US008232274B2

(12) United States Patent
Ting et al.

(10) Patent No.: US 8,232,274 B2

(45) Date of Patent: Jul. 31, 2012

(54) PYRIDAZINONE DERIVATIVES USEFUL AS GLUCAN SYNTHASE INHIBITORS

(75) Inventors: Pauline C. Ting, New Providence, NJ (US); Robert G. Aslanian, Rockaway, NJ (US); Jianhua Cao, Edison, NJ (US); David Won-Shik Kim, Edison, NJ (US); Rongze Kuang, Green Brook, NJ (US); Gang Zhou, Bridgewater, NJ (US); Robert Jason Herr, Voorheesville, NY (US); Andrew John Zych, Albany, NY (US); Jinhai Yang, Guilderland, NY (US); Heping Wu, Edison, NJ (US); Nicolas Zorn, Short Hills, NJ (US)

(73) Assignees: Albany Molecular Research, Inc., Albany, NY (US); Merck Sharp & Dohme Corp., Rahway, NJ (US)

( * ) Notice: Subject to any disclaimer, the term of this patent is extended or adjusted under 35 U.S.C. 154(b) by 514 days.

(21) Appl. No.: 12/046,755

(22) Filed: Mar. 12, 2008

(65) Prior Publication Data

US 2009/0170861 A1 Jul. 2, 2009

Related U.S. Application Data

(60) Provisional application No. 60/918,171, filed on Mar. 15, 2007.

(51) Int. Cl.

| | |
|---|---|
| ***A61K 31/501*** | (2006.01) |
| ***A61K 31/5377*** | (2006.01) |
| ***C07D 401/14*** | (2006.01) |
| ***C07D 403/04*** | (2006.01) |
| ***C07D 403/14*** | (2006.01) |
| ***C07D 409/14*** | (2006.01) |
| ***C07D 413/14*** | (2006.01) |
| *A61P 31/00* | (2006.01) |

(52) U.S. Cl. ................ 514/236.5; 514/252.02; 544/238; 544/121

(58) Field of Classification Search .................. 544/238, 544/121; 514/252.02, 236.5

See application file for complete search history.

(56) References Cited

U.S. PATENT DOCUMENTS

| | | | | |
|---|---|---|---|---|
| 4,532,239 | A * | 7/1985 | Raabe et al. | 514/247 |
| 2009/0143579 | A1 * | 6/2009 | Blake et al. | 544/238 |

FOREIGN PATENT DOCUMENTS

| | | | |
|---|---|---|---|
| EP | 1 479 681 | A1 | 11/2004 |
| ES | 540813 | | 2/1985 |
| JP | 04235975 | * | 8/1992 |
| WO | WO 03027097 | * | 4/2003 |
| WO | WO 03097612 | * | 11/2003 |
| WO | WO 03104225 | * | 12/2003 |
| WO | WO 2005042521 | * | 5/2005 |
| WO | WO 2005117909 | * | 12/2005 |
| WO | WO 2007130383 | A2 * | 11/2007 |

OTHER PUBLICATIONS

Griesser, Chapter 8, The Importance of Solvates (pp. 211-230), in the text, Polymorphism: In the Pharmaceutical Industry, Hilfiker, 2006.*

Cinone, et al., Bioorganic & Medicinal Chemistry (1999), 7(11), 2615-2620.*

Strappaghetti, et al., Eur. J. Med. Chem. (1998), 33(6), 501-508.*

Schmidt, Am. J. Tropical Med. & Hygiene, (1983), 32(2), 231-57.*

Brayman, et al., "Sensitive Assay for Antifungal Activity of glucan Synthase Inhibitors That Uses Germ Tube Formation in *Candida albicans* as an End Point", *Antimicrobial Agents and Chemotherapy*, 47(10): 3305-3310 (Oct. 2003).

Karolyhazy, et al., "Synthesis, in vitro/in vivo Antifungal Evaluation and Structure-Activity Relationship Study of 3(2H)—Pyridazinones", *Arzneimittel-Forschung/Drug Research*, 53(10): 738-743 (2003).

Kondoh, et al., "Piperazine Propanol Derivative as a Novel Antifungal Targeting 1,2-β-D-Glucan Synthase", *Biol. Pharm. Bulletin*, 28(11):2138-2141 (2005).

Ting, et al., "New Agents to Treat Life-Threatening Fungal Infections", *Current Topics in Medicinal Chemistry*, 8:1-11 (2008).

PCT International Search Report mailed Jul. 3, 2008 for corresponding PCT Application No. PCT/US2008/00327.

* cited by examiner

*Primary Examiner* — James O Wilson

*Assistant Examiner* — Cecilia M Jaisle

(74) *Attorney, Agent, or Firm* — Sheldon O. Heber; Raynard Yuro

(57) ABSTRACT

Disclosed is a set of compounds useful as glucan synthase inhibitors having the generic structure of Formula I:

Formula I

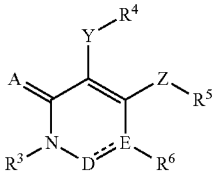

wherein the various moieties A, D, $R^6$, etc., are as defined in the specification. These compounds are useful in treating or preventing fungal infections in a patient.

20 Claims, No Drawings

PYRIDAZINONE DERIVATIVES USEFUL AS GLUCAN SYNTHASE INHIBITORS

The present application claims the benefit of U.S. provisional patent application No. 60/918,171; filed Mar. 15, 2007; which is herein incorporated by reference in its entirety.

FIELD OF THE INVENTION

This invention relates to novel compounds, which are useful as glucan synthase inhibitors, pharmaceutical compositions containing the compounds, and methods of treating or preventing fungal infections. In one embodiment, the compounds are piperazine-substituted pyridazinone compounds.

BACKGROUND OF THE INVENTION

The enzymes involved in fungal cell wall biogenesis are attractive targets for antifungal intervention. These enzymes are unique to fungi and therefore provide highly selective antifungal targets. Furthermore, disruption of cell wall synthesis generally leads to a fungicidal response due to cell lysis induced by the osmotic instability of cells lacking an intact wall. Major structural components of fungal cell walls are β(1,3)-linked D-glucan polymers. These polymers are generated by β(1,3)-D-glucan synthase, an integral membrane protein complex that is required for fungal cell viability. Compounds described as inhibitors of glucan synthase have been described previously. Reference is made to Károlyházy, László et al. *Arzneim.-Forsch./Drug Res.* 2003, Vol. 53, No. 10, 738-743, which discloses 3-(2H)-pyridazinones of the formula:

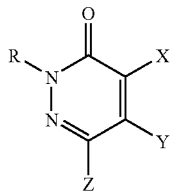

where the various elements are defined therein. An illustrative compound of that series is:

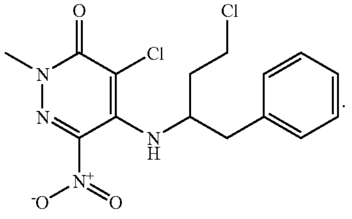

Reference is made to Kondoh, Osamu et al., *Biol. Pharm. Bull.* 2005, 28, 2138-2141, which discloses piperazine propanol derivatives. An illustrative compound of that series is:

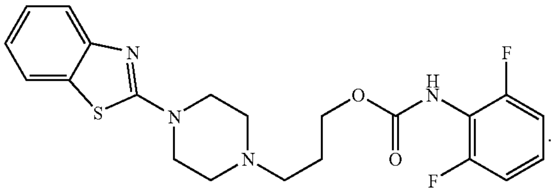

Reference is made to Brayman, Timothy et al., *Antimicrobial Agents and Chemotherapy* 2003 Vol. 47, No. 10, 3305-3310, which discloses the use of several compounds identified as glucan synthase inhibitors to test an assay for antifungal activity of glucan synthase inhibitors that uses germ tube formation in *Candida albicans* as an end point. An illustrative compound used to test the assay is:

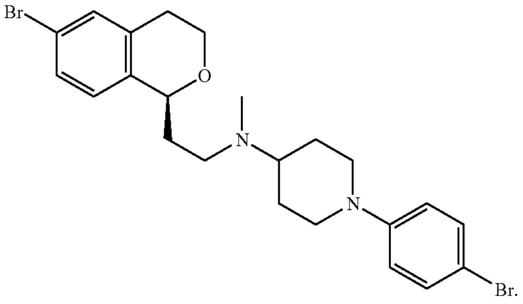

Reference is made to Gomez, Gil et al., ES 540813 1985, which discloses 1,2-diazin-3(2H)-ones as compounds of pharmaceutical interest useful as antihypertensives, β-adrenergic blockers, antiulcer agents or as intermediates thereof. An illustrative compound of that series is:

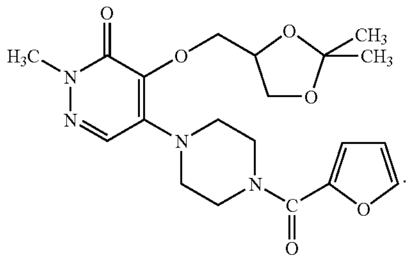

Reference is made to Pauline C. Ting and Scott S. Walker, "New Agents to Treat Life-Threatening Fungal Infections" in Current Topics in Medicinal Chemistry, 2008, which discloses Antifungals that are inhibitors of glucan synthase. These antifungals include cyclic hexapeptides that are either approved for antifungal chemotherapy (caspofungin, micafungin anidulafungin) or under clinical development (aminocandin).

SUMMARY OF THE INVENTION

In its many embodiments, the present invention provides a novel class of compounds, methods of preparing such compounds, pharmaceutical compositions comprising one or more of such compounds, pharmaceutical compositions comprising a combination of one or more of such compounds and other antifungal agents, bacterial agents, and steroids, methods of preparing pharmaceutical formulations comprising one or more of such compounds, and methods of treatment, prevention, inhibition or amelioration of one or more diseases associated with glucan synthase using such compounds or pharmaceutical compositions.

A compound of Formula I:

Formula I

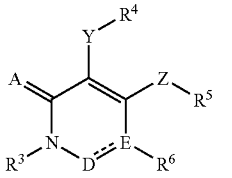

or a pharmaceutically acceptable salt, solvate, ester or prodrug thereof, wherein:

- - - - - - represents a double bond or a single bond, as permitted by the valency requirement, with the proviso that when E is N, the double bond is present and $R^6$ is absent;

A is O or S;

D and E are independently C or N, provided that when D is carbon, D is substituted with hydrogen, alkyl, —Oalkyl, —Nalkyl or —Salkyl;

$R^3$ is a moiety selected from the group consisting of alkyl, alkenyl, aryl, arylalkyl, arylalkenyl, heteroaryl, heteroarylalkyl, heteroarylalkenyl, cycloalkyl, cycloalkylalkyl, cycloalkylalkenyl, cyclenyl, cyclenylalkyl, cyclenylalkenyl, heterocyclyl, heterocyclyalkyl, heterocyclylalkenyl, heterocyclenyl, heterocyclenylalkyl, heterocyclenylalkenyl, arylalkoxylalkyl, arylalkoxylalkenyl, cycloalkoxylalkyl, cycloalkoxylalkenyl, cycloalkenoxylalkyl, and cycloalkenyoxylalkenyl, wherein each of said alkyl, alkenyl, aryl, arylalkyl, arylalkenyl, heteroaryl, heteroarylalkyl, heteroarylalkenyl, cycloalkyl, cycloalkylalkyl, cycloalkylalkenyl, cyclenyl, cyclenylalkyl, cyclenylalkenyl, heterocyclyl, heterocyclylalkyl, heterocyclylalkenyl, heterocyclenyl, heterocyclenylalkyl, heterocyclenylalkenyl, arylalkoxylalkyl, arylalkoxylalkenyl, cycloalkoxylalkyl, cycloalkoxylalkenyl, cycloalkenoxylalkyl, cycloalkenyoxylalkenyl can be unsubstituted or substituted with one or more moieties, which can be the same or different, each moiety being independently selected from the group consisting of alkyl, alkenyl, alkynyl cycloalkyl, halogen, trihaloalkyl, dihaloalkyl, monohaloalkyl, $—NR^9_2$, $—OR^9$, $—SR^9$, $—NO_2$, —CN, $—NR^{16}COR^9$, $—R^{16}SO_2R^9$, $—COR^9$, $—CO_2R^9$, $—SO_2R^9$, $—CONR^9R^{16}$, and —N═C═O;

Y can be present or absent; or

Y is 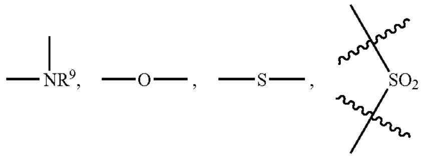 or

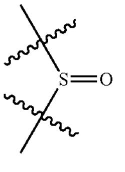

provided that when Y is O, Y—$R^4$ taken together is not alkoxyl of the formula

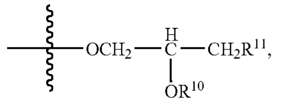

wherein $CH_2R^{11}$ and $—OR^{10}$ together with the CH to which they are attached, form a heterocyclyl that is substituted with one or more moieties, which can be the same or different, selected from the group consisting of alkyl and aryl, or wherein $R^{10}$ is H and $R^{11}$ is hydroxyl or butylamine;

$R^4$ is alkyl, alkenyl, alkynyl, alkoxyalkyl, alkoxyalkoxyalkyl, alkenyl-O-alkyl, alkoxyalkenyl, alkenyl-O-alkenyl, alkynyl-O-alkyl, hydroxyalkyl, hydroxyalkenyl, alkyl-S-alkyl, alkenyl-S-alkyl, alkyl-S-alkenyl, alkenyl-S-alkenyl, alkyl-SO-alkyl, alkenyl-SO-alkyl, alkyl-SO-alkenyl, alkenyl-SO-alkenyl, alkyl-$SO_2$-alkyl, alkenyl-$SO_2$-alkyl, alkyl-$SO_2$-alkenyl, alkenyl-$SO_2$-alkenyl, alkyl-$NR^9$-alkyl, alkenyl-$NR^9$-alkyl, alkyl-$NR^9$-alkenyl, alkenyl-$NR^9$-alkenyl, alkyl-$CO_2$-alkyl, alkenyl-$CO_2$-alkyl, alkyl-$CO_2$-alkenyl, alkenyl-$CO_2$-alkenyl, alkyl-$O_2C$-alkyl, alkenyl-$O_2C$-alkyl, alkyl-$O_2$-alkenyl, alkenyl-$O_2C$-alkenyl, alkyl-NCO-alkyl, alkenyl-NCO-alkyl, alkyl-NCO-alkenyl, alkenyl-NCO-alkenyl, alkyl-CON-alkyl, alkenyl-CON-alkyl, alkyl-CON-alkenyl, alkenyl-CON-alkenyl, alkyl-NCON-alkyl, alkenyl-NCON-alkyl, alkyl-NCON-alkenyl, alkenyl-NCON-alkenyl, alkyl-CO-alkyl, alkenyl-CO-alkyl, alkyl-CO-alkenyl, alkenyl-CO-alkenyl, cycloalkyl, cycloalkylalkyl, spiroheteroaryl, spiroheterocyclenyl, spiroheterocyclyl, spiroheteroarylalkyl, spiroheteroarylalkenyl, spiroheterocyclenylalkyl, spiroheterocyclenylalkenyl, spiroheterocyclylalkyl, spiroheterocyclylalkenyl, spirocycloalkyl, spirocycloalkylalkyl, spirocycloalkylalkenyl, spirocyclenyl, spirocyclenylalkyl, spirocyclenylalkenyl, spiroaryl, spiroarylalkyl, spiroarylalkenyl, alkylcycloalkyl, alkylcycloalkylalkyl, alkylcycloalkylalkenyl, cyclenyl, cyclenylalkyl, cyclenylalkenyl, aryl, arylalkyl, arylalkenyl, heteroaryl, heteroarylalkyl, heteroarylalkenyl, heterocyclyl, heterocyclenyl, heterocyclenylalkyl heterocyclenylalkenyl, heterocyclylalkyl, heterocyclylalkenyl, benzofused-cycloalkyl, benzofused-heterocycloalkyl, benzofused-cycloalkylalkyl or benzofused-heterocycloalkylalkyl;

wherein said alkyl, alkenyl, alkynyl, alkoxyalkyl, alkoxyalkoxyalkyl, alkenyl-O-alkyl, alkoxyalkenyl, alkenyl-O-alkenyl, alkyl-O-alkyl, hydroxyalkyl, hydroxyalkenyl, alkyl-S-alkyl, alkenyl-S-alkyl, alkyl-S-alkenyl, alkenyl-S-alkenyl, alkyl-SO-alkyl, alkenyl-SO-alkyl, alkyl-SO-alkenyl, alkenyl-SO-alkenyl, alkyl-$SO_2$-alkyl, alkenyl-$SO_2$-alkyl, alkyl-$SO_2$-alkenyl, alkenyl-$SO_2$-alkenyl, alkyl-$NR^9$-alkyl, alkenyl-$NR^9$-alkyl, alkyl-$NR^9$-alkenyl, alkenyl-$NR^9$-alkenyl, alkyl-$CO_2$-alkyl, alkenyl-$CO_2$-alkyl, alkyl-$CO_2$-alkenyl, alkenyl-$CO_2$-alkenyl, alkyl-$O_2C$-alkyl, alkenyl-$O_2C$-alkyl, alkyl-$O_2C$-alkenyl, alkenyl-$O_2C$-alkenyl, alkyl-NCO-alkyl, alkenyl-NCO-alkyl, alkyl-NCO-alkenyl, alkenyl-NCO-alkenyl, alkyl-CON-alkyl, alkenyl-CON-alkyl, alkyl-CON-alkenyl, alkenyl-CON-alkenyl, alkyl-NCON-alkyl, alkenyl-NCON-alkyl, alkyl-NCON-alkenyl, alkenyl-NCON-alkenyl, alkyl-CO-alkyl, alkenyl-CO-alkyl, alkyl-CO-alkenyl, alkenyl-CO-alkenyl, cycloalkyl, cycloalkylalkyl, spiroheteroaryl, spiroheterocyclenyl, spiroheterocyclyl, spiroheteroarylalkyl, spiroheteroarylalkenyl, spiroheterocyclenylalkyl, spiroheterocyclenylalkenyl, spiroheterocyclylalkyl, spiroheterocyclylalkenyl, spirocycloalkyl, spirocycloalkylalkyl, spirocycloalkylalkenyl, spirocyclenyl, spirocyclenylalkyl, spirocyclenylalkenyl, spiroaryl, spiroarylalkyl, spiroarylalkenyl, alkylcycloalkyl, alkylcycloalkylalkyl, cyclenyl, cyclenylalkyl, cyclenylalkenyl, aryl, arylalkyl, arylalkenyl, heteroaryl, heteroarylalkyl, heteroarylalkenyl, heterocyclyl, heterocyclenyl, heterocyclenylalkyl, heterocyclenylalkenyl, heterocyclylalkyl, heterocyclylalkenyl, benzofused-cycloalkyl, benzofused-heterocycloalkyl, benzofused-cycloalkylalkyl or benzofused-heterocycloalkylalkyl can be unsubstituted or substituted with at least one moiety independently selected from the group consisting of alkyl, alkenyl, aryl, $OR^9$, arylalkyl, arylalkenyl, cyclenylalkyl, cyclenylalkenyl, cycloalkylalkyl, cycloalkylalkenyl, alkyl$CO_2$alkyl-, halogen, trihaloalkyl, dihaloalkyl, monohaloalkyl, cycloalkyl, cyclenyl, hydroxyalkyl, hydroxyalkenyl, thiohydroxyalkyl, thiohydroxyalkenyl, hydroxyalkenyl, heteroaryl, heteroarylalkyl, heterocyclenyl, heterocyclenylalkyl, heterocyclyl, heterocyclylalkyl, alkoxyalkyl, —CN, $—NO_2$, $—OSiR^9_3$, $—NR^{16}COR^9$, $—OCONR^9_2$, $—NR^{16}CONR^9_2$, $—NR^{16}SO_2R^9$, $—NR^9_2$, —N═C═O,

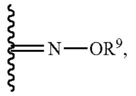

$—NR^{16}CO_2R^9$, $—COR^9$, $—CO_2R^9$, $—OCOR^9$, $—SO_2R^9$, $—SOR^9$, $—SR^9$, $—SO_2N(R^9)_2$ or $CONR^9R^{16}$, wherein each of said alkyl, alkenyl, aryl, arylalkyl, arylalkenyl, cyclenylalkyl, cyclenylalkenyl, cycloalkylalkyl, cycloalkylalkenyl, halogen, trihaloalkyl, dihaloalkyl, monohaloalkyl, cycloalkyl, cyclenyl, hydroxyalkyl, hydroxyalkenyl, thiohydroxyalkyl, thiohydroxyalkenyl, hydroxyalkenyl, heteroaryl, heteroarylalkyl, heterocyclenyl, heterocyclenylalkyl, heterocyclyl, heterocyclylalkyl, alkoxyalkyl, can be unsubstituted or substituted with one or more moieties which can be the same or different, each moiety being independently selected from $R^9$;

Z is a linker attached at either end of said linker to the parent ring of Formula I, wherein said linker is selected from the group consisting of:

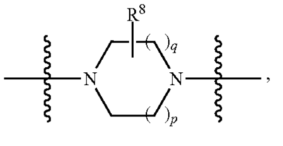

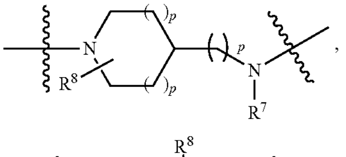

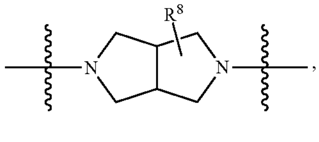

-continued

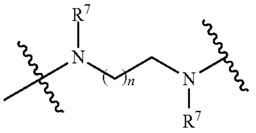

and

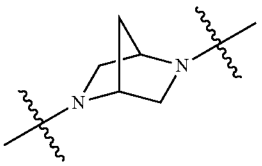

wherein n is 1 to 4, p is 0 to 2, q is 1 to 3;

$R^5$ is

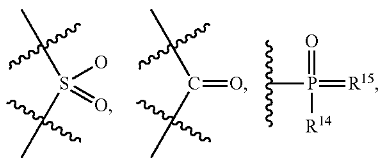

$—CR^9_2$, $—SO_2NR^{13}$-alkyl-C(O)-aryl, or heteroaryl, wherein each of said

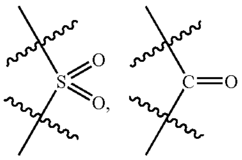

or $—CR^9_2—$ is attached at one end to Z and at the second end substituted with one or more moieties, which can be the same or different, each moiety being independently selected from the group consisting of H, alkyl, alkenyl, cycloalkyl, cyclenyl, aryl, heterocyclyl, heterocyclenyl, heteroaryl, cycloalkylalkyl, cyclenylalkyl, arylalkyl, heterocyclylalkyl, heterocyclenylalkyl, heteroarylalkyl, cycloalkylalkenyl, cyclenylalkenyl, arylalkenyl, heterocyclylalkenyl, heterocyclenylalkenyl, heteroarylalkenyl, $—OR^9$ and $—NR^9_2$, further, wherein each of said alkyl, alkenyl, cycloalkyl, cyclenyl, aryl, heterocyclyl, heterocyclenyl, heteroaryl, cycloalkylalkyl, cyclenylalkyl, arylalkyl, heterocyclylalkyl, heterocyclenylalkyl, heteroarylalkyl, cycloalkylalkenyl, cyclenylalkenyl, arylalkenyl, heterocyclylalkenyl, heterocyclenylalkenyl, or heteroarylalkenyl can be unsubstituted or substituted with one or more moieties, which can be the same or different, each moiety being independently selected from the group consisting of halogen, alkyl, alkenyl, cycloalkyl, $—OR^9$, alkyl$OR^9$, alkyl$CO_2R^9$, alkyl$NR^{16}COR^9$, alkyl$NR^{16}CONR^9$, alkyl$SO_2R^9$, alkyl$COR^9$, alkyl$SO_2NR^9_2$, alkyl$NR^9_2$, alkylaryl, alkylheteroaryl, alkyl$SR^9$, alkyl$SOR^9$, —CN, $—CO_2R^9$, trihaloalkyl, dihaloalkyl, monohaloalkyl, $—NR^{16}COR^9$, $—NR^{16}CONR^9_2$, $—NR^{16}SO_2—R^{13}$, $—SO_2R^9$, $—COR^9$, $—NO_2$, $—SO_2NR^9_2$, aryl, heteroaryl, $—NR^9_2$, $—SR^9$, $—SOR^9$, $—C(═NOH)—NR^{13}$,

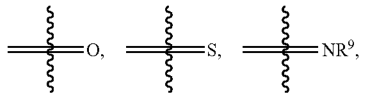

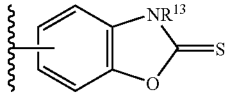 and 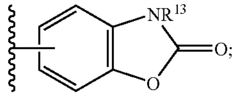;

or Y—$R^4$ taken together are H, provided that $R^6$ is not H; or Y—$R^4$ taken together are H and $R^6$ is H, provided that when Z is

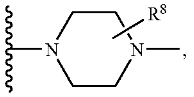

$R^8$ is not H;

or when Y is —O— and $R^5$ is —$SO_2$—, $R^4$ and the second end substituent on $R^5$ together are -alkyl-, -alkenyl-, -alkyl-NH—, or -alkenyl-NH— forming a ring with the —O— and —$SO_2$— groups to which they are attached;

or when $R^3$ is a group having an —$OR^9$ substituent and Y is —O—, $R^4$ and the $R^9$ portion of the $R^3$ group together are a divalent alkyl group, forming a ring with the —O— atoms to which they are attached;

or when Y is —O— and $R^5$ is —$SO_2$—, $R^4$ and the second end substituent of $R^5$ together are an -alkyl-phenylene-alkyl-$NR^{13}$— group or an -alkyl-phenylene-alkyl- group, forming a ring with the —O— and —$SO_2$— groups to which they are attached;

or when Y is —O— and $R^5$ is —$SO_2$—, $R^4$ and the second end substituent of $R^5$ together are an -alkyl-heteroarylene-alkyl- group or an -alkyl-heteroarylene-alkyl-$NR^{13}$— group, forming a ring with the —O— and —$SO_2$— groups to which they are attached;

or Z and $R^5$ taken together is

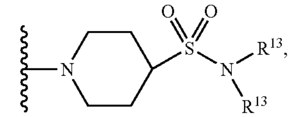 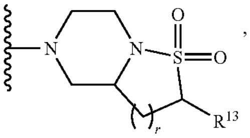,

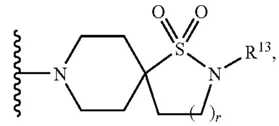 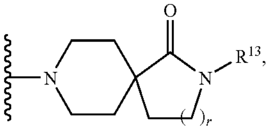

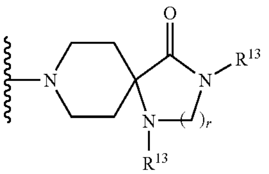 or 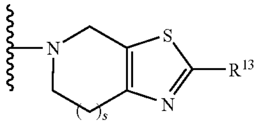, wherein r is 1 or 2;

s is 0 or 1;

or —Y—$R^4$, —$ZR^5$ and the carbons to which they are attached form the group

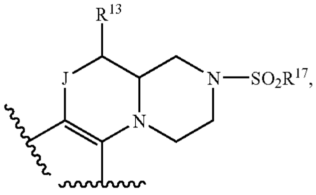

wherein J is —O—, —S— or —$NR^{13}$;

$R^6$ is H, alkyl, aryl, arylalkyl, arylalkenyl, heteroaryl, heteroarylalkyl, heteroarylalkenyl, cycloalkyl, cycloalkylalkyl, cycloalkylalkenyl, arylalkoxylalkyl, arylalkoxylalkenyl, arylalkoxyl, cycloalkoxyl, cycloalkoxylalkyl, cycloalkoxylalkenyl, cycloalkylalkoxyl, cycloalkenoxyl, cycloalkenoxylalkyl, cycloalkenyoxylalkenyl, —$NR^9{}_2$, —$OR^9$, —$NO_2$, —$NR^{16}COR^9$, —$NR^{16}CON(R^{17})_2$, —$NR^{16}SO_2R^9$, —$COR^9$, —$CO_2R^9$ or —$CONR^9R^{16}$;

wherein each of said alkyl, aryl, arylalkyl, arylalkenyl, heteroaryl, heteroarylalkyl, heteroarylalkenyl, cycloalkyl, cycloalkylalkyl, cycloalkylalkenyl, arylalkoxylalkyl, arylalkoxylalkenyl, arylalkoxyl, cycloalkoxyl, cycloalkoxylalkyl, cycloalkoxylalkenyl, cycloalkylalkoxy, cycloalkenoxyl, cycloalkenoxylalkyl, cycloalkenyoxylalkenyl can be unsubstituted or substituted with one or more moieties, which can be the same or different, each moiety being independently selected from the group consisting of halogen, alkyl, trihaloalkyl, dihaloalkyl, monohaloalkyl, —$NR^9{}_2$, —$OR^9$, —$SR^9$, —$NO_2$, —CN, —$NR^{16}COR^9$, —$NR^{16}SO_2R^9$, —$COR^9$, —$CO_2R^9$, —$SO_2R^9$, —$CONR^9R^{16}$ and —$NR^{16}CON(R^{17})_2$;

each $R^7$ is independently selected from the group consisting of H and alkyl;

$R^8$ is one or more moieties, which can be the same or different, each being independently selected from the group consisting of H, aryl, arylalkyl, alkyl,

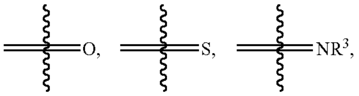

arylalkenyl, heteroaryl, heteroarylalkyl, heteroarylalkenyl, cycloalkyl, cycloalkylalkyl, cycloalkylalkenyl, cyclenyl, cyclenylalkyl, cyclenylalkenyl, alkenyl, alkynyl, trihaloalkyl, dihaloalkyl, monohaloalkyl, $NR^9{}_2$, —$OR^9$, —$SR^9$, —$NR^{16}COR^9$, —$NR^{16}CON(R^{17})_2$, —$NR^{16}SO_2R^9$, —$COR^9$, —$CO_2R^9$, —$SO_2R^9$, and —$CONR^9R^{16}$, wherein each of said aryl, arylalkyl, alkyl, arylalkenyl, heteroaryl, heteroarylalkyl, heteroarylalkenyl, cycloalkyl, cycloalkylalkyl, cycloalkylalkenyl, cyclenyl, cyclenylalkyl, cyclenylalkenyl, alkenyl and alkynyl can be unsubstituted or substituted with one or more moieties which can be the same or different, each moiety being independently selected from the group consisting of halogen, alkyl, trihaloalkyl, dihaloalkyl, monohaloalkyl, —$NR^9{}_2$, —$OR^9$, —$SR^9$, —$NO_2$, —CN, —$NR^{16}COR^9$, —$NR^{16}SO_2R^9$, —$COR^9$, —$CO_2R^9$, —$SO_2R^9$, —$CONR^9R^{16}$ and —$NR^{16}CON(R^{17})_2$;

$R^9$ is one or more moieties, which can be the same or different, each moiety being independently selected from the group consisting of H, alkyl, alkenyl, alkynyl, cycloalkyl, cyclenyl, aryl, heteroalkyl, heterocycloalkyl, heterocyclenyl, heteroaryl, hydroxyalkyl, hydroxyalkenyl, alkylthioalkyl, alkylthioalkenyl, alkenylthioalkyl, alkenylthioalkenyl, alkoxylalkyl, arylalkyl, cycloalkylalkyl, cyclenylalkyl, heterocyclylalkyl, heterocyclenylalkyl, heteroarylalkyl, arylalkenyl, cycloalkyalkenyl, cyclenylalkenyl, heterocyclylalkenyl, heterocyclenylalkenyl, heteroarylalkenyl, alkoxyaryl, trihaloalkyl, trihaloalkenyl, dihaloalkyl, dihaloalkenyl, monohaloalkyl, and monohaloalkenyl, wherein each of said alkyl, alkenyl, alkynyl, cycloalkyl, cyclenyl, aryl, heterocycloalkyl, heterocyclenyl, heteroaryl, hydroxyalkyl, hydroxyalkenyl, alkoxylalkyl, arylalkyl, cycloalkylalkyl, cyclenylalkyl, heterocyclylalkyl, heterocyclenylalkyl, heteroarylalkyl, arylalkenyl, cycloalkyalkenyl, cyclenylalkenyl, heterocyclylalkenyl, heterocyclenylalkenyl, heteroarylalkenyl, and alkoxyaryl can be unsubstituted or substituted with one or more moieties, which can be the same or different, each moiety being independently selected from the group consisting of halogen, trihaloalkyl, dihaloalkyl, monohaloalkyl, trihaloalkenyl, dihaloalkenyl, monohaloalkenyl, hydroxyl, alkoxy, hydroxyalkyl, —$N(R^{12})_2$, alkyl, alkynyl, cycloalkyl, alkenyl, cyclenyl, aryl, heteroaryl, heterocycloalkyl, heterocyclenyl, cycloalkylalkyl, cyclenylalkyl, arylalkyl, heteroarylalkyl, heterocycloalkylalkyl, heterocyclenylalkyl, cycloalkylalkenyl, cyclenylalkenyl, arylalkenyl, heteroarylalkenyl, heterocycloalkylalkenyl, heterocyclenylalkenyl, —CN, —$NO_2$, —$SO_2R^{17}$, —$C(O)N(R^{20})_2$, —$CO_2R^{19}$,

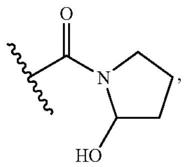

—$NR^{16}$—$C(O)R^{19}$, —$NR^{16}CON(R^{17})_2$, —$NR^{16}SO_2R^{17}$, trihaloalkoxy, dihaloalkoxy, monohaloalkoxy,

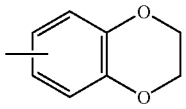 and 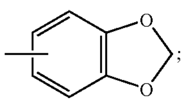;

further wherein when two $R^9$ moieties are attached to a N, the two $R^9$ moieties, together with the N to which they are attached, can form a heterocyclyl or heterocyclenyl ring of 4 to 7 members, wherein 1 or 2 of said ring members can be —O—, —S— or —$NR^{18}$—, provided that there are no heteroatoms adjacent to each other; and wherein the heterocyclyl or heterocyclenyl ring is optionally substituted on 1 or 2 ring carbon atoms by a substituent independently selected from the group consisting of alkyl, alkoxy, —OH and —$NR^{16}$, or two hydrogen atoms on the same carbon are replaced by =O;

each $R^{12}$ is independently selected from the group consisting of H, alkyl, aryl and arylalkyl;

each $R^{13}$ is independently selected from the group consisting of H, alkyl, aryl, arylalkyl, cycloalkyl and cycloalkylalkyl;

$R^{14}$ is alkyl or alkoxy;

$R^{15}$ is aryl, arylalkyl, —$N(R^{13})$aryl —$N(R^{13})$-alkylaryl, —O-aryl or O-alkylaryl;

$R^{16}$ is independently selected from the group consisting of H and alkyl;

$R^{17}$ is alkyl, aryl or arylalkyl;

$R^{18}$ is H, alkyl, —$COOR^{19}$, —$COR^{17}$ or —$CON(R^{17})_2$;

each $R^{19}$ is independently selected from the group consisting of H, alkyl and arylalkyl;

each $R^{20}$ is independently selected from the group consisting of H, alkyl, aryl, arylalkyl, cycloalkyl, cycloalkylalkyl, and alkoxyalkyl;

provided that Formula I does not include the compounds of Table A:

TABLE A

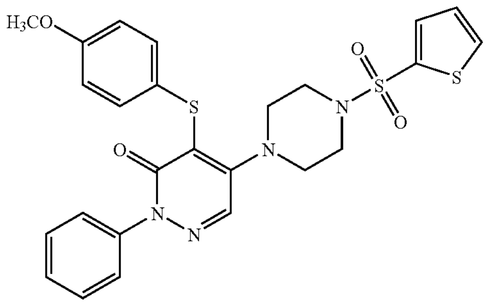

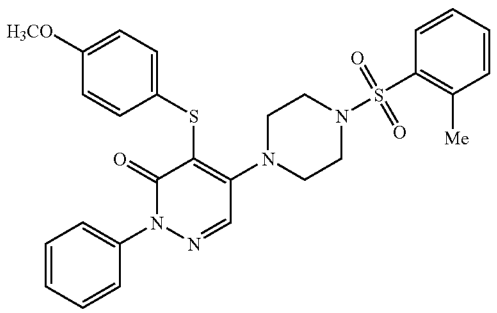

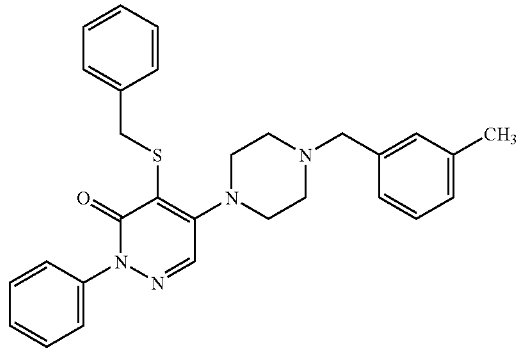

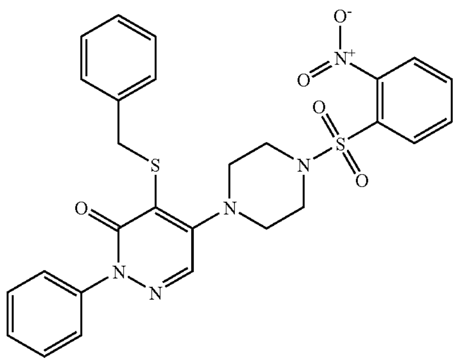

TABLE A-continued
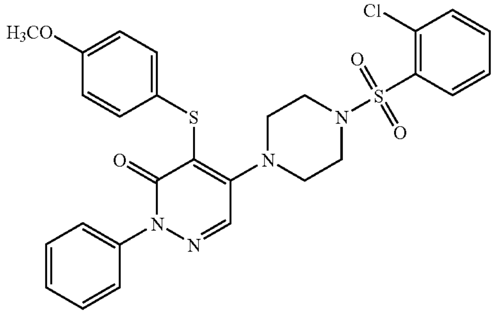
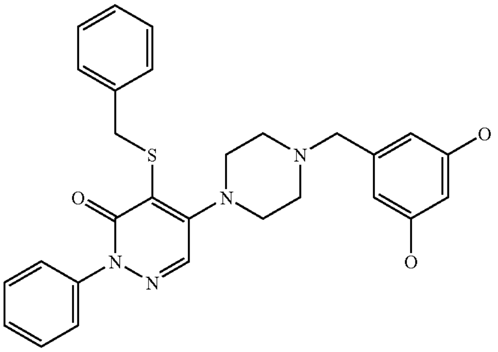
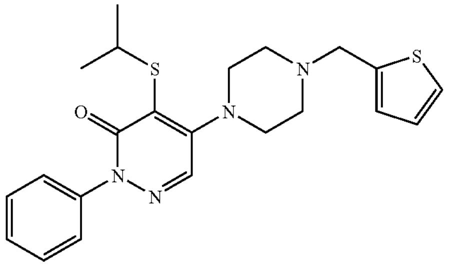
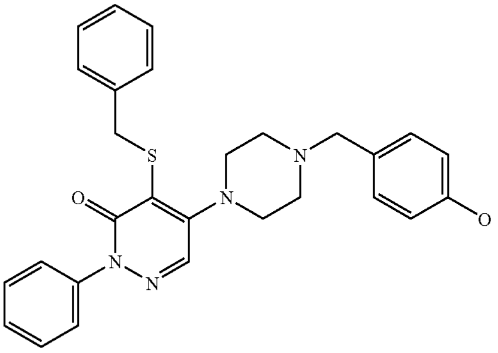
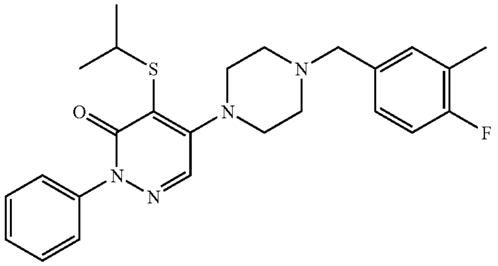
TABLE A-continued
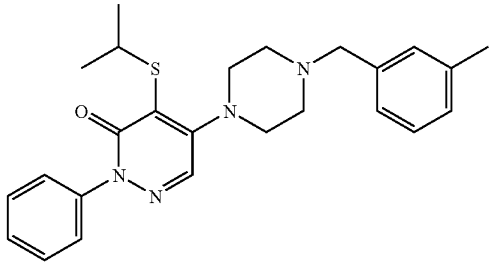
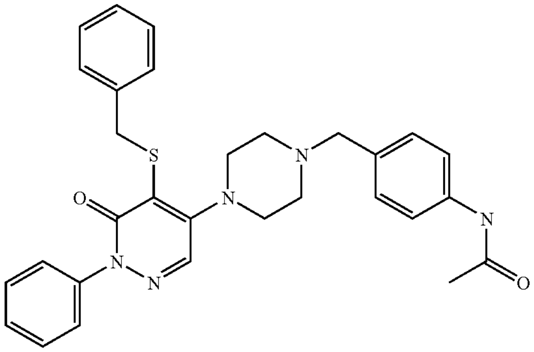
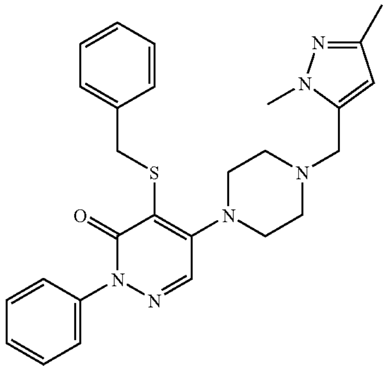
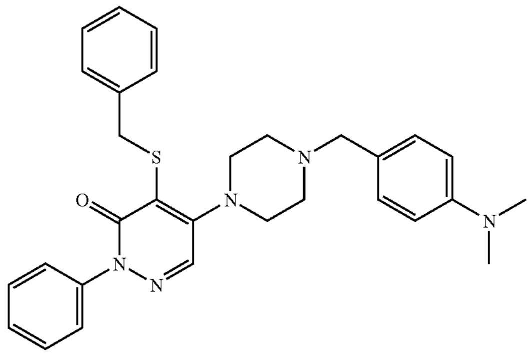

TABLE A-continued
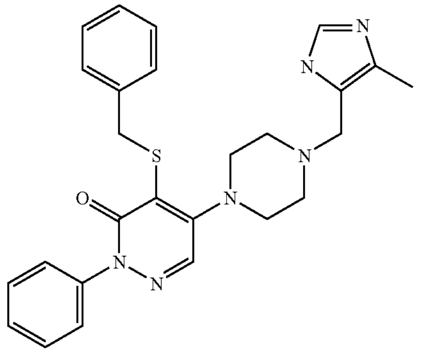
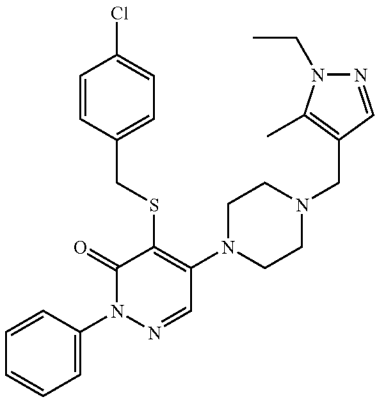
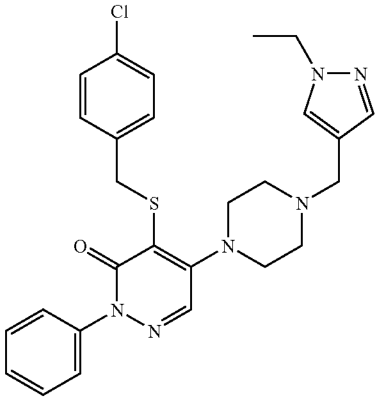
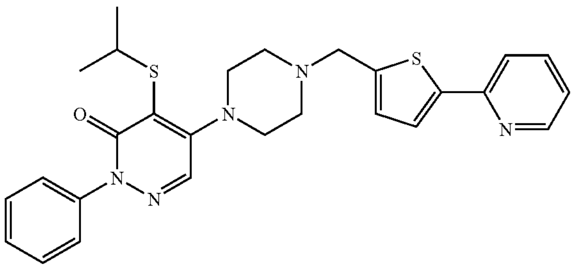
TABLE A-continued
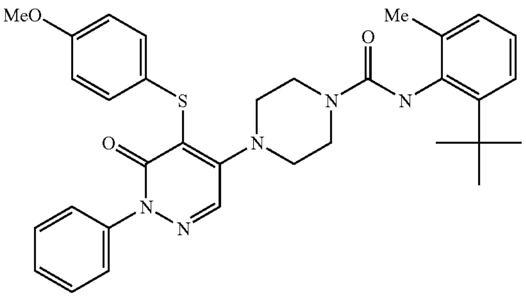
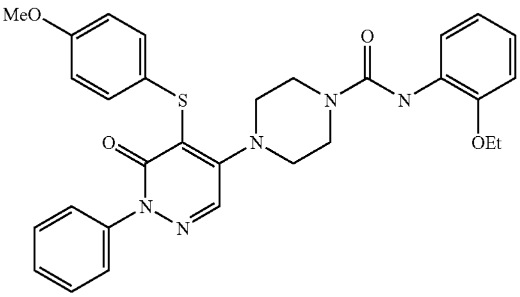
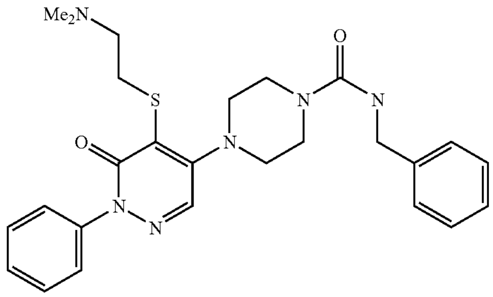
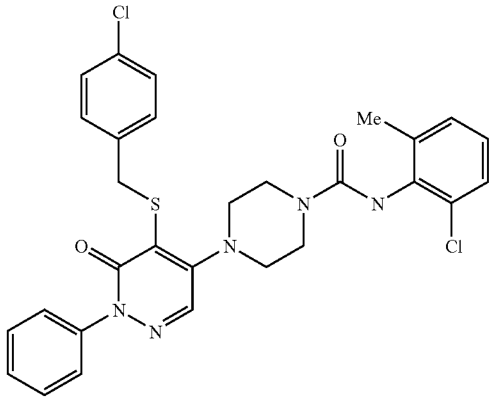

TABLE A-continued
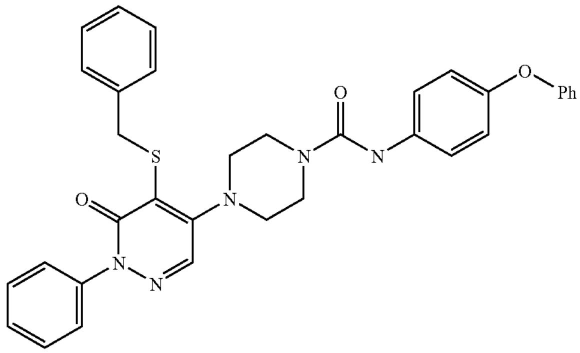
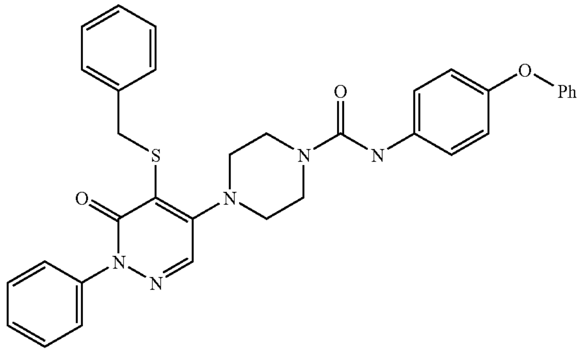
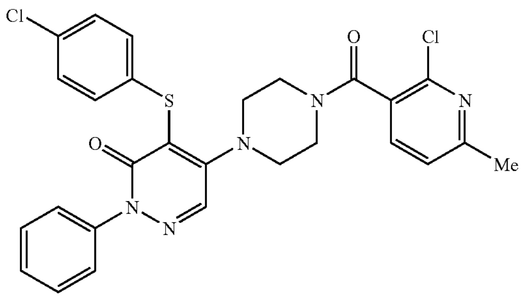
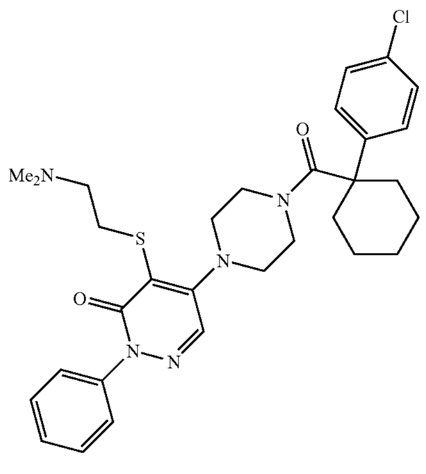
TABLE A-continued
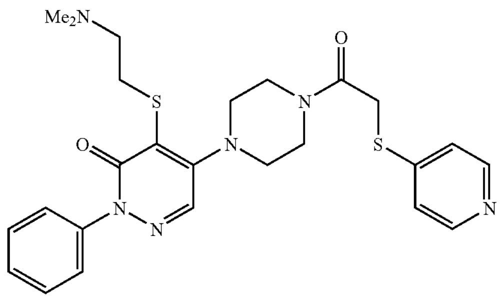
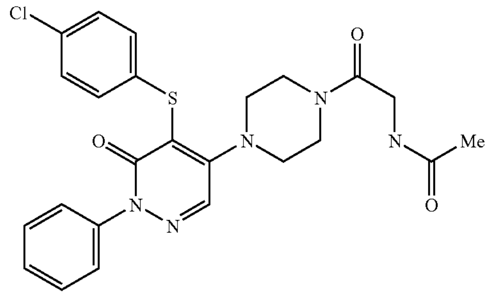
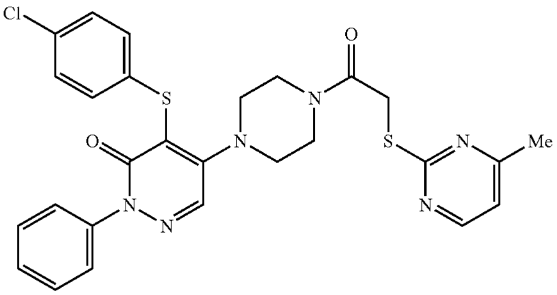
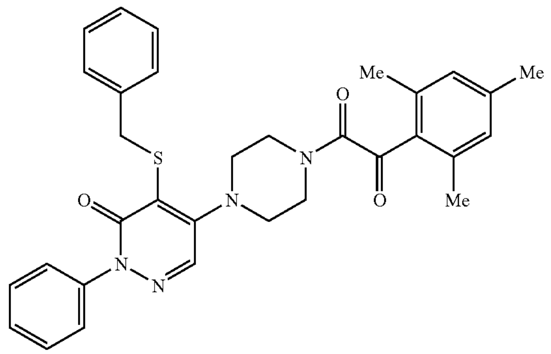

TABLE A-continued
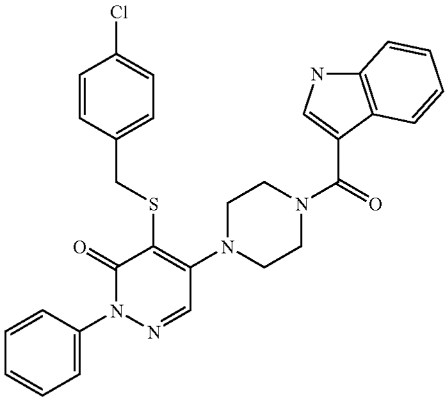
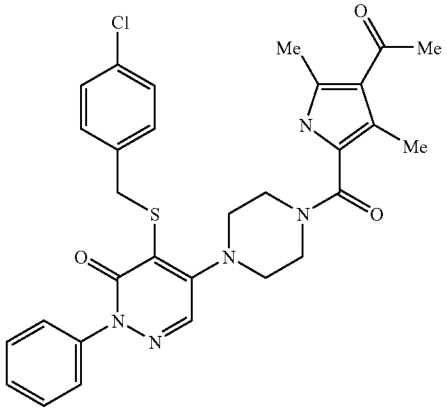
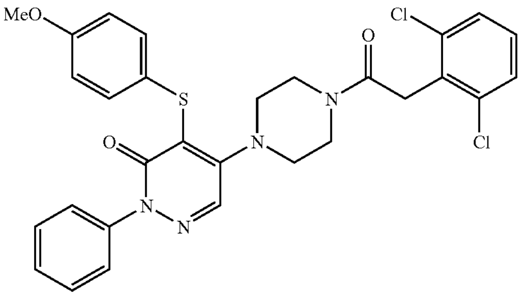
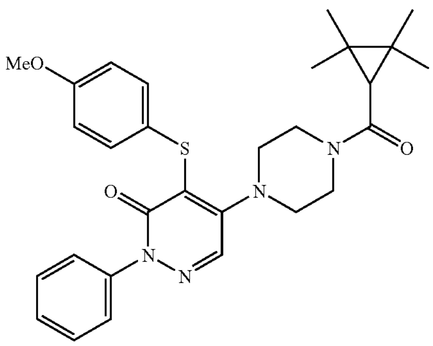
TABLE A-continued
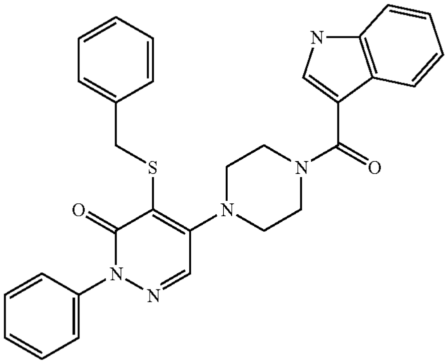
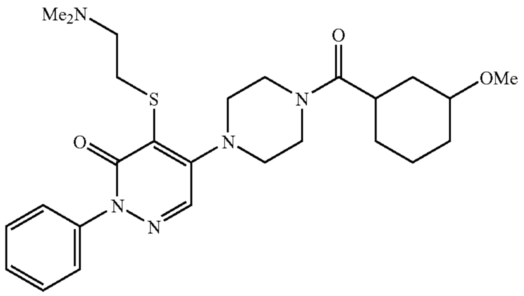
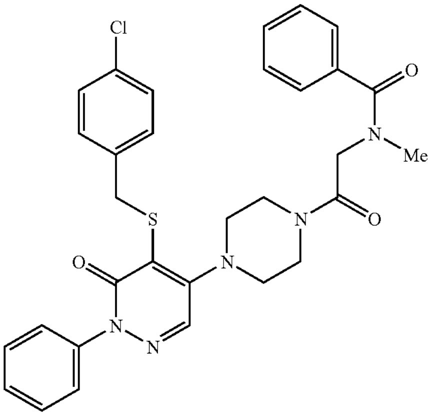
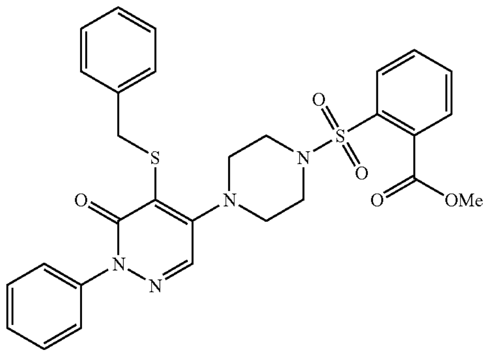

TABLE A-continued
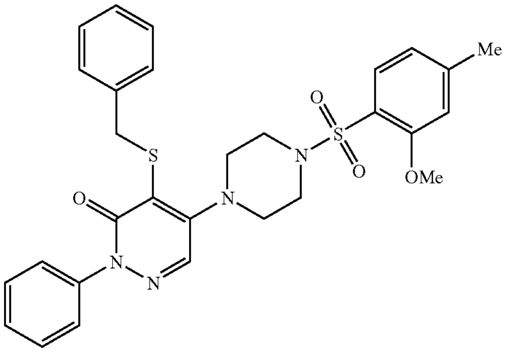
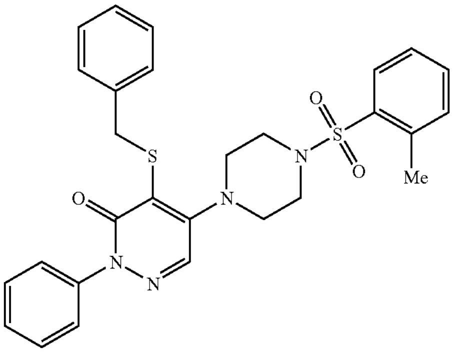
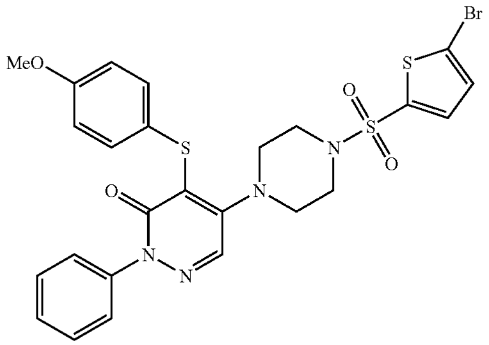
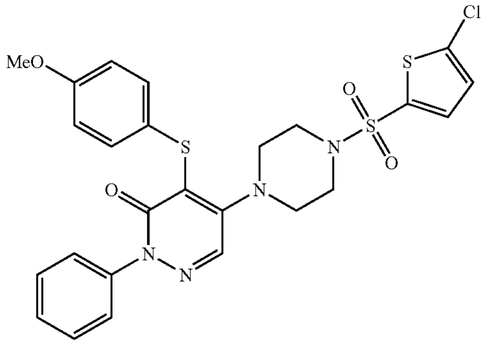
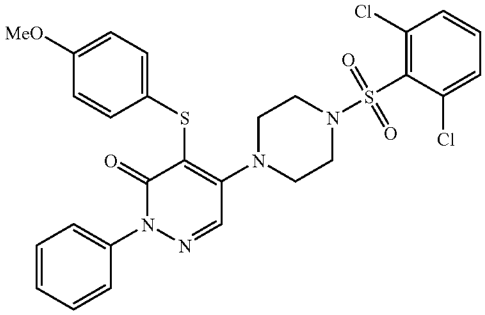
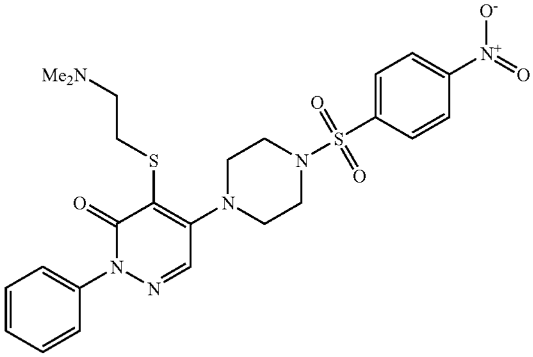
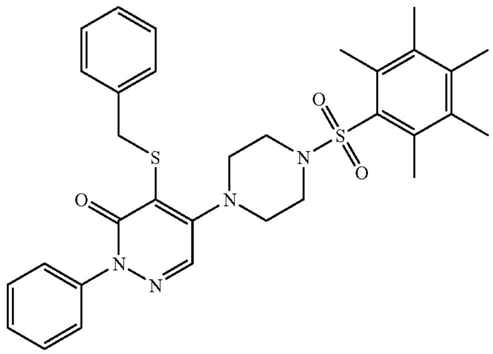
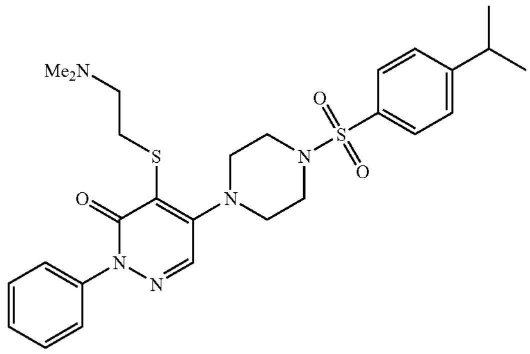

TABLE A-continued
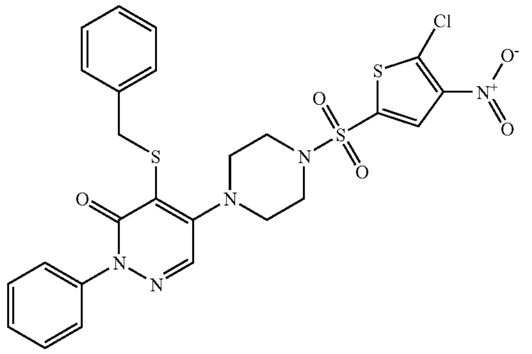
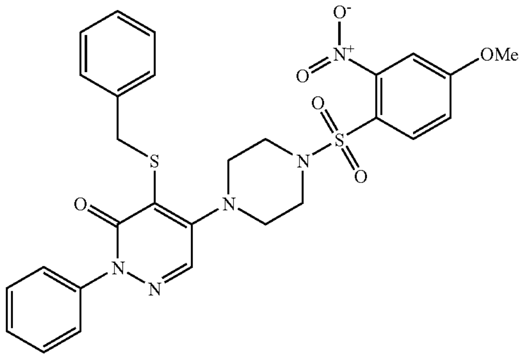
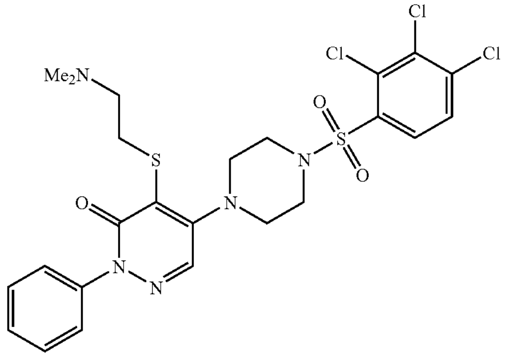
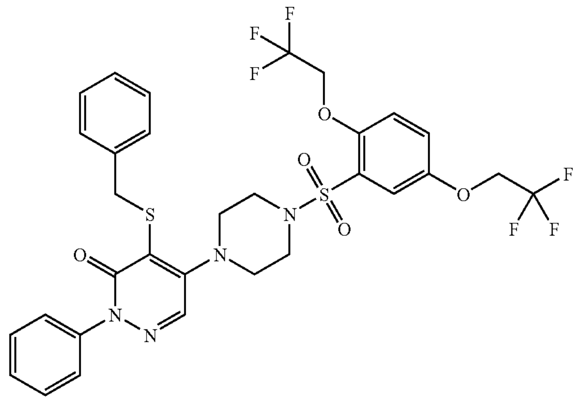
TABLE A-continued
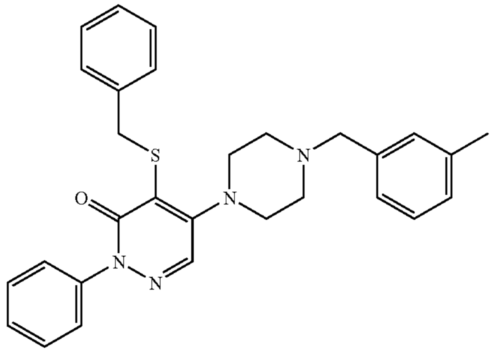
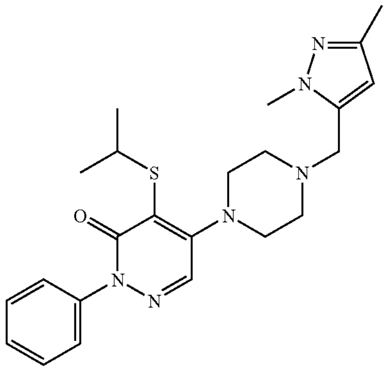
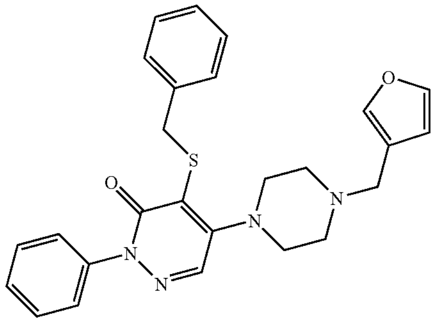
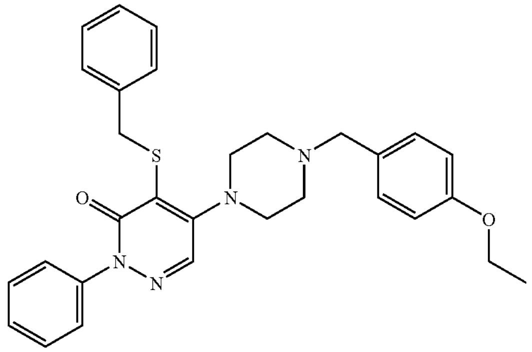

TABLE A-continued
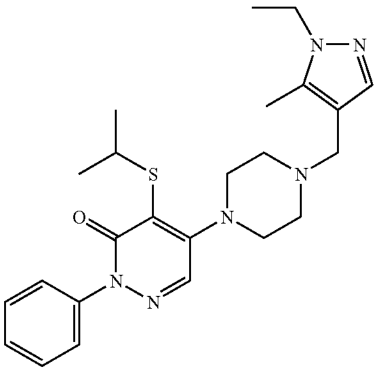
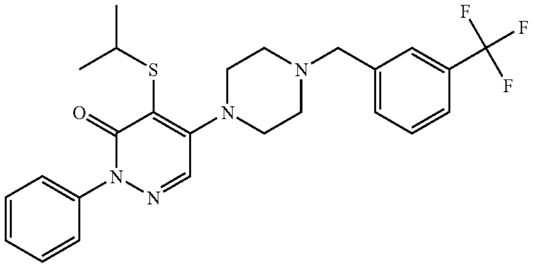
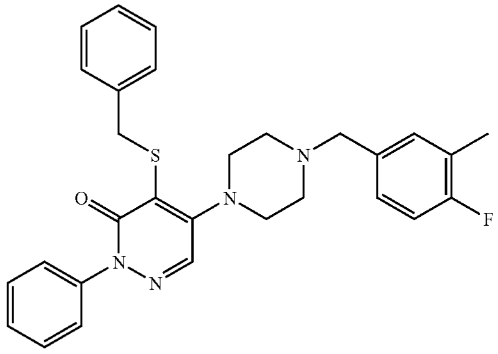
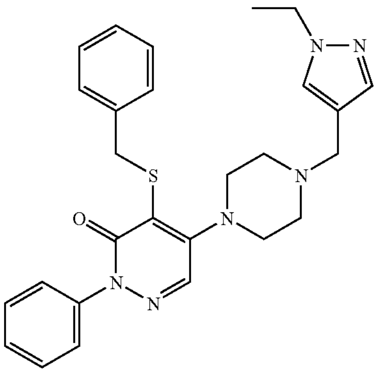
TABLE A-continued
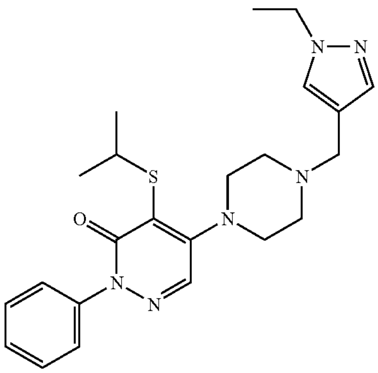
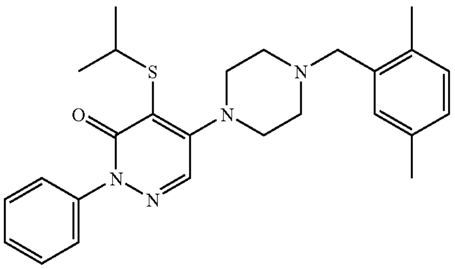
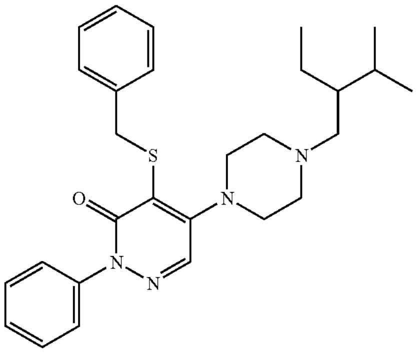
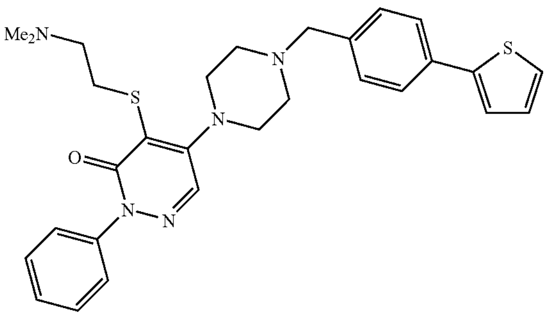

TABLE A-continued
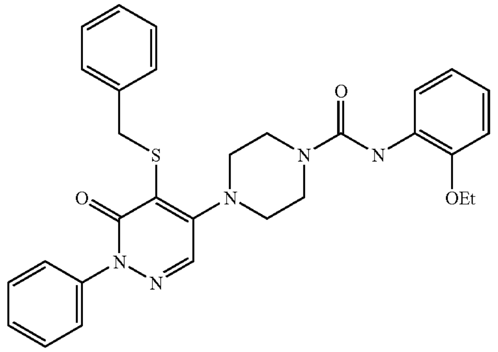
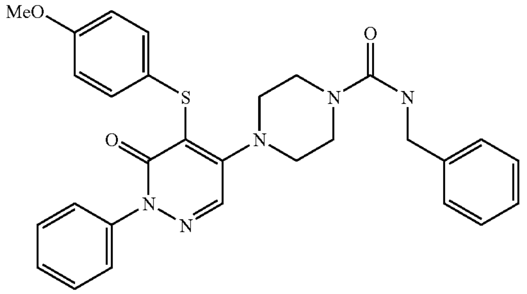
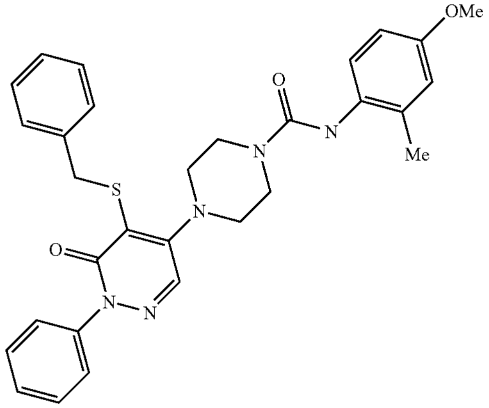
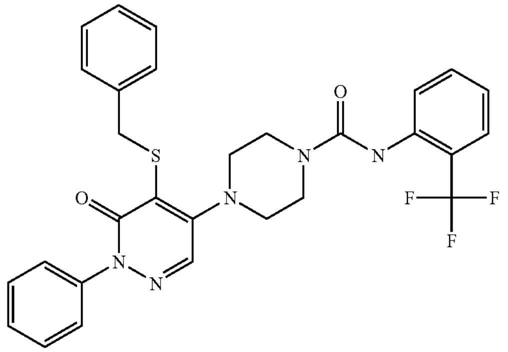
TABLE A-continued
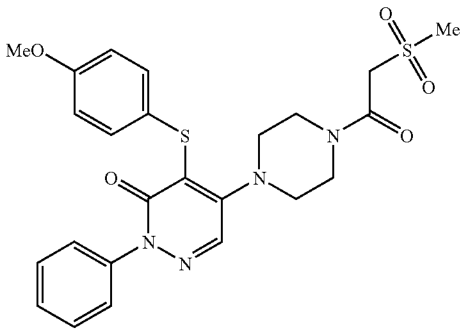
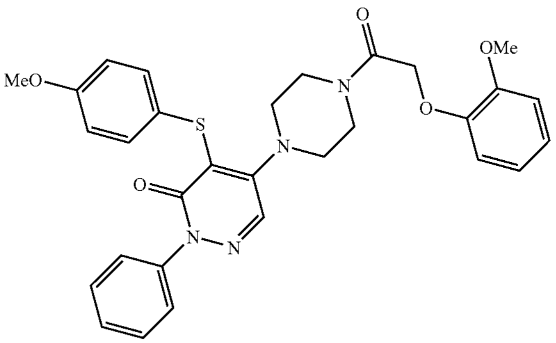
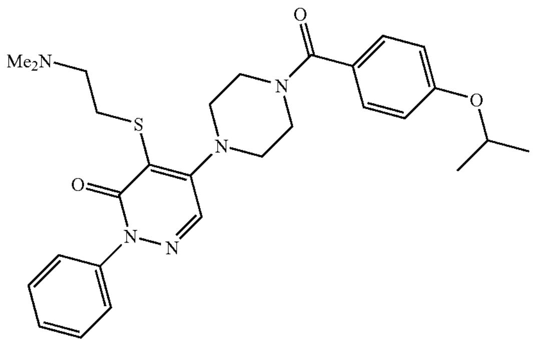
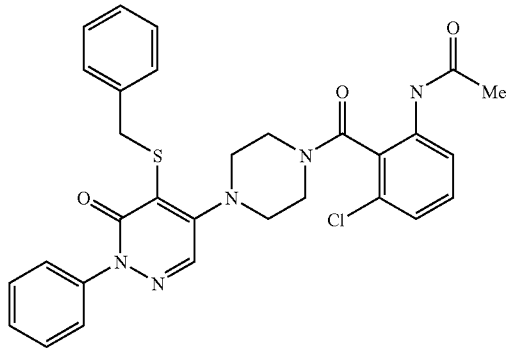

TABLE A-continued
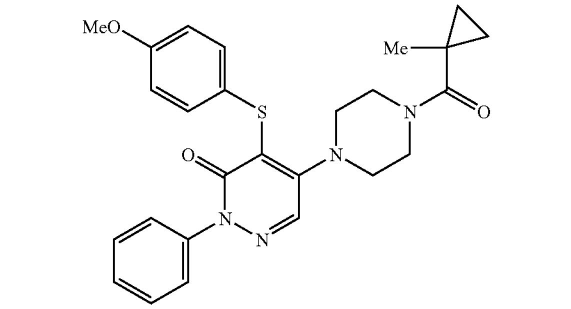
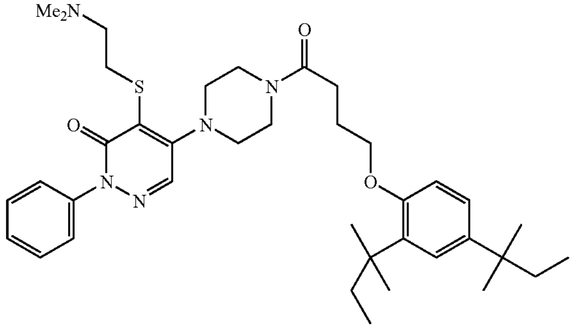
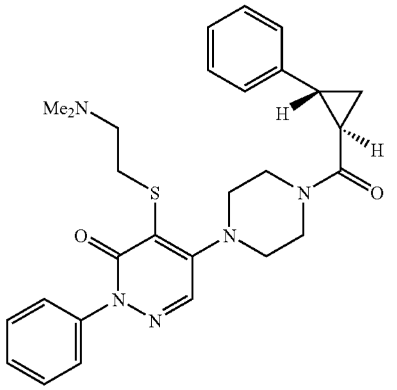
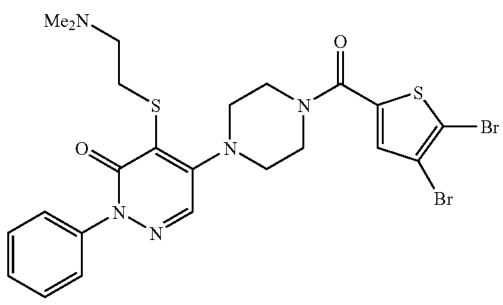
TABLE A-continued
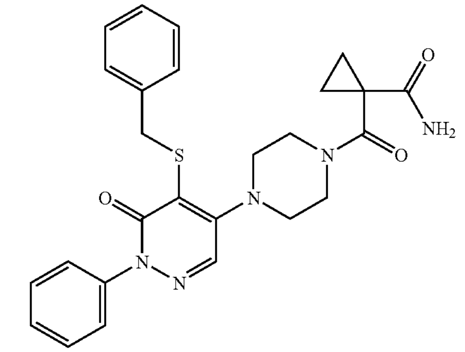
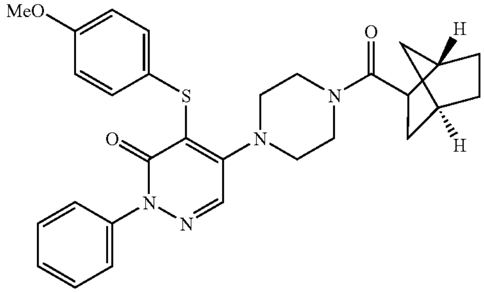
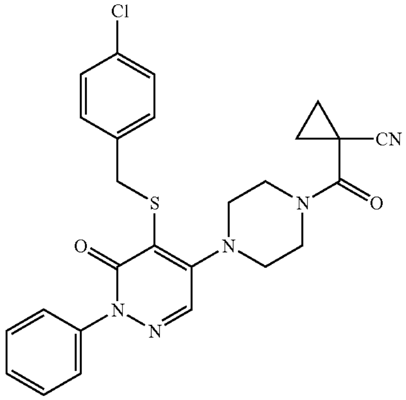
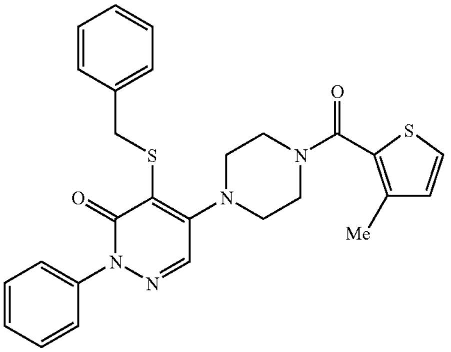

TABLE A-continued
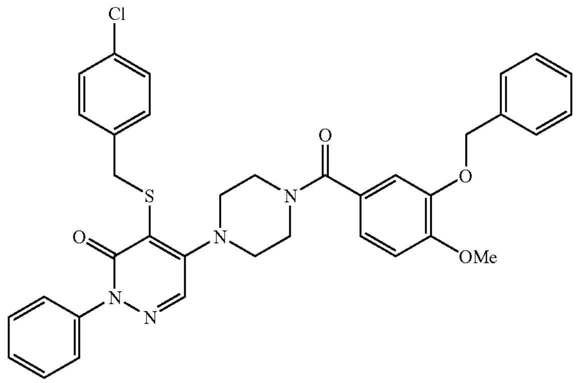
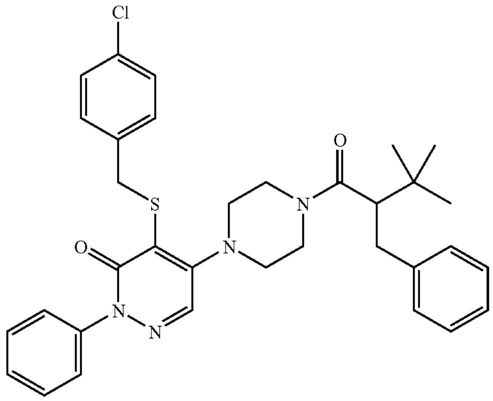
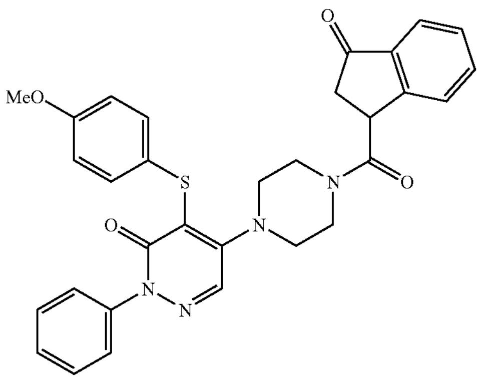
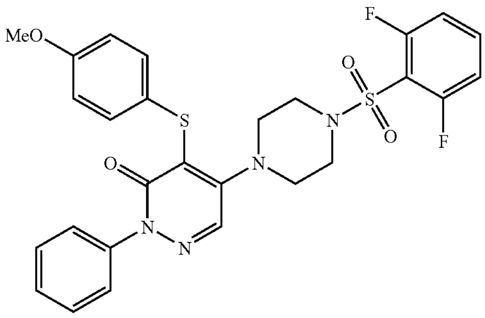
TABLE A-continued
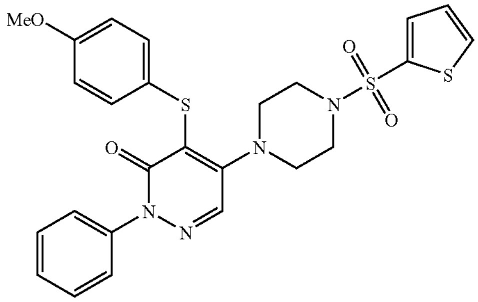
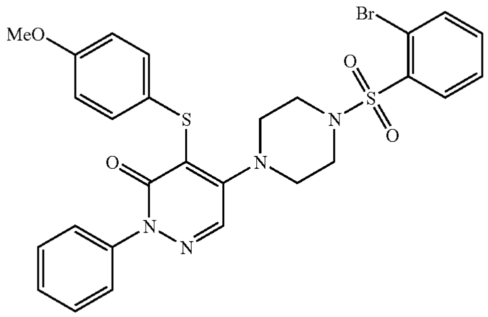
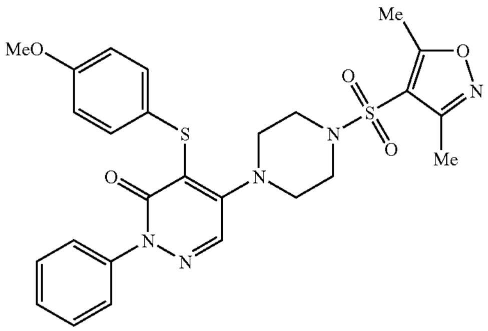
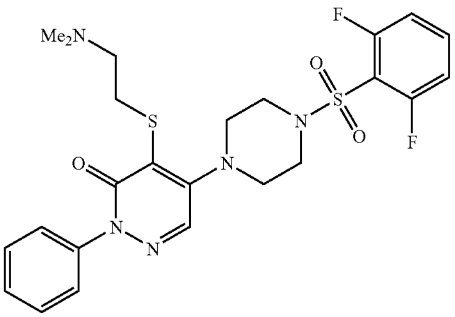
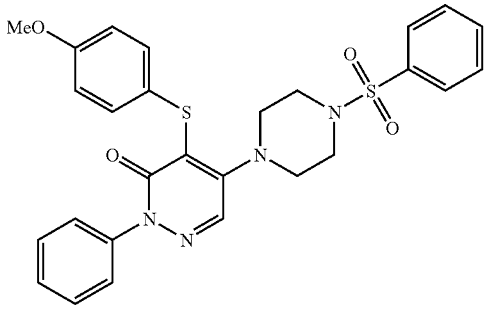

TABLE A-continued
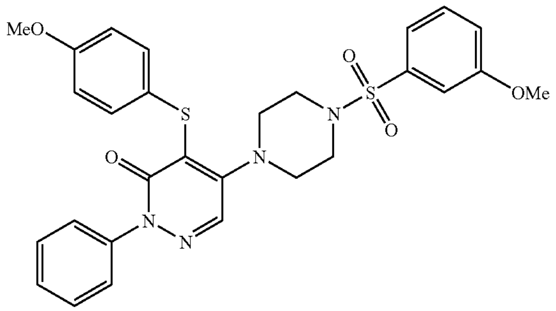
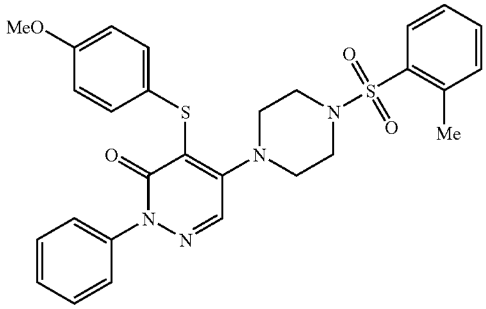
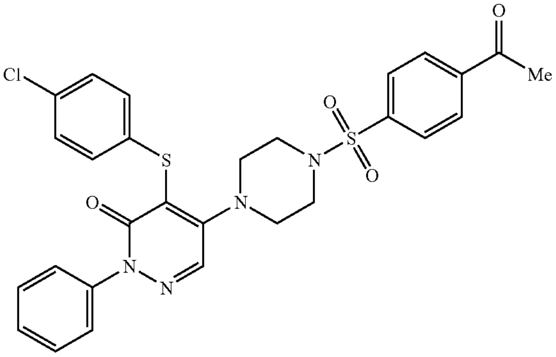
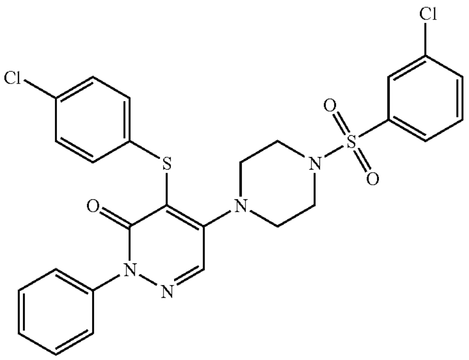
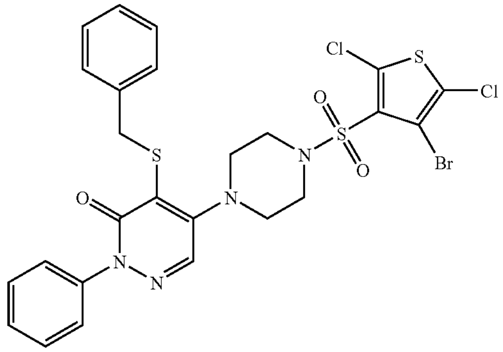
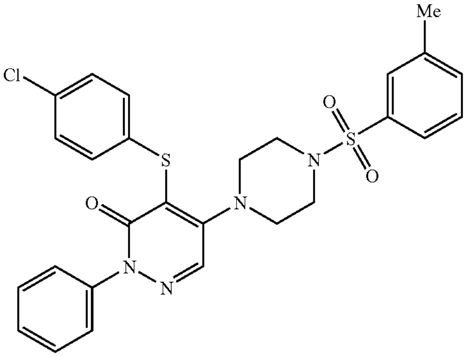
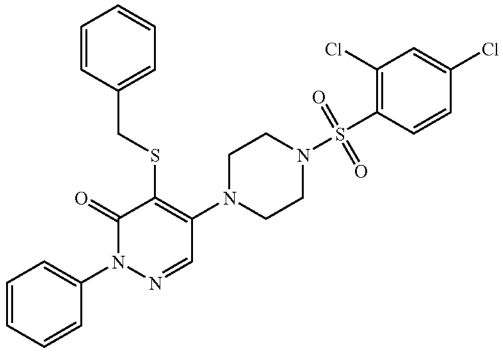
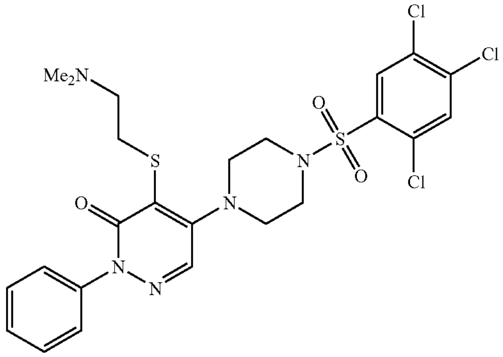

TABLE A-continued
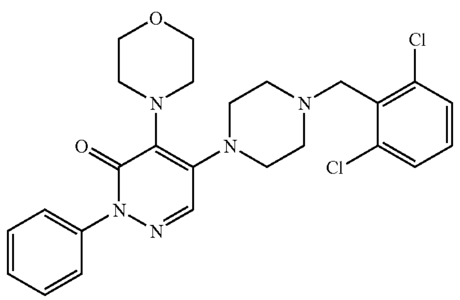
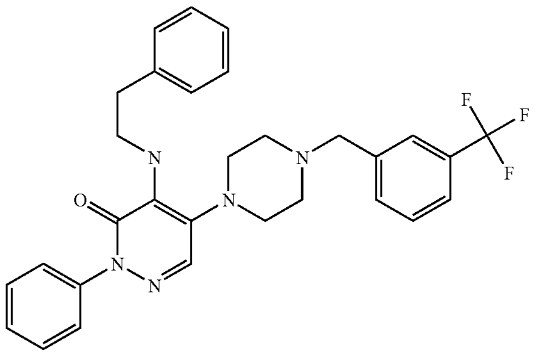
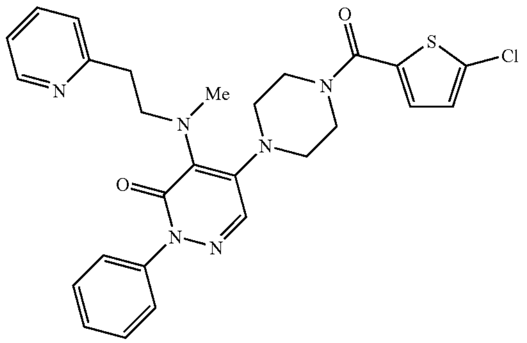
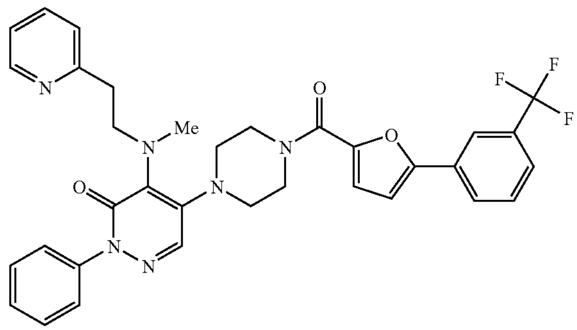
TABLE A-continued
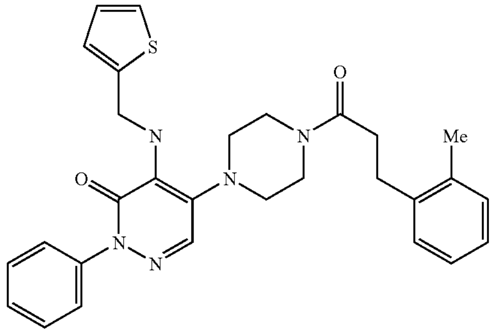
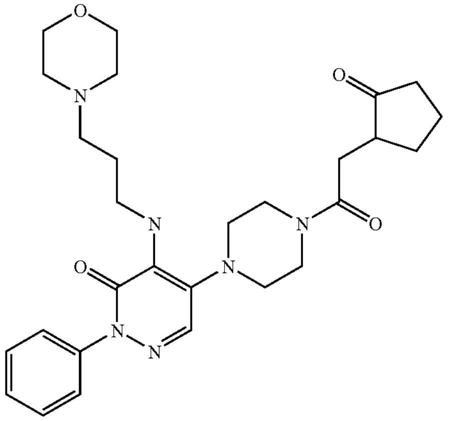
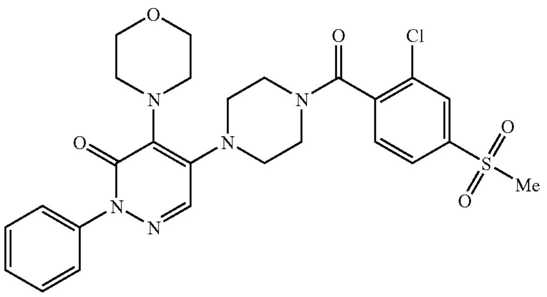
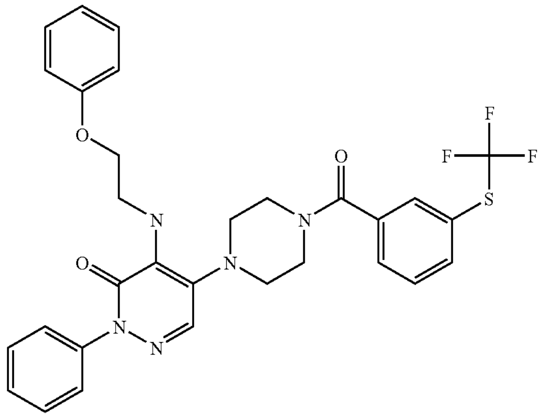

TABLE A-continued
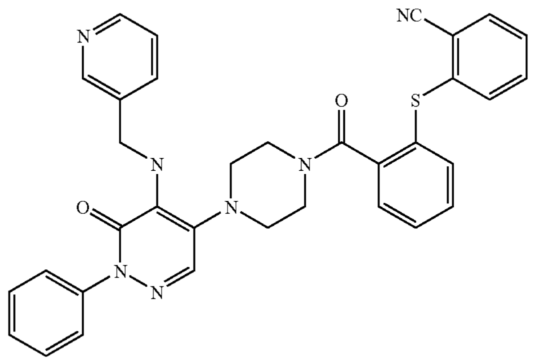
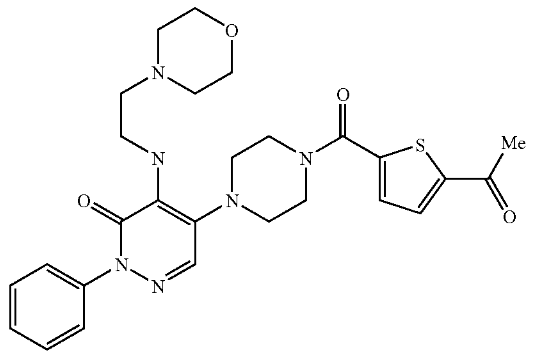
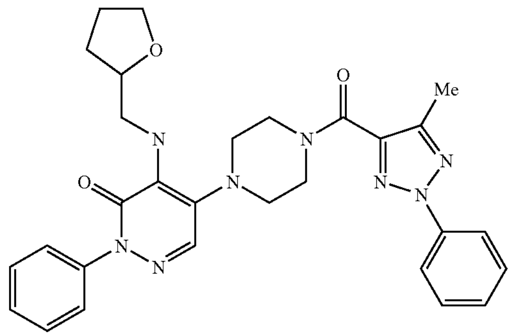
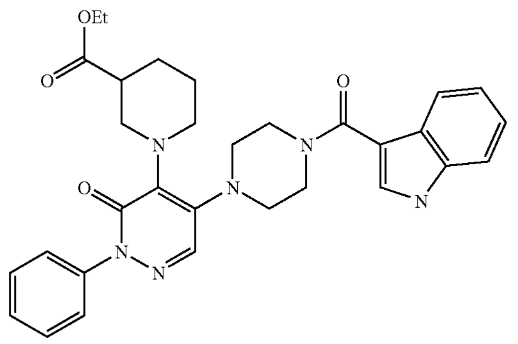
TABLE A-continued
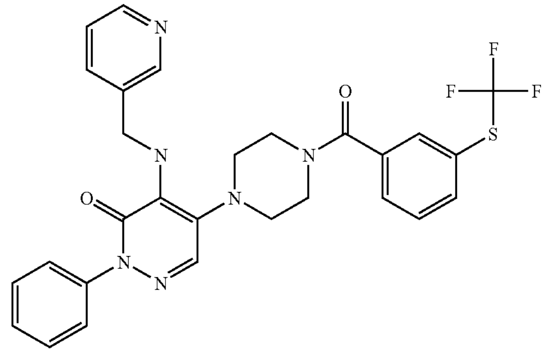
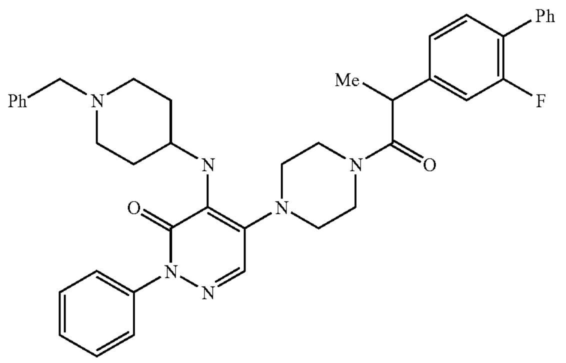
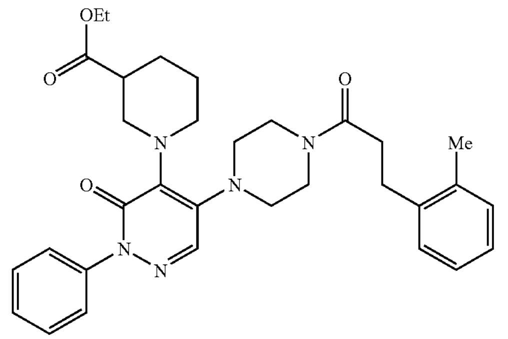
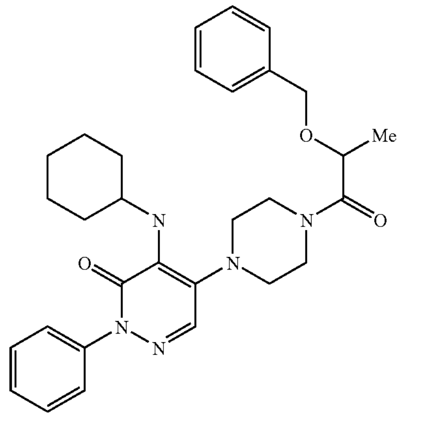

TABLE A-continued
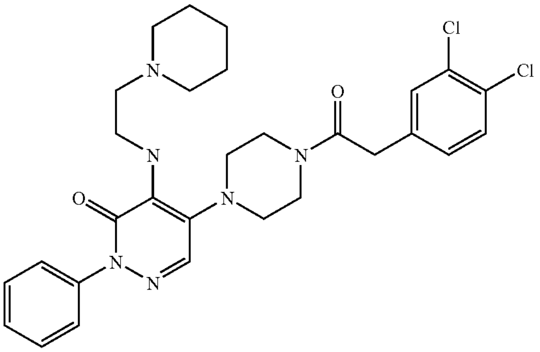
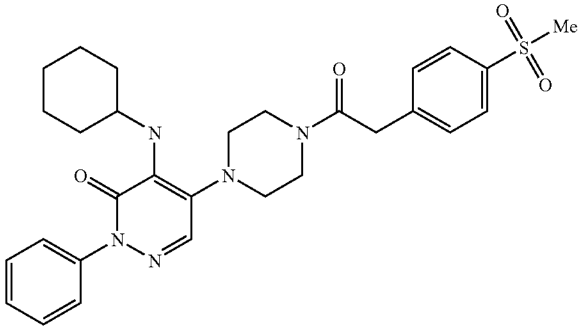
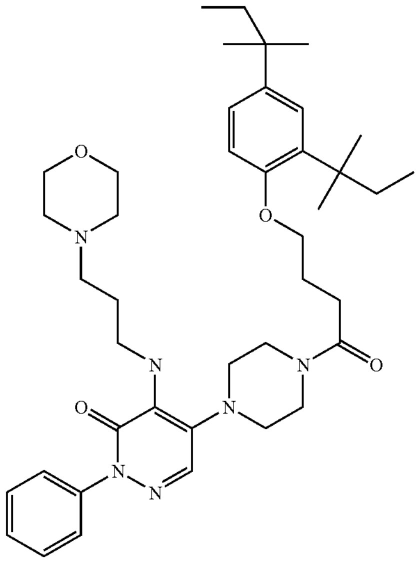
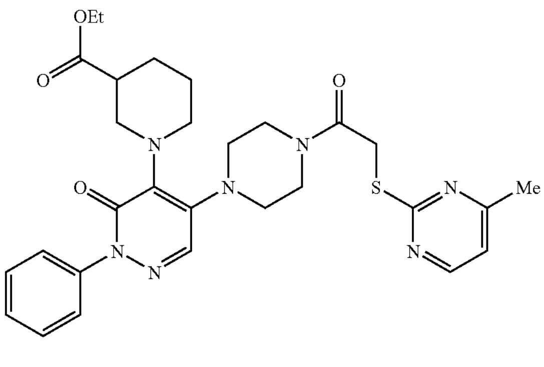
TABLE A-continued
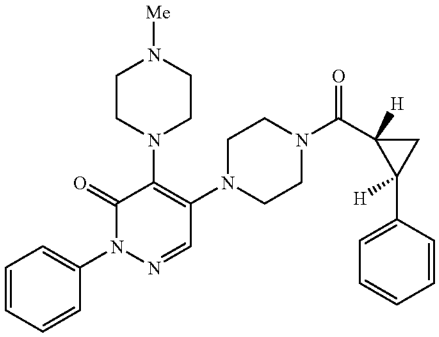
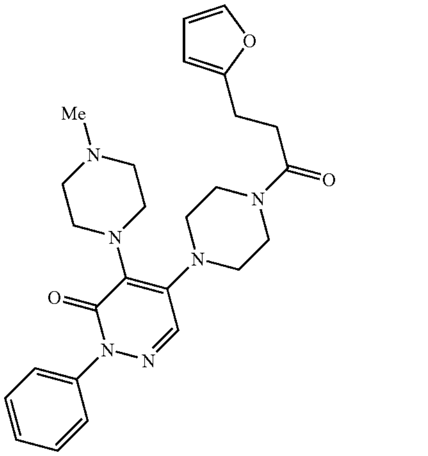
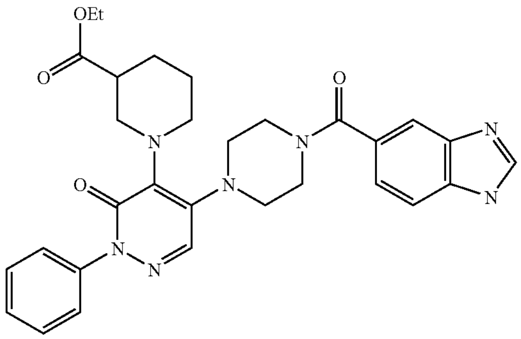
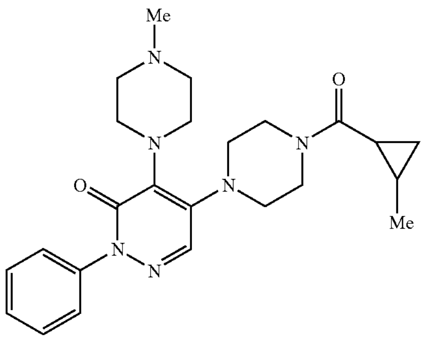

TABLE A-continued
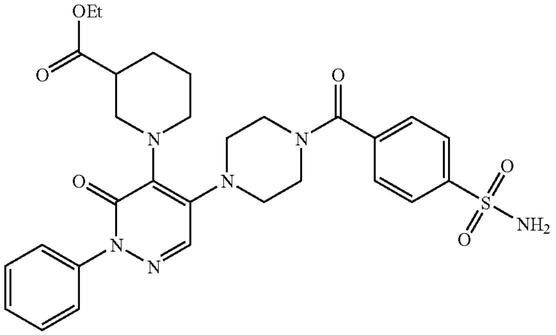
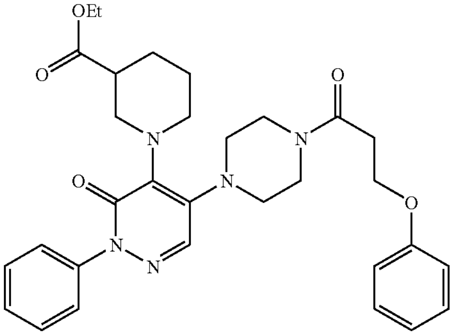
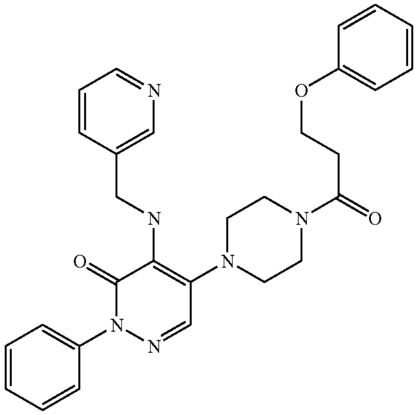
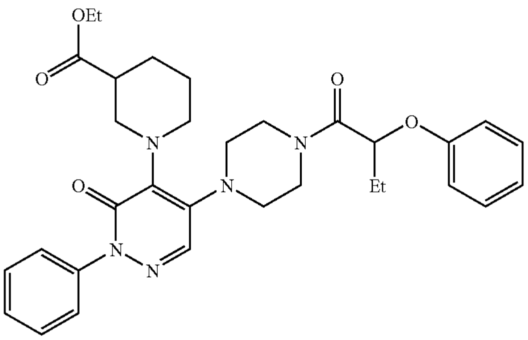
TABLE A-continued
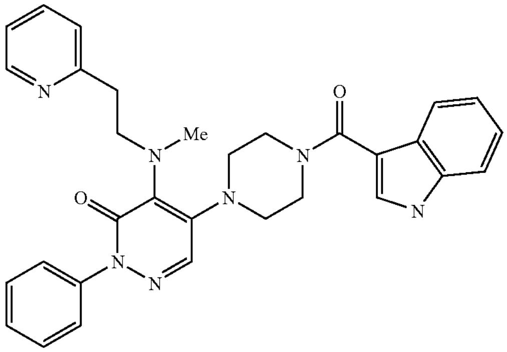
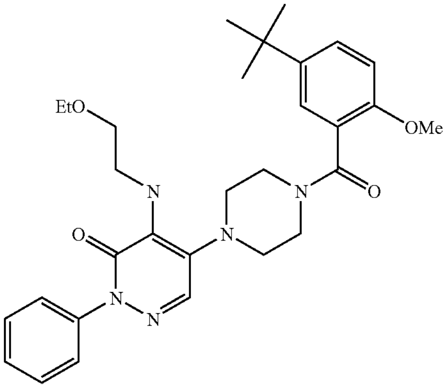
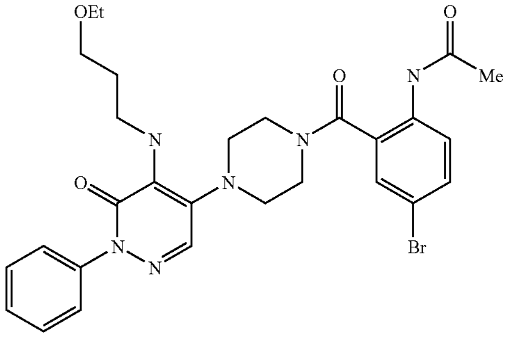
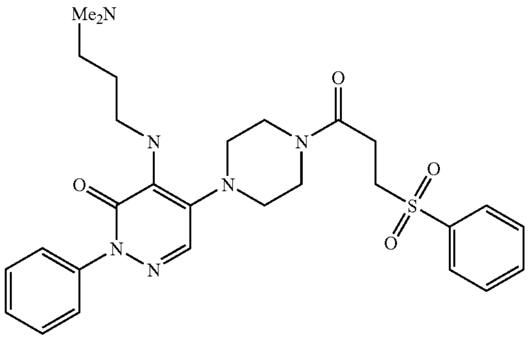

TABLE A-continued
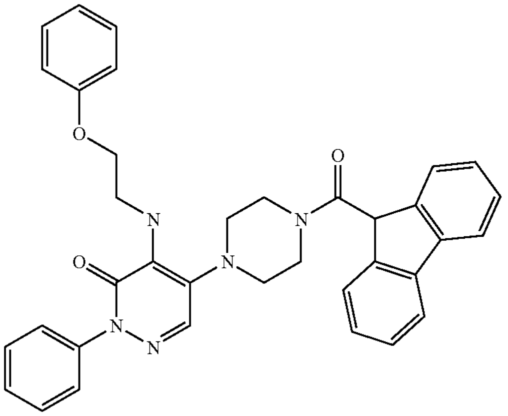
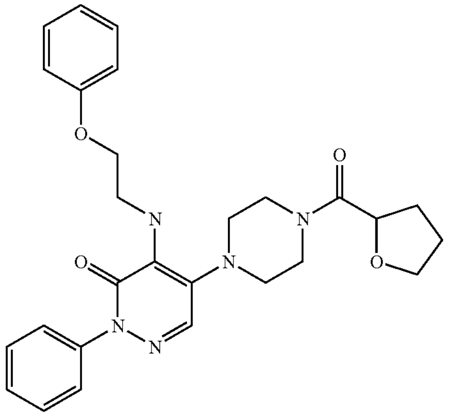
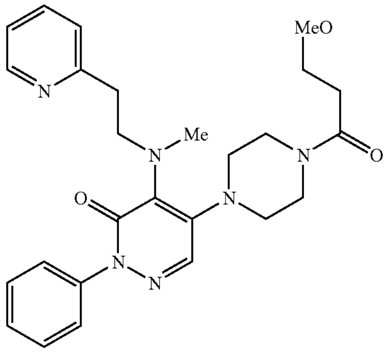
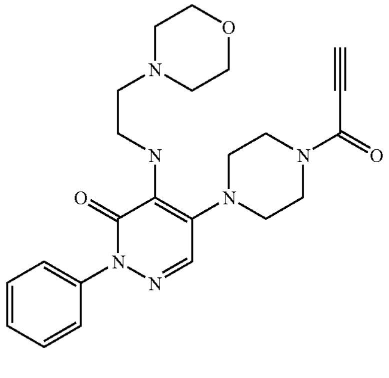
TABLE A-continued
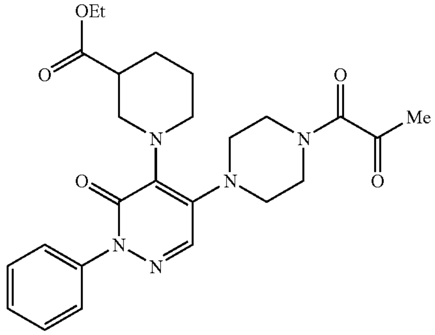
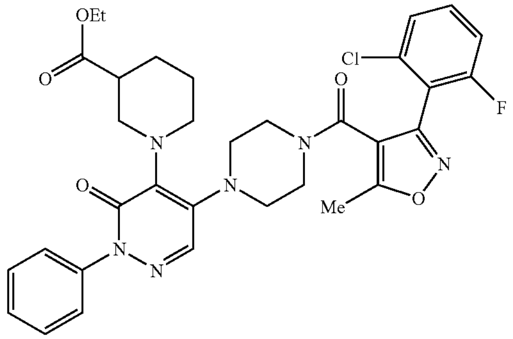
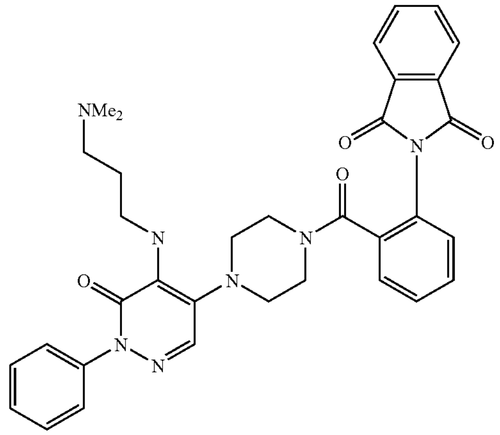
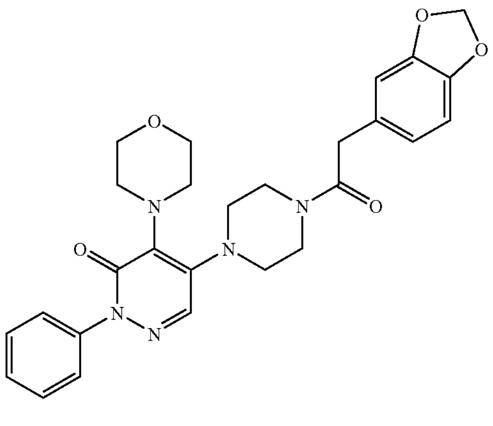

TABLE A-continued
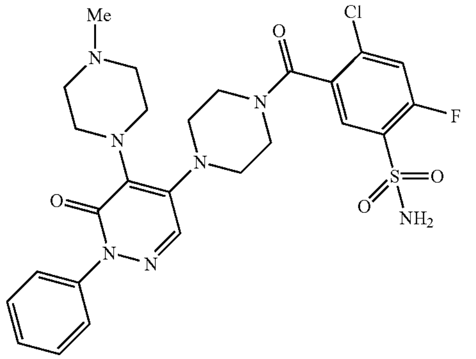
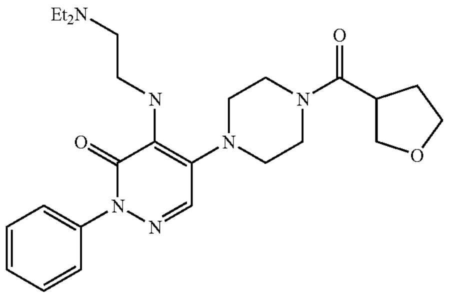
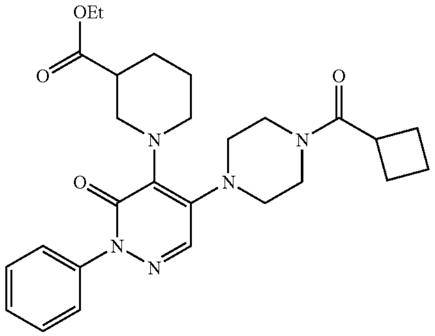
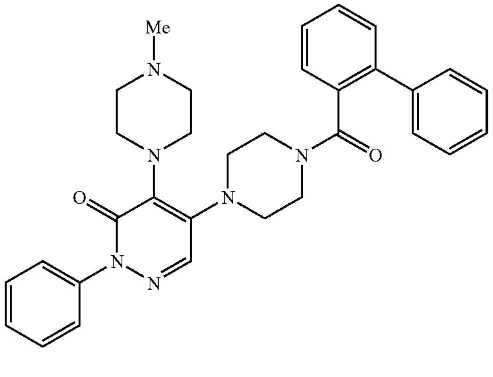
TABLE A-continued
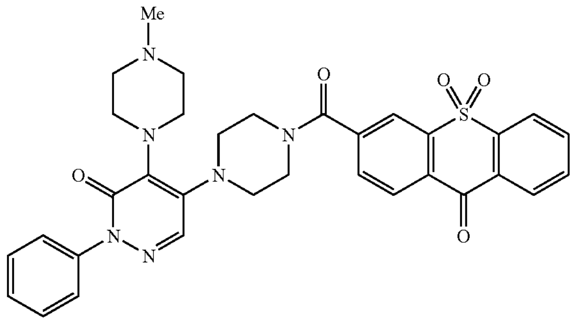
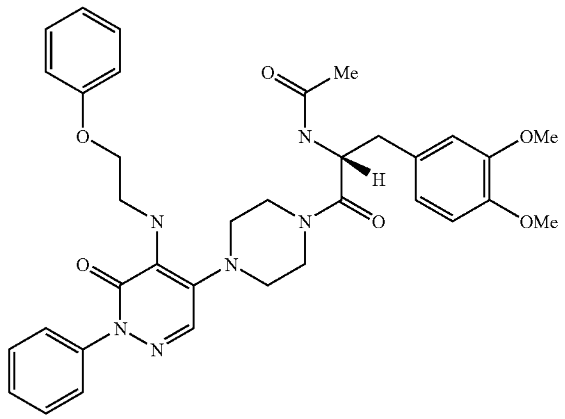
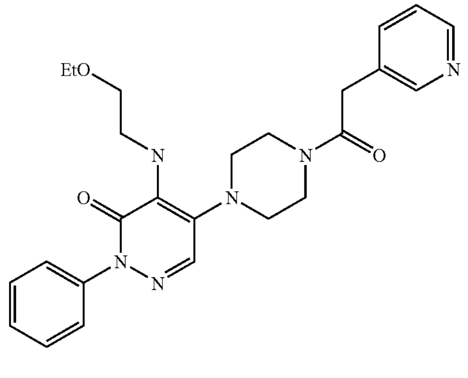
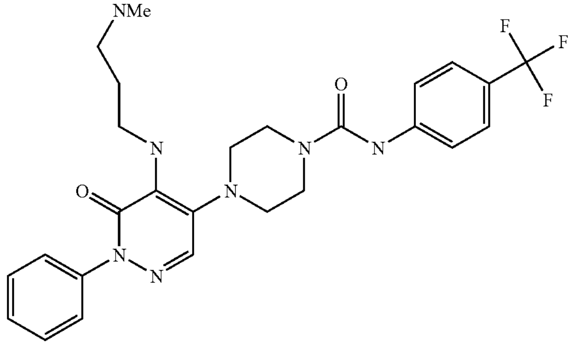

TABLE A-continued
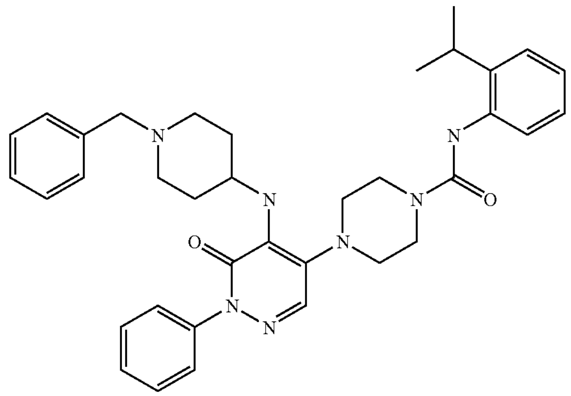
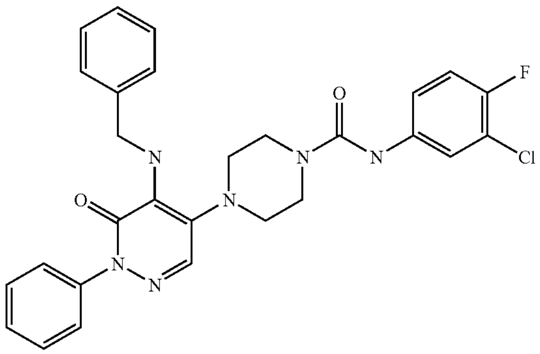
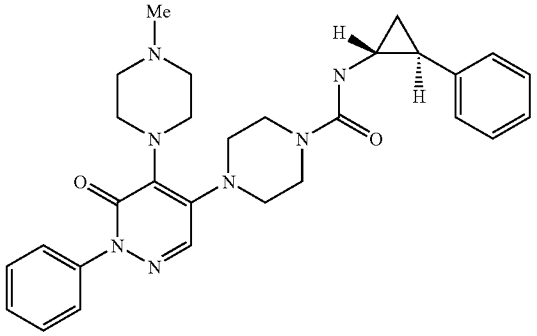
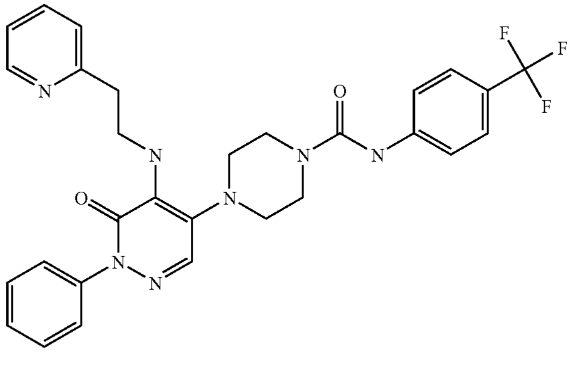
TABLE A-continued
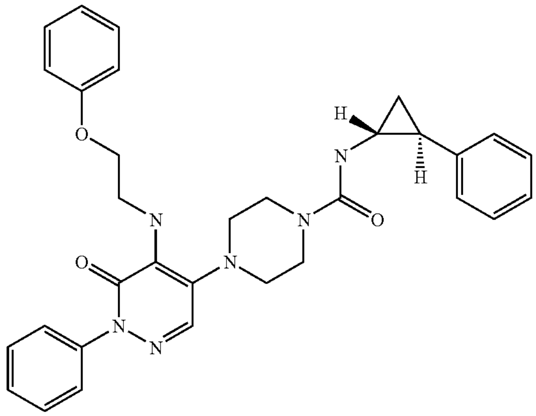
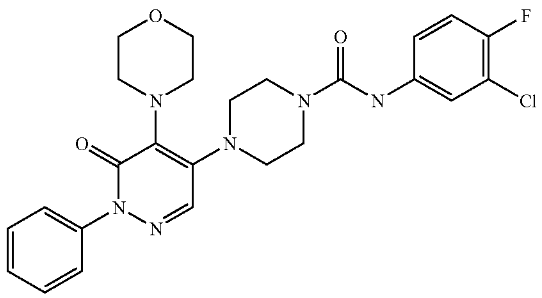
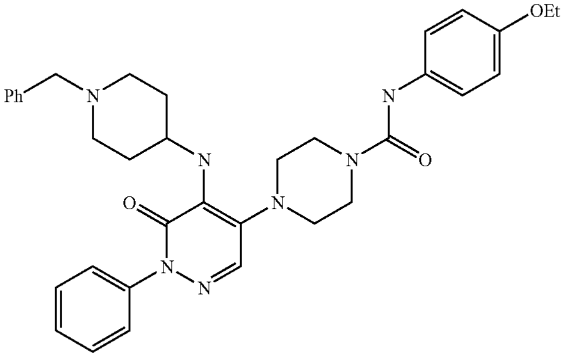
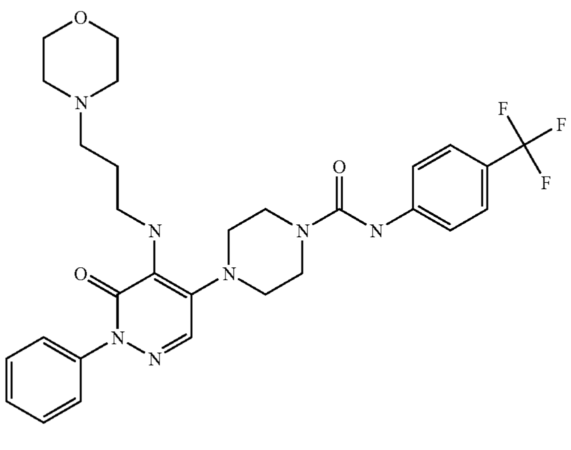

TABLE A-continued
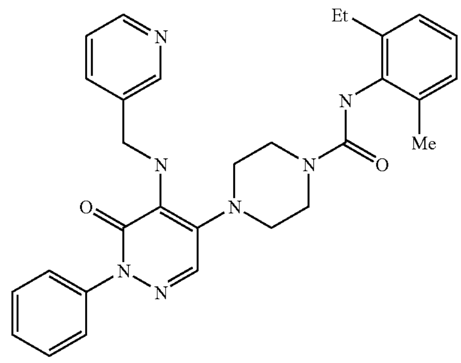
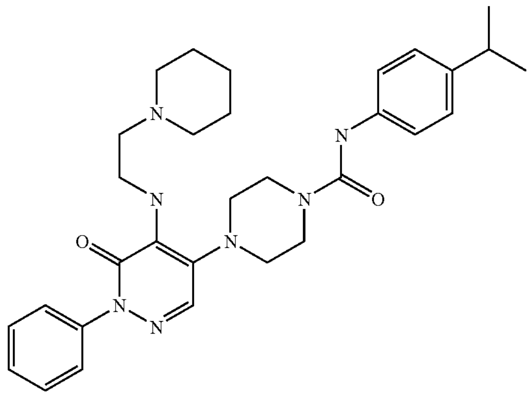
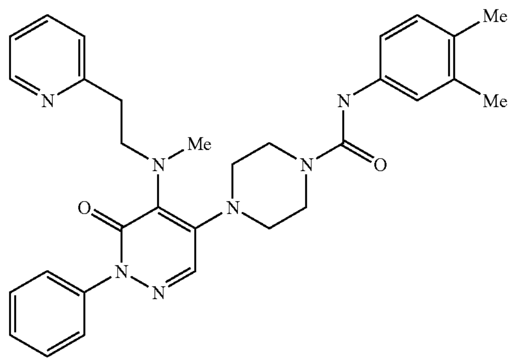
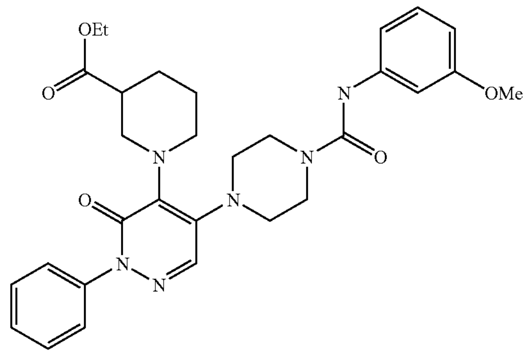
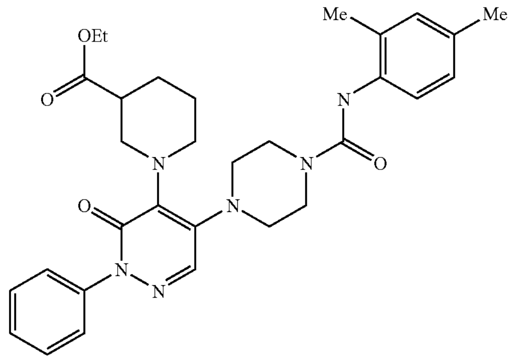
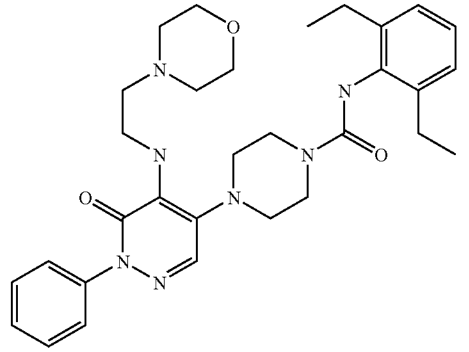
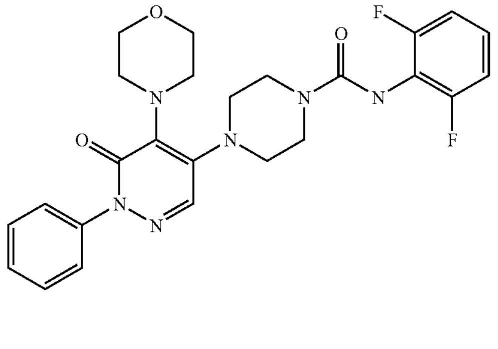
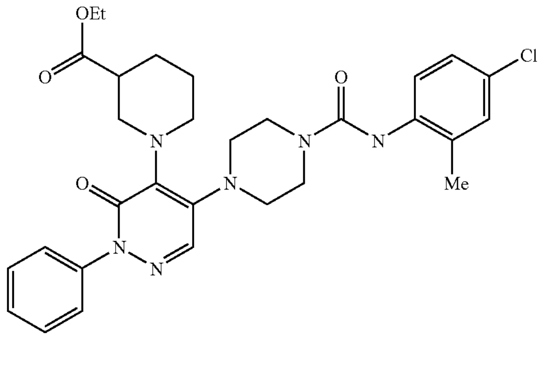

TABLE A-continued
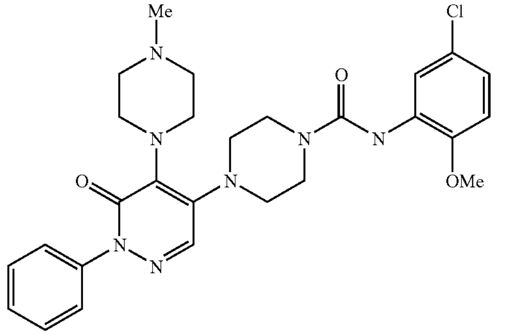
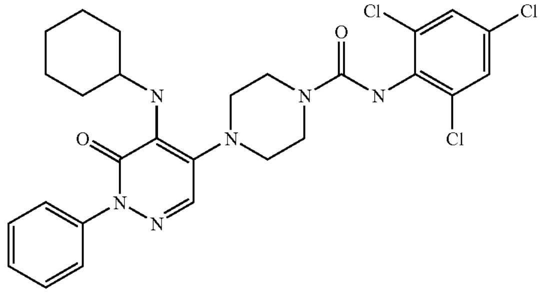
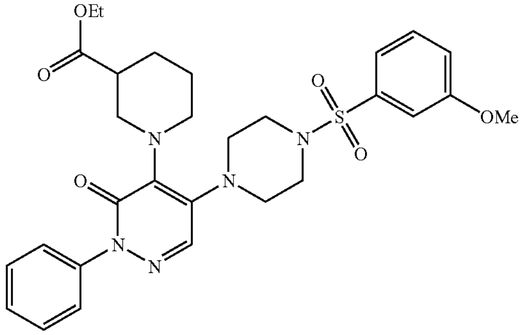
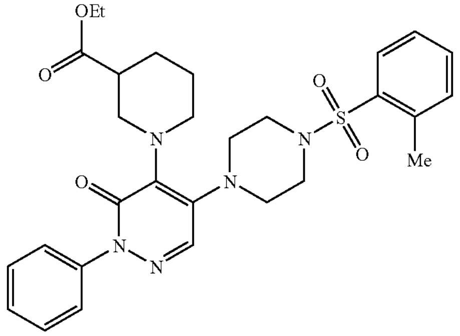
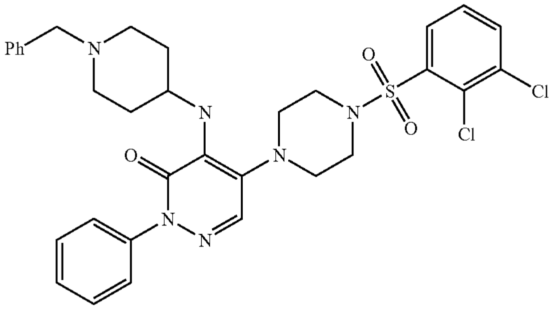
TABLE A-continued
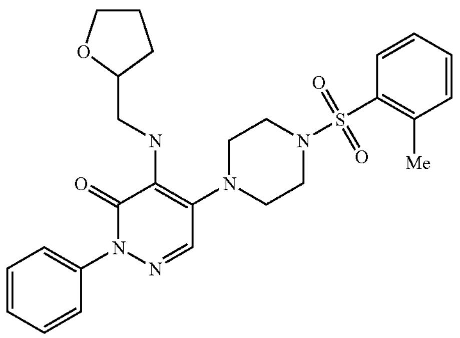
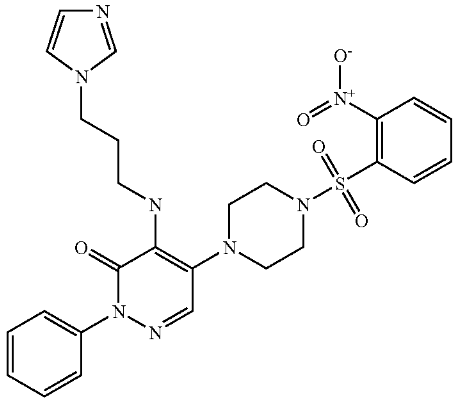
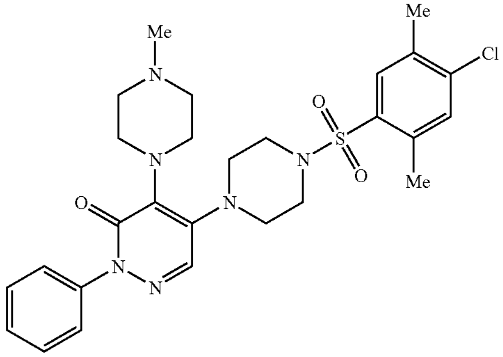
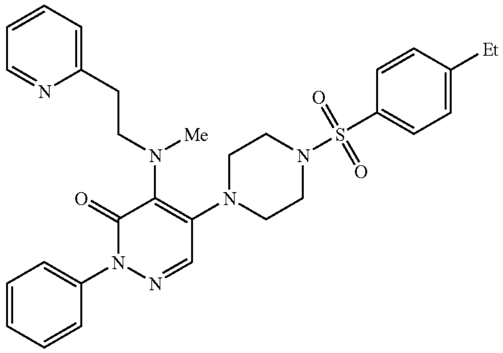

TABLE A-continued
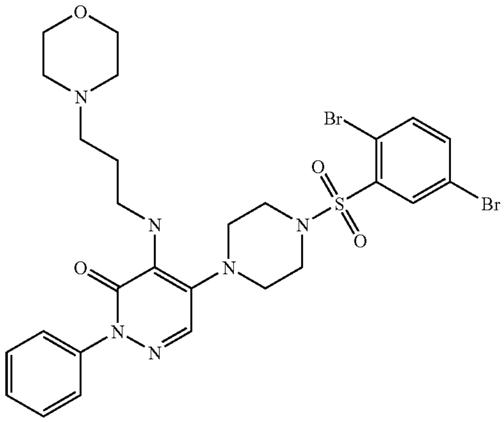
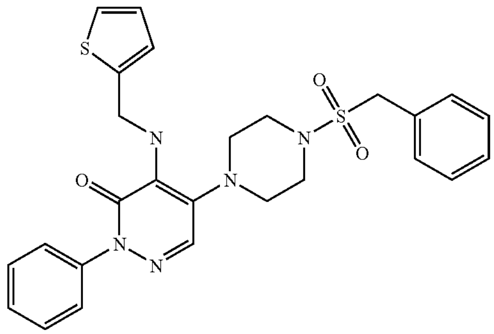
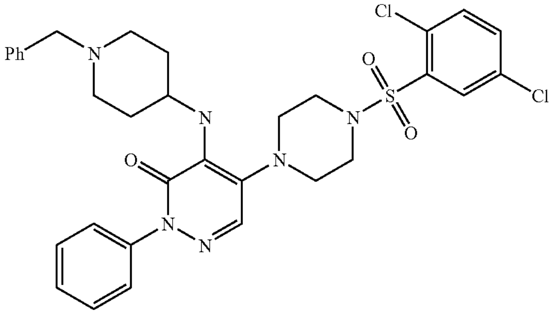
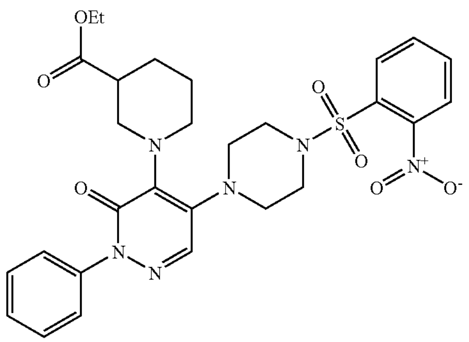
TABLE A-continued
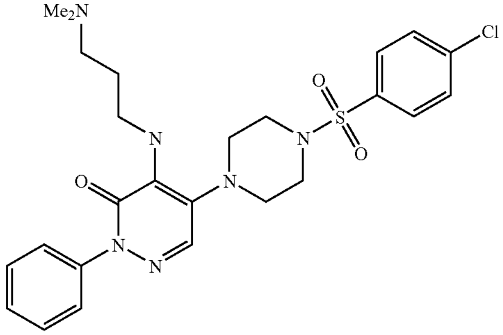
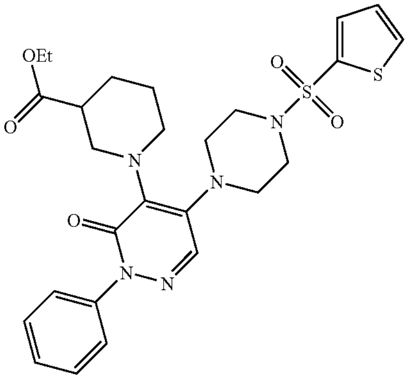
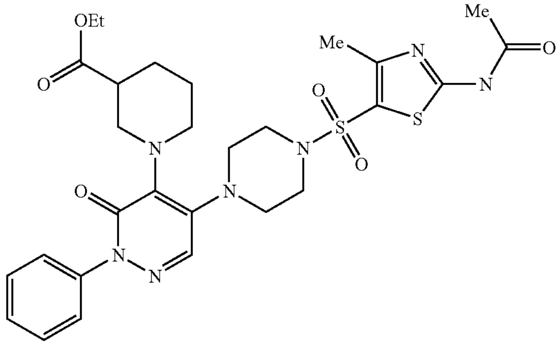
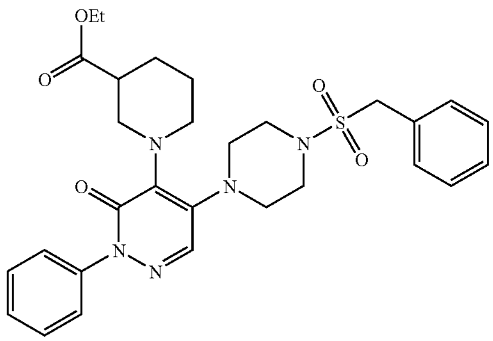

TABLE A-continued
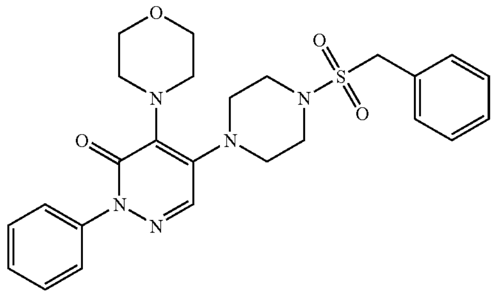
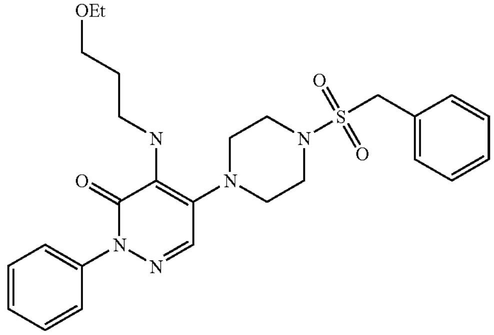
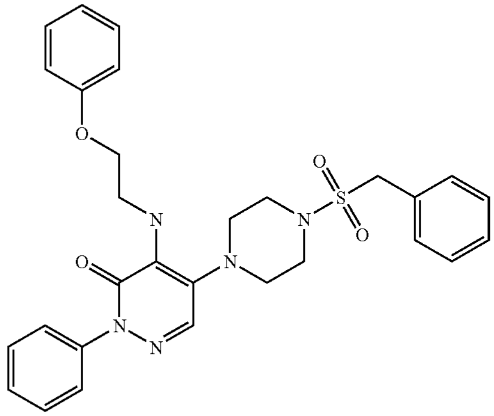
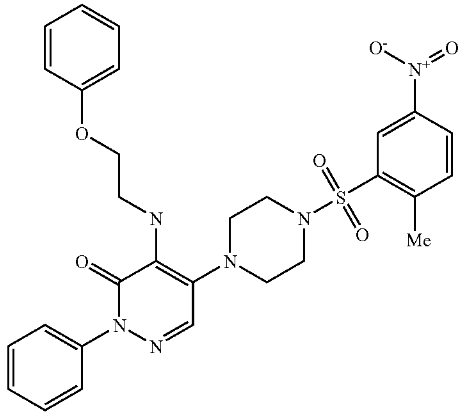
TABLE A-continued
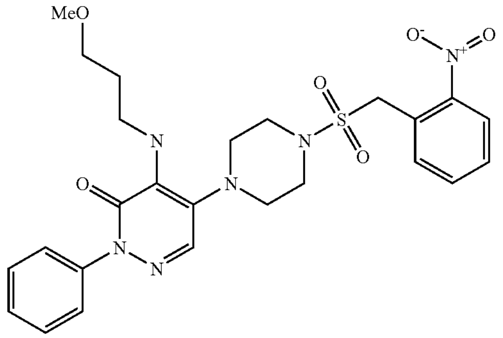
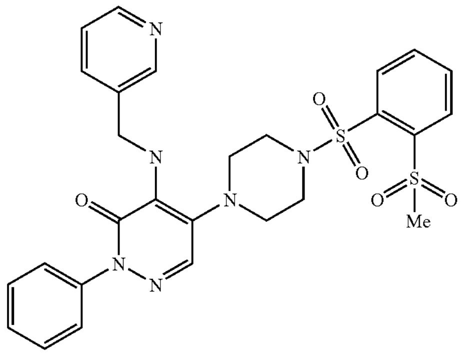
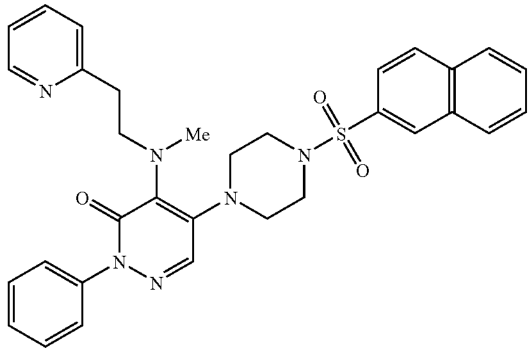
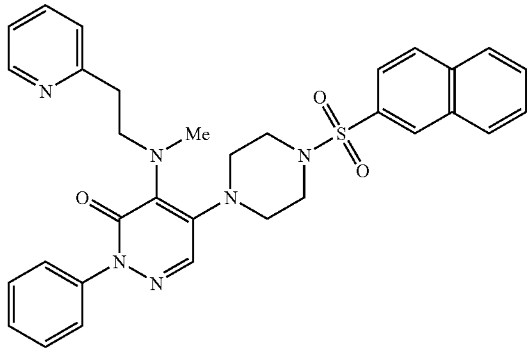

TABLE A-continued
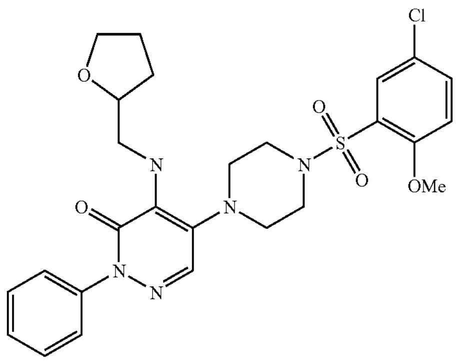
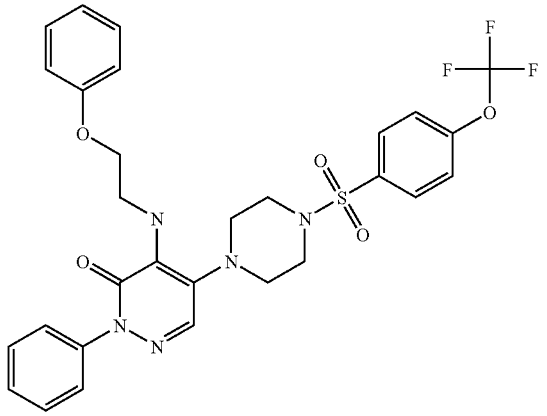
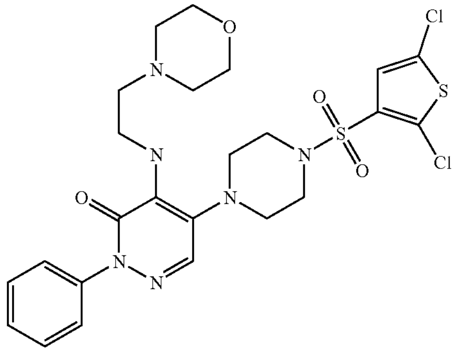
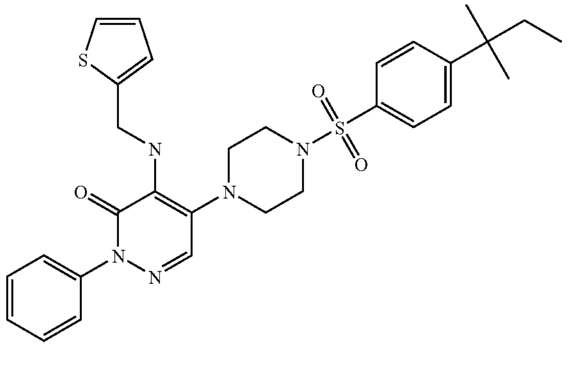
TABLE A-continued
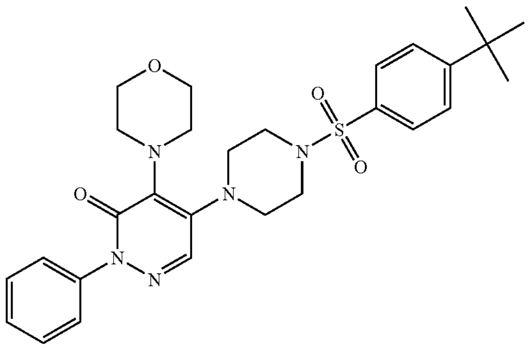
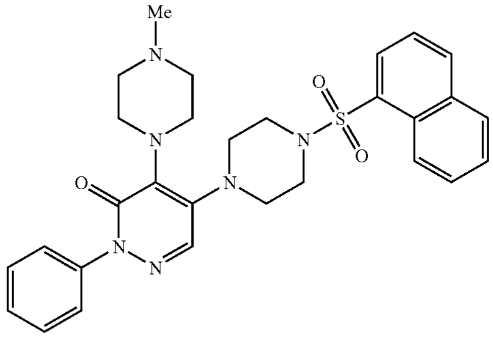
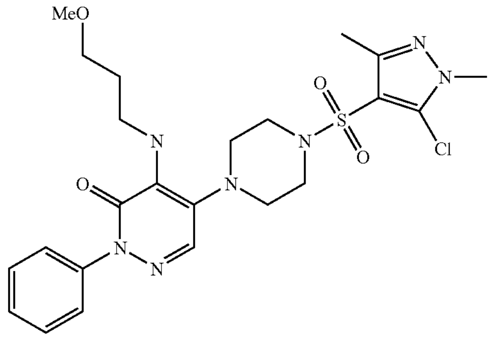
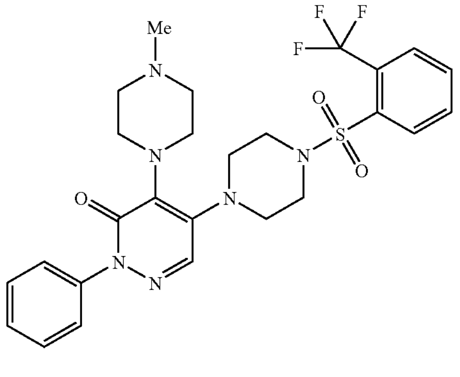

TABLE A-continued
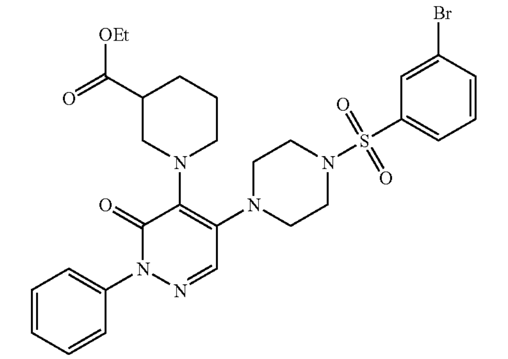
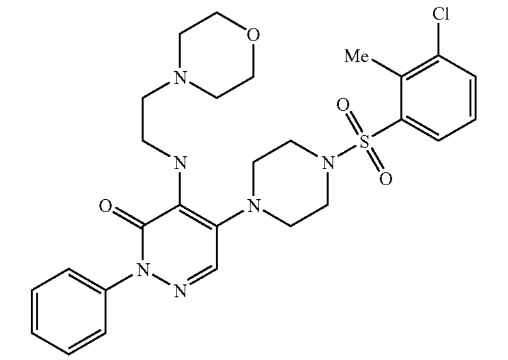
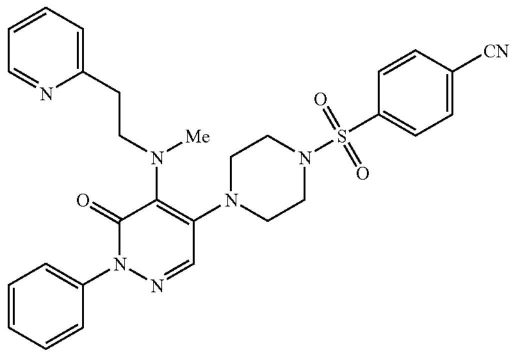
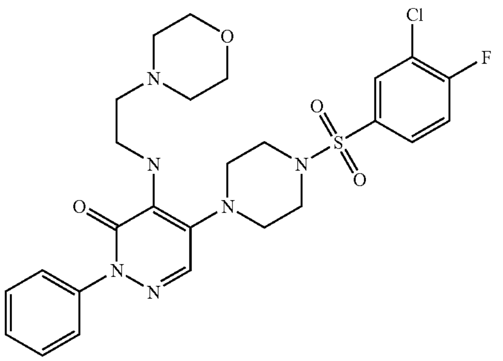
TABLE A-continued
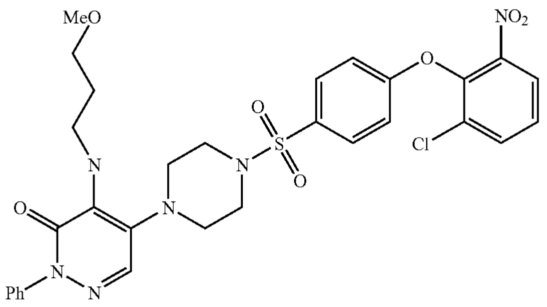
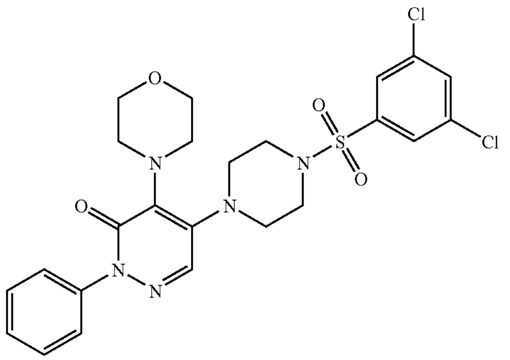
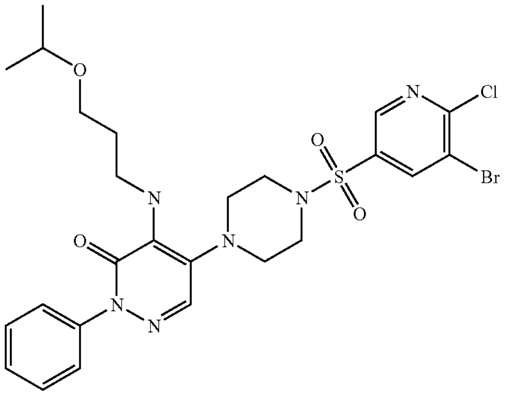
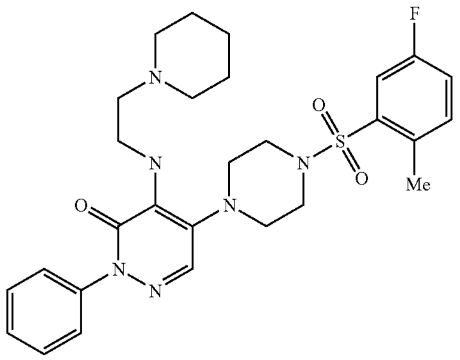

TABLE A-continued
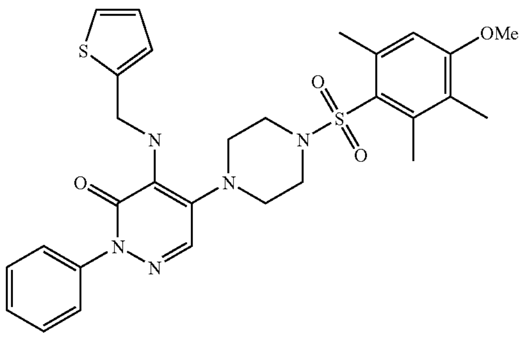
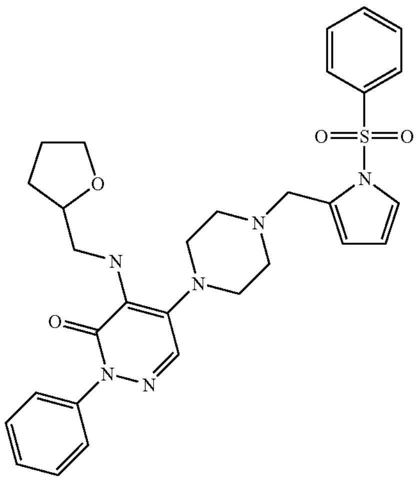
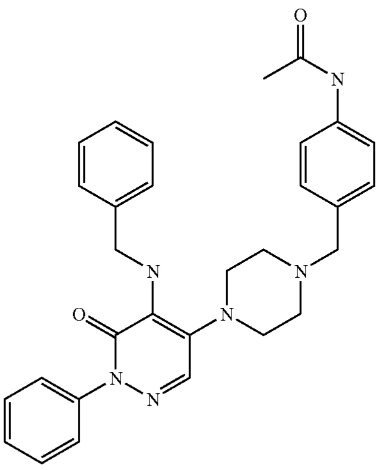
TABLE A-continued
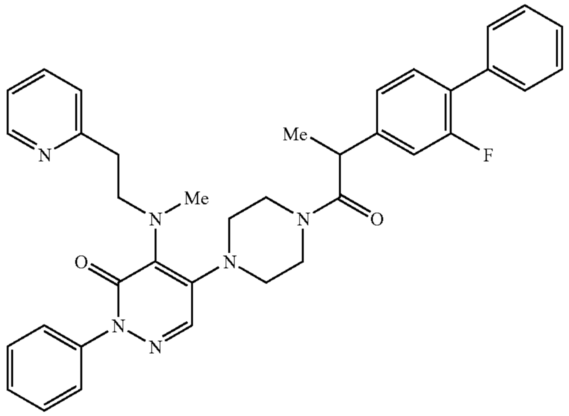
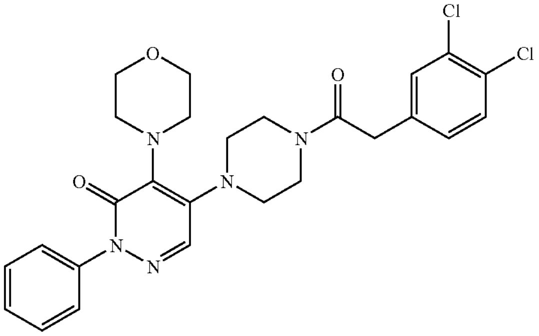
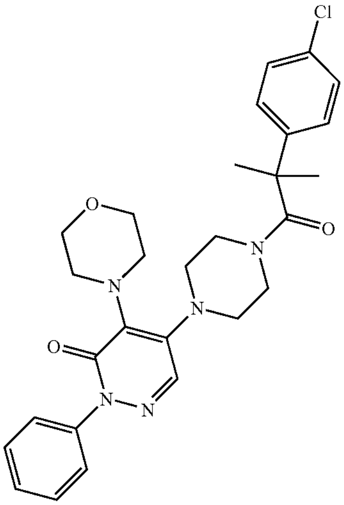
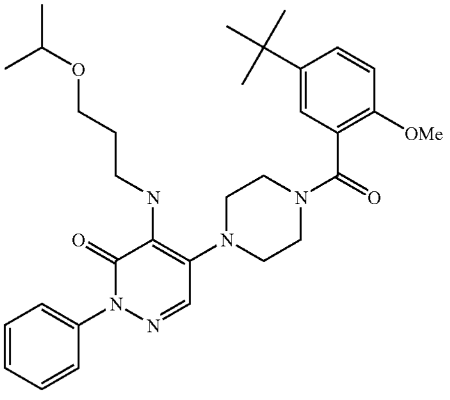

TABLE A-continued
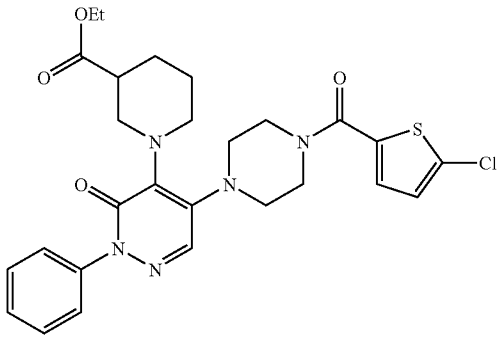
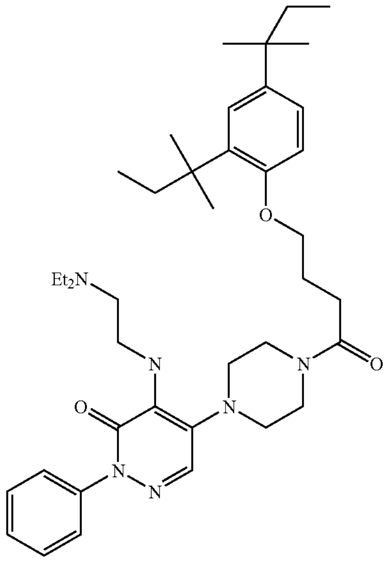
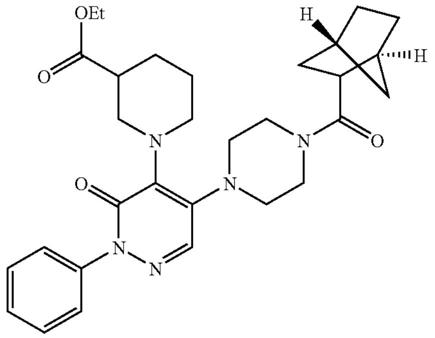
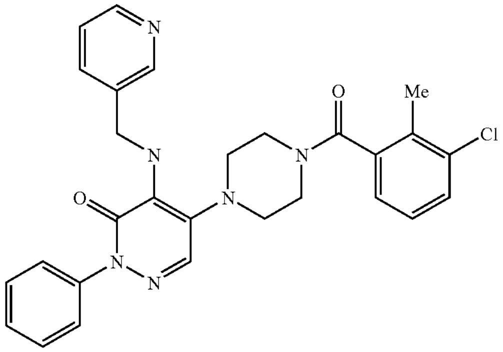
TABLE A-continued
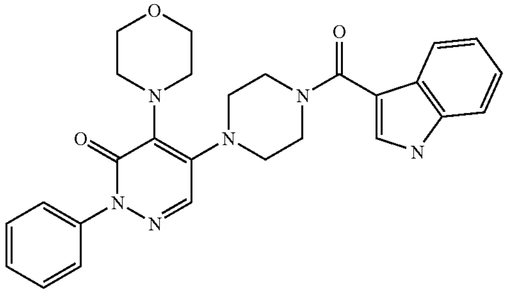
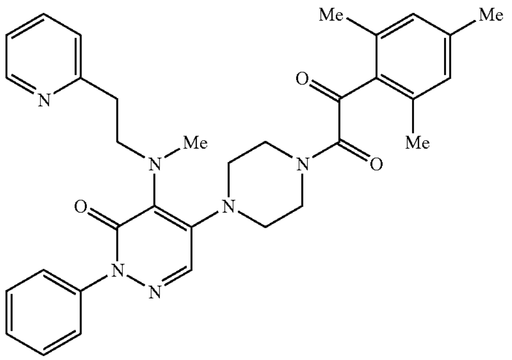
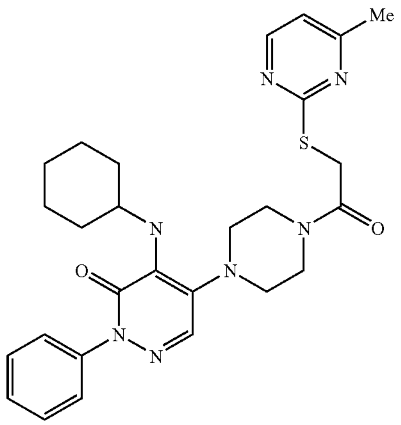
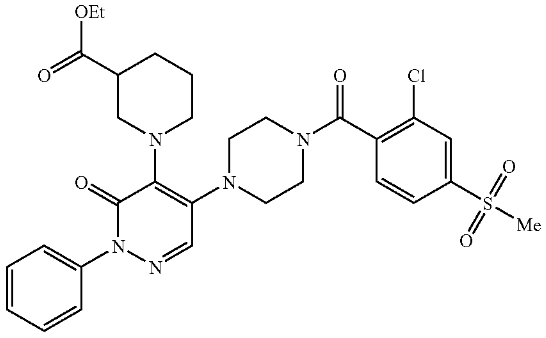

TABLE A-continued
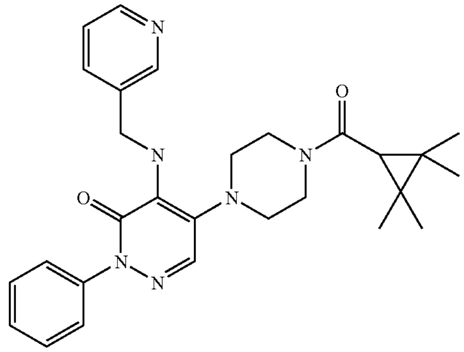
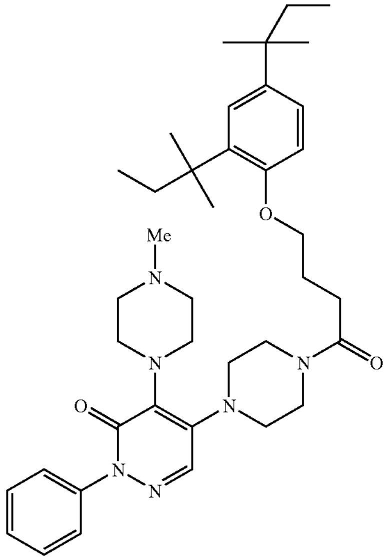
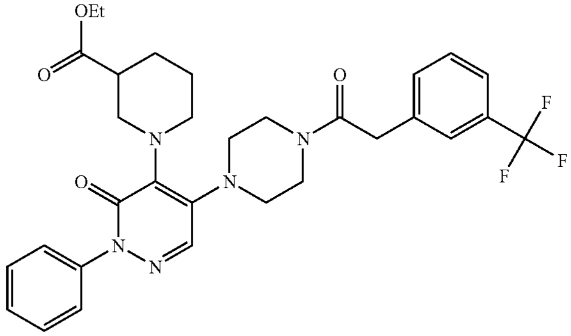
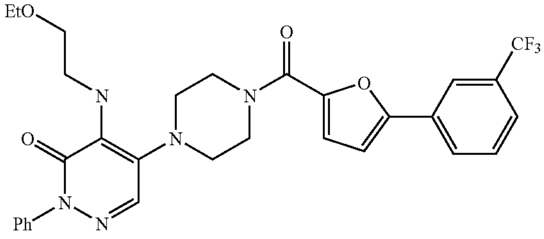
TABLE A-continued
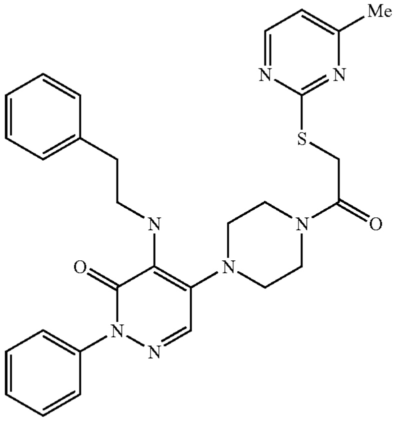
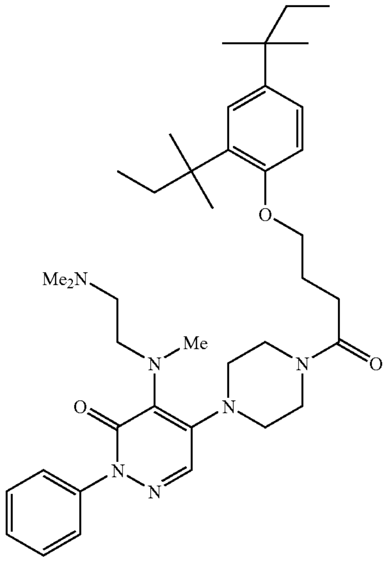
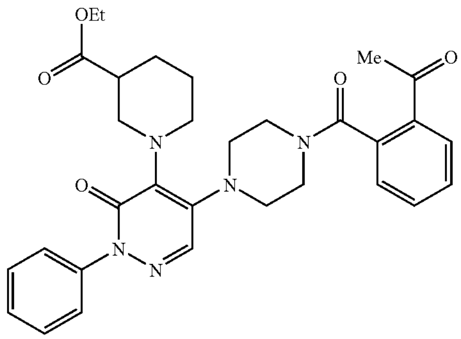

TABLE A-continued
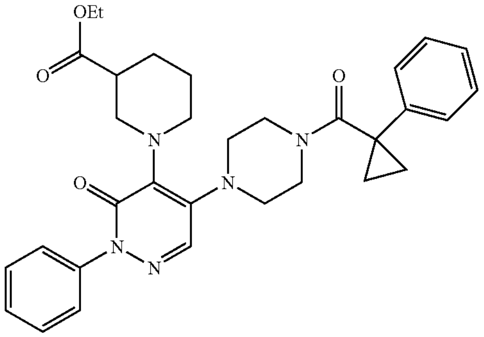
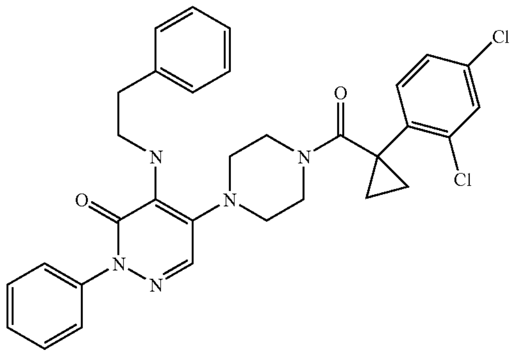
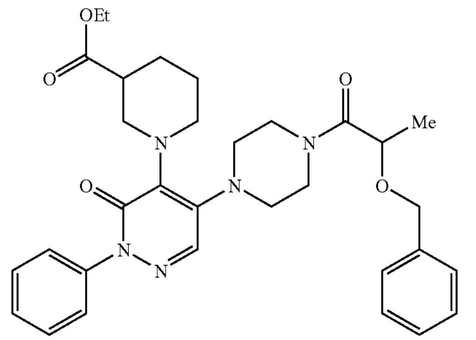
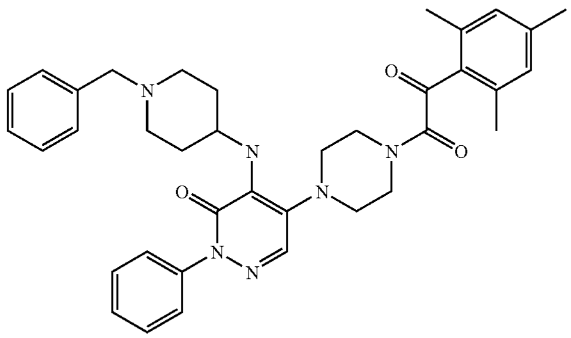
TABLE A-continued
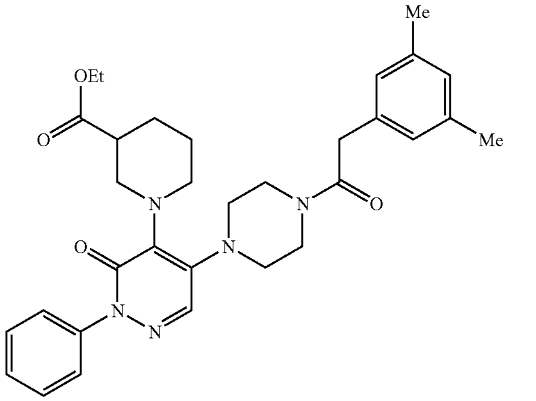
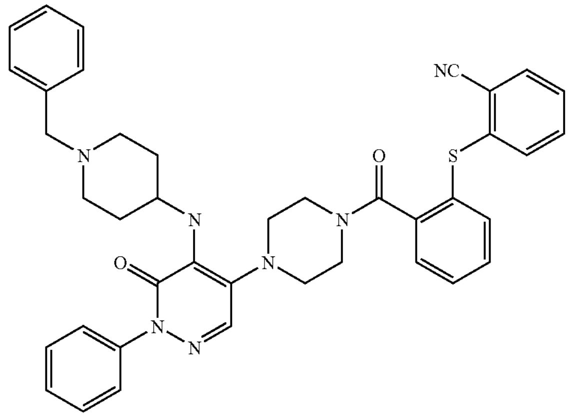
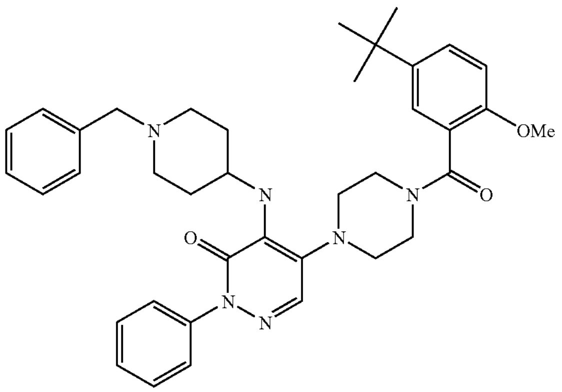
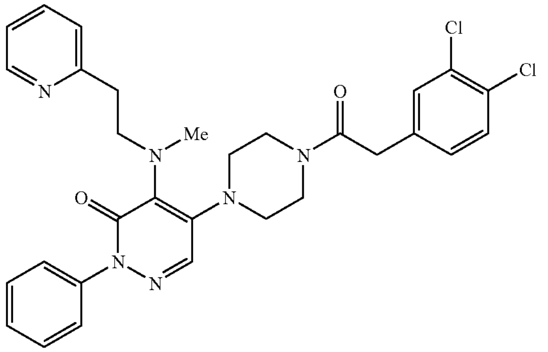

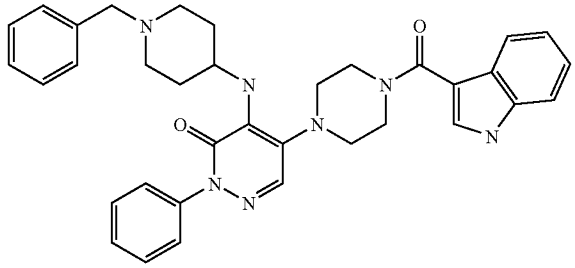
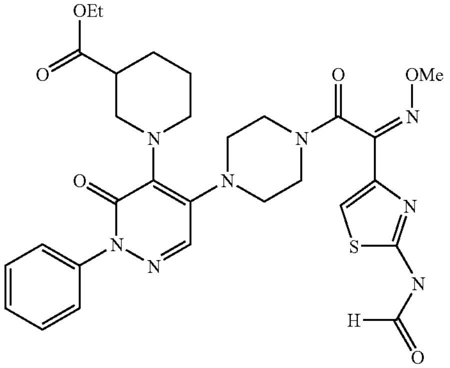
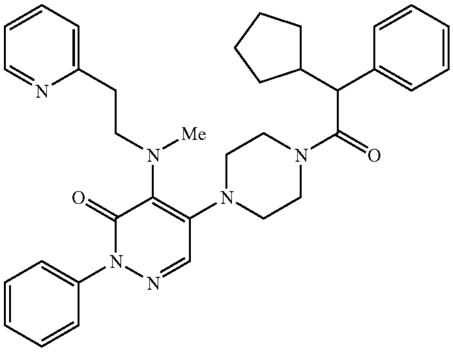
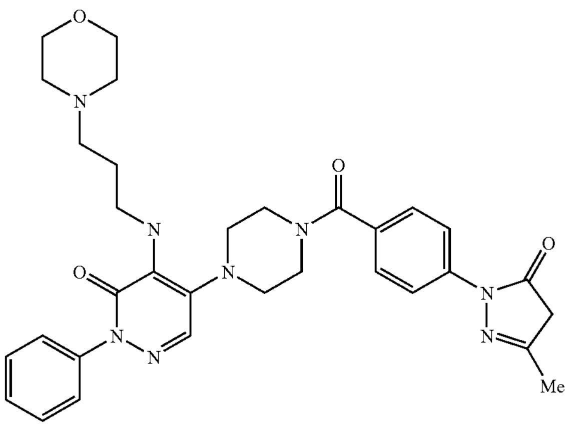
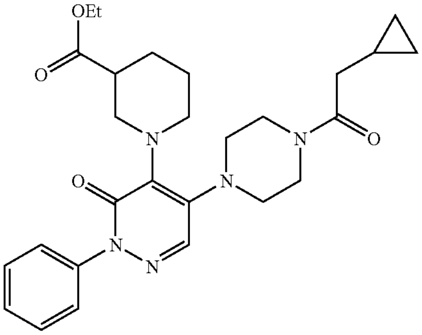
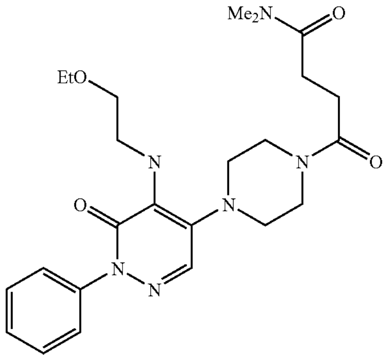
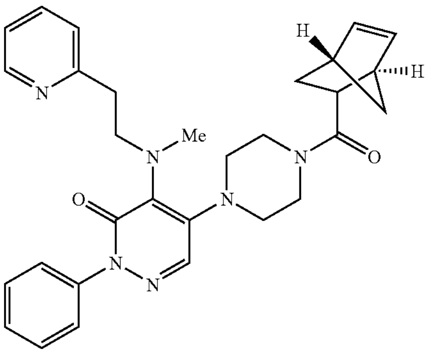
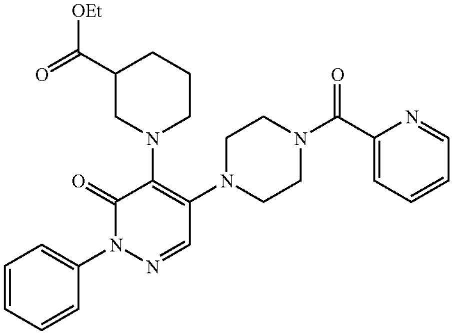

TABLE A-continued
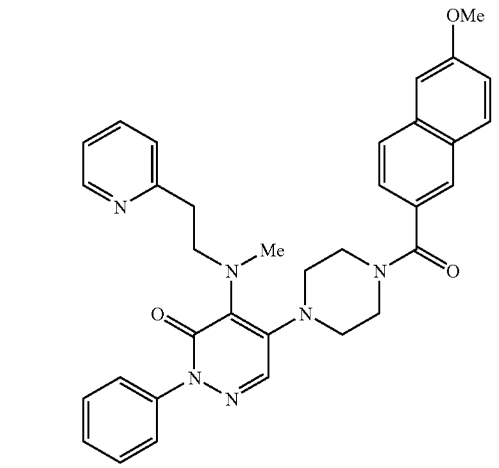
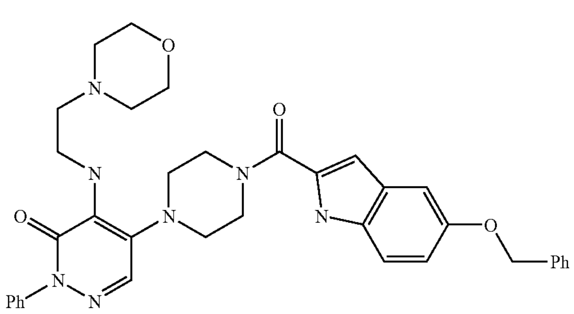
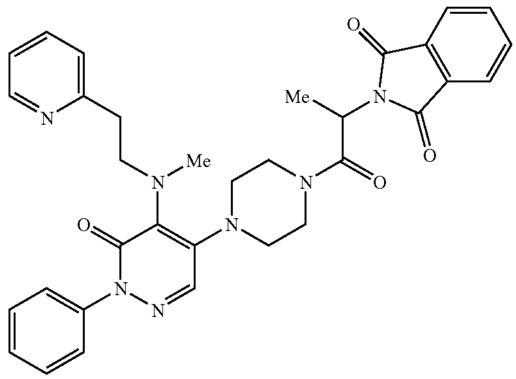
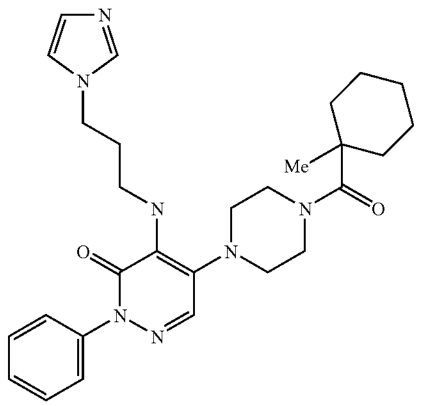
TABLE A-continued
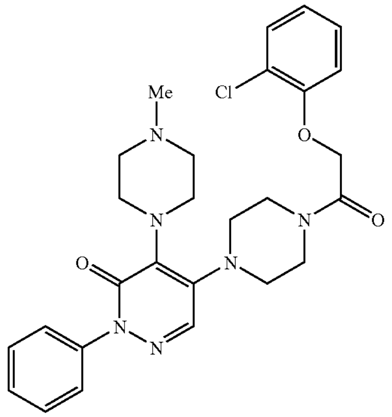
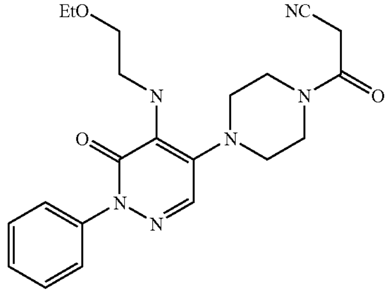
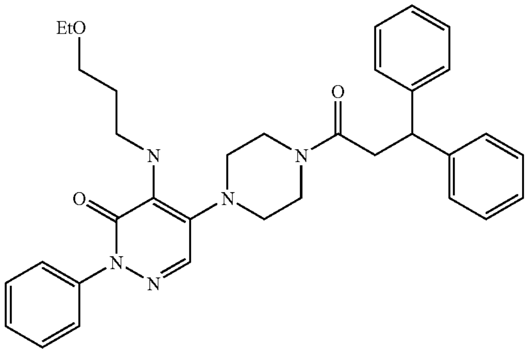
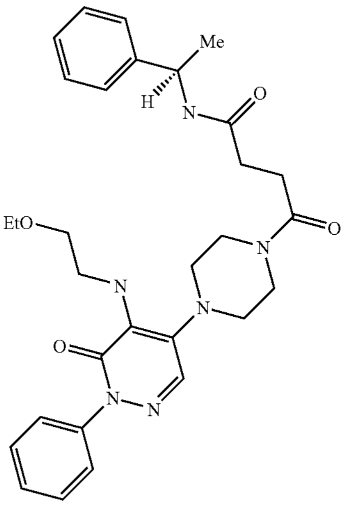

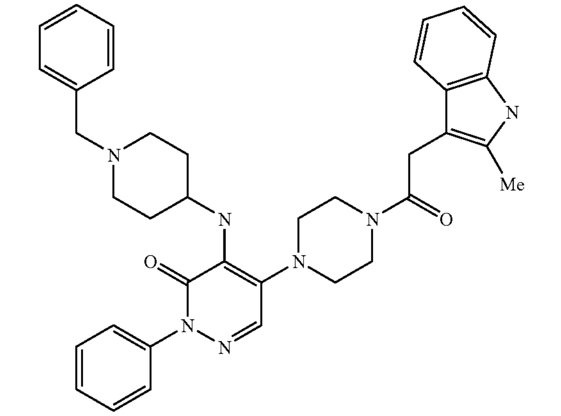
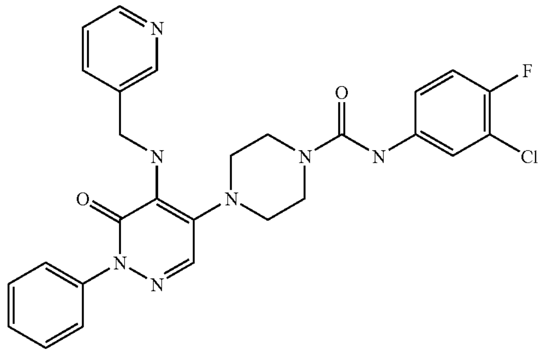
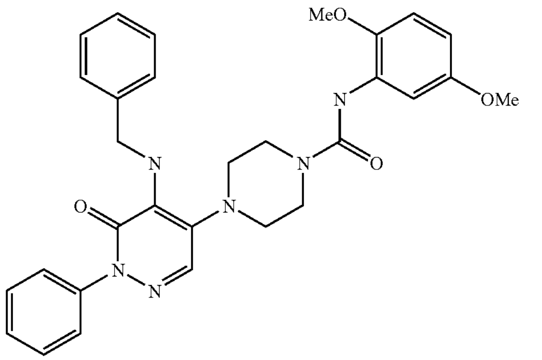
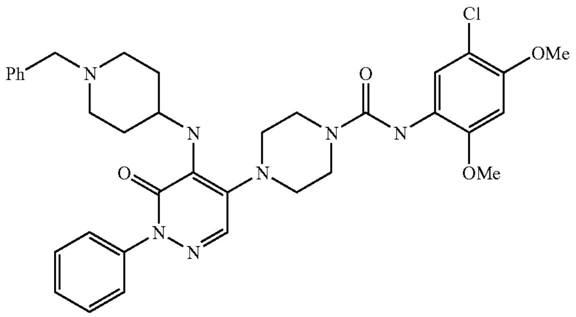
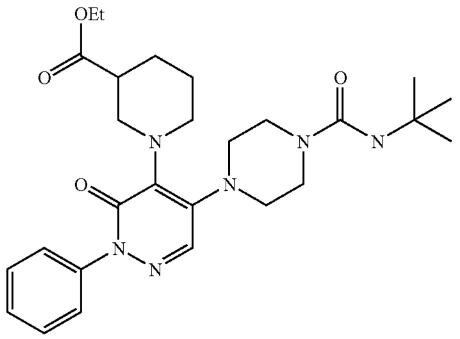
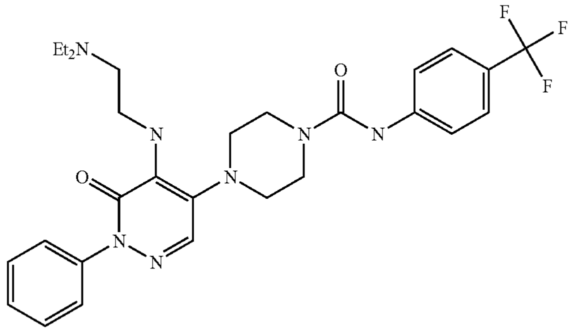
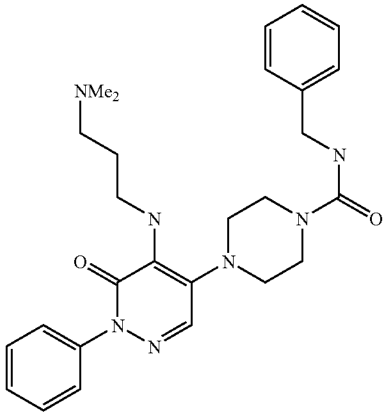
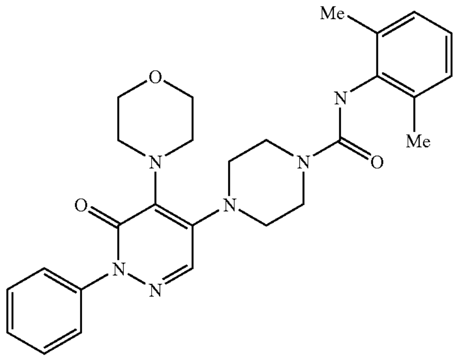

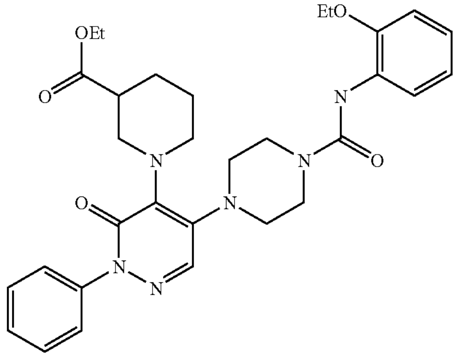
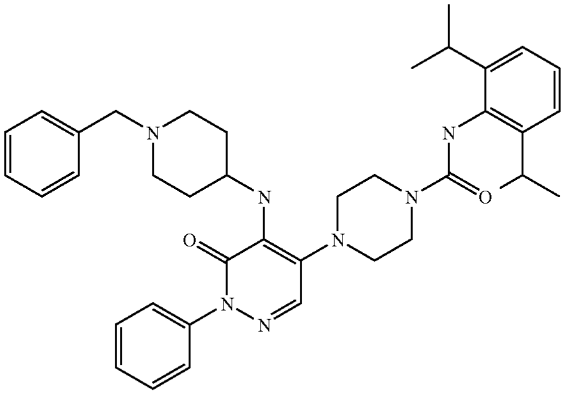
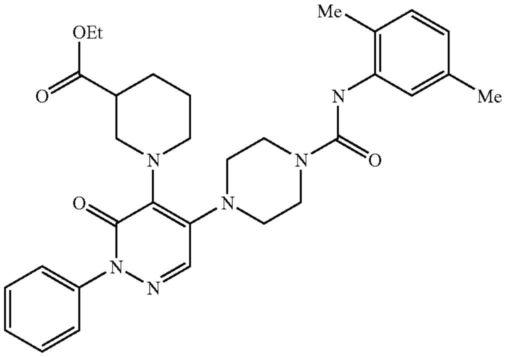
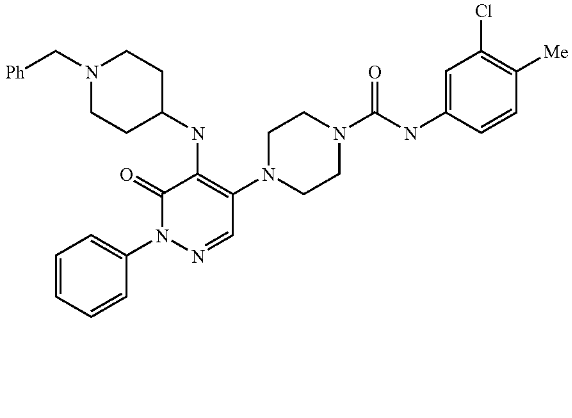
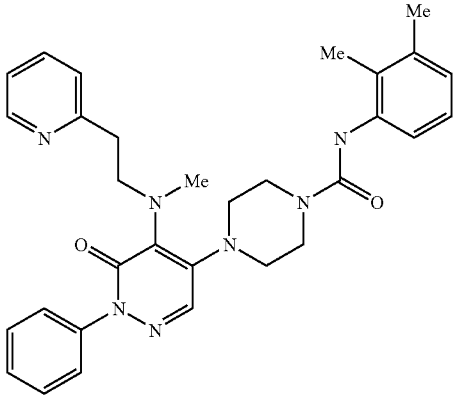
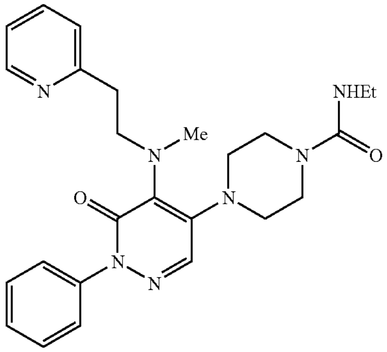
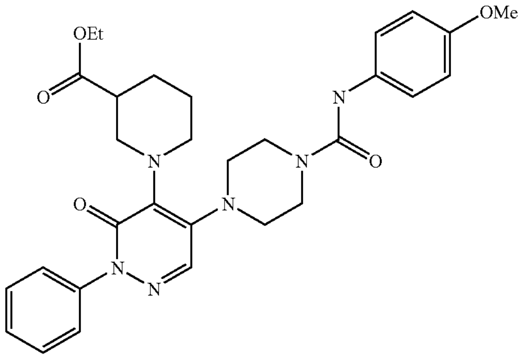
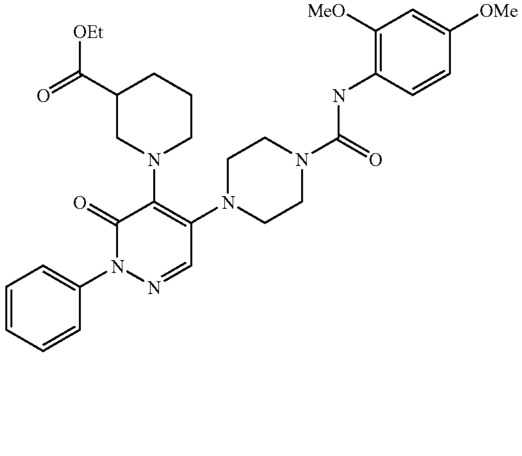

TABLE A-continued
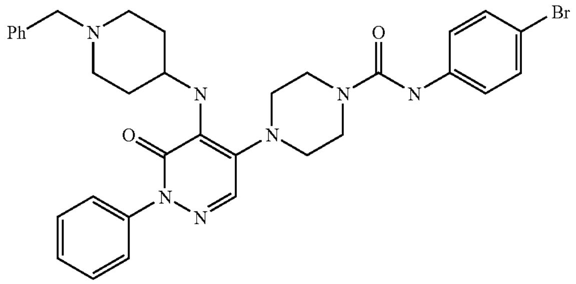
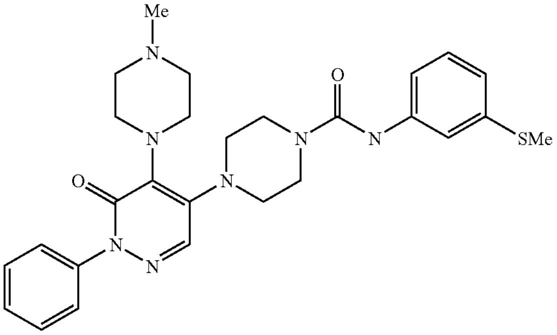
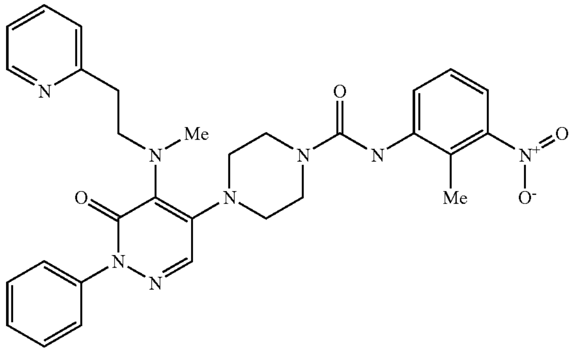
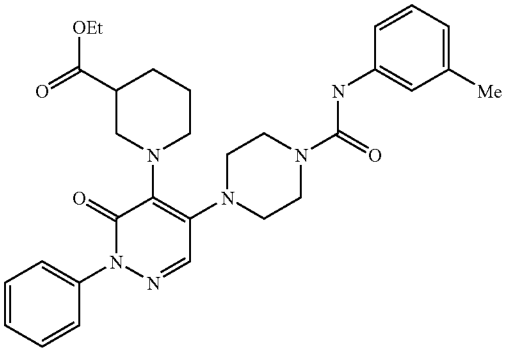
TABLE A-continued
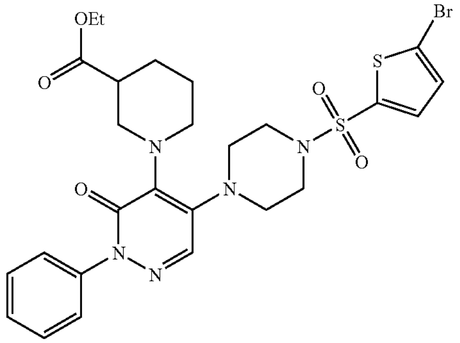
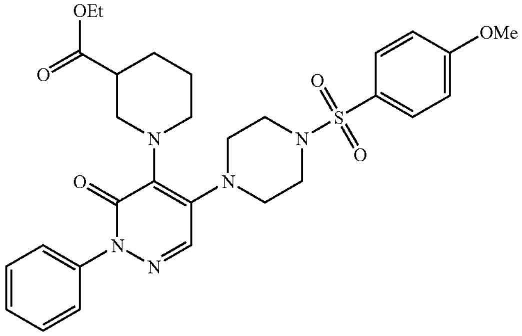
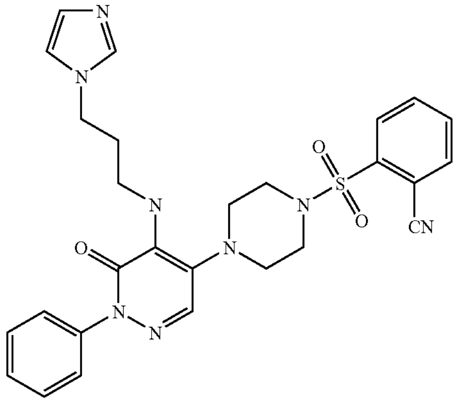
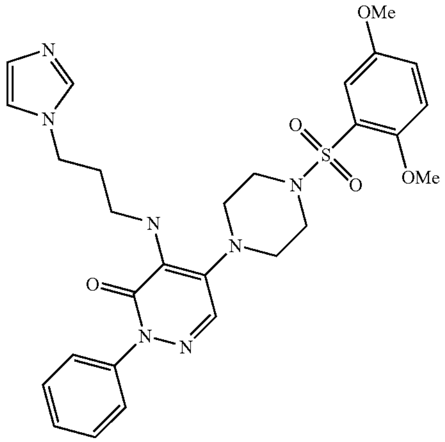

TABLE A-continued
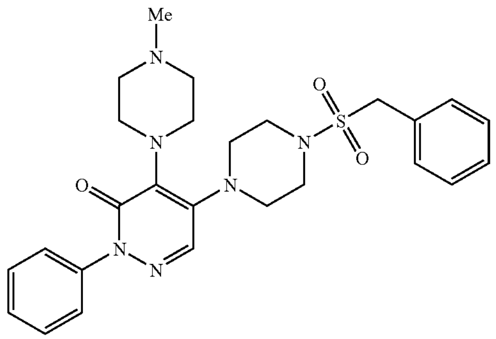
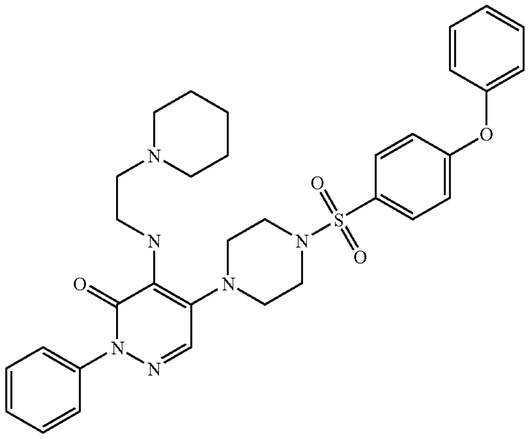
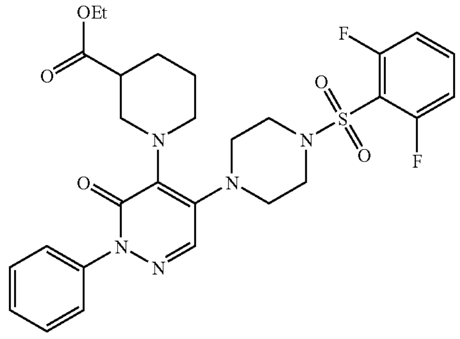
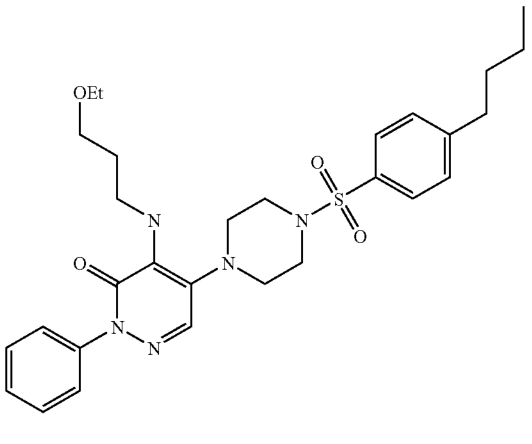
TABLE A-continued
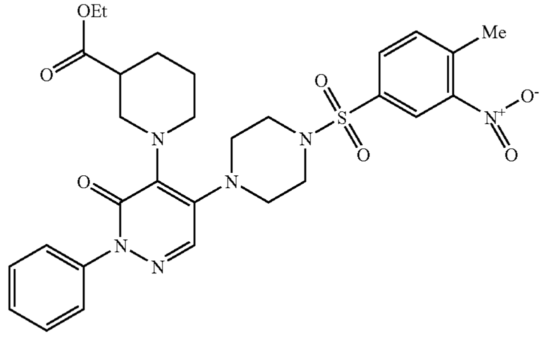
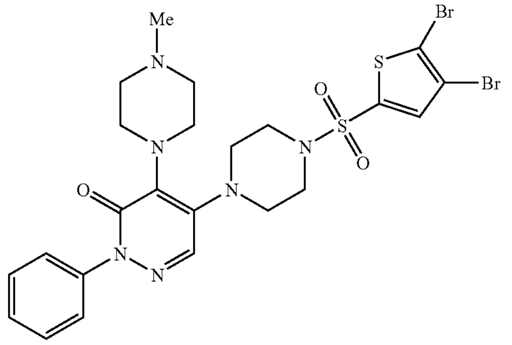
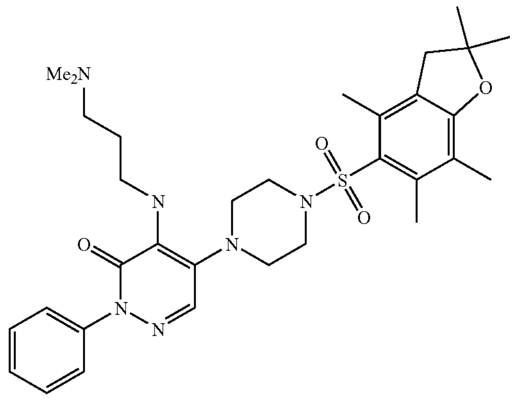
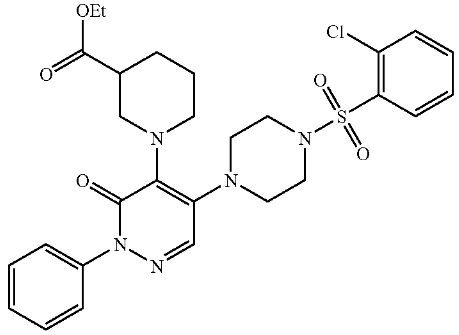

TABLE A-continued
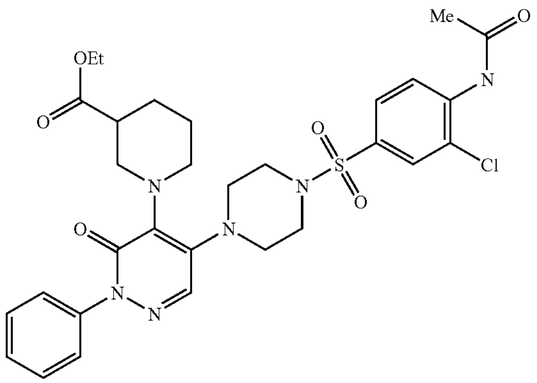
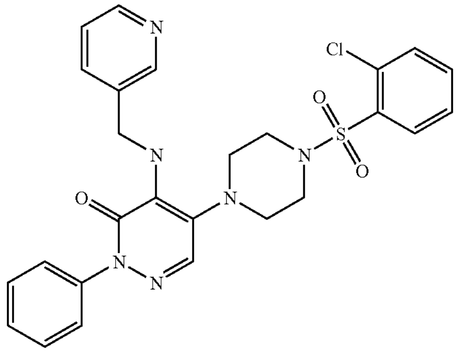
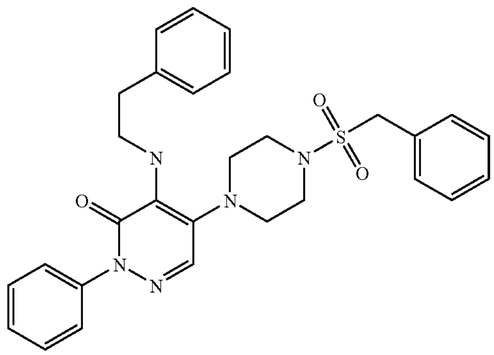
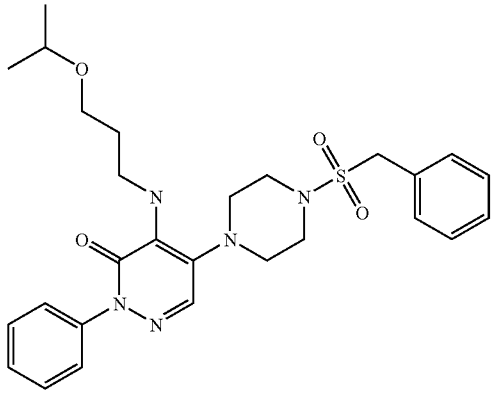
TABLE A-continued
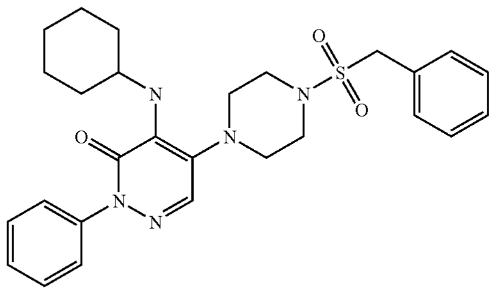
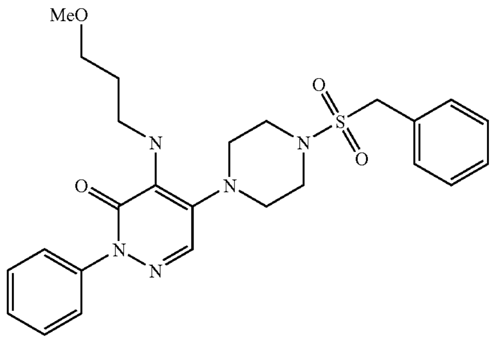
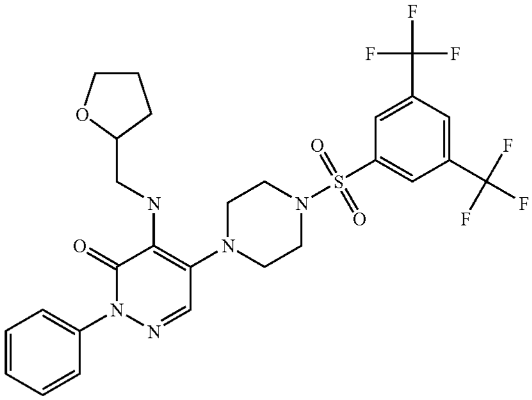
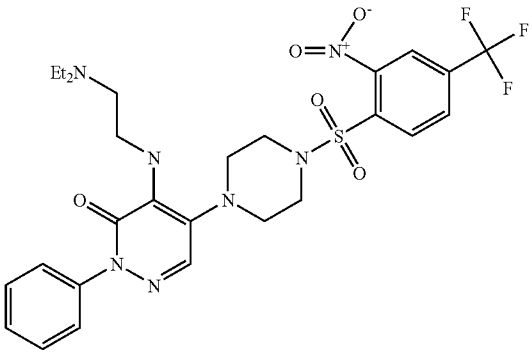

TABLE A-continued
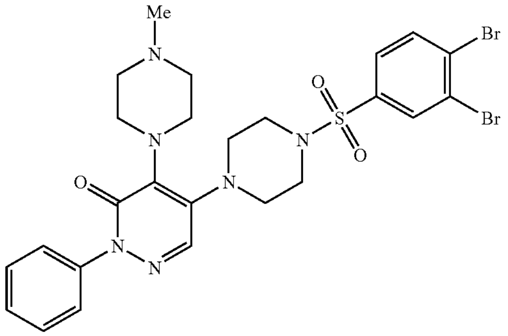
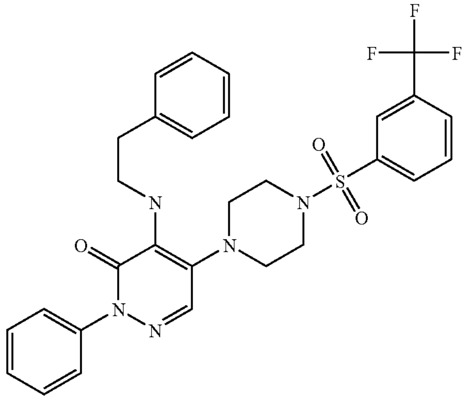
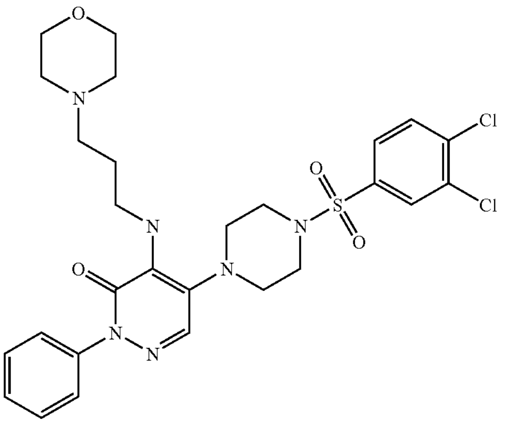
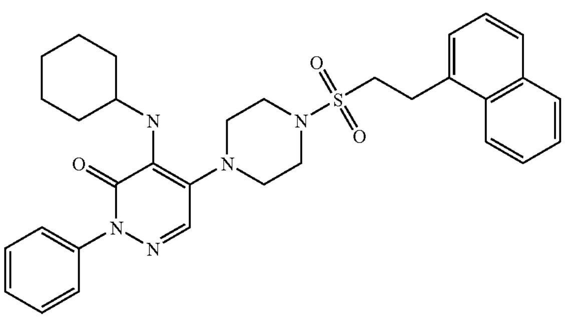
TABLE A-continued
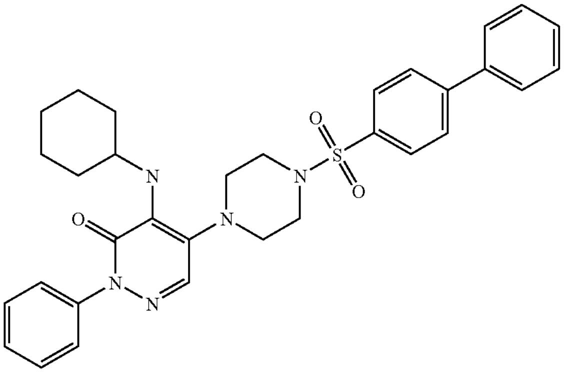
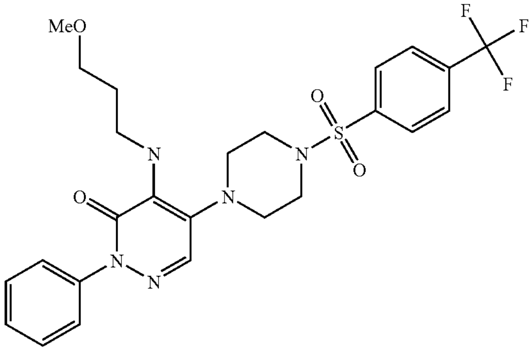
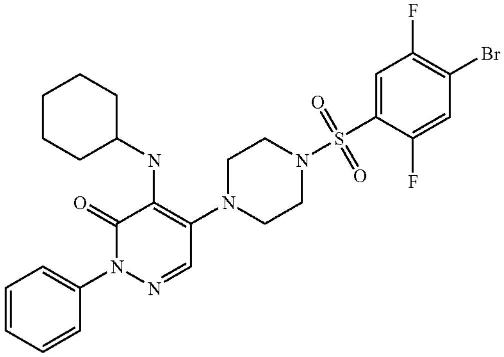
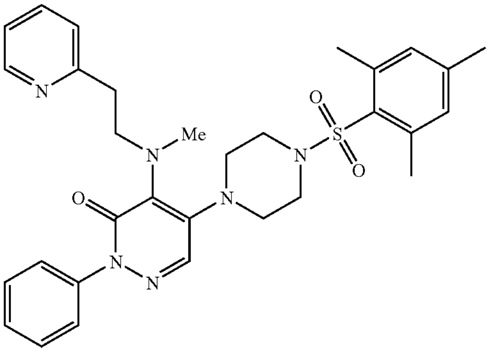

TABLE A-continued
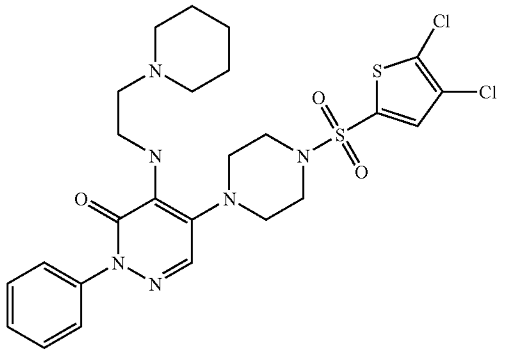
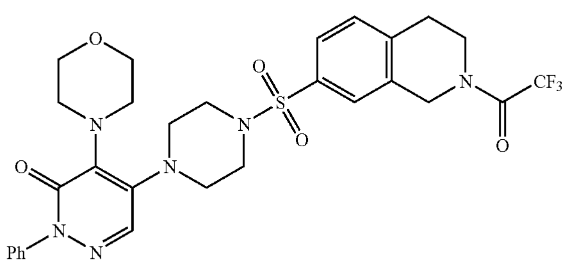
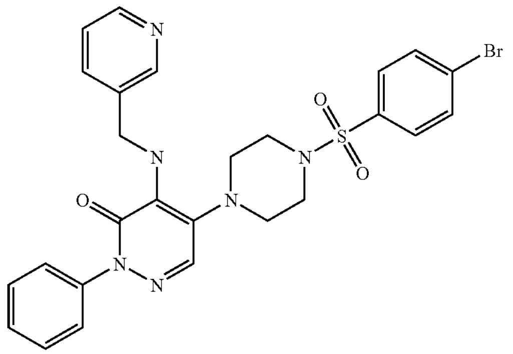
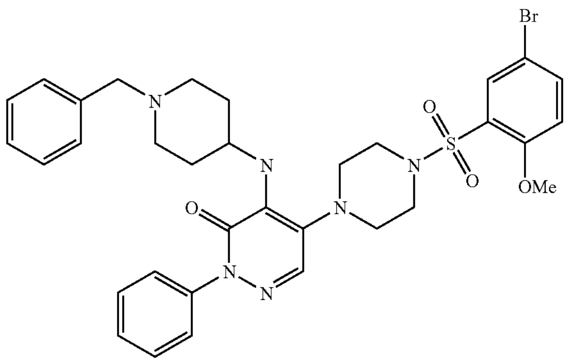
TABLE A-continued
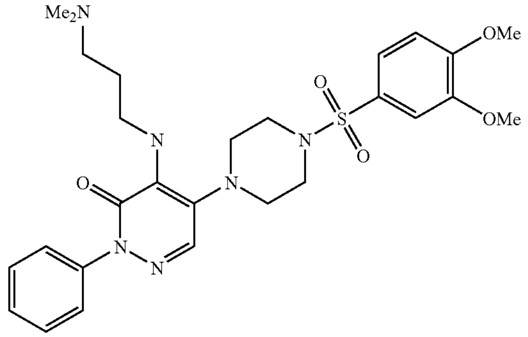
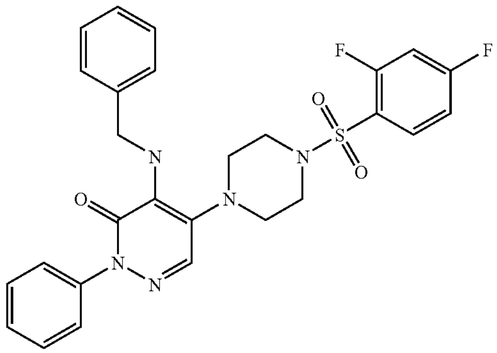
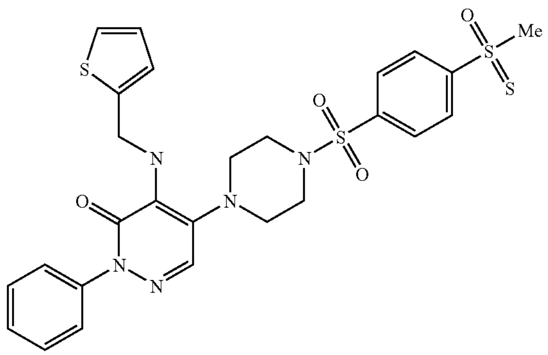
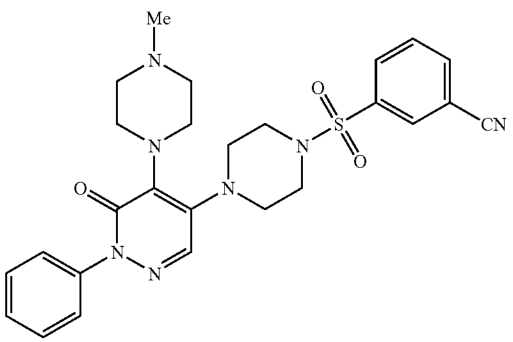

TABLE A-continued
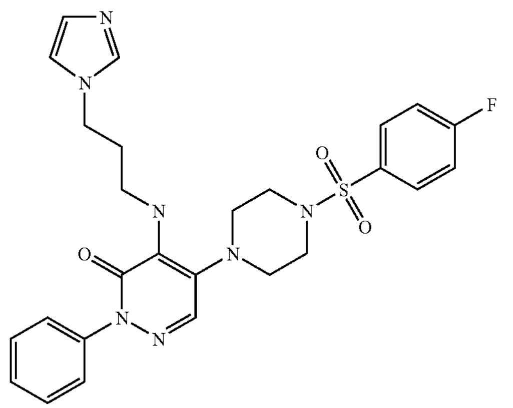
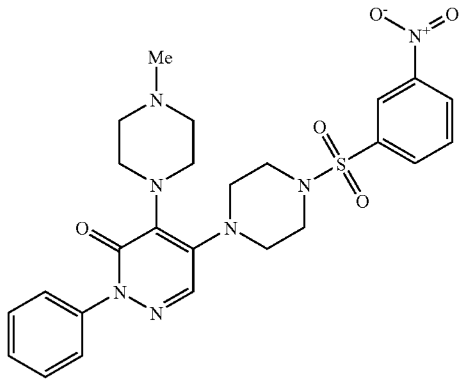
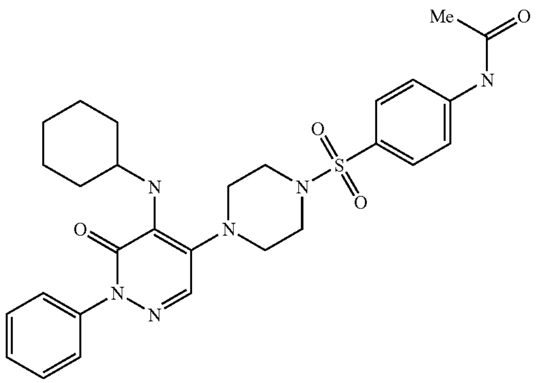
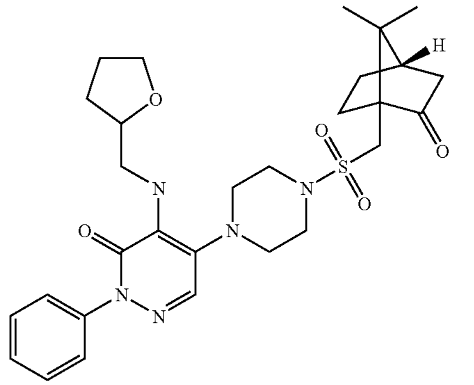
TABLE A-continued
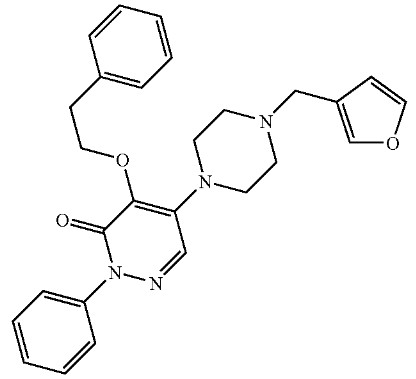
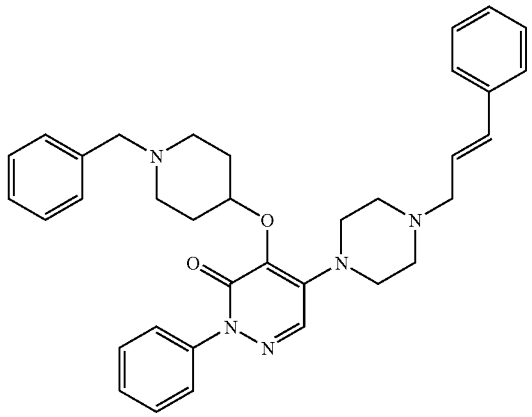
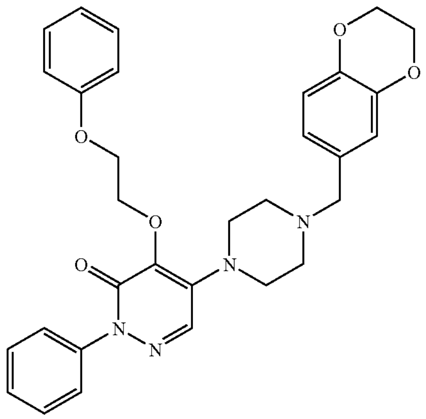
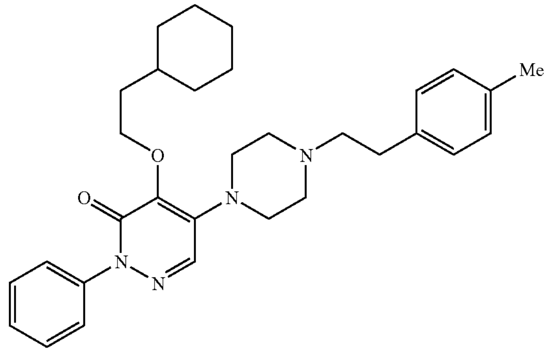

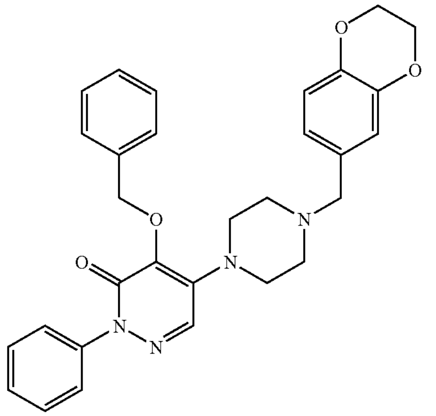
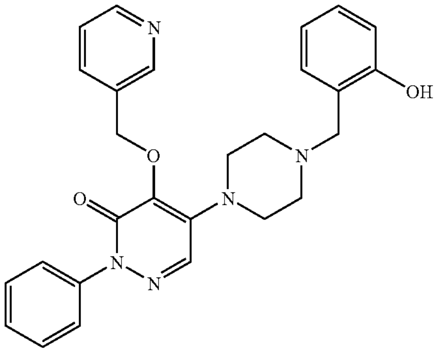
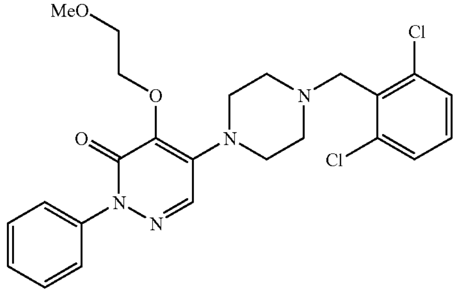
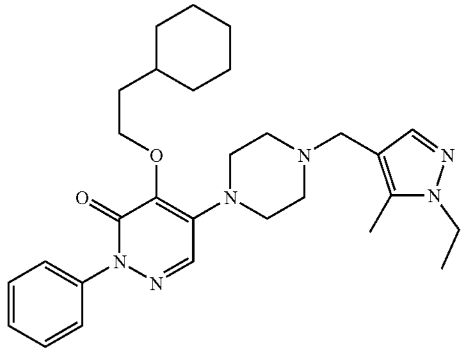
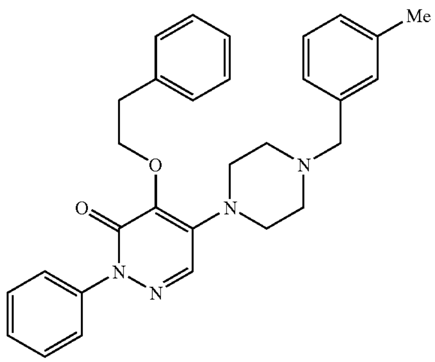
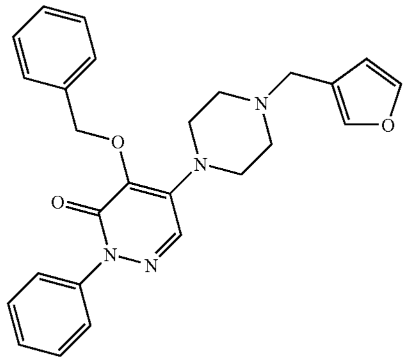
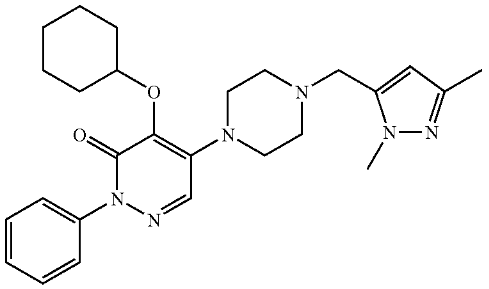
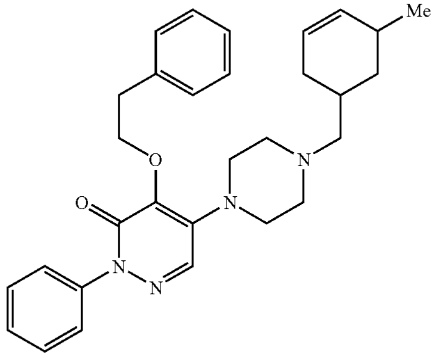

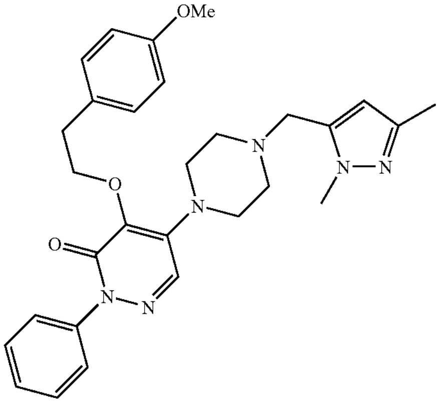
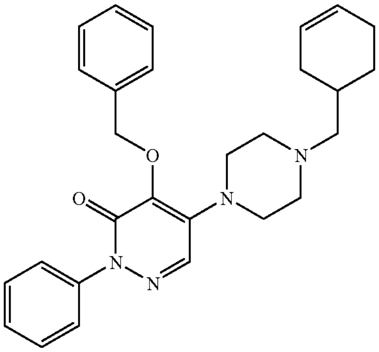
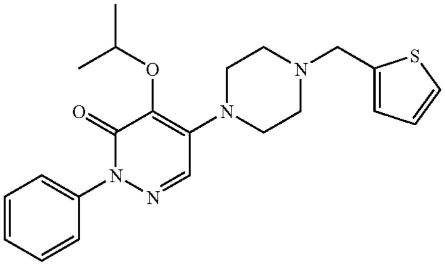
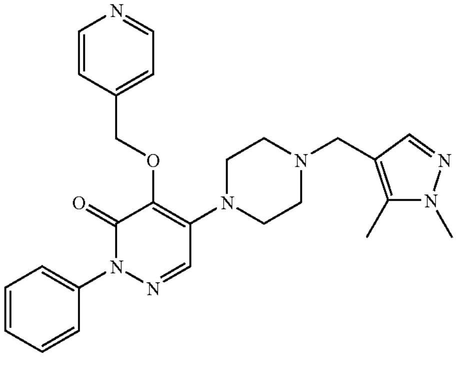
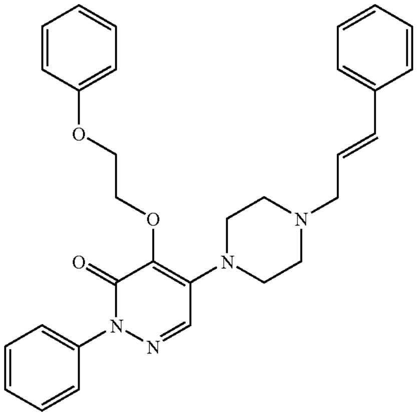
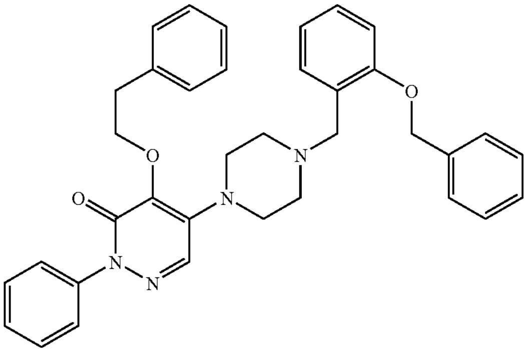
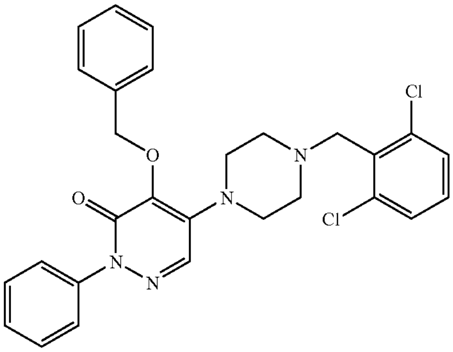
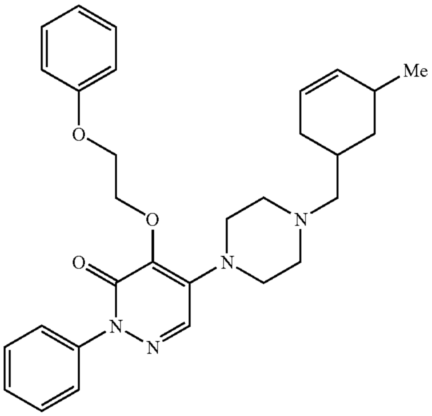

TABLE A-continued
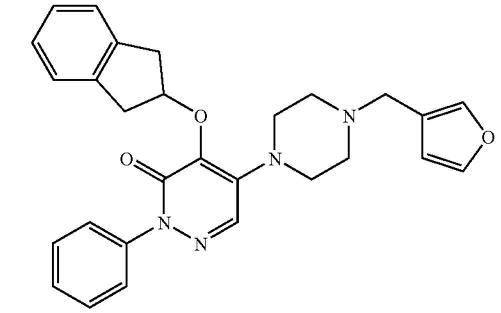
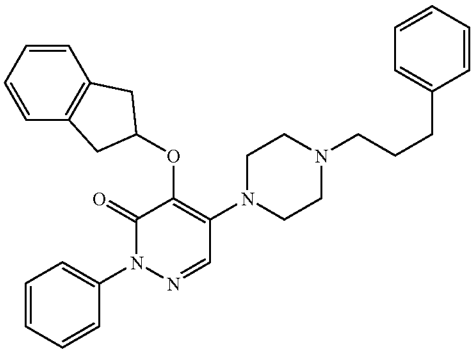
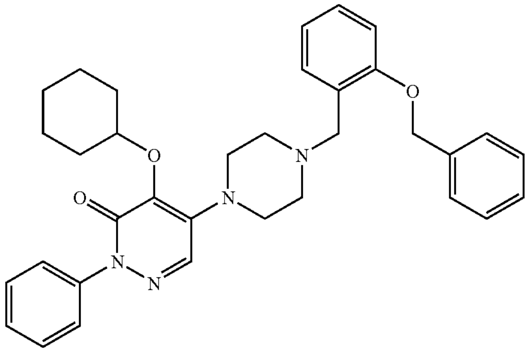
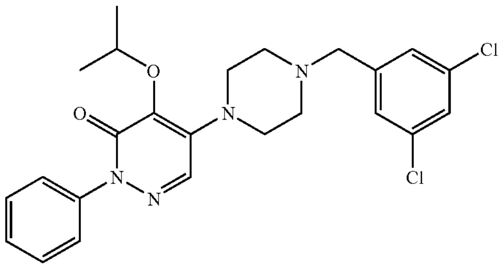
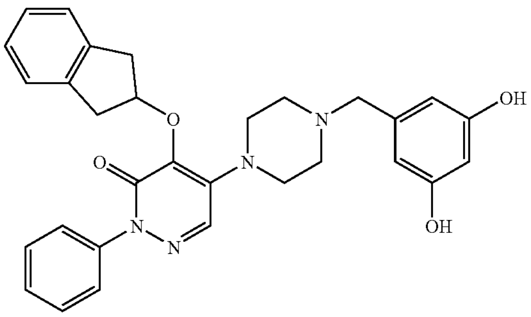
TABLE A-continued
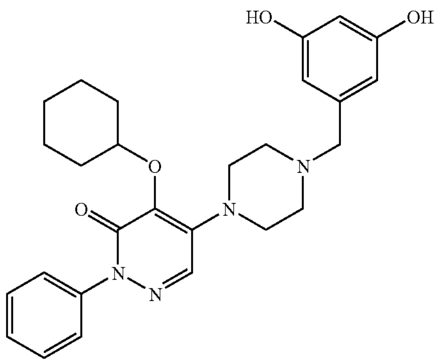
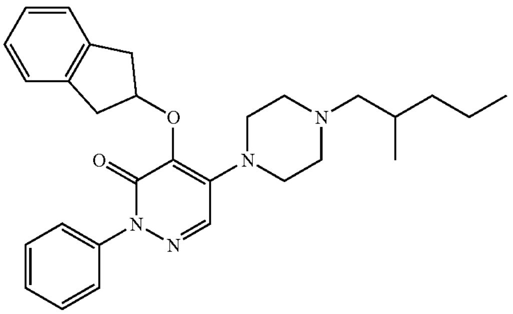
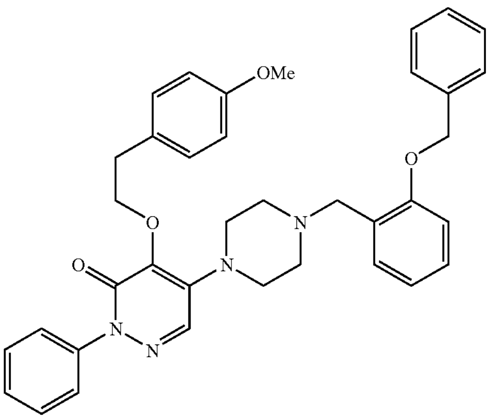
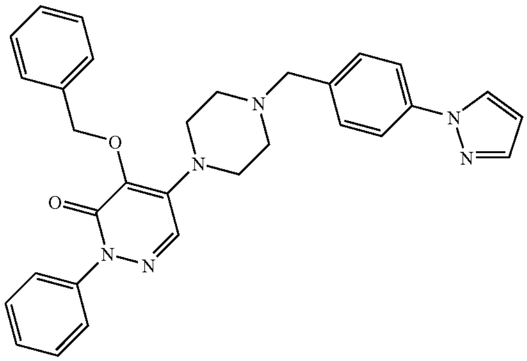

TABLE A-continued
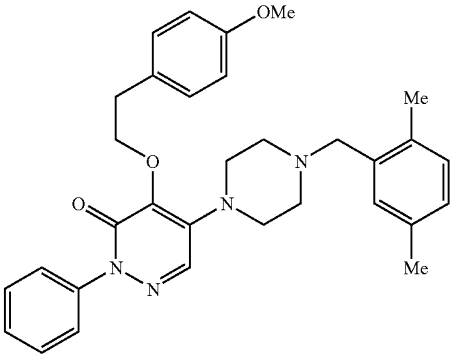
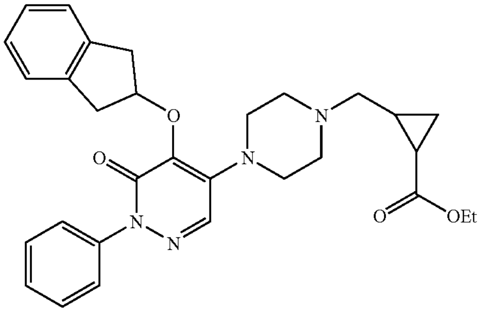
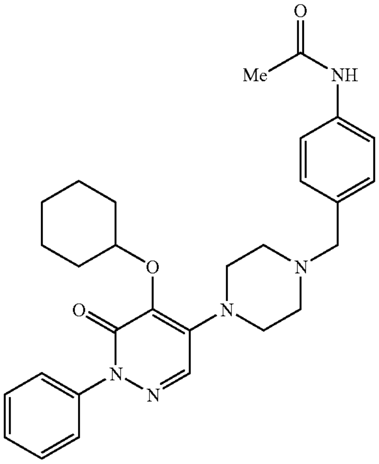
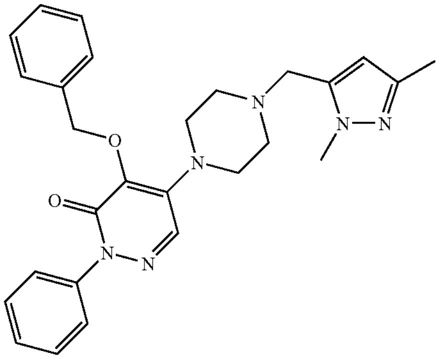
TABLE A-continued
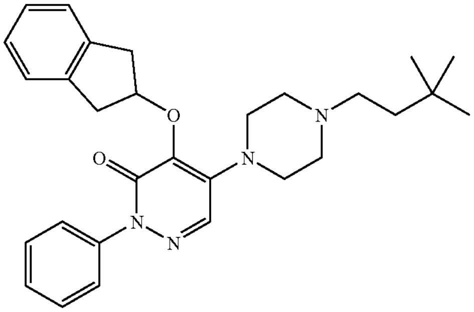
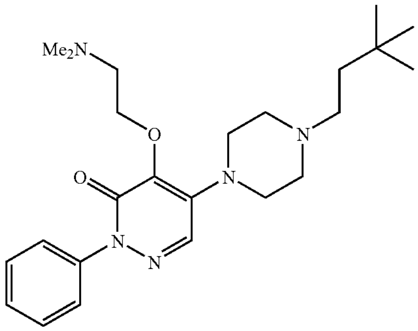
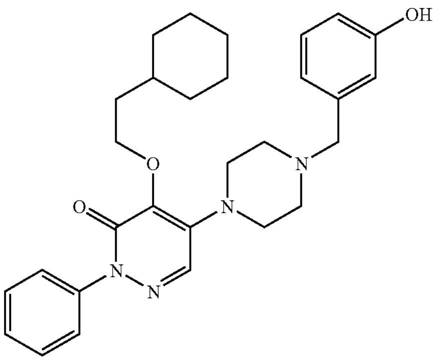
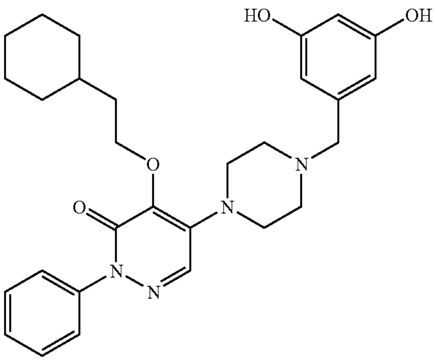

TABLE A-continued
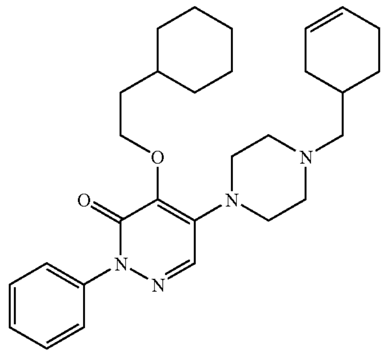
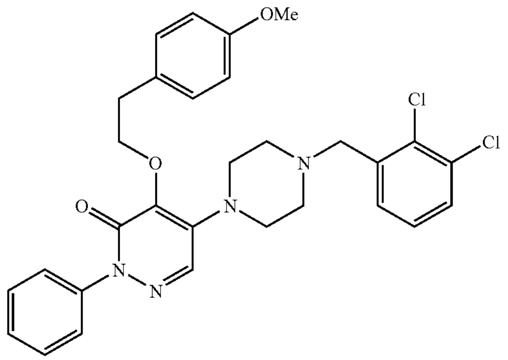
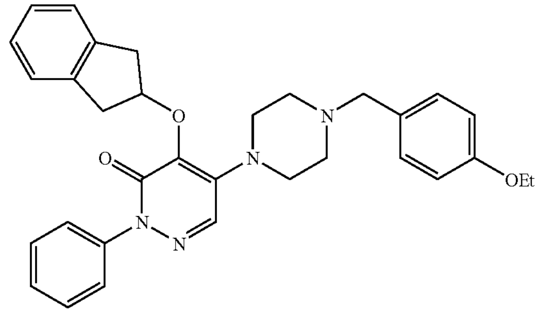
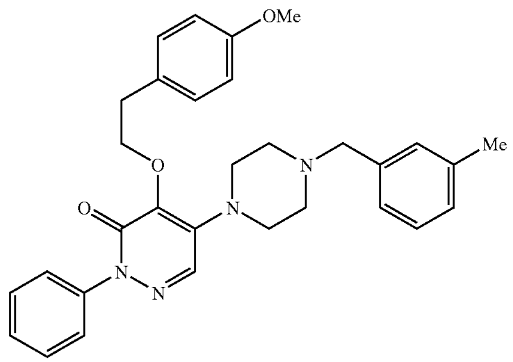
TABLE A-continued
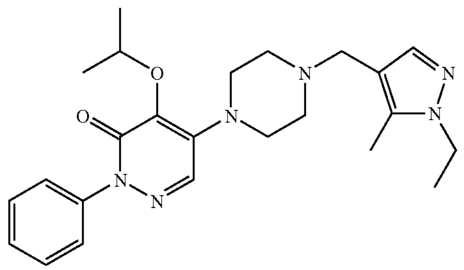
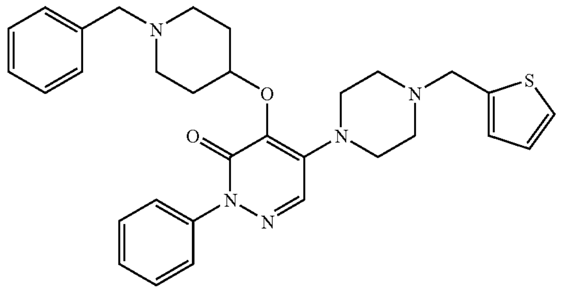
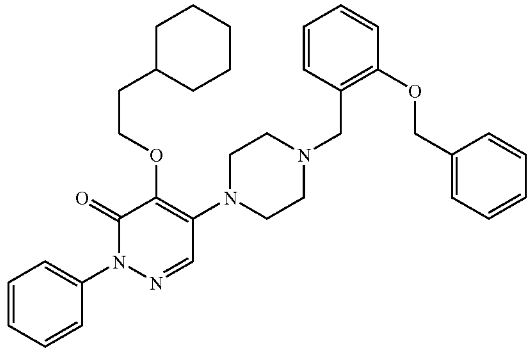
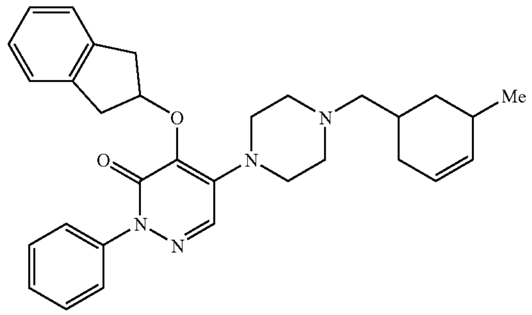
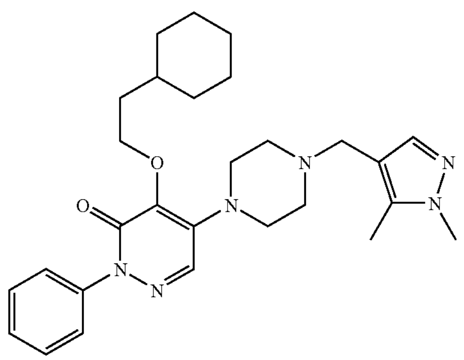

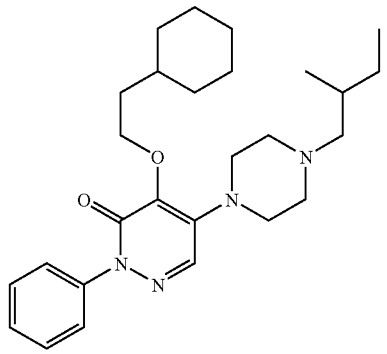
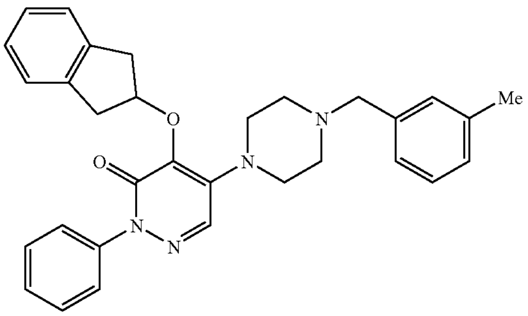
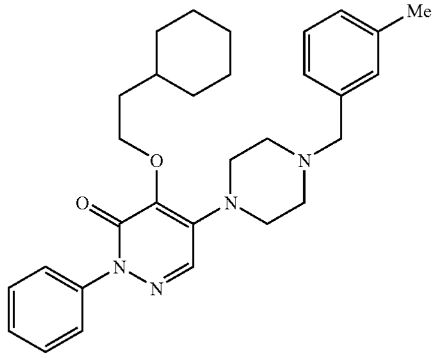
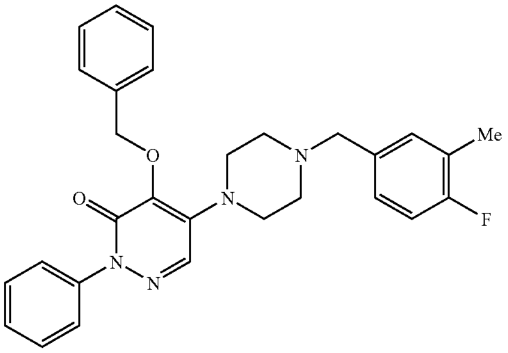
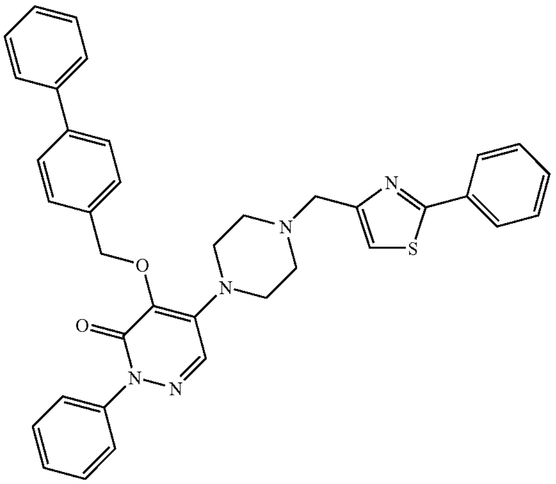
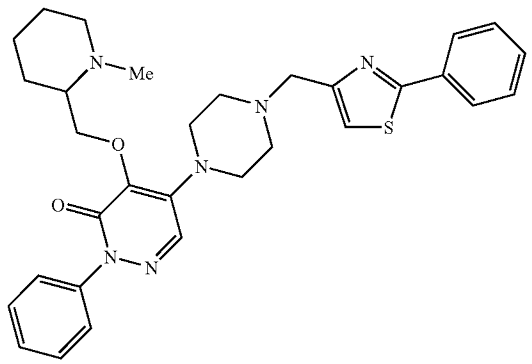
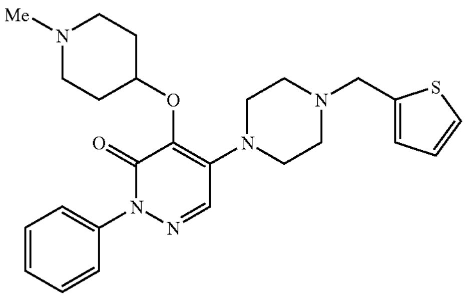
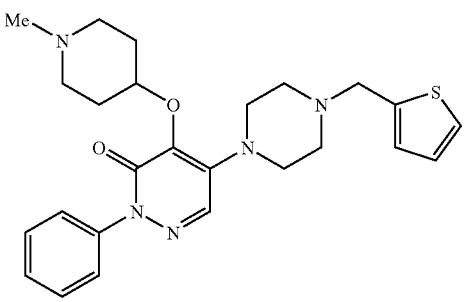

TABLE A-continued
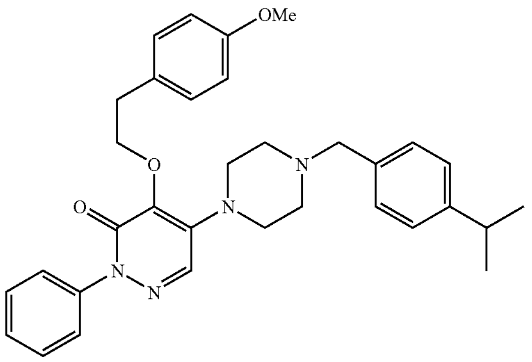
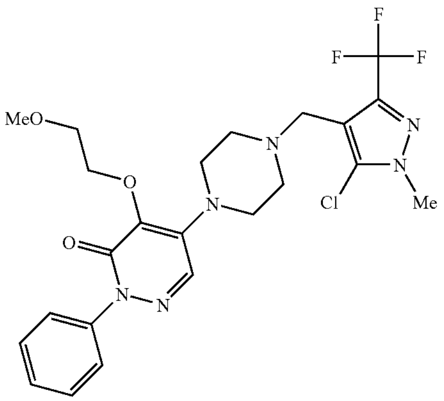
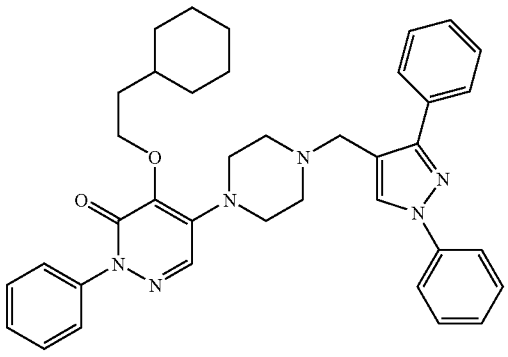
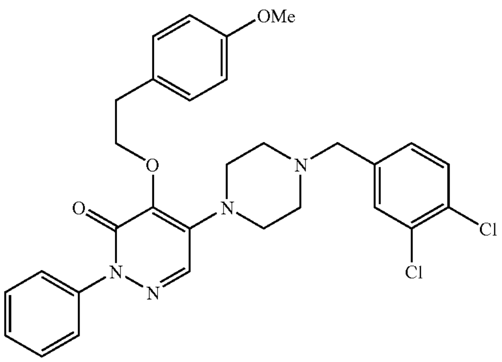
TABLE A-continued
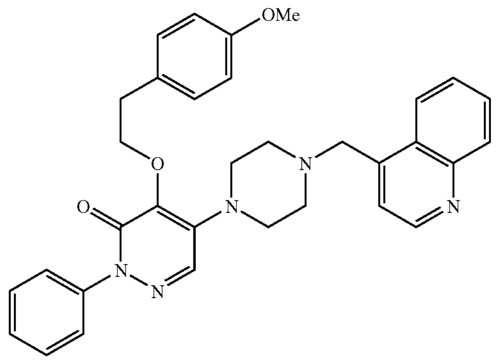
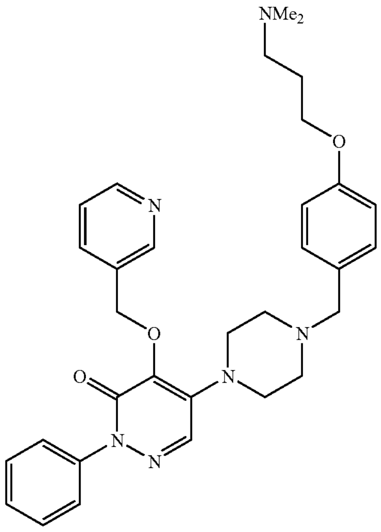
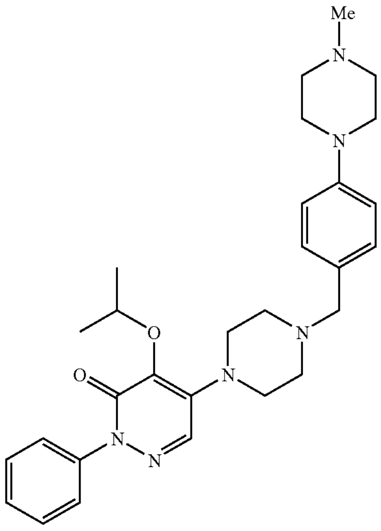

TABLE A-continued
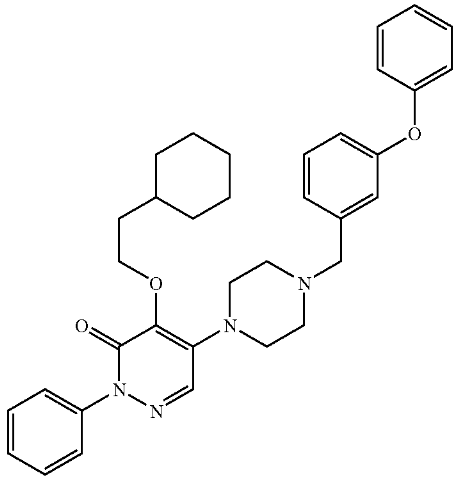
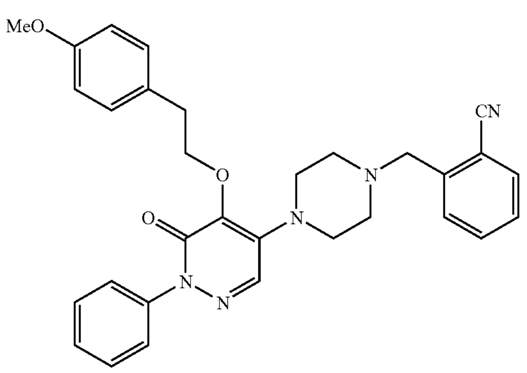
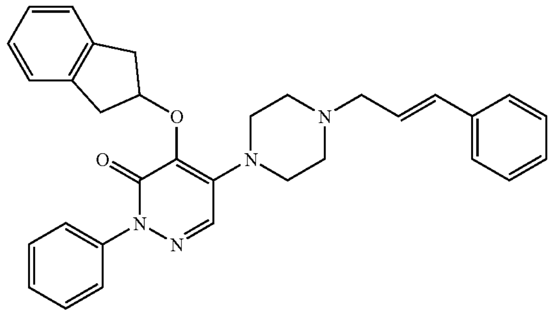
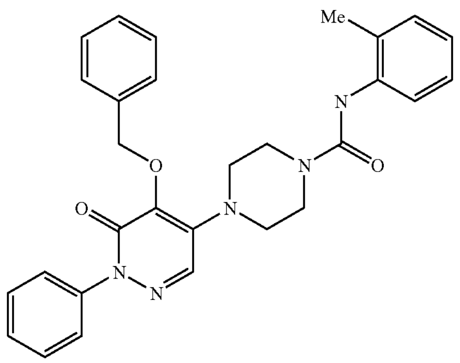
TABLE A-continued
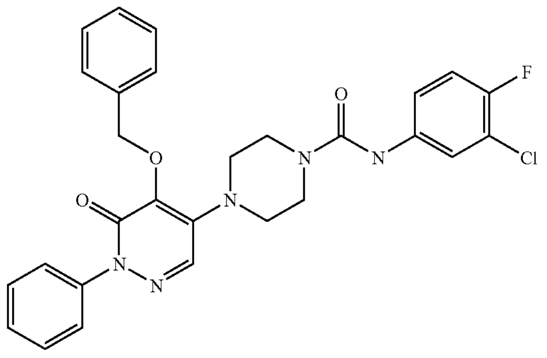
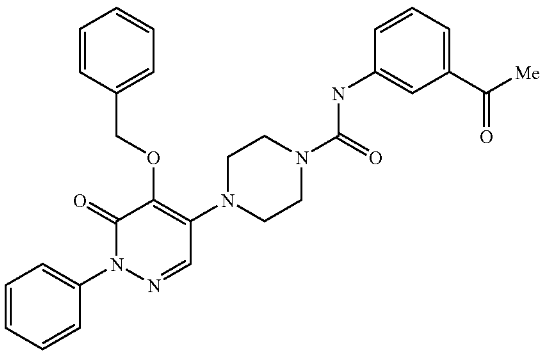
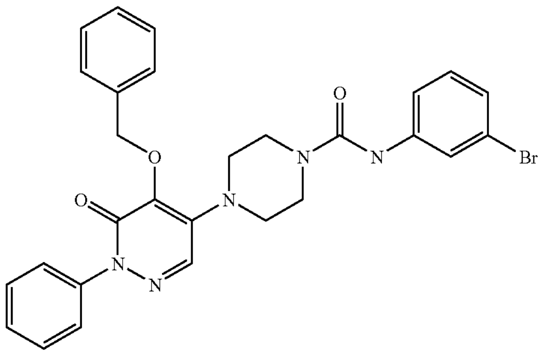
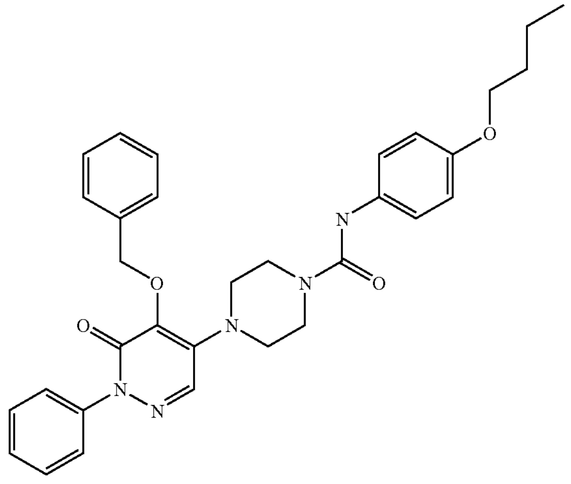

TABLE A-continued
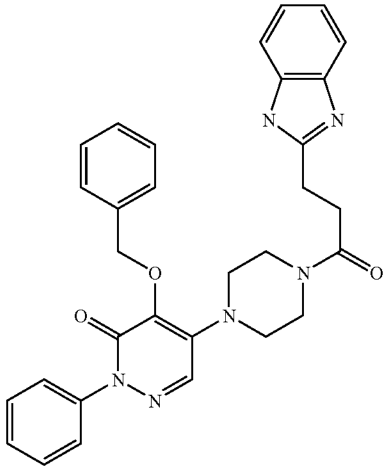
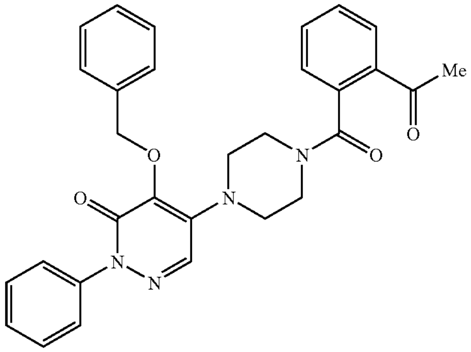
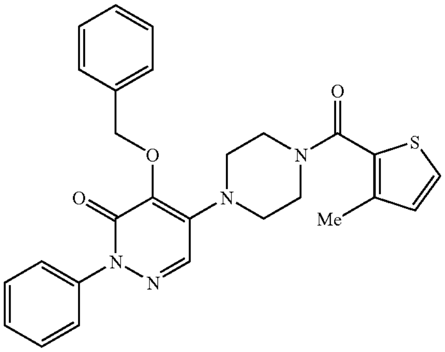
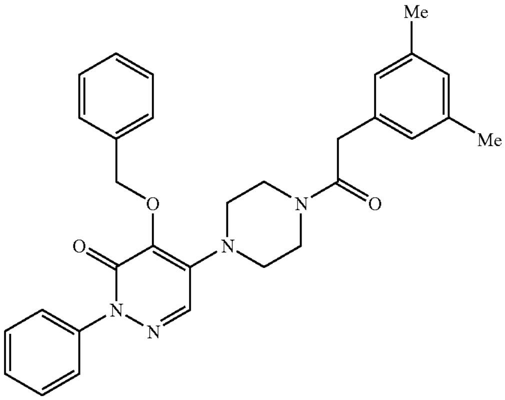
TABLE A-continued
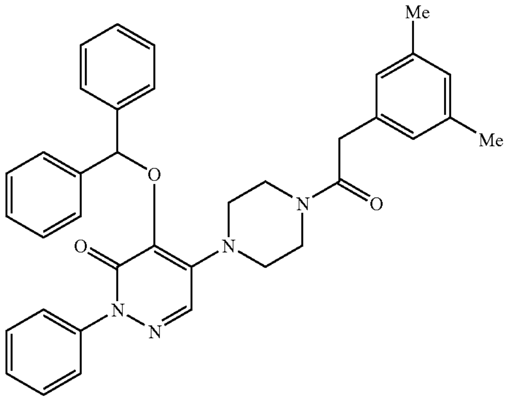
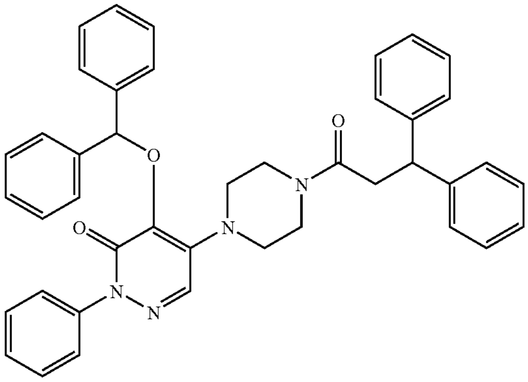
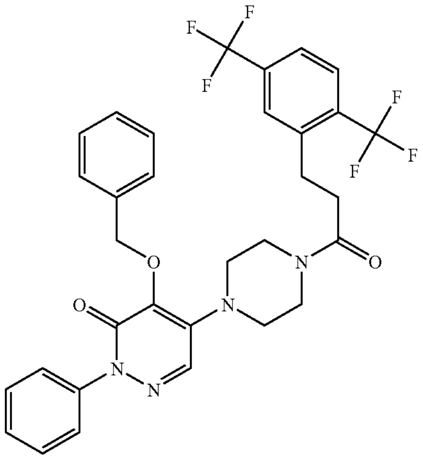
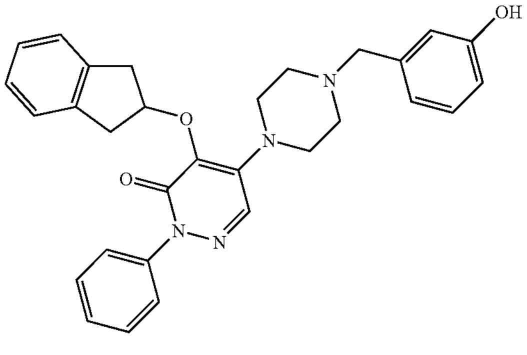

TABLE A-continued
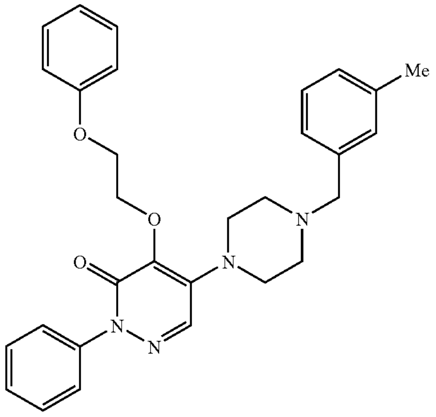
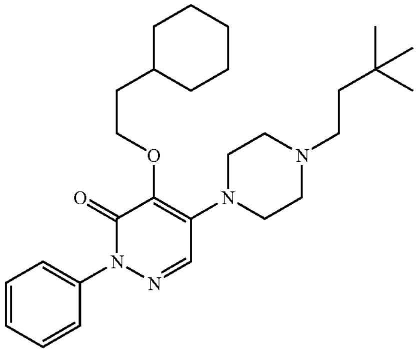
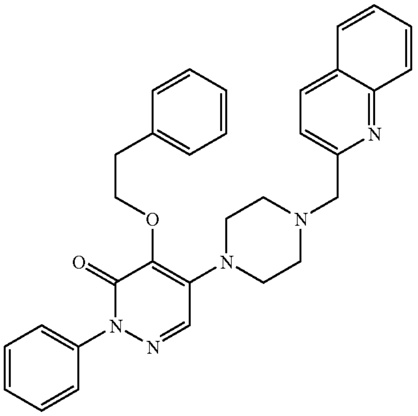
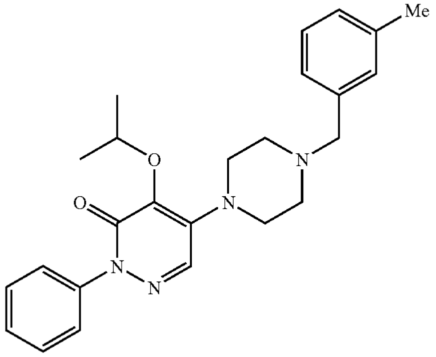
TABLE A-continued
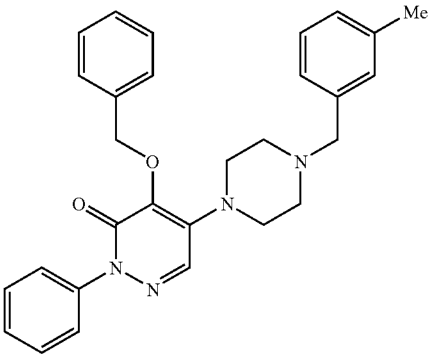
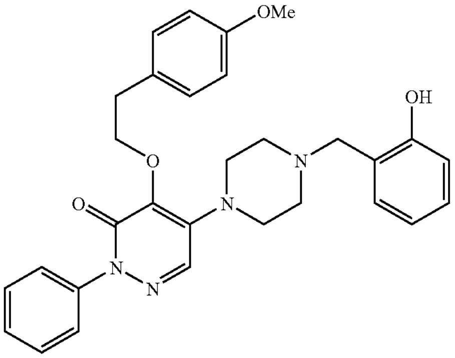
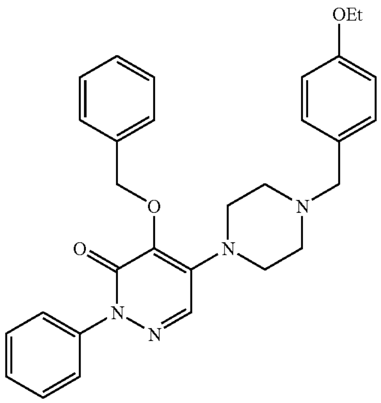
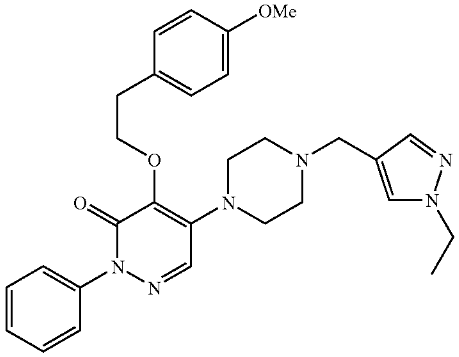

TABLE A-continued
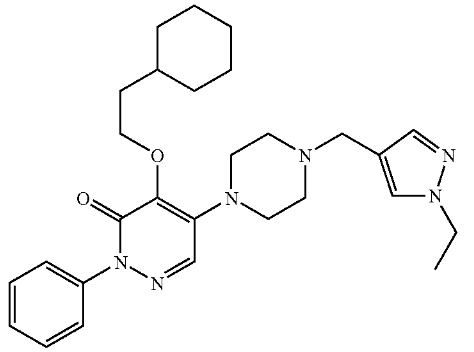
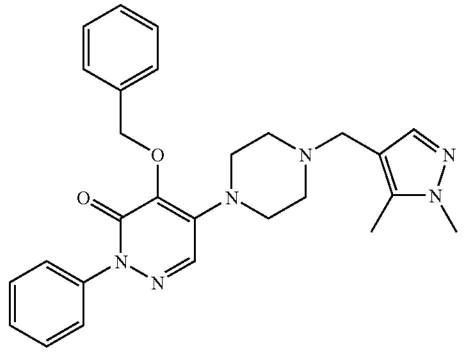
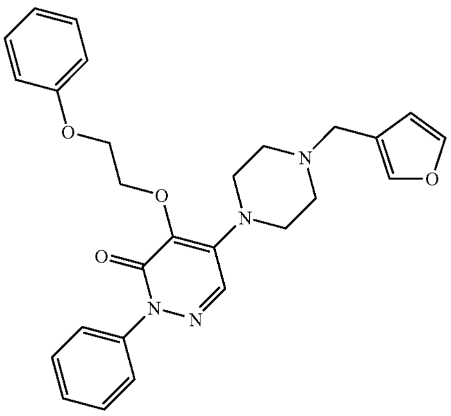
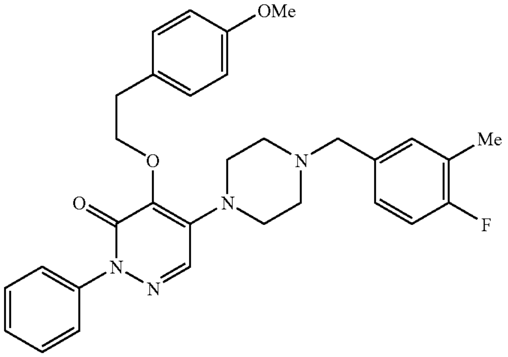
TABLE A-continued
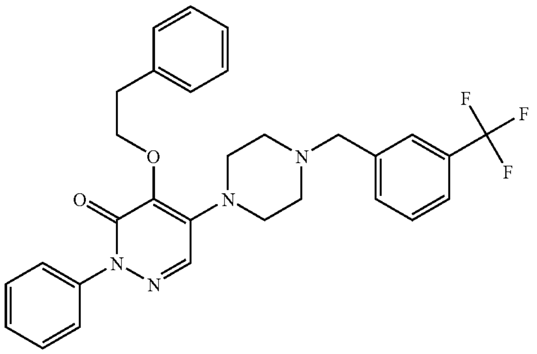
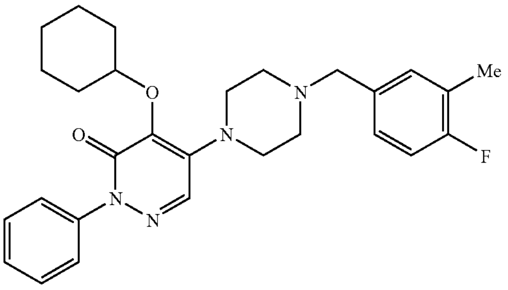
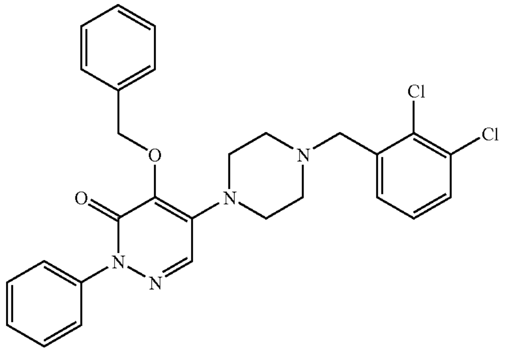
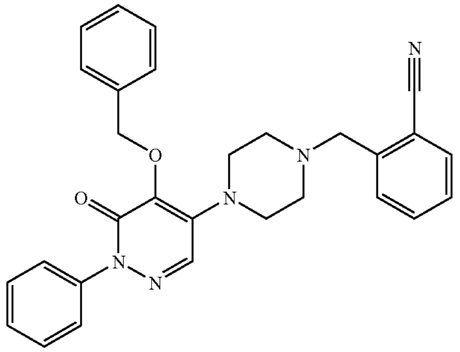

TABLE A-continued
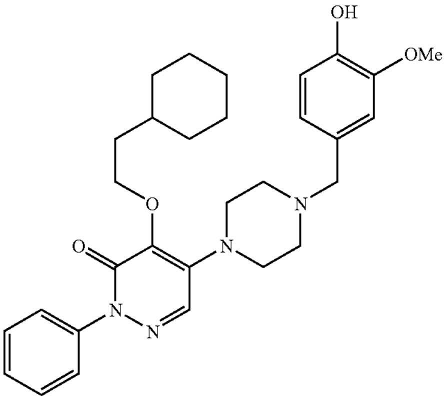
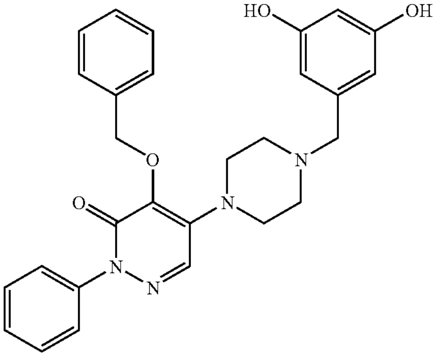
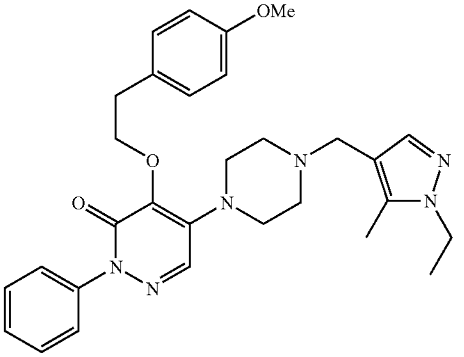
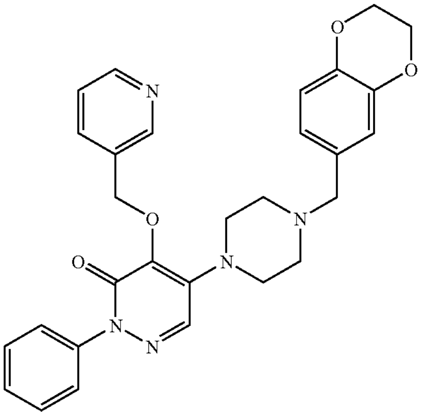
TABLE A-continued
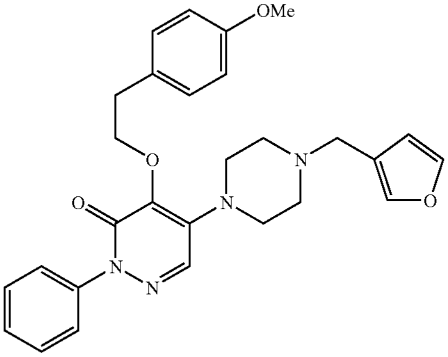
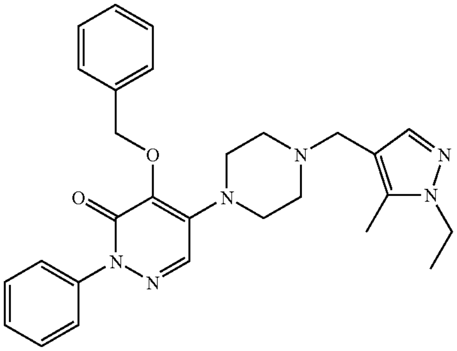
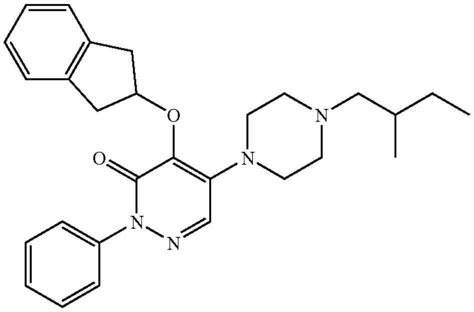
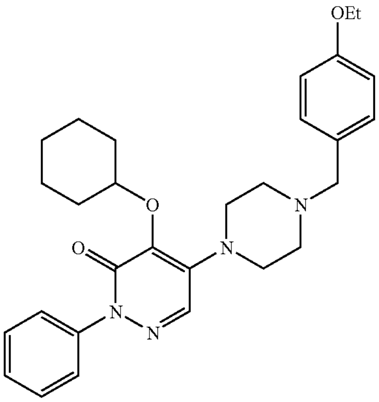

TABLE A-continued
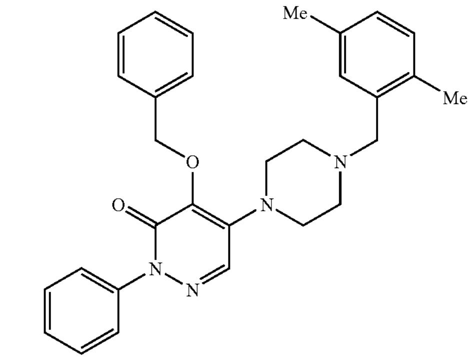
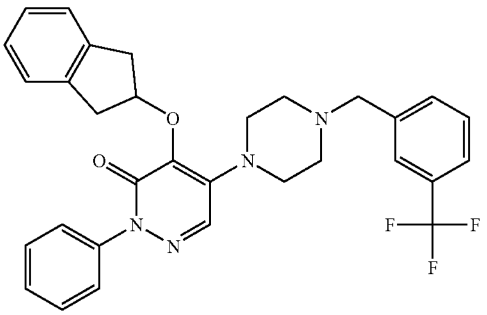
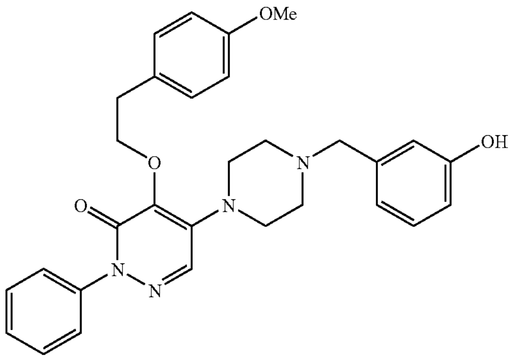
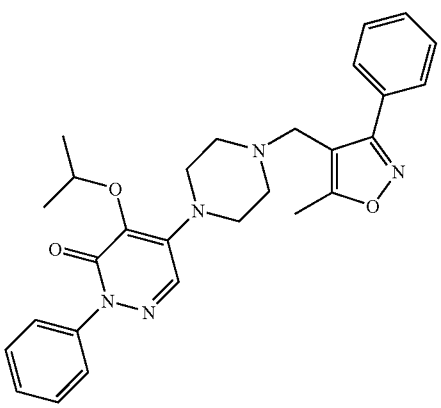
TABLE A-continued
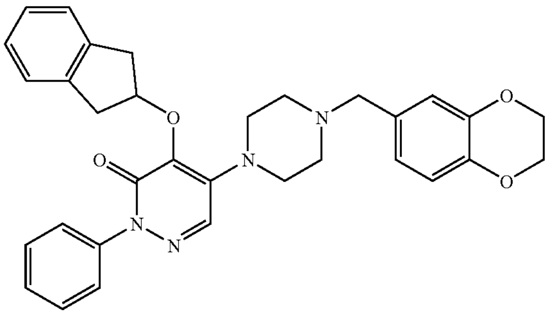
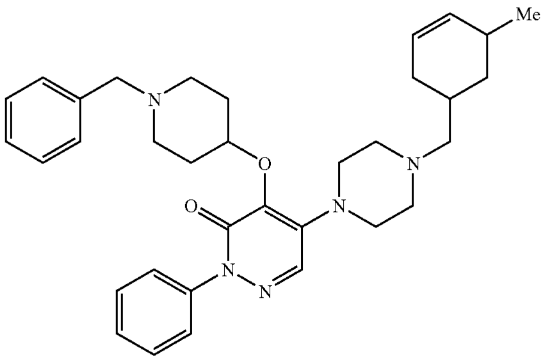
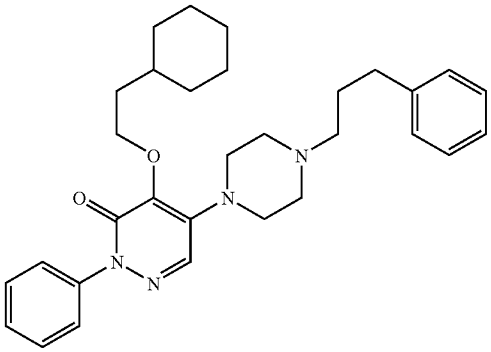
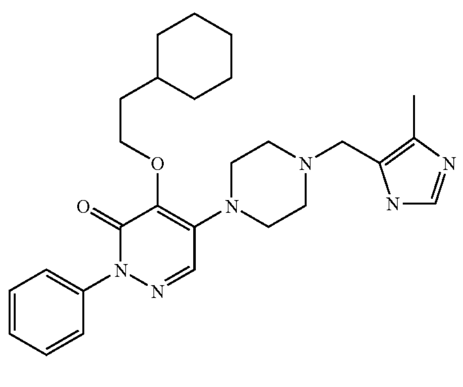

TABLE A-continued
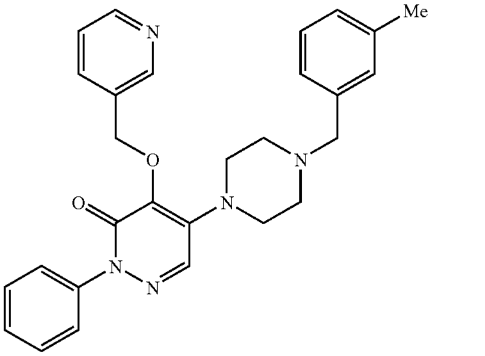
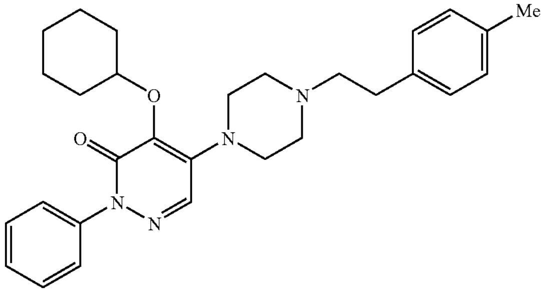
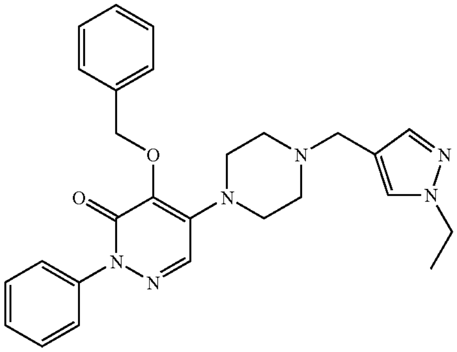
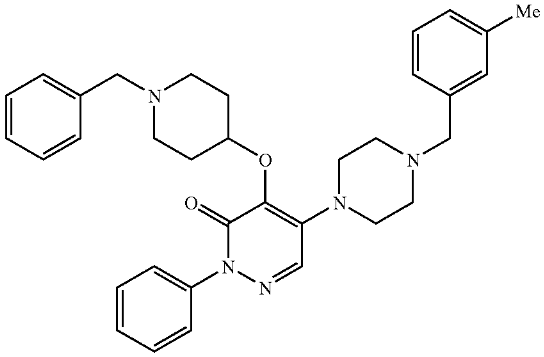
TABLE A-continued
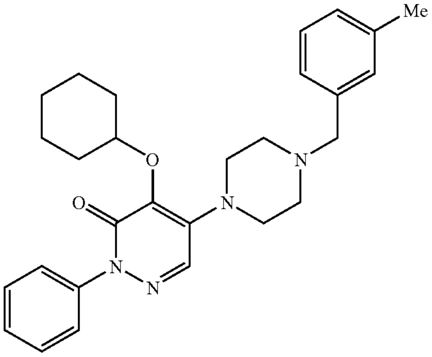
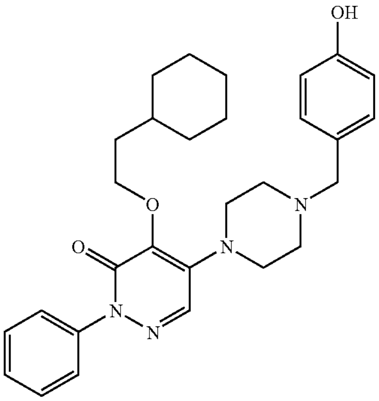
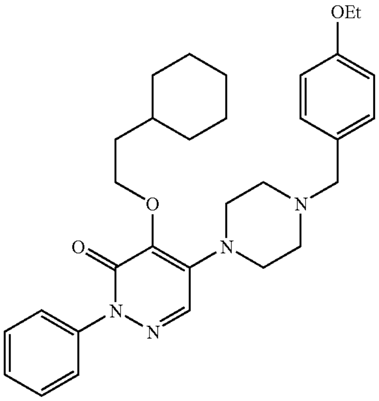
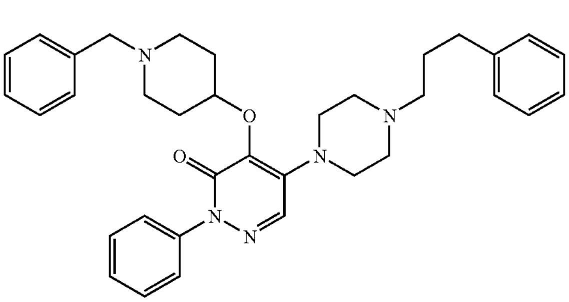

TABLE A-continued
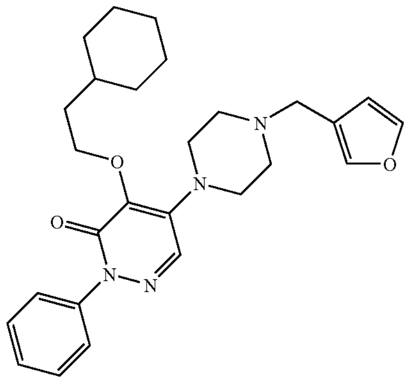
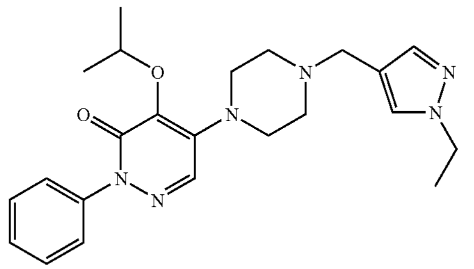
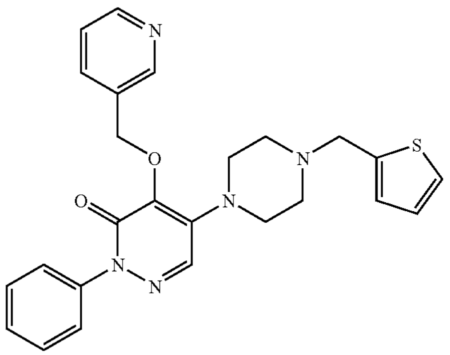
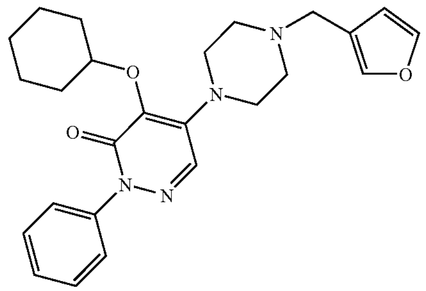
TABLE A-continued
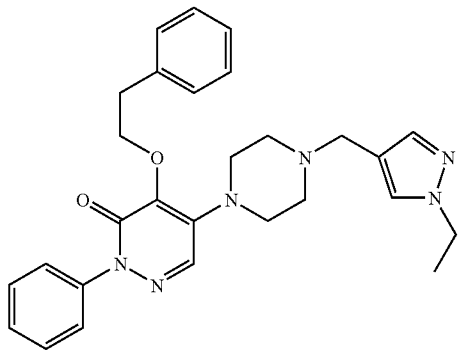
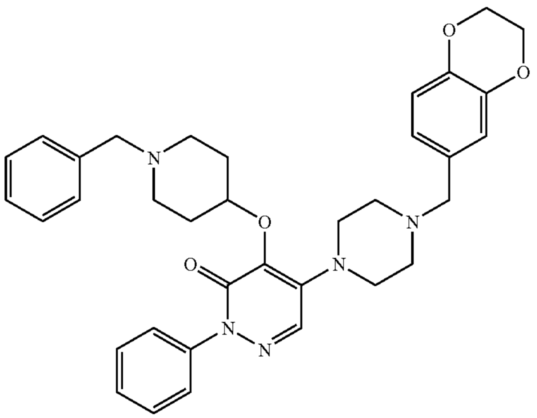
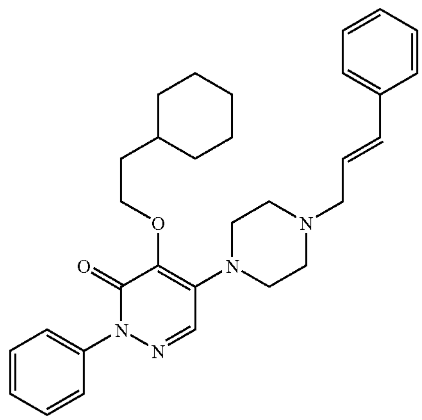
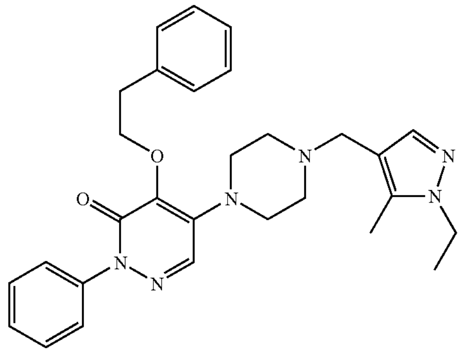

TABLE A-continued
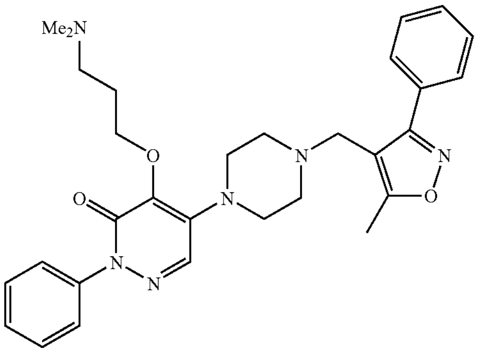
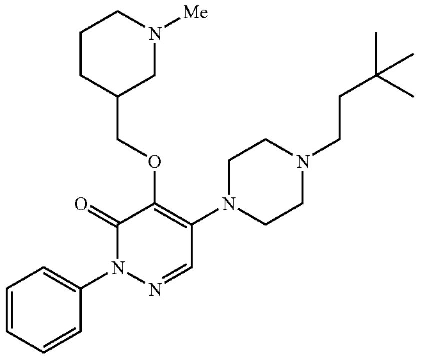
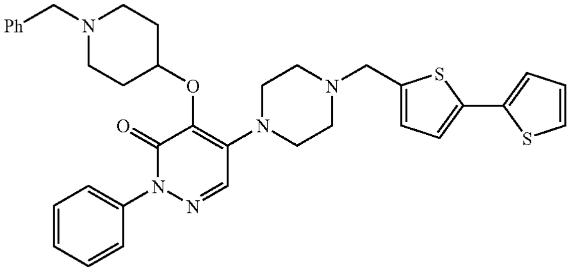
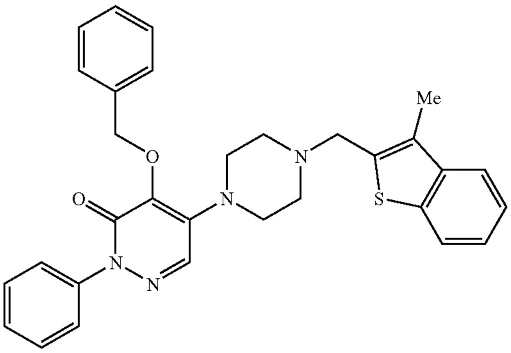
TABLE A-continued
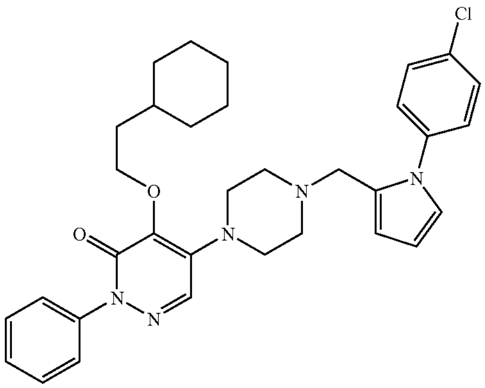
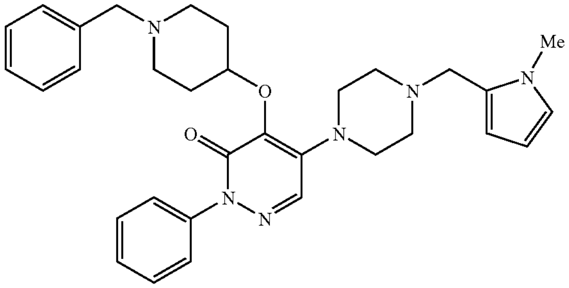
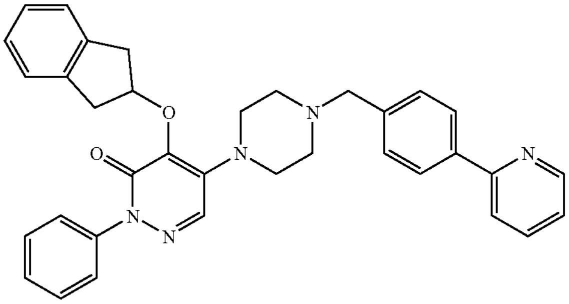
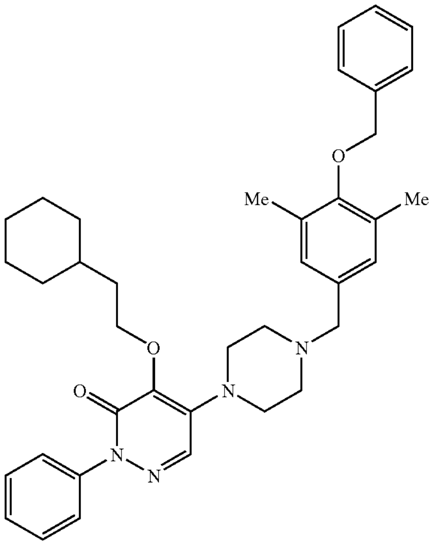

TABLE A-continued
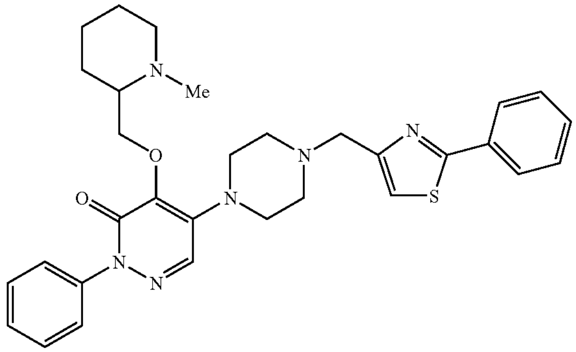
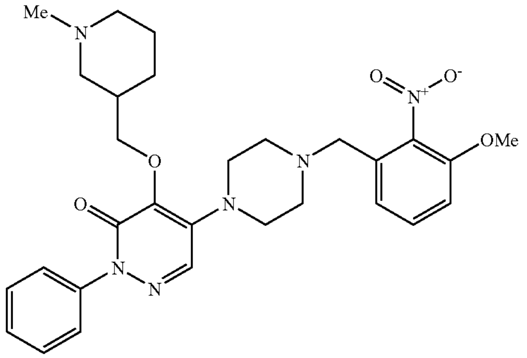
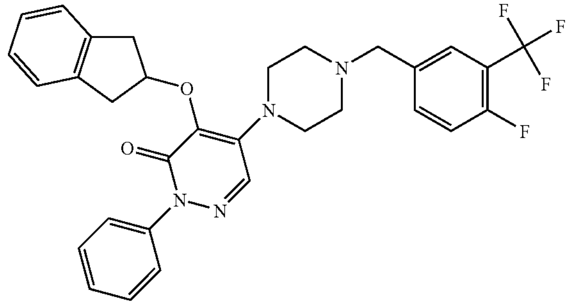
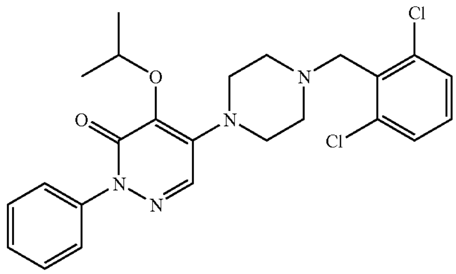
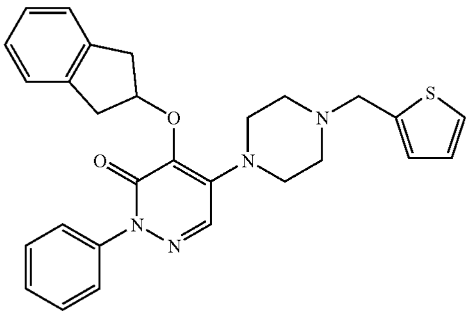
TABLE A-continued
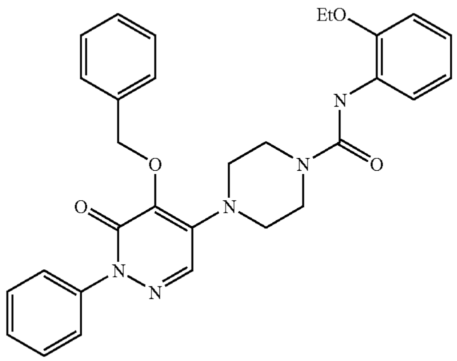
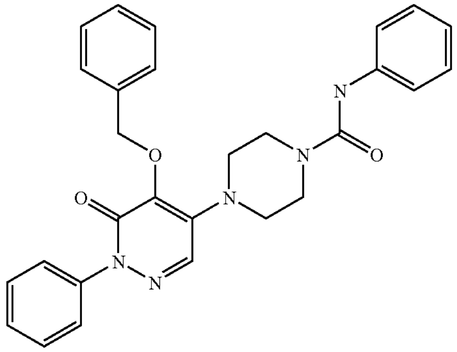
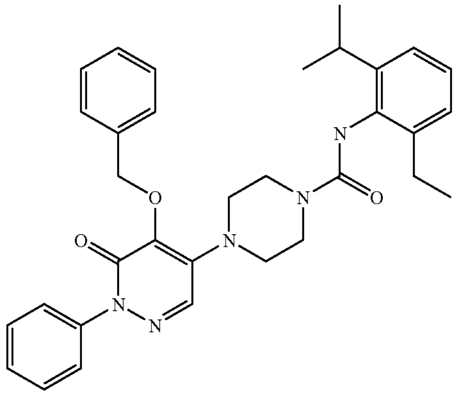
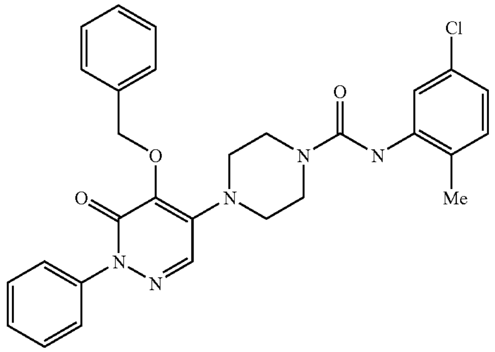

TABLE A-continued

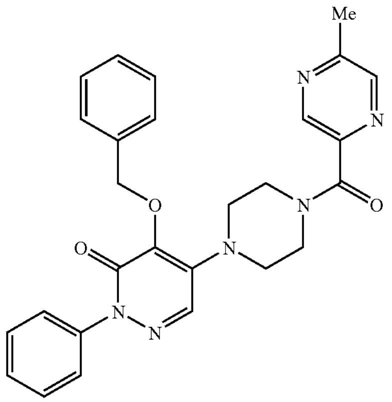

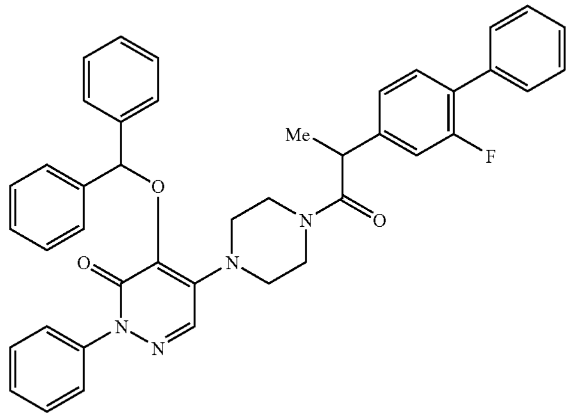

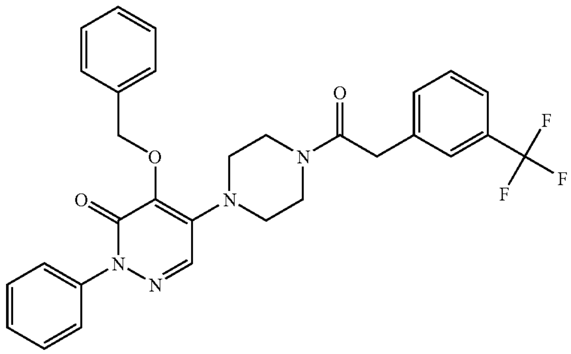

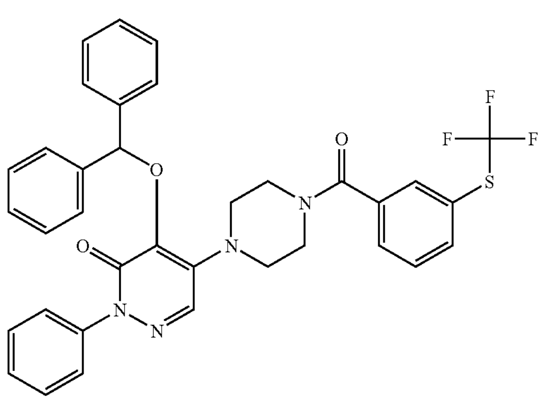

TABLE A-continued

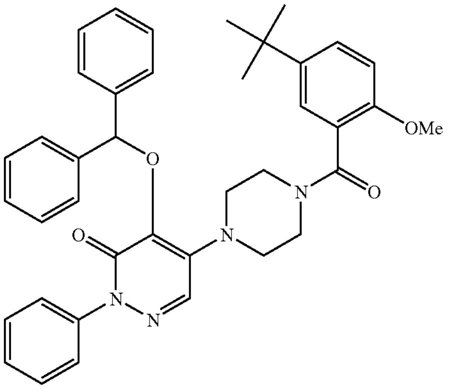

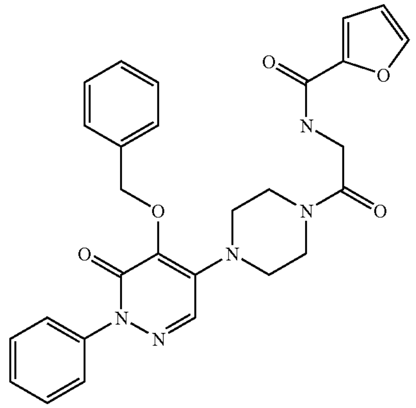

The invention also relates to a pharmaceutical composition for human or veterinary use comprising one or more compounds of Formula I and a pharmaceutically acceptable carrier.

The invention also relates to a pharmaceutical composition for human or veterinary use comprising combination of one or more compounds of Formula I and one or more other antifungal agents with or without a pharmaceutically acceptable carrier.

The invention also relates to a method of treating or preventing growth of fungal pathogens in plants, and to a method of reducing or eliminating fungal growth on inanimate surfaces, comprising applying a compound of Formula I to said plant or surface.

The invention also relates to a method of treating or preventing growth of fungal pathogens on inanimate surface by applying one or more compounds of Formula I to said surface.

Further, the invention relates to a method of treating or preventing growth of fungal pathogens on inanimate surface by applying other antifungal agents along with the compounds of Formula I.

The invention also relates to a method of treating fungal pathogens by administering pharmaceutical compositions for human or veterinary use comprising one or more compounds of Formula I and a pharmaceutically acceptable carrier.

The invention also relates to the use of a glucan synthase inhibitor of Formula I for the preparation of a medicament for treating or preventing fungal infections.

The invention also relates to a method of treating or preventing fungal infections by administering a combination of one or more compounds of Formula I and one or more other antifungal agents.

Further, the invention relates to a method of treating or preventing fungal infections by administering a human or veterinary pharmaceutical composition comprising one or more compounds of Formula I and one or more other antifungal agents in a pharmaceutically acceptable carrier. Also contemplated the method of preparing a kit comprising in a single package, one container comprising one or more compounds of Formula I in a pharmaceutically acceptable carrier, and a separate container comprising one or more other antifungal agents in a pharmaceutically acceptable carrier, with the compounds of Formula I and the other antifungal agents being present in amounts such that the combination is therapeutically effective.

Also, the invention relates to a method of inhibiting one or more glucan synthase comprising administering at least one compound of claim 1 or a pharmaceutically acceptable salt, solvate, ester or prodrug thereof to a patient in need of such inhibition.

DETAILED DESCRIPTION OF THE INVENTION

In an embodiment, the present invention provides novel compounds represented by structural Formula I, or pharmaceutically acceptable salts, solvates, esters or prodrugs thereof, wherein the various moieties are as described above, provided that the compounds of Formula I do not include the compounds of Table A listed above.

In another embodiment, in Formula I, A is O.

In another embodiment, in Formula I, D is N or C.

In another embodiment, in Formula I, D is N.

In another embodiment, in Formula I, D is C.

In another embodiment, in Formula I, E is C.

In another embodiment, in Formula I,

Y is 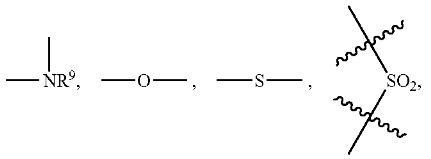

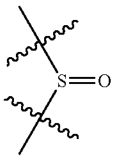 or absent.

In another embodiment, in Formula I, Y is S.

In another embodiment, in Formula I, Y is O.

In another embodiment, in Formula I, Y is

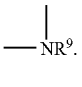

In another embodiment, in Formula I, Y is

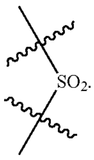

In another embodiment, in Formula I, Y is

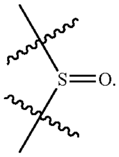

In another embodiment, in Formula I, Y is absent.

In another embodiment, in Formula I, Z is

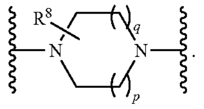

In another embodiment, in Formula I, Z is

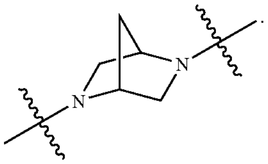

In another embodiment, in Formula I, Z is

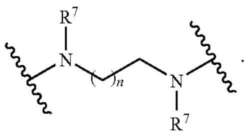

In another embodiment, in Formula I, Z is

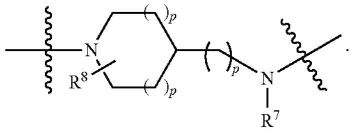

In another embodiment, in Formula I, $R^5$ is

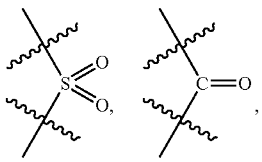

, —$CR^9_2$— or heteroaryl.

In another embodiment, in Formula I, $R^5$ is

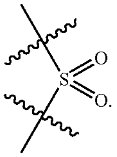

In another embodiment, in Formula I, $R^5$ is

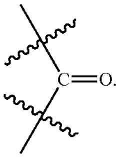

In another embodiment, in Formula I, $R^5$ is —$CR^9_2$—.

In another embodiment, in Formula I, $R^5$ is heteroaryl.

In another embodiment, in Formula I, E is C and $R^6$ is H.

In another embodiment, in Formula I, D is N, E is C, a double bond is present between D and E, and $R^6$ is H.

In another embodiment, this invention discloses a compound of Formula A:

Formula A

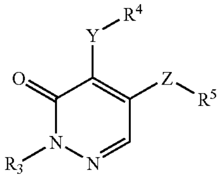

or a pharmaceutically acceptable salt, solvate, ester or prodrug thereof, wherein Y is —O—, provided that Y—$R^4$ taken together is not alkoxyl of the formula

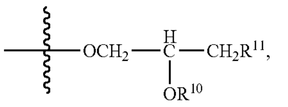

wherein —$CH_2R^{11}$ and $OR^{10}$ together with the CH to which they are attached, form a heterocyclyl that is substituted with one or more moieties, which can be the same or different, selected from the group consisting of alkyl and aryl, or wherein $R^{10}$ is H and $R^{11}$ is hydroxyl or butylamine;

Z is a linker attached at either end of said linker to the parent ring of Formula A, wherein said linker is selected from the group consisting of:

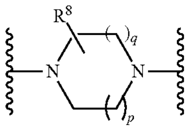
,
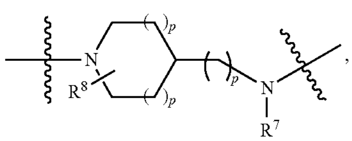
,
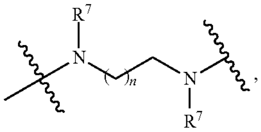
, and
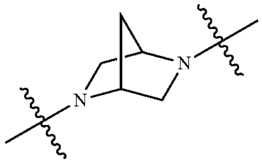

wherein n is 1 to 4, p is 0 to 2, q is 1 to 3:

$R^3$, $R^4$, $R^5$, $R^7$, $R^8$, $R^9$ and $R^{12}$ are as described in Formula I above;

provided that Formula A does not include the compounds of Table A as defined above.

In another embodiment, this invention discloses a compound of Formula B:

Formula B

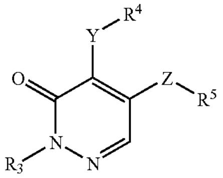

or a pharmaceutically acceptable salt, solvate, ester or prodrug thereof, wherein Y is absent;

$R^3$, $R^4$, $R^5$, $R^7$, $R^8$, $R^9$ and $R^{12}$ are as described in Formula I above;

Z is a linker attached at either end of said linker to the parent ring of Formula B, wherein said linker is selected from the group consisting of:

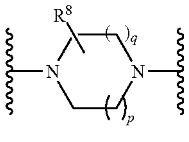
,
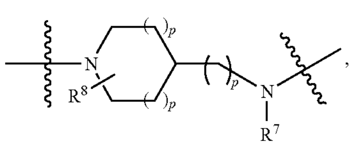
,
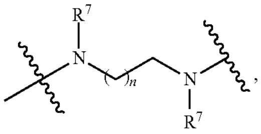
, and

-continued

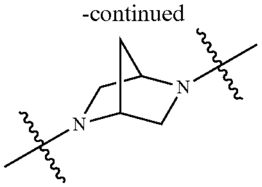

wherein n is 1 to 4, p is 0 to 2, q is 1 to 3;

provided that Formula B does not include the compounds of Table A as defined above.

In another embodiment, this invention discloses a compound of Formula C:

Formula C

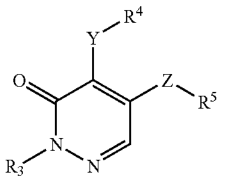

or a pharmaceutically acceptable salt, solvate, ester or prodrug thereof wherein Y is S—,

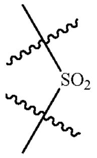 or 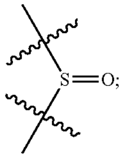

$R^3$, $R^4$, $R^5$, $R^7$, $R^8R^9$ and $R^{12}$ as described in Formula I above;

Z is a linker attached at either end of said tinker to the parent ring of Formula C, wherein said linker is selected from the group consisting of:

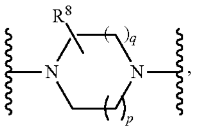, 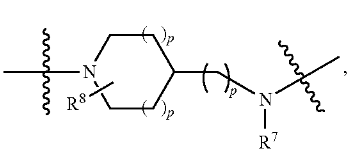,

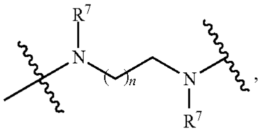, and

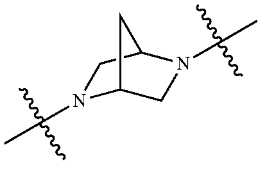

wherein n is 1 to 4, p is 0 to 2, q is 1 to 3;

provided that Formula C does not include the compounds of Table A as defined above.

In another embodiment, this invention discloses compounds of the Formula D:

Formula D

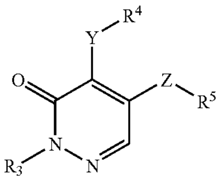

or a pharmaceutically acceptable salt, solvate, ester or prodrug thereof, wherein Y is $NR^9{}_2$;

$R^3$, $R^4$, $R^7$, $R^8R^9$ and $R^{12}$ as described in Formula I above;

Z is a linker attached at either end of said linker to the parent ring of Formula D, wherein said linker is selected from the group consisting of:

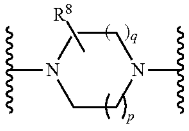, 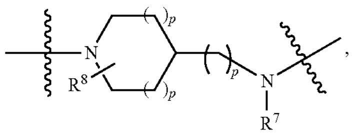,

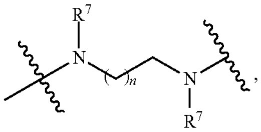, and

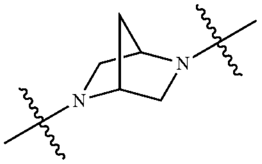

wherein n is 1 to 4, p is 0 to 2, q is 1 to 3;

provided that Formula D does not include the compounds of Table A as defined above.

In another embodiment, this invention discloses compounds of Formula E:

Formula E

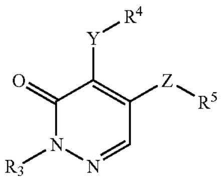

or a pharmaceutically acceptable salt, solvate, ester or prodrug thereof, wherein Y, $R^3$, $R^4$, $R^7$, $R^8$, $R^9$ and $R^{12}$ as described in Formula I above;

Z is a linker attached at either end of said linker to the parent ring of Formula F, wherein said linker is selected from the group consisting of:

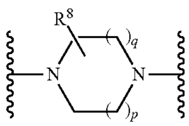,
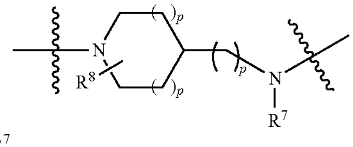,

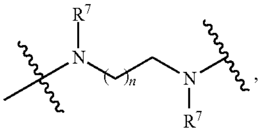, and

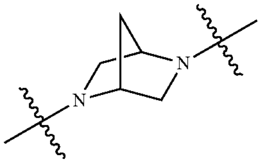

wherein n is 1 to 4, p is 0 to 2, q is 1 to 3;

$R^5$ is

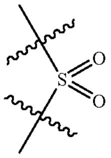

wherein each of said

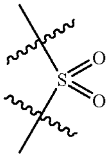

is attached at one end to Z and at the second end substituted with one or more moieties, which can be the same or different, each moiety being independently selected from the group consisting of H, alkyl, alkenyl, cycloalkyl, cyclenyl, aryl, heterocyclyl, heterocyclenyl, heteroaryl, cycloalkylalkyl, cyclenylalkyl, arylalkyl, heterocyclylalkyl, heterocyclenylalkyl, heteroarylalkyl, cycloalkylalkenyl, cyclenylalkenyl, arylalkenyl, heterocyclylalkenyl, heterocyclenylalkenyl, heteroarylalkenyl, —$OR^9$ and —$NR^9_2$, further, wherein each of said alkyl, alkenyl, cycloalkyl, cyclenyl, aryl, heterocyclyl, heterocyclenyl, heteroaryl, cycloalkylalkyl, cyclenylalkyl, arylalkyl, heterocyclylalkyl, heterocyclenylalkyl, heteroarylalkyl, cycloalkylalkenyl, cyclenylalkenyl, arylalkenyl, heterocyclylalkenyl, heterocyclenylalkenyl, or heteroarylalkenyl can be unsubstituted or substituted with one or more moieties, which can be the same or different, each moiety being independently selected from the group consisting of halogen, alkyl, alkenyl, cycloalkyl, —$OR^9$, alkyl$OR^9$, alkyl$CO_2R^9$, alkyl$NR^{16}COR^9$, alkyl$NR^{16}CONR^9$, alkyl$SO_2R^9$, alkyl$COR^9$, alkyl$SO_2NR^9_2$, alkyl$NR^9_2$, alkylaryl, alkylheteroaryl, alkyl$SR^9$, alkyl$SOR^9$, —CN, —$CO_2R^9$, trihaloalkyl, dihaloalkyl, monohaloalkyl, —$NR^{16}COR^9$, —$NR^{16}CONR^9_2$, —$NR^{16}SO_2$—$R^{13}$, —$SO_2R^9$, —$COR^9$, —$NO_2$, —$SO_2NR^9_2$, aryl, heteroaryl, —$NR^9_2$, —$SR^9$, —$SOR^9$, —C(═NOH)—$NR^{13}$, 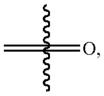, 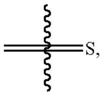,

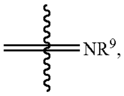, 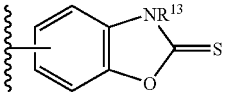 and

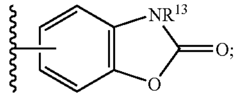;

provided that Formula E does not include the compounds of Table A as defined above.

In another embodiment, this invention discloses compounds of Formula F:

Formula F

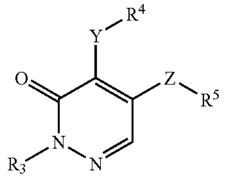

or a pharmaceutically acceptable salt, solvate, ester or prodrug thereof, wherein Y, $R^3$, $R^4$, $R^7$, $R^8$, $R^9$ and $R^{12}$ are as described in Formula I above;

Z is a linker attached at either end of said linker to the parent ring of Formula F, wherein said linker is selected from the group consisting of:

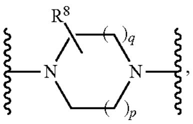,
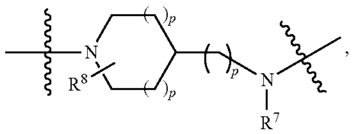,

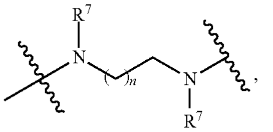, and

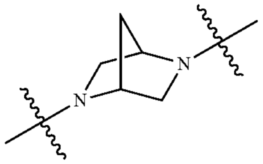

wherein n is 1 to 4, p is 0 to 2, q is 1 to 3;

$R^5$ is heteroaryl, optionally substituted by 1 to 3 ring system substituents, provided that Formula F does not include the compounds of Table A as defined above.

In another embodiment, this invention discloses a compound of Formula G:

Formula G

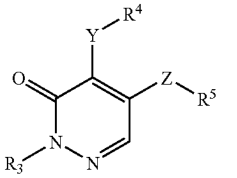

or a pharmaceutically acceptable salt, solvate, ester or prodrug thereof, wherein:

Y, $R^3$, $R^4$, $R^7$, $R^8$, $R^9$ and $R^{12}$ are as described in Formula I above;

Z is a link attached at either end of said linker to the parent ring of Formula G, wherein said linker is selected from the group consisting of:

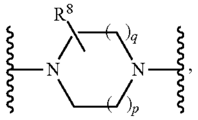,

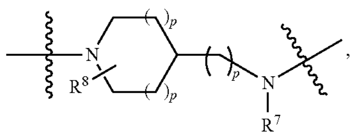,

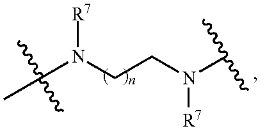, and

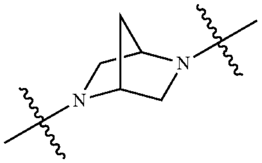

wherein n is 1 to 4, p is 0 to 2, q is 1 to 3;

$R^5$ is

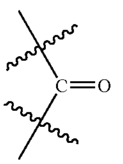

wherein said

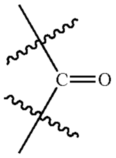

is attached at one end to Z and at the second end substituted with one or more moieties, which can be the same or different, each moiety being independently selected from the group consisting of H, alkyl, alkenyl, cycloalkyl, cyclenyl, aryl, heterocyclyl, heterocyclenyl, heteroaryl, cycloalkylalkyl, cyclenylalkyl, arylalkyl, heterocyclylalkyl, heterocyclenylalkyl, heteroarylalkyl, cycloalkylalkenyl, cyclenylalkenyl, arylalkenyl, heterocyclylalkenyl, heterocyclenylalkenyl, heteroarylalkenyl, —$OR^9$ and —$NR^9{}_2$, further, wherein each of said alkyl, alkenyl, cycloalkyl, cyclenyl, aryl, heterocyclyl, heterocyclenyl, heteroaryl, cycloalkylalkyl, cyclenylalkyl, arylalkyl, heterocyclylalkyl, heterocyclenylalkyl, heteroarylalkyl, cycloalkylalkenyl cyclenylalkenyl, arylalkenyl, heterocyclylalkenyl, heterocyclenylalkenyl, or heteroarylalkenyl can be unsubstituted or substituted with one or more moieties, which can be the same or different, each moiety being independently selected from the group consisting of halogen, alkyl, alkenyl, cycloalkyl, —$OR^9$, alkyl$OR^9$, alkyl$CO_2R^9$, alkyl$NR^{16}COR^9$, alkyl$NR^{16}CONR^9$, alkyl$SO_2R^9$, alkyl$COR^9$, alkyl$SO_2NR^9{}_2$, alkyl$NR^9{}_2$, alkylaryl, alkylheteroaryl, alkyl$SR^9$, alkyl$SO_2R^9$, —CN, —$CO_2R^9$, trihaloalkyl, dihaloalkyl, monohaloalkyl, —$NR^{16}COR^9$, —$NR^{16}CONR^9{}_2$, —$NR^{16}SO_2$—$R^{13}$, —$SO_2R^9$, —$COR^9$, —$NO_2$, —SO—$NR^9{}_2$, aryl, heteroaryl, —$NR^9{}_2$, —$SR^9$, —$SOR^9$, —C(=NOH)—$NR^{13}$, 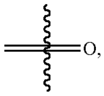, 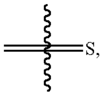,

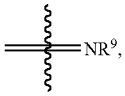, 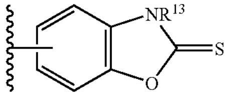 and

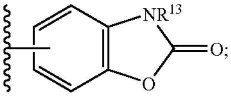;

provided that said Formula G does not include the compounds of Table A as defined above.

In another embodiment, this invention discloses a compound of Formula H:

Formula H

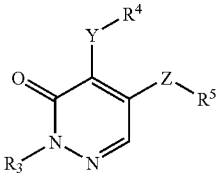

or a pharmaceutically acceptable salt, solvate, ester or prodrug thereof, wherein:

Y, $R^3$, $R^4$, $R^7$, $R^8$, $R^9$ and $R^{12}$ are as described in Formula I above;

Z is a linker attached at either end of said liner to the parent ring of Formula H, wherein said linker is selected from the group consisting of;

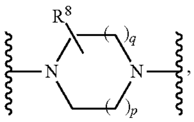
,
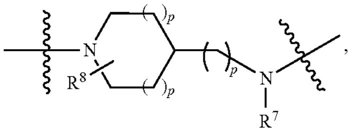
,
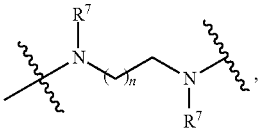
, and
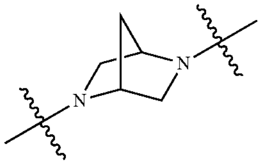

wherein
n is 1 to 4,
p is 0 to 2,
q is 1 to 3;

$R^5$ is —$CR^9_2$— wherein said —$CR^9_2$— is attached at one end to Z and at the second end substituted with one or more moieties, which can be the same or different, each moiety being independently selected from the group consisting of H, alkyl, alkenyl, cycloalkyl, cyclenyl, aryl, heterocyclyl, heterocyclenyl, heteroaryl, cycloalkylalkyl, cyclenylalkyl, arylalkyl, heterocyclylalkyl, heterocyclenylalkyl, heteroarylalkyl, cycloalkylalkenyl, cyclenylalkenyl, arylalkenyl, heterocyclylalkenyl, heterocyclenylalkenyl, heteroarylalkenyl, —$OR^9$ and —$NR^9_2$, further, wherein each of said alkyl, alkenyl, cycloalkyl, cyclenyl, aryl, heterocyclyl, heterocyclenyl, heteroaryl, cycloalkylalkyl, cyclenylalkyl, arylalkyl, heterocyclylalkyl, heterocyclenylalkyl, heteroarylalkyl, cycloalkylalkenyl, cyclenylalkenyl, arylalkenyl, heterocyclylalkenyl, heterocyclenylalkenyl, or heteroarylalkenyl can be unsubstituted or substituted with one or more moieties, which can be the same or different, each moiety being independently selected from the group consisting of halogen, alkyl, alkenyl, cycloalkyl, —$OR^9$, alkyl$OR^9$, alkyl$CO_2R^9$, alkyl$NR^{16}COR^9$, alkyl$NR^{16}CONR^9$, alkyl$SO_2R^9$, alkyl$COR^9$, alkyl$SO_2NR^9_2$, alkyl$NR^9_2$, alkylaryl, alkylheteroaryl, alkyl$SR^9$, alkyl$SOR^9$, —CN, —$CO_2R^9$, trihaloalkyl, dihaloalkyl, monohaloalkyl, —$NR^{16}COR^9$, —$NR^{16}CONR^9_2$, —$NR^{16}SO_2$—$R^{13}$, —$SO_2R^9$, —$COR^9$, —$NO_2$, —$SO_2NR^9_2$, aryl, heteroaryl, —$NR^9_2$, —$SR^9$, —$SOR^9$, —C(=NOH)—$NR^{13}$,
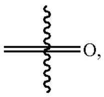
,
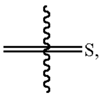
,
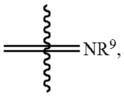
,
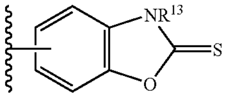
and
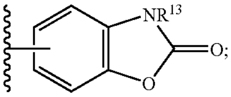
;

provided that Formula H does not include the compounds of Table A as defined above.

In another embodiment, this invention discloses a compound of Formula J

Formula J

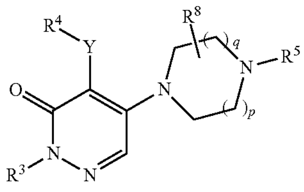

or a pharmaceutically acceptable salt, solvate, ester or prodrug thereof, wherein:

Y, $R^3$, $R^4$, $R^5$, $R^8$, $R^9$ and $R^{12}$ are as described in Formula I above, wherein
q is 1,
p is 0-1, provided that Formula J does not include the compounds of Table A as defined above.

In another embodiment, this invention discloses a compound of Formula K

Formula K

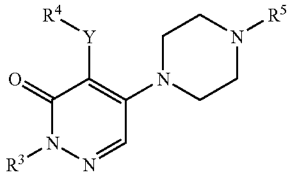

or a pharmaceutically acceptable salt, solvate, ester or prodrug thereof, wherein:

Y is —O— and $R^5$ is —$SO_2$—, and $R^4$ and the second end substituent on $R^5$ together are -alkyl-, -alkenyl-, -alkyl-NH—, or -alkenyl-NH—, forming a ring with the —O— and —$SO_2$— groups to which they are attached;

or Y is —O— and $R^5$ is —$SO_2$—, and $R^4$ and the second end substituent of $R^5$ together are an -alkyl-phenylene-alkyl-$NR^{13}$— group or a -alkyl-phenylene-alkyl- group, forming a ring with the —O— and —$SO_2$— groups to which they are attached;

or Y is —O— and $R^5$ is —$SO_2$—, and $R^4$ and the second end substituent of $R^5$ together are an -alkyl-heteroarylene-alkyl- group or an -alkyl-heteroarylene-alkyl-$NR^{13}$— group, forming a ring with the —O— and —$SO_2$— groups to which they are attached; and $R^3$, $R^7$, $R^8$ and $R^{13}$ are as described in Formula I above;

provided that Formula K does not include the compounds of Table A as defined above.

In another embodiment, this invention discloses a compound of Formula L

Formula L

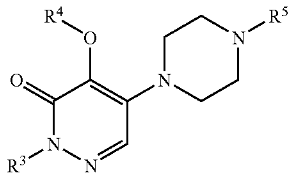

wherein $R^{13}$ is mono- or dihalo-phenyl;

$R^4$ is alkyl, haloalkyl, optionally substituted cycloalkyl, optionally substituted cycloalkylalkyl, optionally substituted benzyl, or optionally substituted benzofused cycloalkyl;

$R^5$ is —$SO_2$— wherein the second end substituent is alkyl, haloalkyl, optionally substituted arylalkyl, or optionally substituted heteroarylalkyl; or —$N(R^9)_2$, wherein one $R^9$ is H and the other is optionally substituted arylalkyl or optionally substituted heteroarylalkyl; or $R^4$ and the second end substituent on $R^5$ together are -alkenyl-;

provided that Formula L does not include the compounds of Table A as defined above.

In each of Formulas I, A, B, C, D, B, F, G, H, J, K and L, $R^3$ is preferably optionally substituted aryl, optionally substituted arylalkyl, optionally substituted heteroaryl or optionally substituted heteroaryl alkyl. $R^3$ is more preferably optionally substituted phenyl, with the preferred optional substituents being 1 or 2 halogens.

In each of Formulas I, A, B, C, D, E, F, G, H, J, K and L, when the $R^4$ group has a substituent that includes an $R^9$ group, $R^9$ is preferably H, alkyl, aryl or arylalkyl, more preferably H, alkyl, phenyl or benzyl.

In each of Formulas I, A, B, C, D, E, F, G, H, J, K and L, $R^6$ is preferably H, alkyl or optionally substituted alkyl (e.g., -alkyl-$OR^9$). When the $R^6$ group has a substituent that includes an $R^9$ group, $R^9$ is preferably H, alkyl, aryl or arylalkyl, more preferably H, alkyl, phenyl or benzyl.

In each of Formulas I, A, B, C, D, E, F, G, H and J, $R^8$ is preferably H or alkyl. When the $R^8$ group has a substituent that includes an $R^9$ group, $R^9$ is preferably H, alkyl, aryl or arylalkyl, more preferably H, alkyl, phenyl or benzyl.

Preferred compounds of Formula I include:

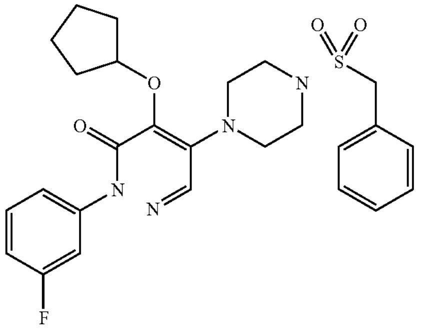

-continued

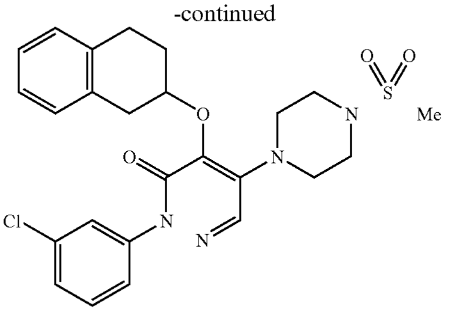

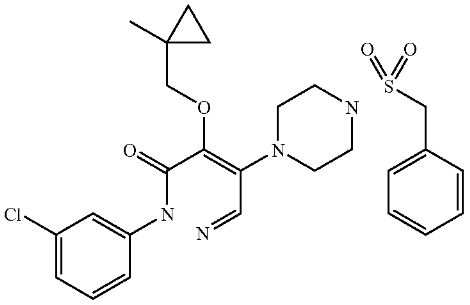

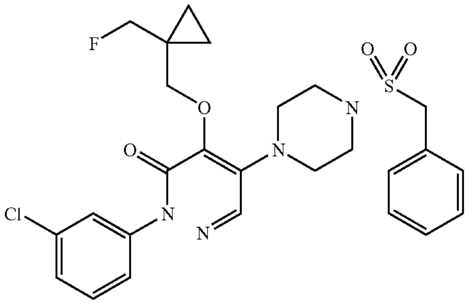

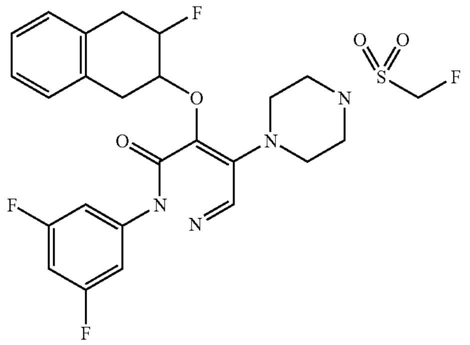

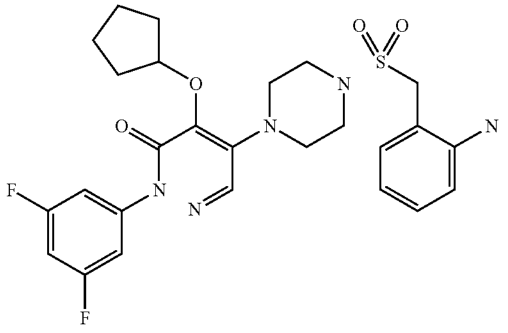

-continued
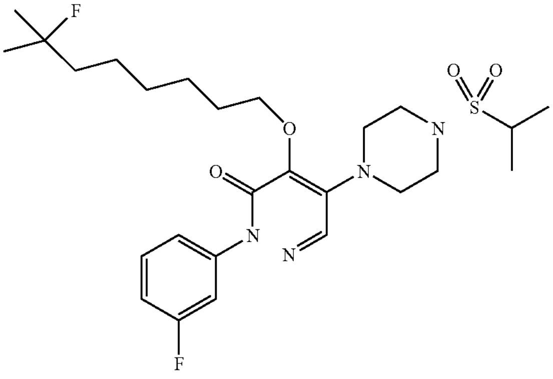
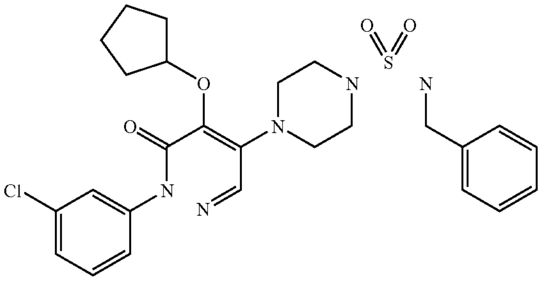
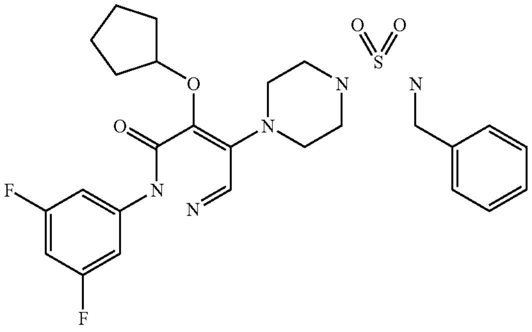
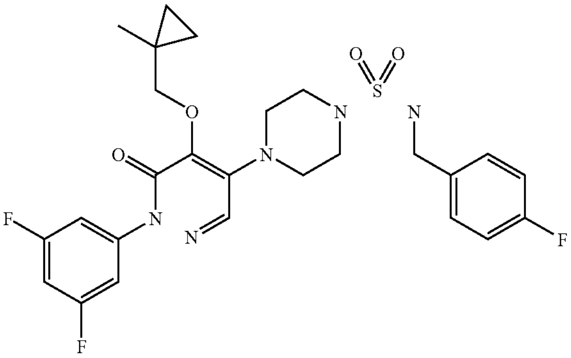
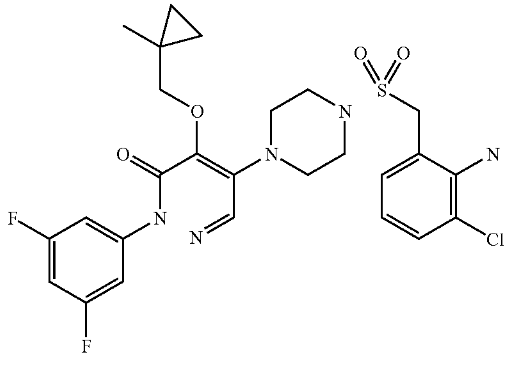
-continued
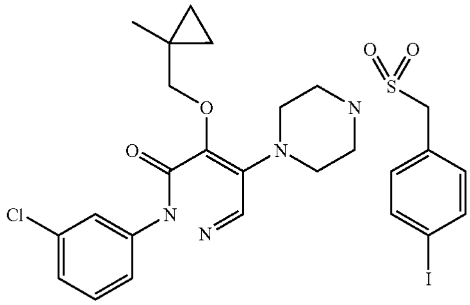
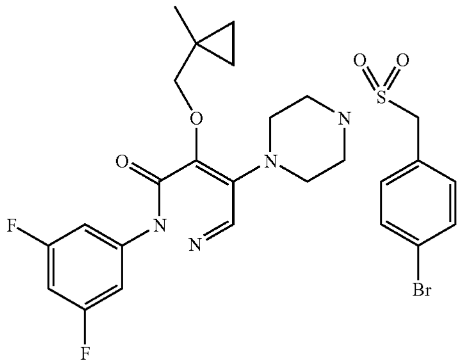
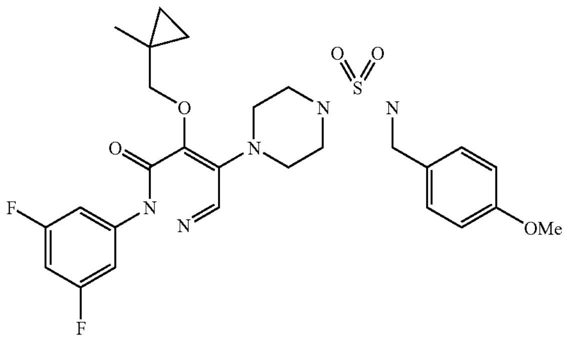
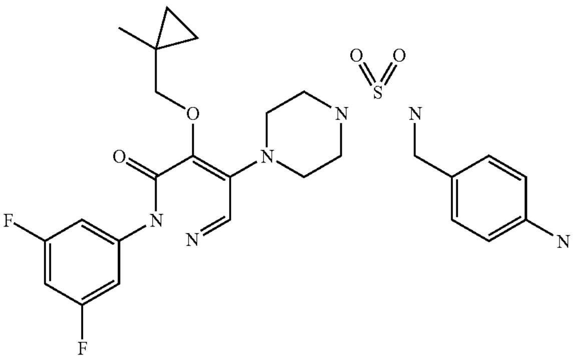
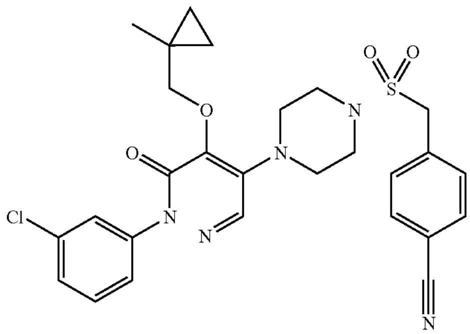

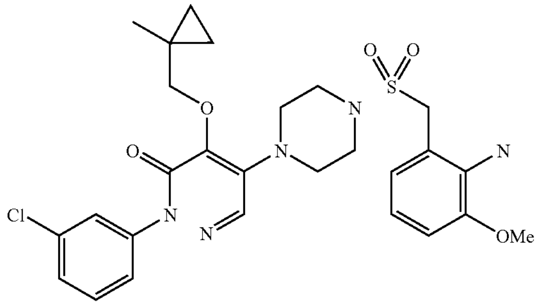
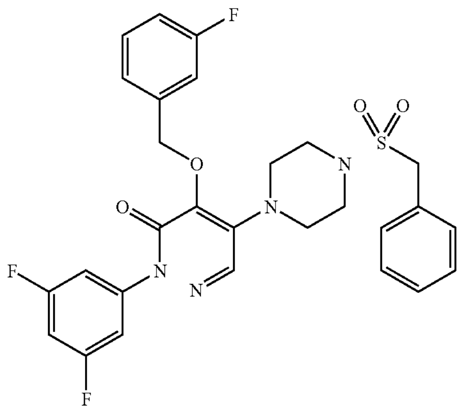
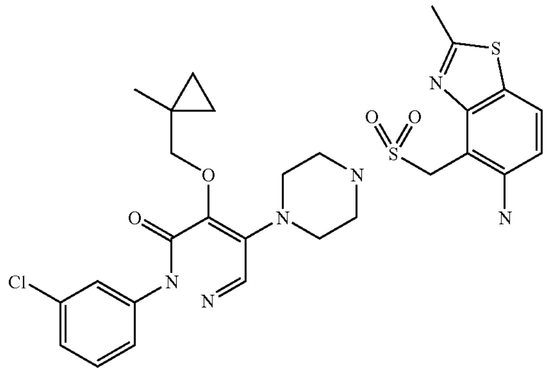
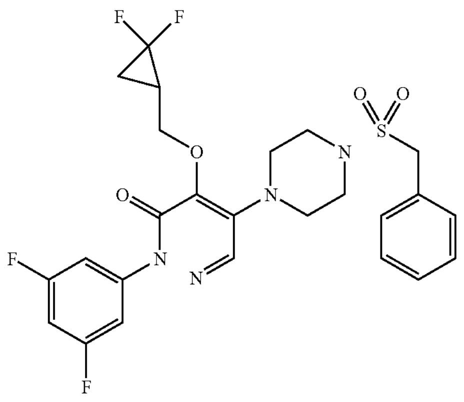
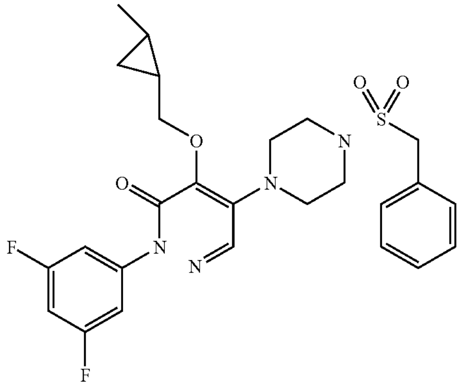
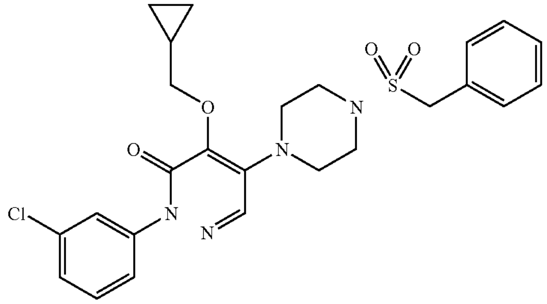
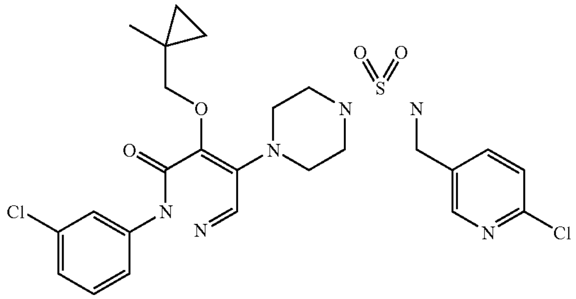
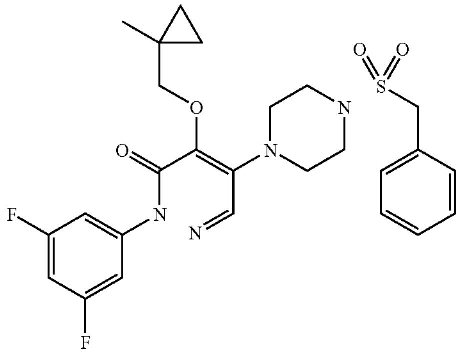
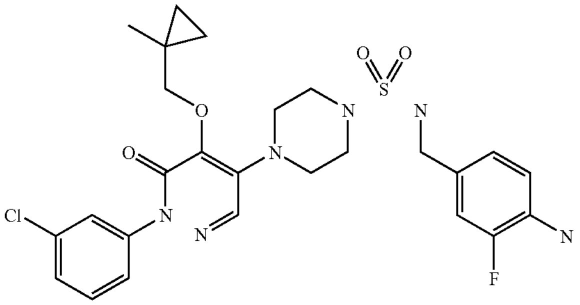

-continued
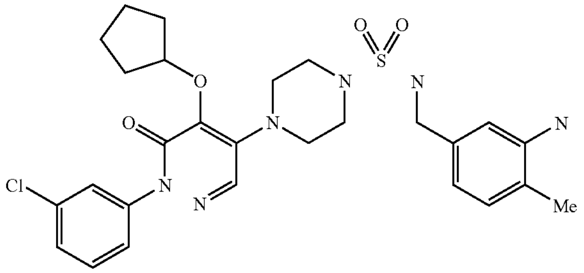
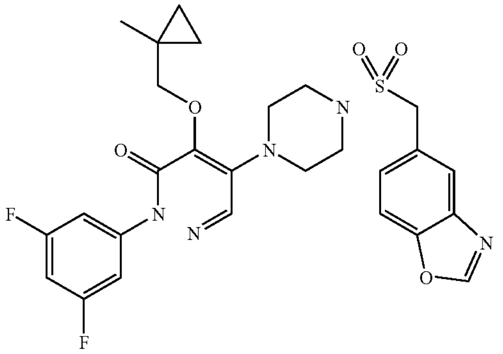
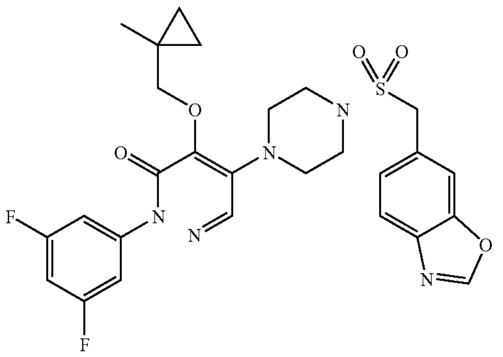
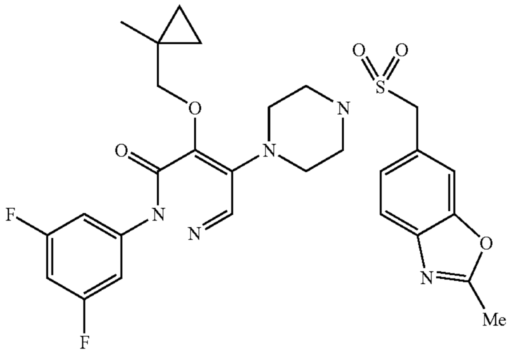
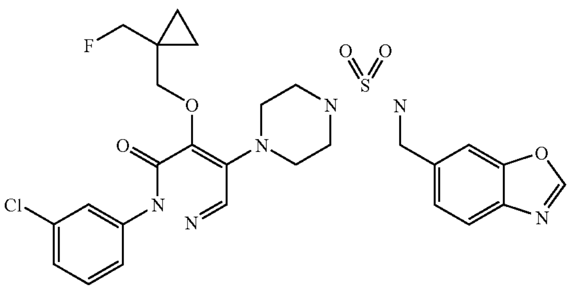
-continued
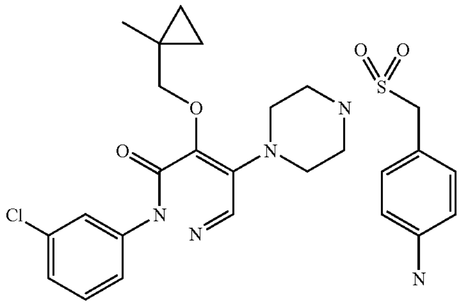
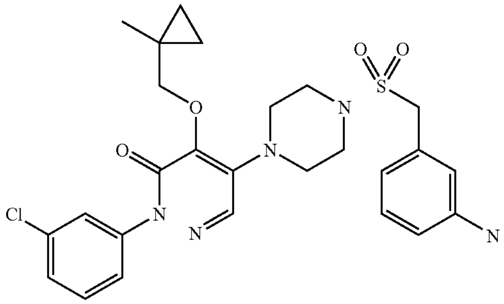
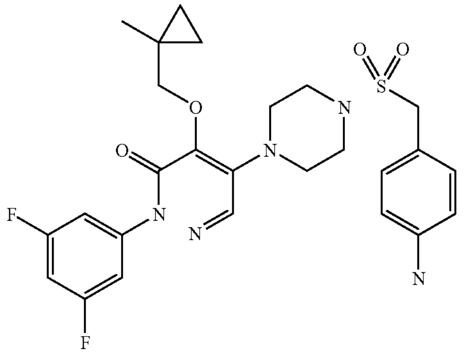
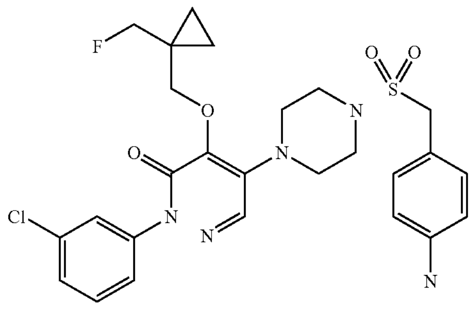
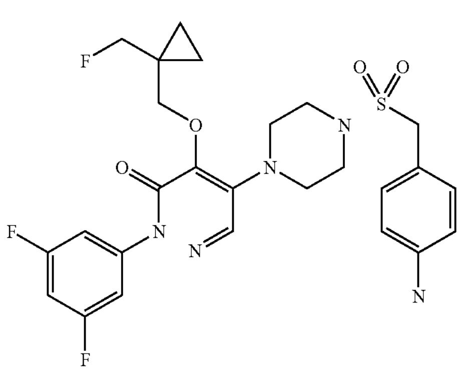

-continued
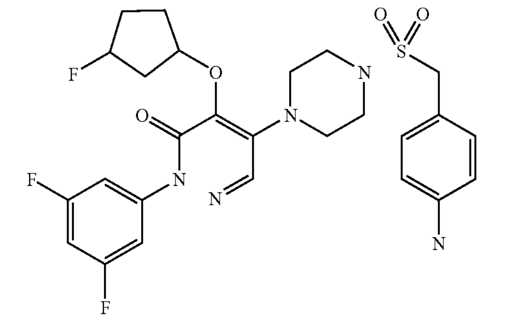
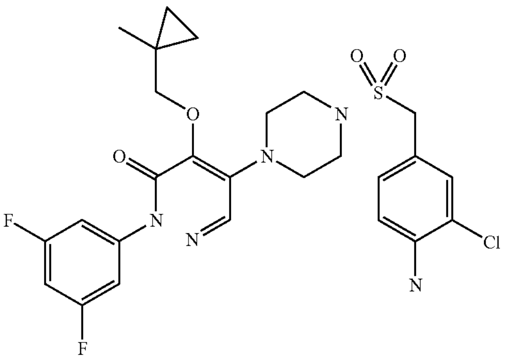
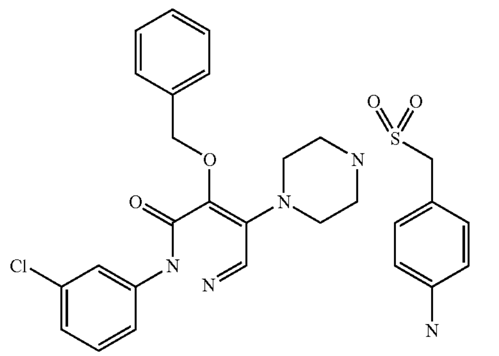
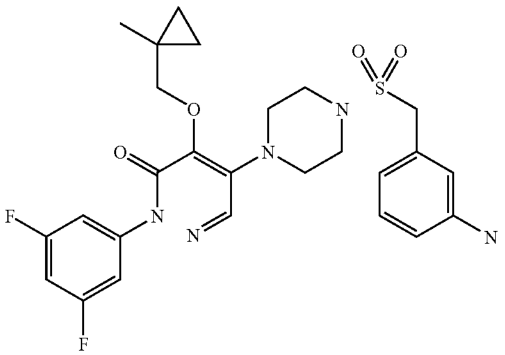
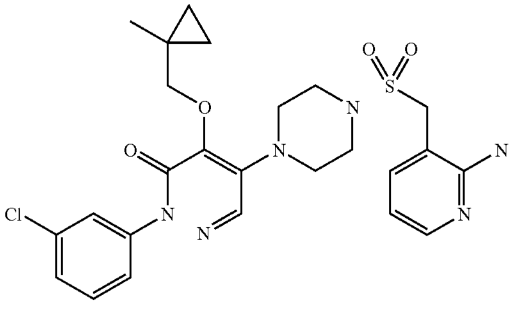
-continued
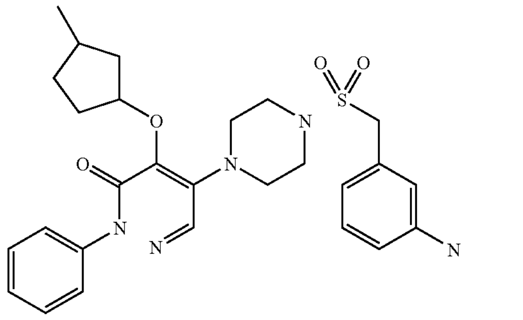
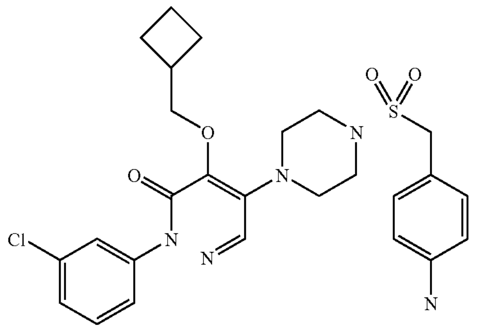
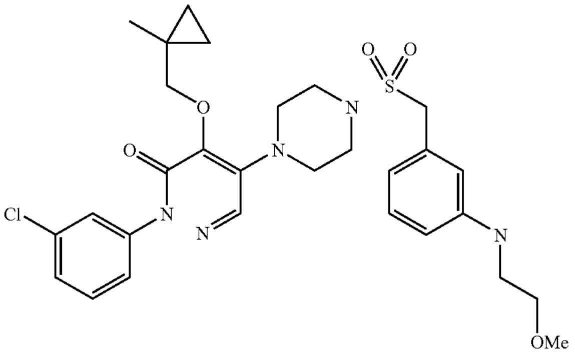
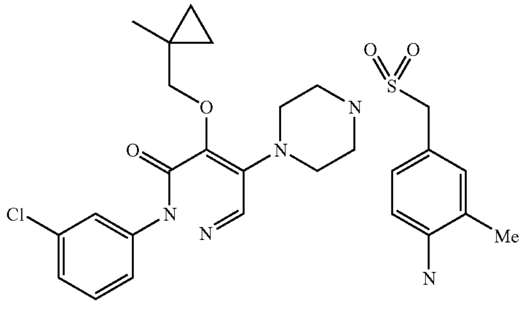
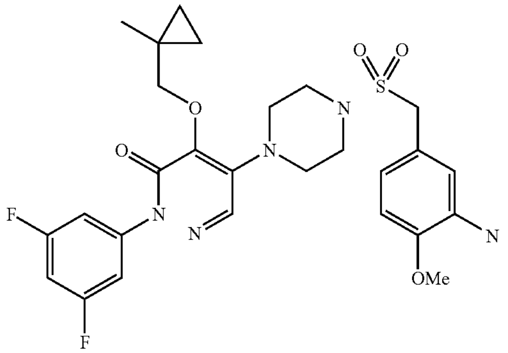

-continued
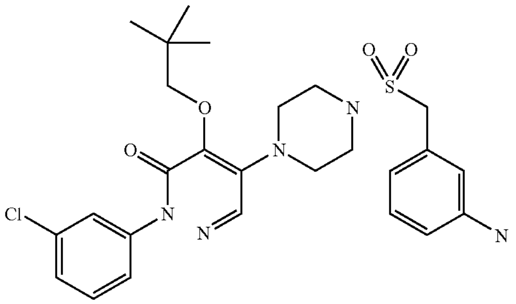
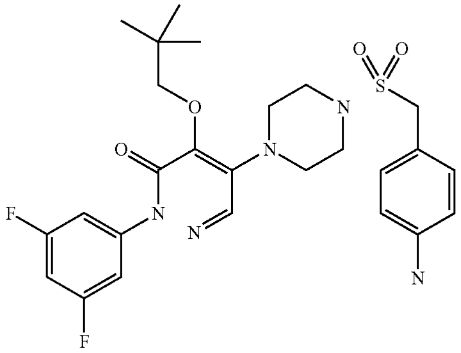
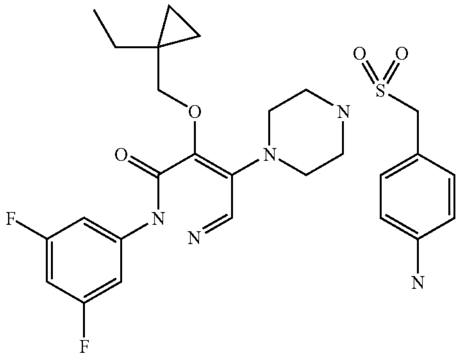
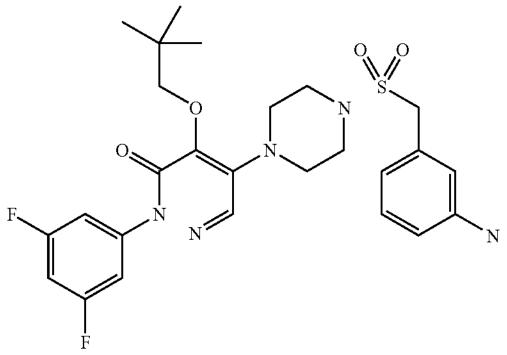
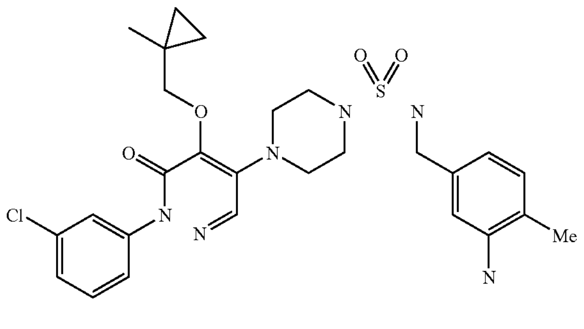
-continued
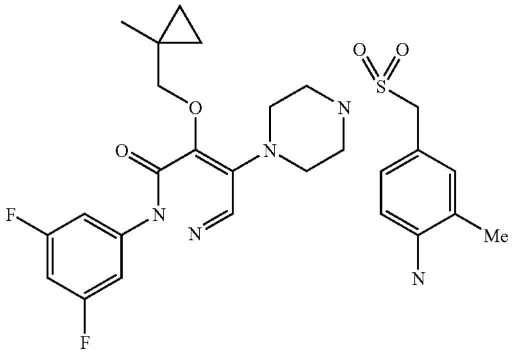
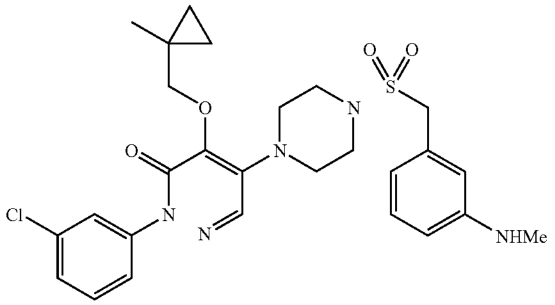
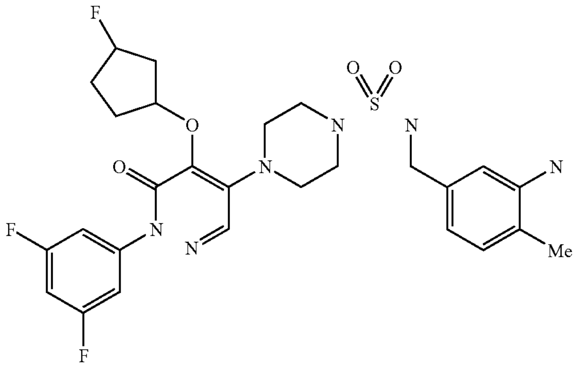
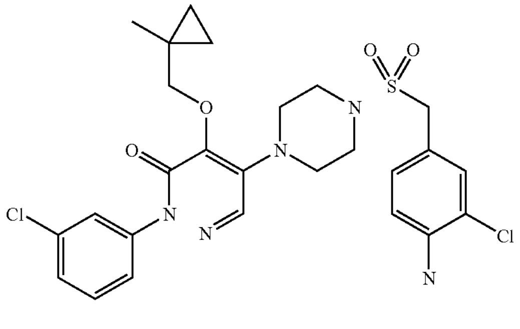
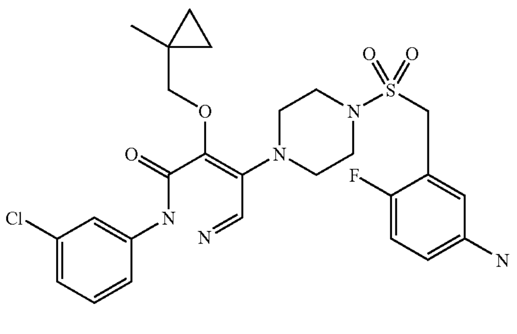

-continued
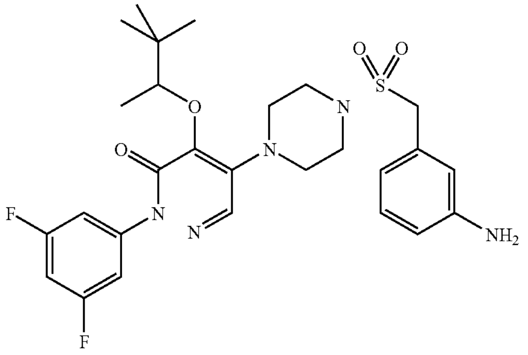
and
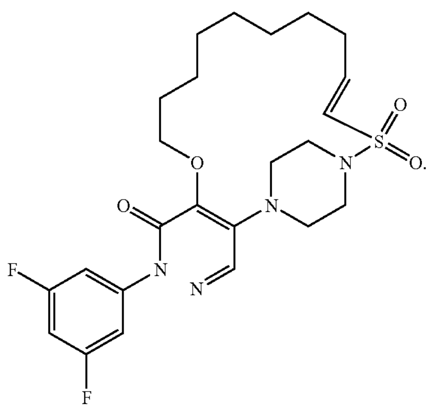
More preferred compounds of Formula I include:
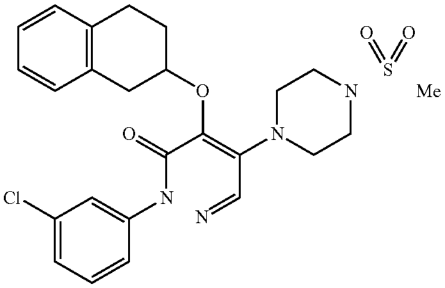
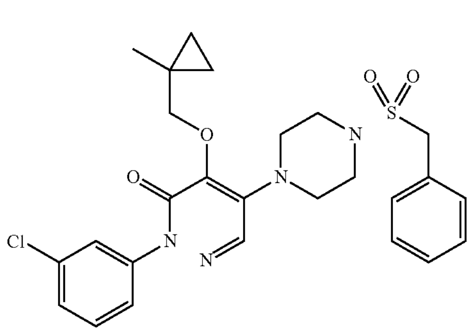
-continued
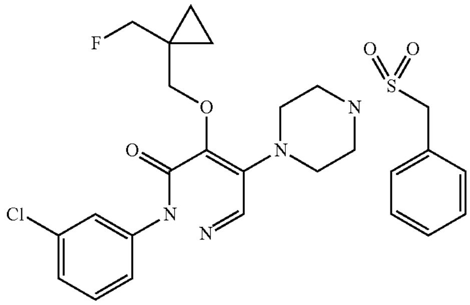
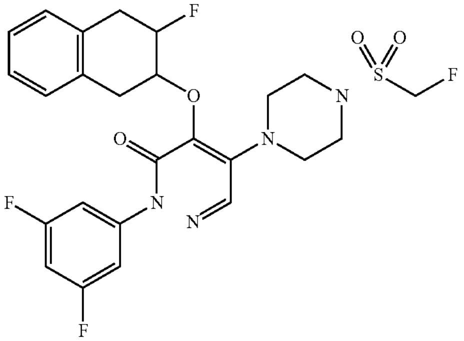
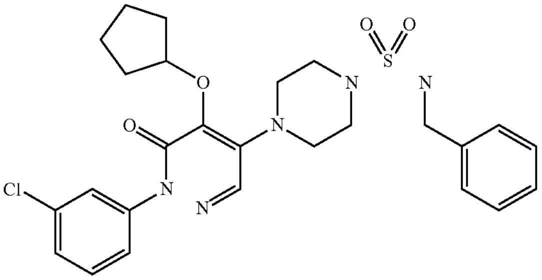
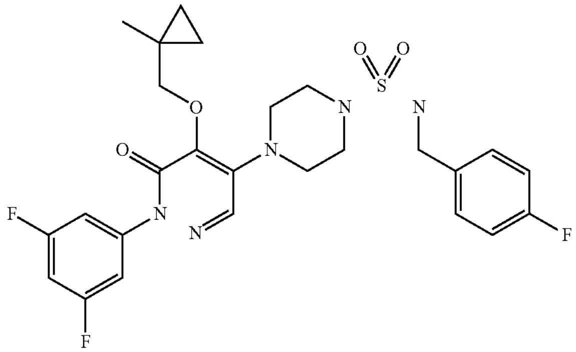
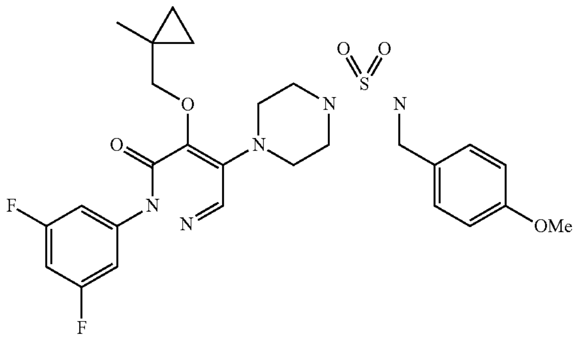

-continued
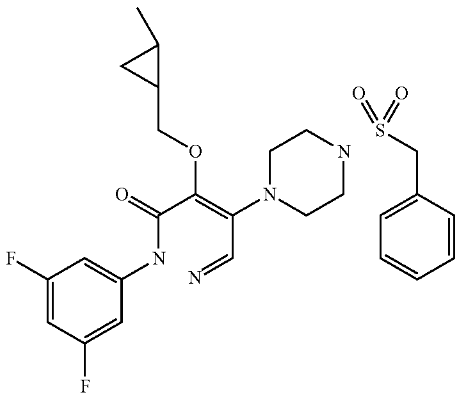
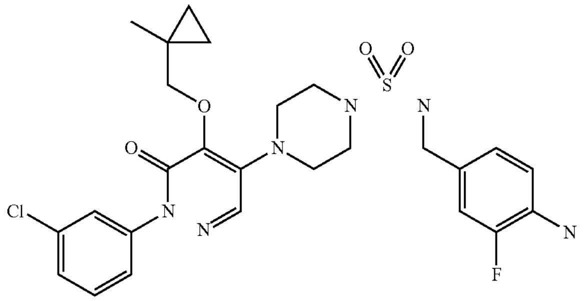
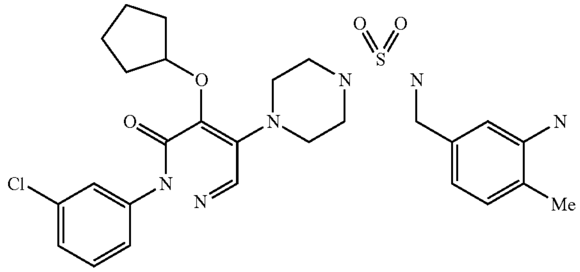
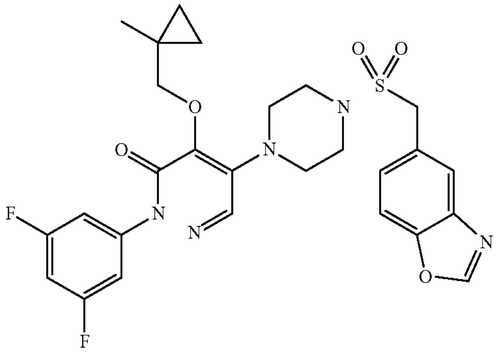
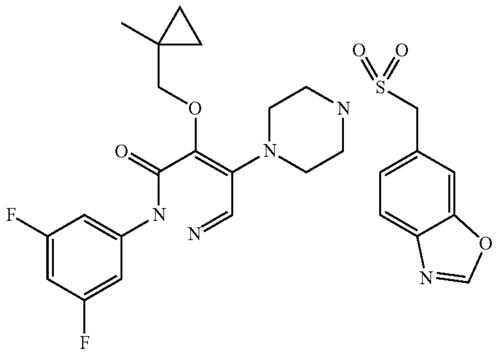
-continued
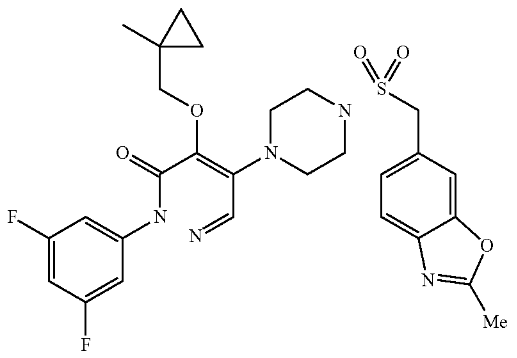
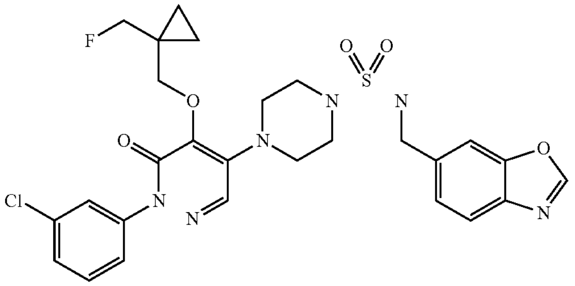
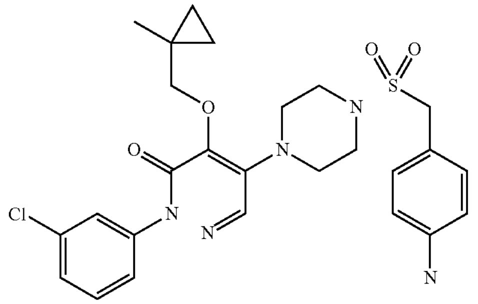
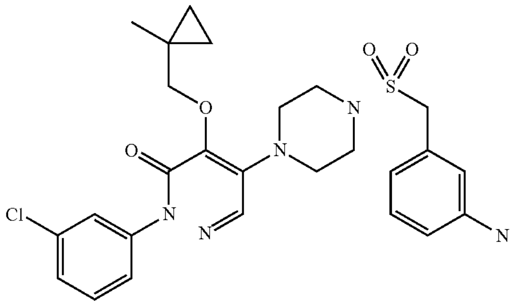
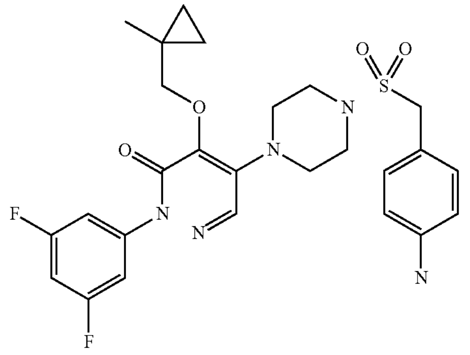

-continued
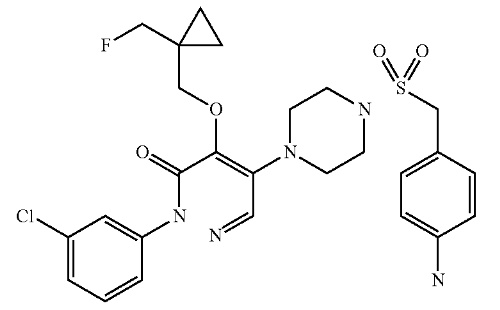
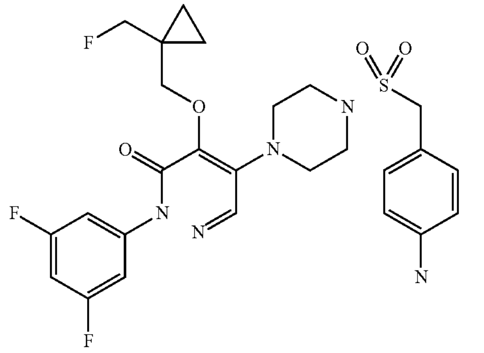
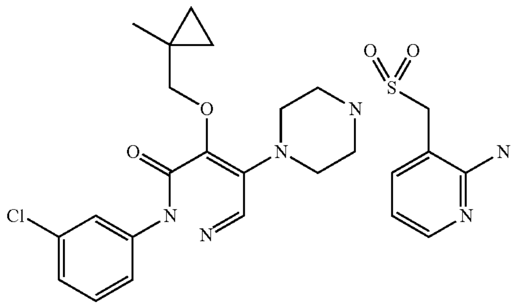
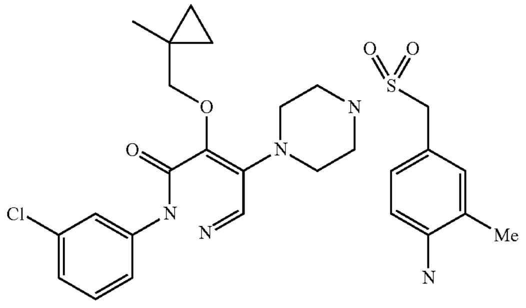
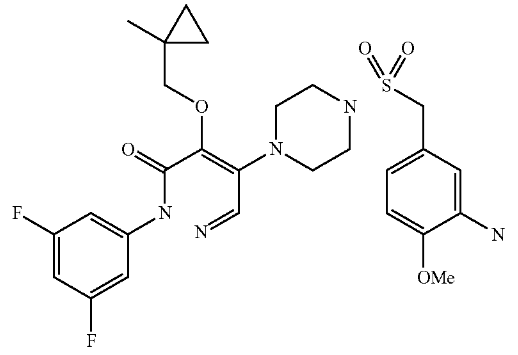
-continued
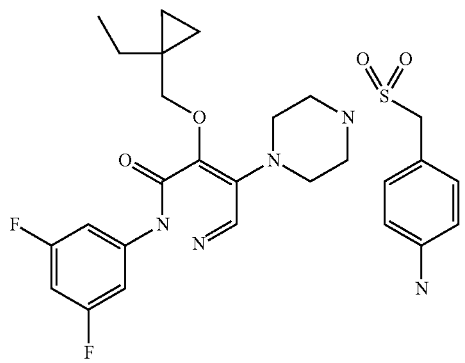
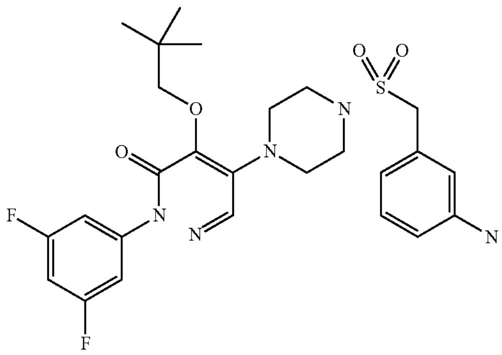
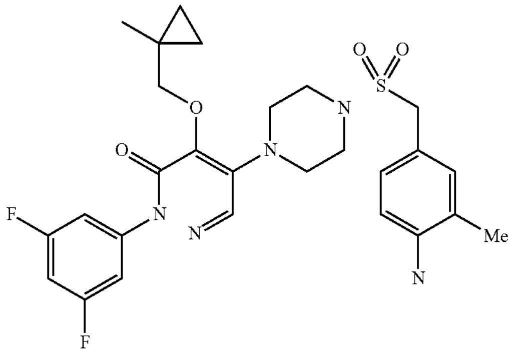
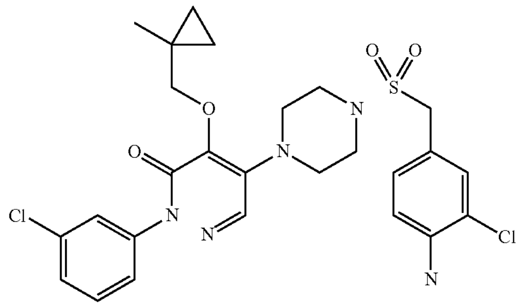
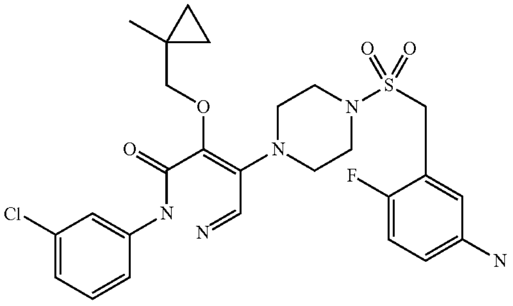
and -continued

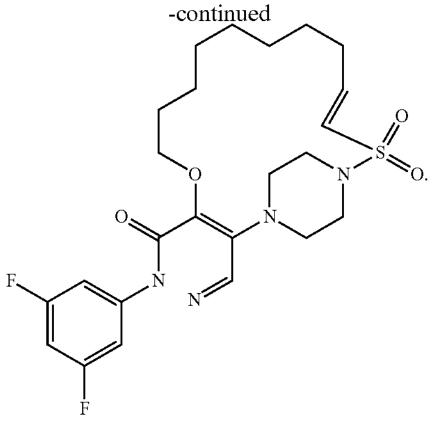

Further, the compounds of the present invention, represented by structural Formulas I, A, B, C, D, E, F, G, H, J, K and L are inhibitors of glucan synthase and therefore are useful in the treatment or prevention of fungal infections caused by pathogens such as *Candida, Cryptococcus, Pichia, Rhodotorula, Saccharomyces, Trichosporon, Absidia, Apophysomyces, Aspergillus, Bjerkandera, Blastomyces, Coccidioides, Cunninghamella, Exophiala, Fusarium, Histoplasma, Microsporum, Mucor, Paecilomyces, Penicillium, Pseudallescheria, Ramichloridium, Rhizomucor, Rhizopus, Saksenaea, Scedosporium, Sporothrix, Trichophyton, Wangiella, Alternaria, Aphanomyces, Ascophyta, Biploaris, Botrytis, Cercospora, Claviceps, Cochlhioobolus, Colletotrichum, Erysiphe, Gibberella, Glomerella, Gomyces, Guignardia, Helminthosporium, Leptosphaeria, Magnaporthe, Microdochium, Monolinia, Mycosphaerella, Nectria, Penicillium, Plasmopara, Podosphaera, Puccinia, Pyrenophora, Pyricularia, Pythium, Phytophthora, Rhizoctonia, Sclerotina, Sclerotium, Septoria, Sphaerotheca, Thielaviopsis, Tilletia, Uncinula, Urocystis, Ustilago, Venturia, Verticillium, Microsporum, Malassezia, Paracoccidioides, Trichosporon, Aureobasidium, Etserophilum*, and *Geotrichum.*

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkoxyalkoxy alkylthio, amine, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Amine" is a type of functional group that contains a nitrogen as the key atom. Structurally it resembles ammonia, wherein one or more hydrogen atoms are replaced by organic substituents such as alkyl, cycloalkyl, aryl or any of the other organic substituents defined herein. "Amino" is the amine, as defined above, as a functional group or substituent.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, primidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, carbazolyl and the like. The term "heteroaryl" also refers to partially saturated heteroaryl moieties such as, for example, tetrahydroisoquinolyl, tetrahydroquinolyl and the like.

"Aralkyl" or "arylalkyl" an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. Arylalkenyl an aryl-alkenyl group in which the aryl and alkenyl are as previously described. The bond to the parent moiety is through the alkyl or alkenyl respectively.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like, "Cycloalkylalkenyl" means a cycloalkyl moiety as defined above linked via an alkenyl moiety (defined above) to a parent core.

"Cycloalkenyl" or "cyclenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" or "cyclenylalkyl" means a cycloalkenyl or cyclenyl moiety as defined above linked via an alkyl moiety (defined above) to a parent core. Non-limiting examples of suitable cycloalkenylalkyls include cyclopentenylmethyl, cyclohexenylmethyl and the like.

"Cycloalkenylalkenyl" or "cyclenylalkenyl" means a cycloalkenyl or cyclenyl moiety as defined above linked via an alkenyl moiety (defined above) to a parent core.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heterorylalkynyl, alkylheteroaryl, hydroxy, hydroxyalkyl, alkoxy, trihaloalkoxy, aryloxy, aralkoxy, alkoxyalkoxy, acyl, aroyl, halo, monohaloalkyl, dihaloalkyl, trihaloalkyl, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, $-C(=N-CN)-NH_2$, $-C(=NH)-NH_2$, $-C(=NH)-NH(alkyl)$, $-NY_1Y_2$, $-alkyl-NY_1Y_2$, $-C(O)NY_1Y_2$ and $-SO_2NY_1Y_2$, wherein $Y_1$ and $Y_2$ can be the same or different and are independently selected from the group consisting of hydrogen, alkyl aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, $-C(CH_3)_2-$ and the like which form moieties such as, for example:

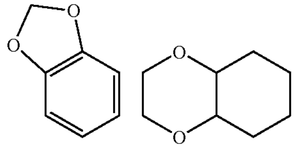

and

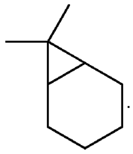

.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heteroalkyl" is a saturated or unsaturated chain containing carbon and at least one heteroatom, wherein one or more of the chain atoms is an element other than carbon, for example nitrogen, oxygen or sulfur, alone or in combination, wherein no two heteroatoms are adjacent. Heteroalkyl chains contain from 2 to 15 member atoms (carbon and heteroatoms) in the chain, preferably 2 to 10, more preferably 2 to 5. For example, alkoxy (i.e., —O-alkyl or —O-heteroalkyl) radicals are included in heteroalkyl. Heteroalkyl chains may be straight or branched. Preferred branched heteroalkyl have one or two branches, preferably one branch. Preferred heteroalkyl are saturated. Unsaturated heteroalkyl have one or more carbon-carbon double bonds and/or one or more carbon-carbon triple bonds. Preferred unsaturated heteroalkyls have one or two double bonds or one triple bond, more preferably one double bond. Heteroalkyl chains may be unsubstituted or substituted with from 1 to 4 substituents. Preferred substituted heteroalkyl are mono-, di-, or tri-substituted. Heteroalkyl may be substituted with lower alkyl, haloalkyl, halo, hydroxy, aryloxy, heteroaryloxy, acyloxy, carboxy, monocyclic aryl, heteroaryl, cycloalkyl, heterocyclyl, spirocycle, amine, acylamino, amido, keto, thioketo, cyano, or any combination thereof.

"Heterocyclyl" or "Heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean heterocyclyl ring wherein a single moiety (e.g., carbonyl) simultaneously replaces two available hydrogens on the same carbon atom on a ring system. Example of such moiety is pyrrolidone:

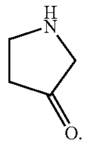

"Heterocyclylalkyl" or "Heterocycloalkylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclylalkenyl" or "Heterocycloalkylalkenyl" means a heterocyclyl moiety as defined above linked via an alkenyl moiety (defined above) to a parent core.

"Heterocyclenyl" or "Heterocycloalkenyl" means a non-aromatic monocyclic or multicyclic ring system comprising about 3 to about 15 ring atoms, preferably about 5 to about 14 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 13 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is a defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a heterocyclenyl ring wherein a single moiety (e.g., carbonyl) simultaneously replaces two available hydrogens on the same carbon atom on a ring system. Example of such moiety is pyrrolidinone:

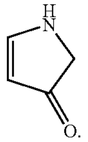

"Heterocyclenylalkyl" means a heterocyclenyl moiety as defined above linked via an alkyl moiety (defined above) to a parent core.

"Heterocyclenylalkenyl" means a heterocyclenyl moiety as defined above linked via an alkenyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

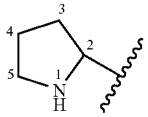

there is no —OH attached directly to carbons marked 2 and 5.

It should also be noted that tautomeric forms such as, for example, the moieties:

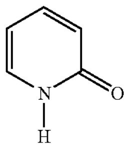
and
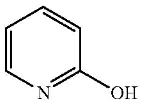

are considered equivalent in certain embodiments of this invention.

"Heterocyclenylalkenyl" means a heterocyclenyl moiety as defined above linked via an alkenyl moiety (defined above) to a parent core.

"Heteroalkyl" is a saturated or unsaturated chain containing carbon and at least one heteroatom, wherein no two heteroatoms are adjacent. Heteroalkyl chains contain from 2 to 15 member atoms (carbon and heteroatoms) in the chain, preferably 2 to 10, more preferably 2 to 5. For example, alkoxy (i.e., —O-alkyl or —O-heteroalkyl) radicals are included in heteroalkyl. Heteroalkyl chains may be straight or branched. Preferred branched heteroalkyl have one or two branches, preferably one branch. Preferred heteroalkyl are saturated. Unsaturated heteroalkyl have one or more carbon-carbon double bonds and/or one or more carbon-carbon triple bonds. Preferred unsaturated heteroalkyls have one or two double bonds or one triple bond, more preferably one double bond. Heteroalkyl chains may be unsubstituted or substituted with from 1 to 4 substituents. Preferred substituted heteroalkyl are mono-, di-, or tri-substituted. Heteroalkyl may be substituted with lower alkyl, haloalkyl, halo, hydroxy, aryloxy, heteroaryloxy, acyloxy, carboxy, monocyclic aryl, heteroaryl, cycloalkyl, heterocycloalkyl, spirocycle, amine, acylamine, amido, keto, thioketo, cyano, or any combination thereof.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Spiro ring systems" have two or more rings linked by one common atom. Preferred spiro ring systems include spiroheteroaryl, spiroheterocyclenyl, spiroheterocyclyl, spirocycloalkyl, spirocyclenyl, and spiroaryl. Non-limiting examples of suitable spiro ring systems include

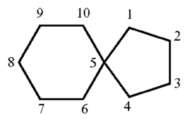

spiro[4.5]decane,

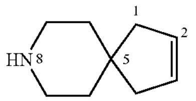

8-azaspiro[4.5]dec-2-ene, and

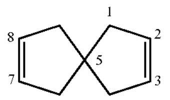

spiro[4.4]nona-2,7-diene.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen. An alkoxy linked directly to another alkoxy is an "alkoxyalkoxy".

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" or "thioalkoxy" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aralkyl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Arylsulfonyl" means an aryl-$S(O_2)$— group. The bond to the parent moiety is through the sulfonyl.

The terms "arylene" and heteroarylene" mean divalent aryl and heteroaryl groups, e.g.,

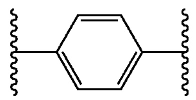 or 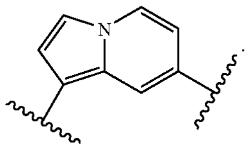.

"Benzofused-cycloalkyl" and benzofused-heterocycloalkyl" mean that a benzene ring is fused to two adjacent carbon atoms of a cycloalkyl or heterocycloalkyl ring. The group is joined to the rest of the molecule through a carbon atom in the cycloalkyl or heterocycloalkyl ring. Both the aromatic and saturated ring moieties are optionally substituted by suitable ring system substituents as defined above. Examples of benzofused-cycloalkyl and benzofused-heterocycloalkyl groups are

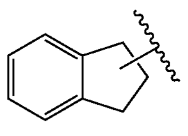 and 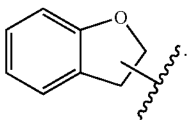.

In the terms above "oxyl" means the same as "oxy", i.e., alkoxyl and alkoxy both refer to an alkyl-O— group.

In the terms above, where a nitrogen atom appears in a chain of atoms and a substituent on the third bond to the nitrogen is not identified, the third bond is understood to be hydrogen, e.g., -alkyl-N-alkyl- is -alkyl-NH-alkyl.

In the terms above, when two $R^9$ groups on a N form a ring, non-limiting examples of such rings are

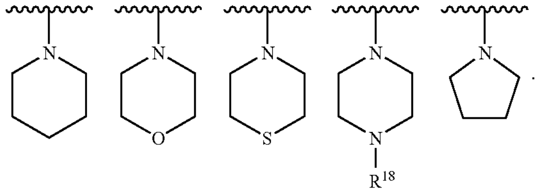

In the terms above, when an nitrogen-containing radical is written as, for example, —$CONR^9R^{16}$, the two "R" groups are each attached to the nitrogen, i.e.,

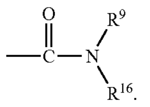

In the definitions above, notably in the "R" groups, where no hyphen is present to indicate the point of attachment and the term is not otherwise defined, the radical is attached to the rest of the molecule through the group on the right side of the term, e.g., "alkylalkenyl" is "alkylalkenyl-".

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups radicals or moieties.

The terms "one or more" and "at least one", when referring to the number of substituents on a group (e.g., alkyl, aryl or heteroaryl) means 1 to 6 substituents, preferably 1 to 3 substituents, unless otherwise specified.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formulas I, A, B, C, D, E, F, G, H, J, K and L, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formulas I, A, B, C, D, E, F, G, H, J, K and L or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula I, Formula A, Formula B, Formula C, Formula D, Formula E, Formula F, Formula G, Formula H, Formula J, Formula K or Formula L or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 11 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminemethyl having from 3 to 9 carbon atoms, 1-(N-(alkoxycarbonyl)amine)ethyl having from 4 to 10 carbon atoms, 3-phthalidyl, 4-crotonolactonyl, gamma-butyrolacton-4-yl, di-N,N—$(C_1-C_2)$alkylamine$(C_2-C_3)$alkyl (such as β-dimethylamineethyl), carbamoyl-$(C_1-C_2)$alkyl, N,N-di$(C_1-C_2)$alkylcarbamoyl-(C1-C2)alkyl and piperidino-, pyrrolidino- or morpholino$(C_2-C_3)$alkyl, and the like.

Similarly, if a compound of Formula I, Formula A, Formula B, Formula C, Formula D, Formula E, Formula F, Formula G, Formula H, Formula J, Formula K or Formula L contains an alcohol functional group, a prodrug can be formed by the replacement of the hydrogen atom of the alcohol group with a group such as, for example, $(C_1-C_6)$alkanoyloxymethyl, 1-($(C_1-C_6)$alkanoyloxy)ethyl, 1-methyl-1-($(C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring, L-amino acids, $P(O)(OH)_2$, —$P(O)(O(C_1-C_6)$alkyl) or glycosyl (the radical resulting from the removal of a hydroxyl group of the hemiacetal form of a carbohydrate) and the like.

If a compound of Formula I, Formula A, Formula B, Formula C, Formula D, Formula E, Formula F, Formula G, Formula U, Formula J, Formula K or Formula L incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$) alkyl, ($C_3$-$C_7$)cycloalkyl, benzyl, or R-carbonyl is a natural α-aminoacyl or natural α-aminoacyl, —C(OH)C(O)O$Y^1$ wherein $Y^1$ is H, ($C_1$-$C_6$)alkyl or benzyl, —C(O$Y^2$)$Y^3$ wherein $Y^2$ is ($C_1$-$C_4$)alkyl and $Y^3$ is ($C_1$-$C_6$)alkyl, carboxy ($C_1$-$C_6$)alkyl, amino($C_1$-$C_4$)alkyl or mono-N— or di-N,N—($C_1$-$C_6$)alkylaminoalkyl, —C($Y^4$)$Y^5$ wherein $Y^4$ is H or methyl and $Y^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for Example, M. Caira et al, *J. Pharmaceutical Sci.* 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm SciTech.,* 5(1), article 12 (2004); and A. L. Bingham et al, *Chem. Commun.,* 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formulas I, A, B, C, D, E, F, G, H, J, K and L can form salts which are also within the scope of this invention. Reference to a compound of Formulas I, A, B, C, D, E, F, G, H, J, K and L herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formulas I, A, B, C, D, E, F, G, H, J, K and L contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formulas I, A, B, C, D, F, F, G, H, J, K and L may be formed, for example, by reacting a compound of Formulas I, A, B, C, D, E, F, G, H, J, K and L with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 1-19; P. Gould, *International of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formulas I, A, B, C, D, E, F, G, H, J, K and L, and salts, solvates, esters and prodrugs thereof, may exist in their tautomeric form (for example, as an amide or imino ether). All such tautomeric forms are contemplated herein as part of the present invention.

The compounds of Formulas I, A, B, C, D, E, F, G, H, J, K and L may contain asymmetric or chiral centers, and, therefore, exist in different stereoisomeric forms. It is intended that all stereoisomeric forms of the compounds of Formulas I, A, B, C, D, F, F, G, H, X, K and L as well as mixtures thereof including racemic mixtures, form part of the present invention. In addition, the present invention embraces all geometric and positional isomers. For example, if a compound of Formulas I, A, B, C, D, F, F, G, H, J, K and L incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g., hydrolyzing) the individual diastereomers to the corresponding pure enantiomers. Also, some of the compounds of Formulas I, A, B, C, D, E, F, G, H, J, K and L may be atropisomers (e.g., substituted biaryls) and are considered as part of this invention. Enantiomers can also be separated by use of chiral HPLC column.

It is also possible that the compounds of Formulas I, A, B, C, D, E, F, G, H, J, K and L may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formulas I, A, B, C, D, F, F, G, H, J, K and L incorporates a double bond or a fused ring, both the cis- and trans-forms, as well as mixtures, are embraced within the scope of the invention. Also, for example all keto-enol and imine-enamine form-s of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formulas I, A, B, C, D, F, F, G, H, J, K and L (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labelled compounds of Formulas I, A, B, C, D, E, F, G, H, J, K and L can generally be prepared by following procedures Analogous to those disclosed in the Schemes and/or in the Examples hereinbelow, by substituting an appropriate isotopically labelled reagent for a non-isotopically labelled reagent.

Polymorphic forms of the compounds of Formulas I, A, B, C, D, E, F, G, H, J, K and L and of the salts, solvates, esters and prodrugs of the compounds of Formulas I, A, B, C, D, F, F, G, H, J, K and L are intended to be included in the present invention.

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gels—refer to the active ingredients dispersed or solubilized in a hydrophillic semi-solid matrix.

Powders for constitution refer to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binders—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d,l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

The compounds listed above are inhibitors of glucan synthase and therefore are useful in the treatment or prevention of fungal infections caused by pathogens such as *Absidia corymbifera; Absidia* spp; *Acrenionium* spp; *Ajellomyces capsulatus; Ajellomyces dermatitidis; Alternaria* spp; *Aphanoascus fulvescens; Apophysomyces* spp; *Arthroderma benhamiae; Arthroderma fulvum; Arthroderma gypseum; Arthroderma incurvatum; Arthroderma otae; Arthroderma vanbreuseghemii; Aspergillus flavus; Aspergillus fumigatus; Aspergillus glaucus; Aspergillus nidulans; Aspergillus niger; Aspergillus oryzae; Aspergillus* spp; *Aspergillus sydowi; Aspergillus terreus; Aspergillus ustus; Aspergillus versicolor; Aureobasidium pullulans; Basidiomycetes; Beauveria* spp; *Bipolaris hawaiiensis; Bipolaris spicifera; Bipolaris* spp; *Bjerkandera adusta; Blastomyces dermatitidis; Blastoschizomyces capitals; Candida albicans; Candida beigelii, Candida colluculosa; Candida dubliniensis; Candida dubliniensis; Candida famata; Candida glabrata; Candida guilliermondii; Candida haemulonii; Candida holmii; Candida inconspicua; Candida intermedia; Candida keyfyr; Candida krusei; Candida lambica; Candida lipolytica; Candida lusitaniae; Candida maris; Candida melibiosica; Candida norvegensis; Candida parapsilosis; Candida pelliculosa; Candida pseudotropicalis; Candida pulcherrima; Candida rugosa; Candida sake; Candida sphaerica; Candida* spp; *Candida stellatoidea; Candida tropicalis; Candida viswanathii; Candida zeylanoides; Chrysosporium* spp; *Cladophialophora bantiana; Cladophialophora carrionii; Cladosporium* spp; *Coccidioides immitis; Cokeromyces recurvatus; Coprinus* spp; *Cryptococcus albidus; Cryptococcus gattii; Cryptococcus laurentii; Cryptococcus neoformans; Cunninghamella bertholletiae; Cunninghamella* spp; *Curvularia lunata; Curvularia* spp; *Dekkera bruxellensis; Epidermopkyton floccosum; Exophiala dermatitidis; Exophiala jeanselmei; Exophiala moniliae; Exserohilum rostratum; Filobasidiella neoformans; Fonsecaea pedrosoi; Fusarium dimerum; Fusarium moniliforme; Fusarium oxysporum; Fusarium proliferatum; Fusarium solani; Fusarium* spp; *Geotrichum canedidum; Geotrichum* spp; *Histoplasma capsulatum; Hortaea werneckii; Issatschenkia orientalis; Kluveromyces lactis; Kluyveromyces marxianus; Madurella grisae; Malassezia furfur; Malassezia globosa; Malassezia obtusa; Malassezia pachydermatis; Malassezia restricta; Malassezia slooffiae; Malassezia sympodialis; Metarrhizium anisopliae; Microsporum audouinii; Microsporum canis; Microsporum fulvum; Microsporum gypseum; Microsporum persicolor; Mucor circinelloides; Mucor hiemalis; Mucor racemosus; Mucor rouxii; Mucor* spp; *Nattrassia mangiferae; Nectria haematococca; Onychocola canadensis; Paecilomyces lilacinus; Paecilomyces* spp; *Paecilomyces variotii; Paracoccidioides brasiliensis; Penicillium marneffei; Penicillium* spp; *Phialophora* spp; *Phialophora verrucosa; Phoma* spp; *Pichia anomala; Pichia etchellsii; Pichia guilliermondii; Pichia ohmeri; Pithomyces* spp; *Pneumocystis carinii; Pseudallescheria boydii; Ramichloridium obovoideum; Rhizomucor miehei; Rhizomucor pusillus; Rhizomucor* spp; *Rhizopus arrhizus; Rhizopus microsporus; Rhizopus oryzae, Rhizopus schipperae; Rhizopus spp; Rhodotorula mucilaginosa; Rhodotorula rubra; Rhodotorula* spp; *Saccharomyces cerevisiae; Saccharomyces* spp; *Sagrahamala* spp; *Saksenaea vasiformis; Scedosporium apiospermum; Scedosporim prolificans; Schizophyllum commune; Schizosaccharomyces pombe; Scopulariopsis brevicaulis; Scytalidium dimidiatum Ulocladium* spp; *Sporobolomyces* spp; *Sporothrix schenckii; Trichoderma* spp; *Trichophyton krajdenii; Trichophyton mentagrophytes; Trichophyton raubitschekii; Trichophyton rubrum; Trichophyton soudanense; Trichophyton* spp; *Trichophyton terrestre; Trichophyton tonsurans; Trichophyton verrucosum; Trichophyton violaceum; Trichosporon asahii; Trichosporon beigelii; Trichosporon capitatum; Trichosporon cutaneum; Trichosporon inkin; Trichosporon mucoides; Trichosporon* spp; *Tritirachium* spp; *Wangiella dermatitidis* and *Yarrowia lipolytica*

For pharmaceutical use, treatment of yeasts (e.g., *Candida, Cryprococcus, Pichia, Rhodotorula, Saccharomyces*, and *Trichosporon*) or moulds (e.g., *Absidia, Alternaria, Apophysomyces, Aspergillus, Bjerkandera, Blastomyces, Coccidioides, Cunninghamella, Exophiala, Fusarium, Histoplasma, Microsporum, Mucor, Paecilomyces, Penicillium, Pseudallescheria, Ramichloridium, Rhizomucor, Rhizopus, Saksenaea, Scedosporium, Sporothrix, Trichophyton* and *Wangiella*) are preferred.

As used herein, the terms "treat" or "treating" mean eliminating the fungal infection, reducing the fungal burden, or stopping the progression of fungal growth.

The terms "prevent" or "preventing", as used herein, mean administering at least one compound listed above before exposure to a potential fungal pathogen. For example at least one compound listed above can be administered to an animal before organ transplant surgery, a procedure known to frequently result in fungal infections, or an animal known to be susceptible to fungal infections can be treated in advance of likely exposure. In the case of fungal plant pathogens, at least one compound listed above can be applied to a plant regularly throughout the growing season, before a potential pathogen can cause any harm to the plant.

When used to treat plant pathogens, at least one compound listed above can be applied to the leaves and stems of the plant using a method well known in the art, for example as a topical spray (e.g., an aqueous solution) or powder, or as a solution or powder added to the soil to allow systemic absorption. Topical application to plants is preferred. Similarly, when applied to the surfaces of inanimate objects to reduce or eliminate fungal growth, at least one compound listed above can be applied as a solution, a spray or a powder.

As indicated above, it is contemplated that more than one compound as listed above can be administered to treat fungal infections. When used herein, the terms "at least one" or "one or more" preferably mean one to three compounds, but more preferably one compound listed above is administered. When administered in combination with another antifungal agent, preferably one compound listed above and one other antifungal agent are administered.

Other antifungal agents for use in combination are: for example azoles (e.g. fluconazole, miconazole, itraconazole, voriconazole, posaconazole), echinocandins (e.g. caspofungin, micafungin, anidulafungin), polyenes (e.g. amphotericin B, including liposomal formulations of amphotericin B, and nystatin), allylamines (e.g. terbinafine), thiocarbamates (e.g. tolnaftate), nikkomycins, pradimicins, 5-fluorocytosines, oxaboroles, ciclopiroxolamine, griseofulvin and morpholines (e.g., fenpropimorph).

As used herein, "animal" means a mammalian or non-mammalian (e.g., birds, fish, crustaceans, reptiles) species, preferably a mammal and more preferably a human. As used herein, "patient" refers to an animal, more preferably a human.

As well known in the art, a bond drawn from a particular atom wherein no moiety is depicted at the terminal end of the bond indicates a methyl group bound through that bond to the atom, unless stated otherwise. For example:

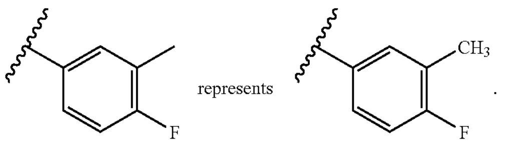

It should also be noted that any carbon or heteroatom with unsatisfied valences in the text, schemes, examples, structural formulae, and any Tables herein is assumed to have the hydrogen atom or atoms to satisfy the valences.

As used herein, the term "composition" is intended to encompass a product comprising the specified ingredients in the specified amounts, as well as any product which results, directly or indirectly, from combination of the specified ingredients in the specified amounts.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

Experimental Procedures

Compounds useful in the method of the invention will show utility as antifungal agents in the following assays.

β(1,3) Glucan Synthase Assay:

1. Preparation of Permeabilized *Saccharomyces cerevisiae* Cells.

Permeabilization of yeast cells was performed according to Crotti et al. (Analytical Biochemistry, 292, 8-16, 2001) with some modifications. A 10 ml-starter culture of the *S. cerevisiae* strain in YPD medium (1% yeast extract, 2% bacto-peptone, 2% dextrose) with $OD_{600}$=3-4 was used to inoculate 1 liter of YPD. The culture was grown at 30° C. until $OD_{600}$=0-0.8. Cells were collected by centrifugation (5,300 g for 15 min at 4° C.) and resuspended in buffer (40 mM EDTA, 100 mM β-mercaptoethanol) at 1 g of cell pellet/3.5 ml buffer. The cell suspension was shaken for 30 min at 30° C., followed by centrifugation at 12,000 g for 10 min at 4° C. The cell pellet was washed with 5 ml 0.8 M sorbitol and resuspended in 6.8 ml of 2.9 mM citric acid, 11.3 mM dibasic sodium phosphate, 1 mM EDTA, 0.8 M sorbitol, with constant shaking at 30)C for 30 min. After centrifugation at 12,000 g for 10 ml at 4° C., the pellet was resuspended in 31.3 ml 50 mM Tris-HCl, pH 7.0, and incubated on ice for 5 min. The mixture was then centrifuged at 12,000 g for 10 min at 4 AC, and the pellet was resuspended in 1 ml of 50 mM Tris-HCl and 33% glycerol, pH 7.5. The permeabilized cell preparation was stored at 80° C. in aliquots.

2. Preparation of Membrane Fraction of Yeast Cells

The protocol was modified from Douglas et al. (Journal of Bacteriology, 176, 5686-5696, 1994). For the preparation of *S. cerevisiae* and *C. albicans* membrane fractions, 1 liter of YPD supplemented with 0.02 mg/mL adenine and 0.08 mg/mL uracil was inoculated with 10 mL starter culture of PM503 ($OD_{600}$=4) or the *C. albicans* strain BWP17 ($OD_{600}$=12) in the same medium and grown at 30° C. until $OD_{600}$ reached about 1. *A. fumigatus* (stain ND158) membranes were prepared by first preparing a spore suspension from agar slants by adding 6 mL of sterile saline, 0.1% Tween-20 solution to each slant, and resuspending by pipetting and scraping. The spore suspensions were used to inoculate two 200 mL flasks containing Sabouraud dextrose broth media. Cultures were incubated at 37° C., 250 rpm for ~8 hrs. All cells, *S. cerevisiae, C. albicans* or *A. fumigatus* were harvested by centrifugation at 5,300 g at 4° C. for 40 minutes. After washing with 100 mL of breakage buffer (0.1 M KPi, pH 7.0, 1 mM EDTA, 1 mM DTT), the cell pellet was resuspended in 50 ml ice-cold breakage buffer. The mixture was transferred to a bead-beater chamber packed in ice (BioSpec Products, Bartlesville, Okla.). To each 50 mL sample was added 50 g of acid-washed glass beads (0.45 μM, Sigma). Cells were disrupted using 12×20 second pulses with 2 min-cooling intervals. Cell debris was removed by centrifugation at 3,000 g for 20 minutes at 4° C., and the supernatant was collected and centrifuged at 100,000 g for 1 hour at 4° C. to pellet the membrane fraction. The pellet was resuspended in 5 mL of ice-cold breakage buffer containing 25% glycerol, homogenized with a Dounce tissue homogenizer and stored at −80° C. in small aliquots.

3. Glucan Synthase Assay and Compound Screening

The assay was performed according to Mo et at (Journal of Biological Chemistry, 269, 31267-31274, 1994) and Taft et al. (The Journal of Antibiotics, 47, 1001-1009, 1994), in a 96-well Optiplate (PerkinElmer). To each well was added 3 μL 10× compound stock (in 100% DMSO), or 3 μL of 30 μg/mL caspofungin in 100% DMSO (as positive control), or 3 μL 100% DMSO (as negative control), followed by the addition of appropriate amount of glucan synthase sources (2 μL permeabilized PM503 cells, or 3 μL membrane preparations from either PM503, BWP17, or ND158). The reaction was initiated by adding 25 μL reaction buffer (0.6 mM UDP-Glucose 0.6 nCi [U-$^{14}$C]DUP-Glucose (327 mCi/mmol, Amersham Bioscience), 20 μM GTP-γ-S, 25 mM NaF, 7.5 mg/mL BSA, 8% glycerol in 75 mM Tris-HCl, pH 7.5). The plate was incubated on a shaker for 1.5 hour at room temperature before being quenched with 250 μL 1% TCA (Trichloroacetic Acid). The quenched reaction was mixed by pipetting, and immediately transferred to a 96-well filter plate (Glass fiber B on 0.65 μm hydrophilic durapore membrane, Millipore) pre-wetted with wash buffer (5% TCA, 60 mM NaPPi). The glucan product was retained on the filter membrane by applying vacuum to the plate using a MultiScreen Resist Vacuum Manifold (Millipore). The filter plate was further washed 4 times with 200 μL wash buffer. The plate was dried at 50° C. for 30 minutes. 100 μL of Microscint-0 (PerkinElmer) was added to each well, and plate was counted in a TopCount NXT plate reader (PerkinElmer).

$IC_{50}$ Determinations:

Dose-response curves were plotted from inhibition data generated. $IC_{50}$ was determined by fitting the CPM versus the Concentration of the test compound plot with the following equation (4-parameter logistic model, ID Business Solutions $XL_{fit}$ 4.2).

Microbroth Susceptibility Testing Methods

Yeast susceptibility testing procedure followed the NCCLS document M27-A2 (*Reference Method for Broth Dilution Antifungal Susceptibility Testing of Yeasts; Approved Standard-Second Edition* (ISBN 1-56238-469-4). NCCLS, 940 West Valley Road, Suite 1400 Wayne, Pa. 19087-1898 USA, 2002) with the following modifications:

1. The final test volume was 100 μl and not 200 μl as stipulated,

2. For testing *Saccharomyces cerevisiae* strain PM503 YPD was used in place of RPMI 1640 broth.

Filamentous fungi susceptibility testing procedure follows the NCCLS document M38-A (*Reference Method for Broth Dilution Antifungal Susceptibility Testing of Filamentous Fungi; Approved Standard* (ISBN 1-56238-470-8). NCCLS, 940 West Valley Road, Suite 1400 Wayne, Pa. 19087-1898 USA, 2002) with the following modifications:

1. The final test volume was 100 μl and not 200 μl as stipulated.

2. The end point used to assess the in vitro activity of glucan synthase inhibitors may require microscopic evaluation of cell morphology in the test wells (Kurtz et al., Antimicrobial Agents and Chemotherapy, 38, 1480-1489, 1994; Arikan et al., Antimicrobial Agents and Chemotherapy, 45, 327-330, 2001). This endpoint, termed the minimum effective concentration (MEC), is characterized by changes in the fungal growth that resulted in truncated and highly branched hyphae.

The invention disclosed herein is exemplified by the following preparations of the inventive compounds and examples which should not be construed to limit the scope of the disclosure. Alternative mechanistic pathways and Analogous structures will be apparent to those skilled in the art.

Scheme 1

SYNTHESIS

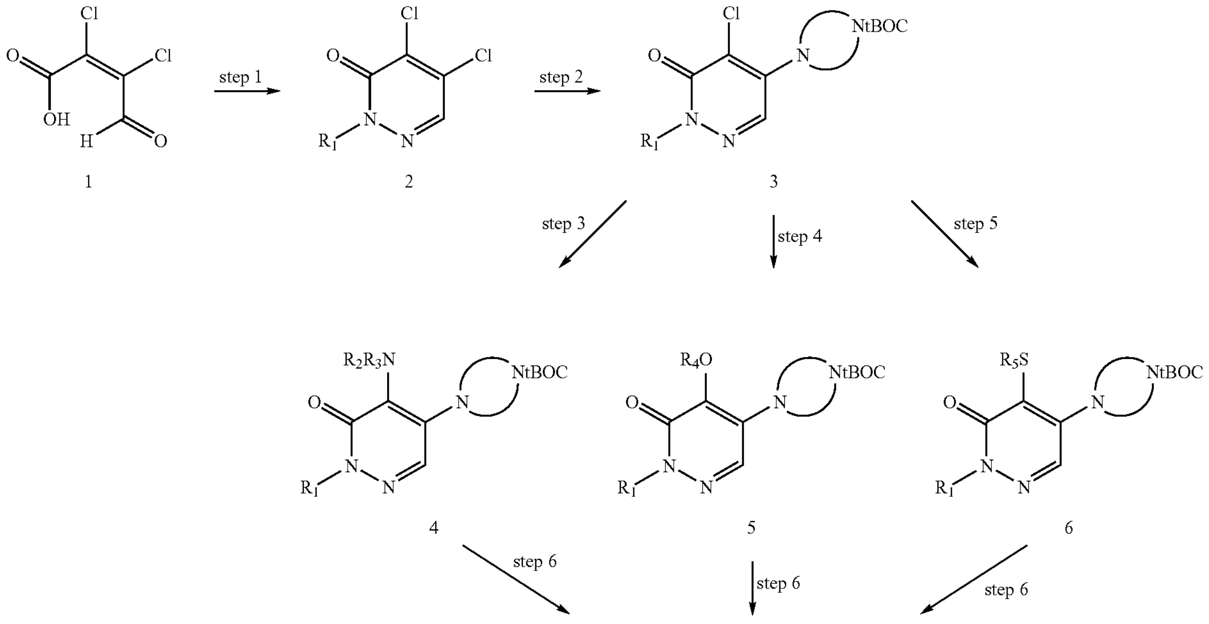

-continued

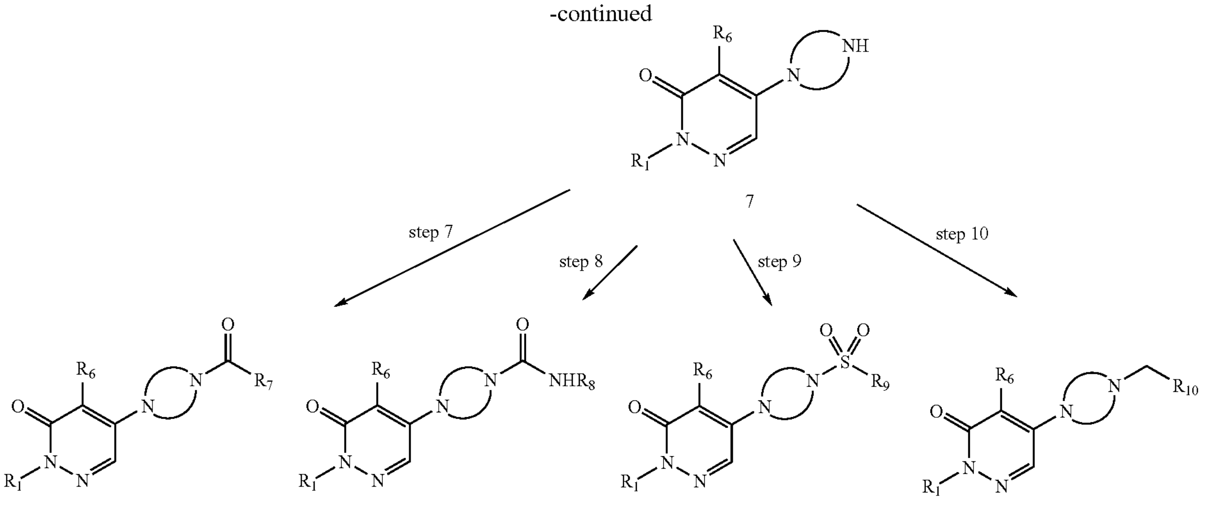

7

8 9 10 11

Step 1:

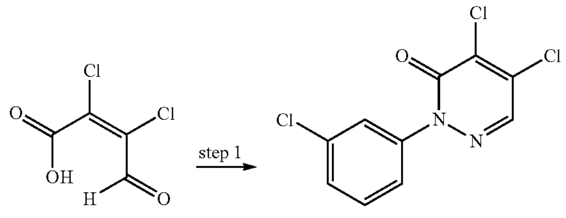

1 2

To a solution of sodium hydroxide (22.3 g, 0559 mol) dissolved in water (50 mL) was added ethanol (300 mL) and 3-chlorophenylhydrazine hydrochloride (100 g, 0.559 mol). The reaction mixture was stirred at room temperature for 15 mins, and then mucochloric acid 1 (94.4, 0.559 mol) was added. The resulting slurry was heated at 100° C. for 24 h then cooled to room temperature. Water (1500 mL) was added. The slurry was stirred and then filtered. The yellow solid was air-dried overnight to give 149.4 g (97%) of the product 2 as a yellow solid. MS (M+1): m/e 277.

Step 2:

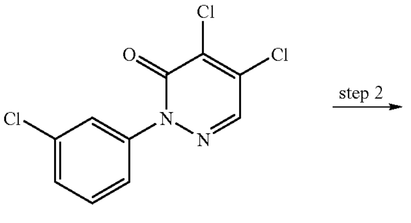

2

-continued

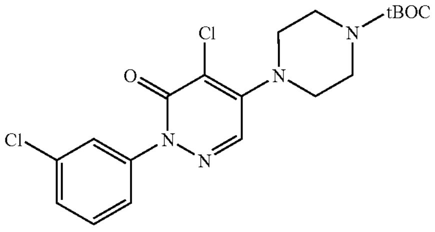

3

To a solution of compound 2 (50.2 g, 0.182 mol) dissolved in ethanol (300 mL) was added N—BOC-piperazine (36.3 g, 0.195 mol) and triethylamine (22.1 g, 30.5 mL, 0.218 mol). The reaction mixture was heated at reflux for 19 h and then cooled to room temperature. The solvent was evaporated, and the solid was triturated with 5% EtOH-$Et_2O$ (800 mL). The product was filtered and air-dried to give 79.7 g (99%) of the product 3 as a beige solid. MS (M+1): m/e 425.

Step 3 (Method 1):

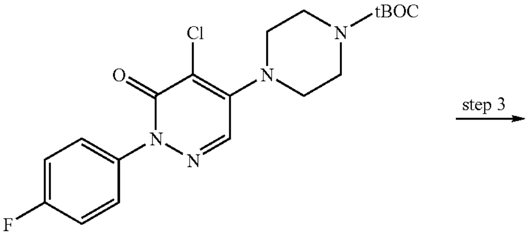

3A

-continued

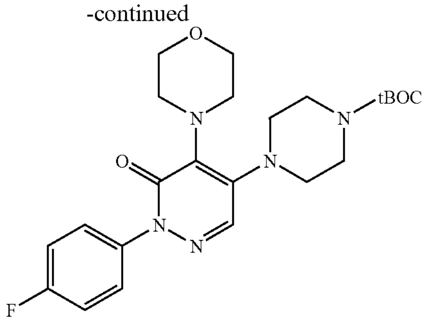

4A

A solution of compound 3A (484 mg, 1.18 mmol) and morpholine (1.04 mL, 11.9 mmol) in 5 mL toluene was heated in a sealed tube in a 138° C. oil bath for 28 h. The mixture was cooled to room temperature and filtered. The solvent was evaporated. Purification by silica gel chromatography (eluant: EtOAc-hexanes gradient) provided 60.7 mg (11% yield) of the product 4A as a solid. MS (M+1): m/e 460.

Step 3 (Method 2):

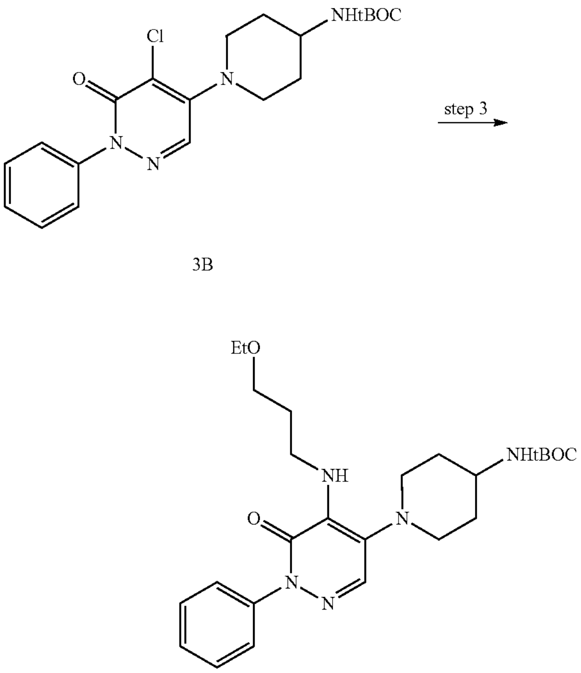

3B

4B

To a solution of compound 3B (1.5 g, 3.70 mmol) dissolved in toluene (35 mL) was added 3-ethoxypropylamine (0.46 g, 4.45 mmol), potassium carbonate (2.6 g, 18.5 mmol), palladium acetate (33 mg, 0.15 mmol), and racemic BINAP (93 mg 0.15 mmol) under a nitrogen atmosphere. The reaction mixture was heated at 120° C. for 40 h then cooled to room temperature. EtOAc was added, and the organic solution was washed with saturated aqueous NaCl, dried ($MgSO_4$), filtered, and concentrated. Purification by silica gel chromatography (eluant: 1-4% MeOH—$CH_2Cl_2$) gave 0.92 g (53%) of the product 4B as a yellow foam. MS (M+1): m/e 472.

Step 4:

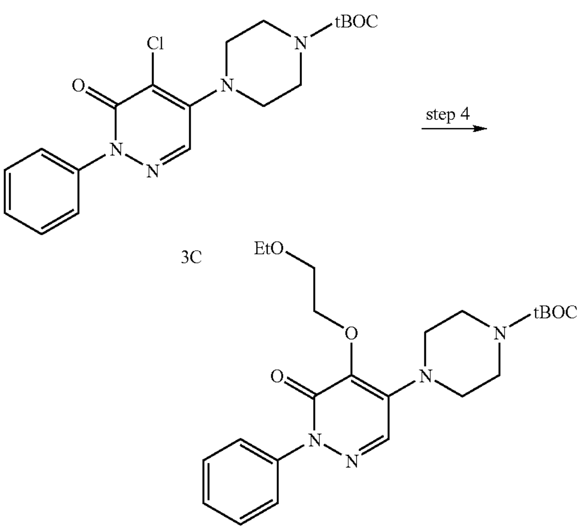

3C

5A

To a solution of 2-ethoxyethanol (0.24 g, 2.69 mmol) dissolved in dry THF (10 mL) under a nitrogen atmosphere was added sodium bis(trimethylsilyl)amide (1 M in THF, 2.3 mL, 2.30 mmol) via syringe. The reaction mixture was stirred at room temperature for 15 mins then compound 3C (0.75 g, 1.92 mmol) was added in dry THF (5 mL). The resulting solution was stirred at room temperature for 16 h. The solvent was evaporated, water (30 mL) was added, and the aqueous solution was extracted with EtOAc. The combined organic extract was dried ($MgSO_4$), filtered, and concentrated. Purification by silica gel chromatography (eluant: 15-40% EtOAc—$CH_2Cl_2$) gave 0.66 g (78%) of the product 5A as a light yellow solid. MS (M+1): m/e 445.

Step 5:

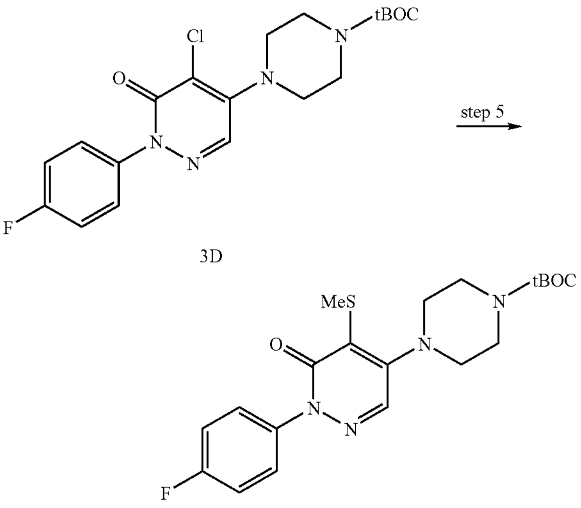

3D

6A

To a solution of compound 3D (242 mg, 0.59 mmol) in methanol (3 mL) was added sodium thiomethoxide (124 mg, 1.77 mmol). The reaction mixture was stirred at reflux for 1 h. The solvent was evaporated. The residue was partitioned between water and ethyl acetate. The organic phase was washed with brine, dried ($Na_2SO_4$), filtered, and concentrated to give 248 mg (100%) of the product 6A as an off-white solid. MS (M+1): m/e 421.

Step 6:

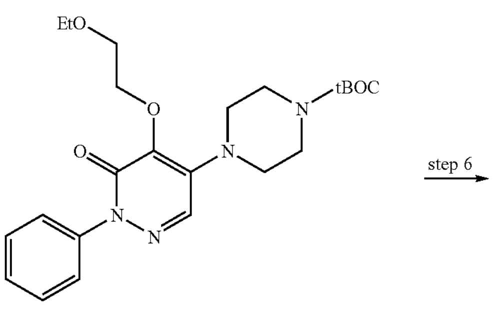

5A

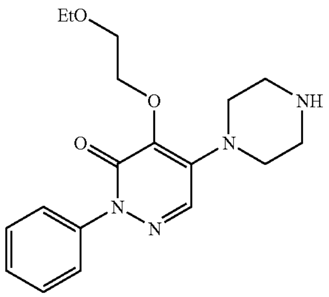

7A

To a solution of compound 5A (0.65 g, 1.46 mmol) dissolved in $CH_2Cl_2$ (10 mL) was added HCl-dioxane (4 N, 3.7 mL, 14.6 mmol). The reaction mixture was stirred at room temperate for 3 h. The solvent was evaporated, and the product was dried under high vacuum to give 0.56 g (100%) of the HCl salt of the product 7A as a white solid. MS (M+1): m/e 345.

Step 7:

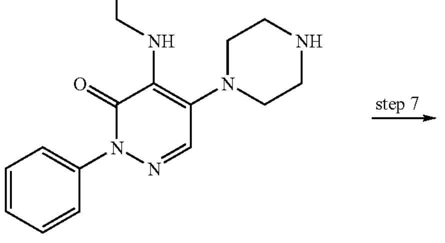

7B

-continued

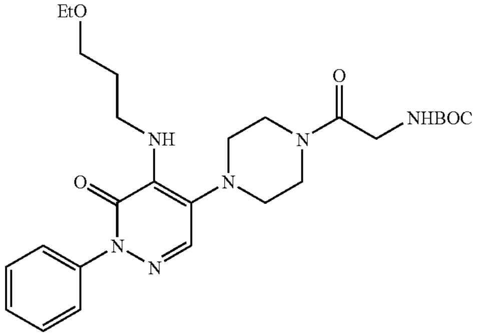

8A

To a solution of compound 7B (107 mg, 0.30 mmol) dissolved in 1:1 DMF:$CH_2Cl_2$ (10 mL) was added Hunig's base (116 mg, 0.16 mL, 0.90 mmol), HATU (171 mg, 0.45 mmol), and BOC-glycine (58 mg, 0.33 mmol). The reaction mixture was stirred at room temperature for 1 h. The solvent was evaporated. Water was added, and the aqueous solution was extracted with $CH_2Cl_2$. The combined organic extract was dried ($MgSO_4$), filtered, and concentrated. Purification by silica gel chromatography (eluant: 10-25% EtOAc—$CH_2Cl_2$ gradient) gave 125 mg (83%) of the product 8A. MS (M+1): m/e 515.

Step 8:

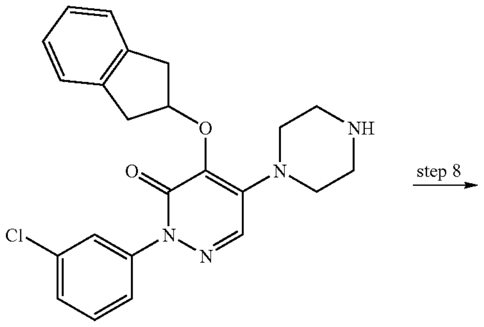

7C

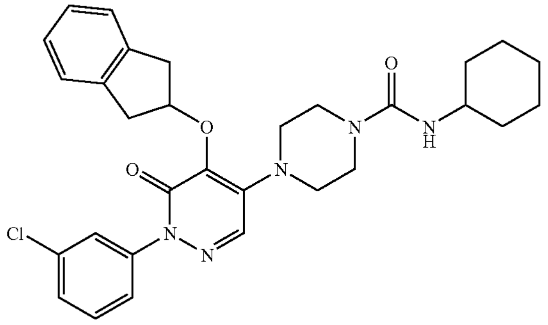

9A

To a solution of compound 7C (65 mg, 0.147 mmol) in dichloromethane (2.5 mL) was added diisopropylethylamine (100 uL) and cyclohexylisocyanate (28 uL, 0.22 mmol). The reaction mixture was stirred at room temperature for 1.5 h. The solvent was evaporated. The residue was dissolved in DMF (2 mL) and purified by chromatography on a C-18 reverse phase column (eluant: acetonitrile/water gradient with 0.1% formic acid). The appropriate fractions were combined and concentrated to give 61.7 mg (79%) of the product 9A as a pale-yellow solid. MS (M+1): m/e 532.

Step 9:

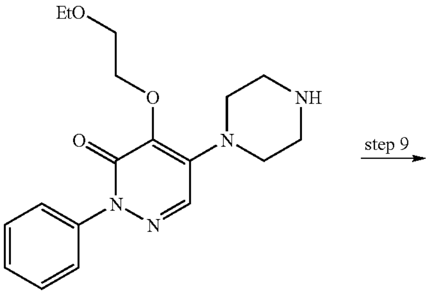

7A

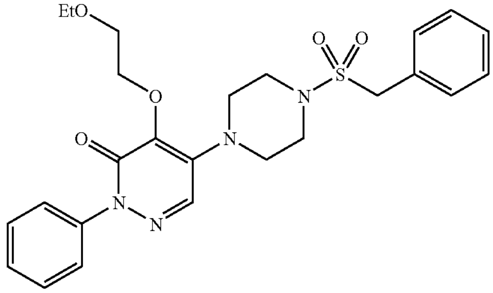

10A

To a solution of the HCl salt of compound 7A (75 mg, 0.197 mmol) dissolved in DMF (1.5 mL) was added Hunigs base (127 mg, 0.16 mL, 0.985 mmol) and α-toluenesulfonyl chloride (56 mg, 0.295 mmol). The reaction mixture was stirred at room temperature for 3 h. The product was purified by chromatography on a C-18 reverse phase column (eluant: acetonitrile/water gradient with 0.1% formic acid) to give 55 mg (56%) of the product 10A as a cream solid. MS (M+1): m/e 499.

Step 10:

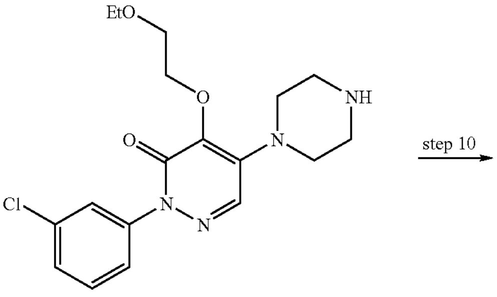

7D

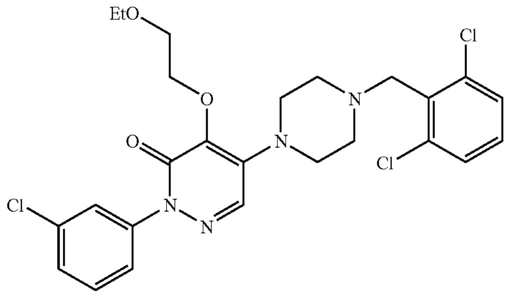

11A

To a solution of compound 7D TFA salt (130 mg, 0.26 mmol) dissolved in toluene (4 mL) was added 2,6-dichlorobenzylchloride (65 mg, 0.33 mmol) and Hunigs base (104 uL, 0.63 mmol). The reaction mixture was heated at reflux for 18 h. The solvent was evaporated. Purification by silica gel chromatography (eluant: 10% MeOH/NH3-$CH_2Cl_2$) gave 50 mg (36%) of the product 1A. MS (M+1): m/e 539.

Scheme 2

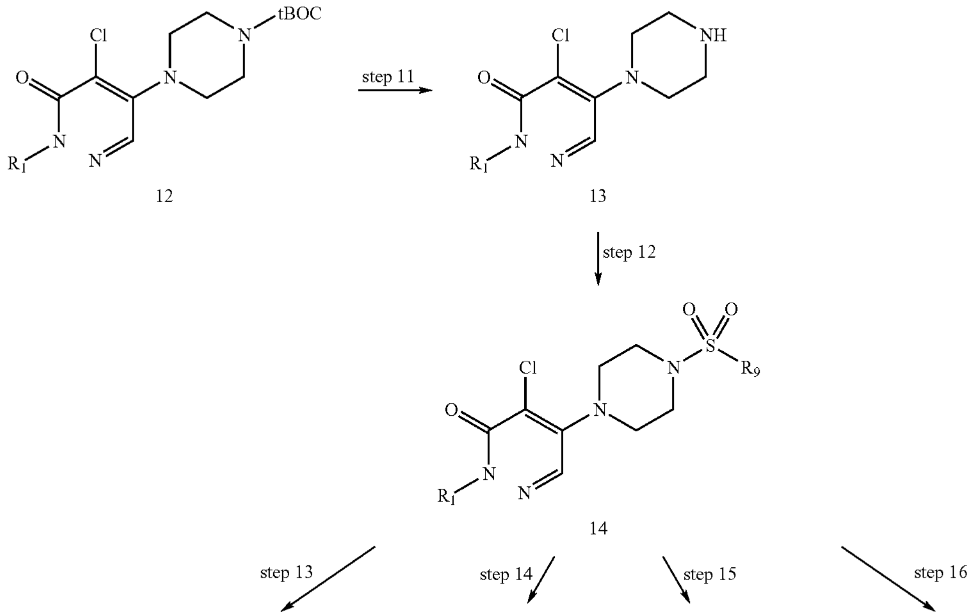

12 13 14

-continued

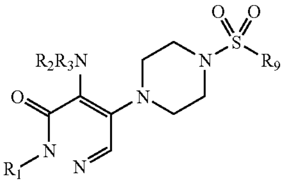

15

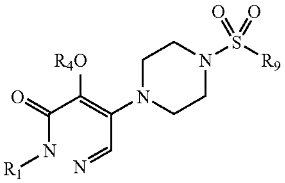

16

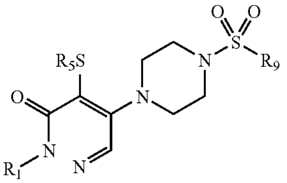

17

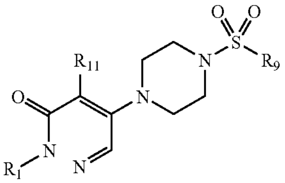

18

Compound 12 can be synthesized using steps 1 and 2 from Scheme 1.

Step 11:

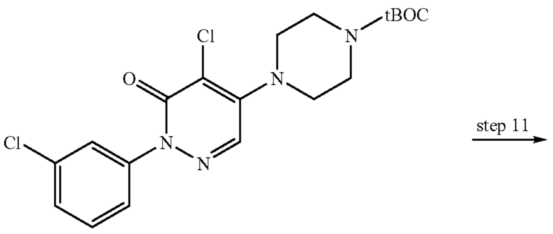

12A

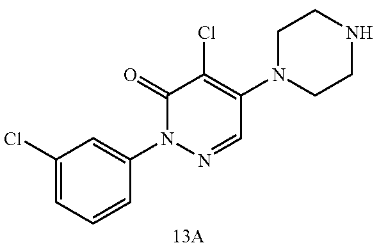

13A

Suspended compound 12A (4.00 g, 9.41 mmol) in $CH_2Cl_2$ (100 mL). Added HCl in dioxane (4 N, 23.5 mL, 94.1 mmol). The reaction mixture was stirred at room temperature for 5 h and precipitate formed. The solvent was evaporated, and the solid was dried under high vacuum to give 3.40 g (100%) of the product 13A as a yellow solid, MS (M+1): m/e 327.

Step 12:

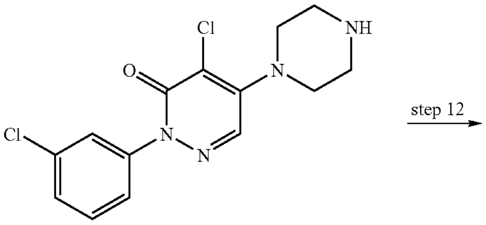

13A

-continued

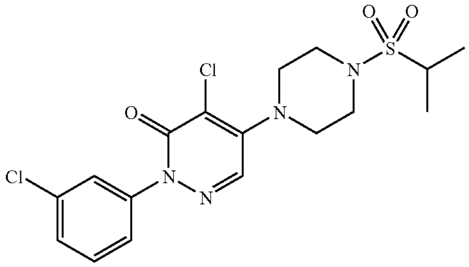

14A

Suspended compound 13A (3.40 g, 9.41 mmol) in $CH_2Cl_2$ (100 mL) and added triethylamine (2.86 g, 3.9 mL, 28.2 mmol). Cooled reaction mixture to 0° C. and added isopropylsulfonyl chloride (1.74 g, 1.4 mL, 12.2 mmol). The reaction mixture was stirred at 0° C. for 30 mins then at room temperature for 24 h. Water (100 mL) was added, and the aqueous solution was extracted with $CH_2Cl_2$. The combined organic extract was dried ($MgSO_4$), filtered, and concentrated. Purification by silica gel chromatography (eluant: 10-20% EtOAc—$Cl_2Cl_2$) gave 2.47 g (61% yield) of the product 14A as a yellow solid. MS (M+1): m/e 431.

Step 13:

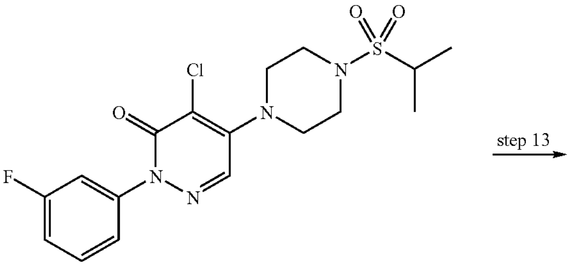

14B

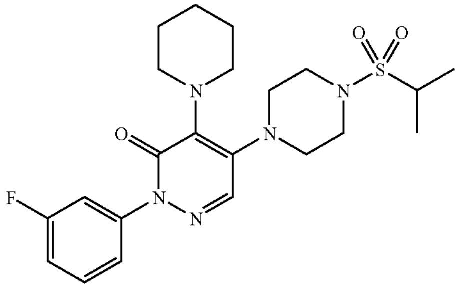

15A

A solution of compound 14B (207 mg, 0.50 mmol) and piperidine (170 mg, 2.0 mmol) dissolved in dichlorobenzene (5 mL) was heated at 250° C. for 60 mins. The reaction mixture was cooled to room temperature. Purification by silica gel chromatography (eluant: EtOAc hexanes gradient) gave 112 mg (48%) of the product 15A. MS (M+1): m/e 464.

Step 14 (Method 1):

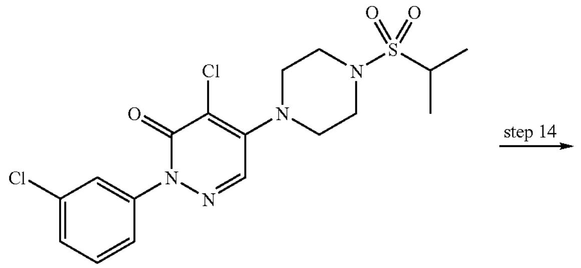

14A

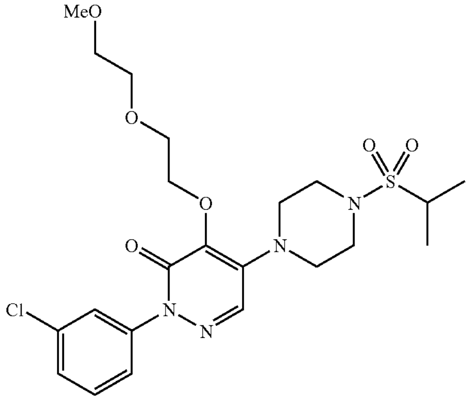

16A

To a solution of 2-(2-methoxyethoxy)ethanol (244 mg, 0.24 mL, 2.03 mmol) dissolved in dry THF (5 mL) was added $NaNTMS_2$ (1 M in THF, 1.74 mL, 1.74 mmol). The reaction mixture was stirred at room temperature for 15 mins then compound 14A (250 mg, 0.580 mmol) was added. The reaction mixture was heated at reflux for 5 h. The solvent was evaporated. Water (25 mL) was added, and the aqueous solution was extracted with EtOAc. The combined organic extract was dried ($MgSO_4$), filtered, and concentrated. Purification by silica gel chromatography (eluant: 20-30% EtOAc-hexanes) gave 233 mg (78%) of the product 16A as an orange solid. MS (M+1): m/e 515.

Step 14 (Method 2):

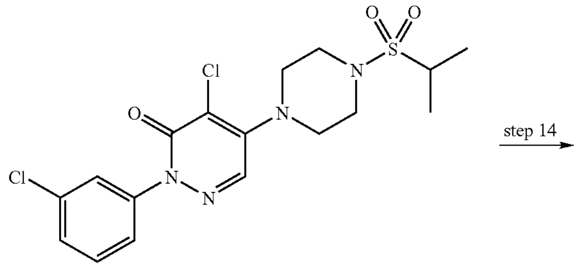

14A

-continued

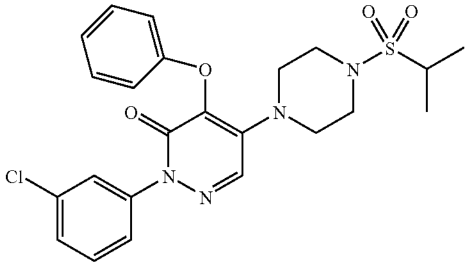

16B

A mixture of anhydrous cesium carbonate (0.114 g, 3.5 mmol) and phenol (0.066 g, 7.0 mmol) in anhydrous methanol (5 mL) was stirred at room temperature for 30 mins. The solvent was evaporated. To the residue at room temperature was added dropwise a solution of compound 14A (0.086 g, 2.0 mmol) in anhydrous DMF (5 mL). The resulting solution was stirred for at 110° C. for 8 h, and then the solvent was evaporated. The residue was quenched with aqueous $NH_4Cl$ solution (10 mL) and extracted with $CH_2Cl_2$ (3×50 mL). The combined organic extract was washed with $H_2O$ (2×10 mL), brine (10 mL), dried over $MgSO_4$, filtered, and concentrated. Purification by silica gel chromatography (1:20 EtOAc-hexanes) gave 42 mg (41%) of the product 16B as a colorless oil. MS (M+1): m/e 489.

Step 15:

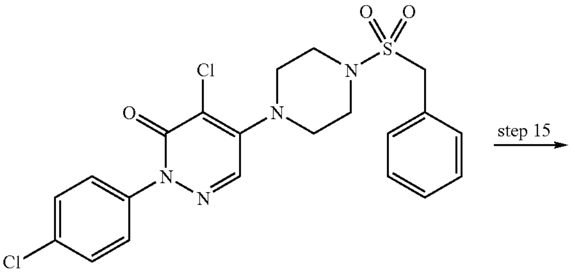

14C

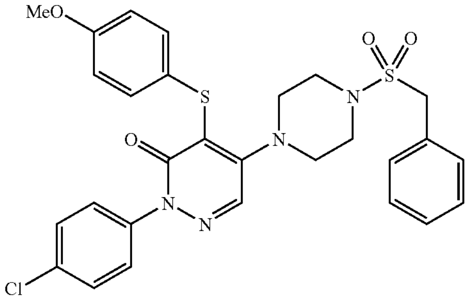

17A

To a solution of compound 14C (240 mg, 0.50 mmol) and potassium carbonate (70 mg, 0.5 mmol) in acetonitrile (2 mL) was added 4-methoxybenzenethiol (100 uL, 0.81 mmol). The reaction mixture was stirred at reflux for 6 h. The solvent was evaporated. The residue was partitioned between water and EtOAc. The organic phase was washed consecutively with water, 1 N sodium hydroxide, and brine, dried ($Na_2SO_4$), filtered, and concentrated. Purification by silica gel chromatography (eluant: EtOAc hexanes gradient) gave 272 mg (93% yield) of the product 17A as a yellow solid. MS (M+1): m/e 583.

Step 16:

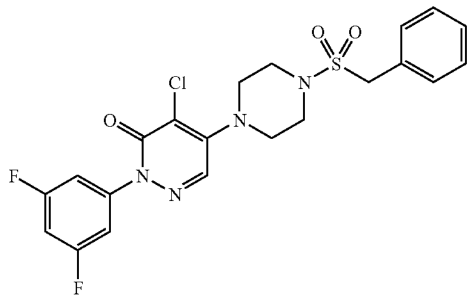

14D step 16

-continued

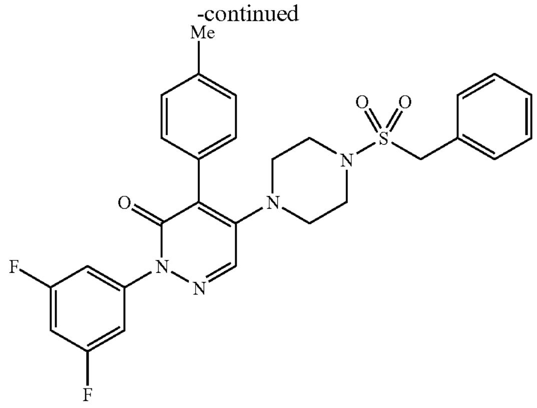

18A

Compound 14D (34 mg 0.070 mmol), 4-methylphenylboronic acid (14 mg, 0.11 mmol), $Na_2CO_3$ (11 mg, 0.11 mmol), and $PdCl_2(PPh_3)_2$ catalyst (2.5 mg, 0.004 mmol) were combined in 5:1 acetonitrile:water (2 mL). The reaction mixture was heated in a microwave at 140° C. for 20 mins then filtered through a Si-carbonate column with $CH_2Cl_2$. Purification by chromatography on a C-18 reverse phase column (eluant: acetonitrile/water gradient with 0.1 formic acid) gave 22 mg (59%) of the product 18A. MS (M+1): m/e 537.

TABLE 1

Sulfur Linked Analogs with Amide
The following compounds can be synthesized
using steps 1, 2, 5, 6, and 7 of Scheme 1.

| Compound No. | Structure | MS M + 1 |
|---|---|---|
| 1Z | 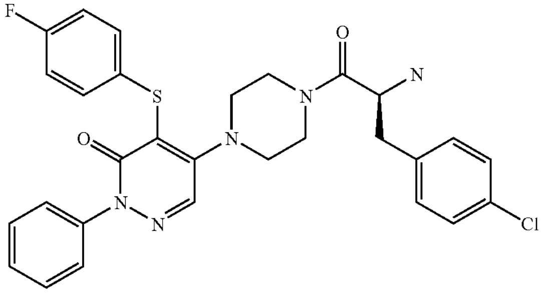 | 564 |
| 2Z | 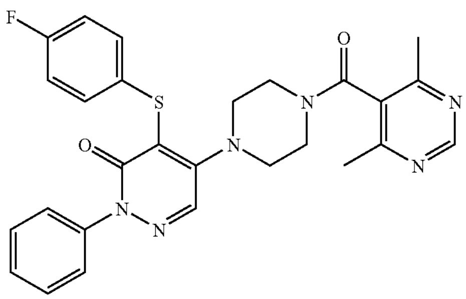 | 517 |

TABLE 2
| Sulfur Linked Analogs with Sulfonamide The following compounds can be synthesized using steps 1, 2, 5, 6, and 9 of Scheme 1 or steps 11, 12, and 15 of Scheme 2. | | |
|---|---|---|
| Comp. No. | Structure | MS M + 1 |
| 3Z | 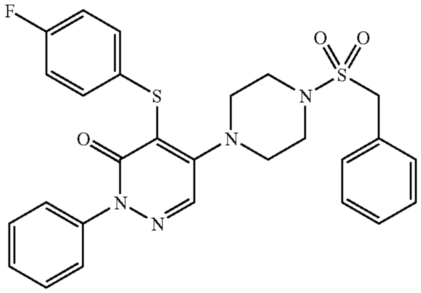 | 537 |
| 4Z | 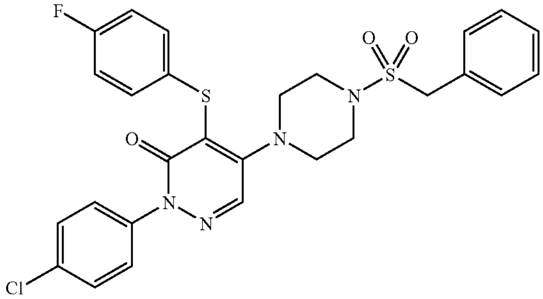 | 571 |
| 5Z | 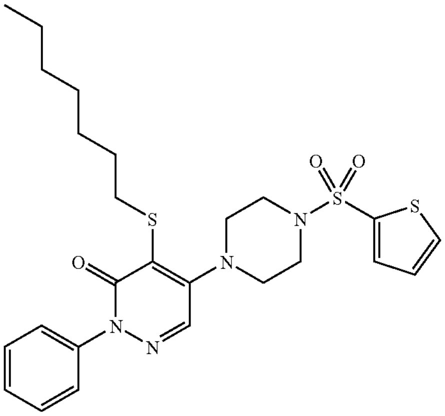 | 533 |
| 6Z | 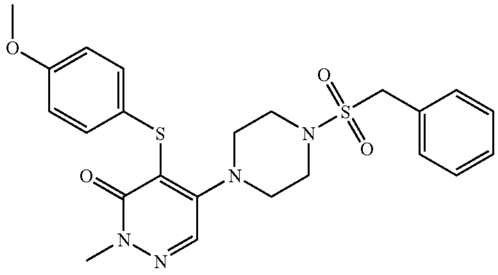 | 487 |

TABLE 2-continued
Sulfur Linked Analogs with Sulfonamide
The following compounds can be synthesized using steps 1, 2, 5, 6, and 9 of Scheme 1 or steps 11, 12, and 15 of Scheme 2.
| Comp. No. | Structure | MS M + 1 |
|---|---|---|
| 7Z | 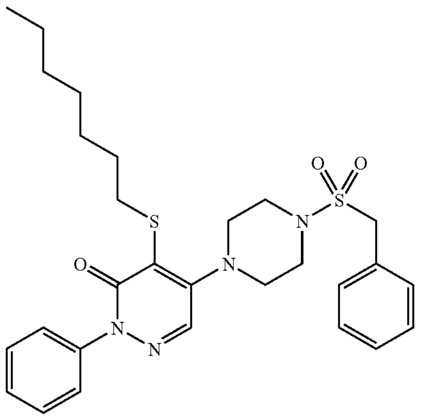 | 541 |
| 8Z | 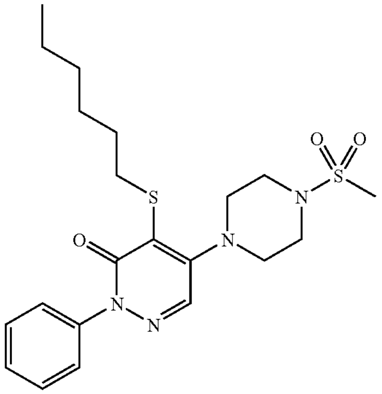 | 451 |
| 9Z | 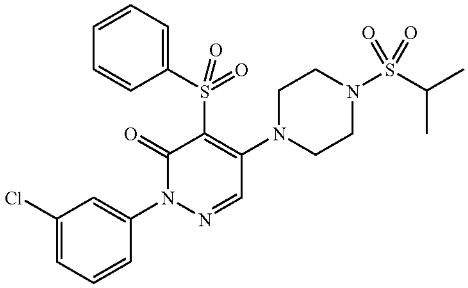 | 537 |
| 10Z | 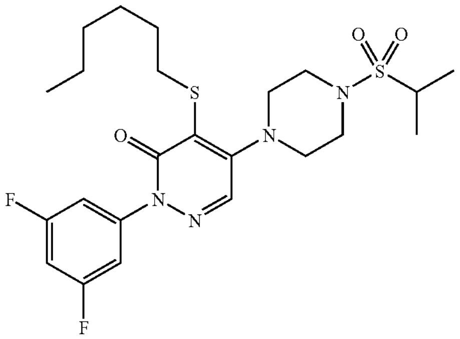 | 515 |

TABLE 2-continued
Sulfur Linked Analogs with Sulfonamide
The following compounds can be synthesized using steps 1, 2, 5, 6, and 9 of Scheme 1 or steps 11, 12, and 15 of Scheme 2.
| Comp. No. | Structure | MS M + 1 |
| --- | --- | --- |
| 11Z | 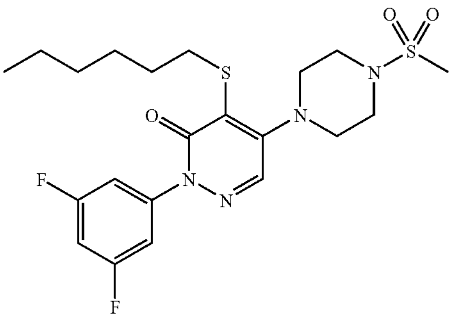 | 487 |
| 12Z | 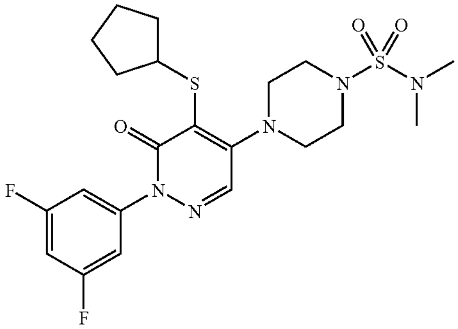 | 500 |
| 13Z | 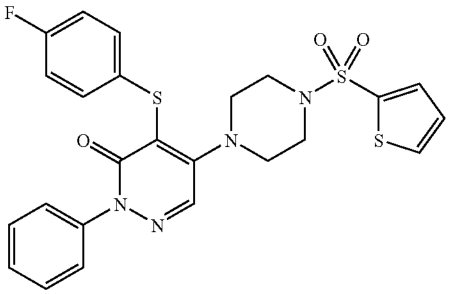 | 529 |
| 14Z | 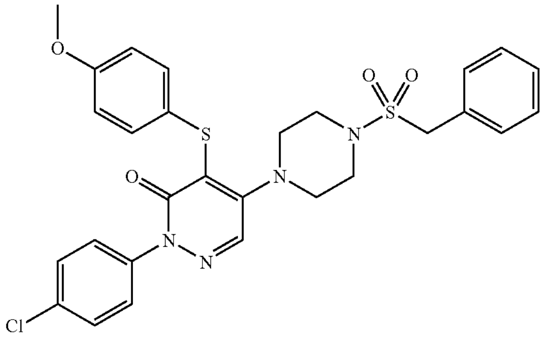 | 583 |

TABLE 2-continued
| Sulfur Linked Analogs with Sulfonamide The following compounds can be synthesized using steps 1, 2, 5, 6, and 9 of Scheme 1 or steps 11, 12, and 15 of Scheme 2. | | |
|---|---|---|
| Comp. No. | Structure | MS M + 1 |
| 15Z | 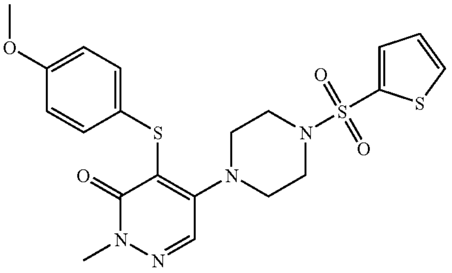 | 479 |
| 16Z | 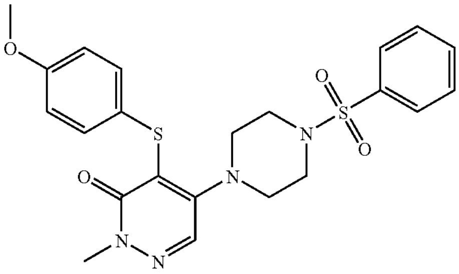 | 473 |
| 17Z | 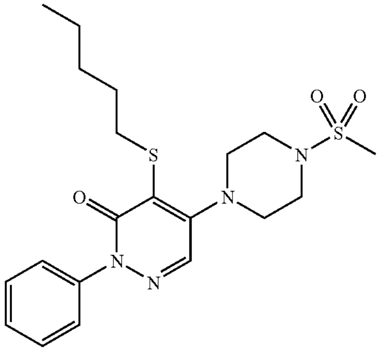 | 437 |
| 18Z | 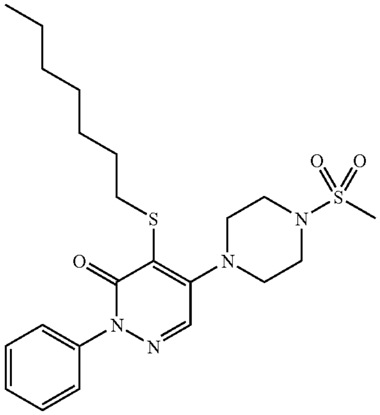 | 465 |

TABLE 2-continued
| Sulfur Linked Analogs with Sulfonamide<br>The following compounds can be synthesized using steps 1, 2, 5, 6, and 9 of Scheme 1 or steps 11, 12, and 15 of Scheme 2. | | |
|---|---|---|
| Comp. No. | Structure | MS M + 1 |
| 19Z | 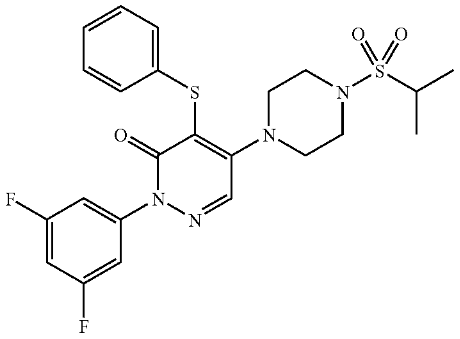 | 507 |
| 20Z | 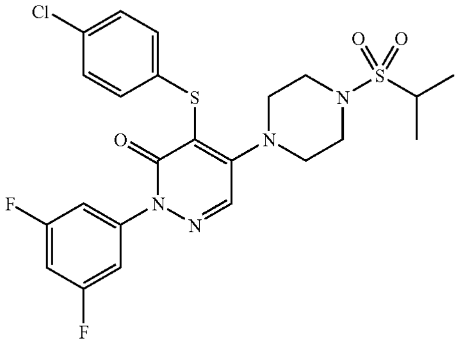 | 541 |
| 21Z | 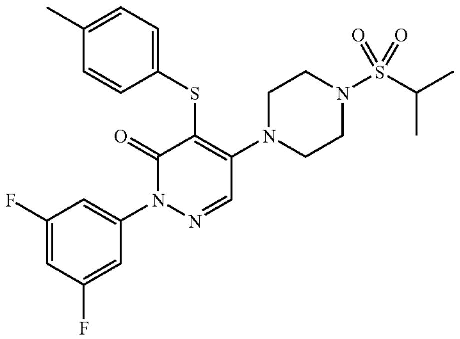 | 521 |

TABLE 3
| Nitrogen Linked Analogs with Amide<br>The following compounds can be synthesized using<br>steps 1, 2, 3, 6, and 7 of Scheme 1. | | |
|---|---|---|
| Comp. No. | Structure | MS M + 1 |
| 22Z | 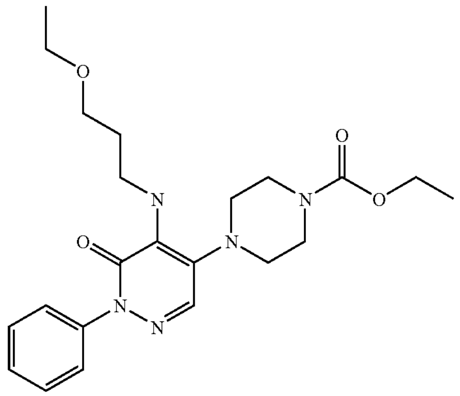 | 403 |
| 23Z | 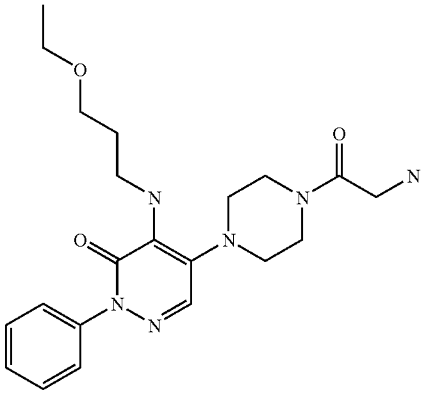 | 415 |
| 24Z | 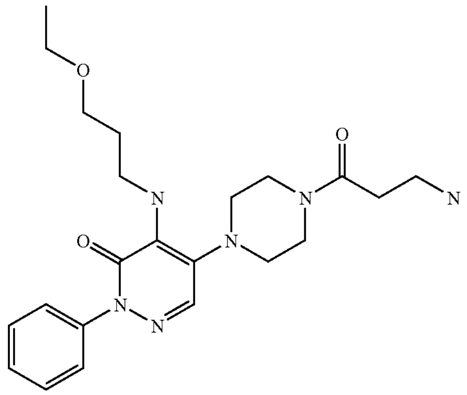 | 429 |

TABLE 3-continued
Nitrogen Linked Analogs with Amide
The following compounds can be synthesized using steps 1, 2, 3, 6, and 7 of Scheme 1.
| Comp. No. | Structure | MS M + 1 |
|---|---|---|
| 25Z | 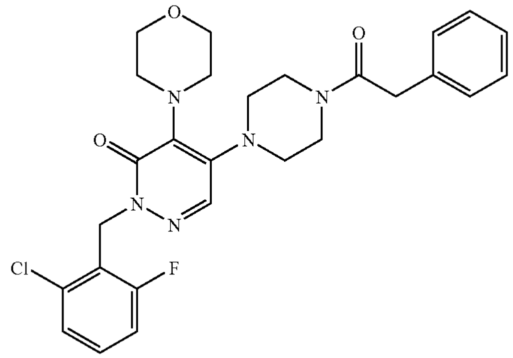 | 529 |
| 26Z | 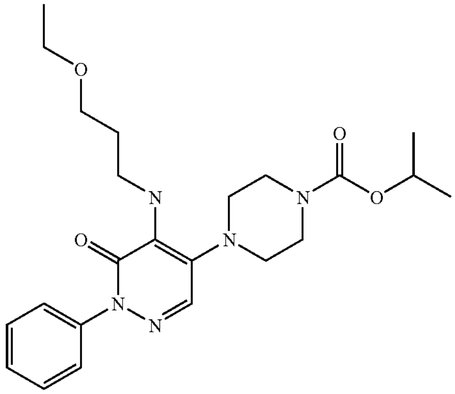 | 444 |
| 27Z | 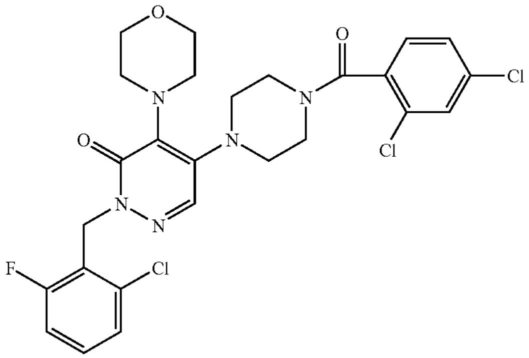 | 472 |
| 28Z | 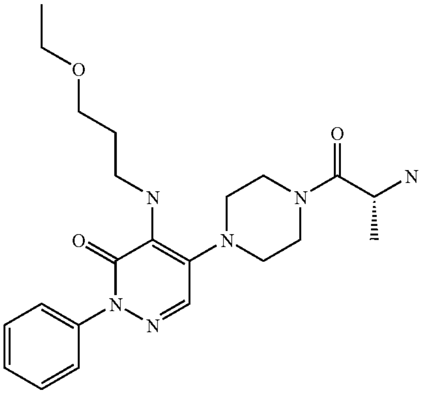 | 429 |

TABLE 3-continued
| Comp. No. | Structure | MS M + 1 |
|---|---|---|
| Nitrogen Linked Analogs with Amide<br>The following compounds can be synthesized using<br>steps 1, 2, 3, 6, and 7 of Scheme 1. | | |
| 29Z | 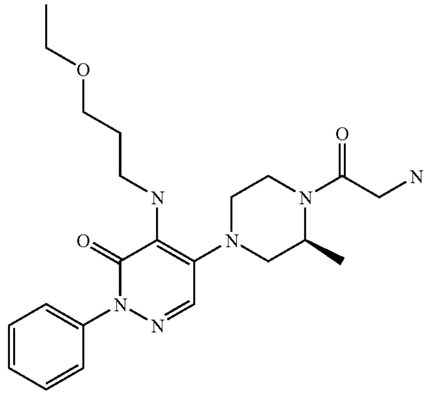 | 429 |
TABLE 4
| Comp. No. | Structure | MS M + 1 |
|---|---|---|
| Nitrogen Linked Analogs with Sulfonamide<br>The following compounds can be synthesized using steps 1, 2,<br>3, 6, and 9 of Scheme 1 or steps 11, 12, and 13 of Scheme 2. | | |
| 30Z | 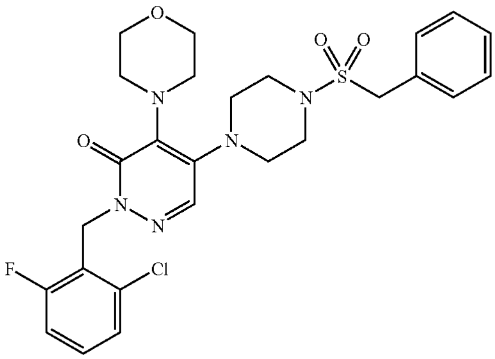 | 562 |
| 31Z | 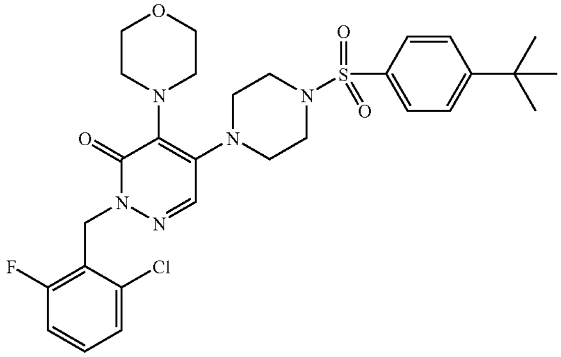 | 604 |

TABLE 4-continued
| Nitrogen Linked Analogs with Sulfonamide The following compounds can be synthesized using steps 1, 2, 3, 6, and 9 of Scheme 1 or steps 11, 12, and 13 of Scheme 2. | | |
|---|---|---|
| Comp. No. | Structure | MS M + 1 |
| 32Z | 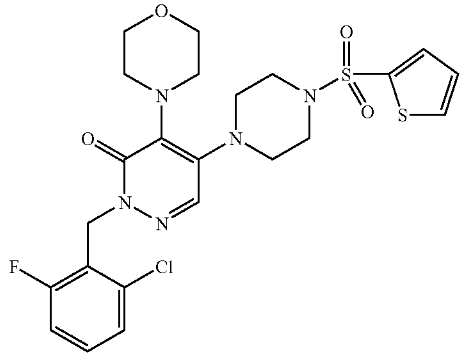 | 554 |
| 33Z | 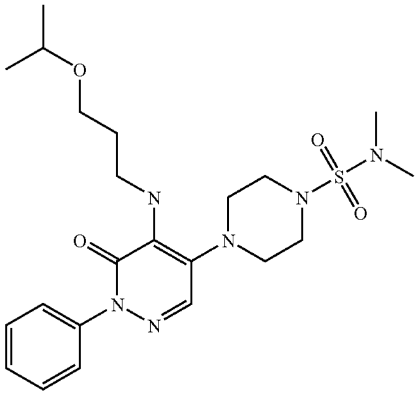 | 479 |
| 34Z | 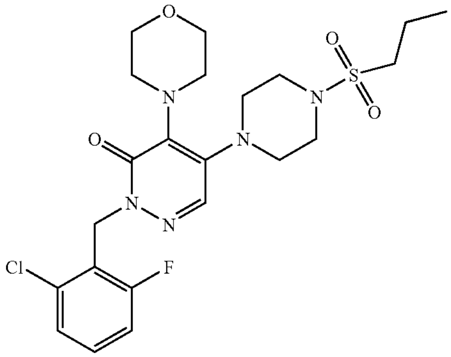 | 514 |
| 35Z | 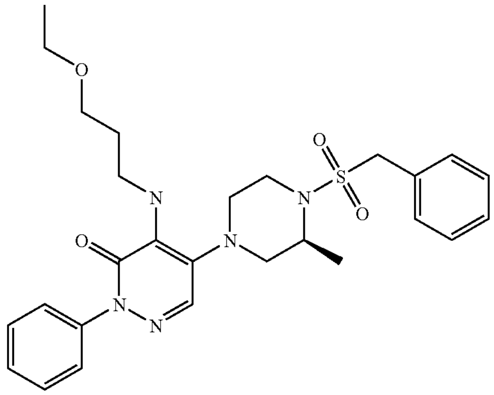 | 526 |

TABLE 4-continued
| Comp. No. | Structure | MS M + 1 |
|---|---|---|
| | Nitrogen Linked Analogs with Sulfonamide<br>The following compounds can be synthesized using steps 1, 2, 3, 6, and 9 of Scheme 1 or steps 11, 12, and 13 of Scheme 2. | |
| 36Z | 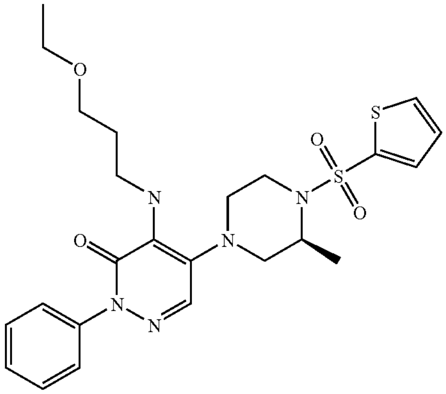 | 518 |
| 37Z | 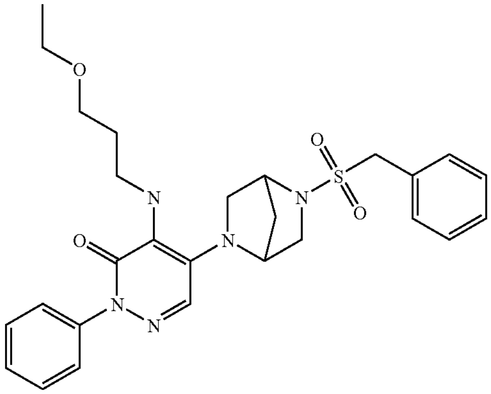 | 524 |
| 38Z | 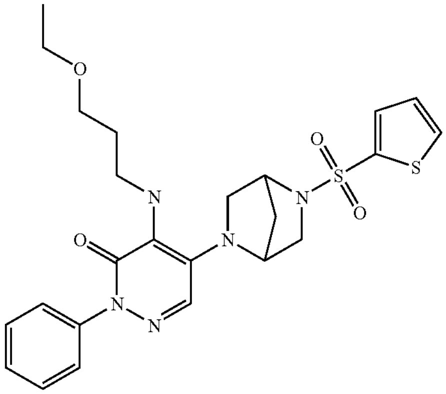 | 516 |

TABLE 4-continued
| Comp. No. | Structure | MS M + 1 |
|---|---|---|
| | Nitrogen Linked Analogs with Sulfonamide<br>The following compounds can be synthesized using steps 1, 2, 3, 6, and 9 of Scheme 1 or steps 11, 12, and 13 of Scheme 2. | |
| 39Z | 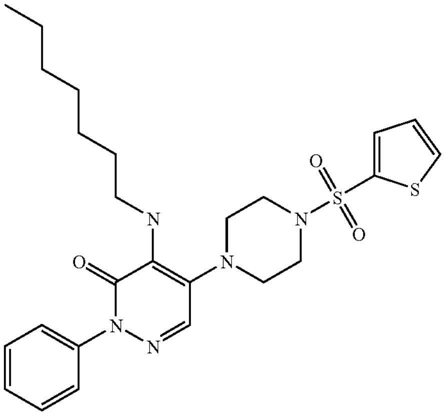 | 516 |
| 40Z | 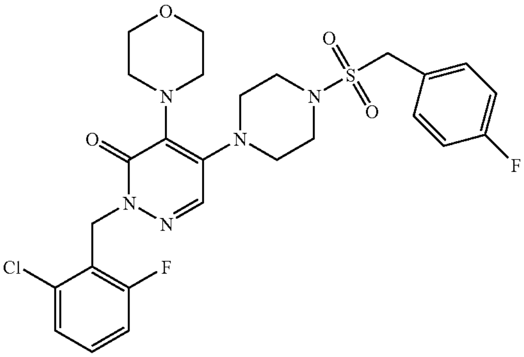 | 580 |
| 41Z | 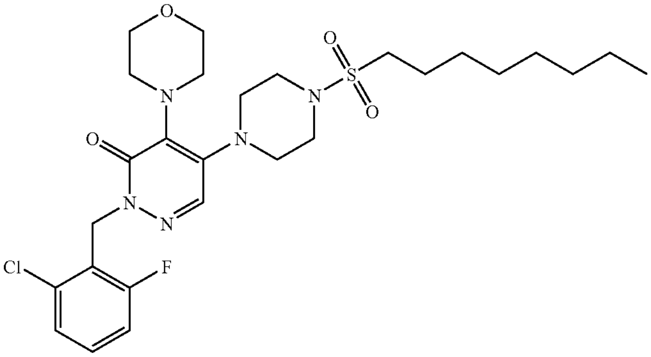 | 584 |
| 42Z | 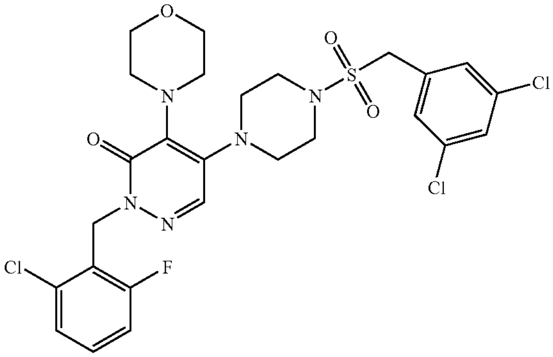 | 632 |

TABLE 4-continued
Nitrogen Linked Analogs with Sulfonamide
The following compounds can be synthesized using steps 1, 2, 3, 6, and 9 of Scheme 1 or steps 11, 12, and 13 of Scheme 2.
| Comp. No. | Structure | MS M + 1 |
|---|---|---|
| 43Z | 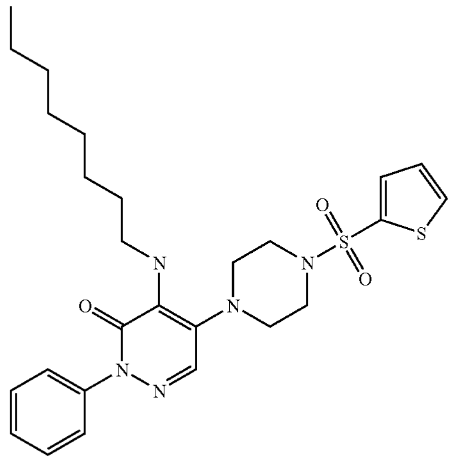 | 530 |
| 44Z | 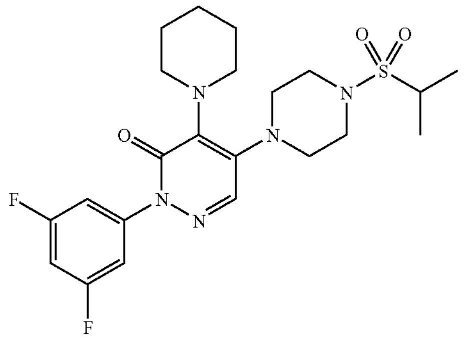 | 482 |
| 45Z | 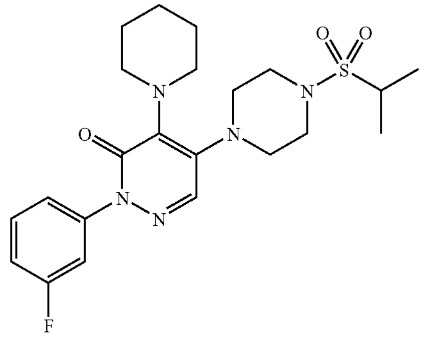 | 464 |
| 46Z | 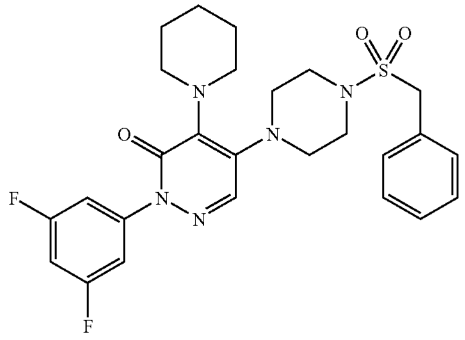 | 530 |

TABLE 4-continued
| Nitrogen Linked Analogs with Sulfonamide The following compounds can be synthesized using steps 1, 2, 3, 6, and 9 of Scheme 1 or steps 11, 12, and 13 of Scheme 2. | | |
|---|---|---|
| Comp. No. | Structure | MS M + 1 |
| 47Z | 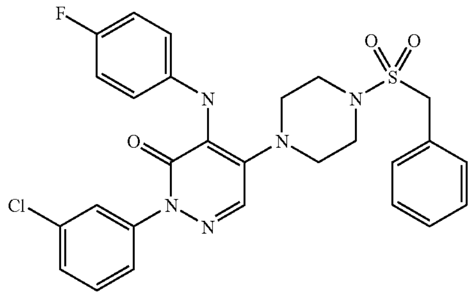 | 554 556 |
| 48Z | 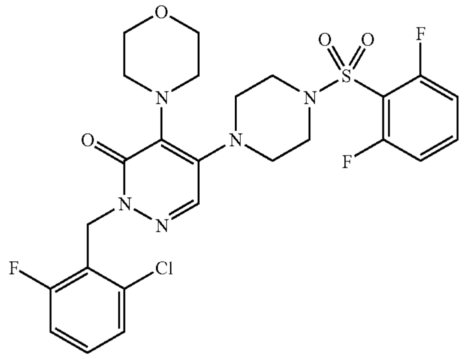 | 584 |
| 49Z | 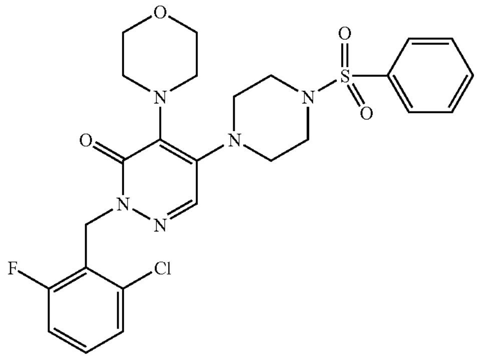 | 548 |
| 50Z | 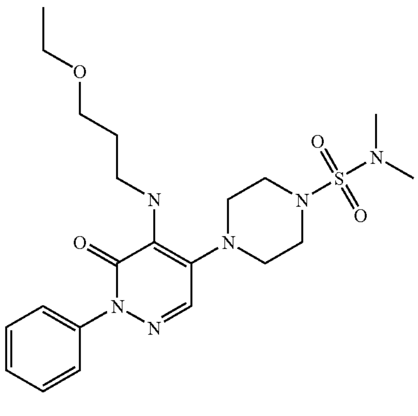 | 465 |

TABLE 4-continued
Nitrogen Linked Analogs with Sulfonamide
The following compounds can be synthesized using steps 1, 2, 3, 6, and 9 of Scheme 1 or steps 11, 12, and 13 of Scheme 2.
| Comp. No. | Structure | MS M + 1 |
|---|---|---|
| 51Z | 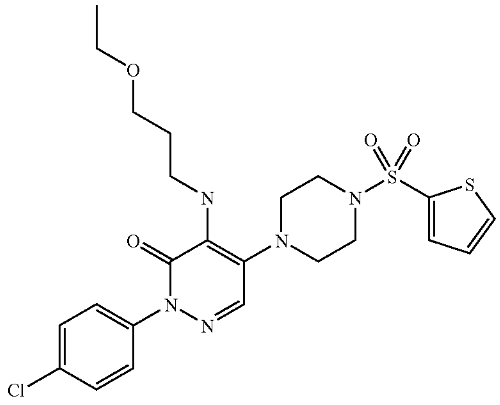 | 538<br>540 |
| 52Z | 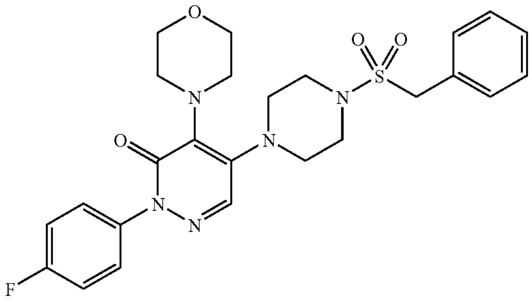 | 514 |
| 53Z | 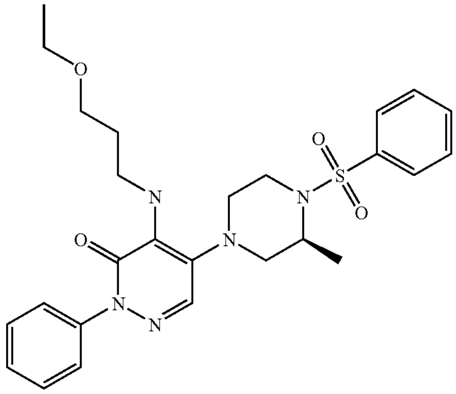 | 512 |
| 54Z | 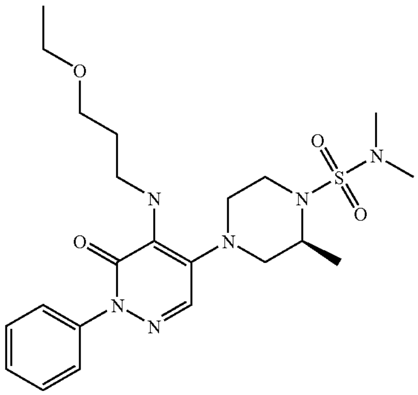 | 479 |

TABLE 4-continued
| Nitrogen Linked Analogs with Sulfonamide<br>The following compounds can be synthesized using steps 1, 2, 3, 6, and 9 of Scheme 1 or steps 11, 12, and 13 of Scheme 2. | | |
|---|---|---|
| Comp. No. | Structure | MS M + 1 |
| 55Z | 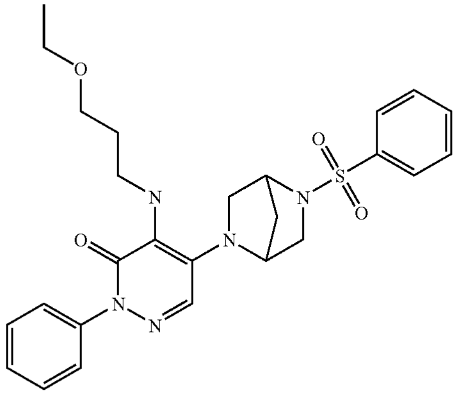 | 510 |
| 56Z | 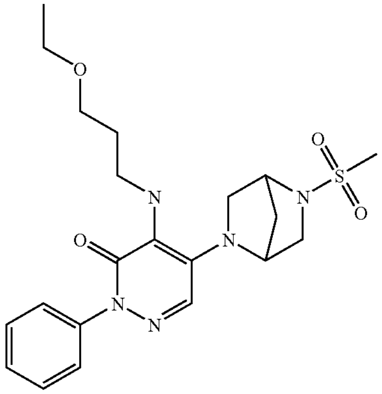 | 448 |
| 57Z | 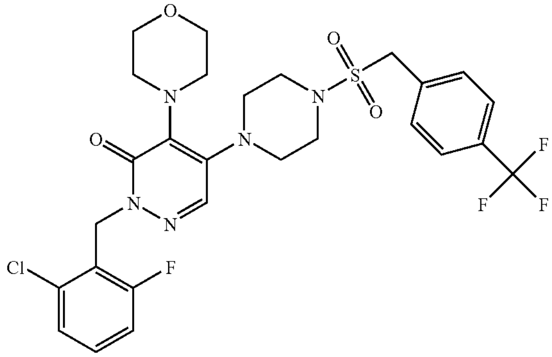 | 630 |
| 58Z | 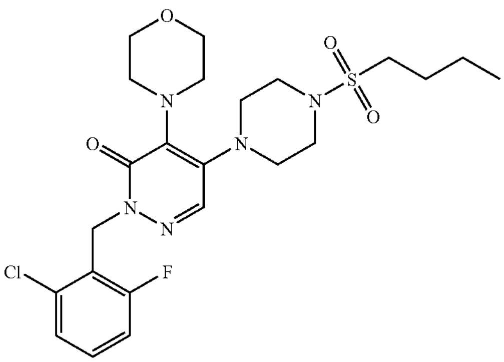 | 528 |

TABLE 4-continued
| Comp. No. | Structure | MS M + 1 |
|---|---|---|
| Nitrogen Linked Analogs with Sulfonamide<br>The following compounds can be synthesized using steps 1, 2, 3, 6, and 9 of Scheme 1 or steps 11, 12, and 13 of Scheme 2. | | |
| 59Z | 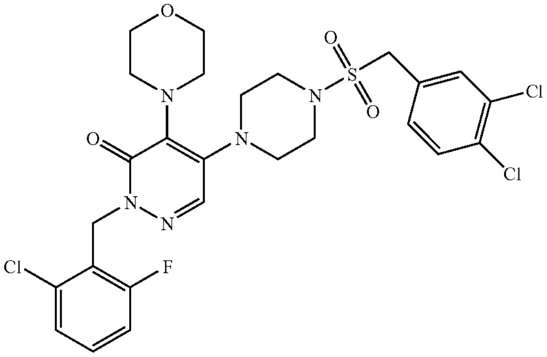 | 632 |
| 60Z | 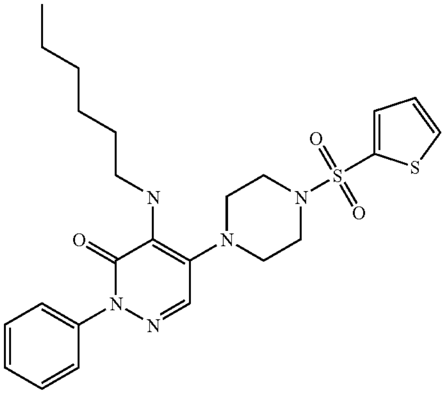 | 502 |
| 61Z | 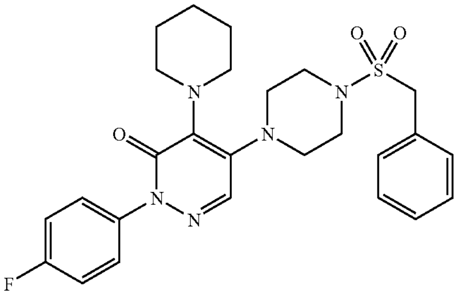 | 512 |
| 62Z | 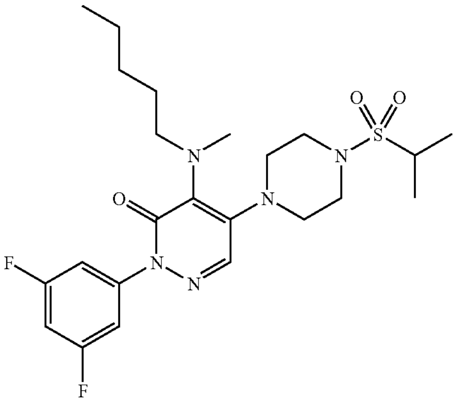 | 498 |

TABLE 4-continued
Nitrogen Linked Analogs with Sulfonamide
The following compounds can be synthesized using steps 1, 2, 3, 6, and 9 of Scheme 1 or steps 11, 12, and 13 of Scheme 2.
| Comp. No. | Structure | MS M + 1 |
|---|---|---|
| 63Z | 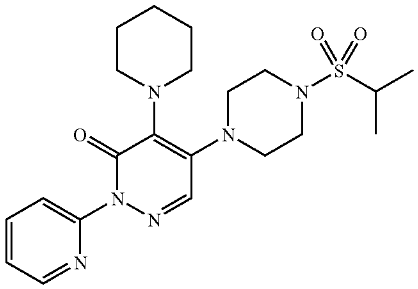 | 447 |
| 64Z | 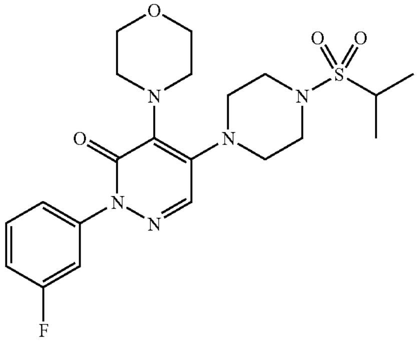 | 466 |
| 65Z | 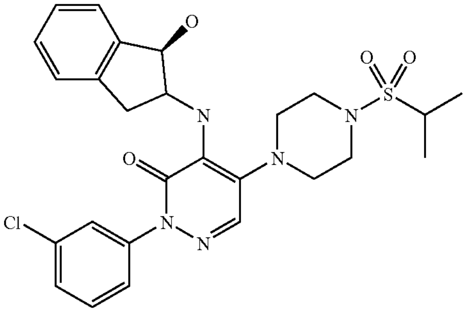 | 544 |
TABLE 5
Carbon Analogs with Sulfonamide
The following compounds can be synthesized by using steps 11, 12, and 16 in Scheme 2.
| Comp. No. | Structure | MS M + 1 |
|---|---|---|
| 66Z | 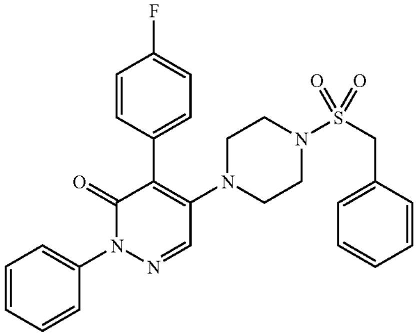 | 505 |

TABLE 5-continued
| Carbon Analogs with Sulfonamide The following compounds can be synthesized by using steps 11, 12, and 16 in Scheme 2. | | |
|---|---|---|
| Comp. No. | Structure | MS M + 1 |
| 67Z | 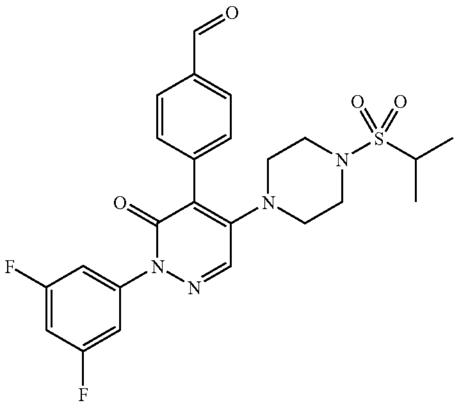 | 503 |
| 68Z | 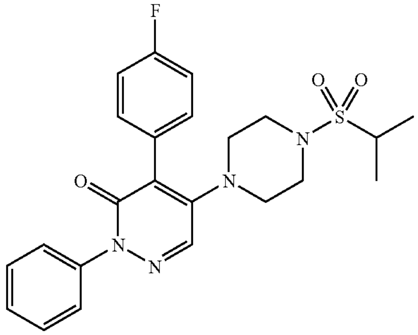 | 457 |
| 69Z | 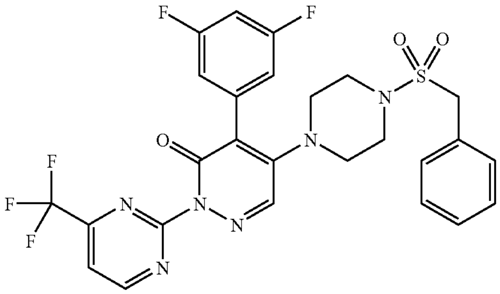 | 593 |
| 70Z | 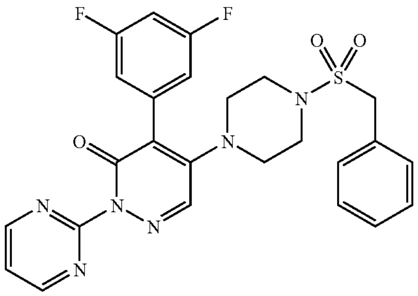 | 525 |

TABLE 5-continued
Carbon Analogs with Sulfonamide
The following compounds can be synthesized
by using steps 11, 12, and 16 in Scheme 2.
| Comp. No. | Structure | MS M + 1 |
|---|---|---|
| 71Z | 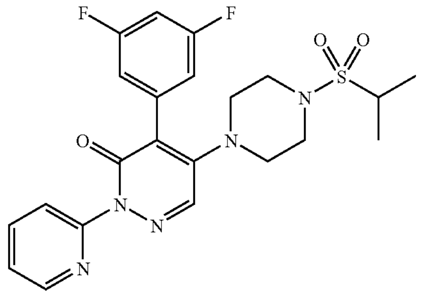 | 476 |
| 72Z | 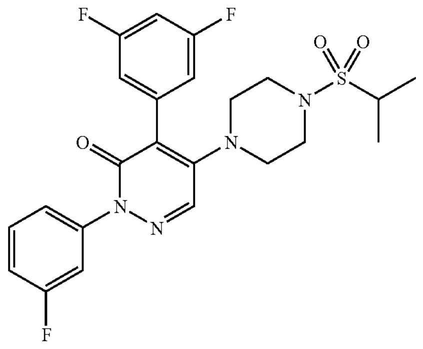 | 493 |
| 73Z | 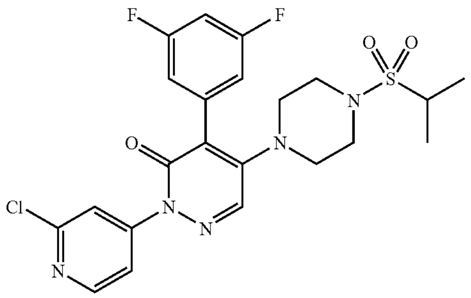 | 510 |
| 74Z | 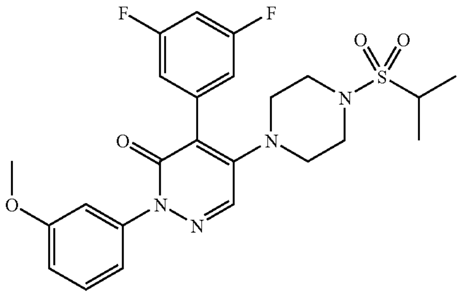 | 505 |

TABLE 5-continued
| Carbon Analogs with Sulfonamide The following compounds can be synthesized by using steps 11, 12, and 16 in Scheme 2. | | |
|---|---|---|
| Comp. No. | Structure | MS M + 1 |
| 75Z | 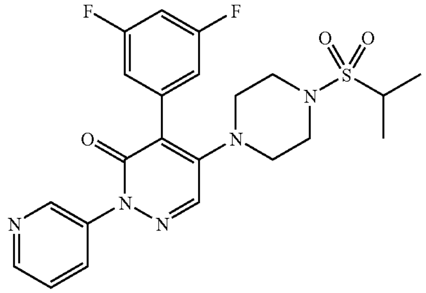 | 476 |
| 76Z | no compound | |
| 77Z | 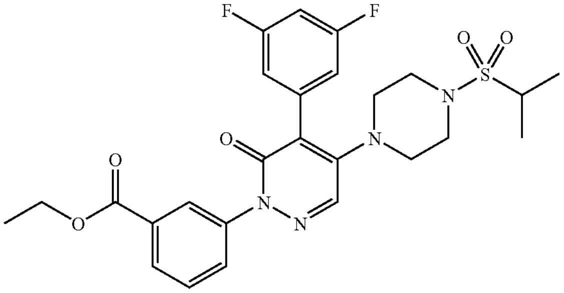 | 547 |
| 78Z | 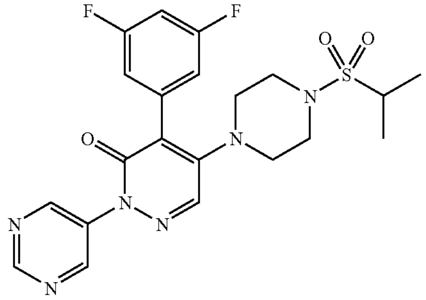 | 477 |
| 79Z | 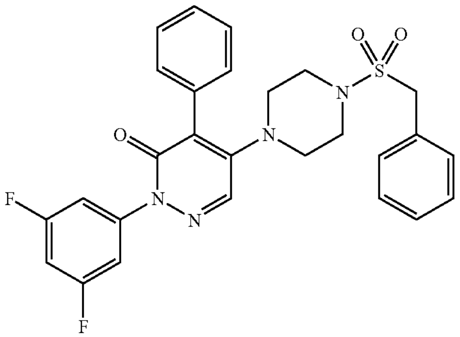 | 523 |

TABLE 5-continued
| Comp. No. | Structure | MS M + 1 |
|---|---|---|
| | Carbon Analogs with Sulfonamide<br>The following compounds can be synthesized by using steps 11, 12, and 16 in Scheme 2. | |
| 80Z | 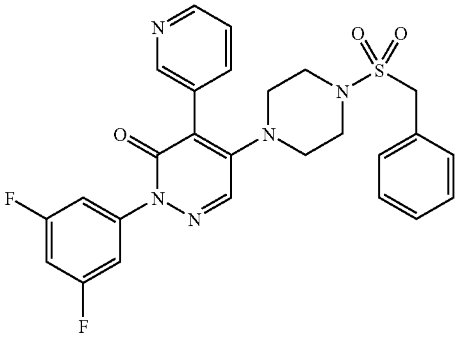 | 524 |
| 81Z | 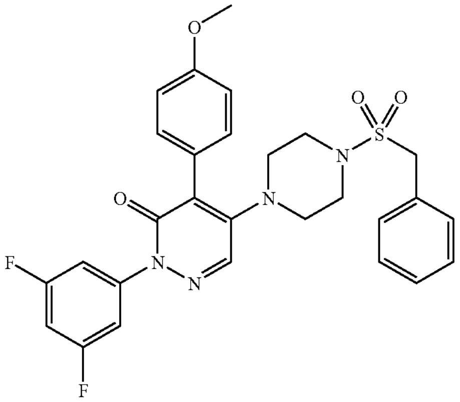 | 553 |
| 82Z | 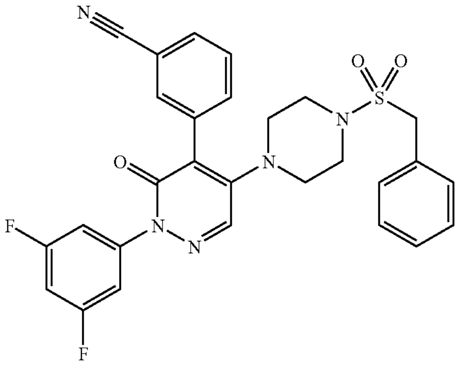 | 548 |
| 83Z | 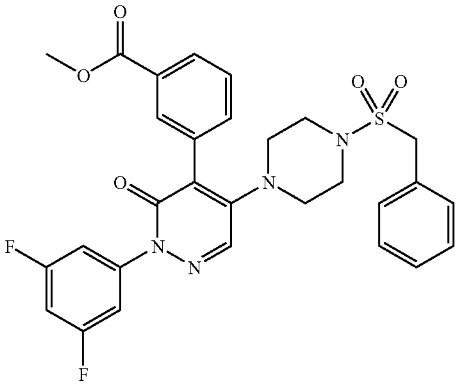 | 581 |

TABLE 5-continued
| Comp. No. | Structure | MS M + 1 |
|---|---|---|
| | Carbon Analogs with Sulfonamide<br>The following compounds can be synthesized<br>by using steps 11, 12, and 16 in Scheme 2. | |
| 84Z | 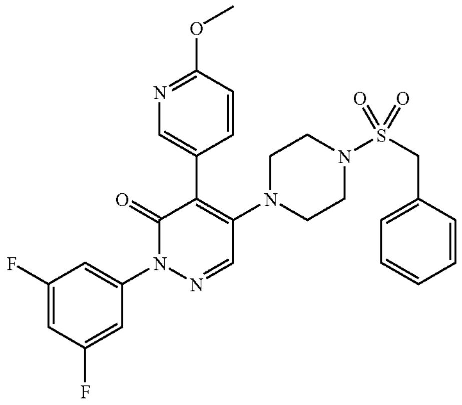 | 554 |
| 85Z | 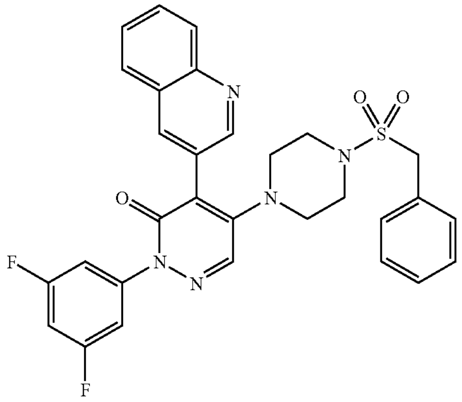 | 574 |
| 86Z | 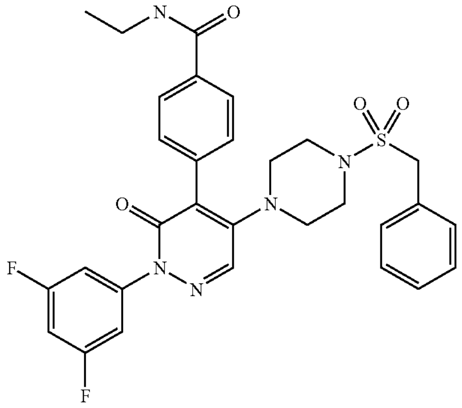 | 594 |

TABLE 5-continued
| Carbon Analogs with Sulfonamide<br>The following compounds can be synthesized<br>by using steps 11, 12, and 16 in Scheme 2. | | |
|---|---|---|
| Comp. No. | Structure | MS M + 1 |
| 87Z | 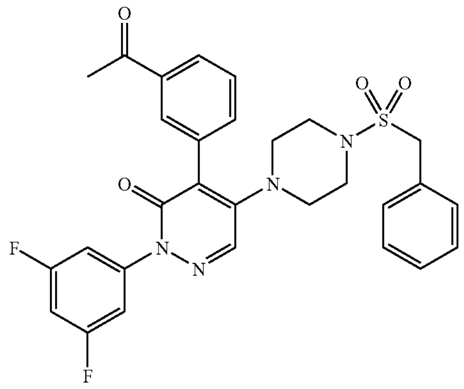 | 565 |
| 88Z | 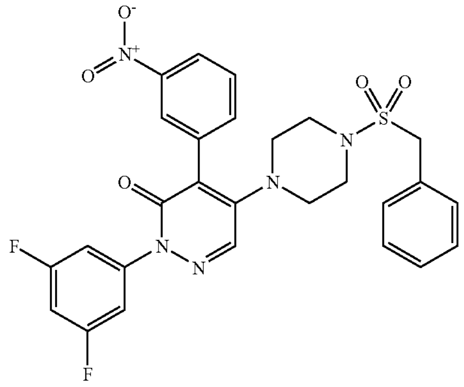 | 568 |
| 89Z | 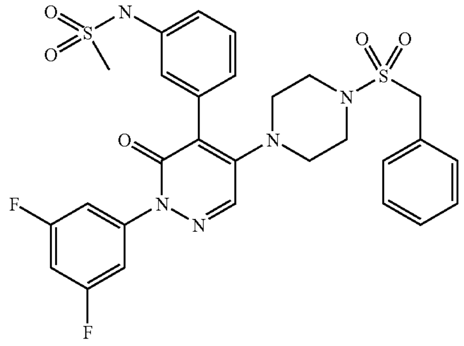 | 616 |
| 90Z | 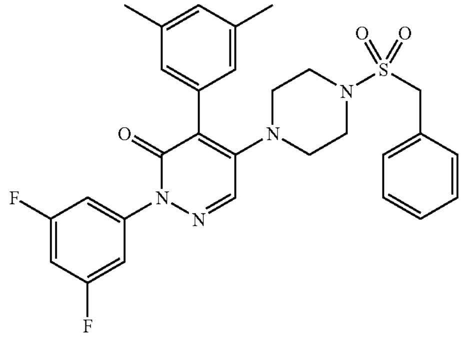 | 551 |

TABLE 5-continued
| Comp. No. | Structure | MS M + 1 |
| --- | --- | --- |
| | Carbon Analogs with Sulfonamide<br>The following compounds can be synthesized<br>by using steps 11, 12, and 16 in Scheme 2. | |
| 91Z | 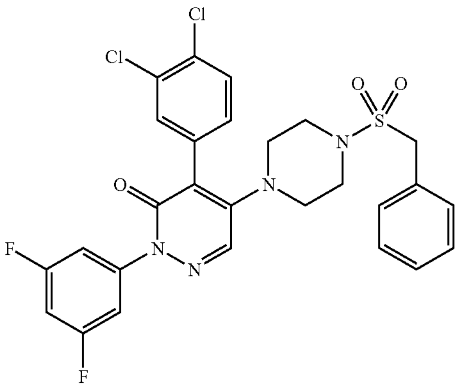 | 591 |
| 92Z | 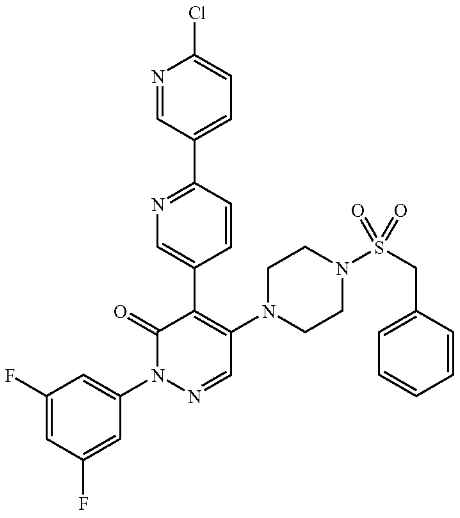 | 635 |
| 93Z | 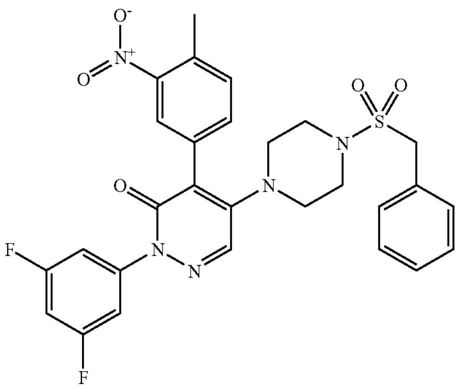 | 582 |

TABLE 5-continued
| Carbon Analogs with Sulfonamide<br>The following compounds can be synthesized<br>by using steps 11, 12, and 16 in Scheme 2. | | |
|---|---|---|
| Comp. No. | Structure | MS M + 1 |
| 94Z | 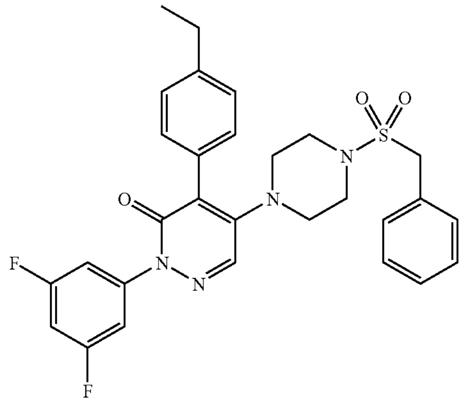 | 551 |
| 95Z | 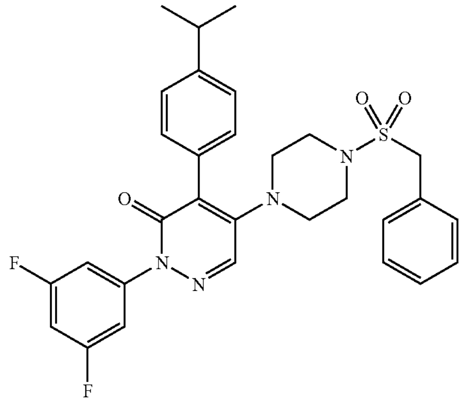 | 565 |
| 96Z | 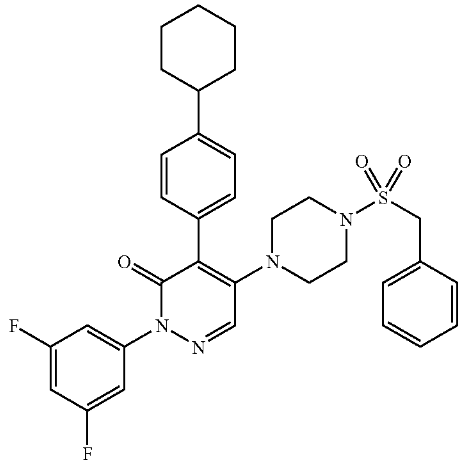 | 605 |

TABLE 5-continued
| Carbon Analogs with Sulfonamide The following compounds can be synthesized by using steps 11, 12, and 16 in Scheme 2. | | |
|---|---|---|
| Comp. No. | Structure | MS M + 1 |
| 97Z | 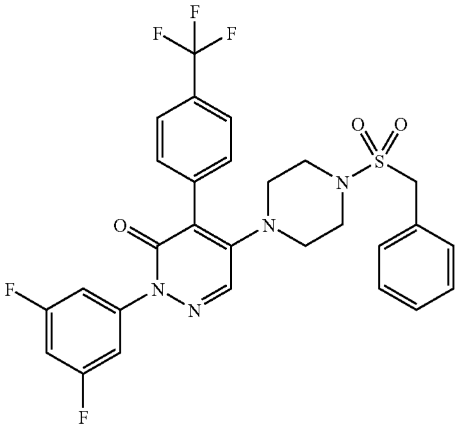 | 591 |
| 98Z | 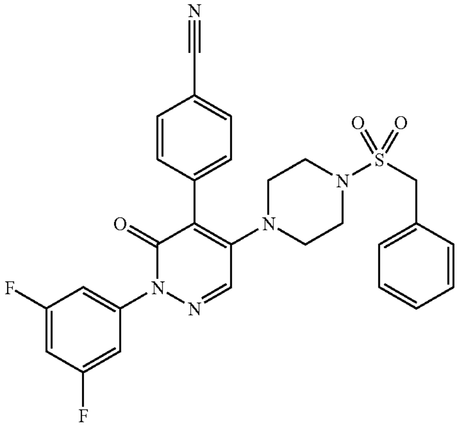 | 548 |
| 99Z | 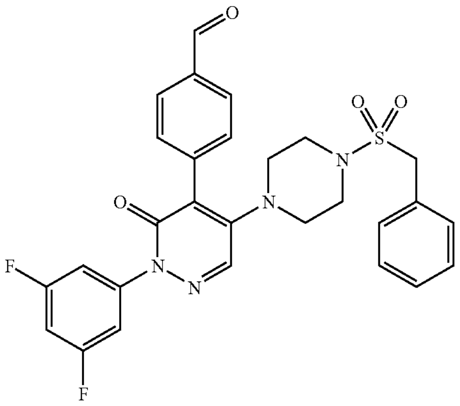 | 551 |

TABLE 5-continued
| Carbon Analogs with Sulfonamide The following compounds can be synthesized by using steps 11, 12, and 16 in Scheme 2. | | |
|---|---|---|
| Comp. No. | Structure | MS M + 1 |
| 100Z | 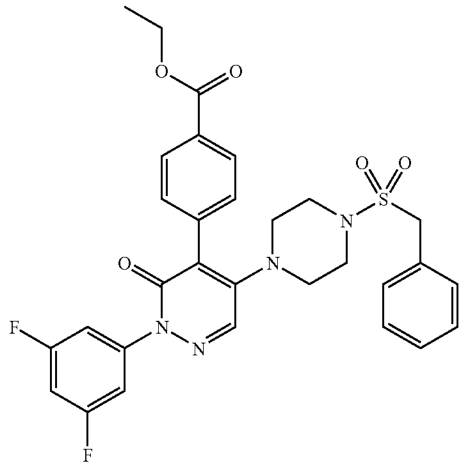 | 595 |
| 101Z | 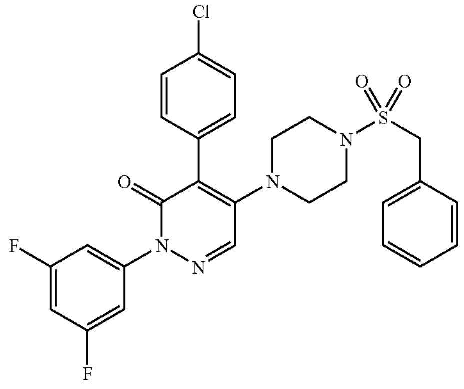 | 557 |
| 102Z | 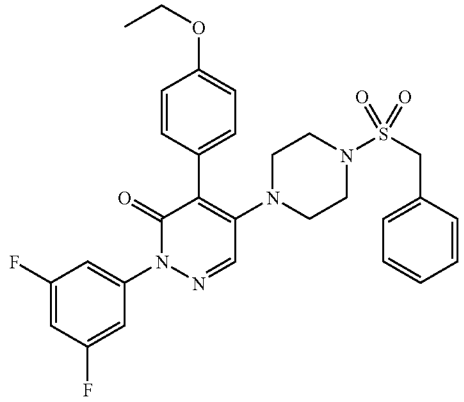 | 567 |

TABLE 5-continued
| Carbon Analogs with Sulfonamide<br>The following compounds can be synthesized<br>by using steps 11, 12, and 16 in Scheme 2. | | |
|---|---|---|
| Comp. No. | Structure | MS M + 1 |
| 103Z | 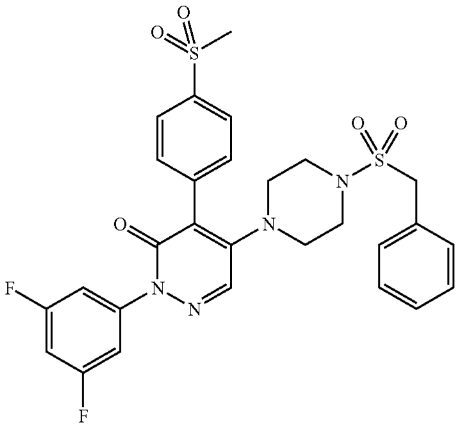 | 601 |
| 104Z | 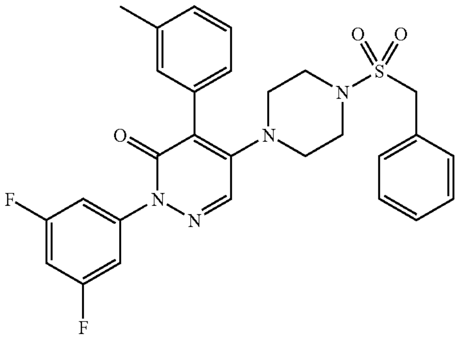 | 537 |
| 105Z | 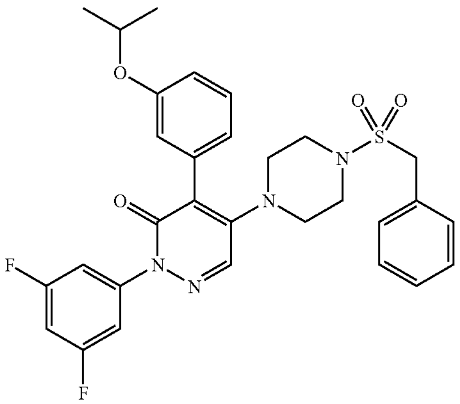 | 581 |
| 106Z | 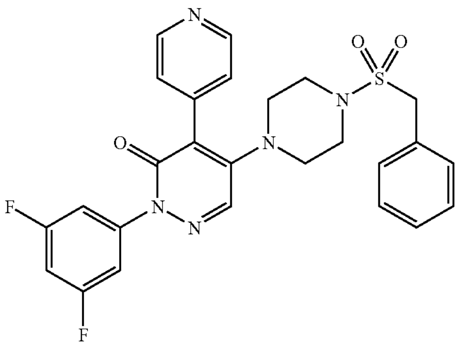 | 524 |

TABLE 5-continued
| Comp. No. | Structure | MS M + 1 |
| --- | --- | --- |
| 107Z | 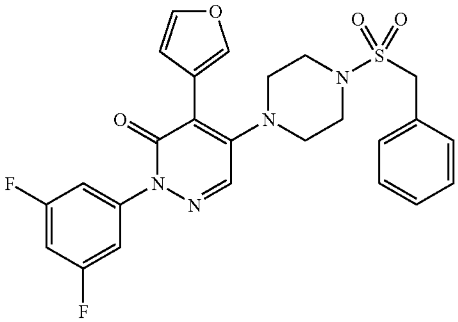 | 513 |
| 108Z | 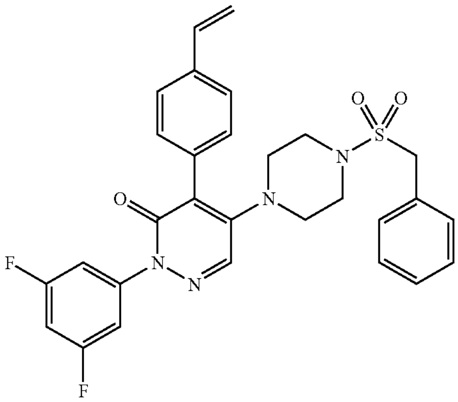 | 549 |
| 109Z | 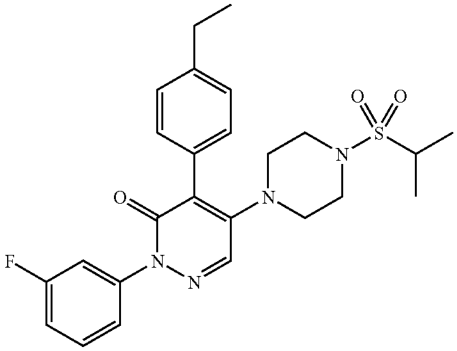 | 485 |
| 110Z | 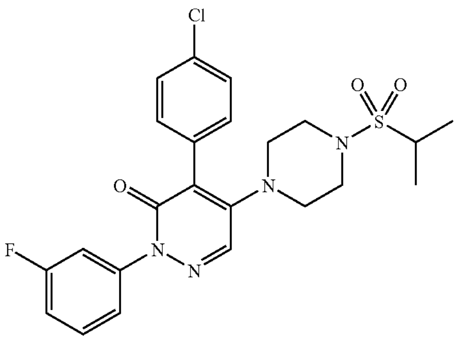 | 491 |
Carbon Analogs with Sulfonamide
The following compounds can be synthesized by using steps 11, 12, and 16 in Scheme 2.

TABLE 5-continued
| Carbon Analogs with Sulfonamide<br>The following compounds can be synthesized<br>by using steps 11, 12, and 16 in Scheme 2. | | |
|---|---|---|
| Comp. No. | Structure | MS M + 1 |
| 111Z | 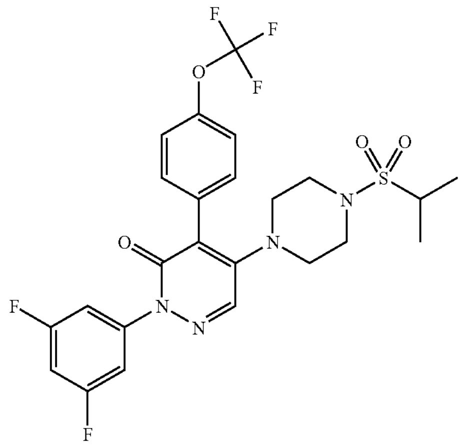 | 559 |
| 112Z | 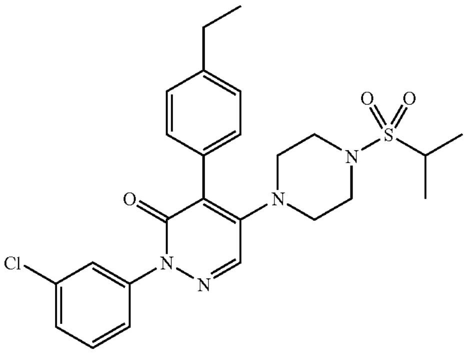 | 501 |
| 113Z | 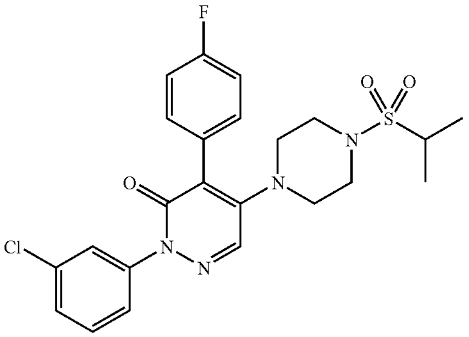 | 491 |
| 114Z | 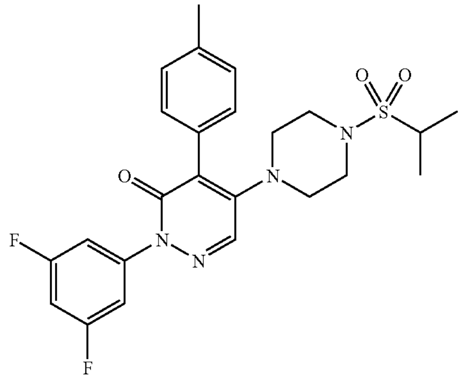 | 489 |

TABLE 5-continued
| Comp. No. | Structure | MS M + 1 |
|---|---|---|
| | Carbon Analogs with Sulfonamide<br>The following compounds can be synthesized<br>by using steps 11, 12, and 16 in Scheme 2. | |
| 115Z | 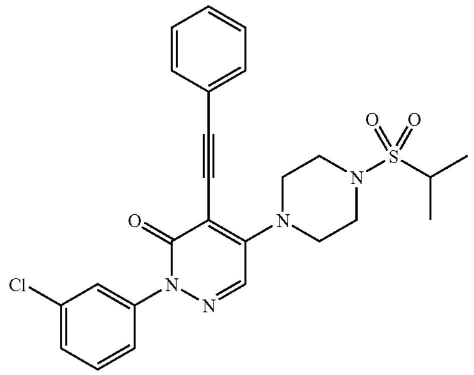 | 497 |
| 116Z | 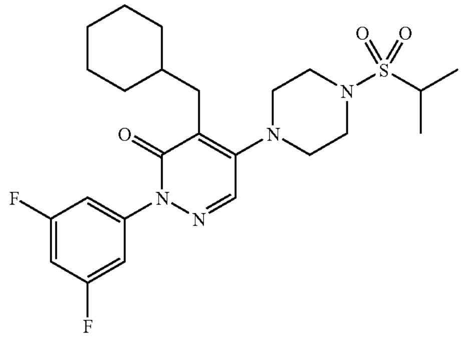 | 495 |
| 117Z | 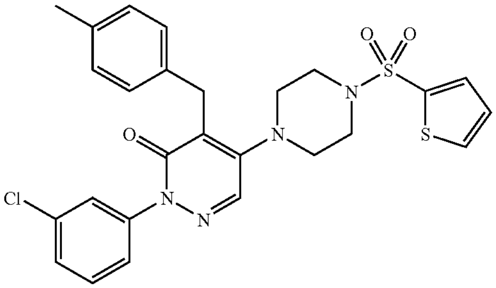 | 541 |
| 118Z | 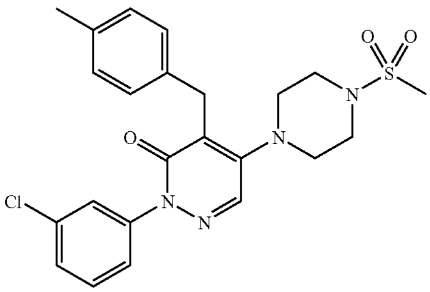 | 473 |

TABLE 5-continued
| Comp. No. | Structure | MS M + 1 |
| --- | --- | --- |
| Carbon Analogs with Sulfonamide The following compounds can be synthesized by using steps 11, 12, and 16 in Scheme 2. | | |
| 119Z | 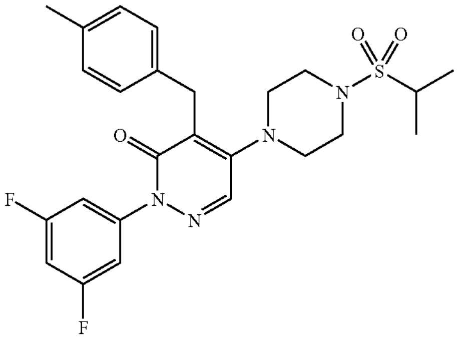 | 503 |
| 120Z | 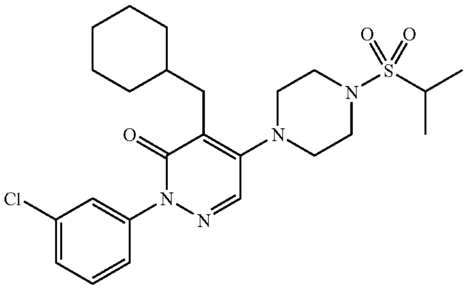 | 493 |
| 121Z | 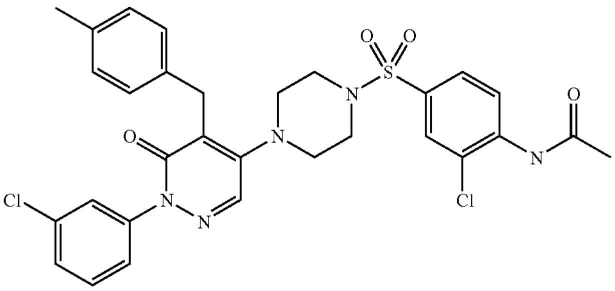 | 626 |
| 122Z | 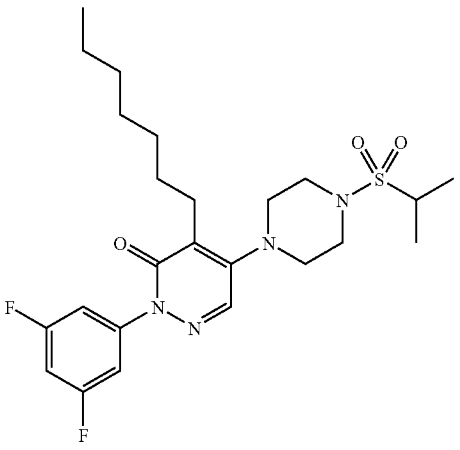 | 483 |

TABLE 5-continued
| Comp. No. | Structure | MS M + 1 |
|---|---|---|
| Carbon Analogs with Sulfonamide<br>The following compounds can be synthesized<br>by using steps 11, 12, and 16 in Scheme 2. | | |
| 123Z | 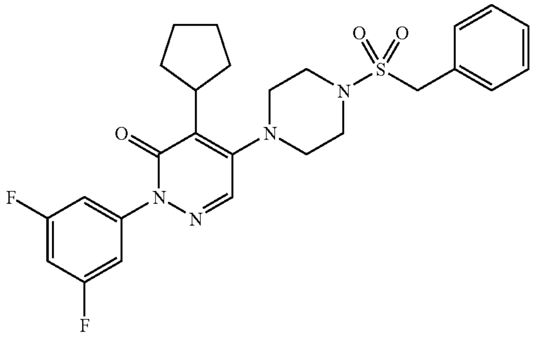 | 515 |
| 124Z | 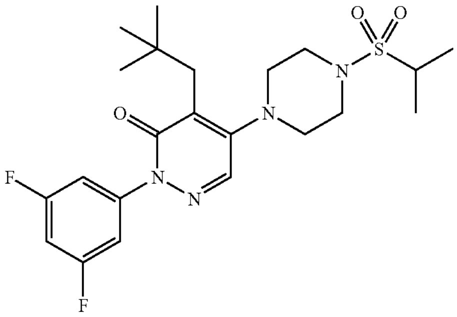 | 469 |
| 125Z | 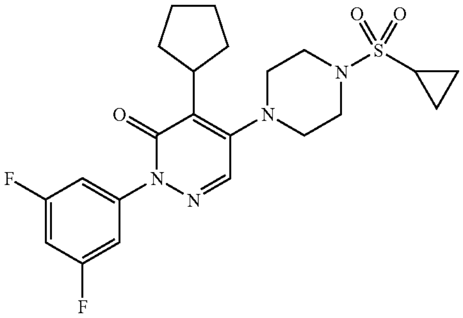 | 465 |
| 126Z | 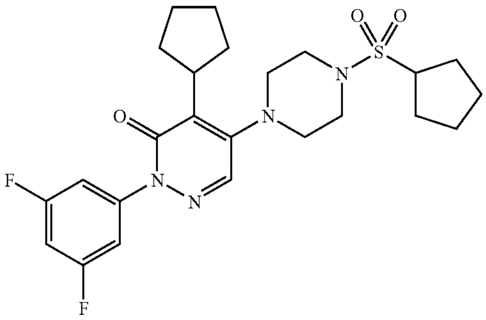 | 493 |

TABLE 5-continued
| Carbon Analogs with Sulfonamide<br>The following compounds can be synthesized<br>by using steps 11, 12, and 16 in Scheme 2. | | |
|---|---|---|
| Comp. No. | Structure | MS M + 1 |
| 127Z | 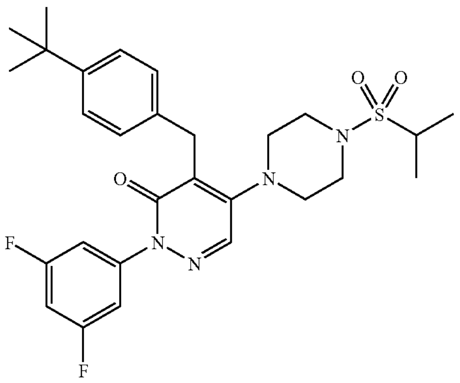 | 545 |
| 128Z | 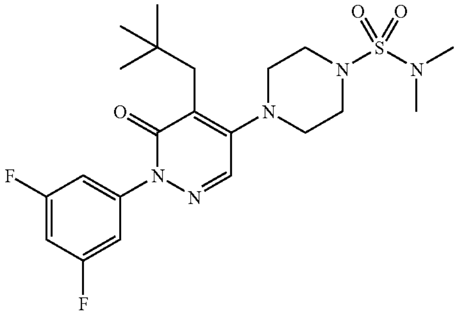 | 470 |
| 129Z | 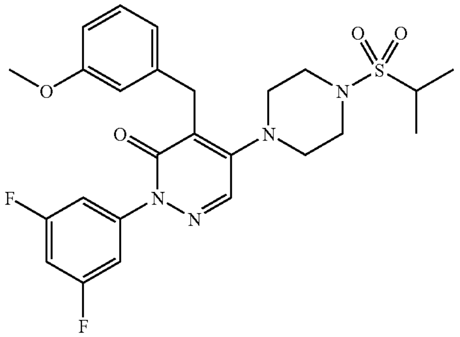 | 519 |
| 130Z | 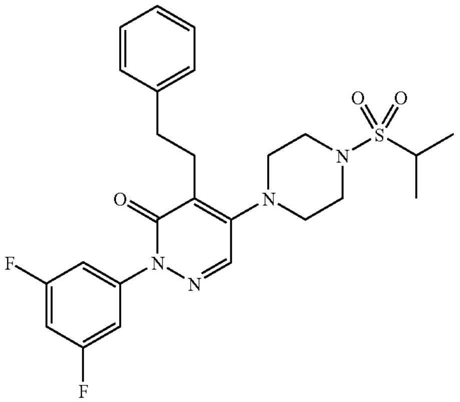 | 503 |

TABLE 5-continued
| Comp. No. | Structure | MS M + 1 |
|---|---|---|
| | Carbon Analogs with Sulfonamide The following compounds can be synthesized by using steps 11, 12, and 16 in Scheme 2. | |
| 131Z | 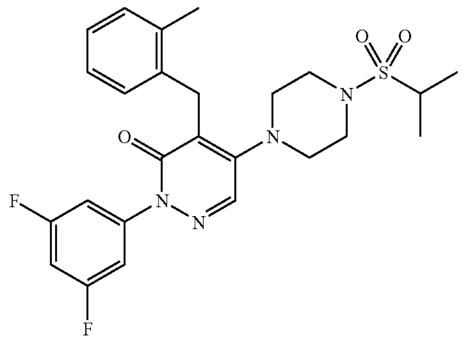 | 503 |
| 132Z | 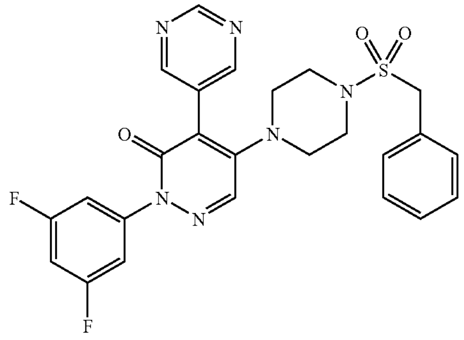 | 525 |
| 133Z | 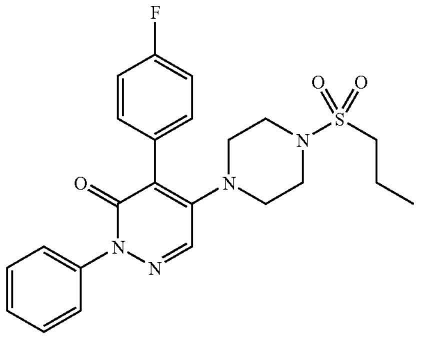 | 457 |
| 134Z | 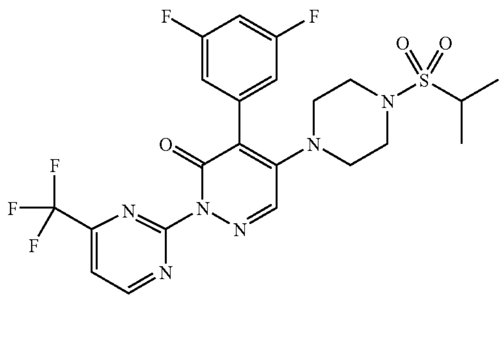 | 545 |

TABLE 5-continued
| Carbon Analogs with Sulfonamide The following compounds can be synthesized by using steps 11, 12, and 16 in Scheme 2. | | |
|---|---|---|
| Comp. No. | Structure | MS M + 1 |
| 135Z | 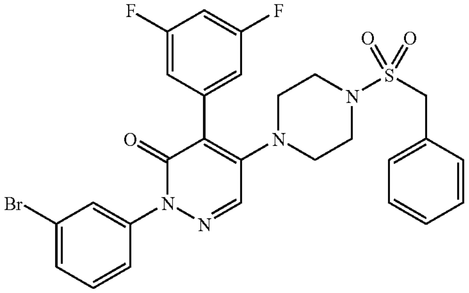 | 603 |
| 136Z | 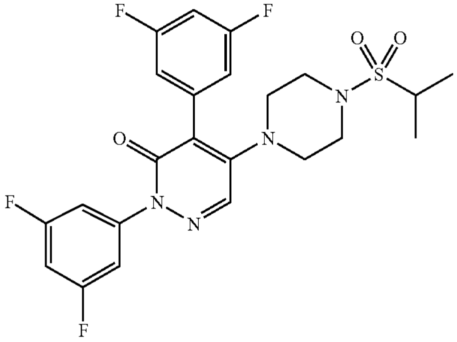 | 511 |
| 137Z | 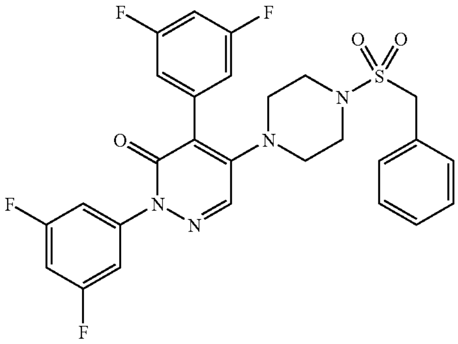 | 559 |
| 138Z | 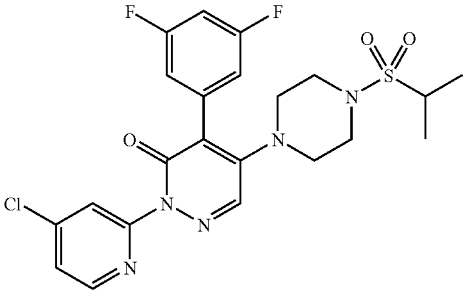 | 510 |

TABLE 5-continued
| Comp. No. | Structure | MS M + 1 |
| --- | --- | --- |
| | Carbon Analogs with Sulfonamide<br>The following compounds can be synthesized<br>by using steps 11, 12, and 16 in Scheme 2. | |
| 139Z | 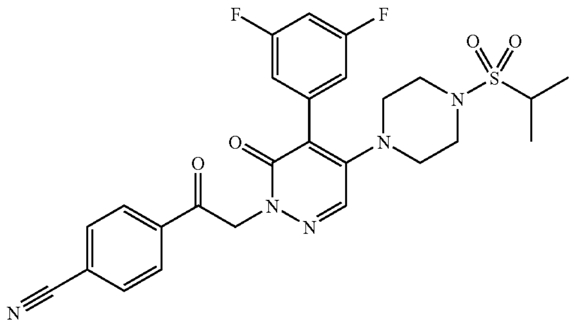 | 542 |
| 140Z | 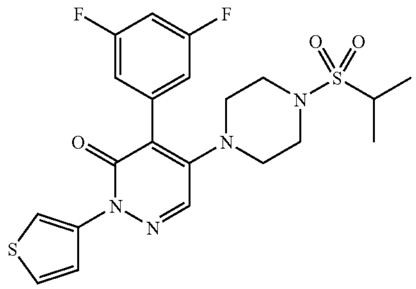 | 481 |
| 141Z | 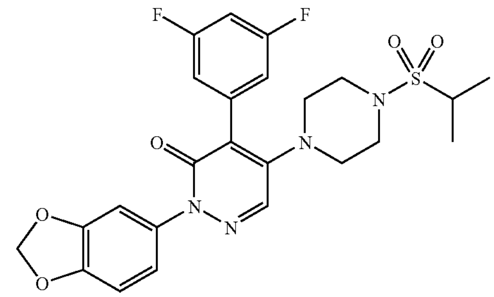 | 519 |
| 142Z | no compound | |
| 143Z | 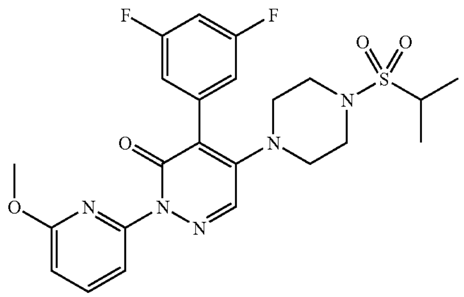 | 506 |

TABLE 5-continued
| Comp. No. | Structure | MS M + 1 |
|---|---|---|
| Carbon Analogs with Sulfonamide The following compounds can be synthesized by using steps 11, 12, and 16 in Scheme 2. | | |
| 144Z | 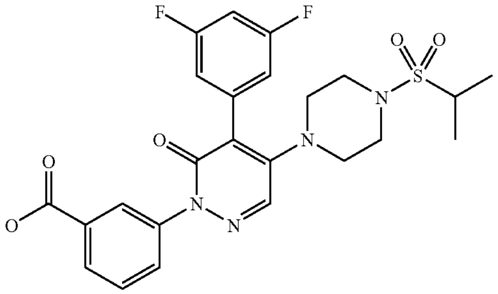 | 519 |
| 145Z | 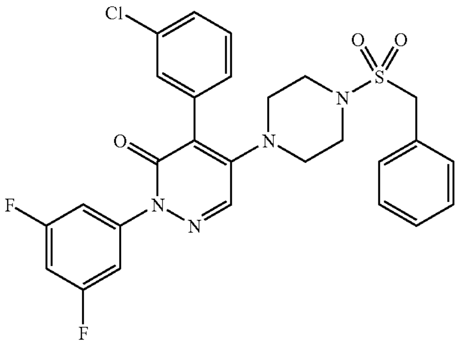 | 557 |
| 146Z | 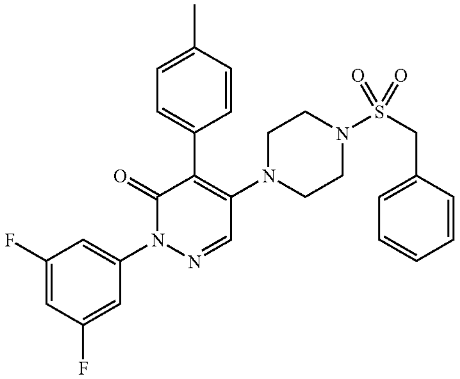 | 537 |
| 147Z | 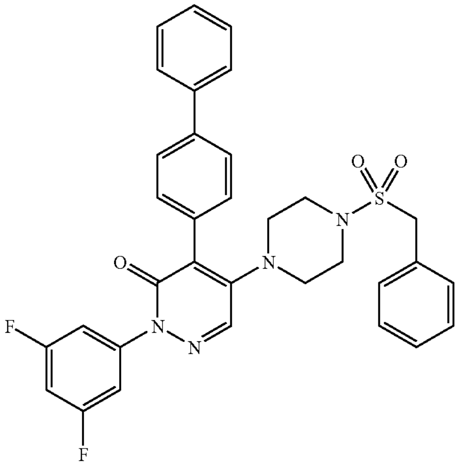 | 599 |

TABLE 5-continued
| Comp. No. | Structure | MS M + 1 |
|---|---|---|
| Carbon Analogs with Sulfonamide<br>The following compounds can be synthesized<br>by using steps 11, 12, and 16 in Scheme 2. | | |
| 148Z | 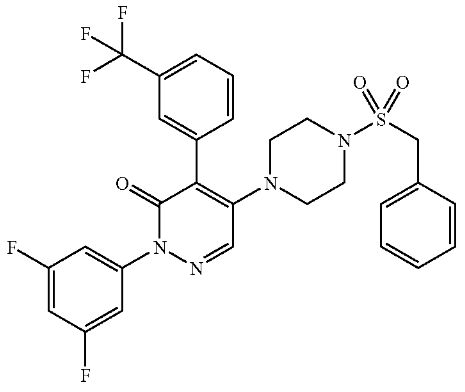 | 591 |
| 149Z | 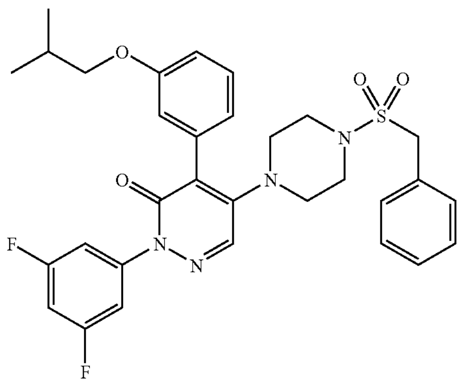 | 595 |
| 150Z | 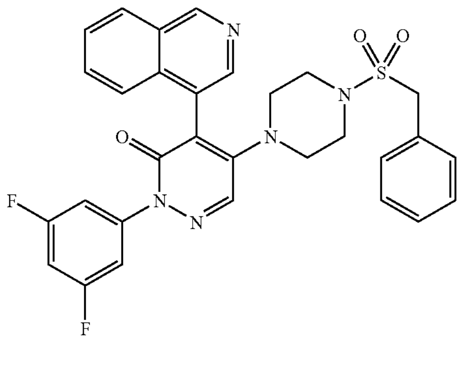 | 574 |

TABLE 5-continued
| Carbon Analogs with Sulfonamide The following compounds can be synthesized by using steps 11, 12, and 16 in Scheme 2. | | |
|---|---|---|
| Comp. No. | Structure | MS M + 1 |
| 151Z | 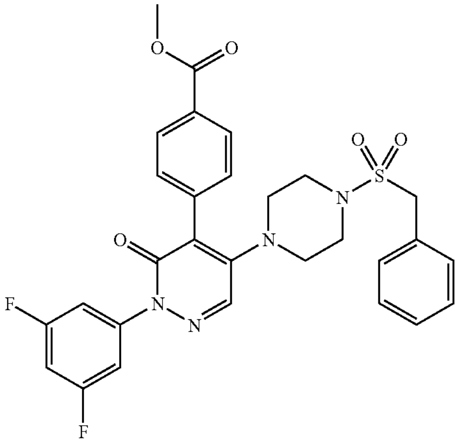 | 581 |
| 152Z | 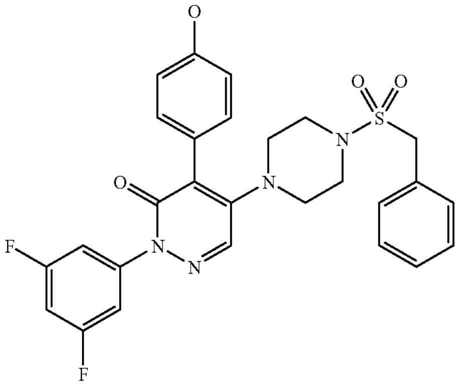 | 539 |
| 153Z | 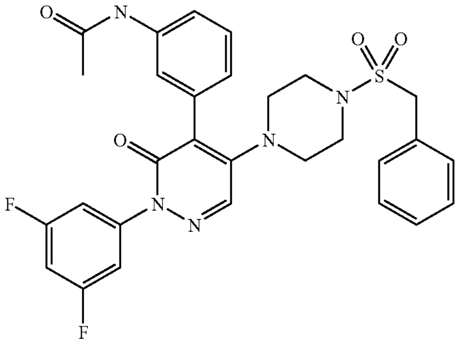 | 580 |

TABLE 5-continued
| Comp. No. | Structure | MS M + 1 |
|---|---|---|
| | Carbon Analogs with Sulfonamide The following compounds can be synthesized by using steps 11, 12, and 16 in Scheme 2. | |
| 154Z | 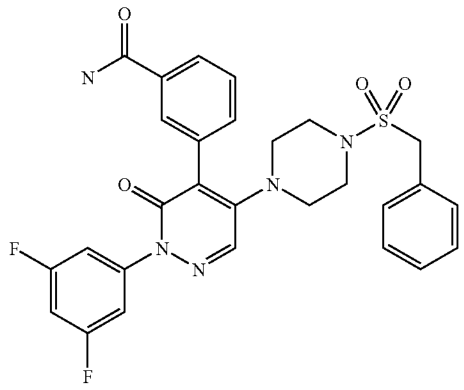 | 566 |
| 155Z | 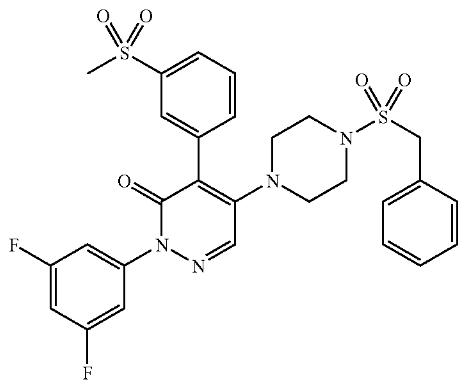 | 601 |
| 156Z | 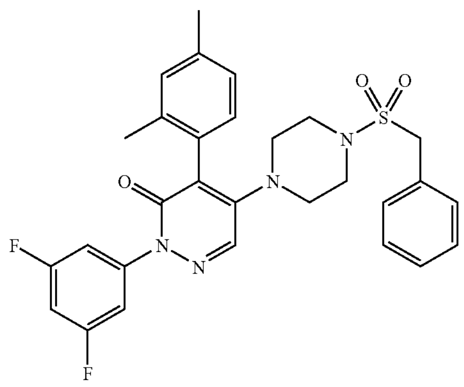 | 551 |

TABLE 5-continued
Carbon Analogs with Sulfonamide
The following compounds can be synthesized
by using steps 11, 12, and 16 in Scheme 2.
| Comp. No. | Structure | MS M + 1 |
|---|---|---|
| 157Z | 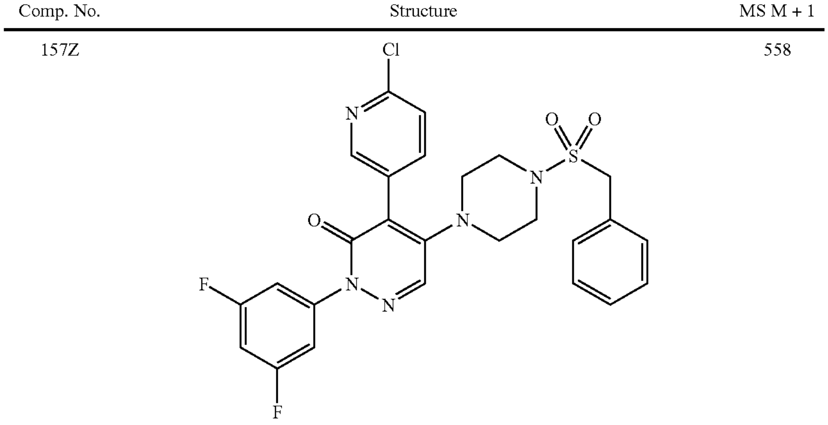 | 558 |
| 158Z | 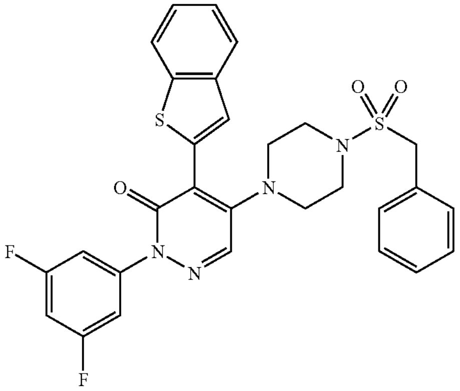 | 579 |
| 159Z | 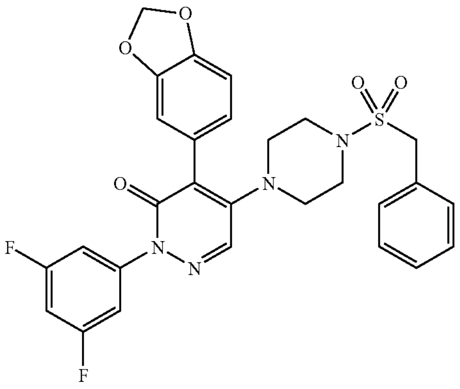 | 567 |
| 160Z | 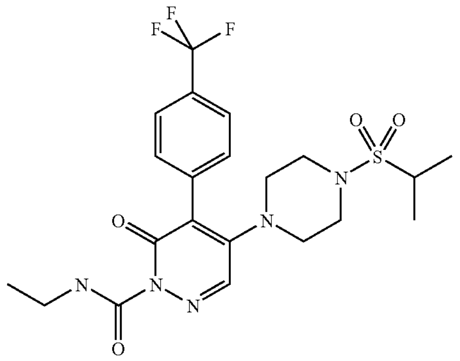 | 502 |

TABLE 5-continued
| Comp. No. | Structure | MS M + 1 |
|---|---|---|
| Carbon Analogs with Sulfonamide<br>The following compounds can be synthesized<br>by using steps 11, 12, and 16 in Scheme 2. | | |
| 161Z | 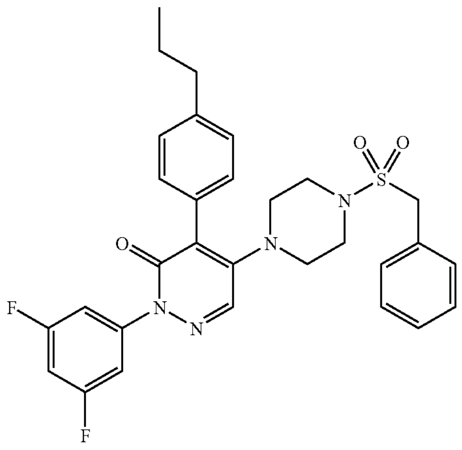 | 565 |
| 162Z | 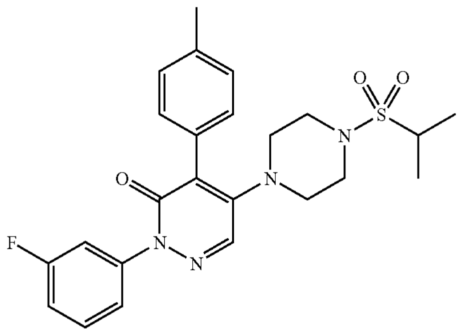 | 471 |
| 163Z | 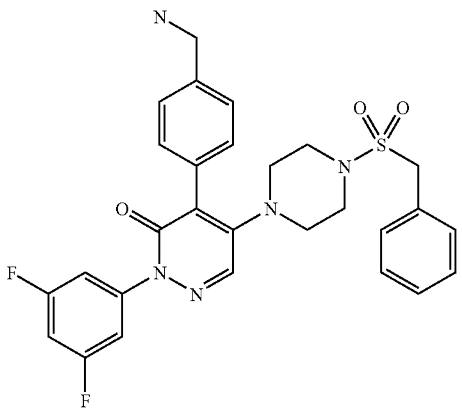 | 552 |

TABLE 5-continued
| Carbon Analogs with Sulfonamide<br>The following compounds can be synthesized<br>by using steps 11, 12, and 16 in Scheme 2. | | |
|---|---|---|
| Comp. No. | Structure | MS M + 1 |
| 164Z | 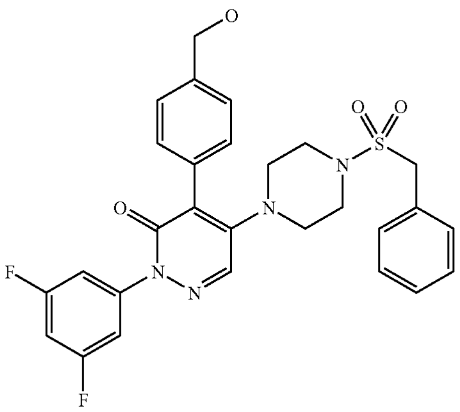 | 553 |
| 165Z | 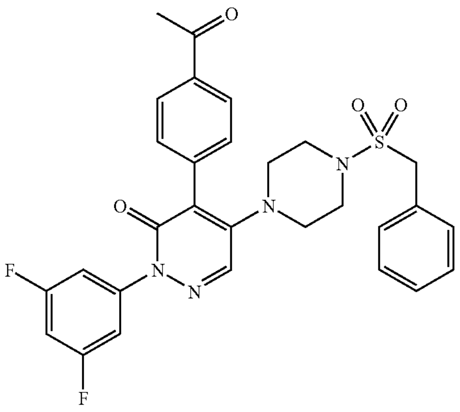 | 565 |
| 166Z | 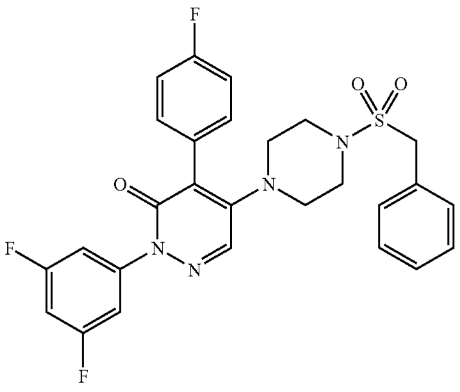 | 541 |

TABLE 5-continued
| Carbon Analogs with Sulfonamide The following compounds can be synthesized by using steps 11, 12, and 16 in Scheme 2. | | |
|---|---|---|
| Comp. No. | Structure | MS M + 1 |
| 167Z | 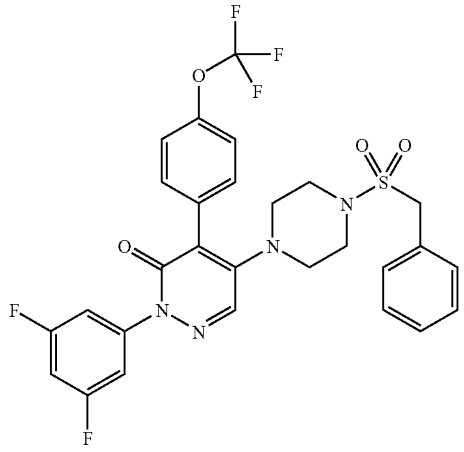 | 607 |
| 168Z | 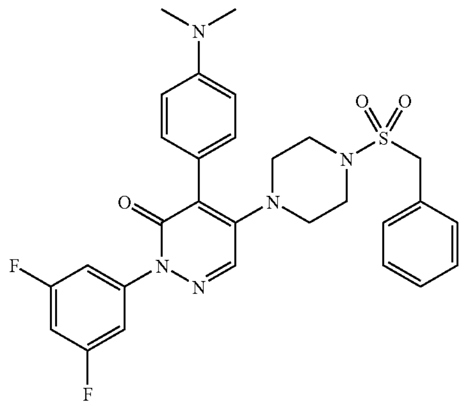 | 566 |
| 169Z | 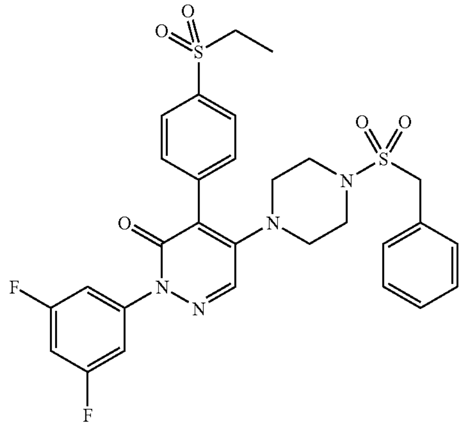 | 615 |

TABLE 5-continued
| Carbon Analogs with Sulfonamide<br>The following compounds can be synthesized<br>by using steps 11, 12, and 16 in Scheme 2. | | |
|---|---|---|
| Comp. No. | Structure | MS M + 1 |
| 170Z | 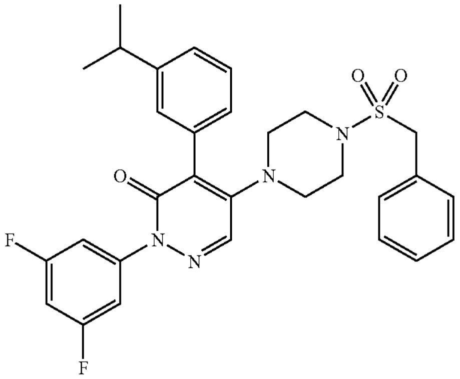 | 565 |
| 171Z | 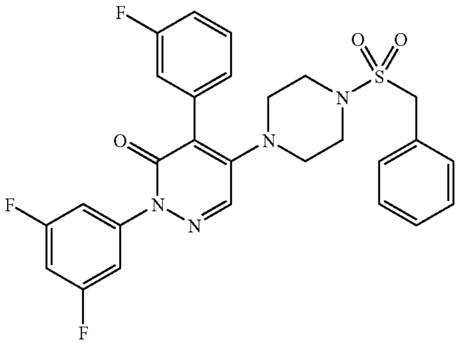 | 541 |
| 172Z | 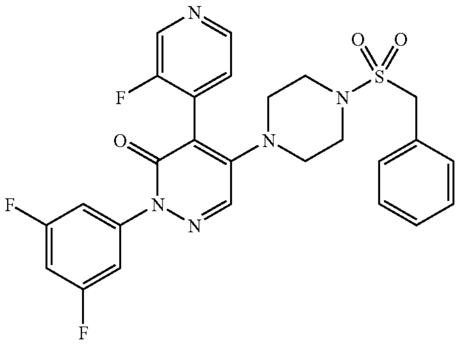 | 565 |
| 173Z | 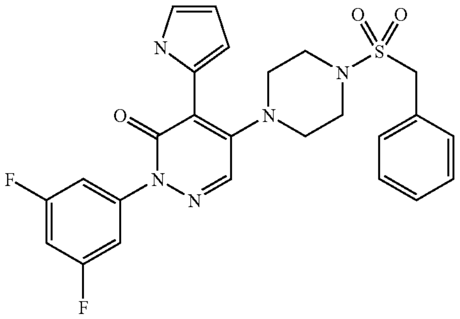 | 512 |

TABLE 5-continued
| Carbon Analogs with Sulfonamide<br>The following compounds can be synthesized<br>by using steps 11, 12, and 16 in Scheme 2. | | |
|---|---|---|
| Comp. No. | Structure | MS M + 1 |
| 174Z | 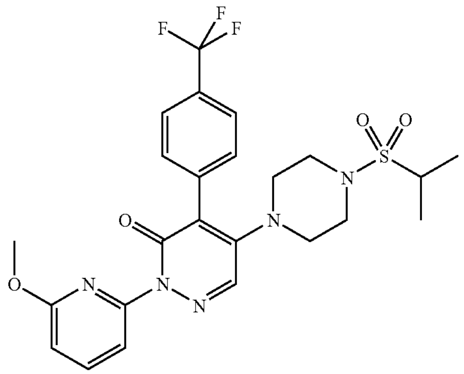 | 538 |
| 175Z | 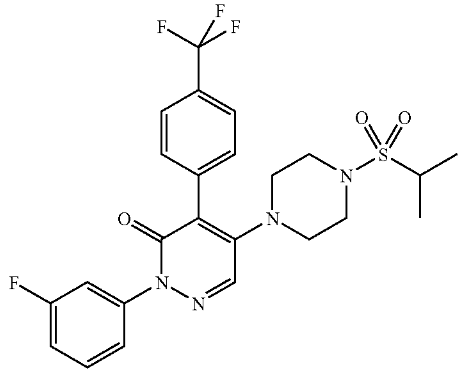 | 525 |
| 176Z | 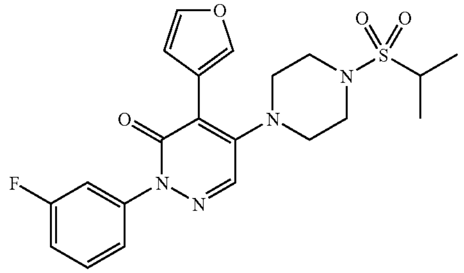 | 447 |
| 177Z | 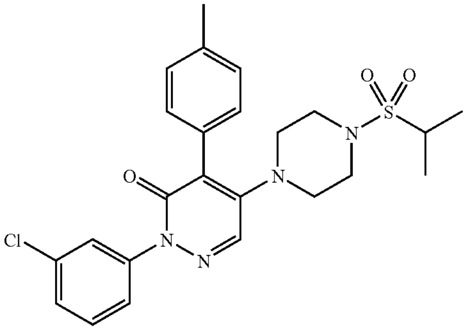 | 487 |

TABLE 5-continued
| Comp. No. | Structure | MS M + 1 |
|---|---|---|
| Carbon Analogs with Sulfonamide The following compounds can be synthesized by using steps 11, 12, and 16 in Scheme 2. | | |
| 178Z | 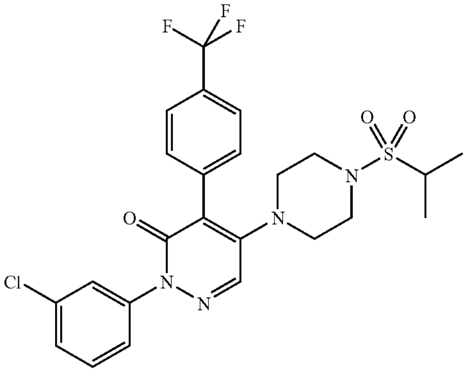 | 541 |
| 179Z | 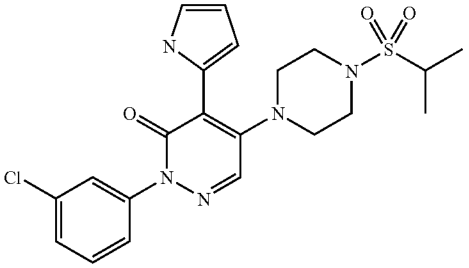 | 462 |
| 180Z | 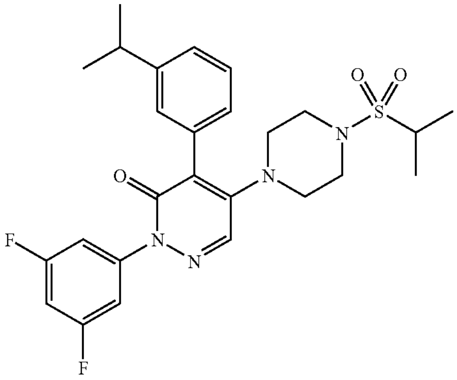 | 517 |
| 181Z | 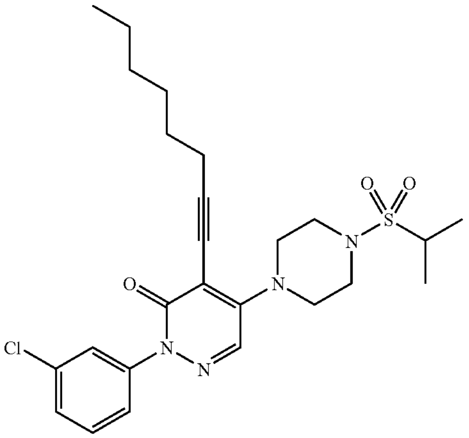 | 505 |

TABLE 5-continued
Carbon Analogs with Sulfonamide
The following compounds can be synthesized by using steps 11, 12, and 16 in Scheme 2.
| Comp. No. | Structure | MS M + 1 |
|---|---|---|
| 182Z | 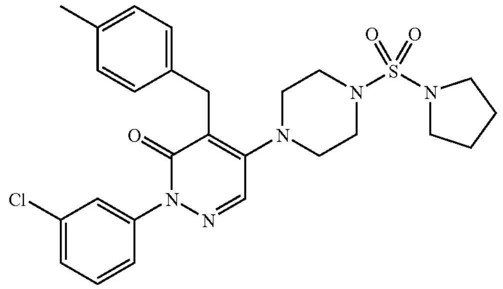 | 528 |
| 183Z | 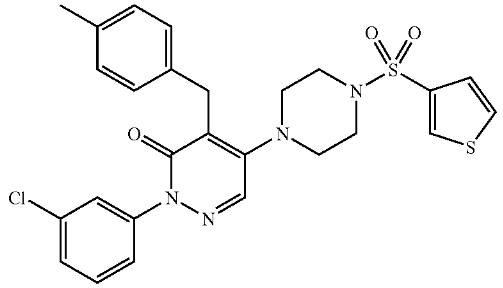 | 541 |
| 184Z | 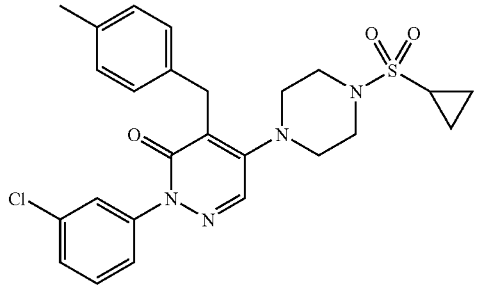 | 499 |
| 185Z | 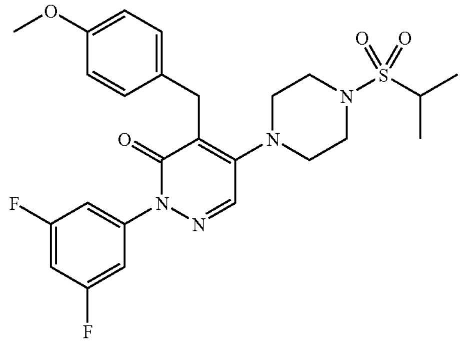 | 519 |
| 186Z | 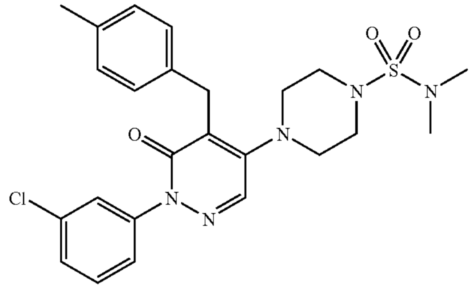 | 502 |

TABLE 5-continued
| Carbon Analogs with Sulfonamide The following compounds can be synthesized by using steps 11, 12, and 16 in Scheme 2. | | |
|---|---|---|
| Comp. No. | Structure | MS M + 1 |
| 187Z | 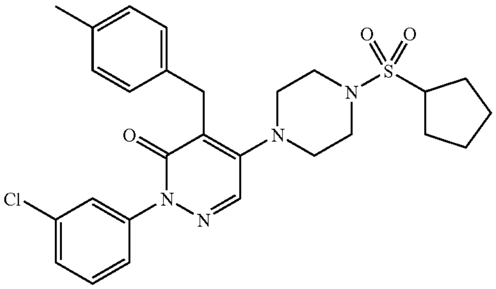 | 527 |
| 188Z | 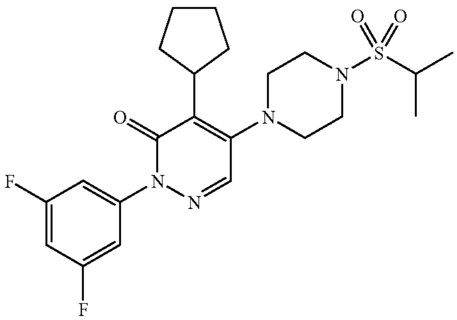 | 467 |
| 189Z | 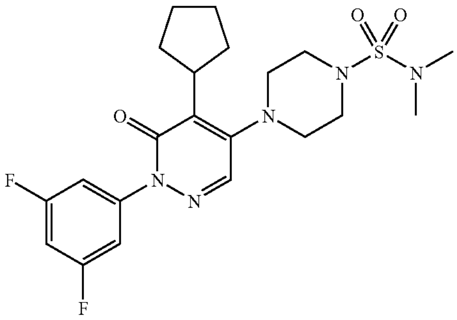 | 468 |
| 190Z | 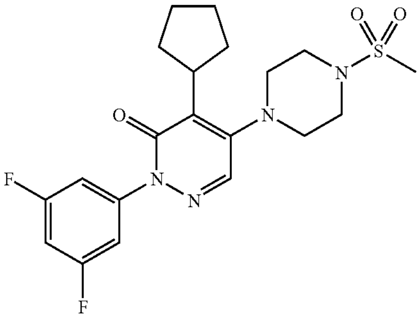 | 439 |

TABLE 5-continued
| Carbon Analogs with Sulfonamide The following compounds can be synthesized by using steps 11, 12, and 16 in Scheme 2. | | |
|---|---|---|
| Comp. No. | Structure | MS M + 1 |
| 191Z | 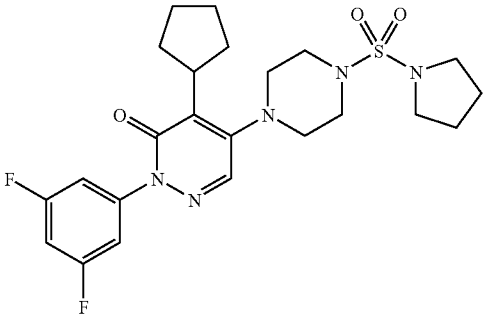 | 494 |
| 192Z | 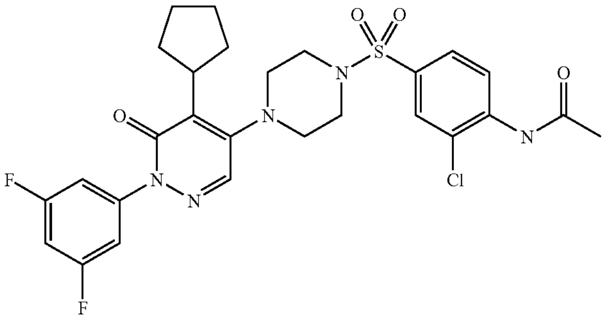 | 592 |
| 193Z | 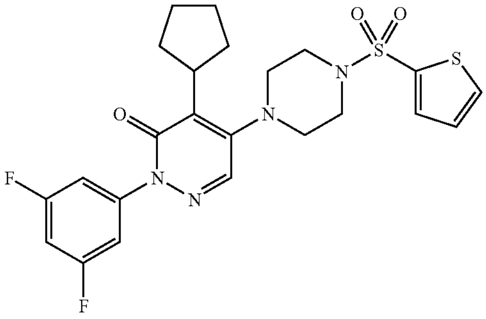 | 507 |
| 194Z | 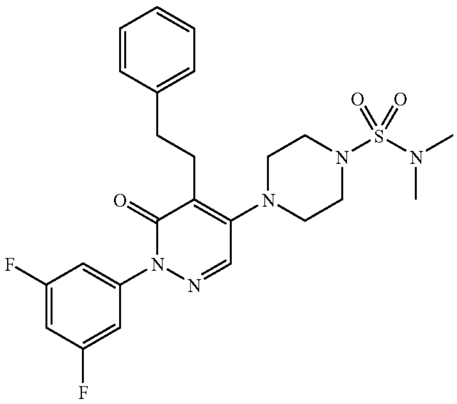 | 504 |

TABLE 5-continued
| Carbon Analogs with Sulfonamide The following compounds can be synthesized by using steps 11, 12, and 16 in Scheme 2. | | |
|---|---|---|
| Comp. No. | Structure | MS M + 1 |
| 195Z | 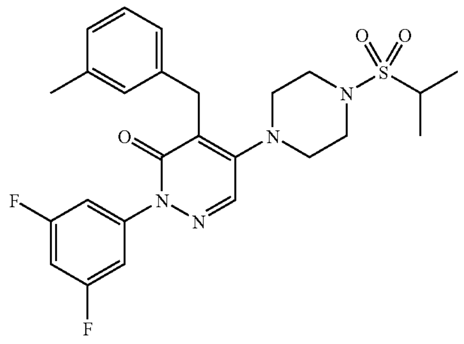 | 503 |
| 196Z | 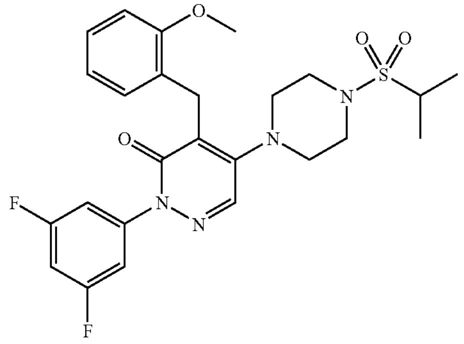 | 519 |
| 196ZA | 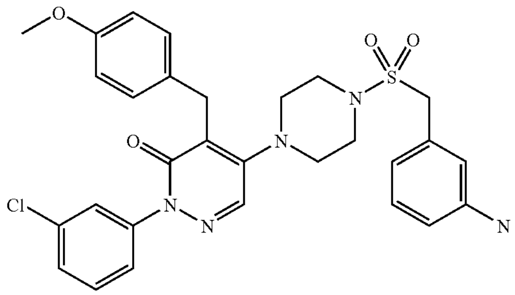 | 580 |
| 196ZB | 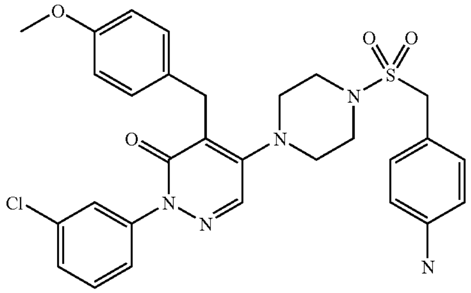 | 580 |

TABLE 5-continued
| Carbon Analogs with Sulfonamide The following compounds can be synthesized by using steps 11, 12, and 16 in Scheme 2. | | |
|---|---|---|
| Comp. No. | Structure | MS M + 1 |
| 196ZC | 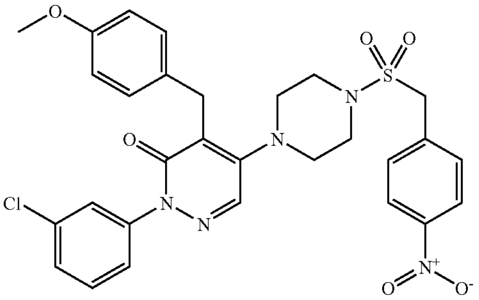 | 610 |
| 196ZD | 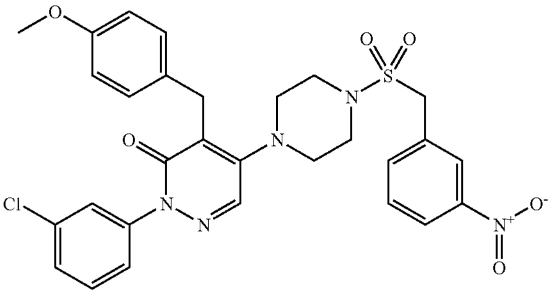 | 610 |
| 196ZE | 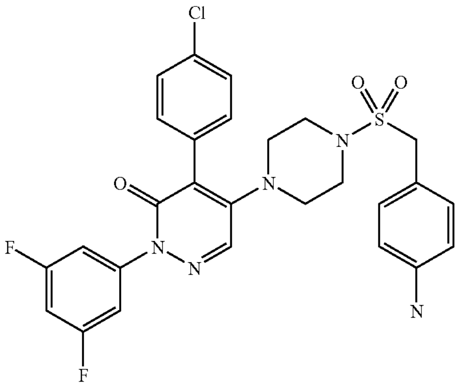 | 572 |
| 196ZF | 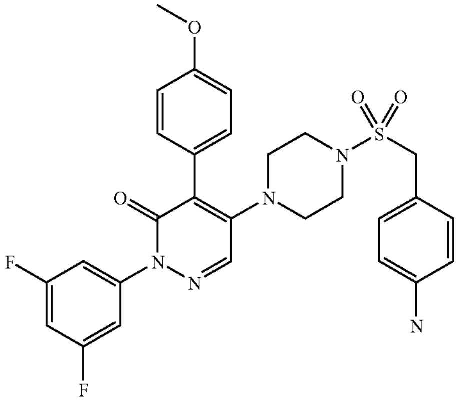 | 568 |

TABLE 5-continued
Carbon Analogs with Sulfonamide
The following compounds can be synthesized
by using steps 11, 12, and 16 in Scheme 2.
| Comp. No. | Structure | MS M + 1 |
|---|---|---|
| 196ZG | 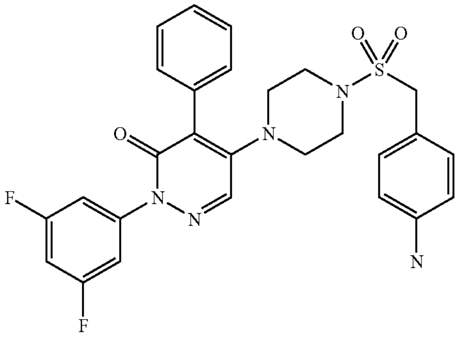 | 538 |
| 196ZH | 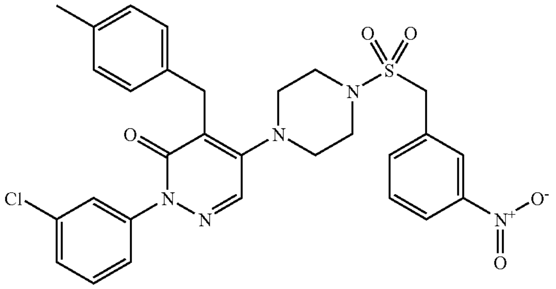 | 594 |
| 196ZI | 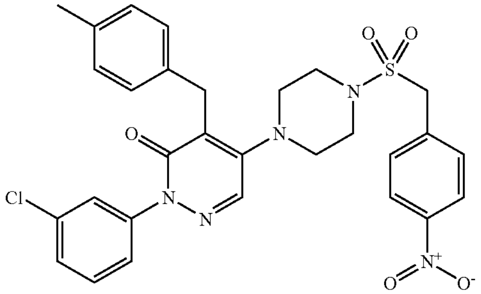 | 594 |
| 196ZJ | 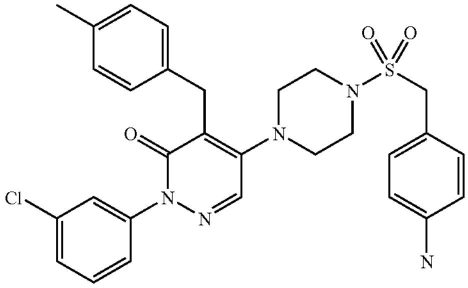 | 564 |
| 196ZK | 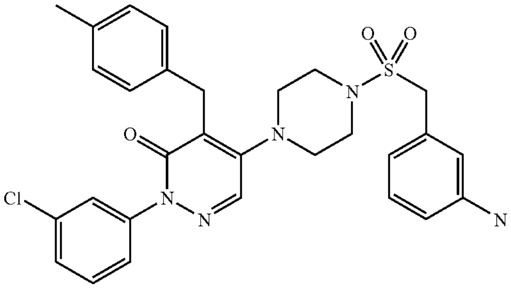 | 564 |

TABLE 5-continued
| Carbon Analogs with Sulfonamide The following compounds can be synthesized by using steps 11, 12, and 16 in Scheme 2. | | |
|---|---|---|
| Comp. No. | Structure | MS M + 1 |
| 196ZL | 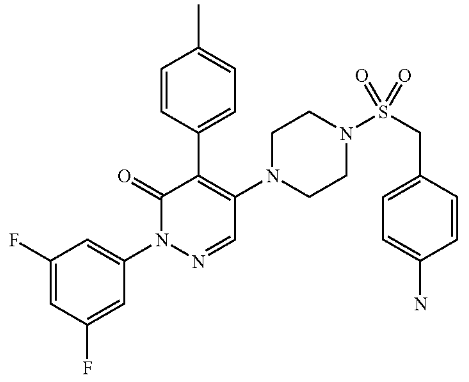 | 552 |
| 196ZM | 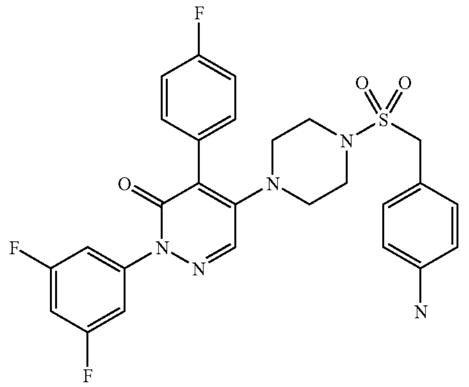 | 556 |
TABLE 6
| Oxygen Linked Analogs with Urea The following compounds can be synthesized by using steps 1, 2, 4, 6, and 8 in Scheme 1. | | |
|---|---|---|
| Comp. No. | Structure | MS M + 1 |
| 197Z | 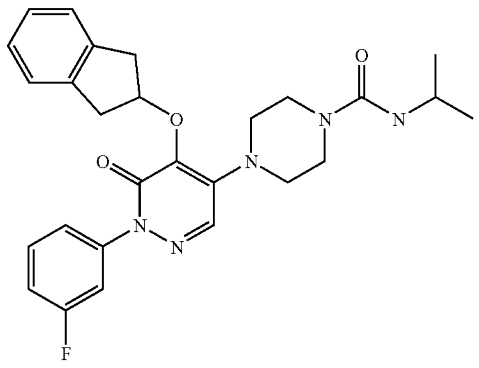 | 492 |

TABLE 6-continued
| Oxygen Linked Analogs with Urea The following compounds can be synthesized by using steps 1, 2, 4, 6, and 8 in Scheme 1. | | |
|---|---|---|
| Comp. No. | Structure | MS M + 1 |
| 198Z | 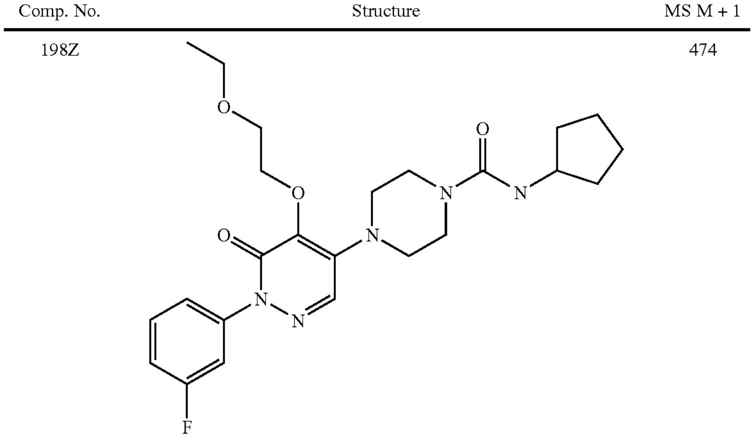 | 474 |
| 199Z | 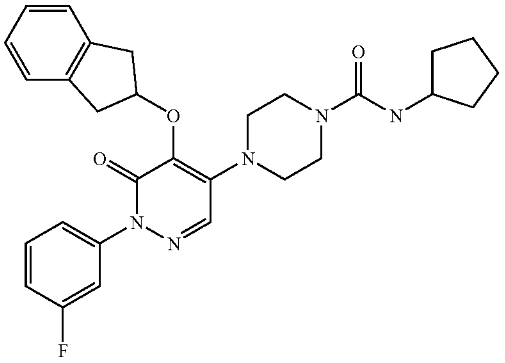 | 518 |
| 200Z | 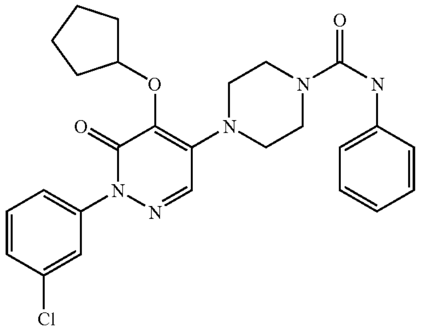 | 494 |
| 201Z | 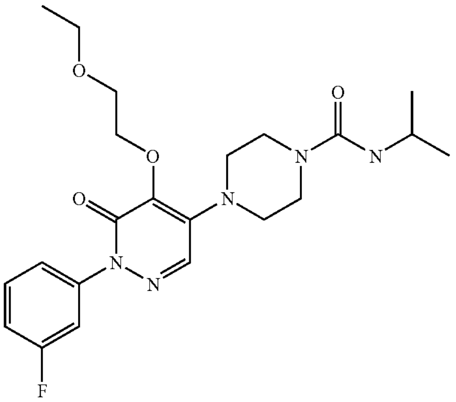 | 448 |

TABLE 6-continued
| Oxygen Linked Analogs with Urea The following compounds can be synthesized by using steps 1, 2, 4, 6, and 8 in Scheme 1. | | |
|---|---|---|
| Comp. No. | Structure | MS M + 1 |
| 202Z | 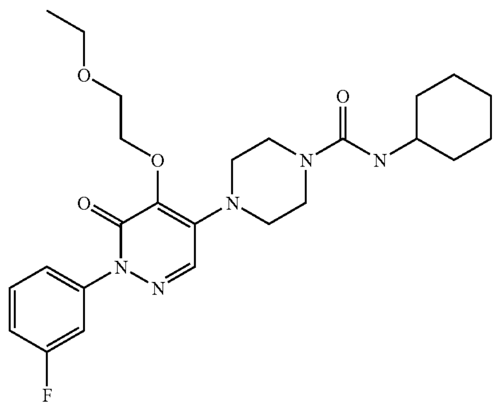 | 488 |
| 203Z | 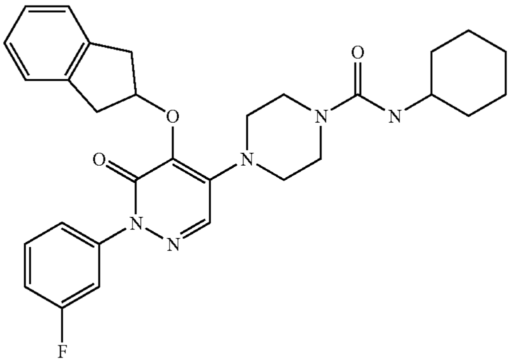 | 532 |
| 204Z | 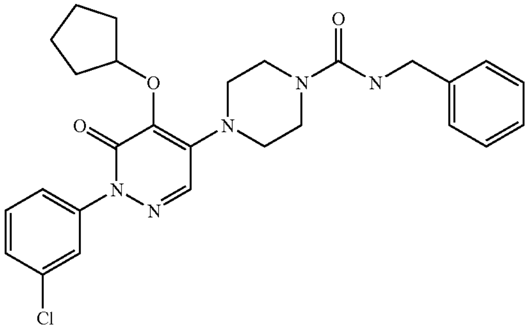 | 508 |

TABLE 6-continued
| Oxygen Linked Analogs with Urea The following compounds can be synthesized by using steps 1, 2, 4, 6, and 8 in Scheme 1. | | |
|---|---|---|
| Comp. No. | Structure | MS M + 1 |
| 204Za | 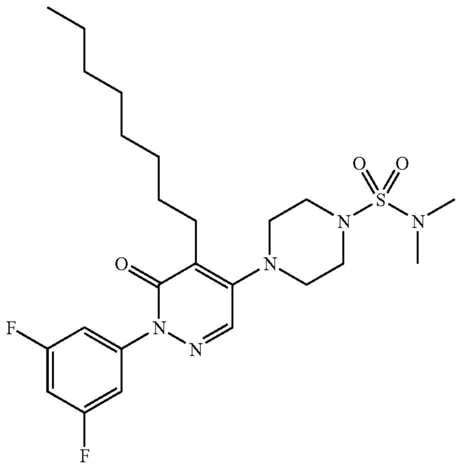 | 512 |
| 204Zb | 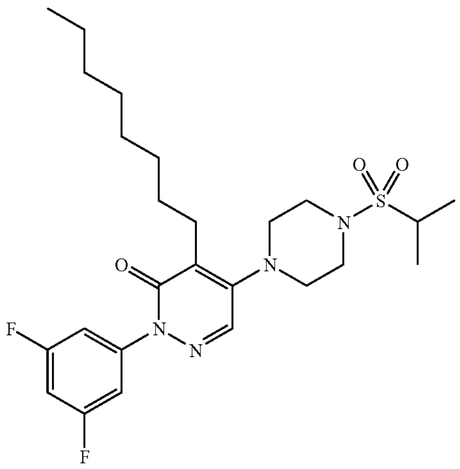 | 511 |
| 204Zc | 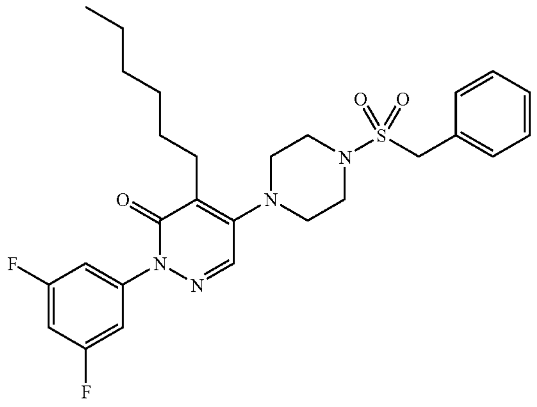 | 531 |

TABLE 6-continued
Oxygen Linked Analogs with Urea
The following compounds can be synthesized by using steps 1, 2, 4, 6, and 8 in Scheme 1.
| Comp. No. | Structure | MS M + 1 |
|---|---|---|
| 204Zd | 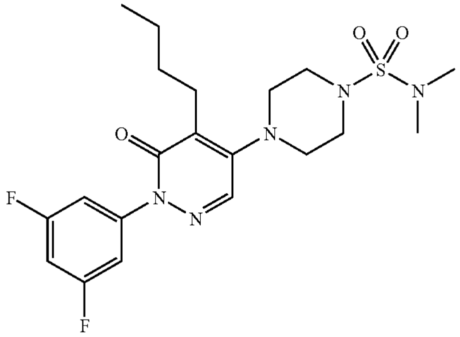 | 456 |
| 204Ze | 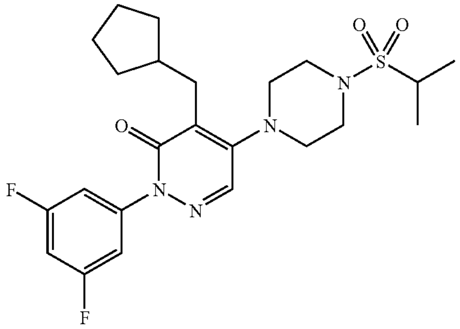 | 481 |
| 204Zf | 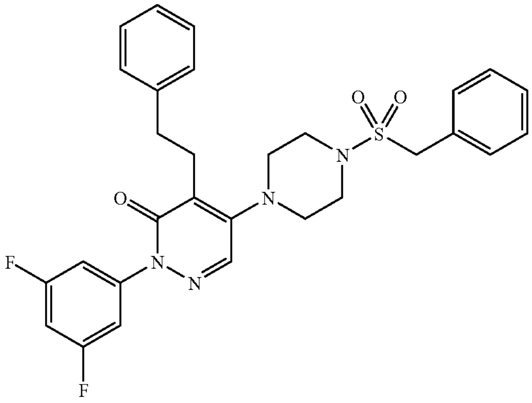 | 551 |
| 204Zg | 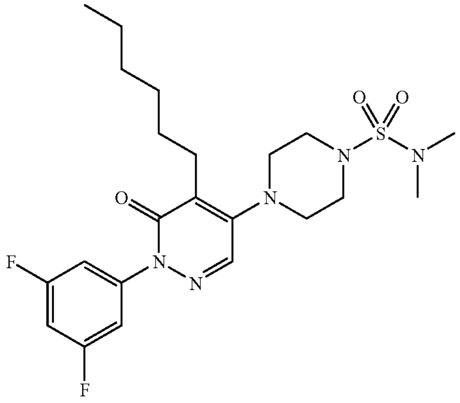 | 484 |

TABLE 6-continued
| Oxygen Linked Analogs with Urea The following compounds can be synthesized by using steps 1, 2, 4, 6, and 8 in Scheme 1. | | |
|---|---|---|
| Comp. No. | Structure | MS M + 1 |
| 204Zh | 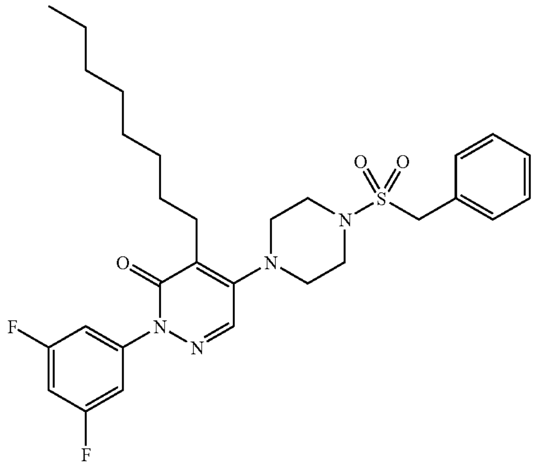 | 559 |
| 204Zi | 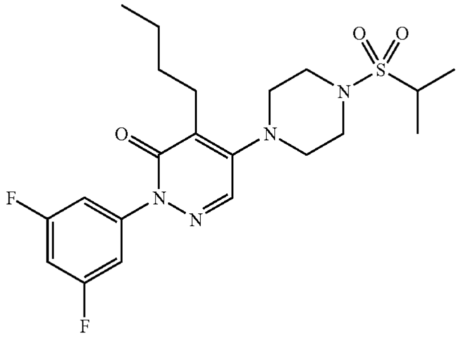 | 455 |
| 204Zj | 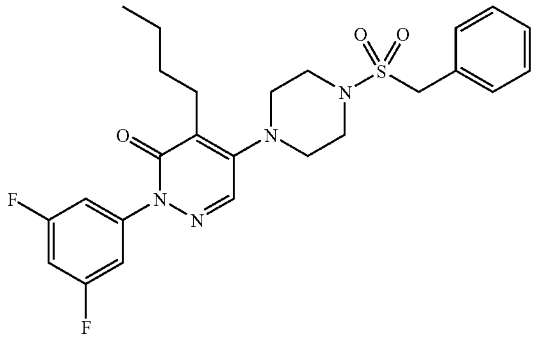 | 503 |
| 204Zk | 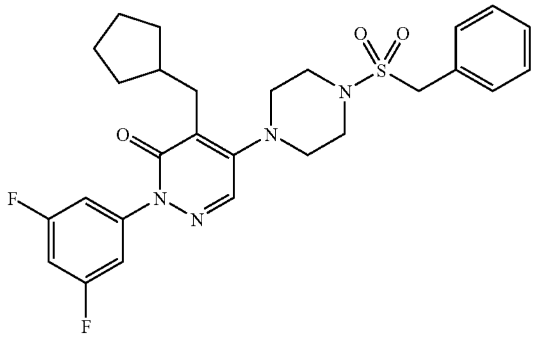 | 529 |

TABLE 7
| Oxygen Analogs with Amine<br>The following compounds can be synthesized<br>by using steps 1, 2, 4, 6, and 10 in Scheme 1. | | |
|---|---|---|
| Comp. No. | Structure | MS M + 1 |
| 205Z | 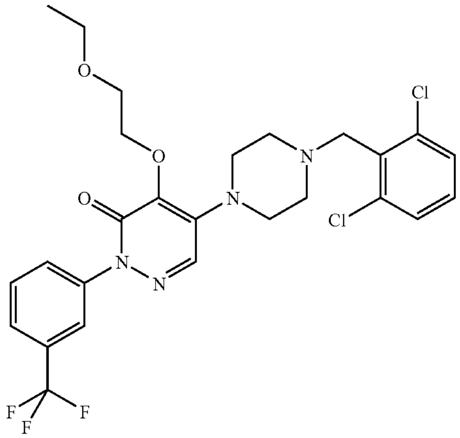 | 571 |
| 206Z | 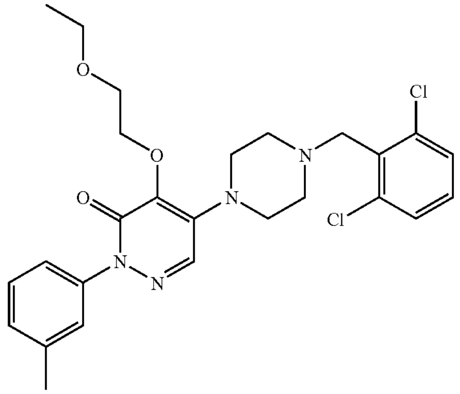 | 517 |
| 207Z | 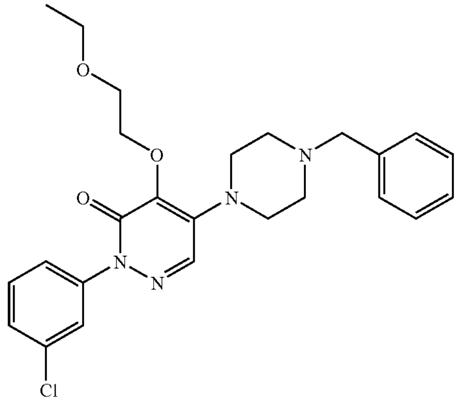 | 469 |

TABLE 7-continued
| Comp. No. | Structure | MS M + 1 |
|---|---|---|
| Oxygen Analogs with Amine<br>The following compounds can be synthesized<br>by using steps 1, 2, 4, 6, and 10 in Scheme 1. | | |
| 208Z | 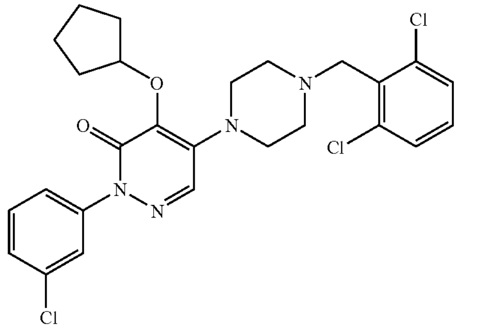 | 533 |
| 209Z | 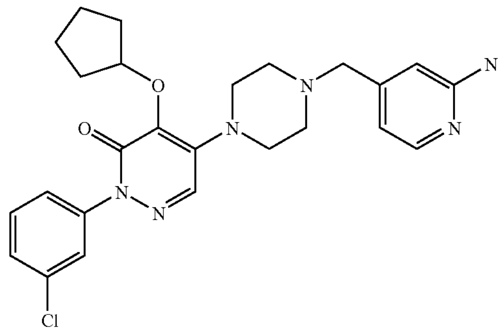 | 481 |
| 210Z | 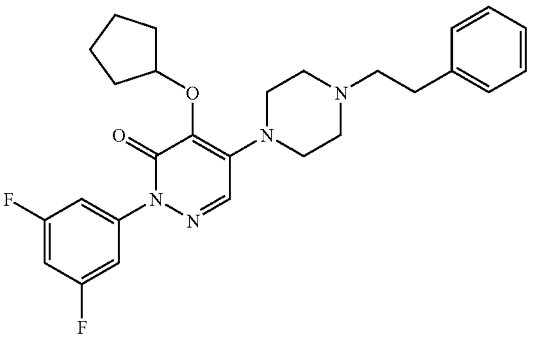 | 481 |
| 211Z | 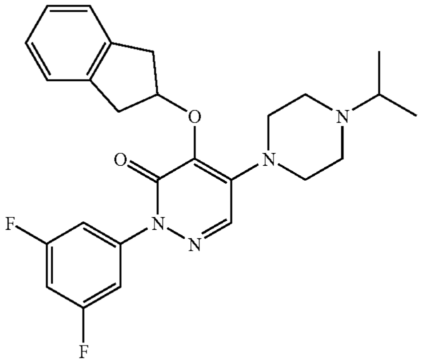 | 467 |

TABLE 7-continued
| Oxygen Analogs with Amine The following compounds can be synthesized by using steps 1, 2, 4, 6, and 10 in Scheme 1. | | |
|---|---|---|
| Comp. No. | Structure | MS M + 1 |
| 212Z | 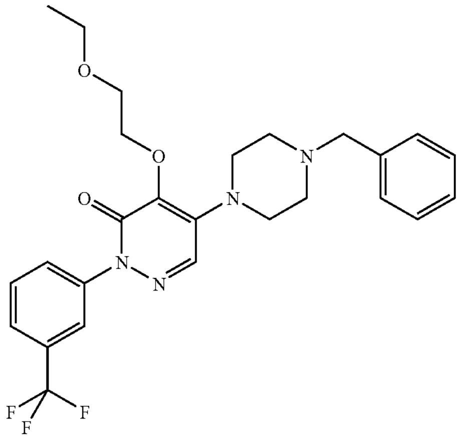 | 503 |
| 213Z | 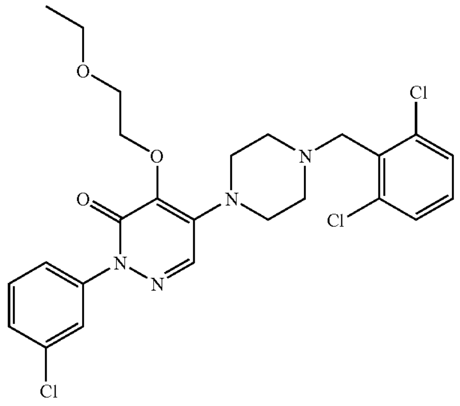 | 539 |
| 214Z | 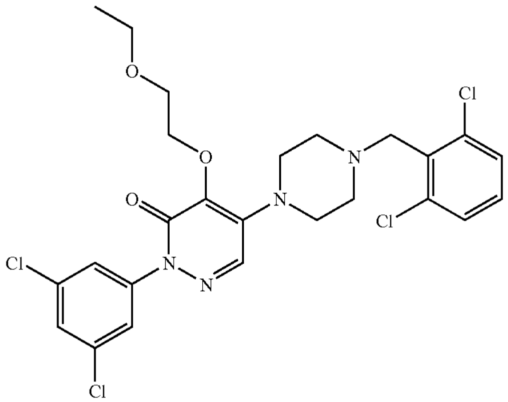 | 573 |

TABLE 7-continued
Oxygen Analogs with Amine
The following compounds can be synthesized by using steps 1, 2, 4, 6, and 10 in Scheme 1.
| Comp. No. | Structure | MS M + 1 |
|---|---|---|
| 215Z | 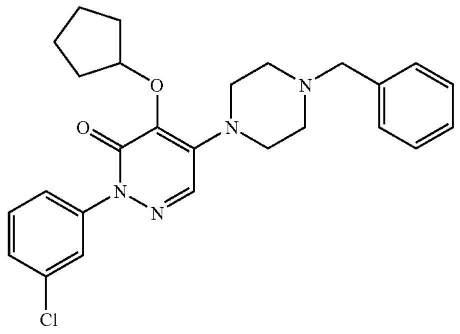 | 465 |
| 216Z | 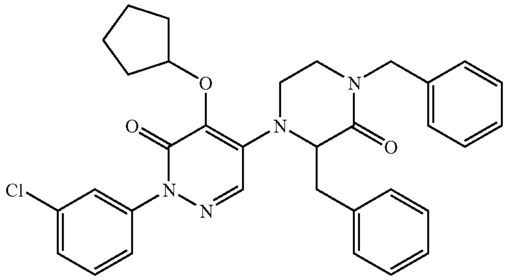 | 570 |
| 217Z | 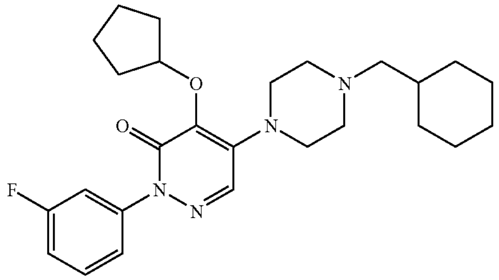 | 455 |
| 217ZA | 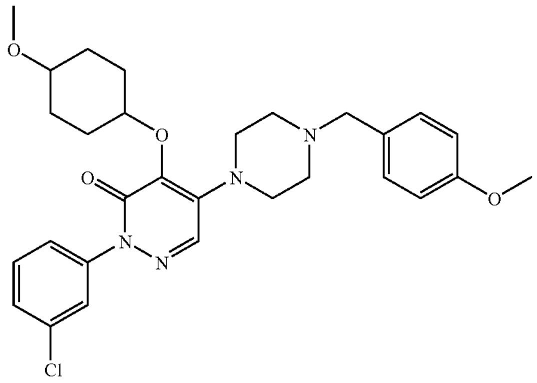 | 539 |

TABLE 8
| Comp. No. | Oxygen Linked Analogs with Amide<br>The following compounds can be synthesized by using steps 1, 2, 4, 6, and 7 in Scheme 1.<br>Structure | MS M + 1 |
|---|---|---|
| 218Z | 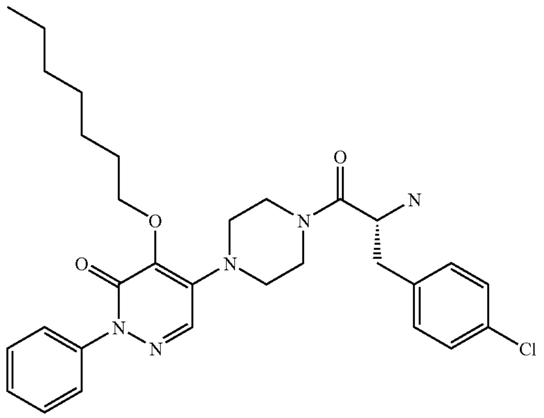 | 552 |
| 219Z | 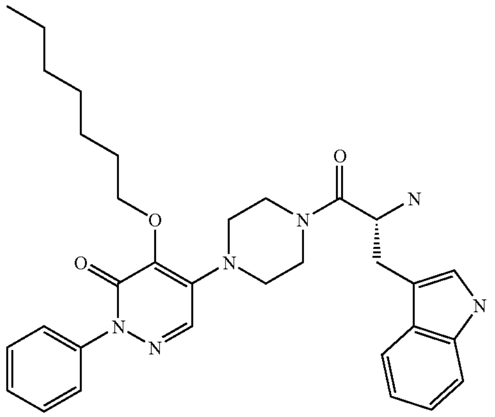 | 557 |
| 220Z | 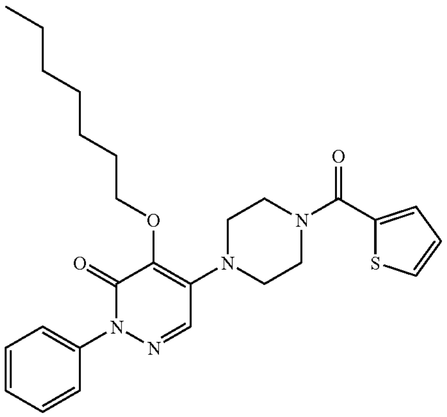 | 481 |

TABLE 8-continued
| Comp. No. | Structure | MS M + 1 |
| --- | --- | --- |
| Oxygen Linked Analogs with Amide. The following compounds can be synthesized by using steps 1, 2, 4, 6, and 7 in Scheme 1. | | |
| 221Z | 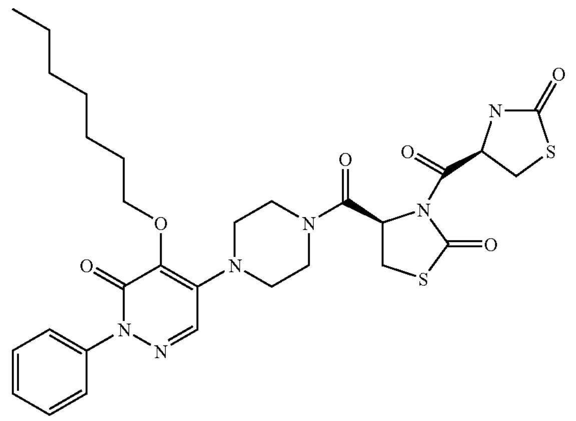 | 629 |
| 222Z | 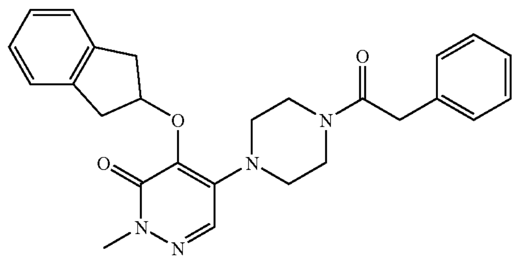 | 445 |
| 223Z | 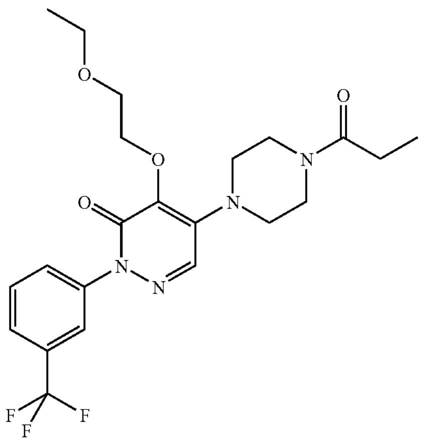 | 469 |

TABLE 8-continued
Oxygen Linked Analogs with Amide
The following compounds can be synthesized by using steps 1, 2, 4, 6, and 7 in Scheme 1.
| Comp. No. | Structure | MS M + 1 |
|---|---|---|
| 224Z | 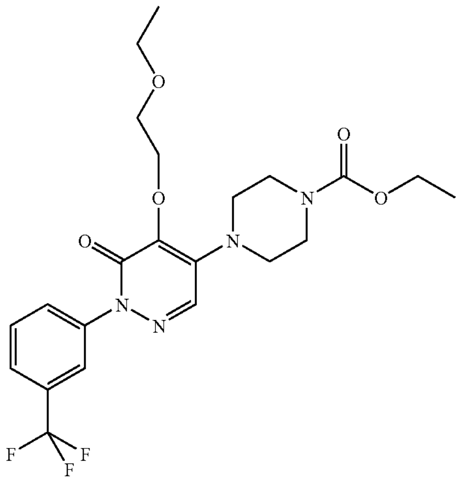 | 485 |
| 225Z | 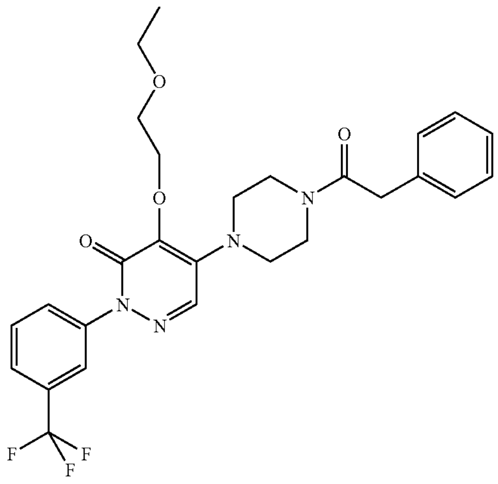 | 531 |
| 226Z | 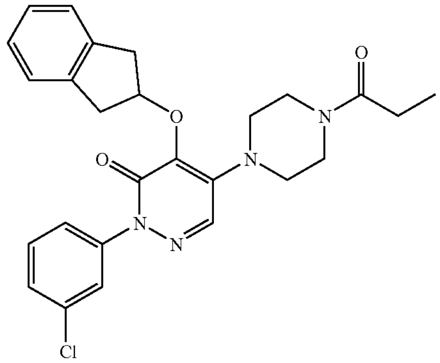 | 479 |

TABLE 8-continued
Oxygen Linked Analogs with Amide
The following compounds can be synthesized by using steps 1, 2, 4, 6, and 7 in Scheme 1.
| Comp. No. | Structure | MS M + 1 |
|---|---|---|
| 227Z | 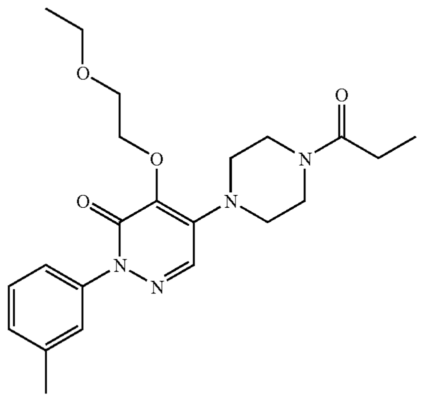 | 415 |
| 228Z | 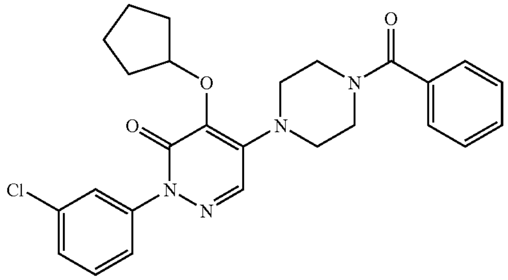 | 479 |
| 229Z | 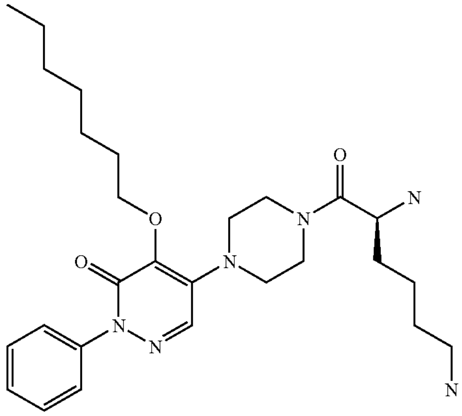 | 499 |
| 230Z | 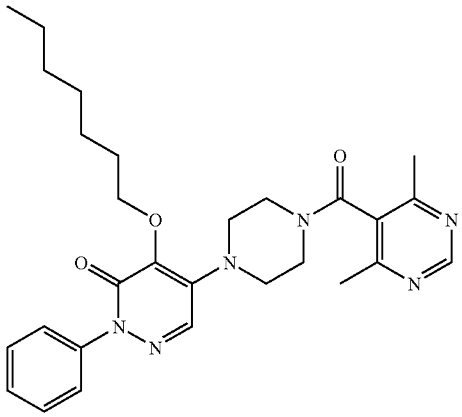 | 505 |

TABLE 8-continued
| Oxygen Linked Analogs with Amide<br>The following compounds can be synthesized by using steps 1, 2, 4, 6, and 7 in Scheme 1. | | |
|---|---|---|
| Comp. No. | Structure | MS M + 1 |
| 231Z | 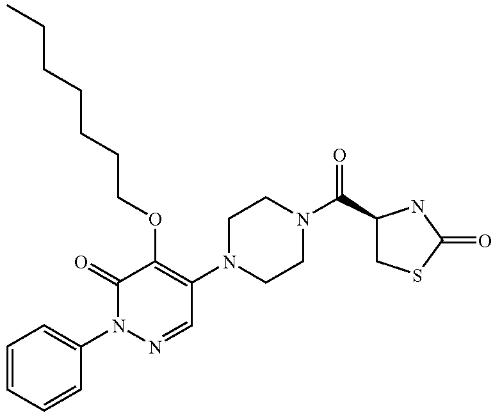 | 500 |
| 232Z | 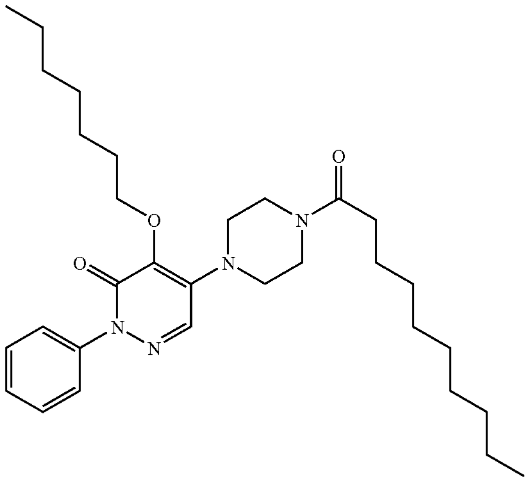 | 525 |
| 233Z | 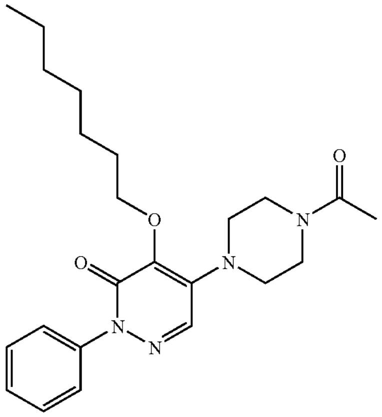 | 413 |

TABLE 8-continued
| Comp. No. | Structure | MS M + 1 |
|---|---|---|
| Oxygen Linked Analogs with Amide. The following compounds can be synthesized by using steps 1, 2, 4, 6, and 7 in Scheme 1. | | |
| 234Z | 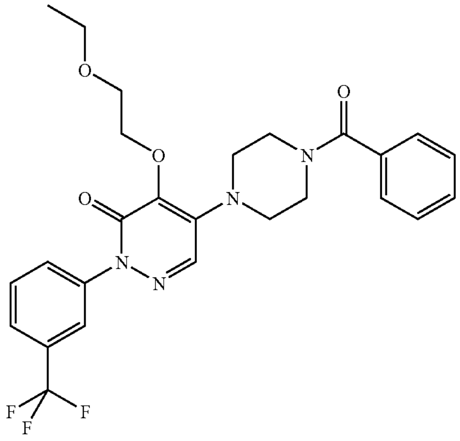 | 517 |
| 235Z | 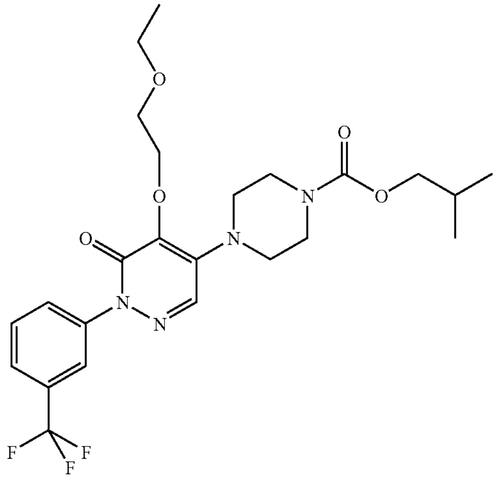 | 513 |
| 236Z | 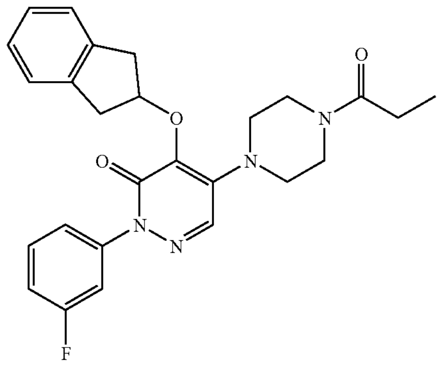 | 463 |

TABLE 8-continued
Oxygen Linked Analogs with Amide
The following compounds can be synthesized by using steps 1, 2, 4, 6, and 7 in Scheme 1.
| Comp. No. | Structure | MS M + 1 |
|---|---|---|
| 237Z | 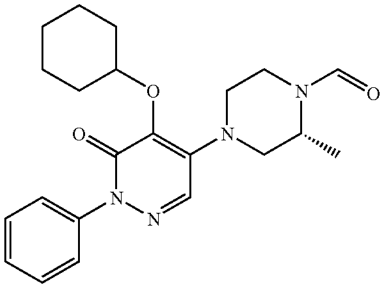 | 524 |
| 238Z | 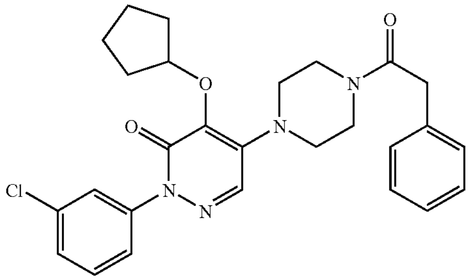 | 493 |
| 238A | 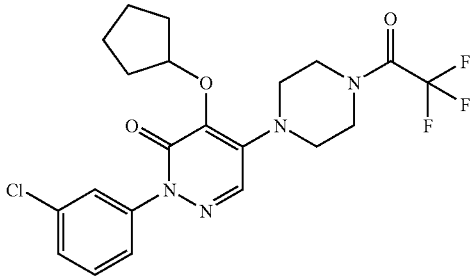 | 471 |
| 238B | 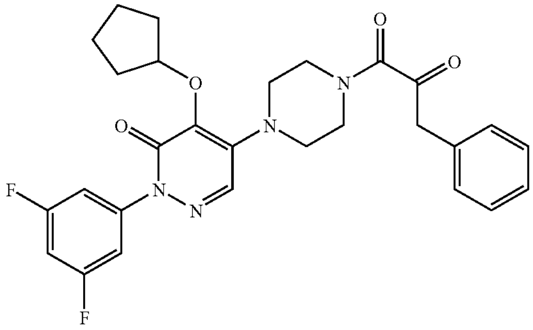 | 523 |

TABLE 8-continued
Oxygen Linked Analogs with Amide
The following compounds can be synthesized by using steps 1, 2, 4, 6, and 7 in Scheme 1.
| Comp. No. | Structure | MS M + 1 |
|---|---|---|
| 238C | 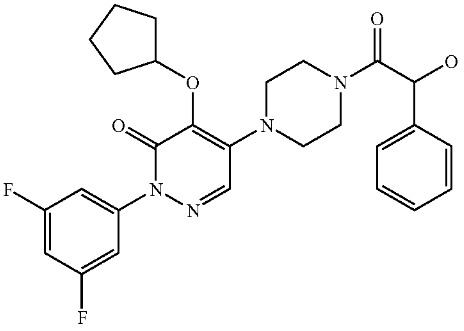 | 511 |
| 238D | 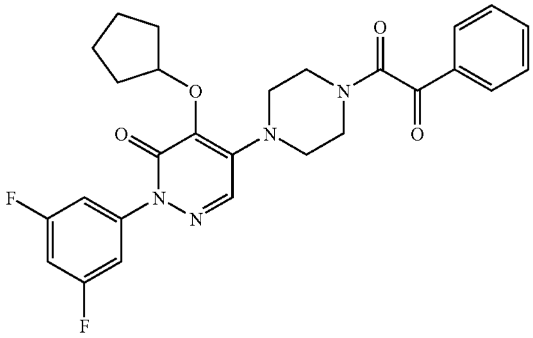 | 509 |
| 238E | 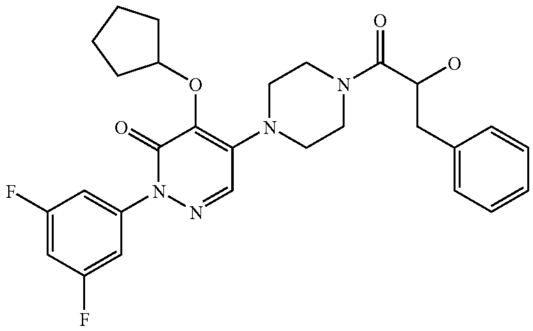 | 525 |
| 238F | 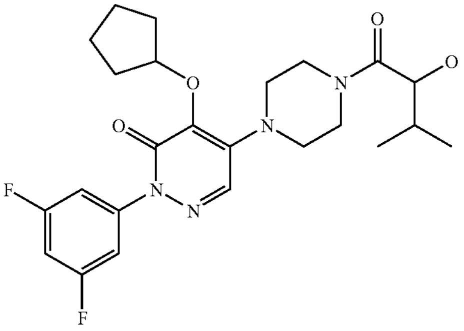 | 477 |

TABLE 8-continued
Oxygen Linked Analogs with Amide
The following compounds can be synthesized by using steps 1, 2, 4, 6, and 7 in Scheme 1.
| Comp. No. | Structure | MS M + 1 |
|---|---|---|
| 238G | 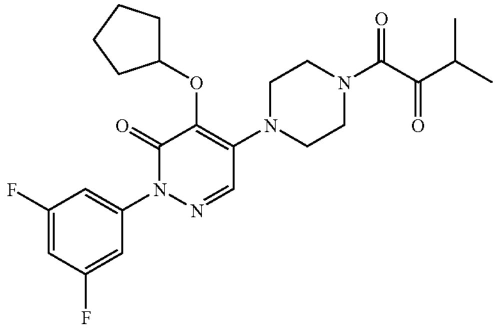 | 475 |
TABLE 9
Oxygen Linked Analogs with Heterocycle
The following compounds can be synthesized by using steps 1, 2, and 4 in Scheme I.
| Compound No. | Structure | MS M + 1 |
|---|---|---|
| 239Z | 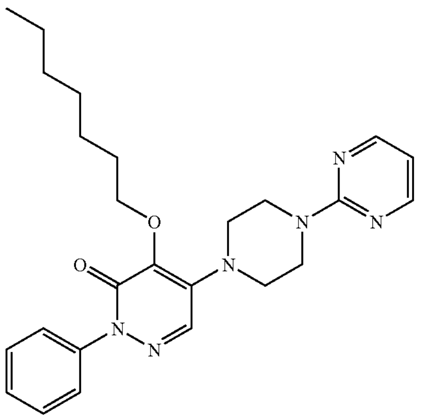 | 449 |
| 240Z | 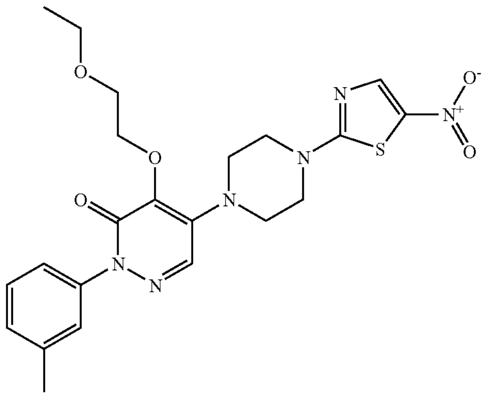 | 487 |

TABLE 9-continued
| Oxygen Linked Analogs with Heterocycle<br>The following compounds can be synthesized by using steps 1, 2, and 4 in Scheme I. | | |
|---|---|---|
| Compound No. | Structure | MS M + 1 |
| 241Z | 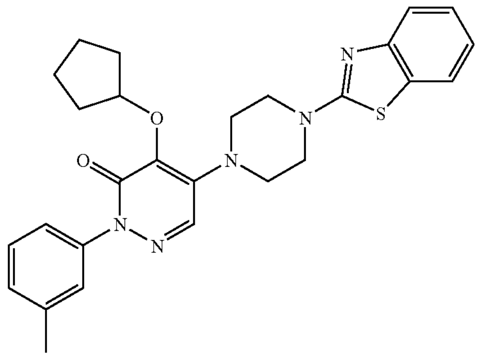 | 488 |
TABLE 10
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 242Z | 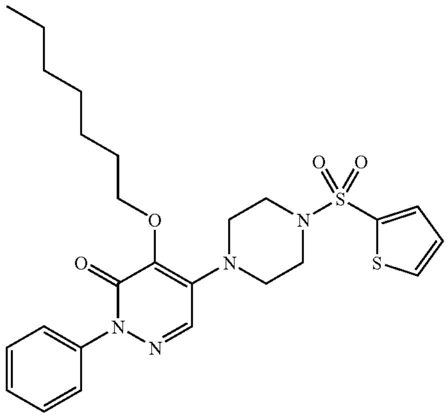 | 517 |
| 243Z | 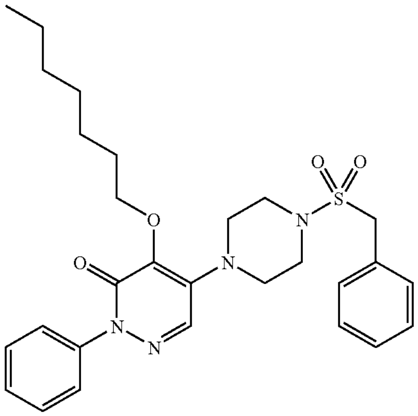 | 525 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 244Z | 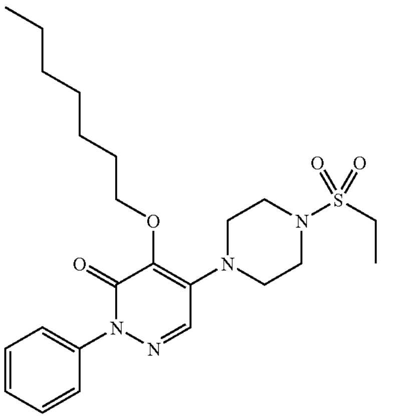 | 463 |
| 245Z | 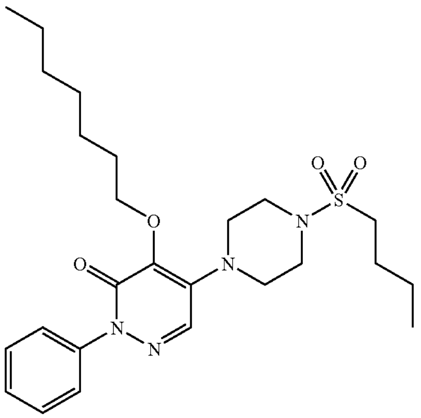 | 491 |
| 246Z | 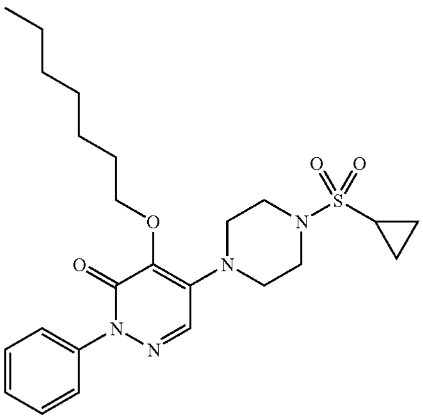 | 475 |

TABLE 10-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 247Z | 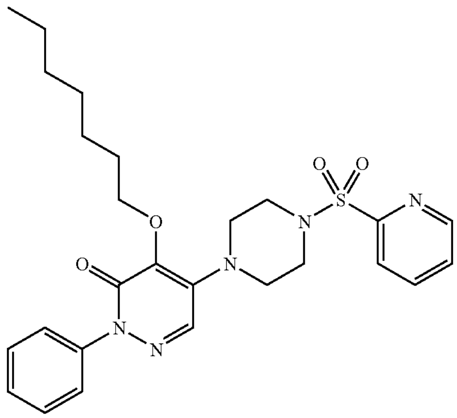 | 512 |
| 248Z | 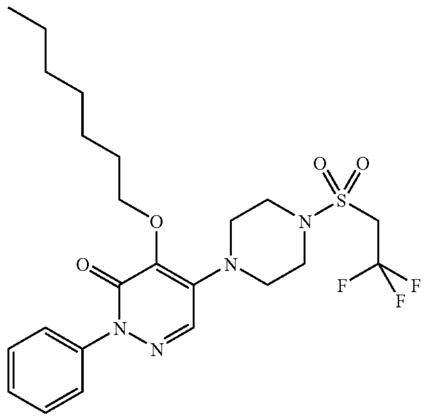 | 517 |
| 249Z | 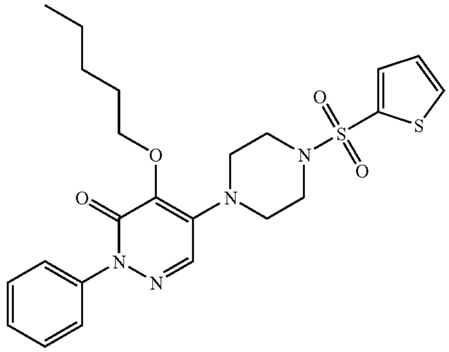 | 489 |

TABLE 10-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 250Z | 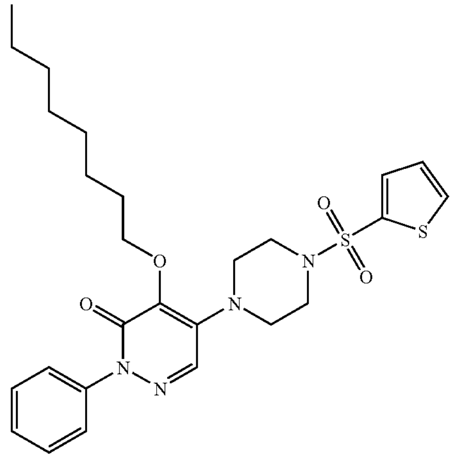 | 531 |
| 251Z | 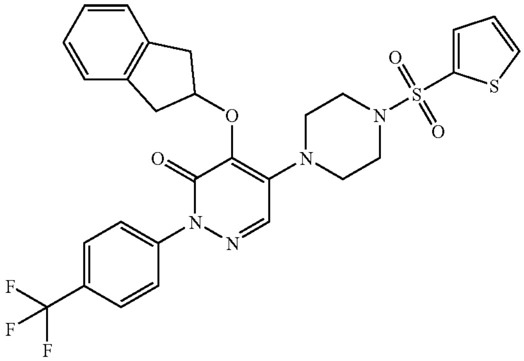 | 603 |
| 252Z | 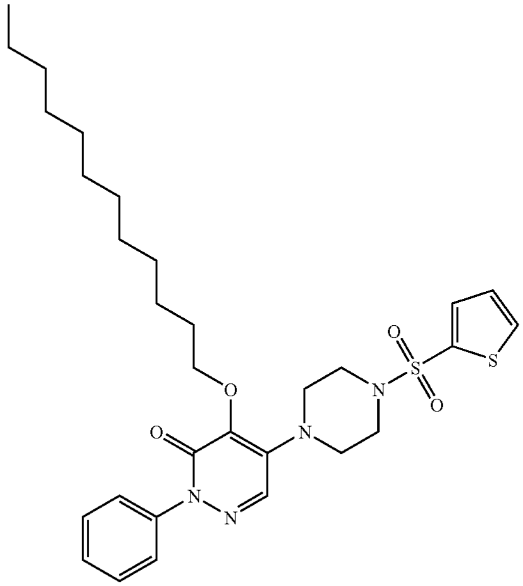 | 587 |

TABLE 10-continued
| Comp. No. | Structure | MS M + 1 |
|---|---|---|
| | Oxygen Linked Analogs with Sulfonamide. The following compounds can be synthesized using steps 1, 2, 4, 6, and 9 of Scheme 1 or steps 11, 12, and 14 of Scheme 2. | |
| 253Z | 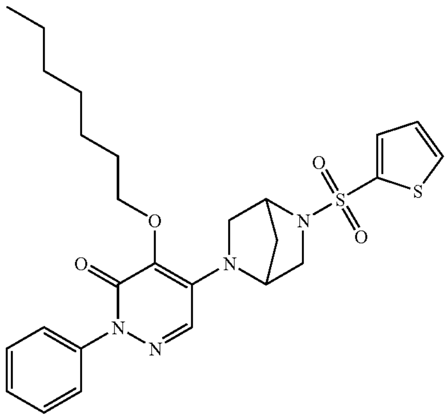 | 529 |
| 254Z | 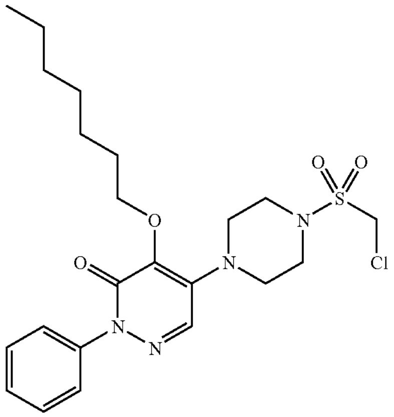 | 483 |
| 255Z | 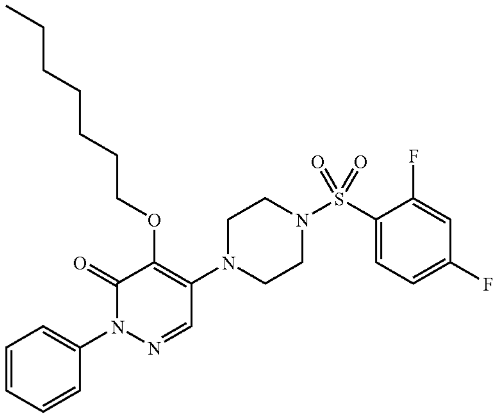 | 547 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 256Z | 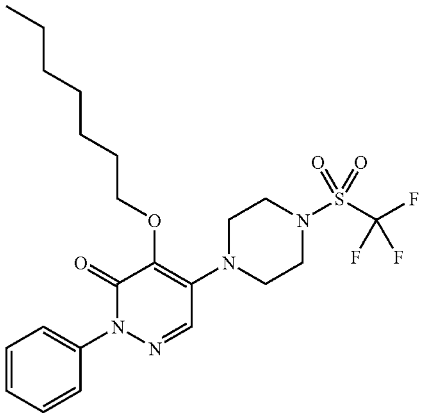 | 503 |
| 257Z | 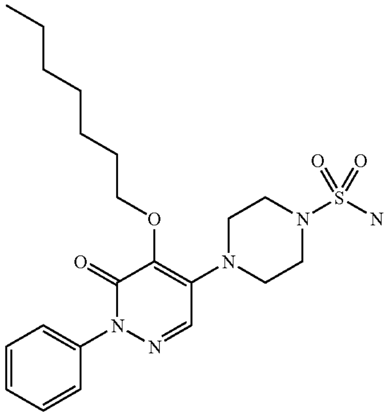 | 450 |
| 258Z | 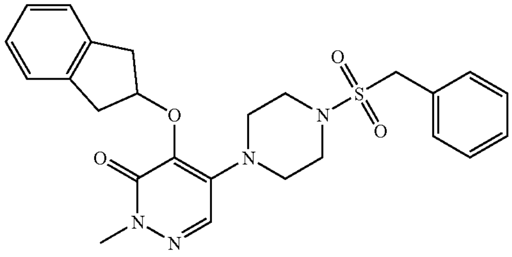 | 481 |
| 259Z | 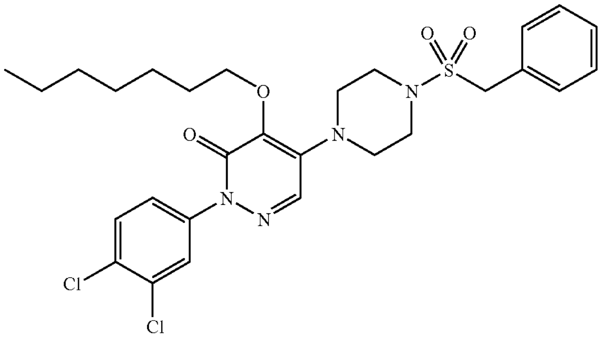 | 593 |

TABLE 10-continued
| Comp. No. | Structure | MS M + 1 |
|---|---|---|
| Oxygen Linked Analogs with Sulfonamide. The following compounds can be synthesized using steps 1, 2, 4, 6, and 9 of Scheme 1 or steps 11, 12, and 14 of Scheme 2. | | |
| 260Z | 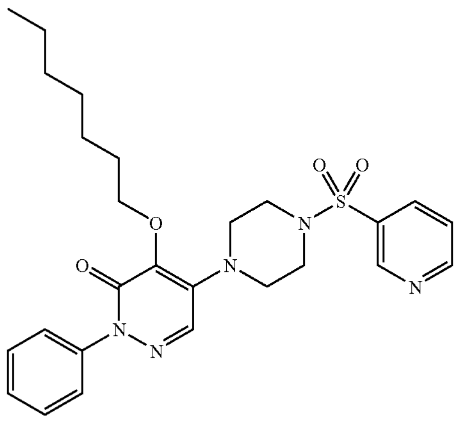 | 512 |
| 261Z | 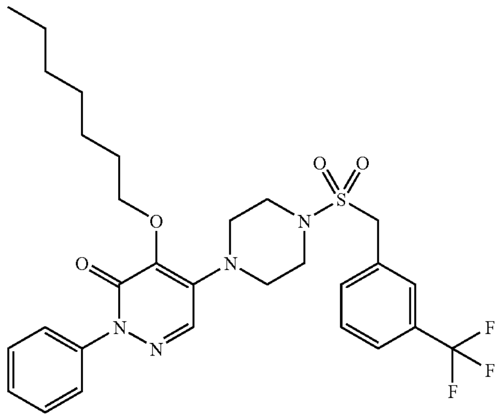 | 593 |
| 262Z | 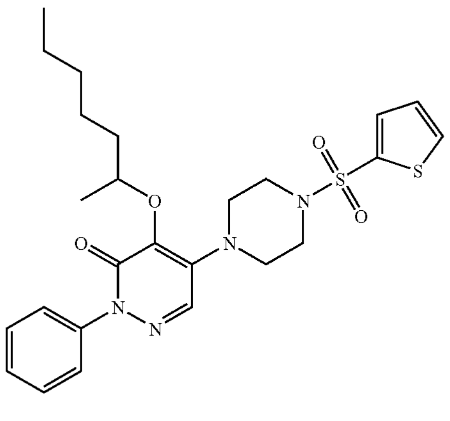 | 517 |

TABLE 10-continued
| Comp. No. | Structure | MS M + 1 |
|---|---|---|
| Oxygen Linked Analogs with Sulfonamide The following compounds can be synthesized using steps 1, 2, 4, 6, and 9 of Scheme 1 or steps 11, 12, and 14 of Scheme 2. | | |
| 263Z | 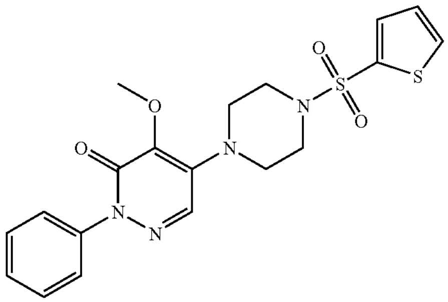 | 433 |
| 264Z | 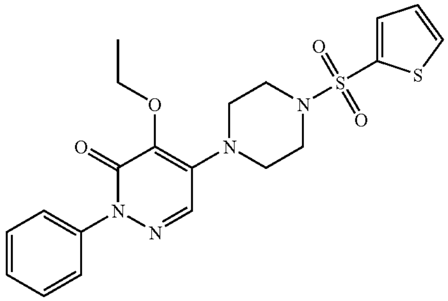 | 447 |
| 265Z | 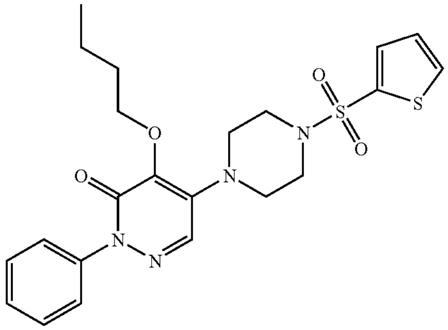 | 475 |
| 266Z | 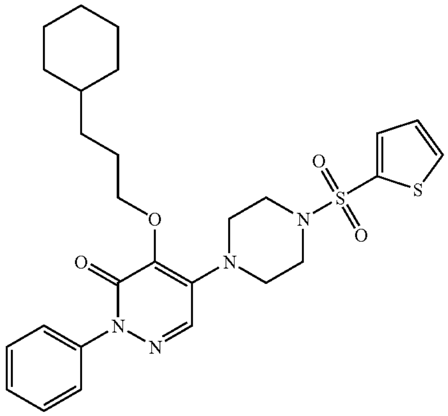 | 557 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 267Z | 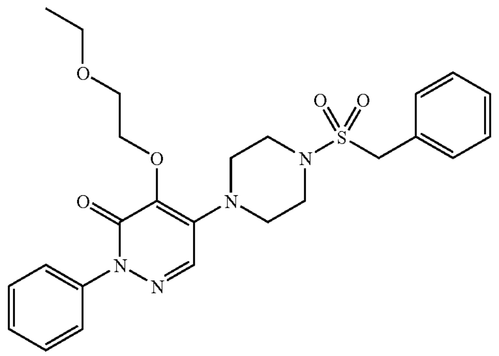 | 499 |
| 268Z | 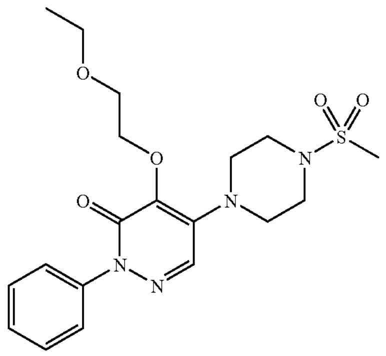 | 423 |
| 269Z | 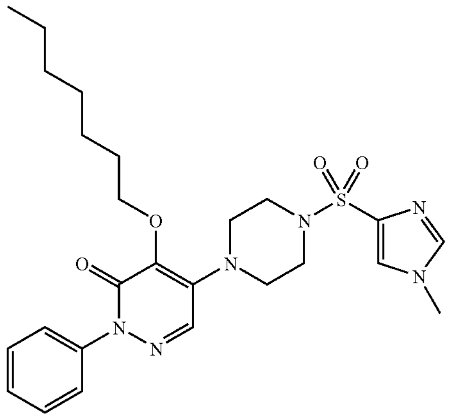 | 515 |

TABLE 10-continued
| Comp. No. | Structure | MS M + 1 |
|---|---|---|
| | Oxygen Linked Analogs with Sulfonamide The following compounds can be synthesized using steps 1, 2, 4, 6, and 9 of Scheme 1 or steps 11, 12, and 14 of Scheme 2. | |
| 270Z | 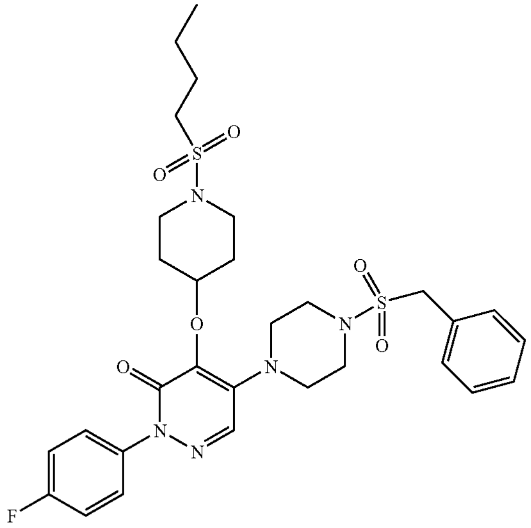 | 648 |
| 271Z | 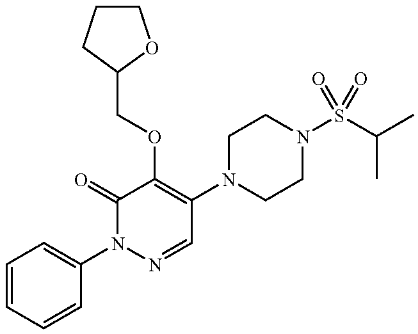 | 463 |
| 272Z | 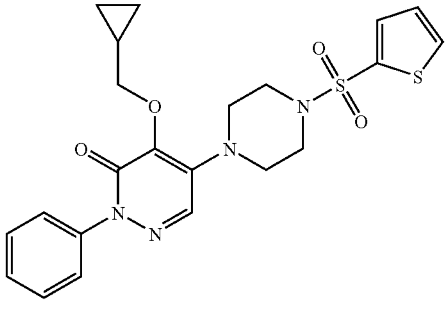 | 473 |

TABLE 10-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 273Z | 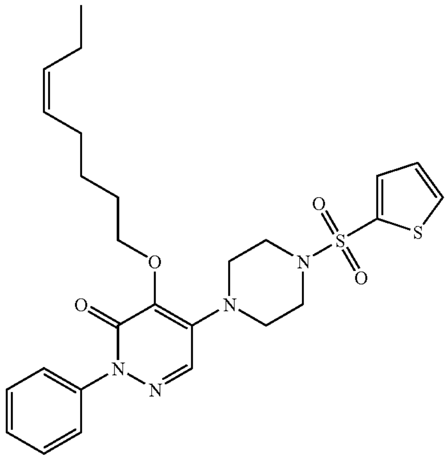 | 529 |
| 274Z | 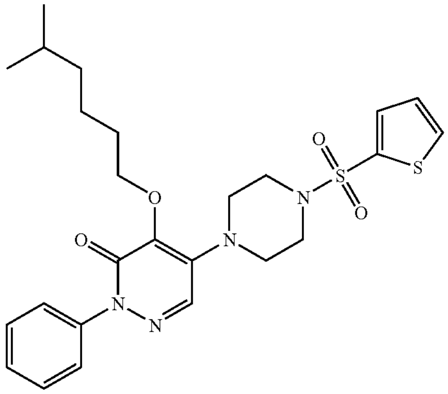 | 517 |
| 275Z | 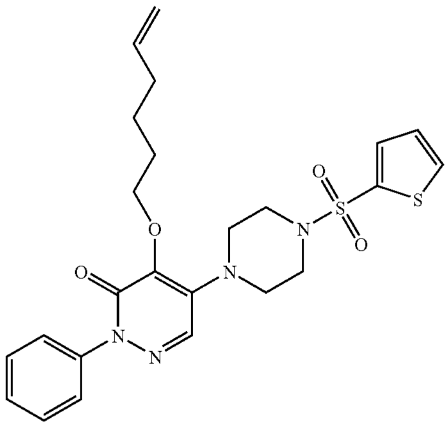 | 501 |

TABLE 10-continued
| Comp. No. | Structure | MS M + 1 |
| --- | --- | --- |
| | Oxygen Linked Analogs with Sulfonamide The following compounds can be synthesized using steps 1, 2, 4, 6, and 9 of Scheme 1 or steps 11, 12, and 14 of Scheme 2. | |
| 276Z | 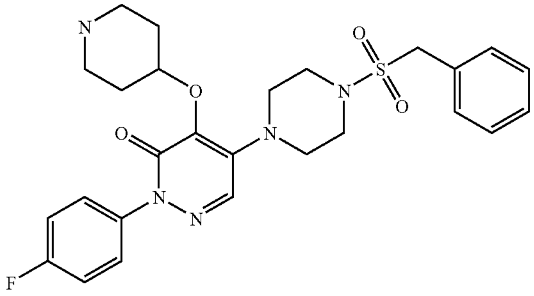 | 528 |
| 277Z | 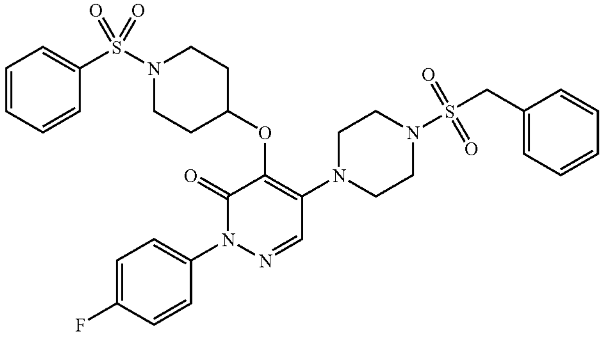 | 668 |
| 278Z | 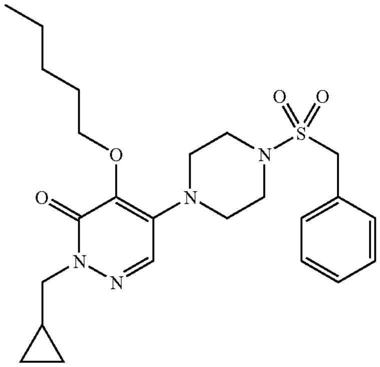 | 475 |
| 279Z | 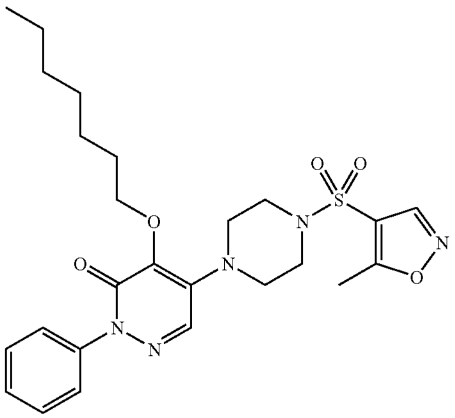 | 516 |

TABLE 10-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 280Z | 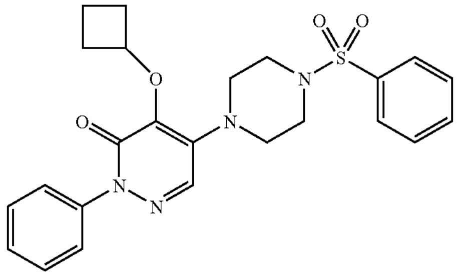 | 467 |
| 281Z | 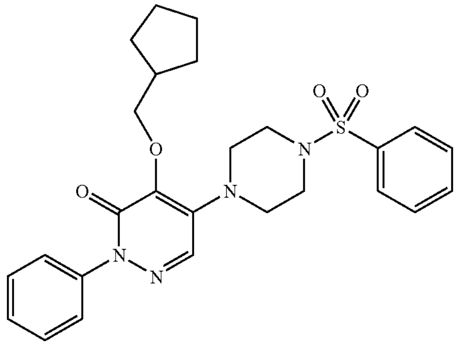 | 495 |
| 282Z | 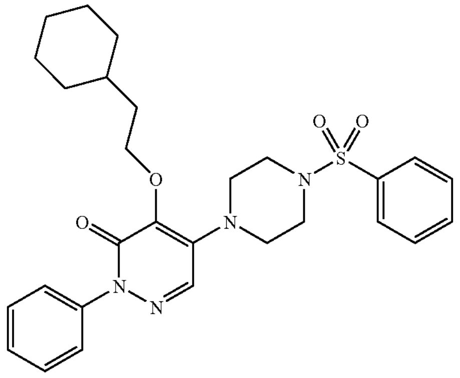 | 509 |
| 283Z | 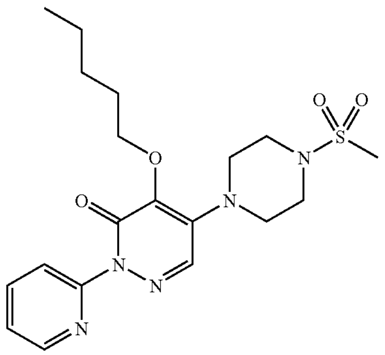 | 422 |

TABLE 10-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 284Z | 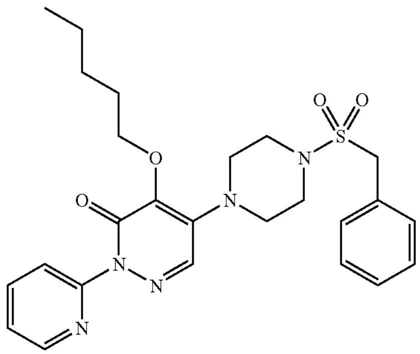 | 498 |
| 285Z | 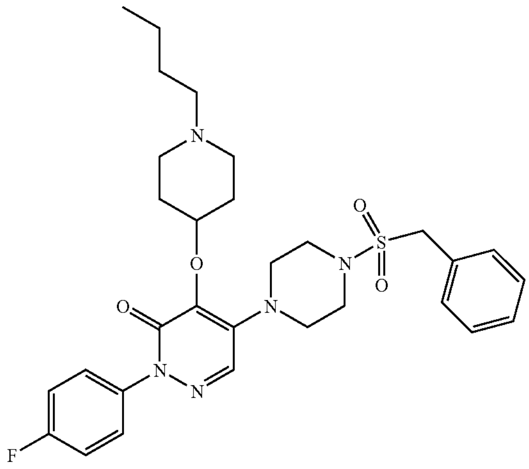 | 584 |
| 286Z | 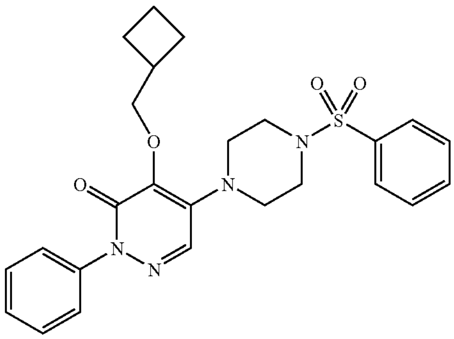 | 481 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 287Z | 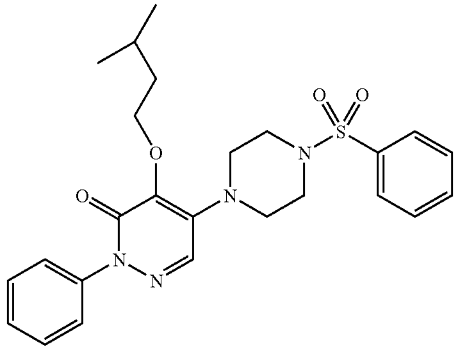 | 483 |
| 288Z | 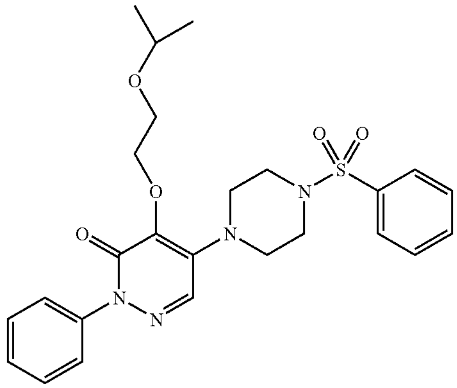 | 499 |
| 289Z | 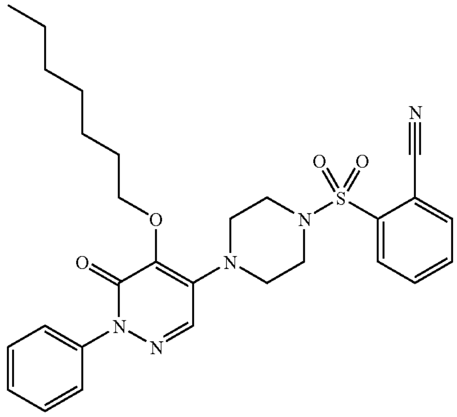 | 536 |
| 290Z | 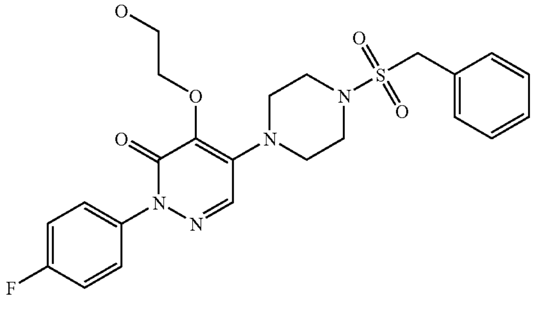 | 489 |

TABLE 10-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 291Z | 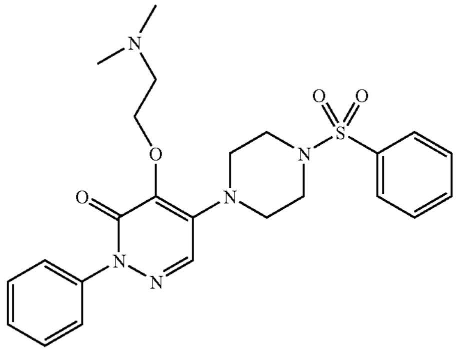 | 484 |
| 292Z | 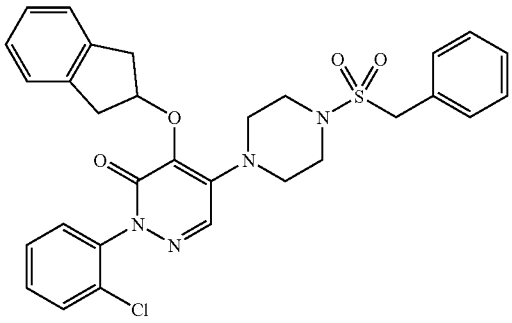 | 577 |
| 293Z | 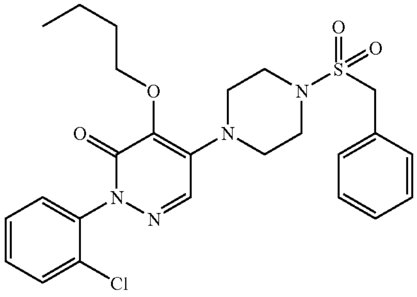 | 517 |

TABLE 10-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 294Z | 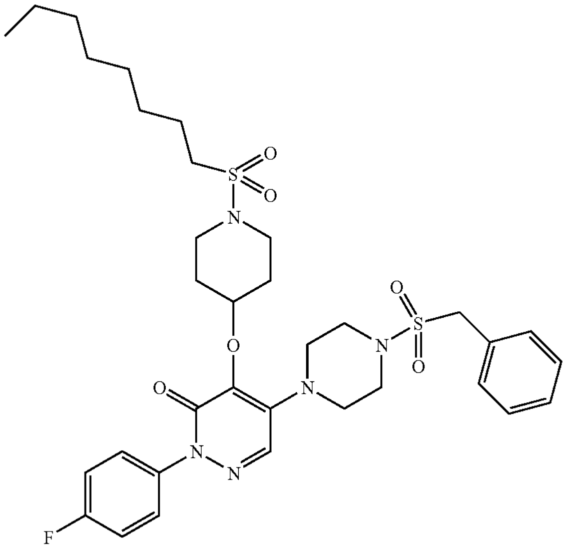 | 704 |
| 295Z | 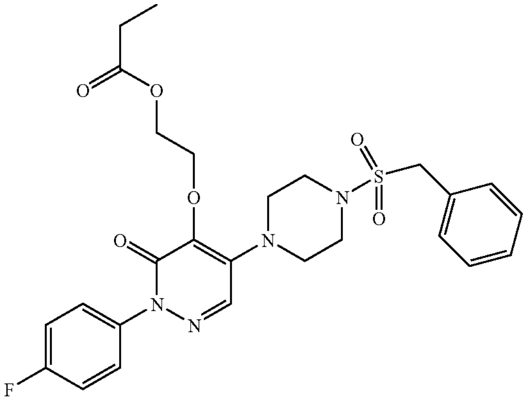 | 545 |
| 296Z | 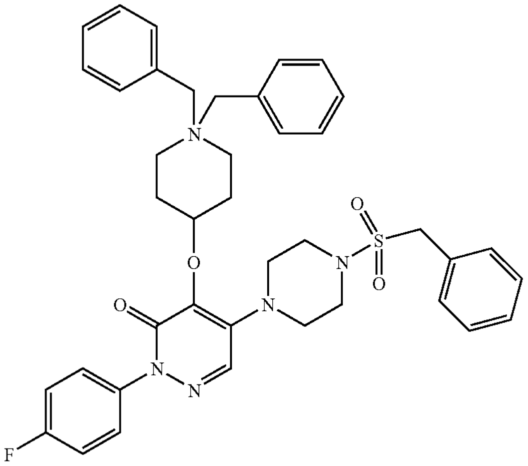 | 708 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 297Z | 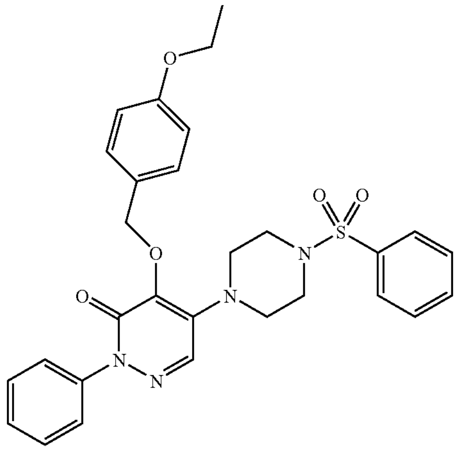 | 547 |
| 298Z | 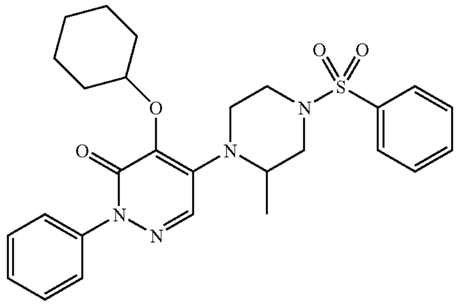 | 509 |
| 299Z | 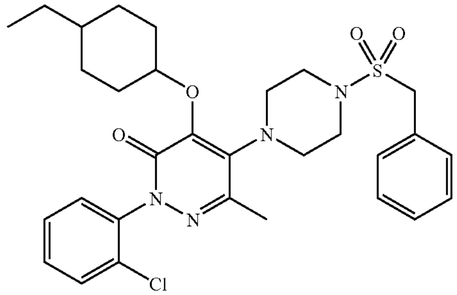 | 571 |
| 300Z | 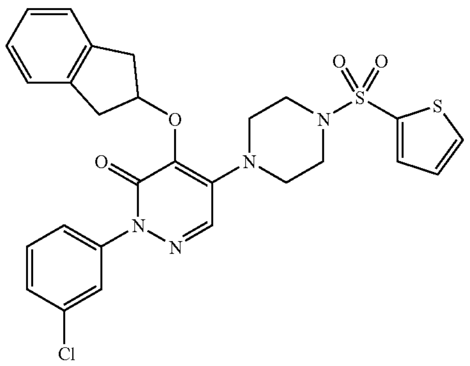 | 569 |

TABLE 10-continued
| Comp. No. | Structure | MS M + 1 |
|---|---|---|
| | Oxygen Linked Analogs with Sulfonamide The following compounds can be synthesized using steps 1, 2, 4, 6, and 9 of Scheme 1 or steps 11, 12, and 14 of Scheme 2. | |
| 301Z | 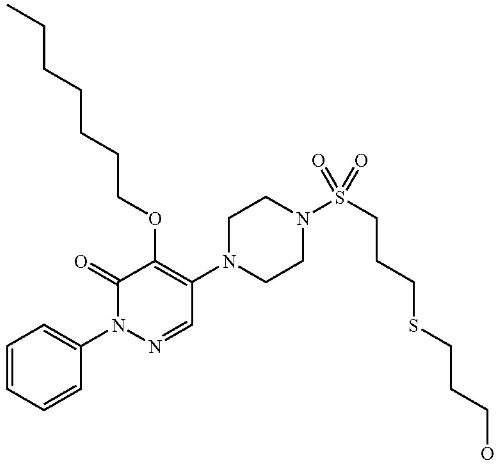 | 567 |
| 302Z | 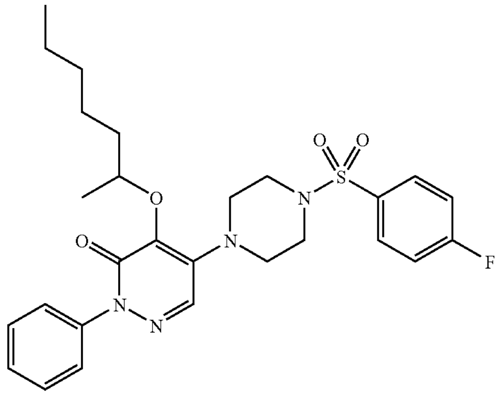 | 529 |
| 303Z | 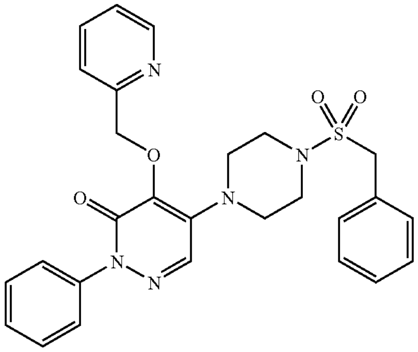 | 518 |
| 304Z | 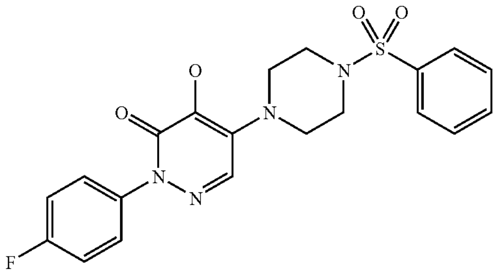 | 431 |

TABLE 10-continued
| Comp. No. | Structure | MS M + 1 |
| --- | --- | --- |
| Oxygen Linked Analogs with Sulfonamide<br>The following compounds can be synthesized using steps 1, 2, 4, 6, and 9 of Scheme 1 or steps 11, 12, and 14 of Scheme 2. | | |
| 305Z | 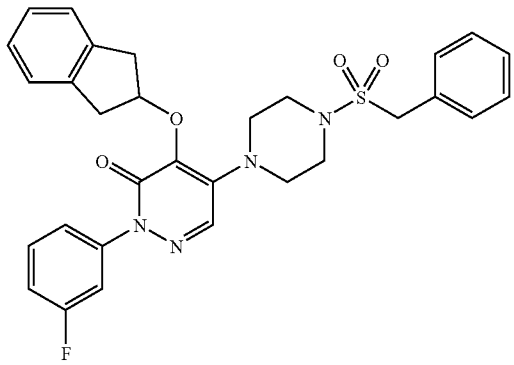 | 561 |
| 306Z | 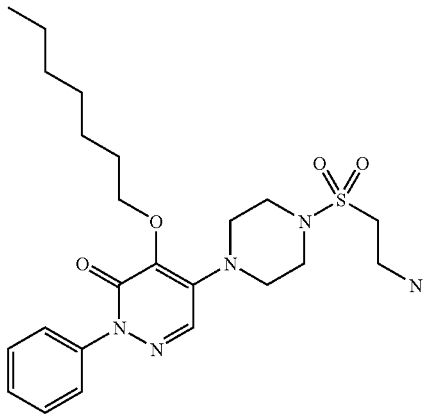 | 478 |
| 307Z | 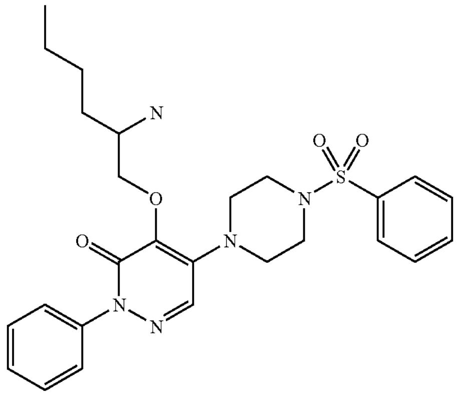 | 512 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
| --- | --- | --- |
| 308Z | 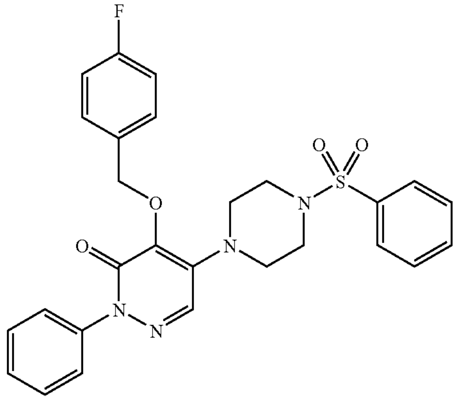 | 521 |
| 309Z | 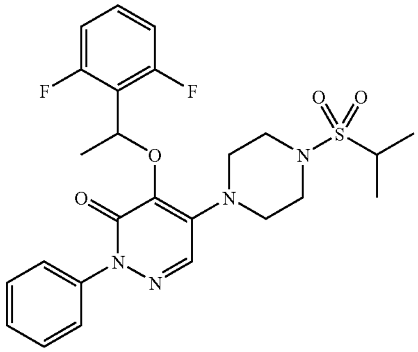 | 519 |
| 310Z | 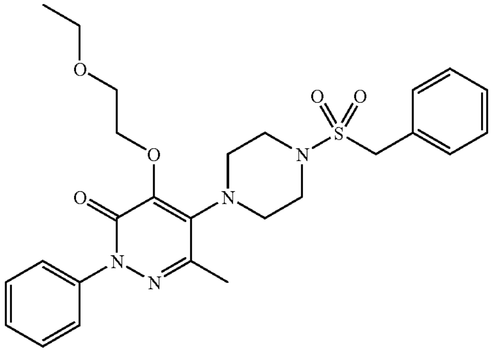 | 535 |
| 311Z | 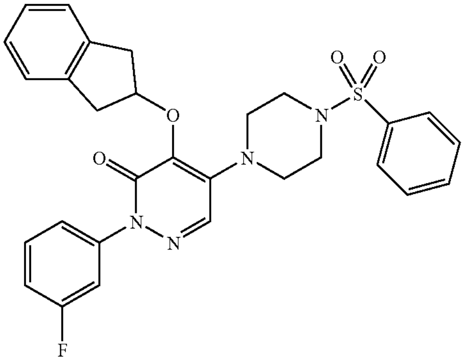 | 547 |

TABLE 10-continued
| Comp. No. | Structure | MS M + 1 |
|---|---|---|
| Oxygen Linked Analogs with Sulfonamide. The following compounds can be synthesized using steps 1, 2, 4, 6, and 9 of Scheme 1 or steps 11, 12, and 14 of Scheme 2. | | |
| 312Z | 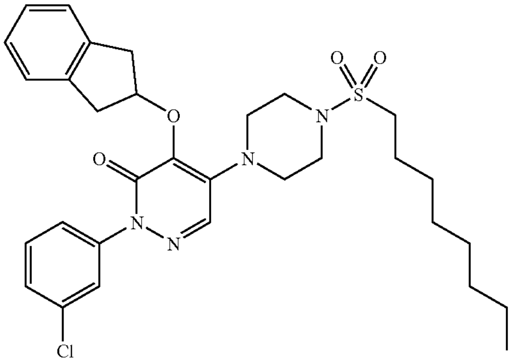 | 599<br>601 |
| 313Z | 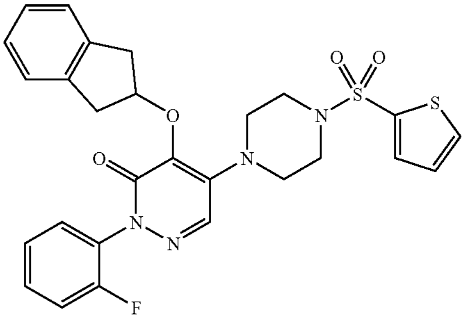 | 553 |
| 314Z | 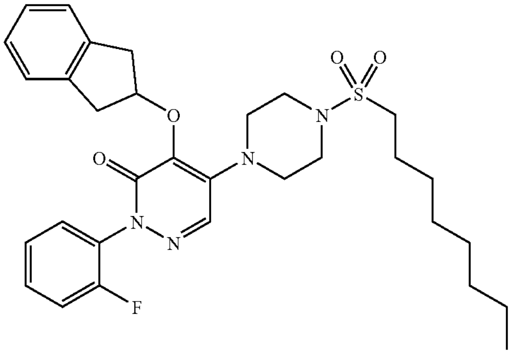 | 583 |
| 315Z | 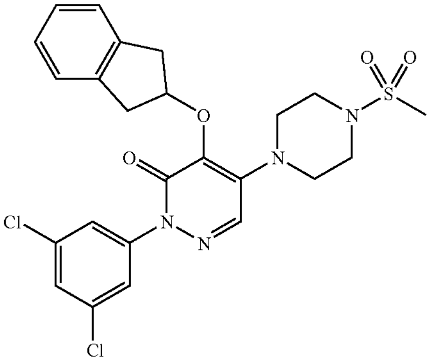 | 535 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 316Z | 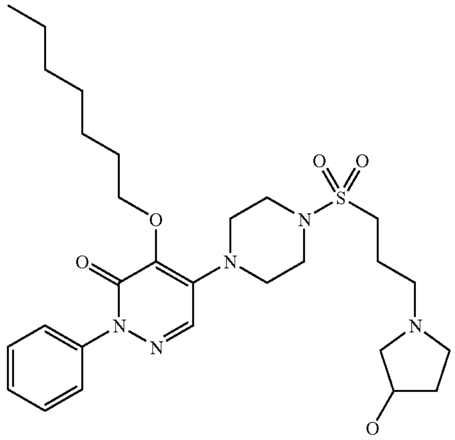 | 562 |
| 317Z | 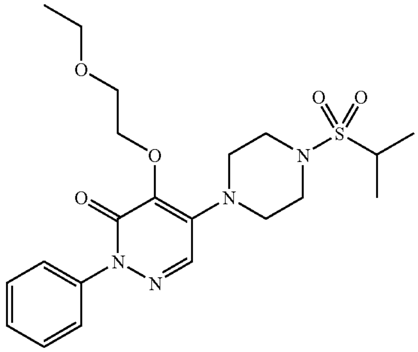 | 451 |
| 318Z | 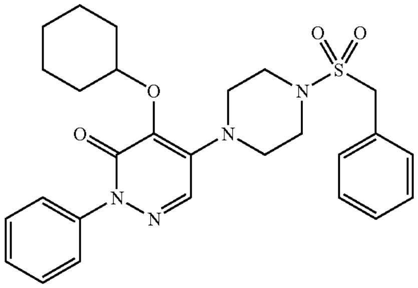 | 509 |
| 319Z | 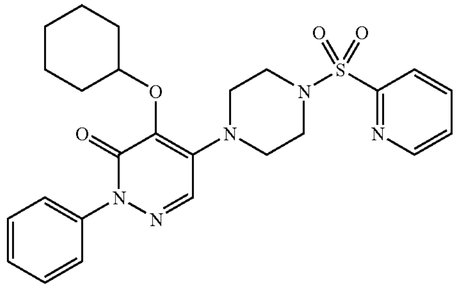 | 496 |

TABLE 10-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 320Z | 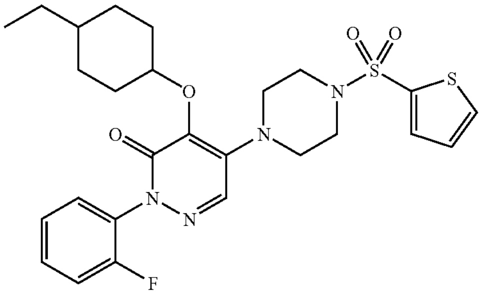 | 547 |
| 321Z | 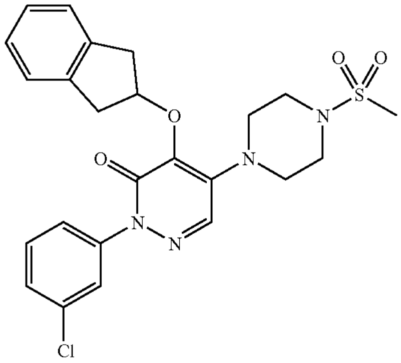 | 501 |
| 322Z | 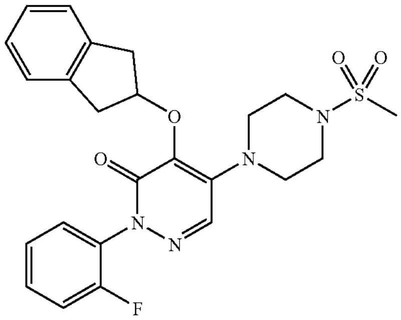 | 485 |
| 323Z | 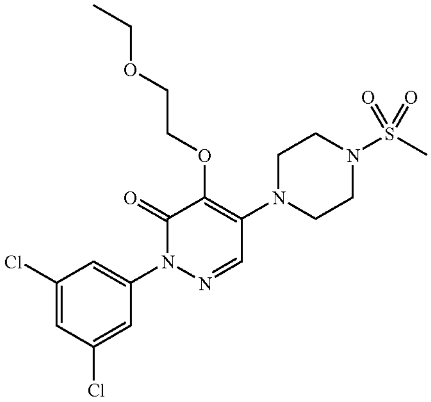 | 491 |

TABLE 10-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 324Z | 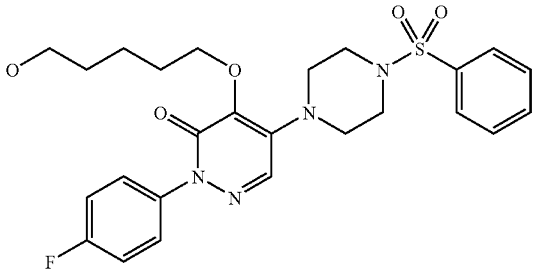 | 517 |
| 325Z | 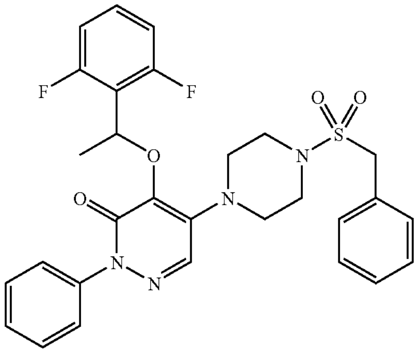 | 567 |
| 326Z | 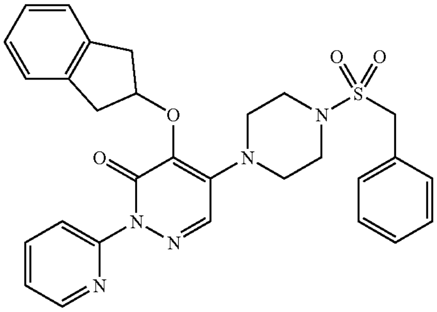 | 544 |
| 327Z | 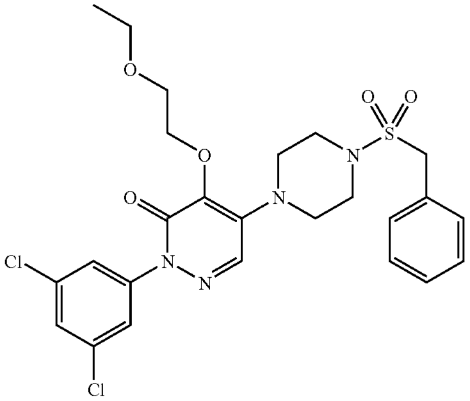 | 567 |

TABLE 10-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 328Z | 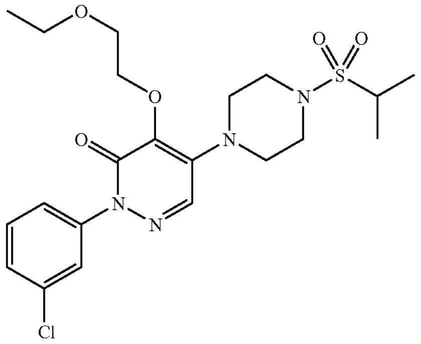 | 485 |
| 329Z | 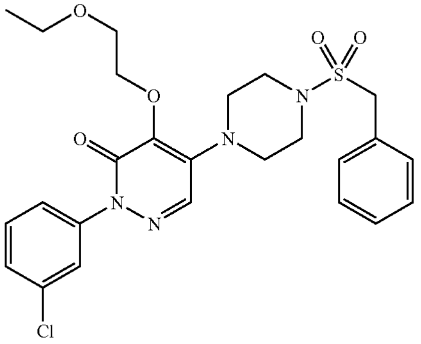 | 533 |
| 330Z | 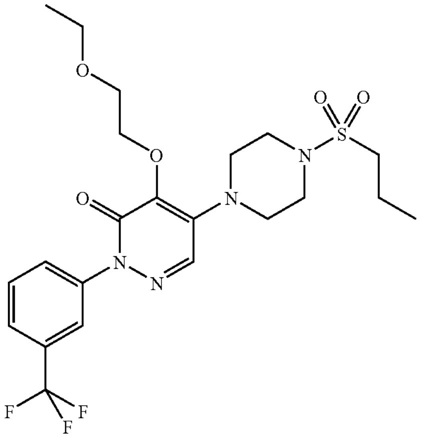 | 519 |
| 331Z | 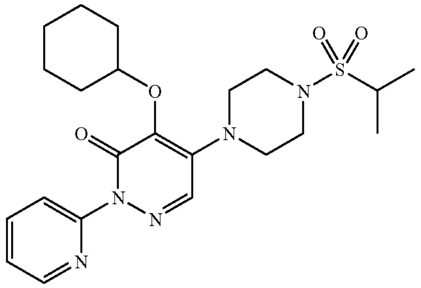 | 462 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 332Z | 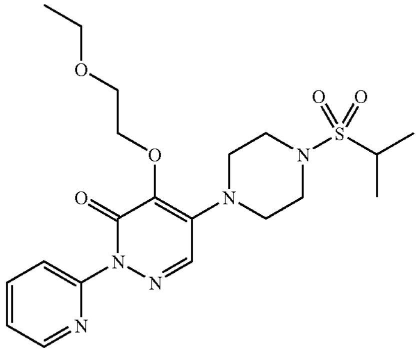 | 452 |
| 333Z | 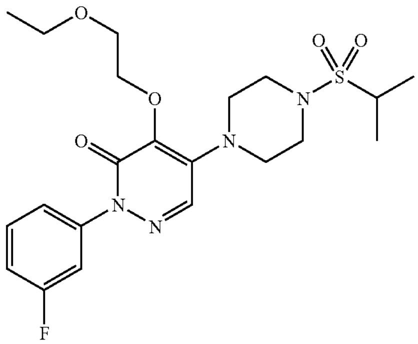 | 469 |
| 334Z | 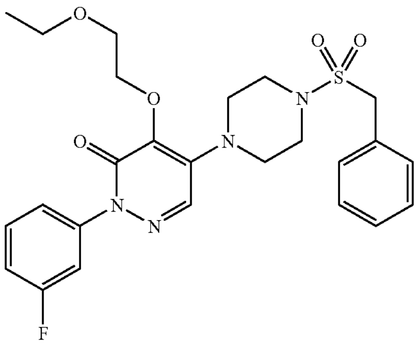 | 517 |
| 335Z | 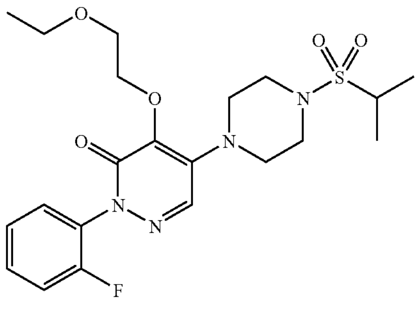 | 469 |

TABLE 10-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 336Z | 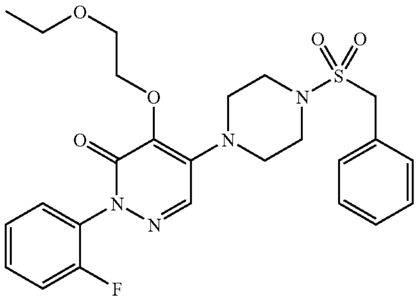 | 517 |
| 337Z | 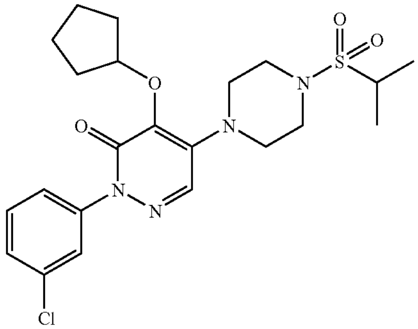 | 481 |
| 338Z | 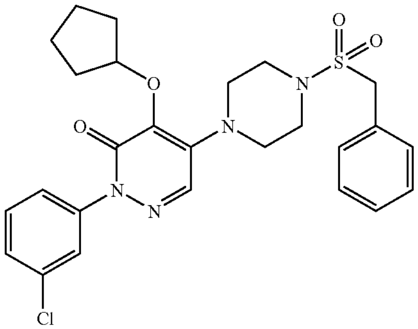 | 529 |
| 339Z | 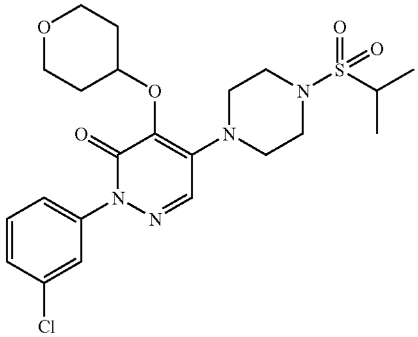 | 497 |

TABLE 10-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 340Z | 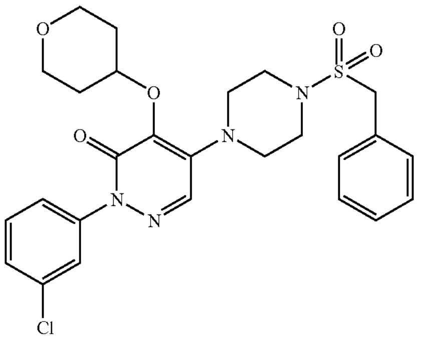 | 545 |
| 341Z | 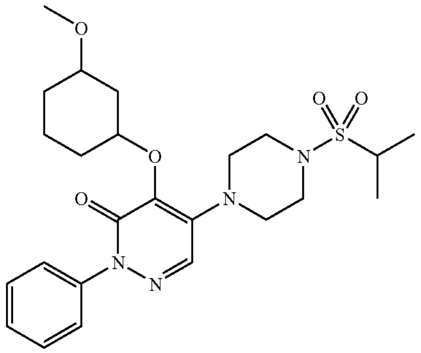 | 491 |
| 342Z | 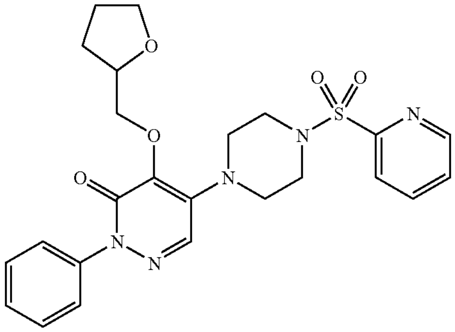 | 498 |
| 343Z | 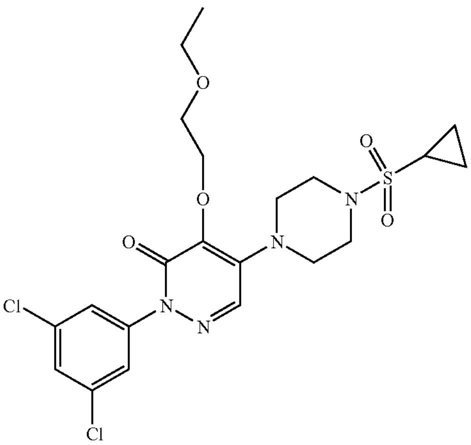 | 517 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 344Z | 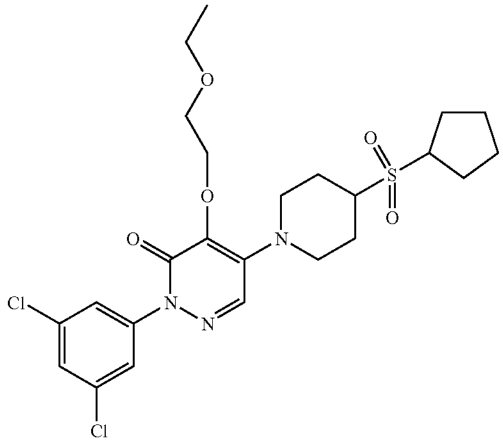 | 545 |
| 345Z | 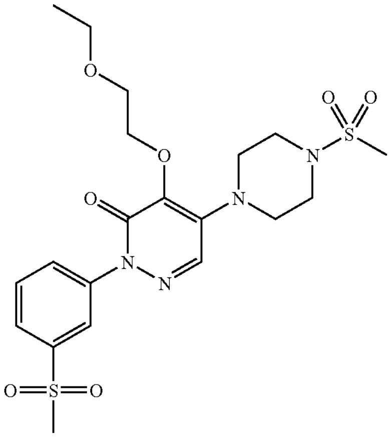 | 501 |
| 346Z | 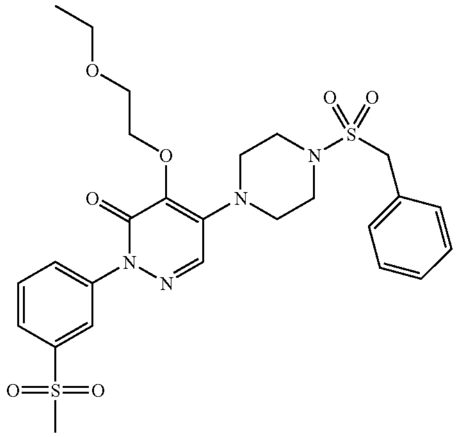 | 577 |

TABLE 10-continued
| Comp. No. | Structure | MS M + 1 |
|---|---|---|
| Oxygen Linked Analogs with Sulfonamide The following compounds can be synthesized using steps 1, 2, 4, 6, and 9 of Scheme 1 or steps 11, 12, and 14 of Scheme 2. | | |
| 347Z | 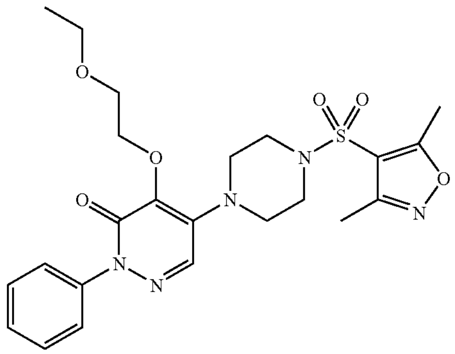 | 504 |
| 348Z | 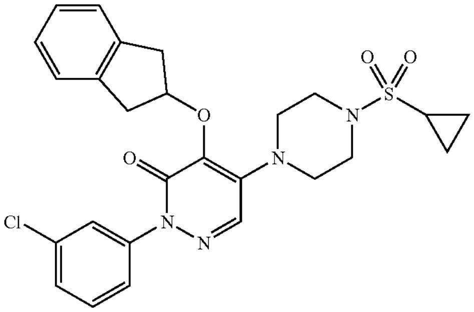 | 527 |
| 349Z | 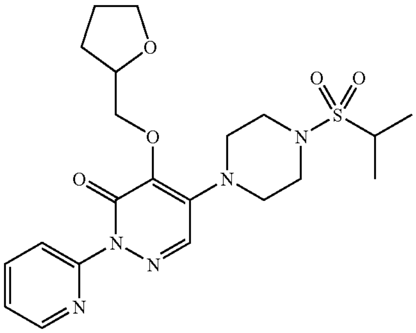 | 464 |
| 350Z | 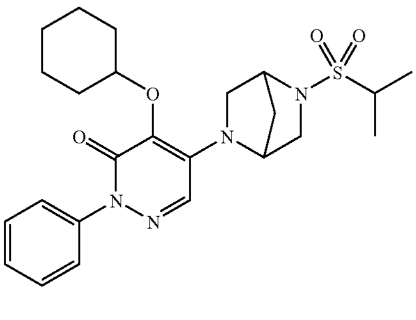 | 473 |

TABLE 10-continued
| Comp. No. | Structure | MS M + 1 |
| --- | --- | --- |
| Oxygen Linked Analogs with Sulfonamide The following compounds can be synthesized using steps 1, 2, 4, 6, and 9 of Scheme 1 or steps 11, 12, and 14 of Scheme 2. | | |
| 351Z | 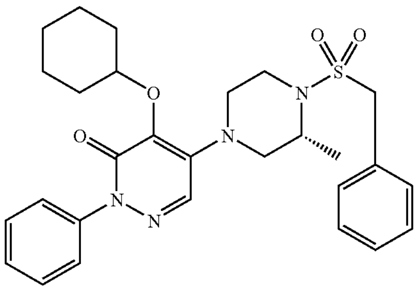 | 523 |
| 352Z | 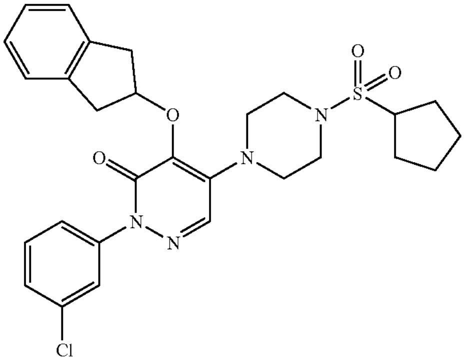 | 555 |
| 353Z | 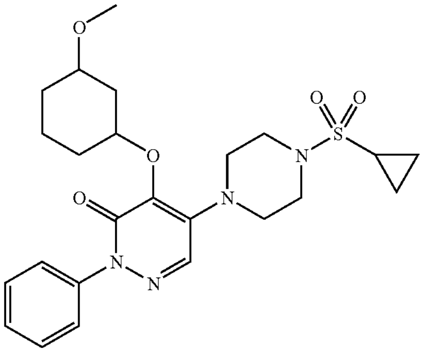 | 489 |
| 354Z | 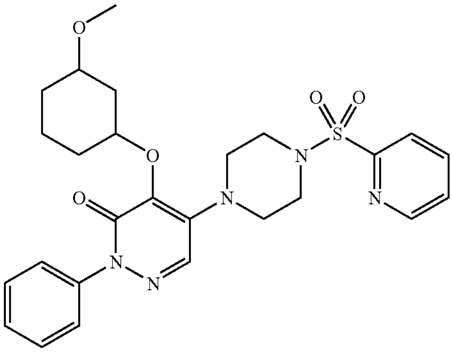 | 526 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 355Z | 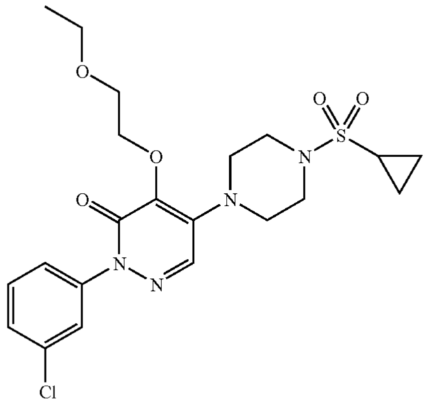 | 483 |
| 356Z | 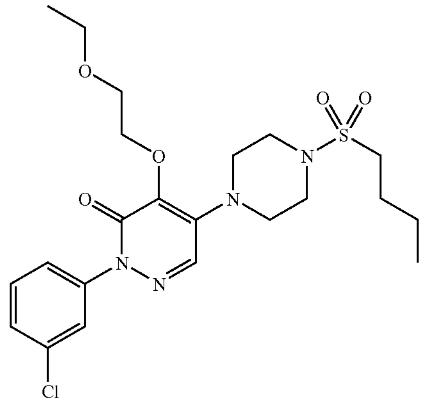 | 499 |
| 357Z | 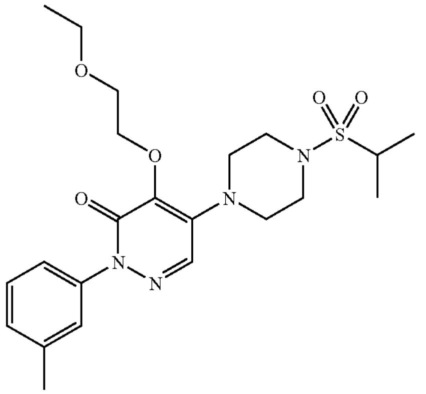 | 465 |
| 358Z | 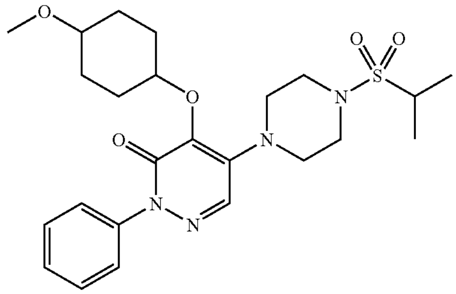 | 491 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 359Z | 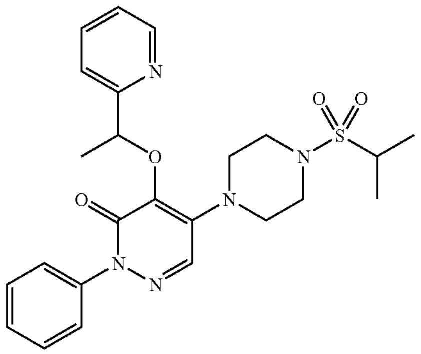 | 484 |
| 360Z | 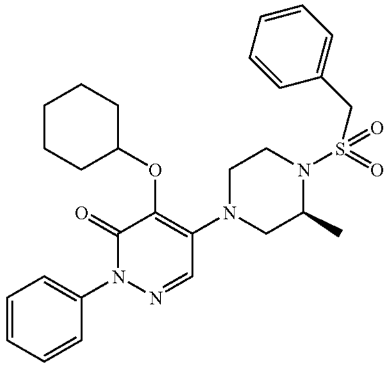 | 523 |
| 361Z | 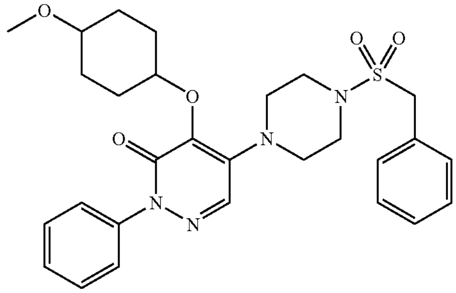 | 539 |
| 362Z | 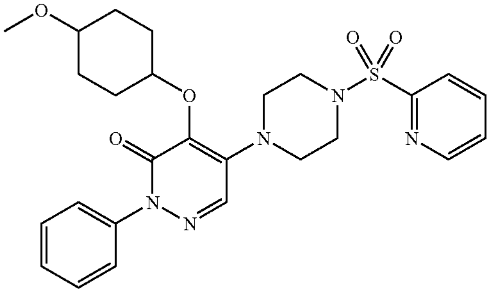 | 526 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 363Z | 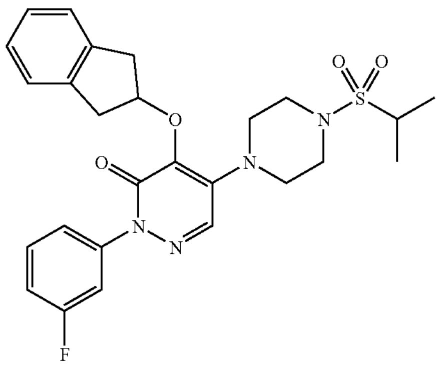 | 513 |
| 364Z | 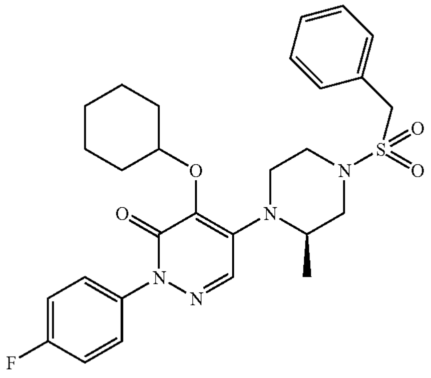 | 541 |
| 365Z | 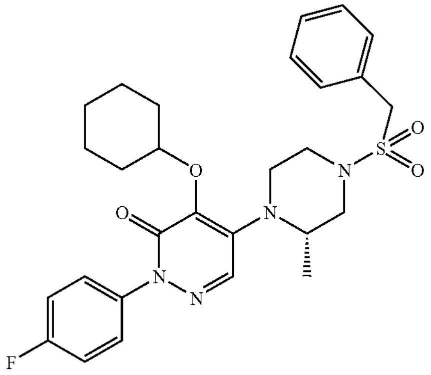 | 541 |
| 366Z | 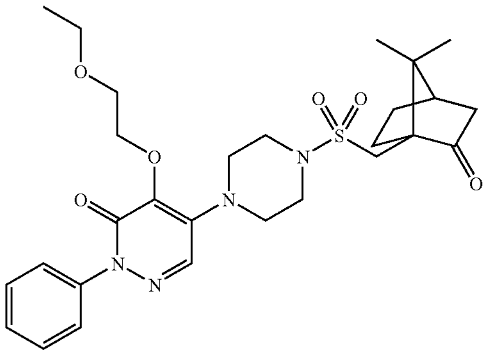 | 559 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 367Z | 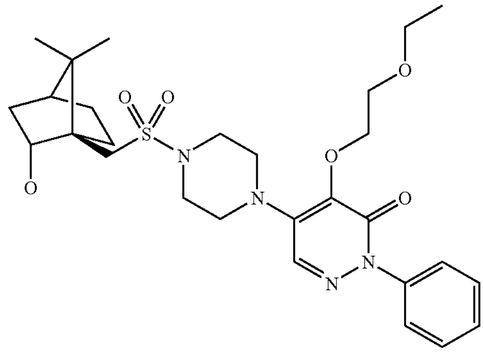 | 561 |
| 368Z | 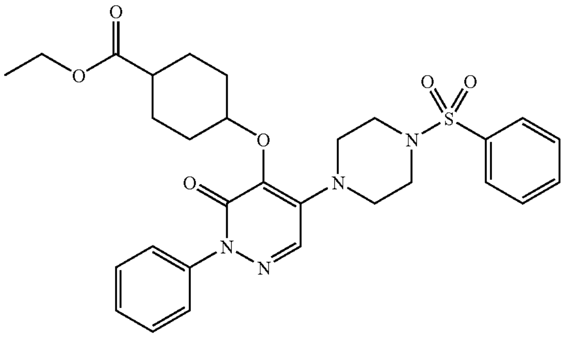 | 567 |
| 369Z | 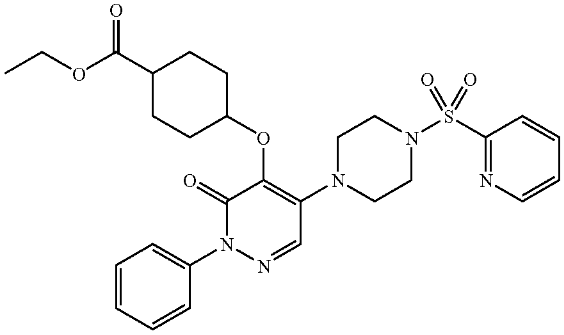 | 568 |
| 370Z | 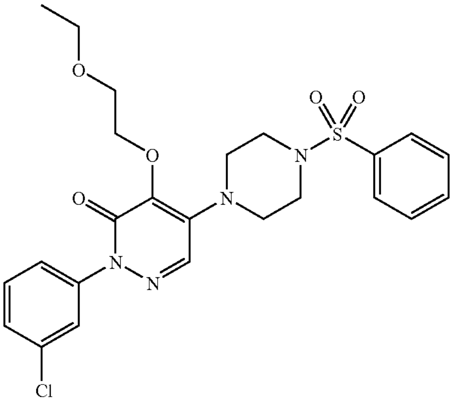 | 519 |

TABLE 10-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 371Z | 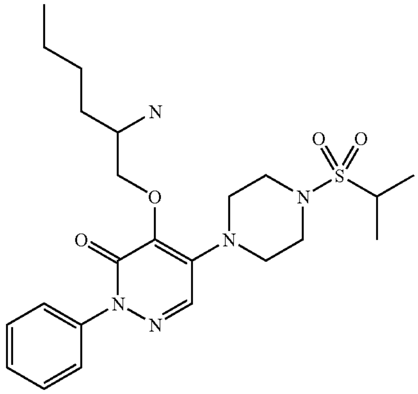 | 478 |
| 372Z | 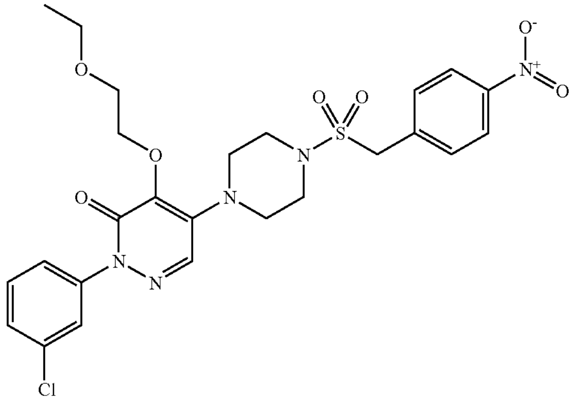 | 578 |
| 373Z | 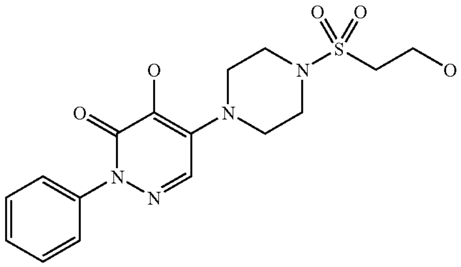 | 381 |
| 374Z | 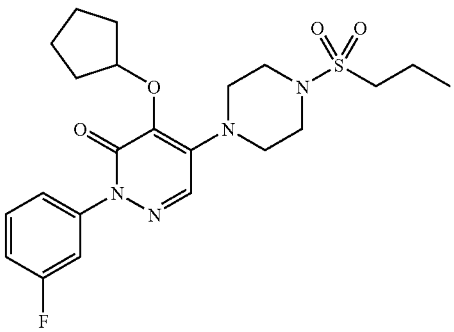 | 465 |

TABLE 10-continued
| Comp. No. | Oxygen Linked Analogs with Sulfonamide The following compounds can be synthesized using steps 1, 2, 4, 6, and 9 of Scheme 1 or steps 11, 12, and 14 of Scheme 2. Structure | MS M + 1 |
|---|---|---|
| 375Z | 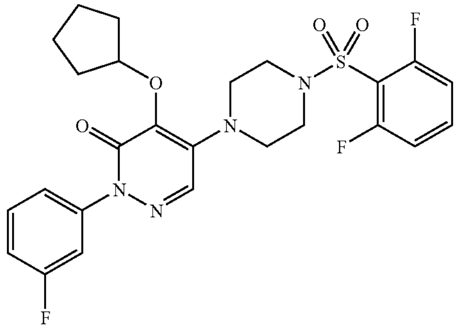 | 535 |
| 376Z | 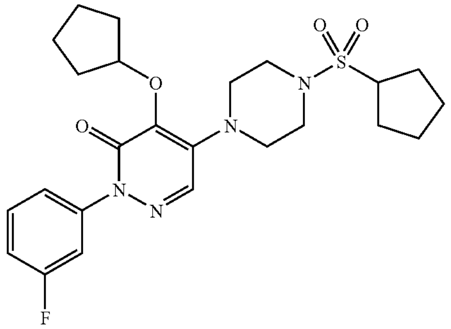 | 491 |
| 377Z | 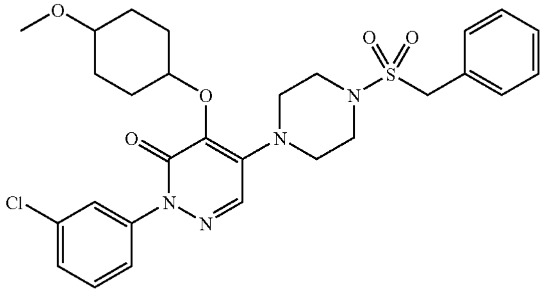 | 573 |
| 378Z | 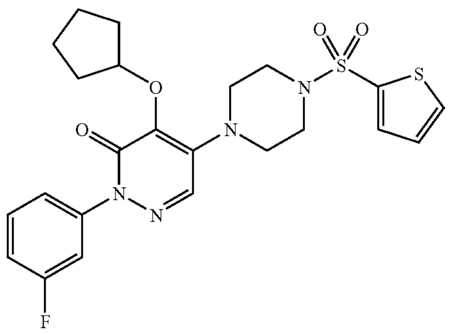 | 505 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
| --- | --- | --- |
| 379Z | 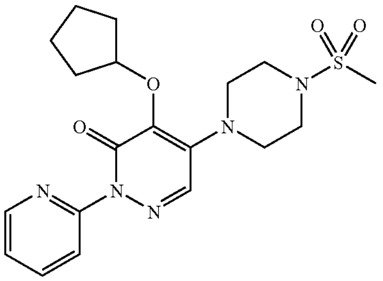 | 442 for M + 1-methyl |
| 380Z | 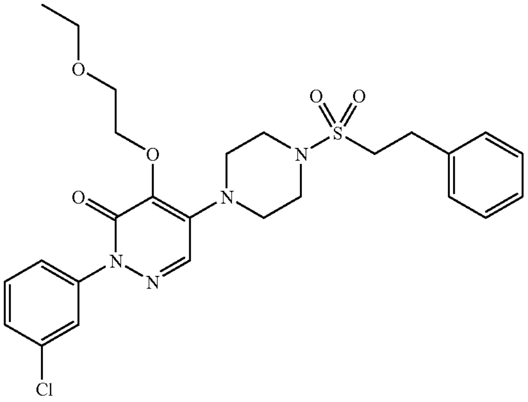 | 547 |
| 381Z | 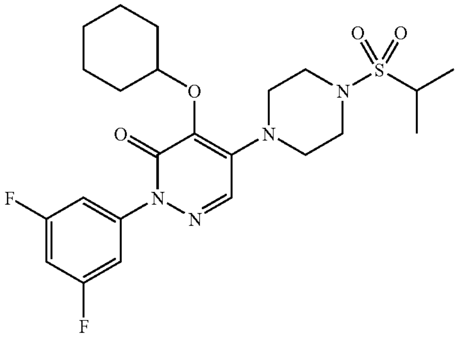 | 497 |
| 382Z | 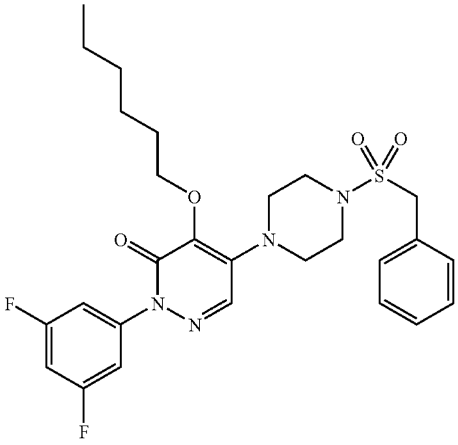 | 547 |

TABLE 10-continued
| Comp. No. | Structure | MS M + 1 |
|---|---|---|
| | Oxygen Linked Analogs with Sulfonamide The following compounds can be synthesized using steps 1, 2, 4, 6, and 9 of Scheme 1 or steps 11, 12, and 14 of Scheme 2. | |
| 383Z | 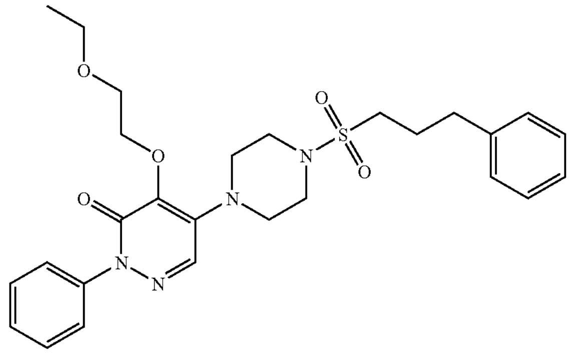 | 527 |
| 384Z | 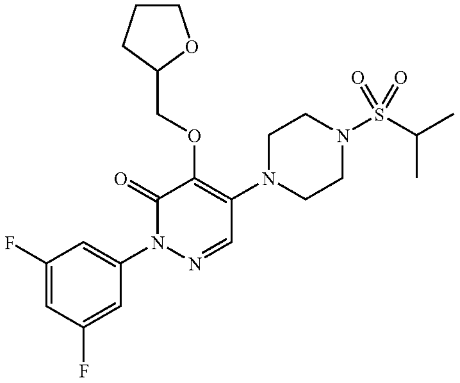 | 499 |
| 385Z | 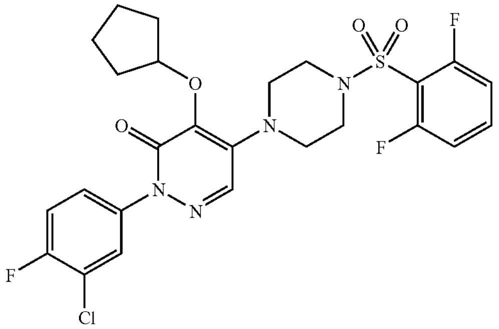 | 569 |
| 386Z | 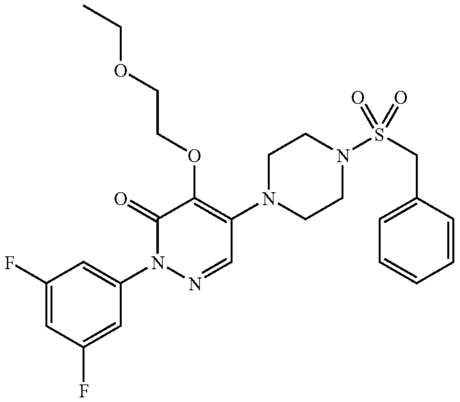 | 535 |

TABLE 10-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 387Z | 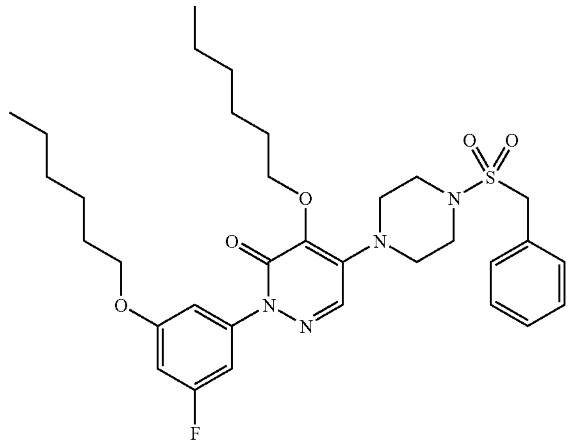 | 629 |
| 388Z | 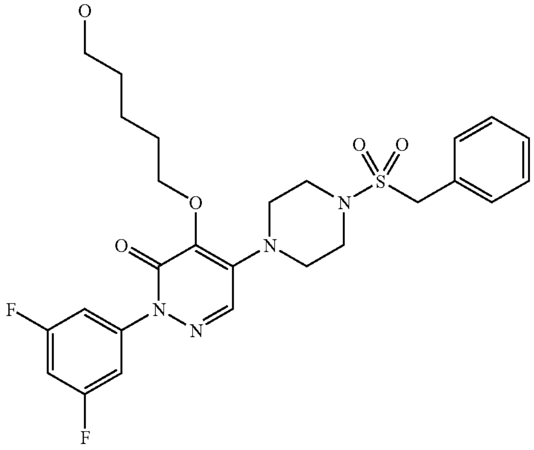 | 549 |
| 389Z | 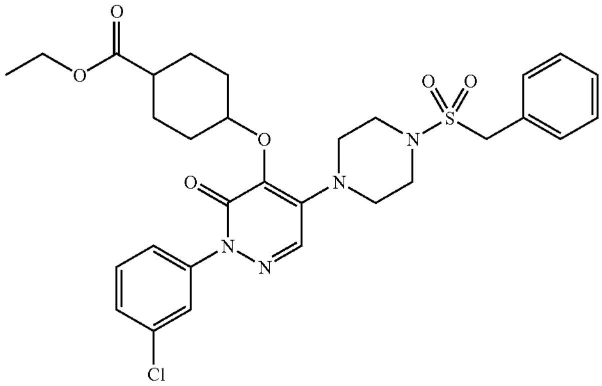 | 615 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 390Z | 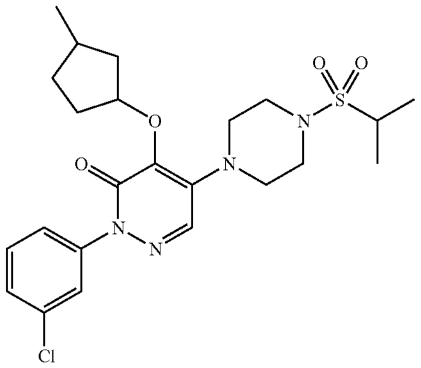 | 495 |
| 391Z | 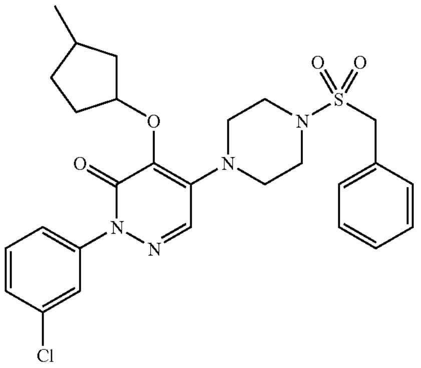 | 543<br>545 |
| 392Z | 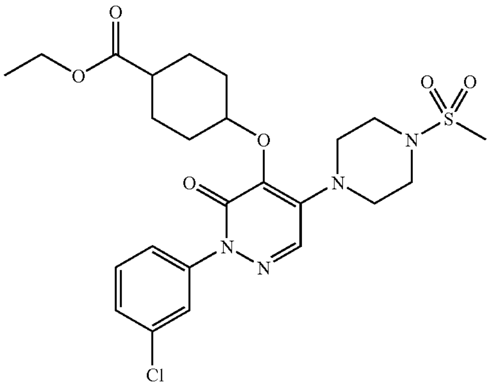 | 539 |
| 393Z | 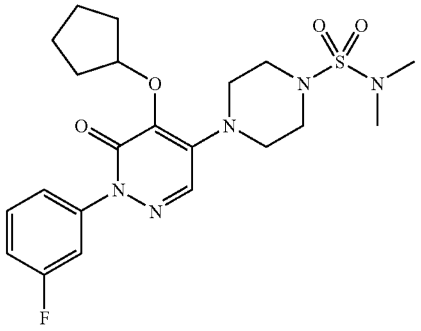 | 466 |

TABLE 10-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 394Z | 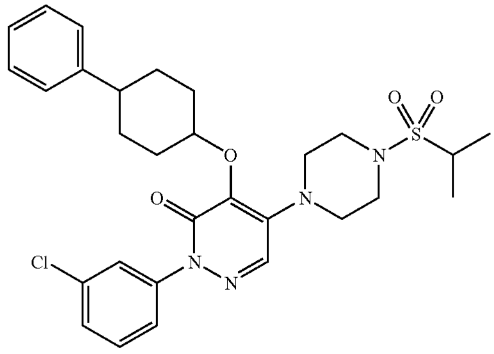 | 571 |
| 395Z | 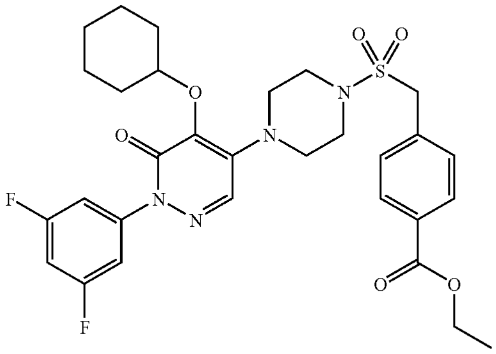 | 617 |
| 396Z | 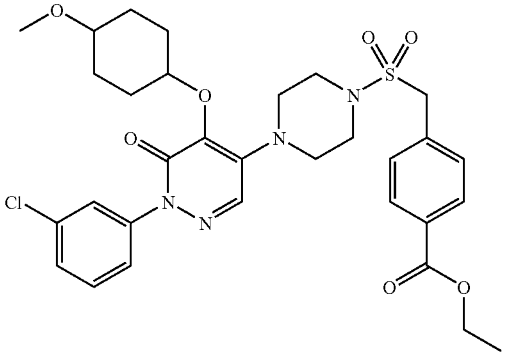 | 645 |
| 397Z | 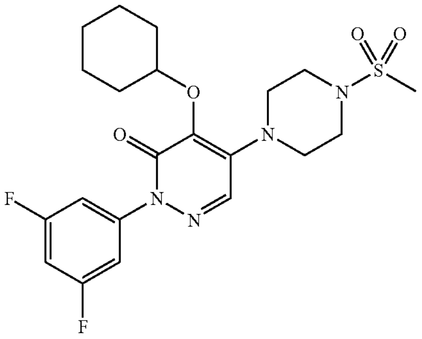 | 469 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 398Z | 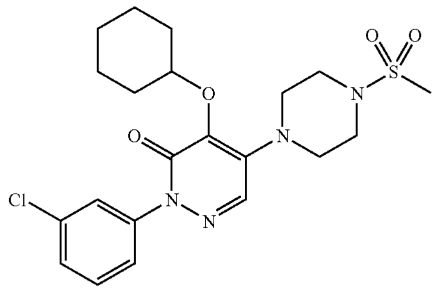 | 467 |
| 399Z | 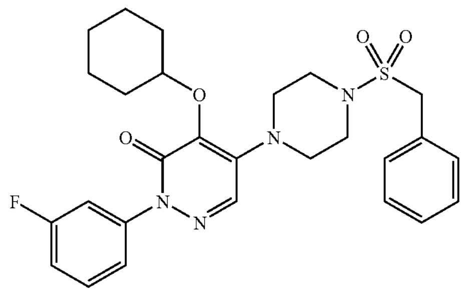 | 527 |
| 400Z | 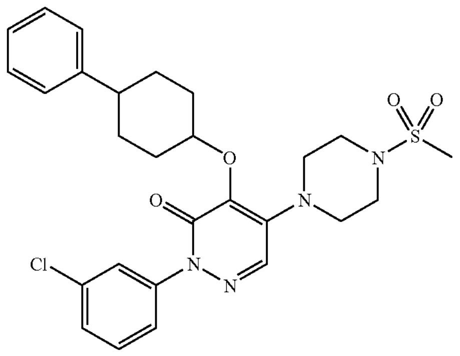 | 543 |
| 401Z | 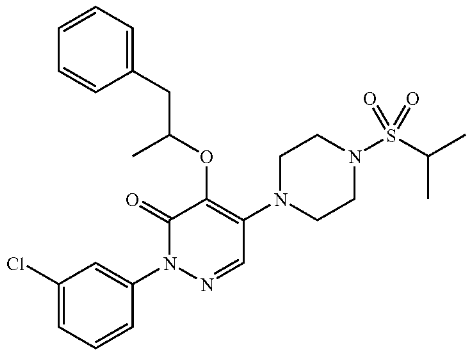 | 531 |

TABLE 10-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 402Z | 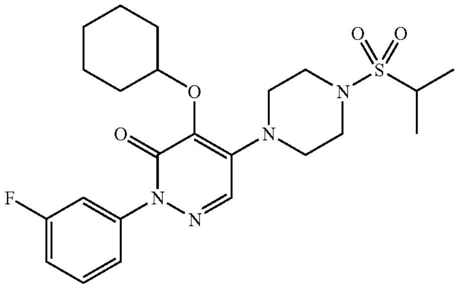 | 479 |
| 403Z | 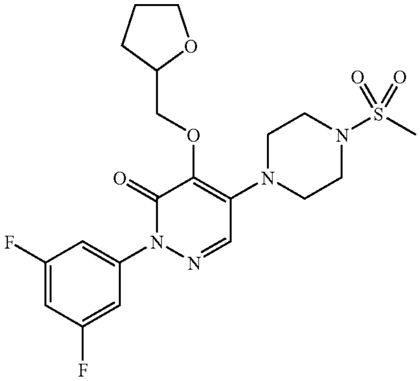 | 471 |
| 404Z | 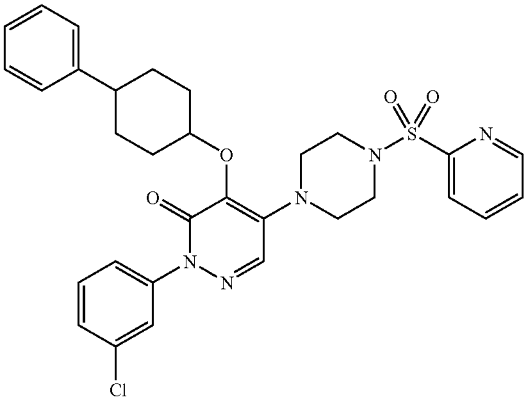 | 606 |
| 405Z | 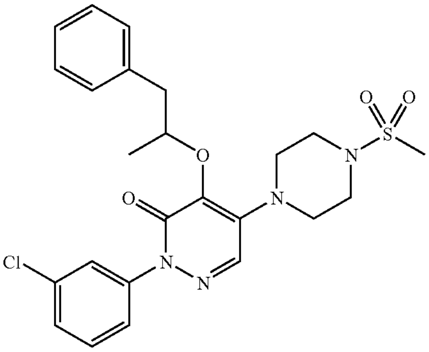 | 503 |

TABLE 10-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 406Z | 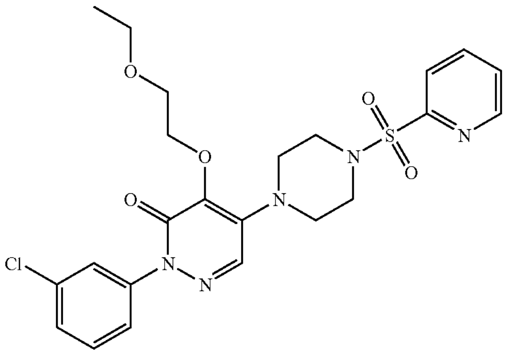 | 520 |
| 407Z | 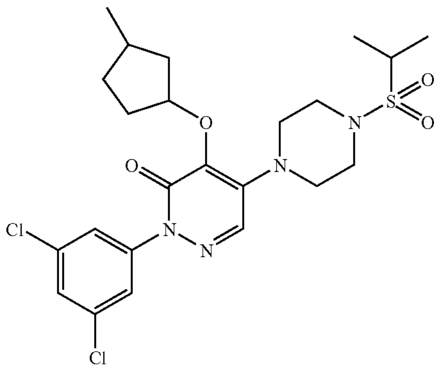 | 529 |
| 408Z | 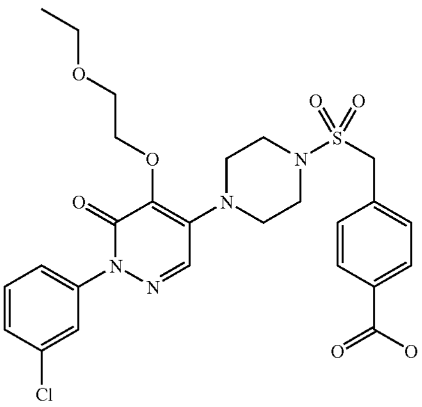 | 577 |

TABLE 10-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 409Z | 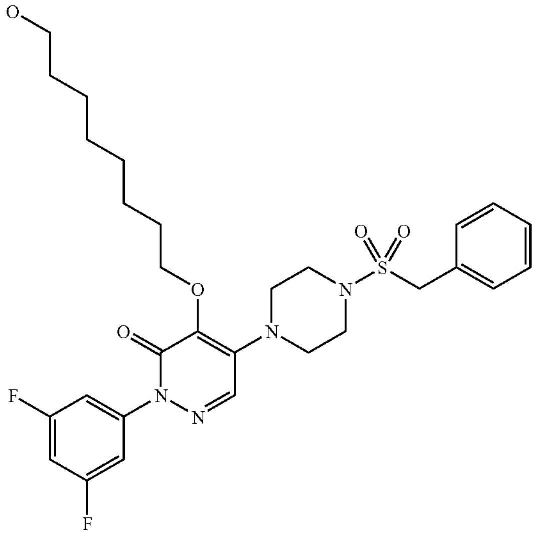 | 591 |
| 410Z | 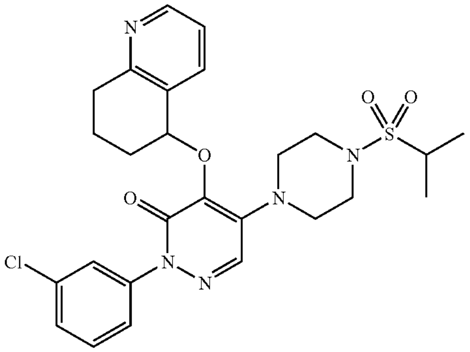 | 544 |
| 411Z | 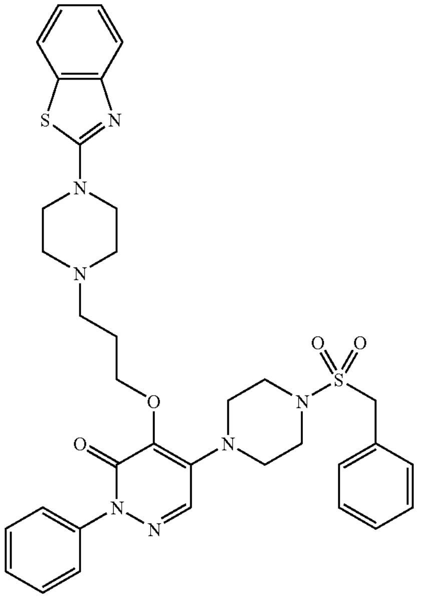 | 686 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
| --- | --- | --- |
| 412Z | 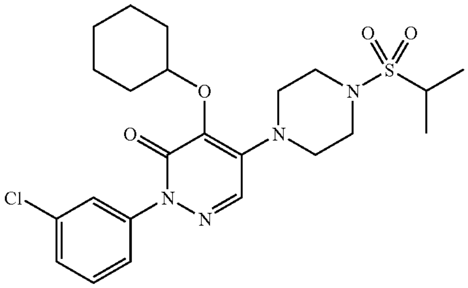 | 495 |
| 413Z | 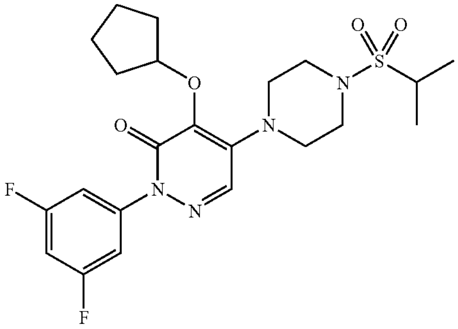 | 531 |
| 414Z | 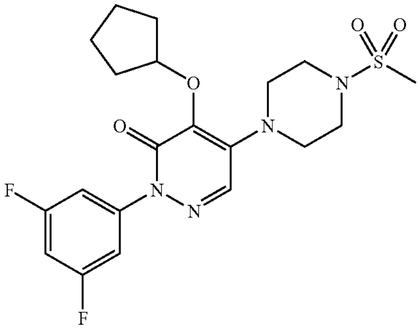 | 455 |
| 415Z | 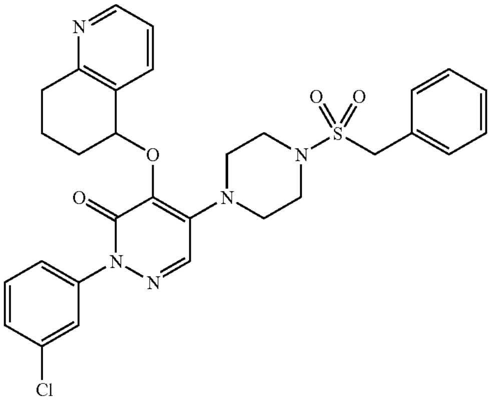 | 592 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 416Z | 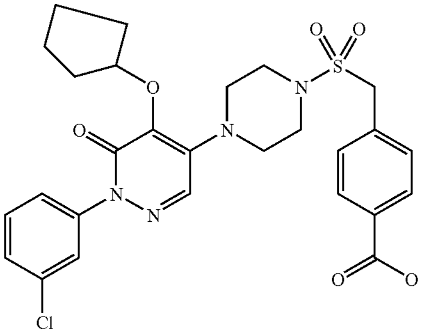 | 573 |
| 417Z | 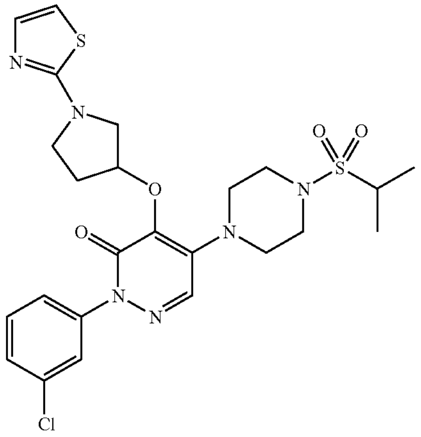 | 565 |
| 418Z | 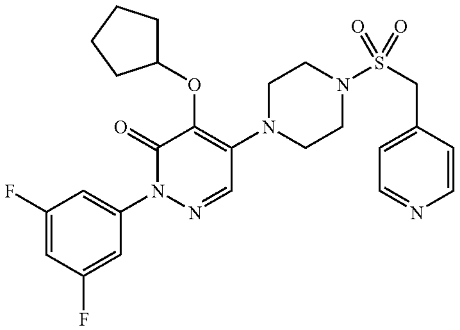 | 532 |
| 419Z | 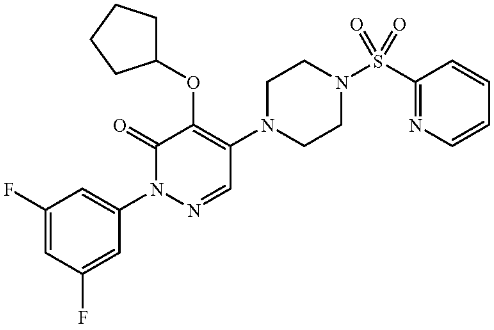 | 518 |

TABLE 10-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 420Z | 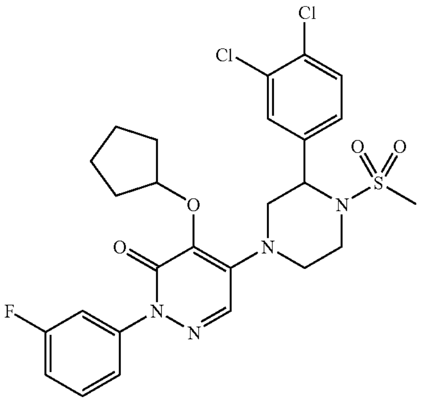 | 581 |
| 421Z | 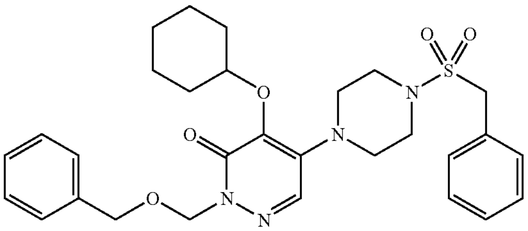 | 553 |
| 422Z | 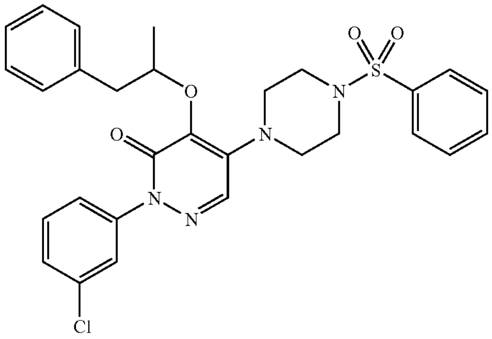 | 566 |
| 423Z | 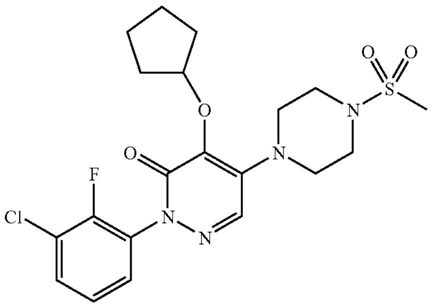 | 471 |

TABLE 10-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 424Z | 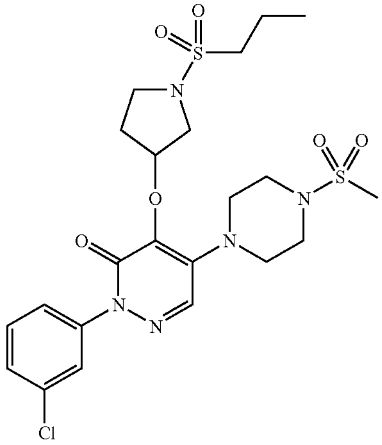 | 560 |
| 425Z | 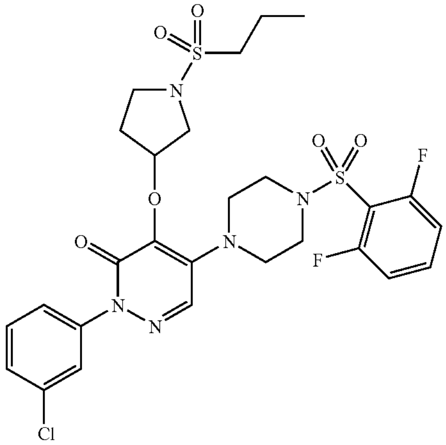 | 658 |
| 426Z | 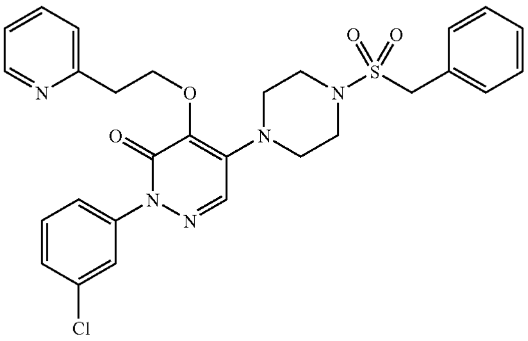 | 566 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
| --- | --- | --- |
| 427Z | 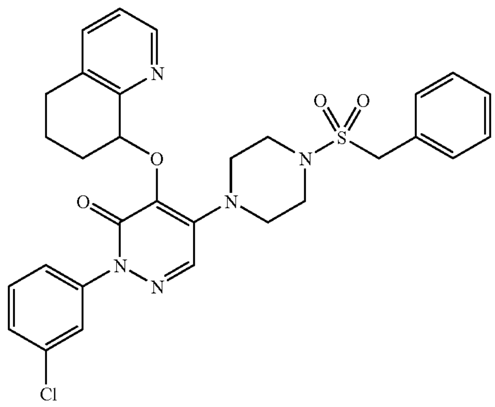 | 592 |
| 428Z | 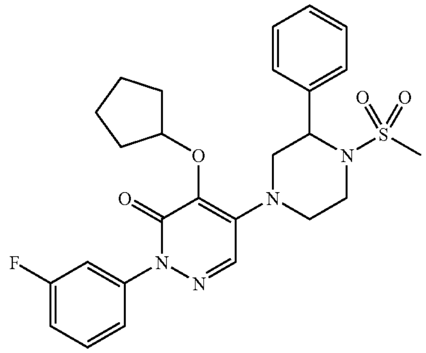 | 513 |
| 429Z | 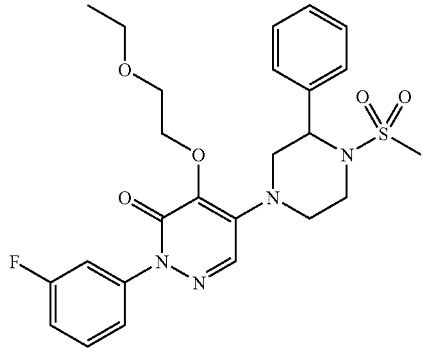 | 517 |
| 430Z | 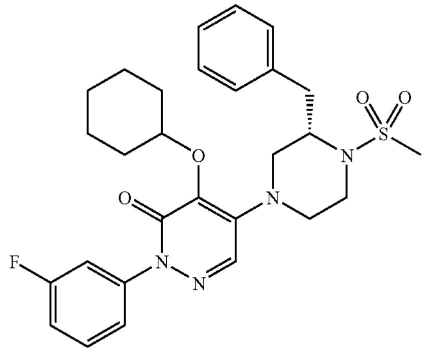 | 541 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 431Z | 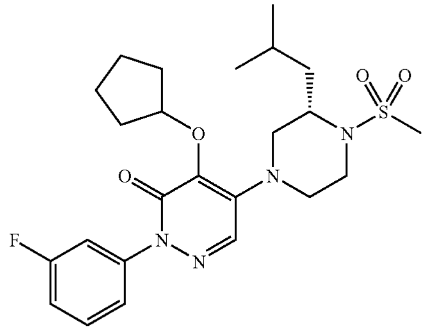 | 493 |
| 432Z | 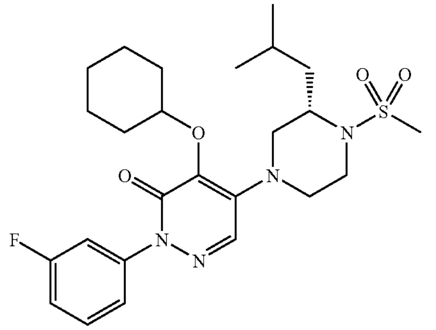 | 507 |
| 433Z | 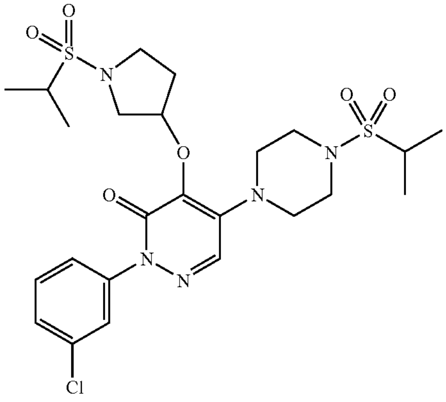 | 588 |
| 434Z | 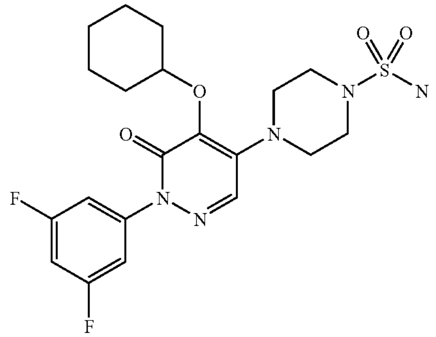 | 470 |

TABLE 10-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 435Z | 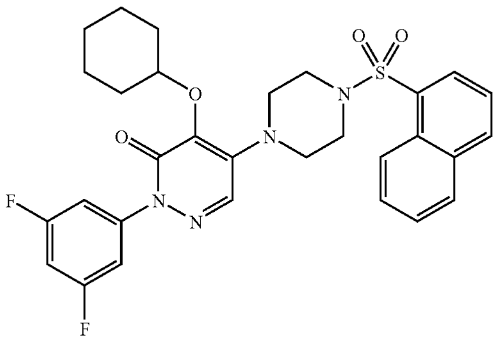 | 581 |
| 436Z | 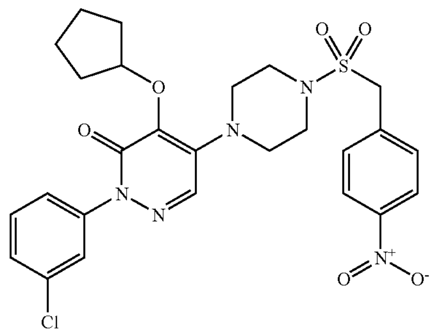 | 574 |
| 437Z | 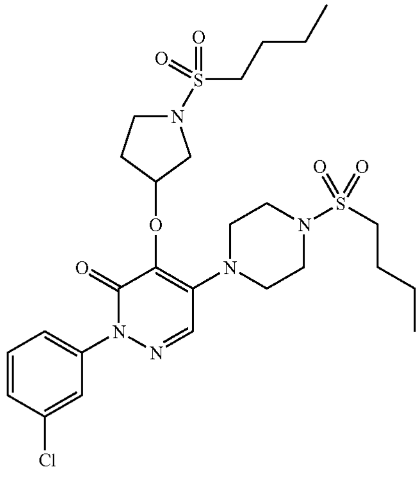 | 616 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 438Z | 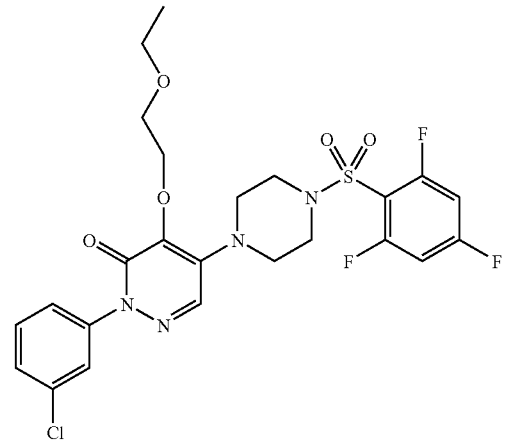 | 573 |
| 439Z | 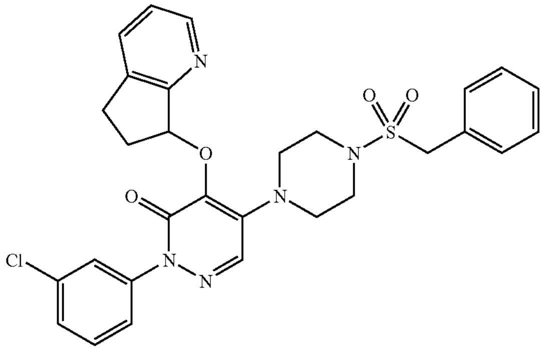 | 578 |
| 440Z | 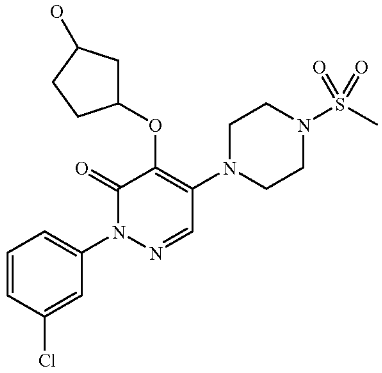 | 469 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 441Z | 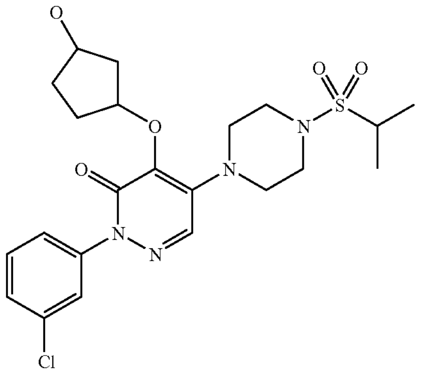 | 497 |
| 442Z | 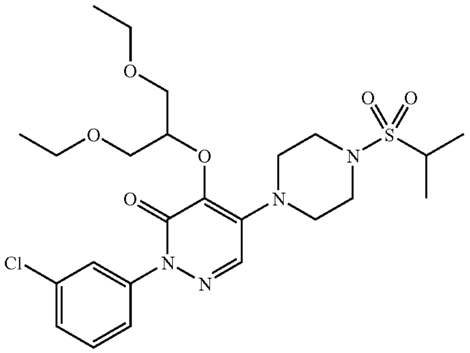 | 543 |
| 443Z | 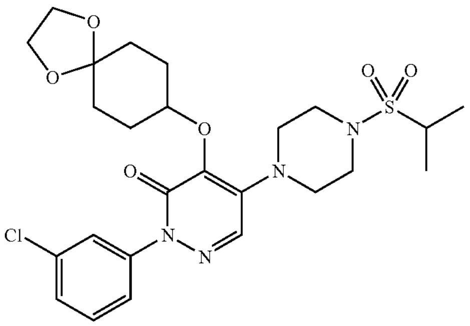 | 553 |
| 444Z | 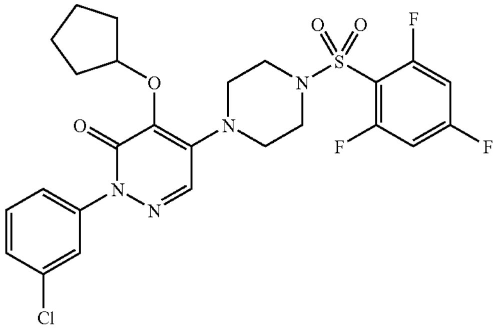 | 569 |

TABLE 10-continued
| Comp. No. | Structure | MS M + 1 |
|---|---|---|
| Oxygen Linked Analogs with Sulfonamide. The following compounds can be synthesized using steps 1, 2, 4, 6, and 9 of Scheme 1 or steps 11, 12, and 14 of Scheme 2. | | |
| 445Z | 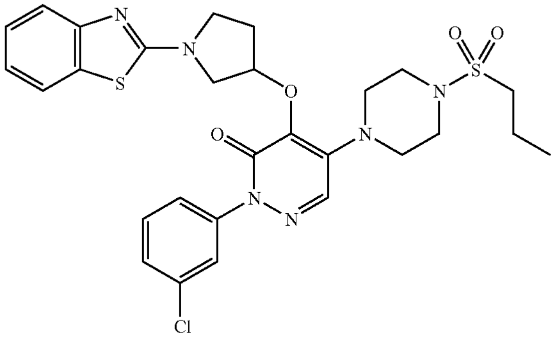 | 615 |
| 446Z | 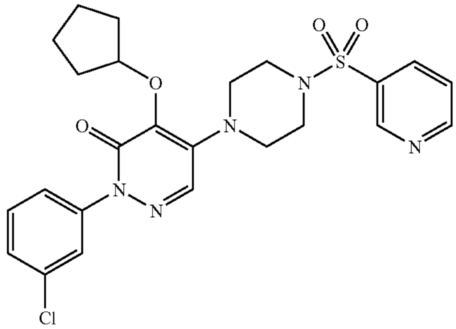 | 516 |
| 447Z | 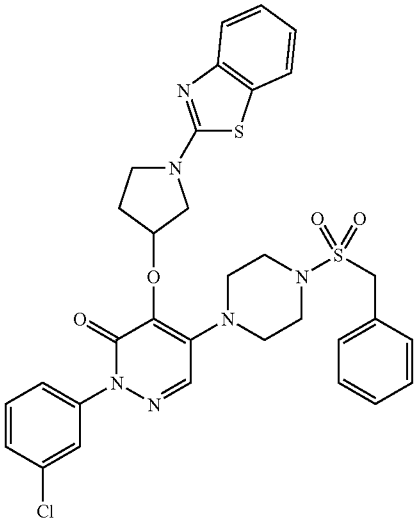 | 663 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 448Z | 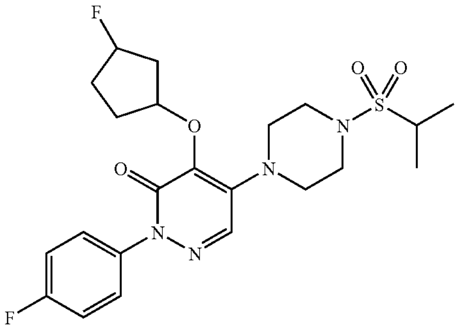 | 483 |
| 449Z | 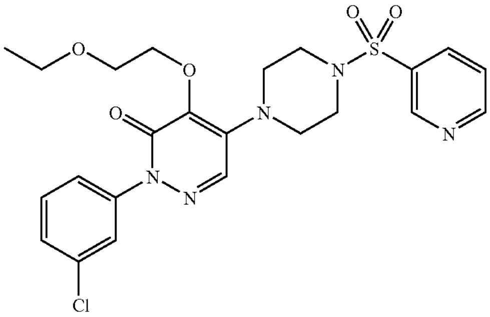 | 520 |
| 450Z | 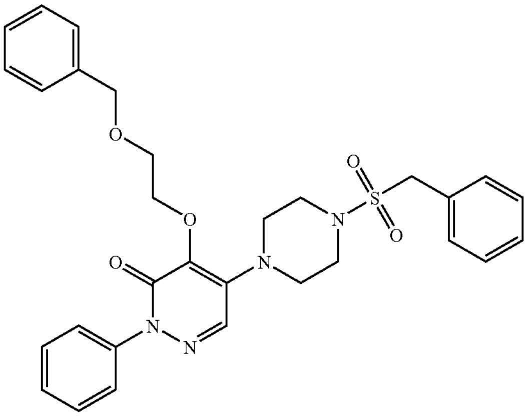 | 561 |
| 451Z | 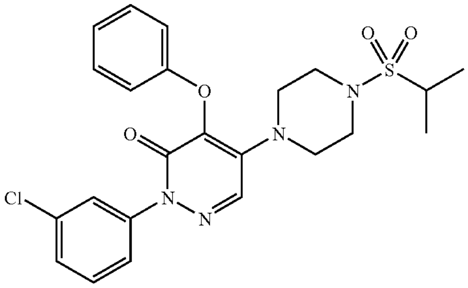 | 489 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
| --- | --- | --- |
| 452Z | 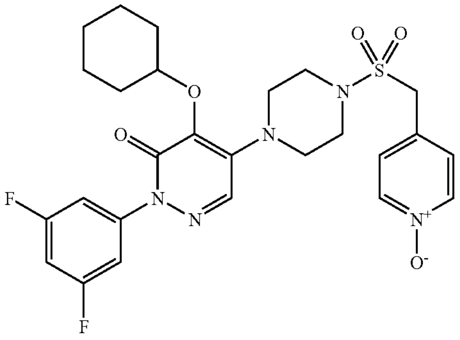 | 562 |
| 453Z | 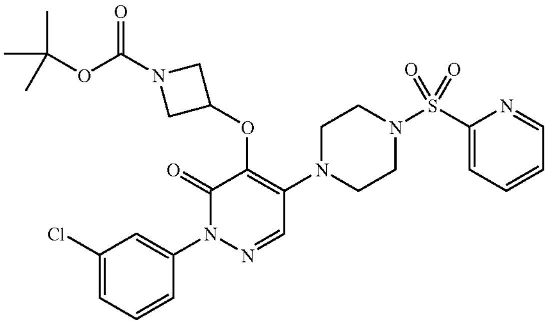 | 603 |
| 454Z | 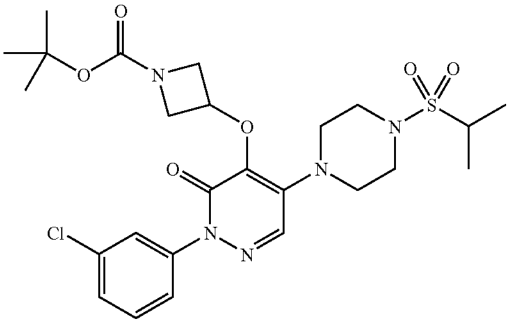 | 568 |
| 455Z | 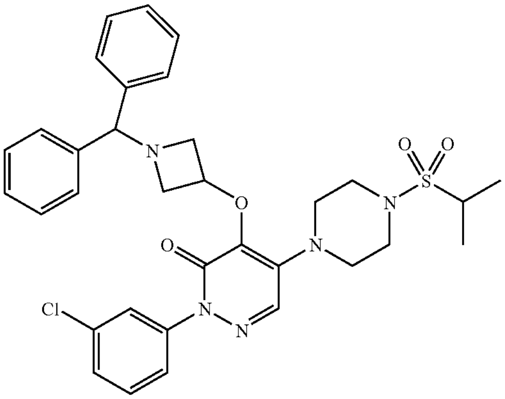 | 636 |

TABLE 10-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 456Z | 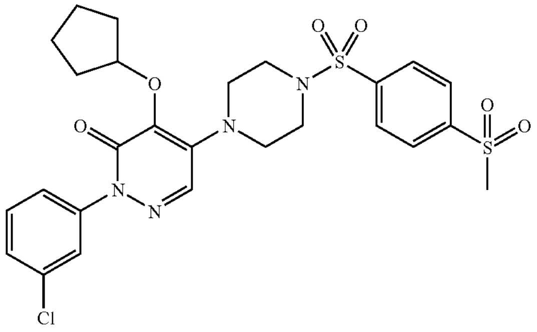 | 593 |
| 457Z | 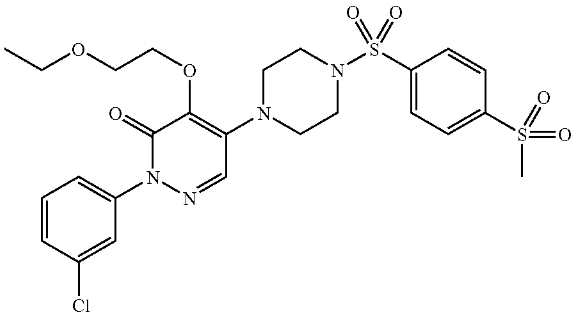 | 570 |
| 458Z | 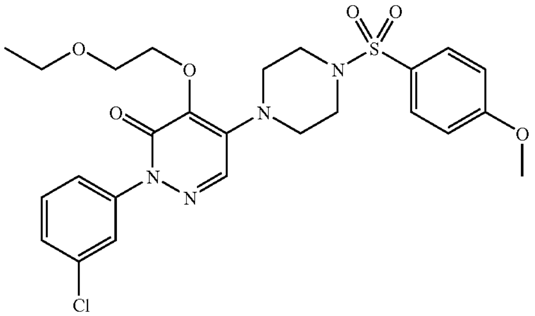 | 549 |
| 459Z | 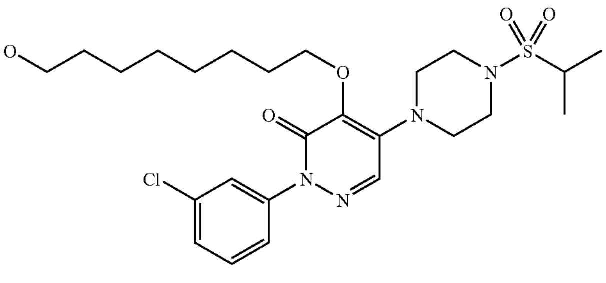 | 541 |

TABLE 10-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 460Z | 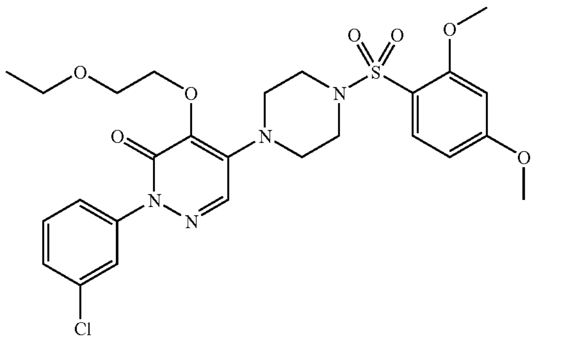 | 579 |
| 461Z | 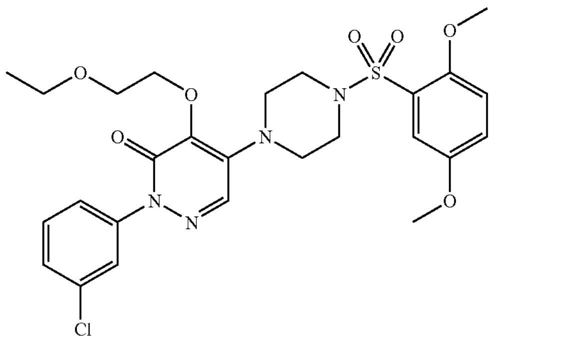 | 579 |
| 462Z | 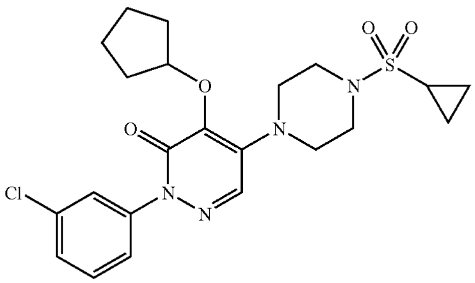 | 479 |
| 463Z | 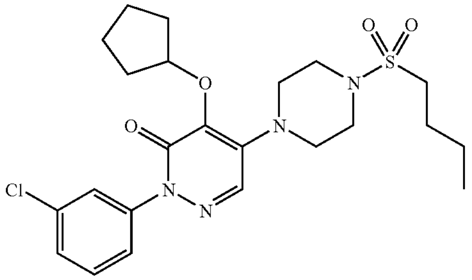 | 495 |

TABLE 10-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 464Z | 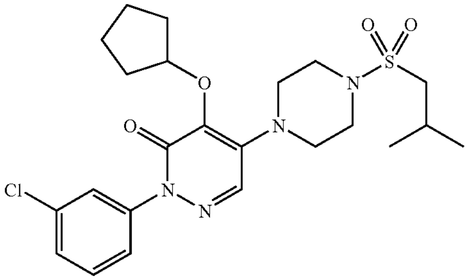 | 495 |
| 465Z | 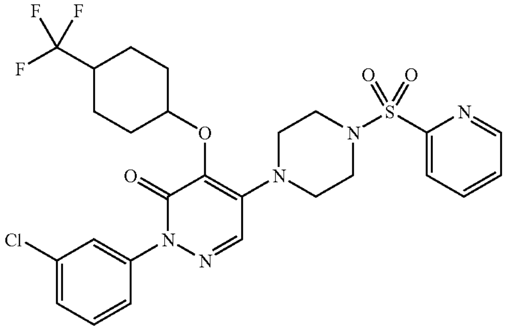 | 598 |
| 466Z | 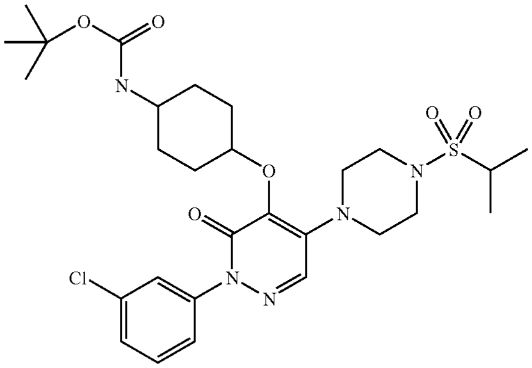 | 610 |
| 467Z | 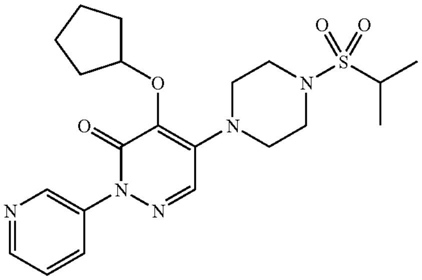 | 448 |

TABLE 10-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 468Z | 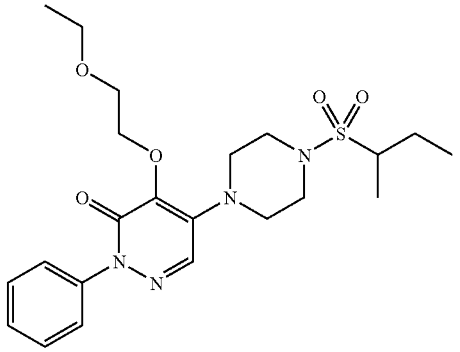 | 465 |
| 469Z | 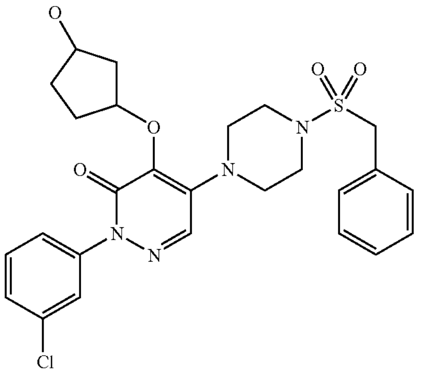 | 545 |
| 470Z | 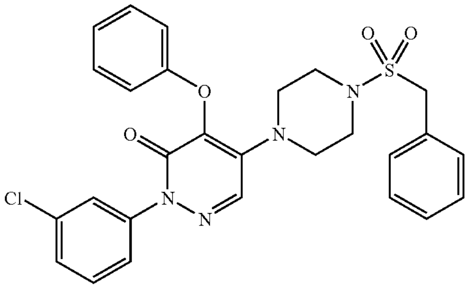 | 537 |
| 471Z | 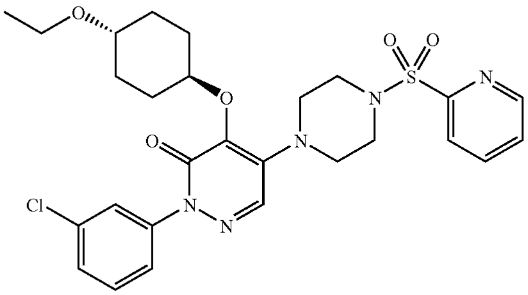 | 574 |

TABLE 10-continued
| Comp. No. | Structure | MS M + 1 |
|---|---|---|
| | Oxygen Linked Analogs with Sulfonamide The following compounds can be synthesized using steps 1, 2, 4, 6, and 9 of Scheme 1 or steps 11, 12, and 14 of Scheme 2. | |
| 472Z | 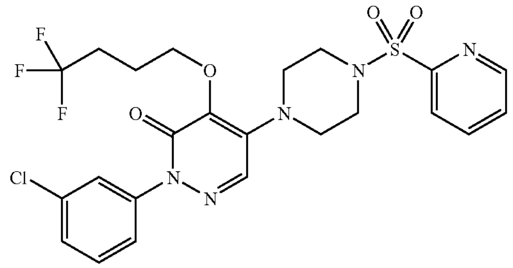 | 558 |
| 473Z | 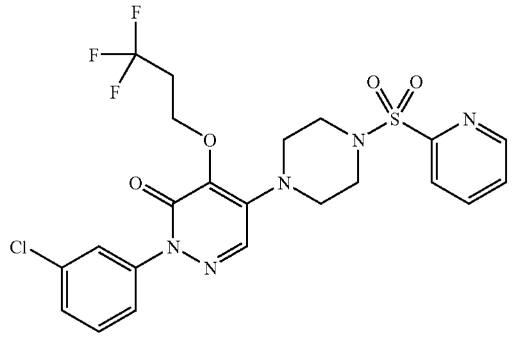 | 544 |
| 474Z | 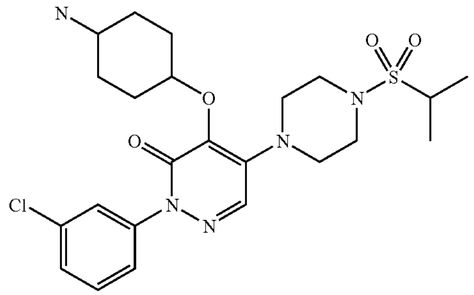 | 525 |
| 475Z | 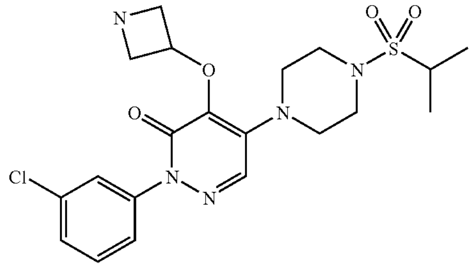 | 466 (M − H) |
| 476Z | 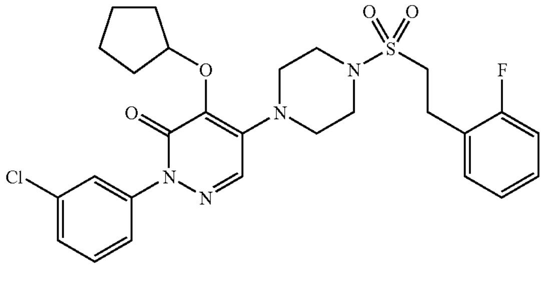 | 561 |

TABLE 10-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 477Z | 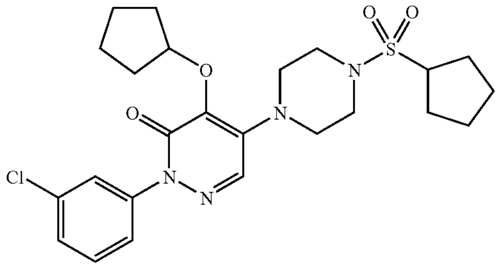 | 507 |
| 478Z | 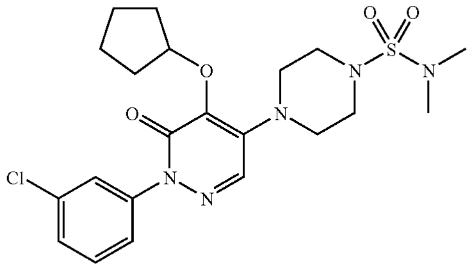 | 482 |
| 479Z | 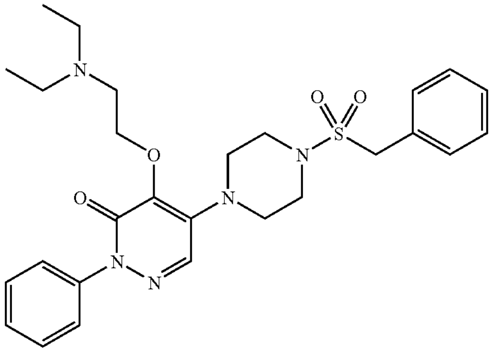 | 526 |
| 480Z | 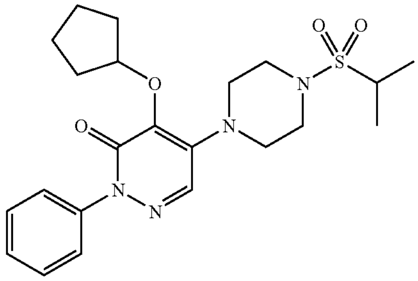 | 447 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 481Z | 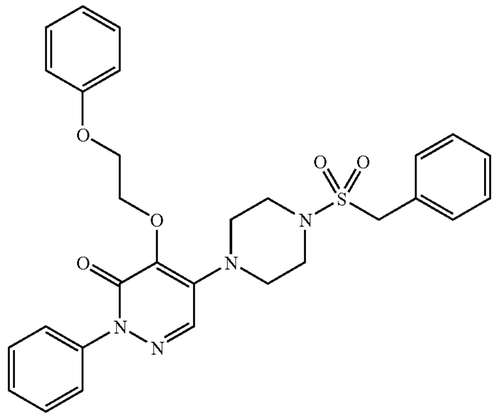 | 547 |
| 482Z | 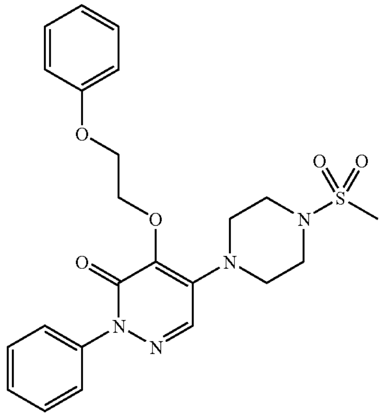 | 471 |
| 483Z | 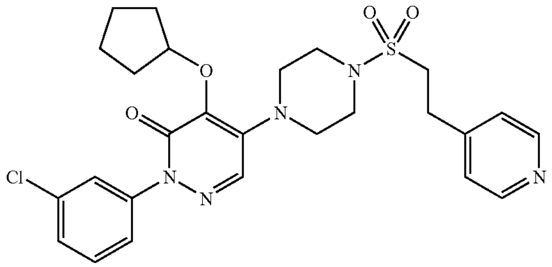 | 544 |
| 484Z | 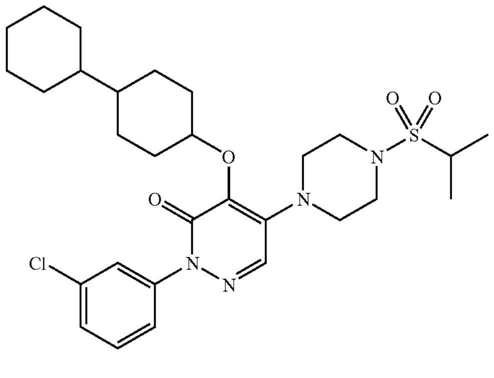 | 577 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 485Z | 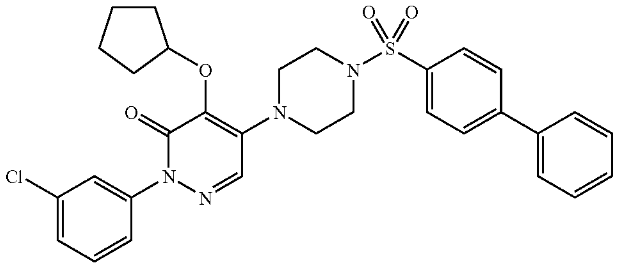 | 591 |
| 486Z | 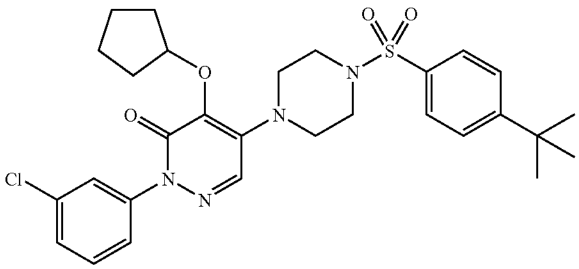 | 571 |
| 487Z | 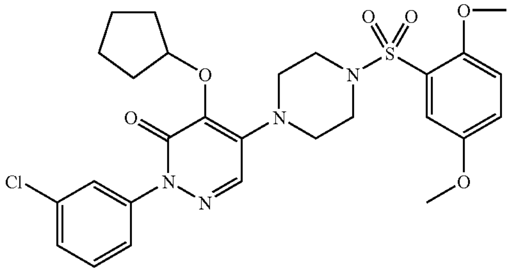 | 575 |
| 488Z | 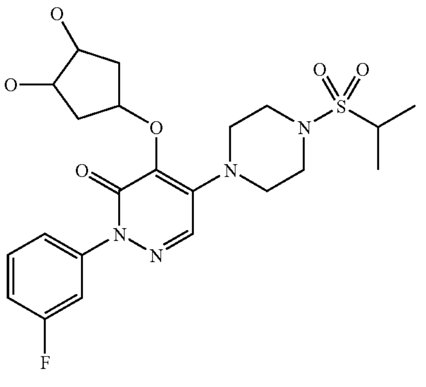 | 497 |

TABLE 10-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 489Z | 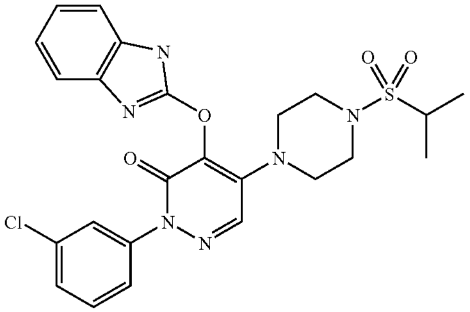 | 529 |
| 490Z | no compound | |
| 491Z | 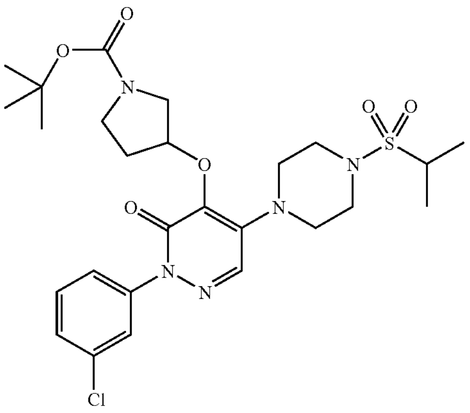 | 482 (M − BOC) |
| 492Z | 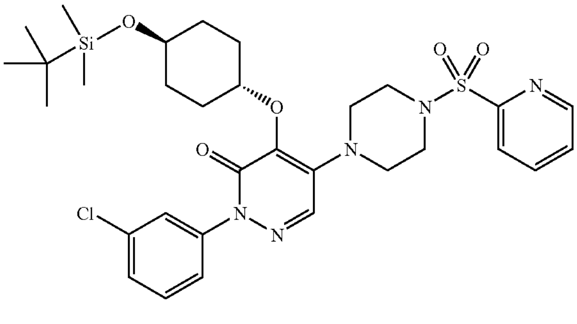 | 661 |
| 493Z | 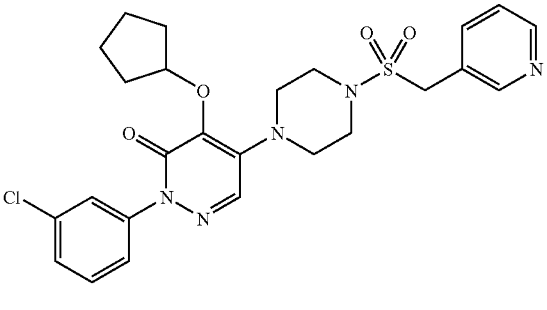 | 530 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
| --- | --- | --- |
| 494Z | 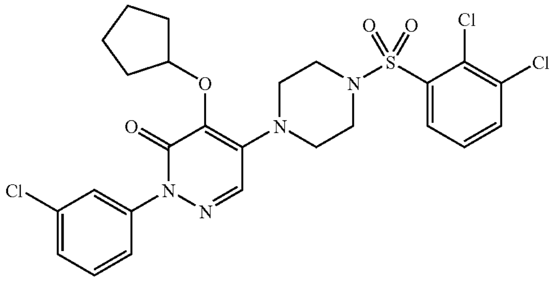 | 583 |
| 495Z | 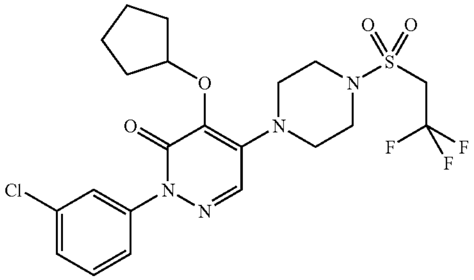 | 521 |
| 496Z | 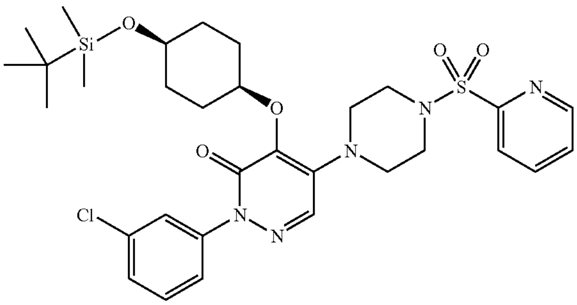 | 660 |
| 497Z | 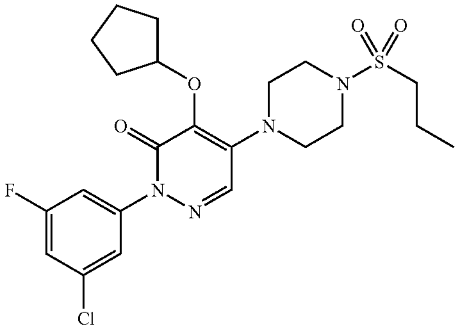 | 499 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 498Z | 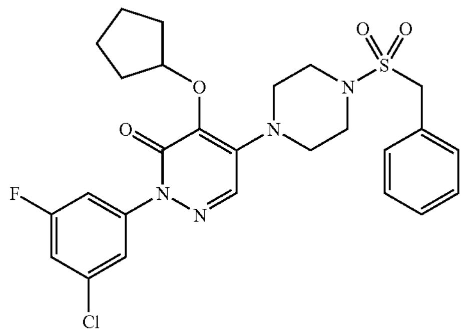 | 547 |
| 499Z | 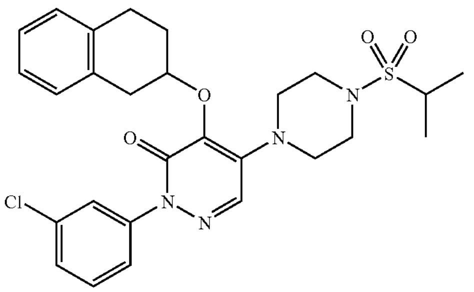 | 543 |
| 500Z | 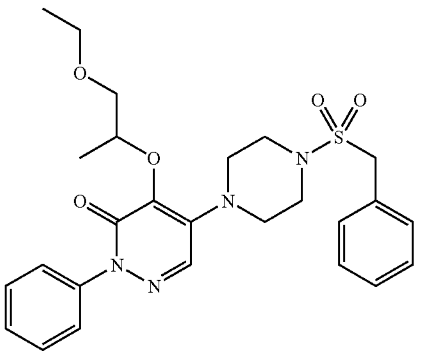 | 513 |
| 501Z | 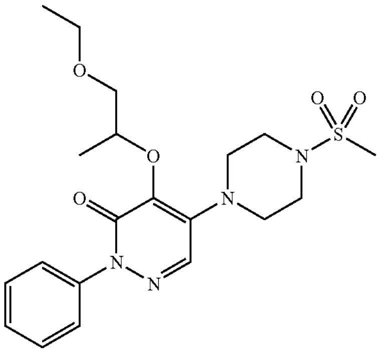 | 437 |

TABLE 10-continued
| Comp. No. | Structure | MS M + 1 |
| --- | --- | --- |
| Oxygen Linked Analogs with Sulfonamide The following compounds can be synthesized using steps 1, 2, 4, 6, and 9 of Scheme 1 or steps 11, 12, and 14 of Scheme 2. | | |
| 502Z | 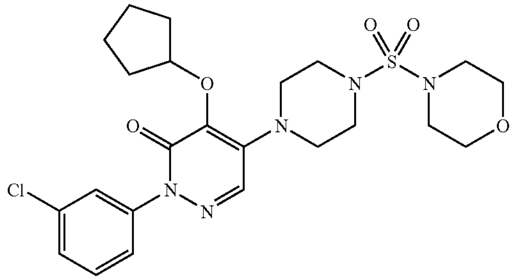 | 524 |
| 503Z | 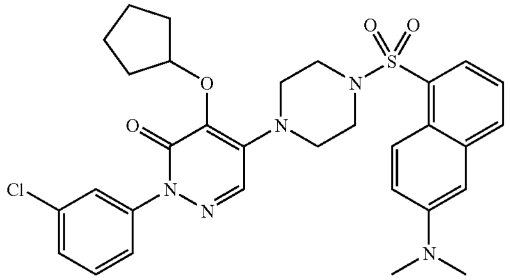 | 608 |
| 504Z | 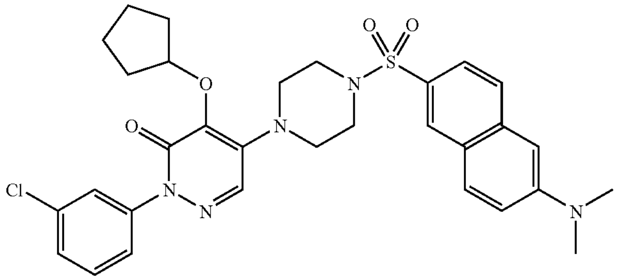 | 608 |
| 505Z | 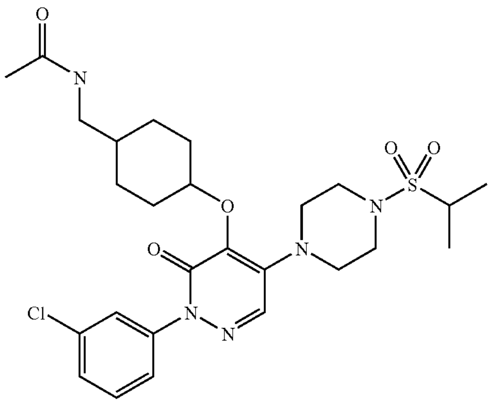 | 568 (M + 2) |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
| --- | --- | --- |
| 506Z | 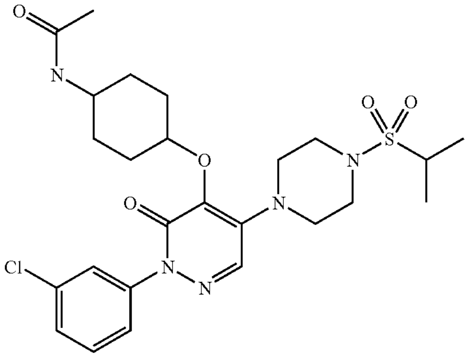 | 552 |
| 507Z | 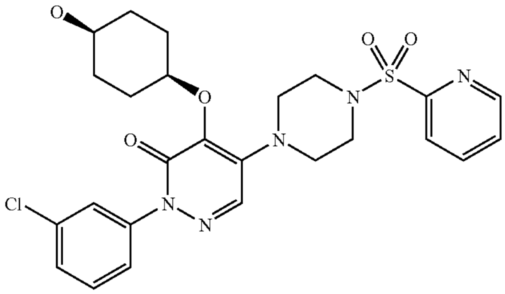 | 546 |
| 508Z | 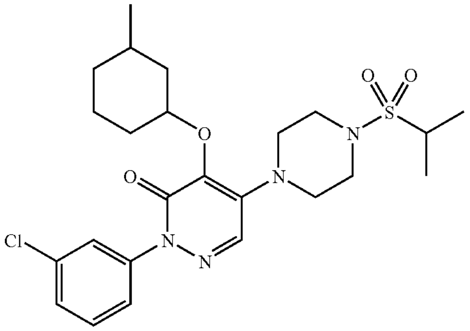 | 510 |
| 509Z | 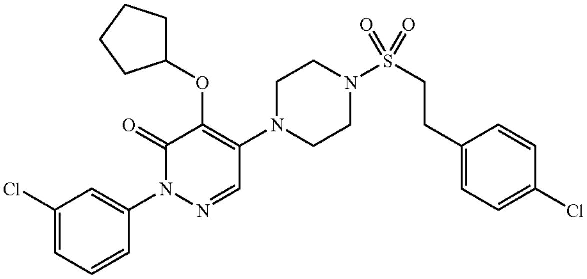 | 577 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 510Z | 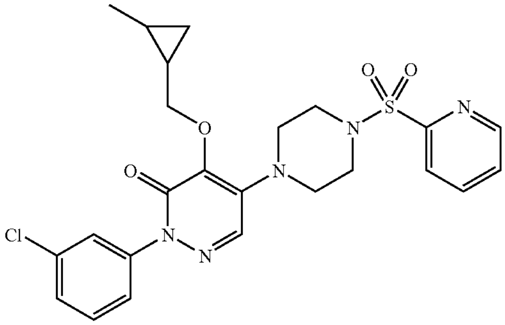 | 516 |
| 511Z | 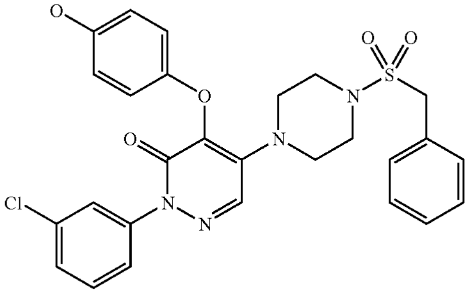 | 553 |
| 512Z | 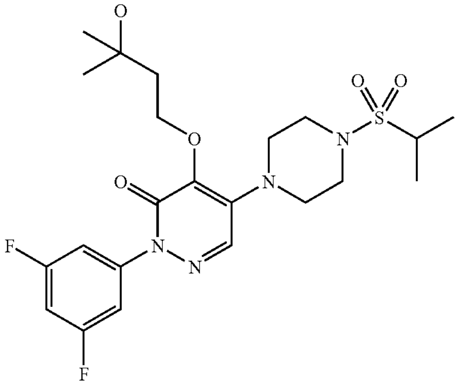 | 501 |
| 513Z | 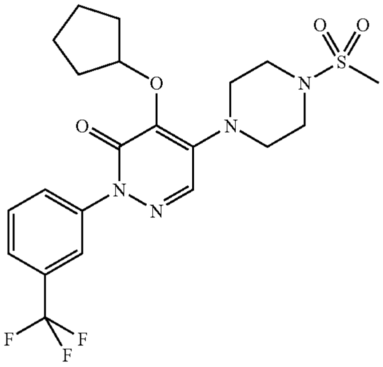 | 487 |

TABLE 10-continued
| Comp. No. | Structure | MS M + 1 |
|---|---|---|
| | Oxygen Linked Analogs with Sulfonamide The following compounds can be synthesized using steps 1, 2, 4, 6, and 9 of Scheme 1 or steps 11, 12, and 14 of Scheme 2. | |
| 514Z | 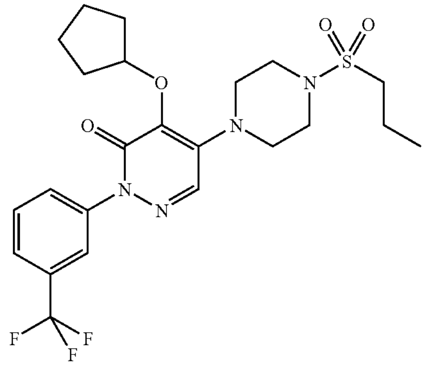 | 515 |
| 515Z | 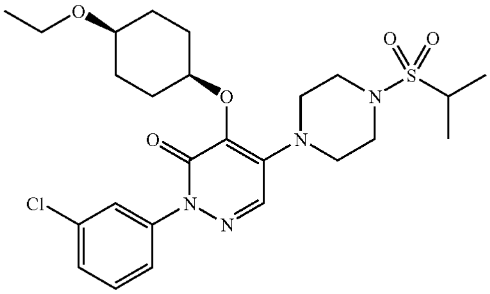 | 539 |
| 516Z | 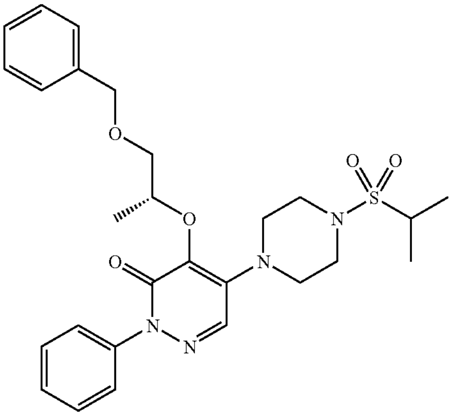 | 527 |
| 517Z | 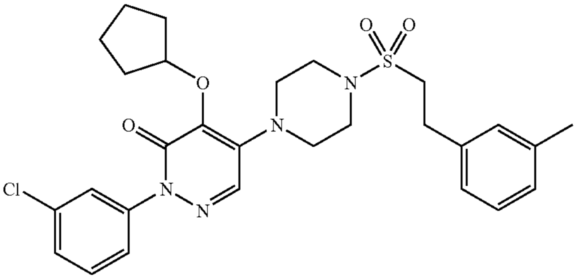 | 557 |

TABLE 10-continued
| Comp. No. | Structure | MS M + 1 |
| --- | --- | --- |
| | Oxygen Linked Analogs with Sulfonamide The following compounds can be synthesized using steps 1, 2, 4, 6, and 9 of Scheme 1 or steps 11, 12, and 14 of Scheme 2. | |
| 518Z | 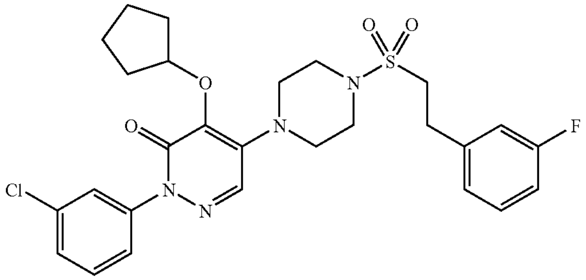 | 561 |
| 519Z | 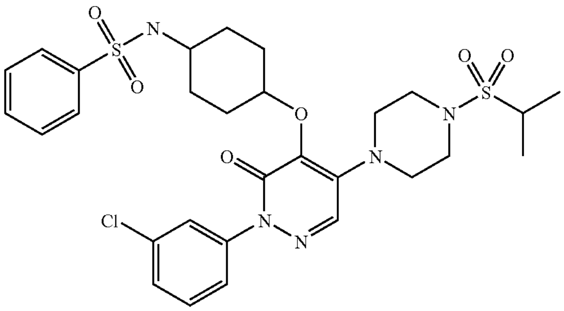 | 650 |
| 520Z | 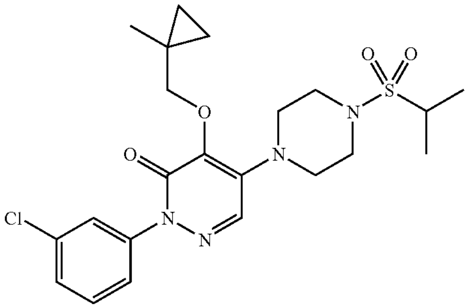 | 481 |
| 521Z | 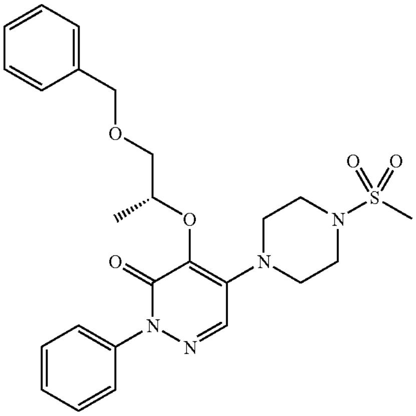 | 499 |

TABLE 10-continued
| Comp. No. | Structure | MS M + 1 |
|---|---|---|
| Oxygen Linked Analogs with Sulfonamide The following compounds can be synthesized using steps 1, 2, 4, 6, and 9 of Scheme 1 or steps 11, 12, and 14 of Scheme 2. | | |
| 522Z | 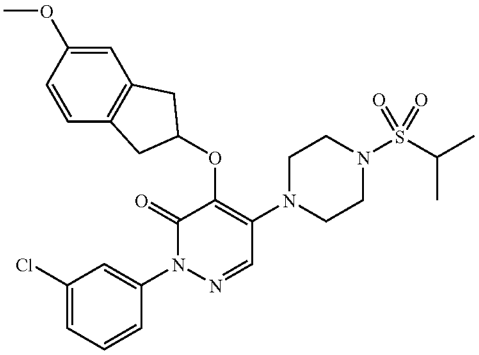 | 559 |
| 523Z | 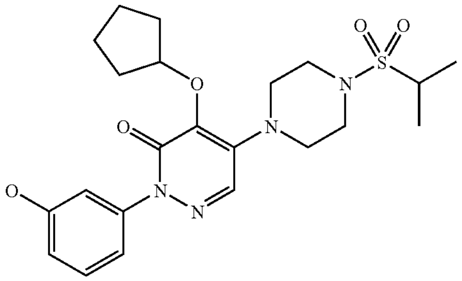 | 463 |
| 524Z | 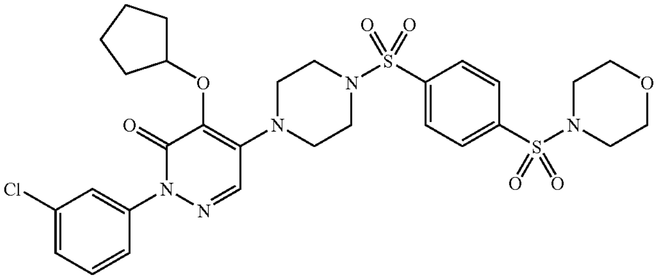 | 664 |
| 525Z | 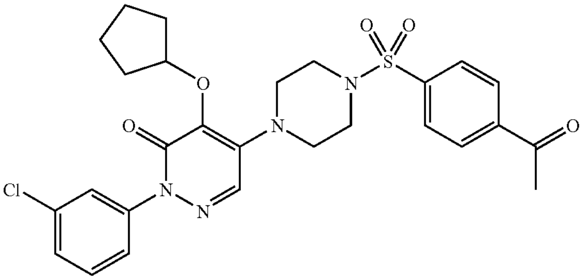 | 557 |
| 526Z | 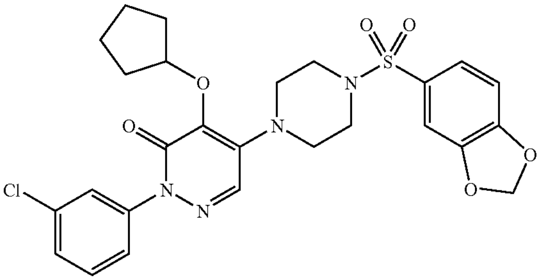 | 559 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 527Z | 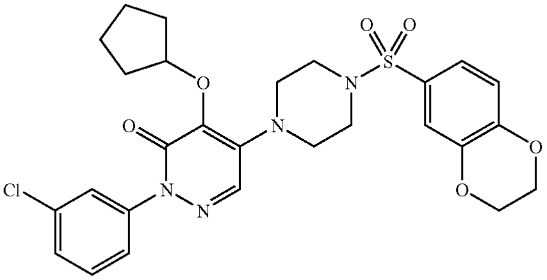 | 573 |
| 528Z | 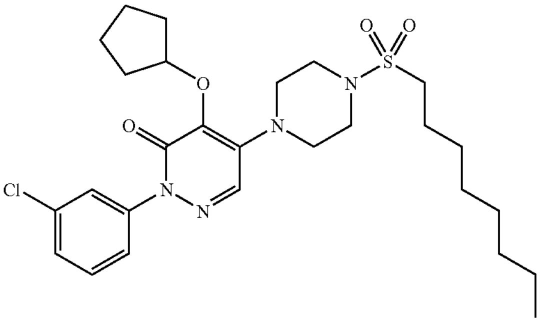 | 551 |
| 529Z | 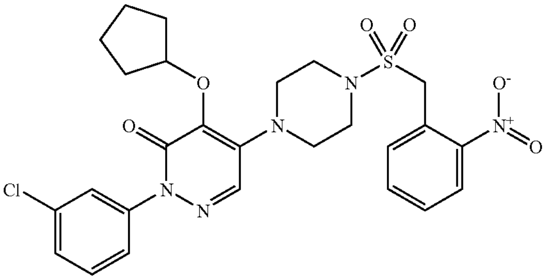 | 574 |
| 530Z | 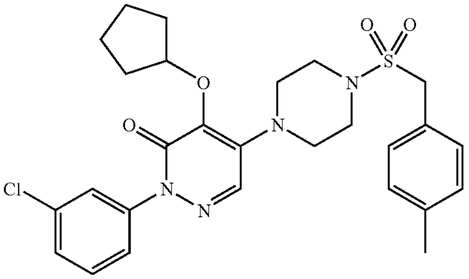 | 543 |
| 531Z | 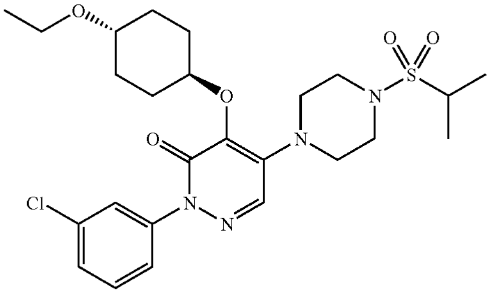 | 539 |

TABLE 10-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 532Z | 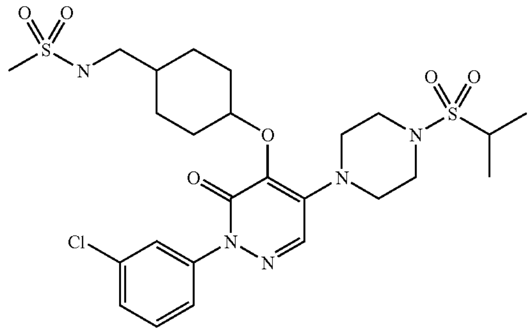 | 603 |
| 533Z | 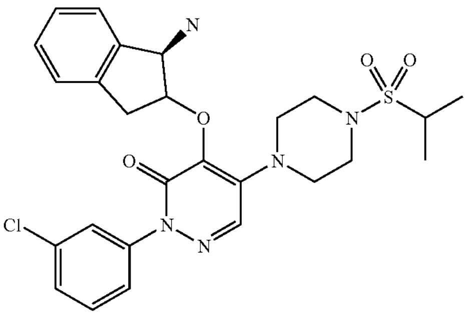 | 544 |
| 534Z | 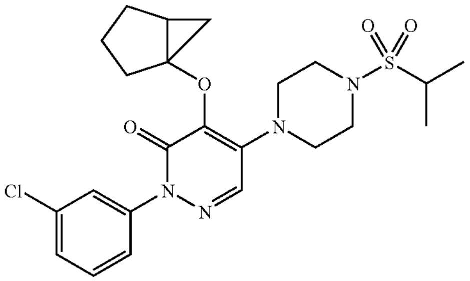 | 493 |
| 535Z | 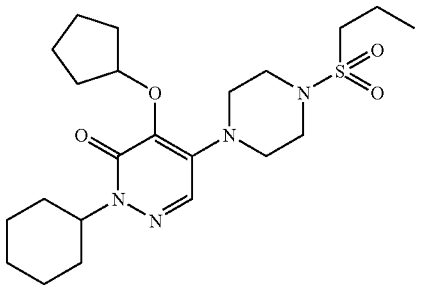 | 425 (M + 1-ethylene) |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 536Z | 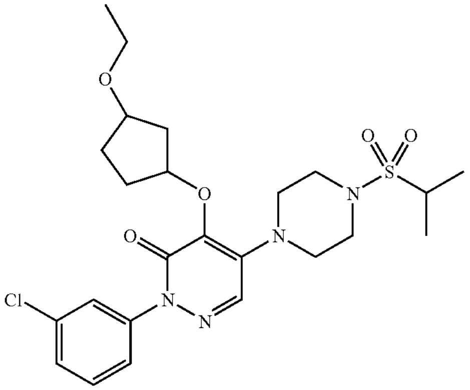 | 525 |
| 537Z | 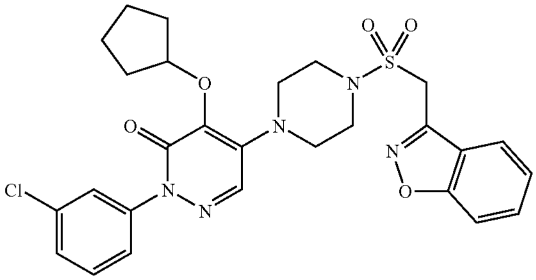 | 570 |
| 538Z | 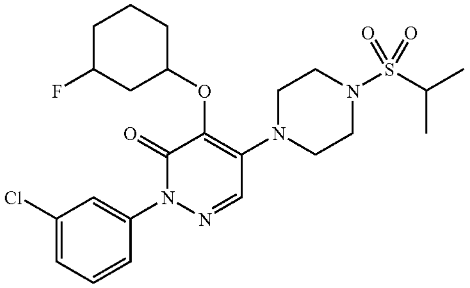 | 513 |
| 539Z | 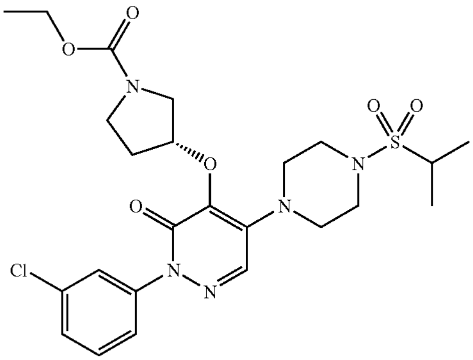 | 554 |

TABLE 10-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 540Z | 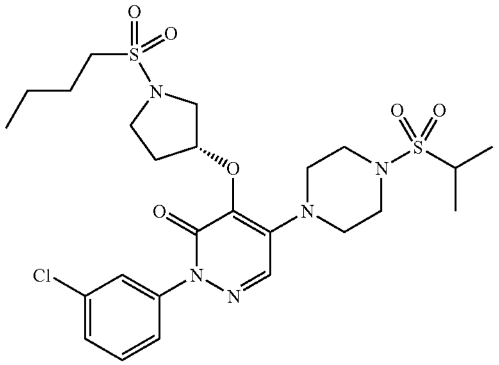 | 602 |
| 541Z | 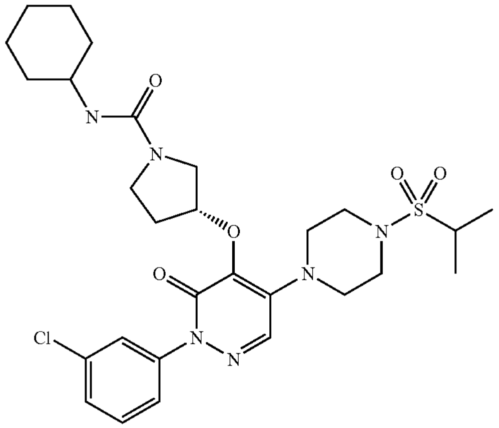 | 607 |
| 542Z | 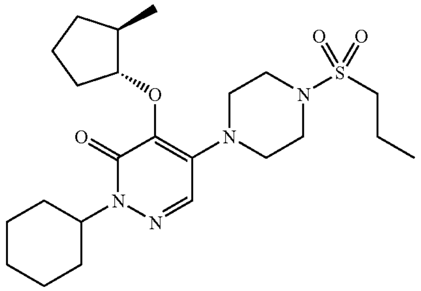 | 467 |
| 543Z | 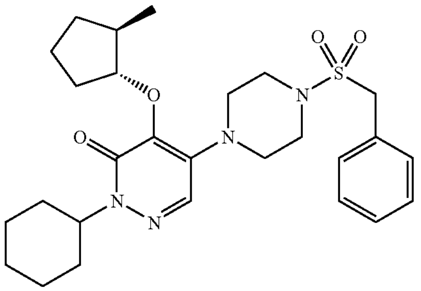 | 515 |

TABLE 10-continued
| Comp. No. | Structure | MS M + 1 |
|---|---|---|
| Oxygen Linked Analogs with Sulfonamide The following compounds can be synthesized using steps 1, 2, 4, 6, and 9 of Scheme 1 or steps 11, 12, and 14 of Scheme 2. | | |
| 544Z | 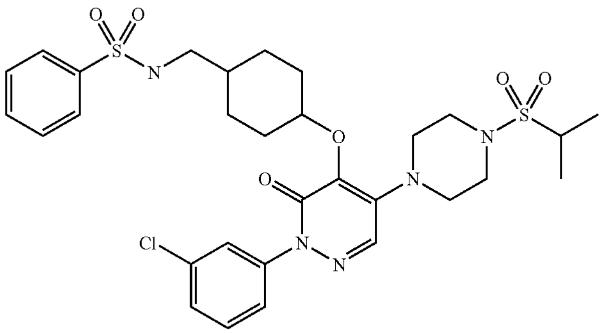 | 664 |
| 545Z | 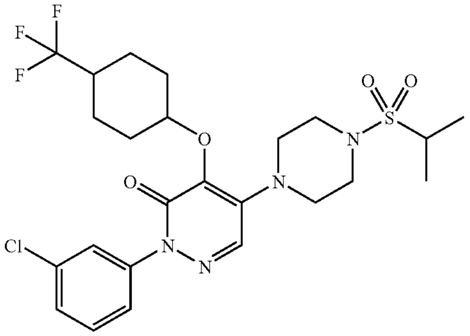 | 563 |
| 546Z | 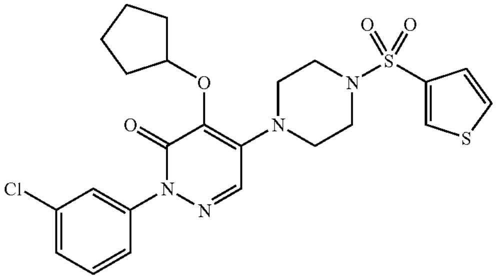 | 521 |
| 547Z | 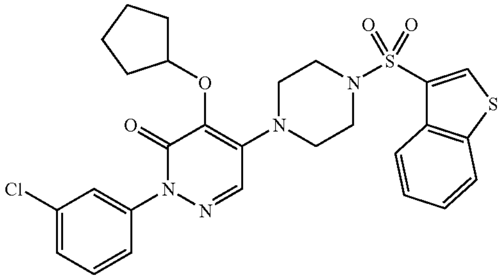 | 571 |

TABLE 10-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 548Z | 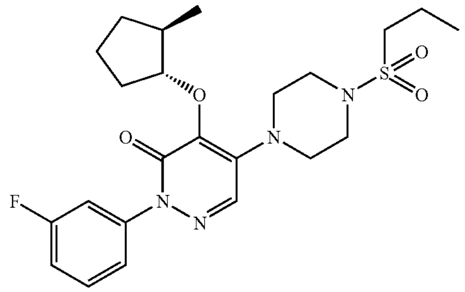 | 479 |
| 549Z | 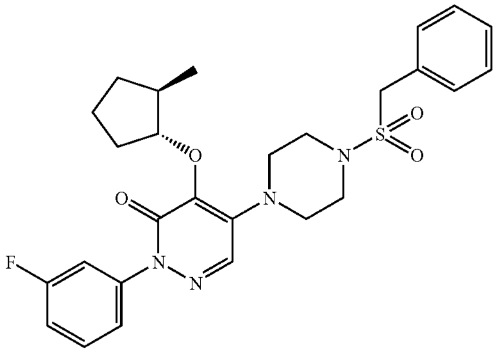 | 527 |
| 550Z | 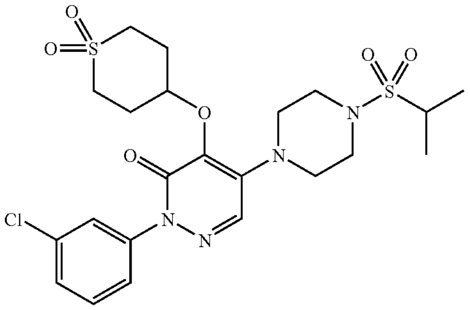 | 545 |
| 551Z | 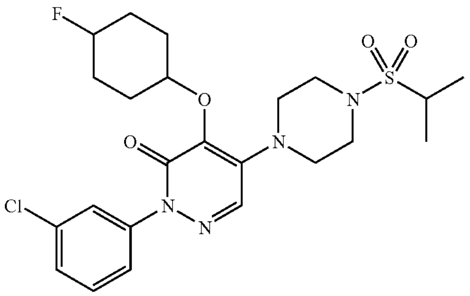 | 513 |

TABLE 10-continued
| Comp. No. | Structure | MS M + 1 |
|---|---|---|
| Oxygen Linked Analogs with Sulfonamide The following compounds can be synthesized using steps 1, 2, 4, 6, and 9 of Scheme 1 or steps 11, 12, and 14 of Scheme 2. | | |
| 552Z | 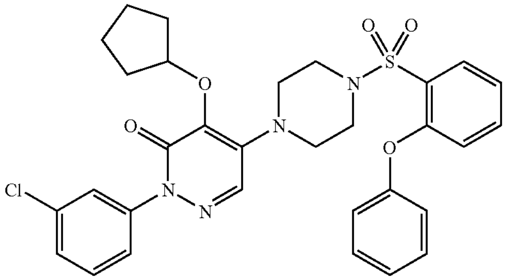 | 607 |
| 553Z | 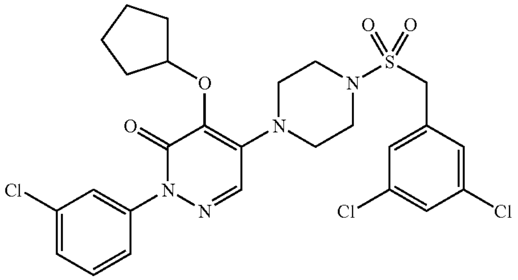 | 597 |
| 554Z | 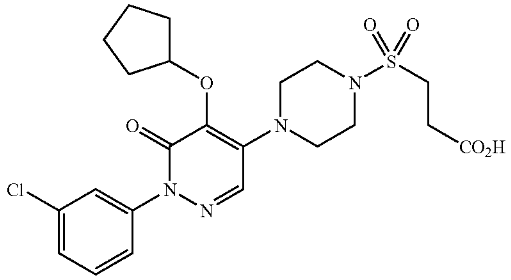 | 509 (M − 1) |
| 555Z | 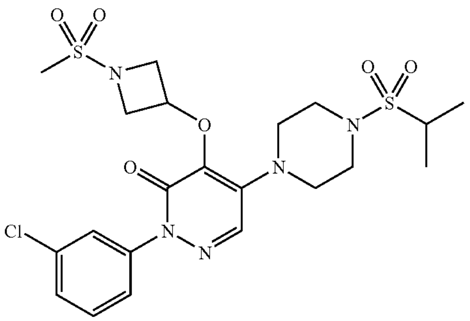 | 547 |

TABLE 10-continued
| Comp. No. | Oxygen Linked Analogs with Sulfonamide<br>The following compounds can be synthesized using steps 1, 2, 4, 6, and 9 of Scheme 1 or steps 11, 12, and 14 of Scheme 2.<br>Structure | MS M + 1 |
|---|---|---|
| 556Z | 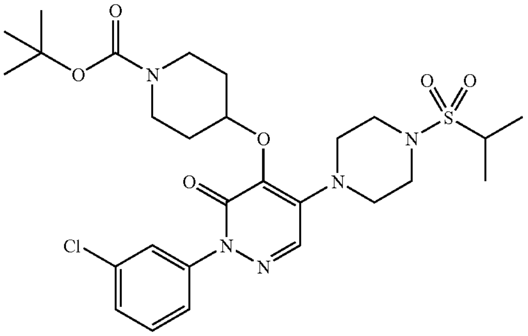 | 596 |
| 557Z | 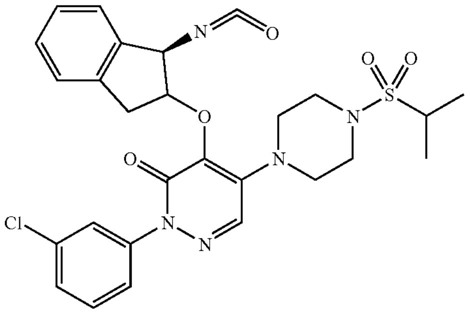 | 570 |
| 558Z | 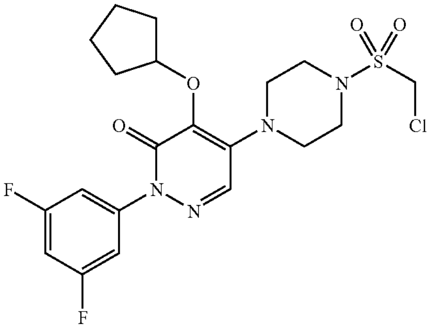 | 489 |
| 559Z | 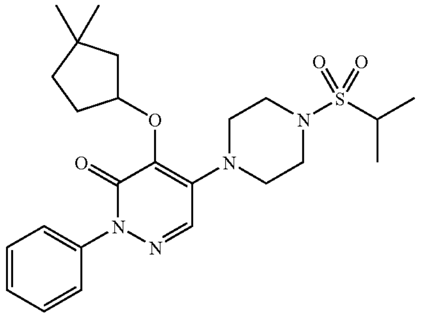 | 475 |

TABLE 10-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 560Z | 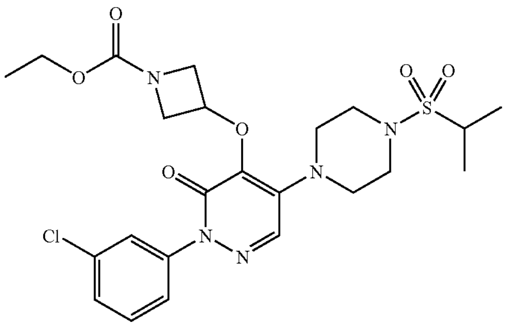 | 540 |
| 561Z | 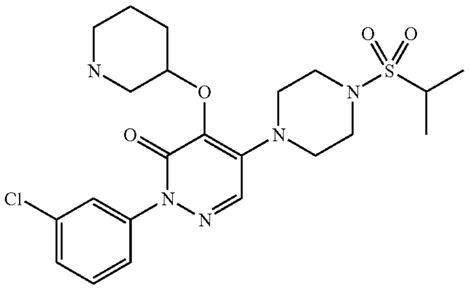 | 496 |
| 562Z | 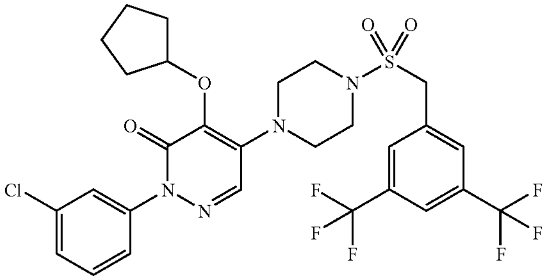 | 665 |
| 563Z | 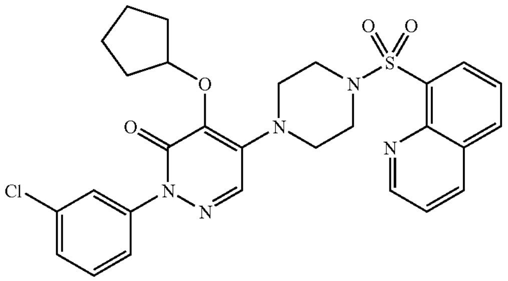 | 566 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 564Z | 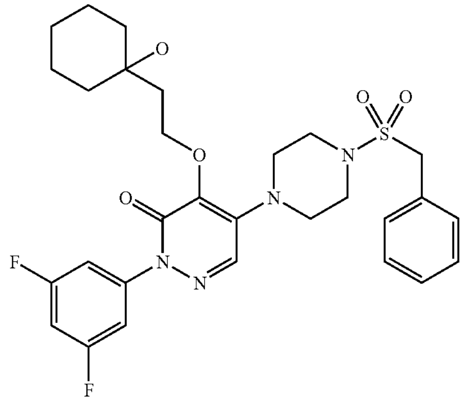 | 589 |
| 565Z | 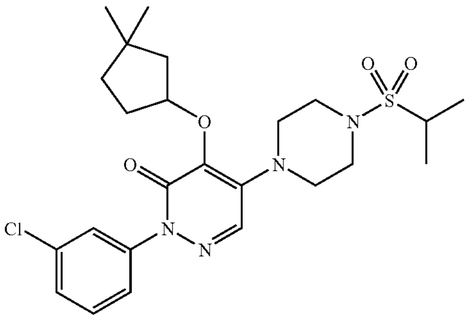 | 509 |
| 566Z | 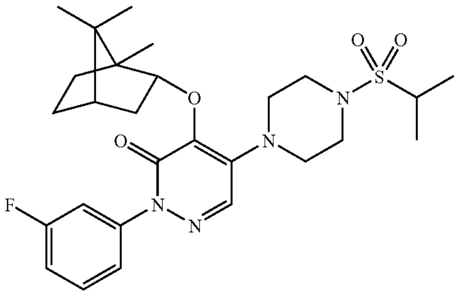 | 533 |
| 567Z | 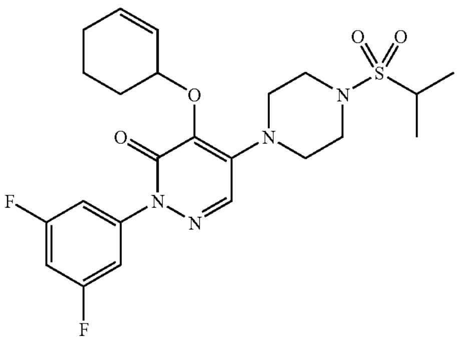 | 495 |

TABLE 10-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 568Z | 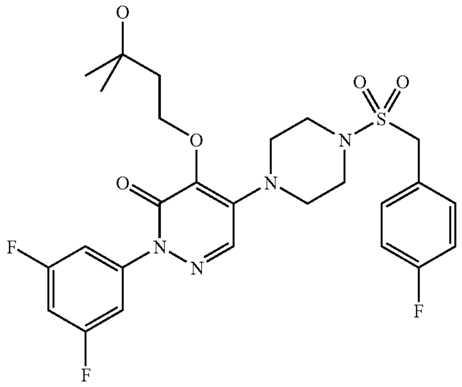 | 567 |
| 569Z | 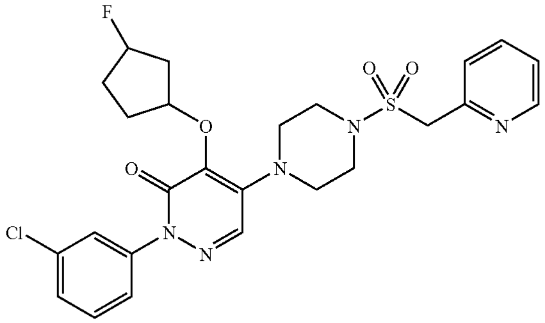 | 584 |
| 570Z | 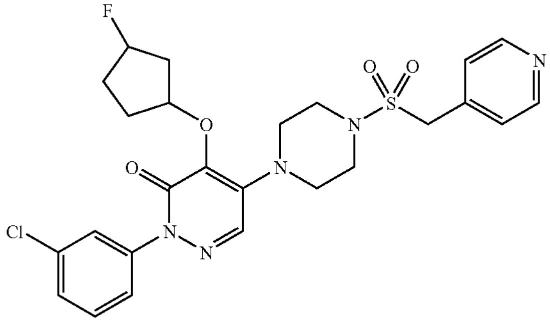 | 548 |
| 571Z | 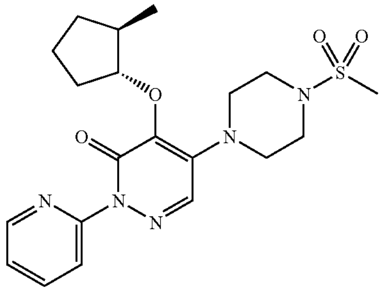 | 434 |

TABLE 10-continued
| Comp. No. | Structure | MS M + 1 |
|---|---|---|
| Oxygen Linked Analogs with Sulfonamide. The following compounds can be synthesized using steps 1, 2, 4, 6, and 9 of Scheme 1 or steps 11, 12, and 14 of Scheme 2. | | |
| 572Z | 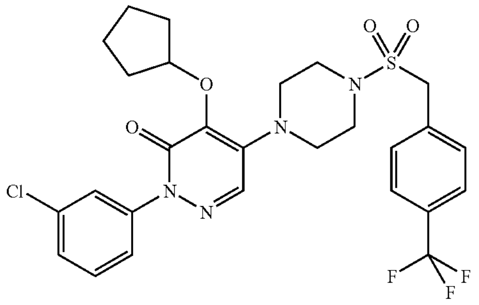 | 597 |
| 573Z | 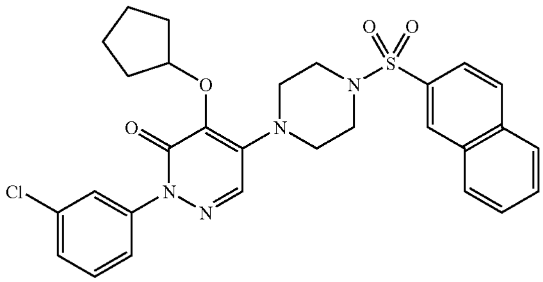 | 565 |
| 574Z | 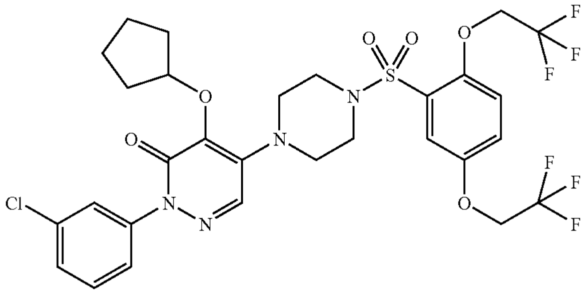 | 711 |
| 575Z | 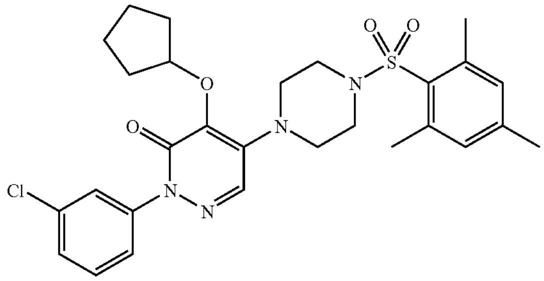 | 557 |

TABLE 10-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 576Z | 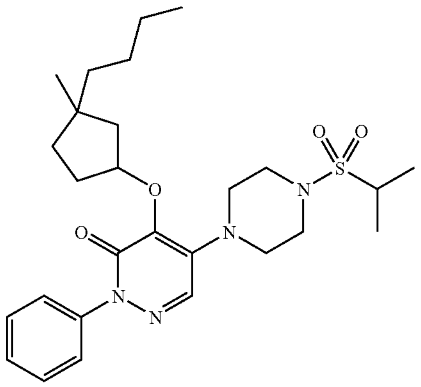 | 517 |
| 577Z | 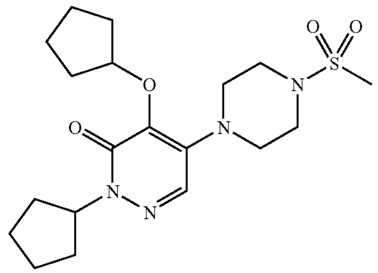 | 411 |
| 578Z | 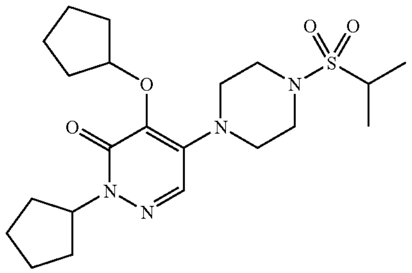 | 439 |
| 579Z | 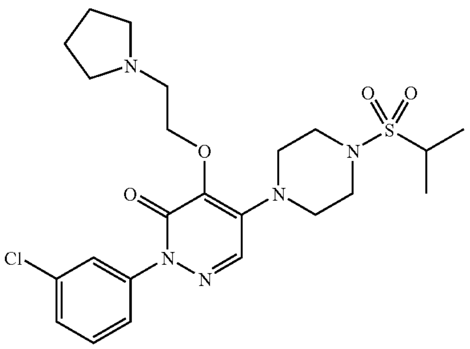 | 510 |

TABLE 10-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 580Z | 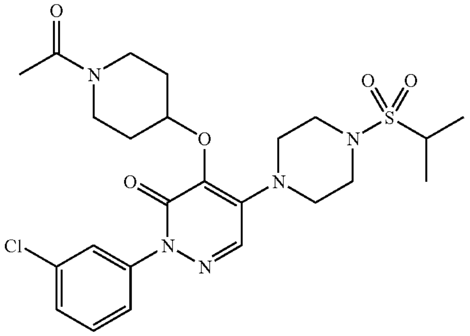 | 538 |
| 581Z | 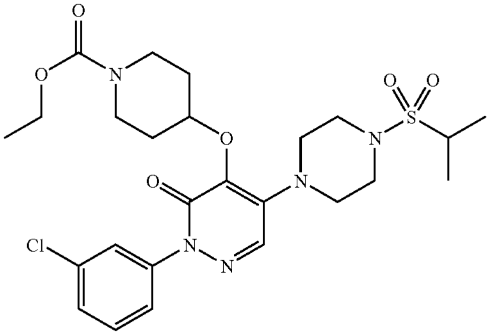 | 568 |
| 582Z | 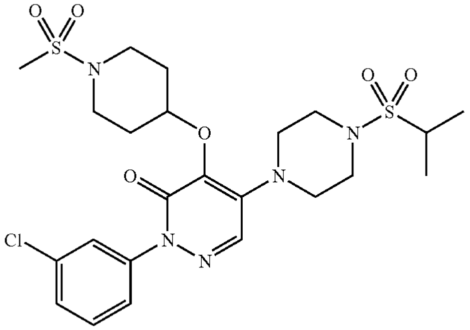 | 574 |
| 583Z | 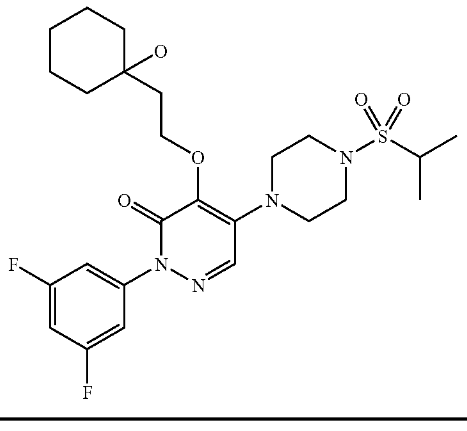 | 541 |

| | | |
|---|---|---|
| 584Z | 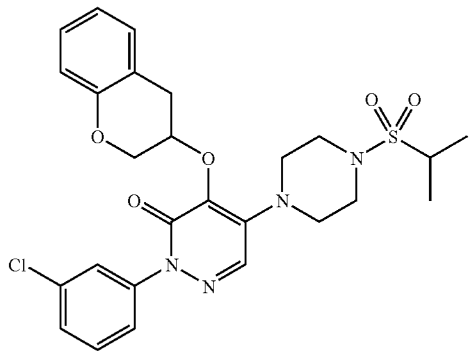 | 545 |
| 585Z | 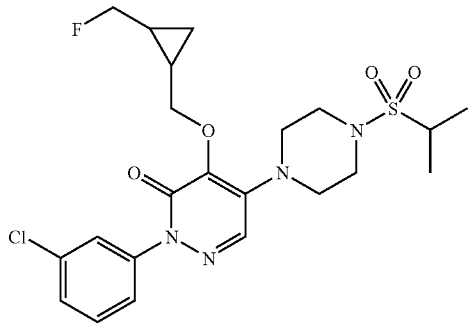 | 499 |
| 586Z | 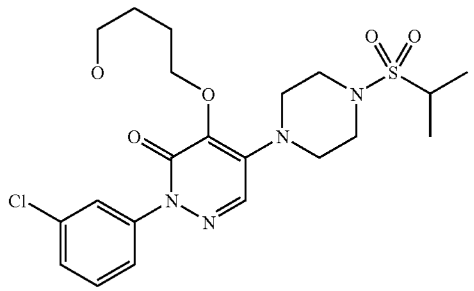 | 485 |
| 587Z | 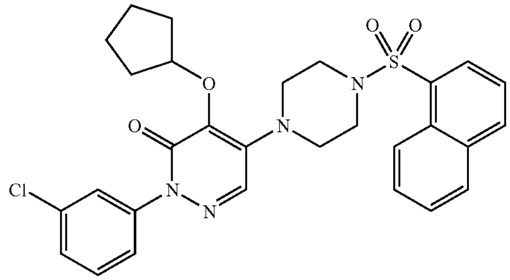 | 565 |
| 588Z | 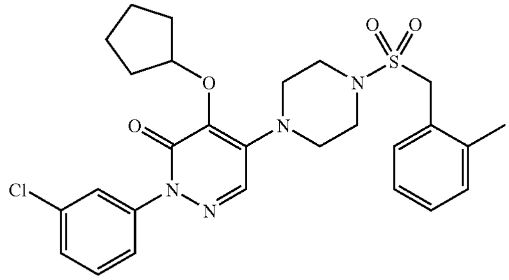 | 543 |

-continued
589Z 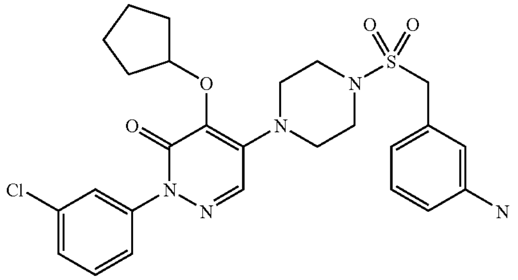 544
590Z 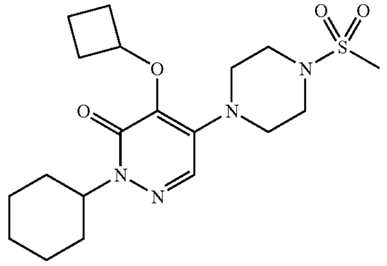 411
591Z 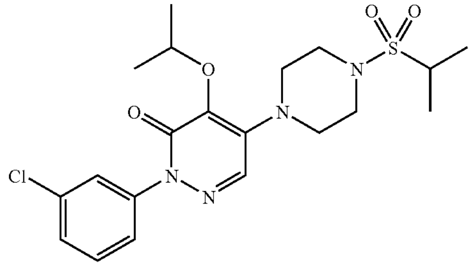 455
592Z 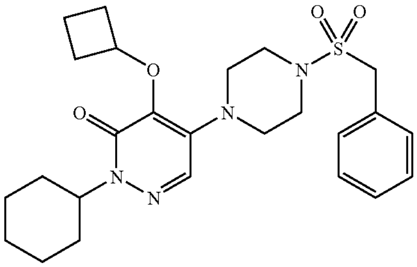 487
593Z 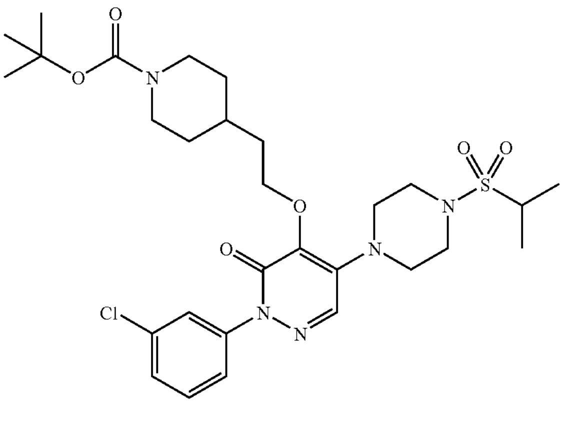 624

-continued
| | | |
|---|---|---|
| 594Z | 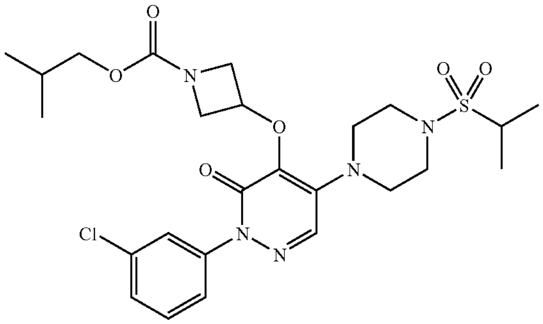 | 568 |
| 595Z | 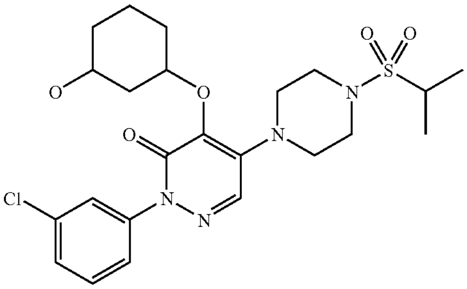 | 511 |
| 596Z | 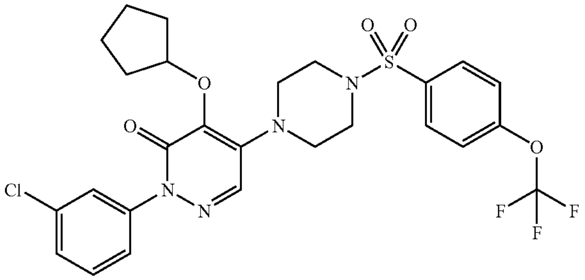 | 599 |
| 597Z | 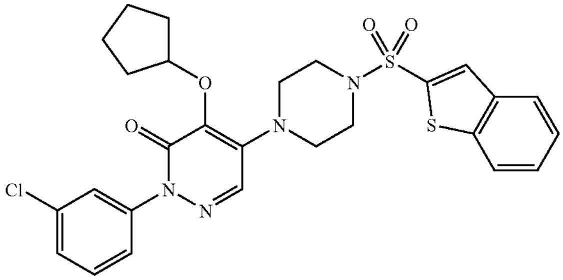 | 571 |
| 598Z | 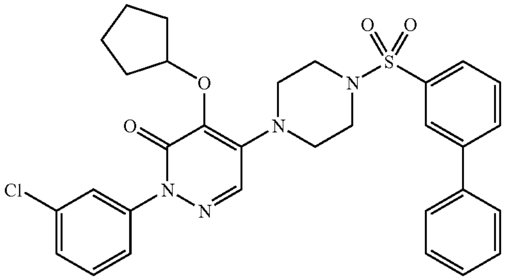 | 591 |

-continued
| | | |
|---|---|---|
| 599Z | 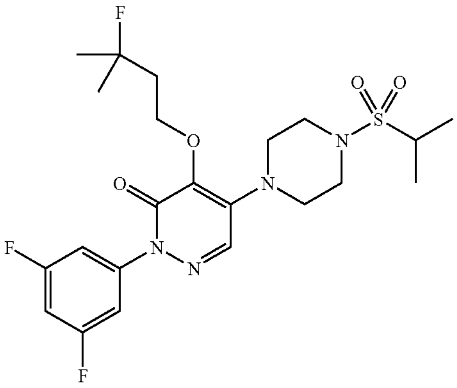 | 503 |
| 600Z | 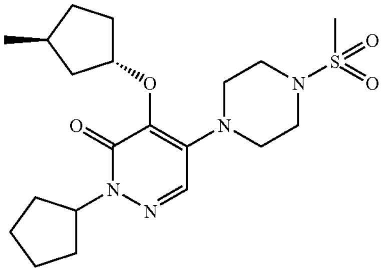 | 425 |
| 601Z | 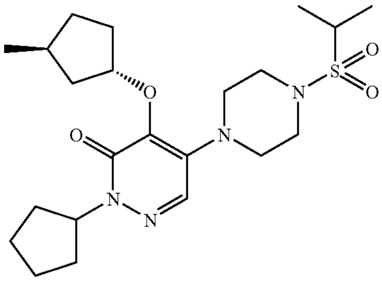 | 453 |
| 602Z | 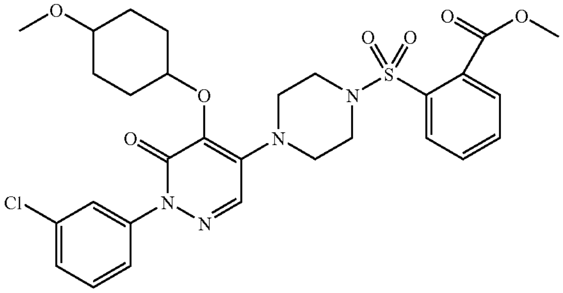 | 617 |
| 603Z | 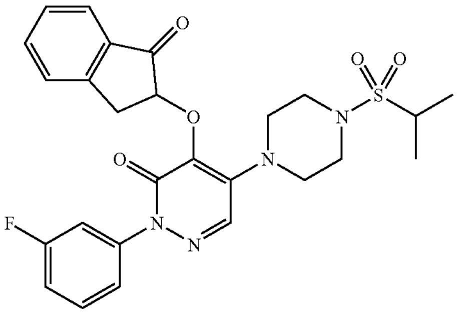 | 527 |

-continued
| | | |
|---|---|---|
| 604Z | 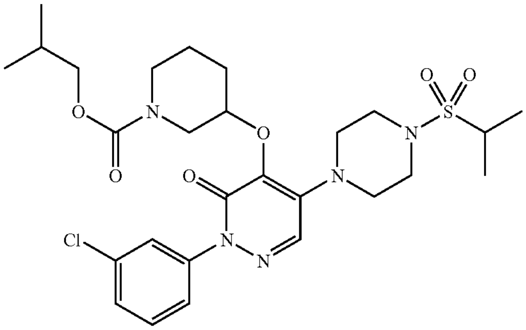 | 596 |
| 605Z | 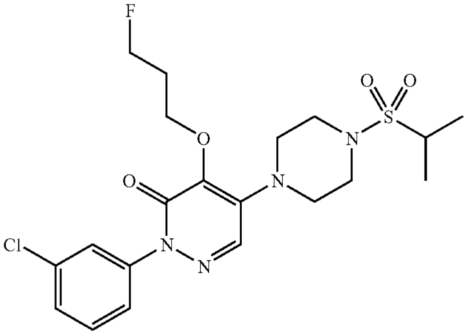 | 473 |
| 606Z | 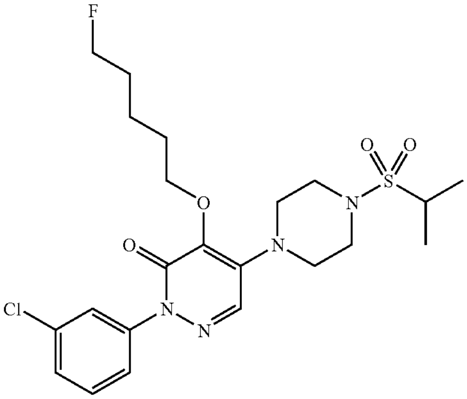 | 501 |
| 607Z | 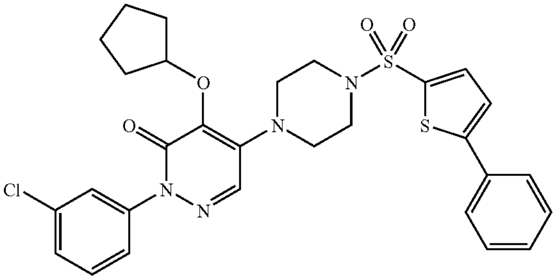 | 597 |
| 608Z | 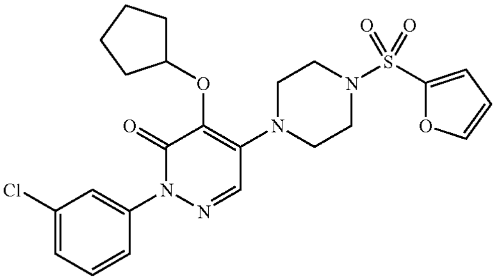 | 505 |

-continued
609Z 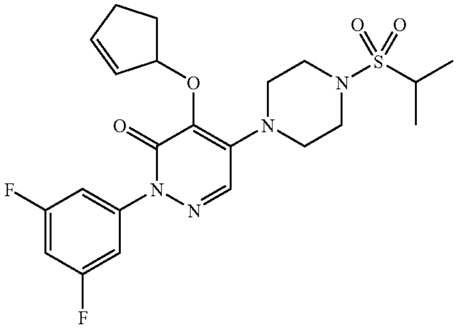 481
610Z 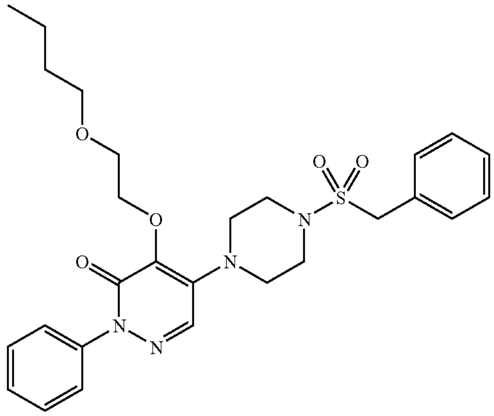 527
611Z 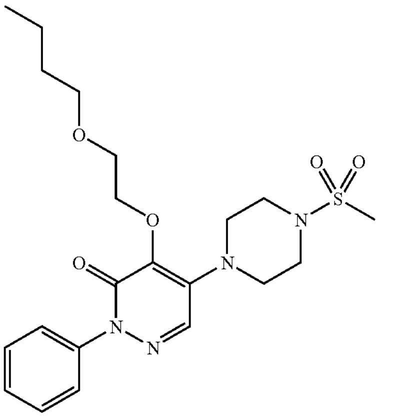 451
612Z 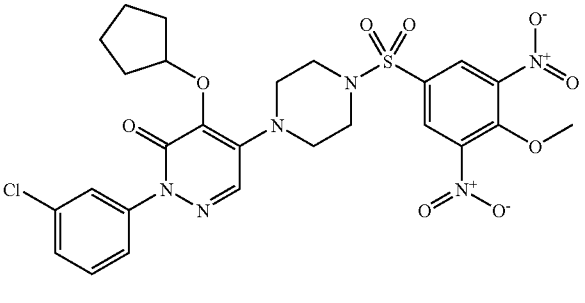 635

-continued
613Z 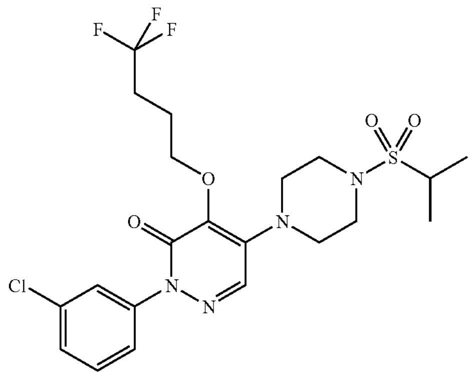 523
614Z 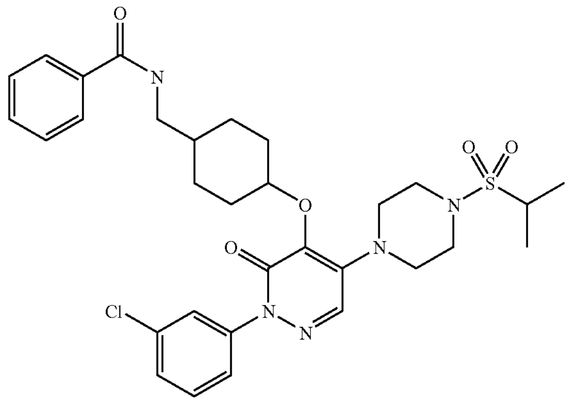 628
615Z 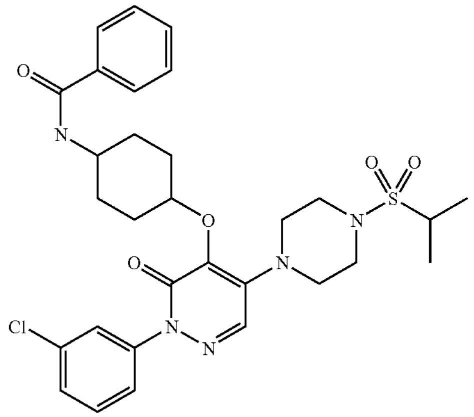 614
616Z 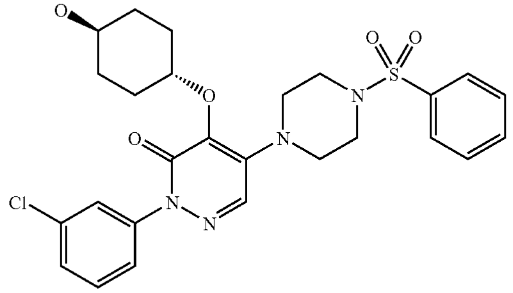 546

-continued
617Z 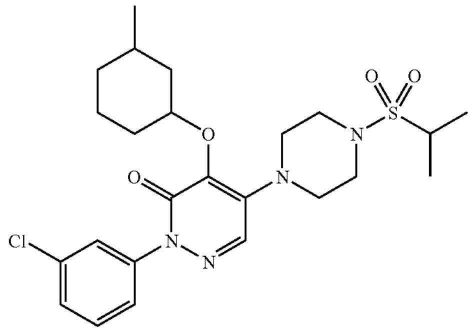 510
618Z 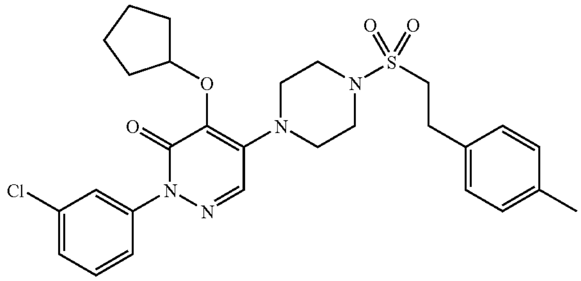 557
619Z 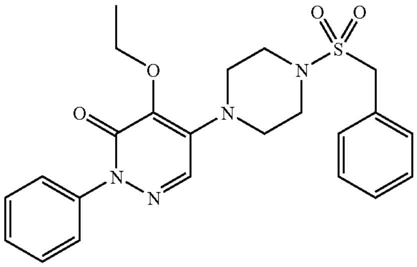 455
620Z 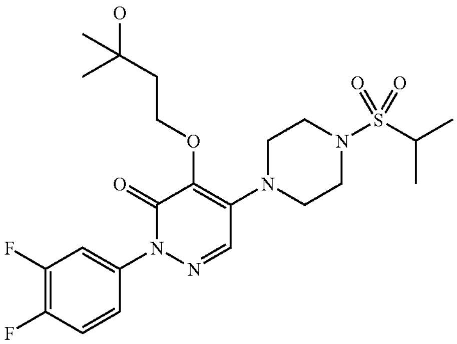 501
621Z 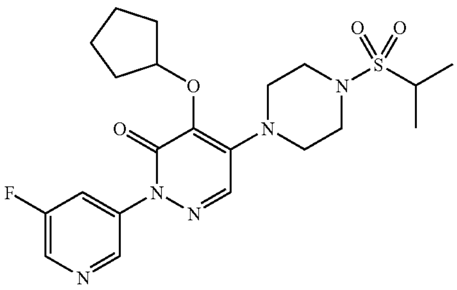 466

-continued
622Z 515
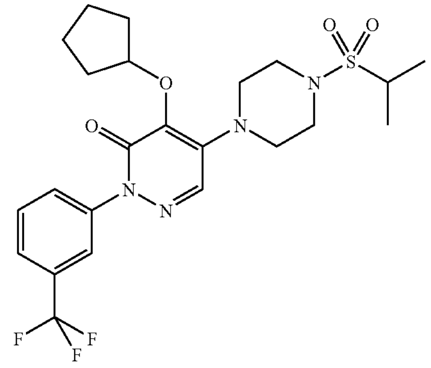
623Z 563
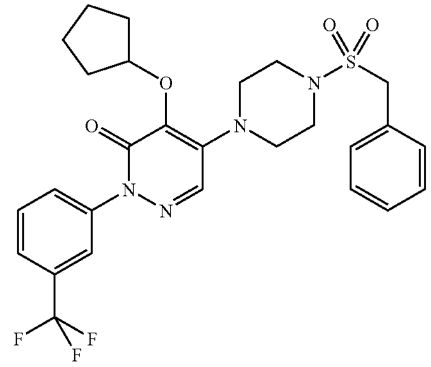
624Z 562
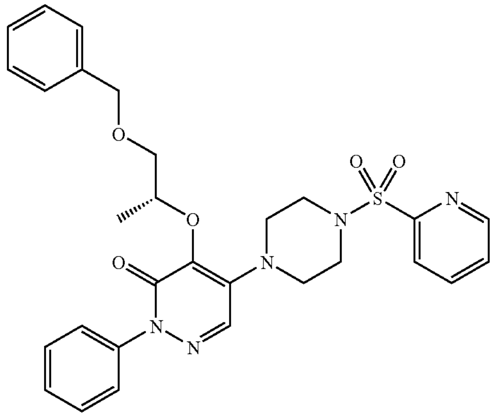
625Z 516
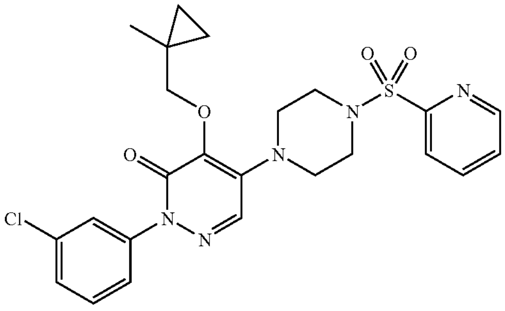

-continued
| | | |
|---|---|---|
| 626Z | 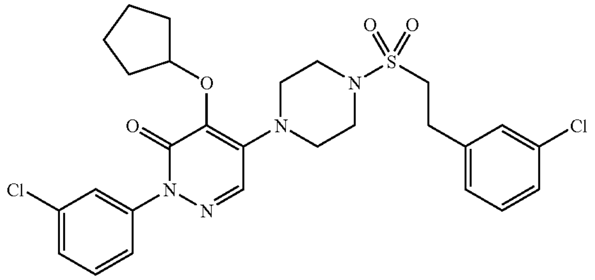 | 577 |
| 627Z | 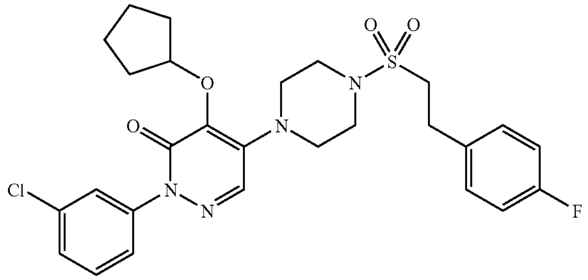 | 561 |
| 628Z | 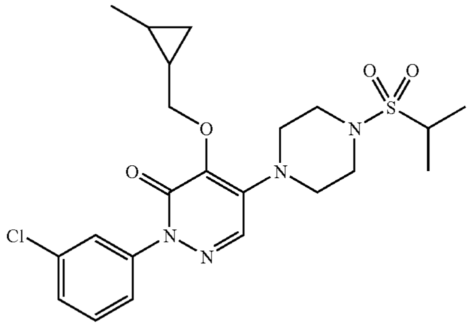 | 481 |
| 629Z | 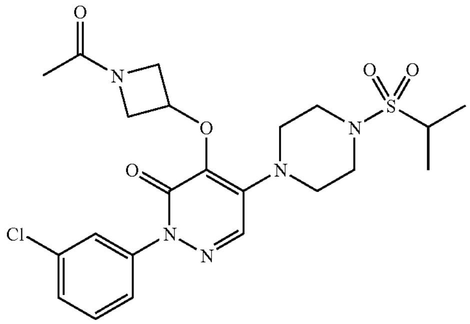 | 512 (M + 2) |
| 630Z | 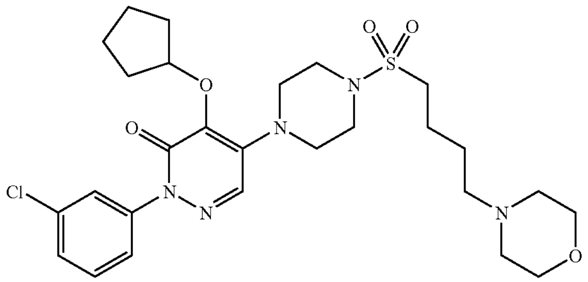 | 580 |

-continued
| | | |
|---|---|---|
| 631Z | 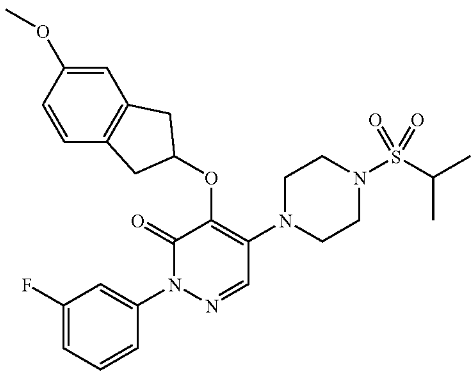 | 543 |
| 632Z | 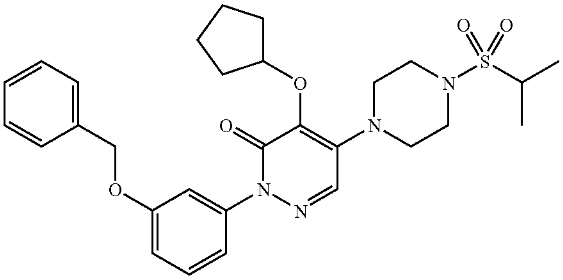 | 553 |
| 633Z | 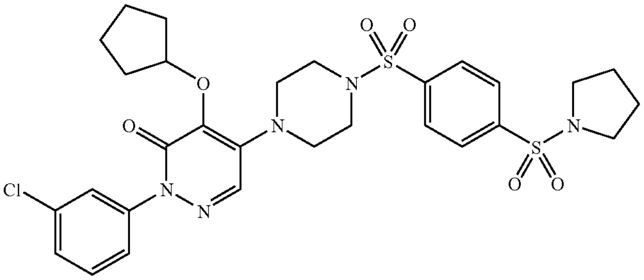 | 648 |
| 634Z | 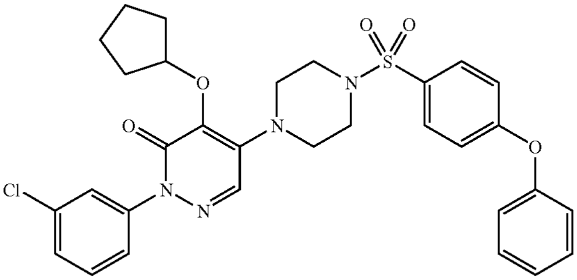 | 607 |
| 635Z | 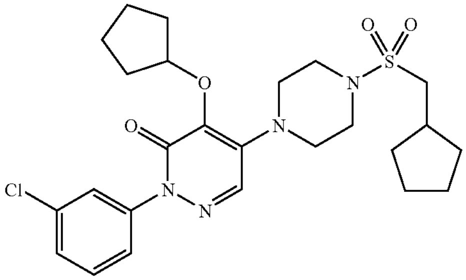 | 521 |

-continued
636Z 586
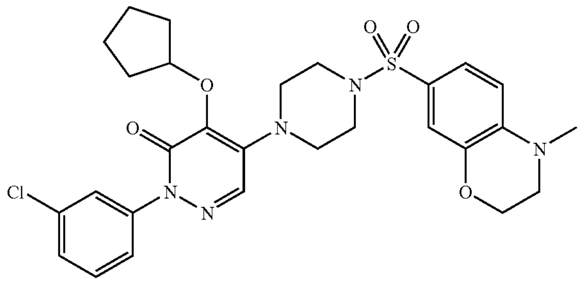
637Z 519
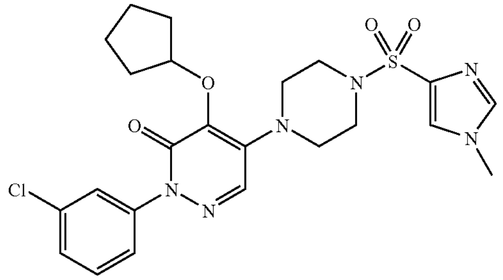
638Z 574
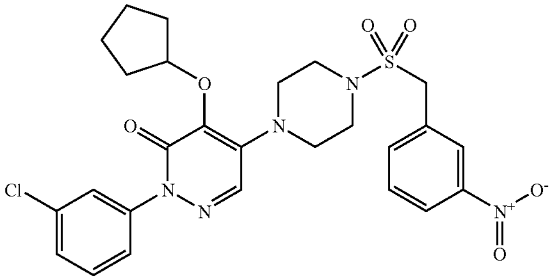
639Z 593
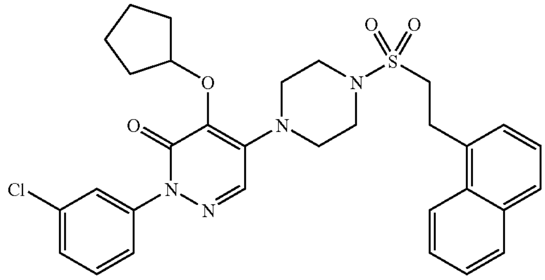
640Z 509
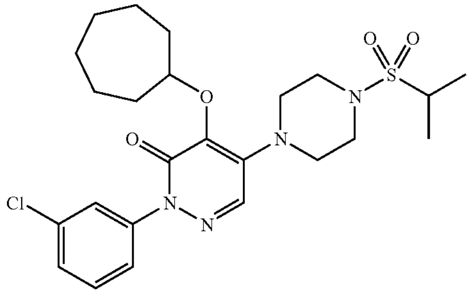

-continued
| | | |
|---|---|---|
| 641Z | 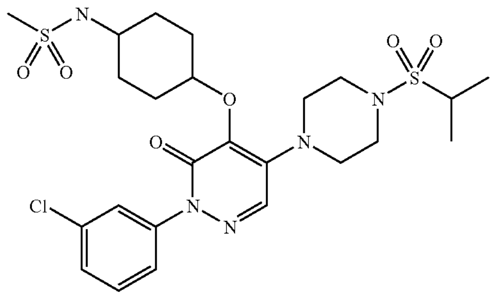 | 588 |
| 642Z | 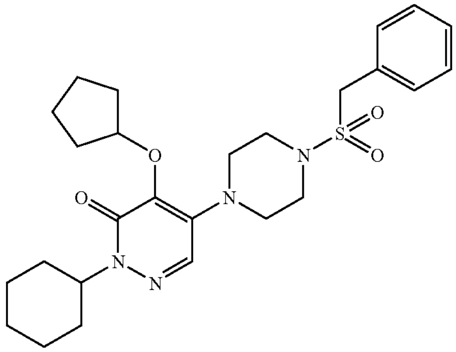 | 501 |
| 643Z | 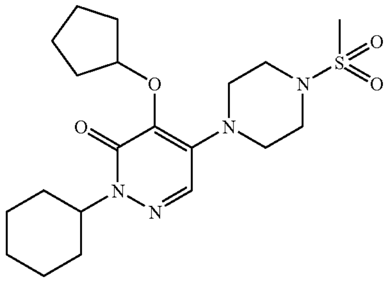 | 467 (M + Na) |
| 644Z | 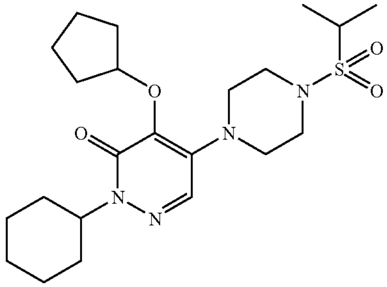 | 453 |
| 645Z | 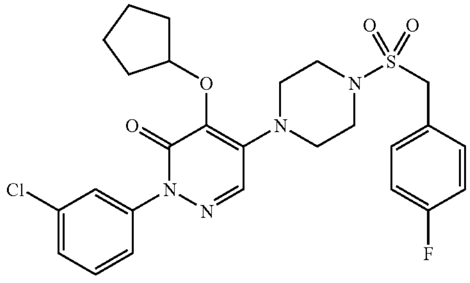 | 547 |

-continued
| | | |
|---|---|---|
| 646Z | 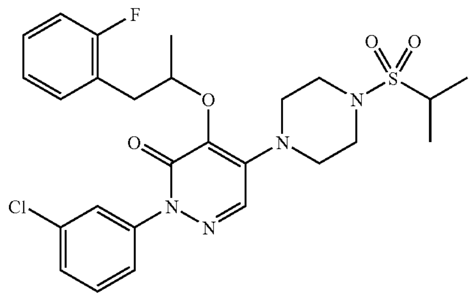 | 549 |
| 647Z | 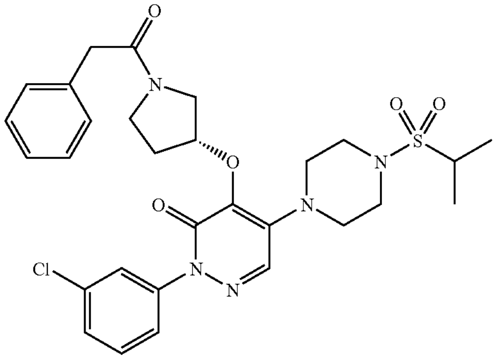 | 600 |
| 648Z | 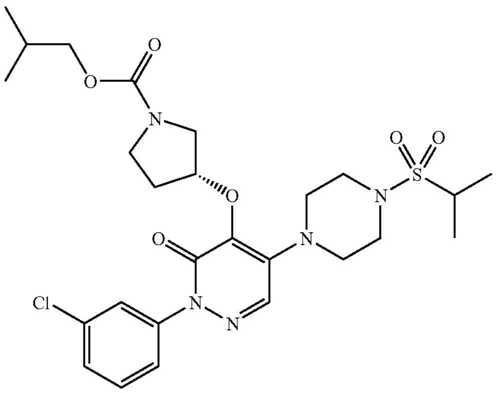 | 582 |
| 649Z | 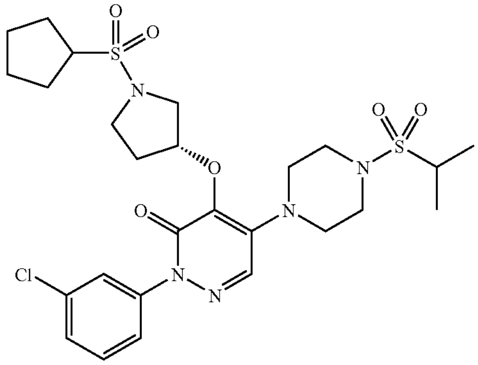 | 614 |

-continued
650Z 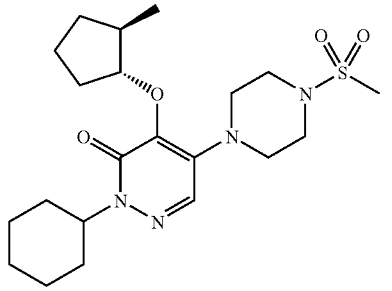 439
651Z 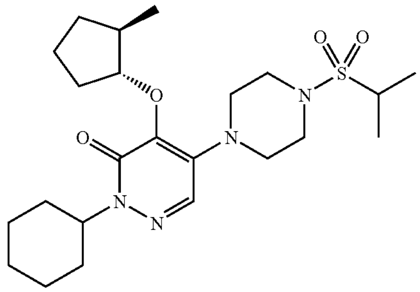 467
652Z 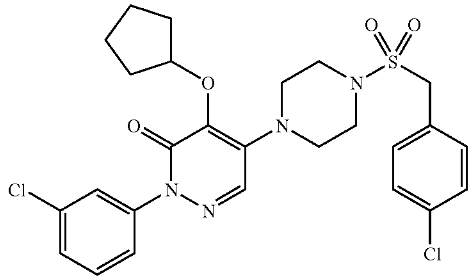 563
653Z 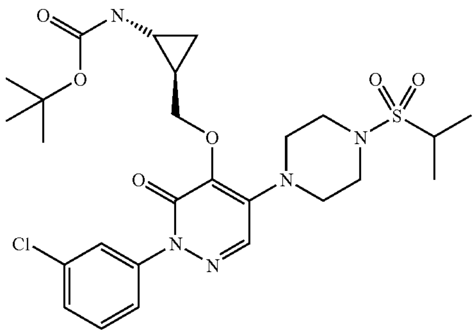 582
654Z 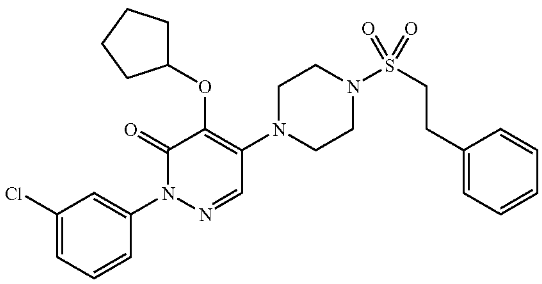 543

-continued
655Z 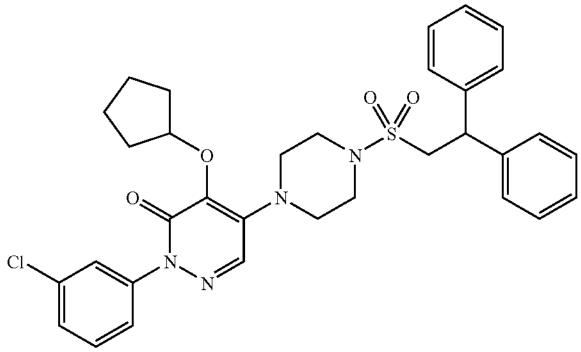 619
656Z 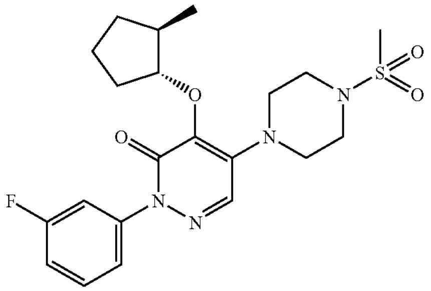 451
657Z 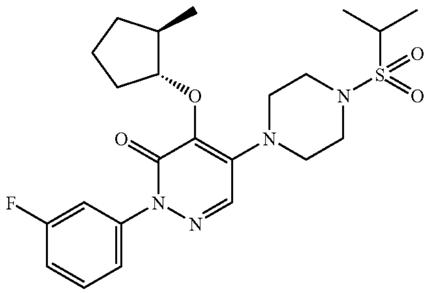 479
658 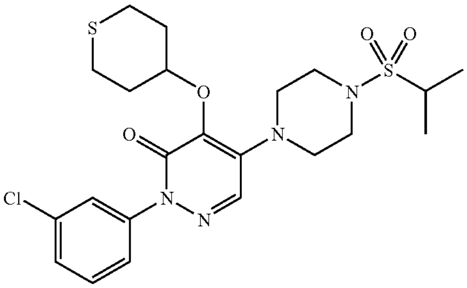 513
659Z 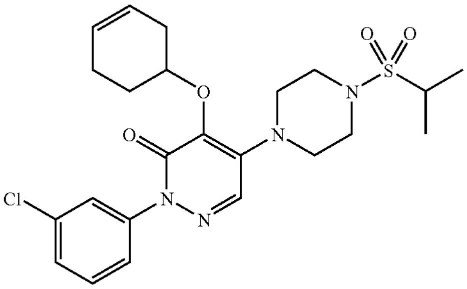 493

-continued
| | | |
|---|---|---|
| 660Z | 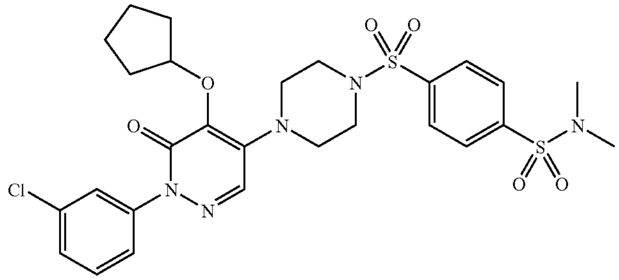 | 622 |
| 661Z | 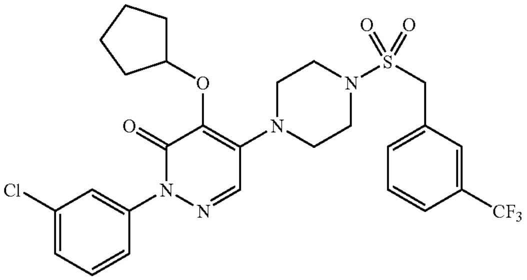 | 597 |
| 662Z | 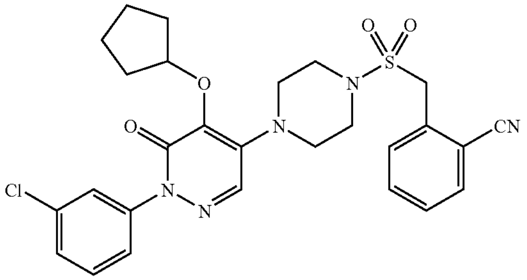 | 554 |
| 663Z | 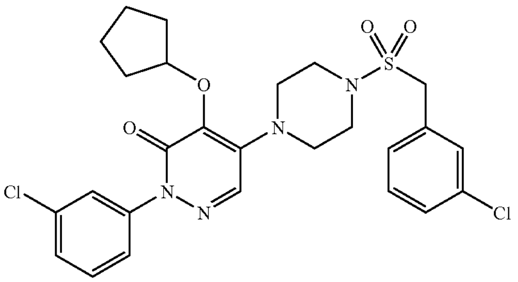 | 565 |
| 664Z | 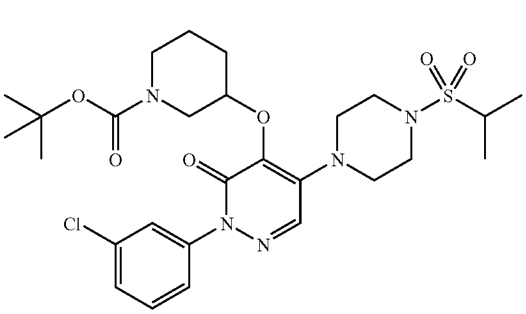 | 497 (M + 1-BOC) |

-continued
665Z 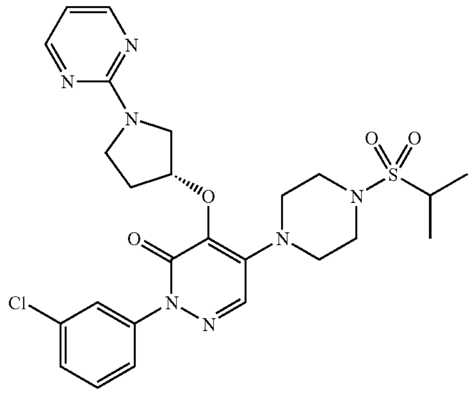 560
666Z 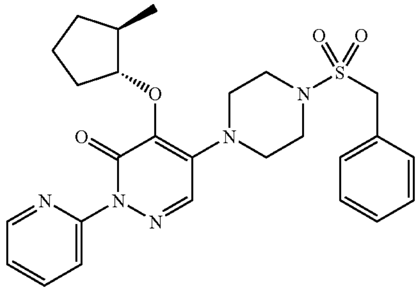 510
667Z 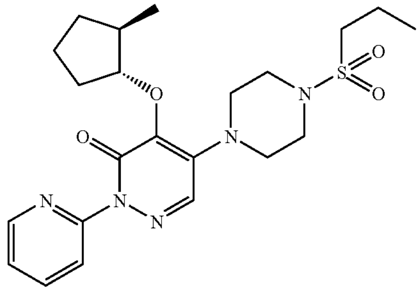 462
668Z 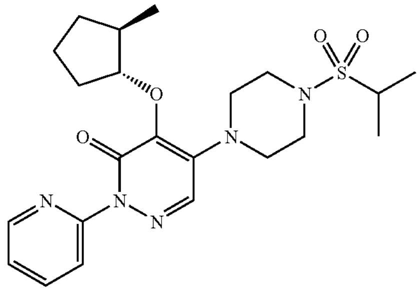 462
669Z 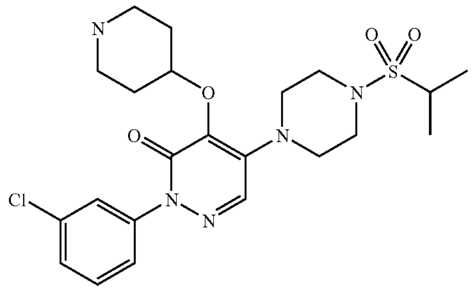 496

-continued
670Z 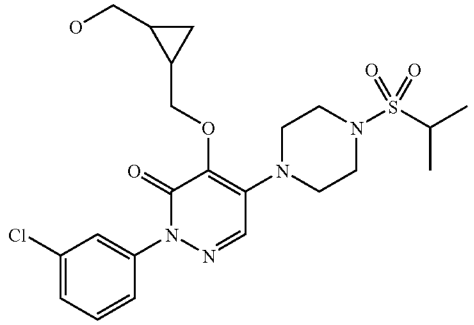 497
671Z 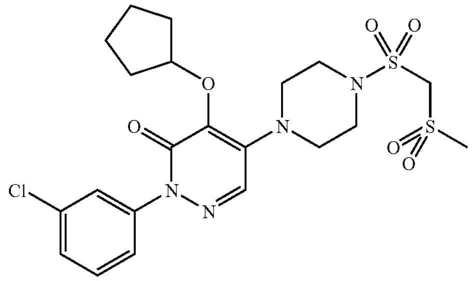 531
672Z 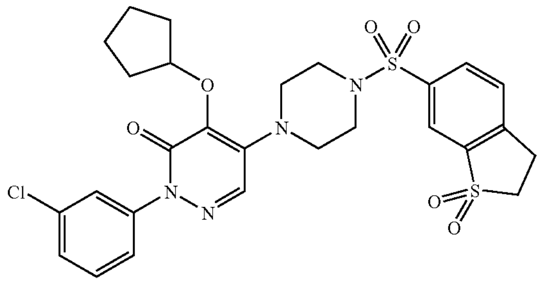 606
673Z 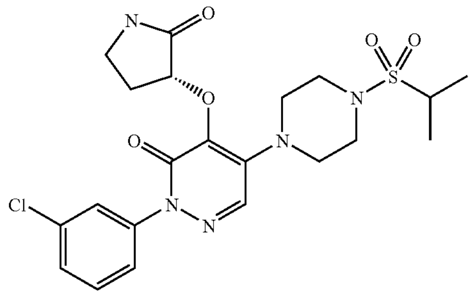 496
674Z 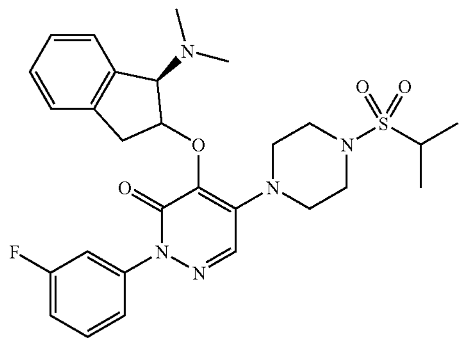 556

-continued
675Z 557
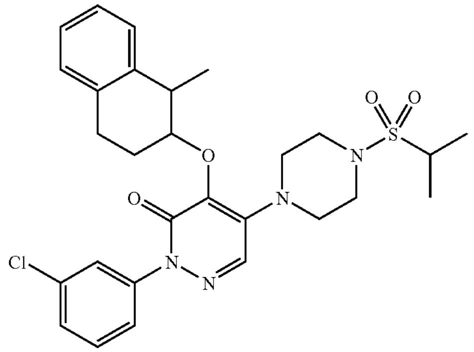
676Z 550
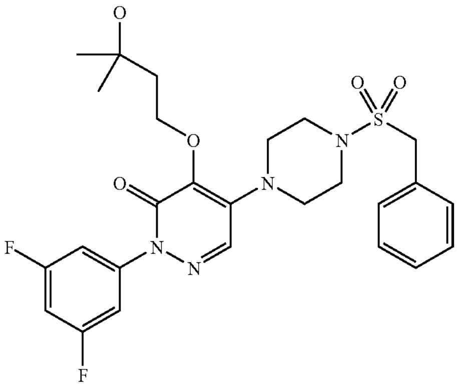
677Z 550
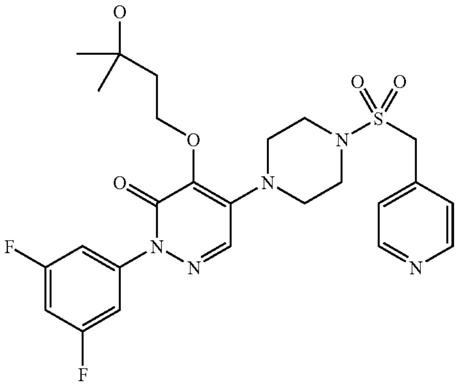
678Z 548
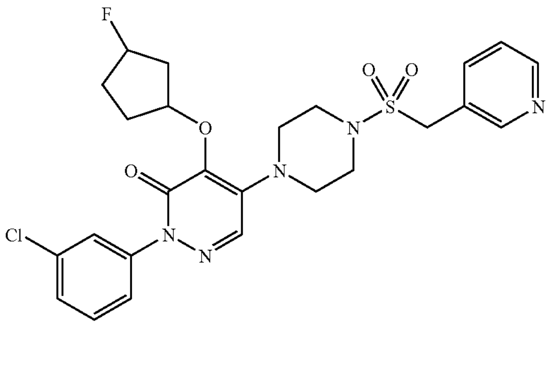

-continued
679Z 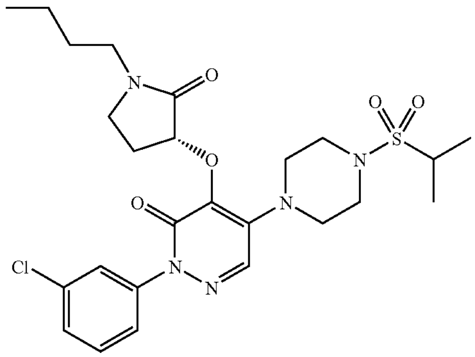 552
680Z 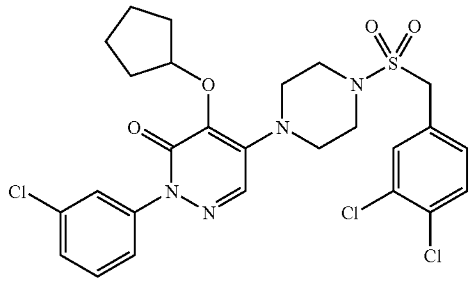 597
681Z 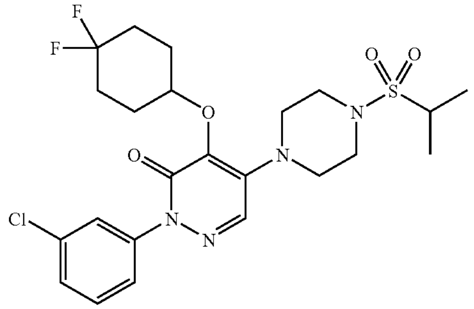 531
682Z 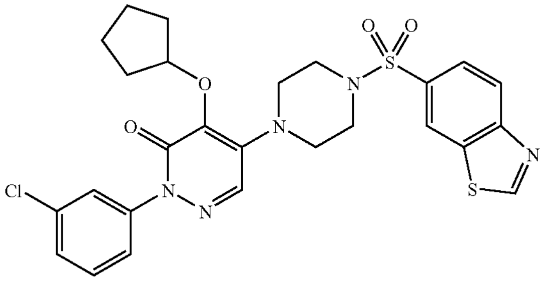 572
683Z 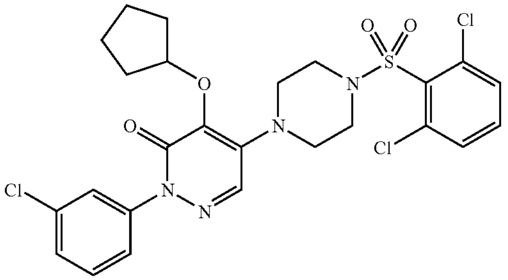 583

-continued
684Z 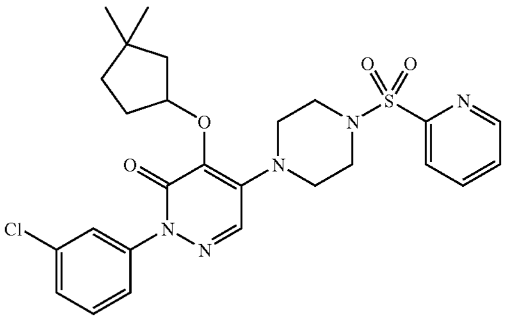 544
685Z 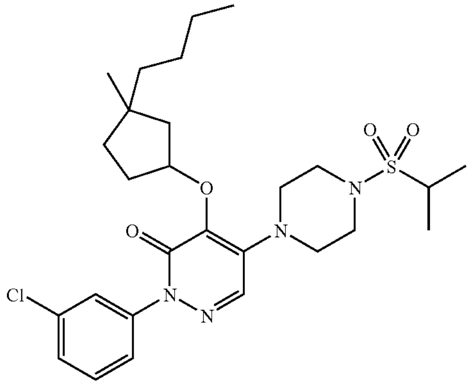 551
686Z 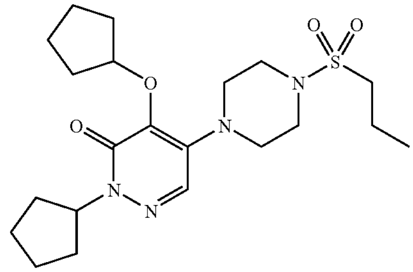 439
687Z 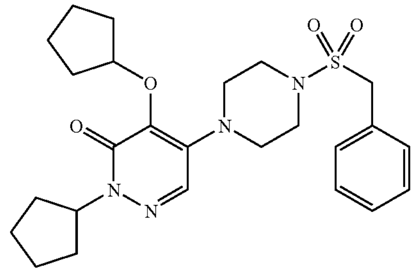 487
688Z 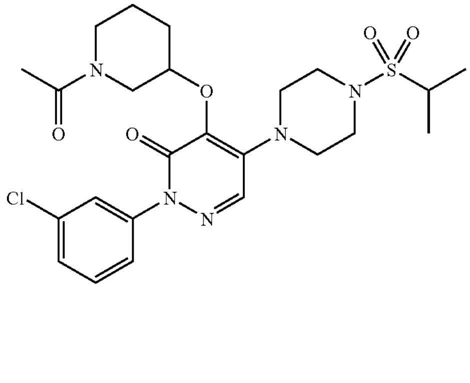 538

-continued
689Z 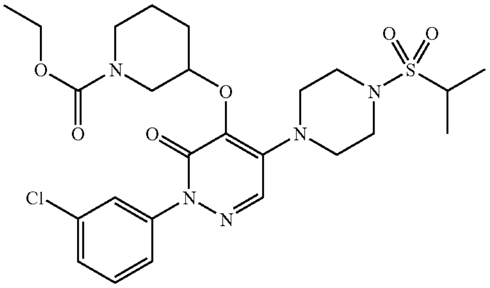 568
690Z 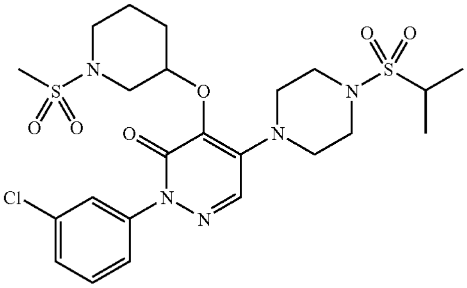 574
691Z 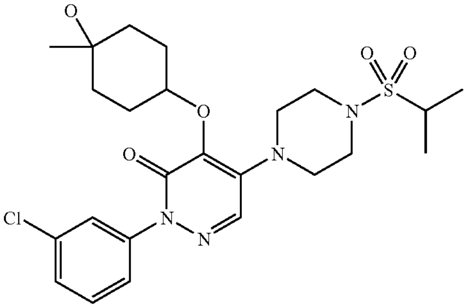 525
692Z 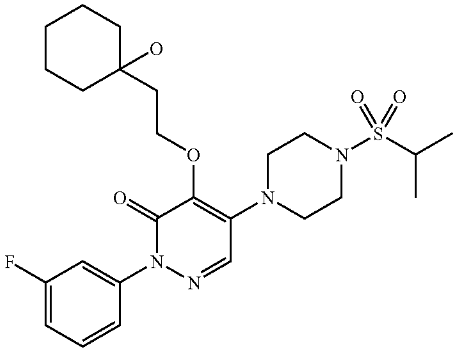 523
693Z 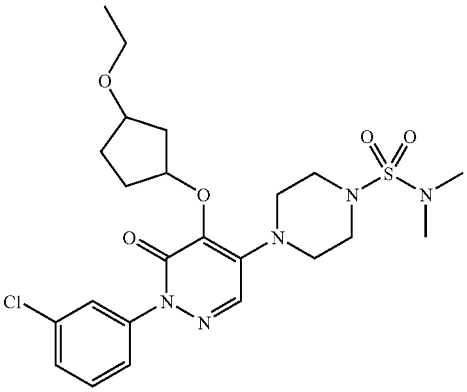 526

-continued
694Z 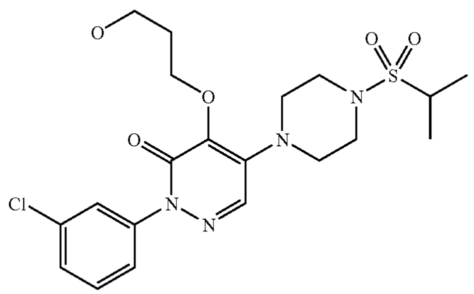 471
695Z 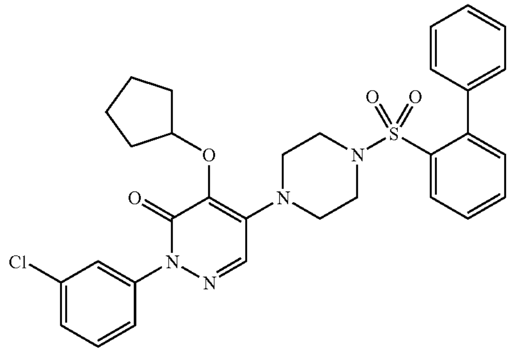 591
696Z 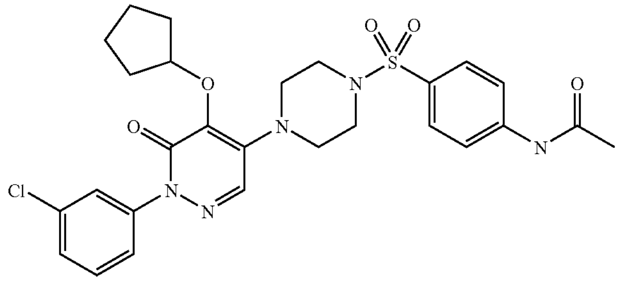 572
697Z 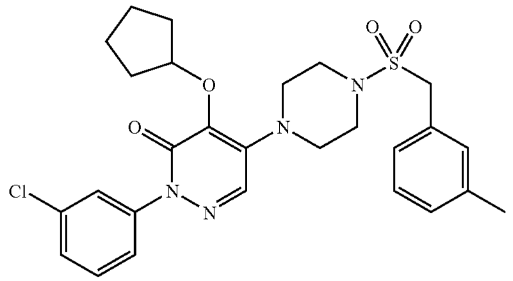 543
698Z 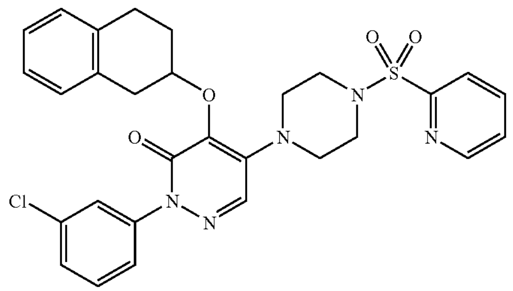 578

-continued
699Z 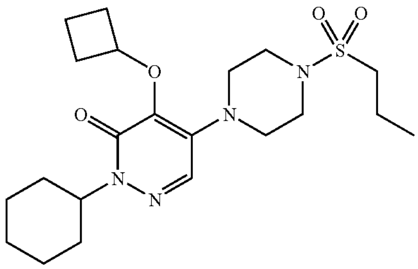 439
700Z 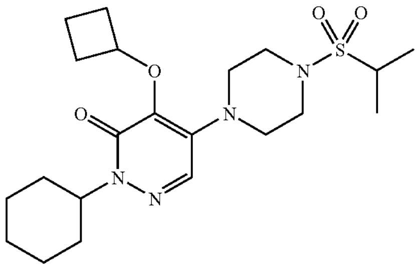 439
701Z 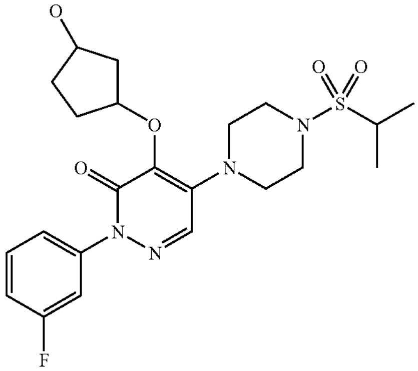 481
702Z 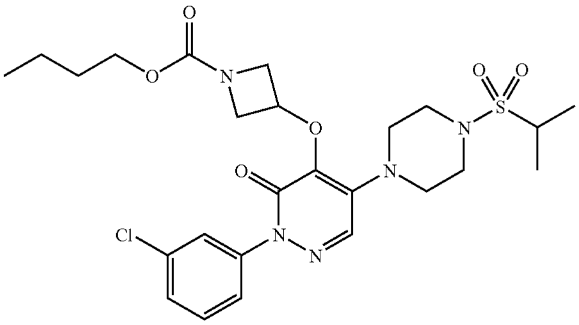 568
703Z 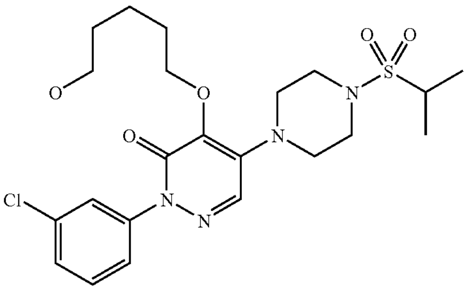 499

-continued
| | | |
|---|---|---|
| 704Z | 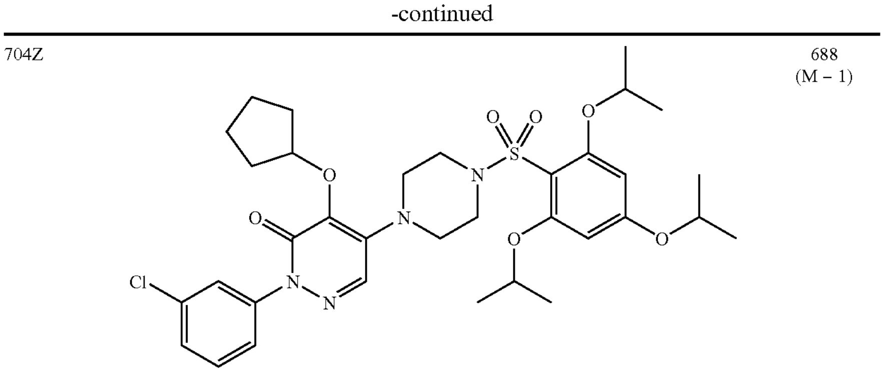 | 688 (M − 1) |
| 705Z | 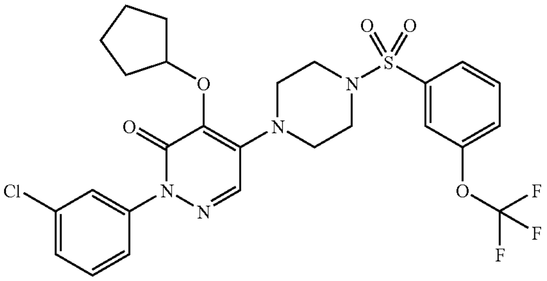 | 599 |
| 706Z | 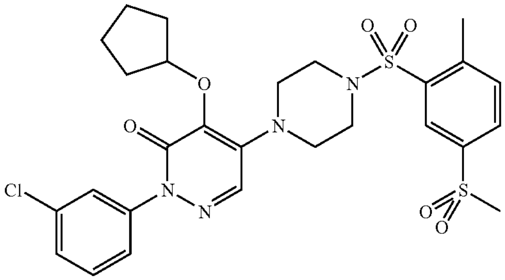 | 607 |
| 707Z | 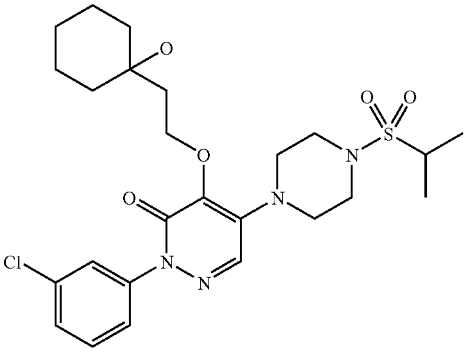 | 539 |
| 708Z | 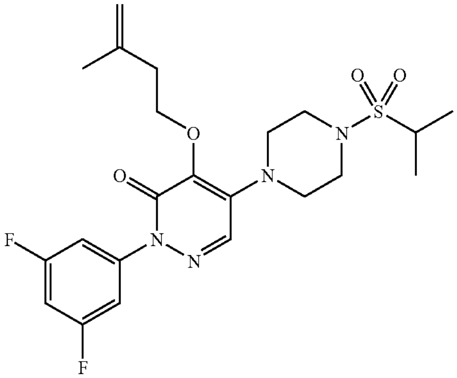 | 483 |

-continued
709Z 453
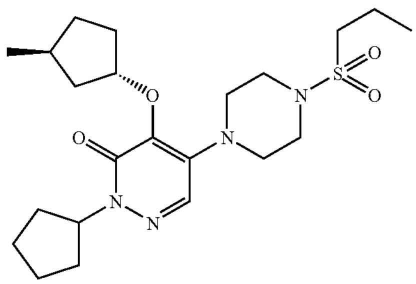
710Z 501
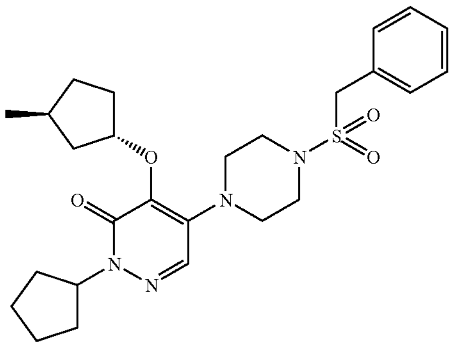
711Z 529
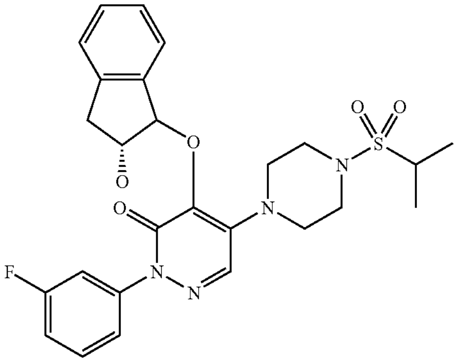
712Z 456 (M + 1-BOC)
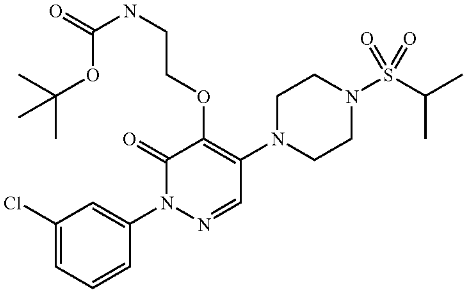

-continued
713Z 596
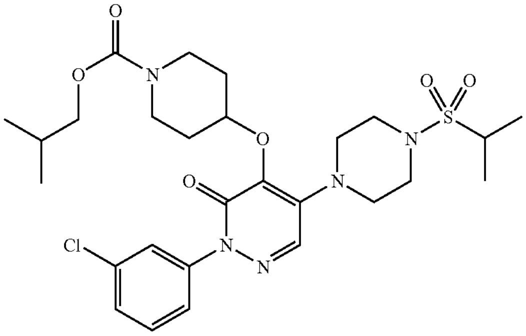
714Z 487
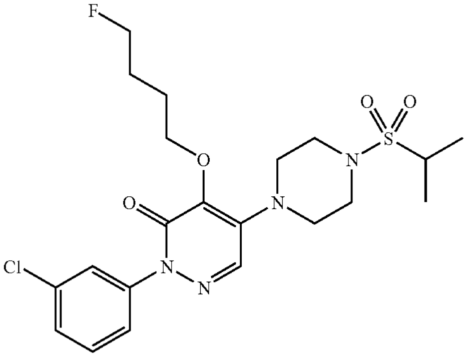
715Z 605
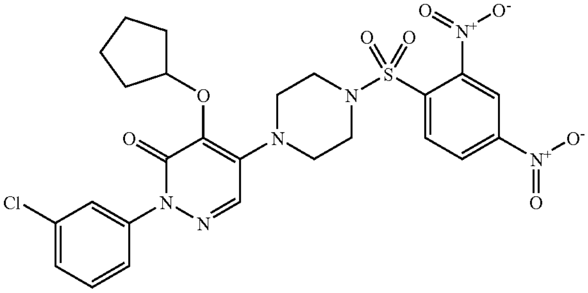
716Z 585
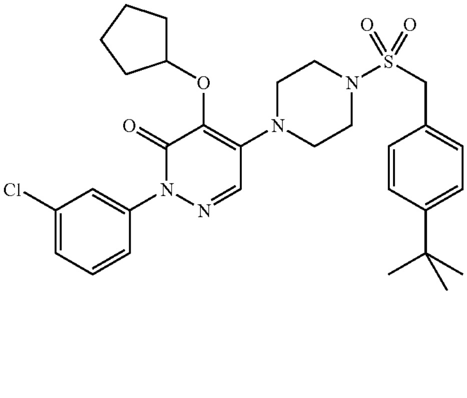

-continued
717Z 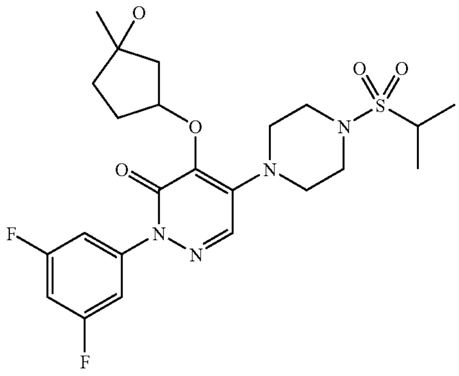 513
718Z 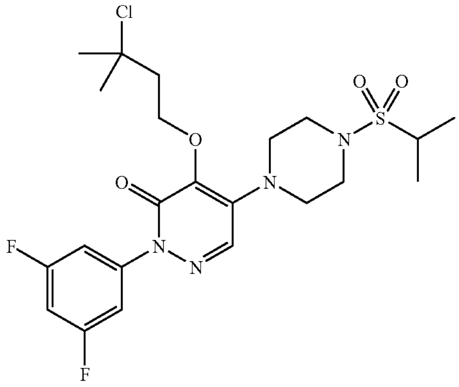 519
719Z 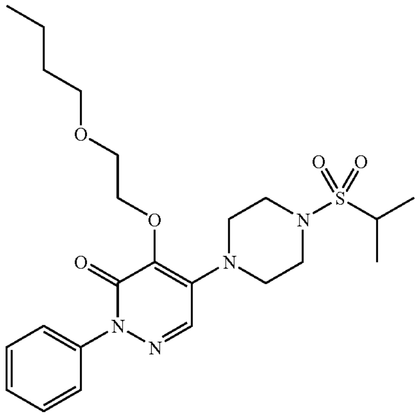 479
720Z 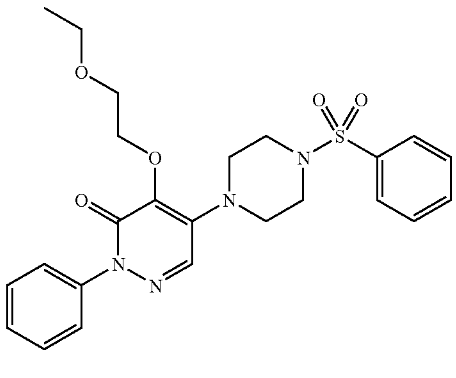 485

-continued
721Z 493
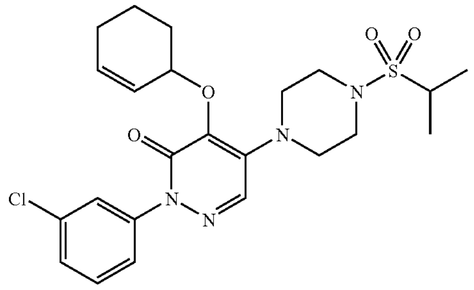
723Z 559
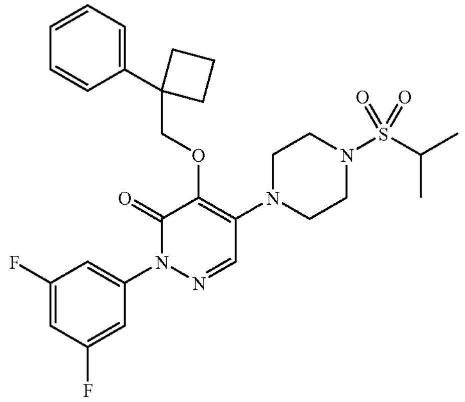
724Z 547
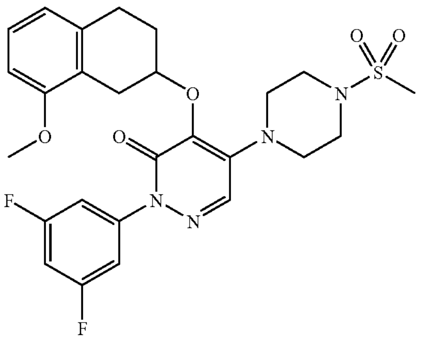
725Z 502
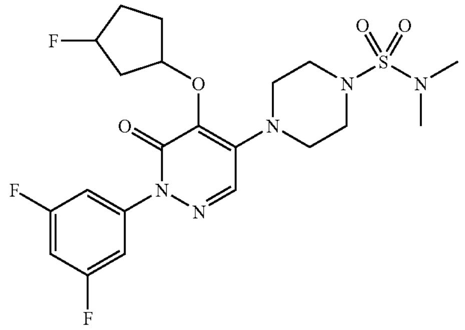

-continued
726Z
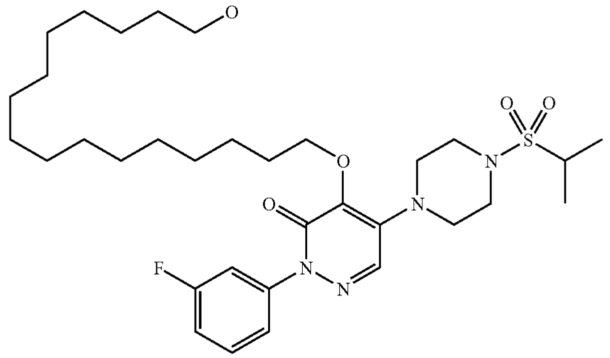
637
727Z
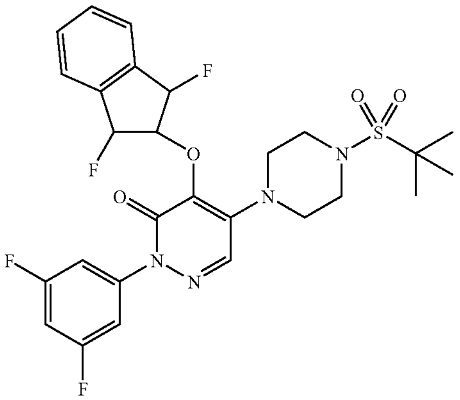
581
728Z
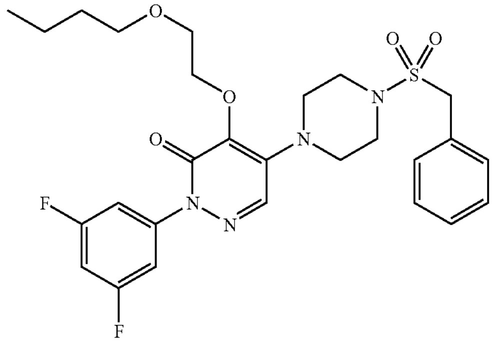
563
729Z
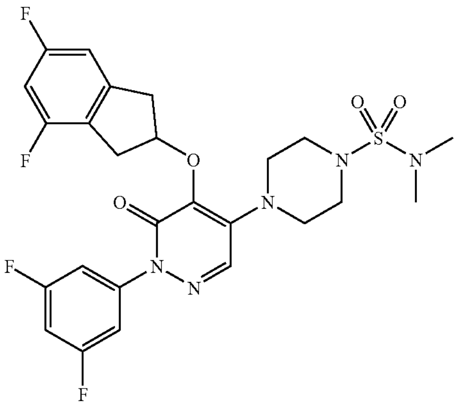
568

-continued
730Z
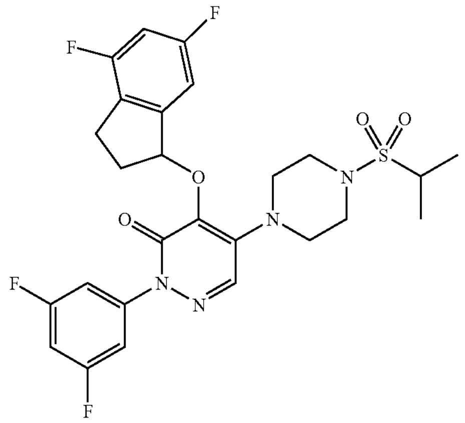
567
731Z
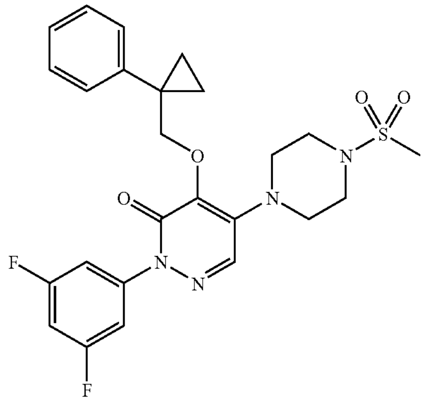
517
732Z
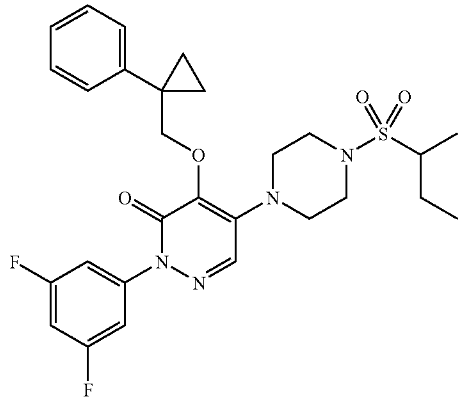
559
733Z
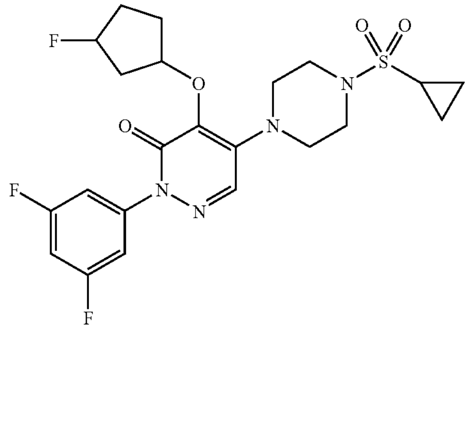
499

-continued
734Z
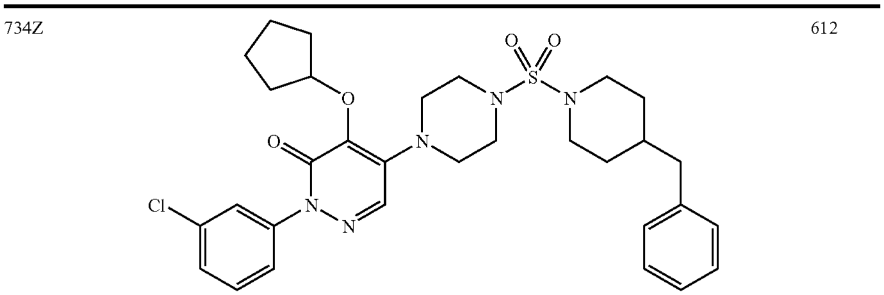
612
735Z
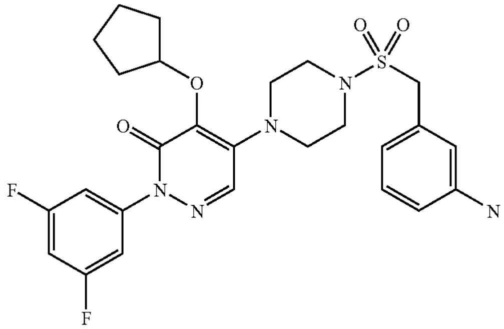
546
738Z
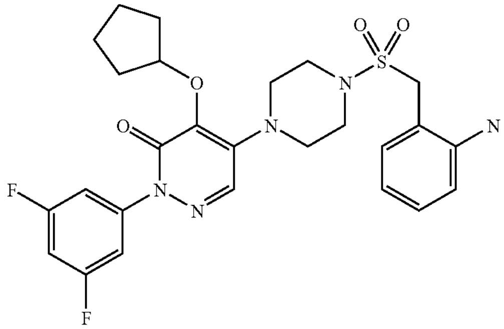
546
739Z
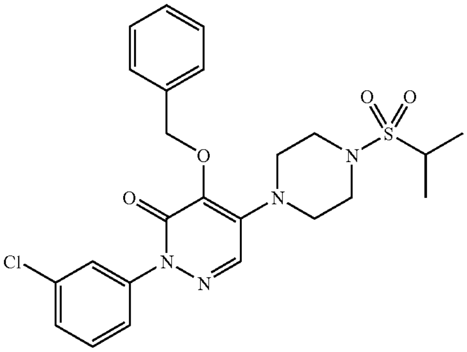
503
740Z
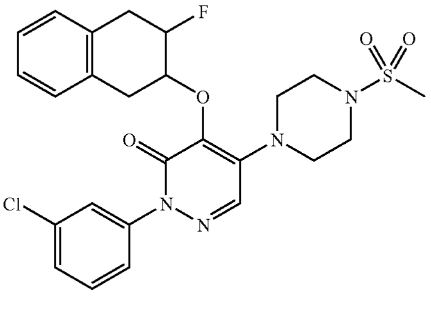
533

-continued
741Z
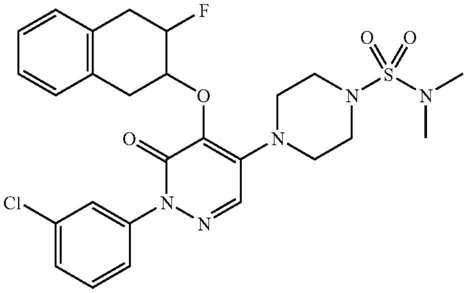
562
742Z
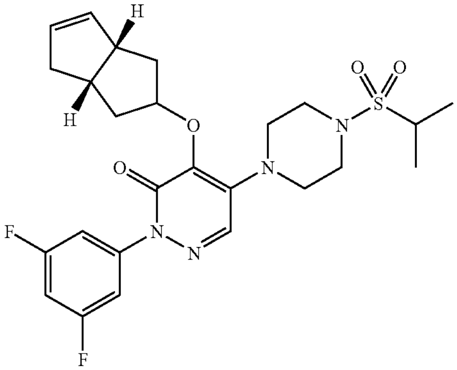
549
743Z
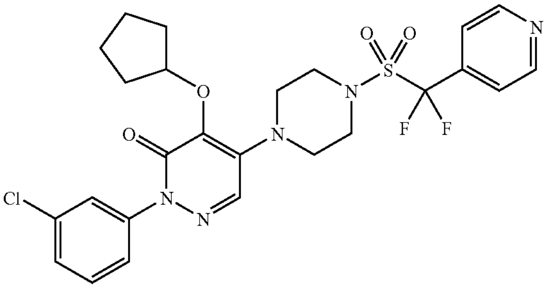
567
744Z
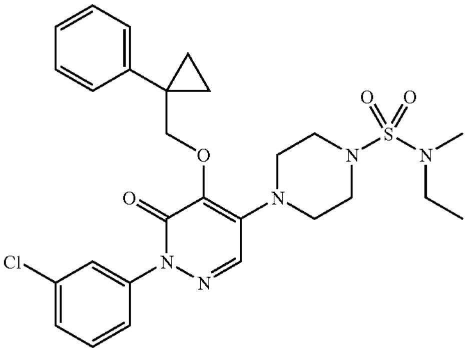
559
745Z
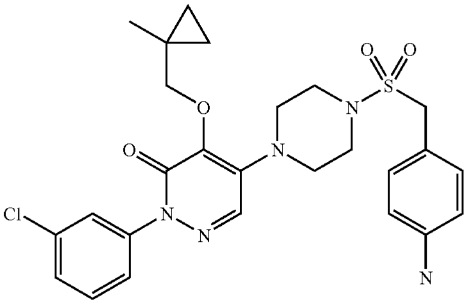
545

-continued
746Z 574
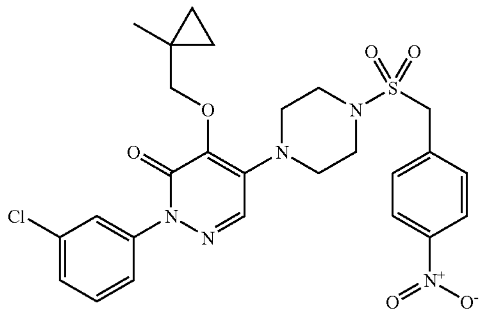
747Z 549
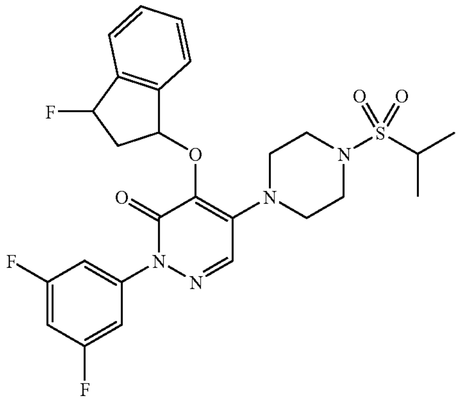
748Z no compound
749Z 553
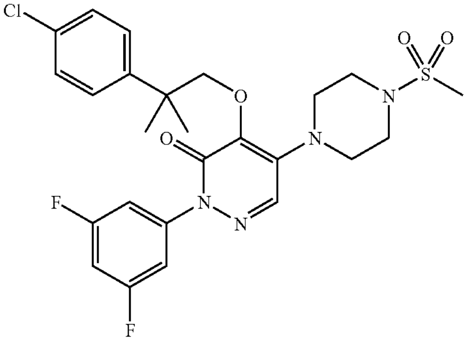
750Z 579
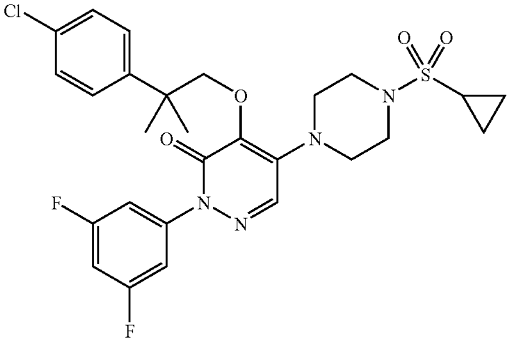

-continued
751Z 469
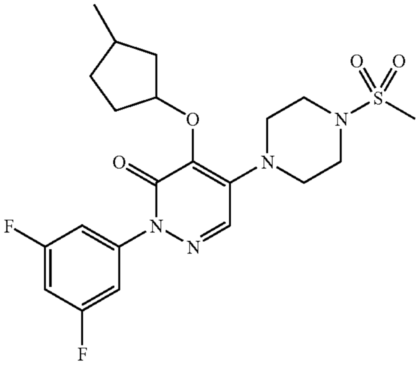
752Z 553
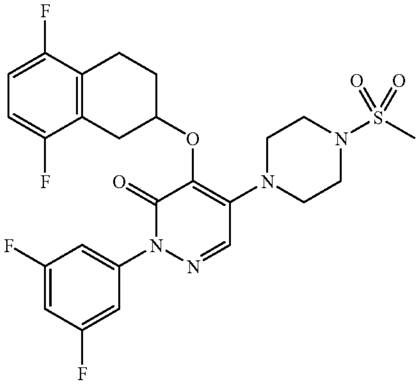
753Z 574
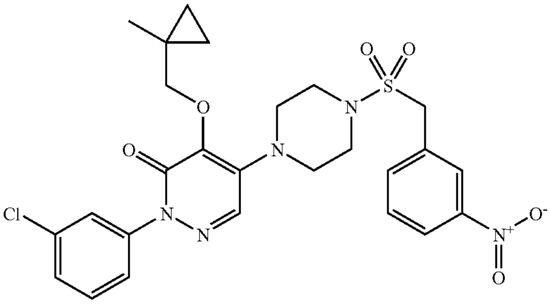
754Z 481
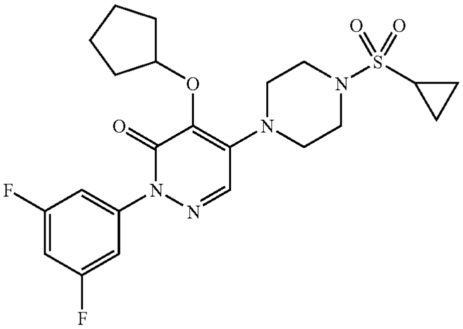

-continued
755Z 545
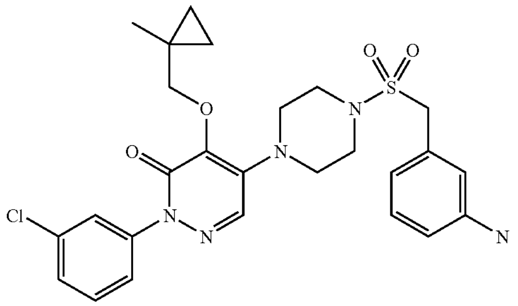
756Z 512
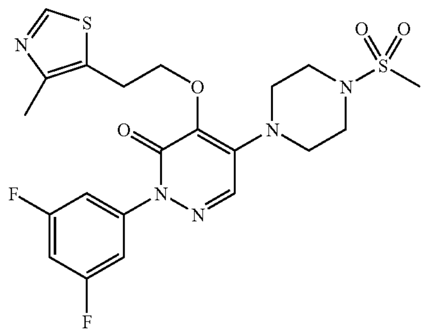
757Z 541
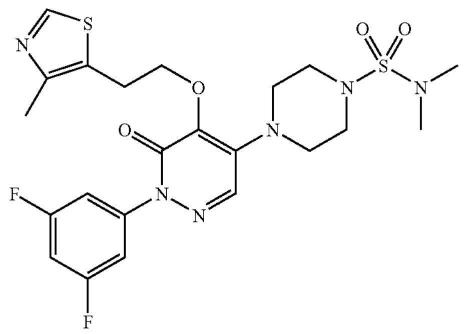
758Z 525
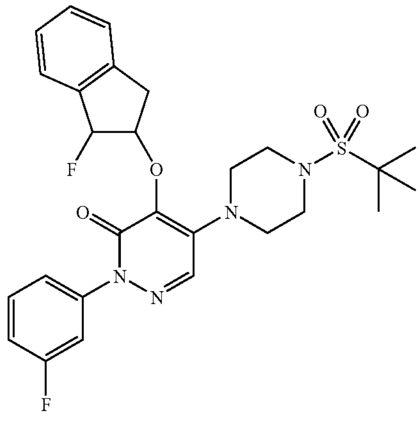

-continued
759Z 538
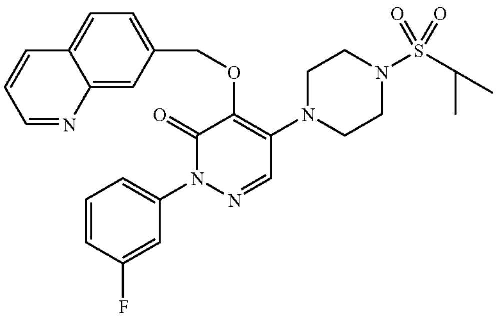
760Z 549
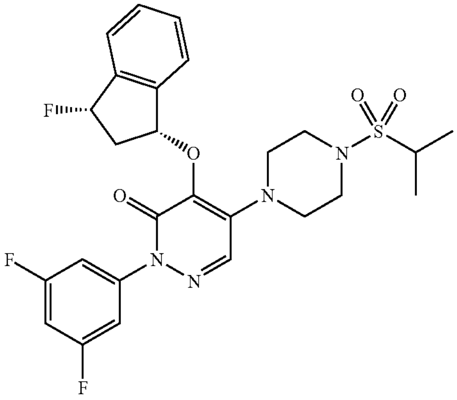
761Z 496
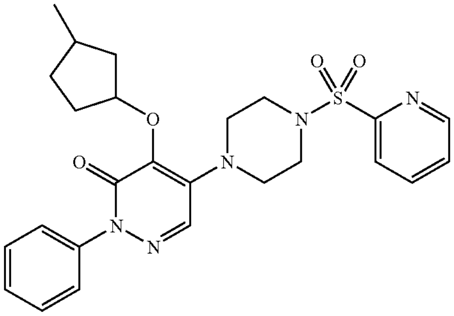
762Z 462
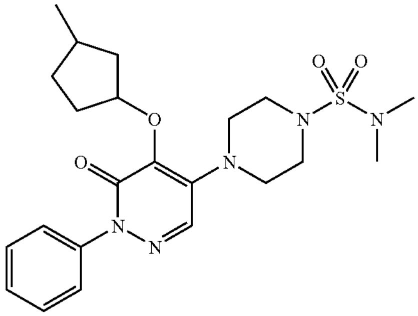

-continued
763Z
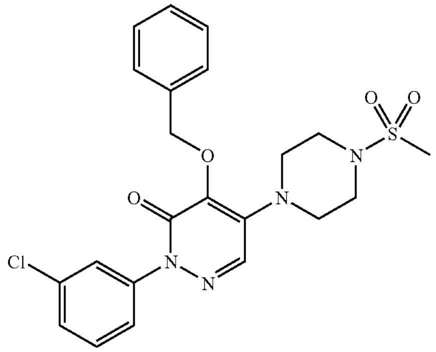
475
764Z
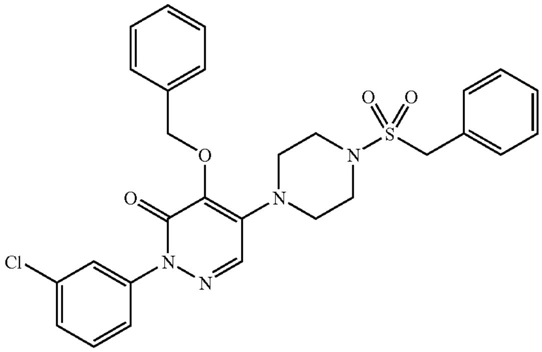
551
765Z
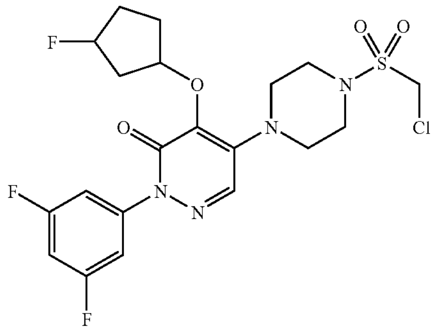
507
766Z
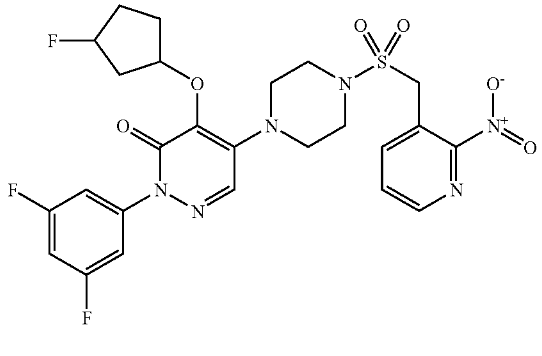
595

-continued
767Z 546
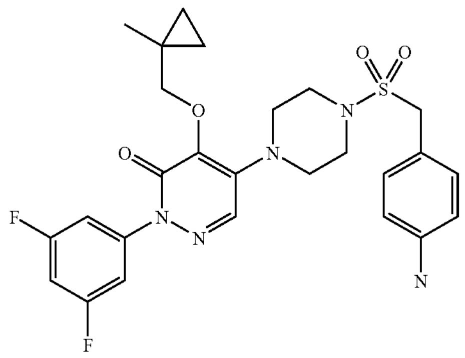
768Z 559
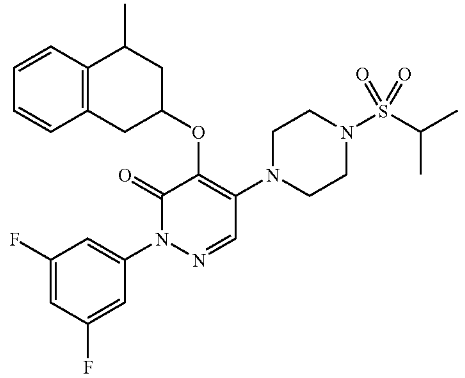
769Z 529
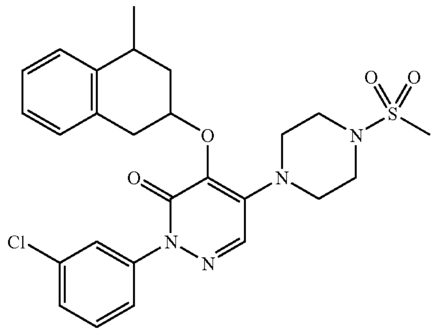
770Z 583
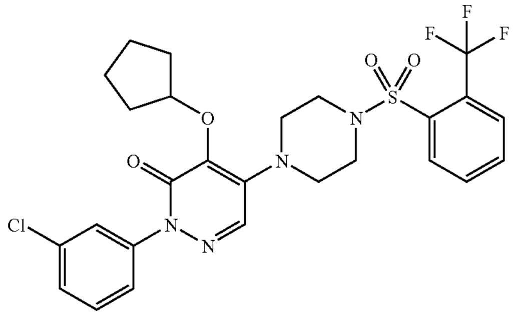

-continued
771Z 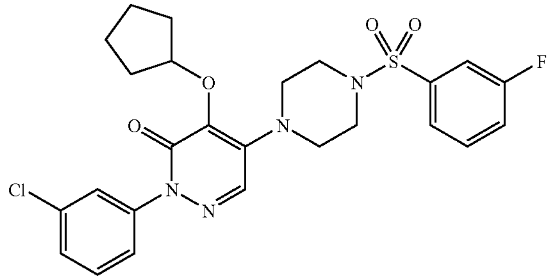 533
772Z 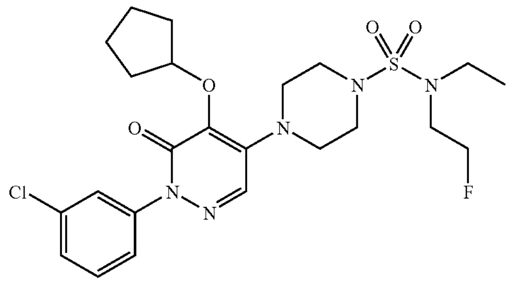 528
773Z 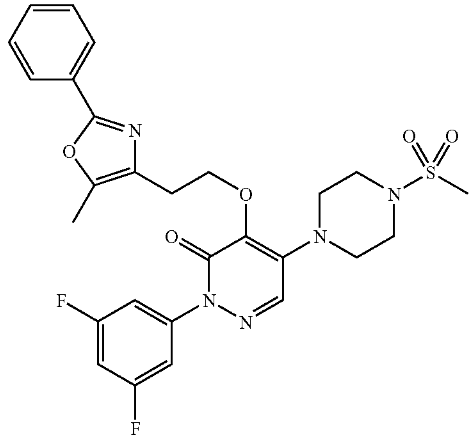 572
774Z 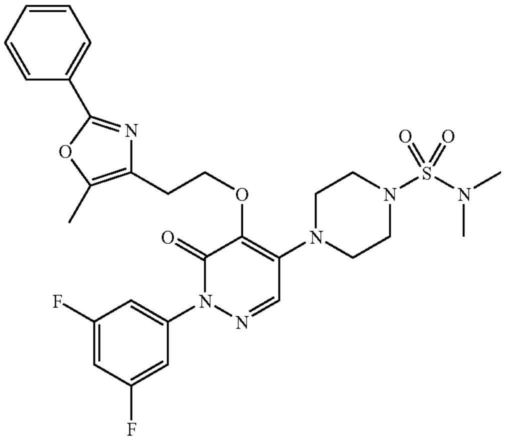 601

-continued
775Z 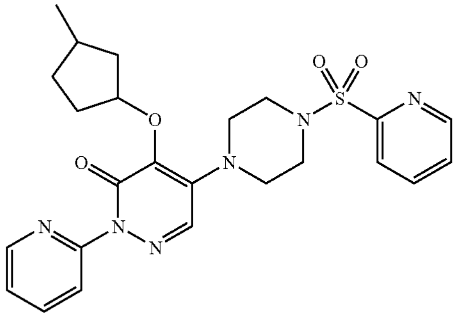 497
776Z 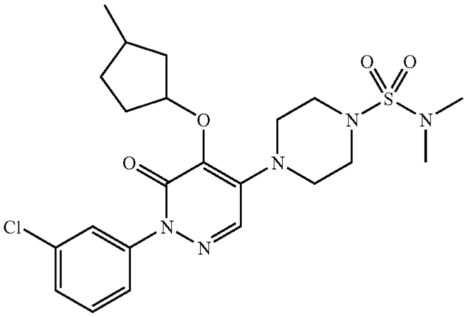 496
777Z 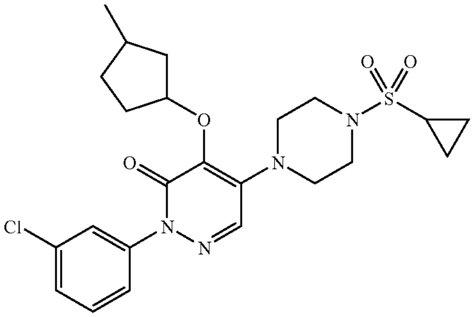 493
778Z 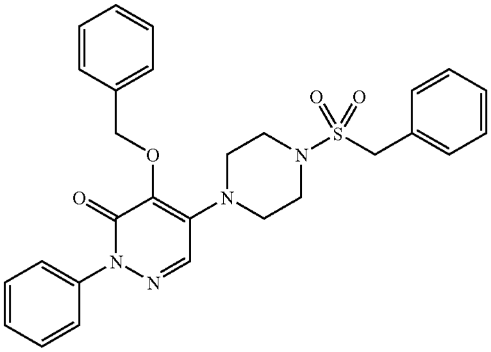 517
779Z 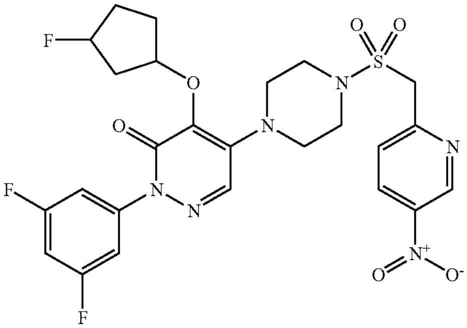 595

-continued
780Z no compound
781Z 529
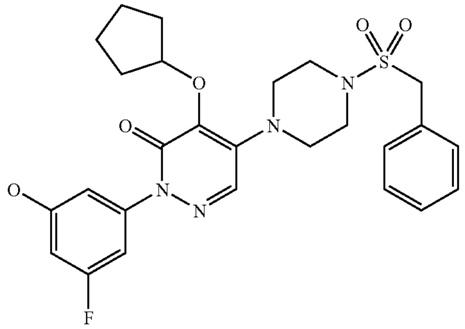
782Z 533
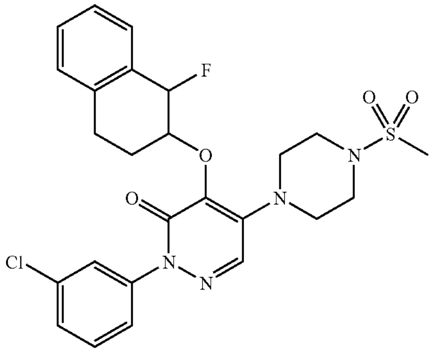
783Z 545
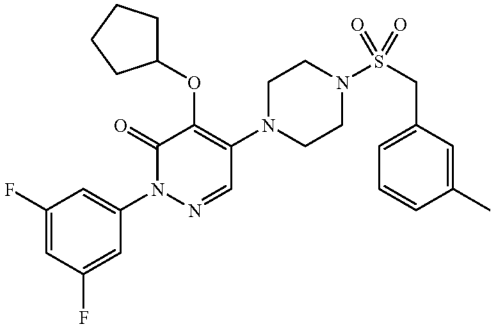
784Z 561
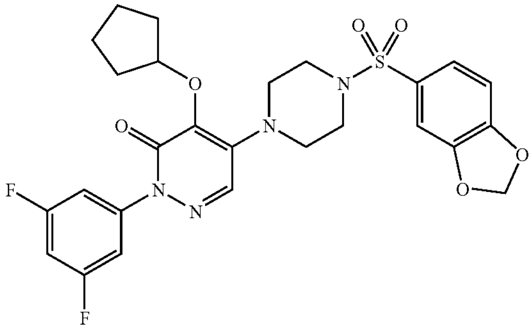

-continued
785Z 548
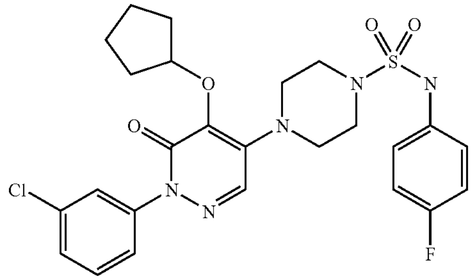
786Z 510
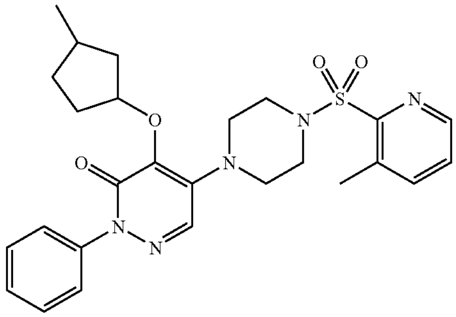
787Z 663
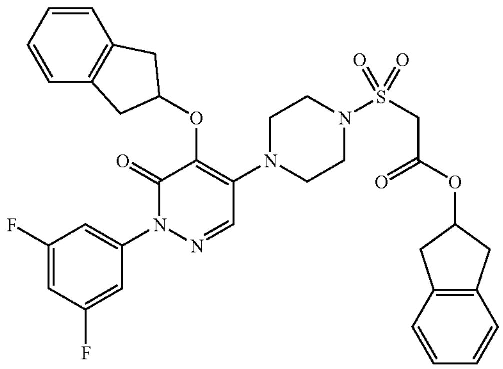
788Z 470
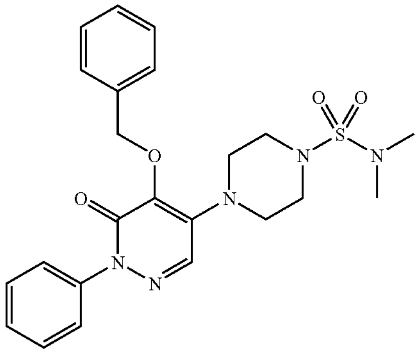

-continued
789Z 504
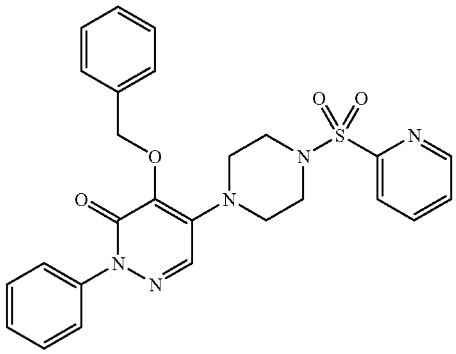
790Z 605
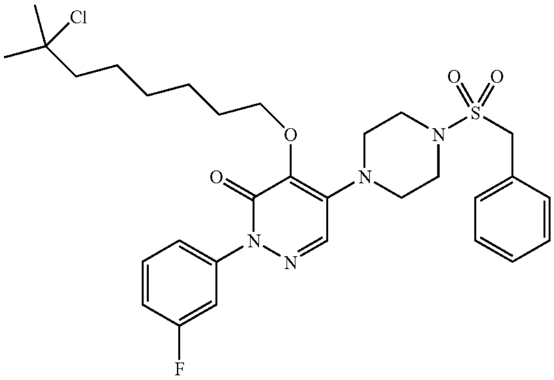
791Z 547
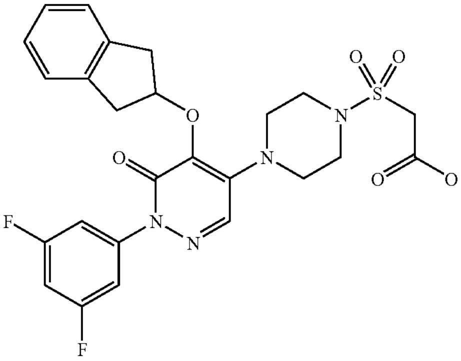
792Z 419
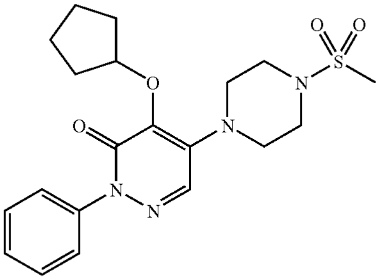

-continued
| | | |
|---|---|---|
| 793Z | 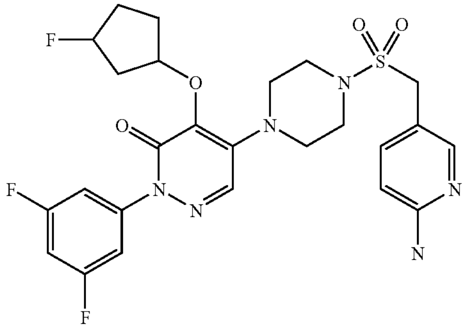 | 565 |
| 794Z | 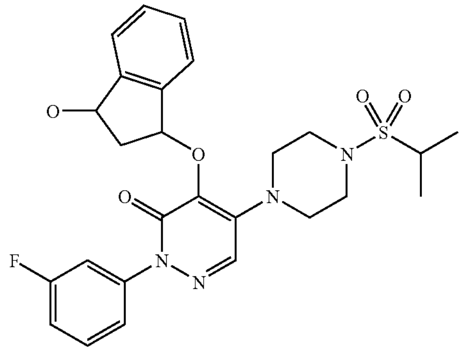 | 529 |
| 795Z | 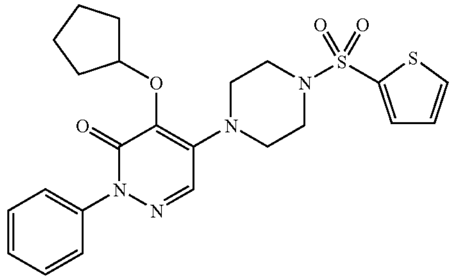 | 487 |
| 796Z | 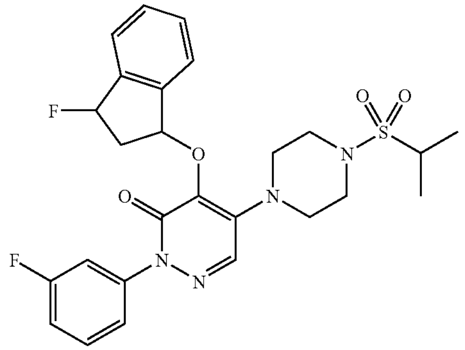 | 531 |
| 797Z | 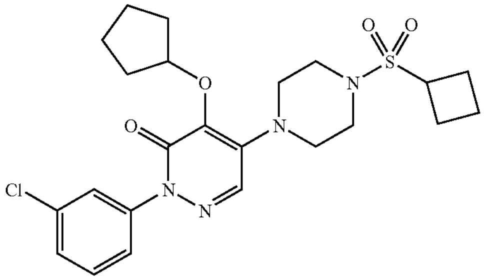 | 493 |

-continued
798Z 529
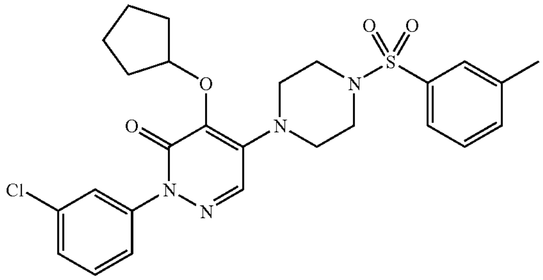
799Z 563
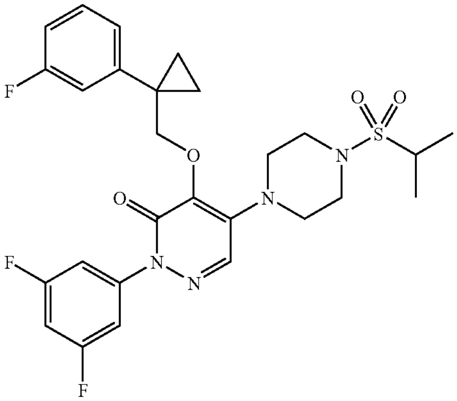
800Z 575
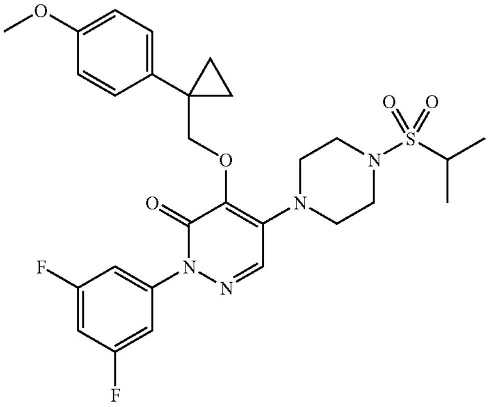
801Z 541
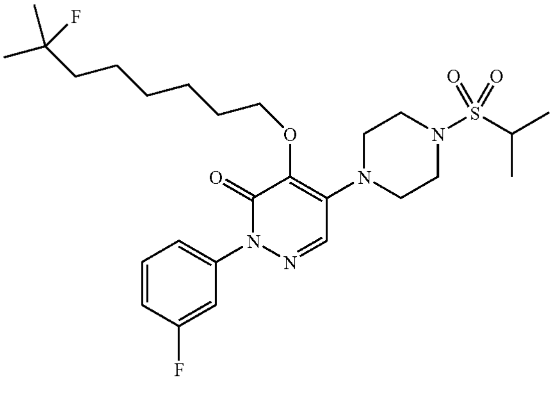

-continued
802Z 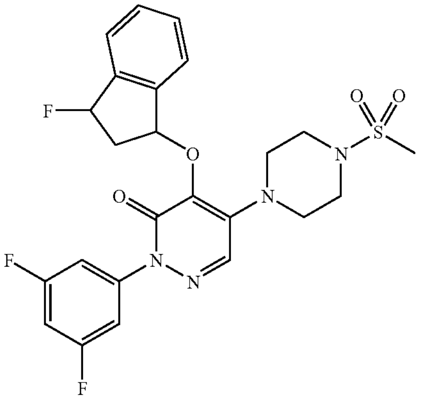 521
803Z 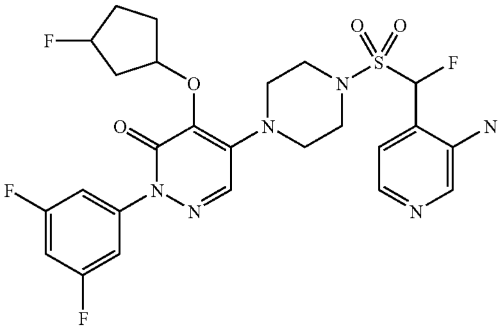 583
804Z 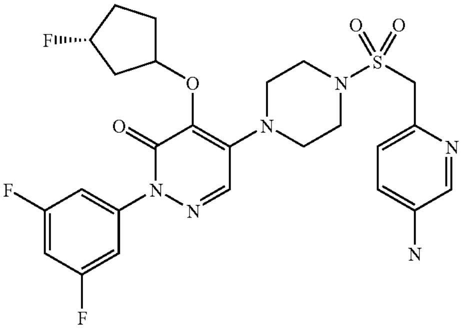 565
805Z 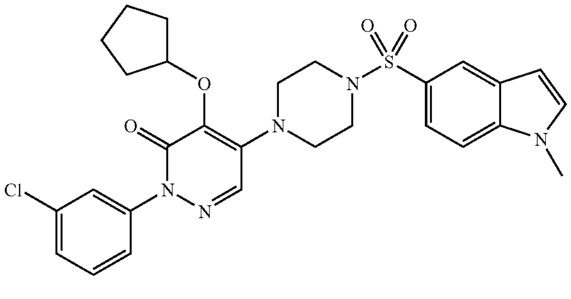 568
806Z 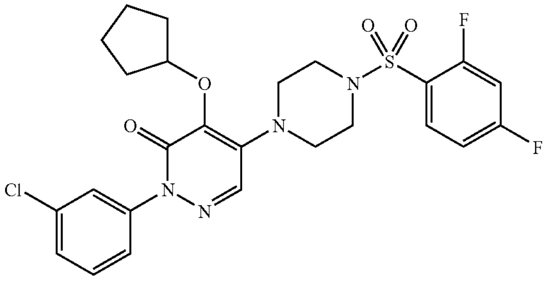 551

-continued
807Z 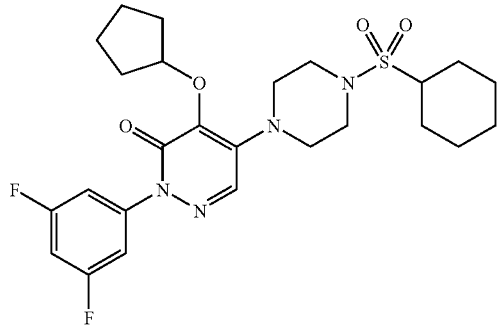 523
808Z 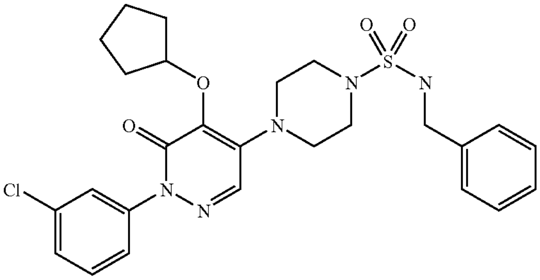 544
809Z 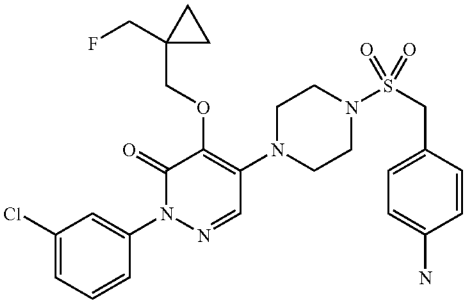 562
810Z no compound
811Z 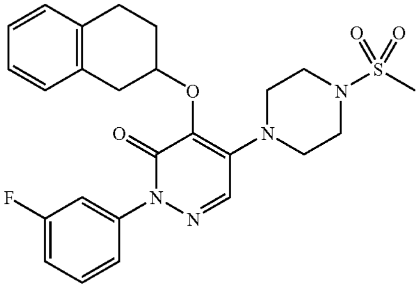 499
812Z 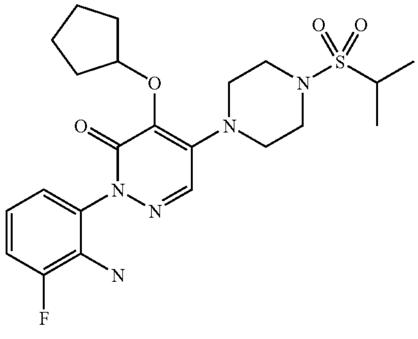 480

-continued
813Z 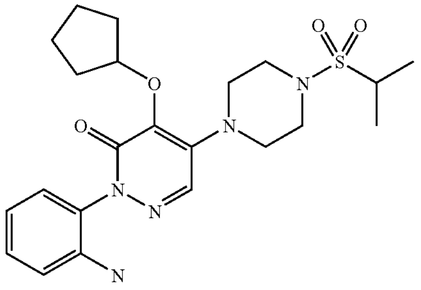 462
814Z no compound
815Z 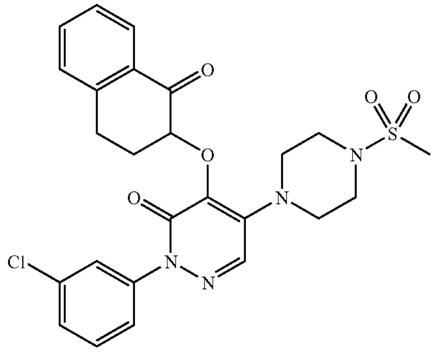 529
816Z no compound
817Z 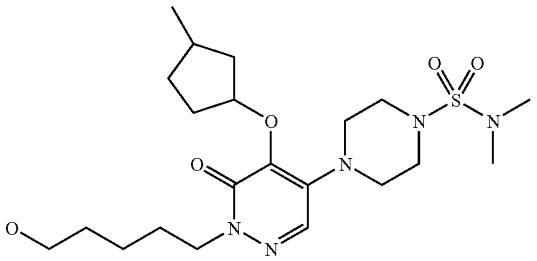 472
818Z no compound
819Z 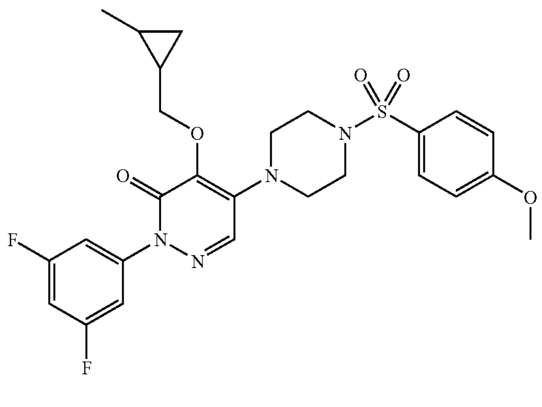 547

-continued
| | | |
|---|---|---|
| 820Z | 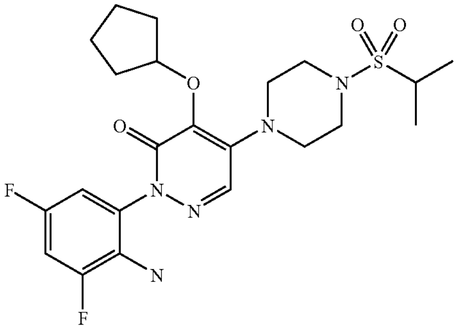 | 498 |
| 821Z | 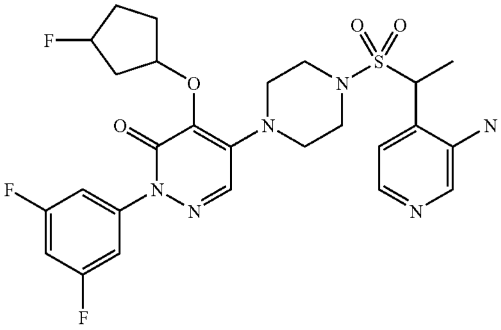 | 579 |
| 822Z | 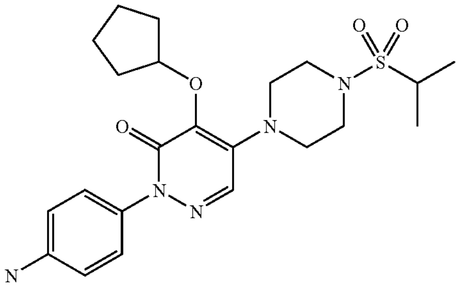 | 462 |
| 823Z | no compound | |
| 824Z | 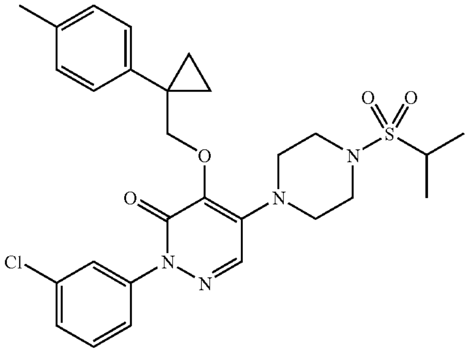 | 558 |
| 825Z | 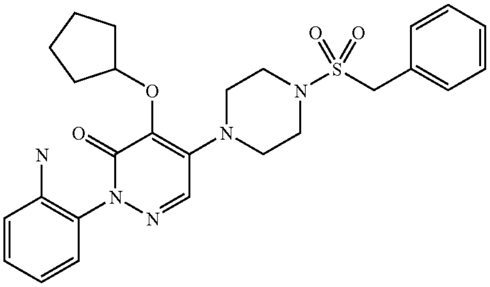 | 510 |

-continued
826Z
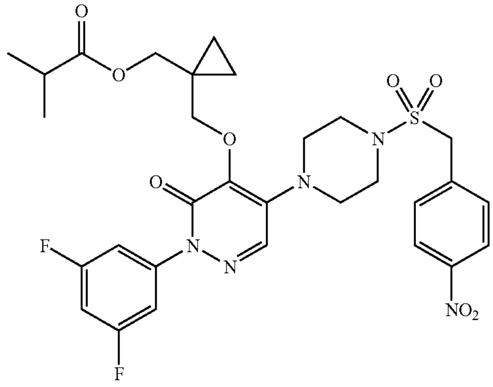
662
827Z
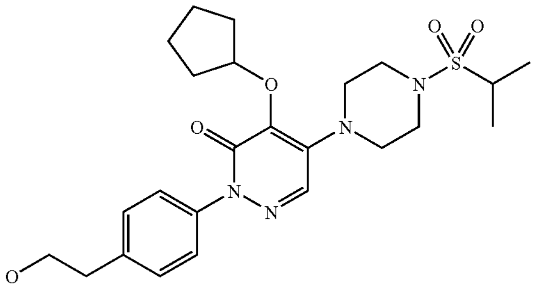
491
828Z
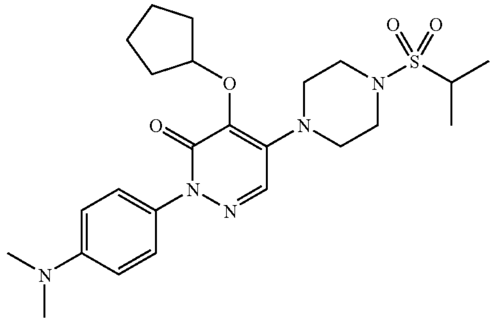
490
829Z
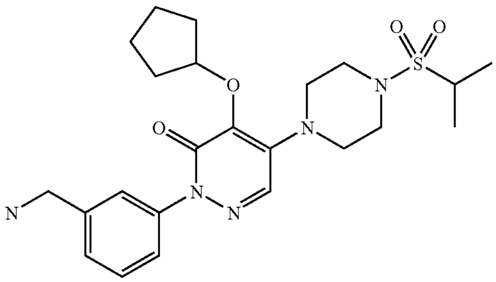
476
830Z
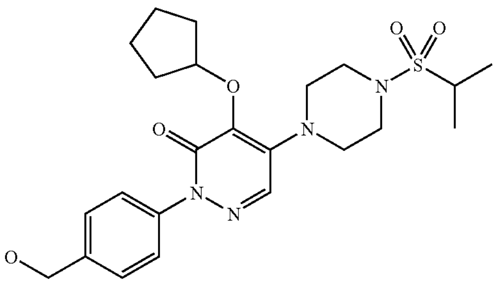
477

-continued
831Z 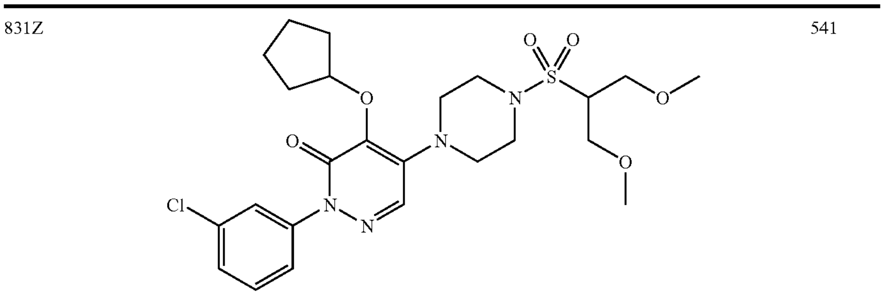 541
832Z 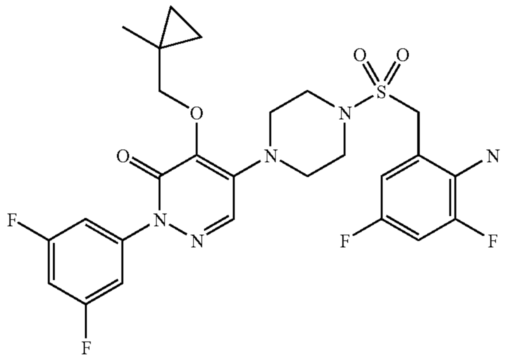 582
833Z 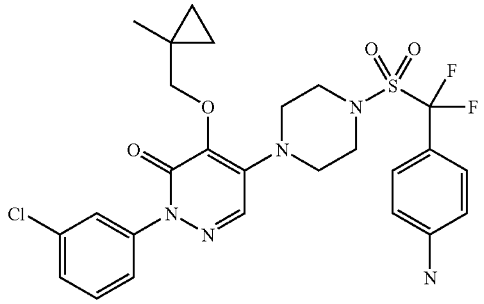 580
834Z 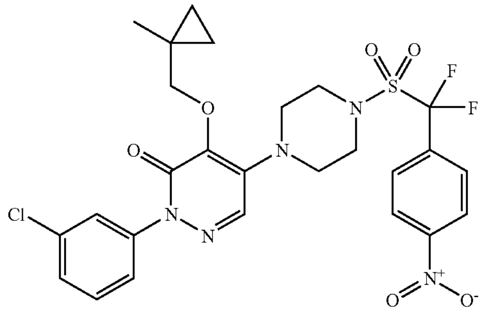 610
835Z 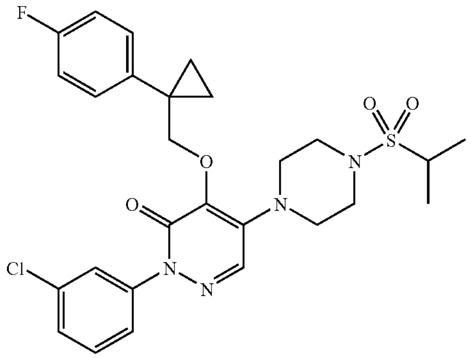 669

-continued
836Z 544
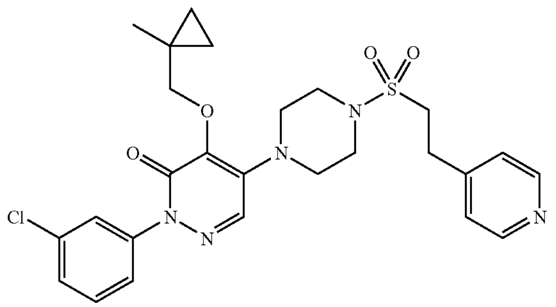
837Z 541
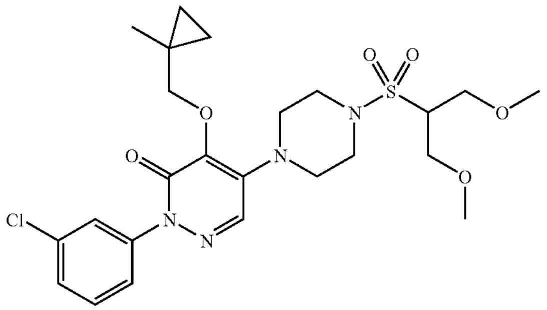
838Z 589
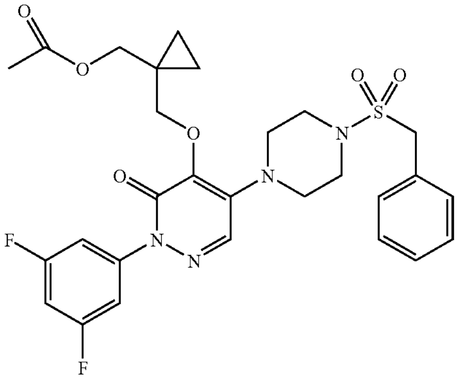
839Z 561
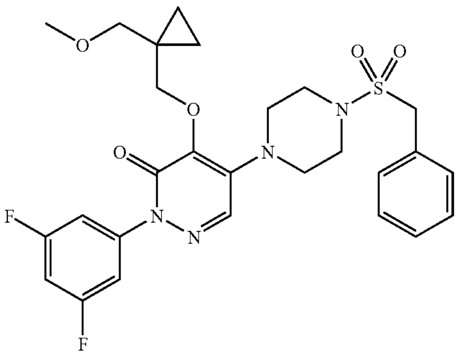

-continued
840Z 619
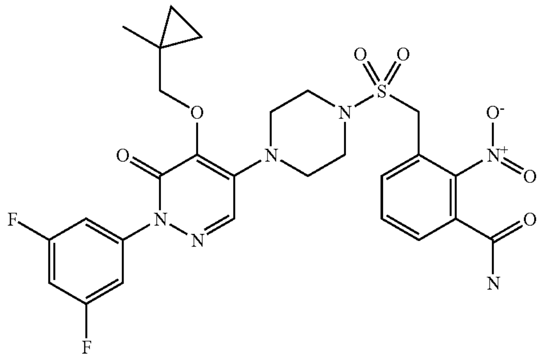
841Z 542
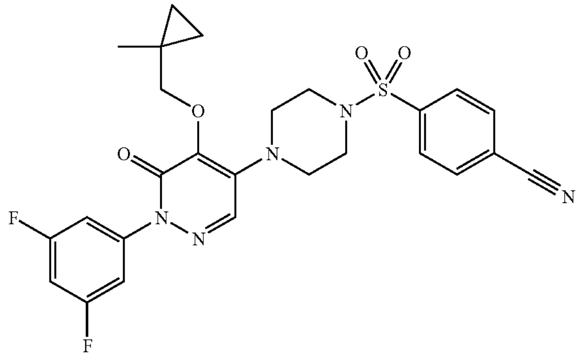
842Z 542
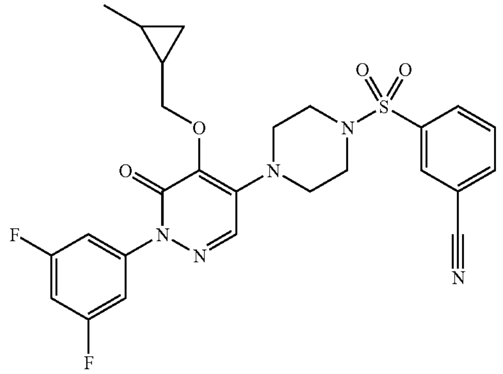
843Z 547
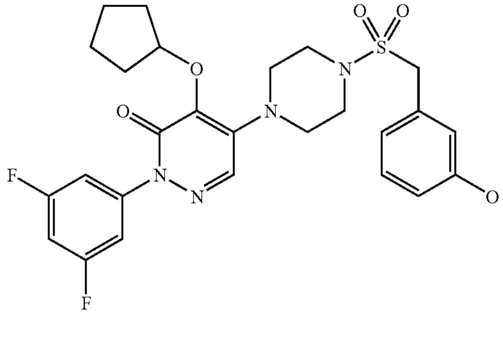

-continued
| | | |
|---|---|---|
| 844Z | no compound | |
| 845Z | 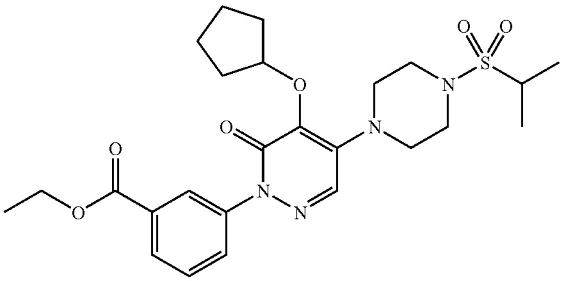 | 519 |
| 846Z | 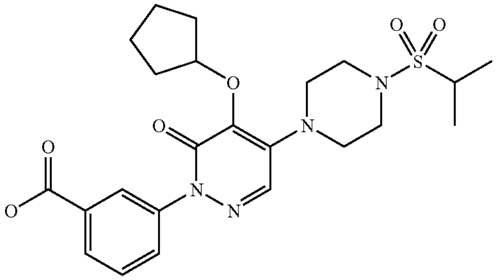 | 491 |
| 847Z | 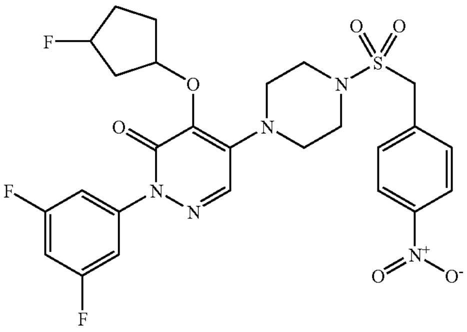 | 594 |
| 848Z | 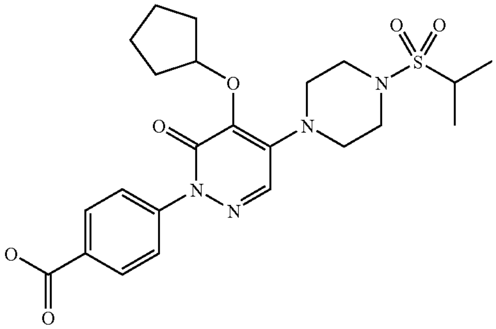 | 491 |
| 849Z | 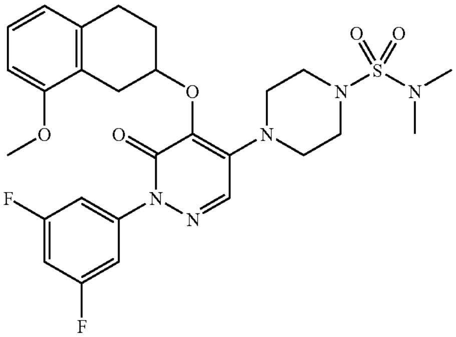 | 576 |

-continued
850Z 499
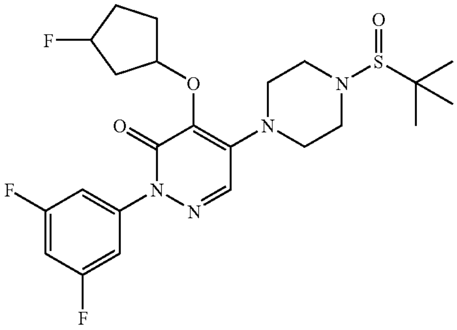
851Z 515
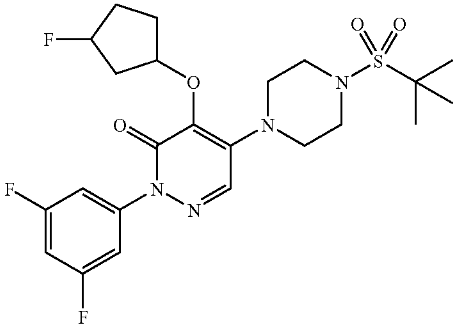
852Z 555
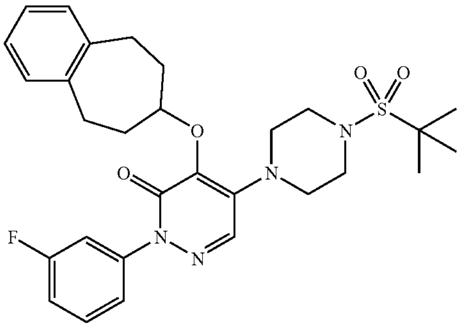
853Z 487
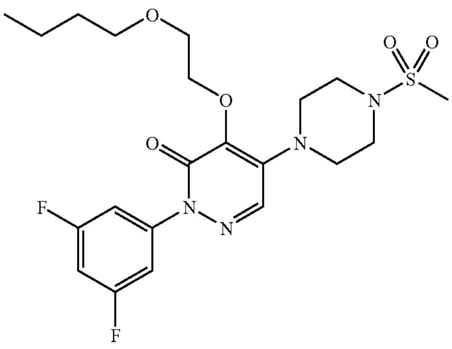

-continued
854Z 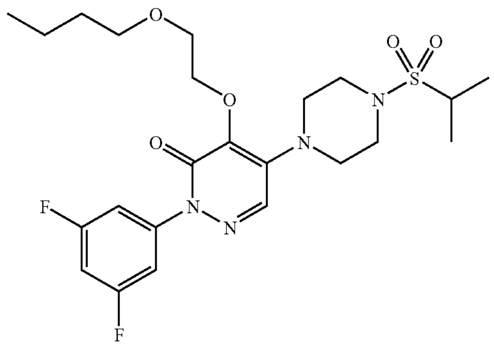 515
855Z 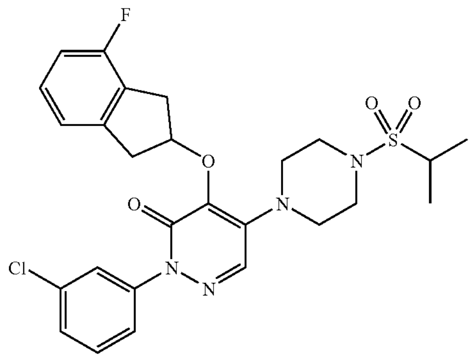 547
856Z 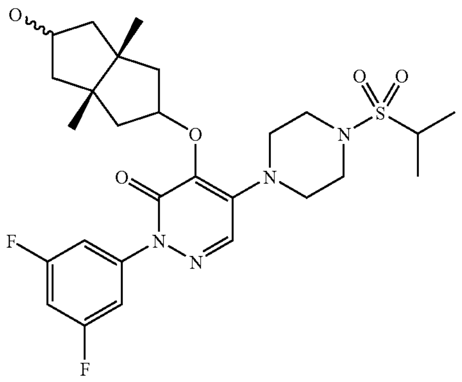 567
857Z 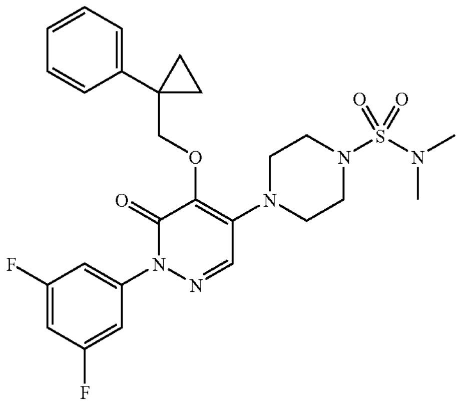 546

-continued
858Z 502
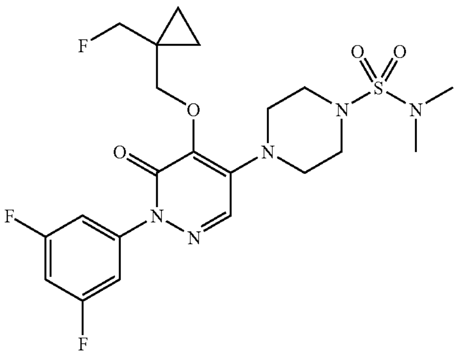
859Z 501
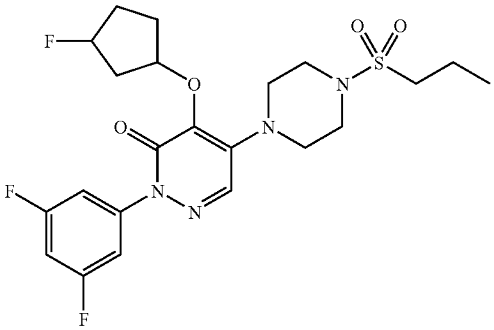
860Z 537
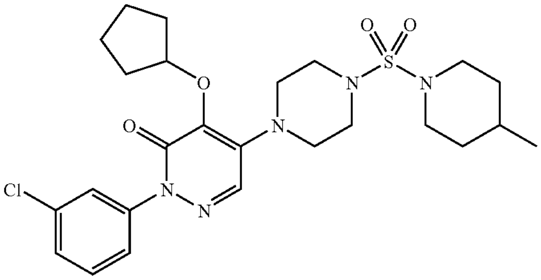
861Z 546
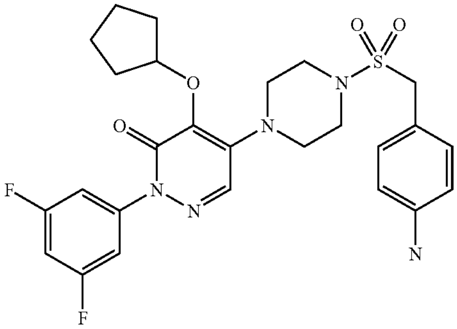

-continued
862Z 581
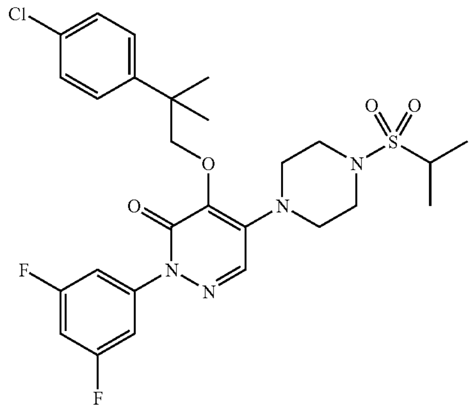
863Z 515
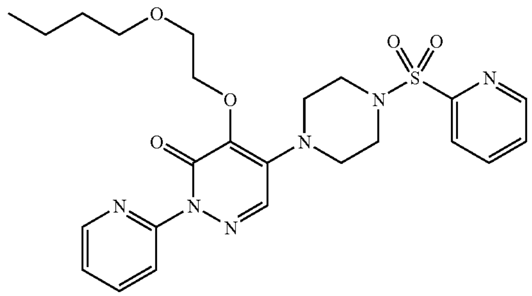
864Z 561
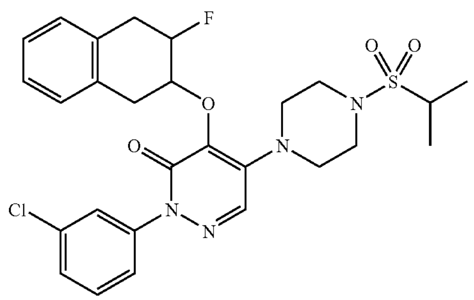
865Z 569
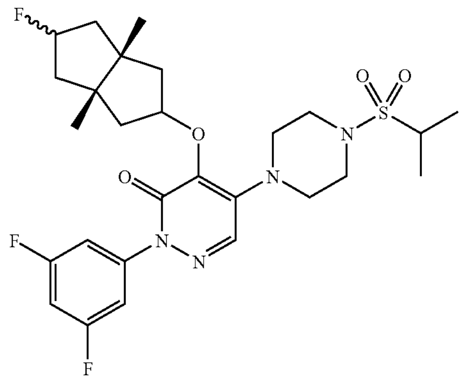

-continued
866Z 532
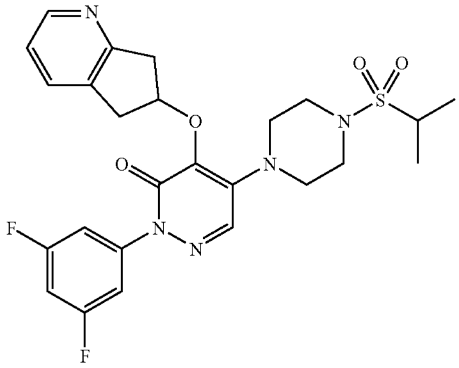
867Z 454
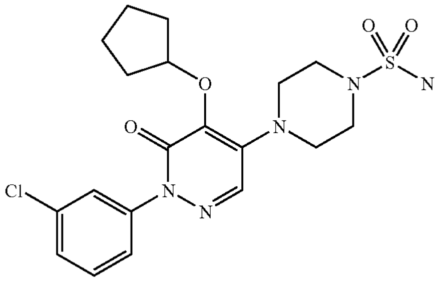
868Z 572
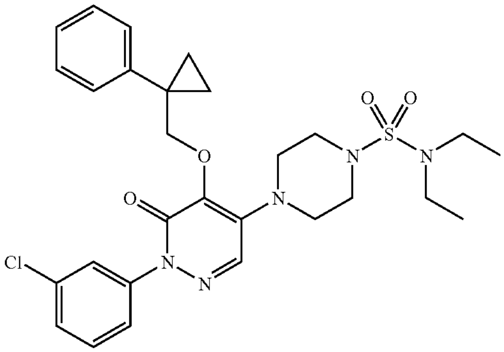
869Z 514
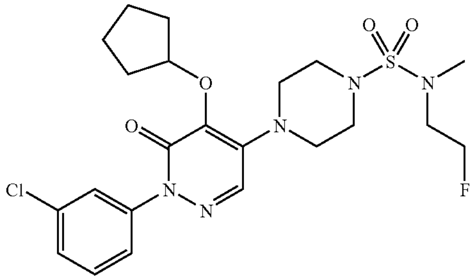

-continued
| | | |
|---|---|---|
| 870Z | 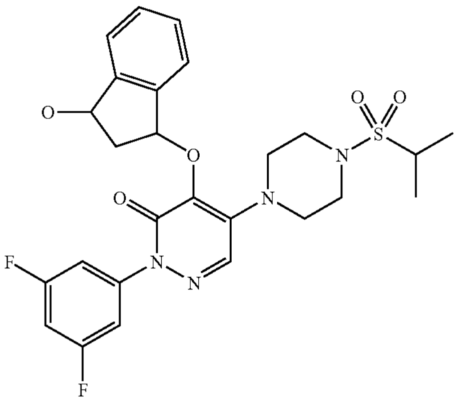 no compound | 529 |
| 871Z | 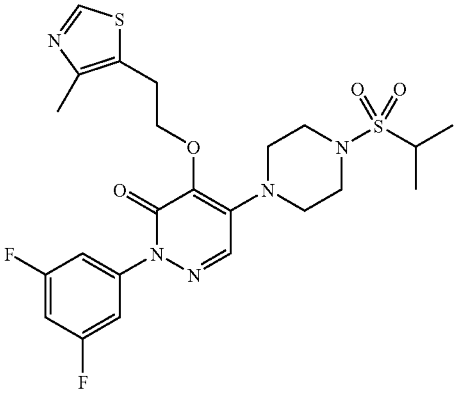 | 540 |
| 872Z | 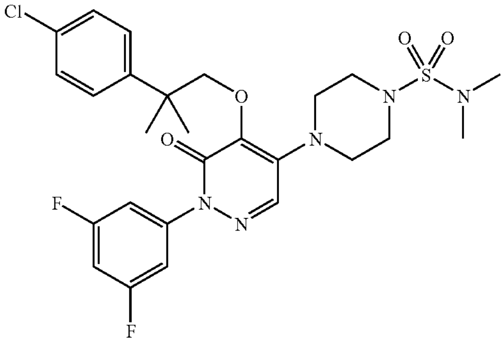 | 582 |
| 873Z | 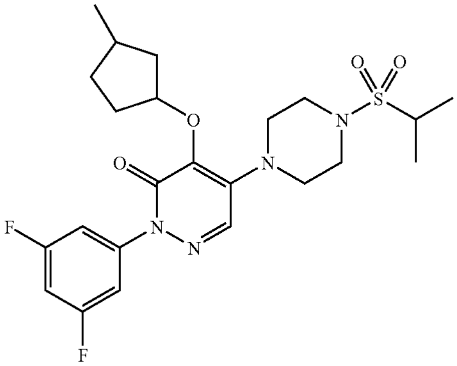 | 497 |

-continued
874Z 545
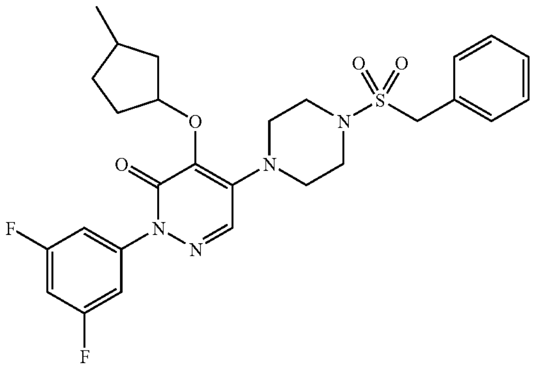
875Z 550
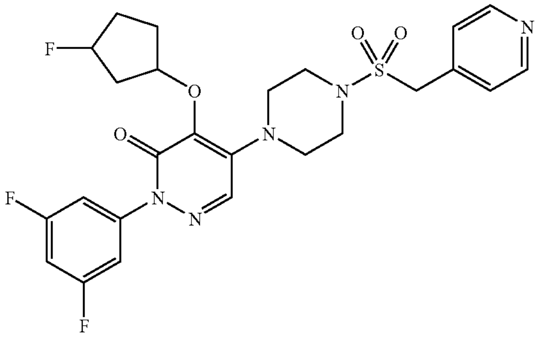
876Z 555
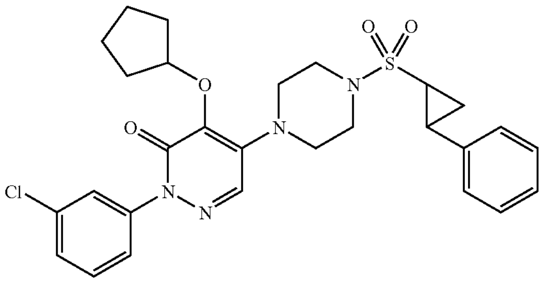
877Z 497
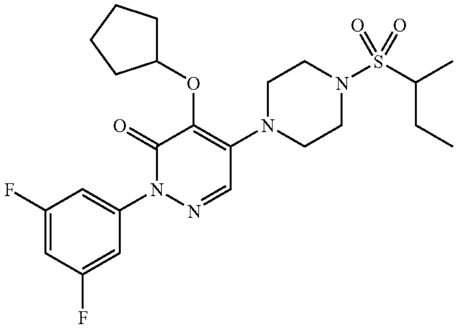

-continued
878Z 483
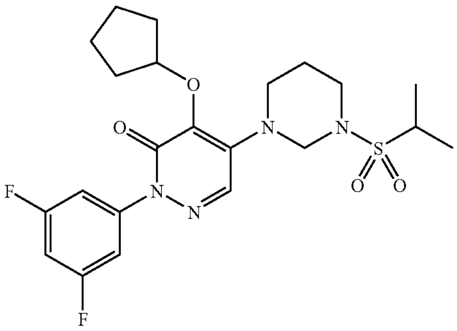
879Z 538
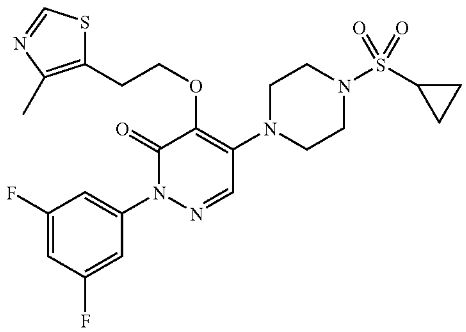
880Z 588
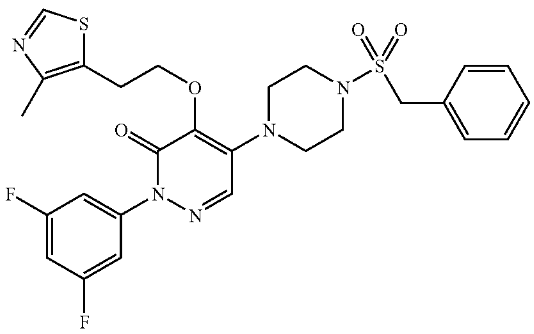
881Z 542
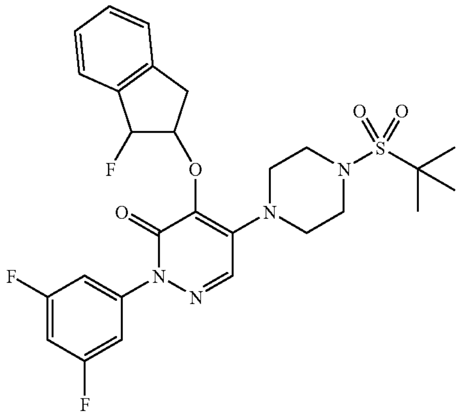

-continued
882Z 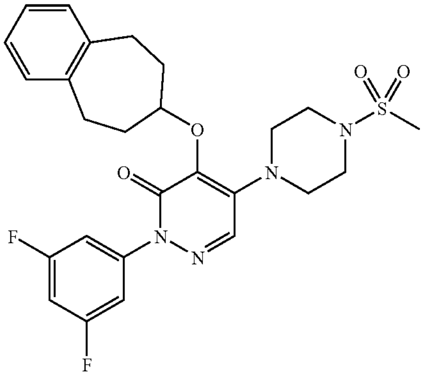 531
883Z 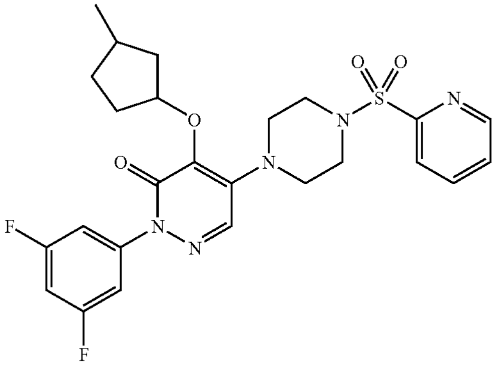 532
884Z 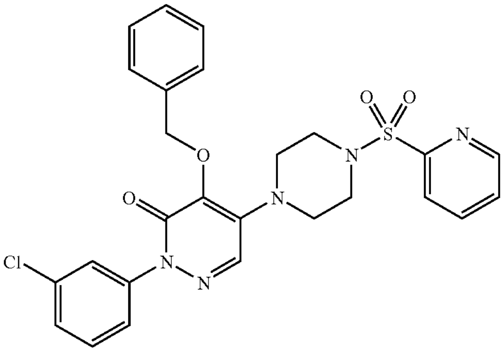 538
885Z 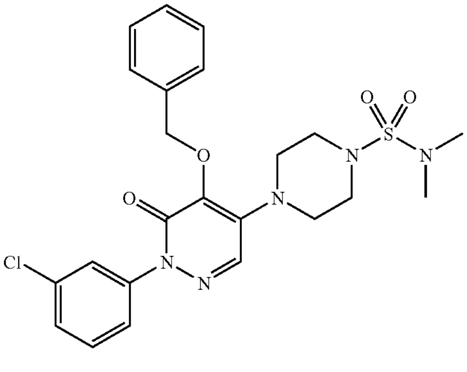 504

-continued
886Z
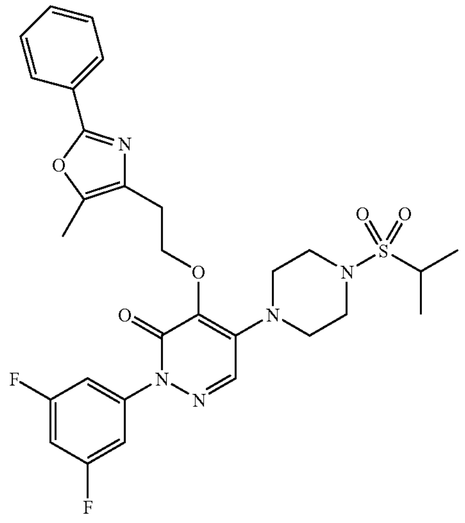
600
887Z
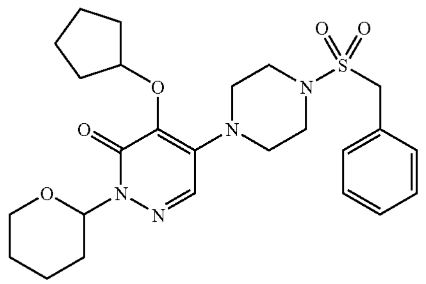
503
888Z
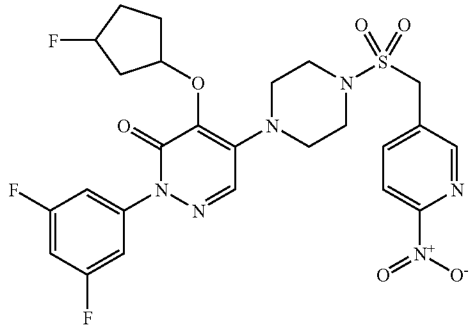
595
889Z
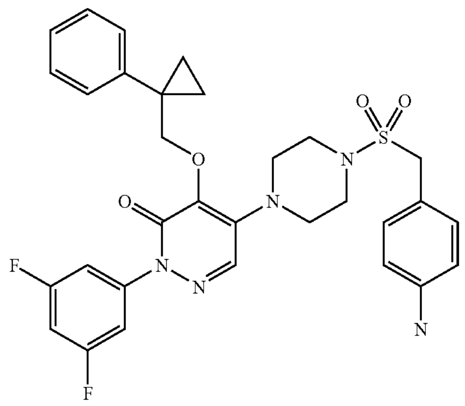
608

-continued
890Z
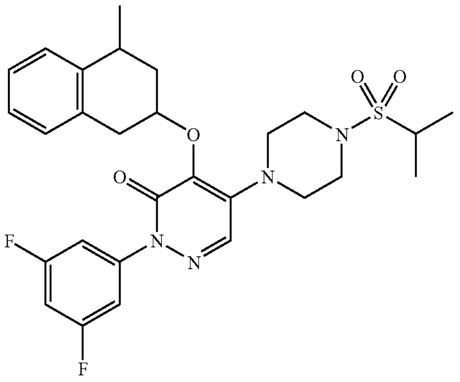
559
891Z
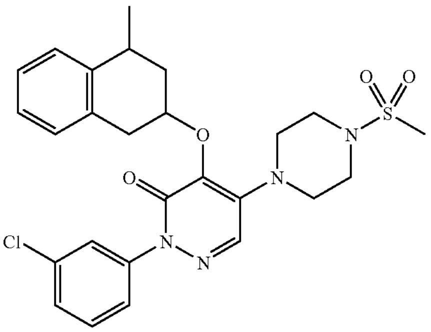
529
892Z
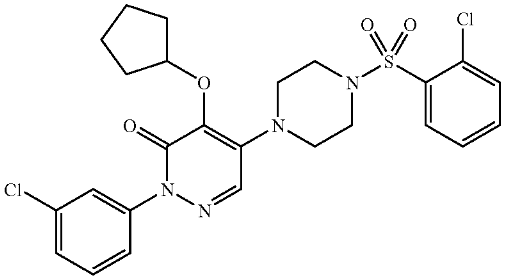
549
893Z
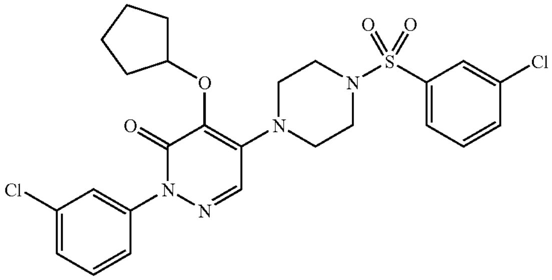
549
894Z
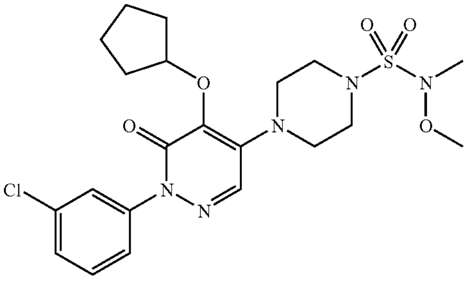
498

-continued
895Z 574
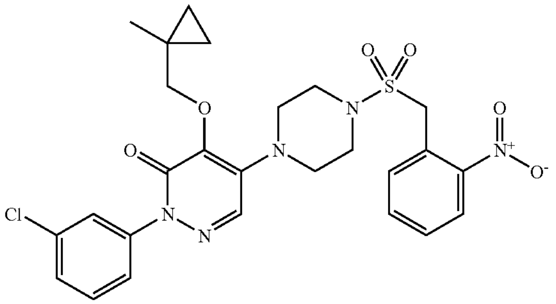
896Z 598
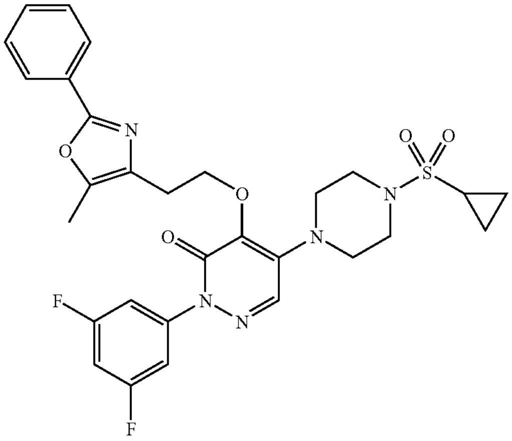
897Z 462
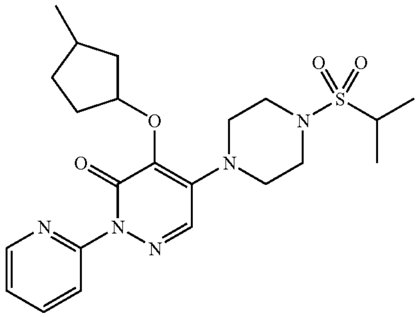
898Z 501
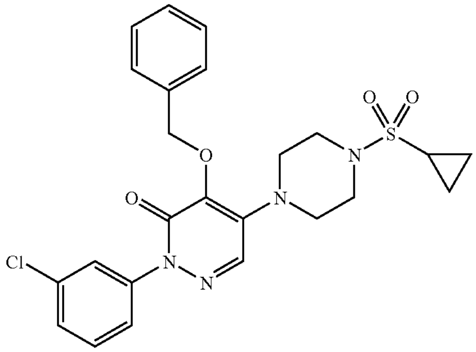

-continued
899Z 530
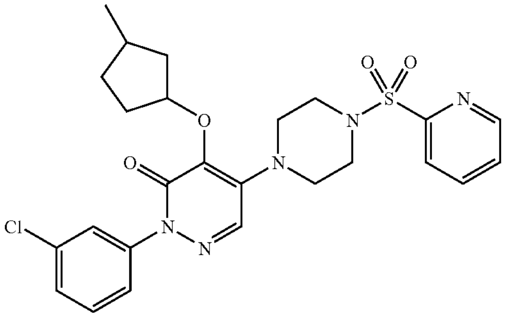
900Z 441
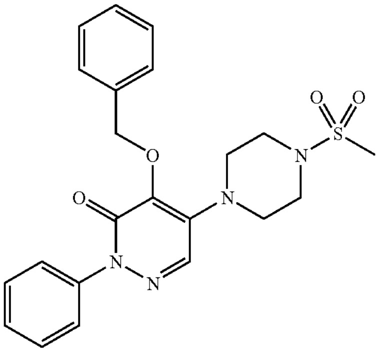
901Z 595
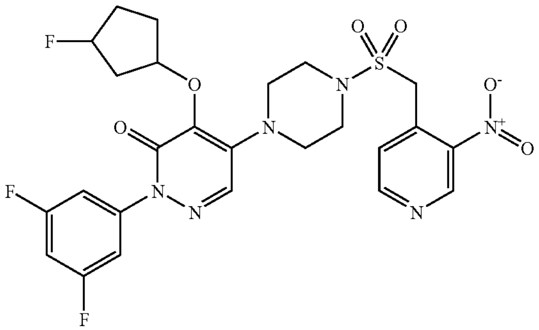
902Z 565
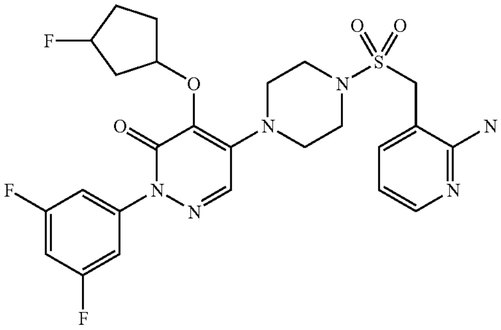

-continued
| | | |
|---|---|---|
| 903Z | no compound | |
| 904Z | 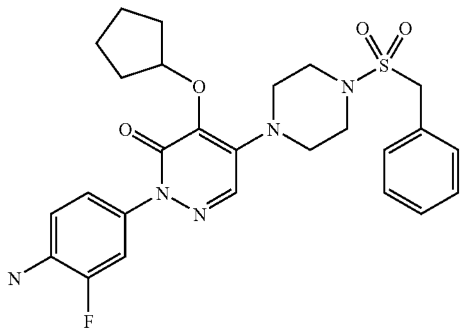 | 528 |
| 905Z | 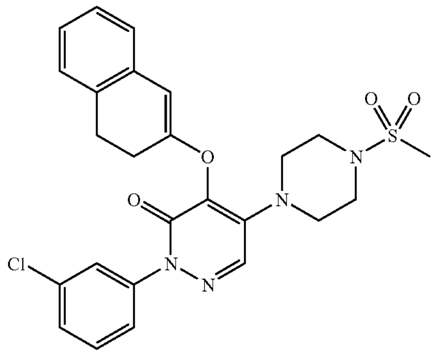 | 513 |
| 906Z | 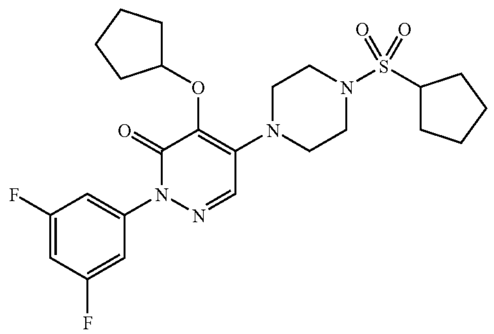 | 509 |
| 907Z | 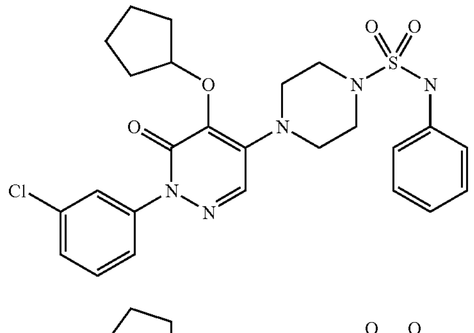 | 530 |
| 908Z | 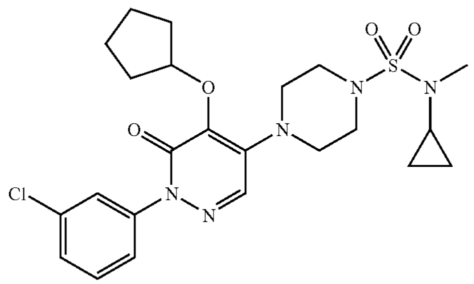 | 508 |

-continued
909Z
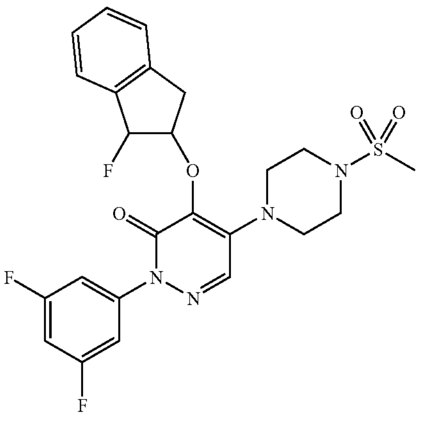
501
910Z
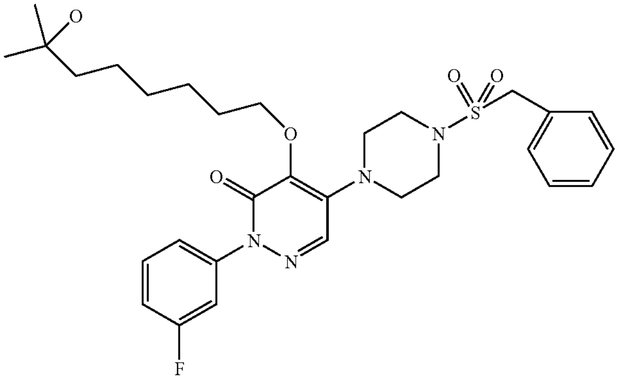
(M − 98) = 489
911Z
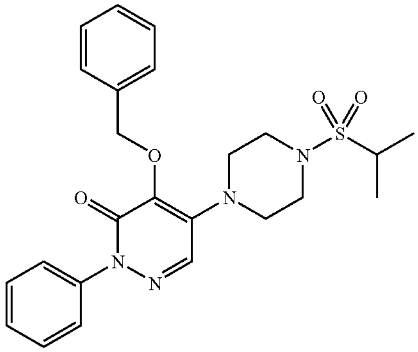
469
912Z
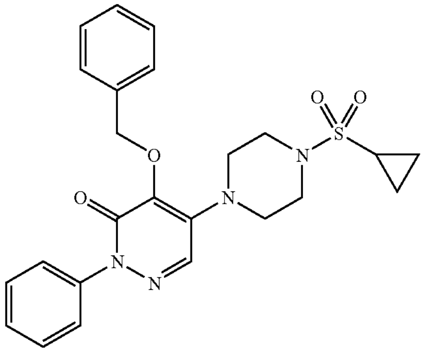
467

-continued
913Z 561
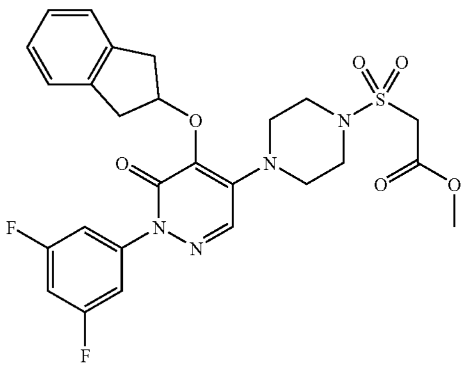
914Z no compound
915Z 445
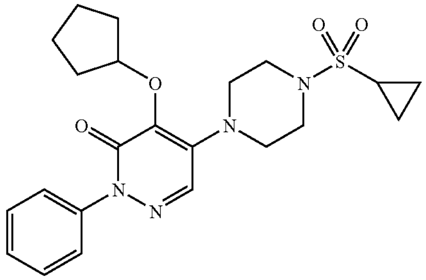
916Z 495
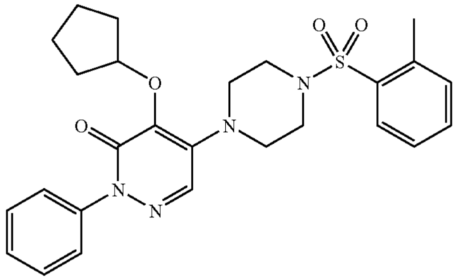
917Z 448
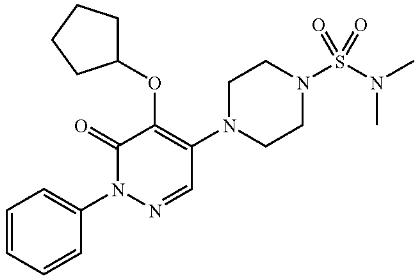

-continued
918Z 519
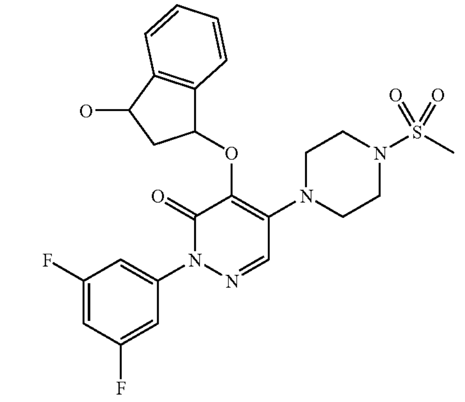
919Z 565
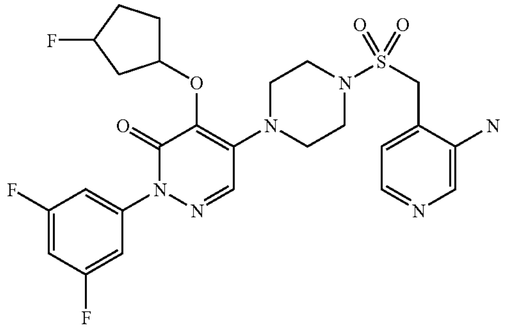
920Z 516
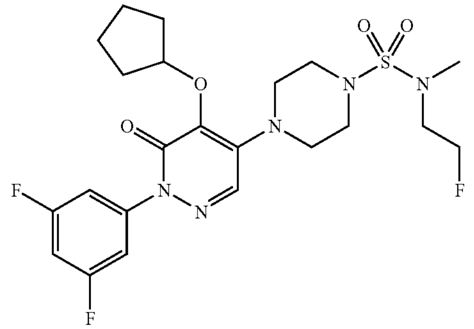
921Z 610
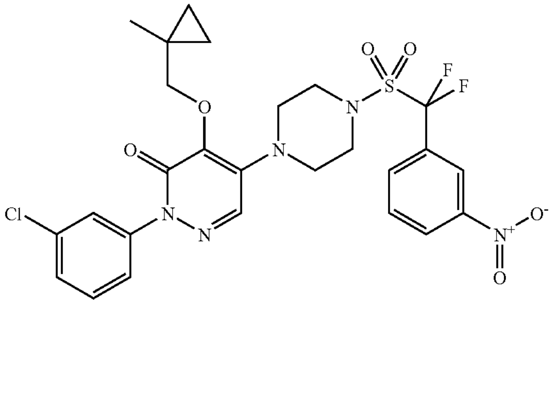

-continued
922Z 563
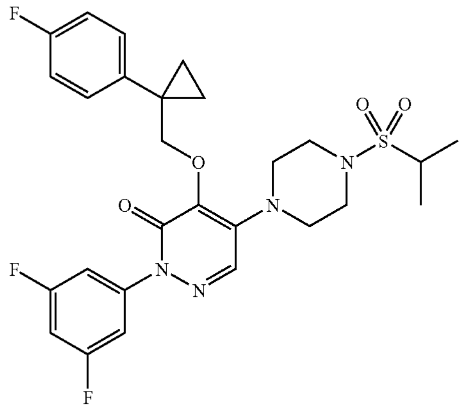
923Z 529
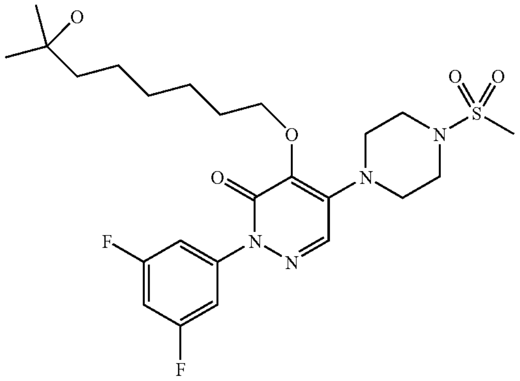
924Z 539
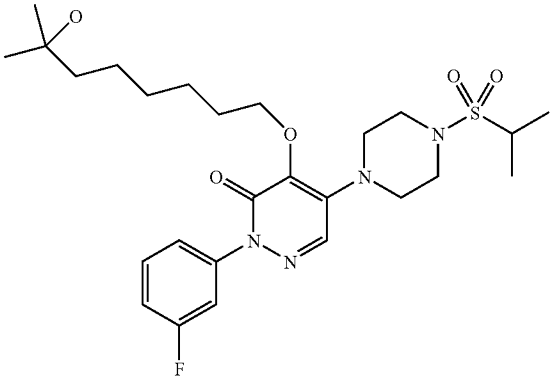
925Z 565
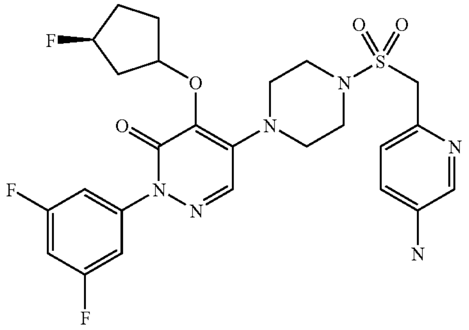
926Z no compound
927Z no compound -continued
928Z 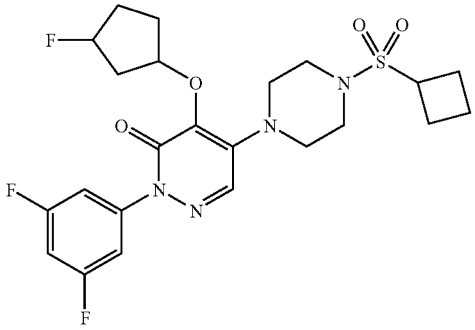 513
929Z 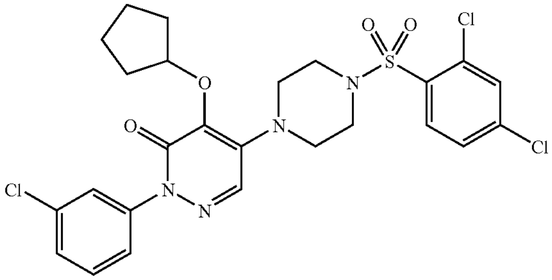 583
930Z 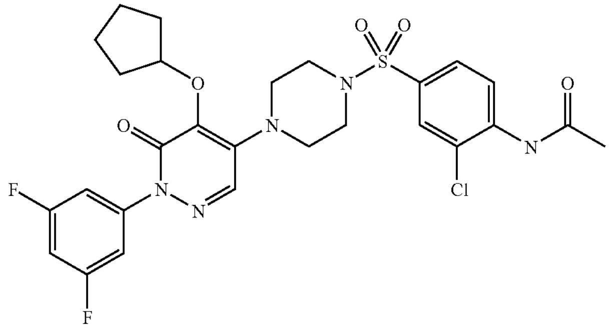 606
931Z 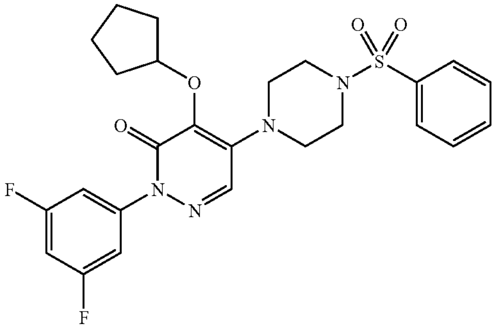 517
932Z 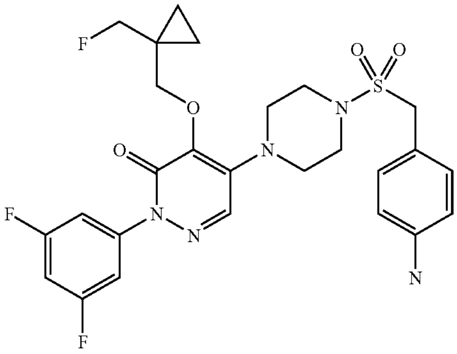 564

-continued
933Z no compound
934Z 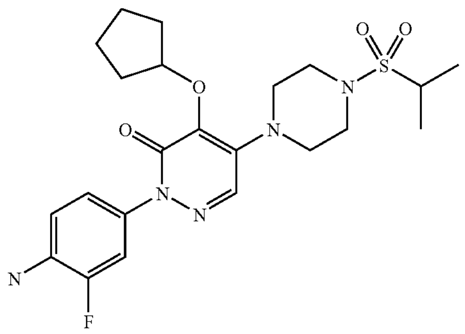 480
935Z no compound
936Z 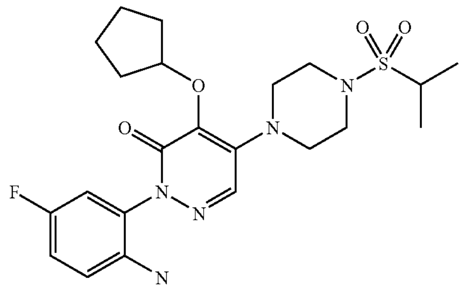 480
937Z 510
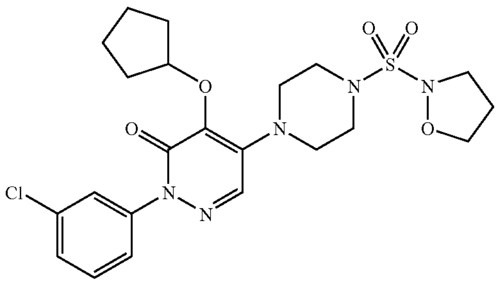
938Z 522
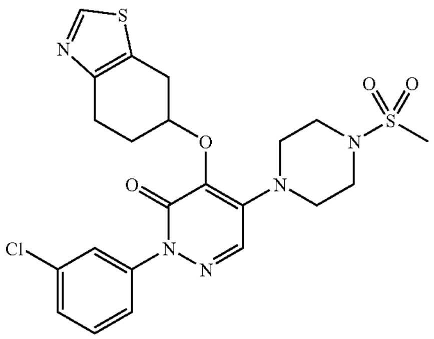

-continued
| | | |
|---|---|---|
| 939Z | no compound | |
| 940Z | 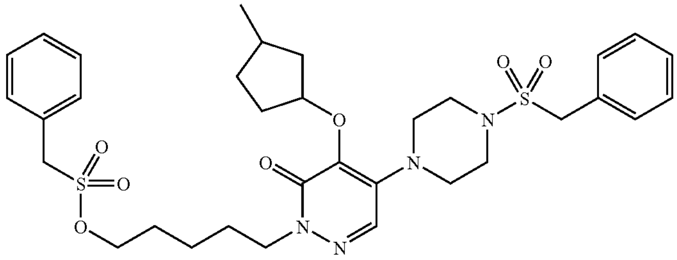 | 673 |
| 941Z | 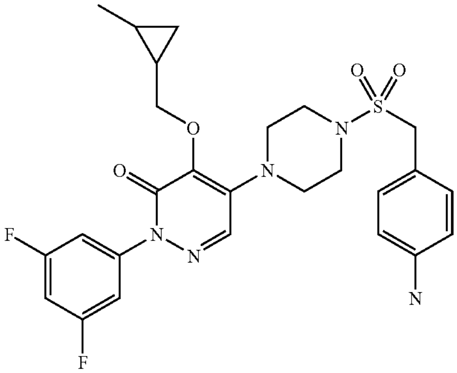 | 546 |
| 942Z | no compound | |
| 943Z | 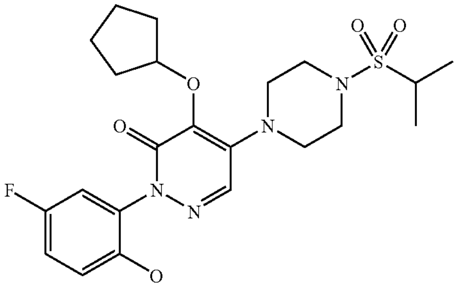 | 481 |
| 944Z | 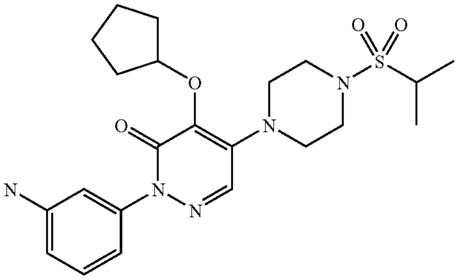 | 462 |
| 945Z | 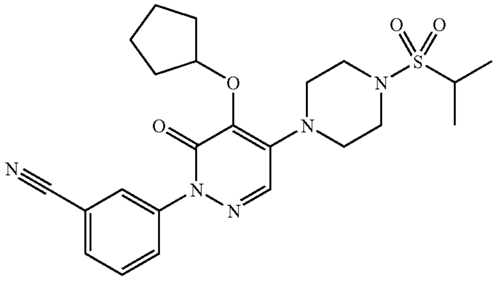 | 493 |

-continued
946Z 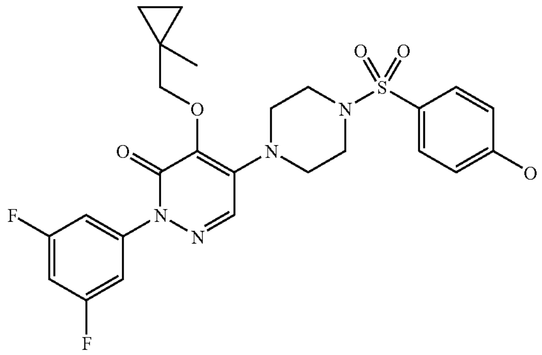 533
947Z 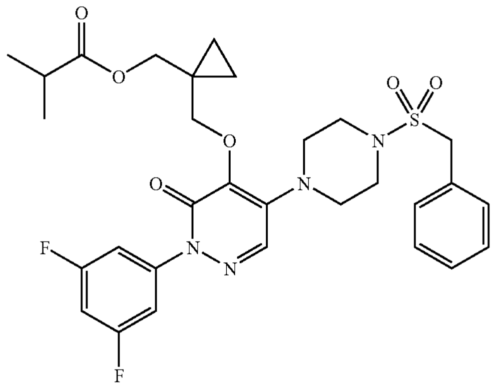 617
948Z 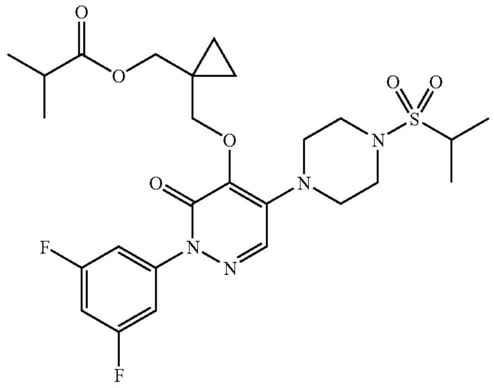 569
949Z 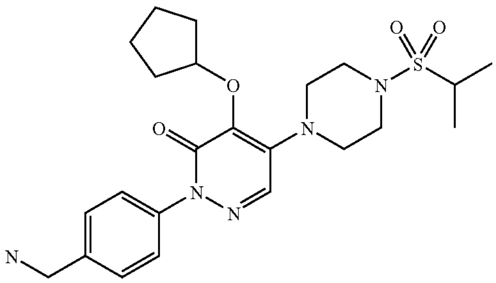 476

-continued
950Z 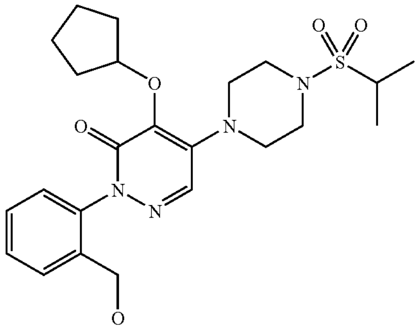 477
951Z 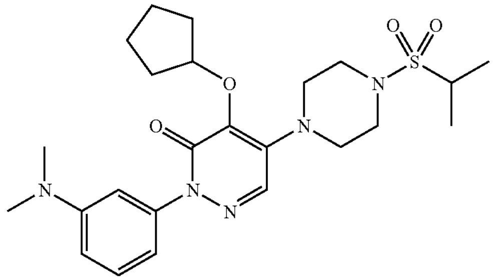 490
952Z 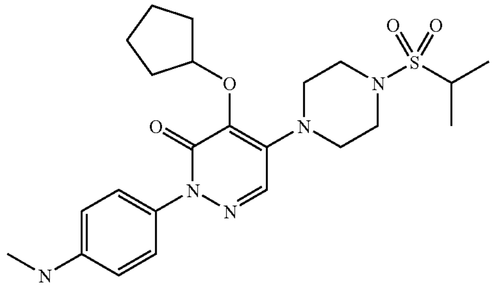 476
953Z 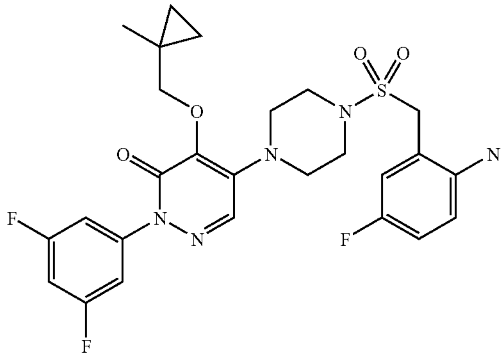 564
954Z 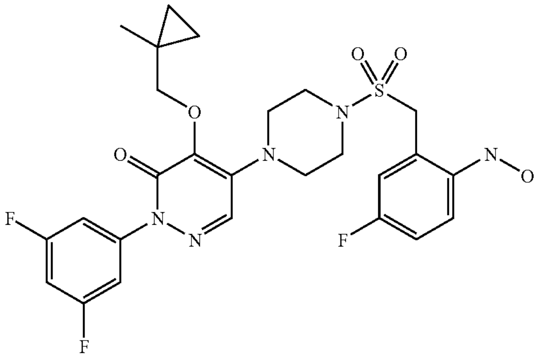 580

-continued
955Z 632
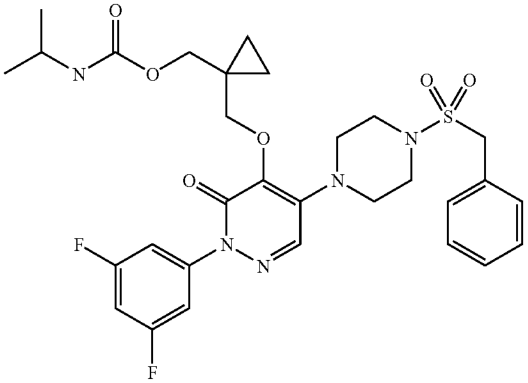
956Z 500
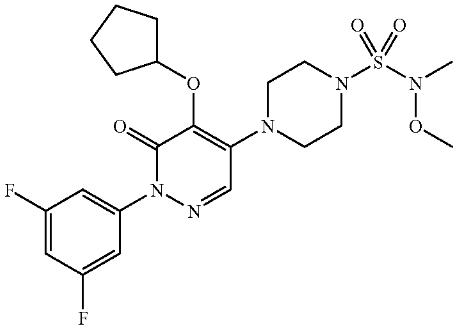
957Z 530
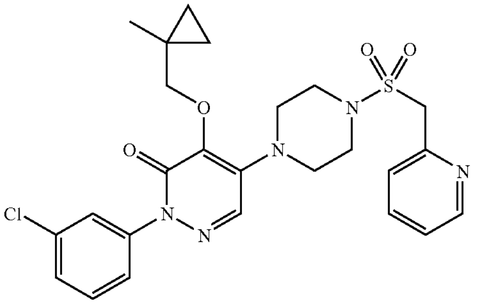
958Z 530
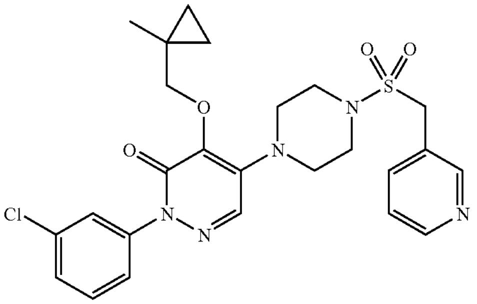

-continued
959Z 530
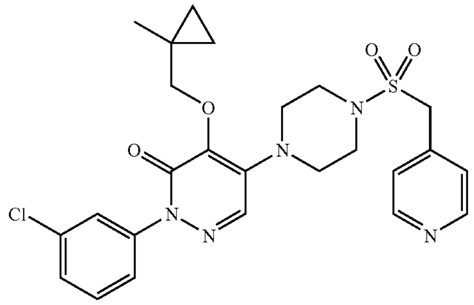
960Z 510
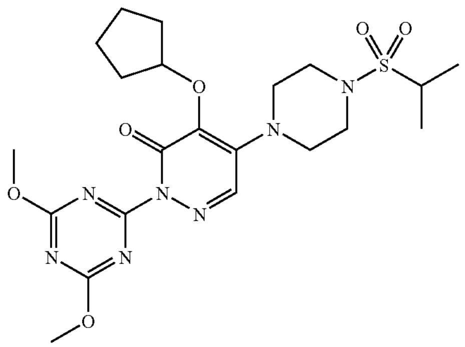
961Z 632
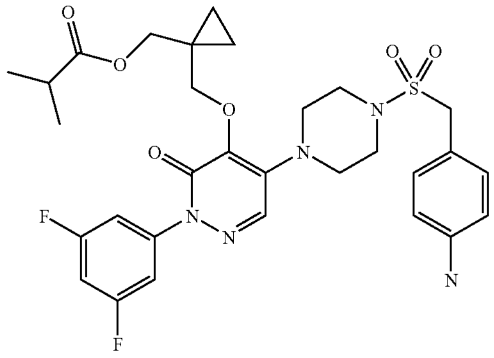
962Z 513
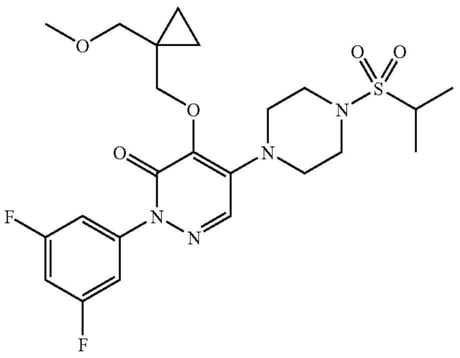

-continued
963Z 594
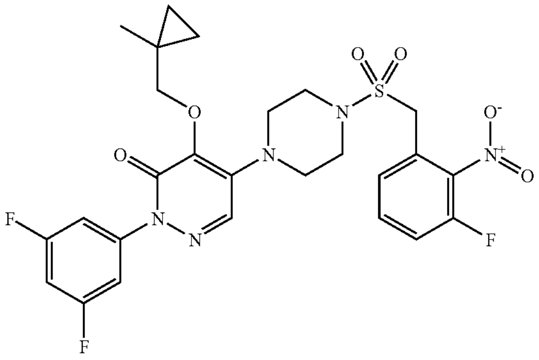
964Z 546
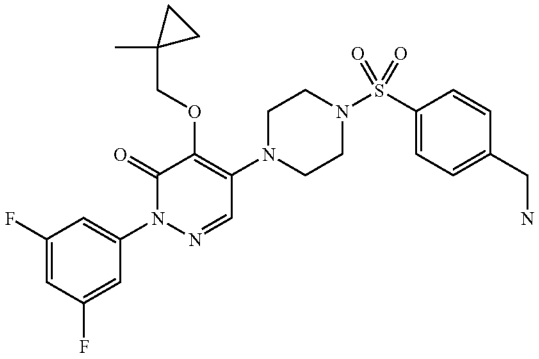
965Z 609
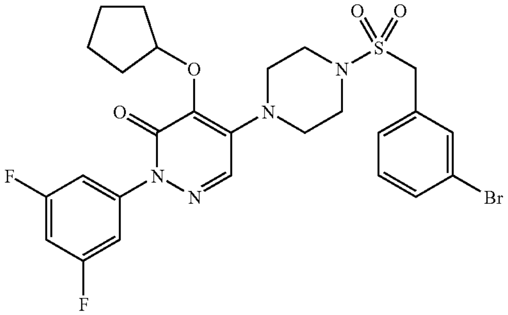
966Z 540
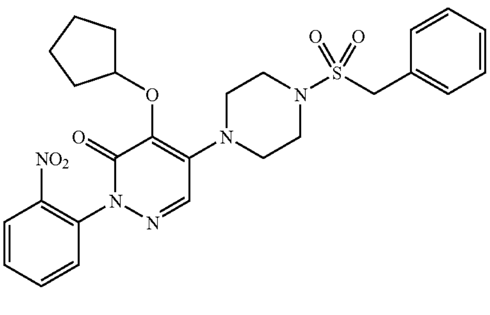

-continued
967Z 584
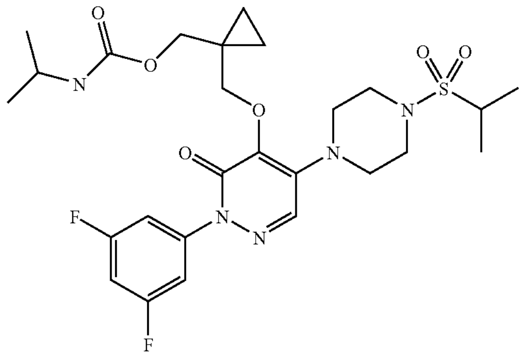
968Z 476
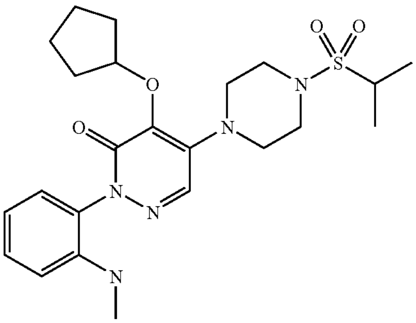
969Z 553
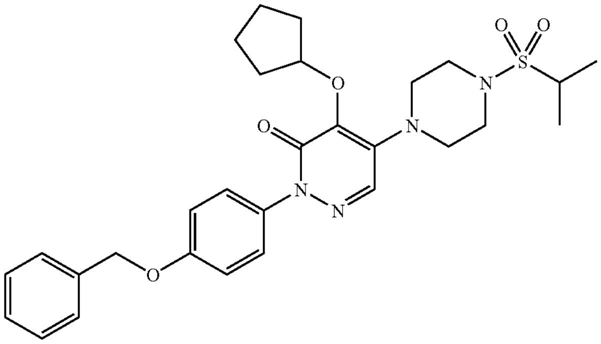
970Z 476
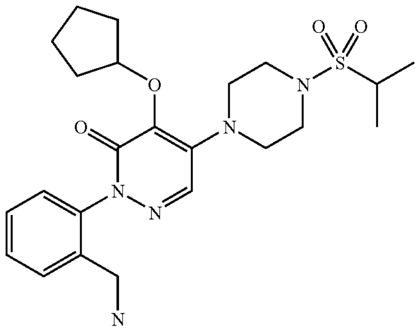

-continued
| | | |
|---|---|---|
| 971Z | 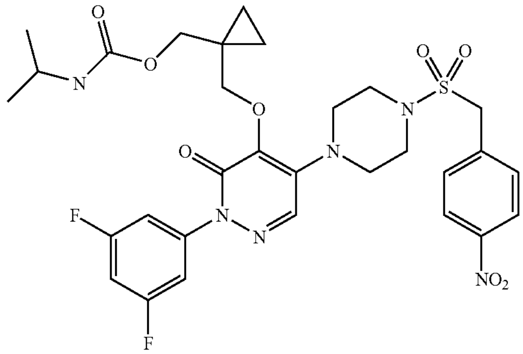 | 677 |
| 971Za | 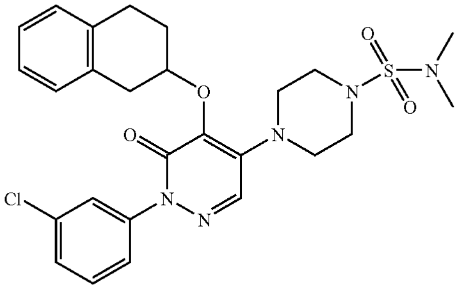 | 545 |
| 971Zb | 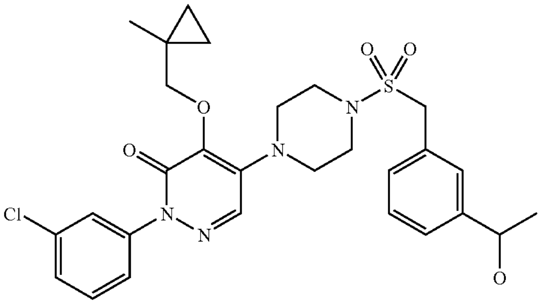 | 573 |
| 971Zc | 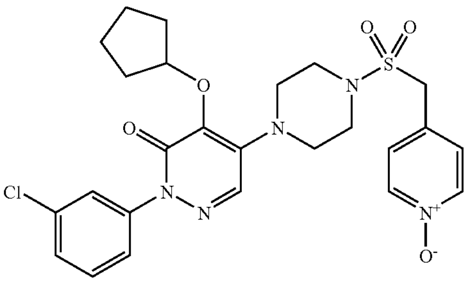 | 546 |
| 971Zd | 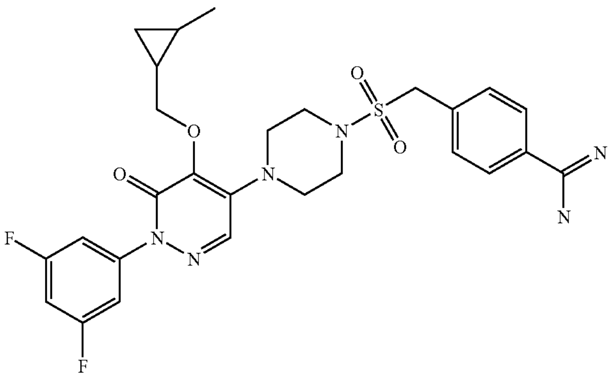 | 573 |

-continued
971Ze 588
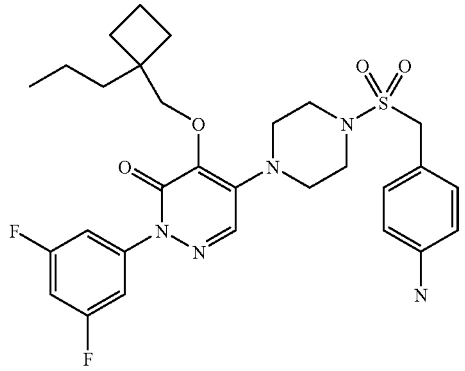
971Zf 562
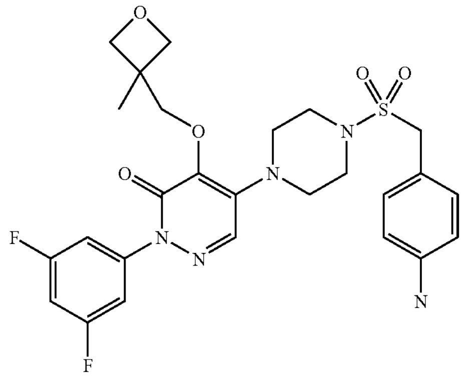
971Zg 561
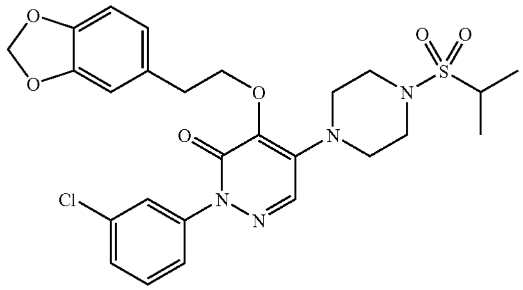
971Zh 576
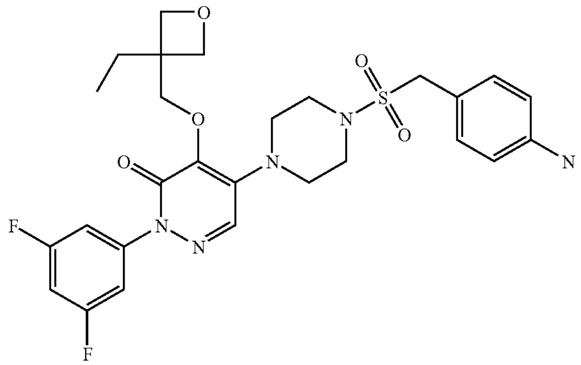

-continued
971Zi 561
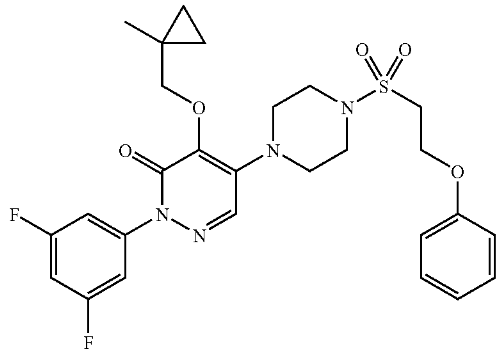
971Zj 467
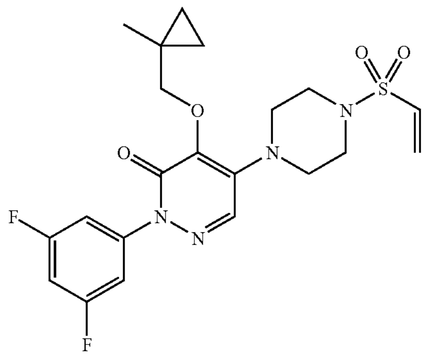
971Zk 465
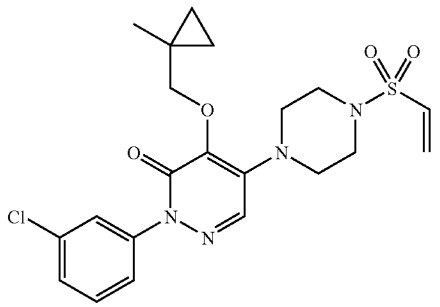
971Zl 559
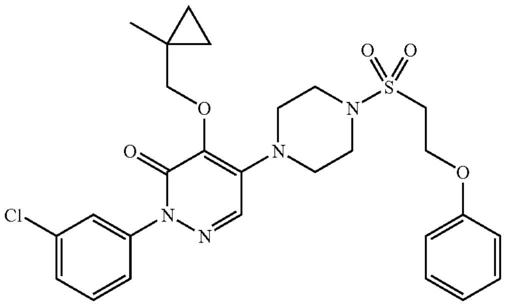

-continued
971Zm 551
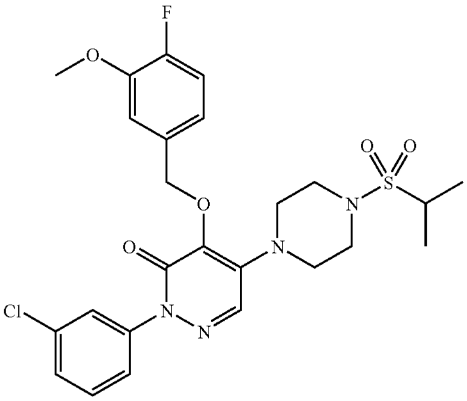
971Zn 558
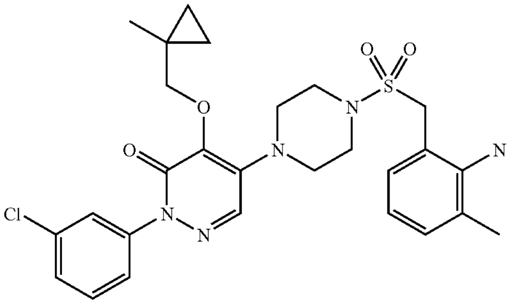
971Zo 563
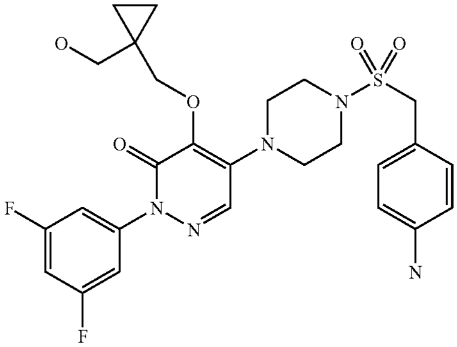
971Zp 574
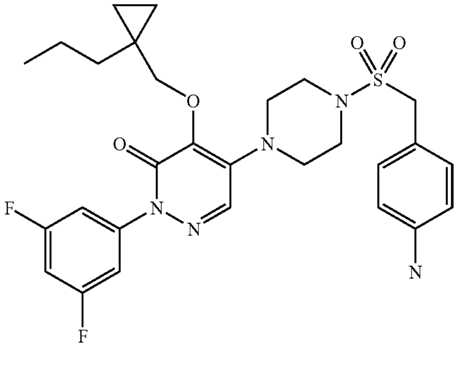

-continued
971Zq 517
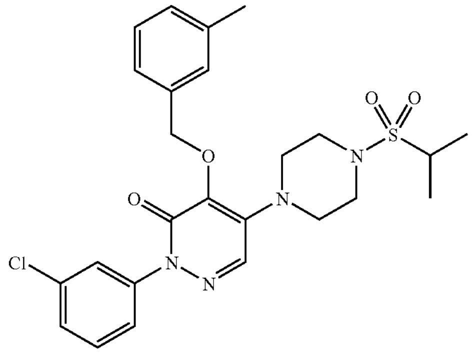
971Zr 579
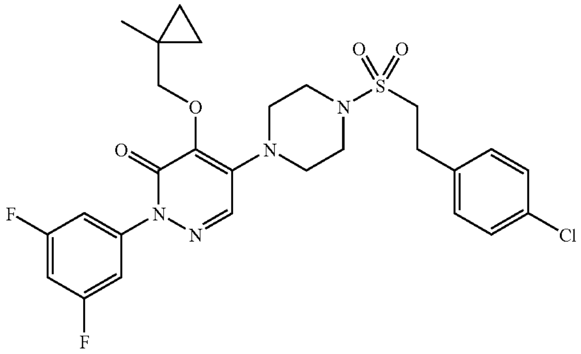
971Zs 590
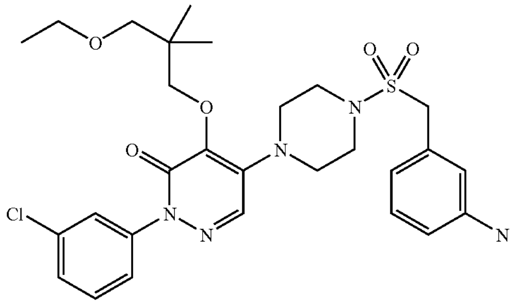
971Zt 545
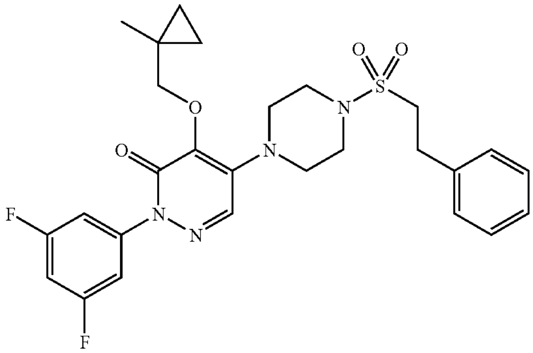

-continued
971Zu 590
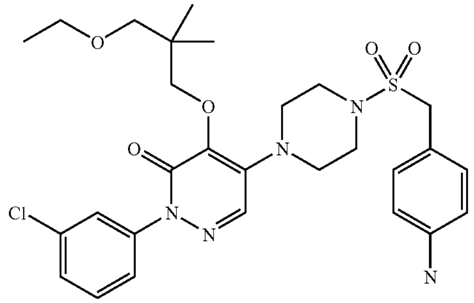
971Zv 563
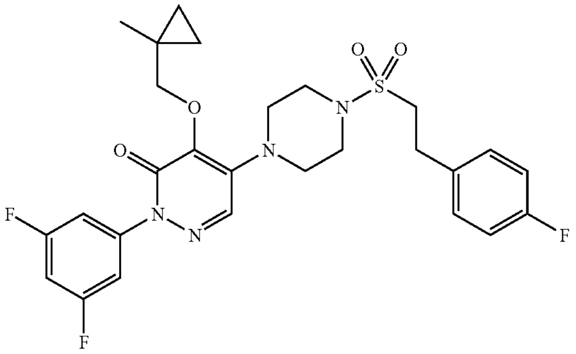
971Zw 609
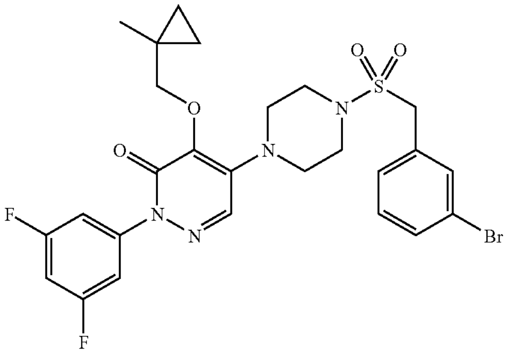
971Zx 577
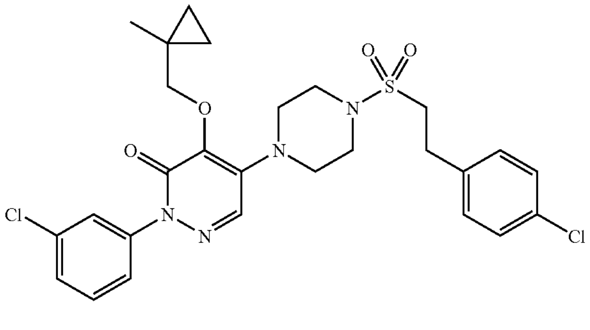

-continued
971Zy
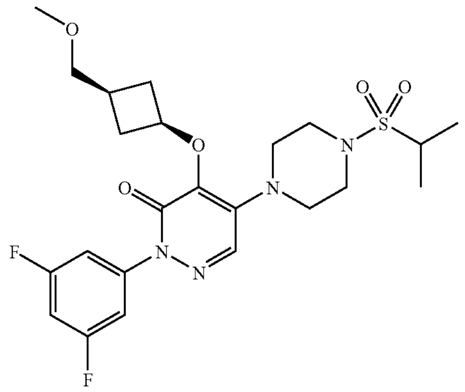
513
971Zz
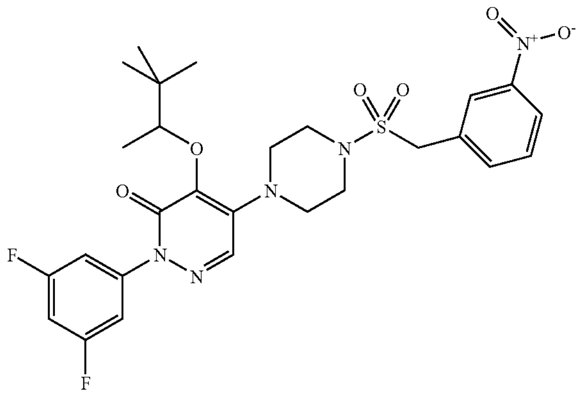
592
971Zaa
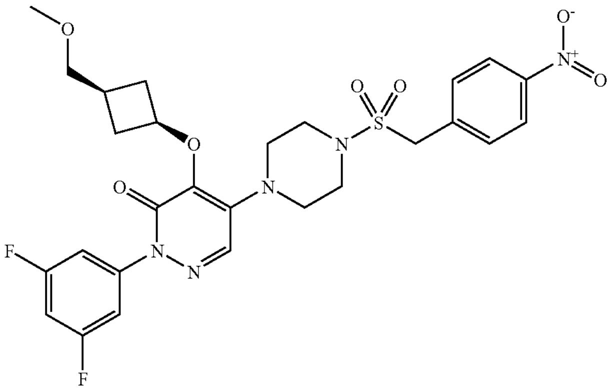
606
971Zbb
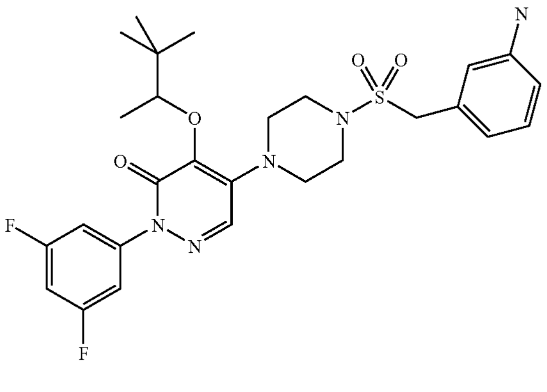
562

-continued
971Zcc 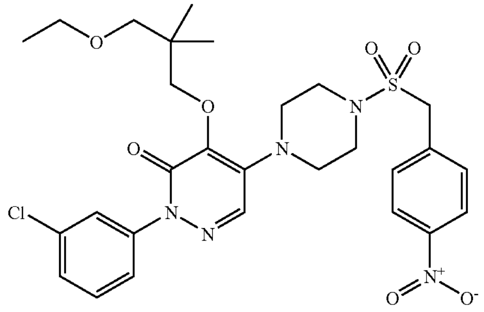 620
971Zdd 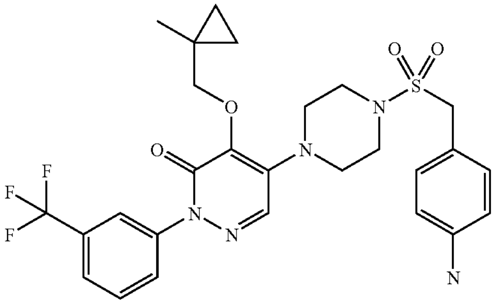 578
971Zee 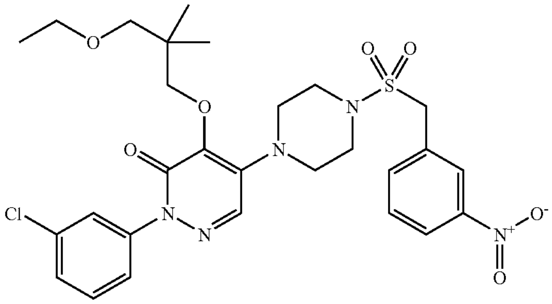 620
971Zff 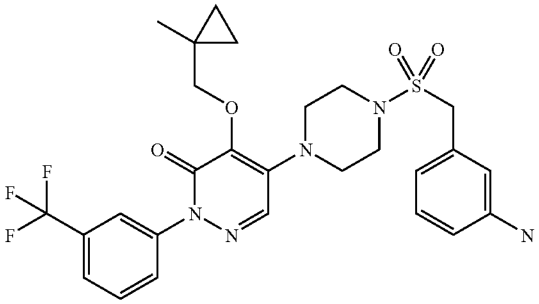 578
971Zgg 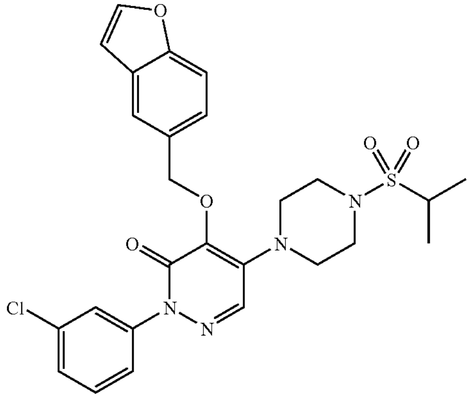 543

-continued
971Zhh 555
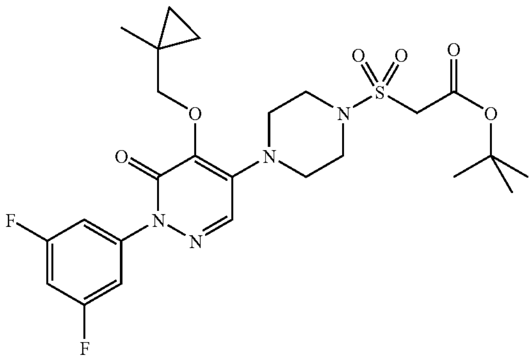
971Zii 560
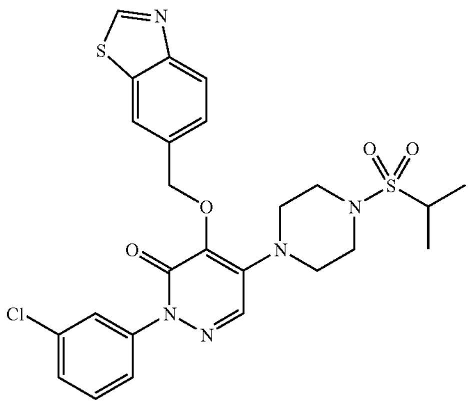
971Zjj 576
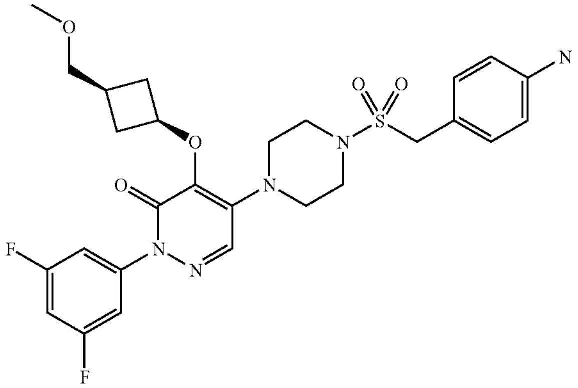
971Zkk 606
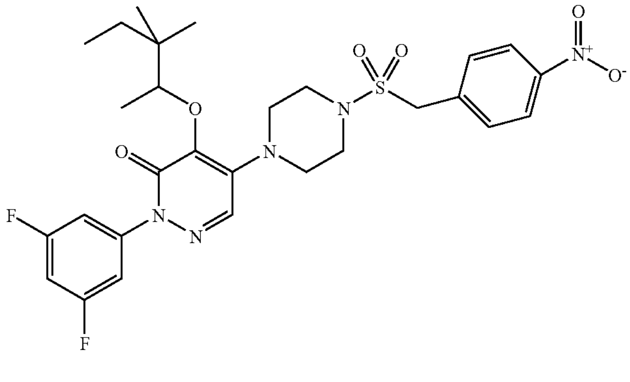

-continued
971Zll 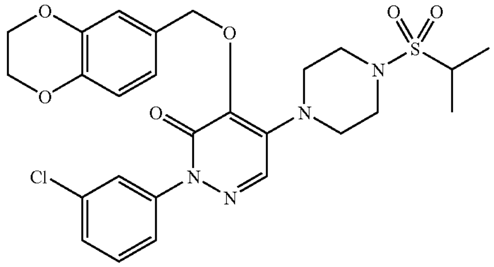 561
971Zmm 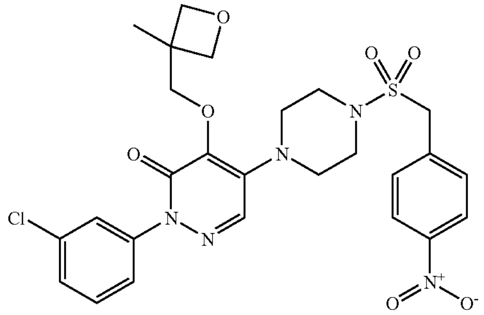 590
971Znn 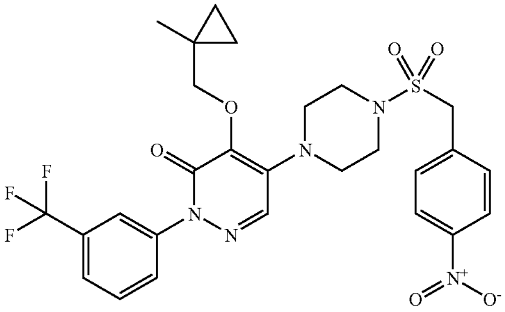 608
971Zoo 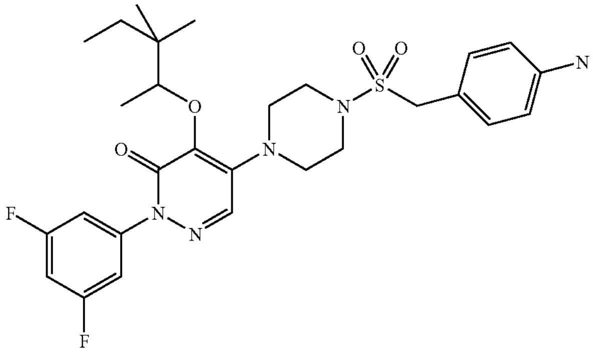 576
971Zpp 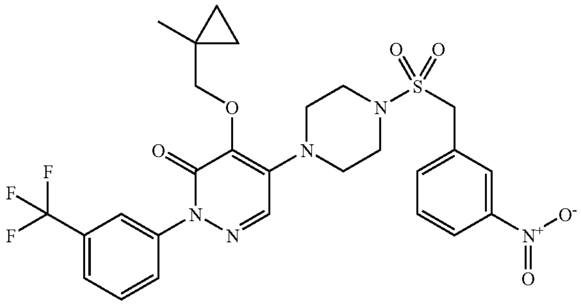 608

-continued
971Zqq 559
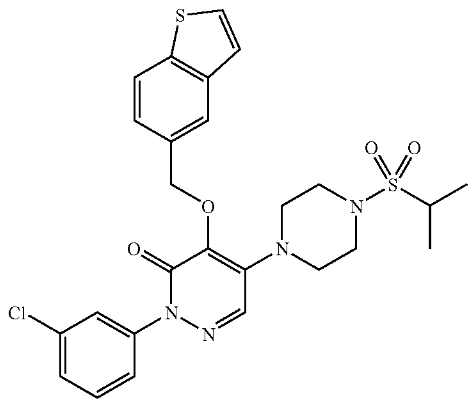
971Zrr 608
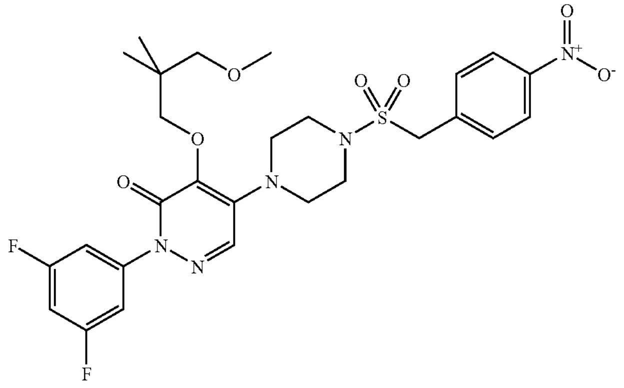
971Zss 572
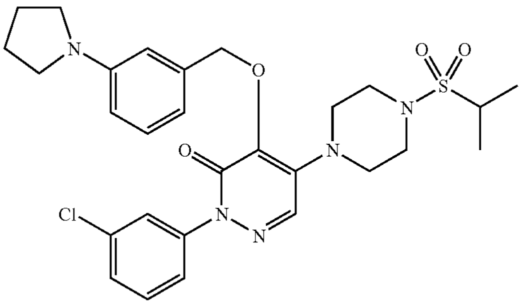
971Ztt 578
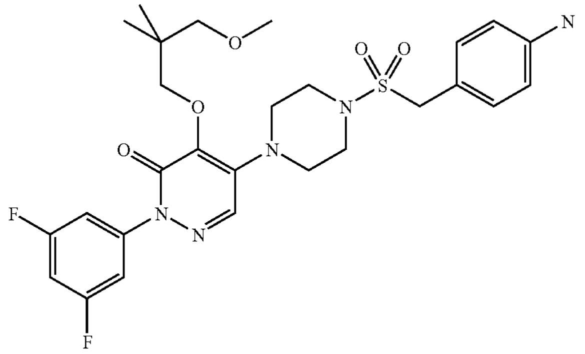

-continued
971Zuu 517
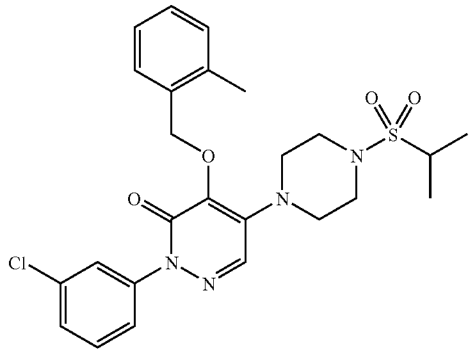
971Zvv 560
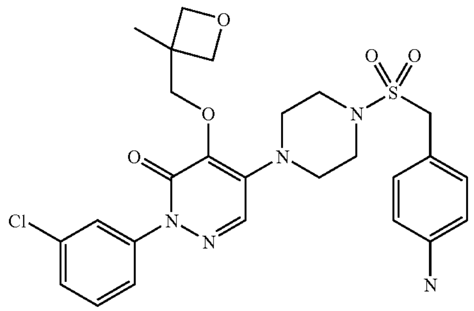
971Zww 517
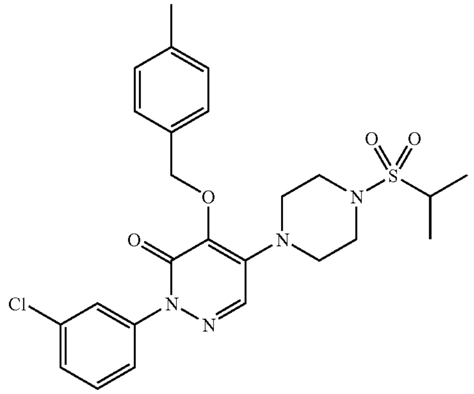
971Zxx 561
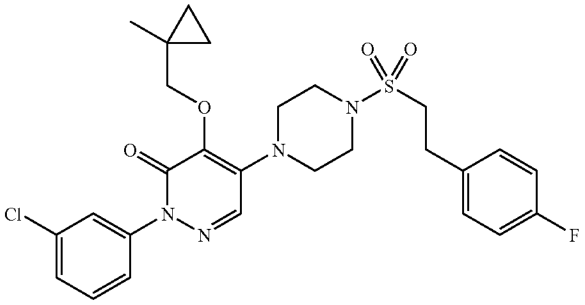

-continued
| | | |
|---|---|---|
| 971Zyy | 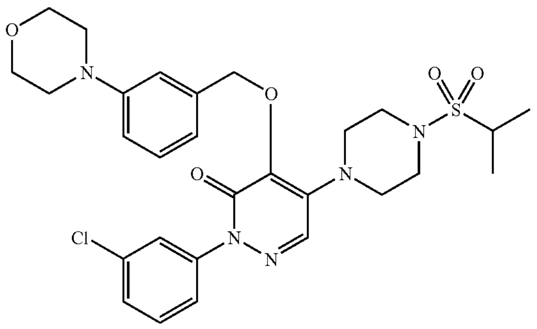 | 588 |
| 971Zzz | 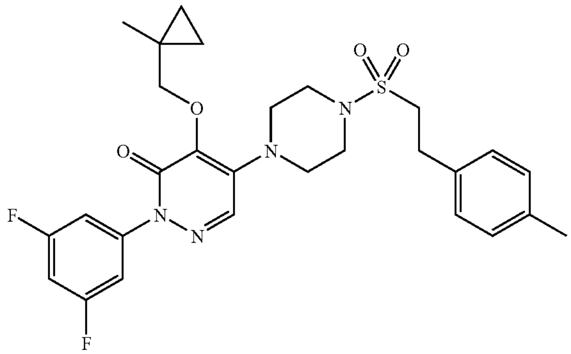 | 559 |
| 971ZA | 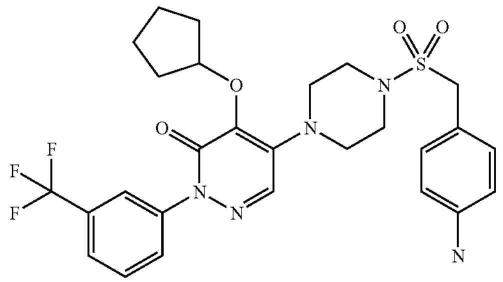 | 578 |
| 971ZB | 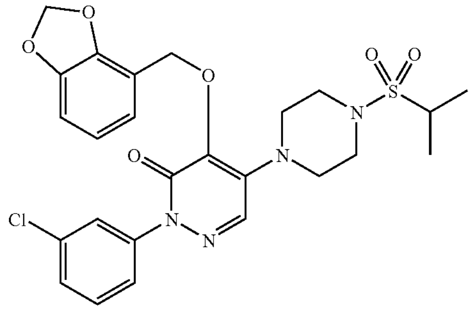 | 547 |
| 971ZC | 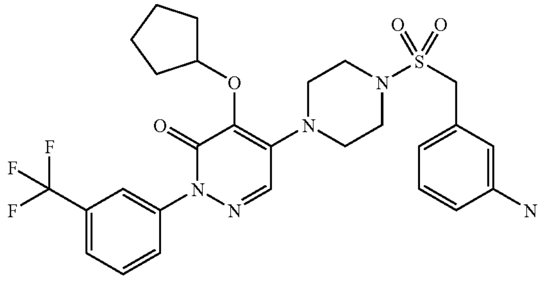 | 578 |

-continued
| | | |
|---|---|---|
| 971ZD | 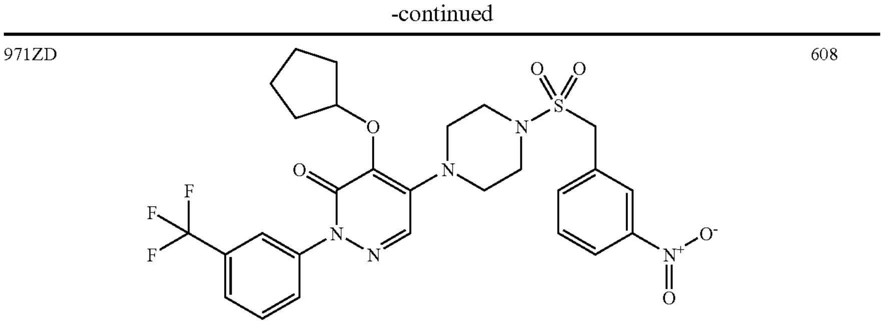 | 608 |
| 971ZE | 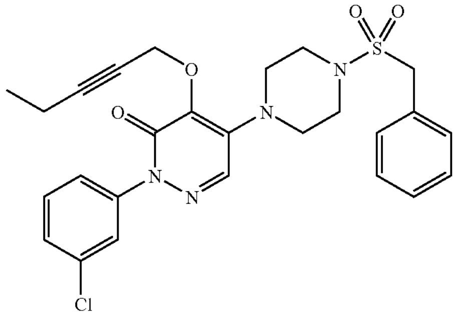 | 527 |
| 971ZF | 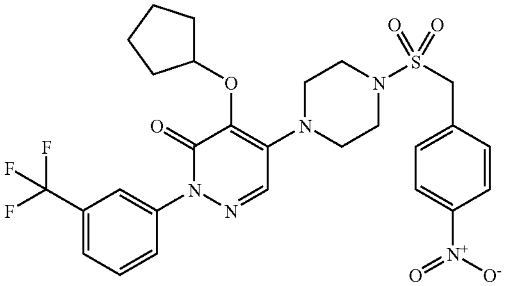 | 608 |
| 971ZG | 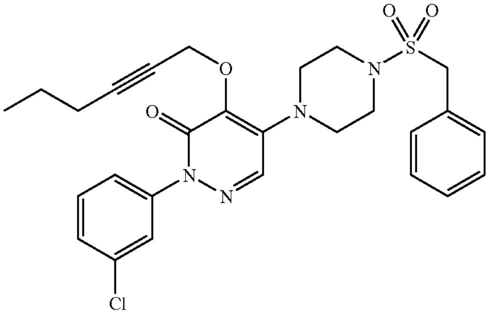 | 541 |
| 971ZH | 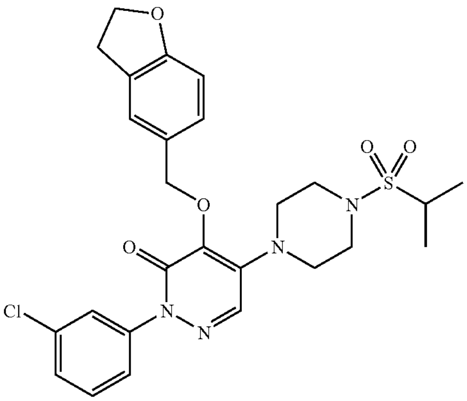 | 475 |

-continued
971ZI 575
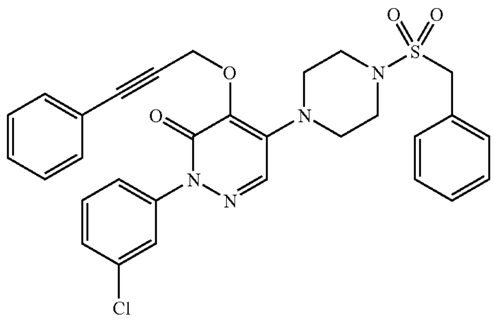
971ZJ 581
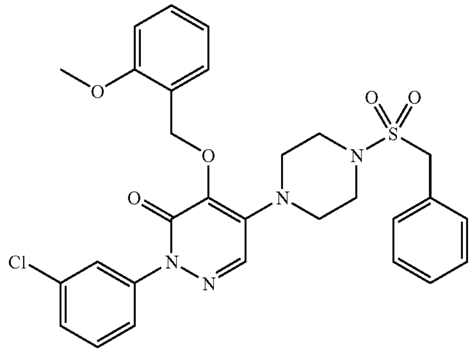
971ZK 581
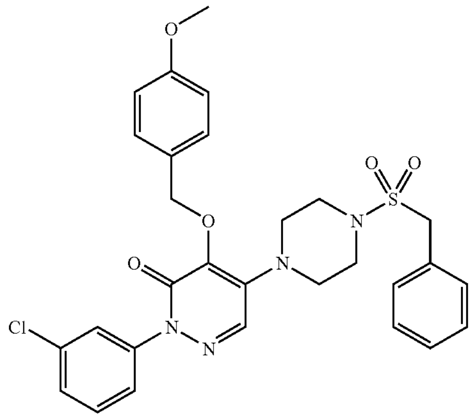
971ZL 581
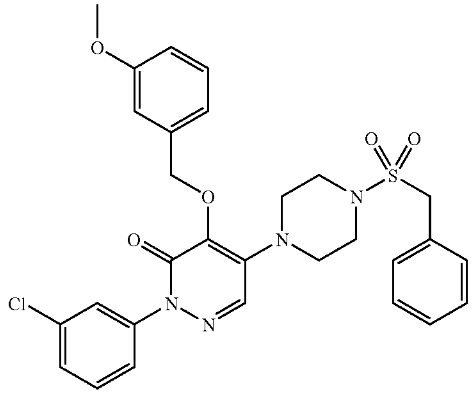

-continued
971ZM 757
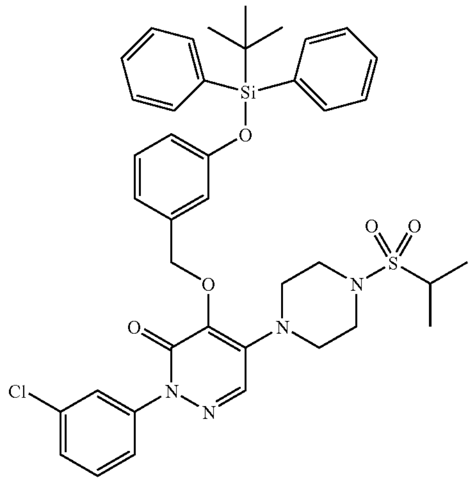
971ZN 595
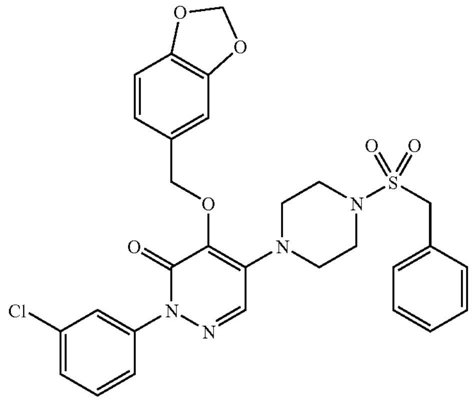
971ZO 519
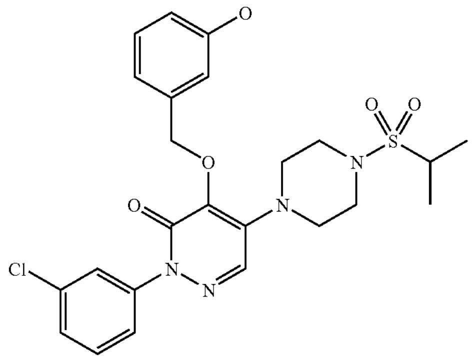
971ZP 547
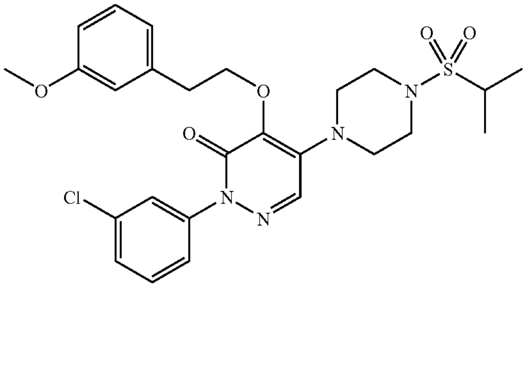

-continued
971ZQ 611
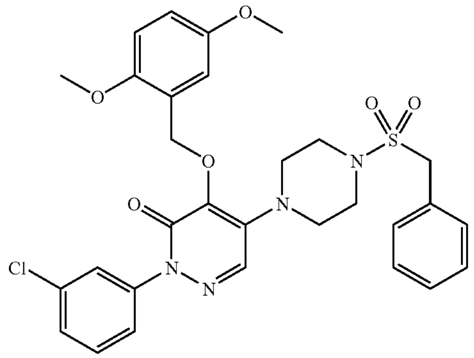
971ZR 548
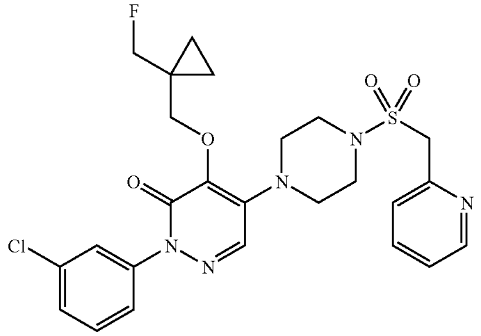
971ZS 548
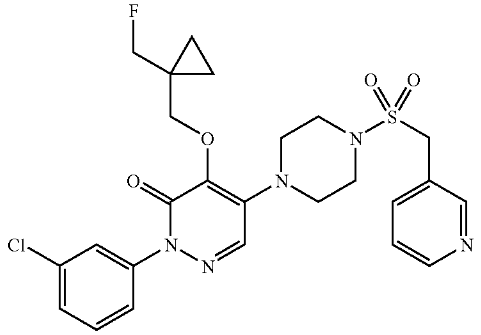
971ZT 548
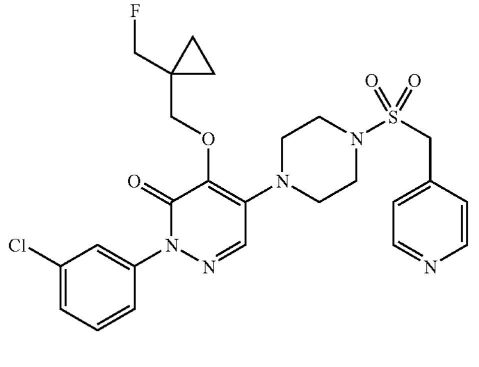

-continued
| | | |
|---|---|---|
| 971ZU | 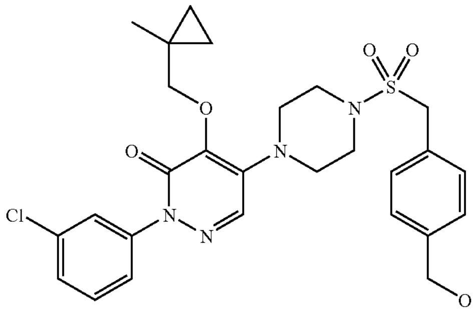 | 559 |
| 971ZV | 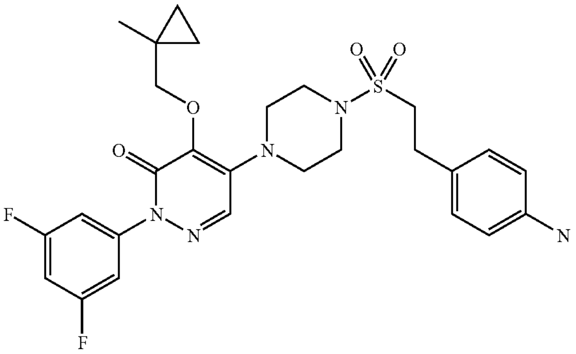 | 560 |
| 971ZW | 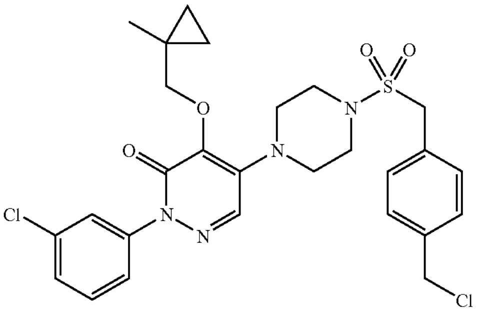 | 577 |
| 971ZX | 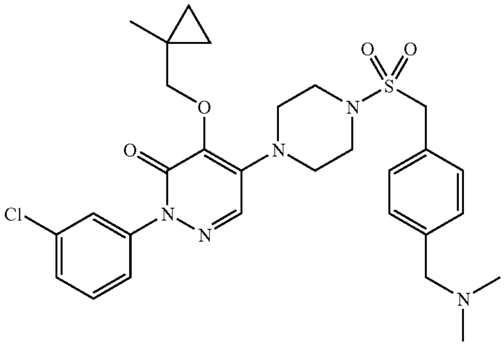 | 586 |

-continued
971ZY 628
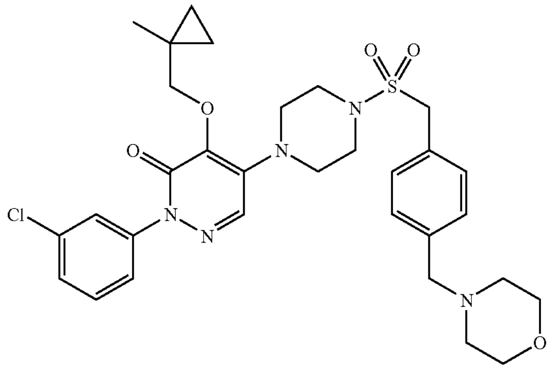
971ZZ 612
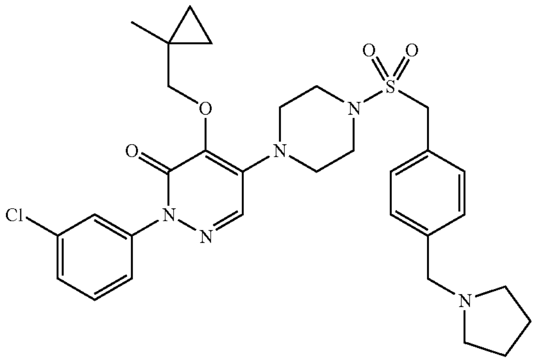
971Za1 557
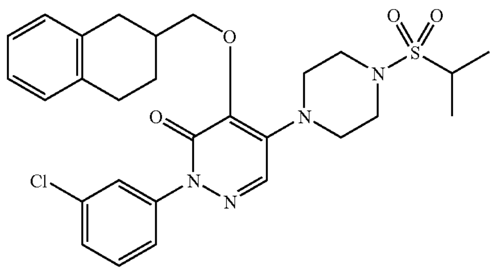
971Zb1 543
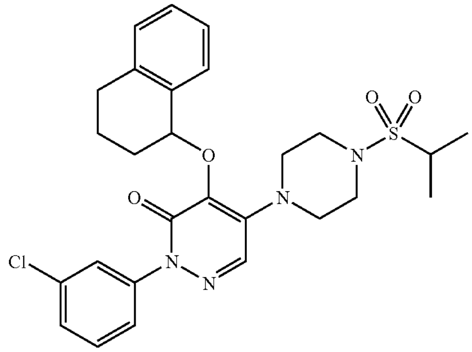

-continued
971Zc1 509
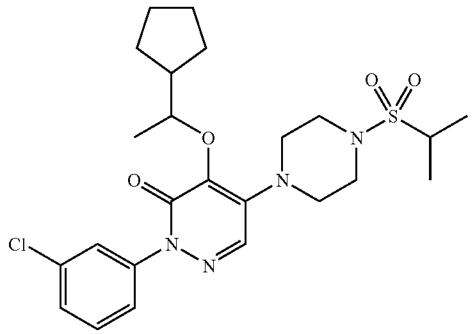
971Zd1 561
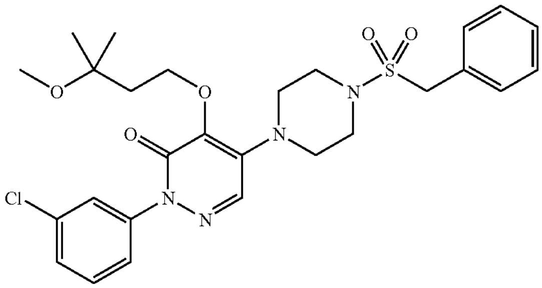
971Ze1 557
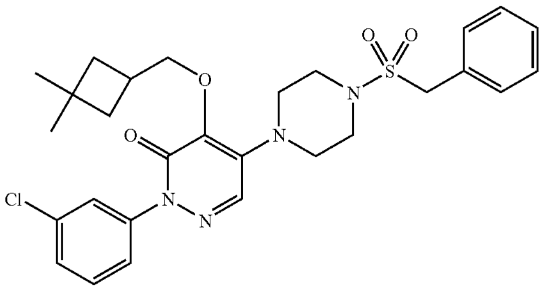
971Zf1 529
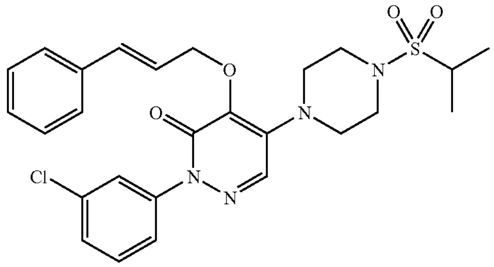
971Zg1 529
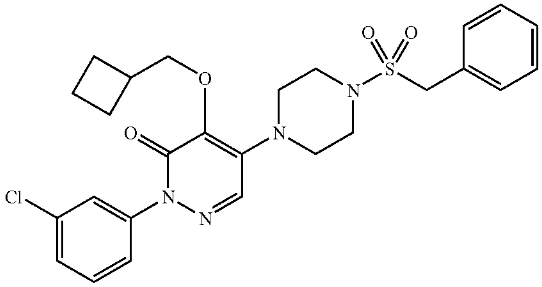

-continued
| | | |
|---|---|---|
| 971Zh1 | 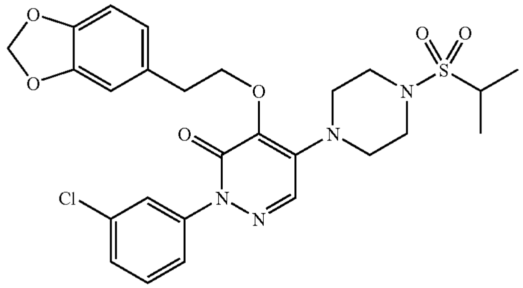 | 561 |
| 971Zi1 | 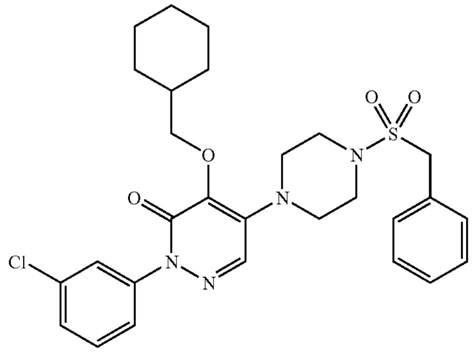 | 557 |
| 971Zj1 | 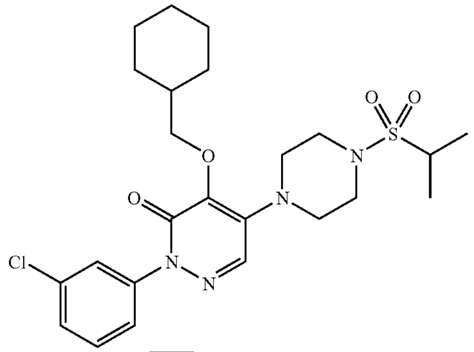 | 509 |
| 971Zk1 | 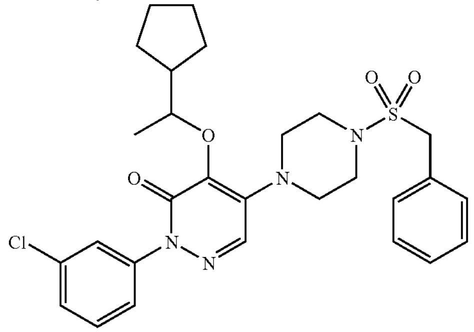 | 557 |
| 971Zl1 | 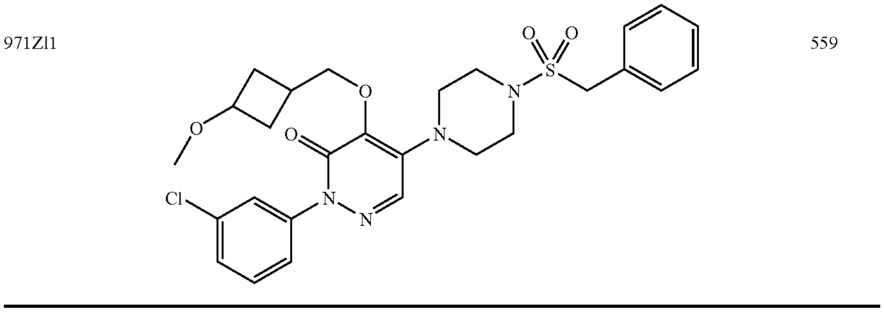 | 559 |

TABLE 11
| Comp. No. | Oxygen Linked Analogs with Sulfonamide<br>The following compounds can be synthesized using steps 1, 2, 4, 6, and 9 of Scheme 1 or steps 11, 12, and 14 of Scheme 2.<br>Structure | MS M + 1 |
|---|---|---|
| 972Z | 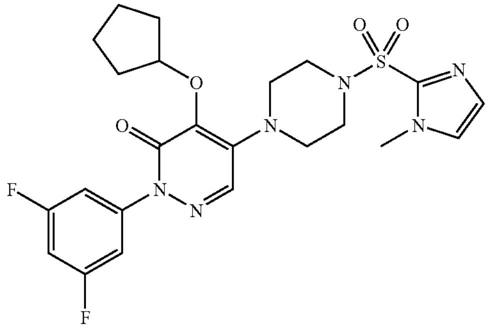 | 521 |
| 973Z | 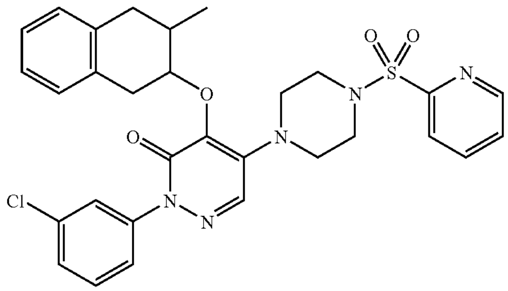 | 592 |
| 974Z | 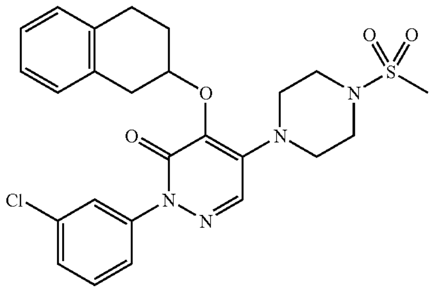 | 515 |
| 975Z | 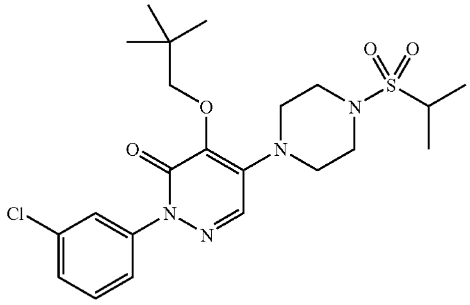 | 483 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 976Z | 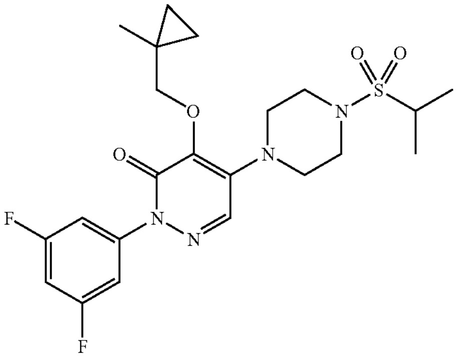 | 483 |
| 977Z | 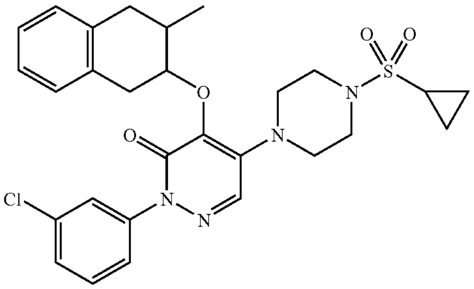 | 555 |
| 978Z | 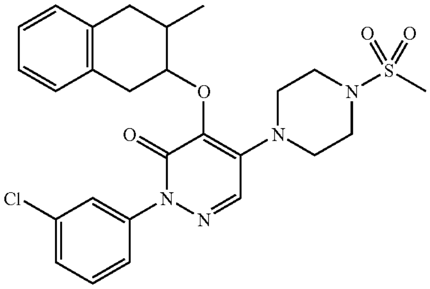 | 529 |
| 979Z | 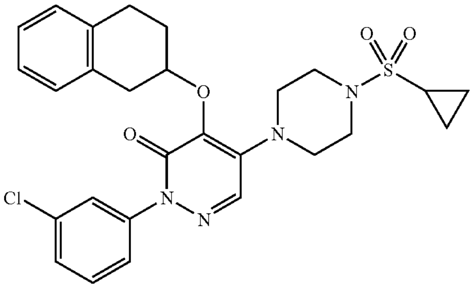 | 541 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
| --- | --- | --- |
| 980Z | 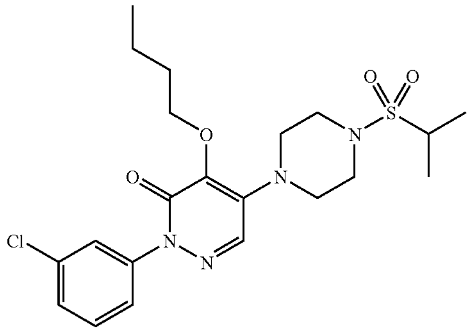 | 469 |
| 981Z | 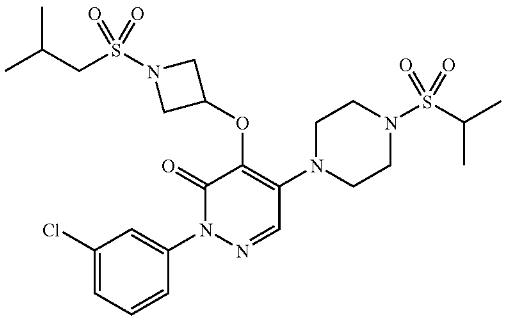 | 589 |
| 982Z | 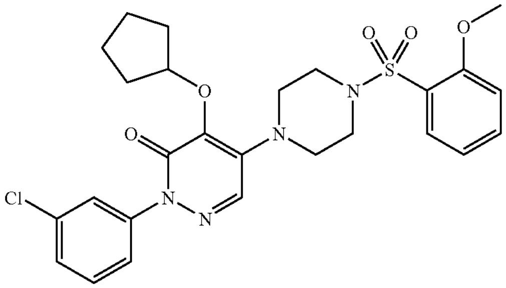 | 545 |
| 983Z | 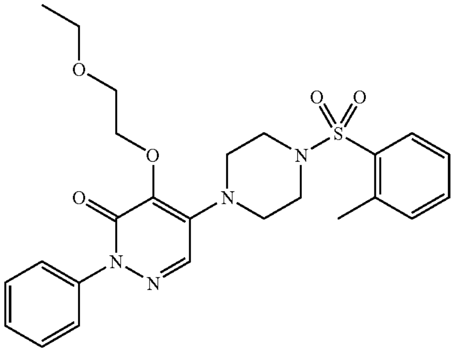 | 499 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 984Z | 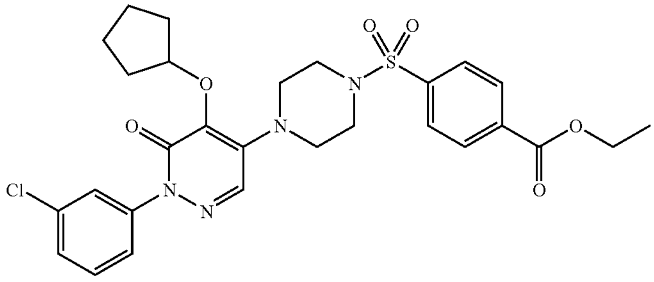 | 587 |
| 985Z | 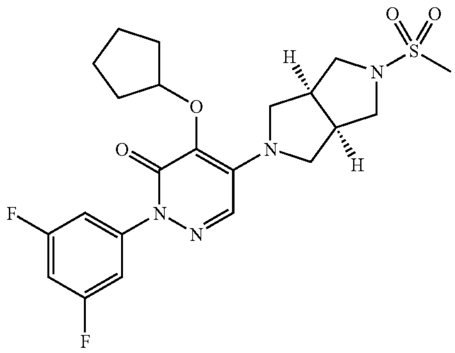 | 481 |
| 986Z | 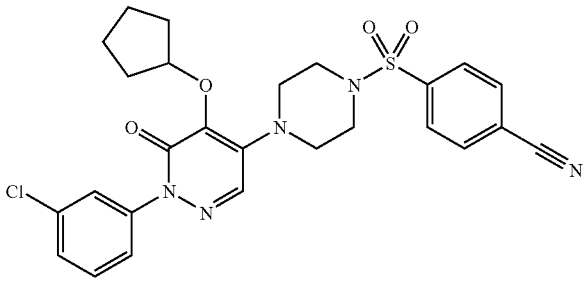 | 540 |
| 987Z | 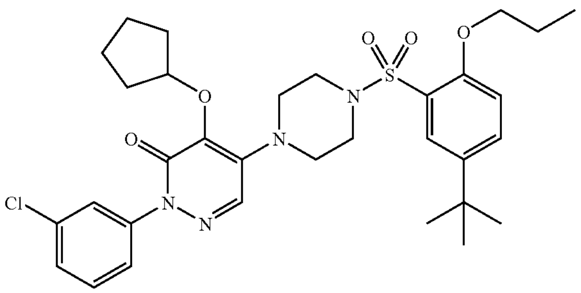 | 629 |

TABLE 11-continued
| Comp. No. | Oxygen Linked Analogs with Sulfonamide<br>The following compounds can be synthesized using steps 1, 2, 4, 6, and 9 of Scheme 1 or steps 11, 12, and 14 of Scheme 2.<br>Structure | MS M + 1 |
|---|---|---|
| 988Z | 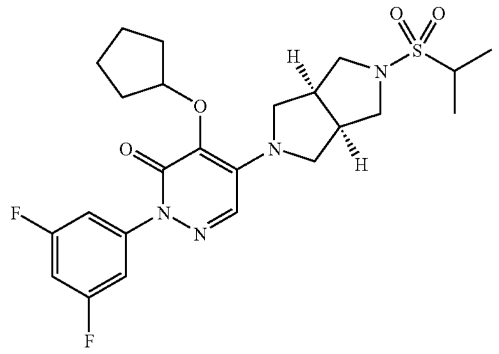 | 509 |
| 989Z | 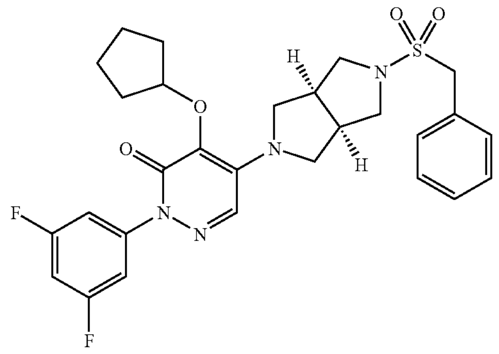 | 557 |
| 990Z | 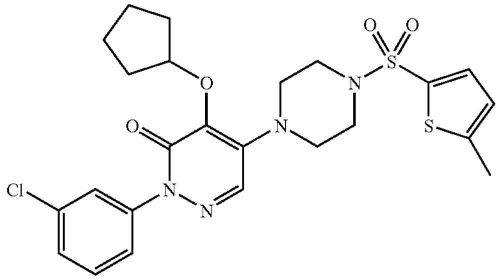 | 535 |
| 991Z | 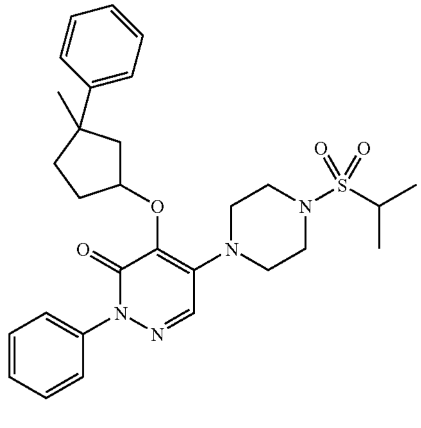 | 537 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
| --- | --- | --- |
| 992Z | 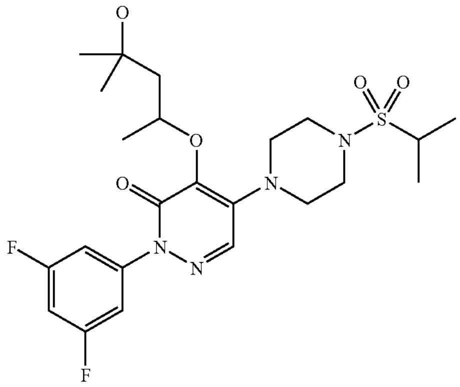 | 515 |
| 993Z | 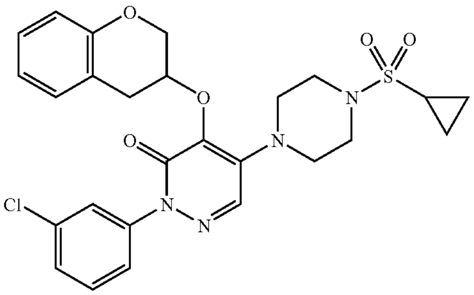 | 543 |
| 994Z | 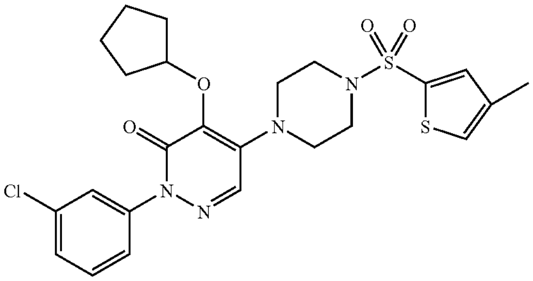 | 535 |
| 995Z | 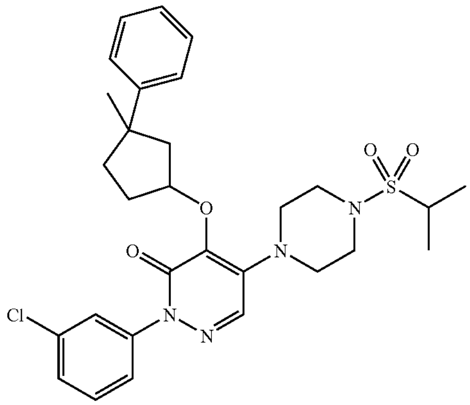 | 571 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 996Z | 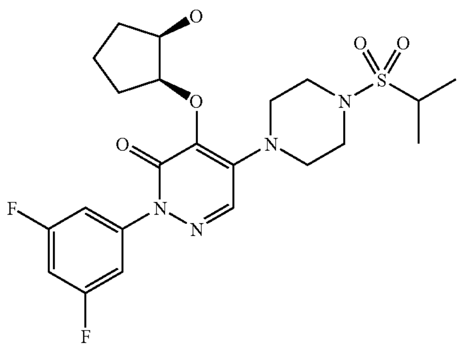 | 499 |
| 997Z | 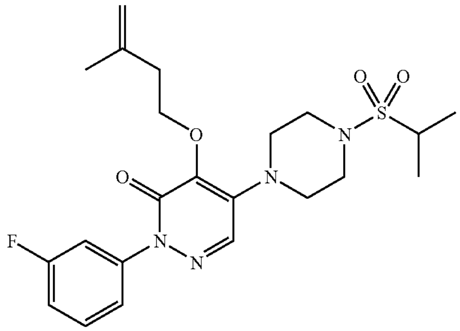 | 465 |
| 998Z | 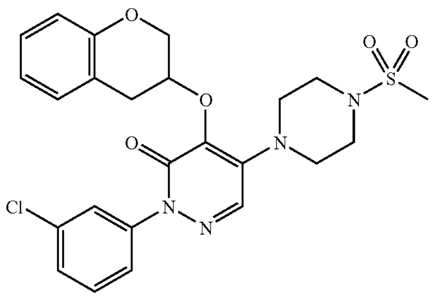 | 517 |
| 999Z | 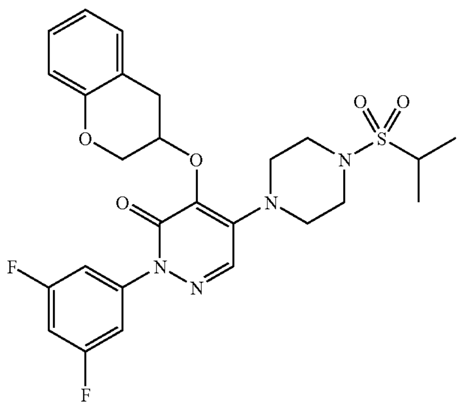 | 547 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1000Z | 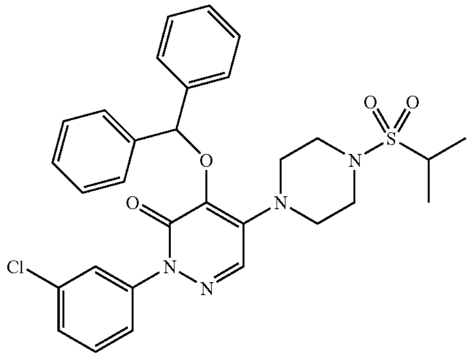 | 580 |
| 1001Z | 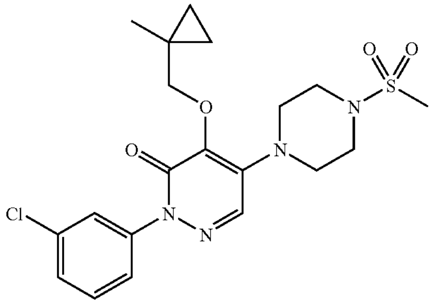 | 453 |
| 1002Z | 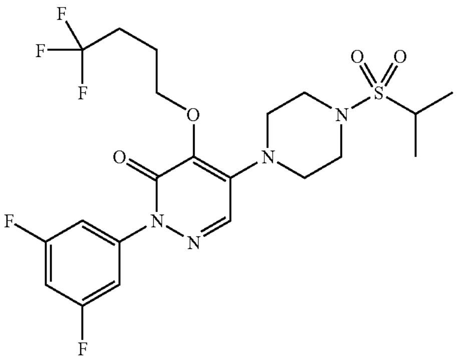 | 525 |
| 1003Z | 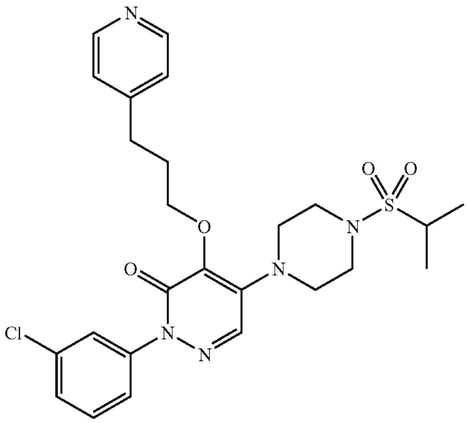 | 533 |

TABLE 11-continued
| Comp. No. | Oxygen Linked Analogs with Sulfonamide The following compounds can be synthesized using steps 1, 2, 4, 6, and 9 of Scheme 1 or steps 11, 12, and 14 of Scheme 2. Structure | MS M + 1 |
|---|---|---|
| 1004Z | 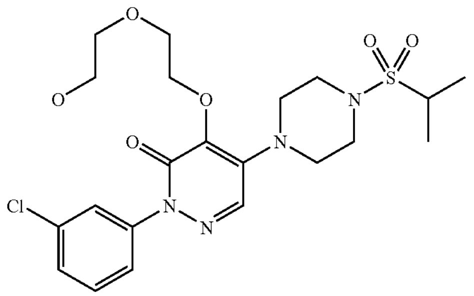 | 501 |
| 1005Z | 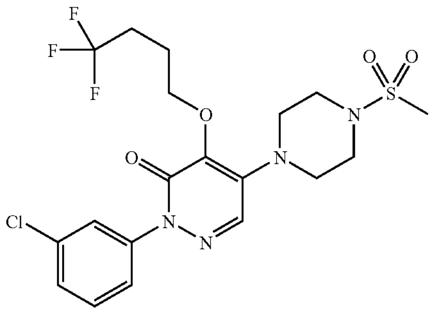 | 495 |
| 1006Z | 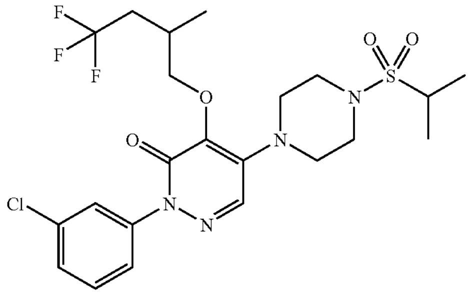 | 537 |
| 1007Z | 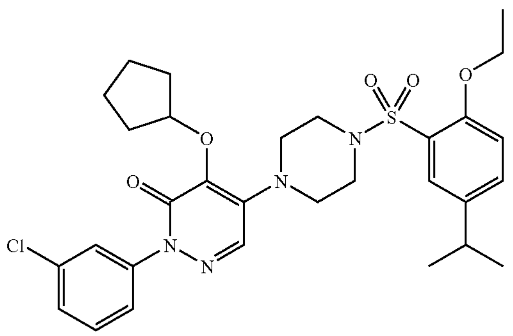 | 601 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1008Z | 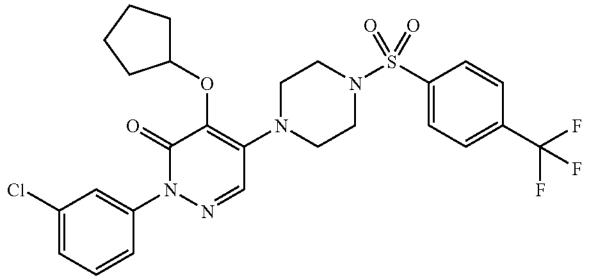 | 583 |
| 1009Z | 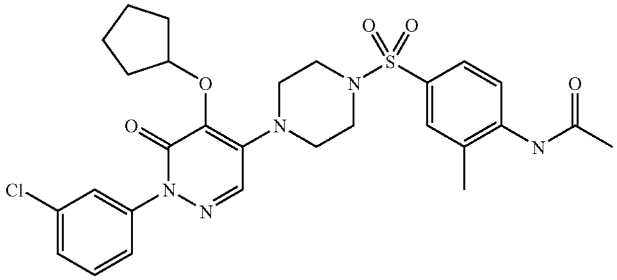 | 586 |
| 1010Z | 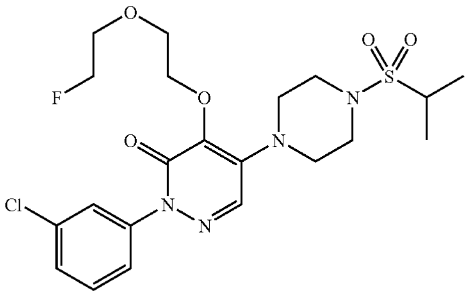 | 503 |
| 1011Z | 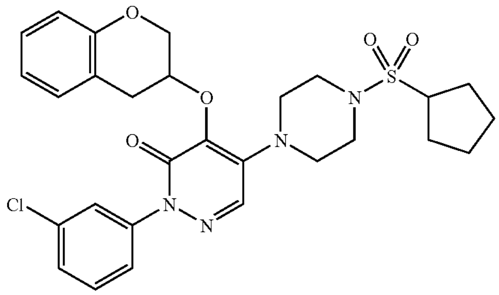 | 571 |
| 1012Z | 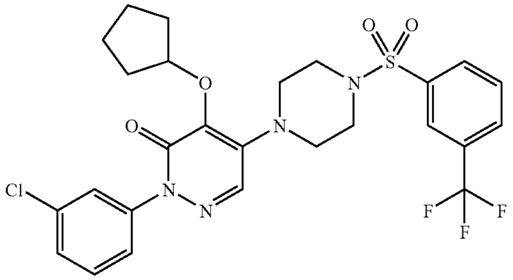 | 583 |

TABLE 11-continued
| Comp. No. | Structure | MS M + 1 |
|---|---|---|
| | Oxygen Linked Analogs with Sulfonamide The following compounds can be synthesized using steps 1, 2, 4, 6, and 9 of Scheme 1 or steps 11, 12, and 14 of Scheme 2. | |
| 1013Z | 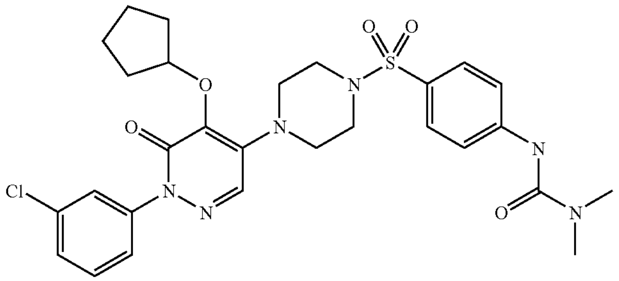 | 601 |
| 1014Z | 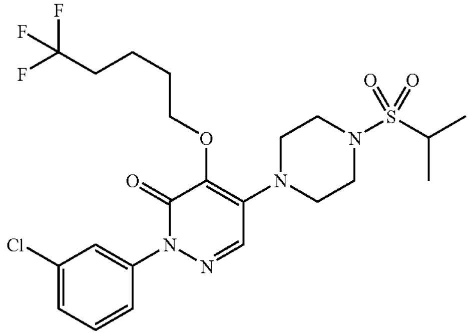 | 537 |
| 1015Z | 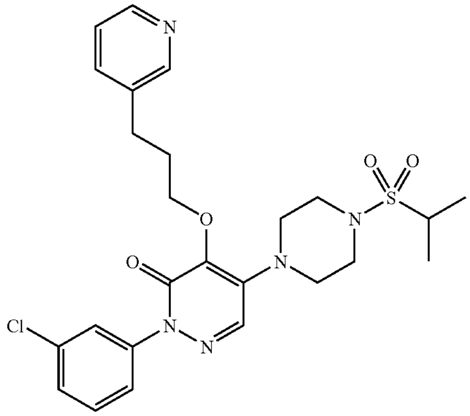 | 532 |
| 1016Z | 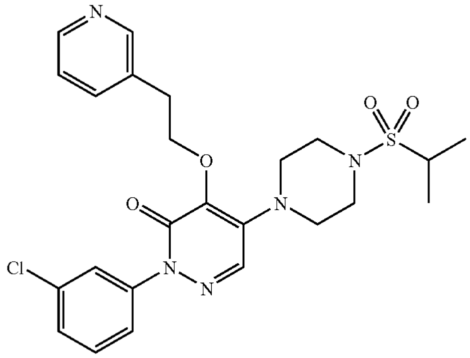 | 518 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1017Z | 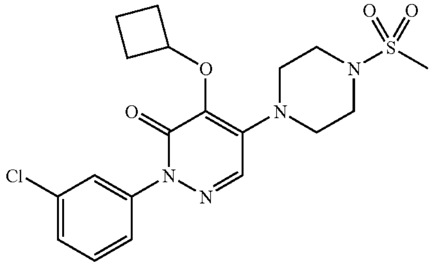 | 439 |
| 1018Z | 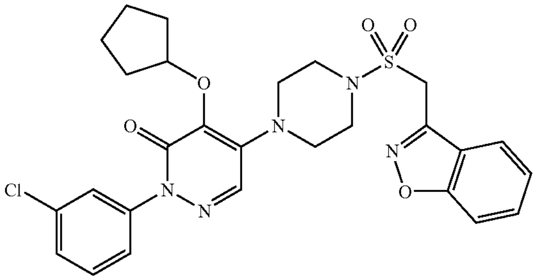 | 570 |
| 1019Z | 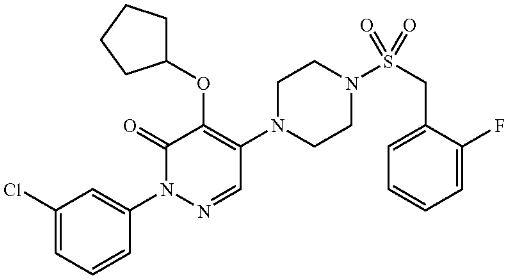 | 547 |
| 1020Z | 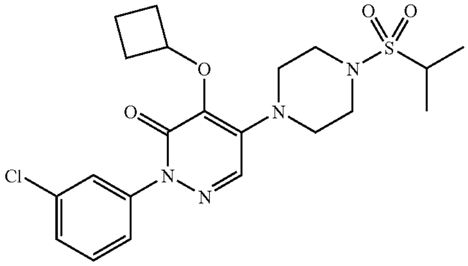 | 467 |
| 1021Z | 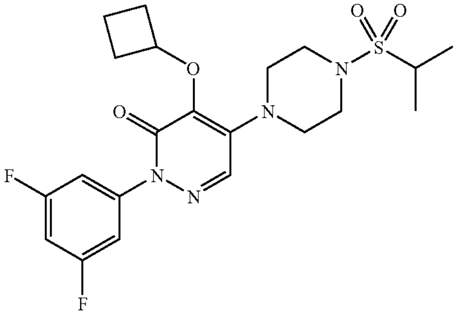 | 469.5 |

TABLE 11-continued
| Comp. No. | Oxygen Linked Analogs with Sulfonamide The following compounds can be synthesized using steps 1, 2, 4, 6, and 9 of Scheme 1 or steps 11, 12, and 14 of Scheme 2. Structure | MS M + 1 |
|---|---|---|
| 1022Z | 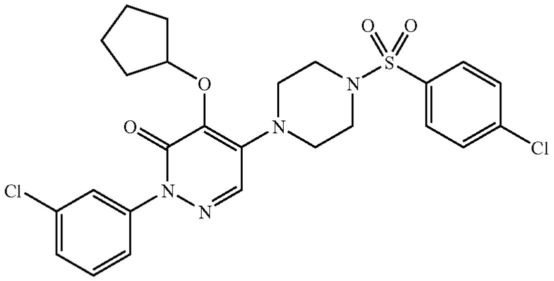 | 549 |
| 1023Z | 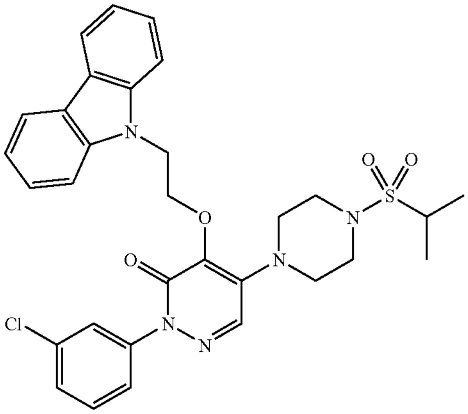 | 606 |
| 1024Z | 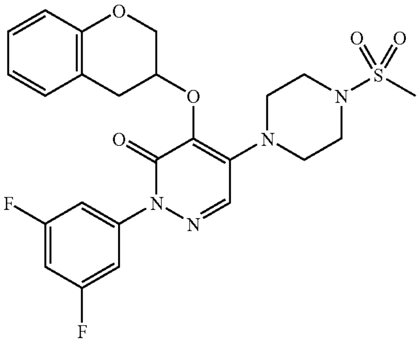 | 519 |
| 1025Z | 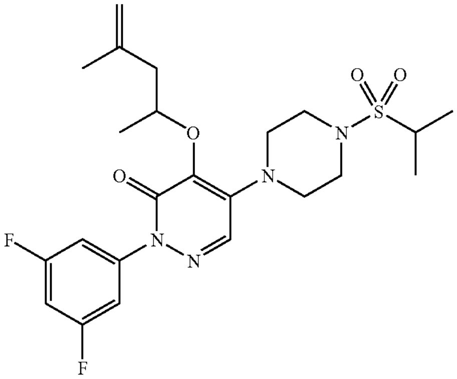 | 497 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1026Z | 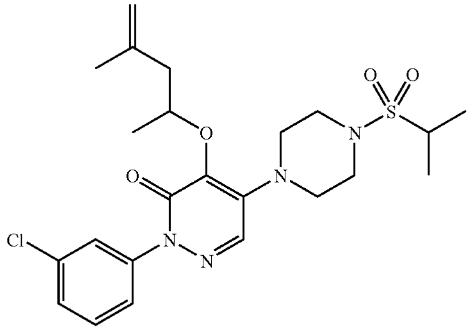 | 495 |
| 1027Z | 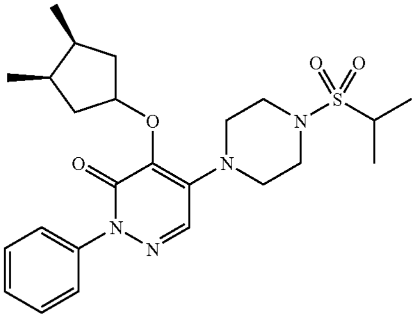 | 475 |
| 1028Z | 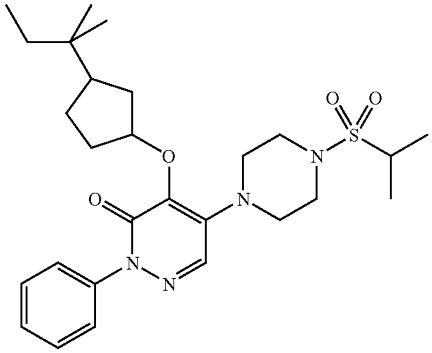 | 517 |
| 1029Z | 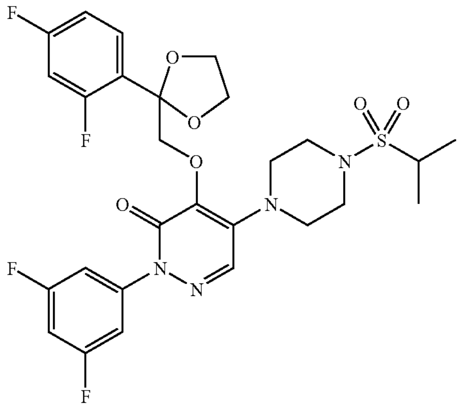 | 613 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
| --- | --- | --- |
| 1030Z | no compound | |
| 1031Z | 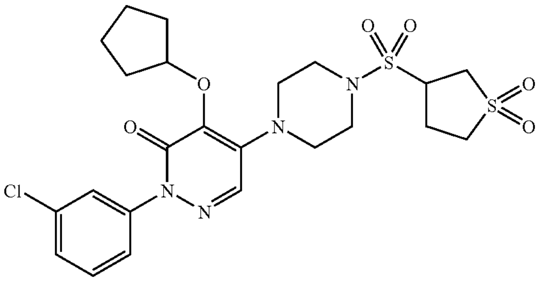 | 557 |
| 1032Z | 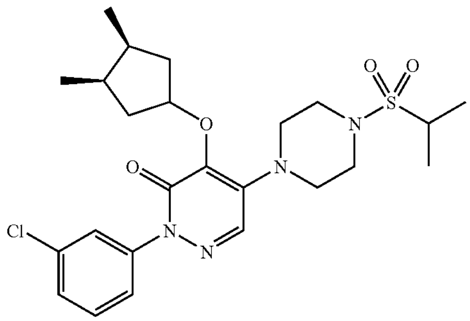 | 509 |
| 1033Z | 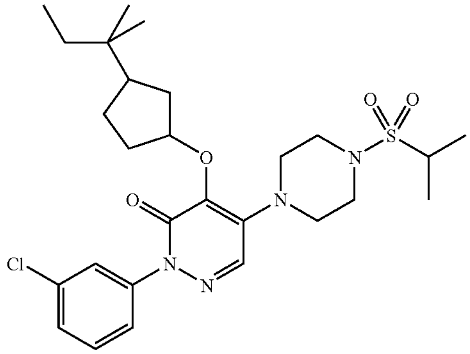 | 551 |
| 1034Z | 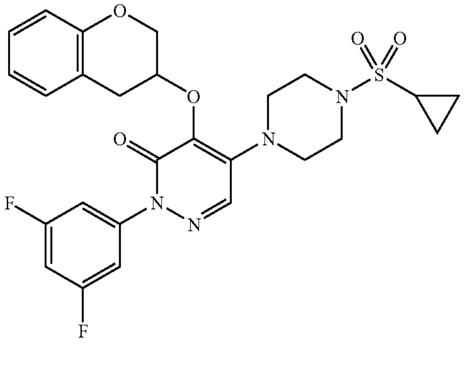 | 545 |

TABLE 11-continued
| Comp. No. | Structure | MS M + 1 |
|---|---|---|
| | Oxygen Linked Analogs with Sulfonamide The following compounds can be synthesized using steps 1, 2, 4, 6, and 9 of Scheme 1 or steps 11, 12, and 14 of Scheme 2. | |
| 1035Z | 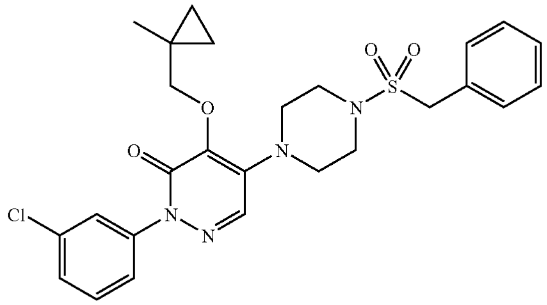 | 529 |
| 1036Z | 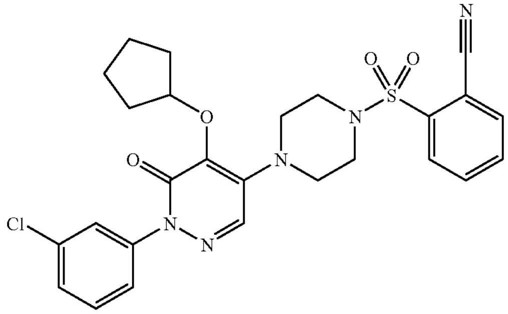 | 540 |
| 1037Z | 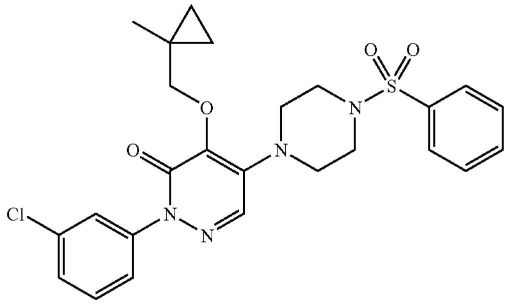 | 515 |
| 1038Z | 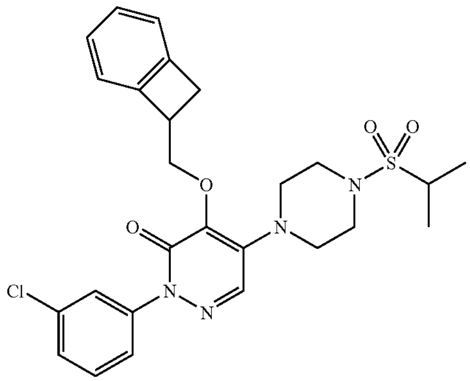 | 529 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1039Z | 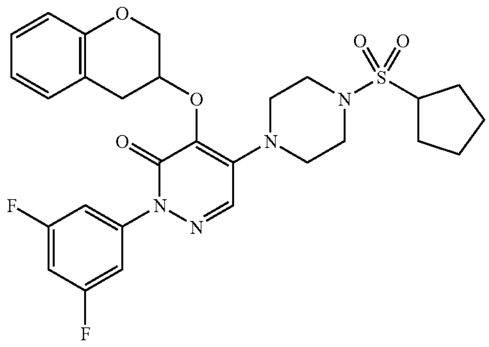 | 573 |
| 1040Z | 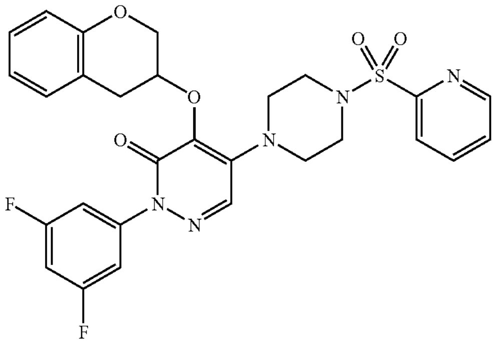 | 582 |
| 1041Z | 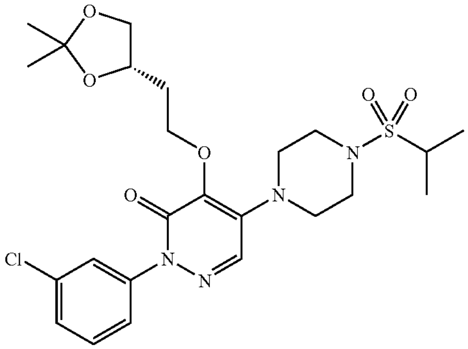 | 541 |
| 1042Z | 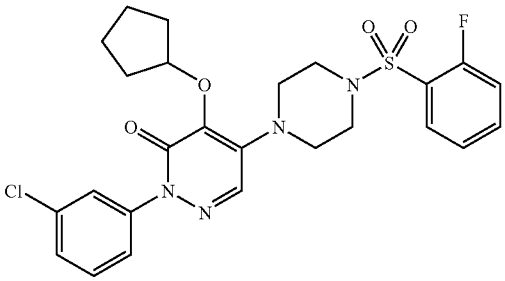 | 533 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1043Z | 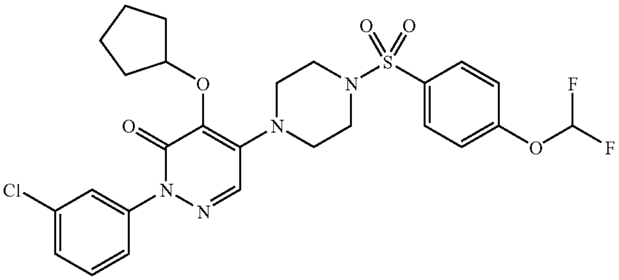 | 581 |
| 1044Z | 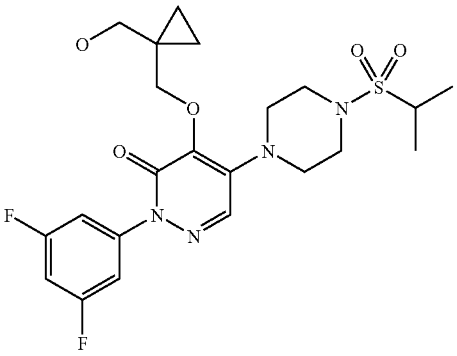 | 481 (M − OH) |
| 1045Z | 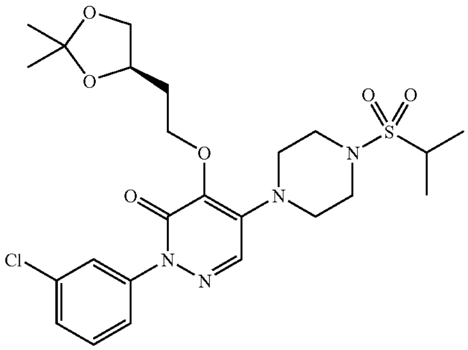 | 541 |
| 1046Z | 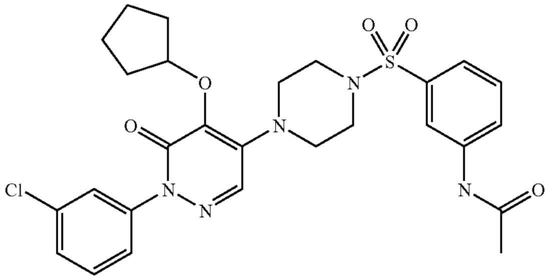 | 572 |

TABLE 11-continued
| Comp. No. | Structure | MS M + 1 |
|---|---|---|
| | Oxygen Linked Analogs with Sulfonamide<br>The following compounds can be synthesized using steps 1, 2, 4, 6, and 9 of Scheme 1 or steps 11, 12, and 14 of Scheme 2. | |
| 1047Z | 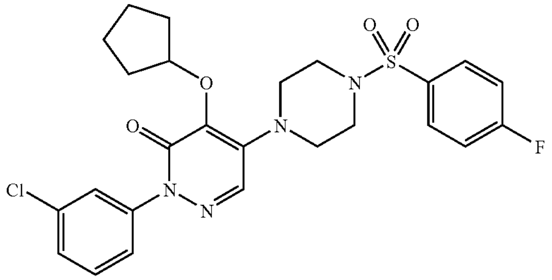 | 533 |
| 1048Z | 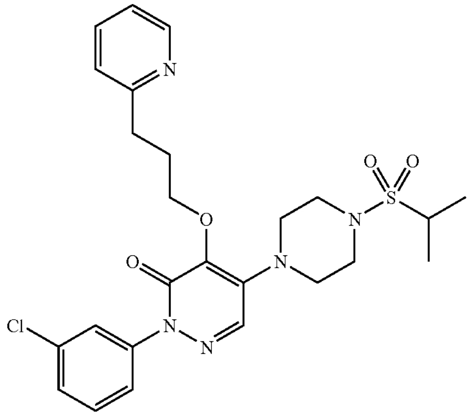 | 532 |
| 1049Z | 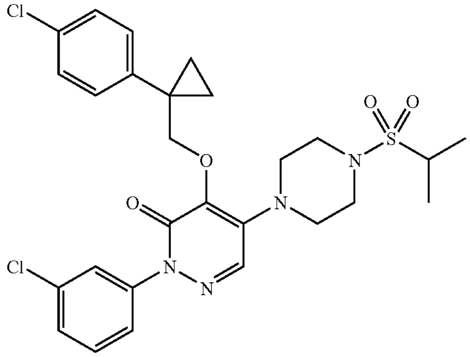 | 577 |
| 1050Z | 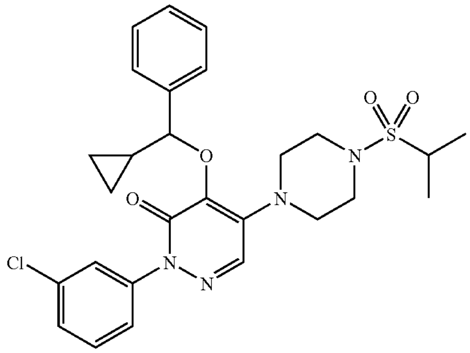 | 543 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
| --- | --- | --- |
| 1051Z | 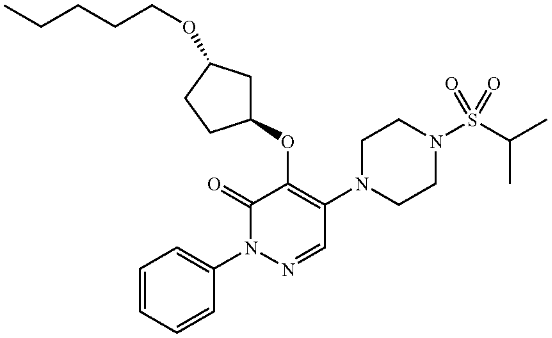 | 533 |
| 1052Z | 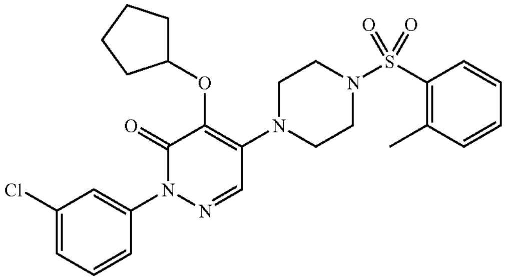 | 529 |
| 1053Z | 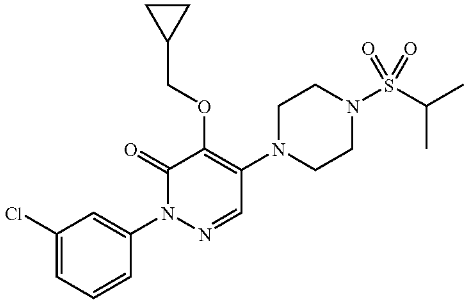 | 467 |
| 1054Z | 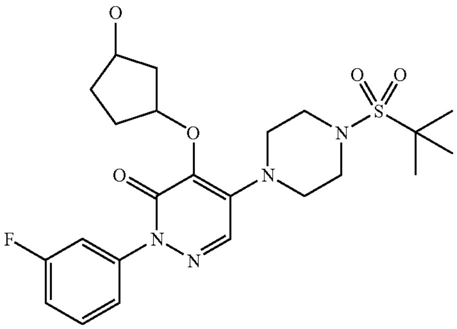 | 495 |

TABLE 11-continued
| Comp. No. | Structure | MS M + 1 |
|---|---|---|
| | Oxygen Linked Analogs with Sulfonamide The following compounds can be synthesized using steps 1, 2, 4, 6, and 9 of Scheme 1 or steps 11, 12, and 14 of Scheme 2. | |
| 1055Z | 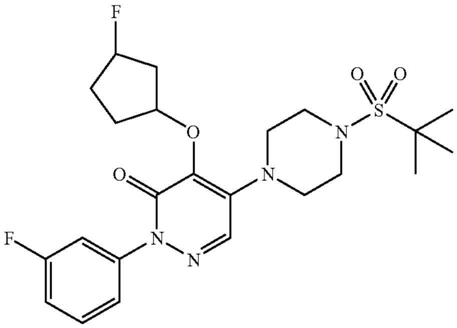 | 497 |
| 1056Z | 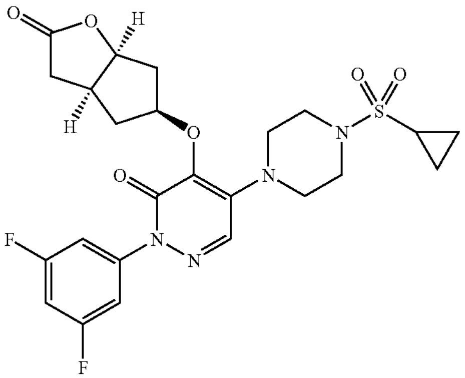 | 537 |
| 1057Z | 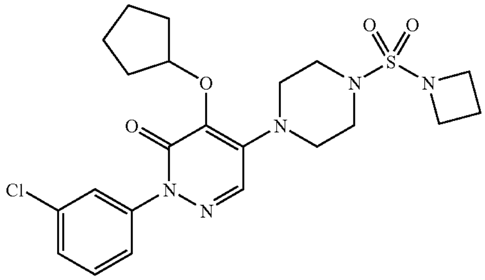 | 494 |
| 1058Z | 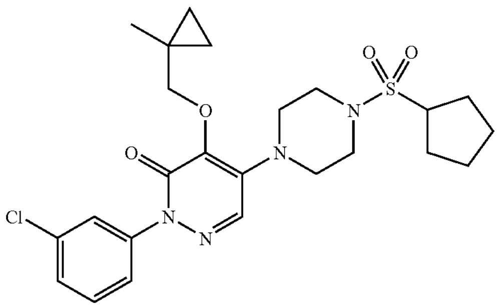 | 507 |

TABLE 11-continued
| Comp. No. | Structure | MS M + 1 |
|---|---|---|
| | Oxygen Linked Analogs with Sulfonamide<br>The following compounds can be synthesized using steps 1, 2, 4, 6, and 9 of Scheme 1 or steps 11, 12, and 14 of Scheme 2. | |
| 1059Z | 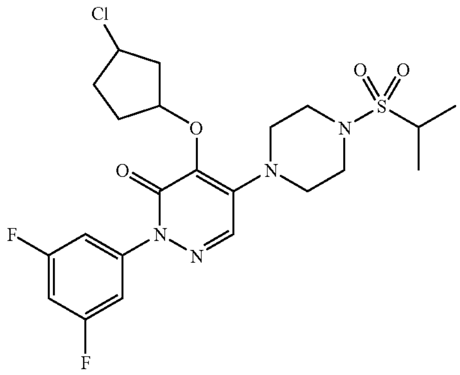 | 517 |
| 1060Z | 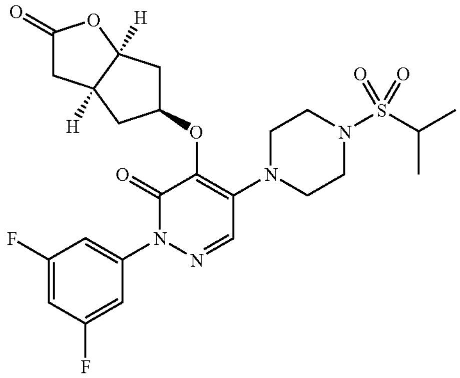 | 539 |
| 1061Z | 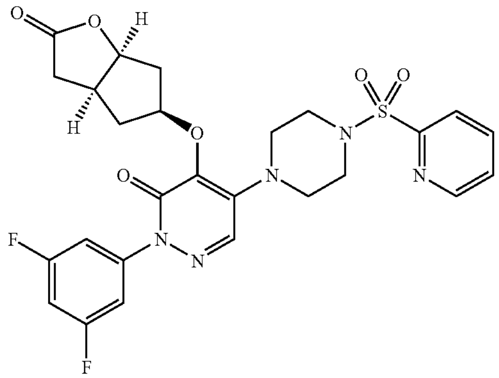 | 574 |
| 1062Z | 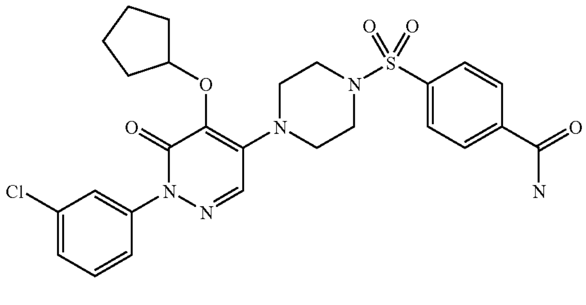 | 558 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1063Z | 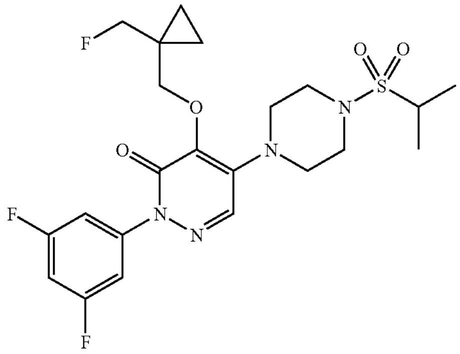 | 501 |
| 1064Z | 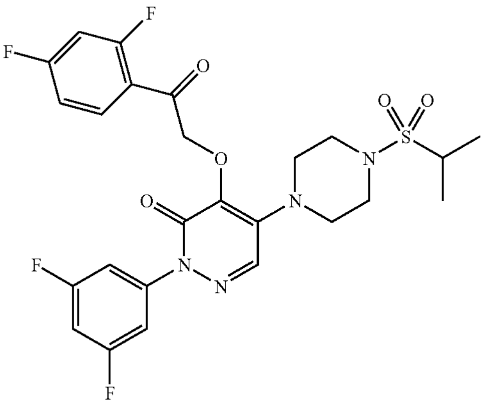 | 569 |
| 1065Z | 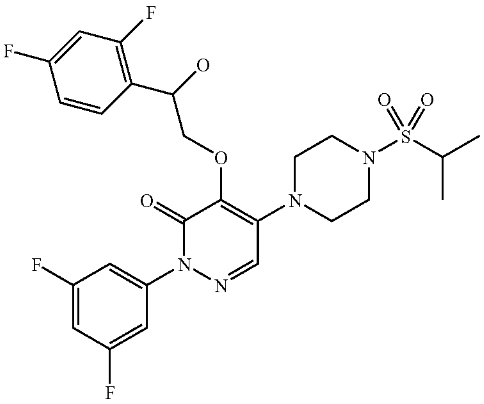 | 571 |
| 1066Z | 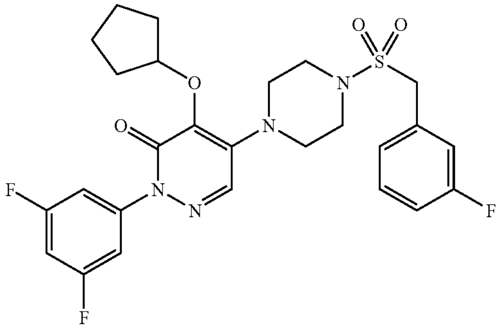 | 549 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1067Z | 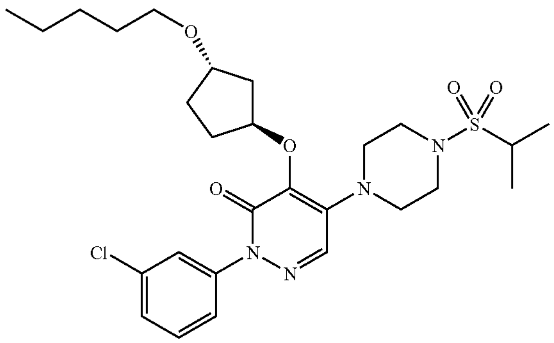 | 567 |
| 1068Z | 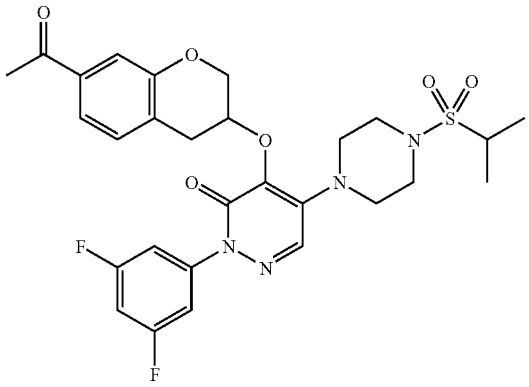 | 589 |
| 1069Z | 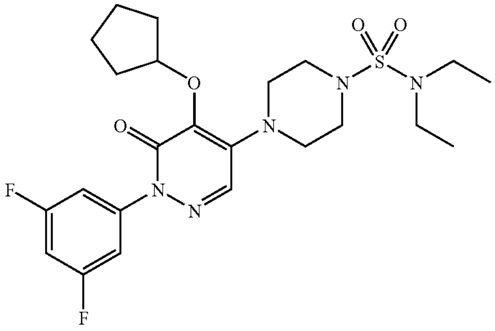 | 512 |
| 1070Z | 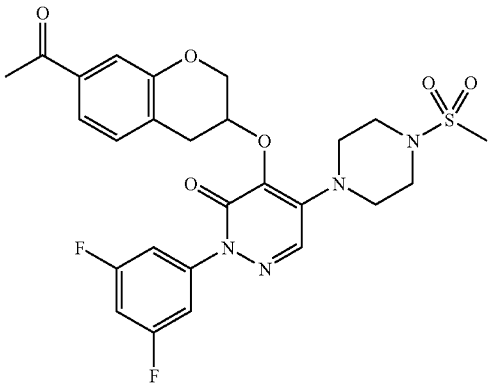 | 561 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1071Z | 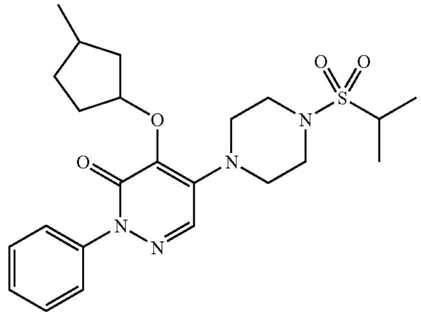 | 461 |
| 1072Z | 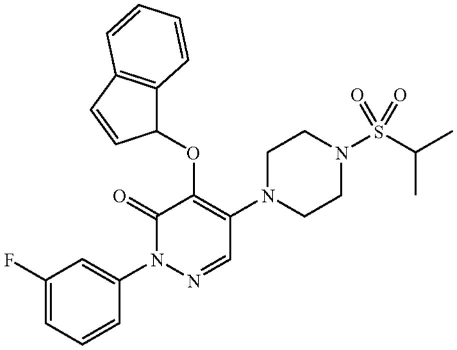 | 511 |
| 1073Z | 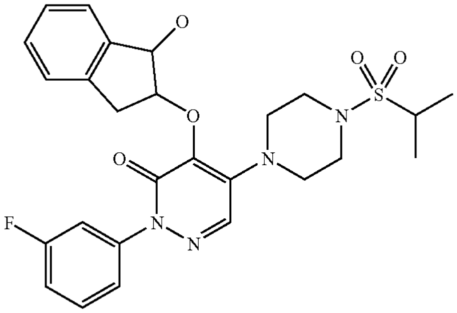 | 529 |
| 1074Z | 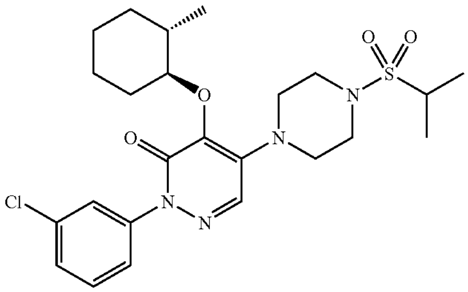 | 509 |

TABLE 11-continued
| Oxygen Linked Analogs with Sulfonamide<br>The following compounds can be synthesized using steps 1, 2,<br>4, 6, and 9 of Scheme 1 or steps 11, 12, and 14 of Scheme 2. | | |
|---|---|---|
| Comp. No. | Structure | MS M + 1 |
| 1075Z | 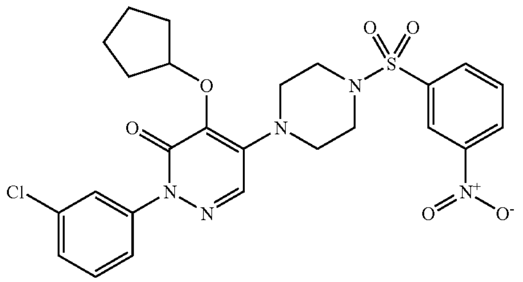 | 560 |
| 1076Z | 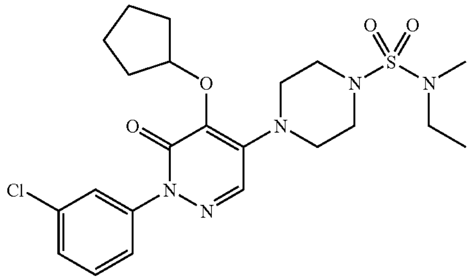 | 496 |
| 1077Z | 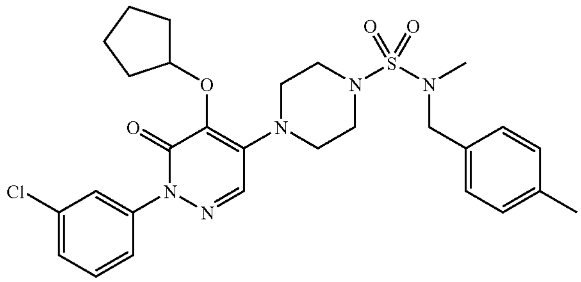 | 572 |
| 1078Z | 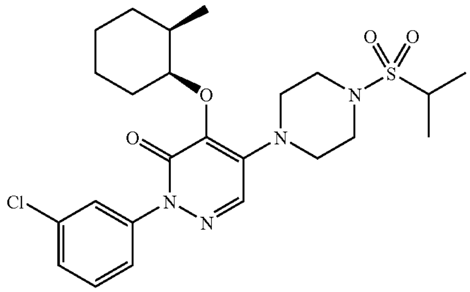 | 509 |
| 1079Z | 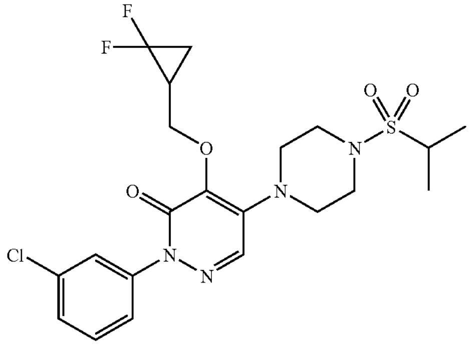 | 503 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1080Z | 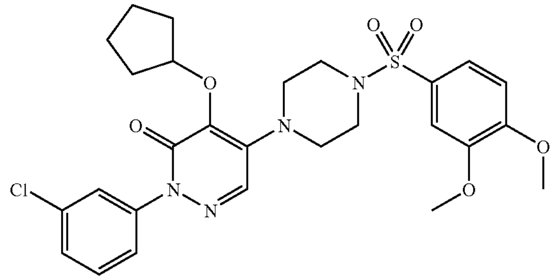 | 575 |
| 1081Z | 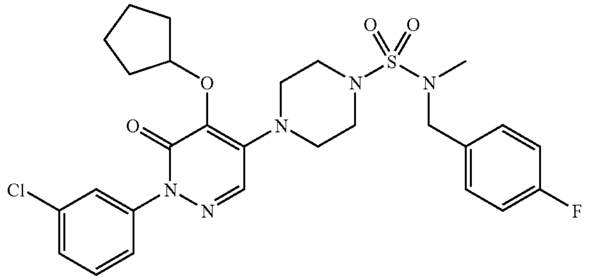 | 576 |
| 1082Z | 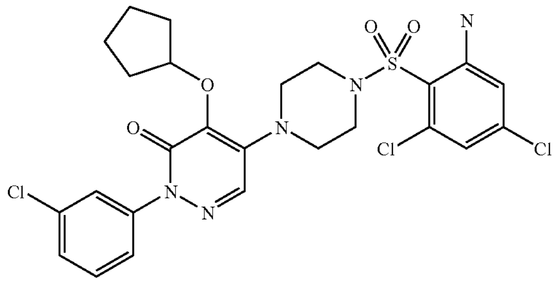 | 598 |
| 1083Z | 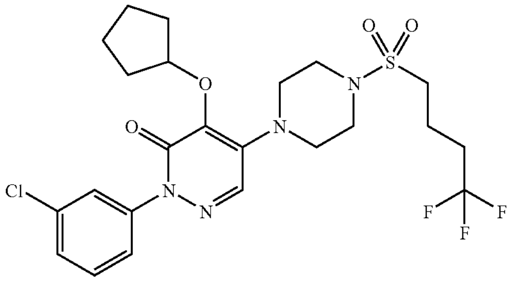 | 549 |
| 1084Z | 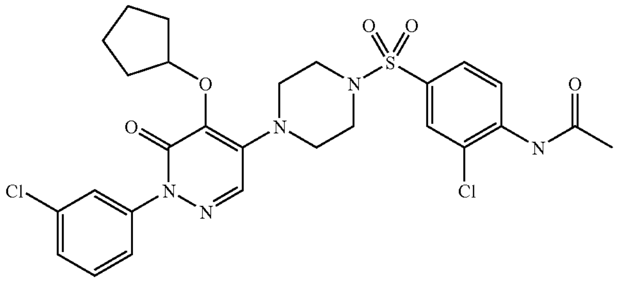 | 606 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1085Z | 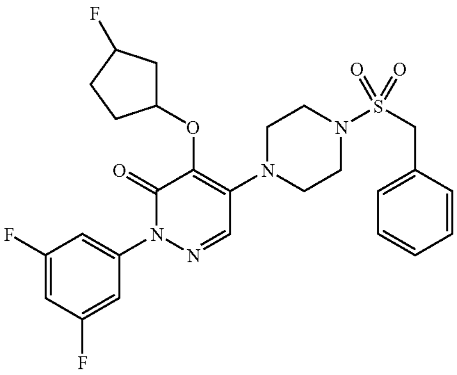 | 549 |
| 1086Z | 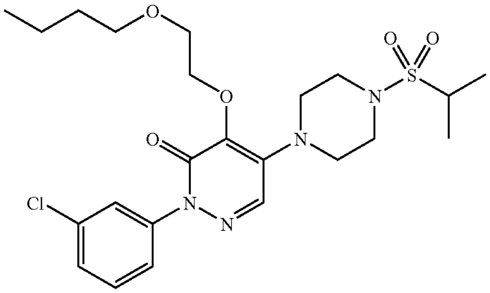 | 513 |
| 1087Z | 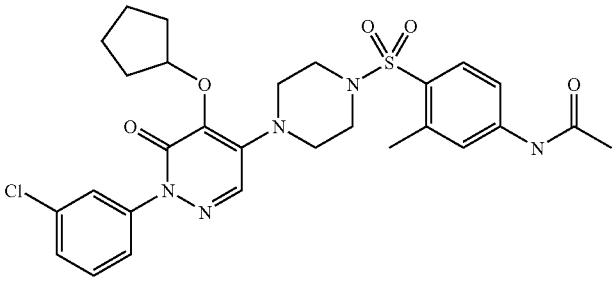 | 586 |
| 1088Z | 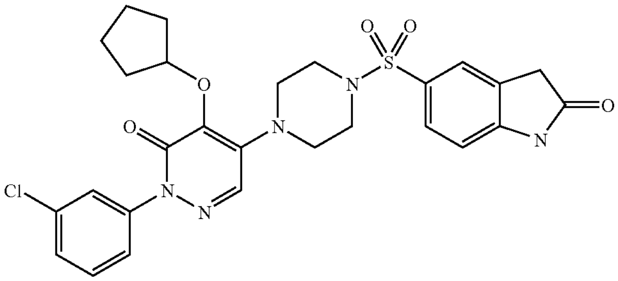 | 570 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1089Z | 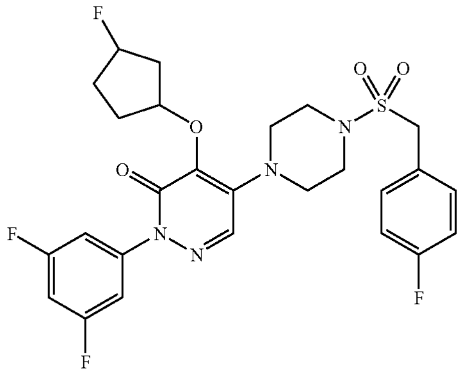 | 567 |
| 1090Z | 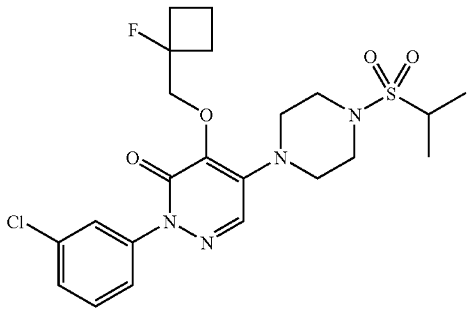 | 499 |
| 1091Z | 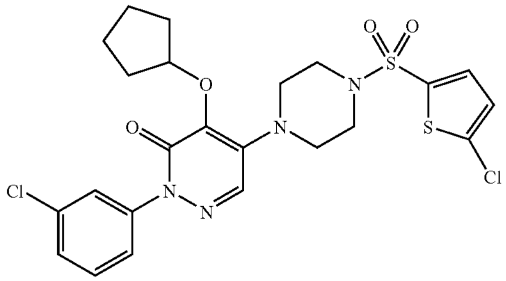 | 555 |
| 1092Z | 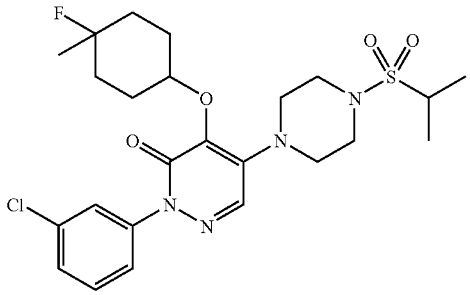 | 527 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1093Z | 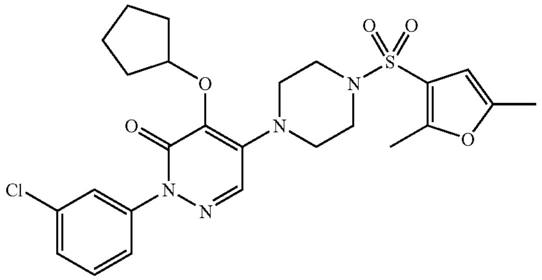 | 533 |
| 1094Z | 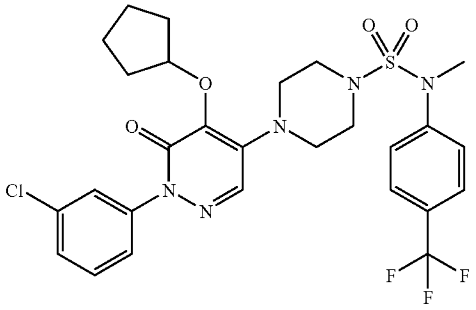 | 612 |
| 1095Z | 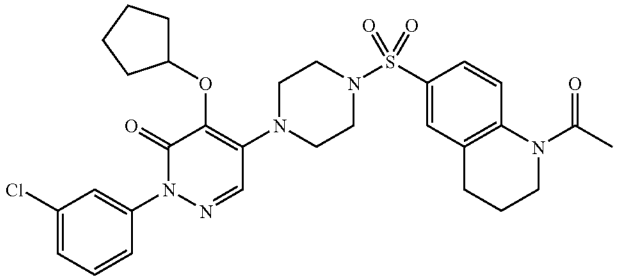 | 612 |
| 1096Z | 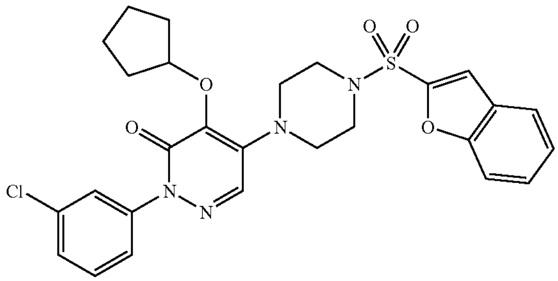 | 555 |
| 1097Z | 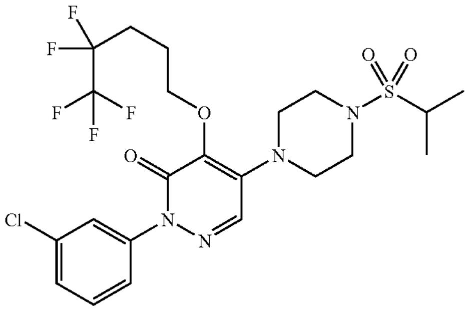 | 573 |

TABLE 11-continued
| Comp. No. | Oxygen Linked Analogs with Sulfonamide<br>The following compounds can be synthesized using steps 1, 2, 4, 6, and 9 of Scheme 1 or steps 11, 12, and 14 of Scheme 2.<br>Structure | MS M + 1 |
|---|---|---|
| 1098Z | 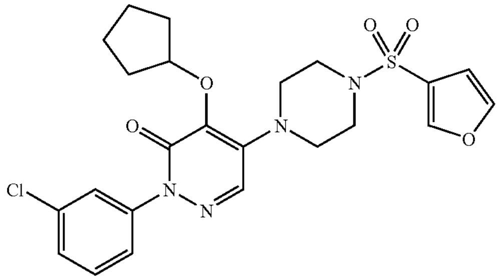 | 505 |
| 1099Z | 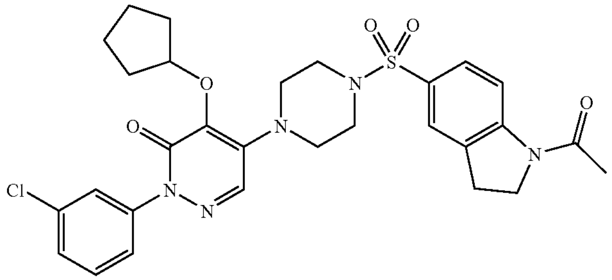 | 598 |
| 1100Z | 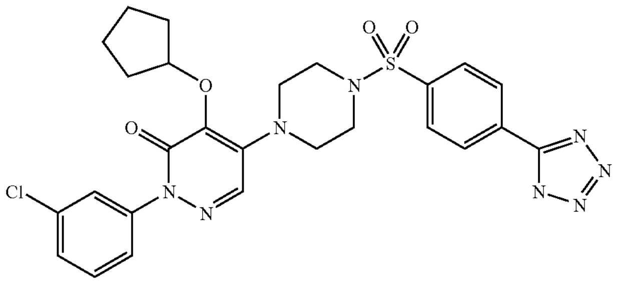 | 583 |
| 1101Z | 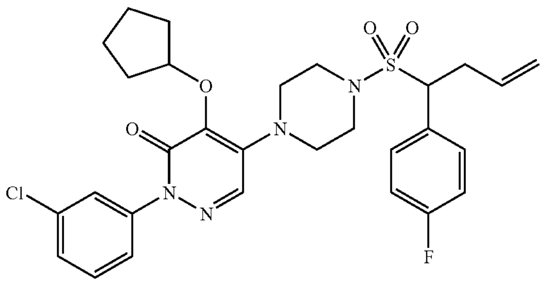 | 587 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1102Z | 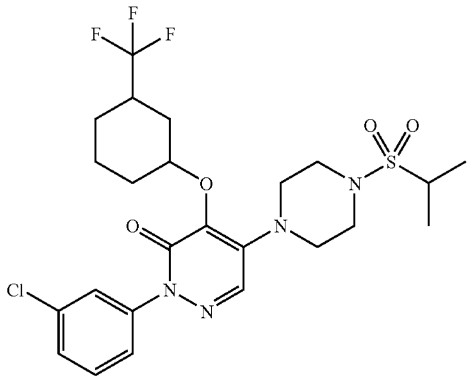 | 563 |
| 1103Z | 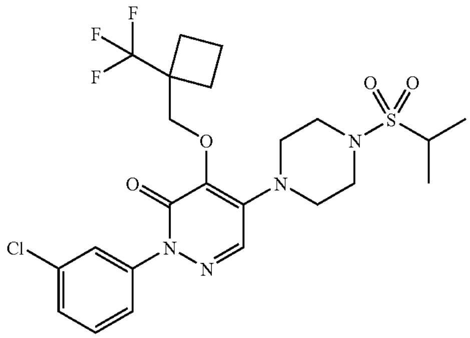 | 549 |
| 1104Z | 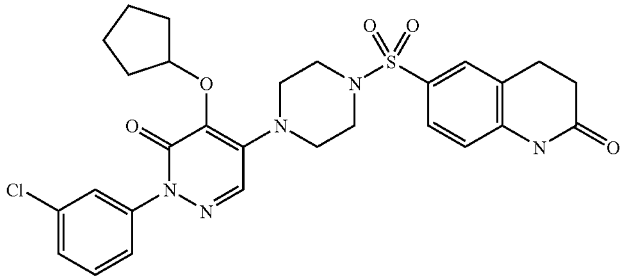 | 584 |
| 1105Z | 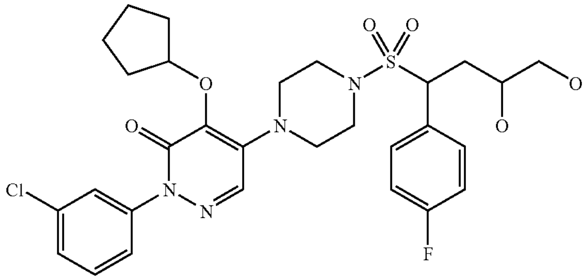 | 621 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1106Z | 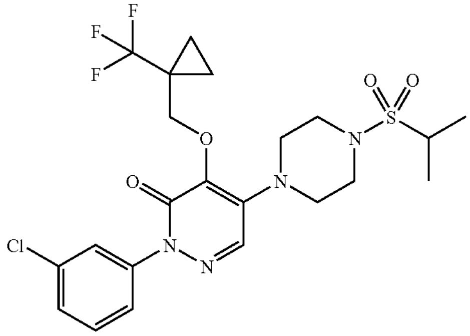 | 535 |
| 1107Z | 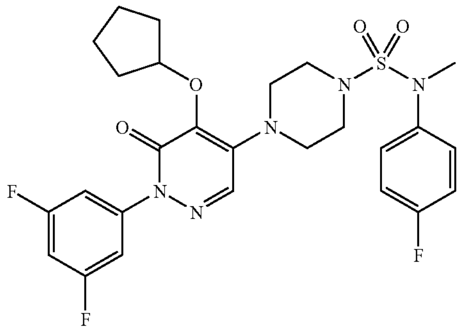 | 564 |
| 1108Z | 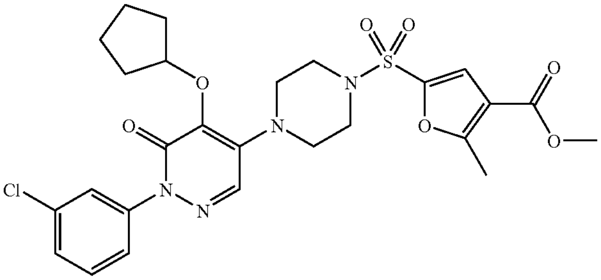 | 577 |
| 1109Z | 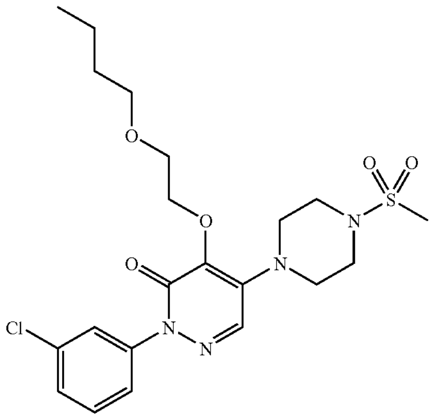 | 485 |

TABLE 11-continued
| Comp. No. | Oxygen Linked Analogs with Sulfonamide The following compounds can be synthesized using steps 1, 2, 4, 6, and 9 of Scheme 1 or steps 11, 12, and 14 of Scheme 2. Structure | MS M + 1 |
|---|---|---|
| 1110Z | 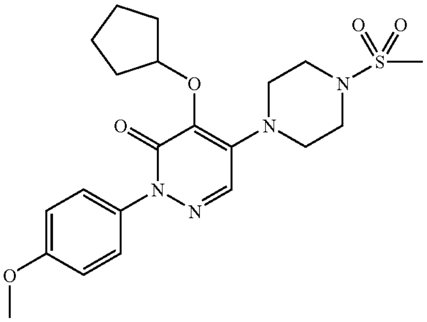 | 449 |
| 1111Z | 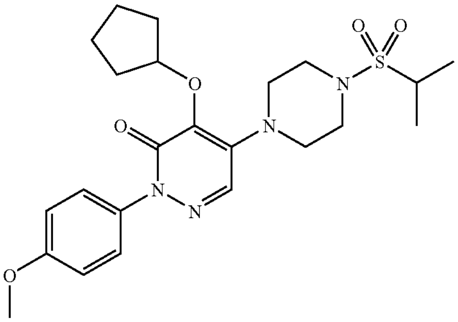 | 477 |
| 1112Z | 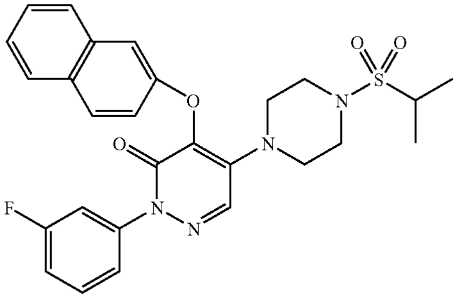 | 523 |
| 1113Z | 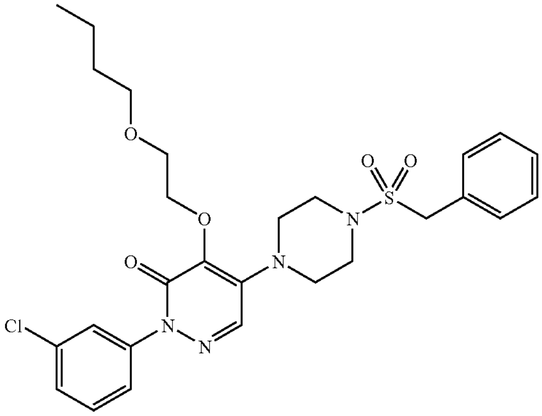 | 561 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1114Z | 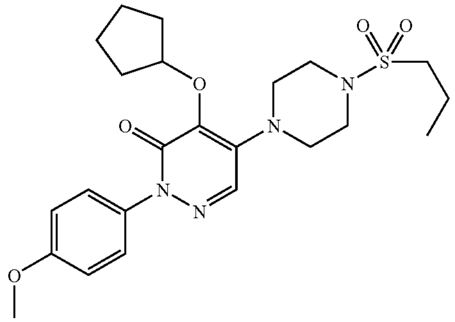 | 477 |
| 1115Z | 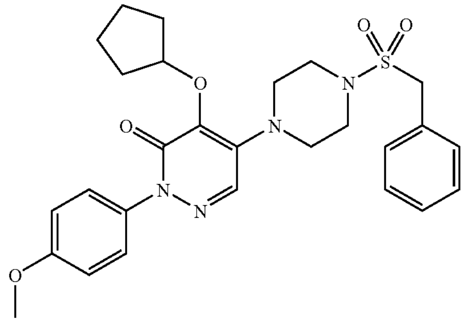 | 525 |
| 1116Z | 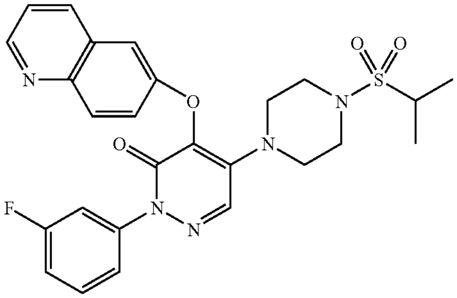 | 524 |
| 1117Z | 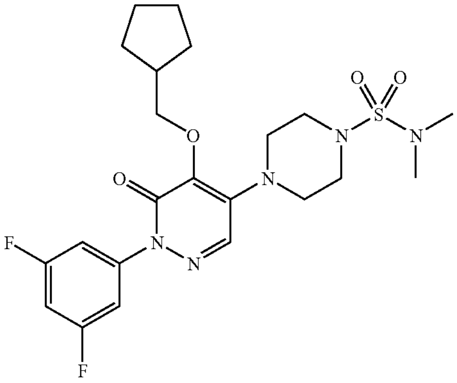 | 498 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1118Z | 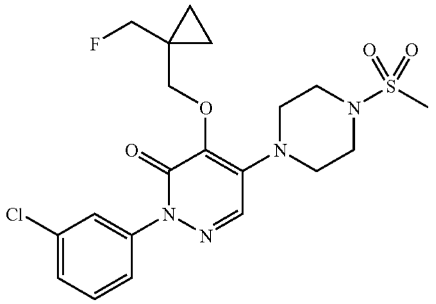 | 471 |
| 1119Z | 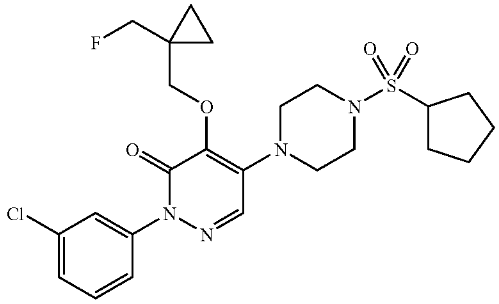 | 525 |
| 1120Z | 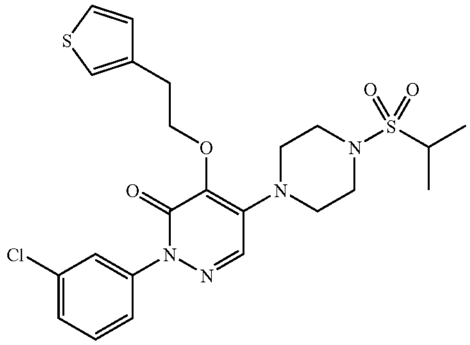 | 523 |
| 1121Z | 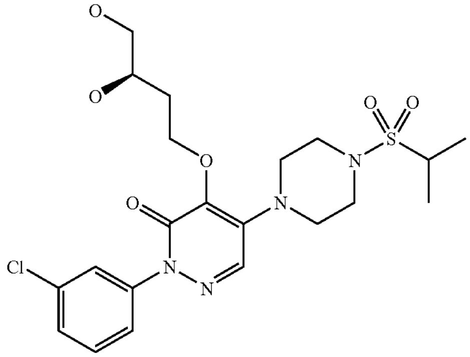 | 501 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
| --- | --- | --- |
| 1122Z | 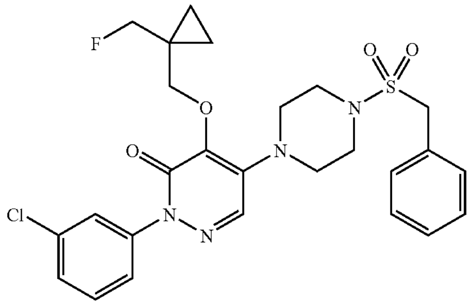 | 547 |
| 1123Z | 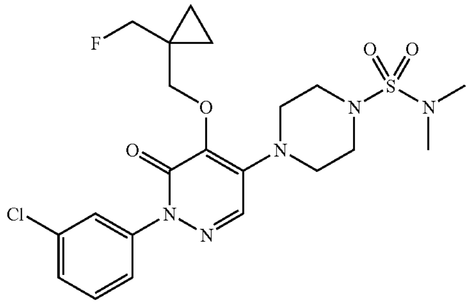 | 500 |
| 1124Z | 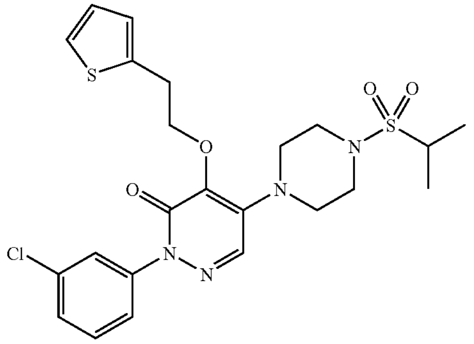 | 523 |
| 1125Z | 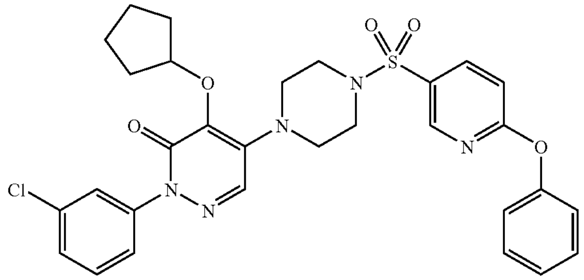 | 608 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1126Z | 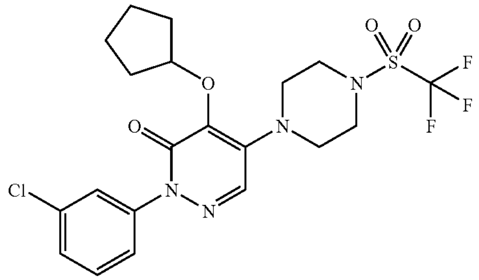 | 507 |
| 1127Z | 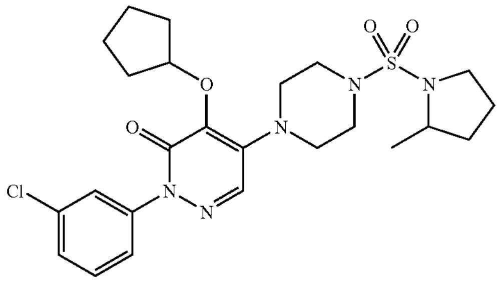 | 522 |
| 1128Z | 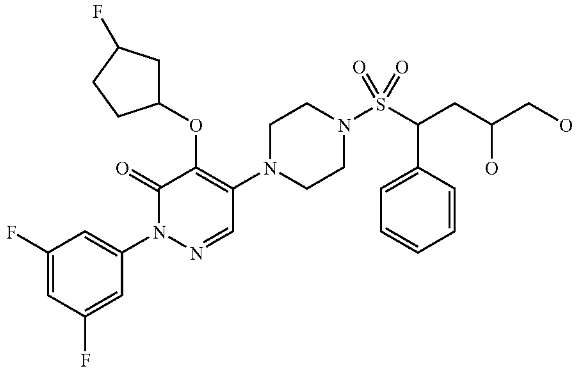 | 623 |
| 1129Z | 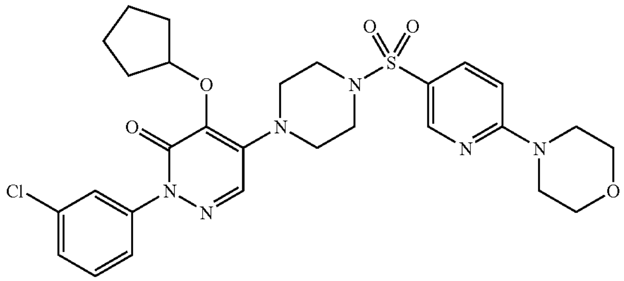 | 601 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1130Z | 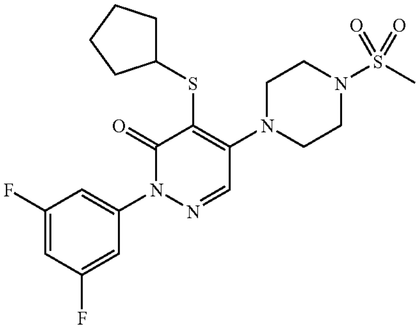 | 471 |
| 1131Z | 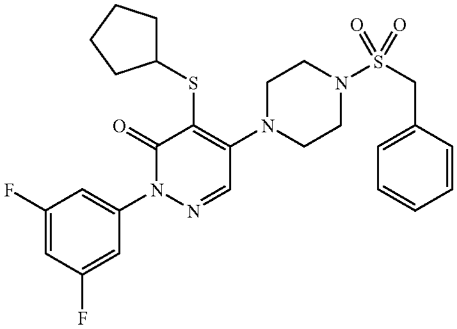 | 547 |
| 1132Z | 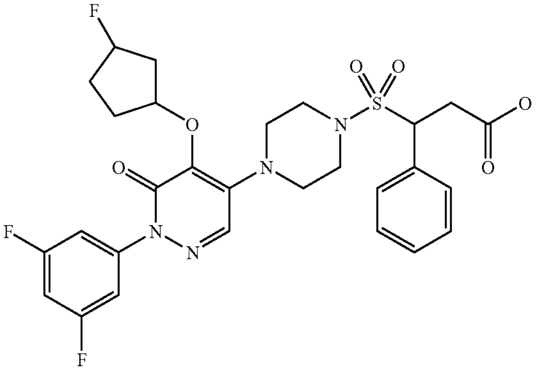 | 607 |
| 1133Z | 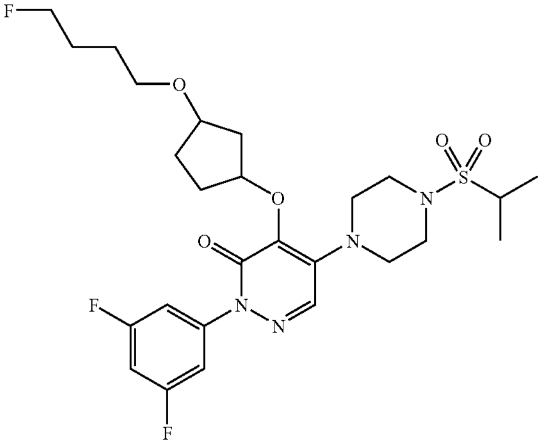 | 501 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1134Z | 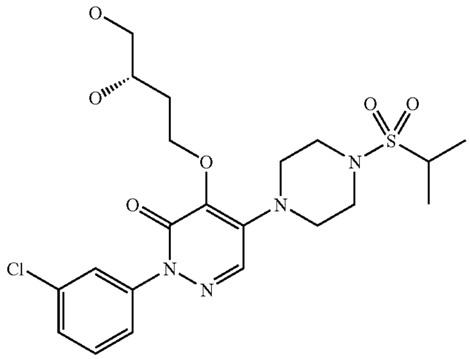 | 501 |
| 1135Z | 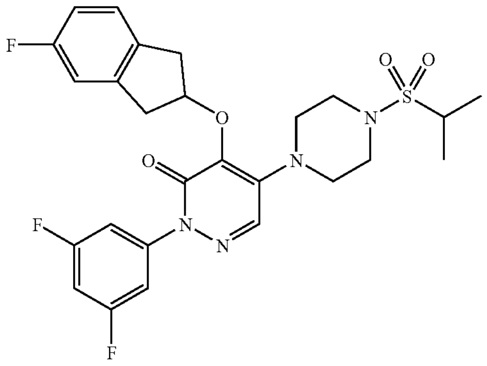 | 549 |
| 1136Z | 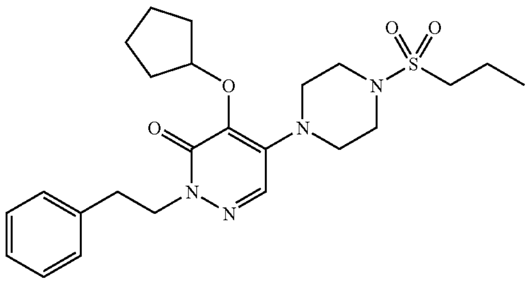 | 475 |
| 1137Z | 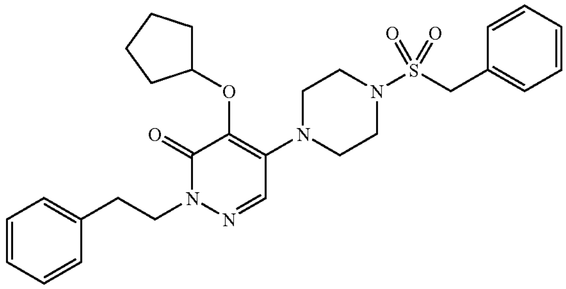 | 523 |

TABLE 11-continued
| Comp. No. | Oxygen Linked Analogs with Sulfonamide The following compounds can be synthesized using steps 1, 2, 4, 6, and 9 of Scheme 1 or steps 11, 12, and 14 of Scheme 2. Structure | MS M + 1 |
|---|---|---|
| 1138Z | 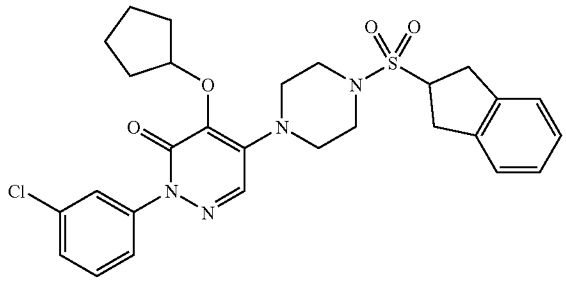 | 555 |
| 1139Z | 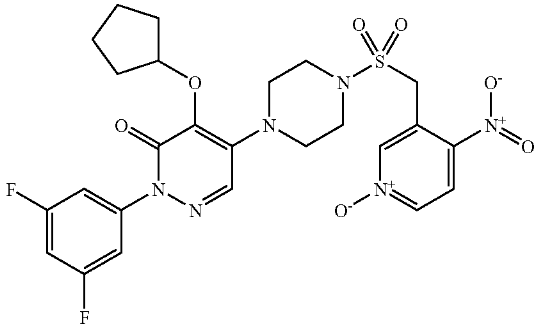 | 593 |
| 1140Z | 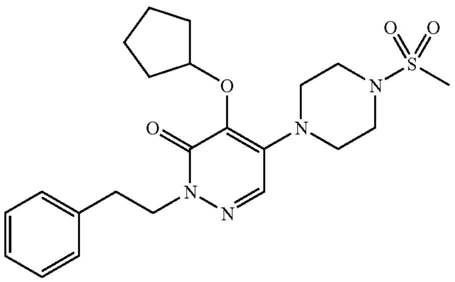 | 447 |
| 1141Z | 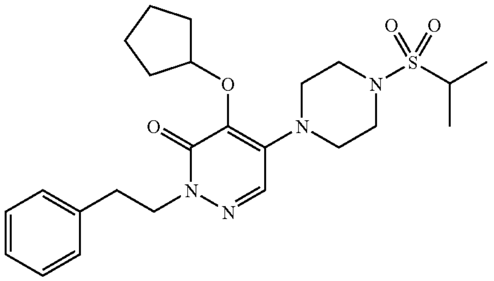 | 475 |

TABLE 11-continued
| Comp. No. | Structure | MS M + 1 |
| --- | --- | --- |
| Oxygen Linked Analogs with Sulfonamide. The following compounds can be synthesized using steps 1, 2, 4, 6, and 9 of Scheme 1 or steps 11, 12, and 14 of Scheme 2. | | |
| 1142Z | 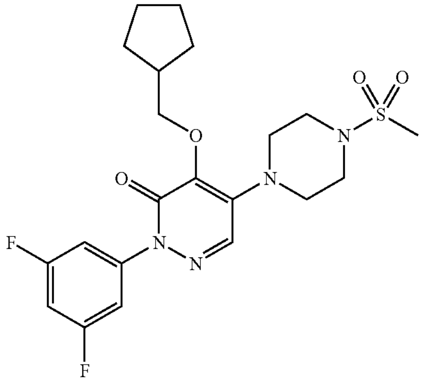 | 469 |
| 1143Z | 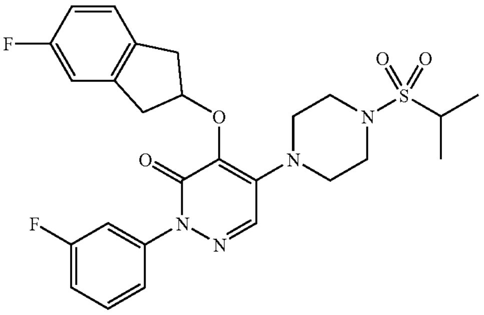 | 531 |
| 1144Z | 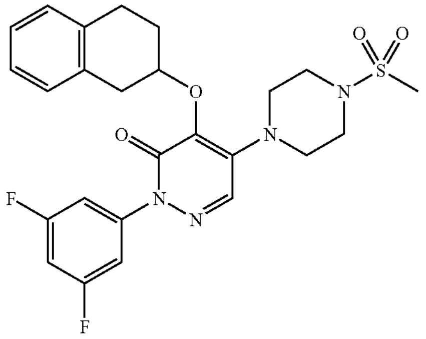 | 517 |
| 1145Z | 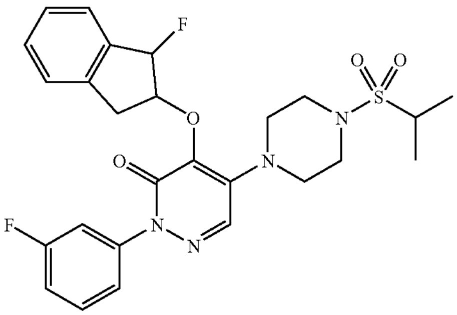 | 511 |

TABLE 11-continued
| Comp. No. | Structure | MS M + 1 |
|---|---|---|
| | Oxygen Linked Analogs with Sulfonamide The following compounds can be synthesized using steps 1, 2, 4, 6, and 9 of Scheme 1 or steps 11, 12, and 14 of Scheme 2. | |
| 1146Z | 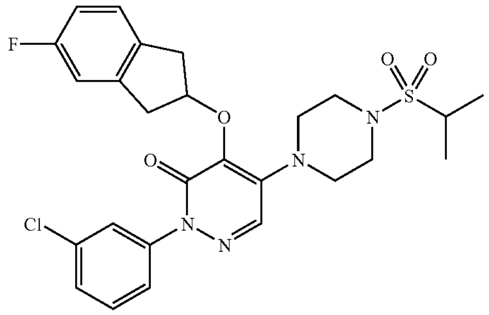 | 547 |
| 1147Z | 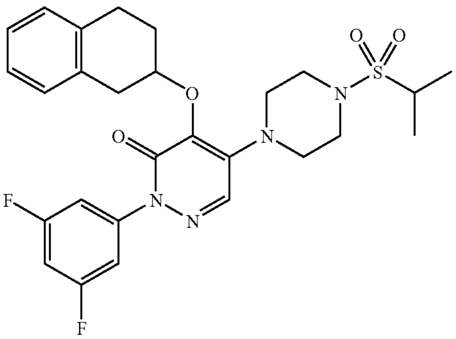 | 545 |
| 1148Z | 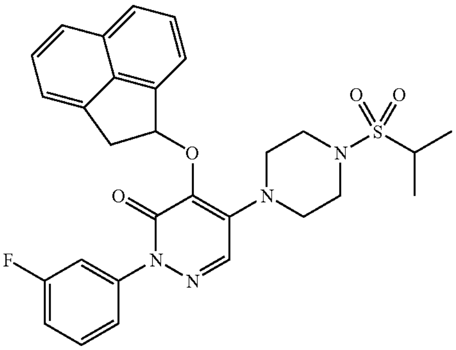 | 549 |
| 1149Z | 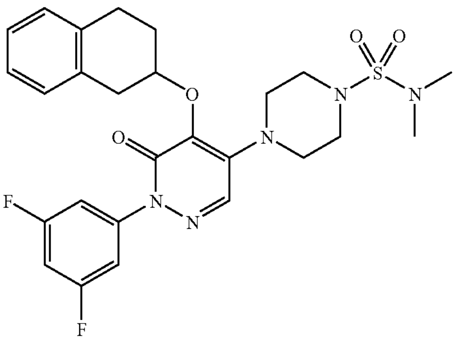 | 546 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1150Z | 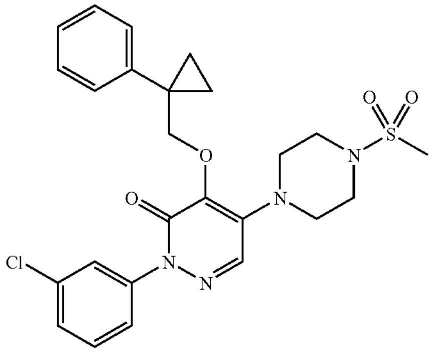 | 515 |
| 1151Z | 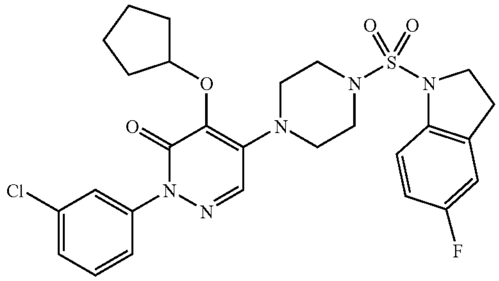 | 574 |
| 1152Z | 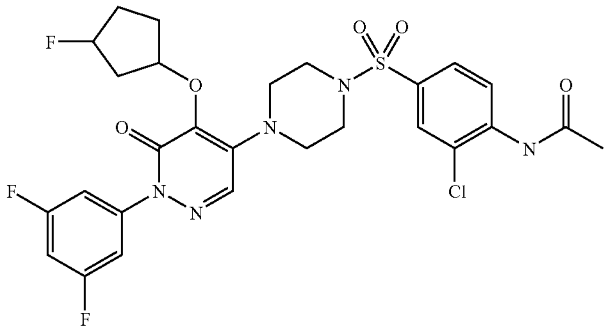 | 626 |
| 1153Z | 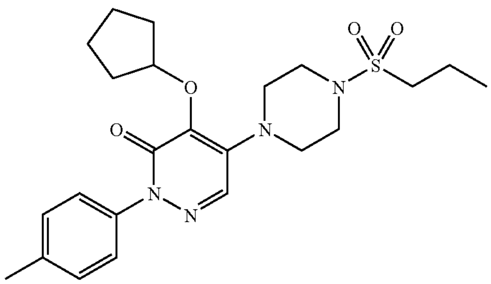 | 461 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
| --- | --- | --- |
| 1154Z | 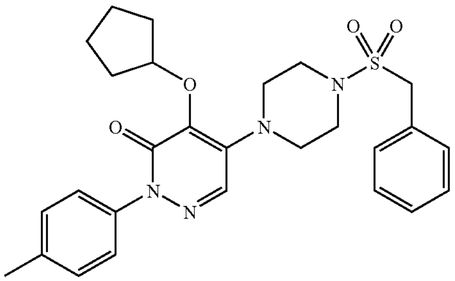 | 509 |
| 1155Z | 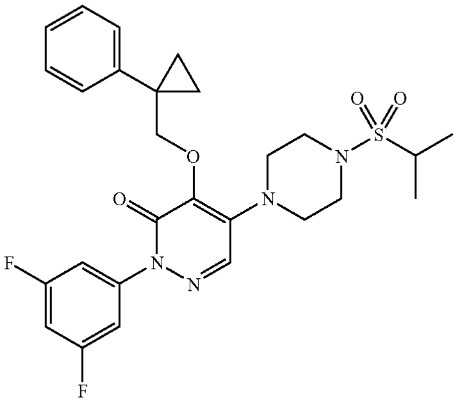 | 545 |
| 1156Z | 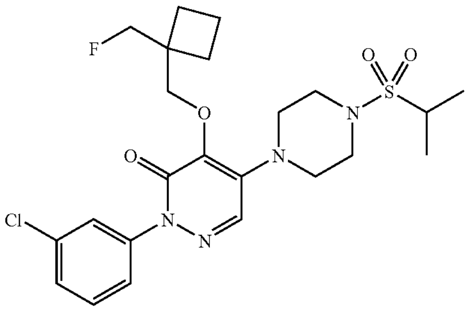 | 513 |
| 1157Z | 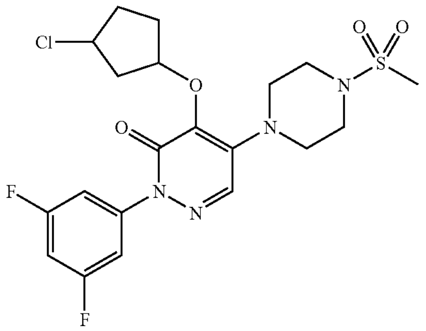 | 489 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1158Z | 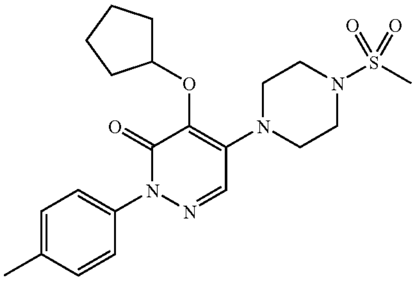 | 433 |
| 1159Z | 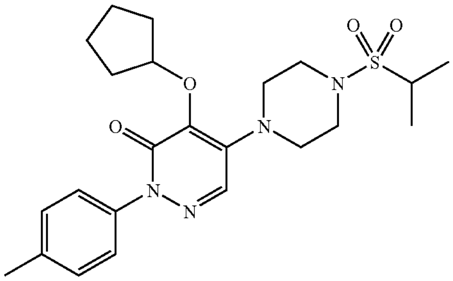 | 461 |
| 1160Z | 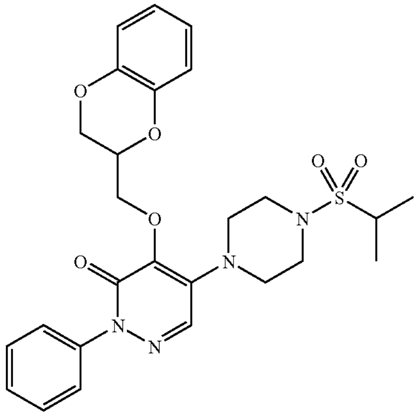 | 527 |
| 1161Z | 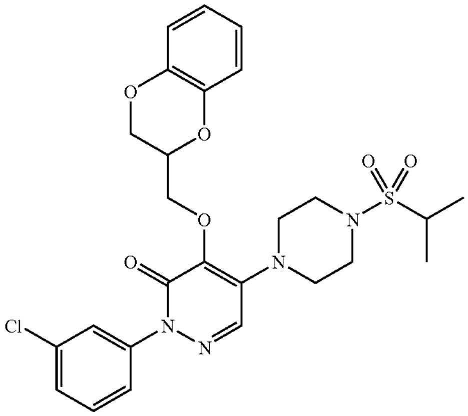 | 561 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1162Z | 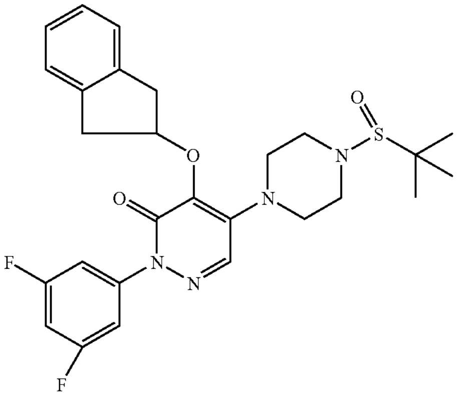 | 529 |
| 1163Z | 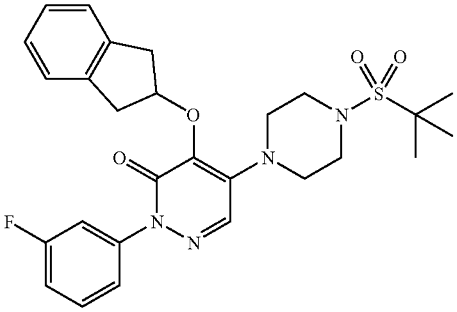 | 527 |
| 1164Z | 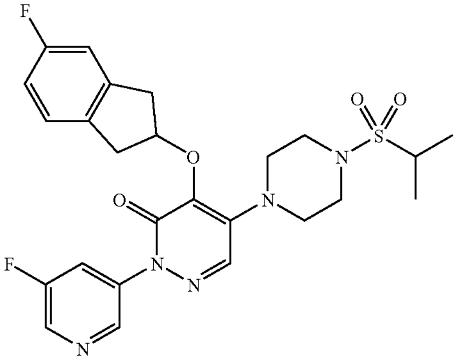 | 532 |
| 1165Z | 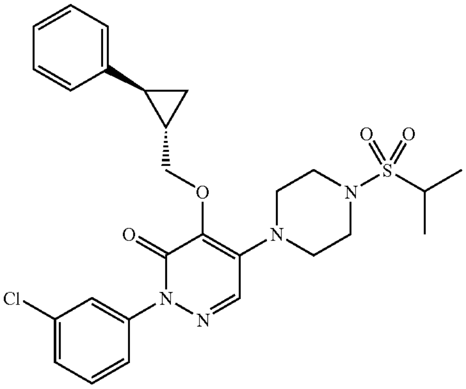 | 543 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1166Z | 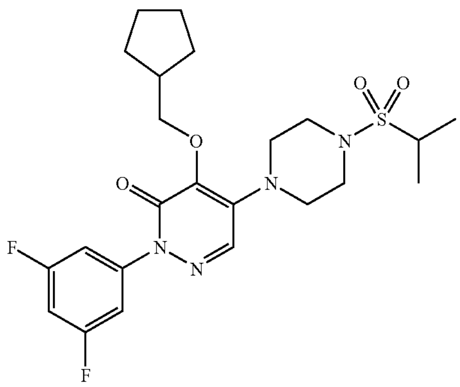 | 497 |
| 1167Z | 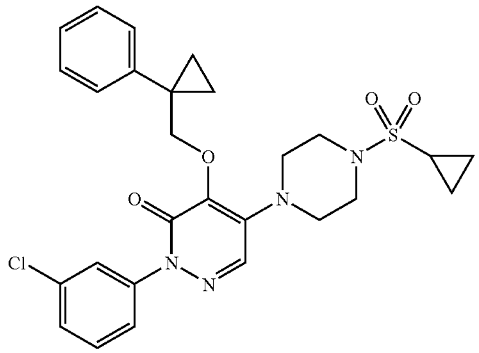 | 541 |
| 1168Z | 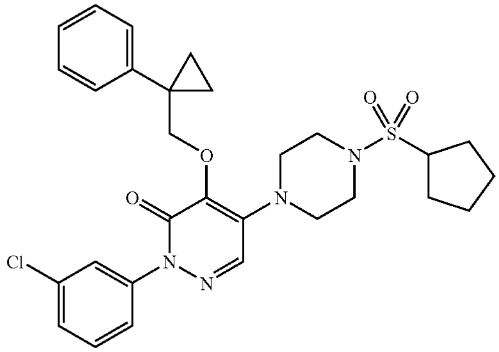 | 569 |

TABLE 11-continued
| Comp. No. | Structure | MS M + 1 |
|---|---|---|
| Oxygen Linked Analogs with Sulfonamide The following compounds can be synthesized using steps 1, 2, 4, 6, and 9 of Scheme 1 or steps 11, 12, and 14 of Scheme 2. | | |
| 1169Z | 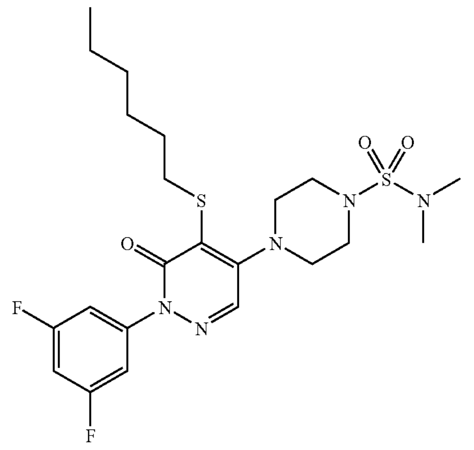 | 516 |
| 1170Z | 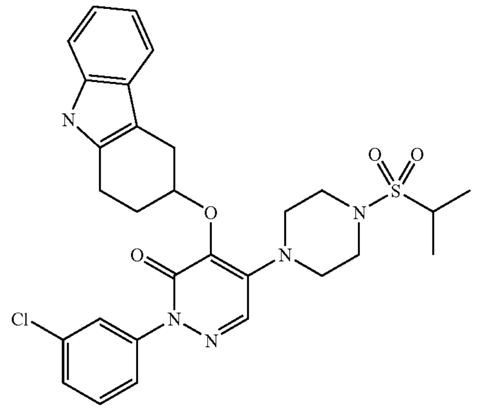 | 582 |
| 1171Z | 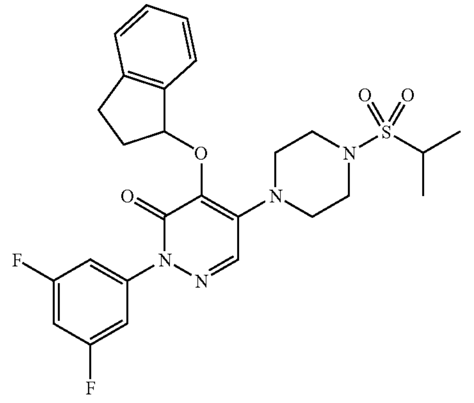 | 529 (M − H) |

TABLE 11-continued
| Comp. No. | Structure | MS M + 1 |
|---|---|---|
| Oxygen Linked Analogs with Sulfonamide The following compounds can be synthesized using steps 1, 2, 4, 6, and 9 of Scheme 1 or steps 11, 12, and 14 of Scheme 2. | | |
| 1172Z | 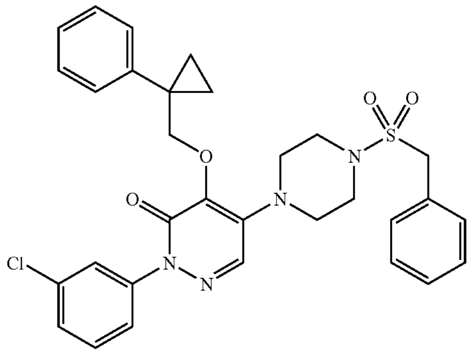 | 591 |
| 1173Z | 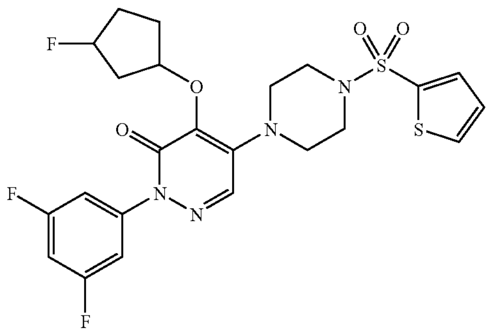 | 541 |
| 1174Z | 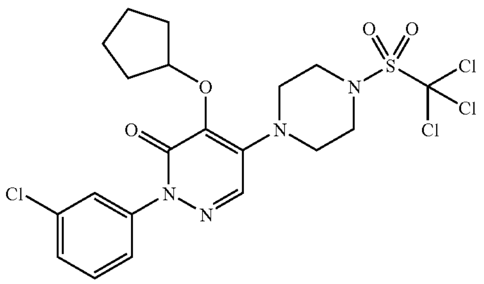 | 555 |
| 1175Z | 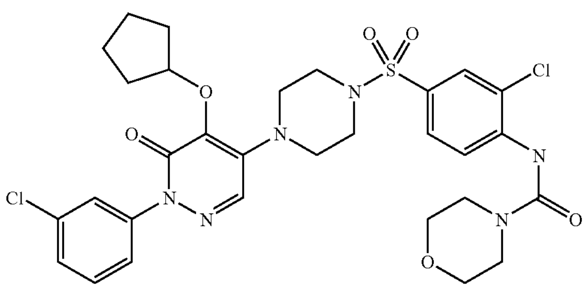 | 677 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1176Z | 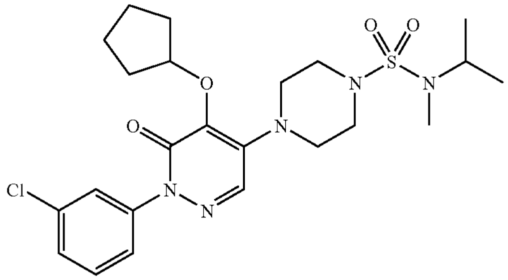 | 510 |
| 1177Z | 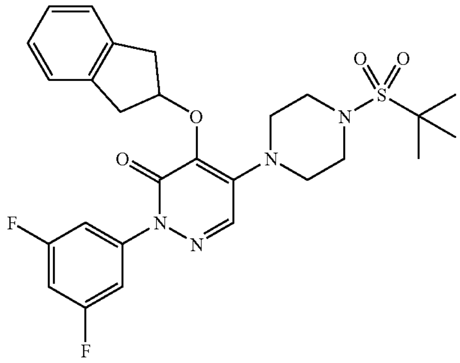 | 545 |
| 1178Z | 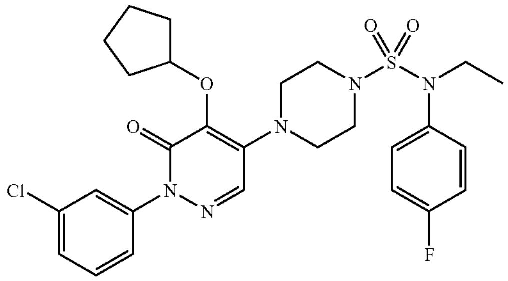 | 576 |
| 1179Z | 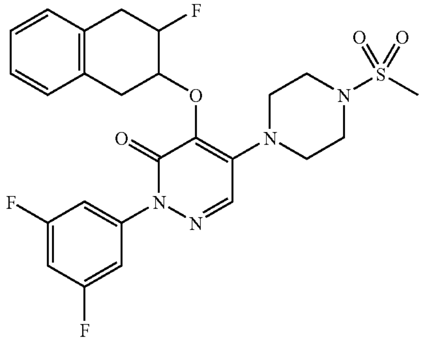 | 535 |

TABLE 11-continued
| Comp. No. | Oxygen Linked Analogs with Sulfonamide The following compounds can be synthesized using steps 1, 2, 4, 6, and 9 of Scheme 1 or steps 11, 12, and 14 of Scheme 2. Structure | MS M + 1 |
|---|---|---|
| 1180Z | 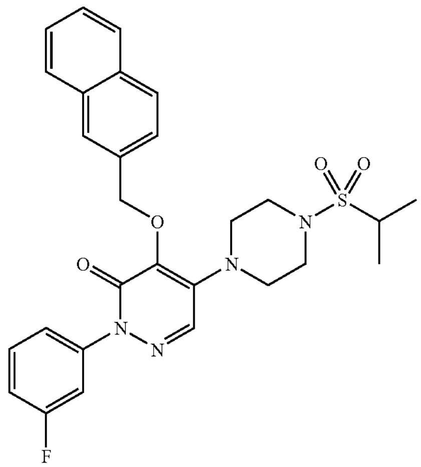 | 537 |
| 1181Z | 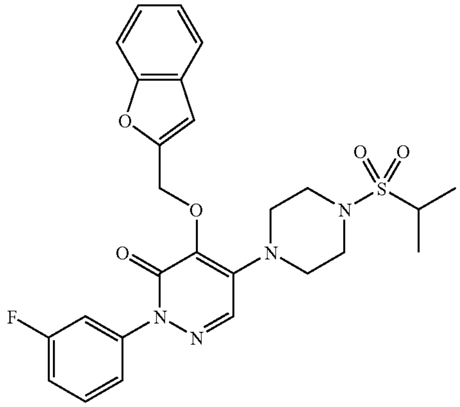 | 527 |
| 1182Z | 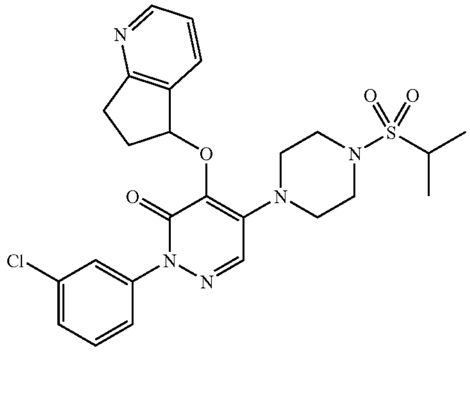 | 530 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1183Z | 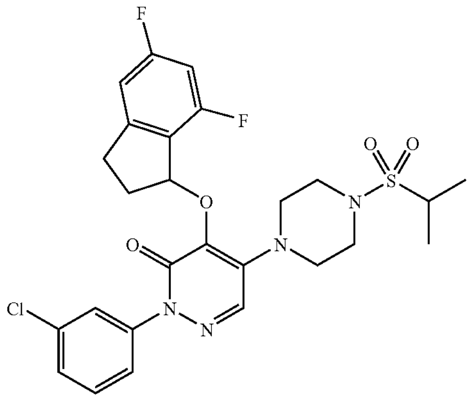 | 565 |
| 1184Z | 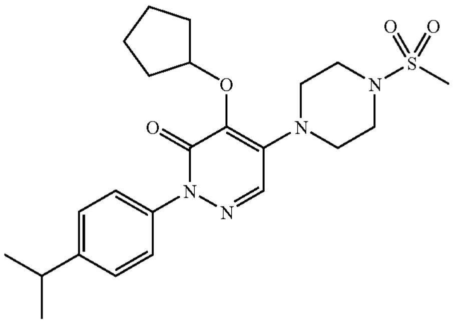 | 461 |
| 1185Z | 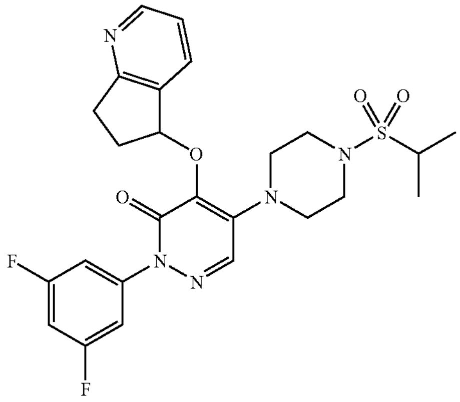 | 532 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1186Z | 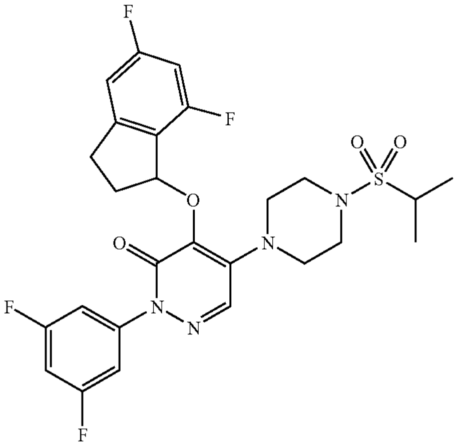 | 567 |
| 1187Z | 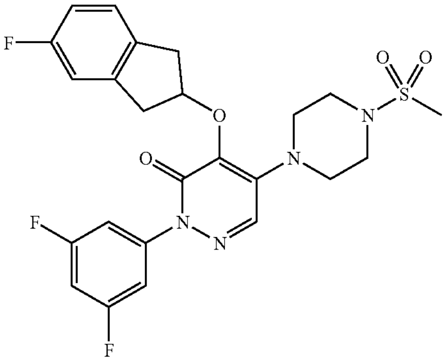 | 521 |
| 1188Z | 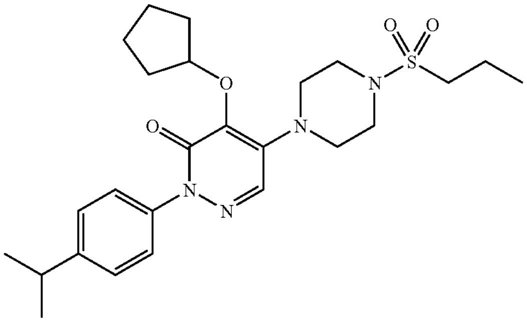 | 489 |
| 1189Z | 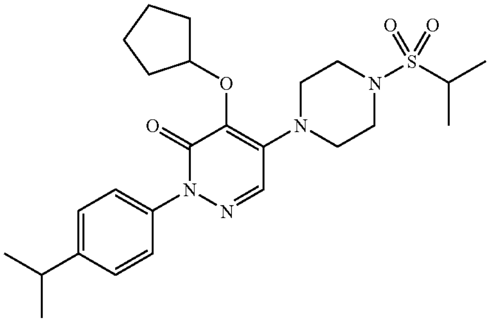 | 489 |

TABLE 11-continued
| Comp. No. | Structure | MS M + 1 |
|---|---|---|
| Oxygen Linked Analogs with Sulfonamide The following compounds can be synthesized using steps 1, 2, 4, 6, and 9 of Scheme 1 or steps 11, 12, and 14 of Scheme 2. | | |
| 1190Z | 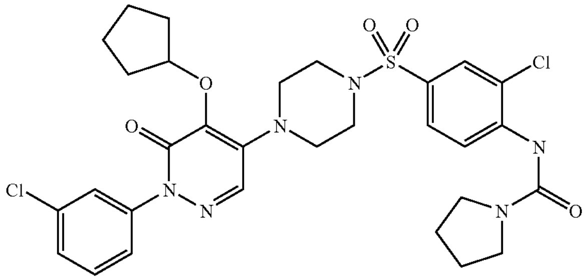 | 677 (M + OH) |
| 1191Z | 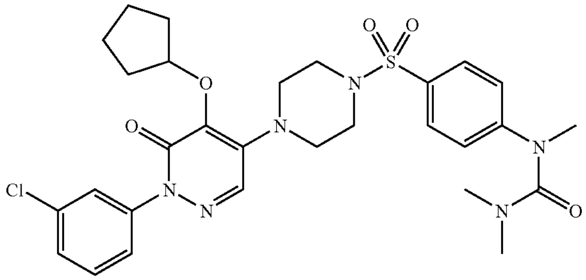 | 616 |
| 1192Z | 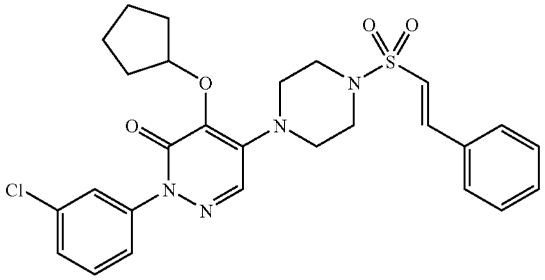 | 541 |
| 1193Z | 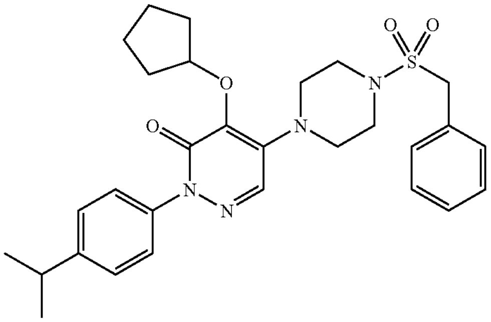 | 537 |

TABLE 11-continued
| Comp. No. | Structure | MS M + 1 |
|---|---|---|
| | Oxygen Linked Analogs with Sulfonamide The following compounds can be synthesized using steps 1, 2, 4, 6, and 9 of Scheme 1 or steps 11, 12, and 14 of Scheme 2. | |
| 1194Z | 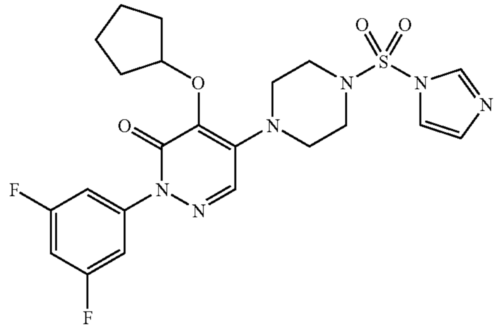 | 507 |
| 1195Z | 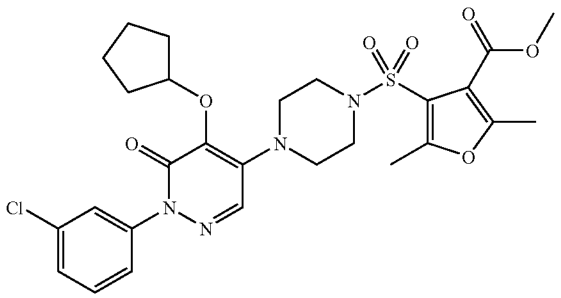 | 592 |
| 1196Z | 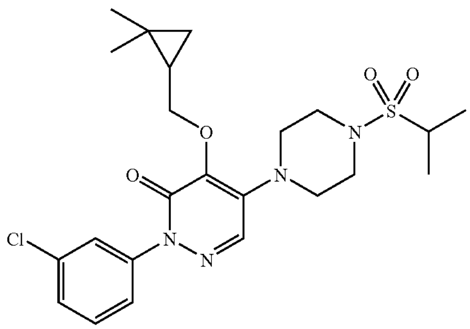 | 495 |
| 1197Z | 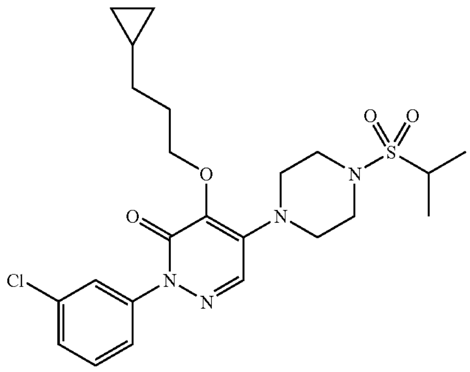 | 495 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1198Z | 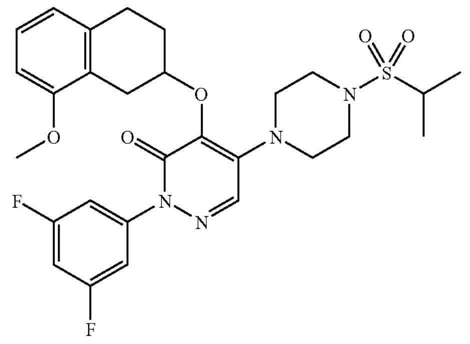 | 575 |
| 1199Z | 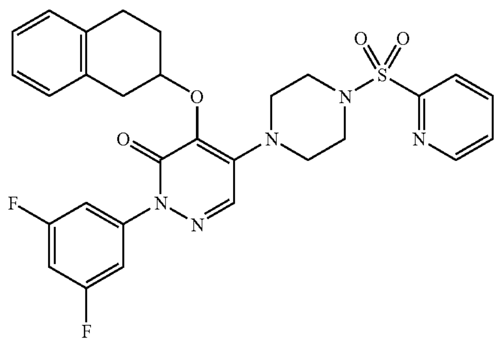 | 580 |
| 1200Z | 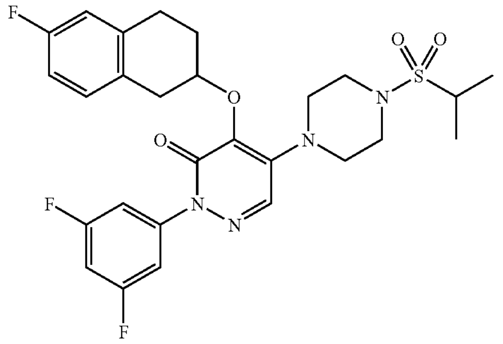 | 563 |
| 1201Z | 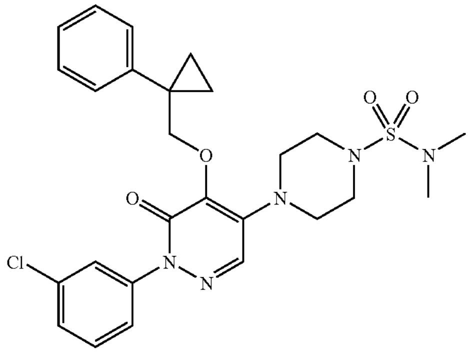 | 544 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1202Z | 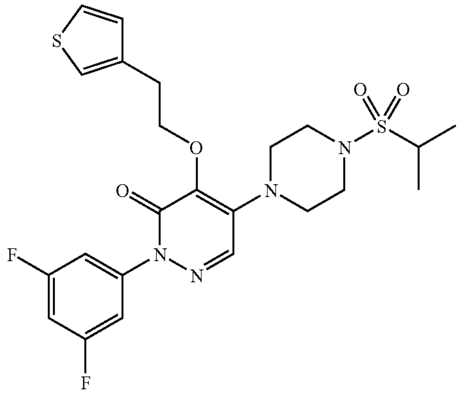 | 525 |
| 1203Z | 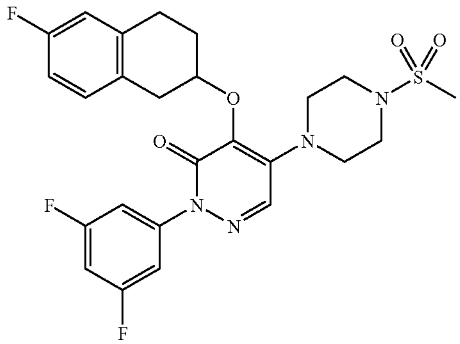 | 535 |
| 1204Z | 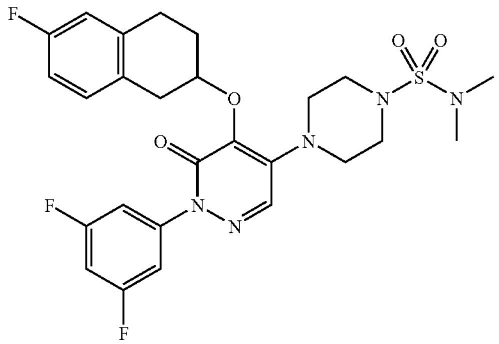 | 564 |
| 1205Z | 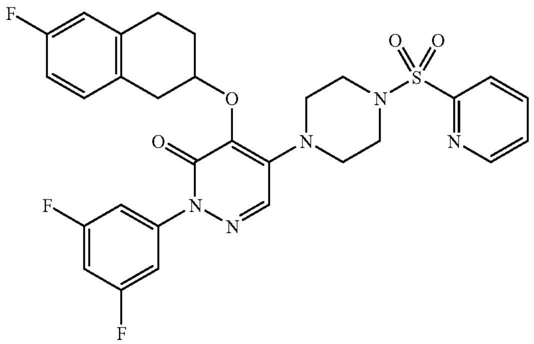 | 598 |

TABLE 11-continued
| Comp. No. | Structure | MS M + 1 |
|---|---|---|
| | Oxygen Linked Analogs with Sulfonamide The following compounds can be synthesized using steps 1, 2, 4, 6, and 9 of Scheme 1 or steps 11, 12, and 14 of Scheme 2. | |
| 1206Z | 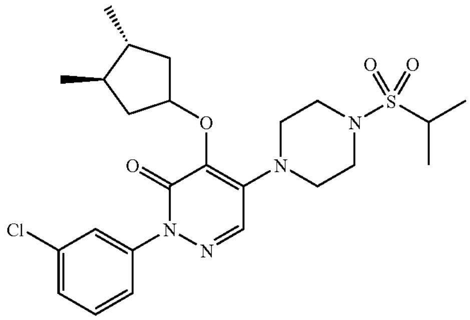 | 509 |
| 1207Z | 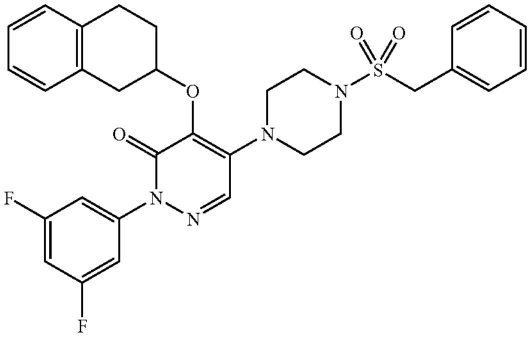 | 593 |
| 1208Z | 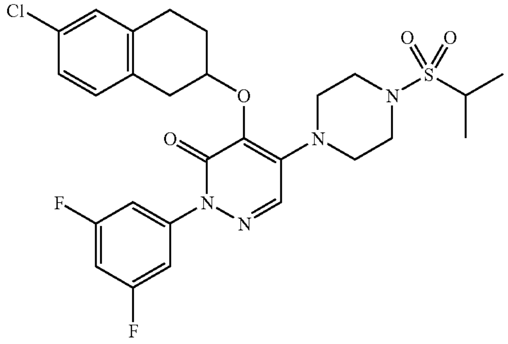 | 579 |
| 1209Z | 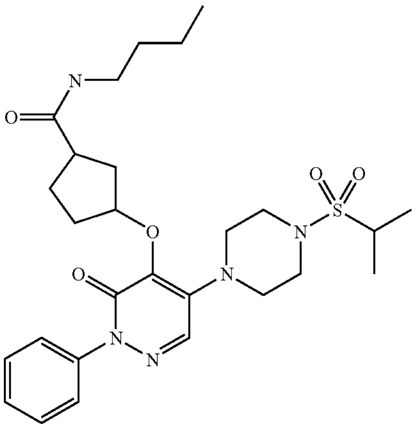 | 546 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1210Z | 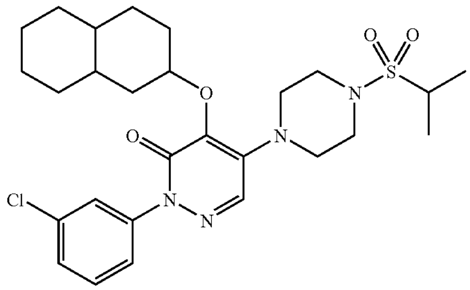 | 549 |
| 1211Z | 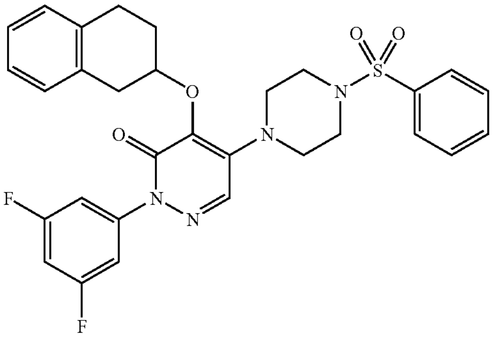 | 579 |
| 1212Z | 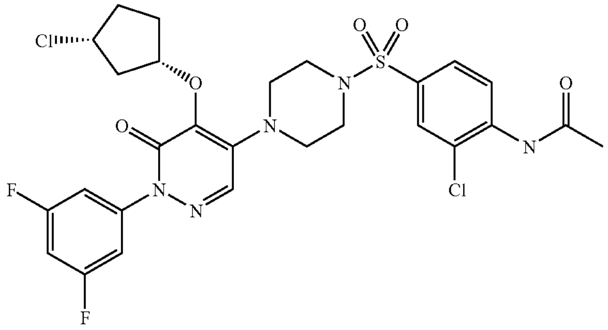 | 642 |
| 1213Z | 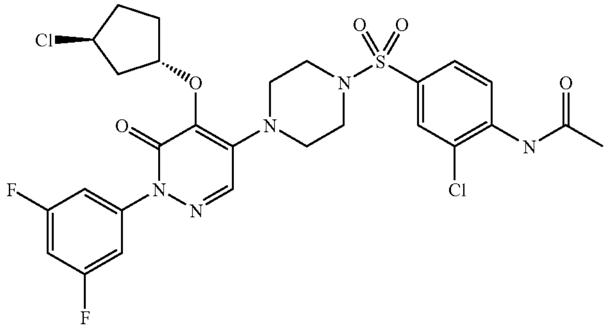 | 642 |

TABLE 11-continued
| Comp. No. | Structure | MS M + 1 |
|---|---|---|
| | Oxygen Linked Analogs with Sulfonamide<br>The following compounds can be synthesized using steps 1, 2, 4, 6, and 9 of Scheme 1 or steps 11, 12, and 14 of Scheme 2. | |
| 1214Z | 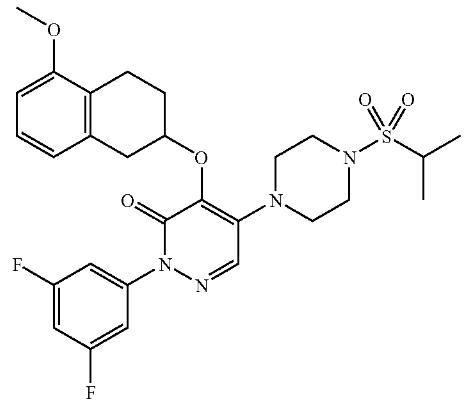 | 575 |
| 1215Z | 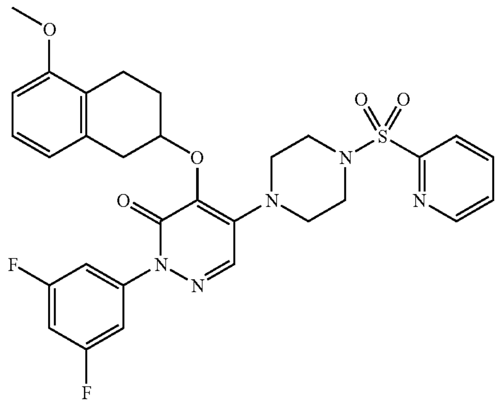 | 610 |
| 1216Z | 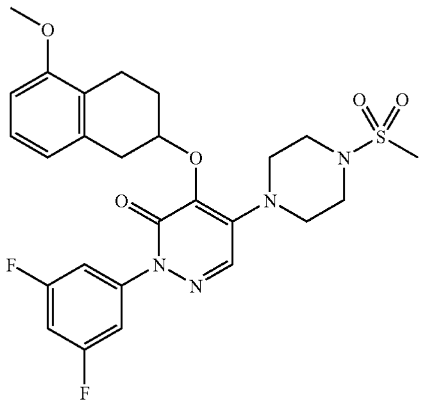 | 547 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1217Z | 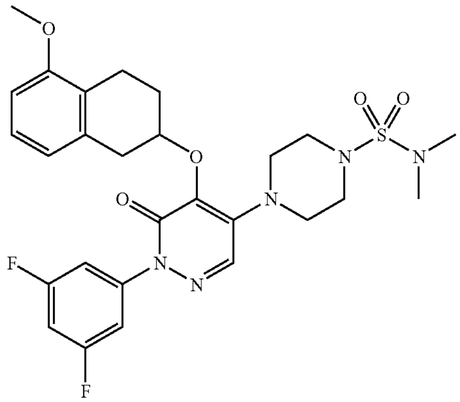 | 576 |
| 1218Z | 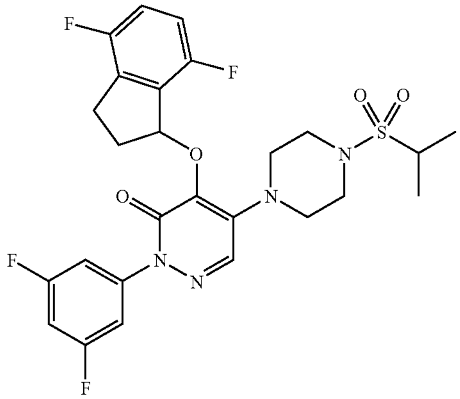 | 567 |
| 1219Z | 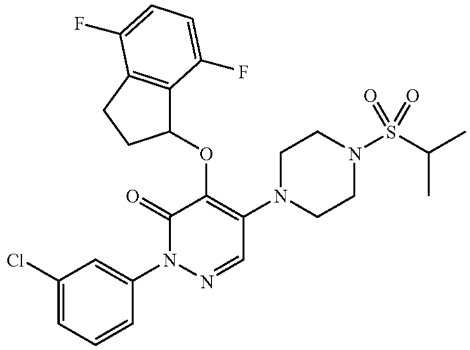 | 565 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
| --- | --- | --- |
| 1220Z | 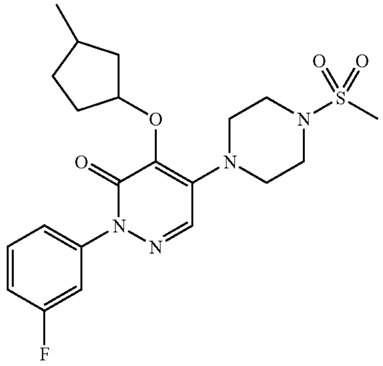 | 451 |
| 1221Z | 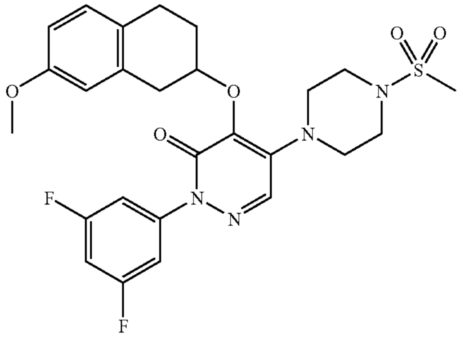 | 547 |
| 1222Z | 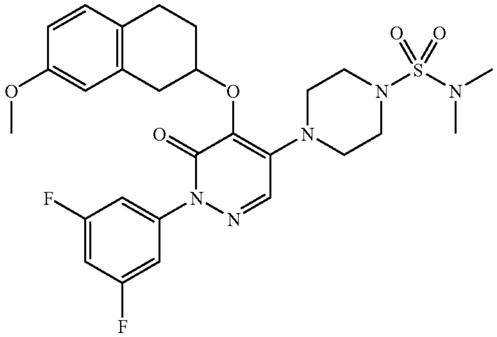 | 576 |
| 1223Z | 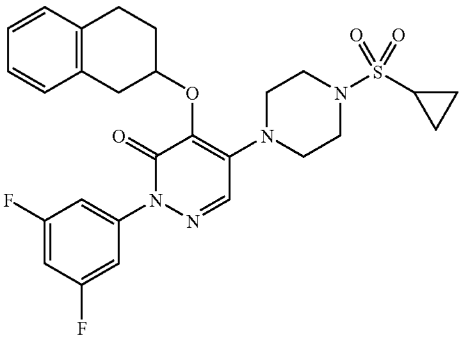 | 543 |

TABLE 11-continued
| Comp. No. | Structure | MS M + 1 |
|---|---|---|
| | Oxygen Linked Analogs with Sulfonamide The following compounds can be synthesized using steps 1, 2, 4, 6, and 9 of Scheme 1 or steps 11, 12, and 14 of Scheme 2. | |
| 1224Z | 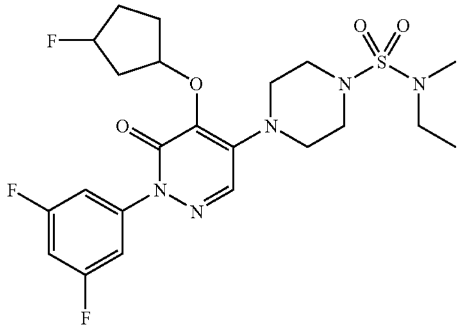 | 516 |
| 1225Z | 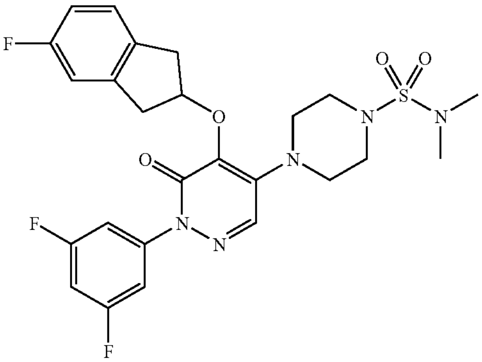 | 550 |
| 1226Z | 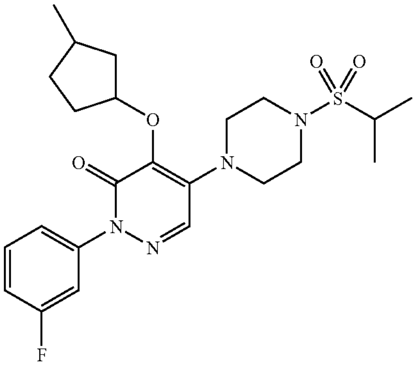 | 479 |
| 1227Z | 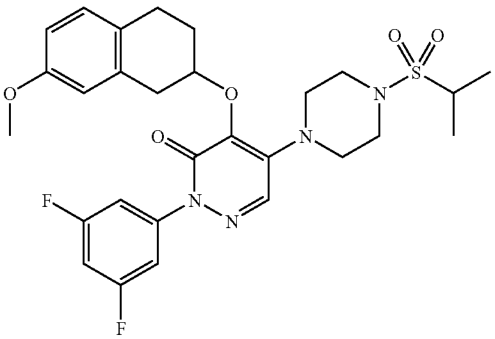 | 575 |

TABLE 11-continued
| Comp. No. | Structure | MS M + 1 |
|---|---|---|
| 1228Z | 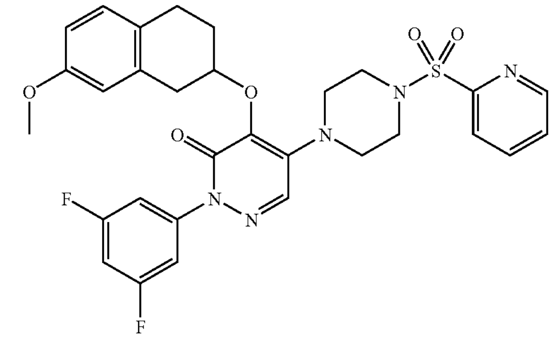 | 610 |
| 1229Z | 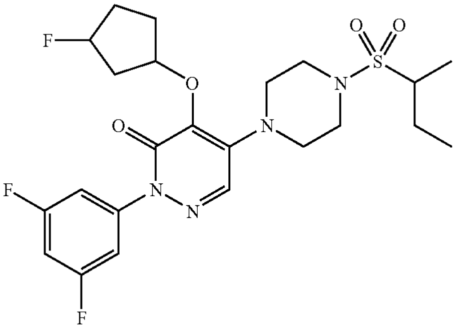 | 515 |
| 1230Z | 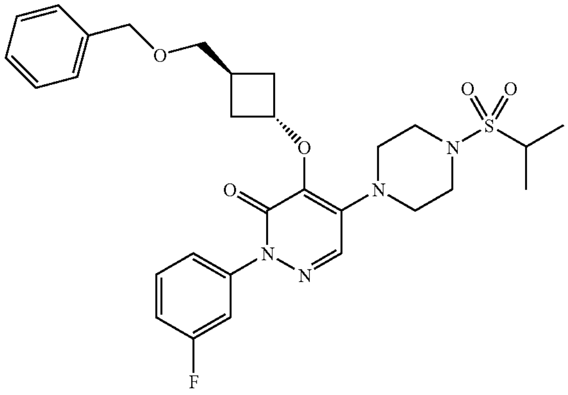 | 571 |
| 1231Z | 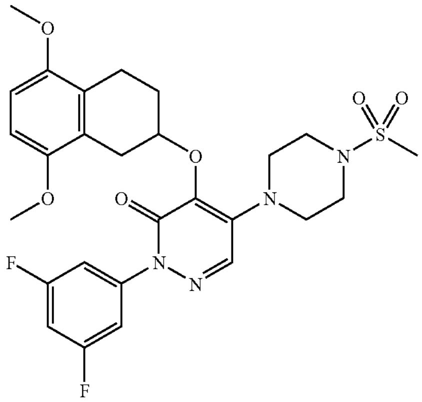 | 577 |
Oxygen Linked Analogs with Sulfonamide
The following compounds can be synthesized using steps 1, 2, 4, 6, and 9 of Scheme 1 or steps 11, 12, and 14 of Scheme 2.

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1232Z | 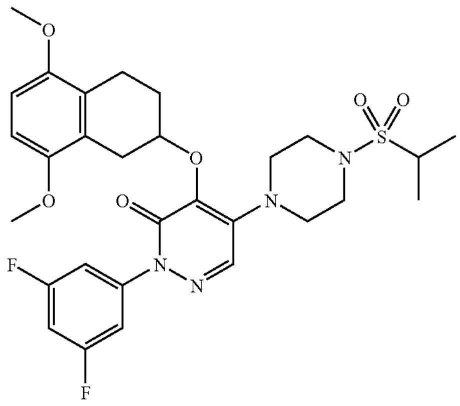 | 605 |
| 1233Z | 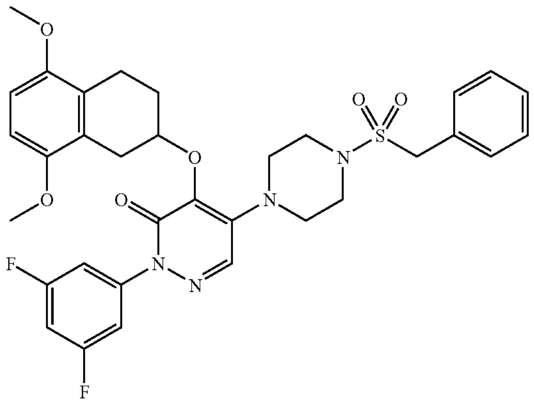 | 653 |
| 1234Z | 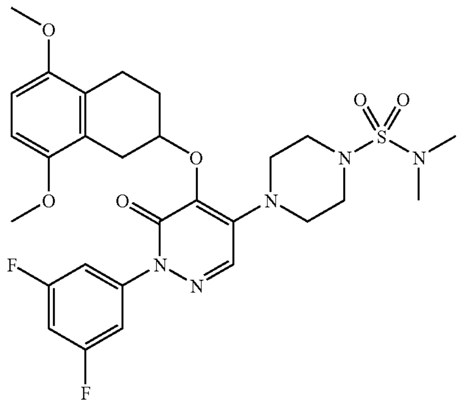 | 606 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1235Z | 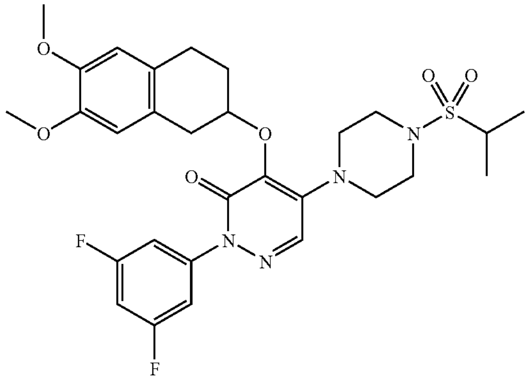 | 605 |
| 1236Z | 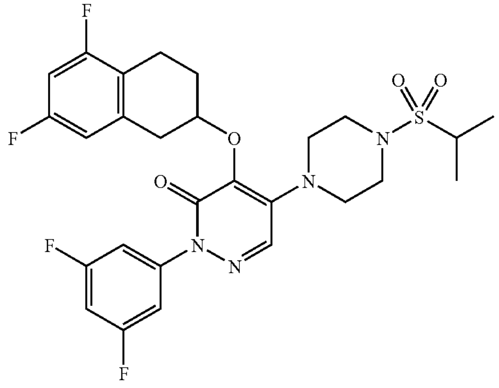 | 581 |
| 1237Z | 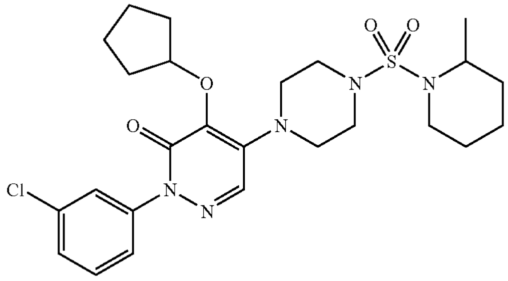 | 536 |
| 1238Z | 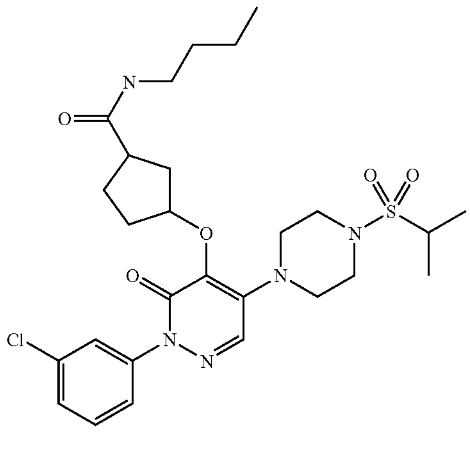 | 580 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1239Z | 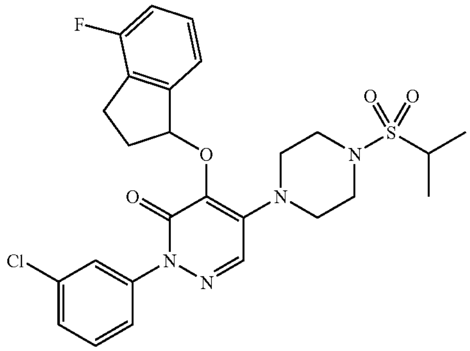 | 547 |
| 1240Z | 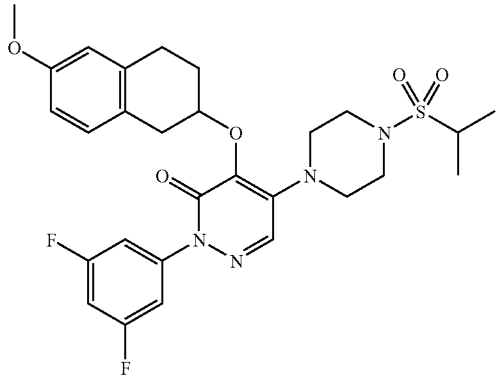 | 575 |
| 1241Z | 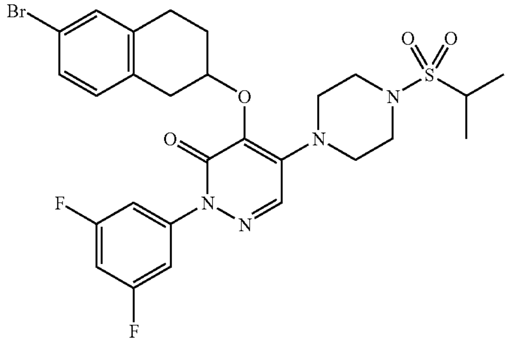 | 623 |
| 1242Z | 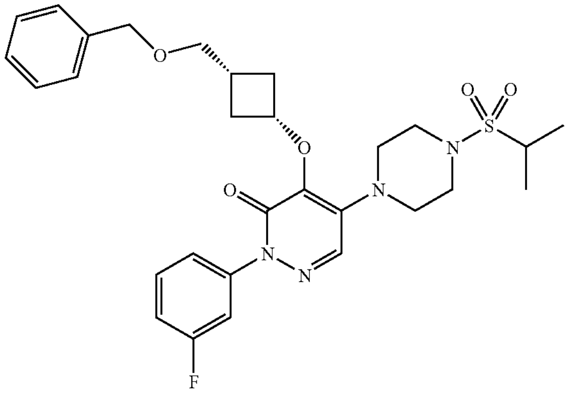 | 571 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1243Z | 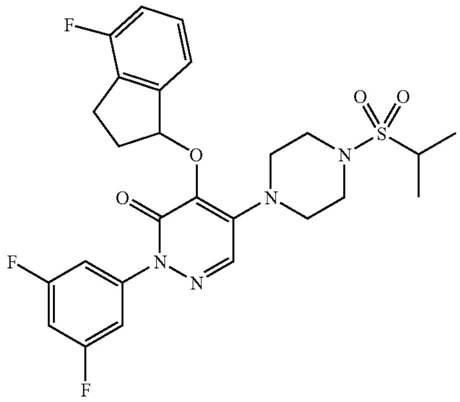 | 549 |
| 1244Z | 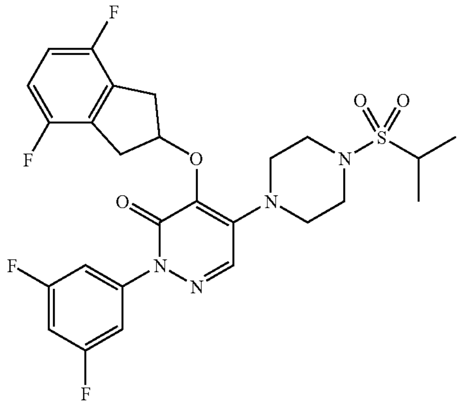 | 567 |
| 1245Z | 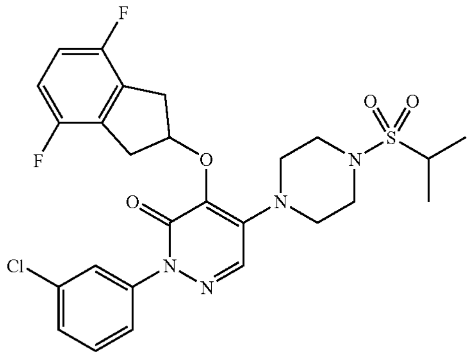 | 565 |
| 1246Z | 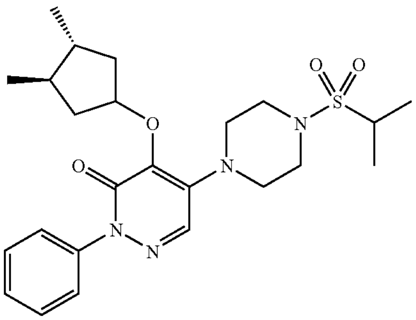 | 475 |

TABLE 11-continued
| Comp. No. | Structure | MS M + 1 |
| --- | --- | --- |
| | Oxygen Linked Analogs with Sulfonamide The following compounds can be synthesized using steps 1, 2, 4, 6, and 9 of Scheme 1 or steps 11, 12, and 14 of Scheme 2. | |
| 1247Z | 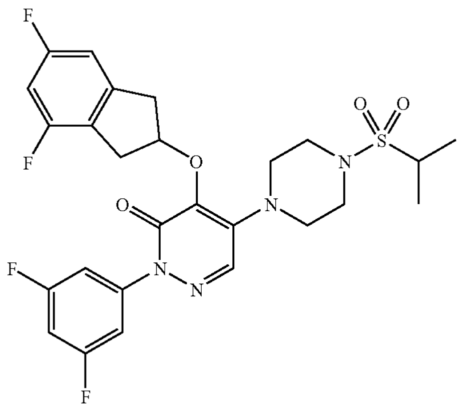 | 567 |
| 1248Z | 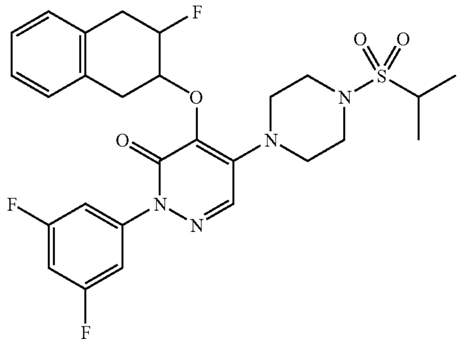 | 563 |
| 1249Z | 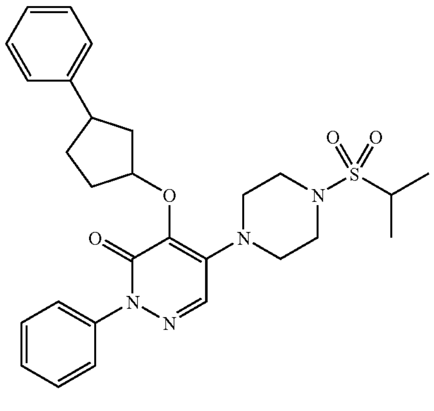 | 523 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1250Z | 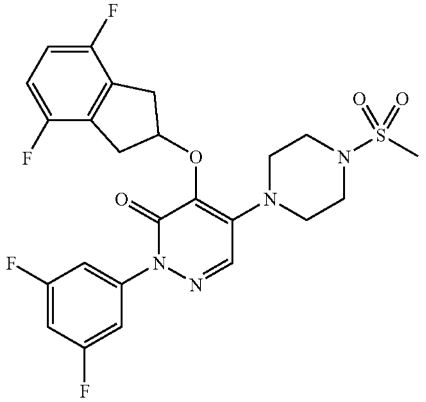 | 539 |
| 1251Z | 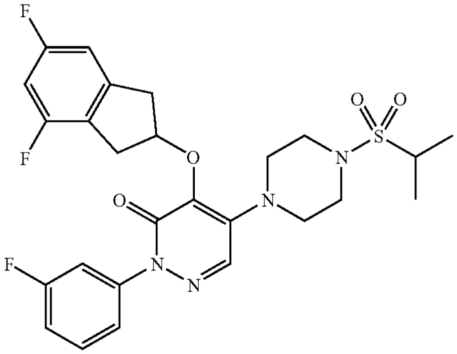 | 549 |
| 1252Z | 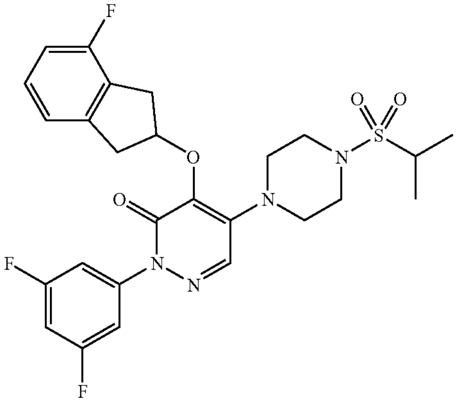 | 549 |
| 1253Z | 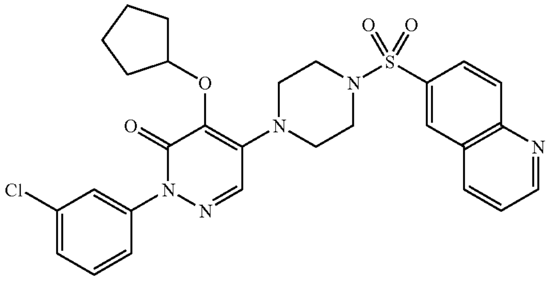 | 566 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1254Z | 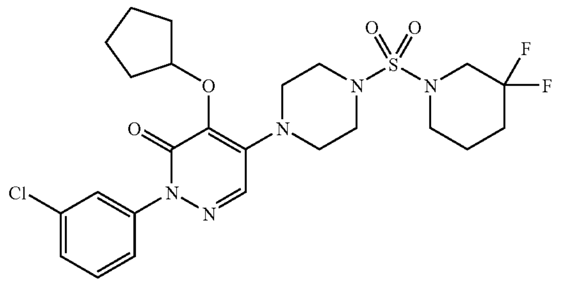 | 559 |
| 1255Z | 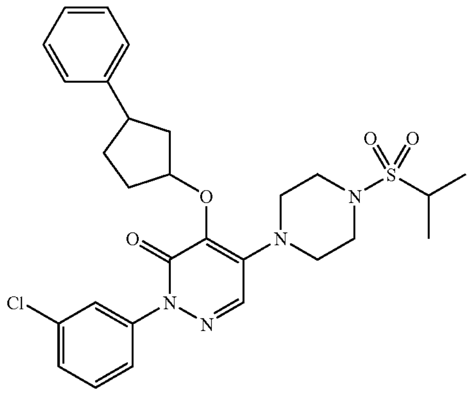 | 557 |
| 1256Z | 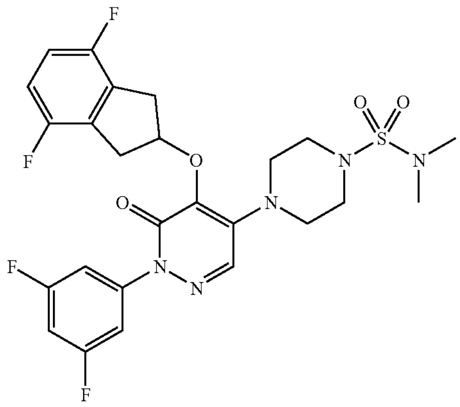 | 568 |
| 1257Z | 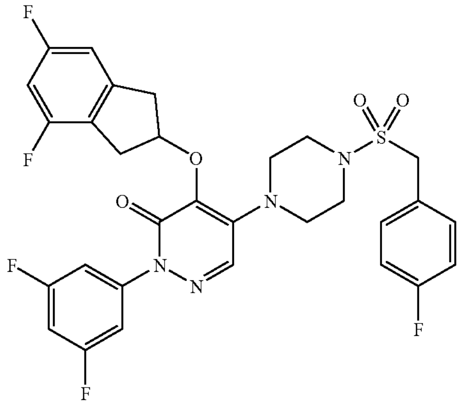 | 633 |

TABLE 11-continued
| Comp. No. | Oxygen Linked Analogs with Sulfonamide<br>The following compounds can be synthesized using steps 1, 2, 4, 6, and 9 of Scheme 1 or steps 11, 12, and 14 of Scheme 2.<br>Structure | MS M + 1 |
|---|---|---|
| 1258Z | 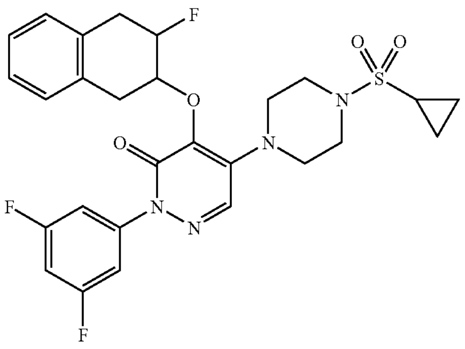 | 561 |
| 1259Z | 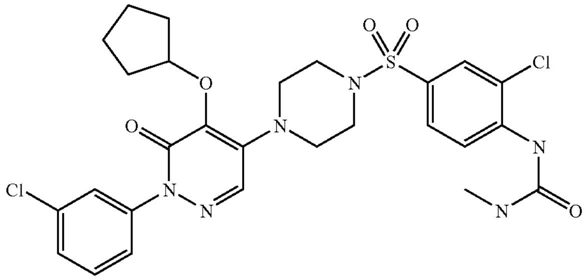 | 621 |
| 1260Z | 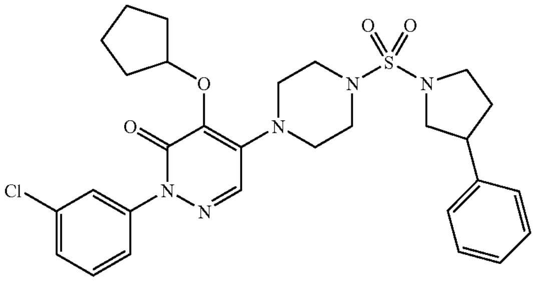 | 584 |
| 1261Z | 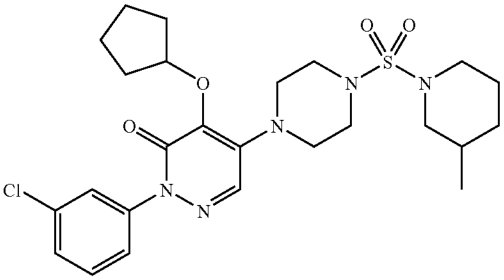 | 536 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1262Z | 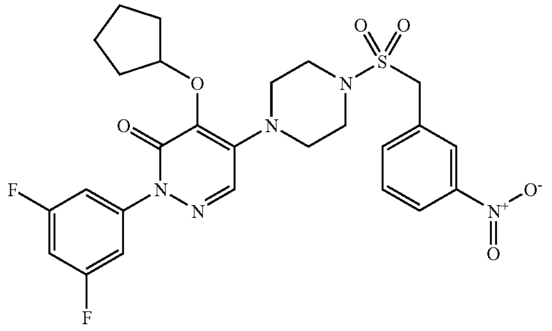 | 576 |
| 1263Z | 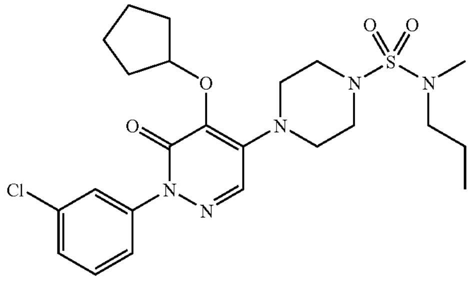 | 510 |
| 1264Z | 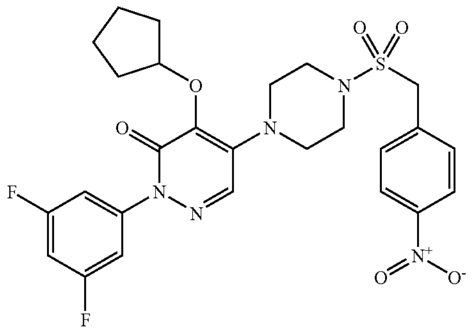 | 576 |
| 1265Z | 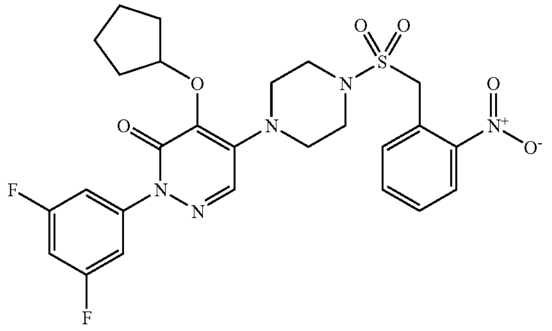 | 576 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1266Z | 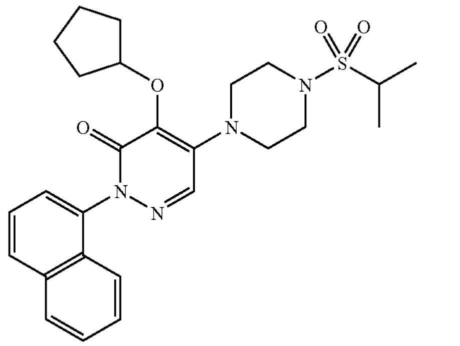 | 497 |
| 1267Z | 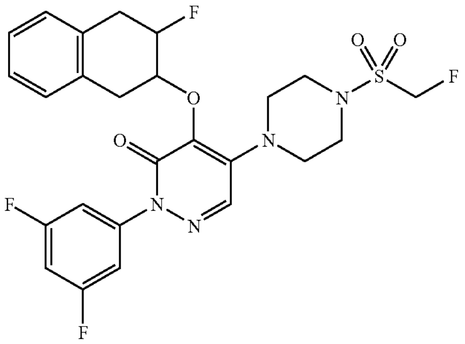 | 553 |
| 1268Z | 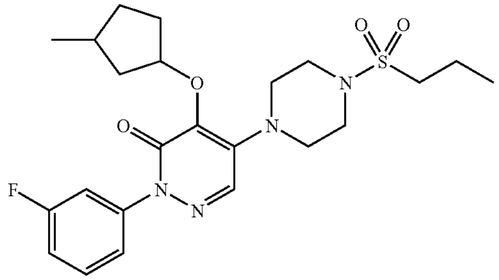 | 479 |
| 1269Z | 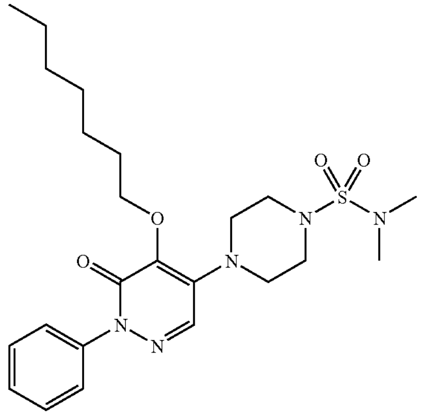 | 478 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1270Z | 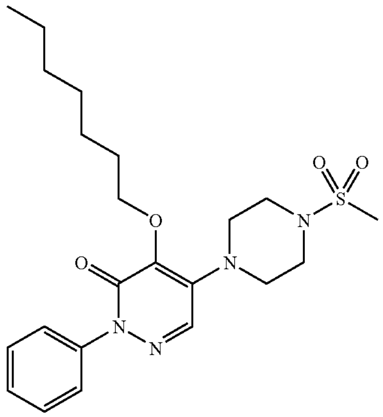 | 449 |
| 1271Z | 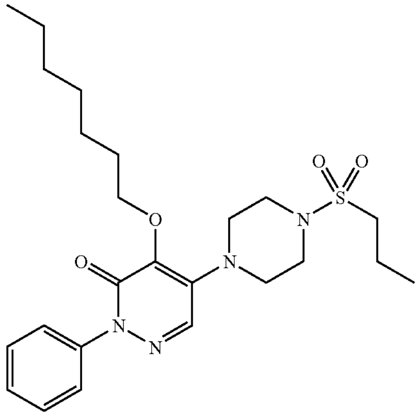 | 477 |
| 1272Z | 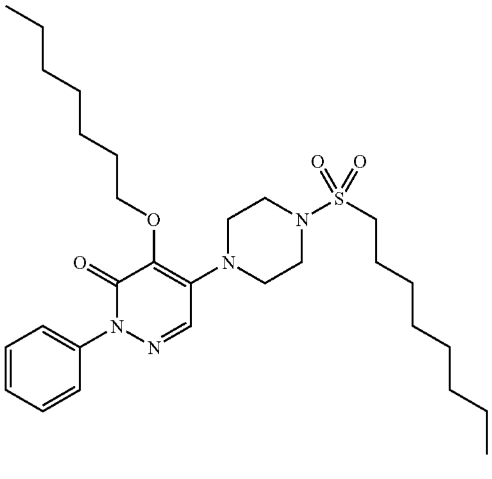 | 547 |

TABLE 11-continued
| Comp. No. | Structure | MS M + 1 |
|---|---|---|
| | Oxygen Linked Analogs with Sulfonamide<br>The following compounds can be synthesized using steps 1, 2, 4, 6, and 9 of Scheme 1 or steps 11, 12, and 14 of Scheme 2. | |
| 1273Z | 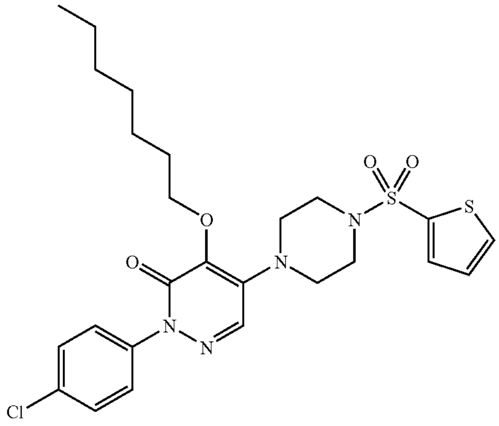 | 551 |
| 1274Z | 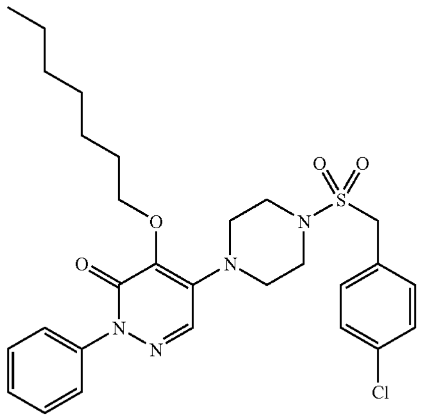 | 559 |
| 1275Z | 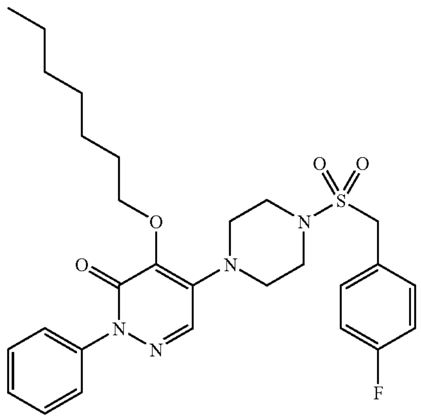 | 543 |

TABLE 11-continued
| Comp. No. | Structure | MS M + 1 |
|---|---|---|
| Oxygen Linked Analogs with Sulfonamide. The following compounds can be synthesized using steps 1, 2, 4, 6, and 9 of Scheme 1 or steps 11, 12, and 14 of Scheme 2. | | |
| 1276Z | 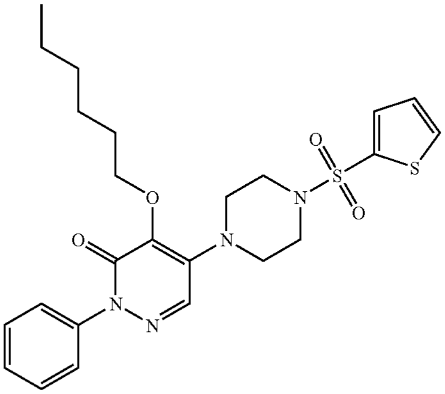 | 503 |
| 1277Z | 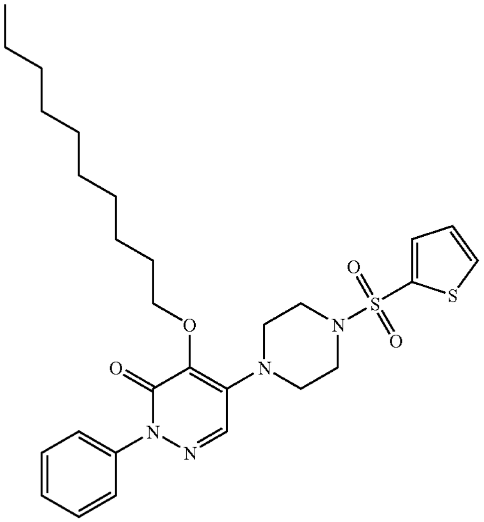 | 559 |
| 1278Z | 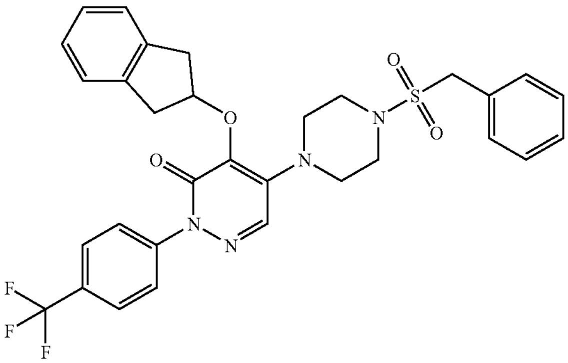 | 611 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1279Z | 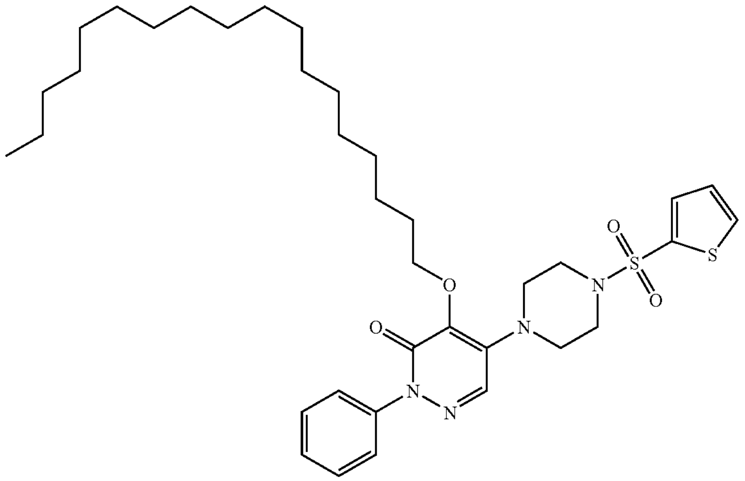 | 671 |
| 1280Z | 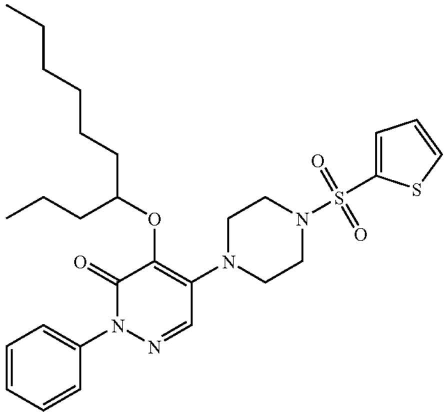 | 559 |
| 1281Z | 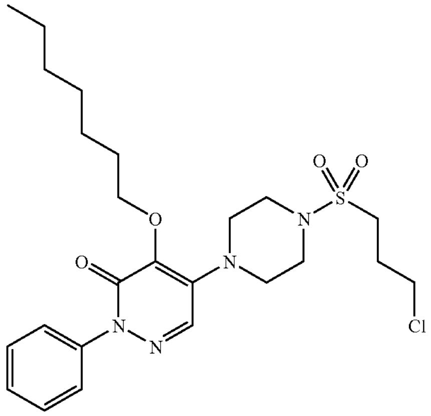 | 511 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1282Z | 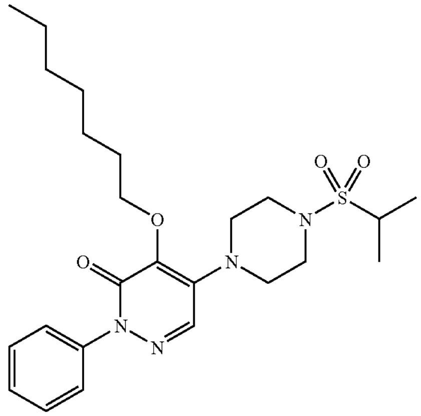 | 477 |
| 1283Z | 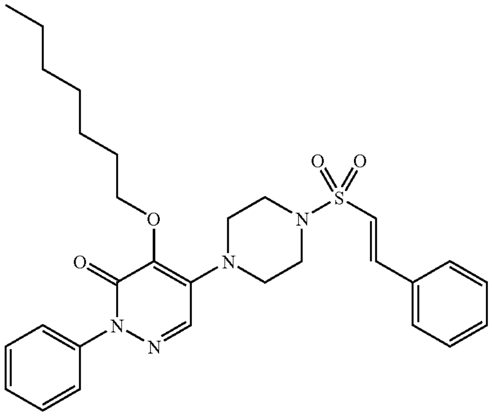 | 537 |
| 1284Z | 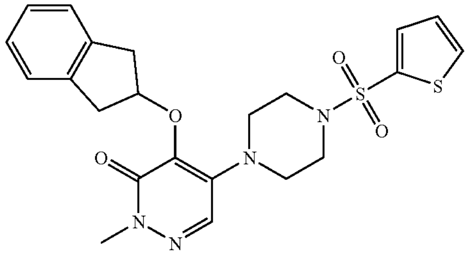 | 573 |
| 1285Z | 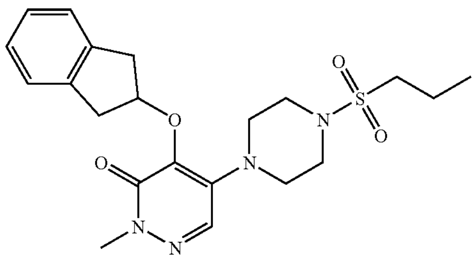 | 432 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1286Z | 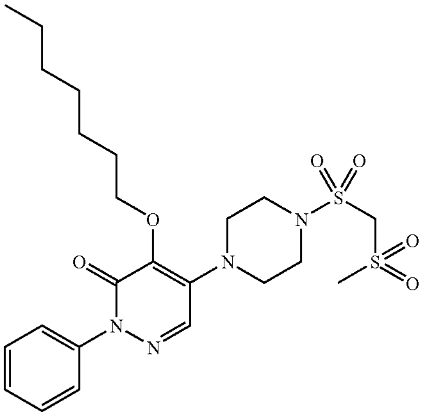 | 527 |
| 1287Z | 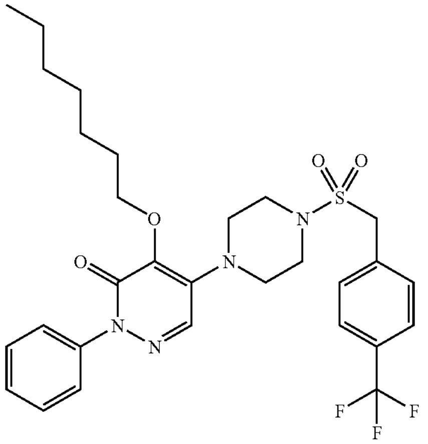 | 593 |
| 1288Z | 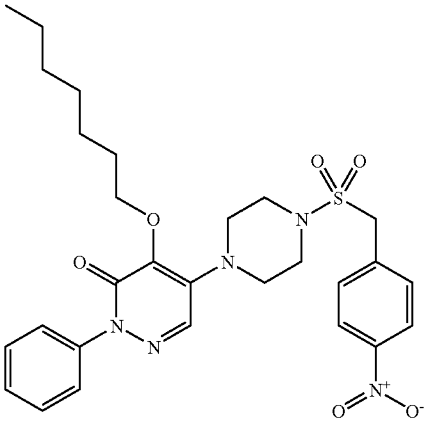 | 570 |

TABLE 11-continued
| Comp. No. | Structure | MS M + 1 |
|---|---|---|
| | Oxygen Linked Analogs with Sulfonamide<br>The following compounds can be synthesized using steps 1, 2, 4, 6, and 9 of Scheme 1 or steps 11, 12, and 14 of Scheme 2. | |
| 1289Z | 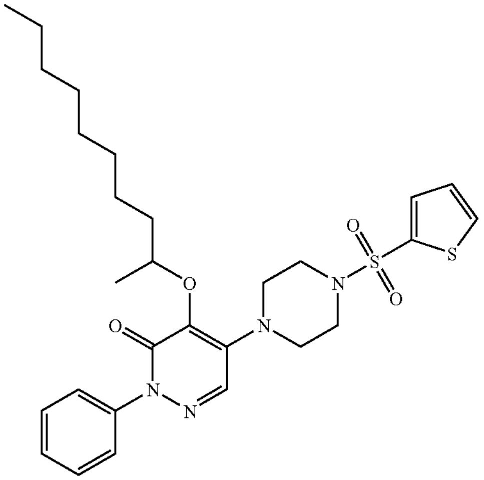 | 531 |
| 1290Z | 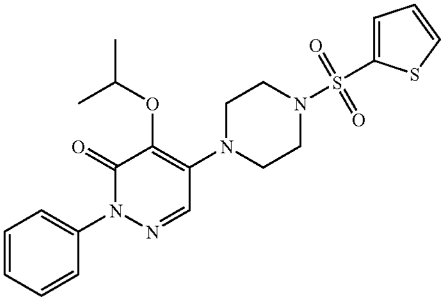 | 461 |
| 1291Z | 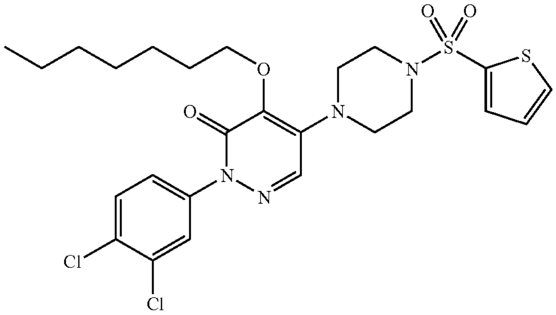 | 585 |
| 1292Z | 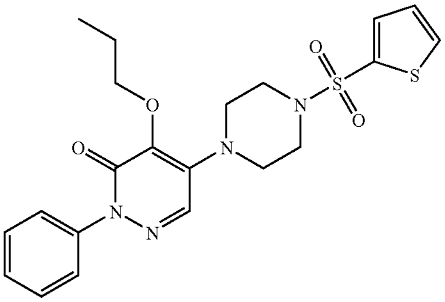 | 461 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1293Z | 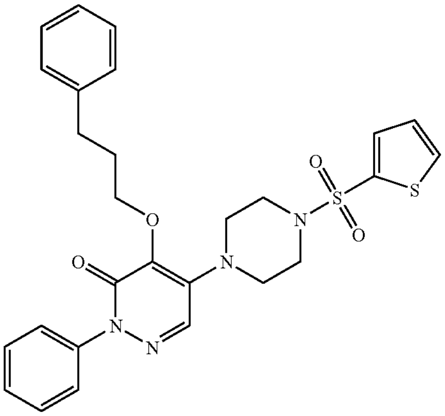 | 551 |
| 1294Z | 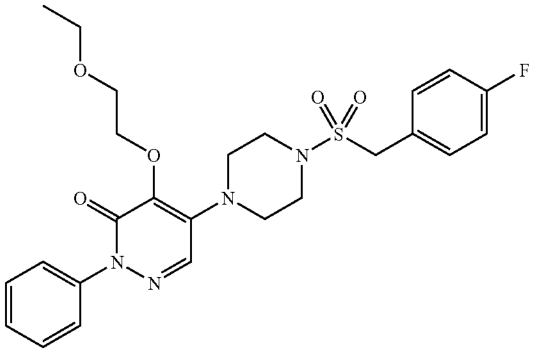 | 517 |
| 1295Z | 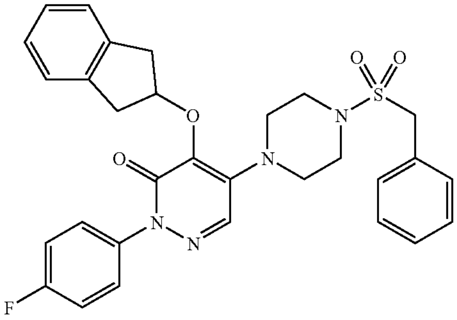 | 561 |

TABLE 11-continued
| Comp. No. | Structure | MS M + 1 |
|---|---|---|
| | Oxygen Linked Analogs with Sulfonamide<br>The following compounds can be synthesized using steps 1, 2, 4, 6, and 9 of Scheme 1 or steps 11, 12, and 14 of Scheme 2. | |
| 1296Z | 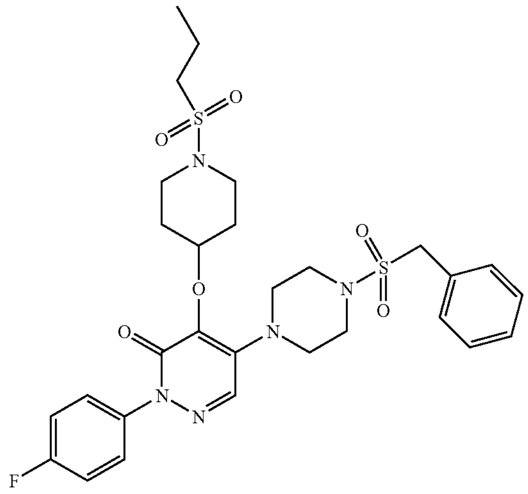 | 634 |
| 1297Z | 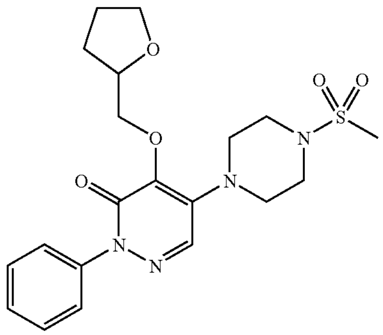 | 435 |
| 1298Z | 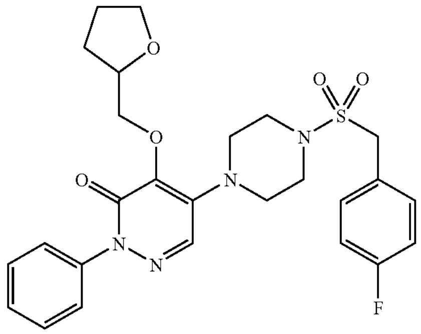 | 529 |
| 1299Z | 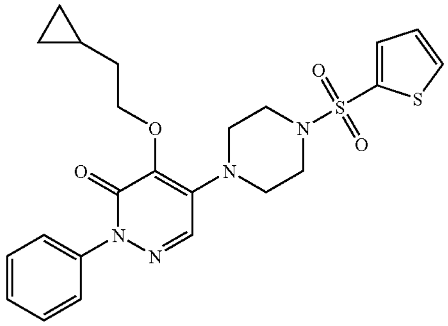 | 487 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1300Z | 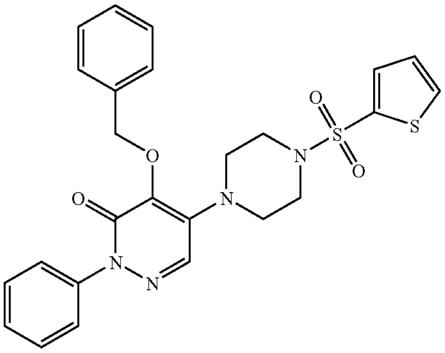 | 509 |
| 1301Z | 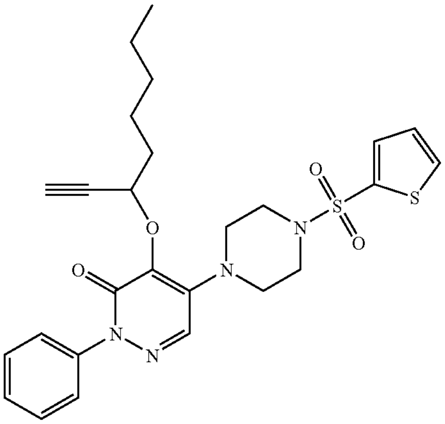 | 527 |
| 1302Z | 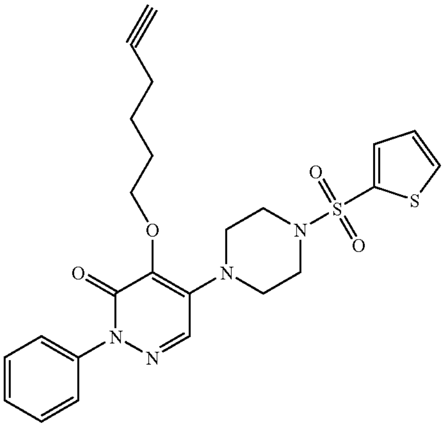 | 499 |

TABLE 11-continued
| Comp. No. | Structure | MS M + 1 |
|---|---|---|
| | Oxygen Linked Analogs with Sulfonamide<br>The following compounds can be synthesized using steps 1, 2, 4, 6, and 9 of Scheme 1 or steps 11, 12, and 14 of Scheme 2. | |
| 1303Z | 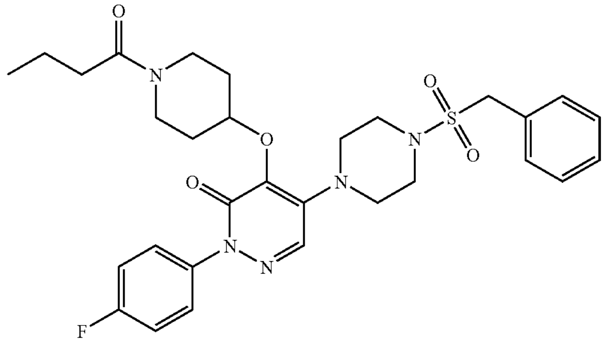 | 598 |
| 1304Z | 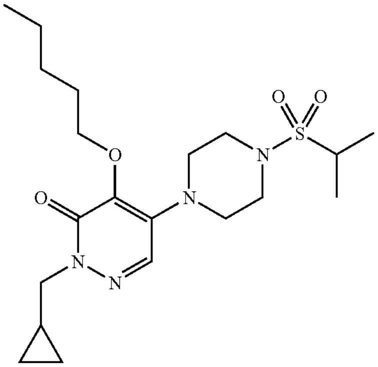 | 427 |
| 1305Z | 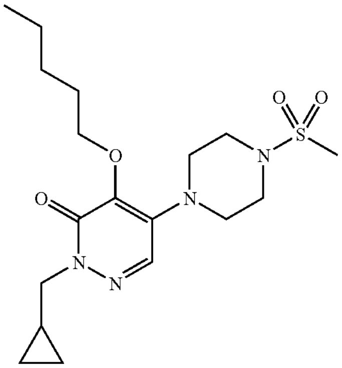 | 399 |
| 1306Z | 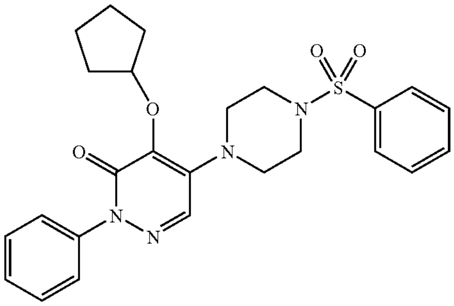 | 481 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1307Z | 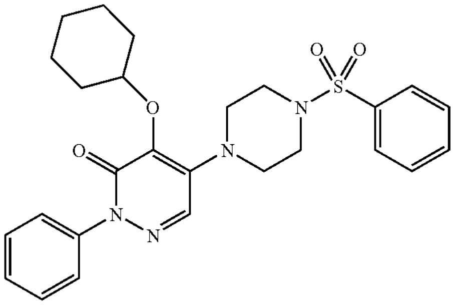 | 495 |
| 1308Z | 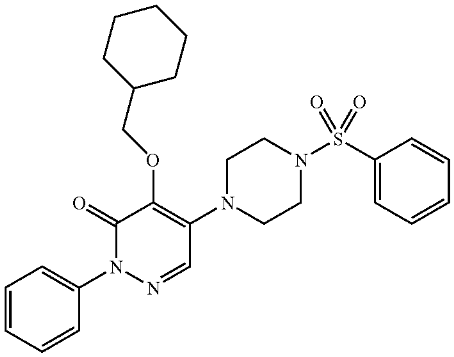 | 509 |
| 1309Z | 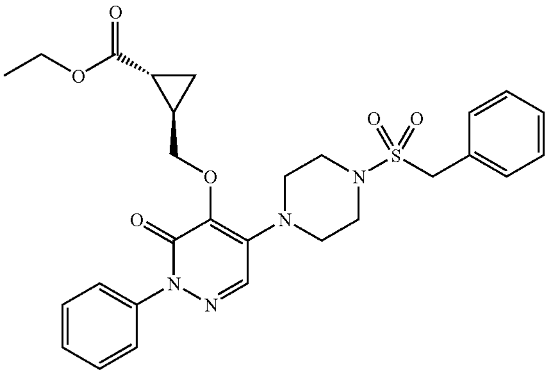 | 553 |
| 1310Z | 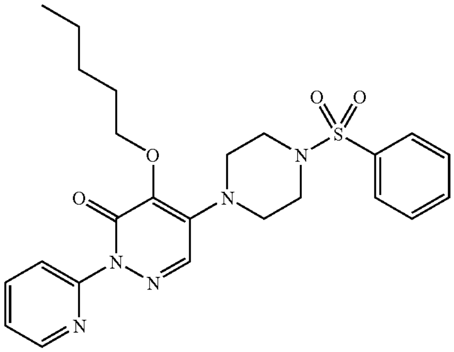 | 484 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1311Z | 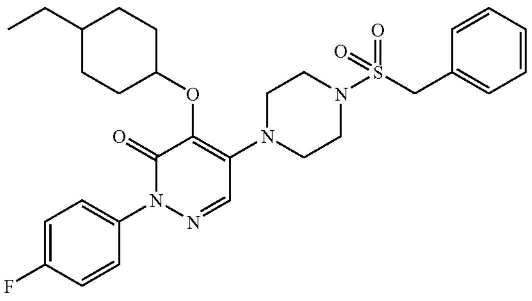 | 555 |
| 1312Z | 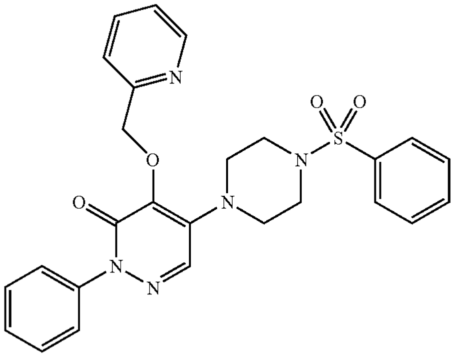 | 504 |
| 1313Z | 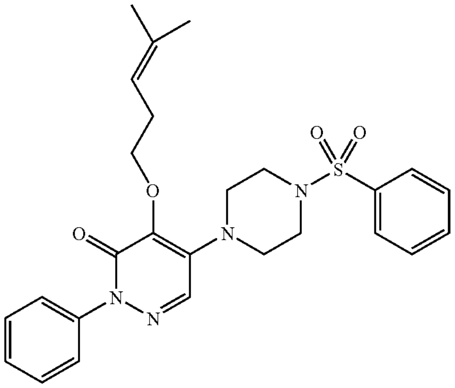 | 495 |
| 1314Z | 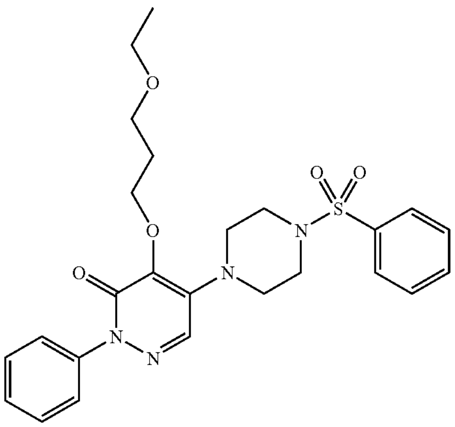 | 499 |

TABLE 11-continued
| Comp. No. | Structure | MS M + 1 |
|---|---|---|
| | Oxygen Linked Analogs with Sulfonamide<br>The following compounds can be synthesized using steps 1, 2, 4, 6, and 9 of Scheme 1 or steps 11, 12, and 14 of Scheme 2. | |
| 1315Z | 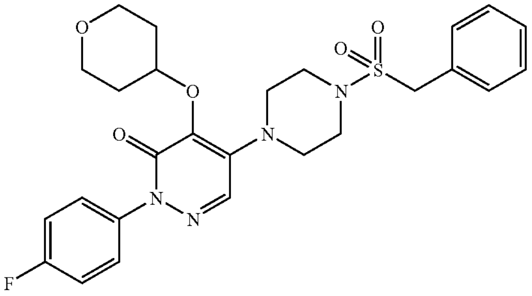 | 529 |
| 1316Z | 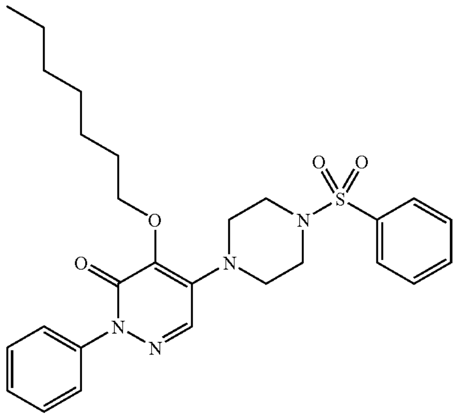 | 511 |
| 1317Z | 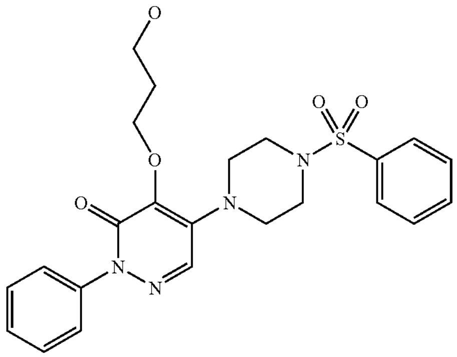 | 471 |
| 1318Z | 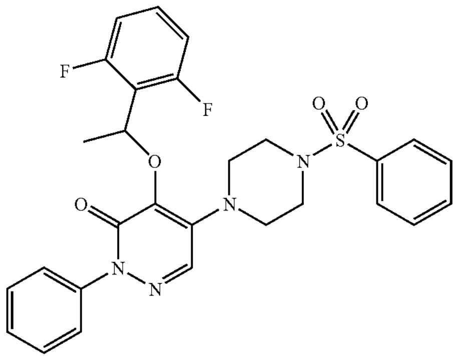 | 553 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1319Z | 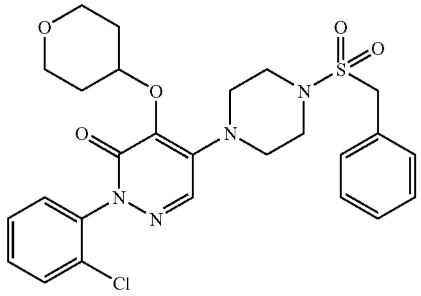 | 545 |
| 1320Z | 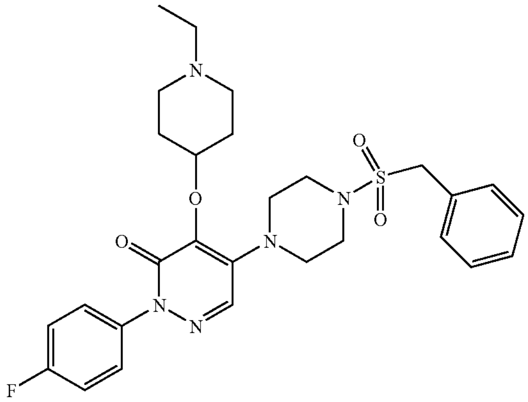 | 556 |
| 1321Z | 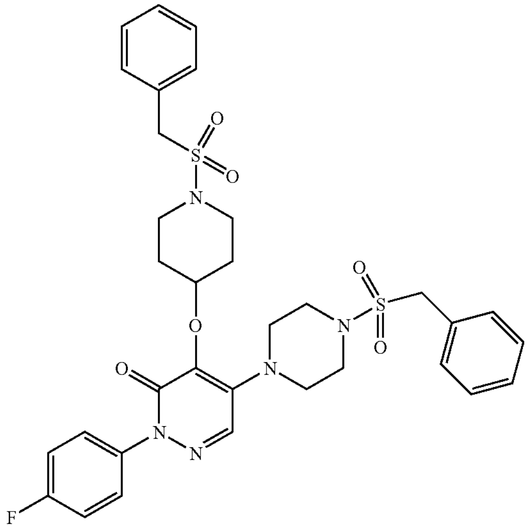 | 682 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1322Z | 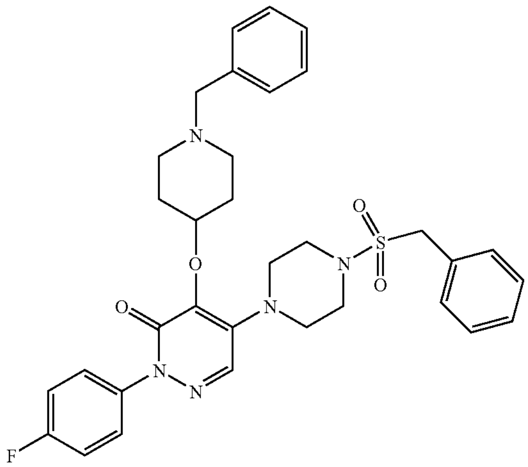 | 618 |
| 1323Z | 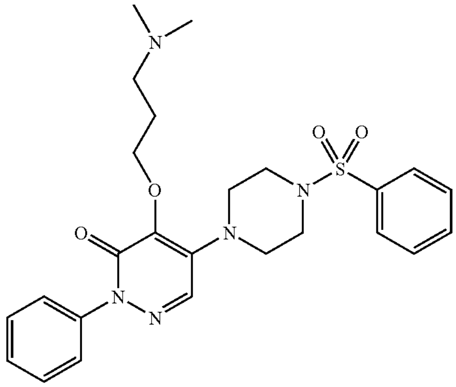 | 498 |
| 1324Z | 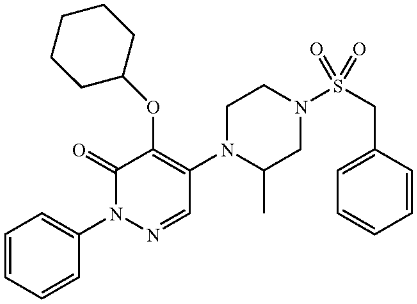 | 523 |
| 1325Z | 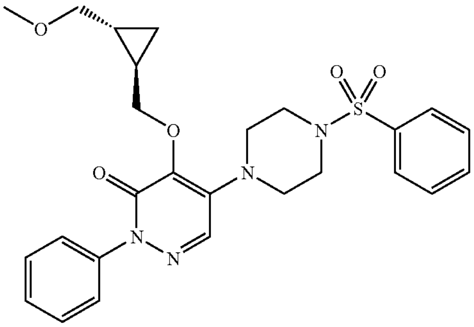 | 511 |

TABLE 11-continued
| Comp. No. | Structure | MS M + 1 |
| --- | --- | --- |
| Oxygen Linked Analogs with Sulfonamide The following compounds can be synthesized using steps 1, 2, 4, 6, and 9 of Scheme 1 or steps 11, 12, and 14 of Scheme 2. | | |
| 1326Z | 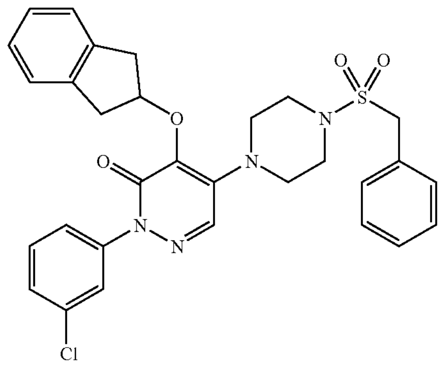 | 577 579 |
| 1327Z | 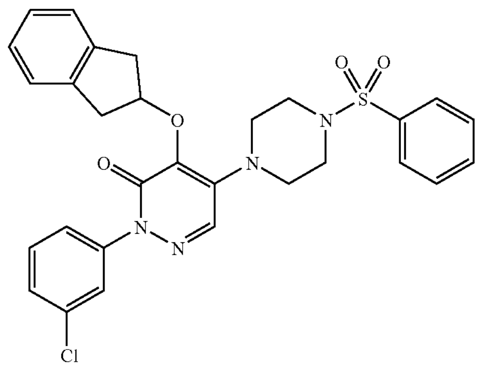 | 563 |
| 1328Z | 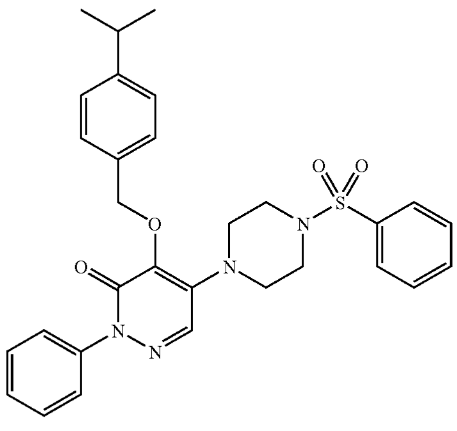 | 545 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1329Z | 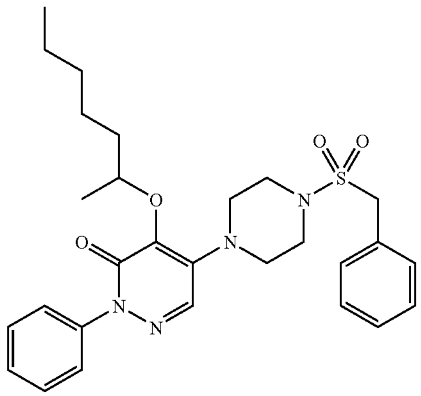 | 525 |
| 1330Z | 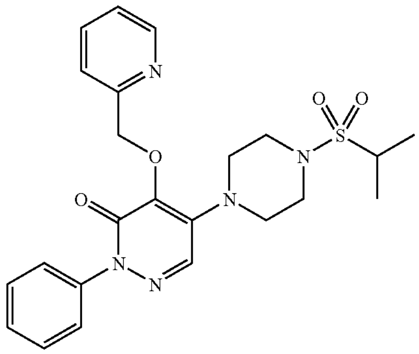 | 470 |
| 1331Z | 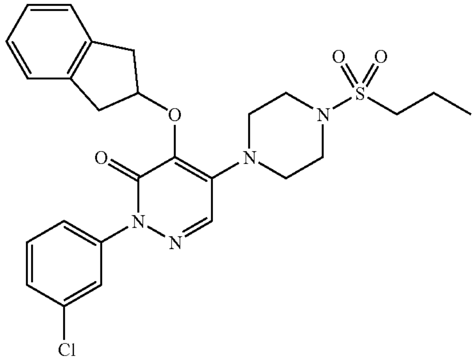 | 529 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1332Z | 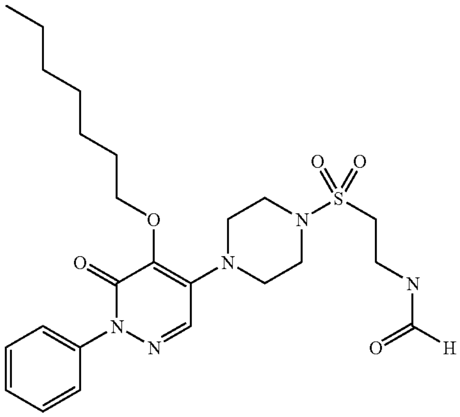 | 506 |
| 1333Z | 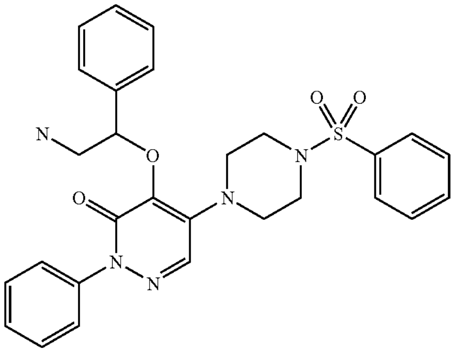 | 532 |
| 1334Z | 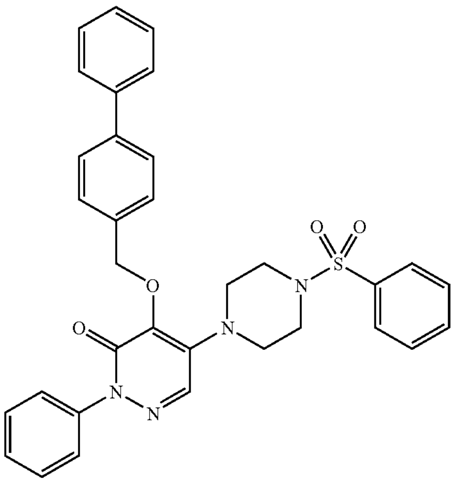 | 579 |

TABLE 11-continued
| Comp. No. | Structure | MS M + 1 |
|---|---|---|
| | Oxygen Linked Analogs with Sulfonamide The following compounds can be synthesized using steps 1, 2, 4, 6, and 9 of Scheme 1 or steps 11, 12, and 14 of Scheme 2. | |
| 1335Z | 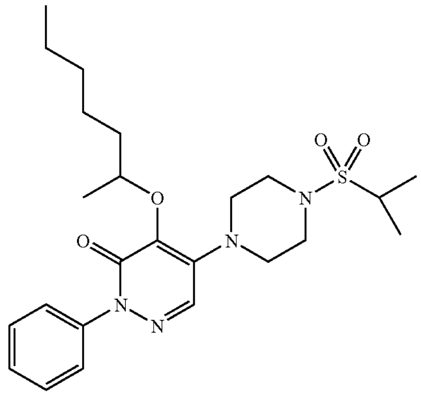 | 477 |
| 1336Z | 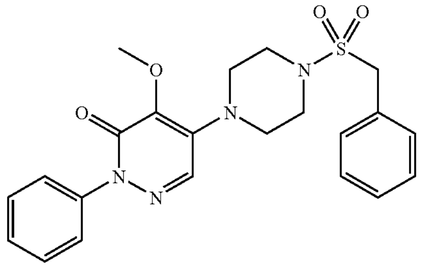 | 441 |
| 1337Z | 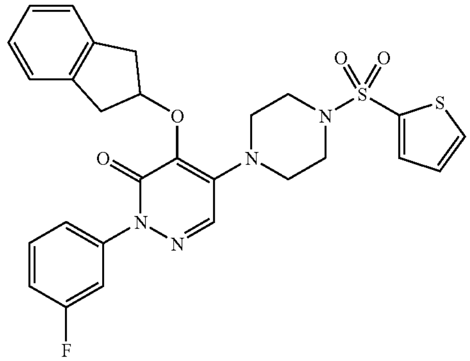 | 553 |
| 1338Z | 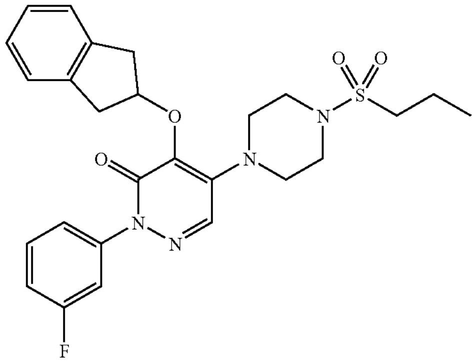 | 513 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1339Z | 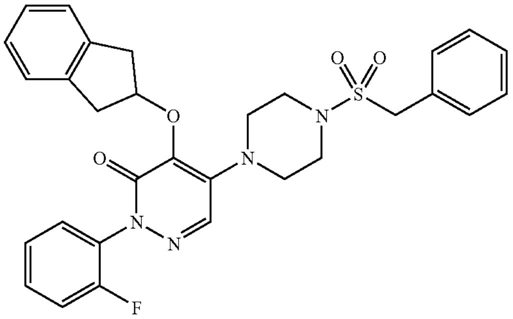 | 561 |
| 1340Z | 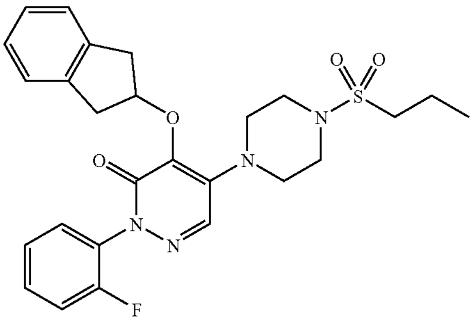 | 513 |
| 1341Z | 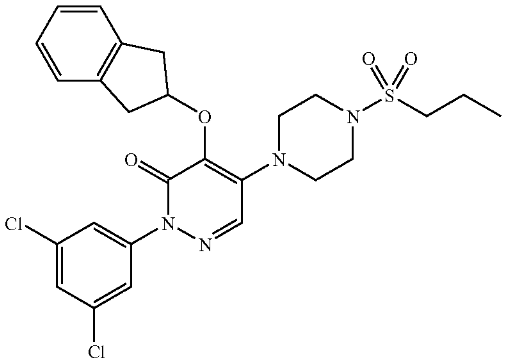 | 563 |
| 1342Z | 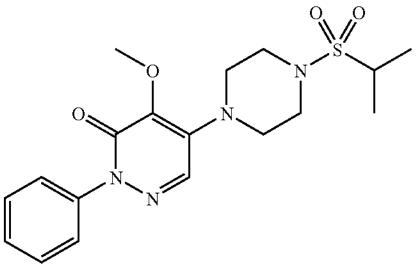 | 393 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1343Z | 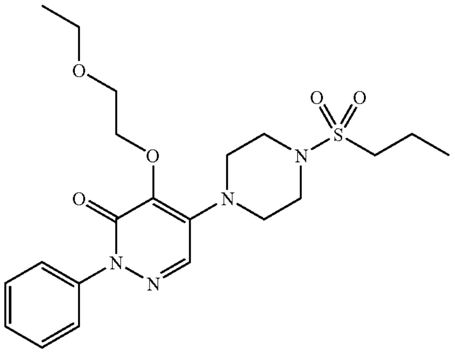 | 451 |
| 1344Z | 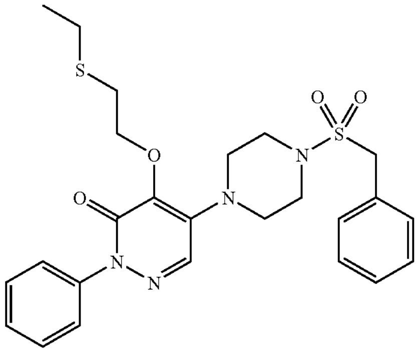 | 515 |
| 1345Z | 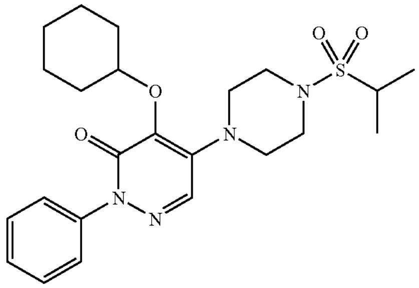 | 461 |
| 1346Z | 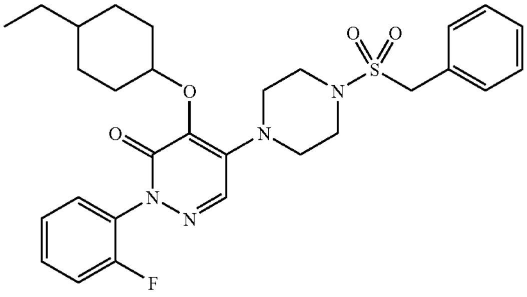 | 555 |

TABLE 11-continued
| Comp. No. | Structure | MS M + 1 |
|---|---|---|
| | Oxygen Linked Analogs with Sulfonamide<br>The following compounds can be synthesized using steps 1, 2, 4, 6, and 9 of Scheme 1 or steps 11, 12, and 14 of Scheme 2. | |
| 1347Z | 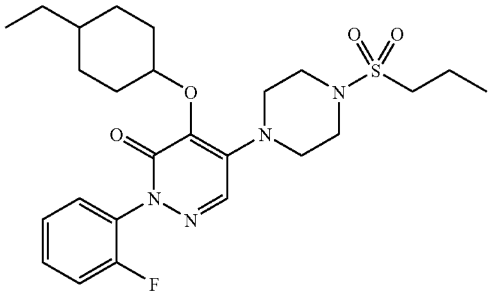 | 507 |
| 1348Z | 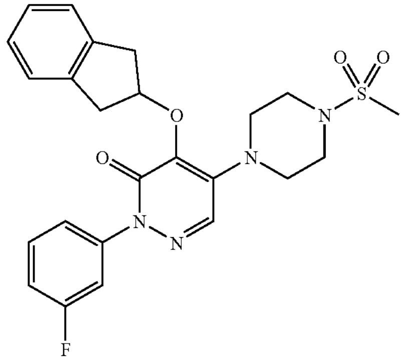 | 485 |
| 1349Z | 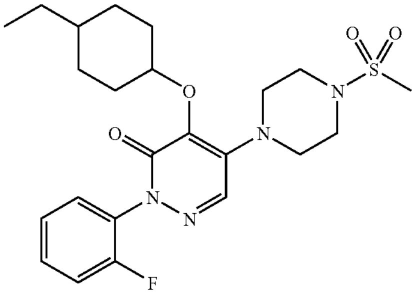 | 479 |
| 1350Z | 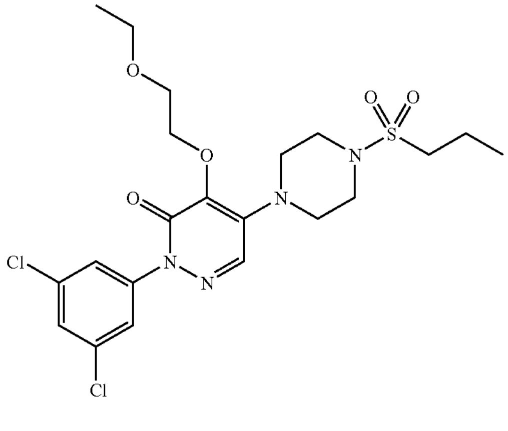 | 519 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1351Z | 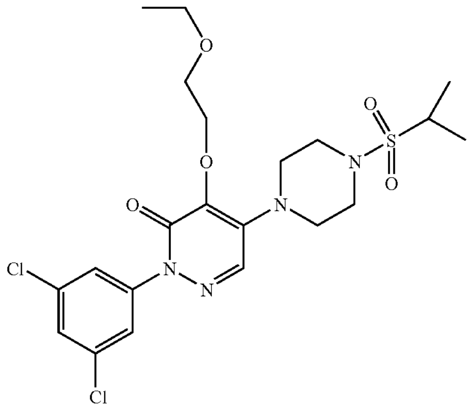 | 519 |
| 1352Z | 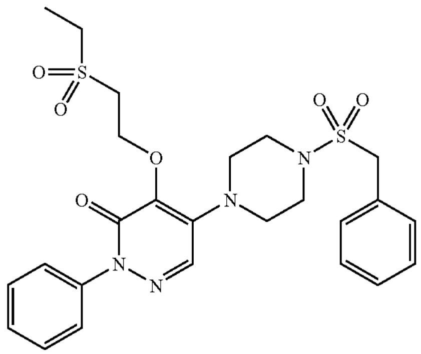 | 547 |
| 1353Z | 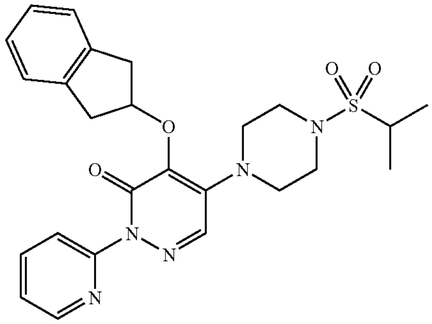 | 496 |
| 1354Z | 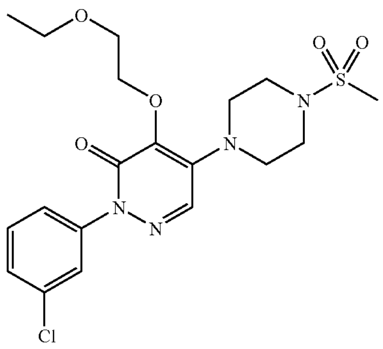 | 457 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1355Z | 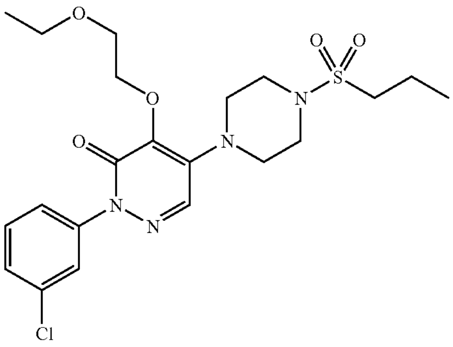 | 485 |
| 1356Z | 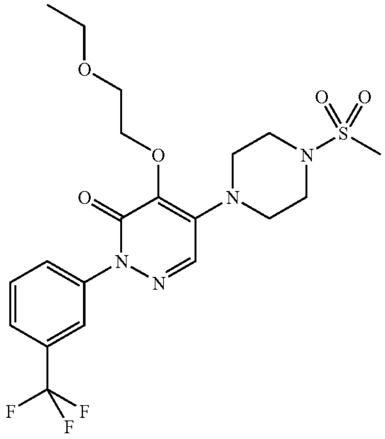 | 491 |
| 1357Z | 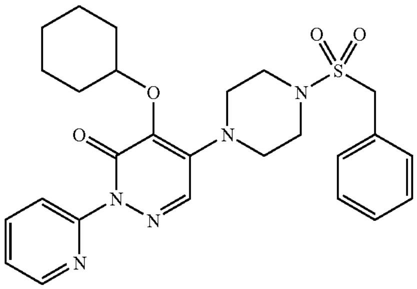 | 510 |
| 1358Z | 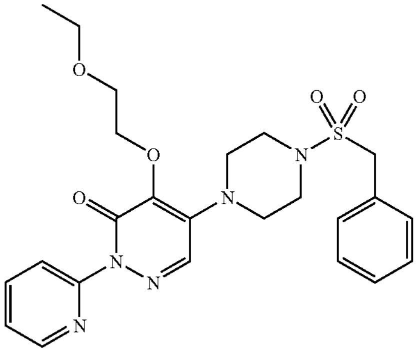 | 500 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
| --- | --- | --- |
| 1359Z | 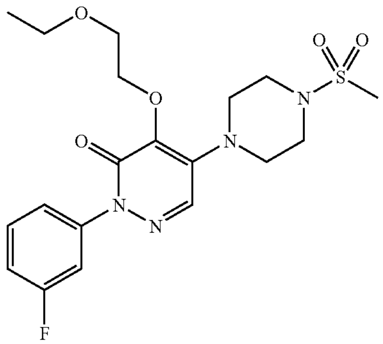 | 441 |
| 1360Z | 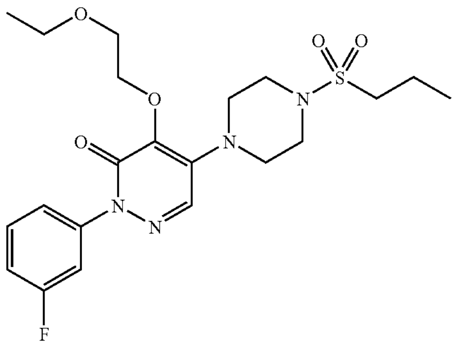 | 469 |
| 1361Z | 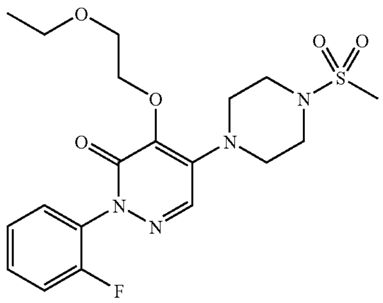 | 441 |
| 1362Z | 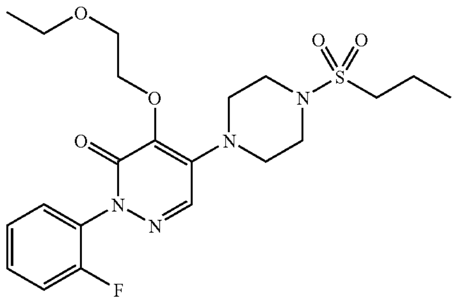 | 469 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1363Z | 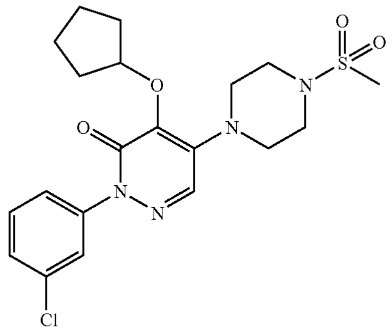 | 453 |
| 1364Z | 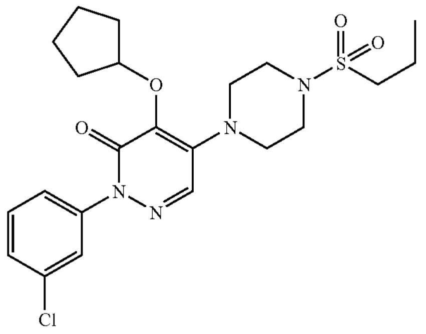 | 481 |
| 1365Z | 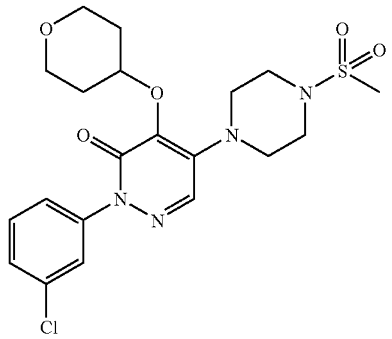 | 469 |
| 1366Z | 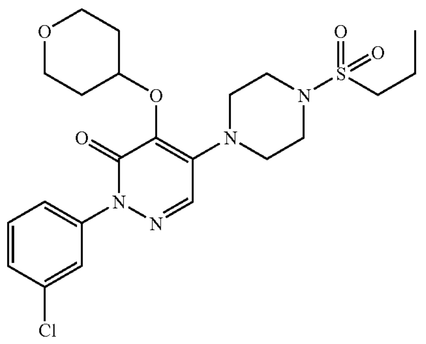 | 497 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1367Z | 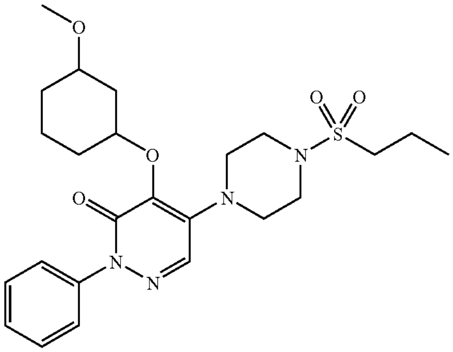 | 491 |
| 1368Z | 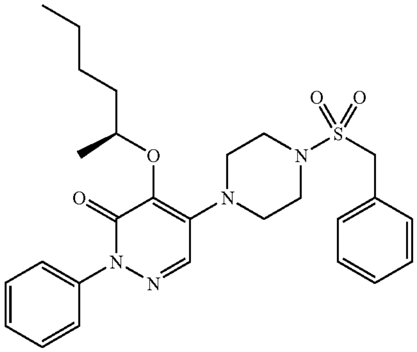 | 511 |
| 1369Z | 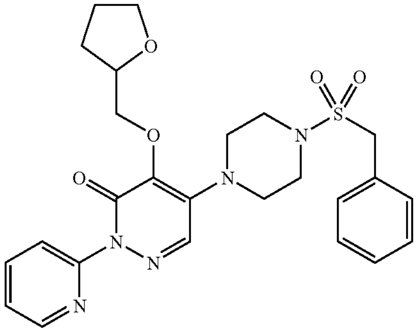 | 512 |
| 1370Z | 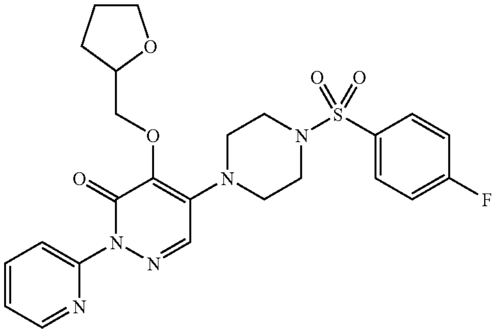 | 516 |

TABLE 11-continued
| Comp. No. | Structure | MS M + 1 |
|---|---|---|
| Oxygen Linked Analogs with Sulfonamide The following compounds can be synthesized using steps 1, 2, 4, 6, and 9 of Scheme 1 or steps 11, 12, and 14 of Scheme 2. | | |
| 1371Z | 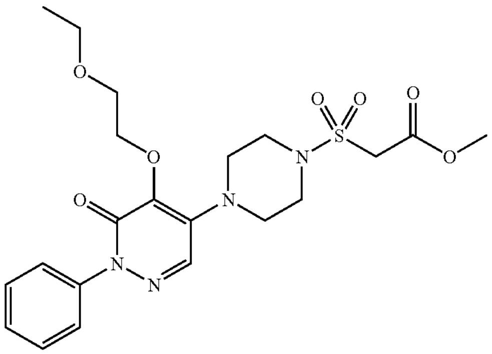 | 481 |
| 1372Z | 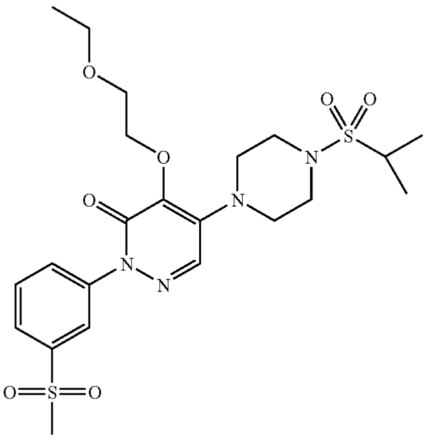 | 529 |
| 1373Z | 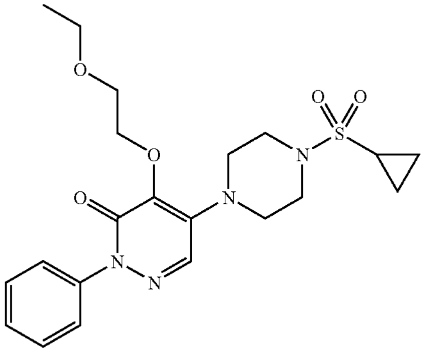 | 449 |
| 1374Z | 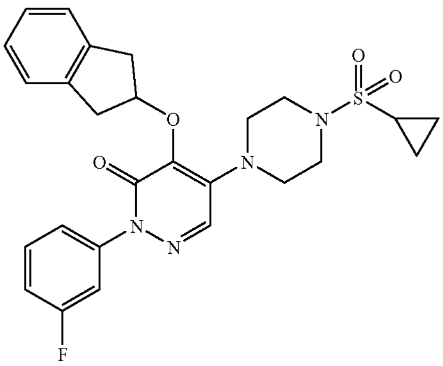 | 511 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1375Z | 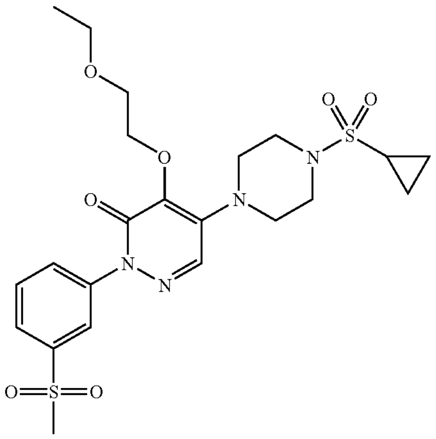 | 527 |
| 1376Z | 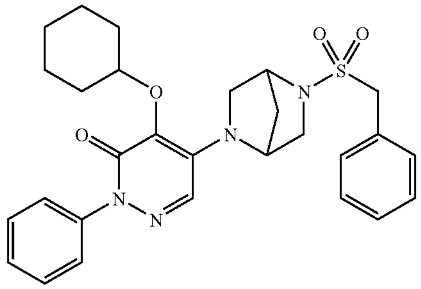 | 521 |
| 1377Z | 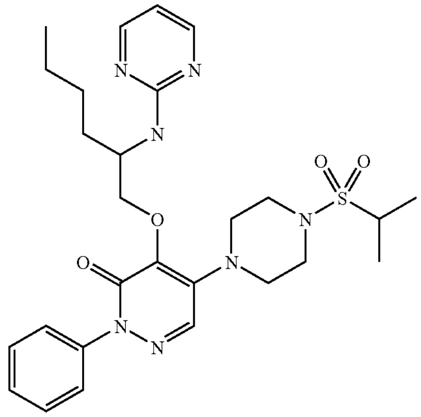 | 556 |

TABLE 11-continued
| Comp. No. | Oxygen Linked Analogs with Sulfonamide<br>The following compounds can be synthesized using steps 1, 2, 4, 6, and 9 of Scheme 1 or steps 11, 12, and 14 of Scheme 2.<br>Structure | MS M + 1 |
|---|---|---|
| 1378Z | 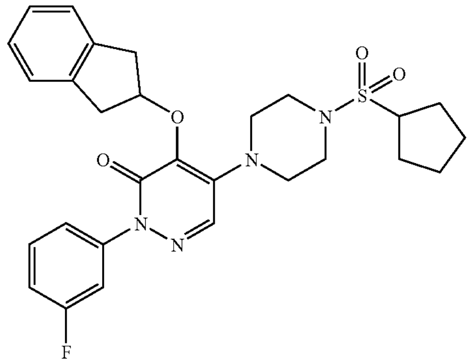 | 539 |
| 1379Z | 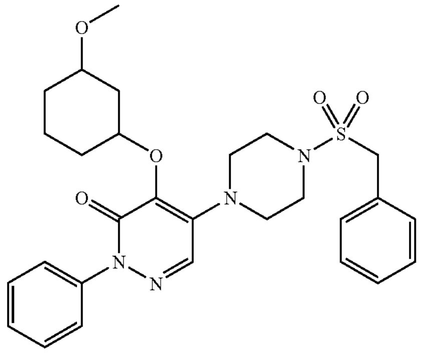 | 539 |
| 1380Z | 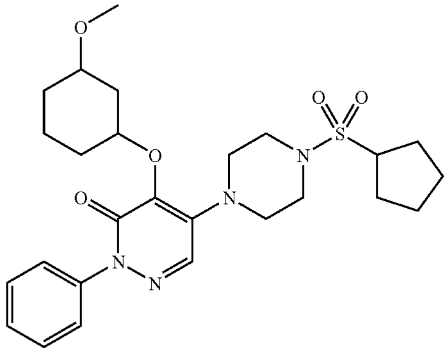 | 517 |
| 1381Z | 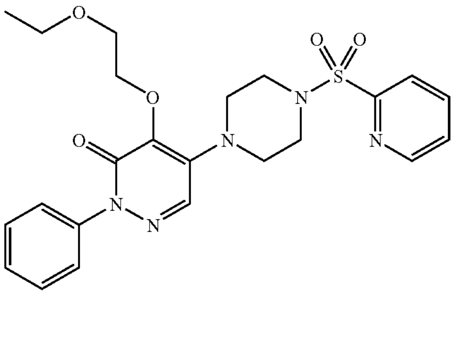 | 486 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1382Z | 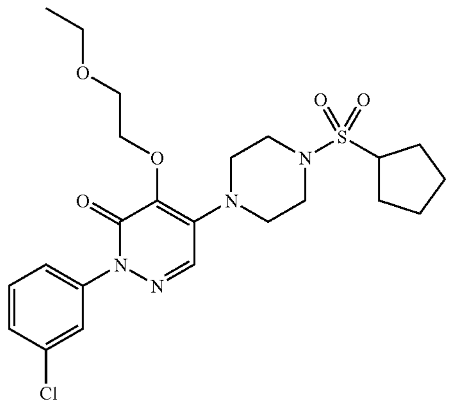 | 511 |
| 1383Z | 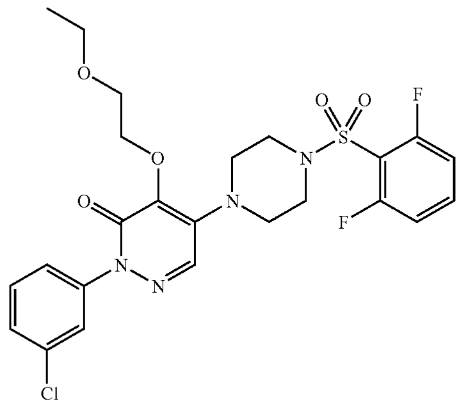 | 555 |
| 1384Z | 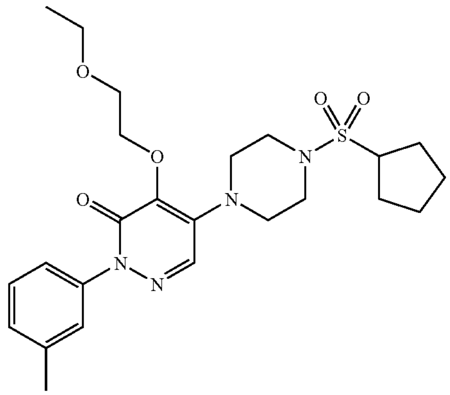 | 491 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1385Z | 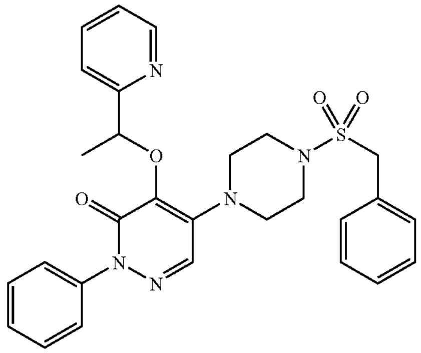 | 532 |
| 1386Z | 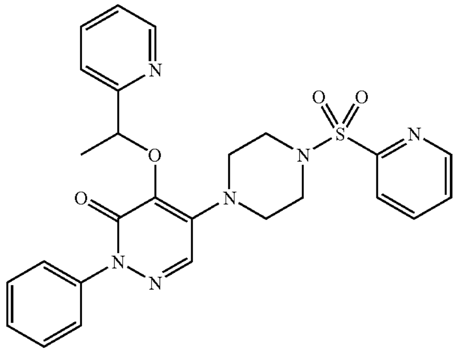 | 519 |
| 1387Z | 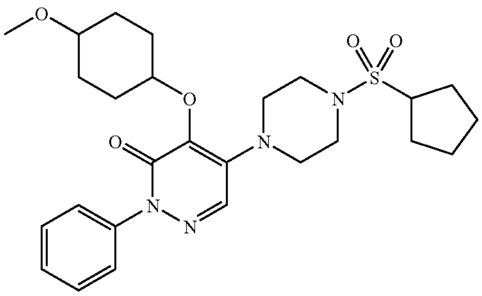 | 517 |
| 1388Z | 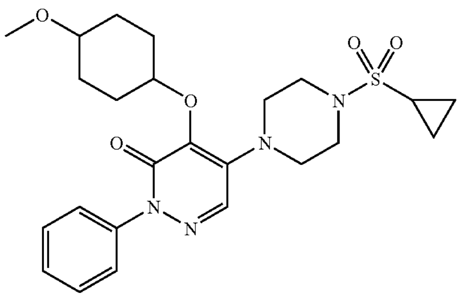 | 489 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1389Z | 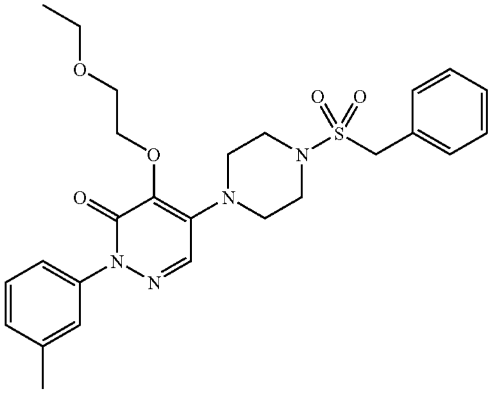 | 513 |
| 1390Z | 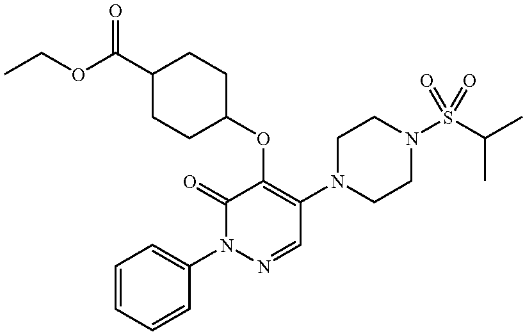 | 533 |
| 1391Z | 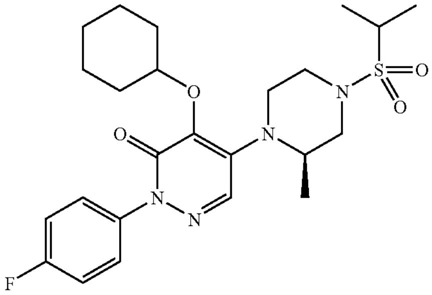 | 493 |
| 1392Z | 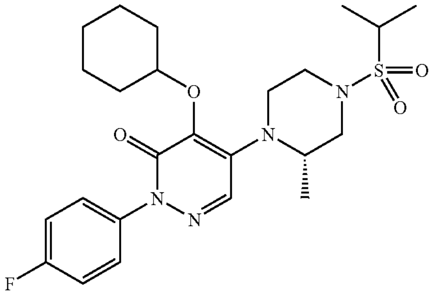 | 493 |

TABLE 11-continued
| Comp. No. | Structure | MS M + 1 |
|---|---|---|
| | Oxygen Linked Analogs with Sulfonamide<br>The following compounds can be synthesized using steps 1, 2, 4, 6, and 9 of Scheme 1 or steps 11, 12, and 14 of Scheme 2. | |
| 1393Z | 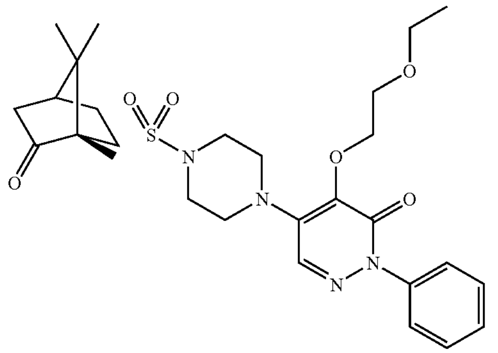 | 559 |
| 1394Z | 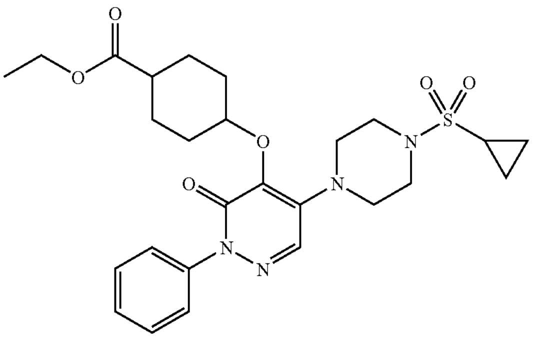 | 531 |
| 1395Z | 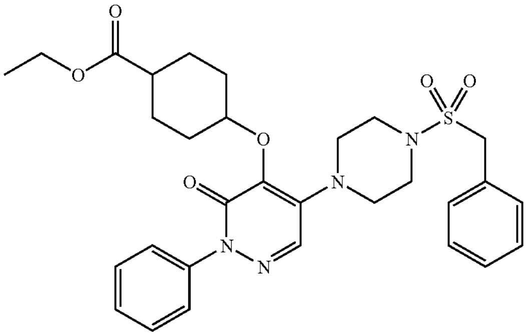 | 581 |
| 1396Z | 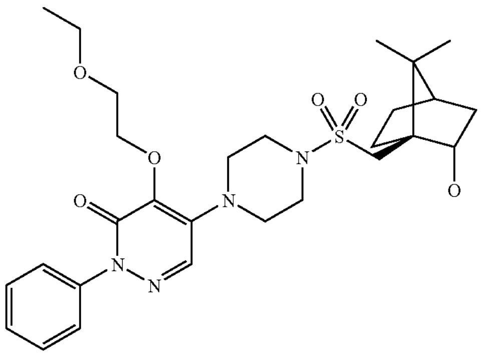 | 561 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1397Z | 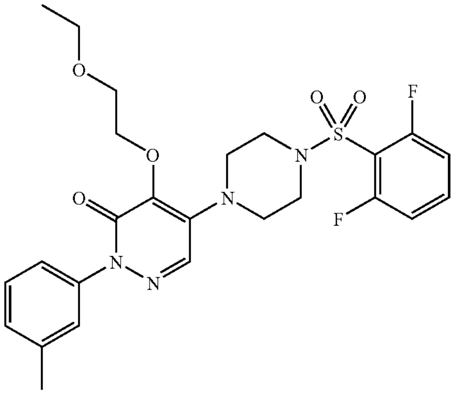 | 535 |
| 1398Z | 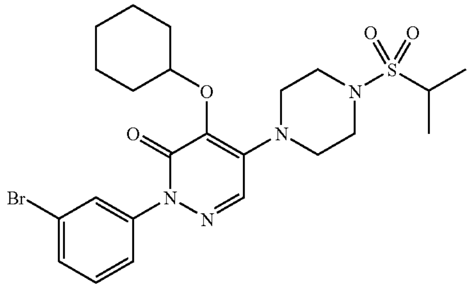 | 541 |
| 1399Z | 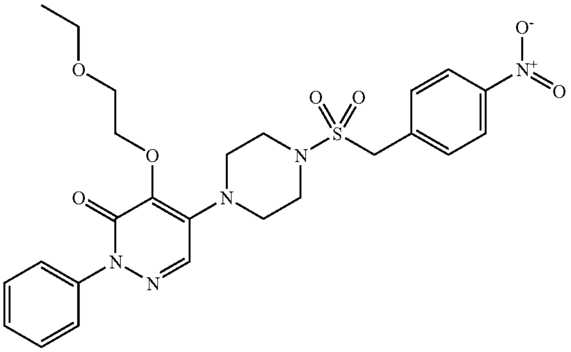 | 544 |
| 1400Z | 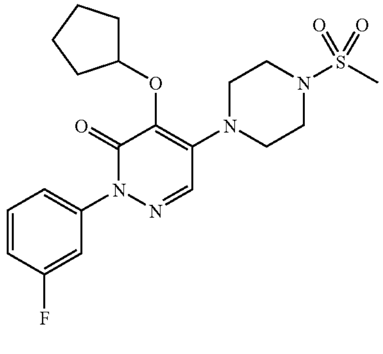 | 437 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1401Z | 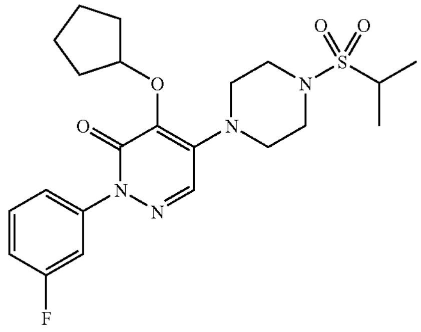 | 465 |
| 1402Z | 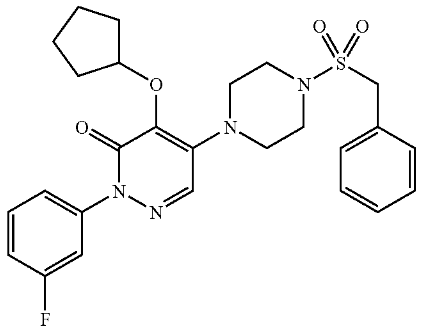 | 513 |
| 1403Z | 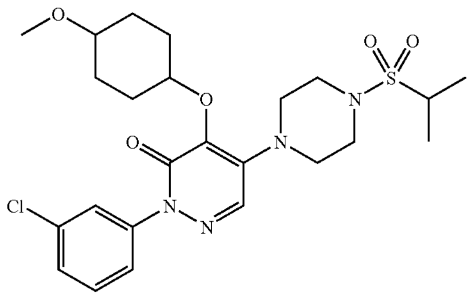 | 525 |
| 1404Z | 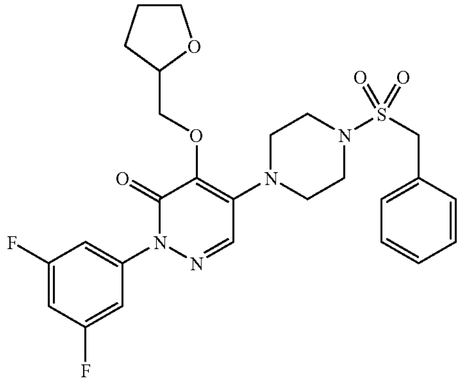 | 547 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1405Z | 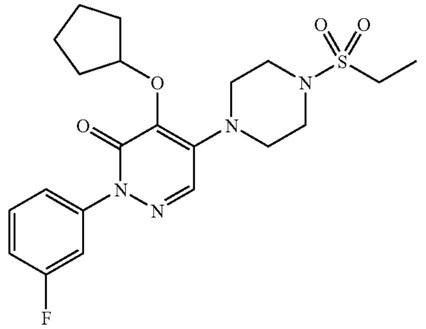 | 451 |
| 1406Z | 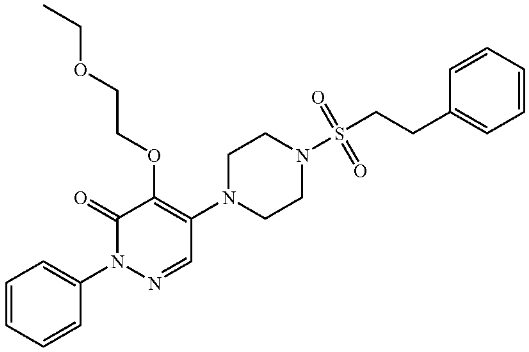 | 513 |
| 1407Z | 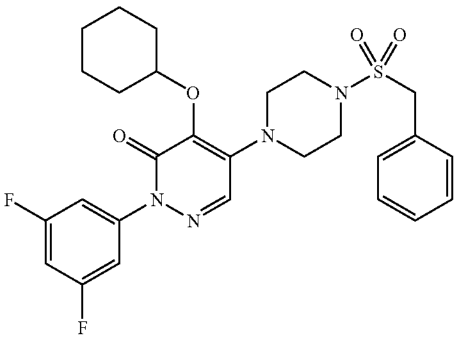 | 545 |
| 1408Z | no compound | |
| 1409Z | 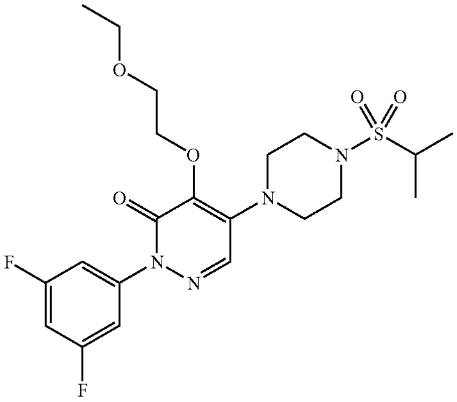 | 557 |

TABLE 11-continued
| Comp. No. | Structure | MS M + 1 |
|---|---|---|
| | Oxygen Linked Analogs with Sulfonamide<br>The following compounds can be synthesized using steps 1, 2, 4, 6, and 9 of Scheme 1 or steps 11, 12, and 14 of Scheme 2. | |
| 1410Z | 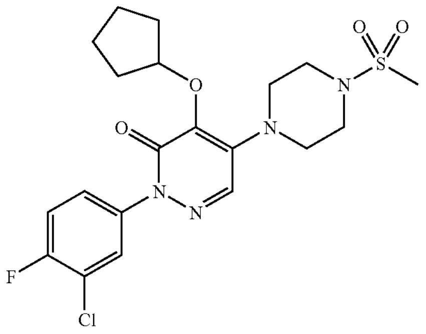 | 471 |
| 1411Z | 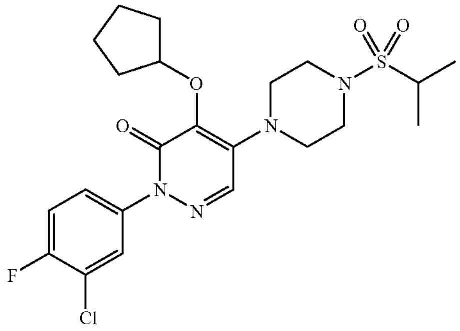 | 499 |
| 1412Z | 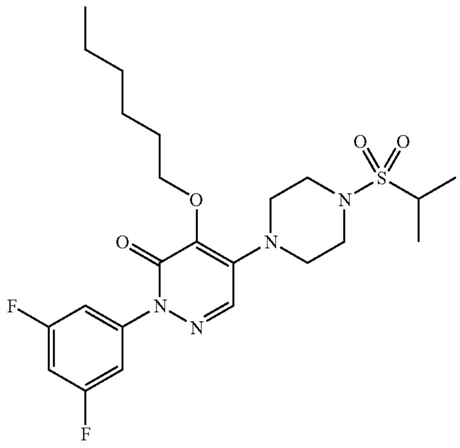 | 499 |

TABLE 11-continued
| Oxygen Linked Analogs with Sulfonamide<br>The following compounds can be synthesized using steps 1, 2,<br>4, 6, and 9 of Scheme 1 or steps 11, 12, and 14 of Scheme 2. | | |
|---|---|---|
| Comp. No. | Structure | MS M + 1 |
| 1413Z | no compound | |
| 1414Z | 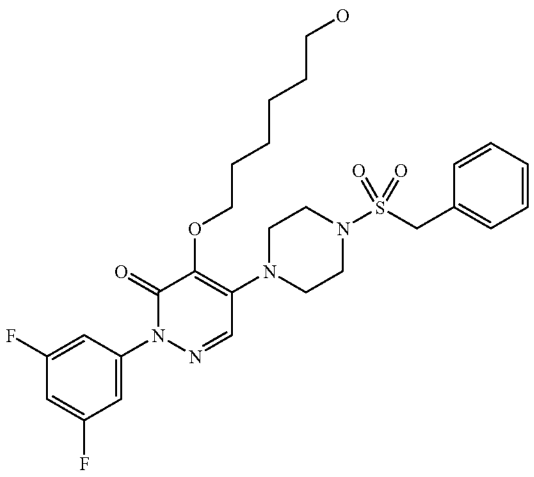 | 563 |
| 1415Z | 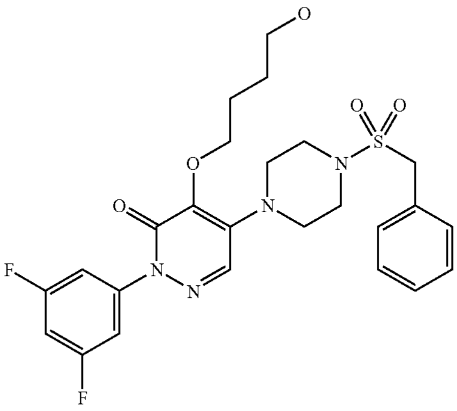 | 535 |
| 1416Z | 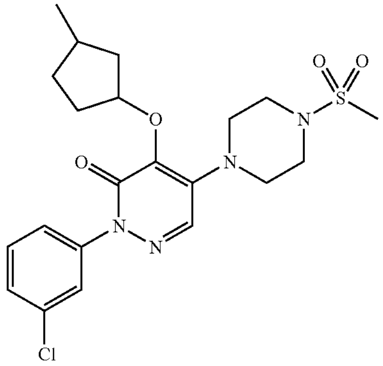 | 467 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1417Z | 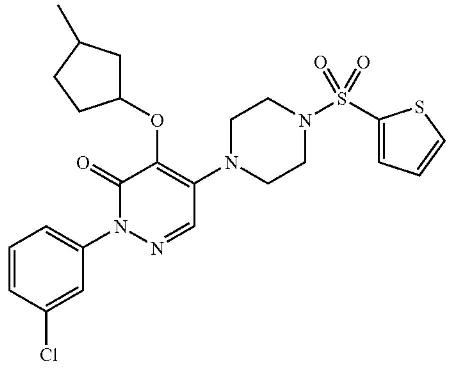 | 535 |
| 1418Z | 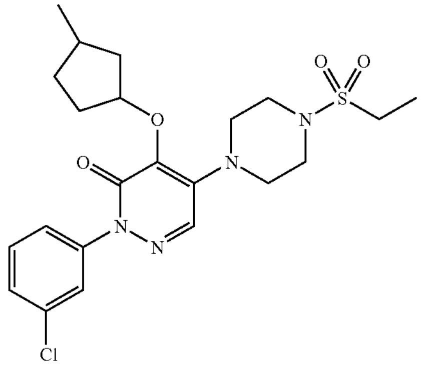 | 481 |
| 1419Z | 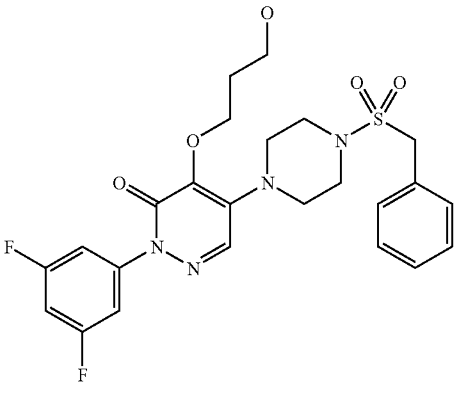 | 521 |

TABLE 11-continued
| Comp. No. | Structure | MS M + 1 |
|---|---|---|
| | Oxygen Linked Analogs with Sulfonamide<br>The following compounds can be synthesized using steps 1, 2, 4, 6, and 9 of Scheme 1 or steps 11, 12, and 14 of Scheme 2. | |
| 1420Z | 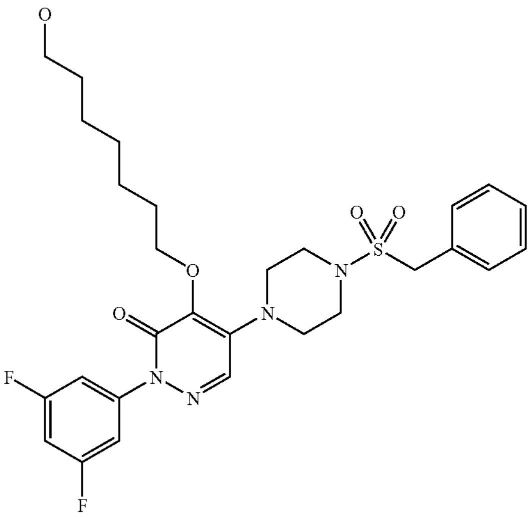 | 577 |
| 1421Z | 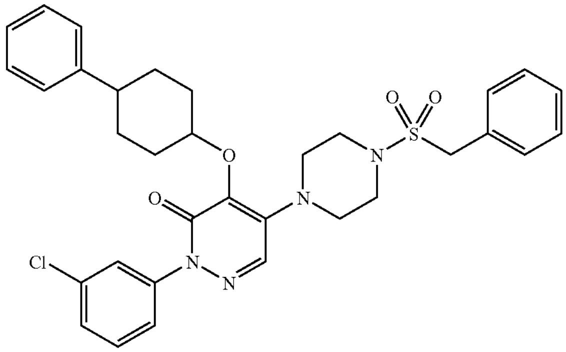 | 619 |
| 1422Z | 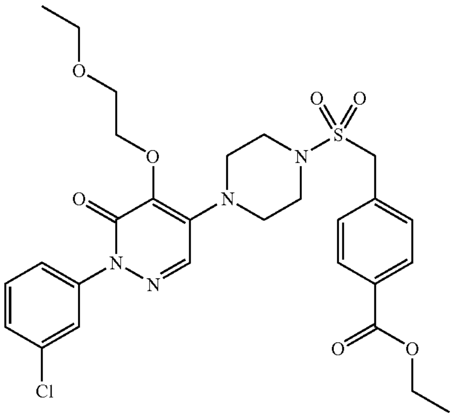 | 605 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1423Z | 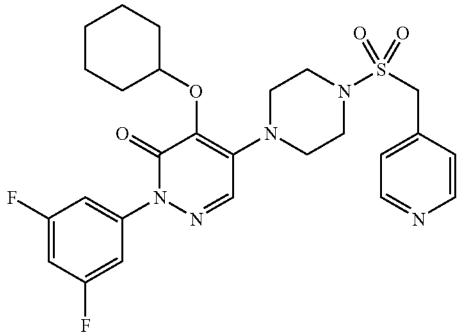 | 546 |
| 1424Z | 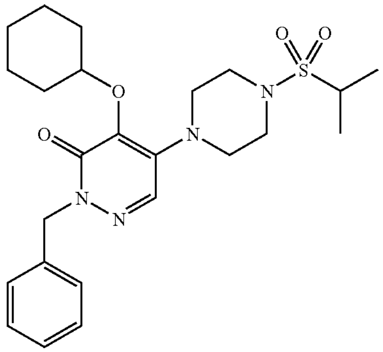 | 475 |
| 1425Z | 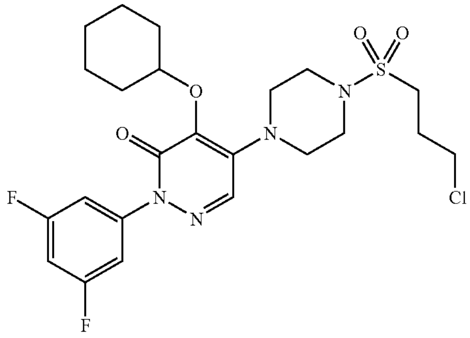 | 531 |
| 1426Z | 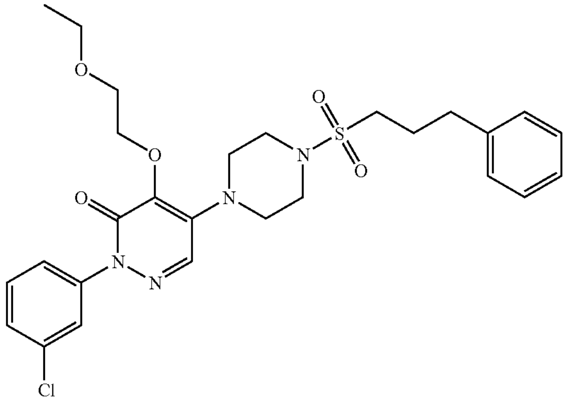 | 561 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1427Z | 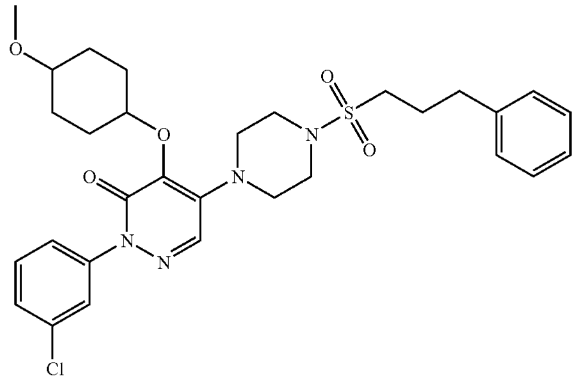 | 601 |
| 1428Z | 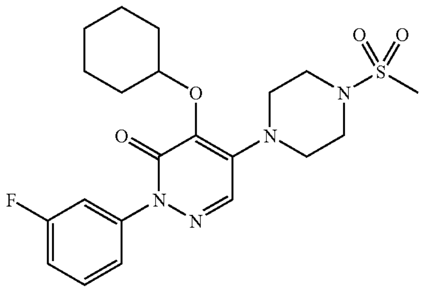 | 451 |
| 1429Z | 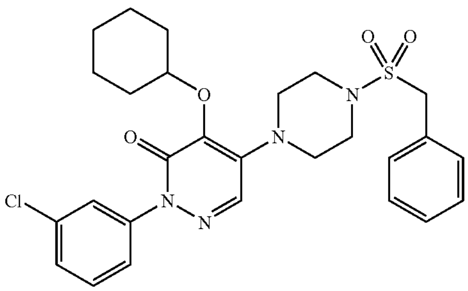 | 543 |
| 1430Z | 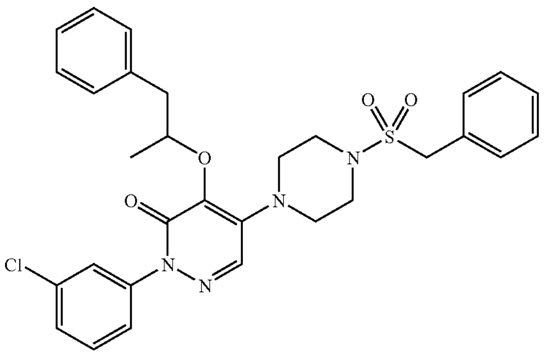 | 579 |

TABLE 11-continued
| Comp. No. | Structure | MS M + 1 |
|---|---|---|
| Oxygen Linked Analogs with Sulfonamide. The following compounds can be synthesized using steps 1, 2, 4, 6, and 9 of Scheme 1 or steps 11, 12, and 14 of Scheme 2. | | |
| 1431Z | 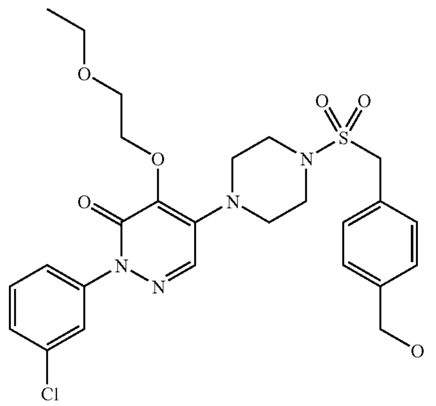 | 563 |
| 1432Z | 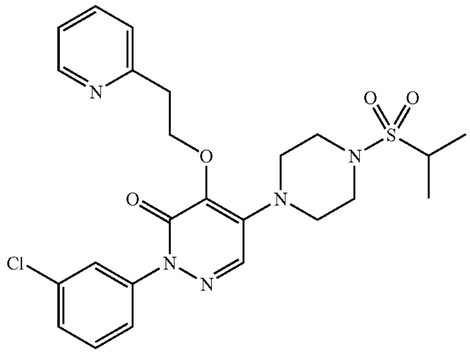 | 518 |
| 1433Z | 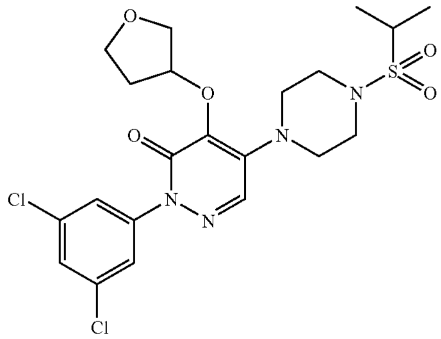 | 517 |
| 1434Z | 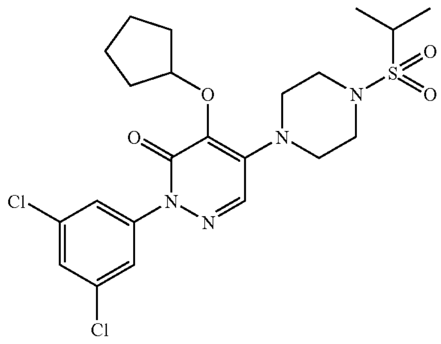 | 515 |

TABLE 11-continued
| Comp. No. | Structure | MS M + 1 |
| --- | --- | --- |
| | Oxygen Linked Analogs with Sulfonamide<br>The following compounds can be synthesized using steps 1, 2, 4, 6, and 9 of Scheme 1 or steps 11, 12, and 14 of Scheme 2. | |
| 1435Z | 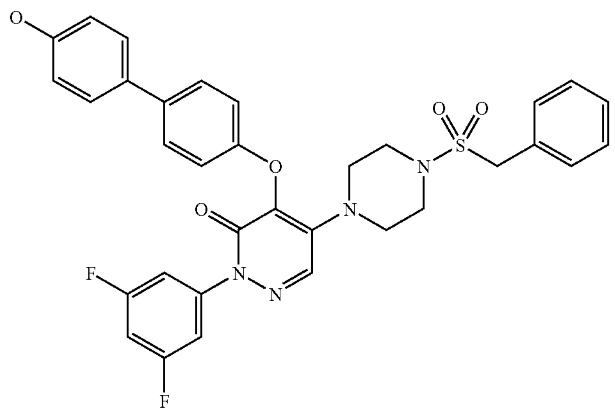 | 631 |
| 1436Z | 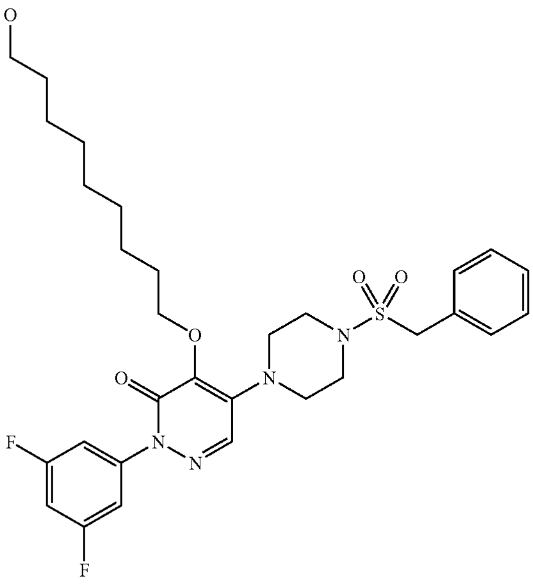 | 605 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1437Z | 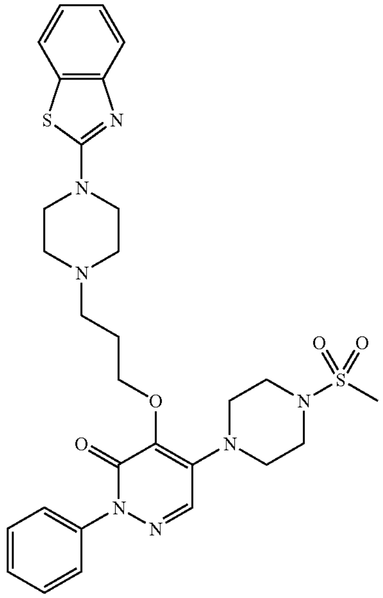 | 610 |
| 1438Z | 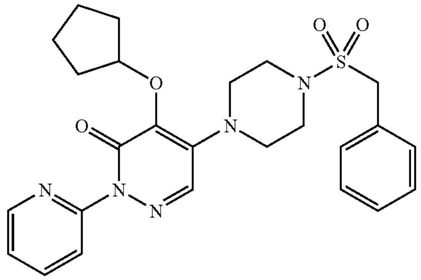 | 496 |
| 1439Z | 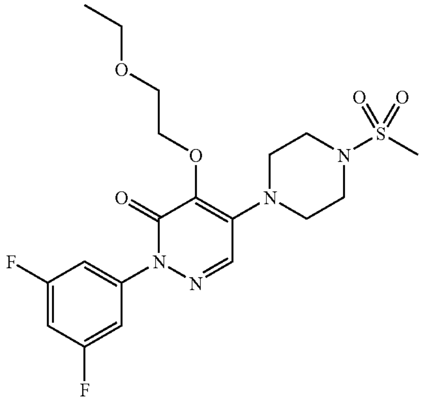 | 459 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1440Z | 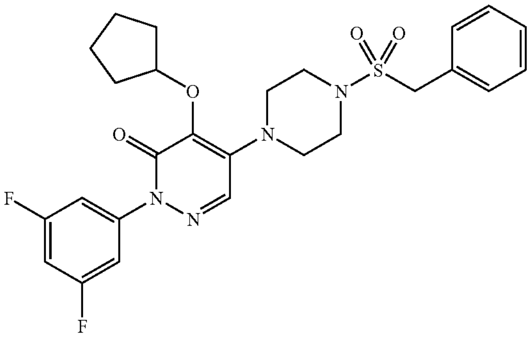 | 483 |
| 1441Z | 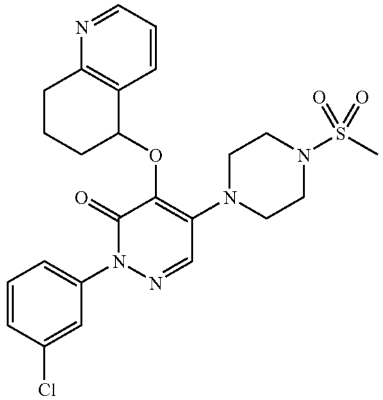 | 516 |
| 1442Z | 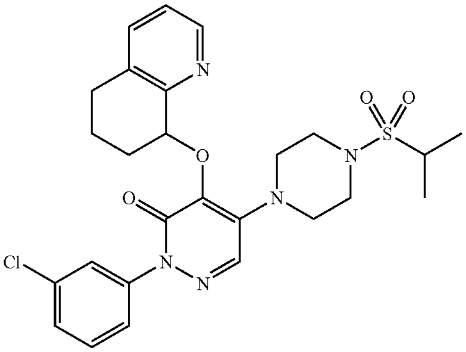 | 544 |
| 1443Z | 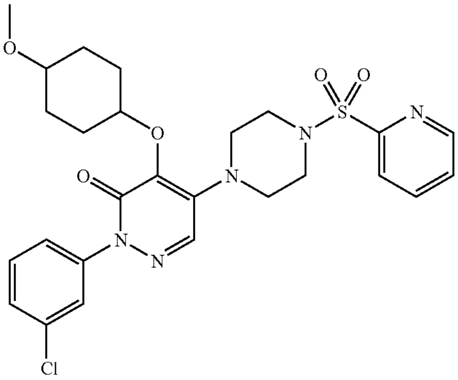 | 560 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1444Z | 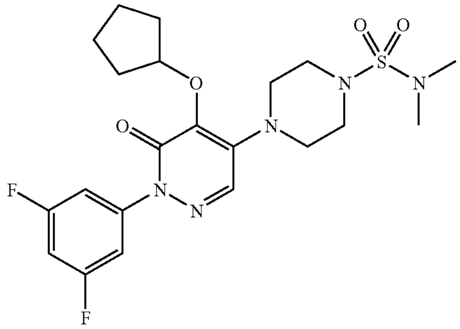 | 484 |
| 1445Z | 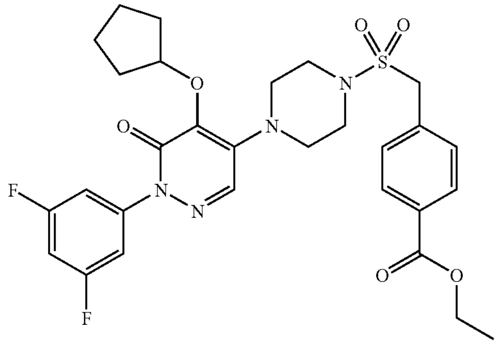 | 603 |
| 1446Z | 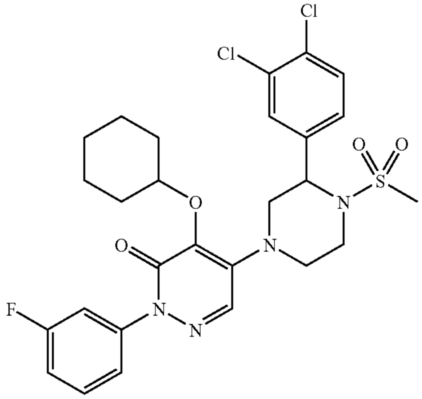 | 595 |
| 1447Z | 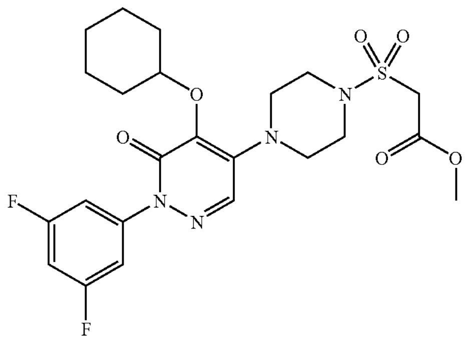 | 527 |

TABLE 11-continued
| Comp. No. | Structure | MS M + 1 |
|---|---|---|
| | Oxygen Linked Analogs with Sulfonamide<br>The following compounds can be synthesized using steps 1, 2, 4, 6, and 9 of Scheme 1 or steps 11, 12, and 14 of Scheme 2. | |
| 1448Z | 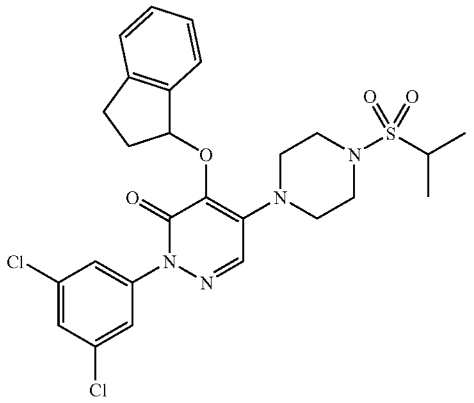 | 563 |
| 1449Z | 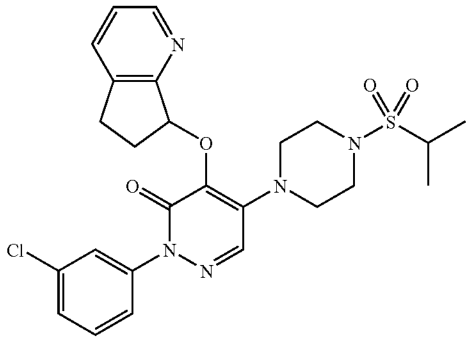 | 530 |
| 1450Z | 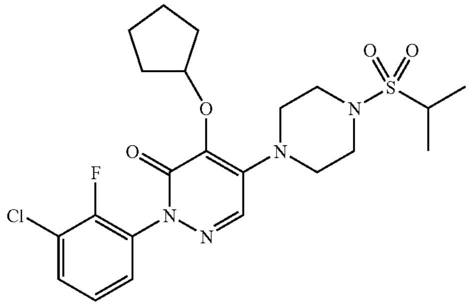 | 499 |
| 1451Z | 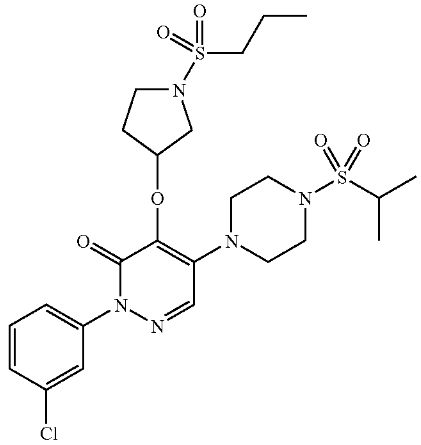 | 588 |

TABLE 11-continued
| Comp. No. | Structure | MS M + 1 |
| --- | --- | --- |
| | Oxygen Linked Analogs with Sulfonamide The following compounds can be synthesized using steps 1, 2, 4, 6, and 9 of Scheme 1 or steps 11, 12, and 14 of Scheme 2. | |
| 1452Z | 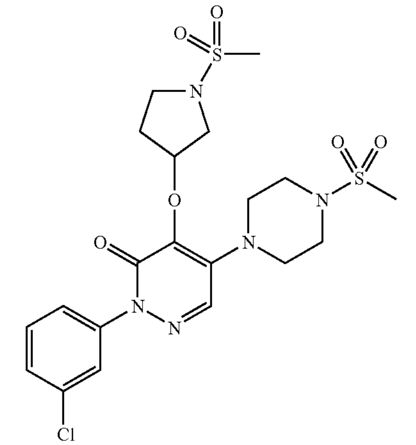 | 532 |
| 1453Z | 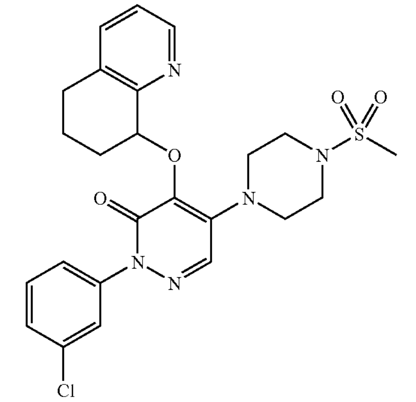 | 516 |
| 1454Z | 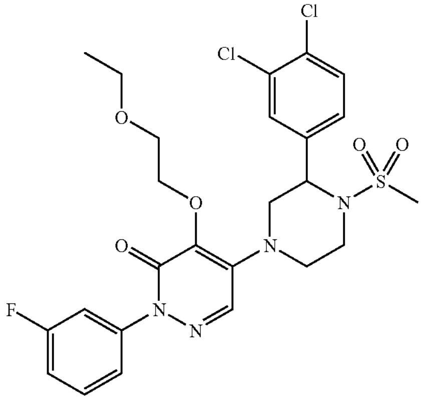 | 585 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1455Z | 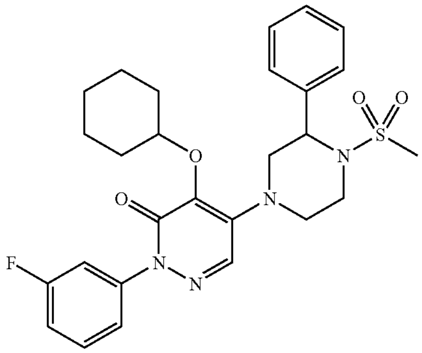 | 527 |
| 1456Z | 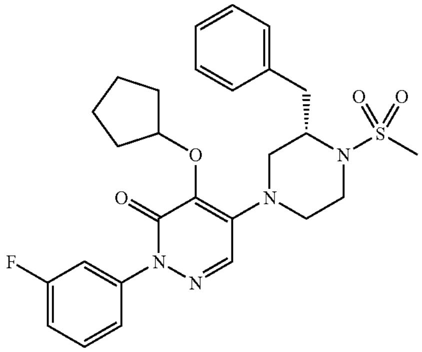 | 527 |
| 1457Z | 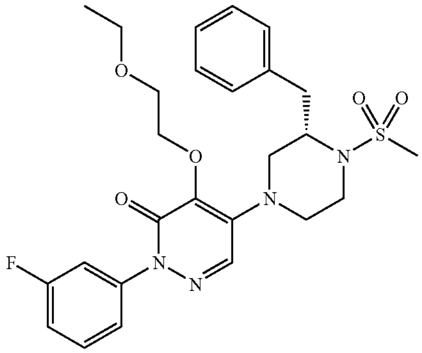 | 531 |
| 1458Z | 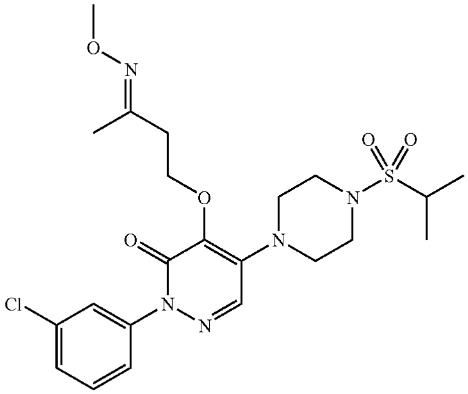 | 512 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
| --- | --- | --- |
| 1459Z | 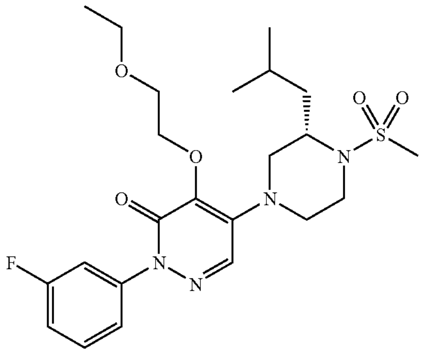 | 497 |
| 1460Z | 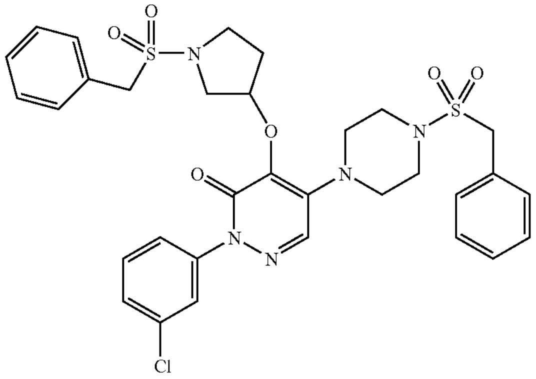 | 684 |
| 1461Z | 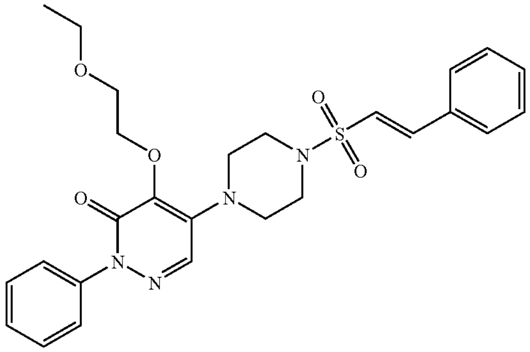 | 511 |
| 1462Z | 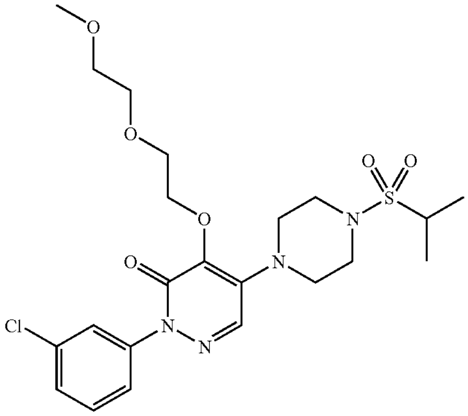 | 515 |

TABLE 11-continued
| Comp. No. | Oxygen Linked Analogs with Sulfonamide The following compounds can be synthesized using steps 1, 2, 4, 6, and 9 of Scheme 1 or steps 11, 12, and 14 of Scheme 2. Structure | MS M + 1 |
|---|---|---|
| 1463Z | 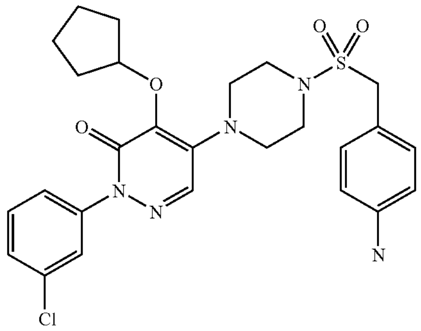 | 544 |
| 1464Z | 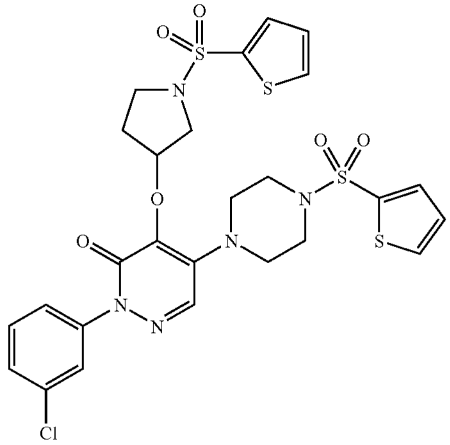 | 668 |
| 1465Z | 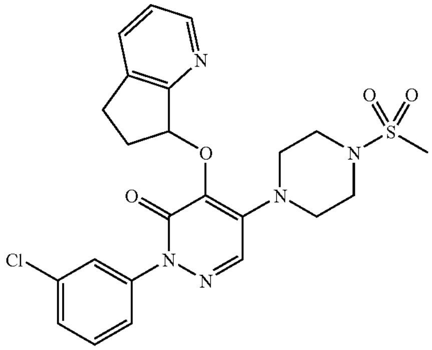 | 502 |

TABLE 11-continued
| Comp. No. | Oxygen Linked Analogs with Sulfonamide The following compounds can be synthesized using steps 1, 2, 4, 6, and 9 of Scheme 1 or steps 11, 12, and 14 of Scheme 2. Structure | MS M + 1 |
|---|---|---|
| 1466Z | 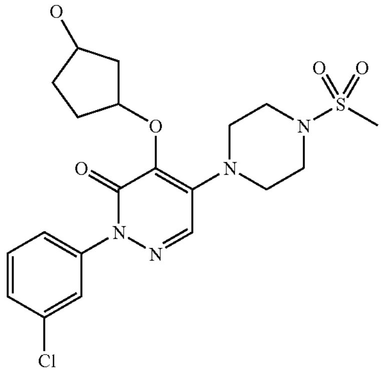 | 469 |
| 1467Z | 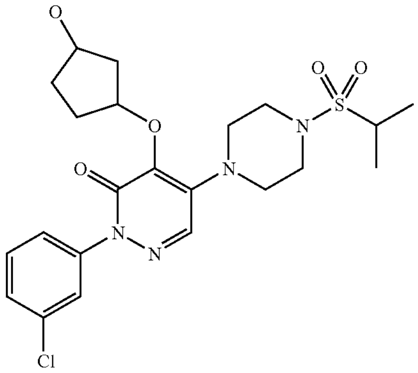 | 497 |
| 1468Z | 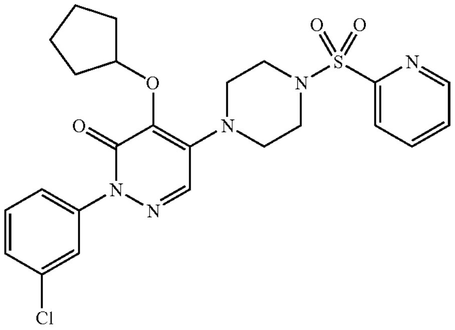 | 516 |
| 1469Z | 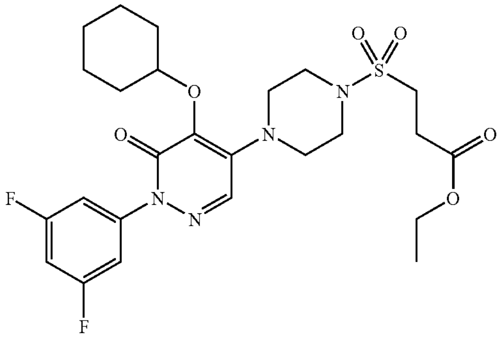 | 555 |

TABLE 11-continued
| Comp. No. | Structure | MS M + 1 |
| --- | --- | --- |
| | Oxygen Linked Analogs with Sulfonamide<br>The following compounds can be synthesized using steps 1, 2, 4, 6, and 9 of Scheme 1 or steps 11, 12, and 14 of Scheme 2. | |
| 1470Z | 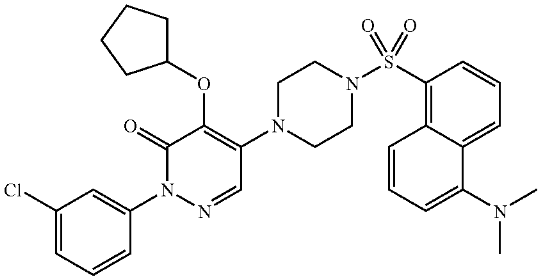 | 608 |
| 1471Z | 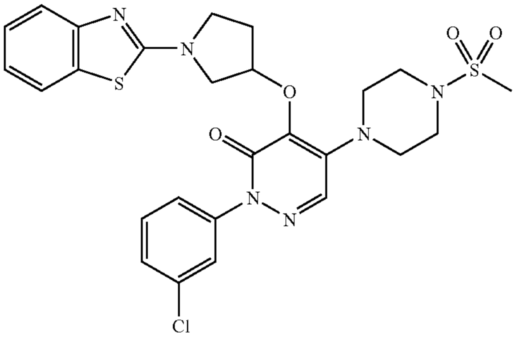 | 587 |
| 1472Z | 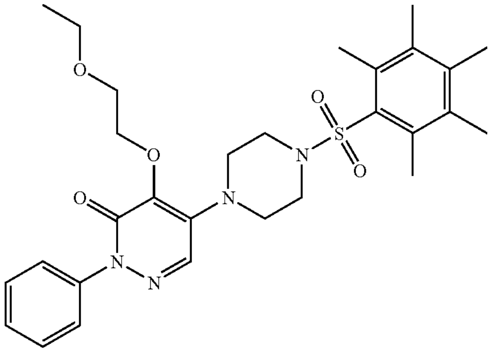 | 555 |
| 1473Z | 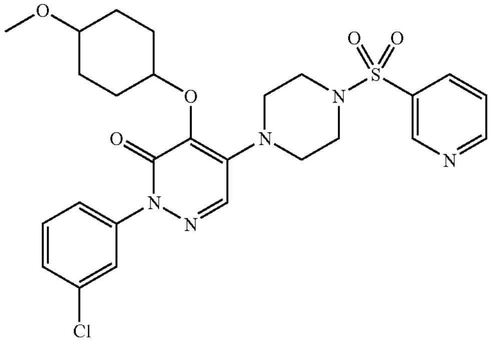 | 560 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1474Z | 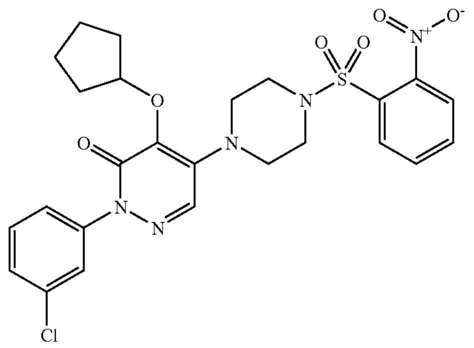 | 560 |
| 1475Z | 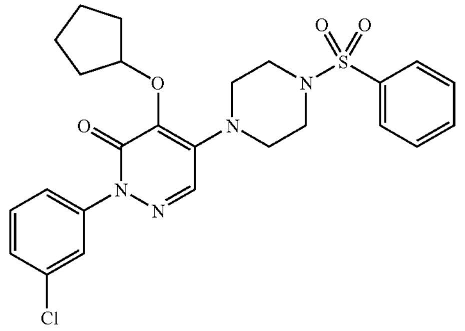 | 515 |
| 1476Z | 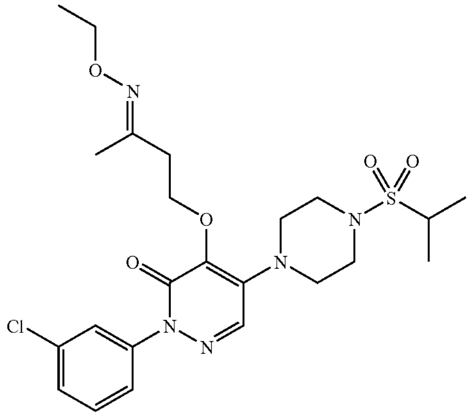 | 526 |
| 1477Z | 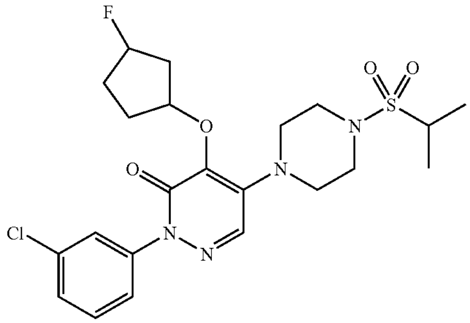 | 499 |

TABLE 11-continued
| Comp. No. | Structure | MS M + 1 |
|---|---|---|
| | Oxygen Linked Analogs with Sulfonamide The following compounds can be synthesized using steps 1, 2, 4, 6, and 9 of Scheme 1 or steps 11, 12, and 14 of Scheme 2. | |
| 1478Z | 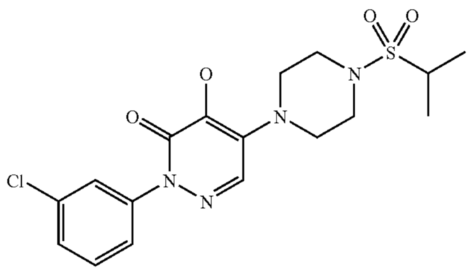 | 413 |
| 1479Z | 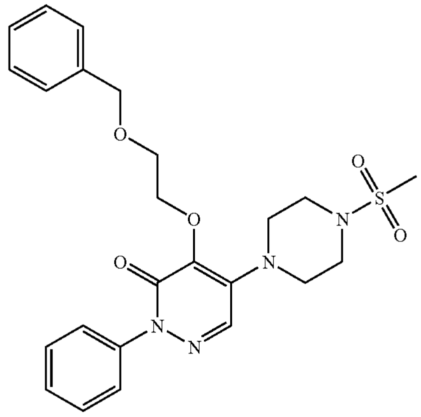 | 485 |
| 1480Z | 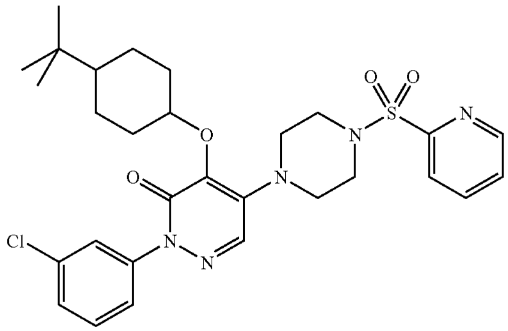 | 586 |
| 1481Z | 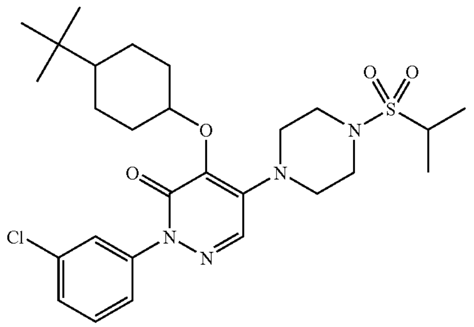 | 551 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1482Z | 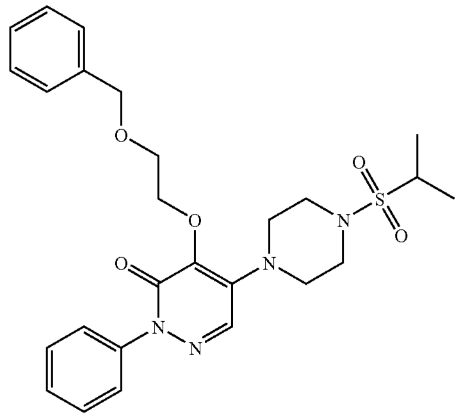 | 513 |
| 1483Z | 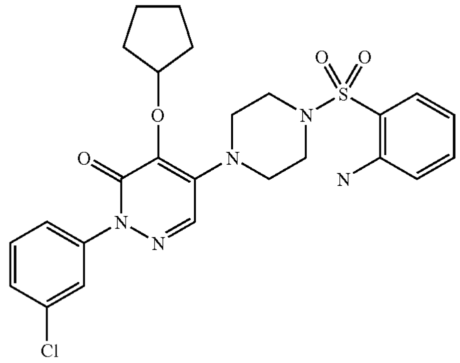 | 530 |
| 1484Z | 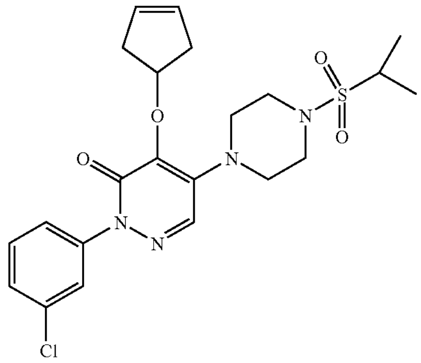 | 479 |
| 1485Z | 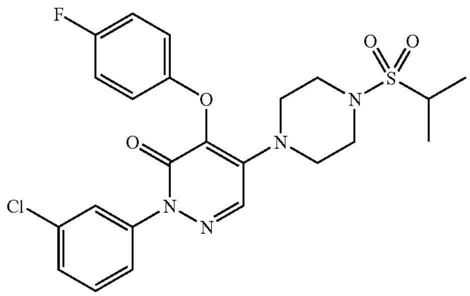 | 507 |

TABLE 11-continued
| Comp. No. | Structure | MS M + 1 |
|---|---|---|
| | Oxygen Linked Analogs with Sulfonamide The following compounds can be synthesized using steps 1, 2, 4, 6, and 9 of Scheme 1 or steps 11, 12, and 14 of Scheme 2. | |
| 1486Z | 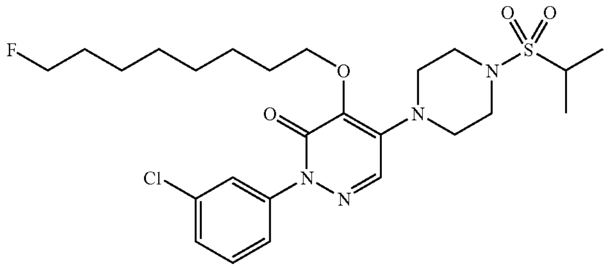 | 543 |
| 1487Z | 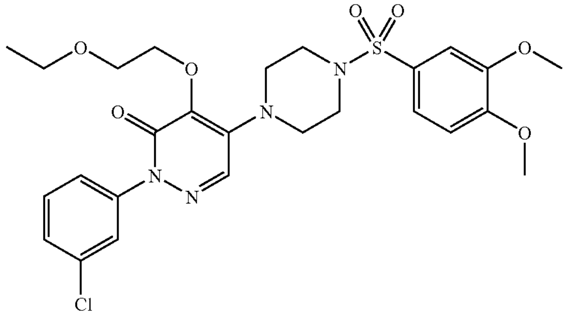 | 579 |
| 1488Z | 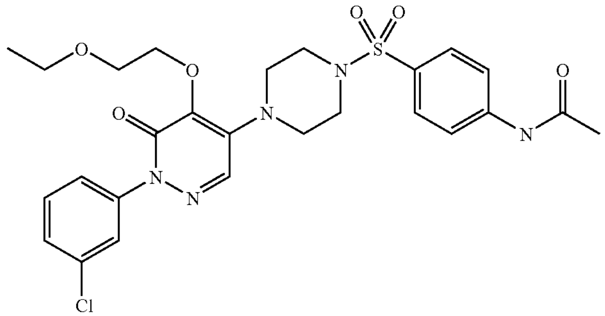 | 576 |
| 1489Z | 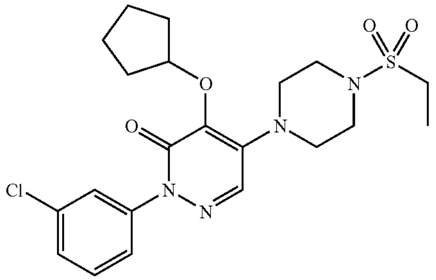 | 467 |
| 1490Z | 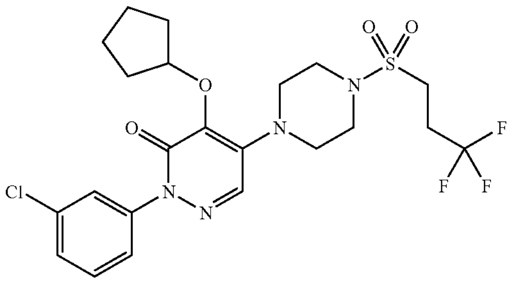 | 535 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1491Z | 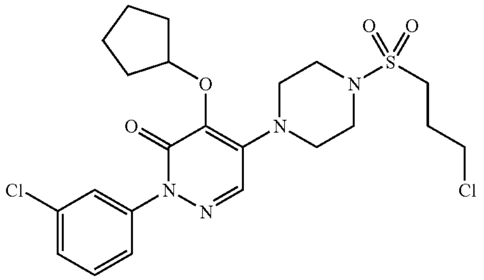 | 515 |
| 1492Z | 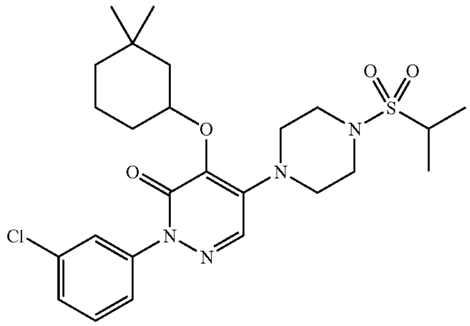 | 523 |
| 1493Z | 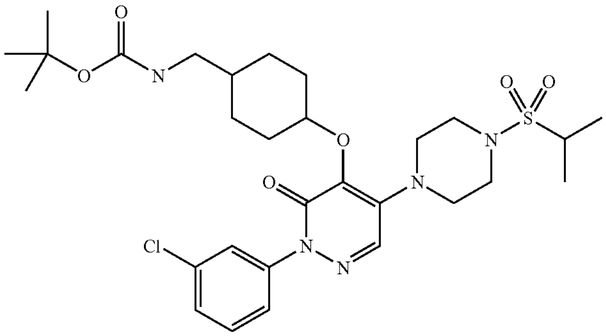 | 624 |
| 1494Z | 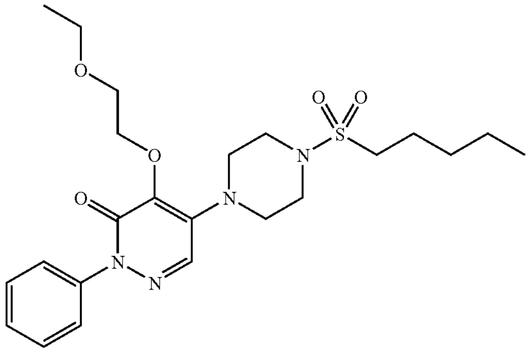 | 479 |

TABLE 11-continued
| Comp. No. | Oxygen Linked Analogs with Sulfonamide The following compounds can be synthesized using steps 1, 2, 4, 6, and 9 of Scheme 1 or steps 11, 12, and 14 of Scheme 2. Structure | MS M + 1 |
|---|---|---|
| 1495Z | 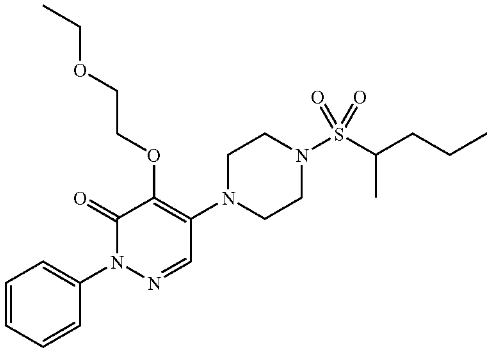 | 479 |
| 1496Z | 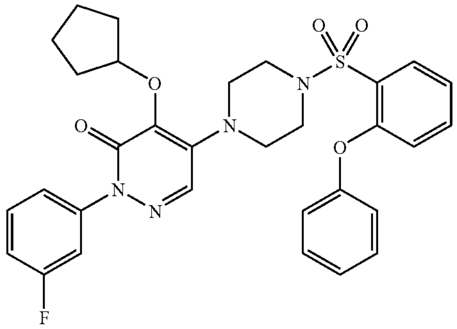 | 591 |
| 1497Z | 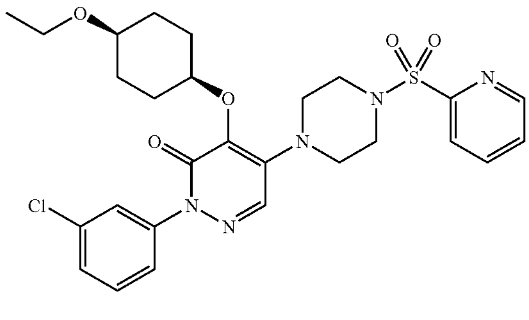 | 574 |
| 1498Z | 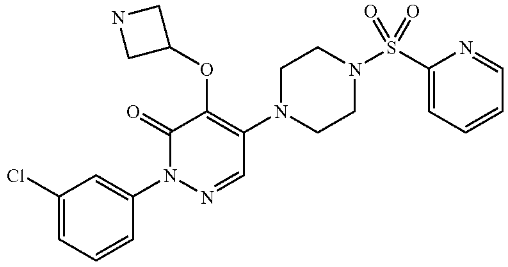 | 503 |

TABLE 11-continued
| Comp. No. | Structure | MS M + 1 |
|---|---|---|
| Oxygen Linked Analogs with Sulfonamide<br>The following compounds can be synthesized using steps 1, 2, 4, 6, and 9 of Scheme 1 or steps 11, 12, and 14 of Scheme 2. | | |
| 1499Z | 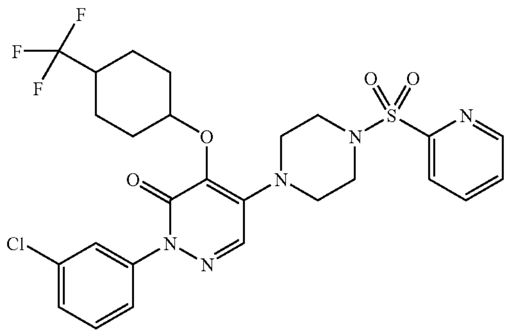 | 598 |
| 1500Z | 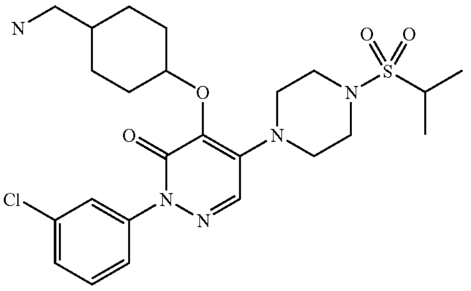 | 524 |
| 1501Z | 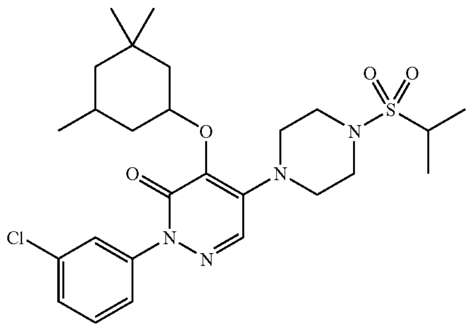 | 537 |
| 1502Z | 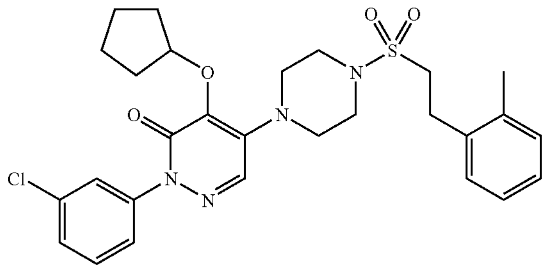 | 557 |
| 1503Z | 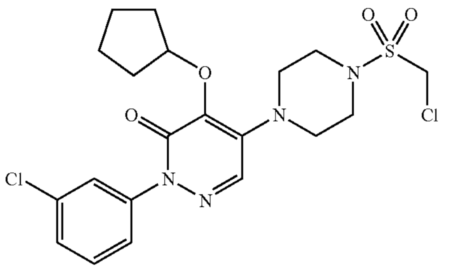 | 487 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1504Z | 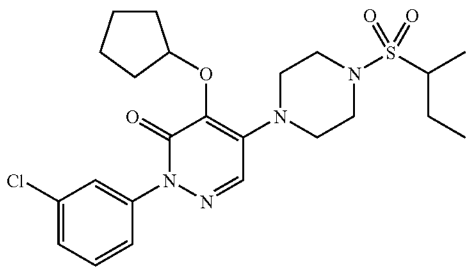 | 495 |
| 1505Z | 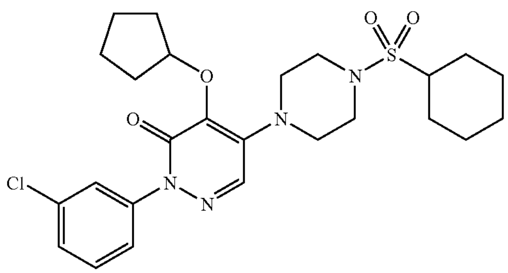 | 521 |
| 1506Z | 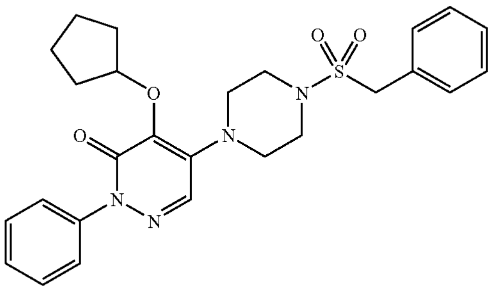 | 495 |
| 1507Z | 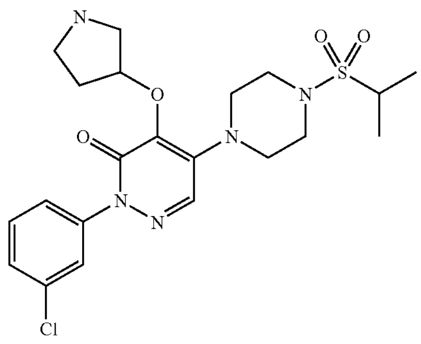 | 482 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1508Z | 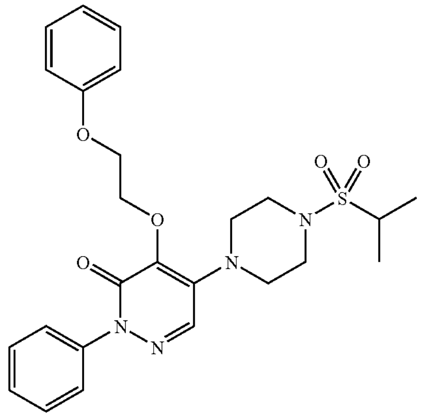 | 499 |
| 1509Z | 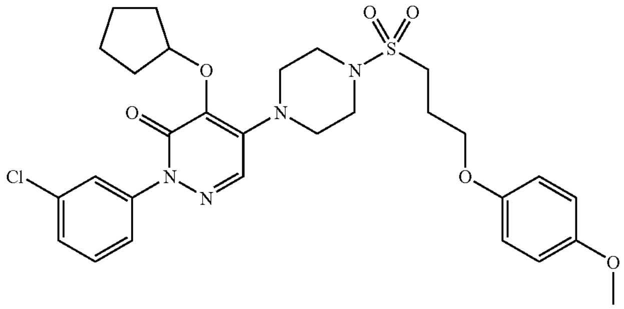 | 603 |
| 1510Z | 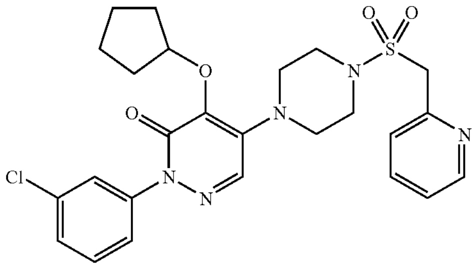 | 530 |
| 1511Z | 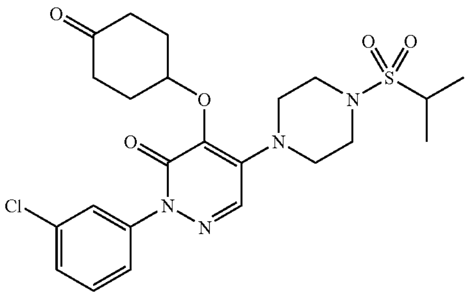 | 509 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1512Z | 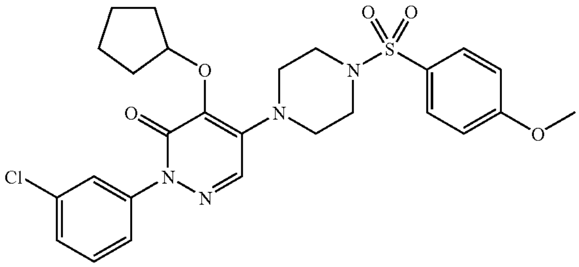 | 545 |
| 1513Z | 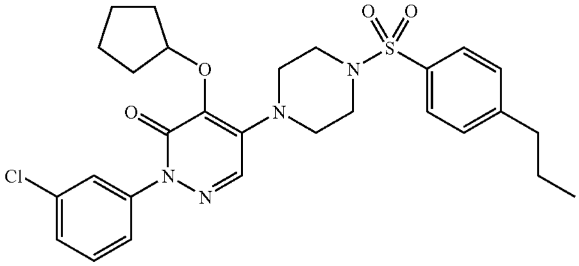 | 557 |
| 1514Z | 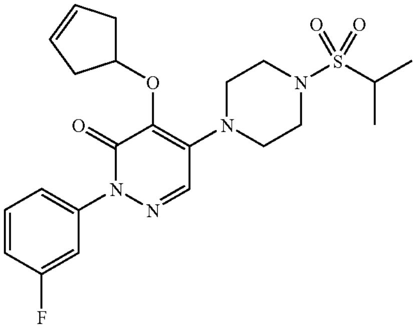 | 463 |
| 1515Z | 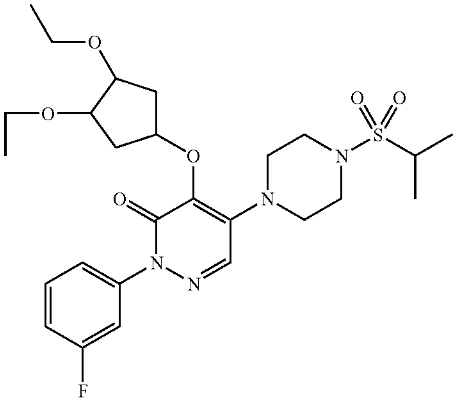 | 553 |

TABLE 11-continued
| Comp. No. | Structure | MS M + 1 |
|---|---|---|
| Oxygen Linked Analogs with Sulfonamide The following compounds can be synthesized using steps 1, 2, 4, 6, and 9 of Scheme 1 or steps 11, 12, and 14 of Scheme 2. | | |
| 1516Z | 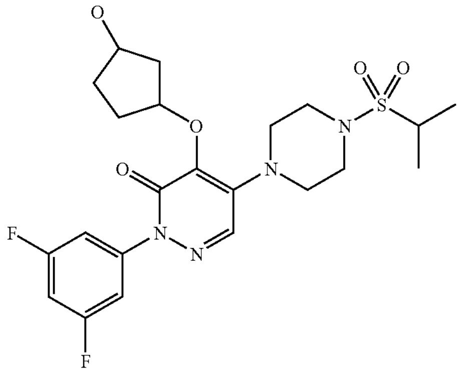 | 481 |
| 1517Z | 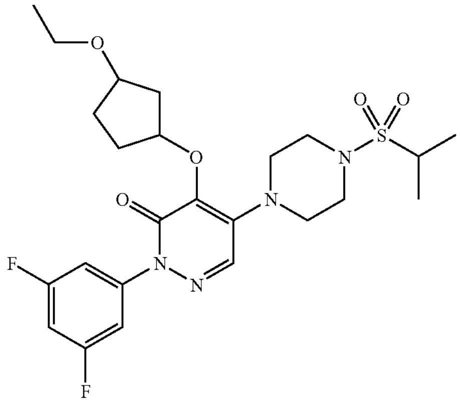 | 527 |
| 1518Z | 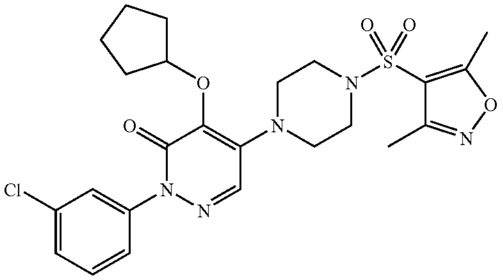 | 534 |
| 1519Z | 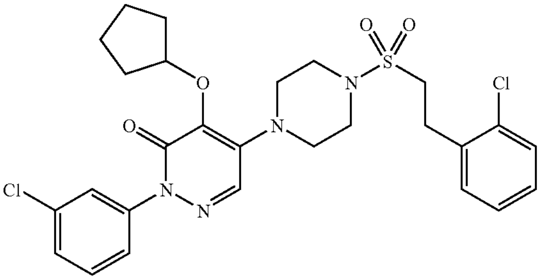 | 577 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
| --- | --- | --- |
| 1520Z | 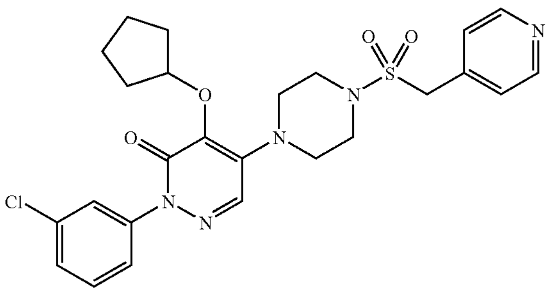 | 530 |
| 1521Z | 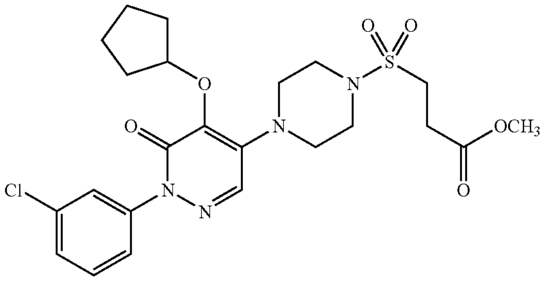 | 525 |
| 1522Z | 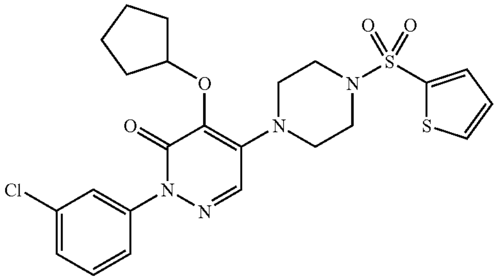 | 521 |
| 1523Z | 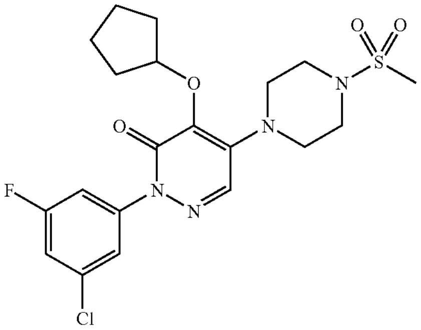 | 471 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
| --- | --- | --- |
| 1524Z | 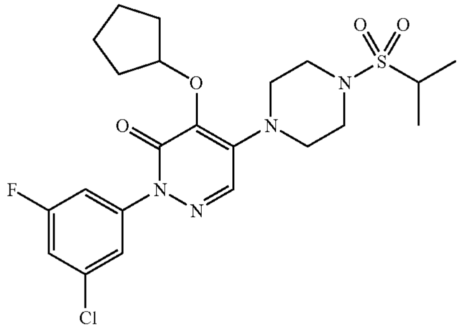 | 499 |
| 1525Z | 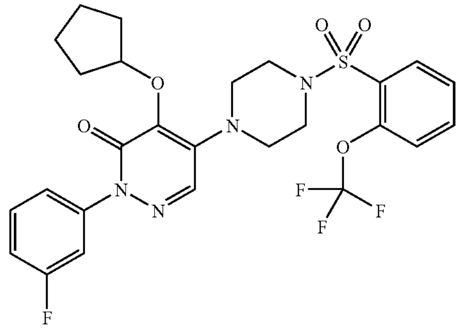 | 583 |
| 1526Z | 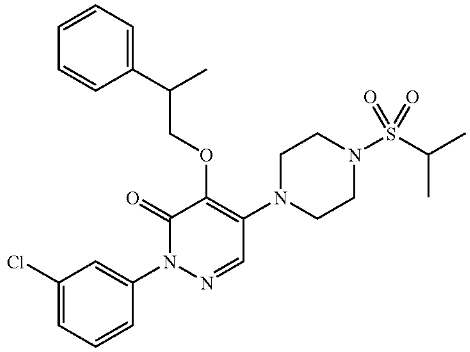 | 531 |
| 1527Z | 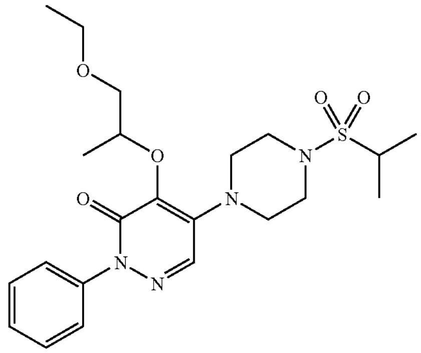 | 465 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1528Z | 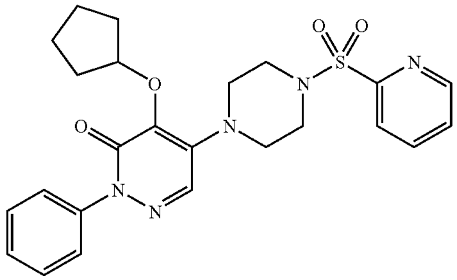 | 482 |
| 1529Z | 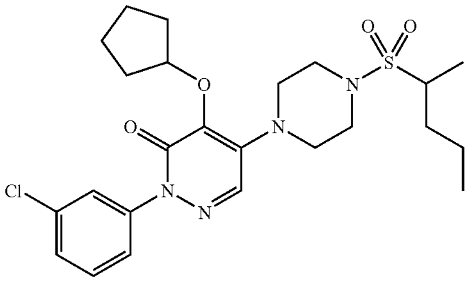 | 509 |
| 1529Z-1 | 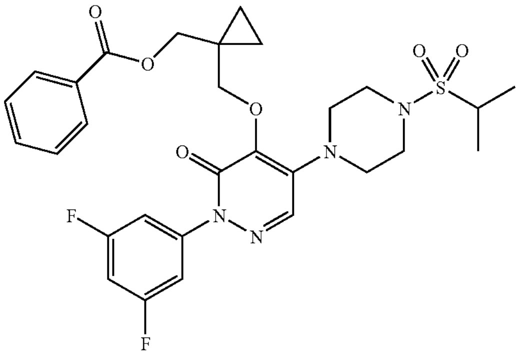 | 603 |
| 1529Z-2 | 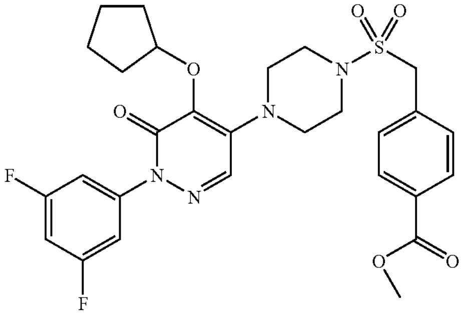 | 589 |

TABLE 11-continued
| Comp. No. | Structure | MS M + 1 |
| --- | --- | --- |
| Oxygen Linked Analogs with Sulfonamide The following compounds can be synthesized using steps 1, 2, 4, 6, and 9 of Scheme 1 or steps 11, 12, and 14 of Scheme 2. | | |
| 1529Z-3 | 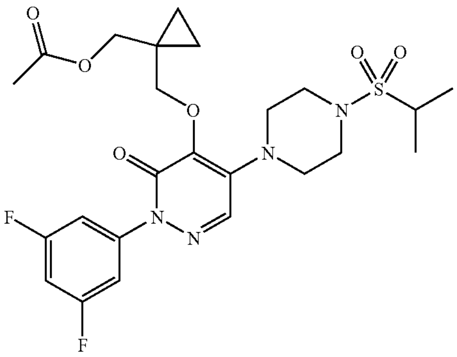 | 541 |
| 1529Z-4 | 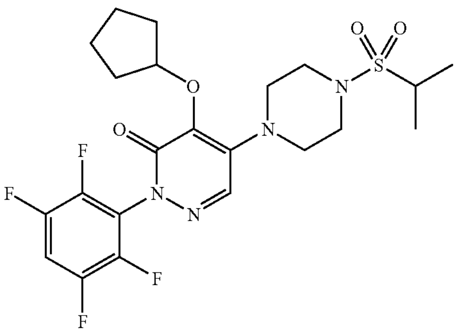 | 519 |
| 1529Z-5 | 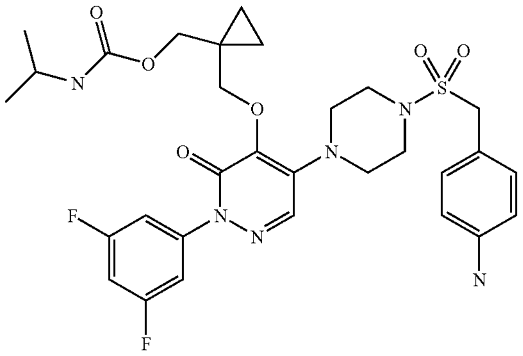 | 647 |
| 1529Z-6 | 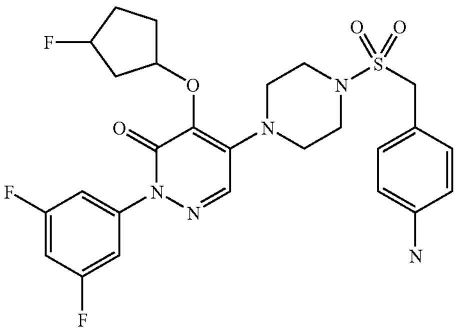 | 564 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-7 | 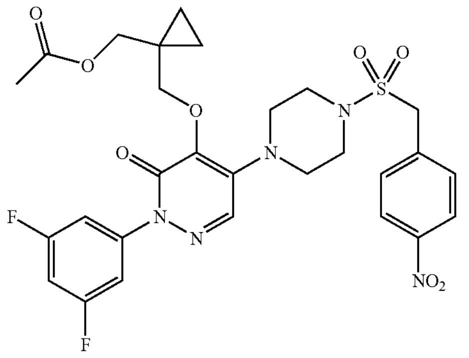 | 634 |
| 1529Z-8 | 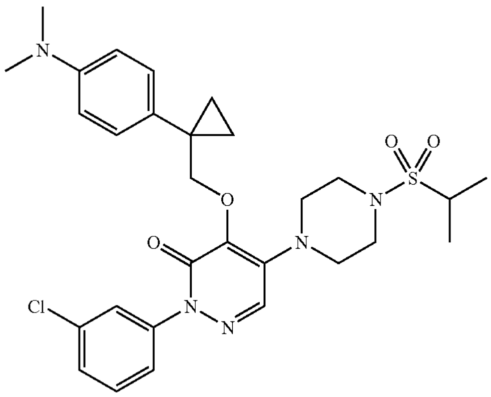 | 586 |
| 1529Z-9 | 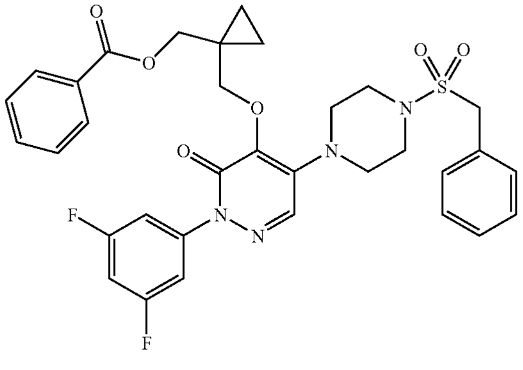 | 651 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1529Z-10 | 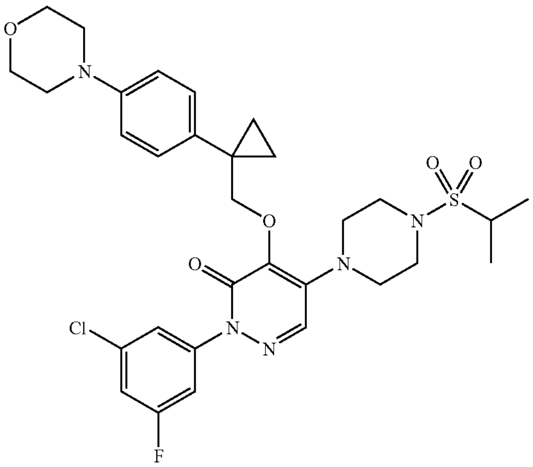 | 628 |
| 1529Z-11 | 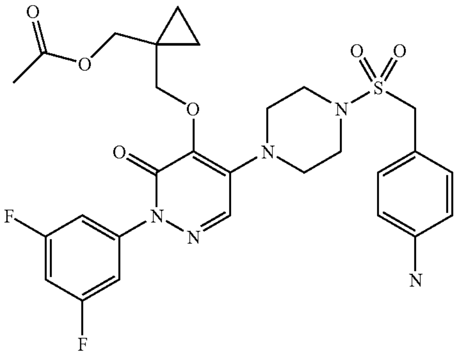 | 604 |
| 1529Z-12 | 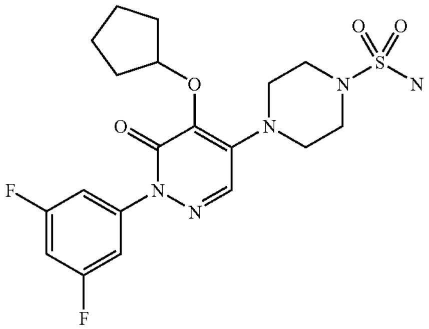 | 454 (M − 1) |
| 1529Z-13 | 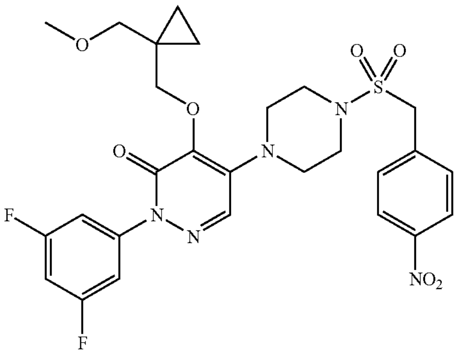 | 606 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1529Z-14 | 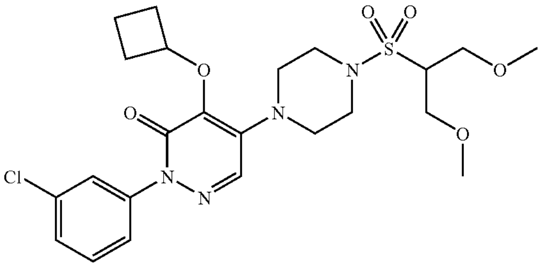 | 527 |
| 1529Z-15 | 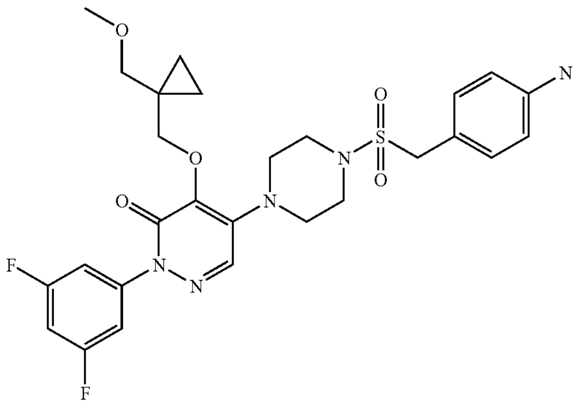 | 576 |
| 1529Z-16 | 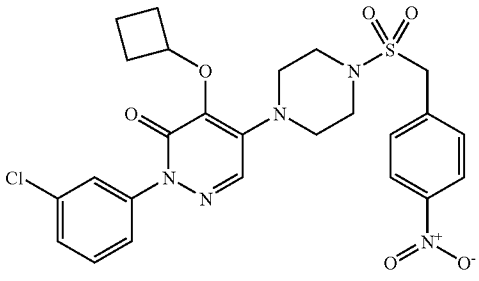 | 550 |
| 1529Z-17 | 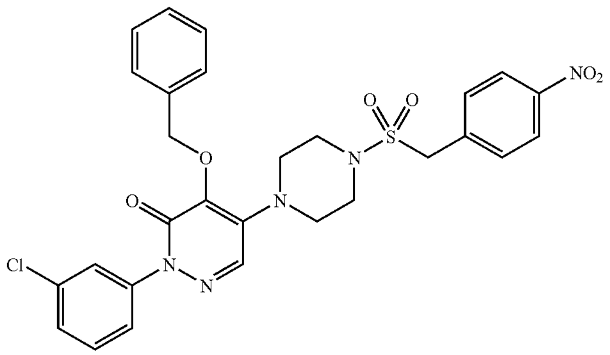 | 596 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-18 | 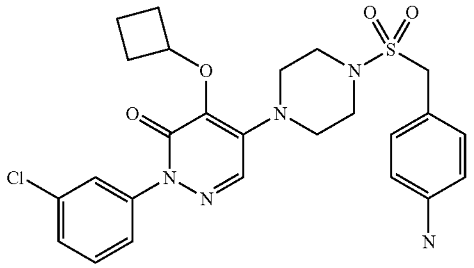 | 530 |
| 1529Z-19 | 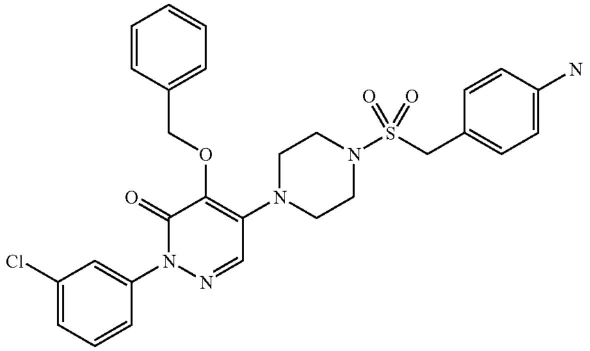 | 566 |
| 1529Z-20 | 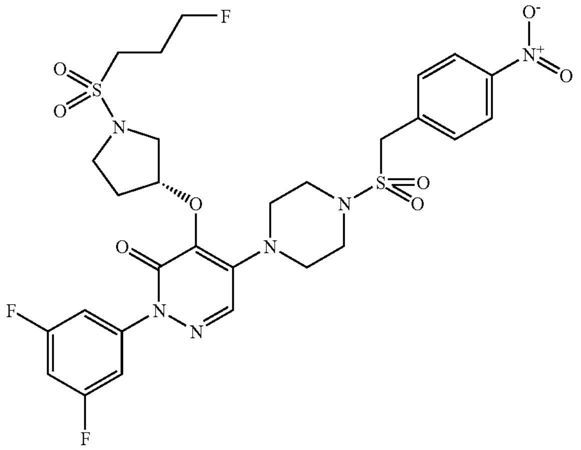 | 701 |
| 1529Z-21 | 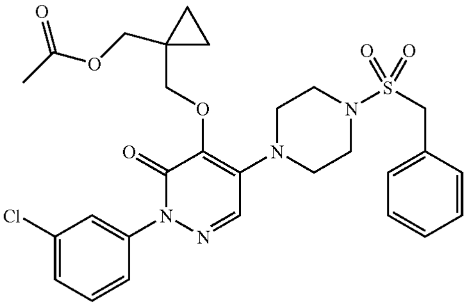 | 587 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1529Z-22 | 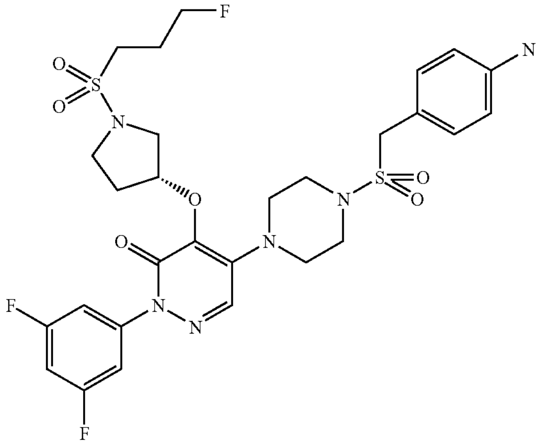 | 671 |
| 1529Z-23 | 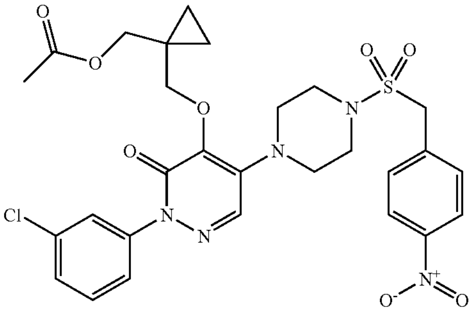 | 632 |
| 1529Z-24 | 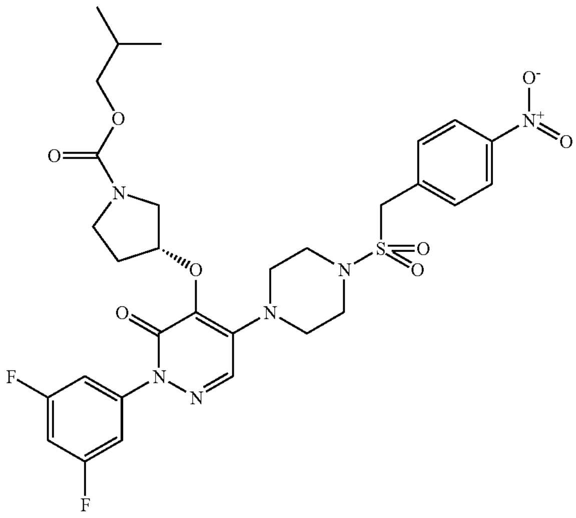 | 677 |

TABLE 11-continued
| Comp. No. | Structure | MS M + 1 |
| --- | --- | --- |
| Oxygen Linked Analogs with Sulfonamide The following compounds can be synthesized using steps 1, 2, 4, 6, and 9 of Scheme 1 or steps 11, 12, and 14 of Scheme 2. | | |
| 1529Z-25 | 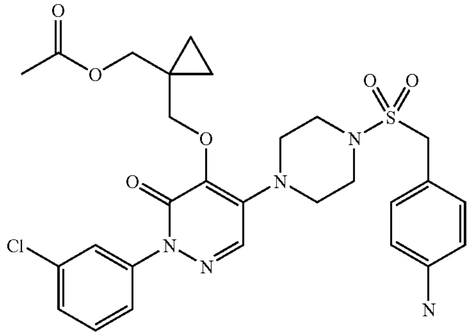 | 602 |
| 1529Z-26 | 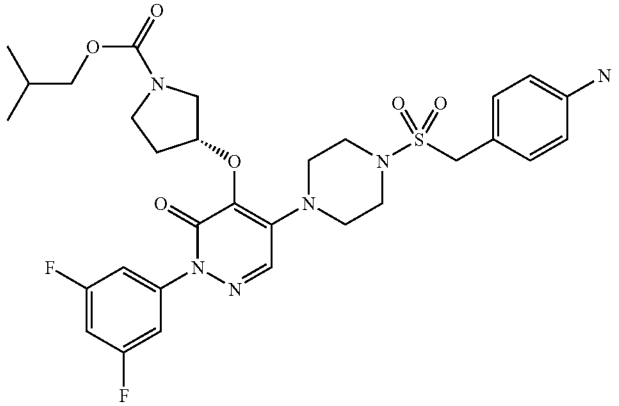 | 647 |
| 1529Z-27 | 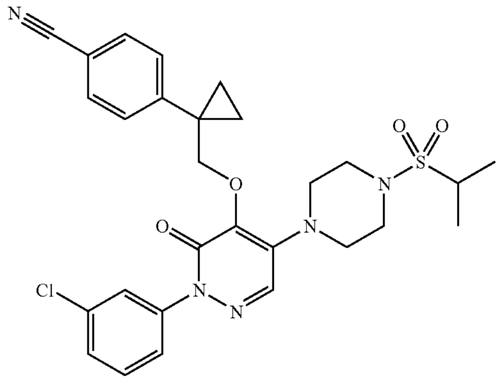 | 568 |
| 1529Z-28 | 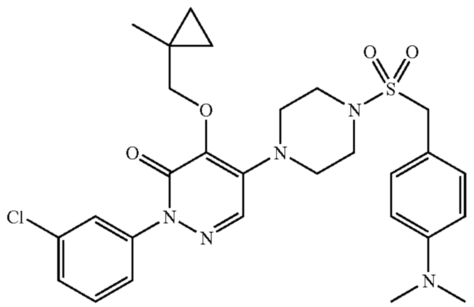 | 572 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1529Z-29 | 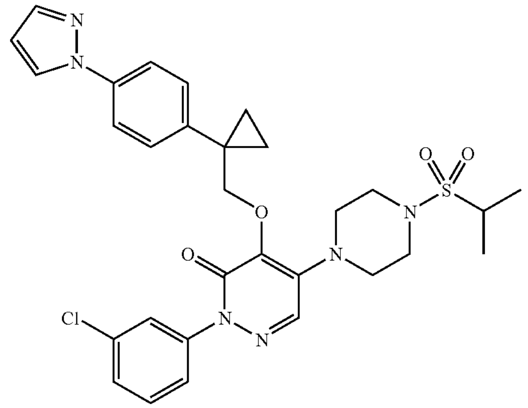 | 609 |
| 1529Z-30 | 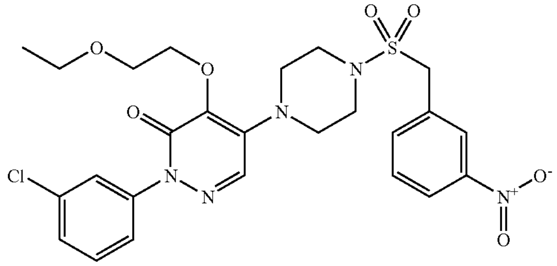 | 578 |
| 1529Z-31 | 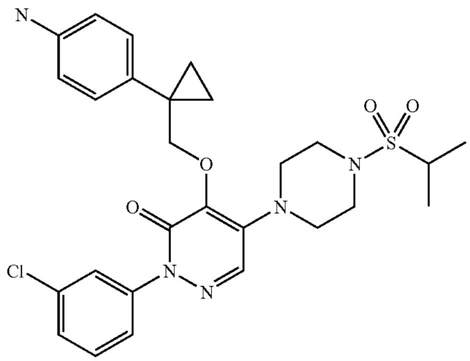 | 558 |
| 1529Z-32 | 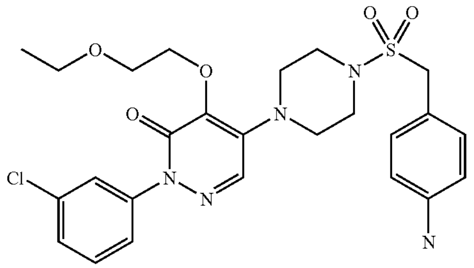 | 548 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
| --- | --- | --- |
| 1529Z-33 | 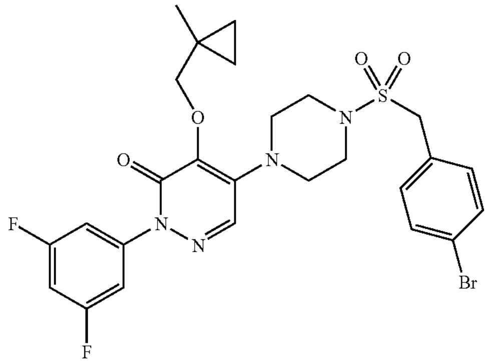 | 611 |
| 1529Z-34 | 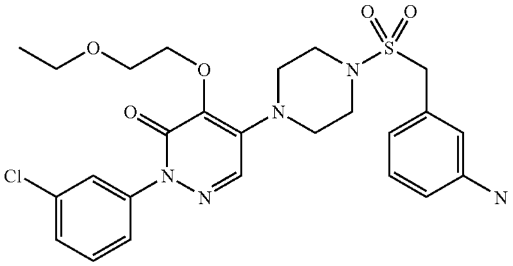 | 548 |
| 1529Z-35 | 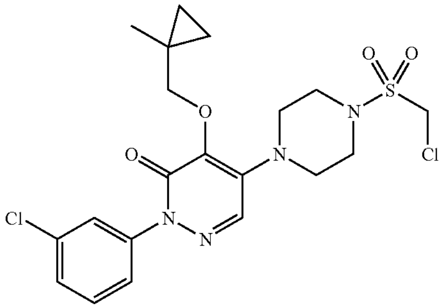 | 487 |
| 1529Z-36 | 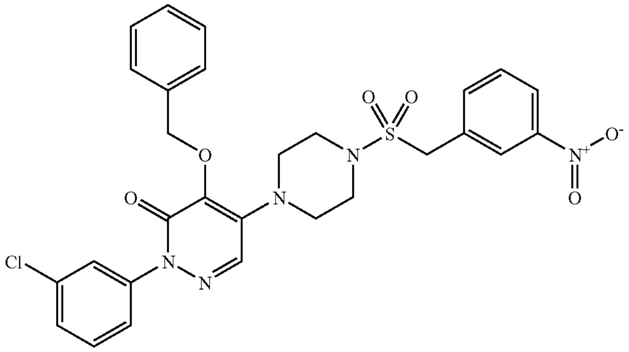 | 596 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-37 | 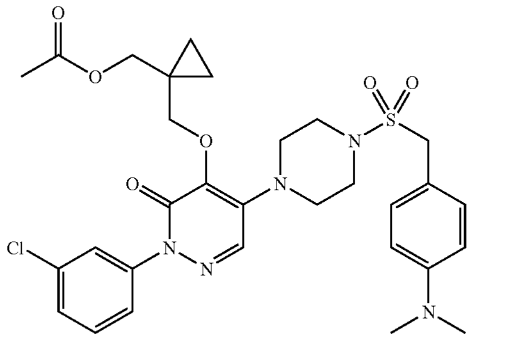 | 630 |
| 1529Z-38 | 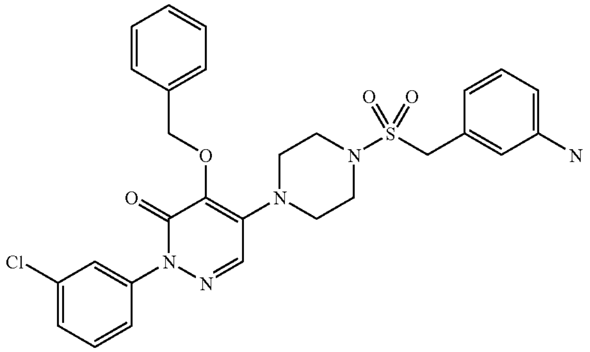 | 566 |
| 1529Z-39 | 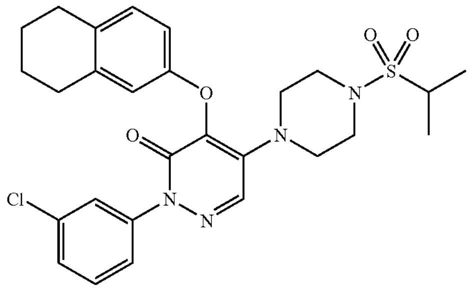 | 543 |
| 1529Z-40 | 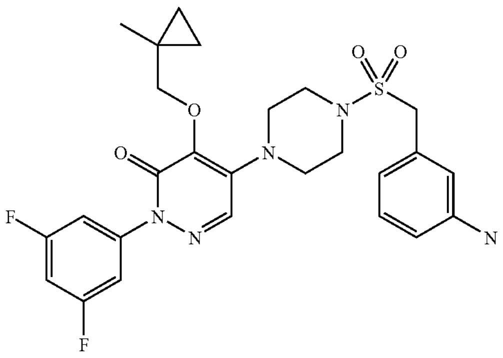 | 546 |

TABLE 11-continued
| Comp. No. | Structure | MS M + 1 |
| --- | --- | --- |
| | Oxygen Linked Analogs with Sulfonamide The following compounds can be synthesized using steps 1, 2, 4, 6, and 9 of Scheme 1 or steps 11, 12, and 14 of Scheme 2. | |
| 1529Z-41 | 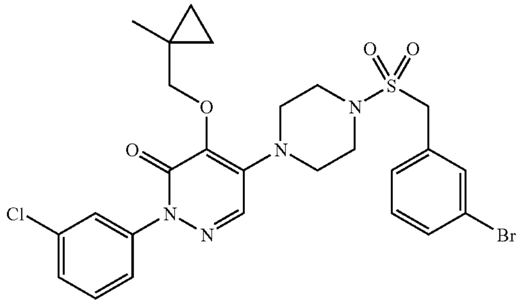 | 605 (M − 1) |
| 1529Z-42 | 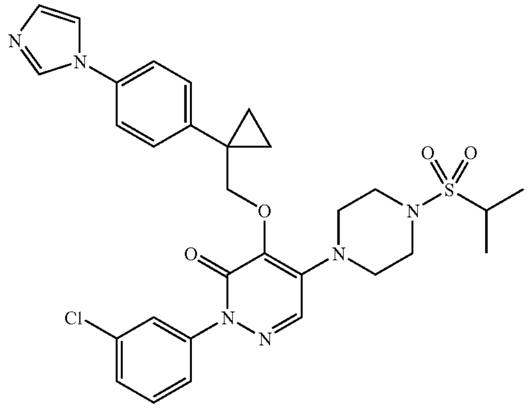 | 609 |
| 1529Z-43 | 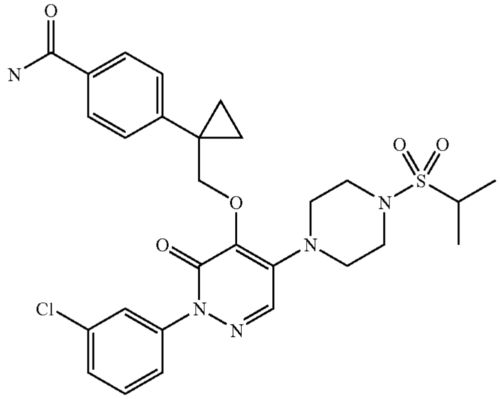 | 586 |
| 1529Z-44 | 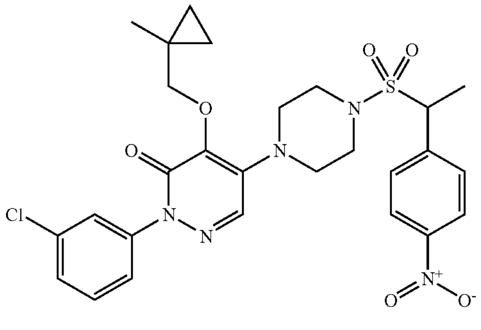 | 588 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-45 | 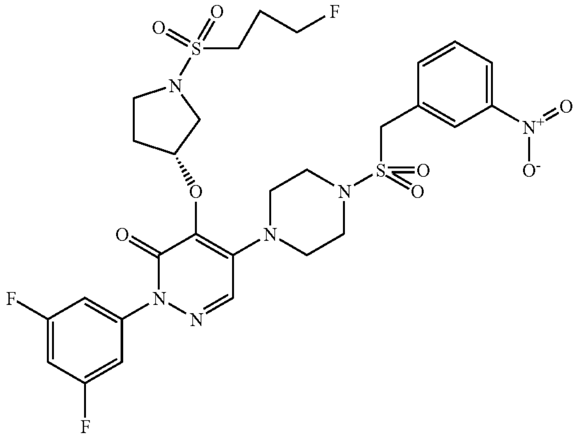 | 701 |
| 1529Z-46 | 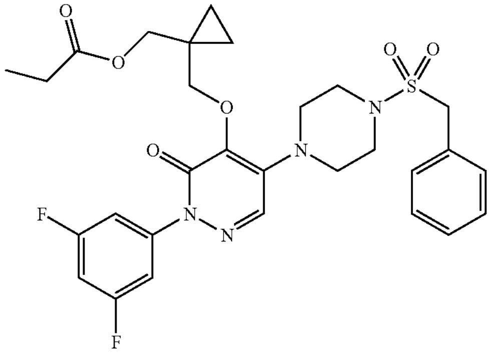 | 603 |
| 1529Z-47 | 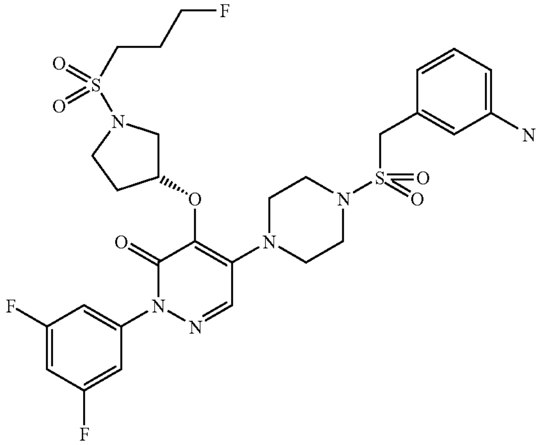 | 671 |

TABLE 11-continued
| Comp. No. | Structure | MS M + 1 |
| --- | --- | --- |
| Oxygen Linked Analogs with Sulfonamide The following compounds can be synthesized using steps 1, 2, 4, 6, and 9 of Scheme 1 or steps 11, 12, and 14 of Scheme 2. | | |
| 1529Z-48 | 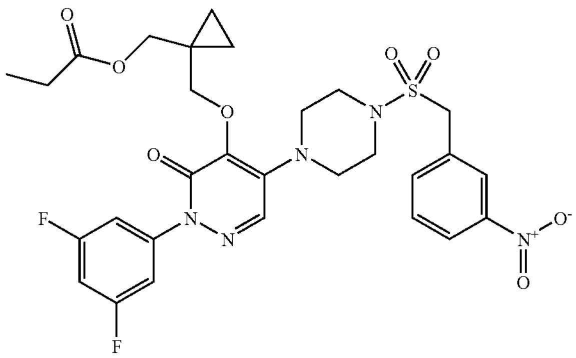 | 648 |
| 1529Z-49 | 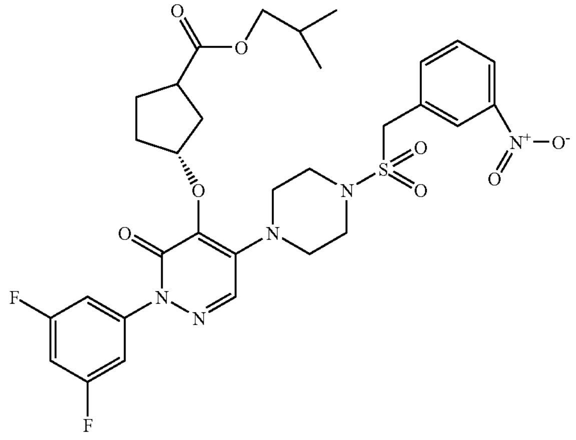 | 677 |
| 1529Z-50 | 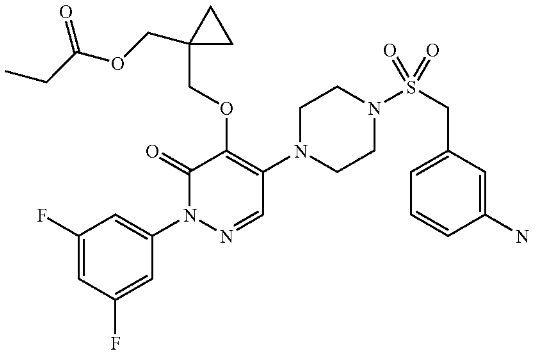 | 618 |

TABLE 11-continued
| Comp. No. | Structure | MS M + 1 |
| --- | --- | --- |
| | Oxygen Linked Analogs with Sulfonamide The following compounds can be synthesized using steps 1, 2, 4, 6, and 9 of Scheme 1 or steps 11, 12, and 14 of Scheme 2. | |
| 1529Z-51 | 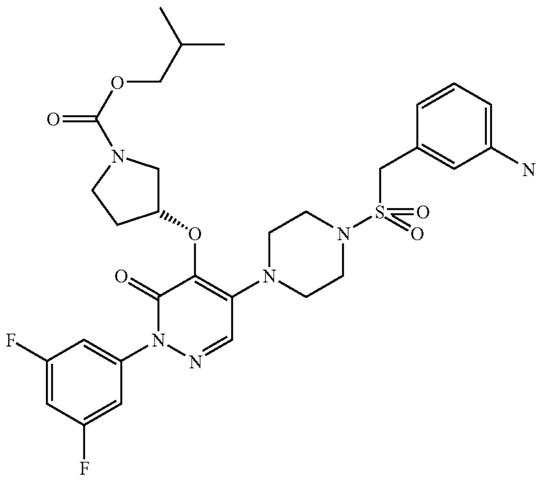 | 647 |
| 1529Z-52 | 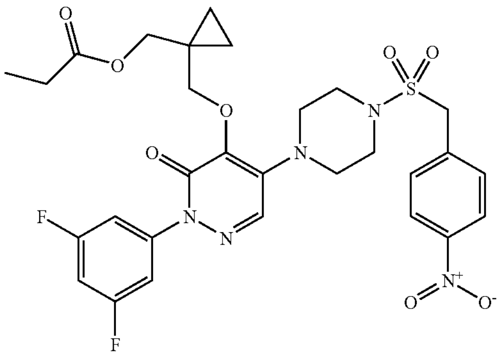 | 648 |
| 1529Z-53 | 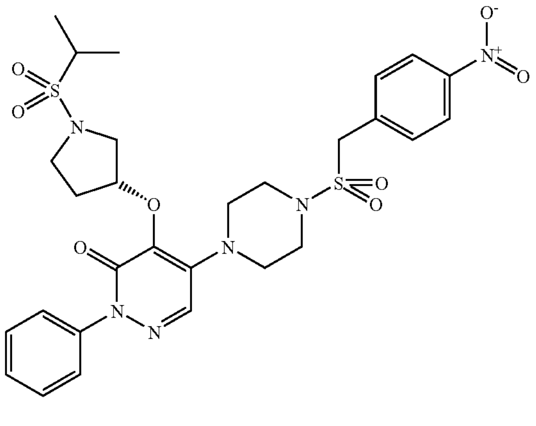 | 647 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-54 | 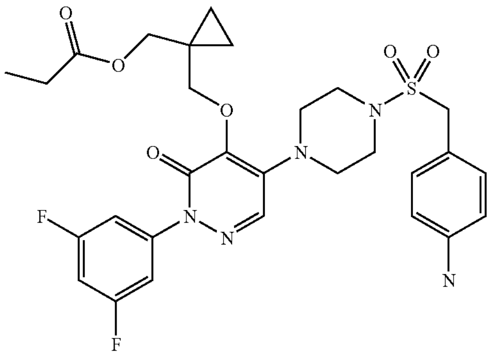 | 618 |
| 1529Z-55 | 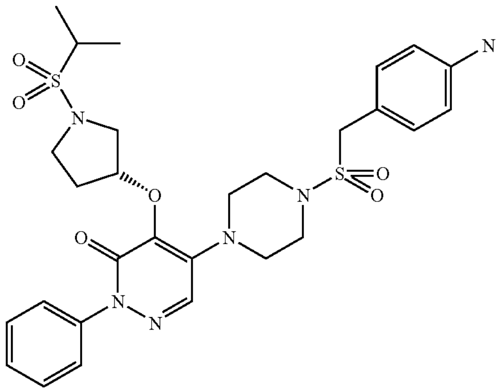 | 617 |
| 1529Z-56 | 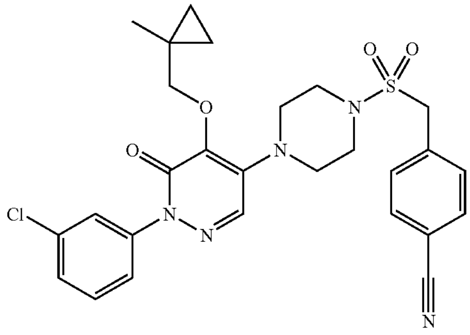 | 554 |
| 1529Z-57 | 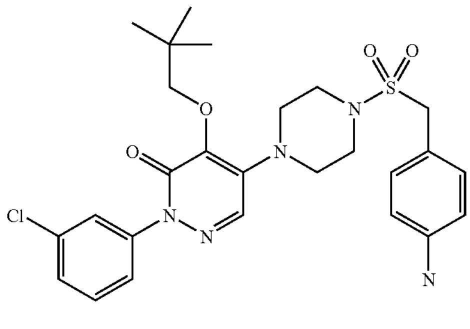 | 546 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-58 | 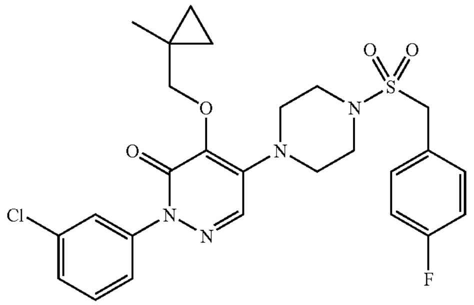 | 547 |
| 1529Z-59 | 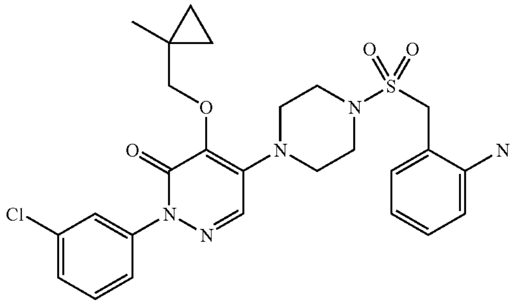 | 544 |
| 1529Z-60 | 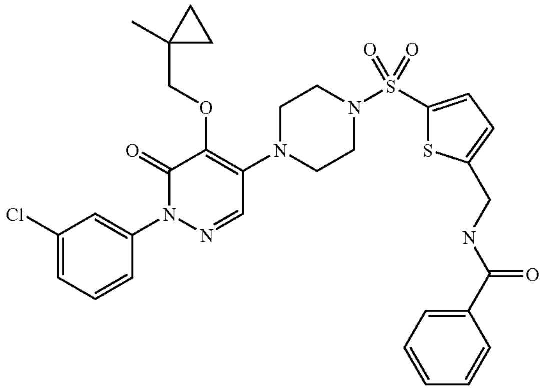 | 654 |
| 1529Z-61 | 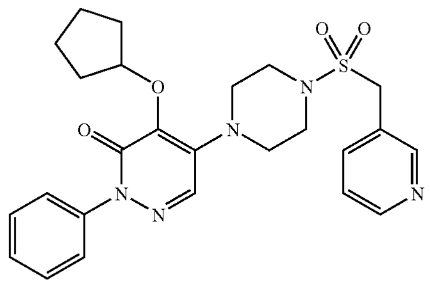 | 496 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-62 | 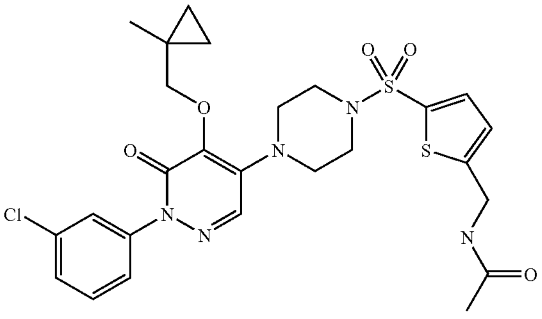 | 592 |
| 1529Z-63 | 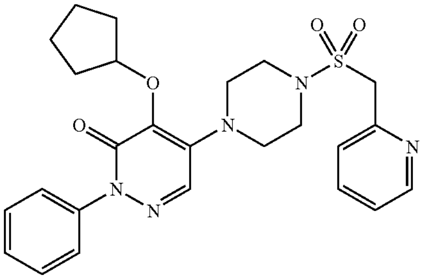 | 496 |
| 1529Z-64 | 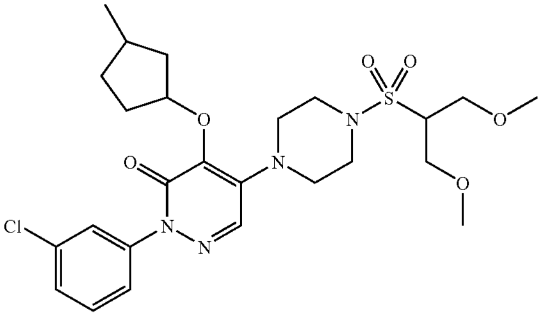 | 521 |
| 1529Z-65 | 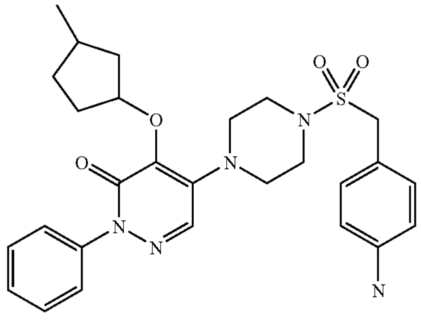 | 524 |

TABLE 11-continued
| Comp. No. | Structure | MS M + 1 |
|---|---|---|
| | Oxygen Linked Analogs with Sulfonamide<br>The following compounds can be synthesized using steps 1, 2, 4, 6, and 9 of Scheme 1 or steps 11, 12, and 14 of Scheme 2. | |
| 1529Z-66 | 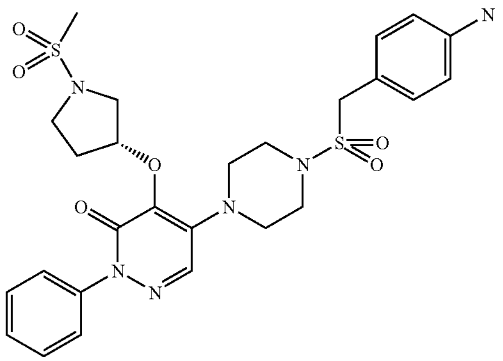 | 589 |
| 1529Z-67 | 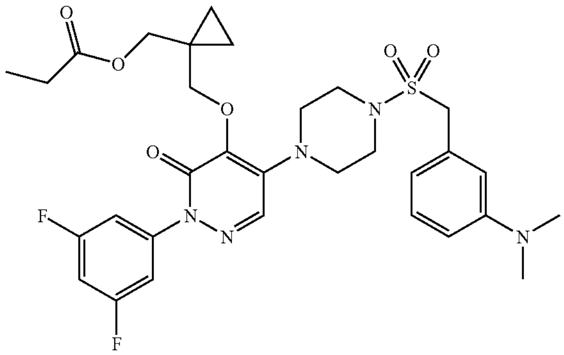 | 646 |
| 1529Z-68 | 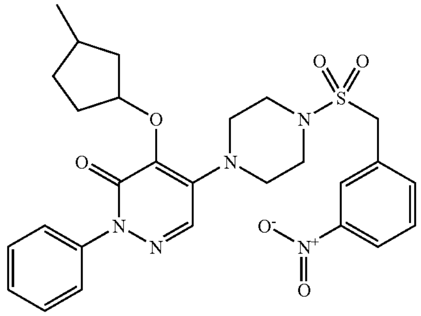 | 554 |
| 1529Z-69 | 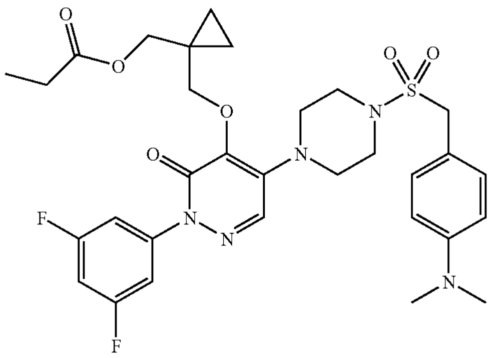 | 646 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-70 | 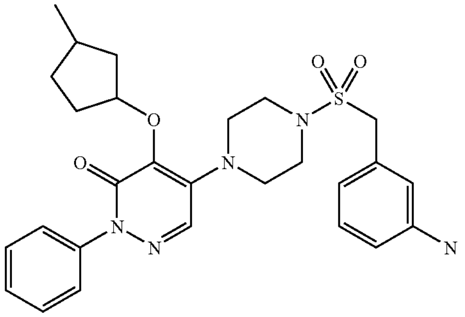 | 524 |
| 1529Z-71 | 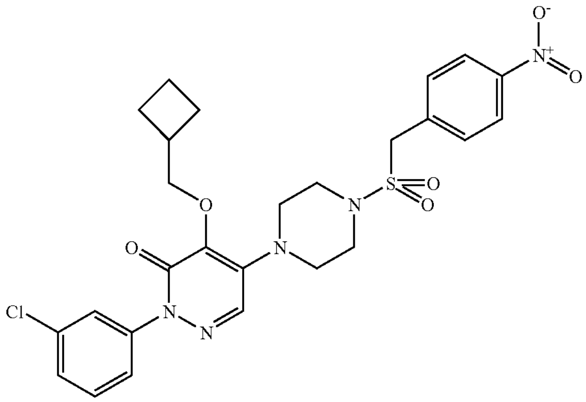 | 574 |
| 1529Z-72 | 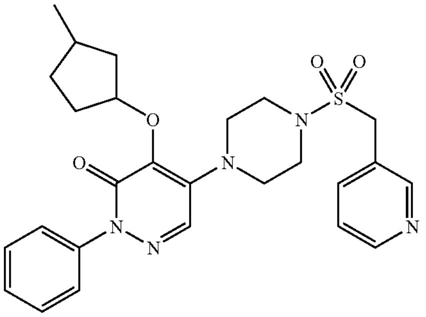 | 510 |
| 1529Z-73 | 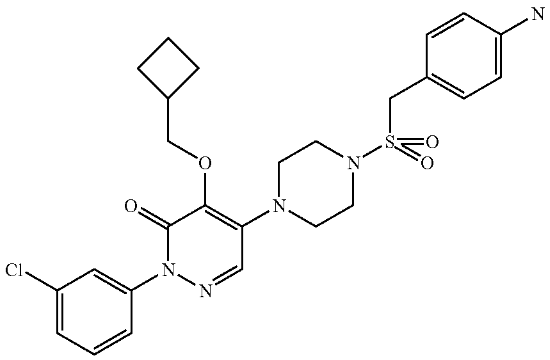 | 544 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1529Z-74 | 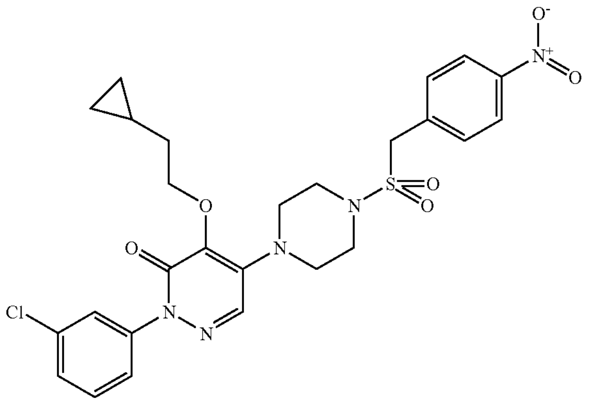 | 574 |
| 1529Z-75 | 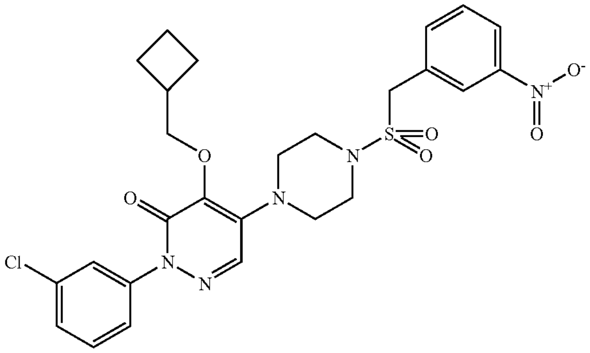 | 574 |
| 1529Z-76 | 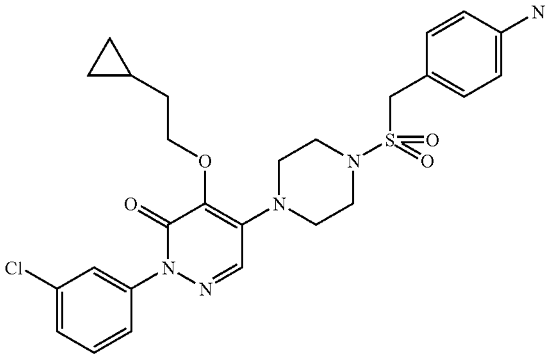 | 544 |
| 1529Z-77 | 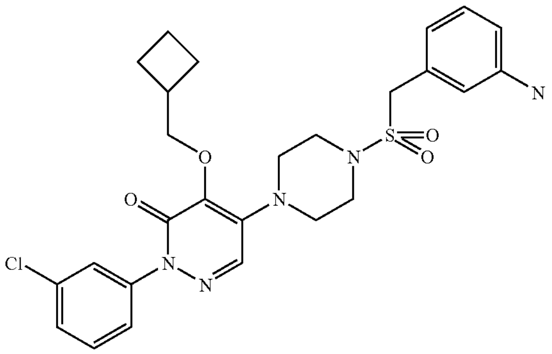 | 544 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
| --- | --- | --- |
| 1529Z-78 | 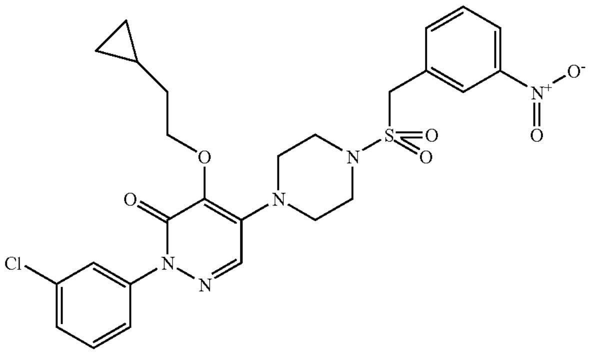 | 574 |
| 1529Z-79 | 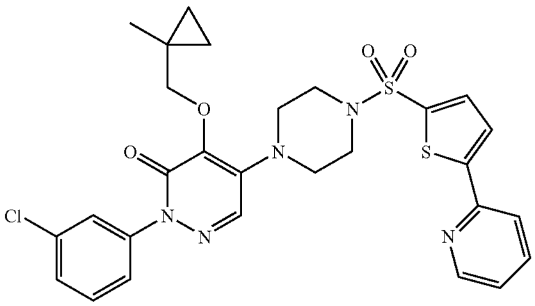 | 598 |
| 1529Z-80 | 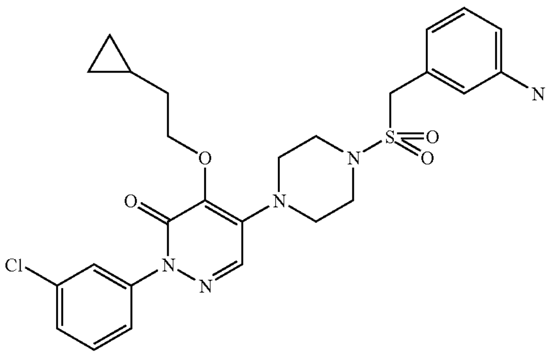 | 544 |
| 1529Z-81 | 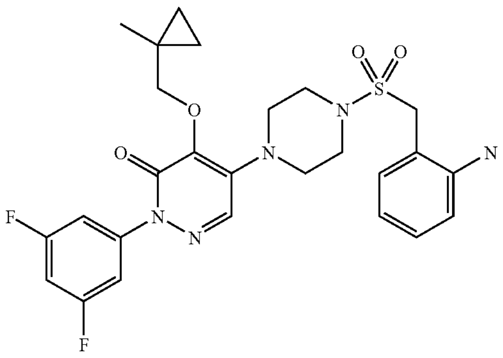 | 546 |

TABLE 11-continued
| Comp. No. | Structure | MS M + 1 |
|---|---|---|
| Oxygen Linked Analogs with Sulfonamide The following compounds can be synthesized using steps 1, 2, 4, 6, and 9 of Scheme 1 or steps 11, 12, and 14 of Scheme 2. | | |
| 1529Z-82 | 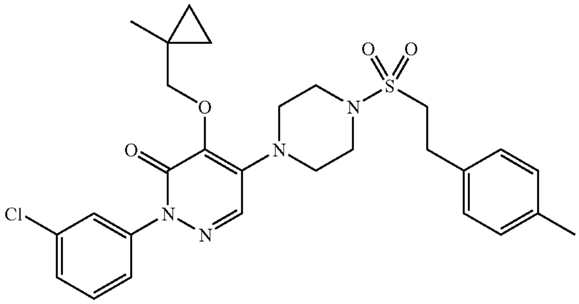 | 557 |
| 1529Z-83 | 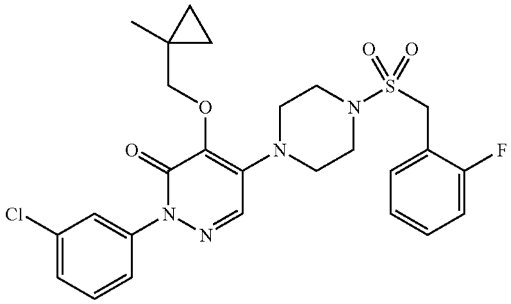 | 547 |
| 1529Z-84 | 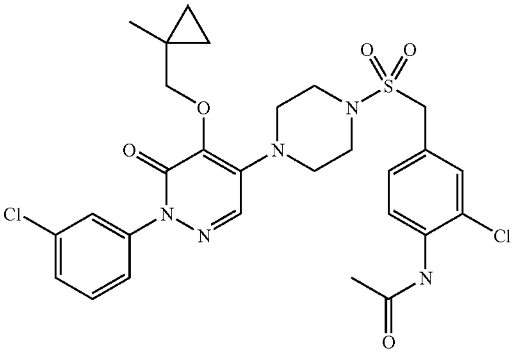 | 618 (M − 1) |
| 1529Z-85 | 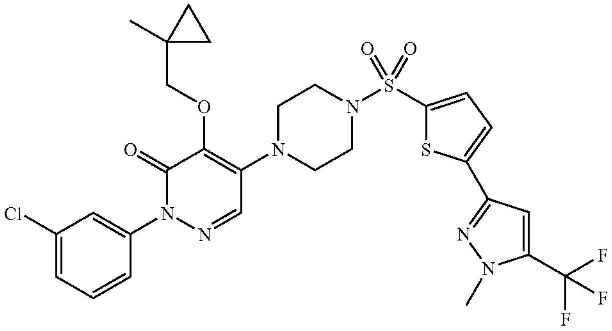 | 669 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-86 | 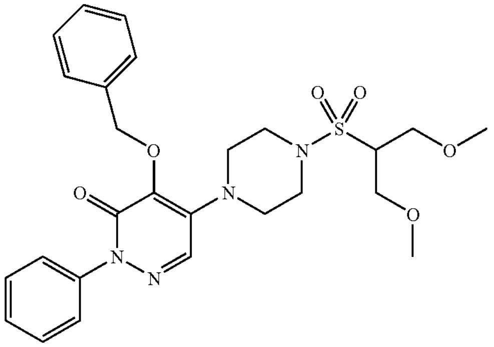 | 529 |
| 1529Z-87 | 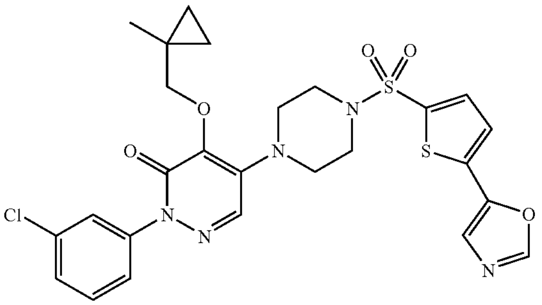 | 588 |
| 1529Z-88 | 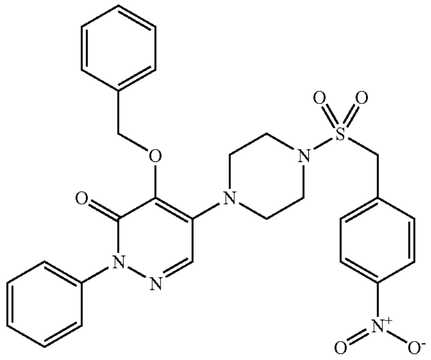 | 562 |
| 1529Z-89 | 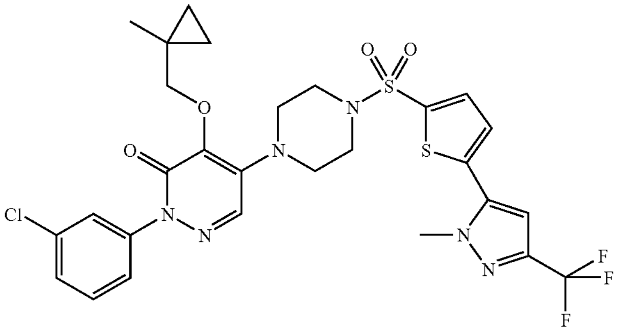 | 669 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-90 | 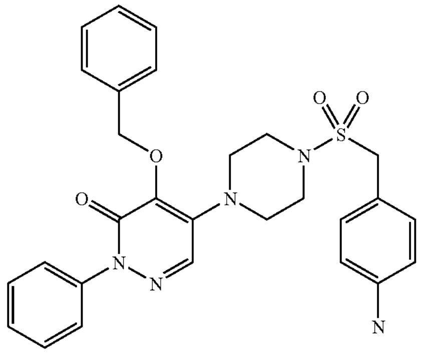 | 532 |
| 1529Z-91 | 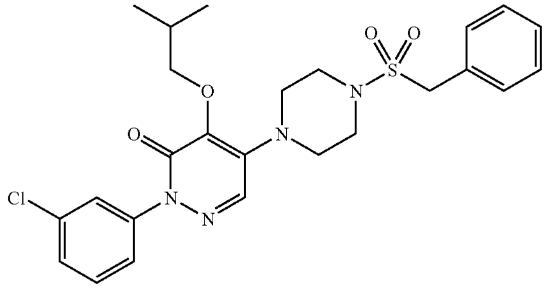 | 517 |
| 1529Z-92 | 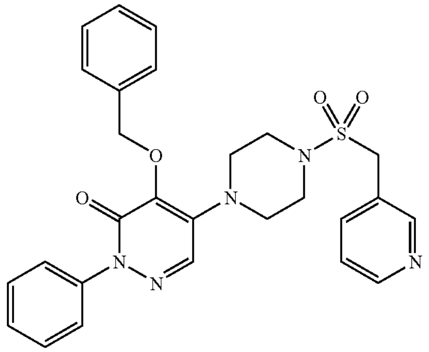 | 518 |
| 1529Z-93 | 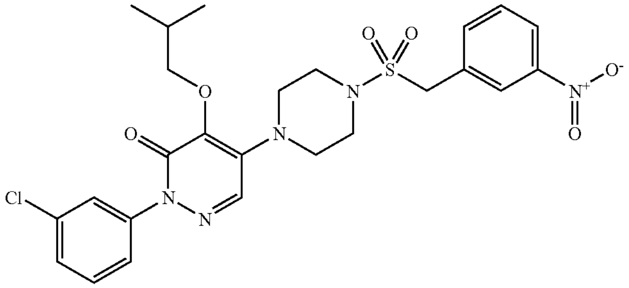 | 562 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-94 | 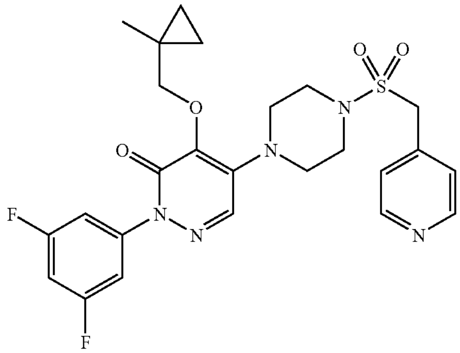 | 532 |
| 1529Z-95 | 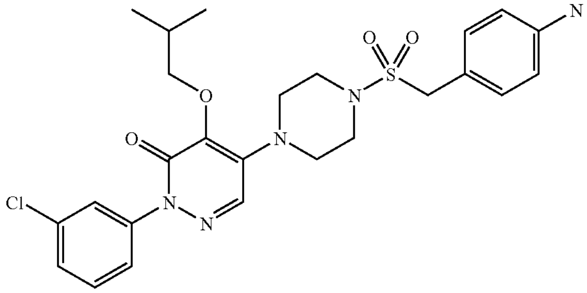 | 532 |
| 1529Z-96 | 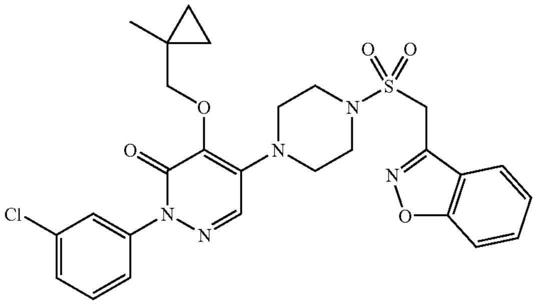 | 570 |
| 1529Z-97 | 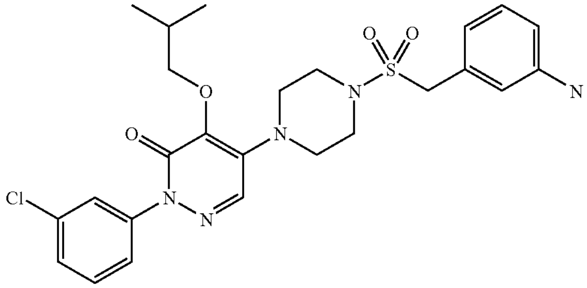 | 532 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-98 | 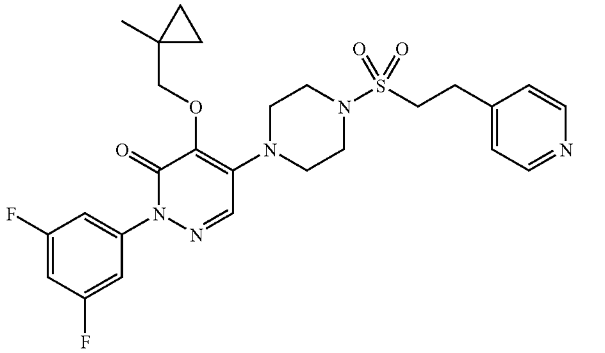 | 547 |
| 1529Z-99 | 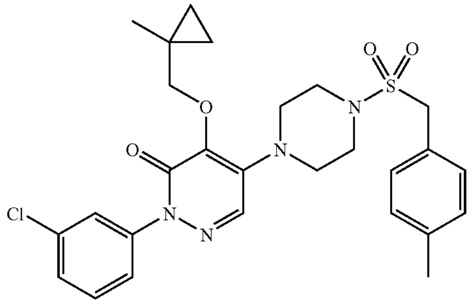 | 543 |
| 1529Z-100 | 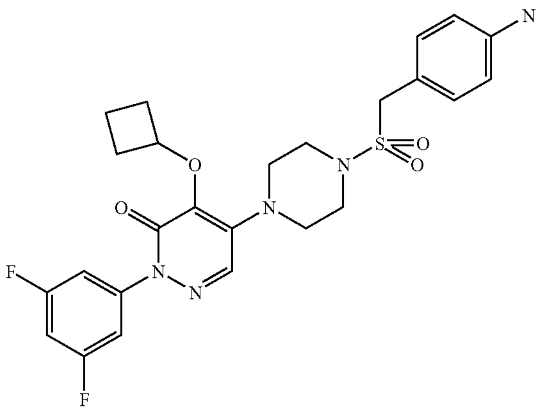 | 532 |
| 1529Z-101 | 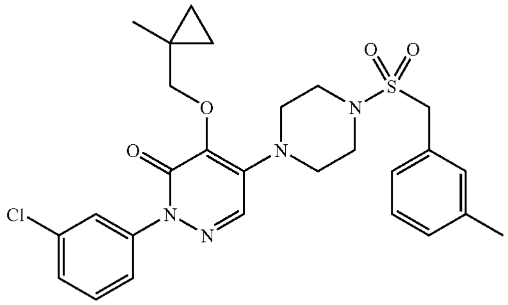 | 543 |

TABLE 11-continued
| Comp. No. | Structure | MS M + 1 |
| --- | --- | --- |
| | Oxygen Linked Analogs with Sulfonamide The following compounds can be synthesized using steps 1, 2, 4, 6, and 9 of Scheme 1 or steps 11, 12, and 14 of Scheme 2. | |
| 1529Z-102 | 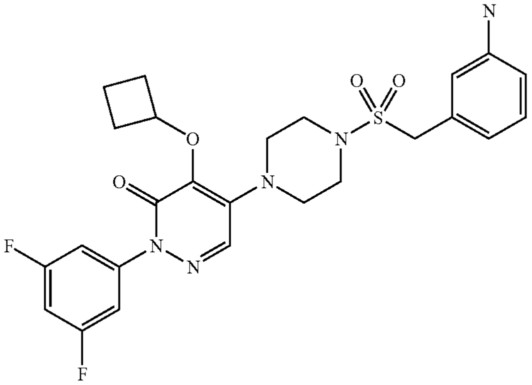 | 532 |
| 1529Z-103 | 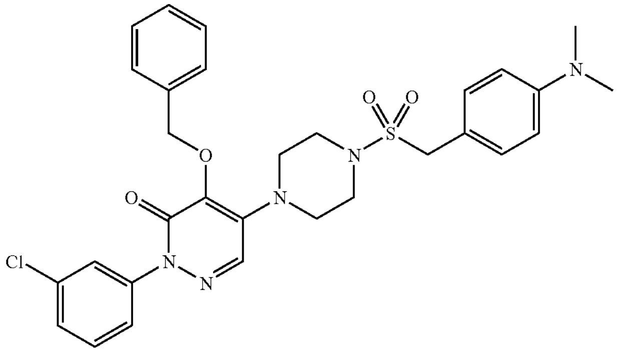 | 594 |
| 1529Z-104 | 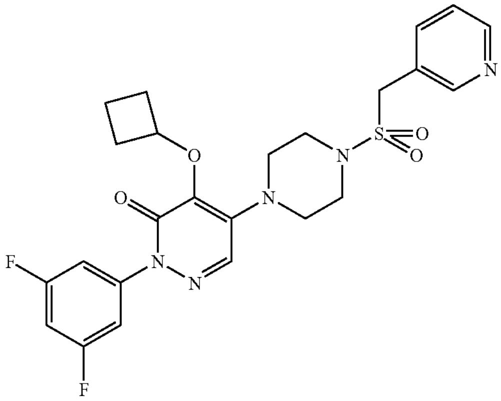 | 518 |
| 1529Z-105 | 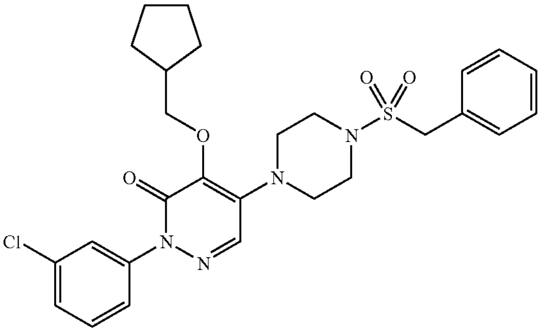 | 543 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-106 | 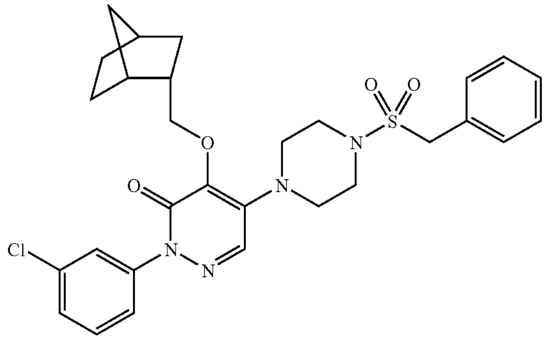 | 569 |
| 1529Z-107 | 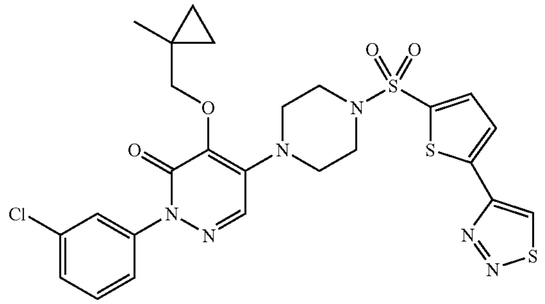 | 605 |
| 1529Z-108 | 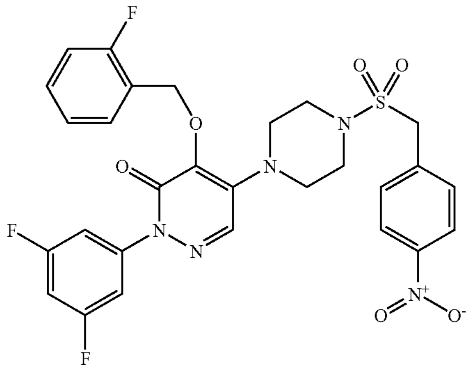 | 616 |
| 1529Z-109 | 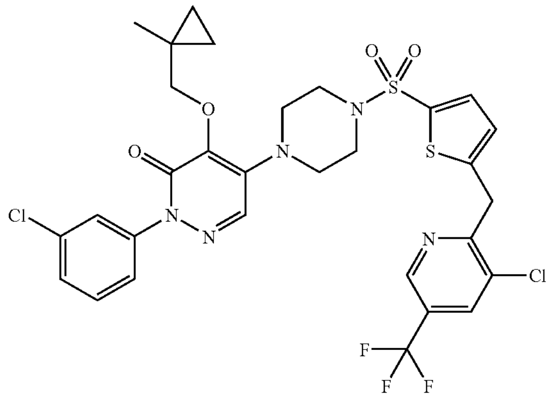 | 714 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1529Z-110 | 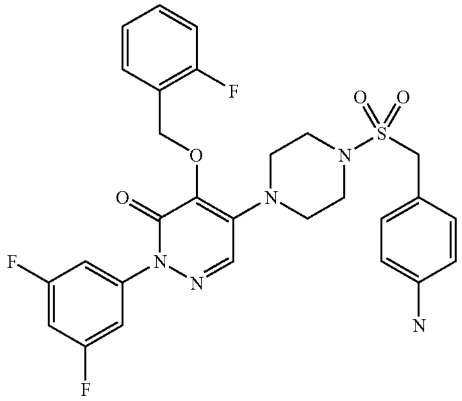 | 586 |
| 1529Z-111 | 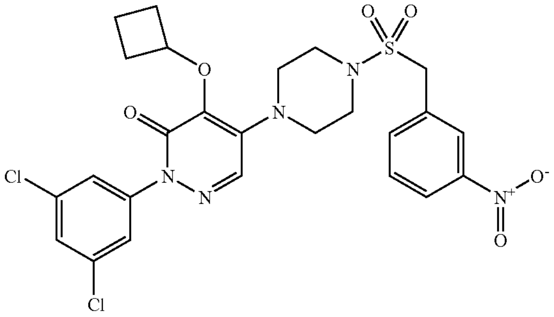 | 560 |
| 1529Z-112 | 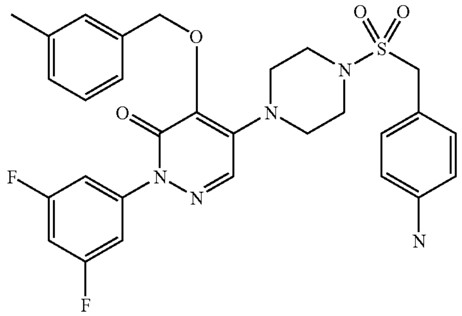 | 582 |
| 1529Z-113 | 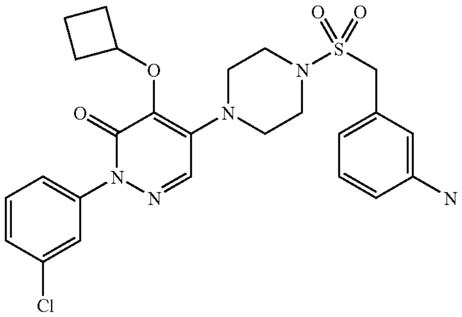 | 530 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
| --- | --- | --- |
| 1529Z-114 | 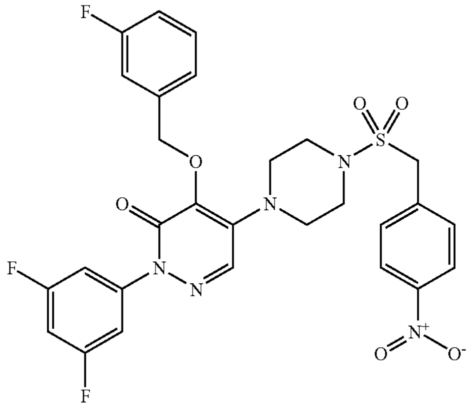 | 616 |
| 1529Z-115 | 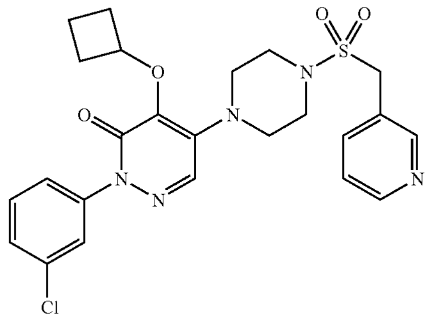 | 516 |
| 1529Z-116 | 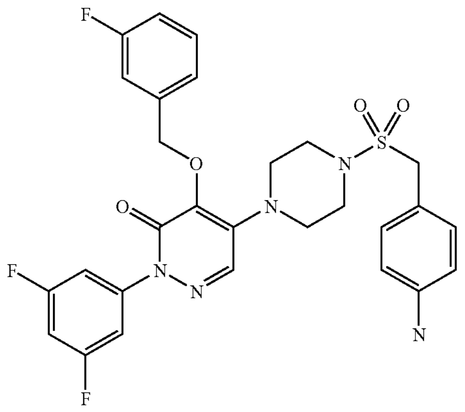 | 586 |
| 1529Z-117 | 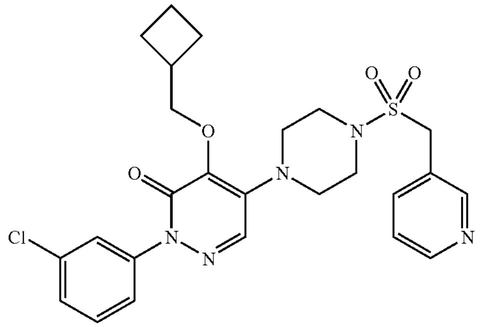 | 530 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1529Z-118 | 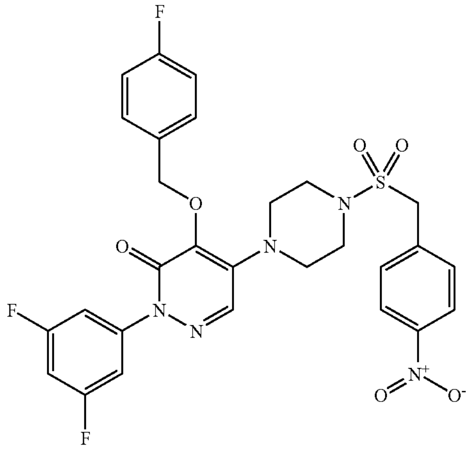 | 616 |
| 1529Z-119 | 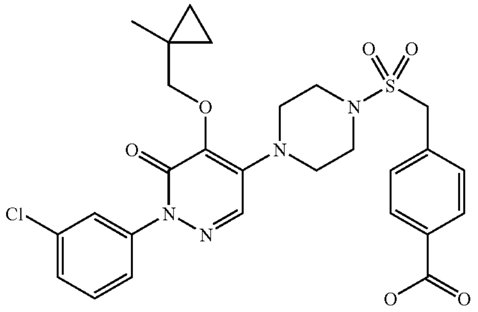 | 571 (M − 1) |
| 1529Z-120 | 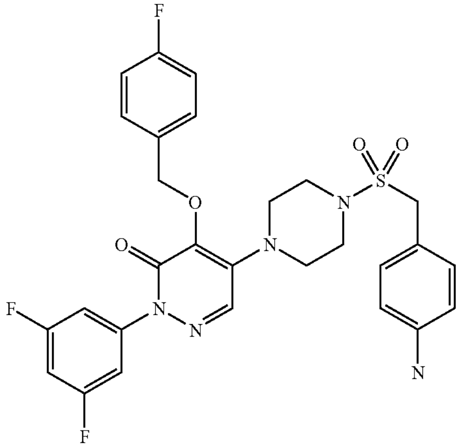 | 586 |

TABLE 11-continued
| Comp. No. | Structure | MS M + 1 |
|---|---|---|
| | Oxygen Linked Analogs with Sulfonamide The following compounds can be synthesized using steps 1, 2, 4, 6, and 9 of Scheme 1 or steps 11, 12, and 14 of Scheme 2. | |
| 1529Z-121 | 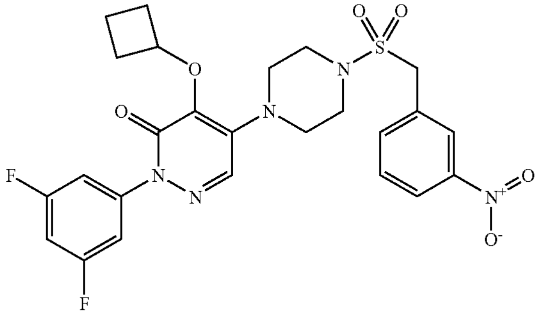 | 562 |
| 1529Z-122 | 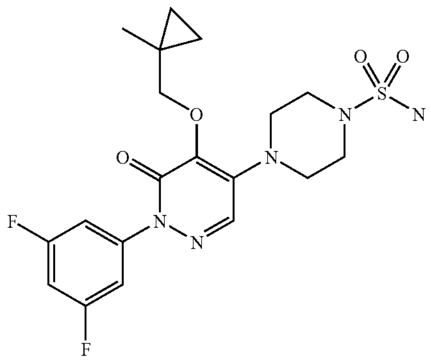 | 456 |
| 1529Z-123 | 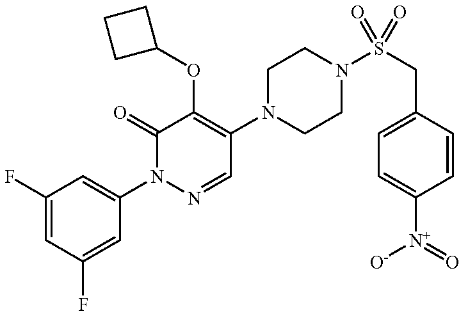 | 562 |
| 1529Z-124 | 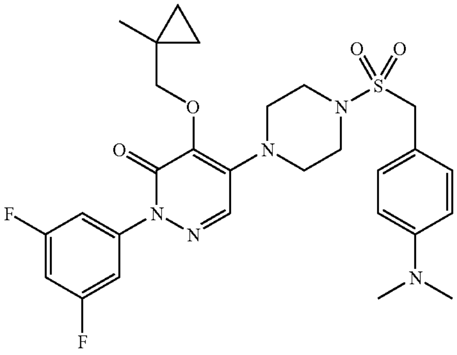 | 574 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-125 | 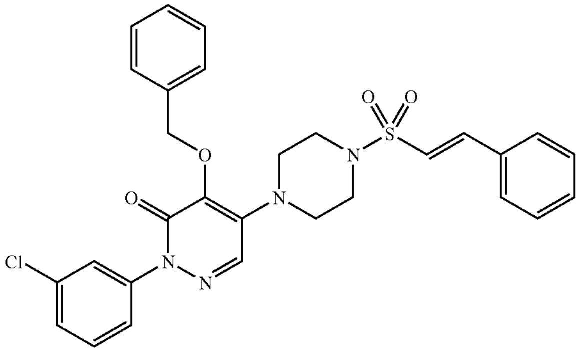 | 563 |
| 1529Z-126 | 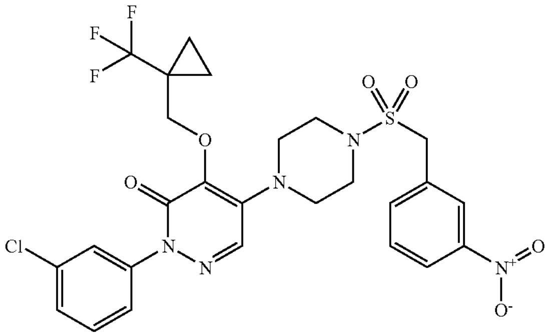 | 628 |
| 1529Z-127 | 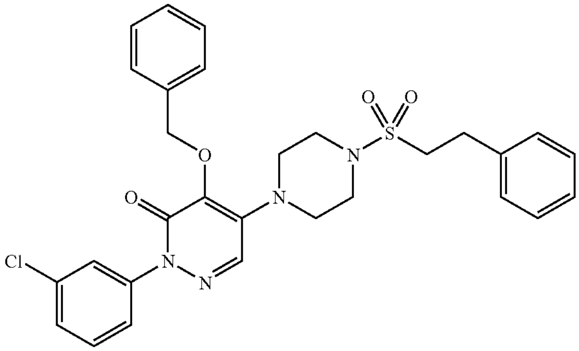 | 565 |
| 1529Z-128 | 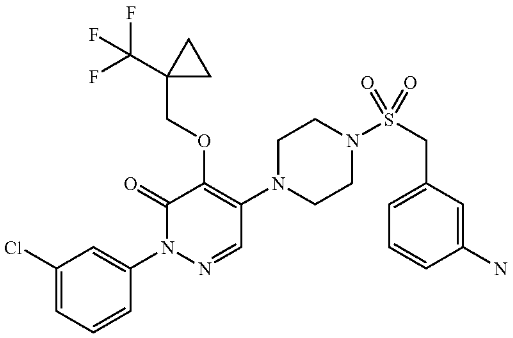 | 598 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-129 | 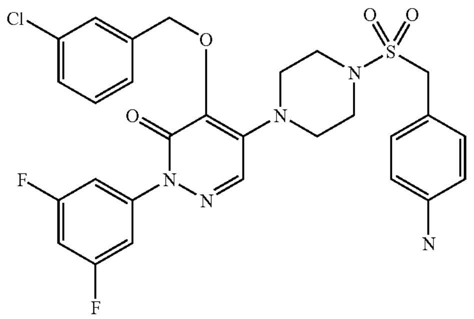 | 602 |
| 1529Z-130 | 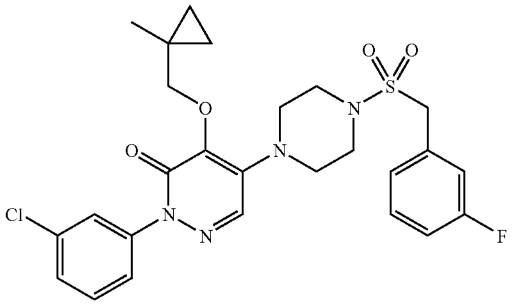 | 547 |
| 1529Z-131 | 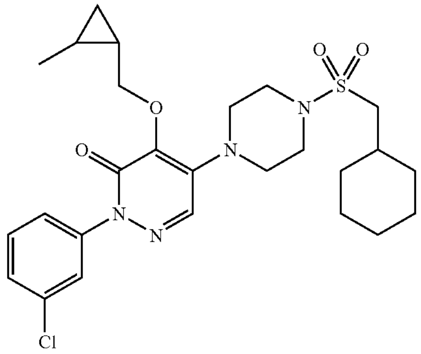 | 535 |
| 1529Z-132 | 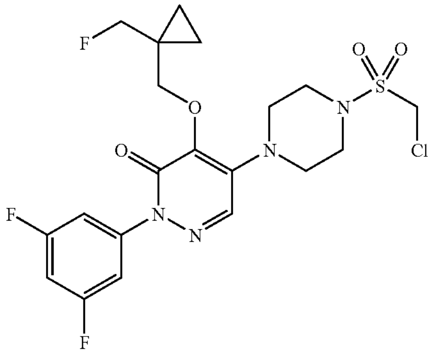 | 507 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1529Z-133 | 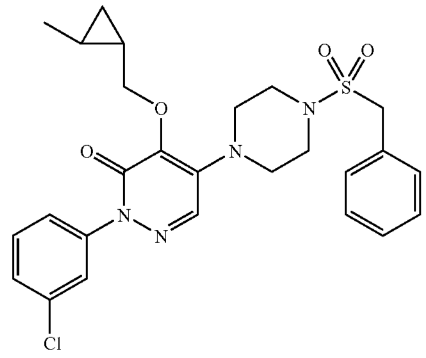 | 530 |
| 1529Z-134 | 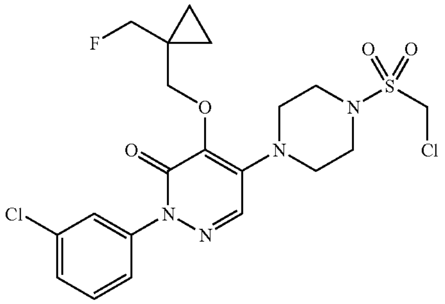 | 505 |
| 1529Z-135 | 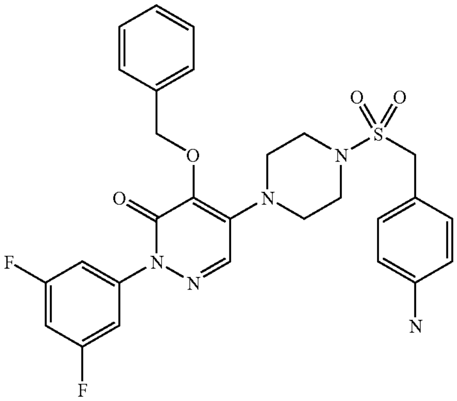 | 568 |
| 1529Z-136 | 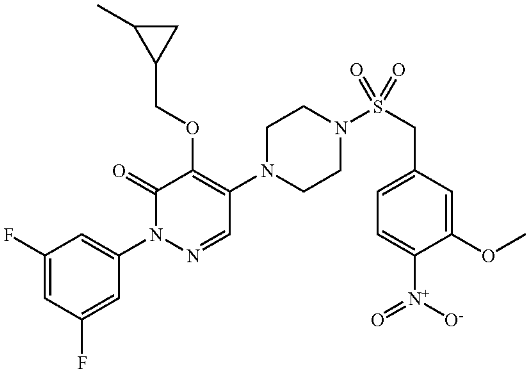 | 607 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
| --- | --- | --- |
| 1529Z-137 | 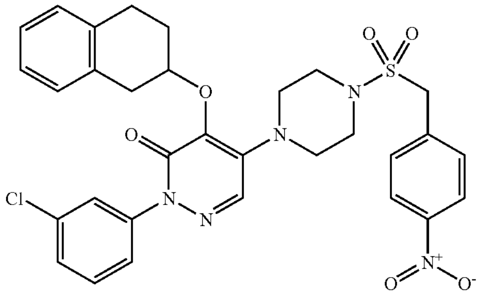 | 636 |
| 1529Z-138 | 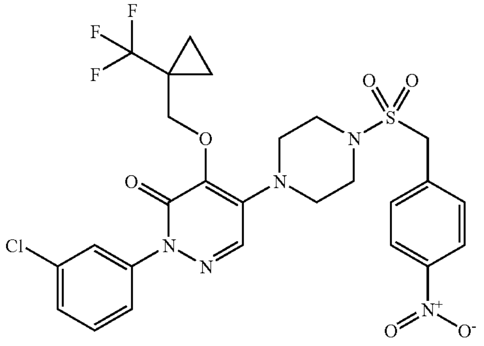 | 628 |
| 1529Z-139 | 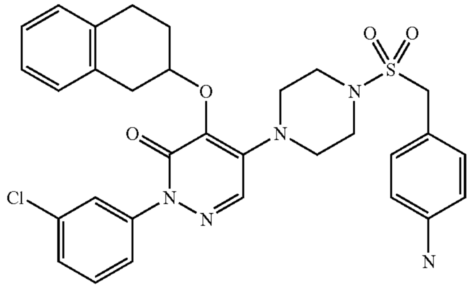 | 606 |
| 1529Z-140 | 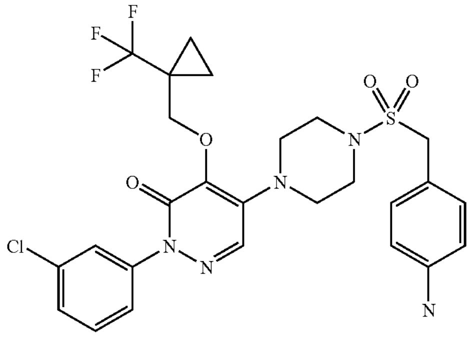 | 598 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-141 | 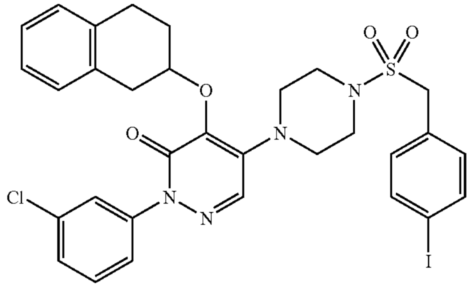 | 717 |
| 1529Z-142 | 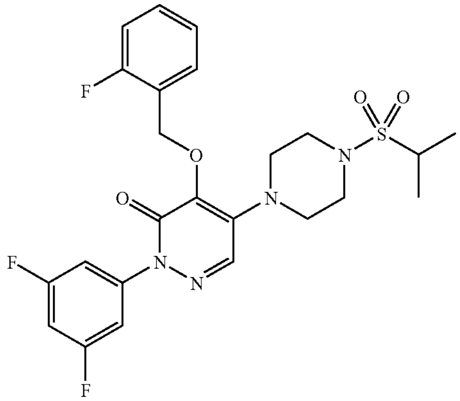 | 523 |
| 1529Z-143 | 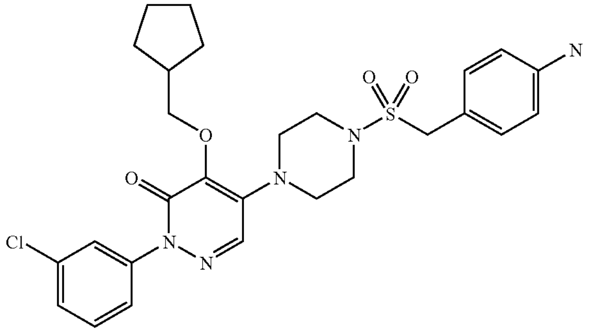 | 558 |
| 1529Z-144 | 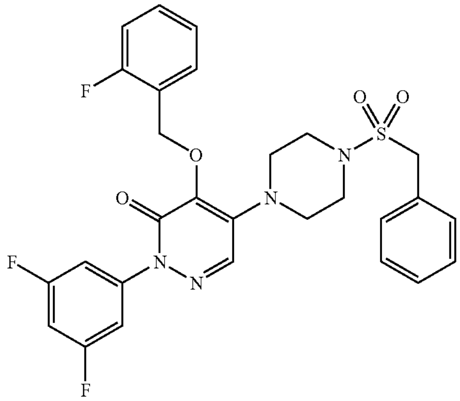 | 571 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-145 | 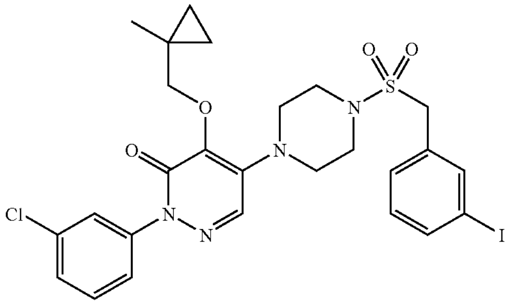 | 653 (M − 1) |
| 1529Z-146 | 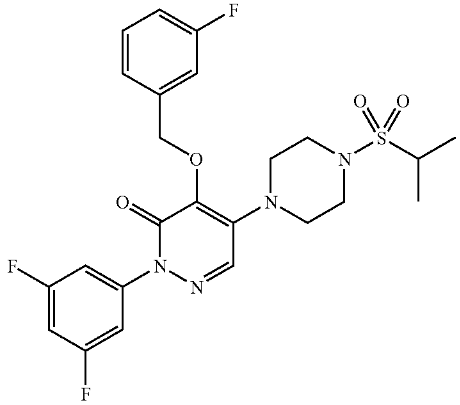 | 523 |
| 1529Z-147 | 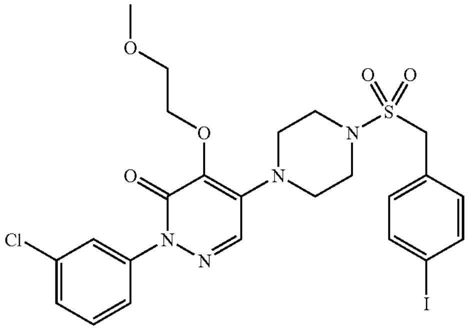 | 645 |
| 1529Z-148 | 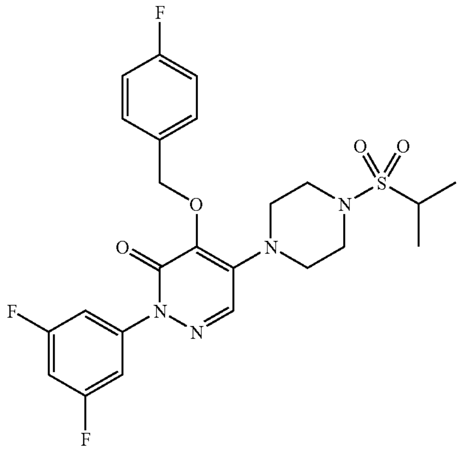 | 523 |

TABLE 11-continued
| Comp. No. | Structure | MS M + 1 |
|---|---|---|
| Oxygen Linked Analogs with Sulfonamide<br>The following compounds can be synthesized using steps 1, 2, 4, 6, and 9 of Scheme 1 or steps 11, 12, and 14 of Scheme 2. | | |
| 1529Z-149 | 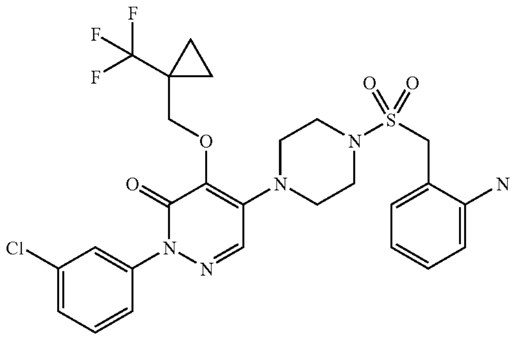 | 599 |
| 1529Z-150 | 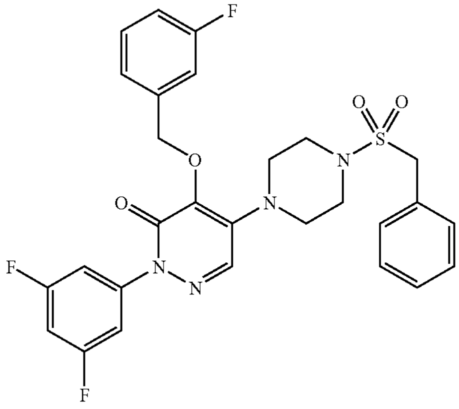 | 571 |
| 1529Z-151 | 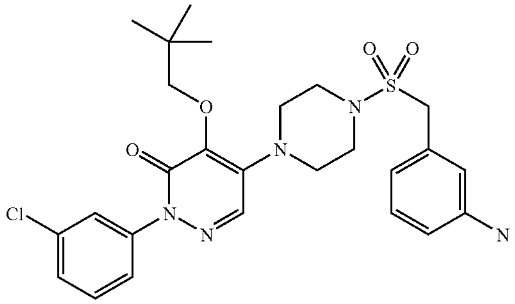 | 546 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1529Z-152 | 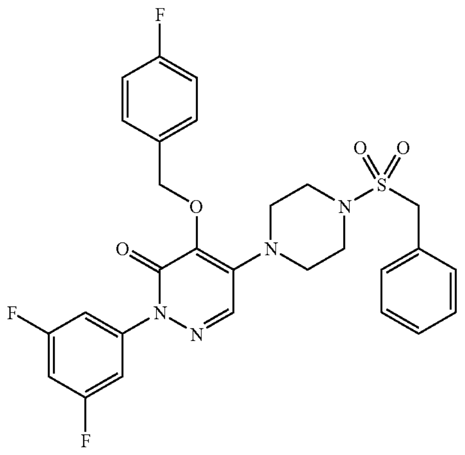 | 571 |
| 1529Z-153 | 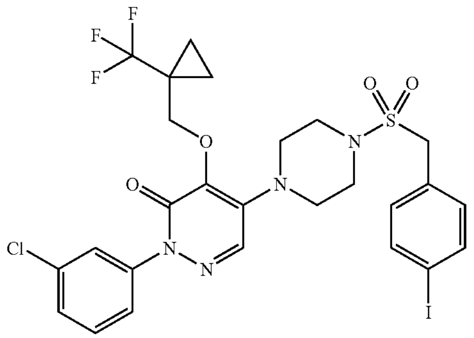 | 709 |
| 1529Z-154 | 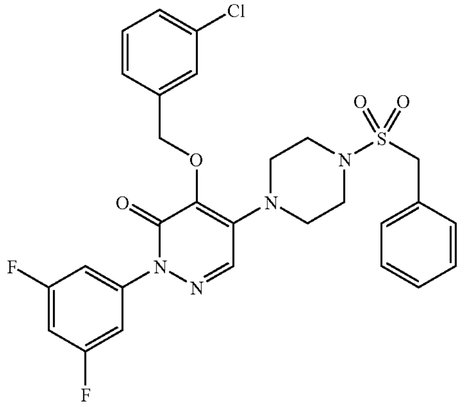 | 587 |
| 1529Z-155 | 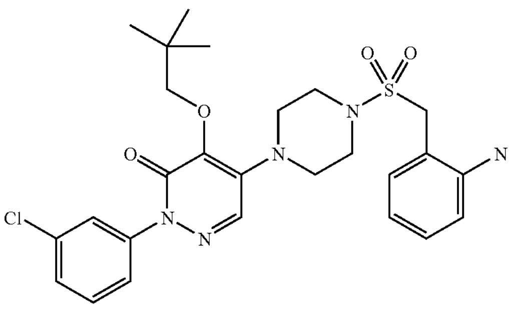 | 546 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-156 | 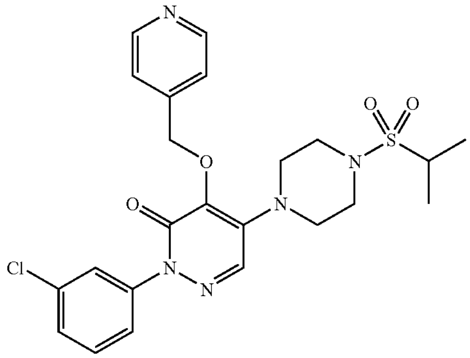 | 504 |
| 1529Z-157 | 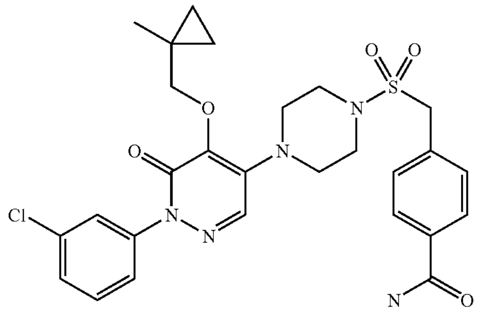 | 572 |
| 1529Z-158 | 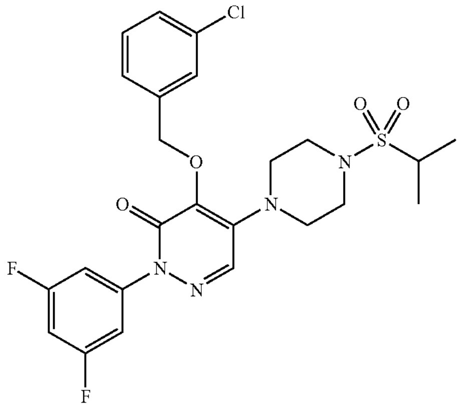 | 539 |
| 1529Z-159 | 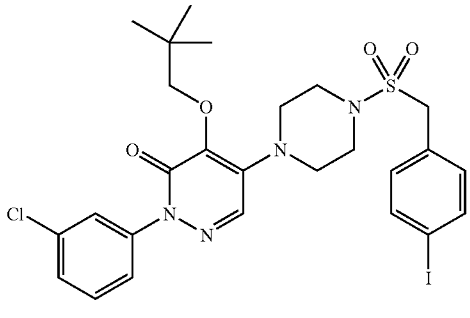 | 657 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-160 | 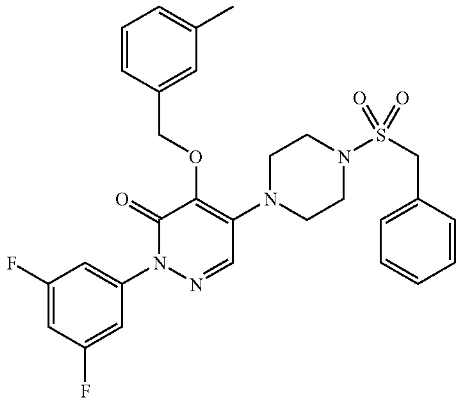 | 567 |
| 1529Z-161 | 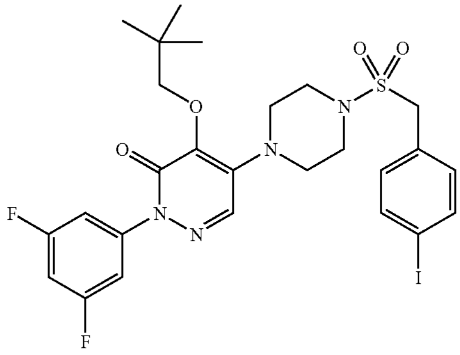 | 659 |
| 1529Z-162 | 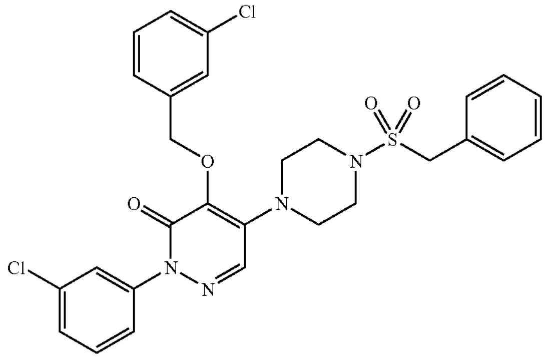 | 585 |
| 1529Z-163 | 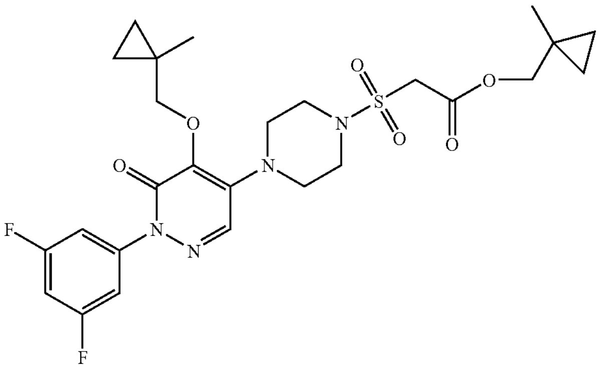 | 567 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-164 | 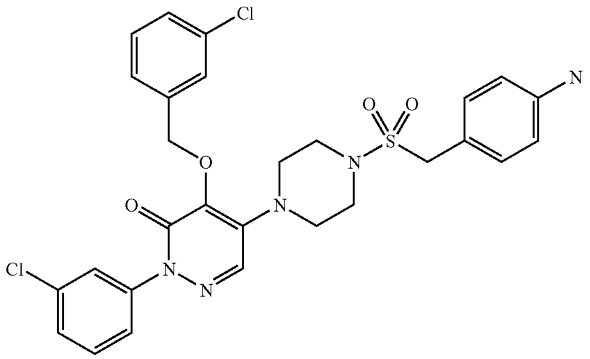 | 600 |
| 1529Z-165 | 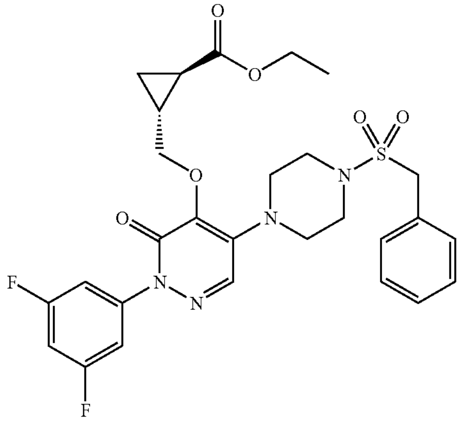 | 589 |
| 1529Z-166 | 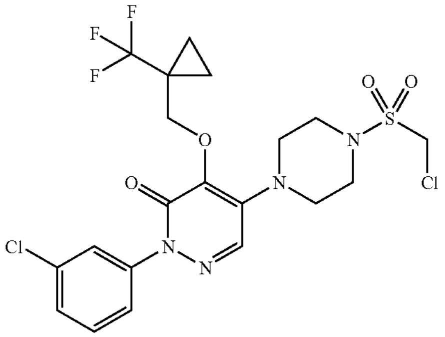 | 541 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-167 | 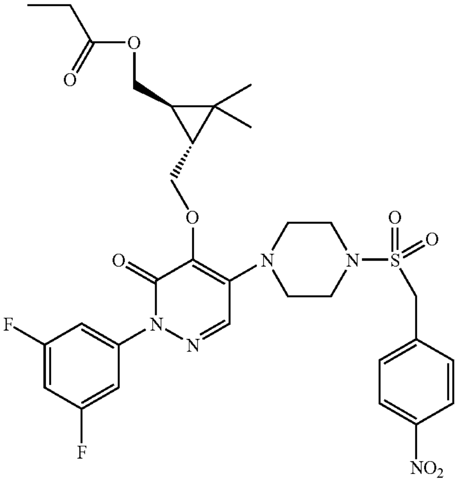 | 676 |
| 1529Z-1689 | 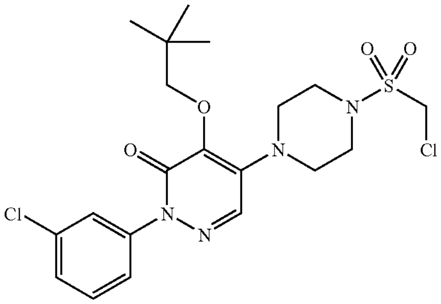 | 489 |
| 1529Z-169 | 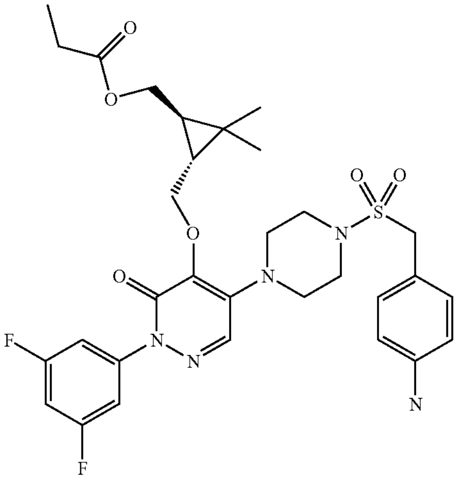 | 646 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1529Z-170 | 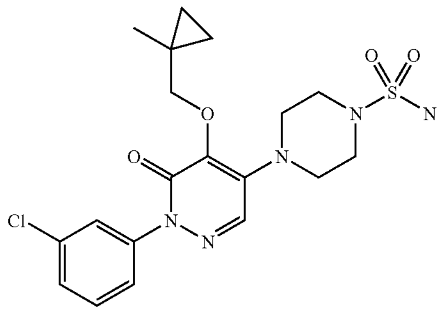 | 454 |
| 1529Z-171 | 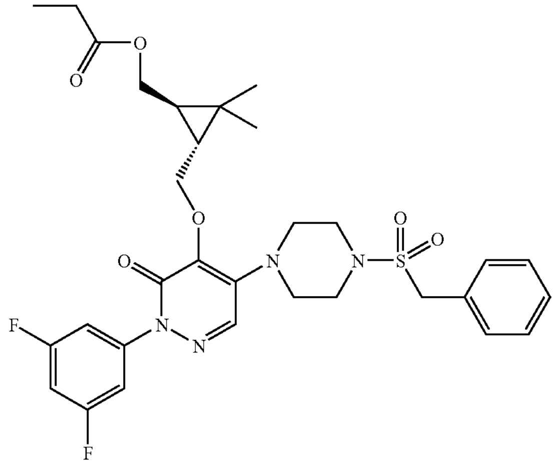 | 631 |
| 1529Z-172 | 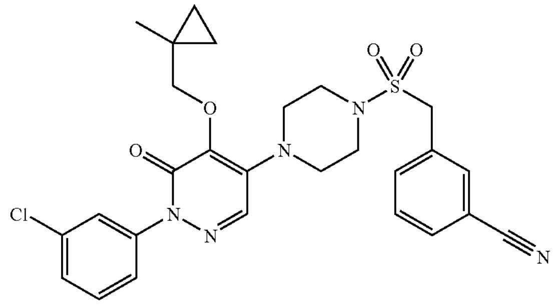 | 554 |
| 1529Z-173 | 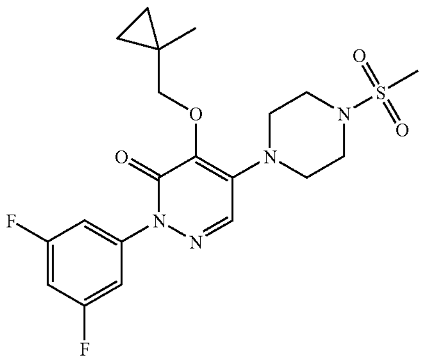 | 455 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-174 | 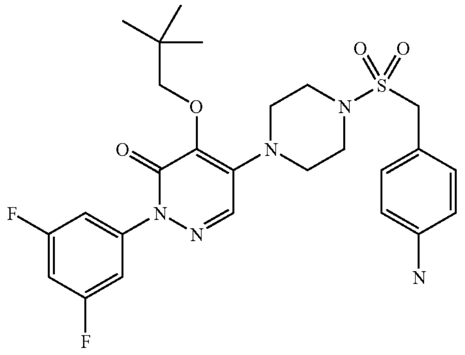 | 548 |
| 1529Z-175 | 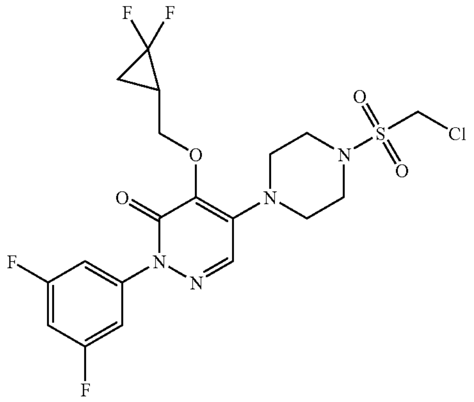 | 511 |
| 1529Z-176 | 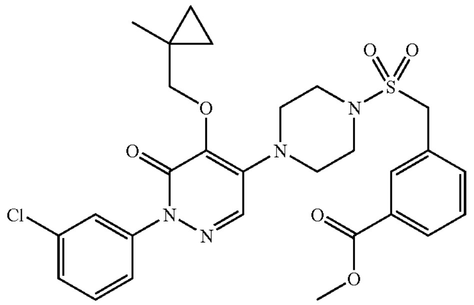 | 587 |
| 1529Z-177 | 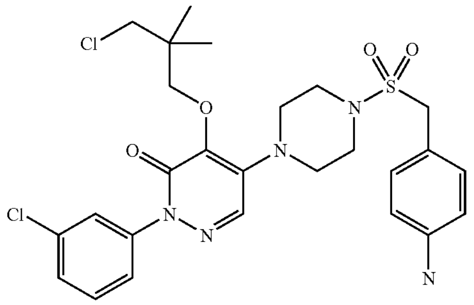 | 580 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-178 | 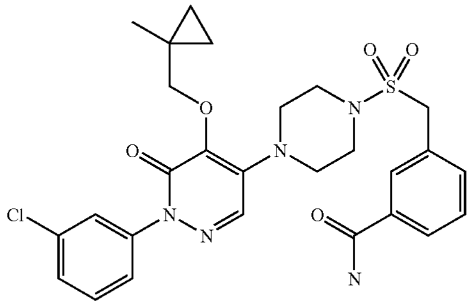 | 572 |
| 1529Z-179 | 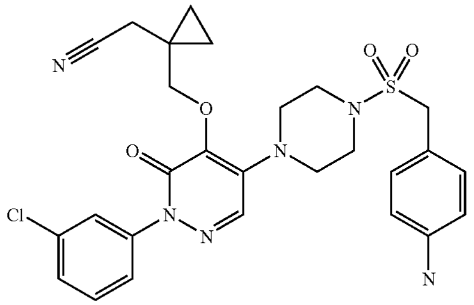 | 569 |
| 1529Z-180 | 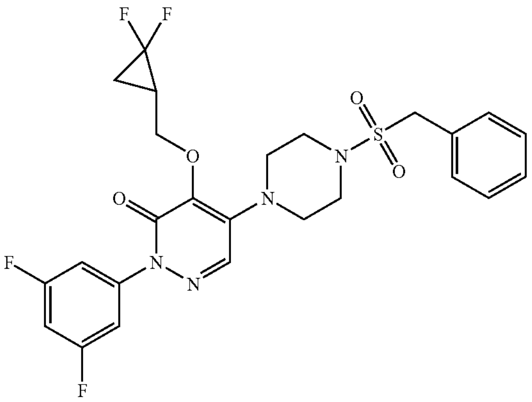 | 553 |
| 1529Z-181 | 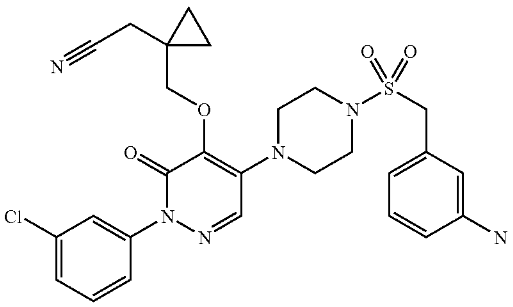 | 569 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1529Z-182 | 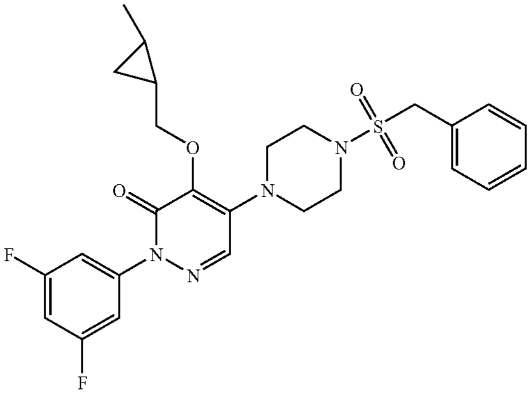 | 531 |
| 1529Z-183 | 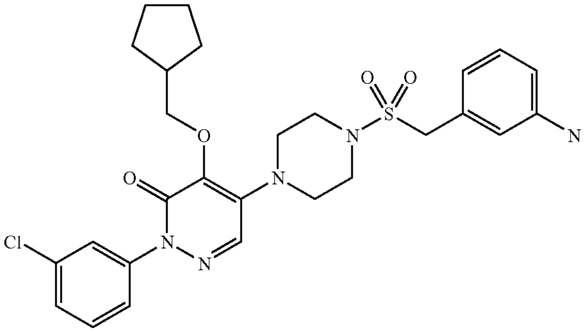 | 558 |
| 1529Z-184 | 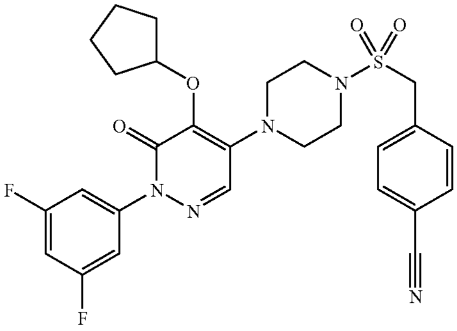 | 556 |
| 1529Z-185 | 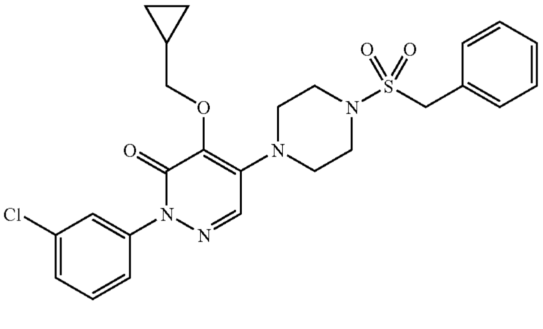 | 515 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1529Z-186 | 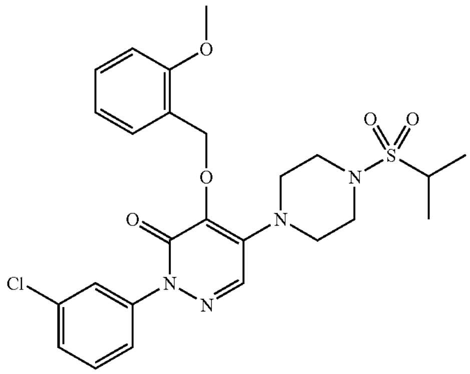 | 533 |
| 1529Z-187 | 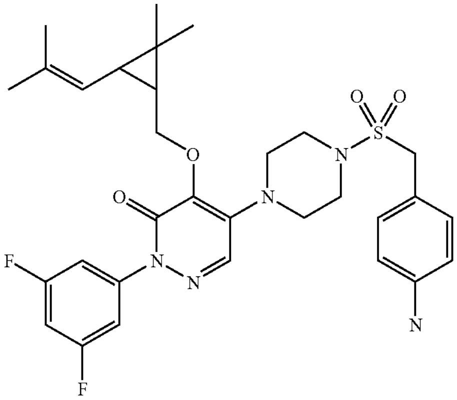 | 614 |
| 1529Z-188 | 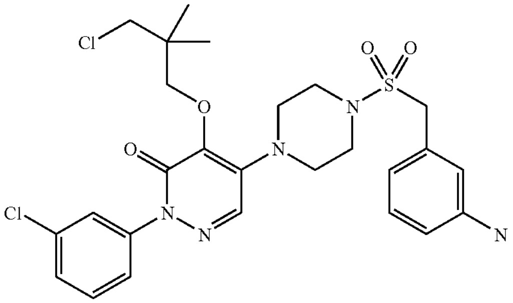 | 580 |
| 1529Z-189 | 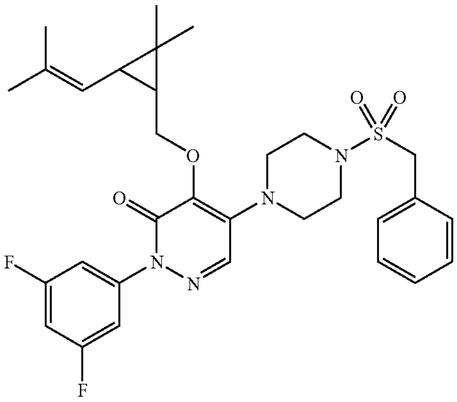 | 599 |

TABLE 11-continued
| Comp. No. | Structure | MS M + 1 |
|---|---|---|
| Oxygen Linked Analogs with Sulfonamide<br>The following compounds can be synthesized using steps 1, 2, 4, 6, and 9 of Scheme 1 or steps 11, 12, and 14 of Scheme 2. | | |
| 1529Z-190 | 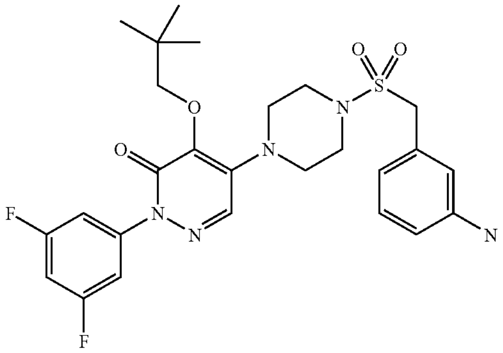 | 548 |
| 1529Z-191 | 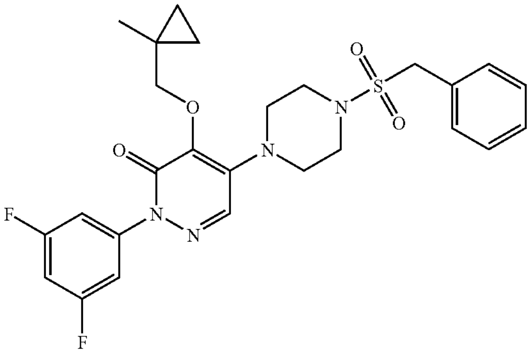 | 531 |
| 1529Z-192 | 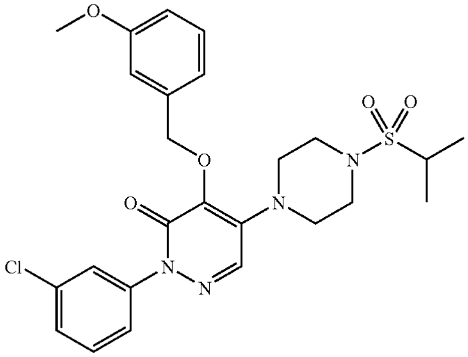 | 533 |
| 1529Z-193 | 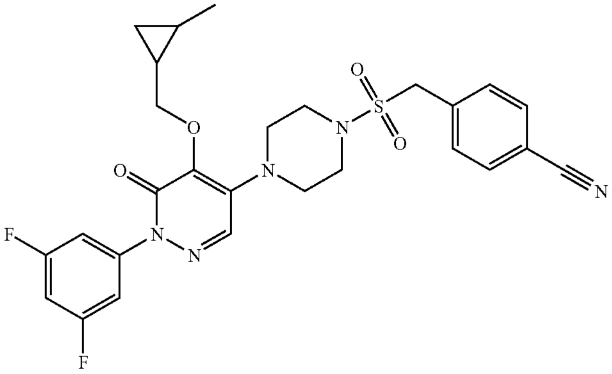 | 556 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-194 | 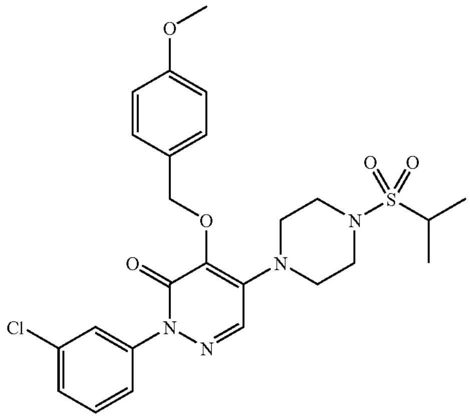 | 533 |
| 1529Z-195 | 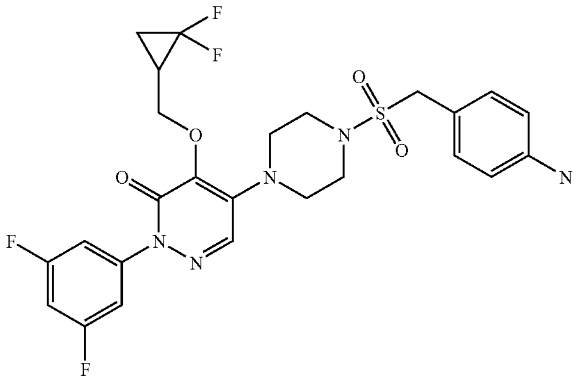 | 568 |
| 1529Z-196 | 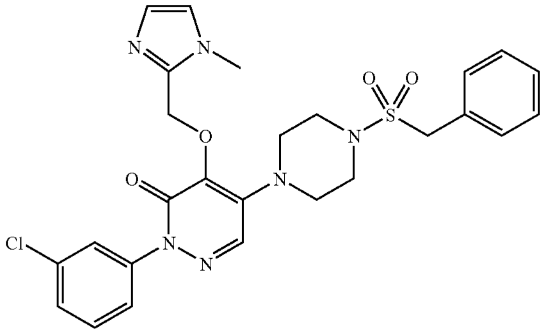 | 555 |
| 1529Z-197 | 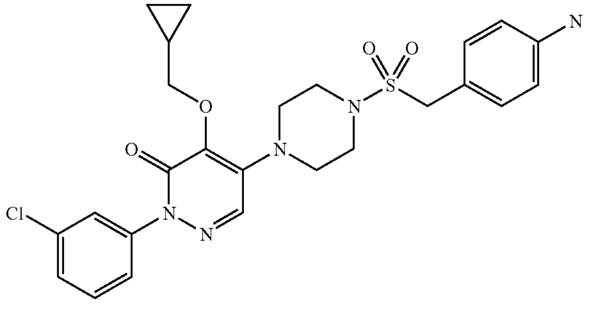 | 530 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-198 | 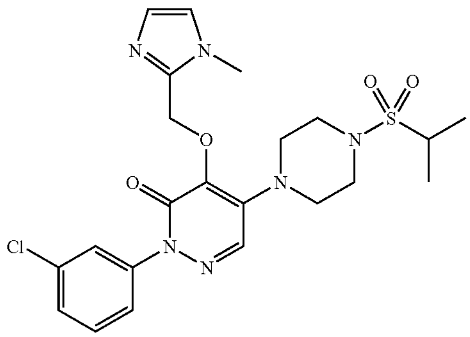 | 507 |
| 1529Z-199 | 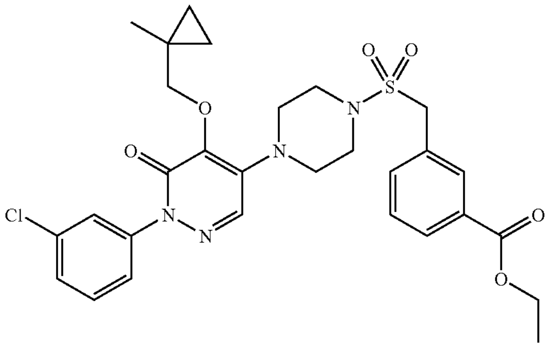 | 601 |
| 1529Z-200 | 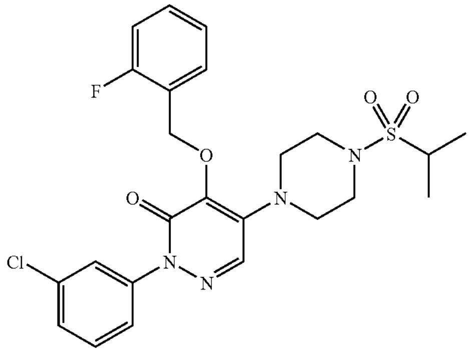 | 521 |
| 1529Z-201 | 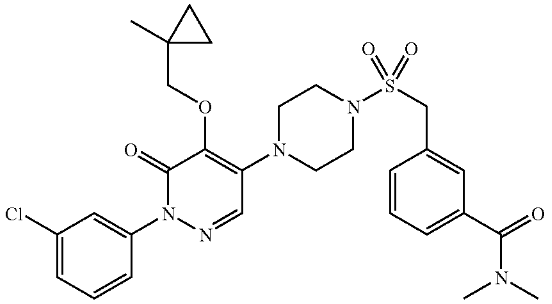 | 600 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-202 | 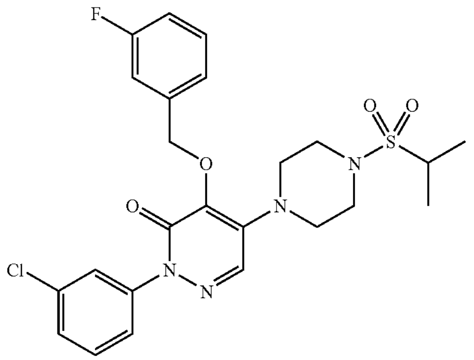 | 521 |
| 1529Z-203 | 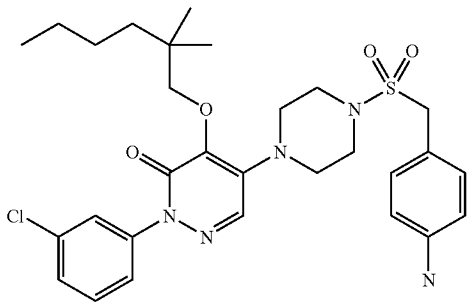 | 588 |
| 1529Z-104 | 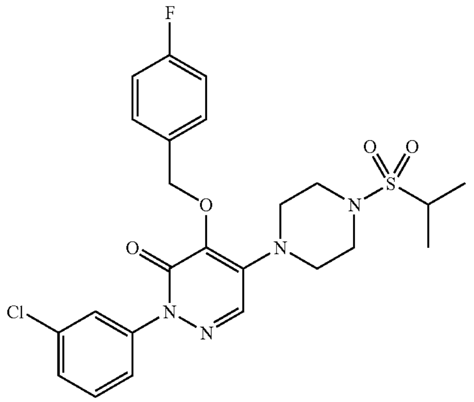 | 521 |
| 1529Z-105 | 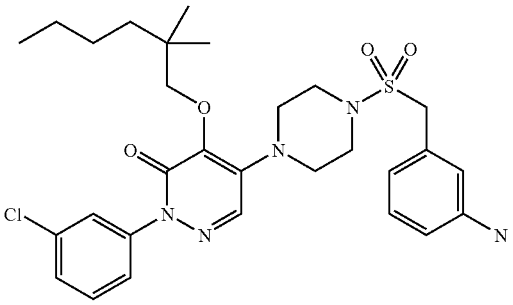 | 588 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
| --- | --- | --- |
| 1529Z-106 | 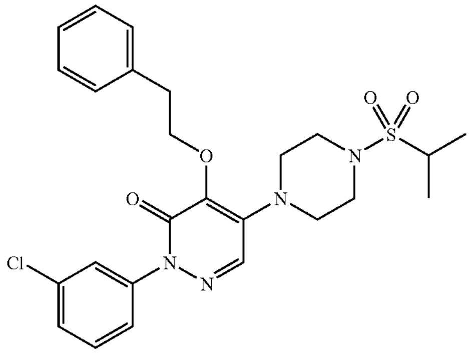 | 517 |
| 1529Z-107 | 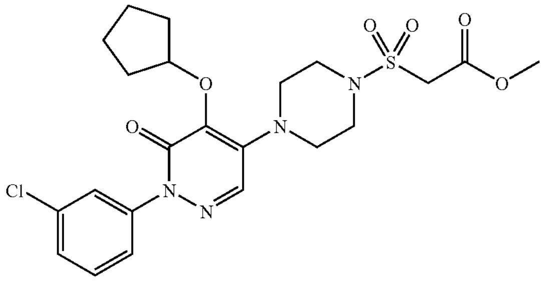 | 511 |
| 1529Z-108 | 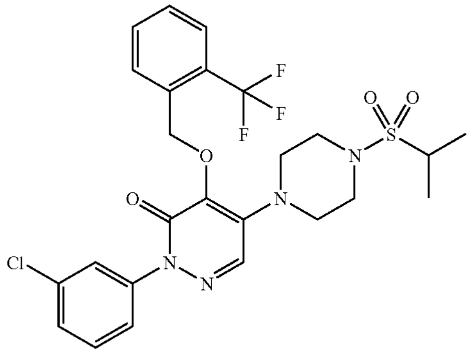 | 571 |
| 1529Z-109 | 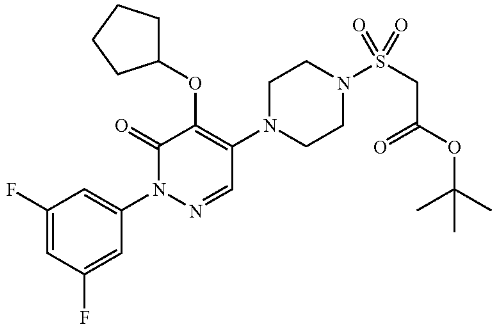 | 555 |

TABLE 11-continued
Oxygen Linked Analogs with Sulfonamide
The following compounds can be synthesized using steps 1, 2, 4, 6, and 9 of Scheme 1 or steps 11, 12, and 14 of Scheme 2.
| Comp. No. | Structure | MS M + 1 |
|---|---|---|
| 1529Z-110 | 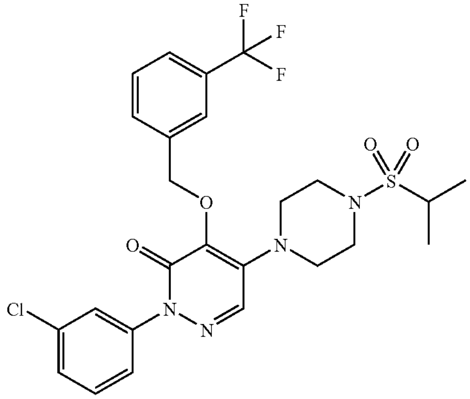 | 571 |
| 1529Z-111 | 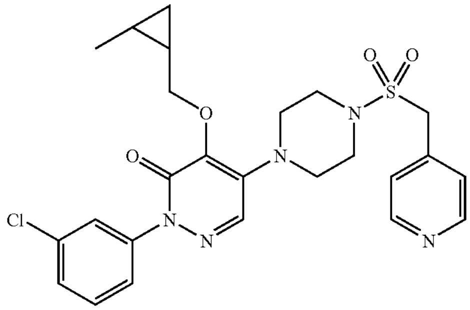 | 530 |
| 1529Z-112 | 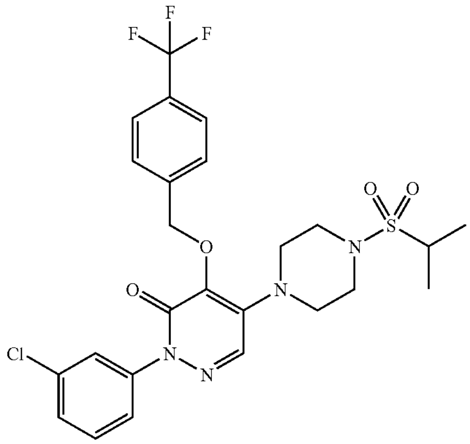 | 571 |
| 1529Z-113 | 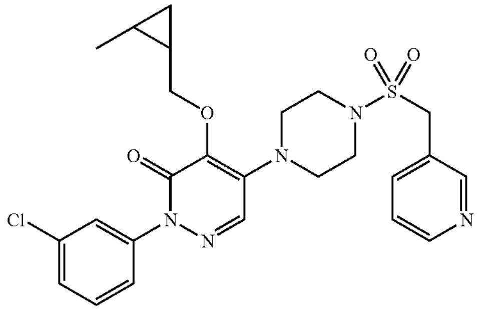 | 530 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-114 | 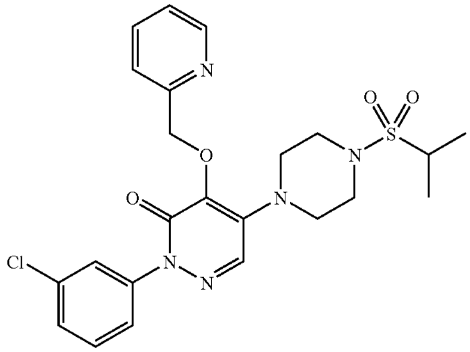 | 504 |
| 1529Z-115 | 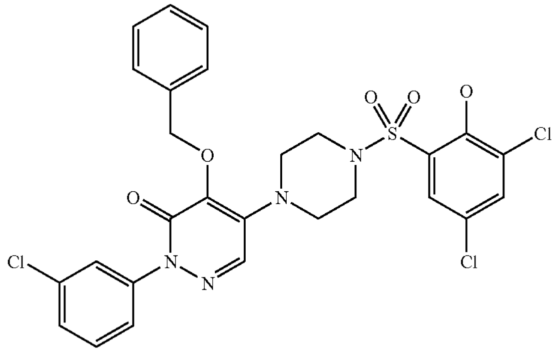 | 621 |
| 1529Z-116 | 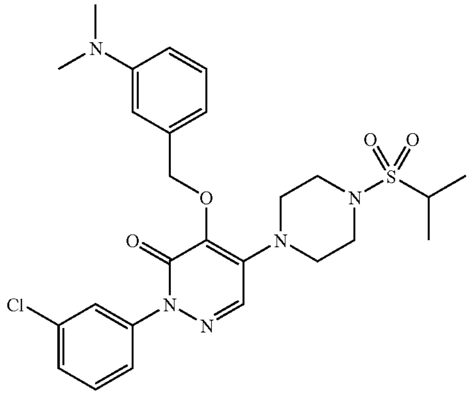 | 546 |
| 1529Z-117 | 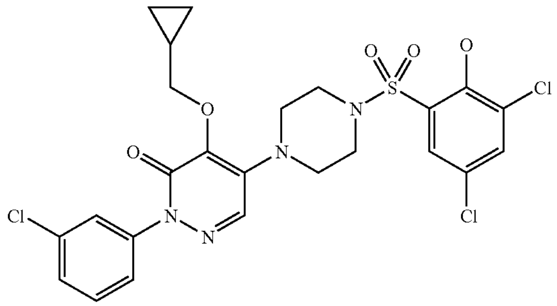 | 585 |

TABLE 11-continued
| Comp. No. | Oxygen Linked Analogs with Sulfonamide<br>The following compounds can be synthesized using steps 1, 2, 4, 6, and 9 of Scheme 1 or steps 11, 12, and 14 of Scheme 2.<br>Structure | MS M + 1 |
|---|---|---|
| 1529Z-118 | 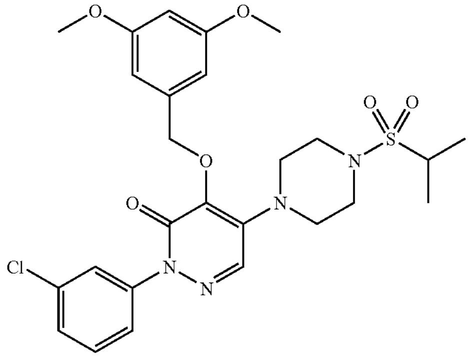 | 563 |
| 1529Z-119 | 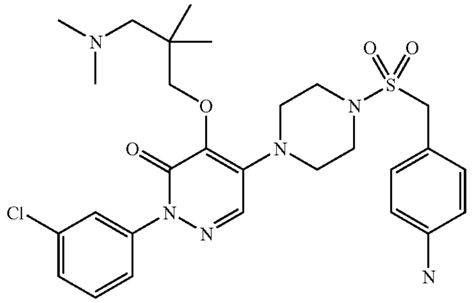 | 589 |
| 1529Z-120 | 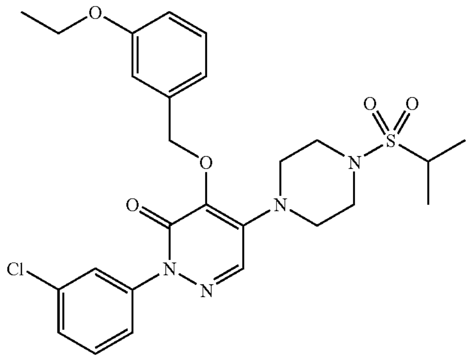 | 547 |
| 1529Z-121 | 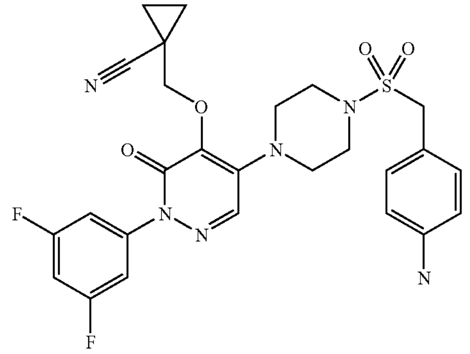 | 558 |

TABLE 11-continued
| Oxygen Linked Analogs with Sulfonamide The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-122 | 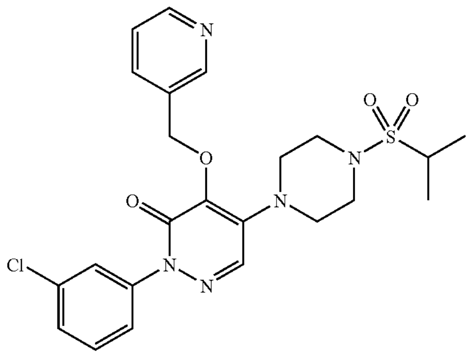 | 504 |
| 1529Z-123 | 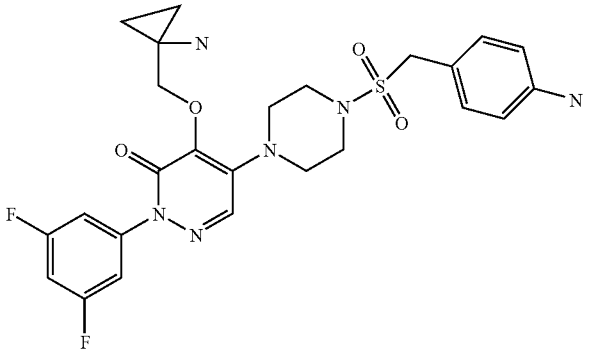 | 561 |
| 1529Z-124 | 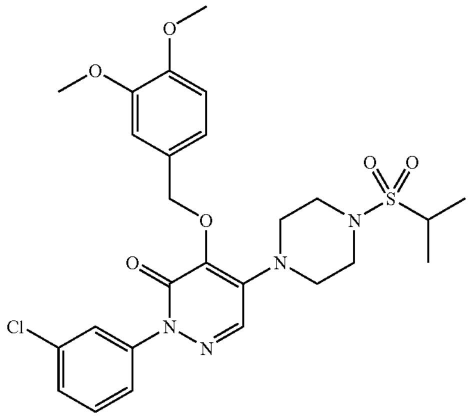 | 563 |
| 1529Z-125 | 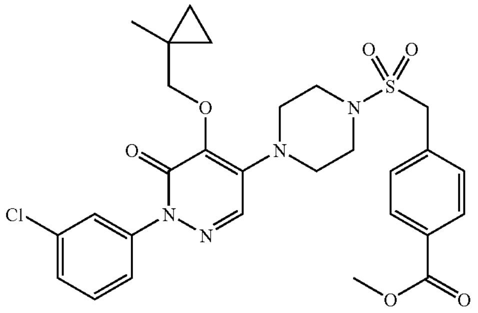 | 585 (M − 1) |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-126 | 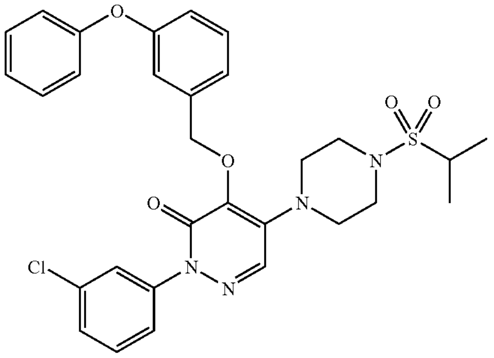 | 595 |
| 1529Z-127 | 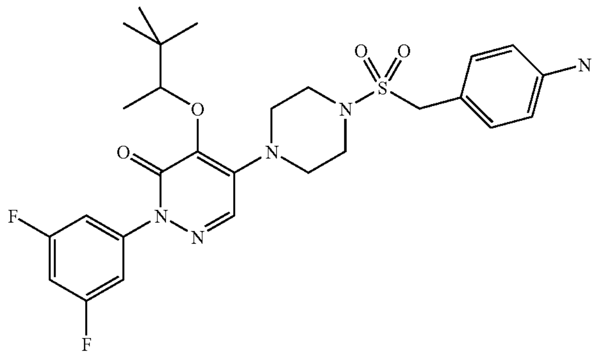 | 562 |
| 1529Z-128 | 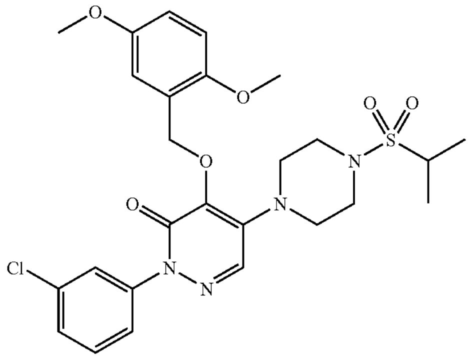 | 563 |
| 1529Z-129 | 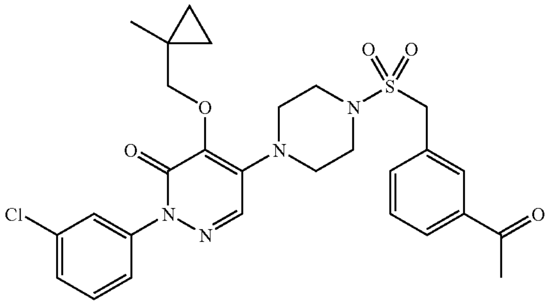 | 571 |

TABLE 11-continued
| Comp. No. | Structure | MS M + 1 |
|---|---|---|
| Oxygen Linked Analogs with Sulfonamide The following compounds can be synthesized using steps 1, 2, 4, 6, and 9 of Scheme 1 or steps 11, 12, and 14 of Scheme 2. | | |
| 1529Z-130 | 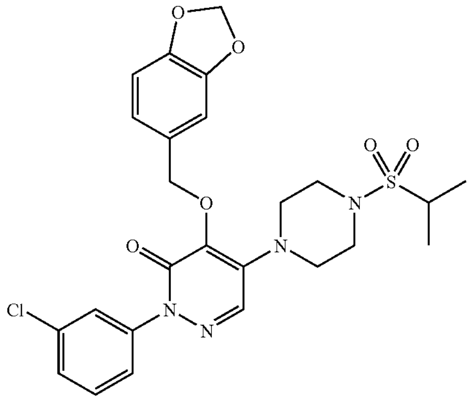 | 547 |
| 1529Z-131 | 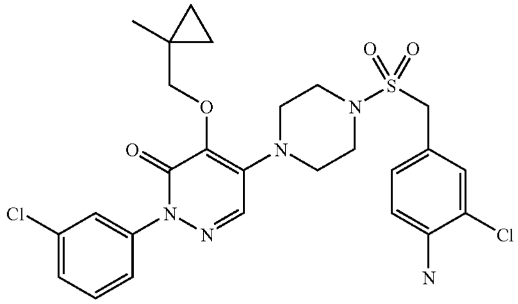 | 578 |
| 1529Z-132 | 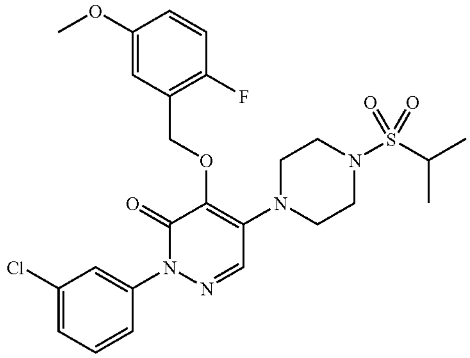 | 551 |
| 1529Z-133 | 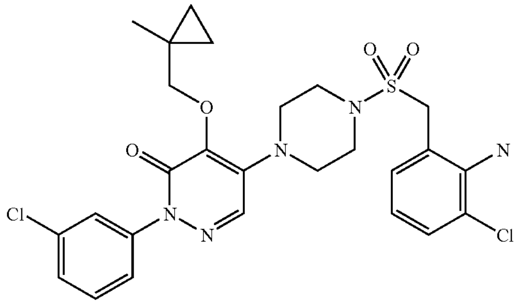 | 578 |

TABLE 11-continued
| Oxygen Linked Analogs with Sulfonamide<br>The following compounds can be synthesized using steps 1, 2, 4, 6, and 9 of Scheme 1 or steps 11, 12, and 14 of Scheme 2. | | |
|---|---|---|
| Comp. No. | Structure | MS M + 1 |
| 1529Z-134 | 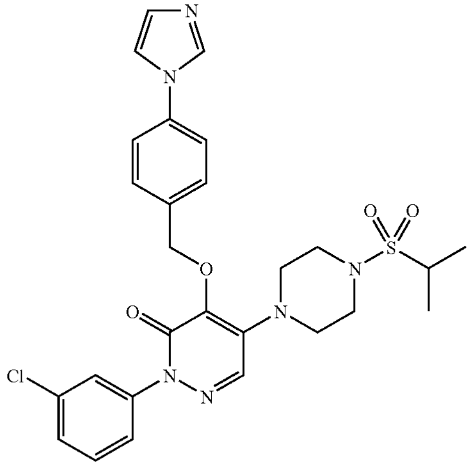 | 569 |
Scheme 3
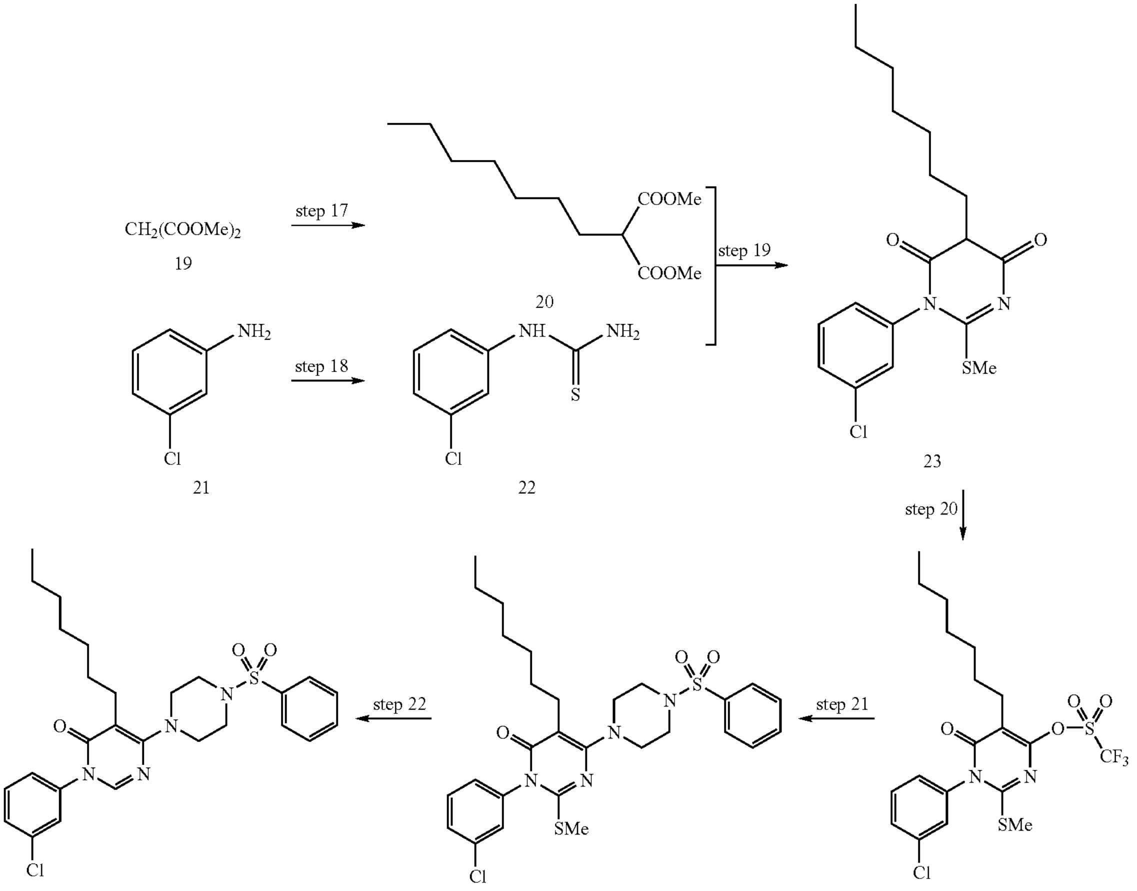
19
20
21
22
23
24
25
26

Step 17:

$CH_2(COOMe)_2$
19

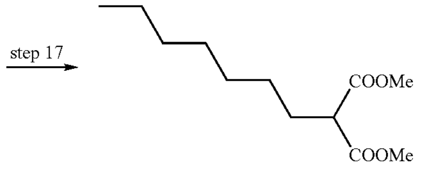

20

To a stirred solution of dimethyl malonate 19 (13.20 g, 0.10 mol) in MeOH (100 mL) was added dropwise sodium methoxide (220 mL, 0.5 M in MeOH, 0.11 mol) and then heptylbromide (16.90 g, 0.09 mol) in MeOH (30 mL). The reaction mixture was heated evaporated and $CHCl_3$ (50 mL) was added to the mixture, the resulting precipitate was removed by filtration. The concentrated filtrate was distilled under vacuum (140° C./14 mmHg) to give the product 20 as a colorless oil (21.0 g, 90.9%). MS (M+1): m/e 231.

Step 18:

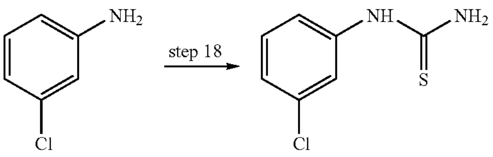

21 22

To a mixture of chloroaniline 21 (25.0 g, 0.20 mol) and KSCN (30.0 g, 0.30 mol) in anhydrous THF (50 mL) cooled to 0° C. was added dropwise 4N HCl in dioxane (50 mL, 0.20 mol). After the reaction mixture was heated at 80° C. for 20 h. the solvent was evaporated, and water (20 mL) was added to the residue. After filtration, the precipitate was washed with water (20 mL) and dried to gave a yellow solid. This solid was further washed with hot ethyl acetate and dried to give the product 22 (20.5 g, 55%) as a white solid.

Step 19:

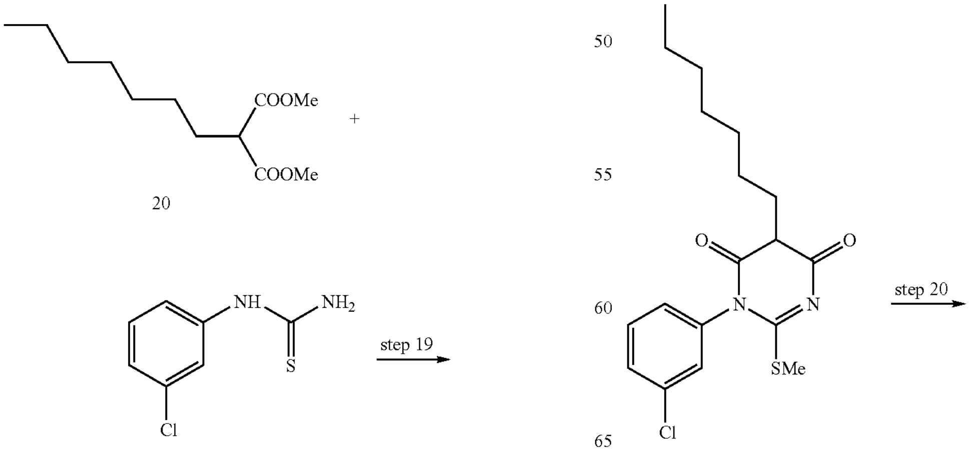

20 + 22 23

-continued

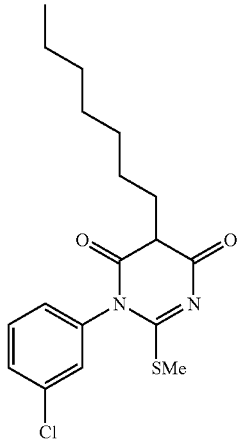

23

To a solution of thiourea 22 (1.86 g, 0.010 mol) dissolved in anhydrous MeOH (20 mL), was added sodium methoxide (1.08 g, 0.020 mol) and compound 20 (2.30 g, 0.010 mol) at once. After the reaction mixture was heated at 65° C. for 3 h, methyl iodide (1.42 g, 0.010 mol) was added to the reaction mixture slowly over 10 min at 50° C. The reaction mixture was further stirred at 50° C. for 30 min. The solvent was evaporated, and water (20 mL) was added. After neutralization with cold acetic acid, the white precipitate was filtered and dried under vacuum to give the desired compound 23 (3.12 g, 85%) as a white solid. MS (M+1): m/e 367.

Step 20:

-continued

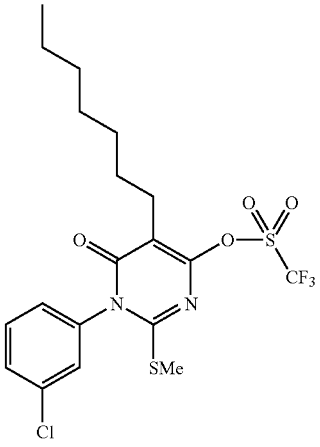

24

To a solution of compound 23 (1.46 g, 4.0 mmol) in anhydrous $CH_2Cl_2$ (15 mL) was added dropwise triflic acid (0.7 mL, 4.2 mmol) and 2,6-lutidine (0.93 mL, 8.0 mmol) at −78° C. The resulting solution was stirred for 2 h at 78° C., and then allowed to warm to room temperature for 12 h. The reaction was quenched with aqueous $NH_4Cl$ solution (10 mL) and extracted with $CH_2Cl_2$ (3×50 mL). The combined organic extract was washed with 1 N HCl (10 mL), $H_2O$ (10 mL), brine (10 mL), dried (MgSO4), filtered, and concentrated. Purification by silica gel chromatography (eluant: 1:10 EtOAc:hexanes) gave the desired product 24 as a white solid (1.5 g, 75%). MS (M+1): m/e 499.

Step 21:

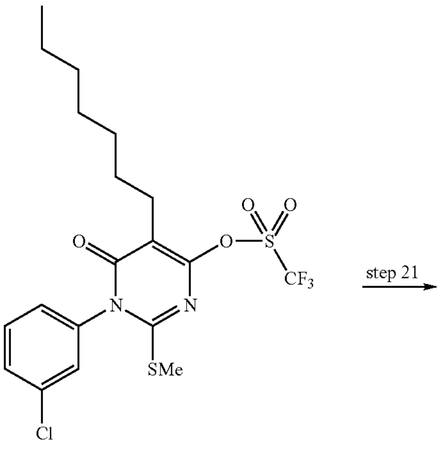

24

-continued

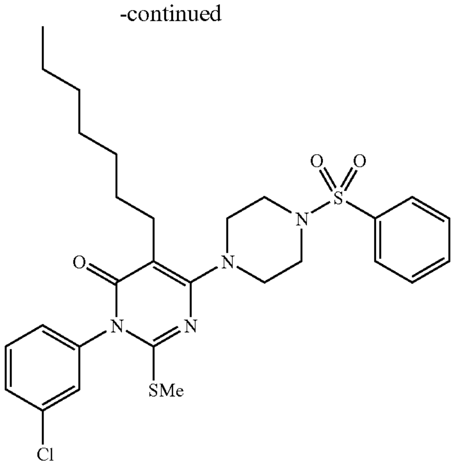

25

To a solution of compound 24 (0.498 g, 0.001 mol) in anhydrous chlorobenzene (10 mL) in a microwave tube was added diisopropylethyl amine (1.29 g, 0.010 mol) and benzenesulfonylpiperizine (2.26 g, 0.010 mol). After the reaction mixture was stirred at 160° C. for 2 h under microwave irradiation, the chlorobenzene was removed under vacuum. Purification by silica gel chromatography (1:5 EtOAc:hexanes) gave the desired compound 25 (0.345 g, 60%) as a light yellow oil. MS (M+1): m/e 575.

Step 22:

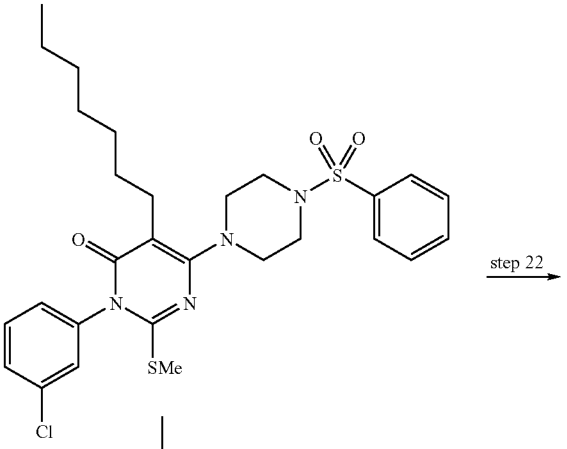

25

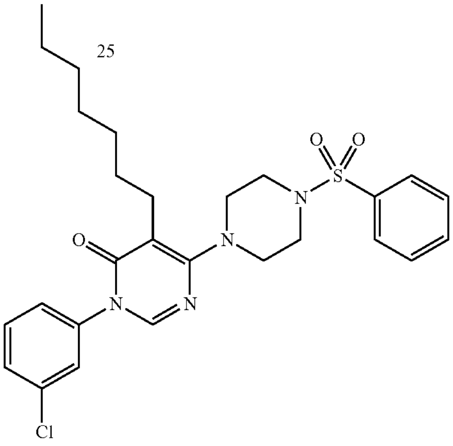

26

To a solution of compound 25 (0.058 g, 0.1 mmol) in anhydrous 3:1 MeOH:THF (10 mL) was added slowly $NiCl_2.6H_2O$ (0.237 g, 1.0 mmol) and $NaBH_4$ (0.038 g, 1.0 mmol). After the reaction mixture was stirred at 0° C. for 1 h, the reaction mixture was filtered through celite and washed with 1:1 MeOH:THF (100 mL). The solvent was evaporated, and the resulting residue was purified by silica gel chromatography (1:5 EtOAc:hexanes) to give the desired compound 26 (0.030 g, 52%) as a light yellow oil. MS (M+1): m/e 529.

TABLE 12

Carbon Linked Analogs with Sulfonamide

The following compounds can be synthesized using the steps of Scheme 3.

| Comp. No. | Structure | MS M + 1 |
|---|---|---|
| 1530Z | 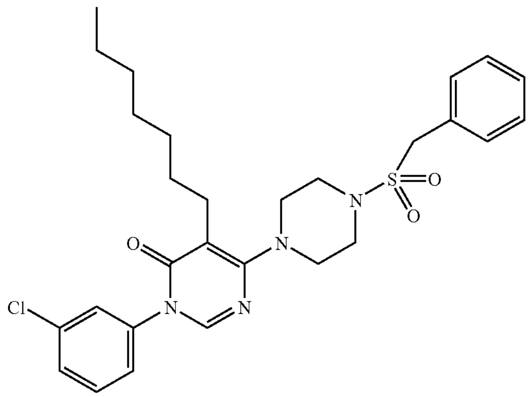 | 543 |
| 1531Z | 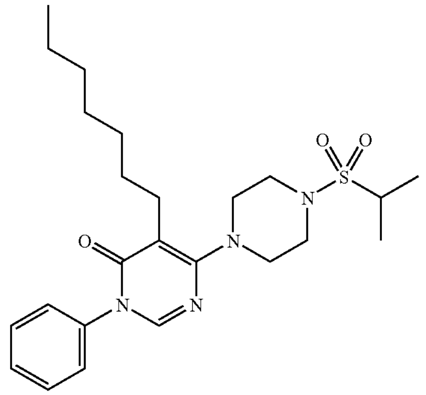 | 461 |
| 1532Z | 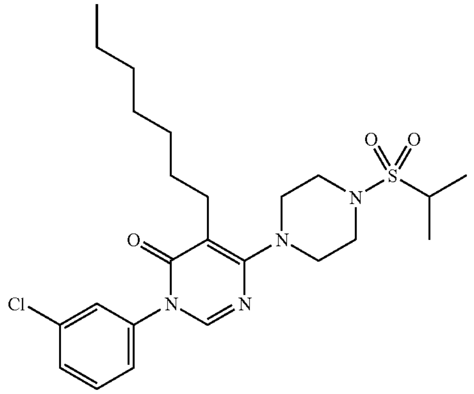 | 495 |

TABLE 12-continued

| Carbon Linked Analogs with Sulfonamide The following compounds can be synthesized using the steps of Scheme 3. | | |
|---|---|---|
| Comp. No. | Structure | MS M + 1 |
| 1533Z | 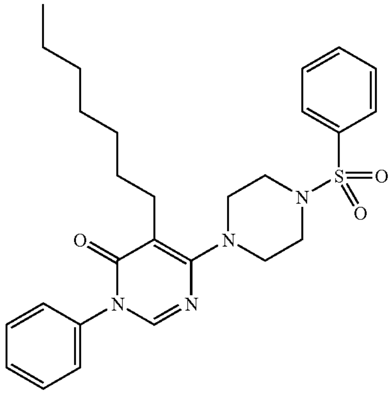 | 495 |

Scheme 4

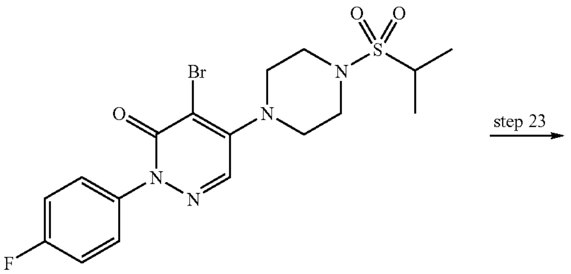

27

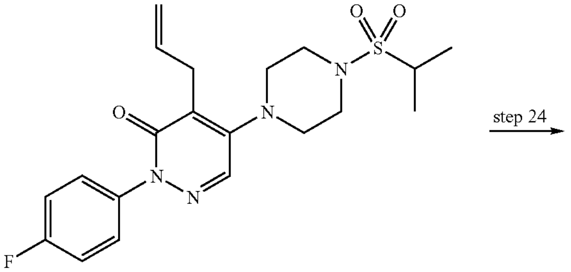

28

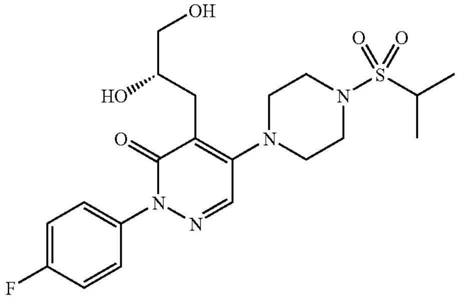

29

-continued

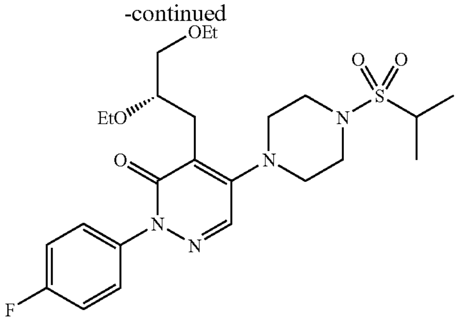

30

Compound 27 can be synthesized using steps 1 and 2 from Scheme 1 and steps 11 and 12 from Scheme 2.

Step 23:

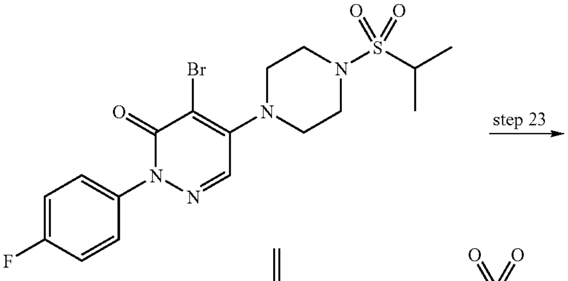

27

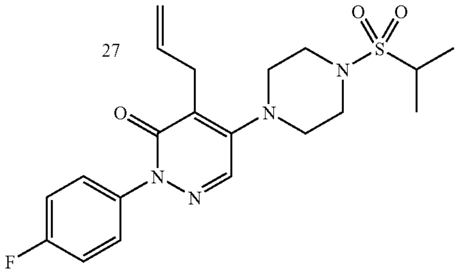

28

To a solution of compound 27 (0.290 g, 0.60 mmol), diisopropylethyl amine (0.154 g, 1.2 mmol) in 4:1 α,α,αtrifluorotoluene:toluene (10 mL) in a microwave tube, allyl tributyltin (0.397 g, 1.2 mmol) and $Pd(PPh_3)_4$ (0.080 g, 0.07 mmol) was added successively under an argon atmosphere. After the reaction mixture was stirred at 165° C. for 40 min under microwave irradiation, the reaction mixture was filtered through short path of silica gel, and the solvent was evaporated. Purification by silica gel chromatography (1:5 EtOAc: hexanes) gave the desired compound 28 (0.220 g, 87%) as a yellow oil. MS (M+1): m/e 421.

Step 24:

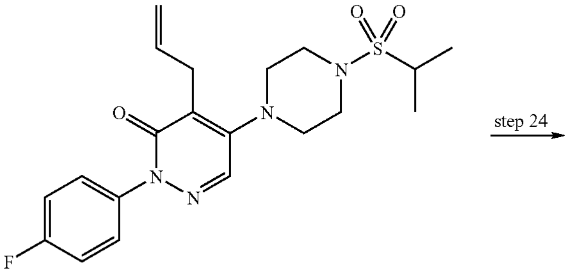

28

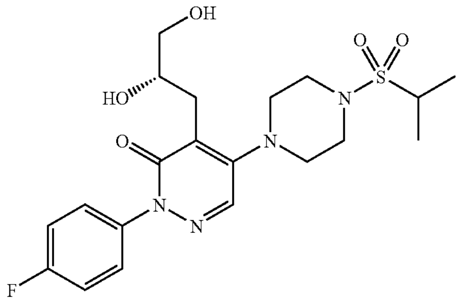

29

To a solution of the pyridazinone 28 (0.210 g, 0.50 mmol) in 10:1 acetone:$H_2O$ (5 mL) was added NMO (0.073 g, 1.5 mmol) and $OsO_4$ (0.025 g, 0.1 mmol) at 20° C. under a nitrogen atmosphere. The reaction mixture was stirred for 2 h at −20° C. to 0° C. then treated with saturated aqueous $Na_2SO_3$ solution (10 mL) and extracted with EtOAc (6×50 mL). The combined organic extract was dried ($MgSO_4$), filtered, and concentrated. Purification by silica gel chromatography (eluant: EtOAc) gave the product 29 (0.182 g, mg, 80%) as a white solid. (M+1): m/e 456.

Step 25:

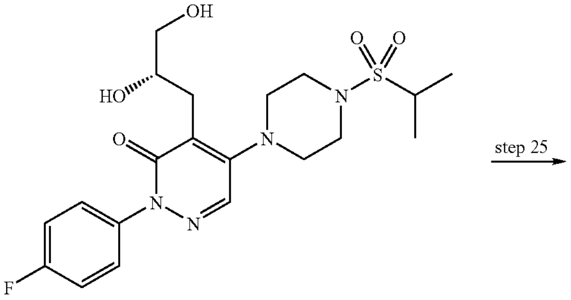

29

-continued

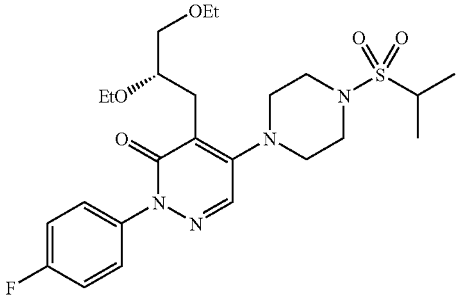

30

To a solution of compound 29 (0.090 g, 0.20 mmol), diisopropylethyl amine (0.077 g, 0.60 mmol) in $CH_2Cl_2$ (10 mL), triethyloxonium tetrafluoroborate (0.114 g, 0.60 mmol) was added at 0° C. The reaction mixture was stirred at 0° C. to room temperature for 24 h then treated with saturated aqueous $NaHCO_3$ solution (10 mL), and the aqueous phase was extracted with $CH_2Cl_2$ (50 mL). The combined organic extract was washed with $H_2O$ (2×10 mL), brine (10 mL), dried ($MgSO_4$), filtered, and concentrated. Purification by silica get chromatography (1:10 EtOAc:hexanes) gave the desired compound 30 (0.220 g, 87%) as a colorless oil. MS (M+1): m/e 511.

TABLE 13

Carbon Linked Analogs with Sulfonamide
The following compounds can be synthesized using the steps of Scheme 4.

| Compound No. | Structure | MS M + 1 |
|---|---|---|
| 1534Z | 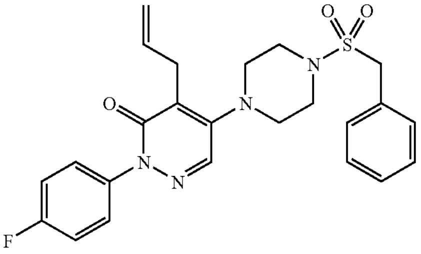 | 429 |
| 1535Z | 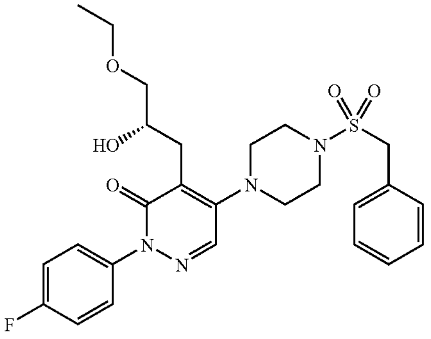 503 | 531 |

TABLE 13-continued
Carbon Linked Analogs with Sulfonamide
The following compounds can be synthesized using the steps of Scheme 4.
| Compound No. | Structure | MS M + 1 |
|---|---|---|
| 1537Z | 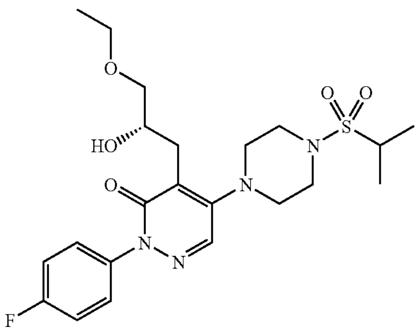 | 483 |
Scheme 5
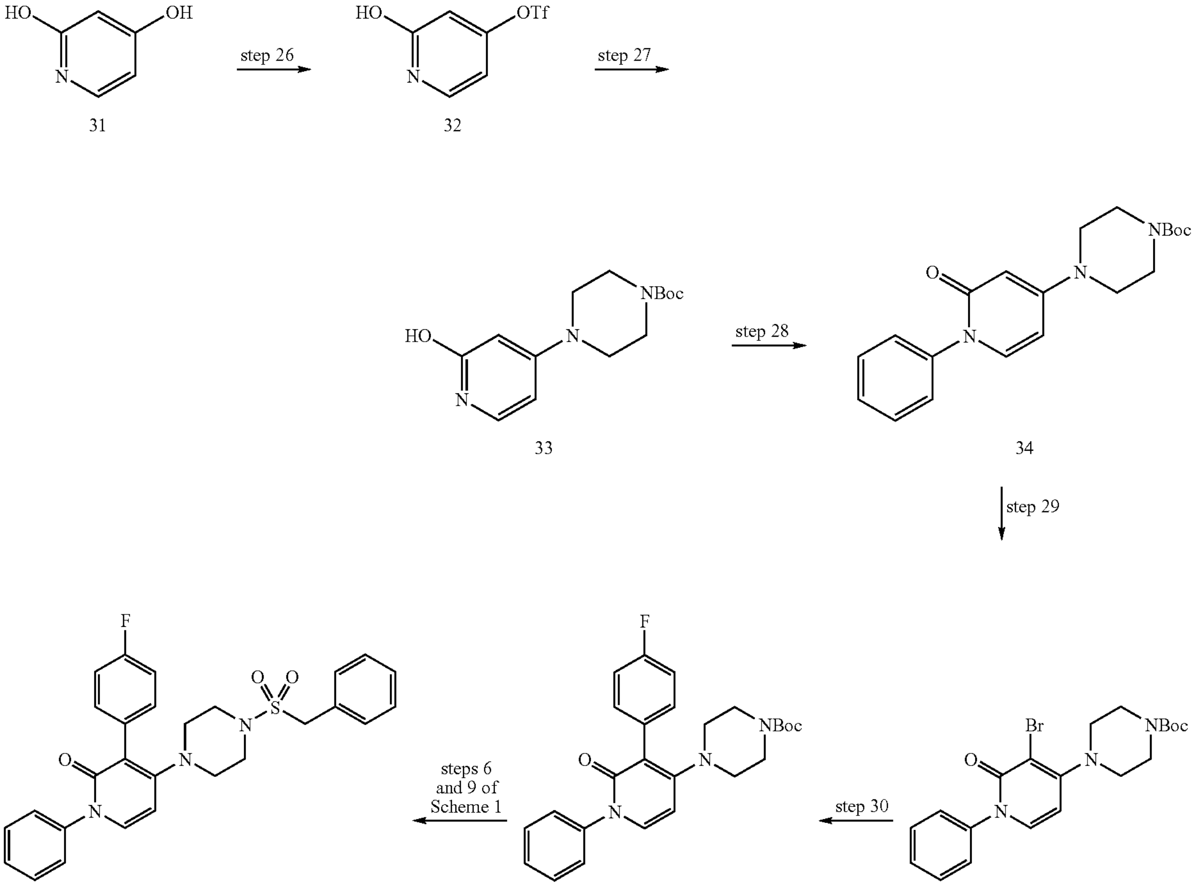
31 32 33 34 35 36 37

Steps 26 and 27:

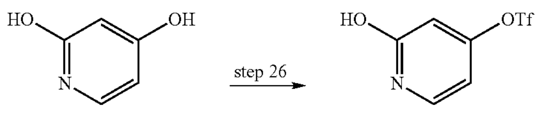

31 32

To a solution of 2,4-dihydroxypyridine 31 (10 g, 0.090 mol) and DMF (120 mL) was added in 4 portions NaH (60%, 4.32 g, 0.108 mol) at room temperature. The reaction mixture was cooled to 0° C. N-Phenyltrifluoromethanesulfonimide (35.4 g, 0.099 mol) was then added in four separate portions. The reaction was warmed to room temperature and stirred for 5 h then quenched with saturated $NH_4Cl$ (50 mL). EtOAc (200 mL) was added, and the organic layer was washed with brine (3×100 mL), dried ($MgSO_4$), filtered, and concentrated. To the crude was added DMF (120 mL) and BOC piperazine (21.1 g, 0.113 mol). The reaction mixture was heated to 80° C. for 6 h then cooled to room temperature. EtOAc (200 mL) was added, and the organic layer was washed with brine (3×100 mL), dried ($MgSO_4$), filtered, and concentrated. Purification by silica gel chromatography (eluant: 10-30%% MeOH-EtOAc) to gave compound 32 (21.3 g) as a orange-white solid. MS (M+1): m/e 280.

Step 28:

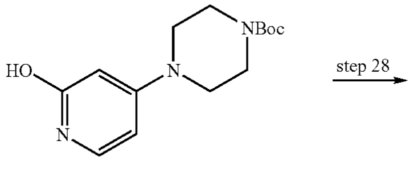

33

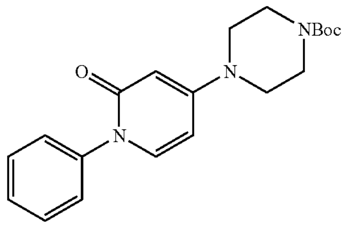

34

To a solution of compound 33 (2.74 g, 9.81 mmol) in $CH_2Cl_2$ (120 mL) was added phenyl boronic acid (2.40 g, 19.68 mmol), $Cu(OAC)_2$ (3.56 g, 19.560 mmol), 4 Å MS (11 g), pyridine (1.6 mL, 19.78 mmol), and triethylamine (2.7 mL, 19.37 mmol). The reaction mixture was stirred at room temperature for 72 h then filtered through celite, concentrated, and purified by silica gel chromatography (1:1 hexanes:EtOAc to 5% MeOH in EtOAc) to give compound 34 (1.65 g) as a brown oil. MS (M+1): m/e 356.

Step 29:

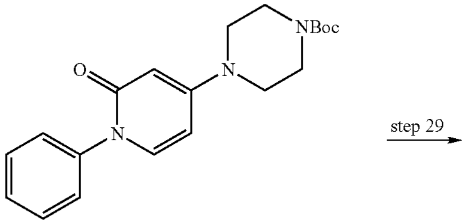

34

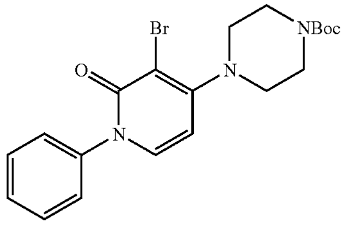

35

To a solution of compound 34 (186.5 mg, 0.525 mmol) in AcOH (8 mL) was added NBS (121.4 mg, 0.682 mmol) and stirred at room temperature for 3 h. The reaction mixture was evaporated and purified by silica gel chromatography (3:1 to 1:1 hexanes:EtOAc) to give compound 35 (149.9 mg) as a light yellow solid. MS (M+1): m/e 434.

Step 30:

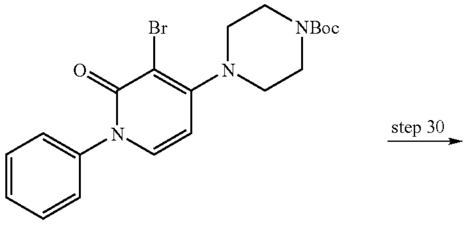

35

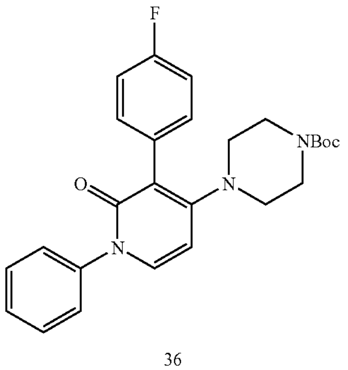

36

To a solution of compound 35 (144.6 mg) in degassed THF (10 mL) was added LiCl (28 mg, 0.661 mmol), tributyl(4-fluorophenyl)stannane (640 mg, 1.66 mmol), and tetrakis (triphenylphosphine)palladium(0) (42 mg, 0.036 mmol). The reaction mixture was heated at reflux for 42 h. The reaction was then cooled to room temperature, quenched with 1 N HCl (3 mL), and extracted with EtOAc (3×20 mL). The combined organic extract was washed with brine (20 mL), dried ($MgSO_4$), filtered, and concentrated. Purification by preparative TLC (eluted twice with 5% acetone in $CH_2Cl_2$) gave compound 36 (24.3 mg) as a white solid. MS (M+1): m/e 450.
Steps 6 and 9 of Scheme 1:
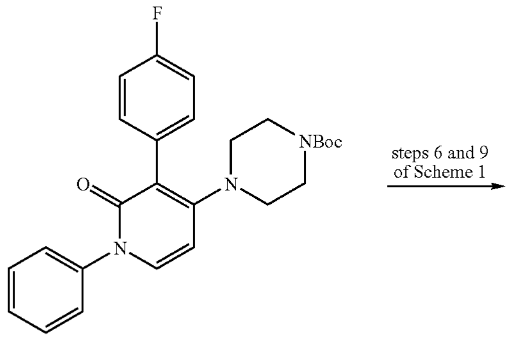
36
-continued
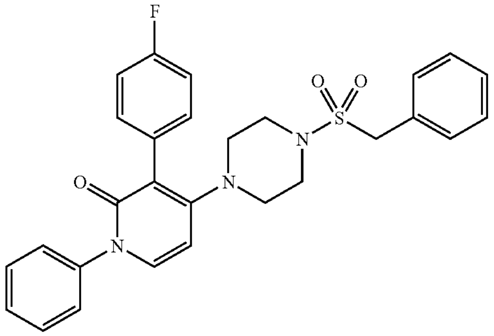
37
Using the procedures described above, compound 37 was synthesized. MS (M+1): m/e 504.
Scheme 6
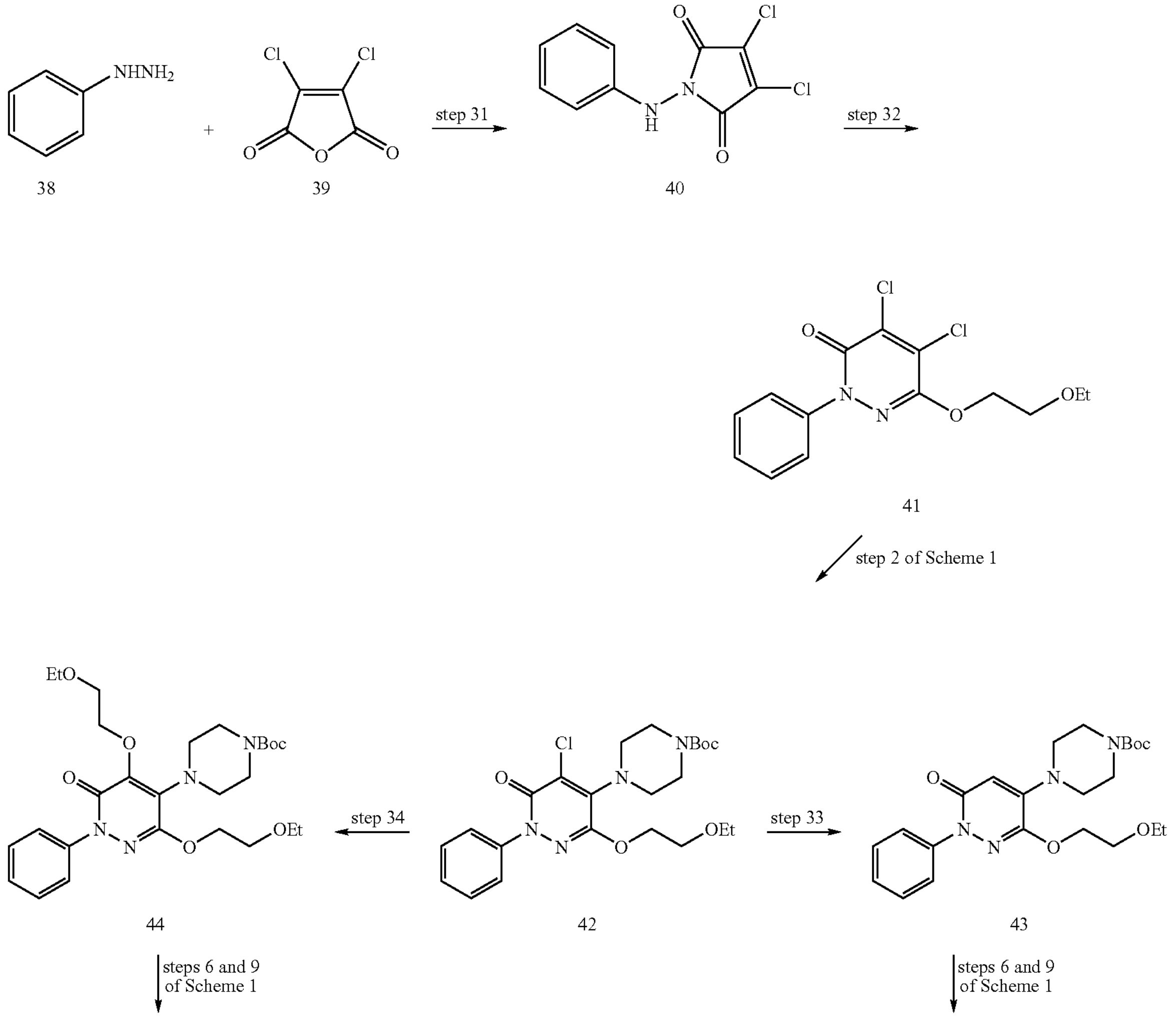
38 39 40
41
44 42 43

-continued

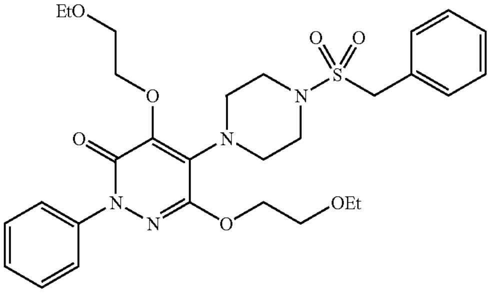

46

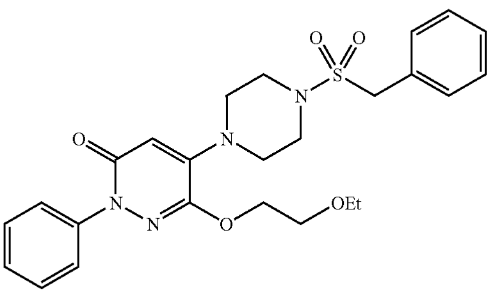

45

Step 31:

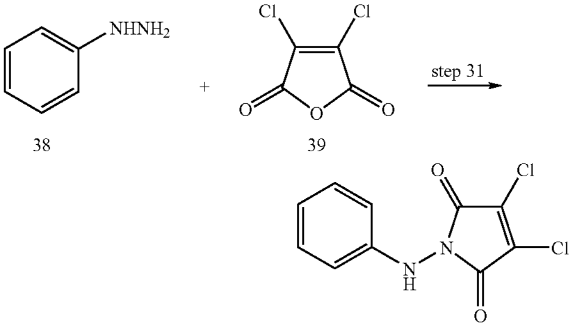

38 39 40

A solution of compound 39 (5.0 g, 0.030 mol) in AcOH (20 mL) was heated at 60° C. for 30 min then cooled to room temperature. Compound 38 (4.33 g, 0.030 mol) was then added, and the reaction mixture was heated at 120° C. for 1 h. The reaction mixture was cooled to room temperature, and the resulting solid was filtered and washed with AcOH to give compound 40 (6.47 g) as a white solid. MS (M+1): m/e 257.

Step 32:

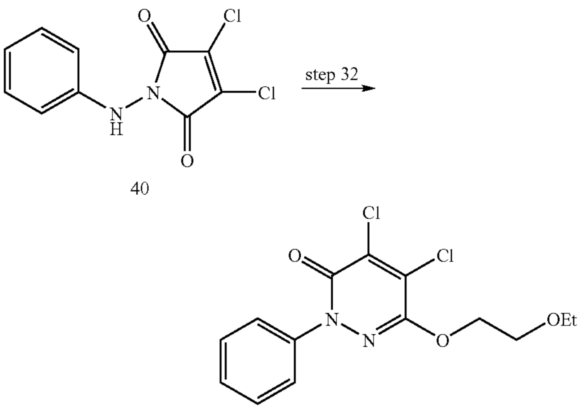

40 41

To a solution of compound 40 (1.0 g, 3.89 mmol) in DMF (30 mL) was added NaH (60%, 2-33 mg, 5.83 mmol) and stirred at room temperature for 15 h. The reaction was then quenched with saturated $NH_4Cl$ (10 mL). EtOAc (250 mL) was added, and the organic layer was washed with brine (3×50 mL), dried ($MgSO_4$), filtered, and concentrated. Purification by silica gel chromatography (8:1 hexanes:EtOAc) gave compound 41 (177.4 mg) as a light yellow solid. MS (M+1): m/e 533.

Step 2 of Scheme 1:

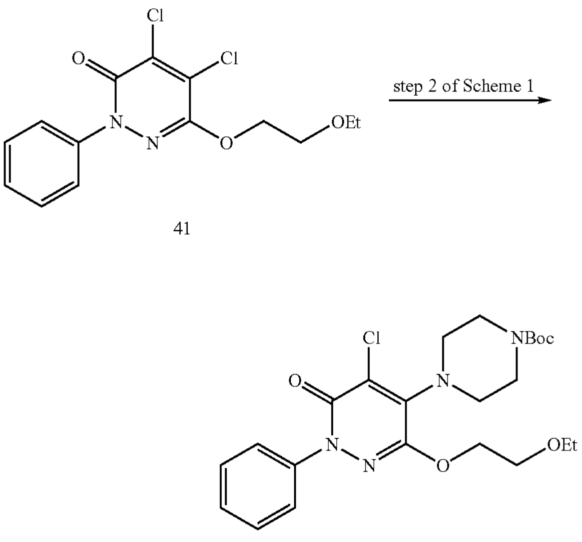

41 42

Using the procedure described above, compound 42 was synthesized. MS (M+1): m/e 480.

Step 33:

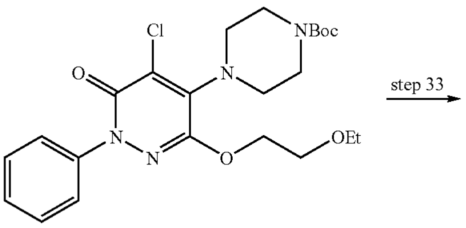

42

-continued

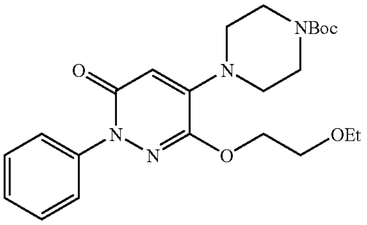

43

To a solution of compound 42 (94.3 mg, 0.197 mmol) in EtOH (10 mL) was added $Pd(OH)_2/C$ (20%, 70 mg) and stirred under $H_2$ (50 psi) at room temperature for 6 h, then filtered through celite. The solvent was evaporated, and purification by silica gel chromatography (2:1 to 1:1 hexanes: EtOAc) gave compound 43 (65.5 mg) as a colorless oil. MS (M+1): m/e 445.

Step 34:

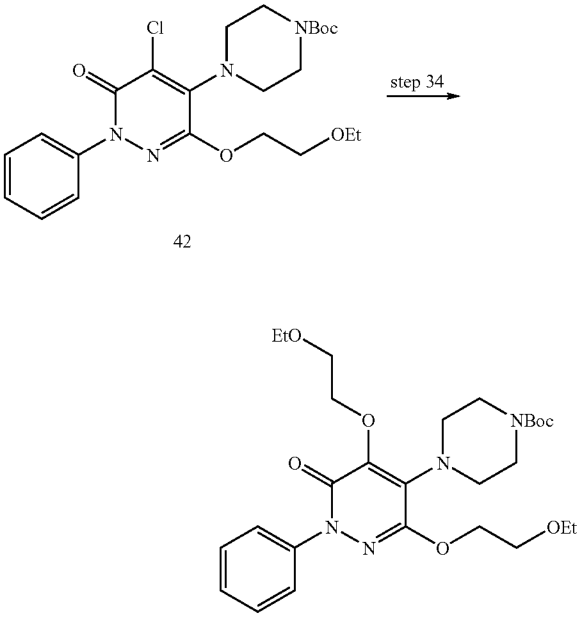

42

44

To a solution of compound 42 (102.3 mg, 0.214 mmol) and 2-ethoxyethanol (111.5 uL, 0.779 mmol) in THF (20 mL) was added NaH (60%, 37 mg, 0.925 mmol) and stirred at room temperature for 17 h. The reaction was then quenched with saturated $NH_4Cl$ (10 mL) and extracted with EtOAc (3×20 mL). The combined organic extract was washed with brine (20 mL), dried ($MgSO_4$), filtered, and concentrated. Purification by silica gel chromatography (3:1 to 2:1 hexanes:EtOAc) gave compound 44 (98.2 mg) as a colorless oil. MS (M+1): m/e 533.

Steps 6 and 9 of Scheme 1:

TABLE 13A

Sulfonamide analogs

The following compounds can be synthesized using the steps of Scheme 6.

| Compound No. | Structure | MS M + 1 |
|---|---|---|
| 1537Za | 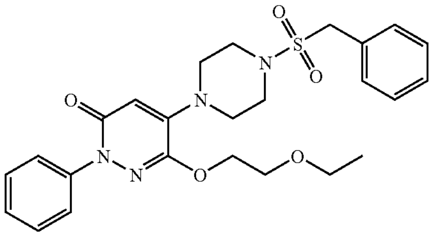 | 499 |
| 1537Zb | 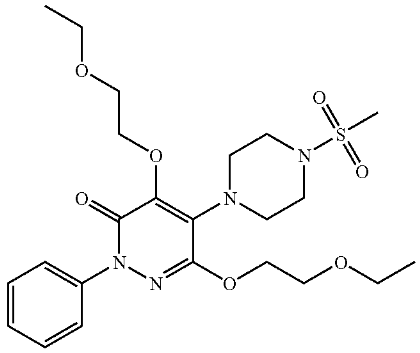 | 511 |
| 1537Zc | 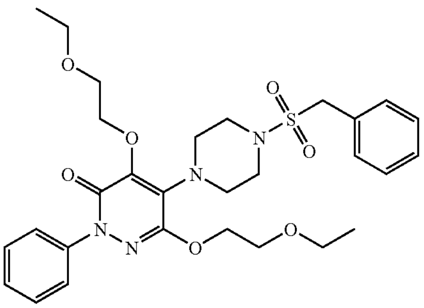 | 587 |

Scheme 7

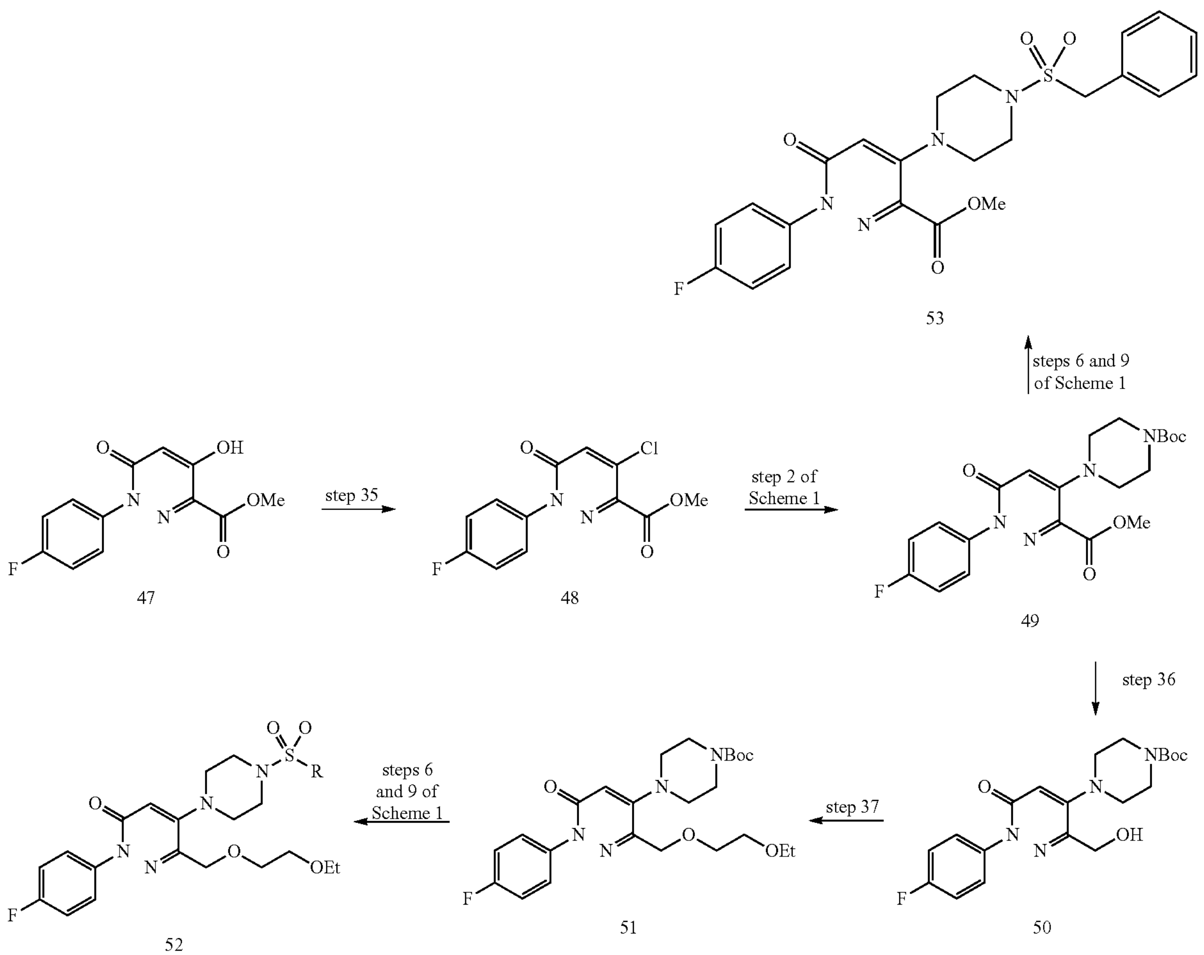

47 48 49 50 51 52 53

Step 35:

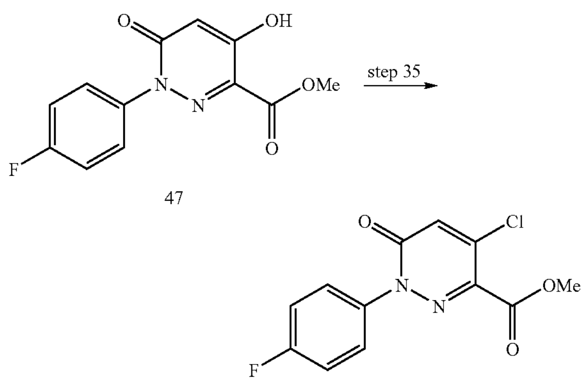

47 48

A solution of compound 47 (3.46 g, 0.013 mol) in $POCl_3$ (25 mL) was heated at 100° C. for 2 h. The reaction mixture was cooled to room temperate then concentrated. Saturated $NaHCO_3$ (50 mL) was added, and the aqueous solution was extracted with $CH_2Cl_2$ (3×100 mL). The combined organic extract was washed with brine (100 mL), dried ($MgSO_4$), filtered, and concentrated. Purification by silica gel chromatography (8:1 to 1:1 gradient of hexanes:EtOAc) gave compound 48 (2.82 g) as an orange solid. MS (M+1): m/e 283.

Step 2 of Scheme 1;

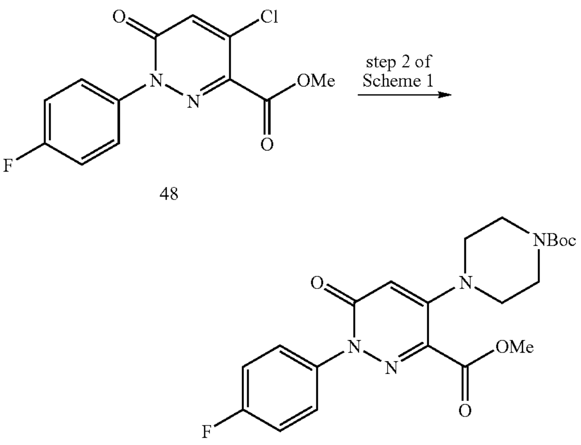

48 49

Using the procedure described above, compound 49 was synthesized. MS (M+1): m/e 433.

Step 36:

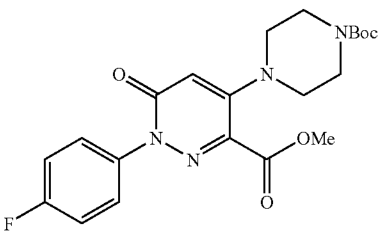

49

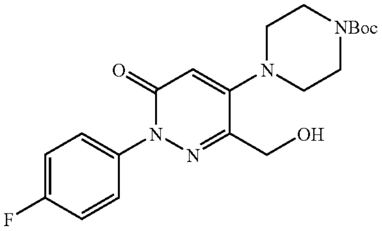

50

To a solution of compound 49 (100 mg, 0.231 mmol) in EtOH (10 mL) at 0° C. was added $NaBH_4$ (88 mg, 2.33 mmol). The reaction mixture was slowly warmed to room temperature and then stirred for 17 h. The reaction was quenched with saturated Rochelle's salt at 0° C. and extracted with EtOAc (3×20 mL). The combined organic extract was washed with brine (20 mL), dried ($MgSO_4$), filtered, and concentrated. Purification by silica gel chromatography (2:1 to 1:2 hexanes:EtOAc) gave compound 50 as a white foam. MS (M+1): m/e 405.

Step 37:

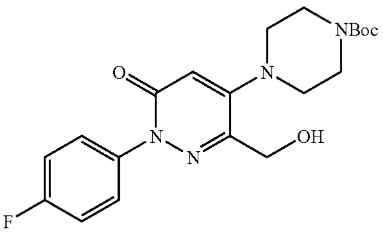

50

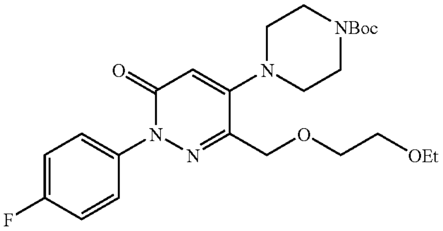

51

To a solution of compound 50 (80.3 mg, 0.199 mmol) in DMF (7 mL) at 0° C. was added NaH (60%, 24 mg, 0.600 mmol). Bromoethylether (134 uL, 1.19 mmol) was then added and the reaction mixture stirred at room temperature for 17 h. The reaction was quenched with saturated $NH_4Cl$ (5 mL) and extracted with EtOAc (3×15 mL). The combined organic extract was washed with brine (20 mL), dried ($MgSO_4$), filtered, and concentrated. Purification by silica gel chromatography (3:1 to 1:1 hexanes:EtOAc) gave compound 51 (93.9 mg) as a light yellow oil. MS (M+1): m/e 477.

Steps 6 and 9 of Scheme 1:

TABLE 14

Sulfonamide Analogs

The following compouns can be synthesized using the steps of Scheme 7.

| Compound No. | Structure | MS M + 1 |
|---|---|---|
| 1538Z | 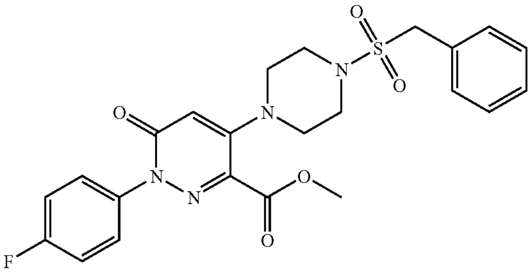 | 487 |
| 1539Z | 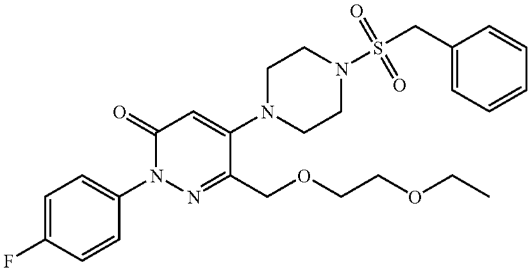 | 531 |

TABLE 14-continued

| Sulfonamide Analogs<br>The following compouns can be synthesized using the steps of Scheme 7. | | |
|---|---|---|
| Compound No. | Structure | MS M + 1 |
| 1540Z | 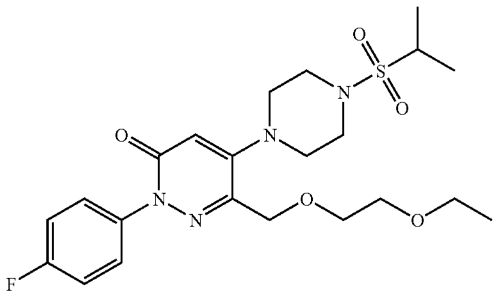 | 483 |

Scheme 8

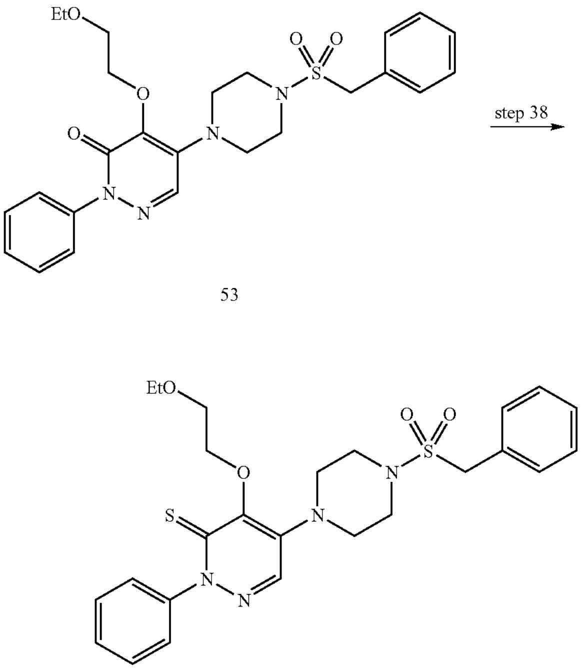

53

54

Compound 53 can be synthesized using steps 1, 2, 4, 6, and 9 of Scheme 1.

Step 38:

To a solution of compound 53 (31.5 mg, 0.063 mmol) in toluene (5 mL) was added Lawesson's reagent (26.0 mg, 0.064 mmol). The reaction mixture was heated to reflux (120° C.) for 48 h then cooled to room temperature and concentrated. Purification by Gilson reverse phase HPLC gave compound 54 (10.0 mg) as a light yellow oil. MS (M+1): m/e 515.

Scheme 9

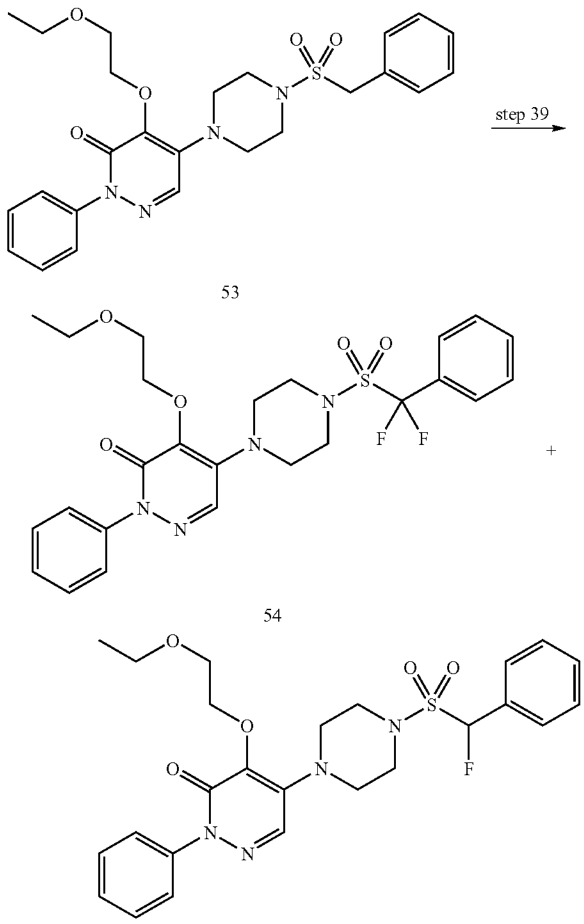

53

54

55

Step 39:

To a solution of compound 53 (100 mg, 0.201 mmol) in THF (20 mL) was added N-fluorobenzenesulfonimide (189.7 mg, 0.602 mmol), and the reaction mixture was cooled to −78° C. NaHMDS (1 M, 421.2 uL, 0.421 mmol) was added slowly over 30 min to the reaction mixture then gradually warmed to room temperature and stirred overnight for 15 h. The reaction was quenched with saturated $NH_4Cl$ (10 mL) and extracted with ethyl acetate (3×25 mL). The combined organic extract was washed with brine (25 mL), ($MgSO_4$), filtered, and concentrated. Purification by prep TLC (112 hexanes:ethyl acetate) gave compound 54 (20.2 mg) as a yellow solid and compound 55 (8.2 mg) as yellow oils. MS (M+1): m/e 535, m/e 517.

TABLE 15

Oxygen Linked Analogs with Sulfonamide
Using similar procedures described above, the following compounds were synthesized.

| Compound No. | Structure | MS M + 1 |
|---|---|---|
| 1541Z | 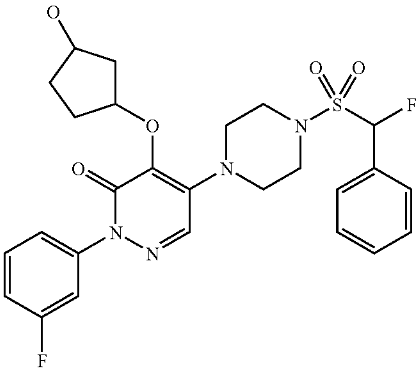 | 547 |
| 1542Z | 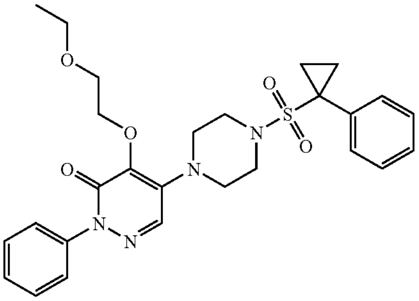 | 525 |
| 1543Z | 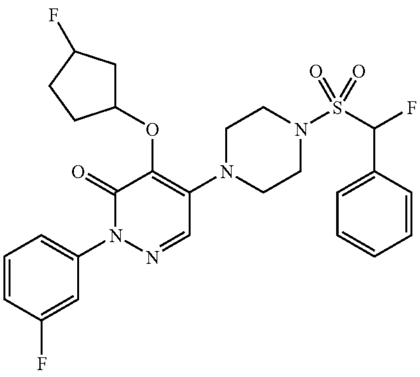 | 549 |

Scheme 10

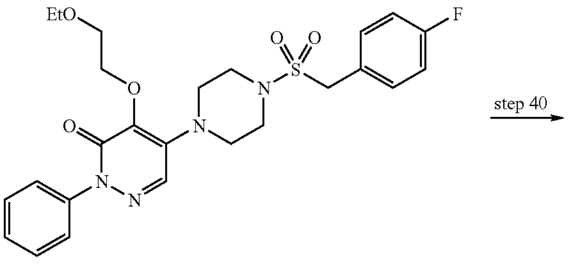

56

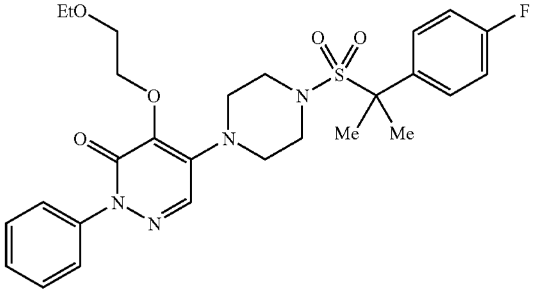

57

+

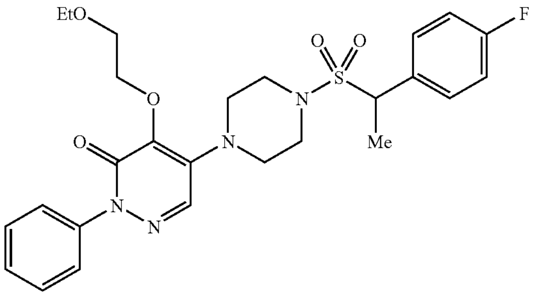

58

Step 40:

To a solution of compound 56 (150 mg, 0.290 mmol) dissolved in dry DMF (4 mL) was added methyl iodide (124 mg, 0.054 mL, 0.871 mmol) and potassium t-butoxide (1 M in THF, 0.87 mL, 0.87 mmol) under a nitrogen atmosphere. The reaction was stirred at room temperature for 24 h. The solvent was evaporated, water (25 mL) was added, and the aqueous solution was extracted with $CH_2Cl_2$. The combined organic extract was dried ($MgSO_4$), filtered, and concentrated. Purification by reverse phase chromatography (eluant: acetonitrile:water gradient with 0.1% formic acid) gave 90 mg (57%) of compound 57 and 37 mg (24%) of compound 58 as colorless oils. MS (M+1): m/e 545 for compound 57 and 531 for compound 58.

Using similar procedures described above, the following compounds were synthesized.

| Cmpd. No. | Structure | MS M + 1 |
|---|---|---|
| 1543Za | 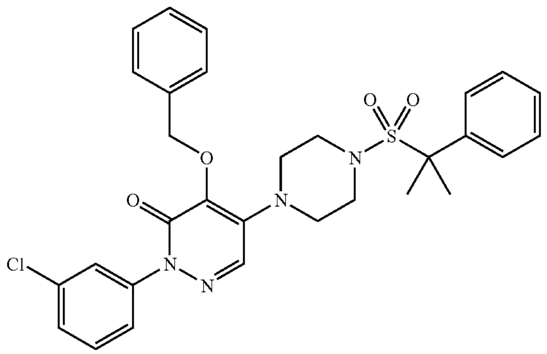 | 579 |
| 1543Zb | 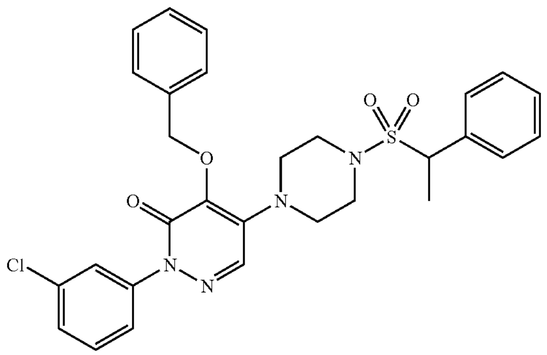 | 565 |
Scheme 11
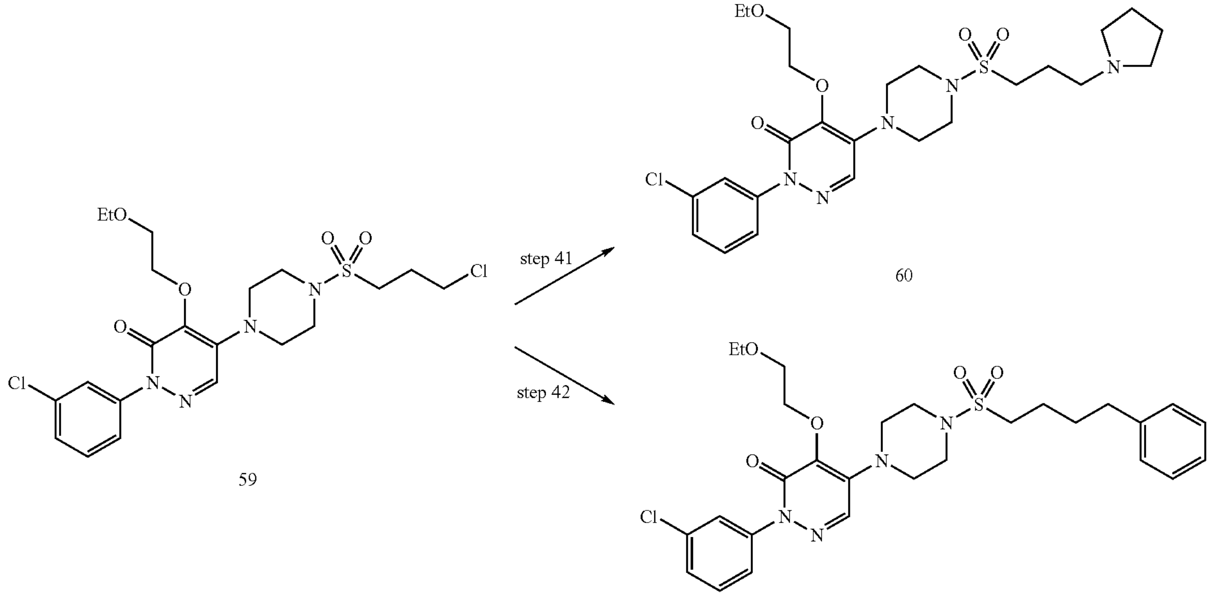
59
60
61

Compound 59 can be synthesized using steps 1, 2, 4, 6, and 9 of Scheme 1.

Step 41:

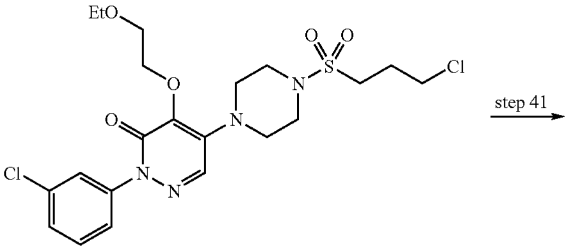

59

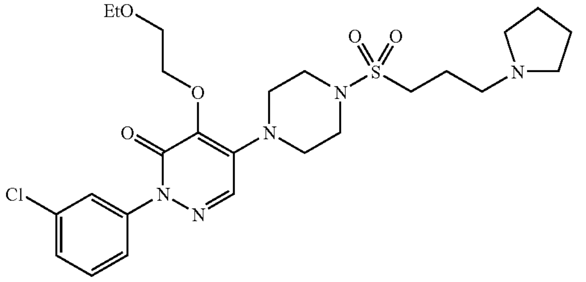

60

To a solution of compound 59 (150 mg, 0.289 mmol) dissolved in dry THF (4 mL) was added pyrrolidine (103 mg, 0.12 mL, 1.44 mmol). The reaction mixture was heated at reflux for 18 h. The solvent was evaporated, and purification by silica gel chromatography (eluant: 5-10% MeOH/$NH_3$—$CH_2Cl_2$) gave 133 mg (83%) of the product 60 as a colorless oil. MS (M+1): m/e 554.

Step 42:

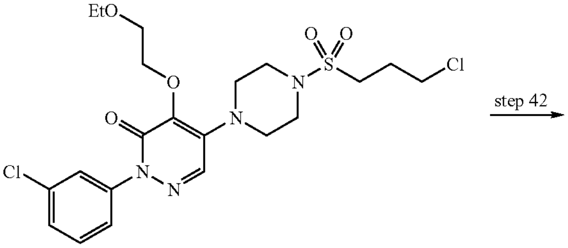

59

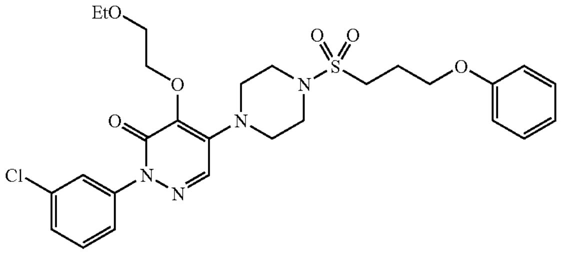

61

To a solution of compound 59 (250 mg, 0.481 mmol) dissolved in dry DMF (5 mL) was added potassium carbonate (200 mg, 1.44 mmol), potassium iodide (20 mg, 0.120 mmol), and phenol (136 mg, 1.44 mmol). The reaction mixture was heated at 100° C. for 16 h. The solvent was evaporated, water (25 mL) was added, and the aqueous solution was extracted with $CH_2Cl_2$. The combined organic extract was dried ($MgSO_4$), filtered, and concentrated. Purification by silica gel chromatography (eluant: 20-30% EtOAc-hexanes) gave 212 mg (76%) of the product 61 as a yellow solid. MS (M+1): m/e 599.

TABLE 16

Oxygen Linked Analogs with Sulfonamide

Using similar procedures described above, the following compound was synthesized.

| Compound No. | Structure | MS M + 1 |
|---|---|---|
| 1544Z | 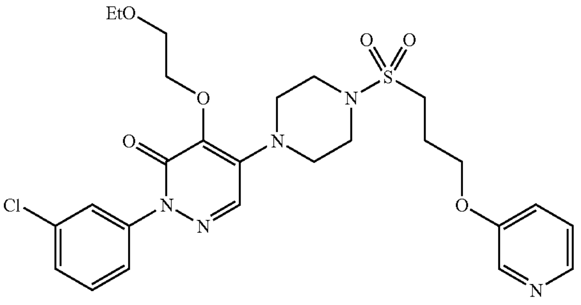 | 578 |

Scheme 12

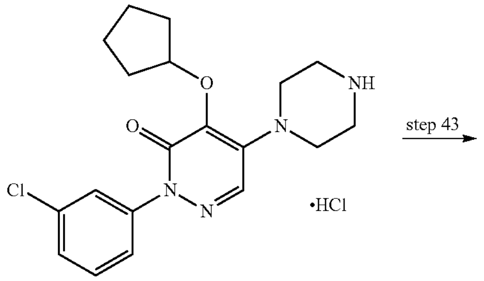

62

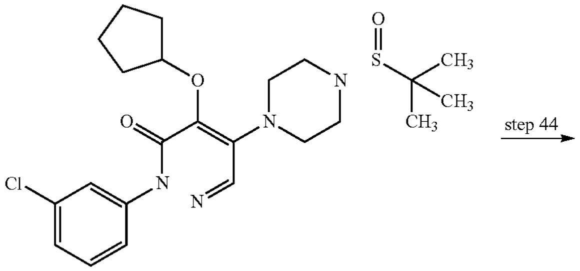

63

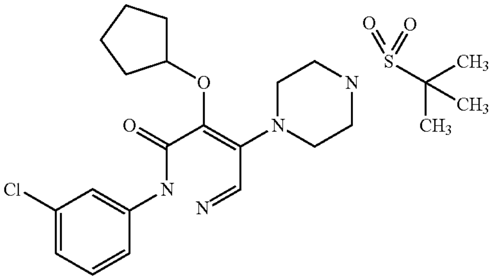

64

Compound 62 can be synthesized using steps 1, 2, 4, and 6 of Scheme 1.

Step 43:

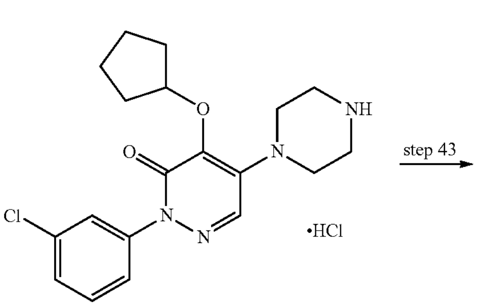

62

-continued

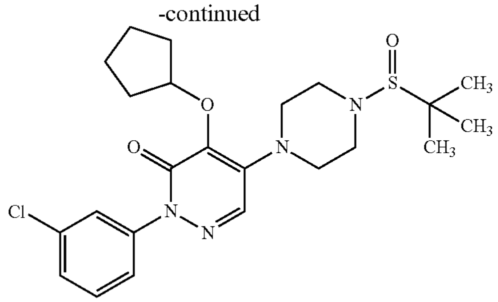

63

Diisopropylethylamine (0.17 mL, 1.0 mmol) was added to a suspension of tert-butylsulfinyl chloride (0.04 mL, 0.30 mmol) and compound 62 (150 mg, 0.36 mmol) in anhydrous $CH_2Cl_2$ (5 mL) at room temperature under nitrogen. The mixture was stirred for 22 h after which it was directly purified by CombiFlash Companion (40-g silica gel cartridge, eluant: 2:8 to 7:3 gradient ethyl acetate/hexanes), to provide sulfinamide 63 (120 mg, 82%) as a white solid: APCI MS m/z 479 $[M+H]^+$.

Step 44:

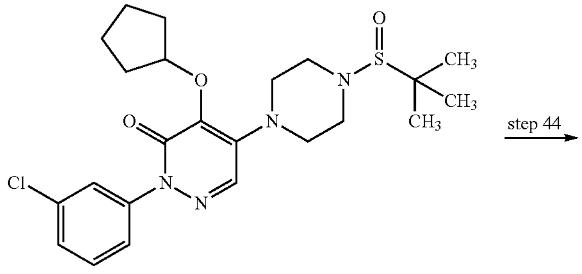

63

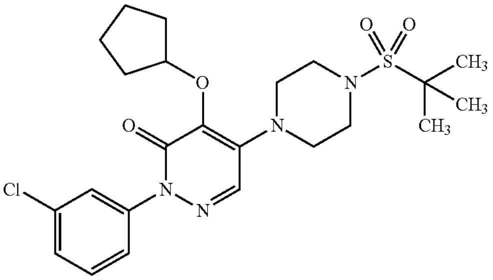

64 meta-Chloroperoxylbenzoic acid (190 mg, 0.78 mmol) was added to a solution of compound 63 (310 mg, 0.65 mmol) in anhydrous $CH_2Cl_2$ (10 mL) at room temperature under nitrogen. The mixture was stirred for 2.5 h after which it was diluted with $CH_2Cl_2$ (50 mL), washed with saturated aqueous sodium bisulfite solution (50 mL) and the solvents were evaporated. The residue was purified by CombiFlash Companion (80-g silica gel cartridge, eluant 1:9 to 7:3 gradient ethyl acetate/hexanes) to provide product 64 (290 mg, 91%) as a white solid: APCI MS m/z 495 $[M+H]^+$.

Scheme 13

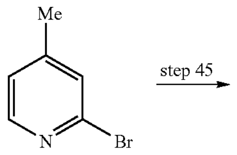

65

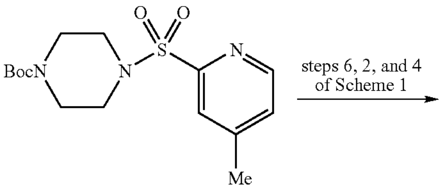

66

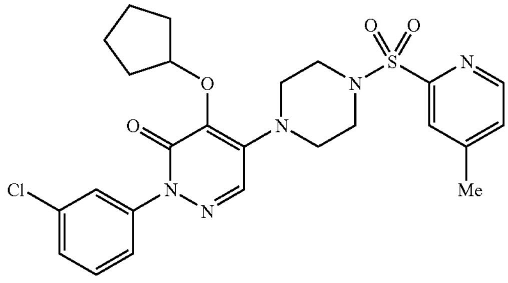

67

Step 45:

To a solution of 2-bromo-4-methylpyridine 65 (1.0 g, 5.81 mmol) in THF (20 mL) was added at room temperature isopropyl magnesium chloride (2 M, 3.2 mL, 6.40 mmol). The reaction mixture was heated to reflux for 3 h then cooled to −40° C. $SO_2$(g) was bubbled through the reaction mixture for 5 min then stirred at −40° C. for 1 h. $SO_2Cl_2$ (607 uL, 7.49 mmol) was added, and the reaction mixture was stirred for 30 min. BOC piperazine (3.2 g, 17.2 mmol) was then added, and the reaction mixture was slowly warmed to room temperature and stirred for 17 h. Water was added, and the aqueous solution was extracted with EtOAc (3×30 mL). The combined organic extract was washed with brine (30 mL), dried ($MgSO_4$), filtered, and concentrated. Purification by silica gel chromatography (3:1 to 1:1 hexanes:EtOAc) gave compound 67 (1.41 g) as a colorless oil. MS (M+1): m/e 342.

Steps 6, 2, and 4 of Scheme 1;

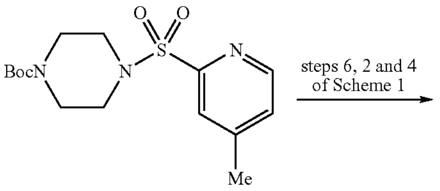

66

-continued

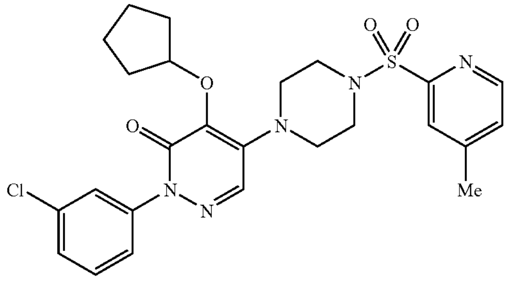

67

TABLE 17

Oxygen Linked Analogs with Sulfonamide
Using the procedures described above, the following compounds were synthesized.

| Compound No. | Structure | MS M + 1 |
|---|---|---|
| 1545Z | 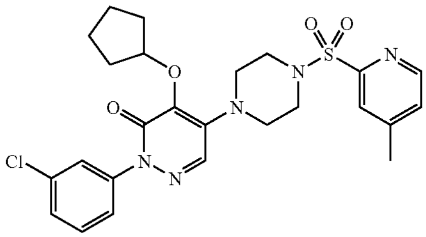 | 530 |
| 1546Z | 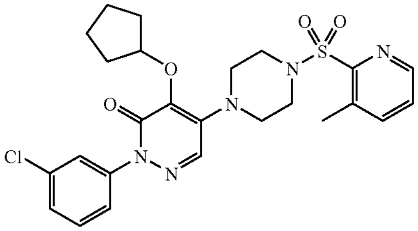 | 530 |
| 1547Z | 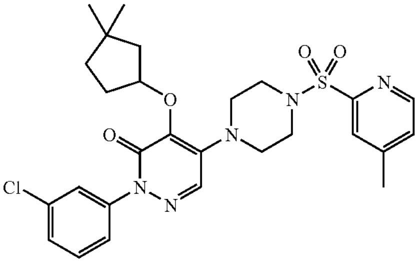 | 558 |
| 1548Z | 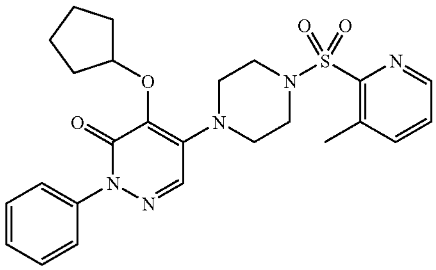 | 496 |

TABLE 17-continued

| Oxygen Linked Analogs with Sulfonamide Using the procedures described above, the following compounds were synthesized. | | |
|---|---|---|
| Compound No. | Structure | MS M + 1 |
| 1549Z | 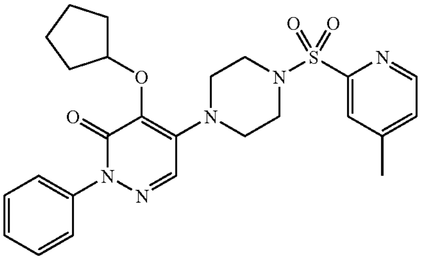 | 496 |

Scheme 14

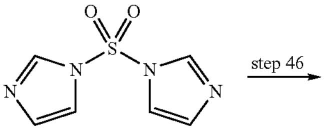

68

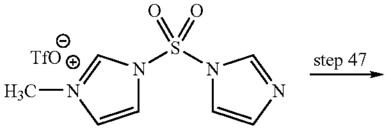

69

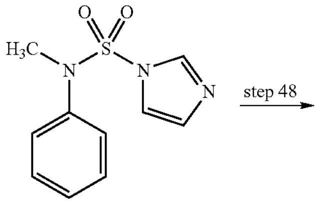

70

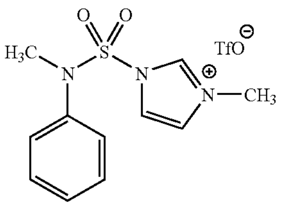

71

-continued

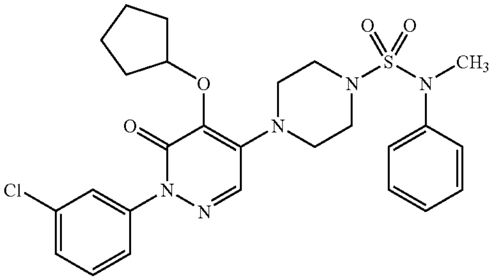

72

Step 46:

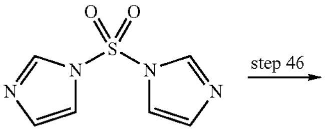

68

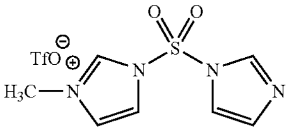

69

To a solution of N,N'-sulfuryldiimidazole 68 (2.00 g, 10.1 mmol) in anhydrous methylene chloride (40 mL) at 0° C. under nitrogen was added dropwise methyl triflate (1.4 mL, 12.4 mmol). The mixture was stirred at 0° C. for 3 h after which the solid was collected by vacuum filtration to provide product 69 (3.33 g, 91%) as a white solid.

Step 47:

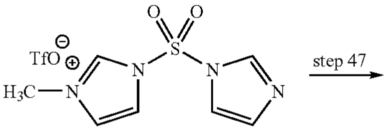

69

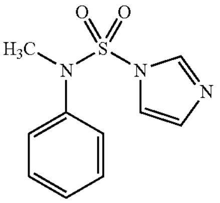

70

To a solution of compound 69 (2.09 g, 5.77 mmol) in anhydrous acetonitrile (15 mL) at room temperature under nitrogen was added N-methylaniline (414 mg, 3.86 mmol). The mixture was stirred for 2.5 h after which the solvent was evaporated. The residue was purified by CombiFlash Companion (40-g silica gel cartridge, eluant 9:1 to 1:1 gradient hexanes/ethyl acetate) to provide product 70 (372 mg, 47%) as a viscous orange oil.

Step 48:

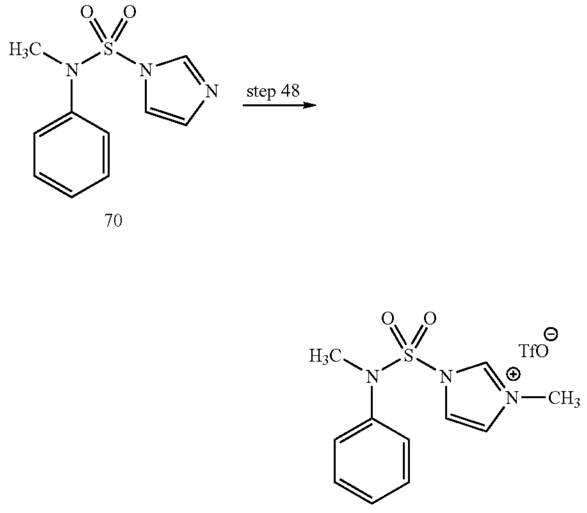

70

71

To a solution of compound 70 (372 mg, 1.57 mmol) in anhydrous methylene chloride (7 mL) at 0° C. under nitrogen was added methyl triflate (0.25 mL, 2.21 mmol). The mixture was stirred at 0° C. for 2 h after which the solvent was removed under reduced pressure to provide product 71 (373 mg, 59%) as a light-brown solid.

Step 49:

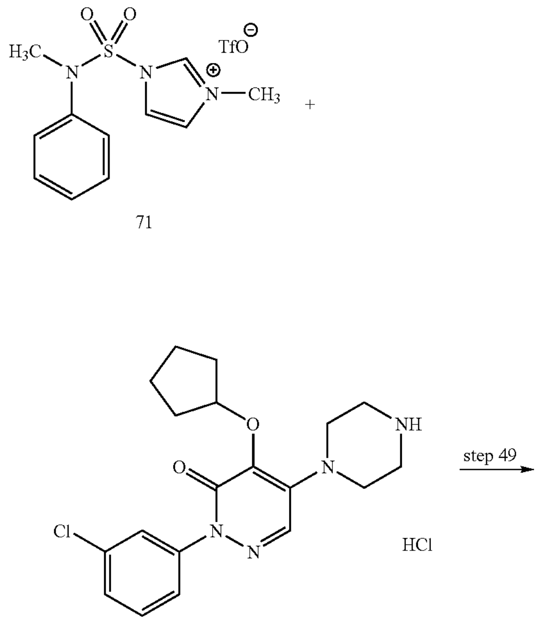

71

73

-continued

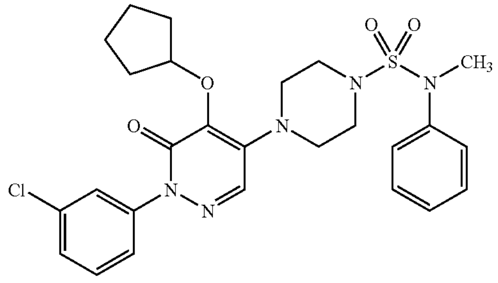

72

To a solution of compound 71 (373 mg, 0.93 mmol) in anhydrous methylene chloride (3 mL) at room temperature under nitrogen was added a solution of compound 73 (255 mg, 0.62 mmol) and N,N-diisopropylethylamine (0.11 mL, 0.631 mmol) in $CH_2Cl_2$ (3 mL). The mixture was stirred for 6 h after which the solvent was removed under reduced pressure. The residue was purified by CombiFlash Companion (40-g silica gel cartridge, eluant 9:1 to 3:1 gradient hexanes/ethyl acetate) to provide product 72 (249 mg, 74%) as a white solid: APCI MS m/z 544 $[M+H]^+$.

TABLE 18

Oxygen Linked Analogs with Sulfonamide

Using the procedures described above, the following compounds were synthesized.

| Comp. No. | Structure | MS M + 1 |
|---|---|---|
| 1550Z | 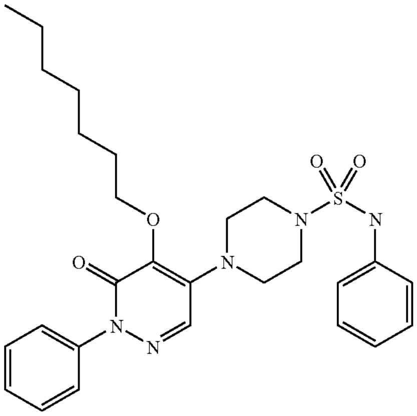 | 526 |
| 1551Z | 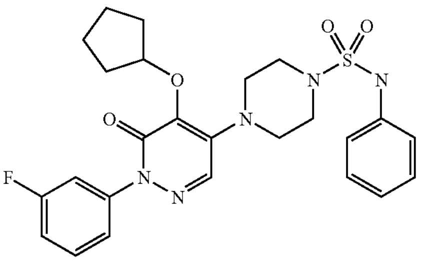 | 514 |

Scheme 15
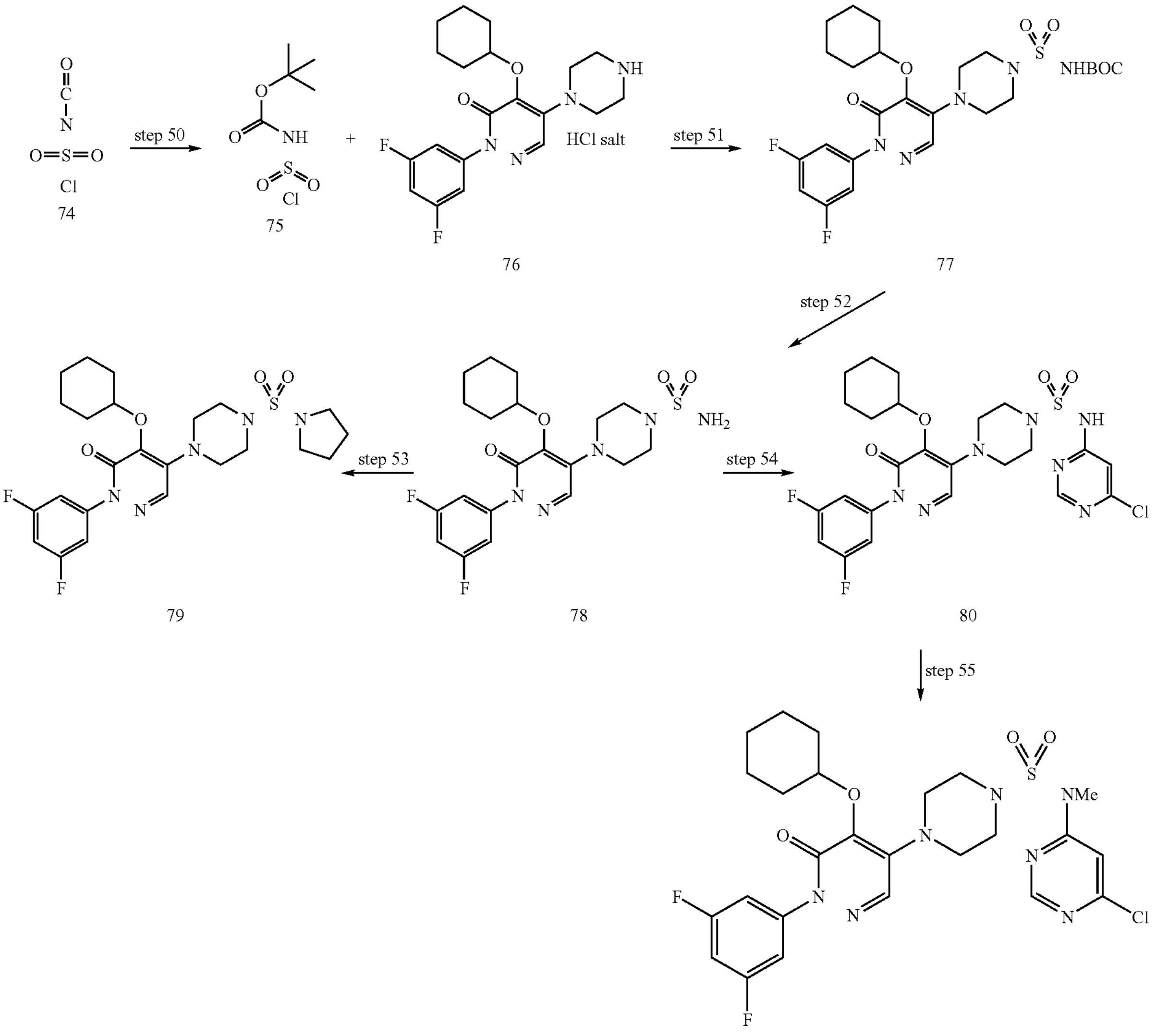
74 75 76 77 79 78 80 81
Step 50:
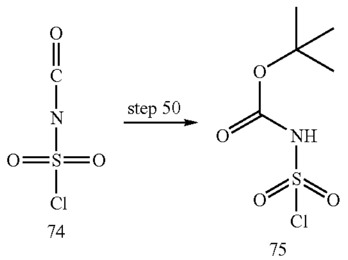
74 75
Dry t-butanol (0.96 mL, 10 mmol) in 20 mL of dry methylene chloride was cooled to 0° C. Chlorosulfonyl isocyanate 74 (0.9 mL, 10 mmol) was then added dropwise. The resulting solution was stirred at 0° C. for 30 min, then at room temperature for 1 h. This 0.5 M solution of compound 75 was used directly in the next step.
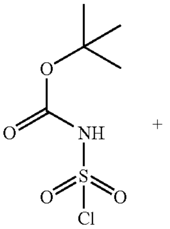
75

-continued

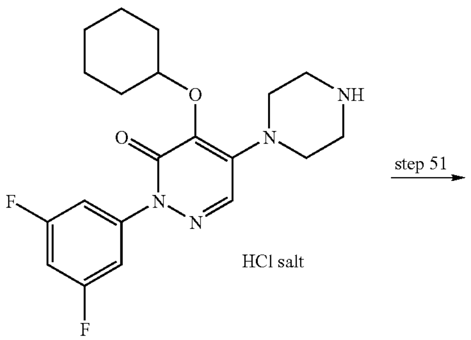

76

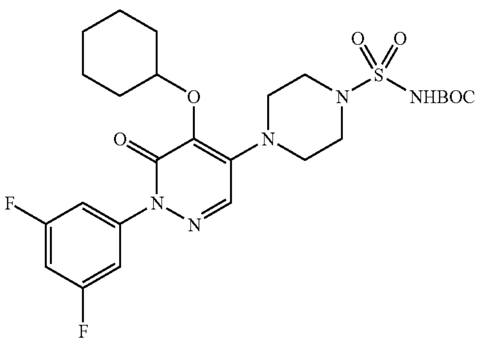

77

Step 51:

Compound 76 (0.43 g, 1.0 mmol) in 10 mL of dry methylene chloride was mixed with diisopropylethylamine (0.52 mL, 3.0 mmol). A 0.5 M solution of compound 75 in methylene chloride (2.4 mL, 1.2 mmol) was added dropwise. The resulting mixture was then stirred at room temperature for 16 h. EtOAc was added, and the organic solution was washed with 1 N HCl, then dried ($Na_2SO_4$), filtered, and concentrated to give quantitative yield of product 77 as a white solid.

Step 52:

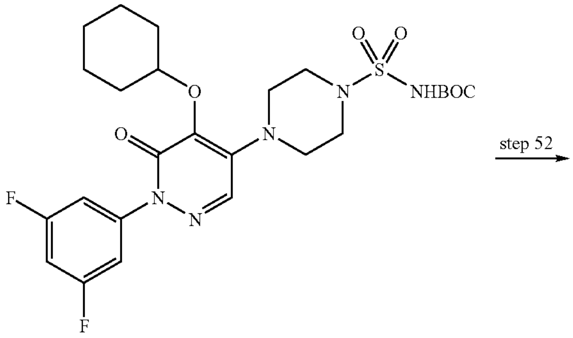

77

-continued

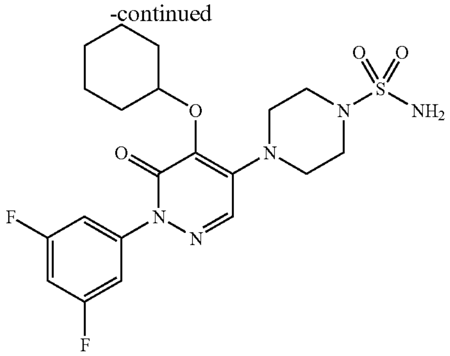

78

To compound 77 (1.0 mmol) dissolved in methylene chloride was added 4 N HCl in dioxane at room temperature and stirred overnight. The solvent was evaporated, and purification by silica gel chromatography gave 0.45 g (96% from 76) of product 78 as a white solid. MS (M+1): m/e 470.

Step 53:

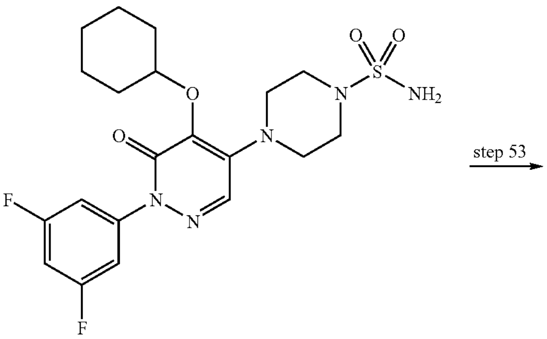

78

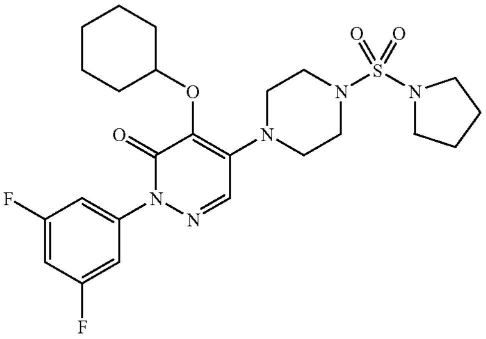

79

To compound 78 (52 mg, 0.11 mmol) dissolved in DMF (1 mL) was added 1,4-diiodobutane (0.015 mL, 0.11 mmol) and NaH (60%, 10 mg, 0.22 mmol). The resulting mixture was stirred at room temperature for 16 h, EtOA was added, and the organic solution was washed with brine, dried ($Na_2SO_4$), filtered, and concentrated. Purification by silica gel chromatography gave 48 mg (83%) of product 79 as a white solid. MS (M+1): m/e 524.

TABLE 19

| Compound No. | Structure | MS M + 1 |
|---|---|---|
| Oxygen Linked Analog with Sulfonamide Using the procedures described above, the following compound was synthesized. | | |
| 1552Z | 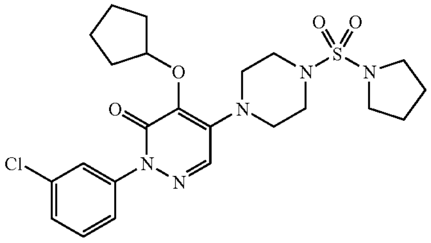 | 508 |

Step 54:

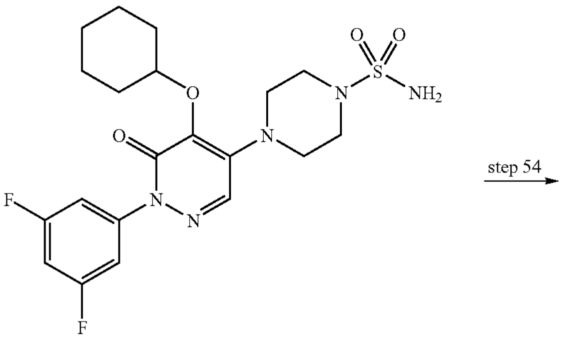

78

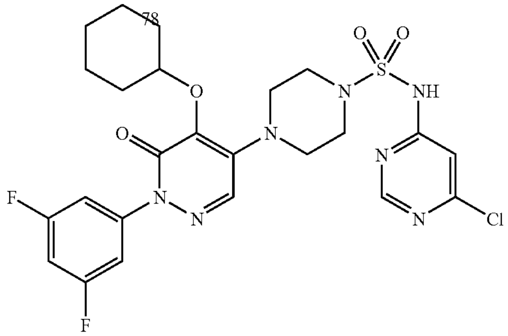

80

Compound 78 (50 mg, 0.1 mmol) was mixed with 4,6-dichloropyrimidine (20 mg, 0.13 mmol) in 1 mL of dry DMF. Phosphazene base P1-t-Bu (0.038 mL, 0.15 mmol) was added. The mixture was stirred at room temperature for 16 h. The crude mixture was purified by prep HPLC to give 0.033 g of product 80 as a white solid. MS (M+1): m/e 582.

Step 55:

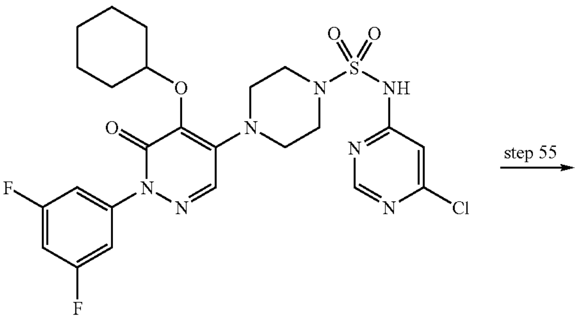

80

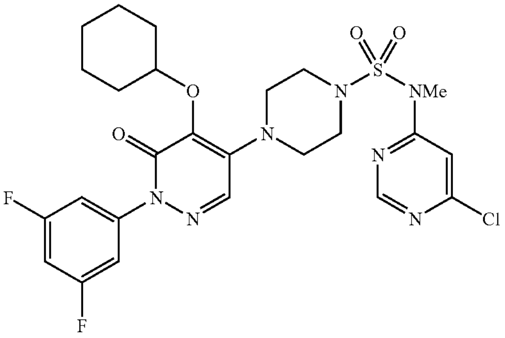

81

To compound 80 in dry DMF was added methyl iodide (0.1 mL), and the resulting mixture was stirred at room temperature for 3 days. The crude mixture was purified by prep HPLC to give 0.035 g of product 81 as a white solid. MS (M+1): m/e 596.

Scheme 16

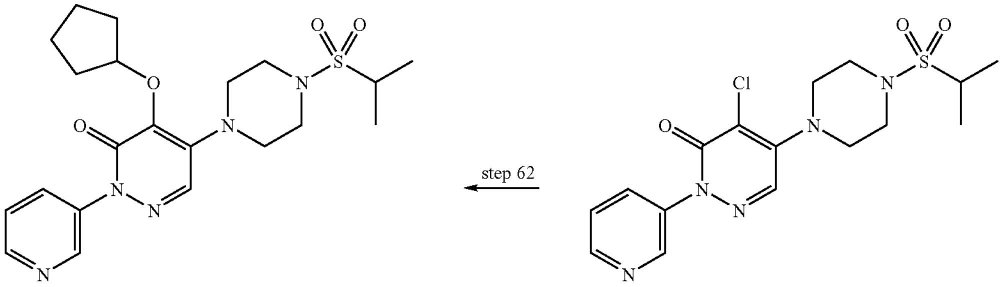

89 88

-continued

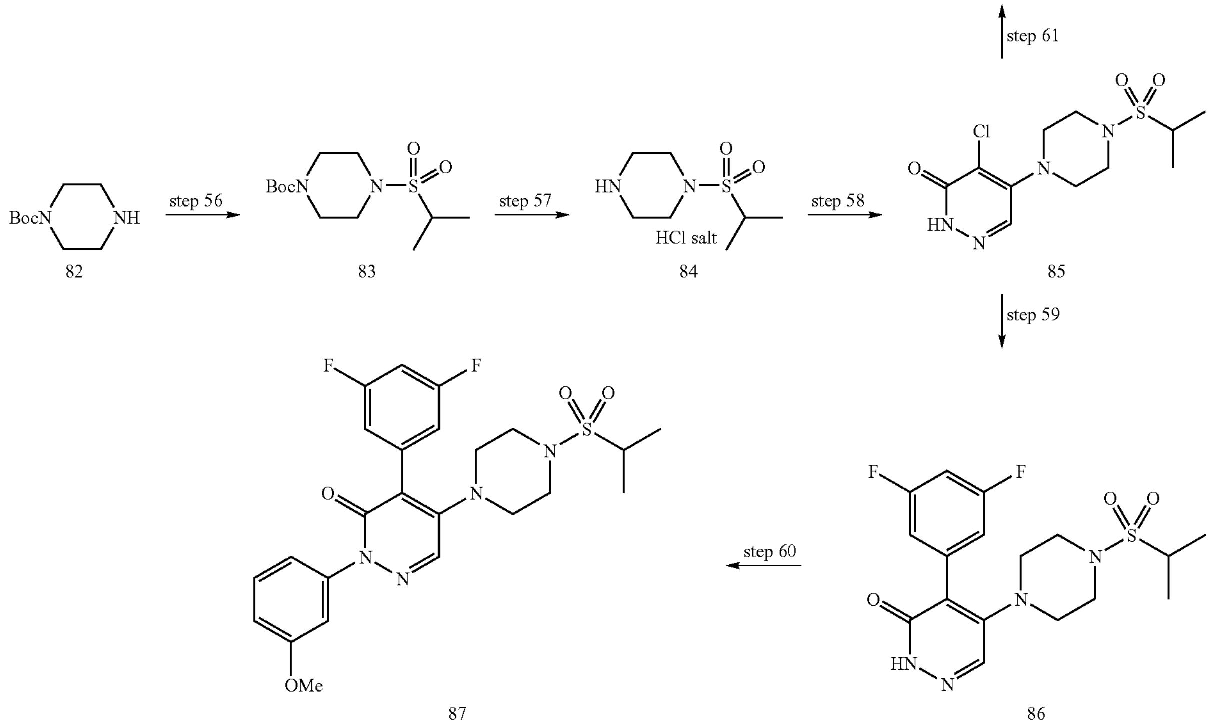

82 83 84 85 86 87

Step 56:

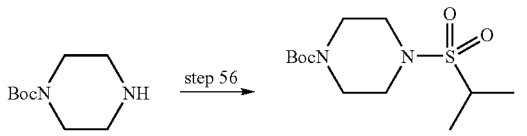

82 83

1-Boc-piperazine 82 (25.0 g, 0.13 mol) was mixed with diisopropylethylamine (28 mL, 0.16 mol) in dry methylene chloride (40 mL), and the mixture was cooled to −25° C. 2-Isopropanesulfonyl chloride (16.5 mL, 0.15 mol) was added dropwise. The resulting mixture was slowly warmed up to room temperature, and stirred for 16 h. The solvent was evaporated, and EtOAc was added. The organic solution was washed with 1 N HCl, brine, dried ($Na_2SO_4$), filtered, and concentrated to give 39 g of product 83 as white solid. MS (M+1): m/e 293.

Step 57:

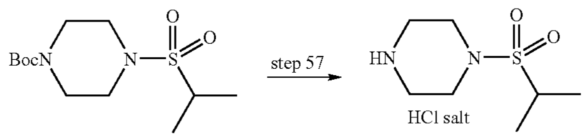

83 84

To compound 83 dissolved in methylene chloride (30 mL) was added of 4 N HCl in dioxane (100 mL). The resulting mixture was stirred at room temperature for 16 h. The solvent was evaporated, and diethyl ether was added. The precipitate was collected by filtration and dried in a vacuum oven at 50° C. for two days to give 28.6 g of product 84 as the HCl salt. MS (M+1): m/e 193.

Step 58:

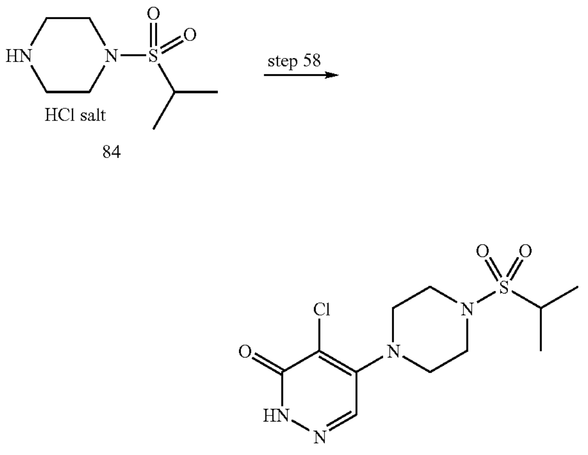

84 85

Compound 84 (9.6 g, 42 mmol) was mixed with 4,5-dichloro-3-hydroxy pyridazine (6.6 g, 40 mmol) and TEA (11.4 mL, 82 mmol) in ethanol (80 mL). The resulting mixture was stirred at 70° C. for 2 days then cooled to room temperature and diluted with water (160 mL). The precipitate was collected by filtration, washed with water/ethanol (1:1), and dried in a vacuum oven at 50° C. for 2 days to give 7.8 g of product 85 as a white solid. MS (M+1): m/e 321.

Step 59:

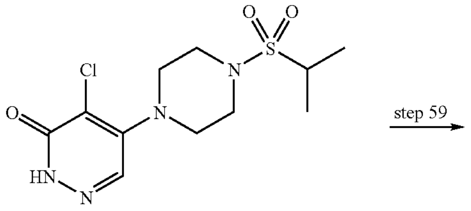

85

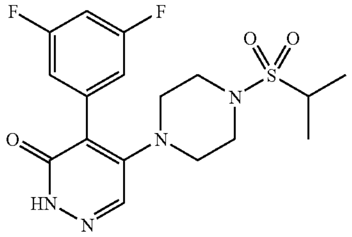

86

A 20-mL microwave reaction vial was charged with compound 85 (1.92 g, 6.0 mmol), 3,5-difluorophenyl boronic acid (1.04 g, 6.6 mmol), sodium carbonate (1.33 g, 12.6 mmol), and $Pd(PPh_3)_2Cl_2$ (0.21 g, 0.3 mmol) in 1:1 $CH_1CN$:$H_2O$ (16 mL). The reaction mixture was heated in the microwave with stirring at 150° C. for 12 mins. After cooling to room temperature, EtOAc was added. The organic solution was washed with 1 N HCl then brine, dried ($Na_2SO_4$), filtered, and concentrated. Purification by silica get chromatography gave 1.35 g of the product 86 as a white solid. MS (M+1): m/e 399.

Step 60:

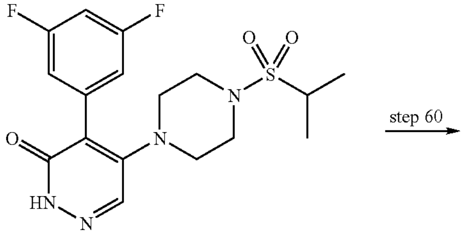

86

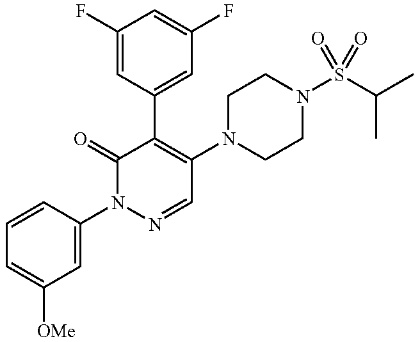

87

A 5-mL microwave reaction vial was charged with compound 86 (50 mg, 0.125 mmol), 3-methoxybromobenzene (0.12 mL), Cu powder (10 mg), anhydrous potassium carbonate (40 mg), and dry pyridine (3 mL). The reaction mixture was heated in the microwave with stirring at 190° C. for 15 min. After cooling to room temperature, the mixture was filtered, and the solution was concentrated. The residue was dissolved in DMF and purification by reverse phase chromatography on a Gilson prep HPLC gave 50.5 mg of product 87 as light-yellow solid. MS (M+1): m/e 505.

Step 61:

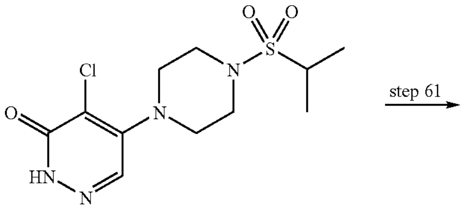

85

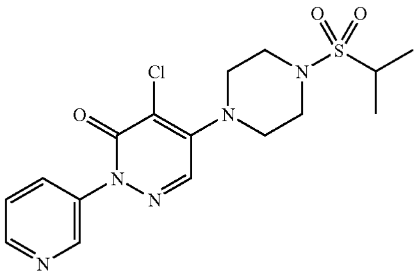

88

A 5-mL microwave reaction vial was charged with compound 85 (100 mg, 0.3 mmol), 3-bromopyridine (0.3 mL), Cu powder (20 mg), anhydrous potassium carbonate (100 mg), and dry pyridine (4 mL). The reaction mixture was heated in a microwave with stirring at 200° C. for 30 min. After cooling to room temperature, the mixture was filtered, and the solution was concentrated. Purification by silica gel chromatography gave 103 ma of product 88 as light-yellow solid. MS (M+1): m/e 398.

Step 62:

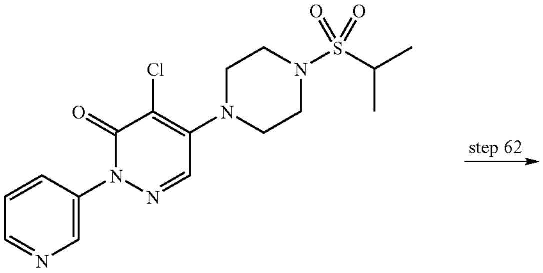

88

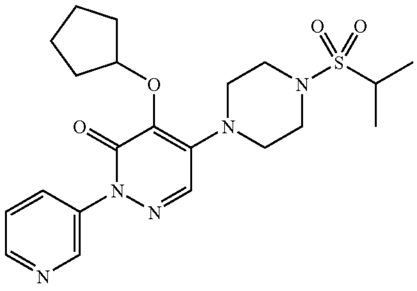

89

Compound 88 (85 mg, 0.21 mmol) and was mixed with cyclopentanol (55 mg, 0.63 mmol) in dry THF (2 mL). Sodium hydride (60 wt % in oil, 20 mg) was added. The reaction mixture was stirred at room temperature for 16 h. EtOAc was added, and the organic solution was washed with water and brine, dried ($Na_2SO4$), filtered, and concentrated. Purification by silica gel chromatography gave 83 mg of product 89 as a light-yellow solid. MS (M+1): m/e 448.

TABLE 20

Oxygen Linked Analog with Sulfonamide
Using the procedures described above, the follow compound was synthesized.

| Compound No. | Structure | MS M + 1 |
|---|---|---|
| 1553Z | 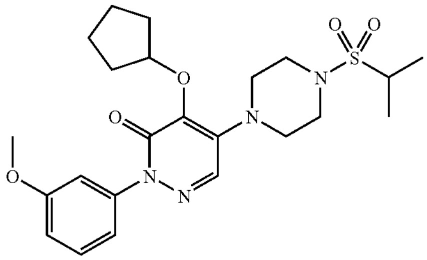 | 478 |

Scheme 17

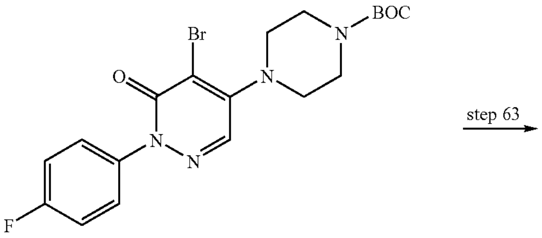

90

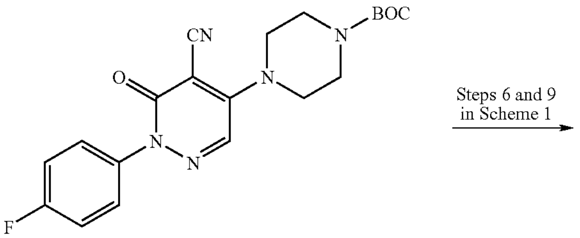

91

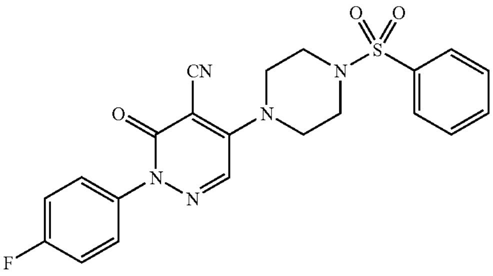

92

Compound 90 can be synthesized using steps 1 and 2 of Scheme 1.

Step 63:

A mixture of anhydrous KCN (0.065 g, 1.0 mmol) and compound 90 (0.451 g, 1.0 mmol) in DMSO (5 mL) was stirred at room temperature for 24 h. The resulting solution was poured into ice $H_2O$ (10 mL), and a white precipitate formed. The solid was filtered and dried under vacuum. Purification by silica eel chromatography (1:10 EtOAc:hexanes) gave the product 91 as a white solid (0.320 g, 80%). MS (M+1): m/e 400.

Steps 6 and 9 of Scheme 1:

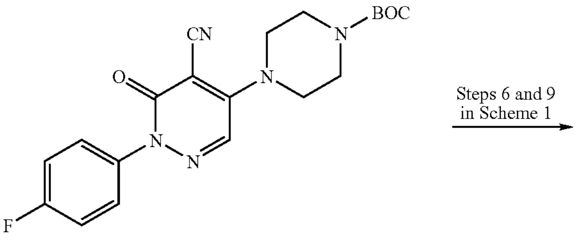

91

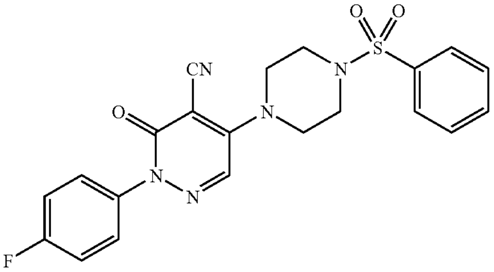

92

Using the procedure described above, compound 92 was synthesized. MS (M+1): m/e 440.

Scheme 18

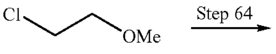

93

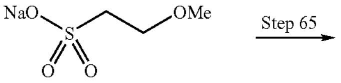

94

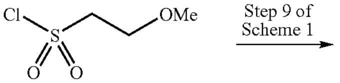

95

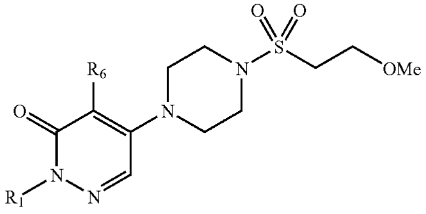

96

Step 64:

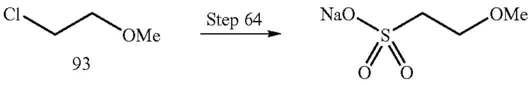

93 94

A mixture of 2-chloroethyl methyl ether 93 (25 g) and $Na_2SO_3$ (33 g) dissolved in $H_2O$ (100 mL) was heated at reflux for 24 h. After cooling to room temperature, the solid was filtered, washed with ether/toluene (5:1), and dried under vacuum to give product 94.

Step 65:

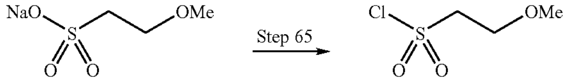

94 95

Compound 94 was added in small portions to $POCl_3$ (60 mL). The resulting heterogeneous mixture was stirred at room temperature for 16 h and then heated at reflux for 12 h. $CH_2Cl_2$ (100 mL) was added to the reaction mixture. After filtration, ethyl acetate was added to the residue and then poured into crushed ice. The organic phase was separated and washed with brine (2×50 mL), dried ($MgSO_4$), filtered, and concentrated to give product 95.

TABLE 21

Oxygen Linked Analogs with Sulfonamide

The following compounds can be synthesized by using compound 95 in step 9 of Scheme 1.

| Compound No. | Structure | MS M + 1 |
|---|---|---|
| 1554Z | 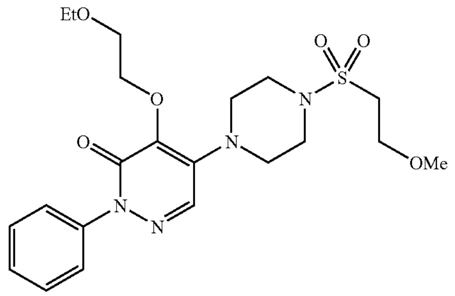 | 467 |
| 1555Z | 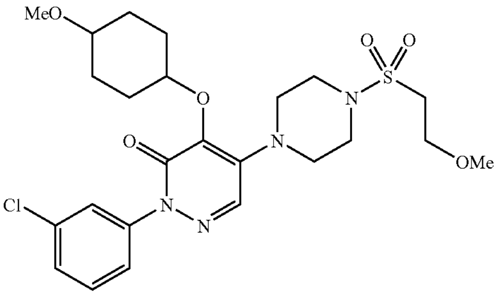 | 541 |
| 1556Z | 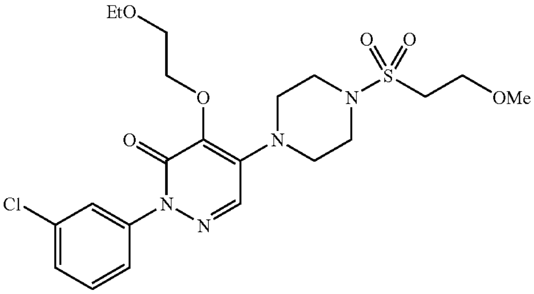 | 501 |

TABLE 21-continued

| Compound No. | Structure | MS M + 1 |
|---|---|---|
| Oxygen Linked Analogs with Sulfonamide. The following compounds can be synthesized by using compound 95 in step 9 of Scheme 1. | | |
| 1557Z | 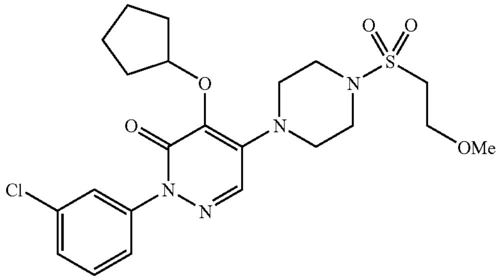 | 497 |

Scheme 19

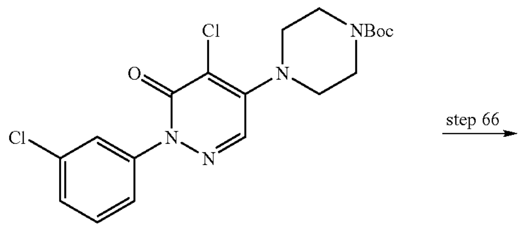

3

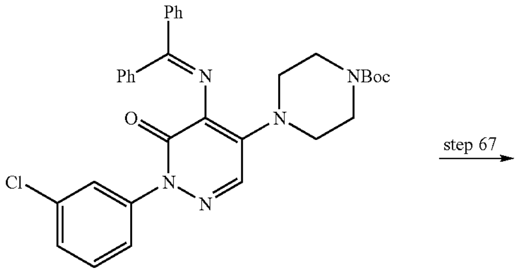

97

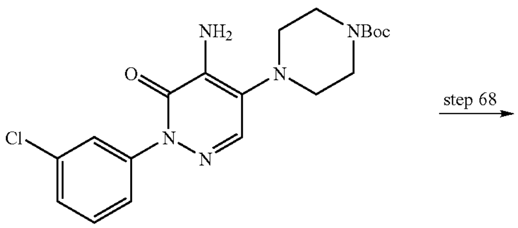

98

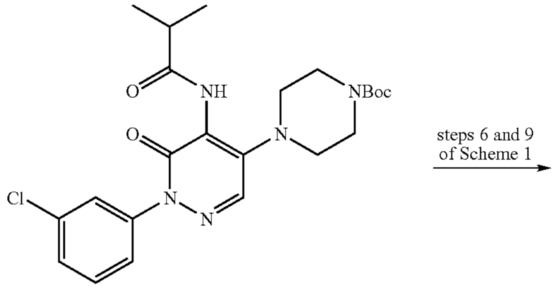

99

-continued

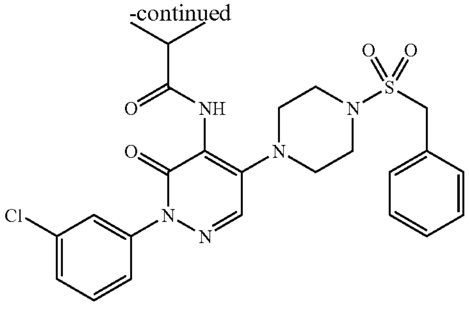

100

Step 66:

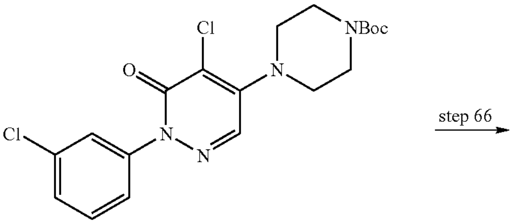

3

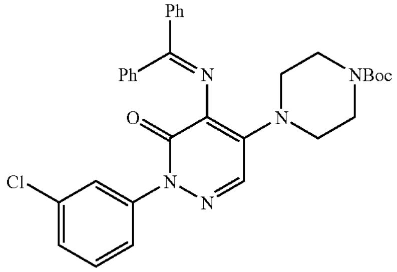

97

Compound 3 (0.43 g, 1 mmol) was mixed with $Pd(OAc)_2$ (4.5 mg), (±) BINAP (12.5 mg), $Ph_2C{=}NH$ (0.2 mL, 1.2 mmol), and potassium carbonate (0.7 g, 5 mmol) in dry toluene (9 mL). The reaction mixture was heated at 110° C. under nitrogen for 2 days. After cooling to room temperature, the mixture was filtered, and the solid was washed with methylene chloride. The combined filtrate was concentrated, and purification by silica gel chromatography gave 0.21 g of product 97 and 0.15 g of product 98. For compound 97: MS (M+1): m/e 570 and for compound 98; MS (M+1): m/e 406.

Step 67:

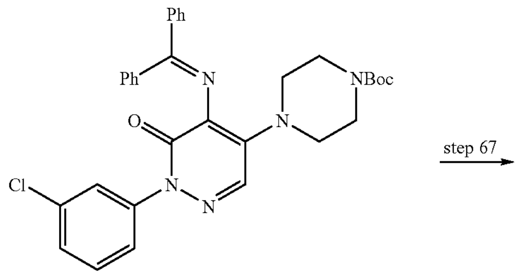

97

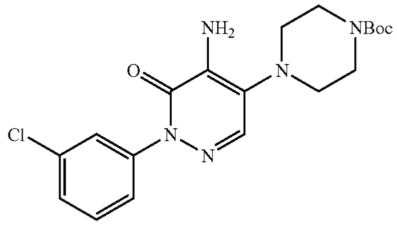

98

Compound 97 (0.15 mg) dissolved in methanol (2 mL) was treated with 2 N HCl (4 mL), and the reaction mixture was stirred at room temperature for 16 h. The reaction mixture was extracted with ethyl acetate and washed with brine. The organic extract was evaporated, and purification by silica gel chromatography gave the product 3 (100%).

Step 68:

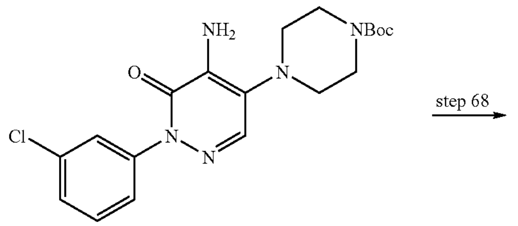

98

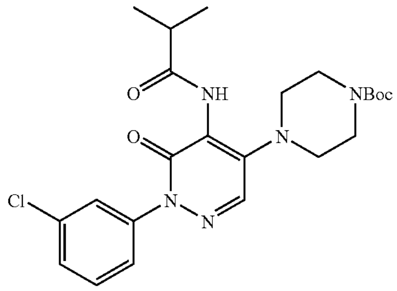

99

To a solution of compound 98 (0.13 g, 0.3 mmol) in dry DMF (2 mL) was added diisopropylethylamine (0.2 mL) and isobutyryl chloride (0.035 mL, 0.33 mmol). The reaction mixture was stirred at room temperature for 3 days. The mixture was diluted with ethyl acetate, and washed with saturated sodium bicarbonate solution, water, 1 N HCl, and brine. The organic solution was evaporated to give the product 99 which was used in the next step without further purification.

Steps 6 and 9 of Scheme 1:

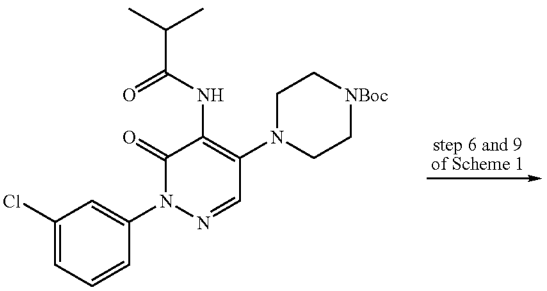

99

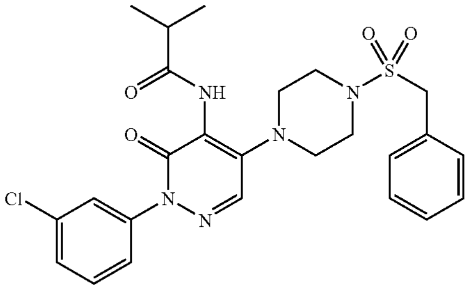

100

Using the procedures described above, compound 100 was synthesized. MS (M+1): m/e 530.

Scheme 20

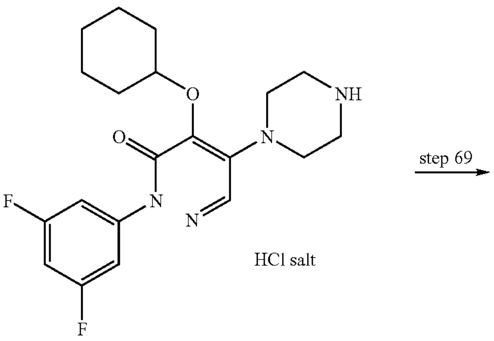

76

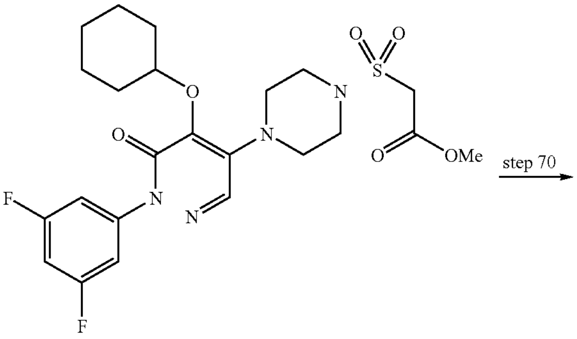

101

-continued

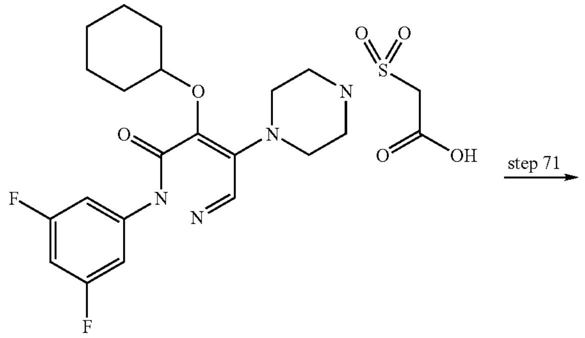

102

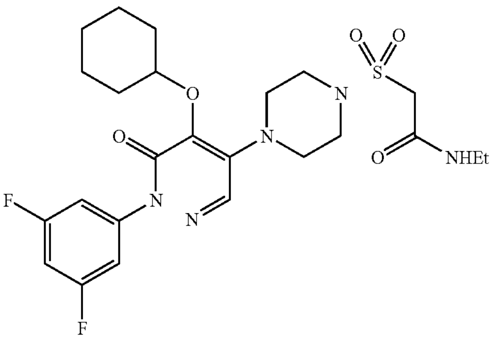

103

Step 69:

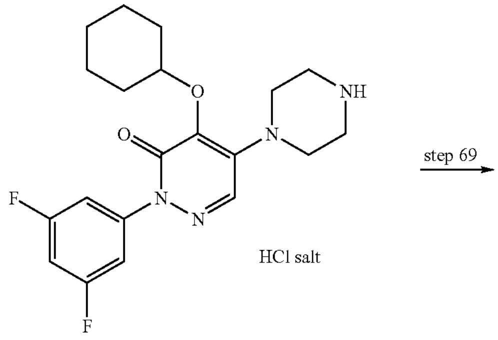

76

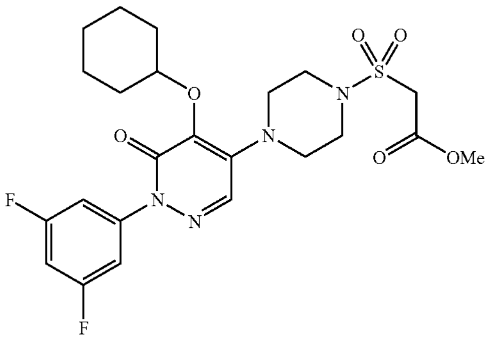

101

Chlorosulfonylacetyl chloride (0.16 mL, 1.5 mmol) in dry diethyl ether (2 mL) was cooled to −78° C., and methanol (1.5 mmol) in dry ether (1 mL) was added. After warming to room temperature, the mixture was stirred at room temperature for 1 h, then added to a solution of compound 76 and diisopropylethylamine (0.88 mL, 5 mmol) in DMF (3 mL). The resulting mixture was stirred at room temperature for 16 h. EtOAc was added, and the organic solution was washed with 1 N HCl and brine, dried ($Na_2SO_4$), filtered and concentrated. Purification by silica gel chromatography gave 0.2 g of product 101 as a white solid. MS (M+1): m/e 527.

Step 70:

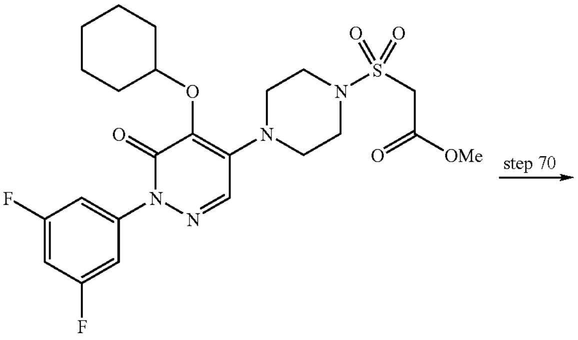

101

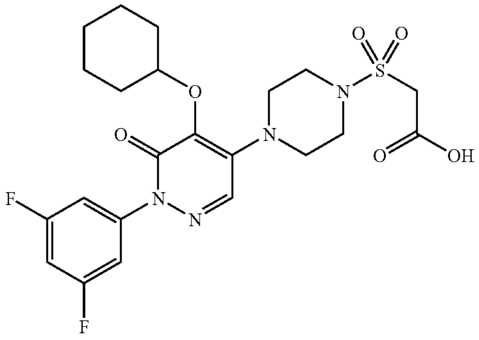

102

To compound 101 (0.17 g) dissolved in THF (3.8 mL) and water (1.5 mL) was added lithium hydroxide (0.019 g). The resulting mixture was stirred at room temperature for 3 h. 1 N HCl (5 mL) was added, and the aqueous solution was extracted with EtOAc. The combined organic extract was dried ($Na_2SO_4$), filtered, and concentrated to give the product 102. MS M+1): m/e 513.

Step 71:

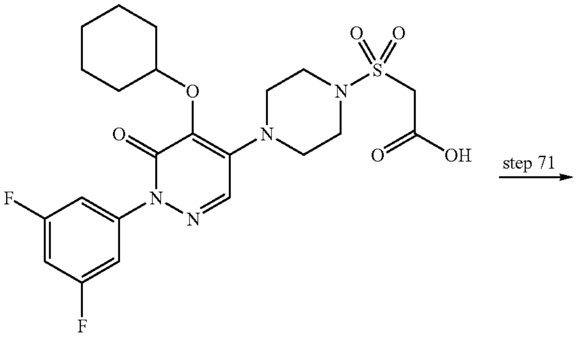

102

-continued

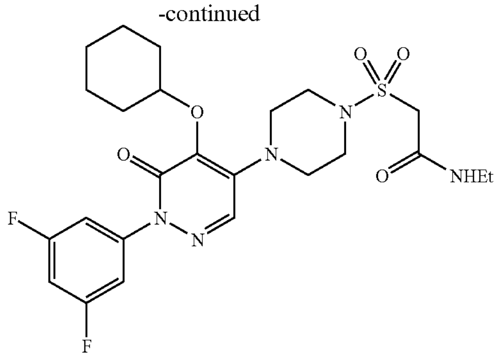

103

Compound 102 (40 mg) was mixed with ethyl amine (0.5 mmol), diisopropylethylamine (0.1 mL), and HATU (0.3 g) in DMF (1 mL). The mixture was stirred at room temperature for 16 h, then purified directly with the Gilson reverse phase prep HPLC (acetonitrile-water gradient with 0.1% formic acid) to give 21 mg of the product 103 as light-yellow solid. MS (M+1): m/e 640.

TABLE 22

Oxygen Linked Analog with Sulfonamide

Using the procedures described above, the follow compound was synthesized.

| Compound No. | Structure | MS M + 1 |
|---|---|---|
| 1558Z | 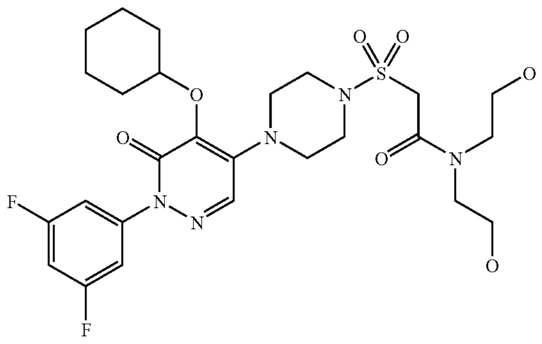 | 600 |

Scheme 21
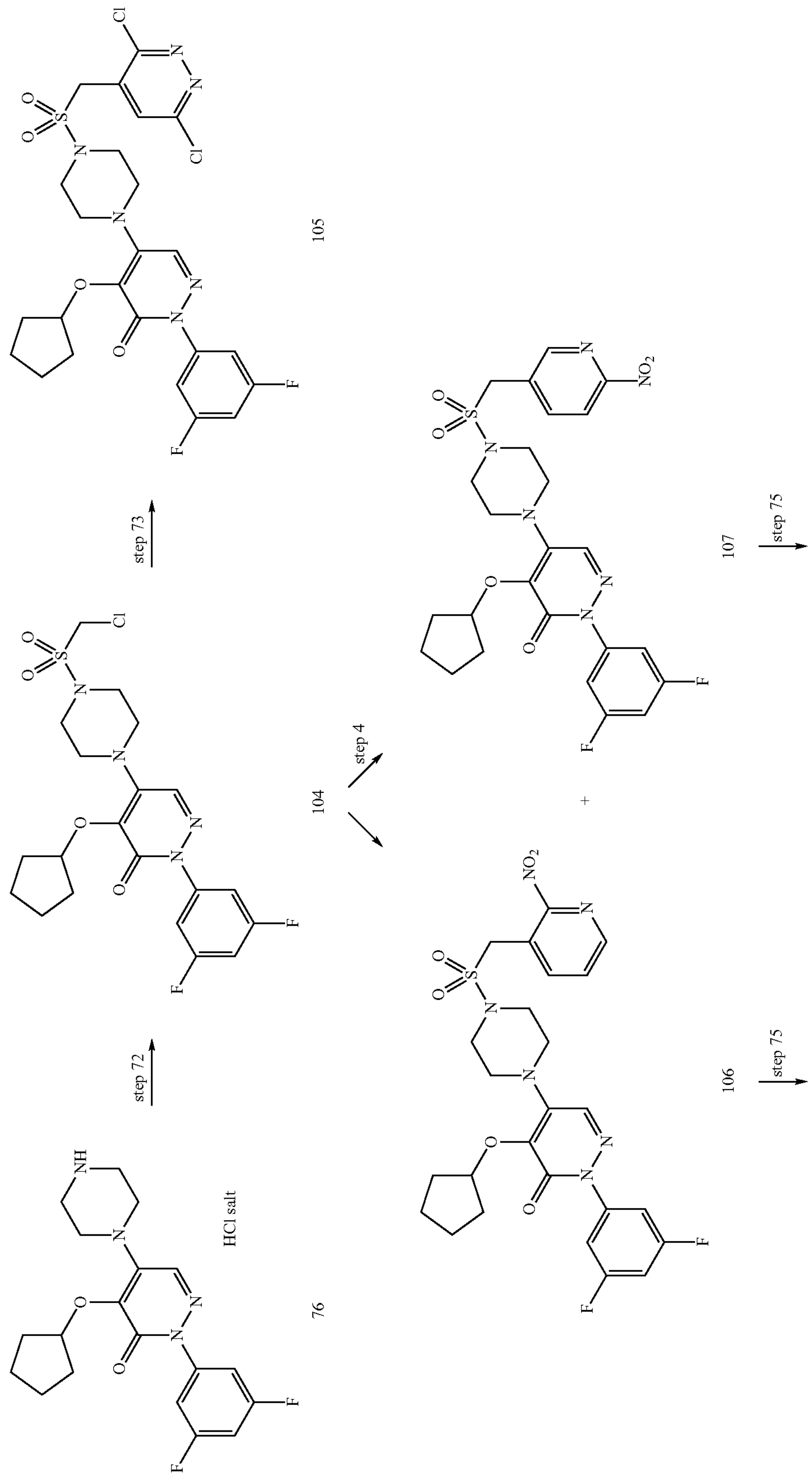
76
104
105
106
107

-continued
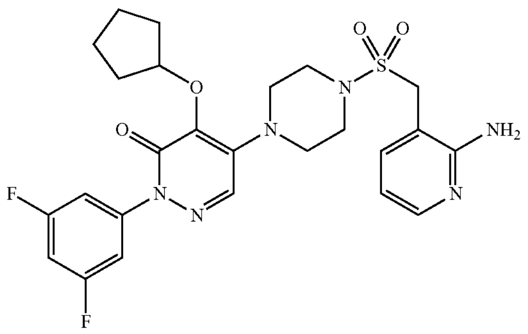
108
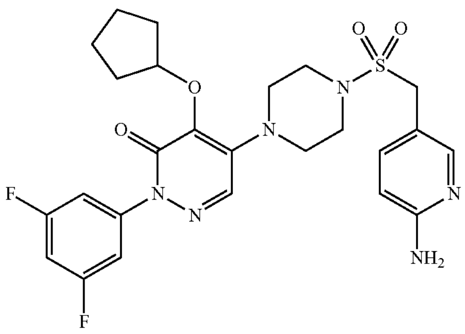
109

Step 72:

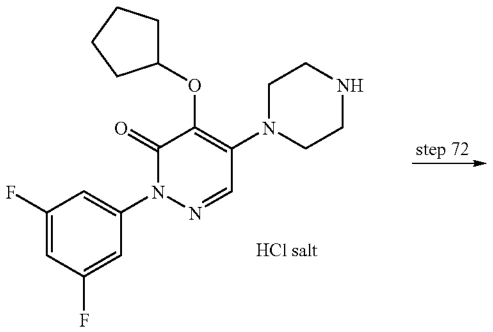

76

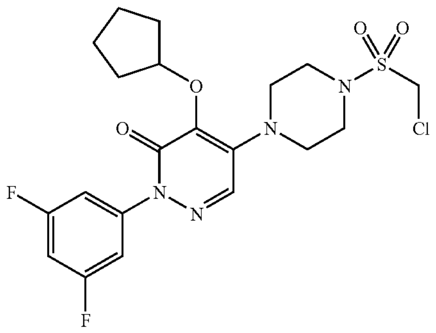

104

Compound 76 (2.1 g, 5.1 mmol) was mixed with diisopropylethylamine (2.1 mL, 12.7 mmol) in 1:1 DMF:$CH_2Cl_2$ (20 mL) and cooled to −30° C. Chloromethanesulfonyl chloride (0.91 g, 6.11 mmol) was added, and the resulting mixture was slowly warmed up to room temperature and stirred for 16 h. EtOAc was added, and the organic solution was washed with 1 N HCl, water, and brine, dried ($Na_2SO_4$), and concentrated. Purification by silica gel chromatography gave 2.3 g of the product 104 as a white solid MS (M+1): m/e 489.

Step 73:

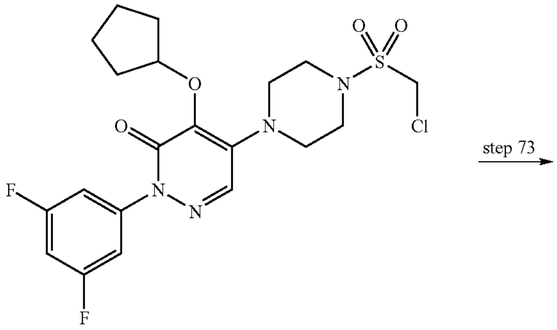

104

-continued

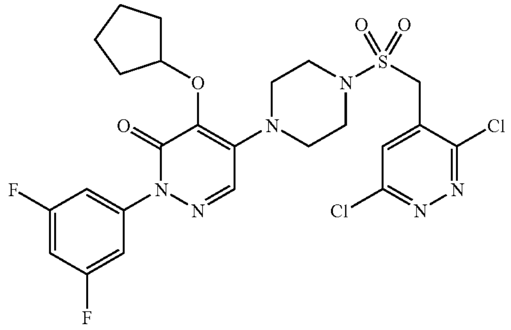

105

Potassium tertbutoxide (0.22 g, 2 mmol) was dissolved in dry THF (4 mL) and cooled to −78° C. A solution of compound 104 (0.24 g, 0.5 mmol) and 3,6-dichloropyridazine (0.10 g, 0.65 mmol) dissolved in dry THF (2 mL) was added. The reaction mixture was stirred at −78° C. for 1 h, and then 1 N aqueous HCl (4 mL) was added. EtOAc was added, and the organic solution was washed with water and brine, dried ($Na_2SO_4$), filtered, and concentrated. Purification by silica gel chromatography gave 0.25 g of the product 105 as white solid. MS (M+1): m/e 601.

Step 74:

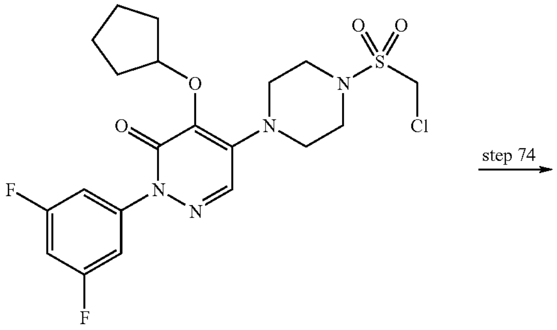

104

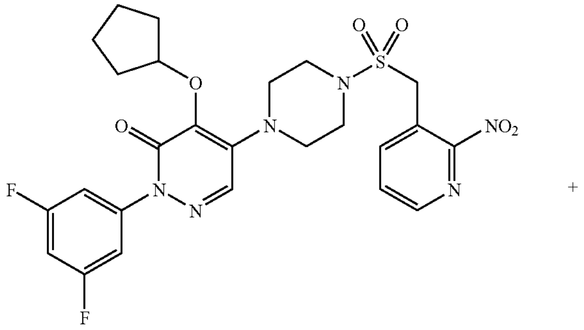

106

-continued

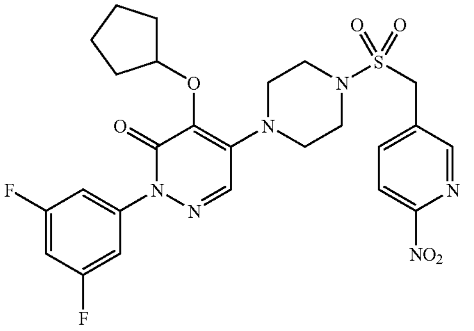

107

To compound 104 (0.24 g, 0.5 mmol) and 2-nitropyridine (0.12 g, 1.0 mmol) dissolved in DMSO (3 mL) was added potassium tert-butoxide (0.22 g, 2 mmol) was added portion-wise at room temperature. After stirring for 5 mins, 1 N aqueous HCl (5 mL) was added. EtOAc was added, and the organic solution was washed with water and brine, dried ($Na_2SO_4$), filtered, and concentrated. Purification by silica gel chromatography (10% hexane/$CH_2CH_2$ to 10% EtOAc/$CH_2CH_2$) gave 0.12 g of the product 106 as a white solid and 0.065 g of the product 107 as a white solid.

The structure of each isomer was assigned by its $^1$H NMR spectrum.

MS (M+1): m/e 577 (compound 106) and 577 (compound 107).

Step 75:

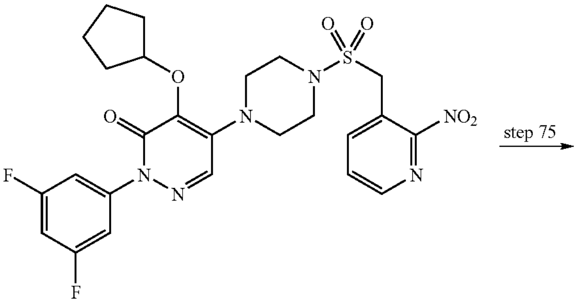

106

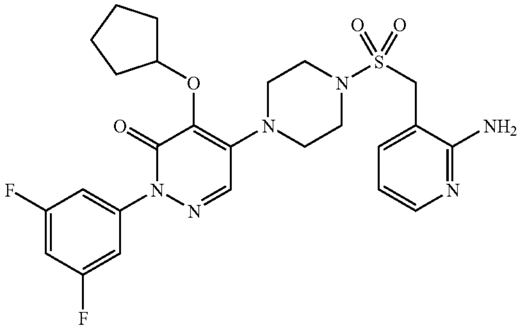

108

To compound 106 (100 mg) dissolved in THF (10 mL) was added 10% Pd/C (200 mg). The reaction mixture was stirred under a balloon of hydrogen gas at room temperature for 2 h. The catalyst was removed by filtration and washed with EtOAc. The filtrate was concentrated, and purification by silica gel chromatography gave 0.085 g of the product 108 as white solid. MS (MM+1): m/e 547.

TABLE 23

Oxygen Linked Analogs with Sulfonamide

Using the procedures described above, the following compounds were synthesized.

| Comp. No. | Structure | MS M + 1 |
|---|---|---|
| 1559Z | 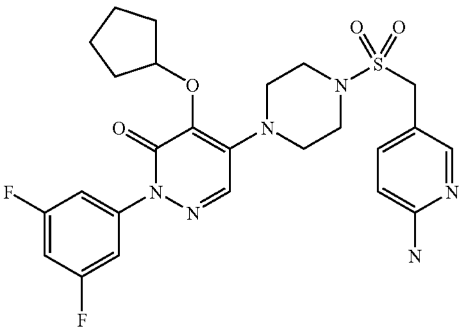 | 547 |

TABLE 23-continued
Oxygen Linked Analogs with Sulfonamide
Using the procedures described above, the following compounds were synthesized.
| Comp. No. | Structure | MS M + 1 |
|---|---|---|
| 1560Z | 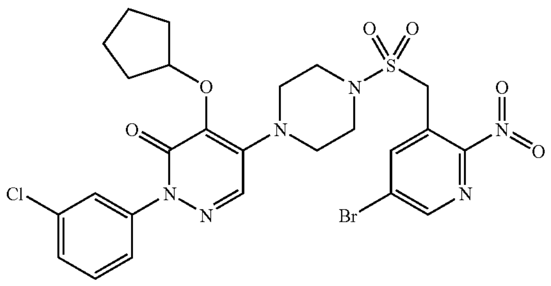 | 655 |
| 1561Z | 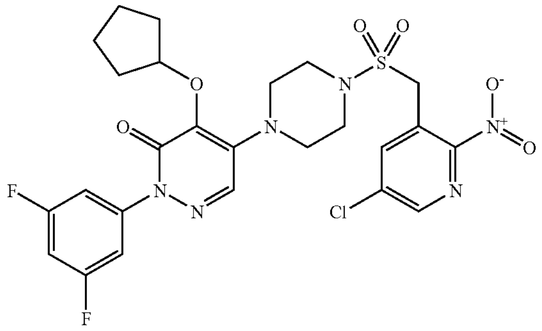 | 612 |
| 1562Z | 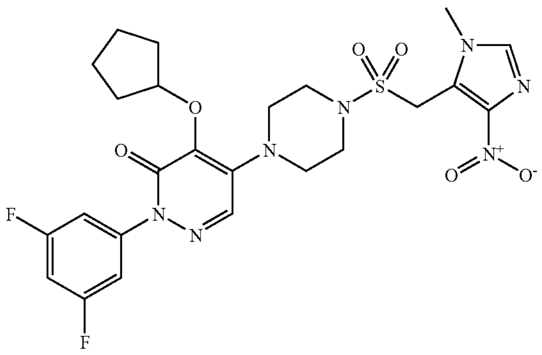 | 580 |
| 1563Z | 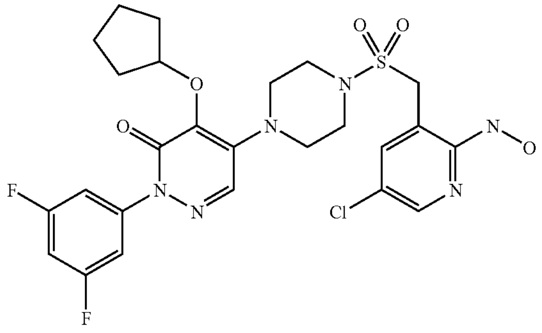 | 597 |

TABLE 23-continued
| Oxygen Linked Analogs with Sulfonamide<br>Using the procedures described above, the following compounds were synthesized. | | |
|---|---|---|
| Comp. No. | Structure | MS M + 1 |
| 1564Z | 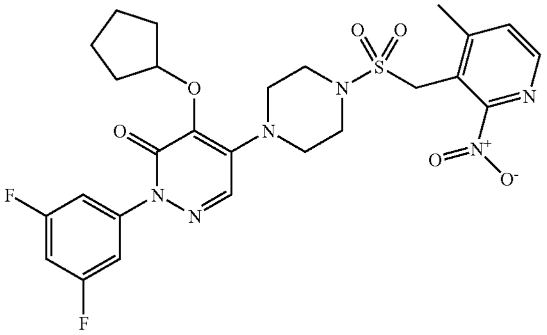 | 591 |
| 1565Z | 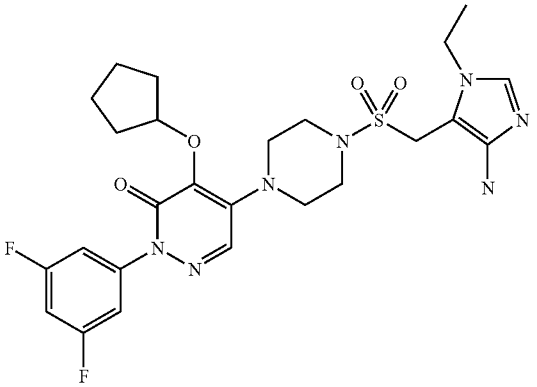 | 564 |
| 1566Z | 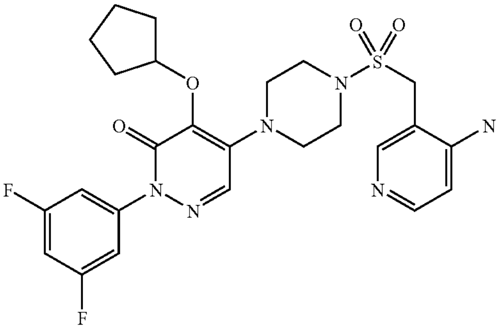 | 547 |
| 1567Z | 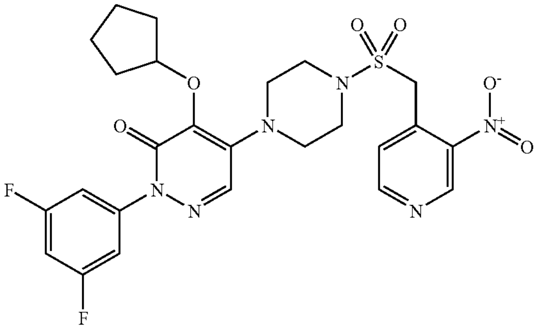 | 577 |

TABLE 23-continued
| Comp. No. | Structure | MS M + 1 |
| --- | --- | --- |
| | Oxygen Linked Analogs with Sulfonamide<br>Using the procedures described above, the following compounds were synthesized. | |
| 1568Z | 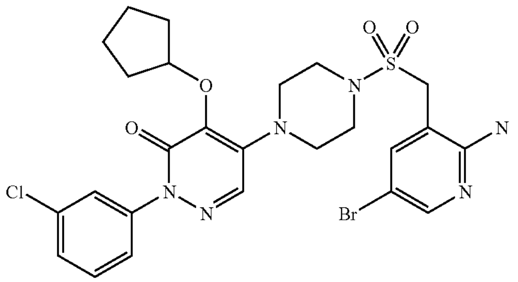 | 625 |
| 1569Z | 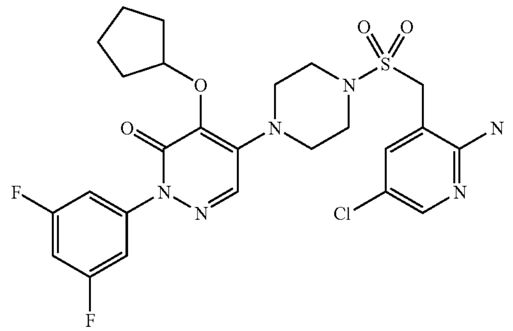 | 582 |
| 1570Z | 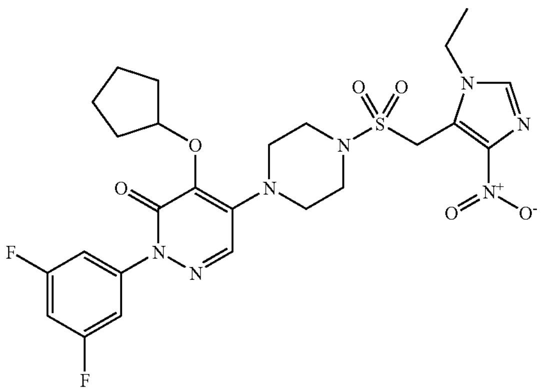 | 594 |
| 1571Z | 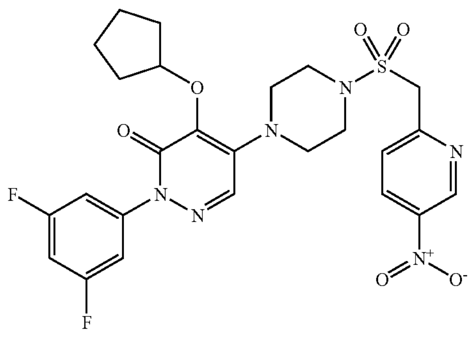 | 577 |

TABLE 23-continued
| Oxygen Linked Analogs with Sulfonamide Using the procedures described above, the following compounds were synthesized. | | |
|---|---|---|
| Comp. No. | Structure | MS M + 1 |
| 1572Z | 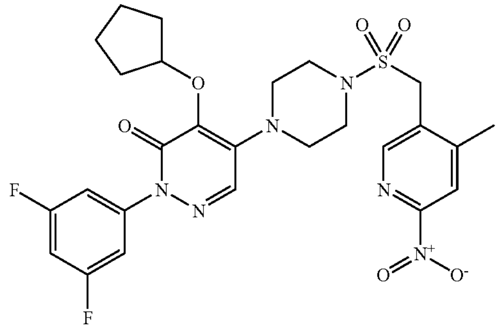 | 591 |
| 1573Z | 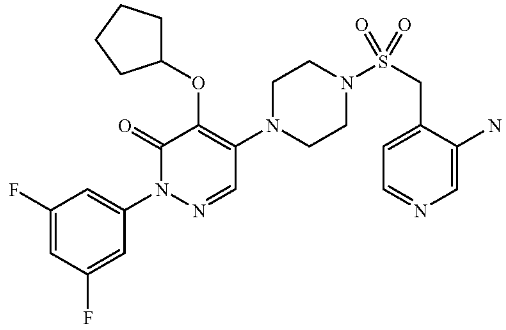 | 547 |
| 1574Z | 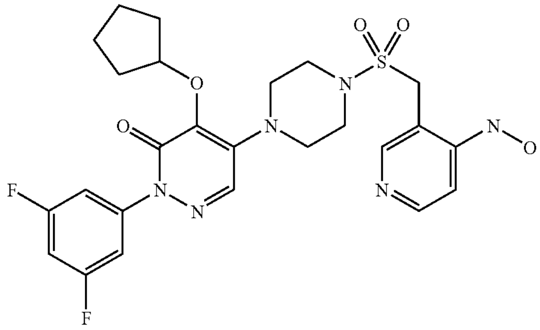 | 563 |
| 1574Za | 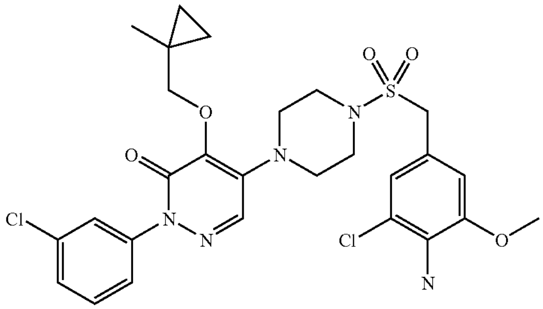 | 608 |

TABLE 23-continued
| Oxygen Linked Analogs with Sulfonamide Using the procedures described above, the following compounds were synthesized. | | |
|---|---|---|
| Comp. No. | Structure | MS M + 1 |
| 1574Zb | 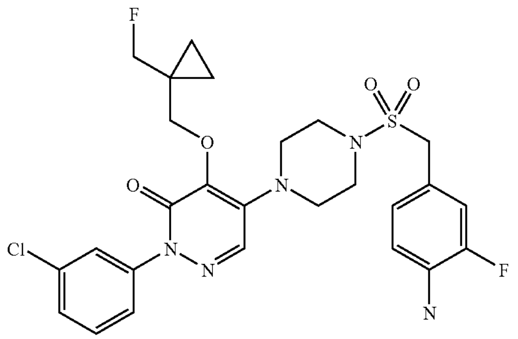 | 580 |
| 1574Zc | 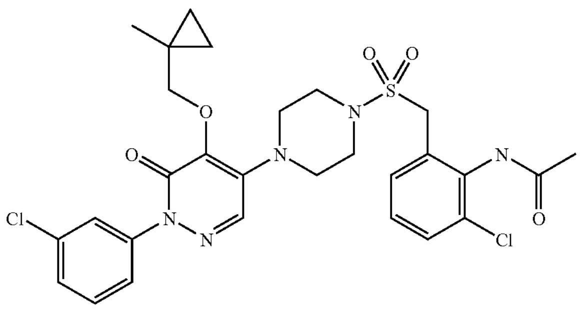 | 618 (M − 1) |
| 1574Zd | 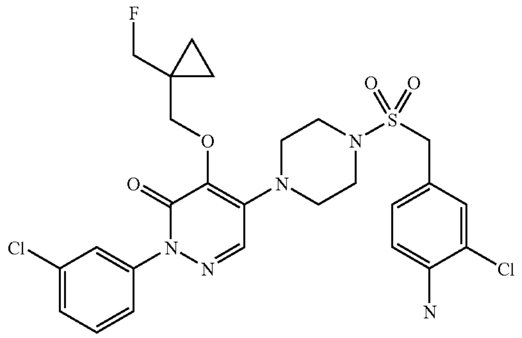 | 596 |
| 1574Ze | 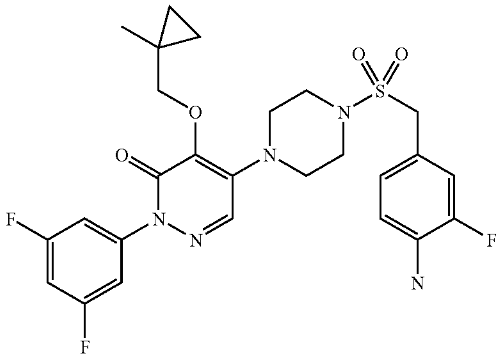 | 564 |

TABLE 23-continued
| Oxygen Linked Analogs with Sulfonamide<br>Using the procedures described above, the following compounds were synthesized. | | |
|---|---|---|
| Comp. No. | Structure | MS M + 1 |
| 1574Zf | 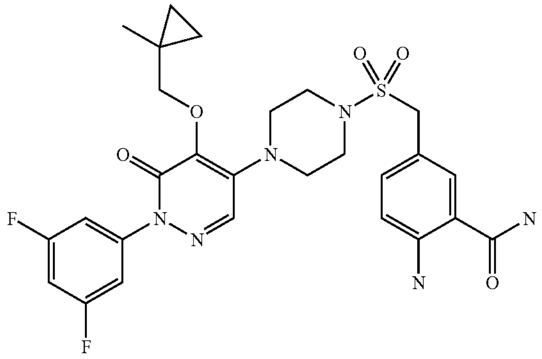 | 589 |
| 1574Zg | 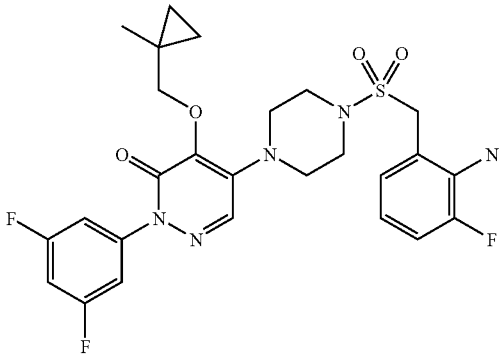 | 564 |
| 1574Zh | 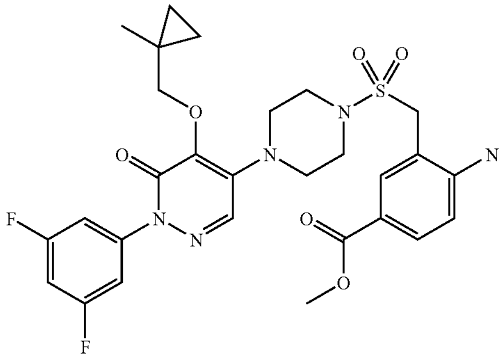 | 604 |
| 1574Zi | 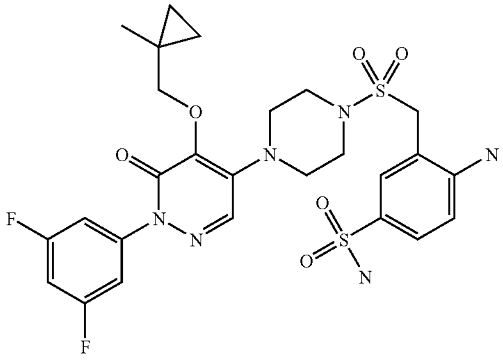 | 625 |

TABLE 23-continued
| Comp. No. | Oxygen Linked Analogs with Sulfonamide<br>Using the procedures described above, the following compounds were synthesized.<br>Structure | MS M + 1 |
|---|---|---|
| 1574Zj | 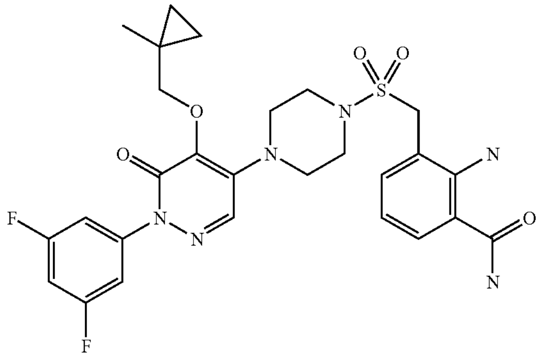 | 589 |
| 1574Zk | 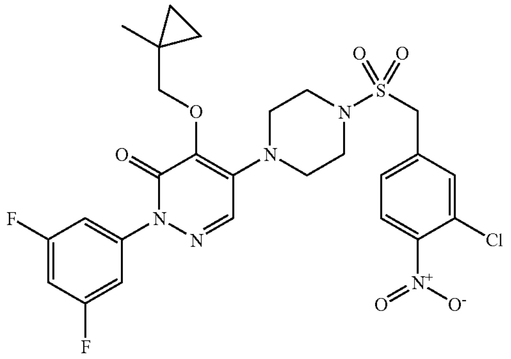 | 610 |
| 1574Zl | 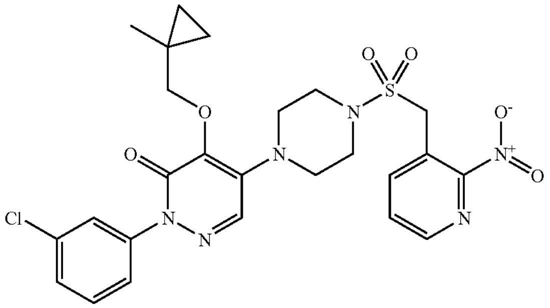 | 575 |
| 1574Zm | 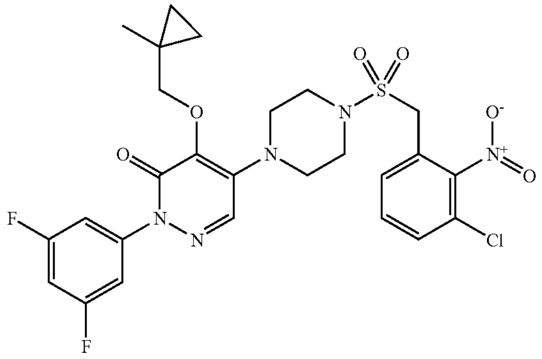 | 610 |

TABLE 23-continued
| Oxygen Linked Analogs with Sulfonamide<br>Using the procedures described above, the following compounds were synthesized. | | |
|---|---|---|
| Comp. No. | Structure | MS M + 1 |
| 1574Zn | 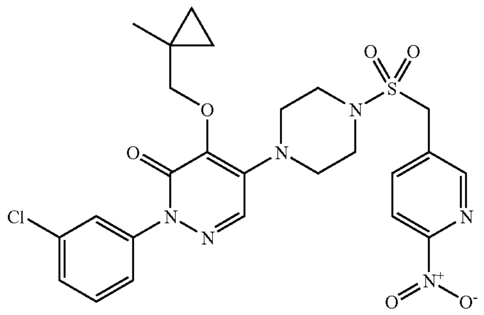 | 575 |
| 1574Zo | 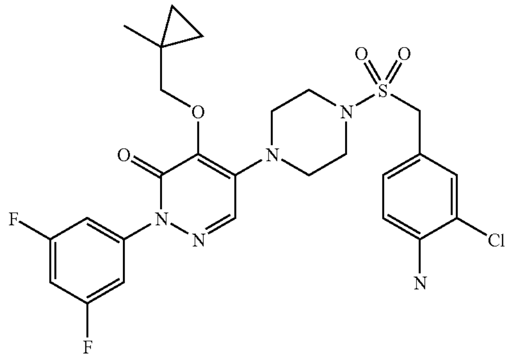 | 580 |
| 1574Zp | 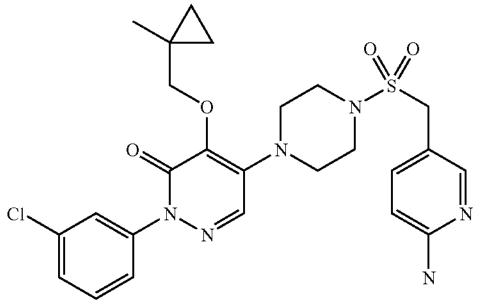 | 545 |
| 1574Zq | 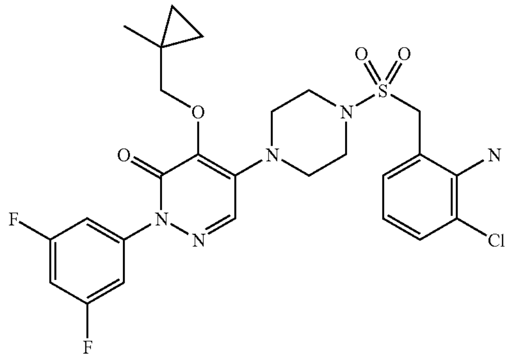 | 580 |

TABLE 23-continued
| Comp. No. | Oxygen Linked Analogs with Sulfonamide Using the procedures described above, the following compounds were synthesized. Structure | MS M + 1 |
|---|---|---|
| 1574Zr | 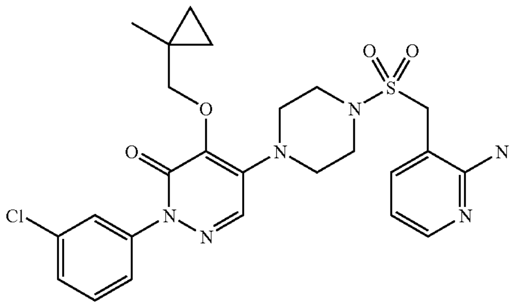 | 545 |
| 1574Zs | 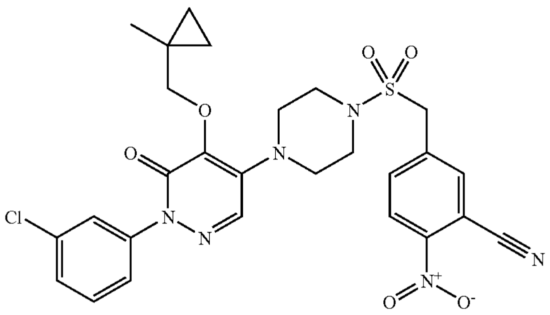 | 599 |
| 1574Zt | 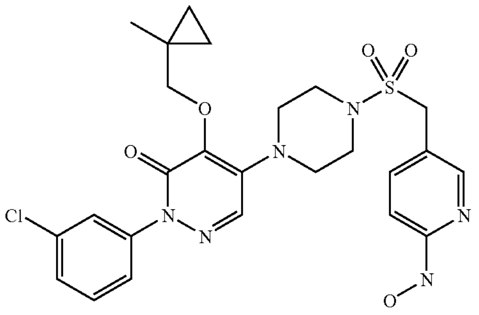 | 561 |
| 1574Zu | 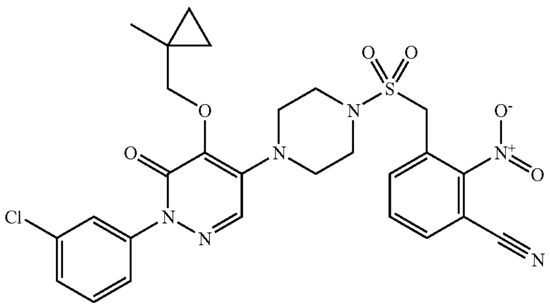 | 599 |

TABLE 23-continued
| Oxygen Linked Analogs with Sulfonamide<br>Using the procedures described above, the following compounds were synthesized. | | |
|---|---|---|
| Comp. No. | Structure | MS M + 1 |
| 1574Zv | 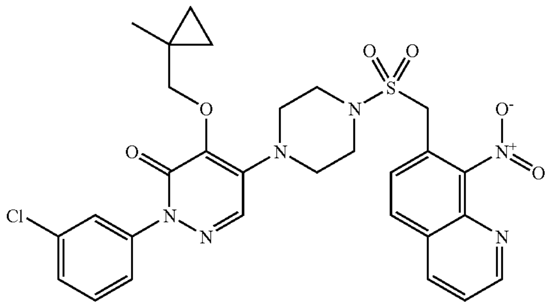 | 625 |
| 1574Zw | 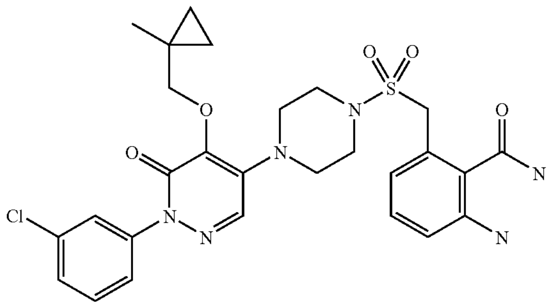 | 569 |
| 1574Zx | 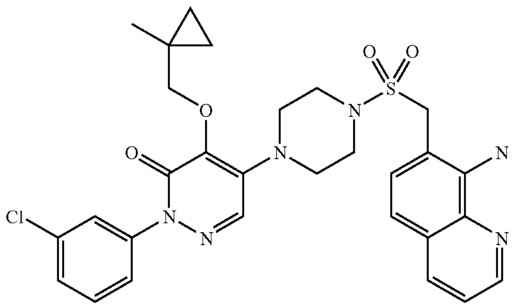 | 595 |
| 1574Zy | 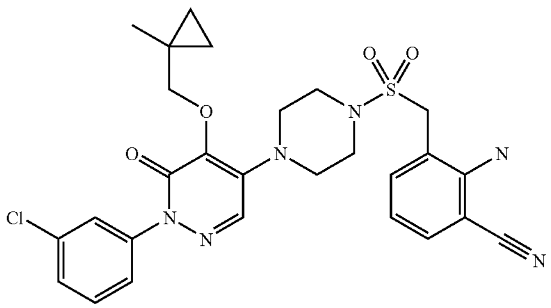 | 587 |

TABLE 23-continued
| Comp. No. | Structure | MS M + 1 |
|---|---|---|
| | Oxygen Linked Analogs with Sulfonamide Using the procedures described above, the following compounds were synthesized. | |
| 1574Zz | 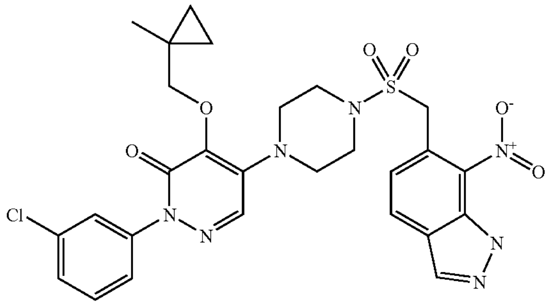 | 614 |
| 1574ZA | 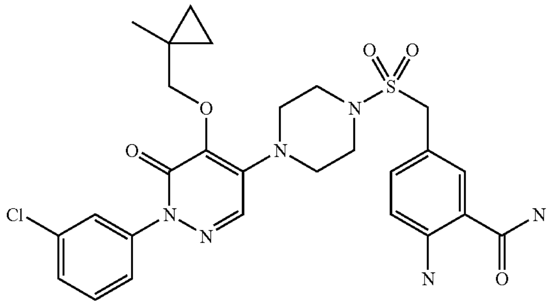 | 587 |
| 1574ZB | 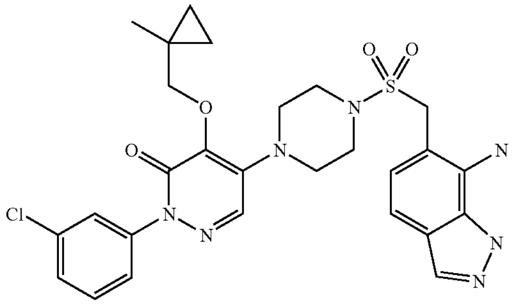 | 584 |
| 1574ZC | 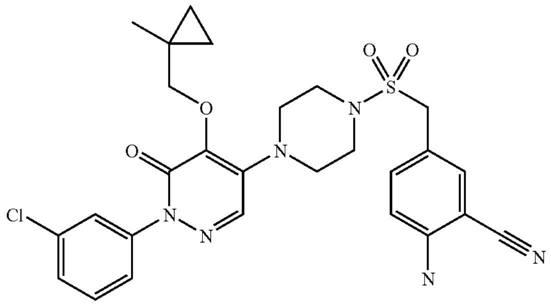 | 569 |

TABLE 23-continued
| Oxygen Linked Analogs with Sulfonamide Using the procedures described above, the following compounds were synthesized. | | |
|---|---|---|
| Comp. No. | Structure | MS M + 1 |
| 1574ZD | 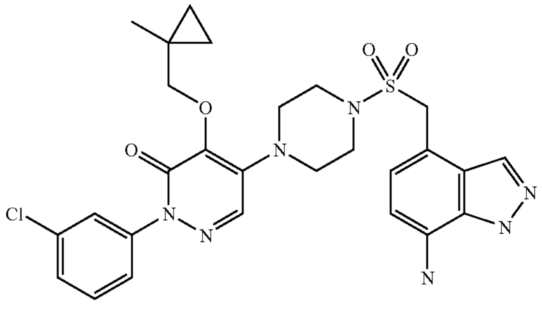 | 584 |
| 1574ZE | 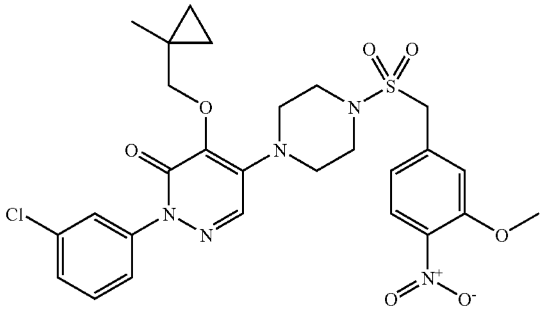 | 604 |
| 1574ZF | 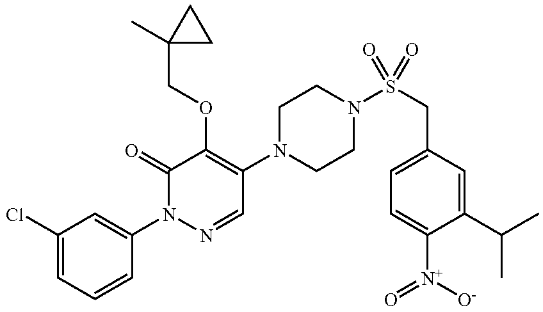 | 616 |
| 1574ZG | 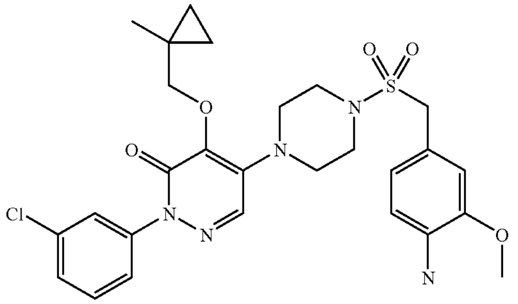 | 574 |

TABLE 23-continued
| Oxygen Linked Analogs with Sulfonamide<br>Using the procedures described above, the following compounds were synthesized. | | |
|---|---|---|
| Comp. No. | Structure | MS M + 1 |
| 1574ZH | 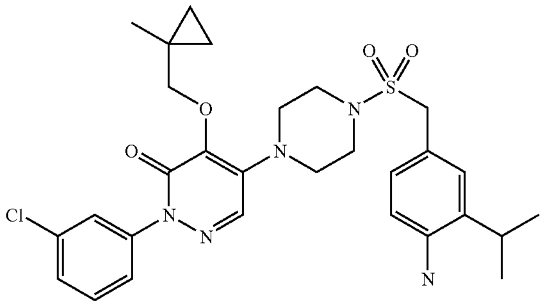 | 586 |
| 1574ZI | 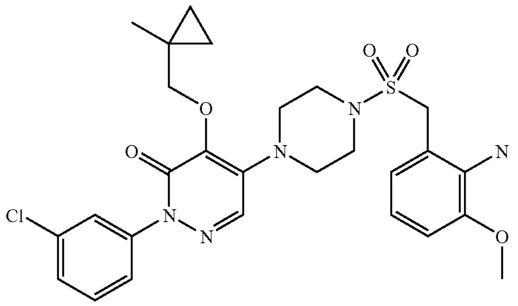 | 574 |
| 1574ZJ | 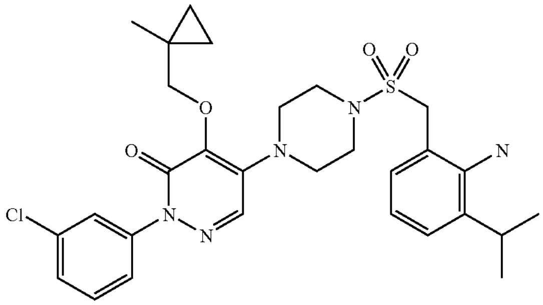 | 586 |
| 1574ZK | 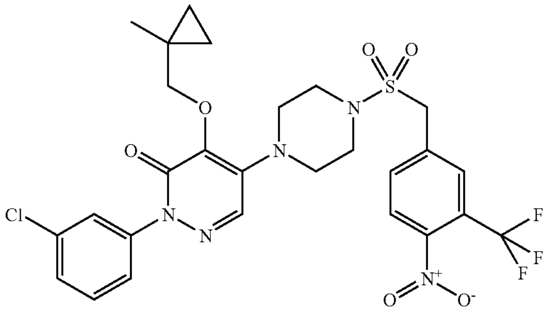 | 642 |

TABLE 23-continued
| Oxygen Linked Analogs with Sulfonamide Using the procedures described above, the following compounds were synthesized. | | |
|---|---|---|
| Comp. No. | Structure | MS M + 1 |
| 1574ZL | 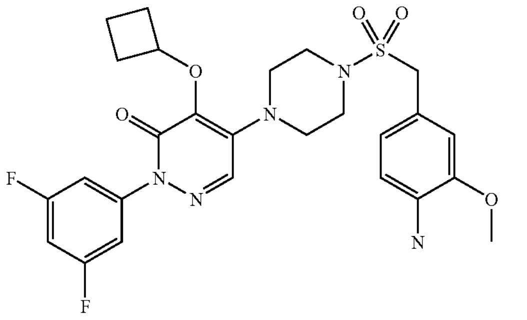 | 562 |
| 1574ZM | 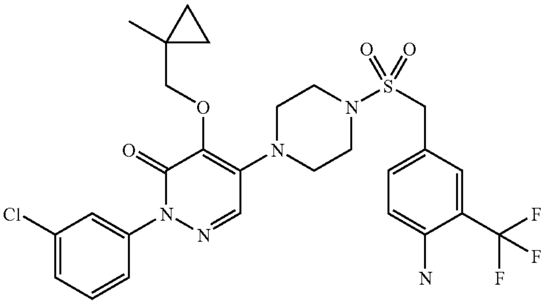 | 586 |
| 1574ZN | 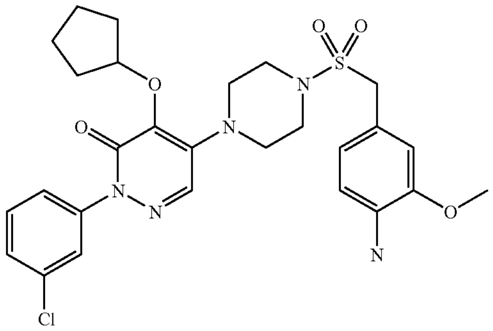 | 574 |
| 1574ZO | 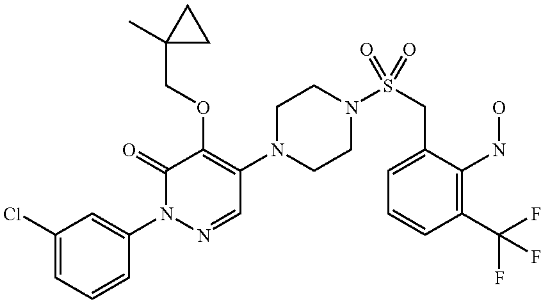 | 628 |

TABLE 23-continued
| Oxygen Linked Analogs with Sulfonamide Using the procedures described above, the following compounds were synthesized. | | |
|---|---|---|
| Comp. No. | Structure | MS M + 1 |
| 1574ZP | 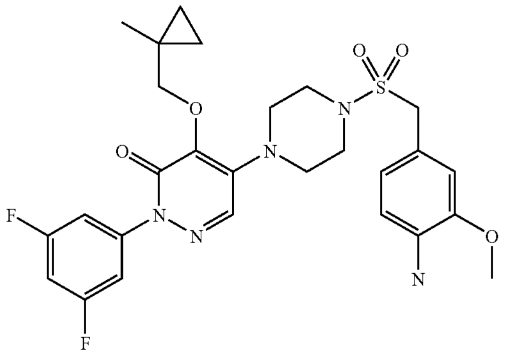 | 576 |
| 1574ZQ | 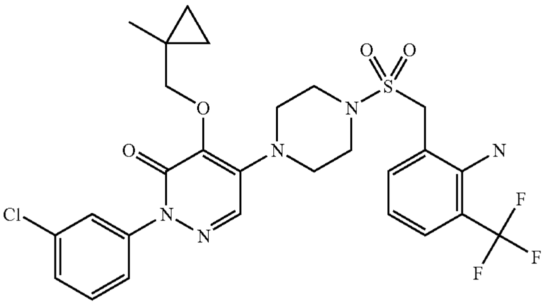 | 586 |
| 1574ZR | 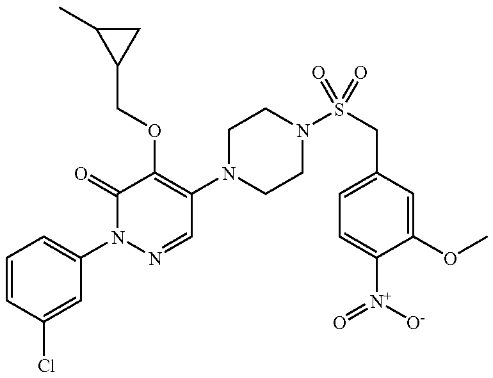 | 604 |
| 1574ZS | 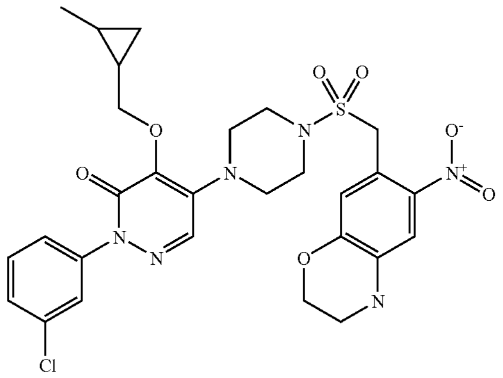 | 629 |

TABLE 23-continued
| Comp. No. | Structure | MS M + 1 |
| --- | --- | --- |
| | Oxygen Linked Analogs with Sulfonamide<br>Using the procedures described above, the following compounds were synthesized. | |
| 1574ZT | 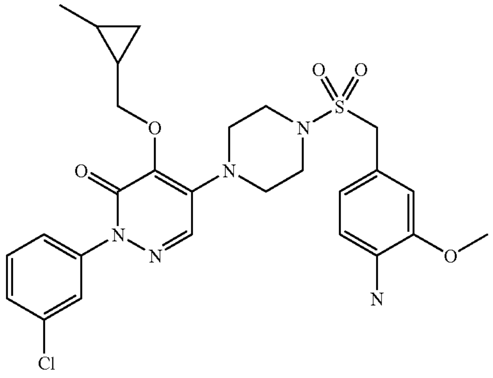 | 574 |
| 1574ZU | 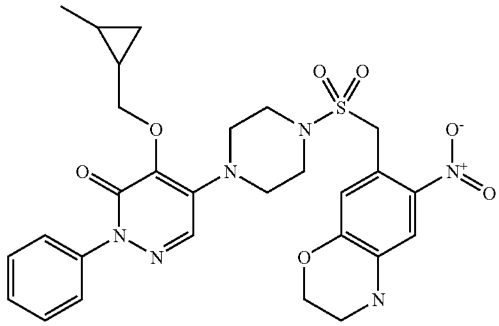 | 597 |
| 1574ZV | 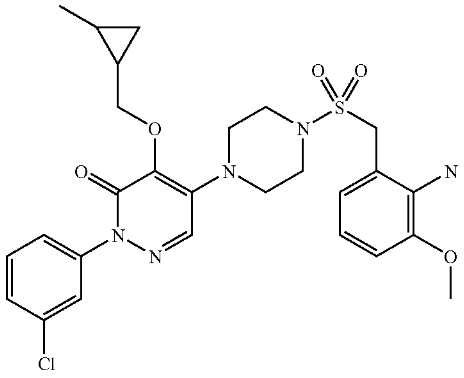 | 574 |
| 1574ZW | 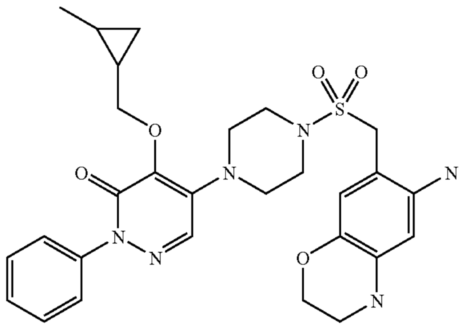 | 567 |

TABLE 23-continued
| Comp. No. | Structure | MS M + 1 |
|---|---|---|
| | Oxygen Linked Analogs with Sulfonamide<br>Using the procedures described above, the following compounds were synthesized. | |
| 1574ZX | 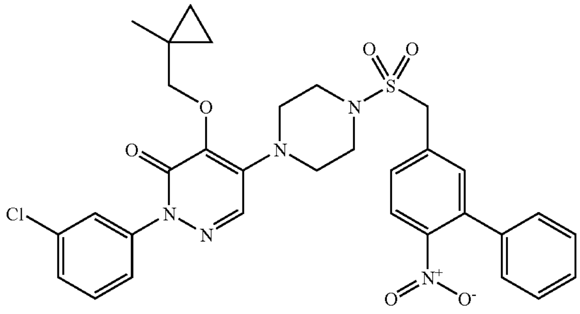 | 650 |
| 1574ZY | 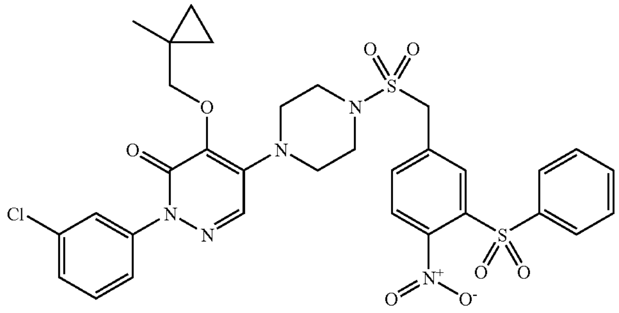 | 714 |
| 1574ZZ | 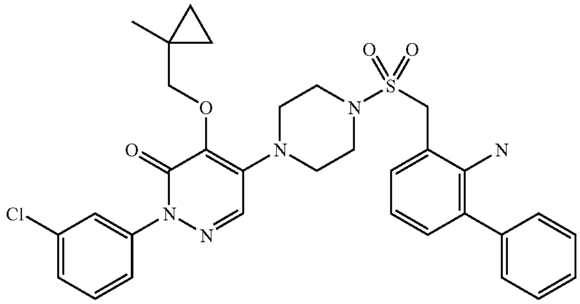 | 620 |
| 1574Z-1 | 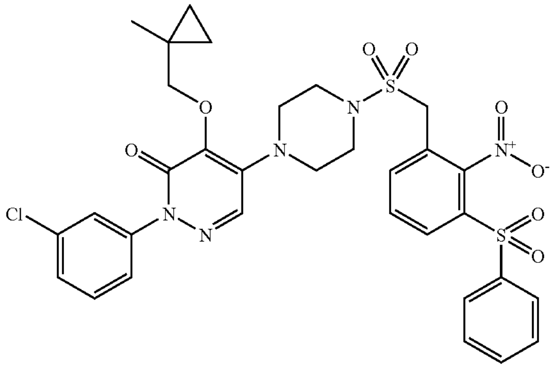 | 714 |

TABLE 23-continued
| Comp. No. | Structure | MS M + 1 |
|---|---|---|
| | Oxygen Linked Analogs with Sulfonamide Using the procedures described above, the following compounds were synthesized. | |
| 1574Z-2 | 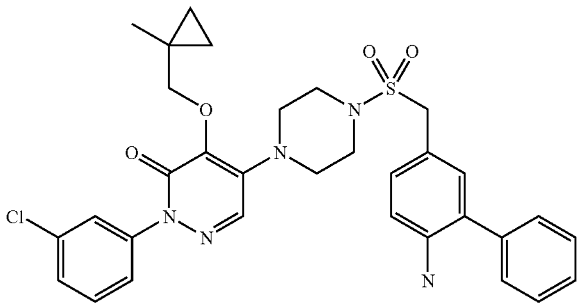 | 620 |
| 1574Z-3 | 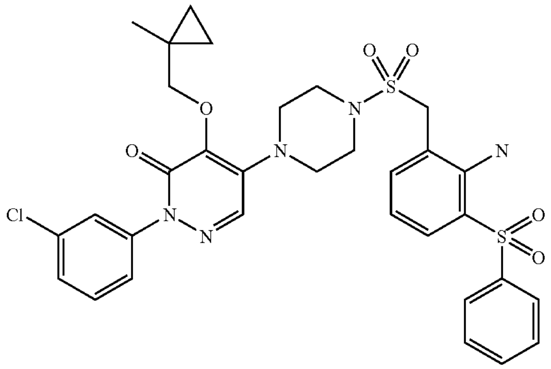 | 684 |
| 1574Z-4 | 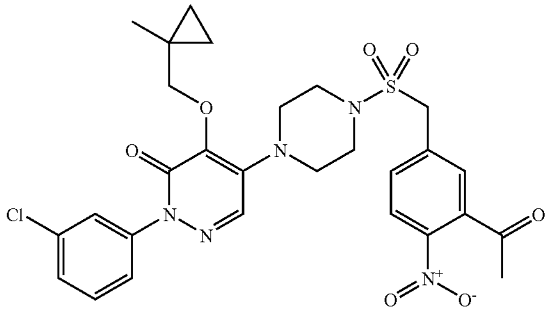 | 616 |
| 1574Z-5 | 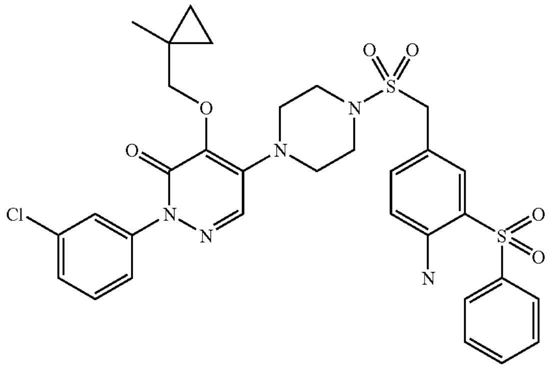 | 684 |

TABLE 23-continued
Oxygen Linked Analogs with Sulfonamide
Using the procedures described above, the following compounds were synthesized.
| Comp. No. | Structure | MS M + 1 |
|---|---|---|
| 1574Z-6 | 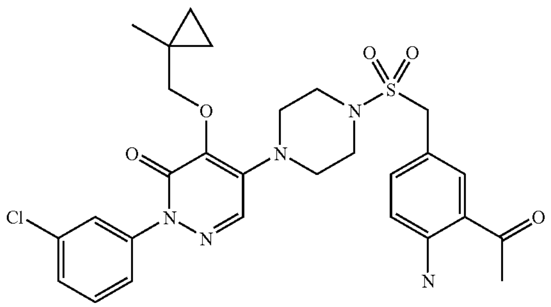 | 568 |
| 1574Z-7 | 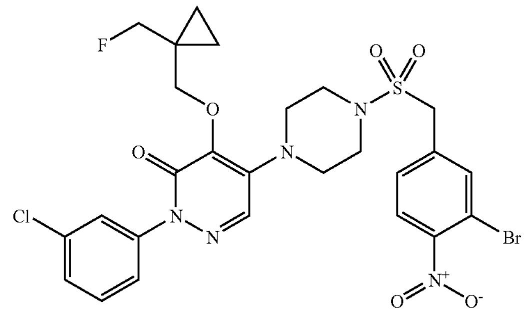 | 672 |
| 1574Z-8 | 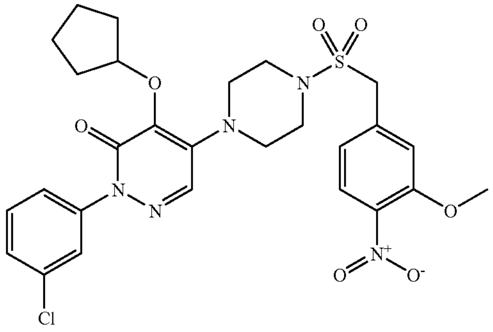 | 604 |
| 1574Z-9 | 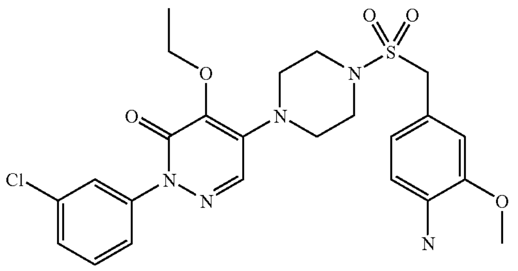 | 534 |

TABLE 23-continued
| Oxygen Linked Analogs with Sulfonamide<br>Using the procedures described above, the following compounds were synthesized. | | |
|---|---|---|
| Comp. No. | Structure | MS M + 1 |
| 1574Z-10<br>1401482 | 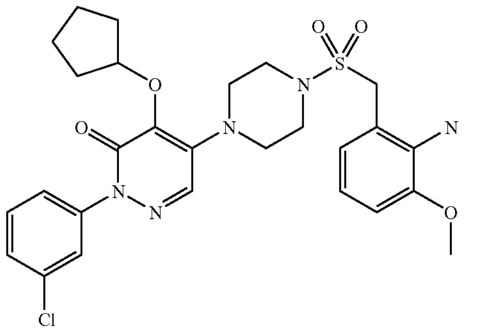 | 574 |
| 1574Z-11 | 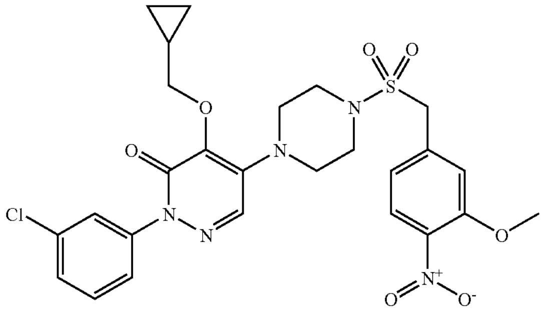 | 604 |
| 1574Z-12 | 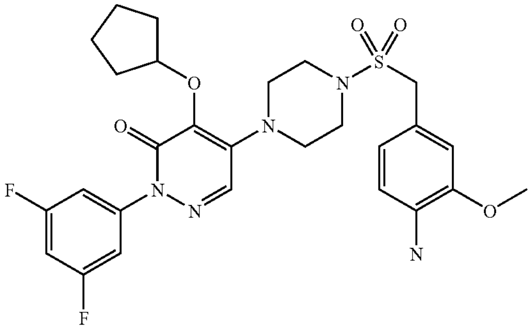 | 576 |
| 1574Z-13 | 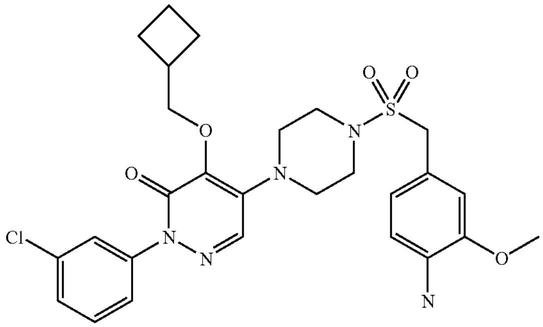 | 574 |

TABLE 23-continued
Oxygen Linked Analogs with Sulfonamide
Using the procedures described above, the following compounds were synthesized.
| Comp. No. | Structure | MS M + 1 |
|---|---|---|
| 1574Z-14 | 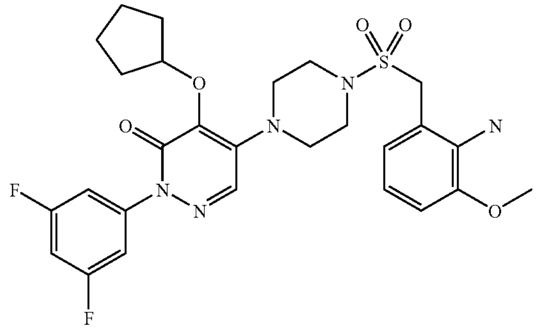 | 576 |
| 1574Z-15 | 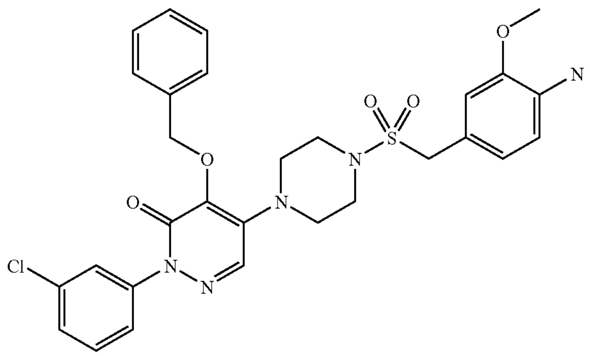 | 596 |
| 1574Z-16 | 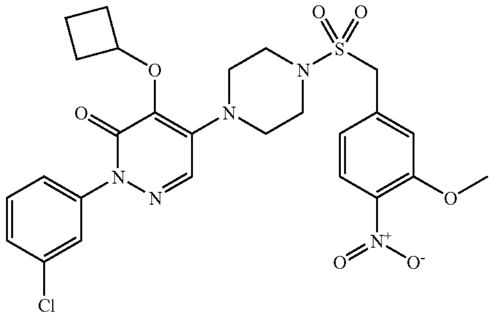 | 590 |
| 1575Z-17 | 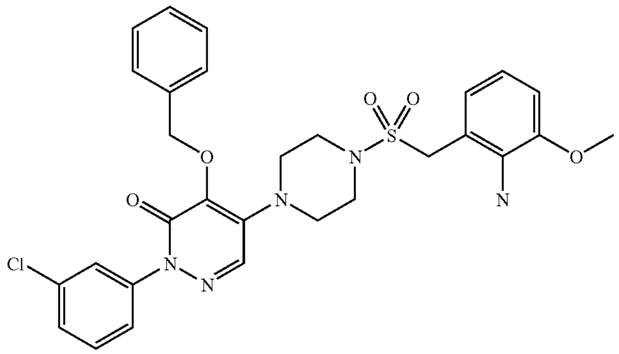 | 596 |

TABLE 23-continued
| Comp. No. | Structure | MS M + 1 |
|---|---|---|
| | Oxygen Linked Analogs with Sulfonamide<br>Using the procedures described above, the following compounds were synthesized. | |
| 1574Z-18 | 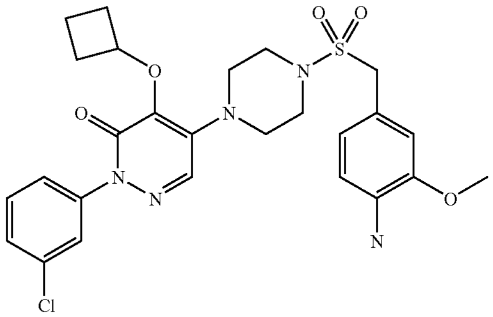 | 545 |
| 1574Z-19 | 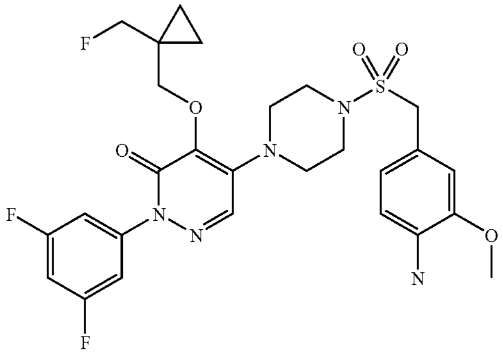 | 594 |
| 1574Z-20 | 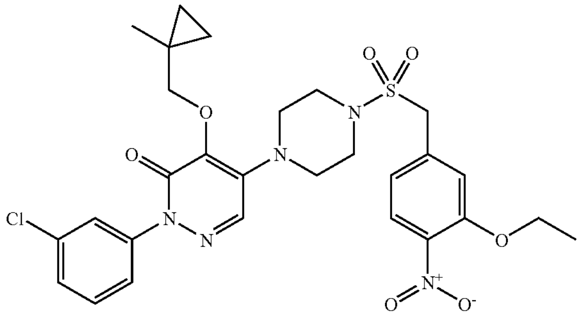 | 618 |
| 1574Z-21 | 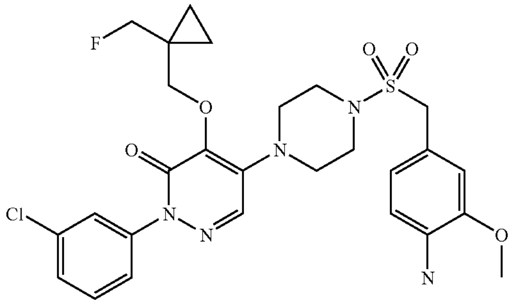 | 592 |

TABLE 23-continued
Oxygen Linked Analogs with Sulfonamide
Using the procedures described above, the following compounds were synthesized.
| Comp. No. | Structure | MS M + 1 |
|---|---|---|
| 1574Z-22 | 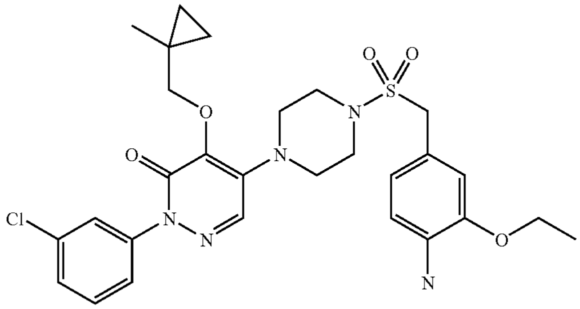 | 588 |
| 1574Z-23 | 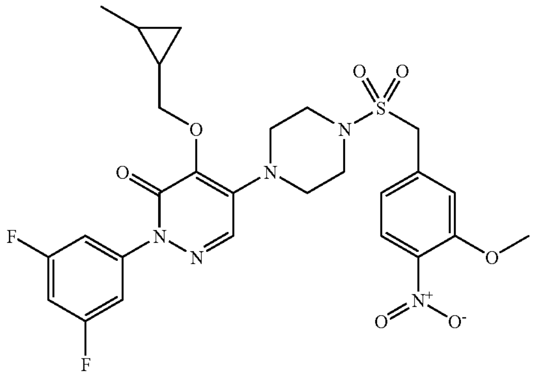 | 607 |
| 1574Z-24 | 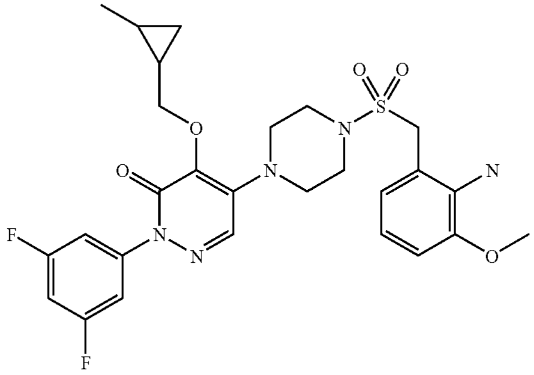 | 574 |
| 1574Z-25 | 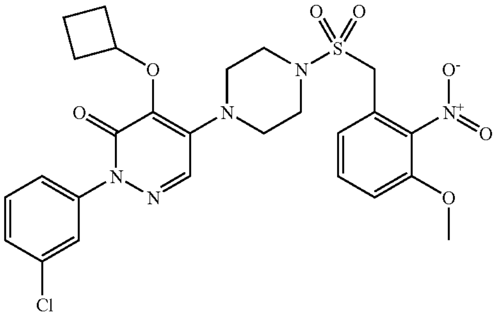 | 590 |

TABLE 23-continued
Oxygen Linked Analogs with Sulfonamide
Using the procedures described above, the following compounds were synthesized.
| Comp. No. | Structure | MS M + 1 |
| --- | --- | --- |
| 1574Z-26 | 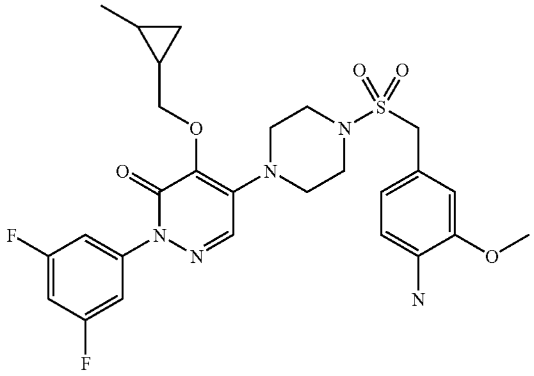 | 574 |
| 1574Z-27 | 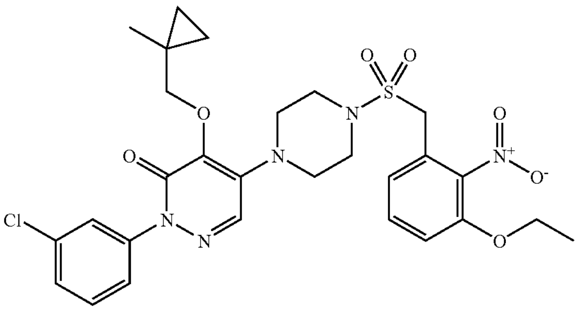 | 618 |
| 1574Z-28 | 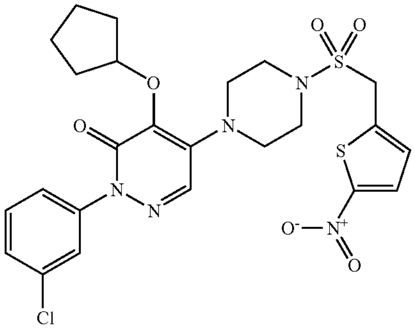 | 580 |
| 1574Z-29 | 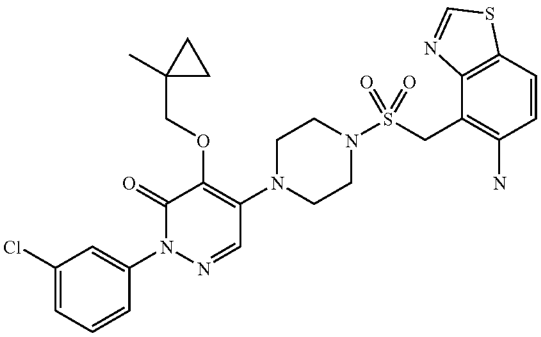 | 601 |

TABLE 23-continued
| Oxygen Linked Analogs with Sulfonamide Using the procedures described above, the following compounds were synthesized. | | |
|---|---|---|
| Comp. No. | Structure | MS M + 1 |
| 1574Z-30 | 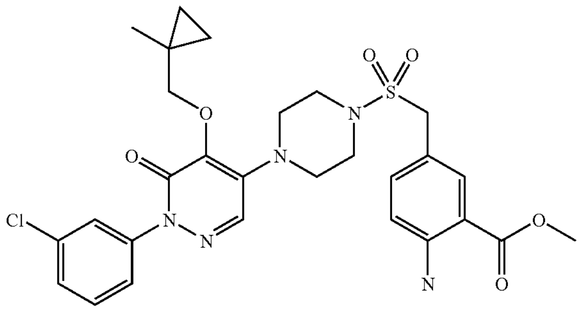 | 602 |
| 1574Z-31 | 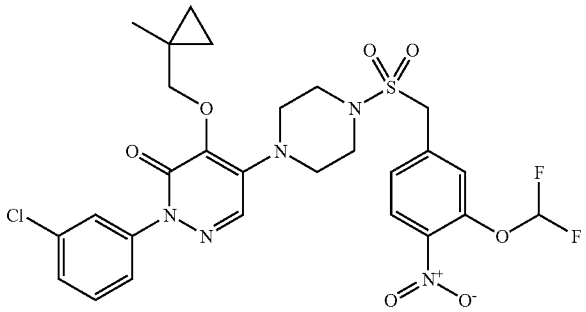 | 640 |
| 1574Z-32 | 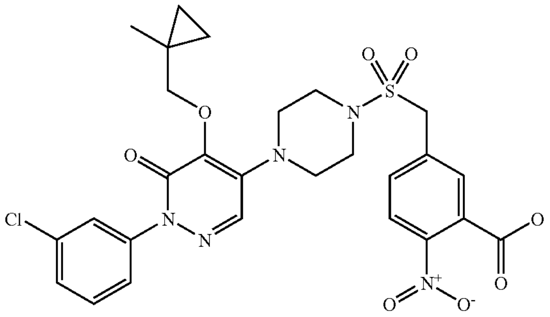 | 602 |
| 1574Z-33 | 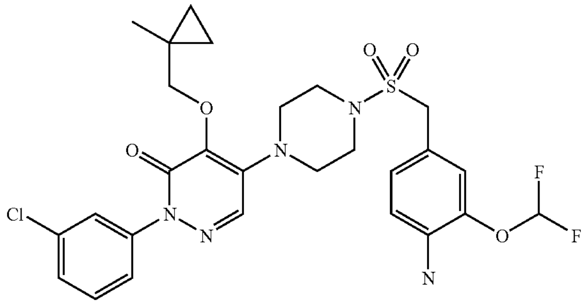 | 610 |

TABLE 23-continued
| Oxygen Linked Analogs with Sulfonamide<br>Using the procedures described above, the following compounds were synthesized. | | |
|---|---|---|
| Comp. No. | Structure | MS M + 1 |
| 1574Z-34 | 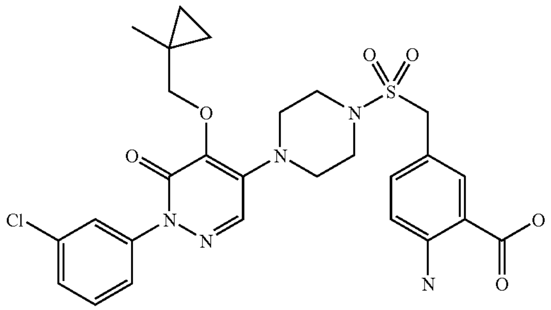 | 588 |
| 1574Z-35 | 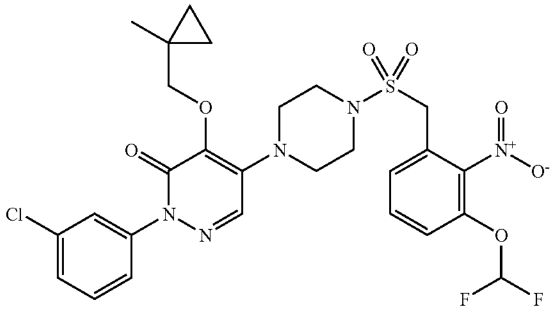 | 640 |
| 1574Z-36 | 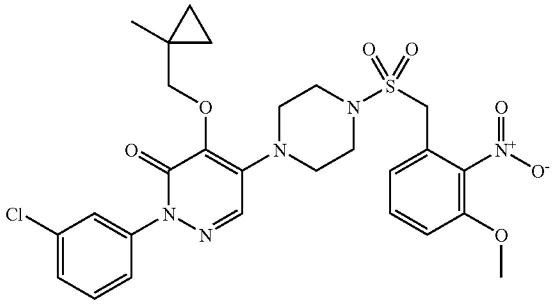 | 604 |
| 1574Z-37 | 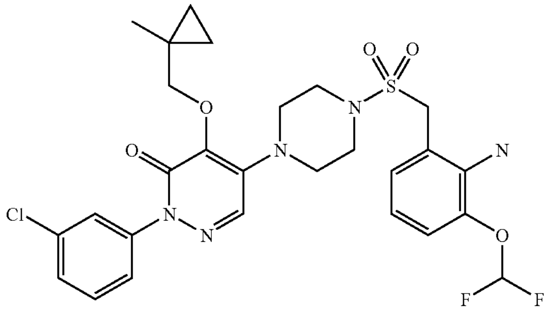 | 610 |

TABLE 23-continued
| Comp. No. | Structure | MS M + 1 |
|---|---|---|
| | Oxygen Linked Analogs with Sulfonamide Using the procedures described above, the following compounds were synthesized. | |
| 1574Z-38 | 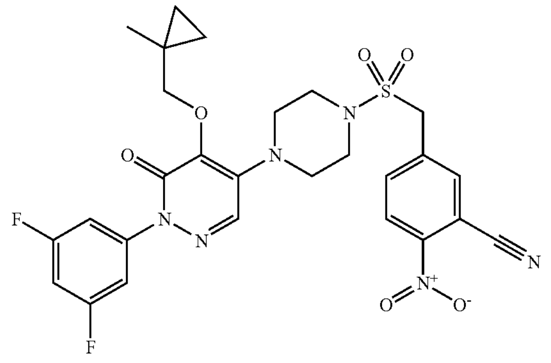 | 601 |
| 15742-39 | 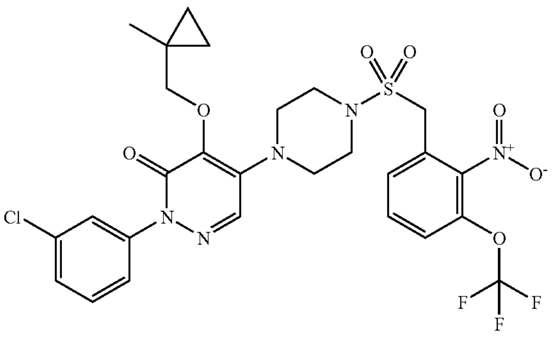 | 658 |
| 1574Z-40 | 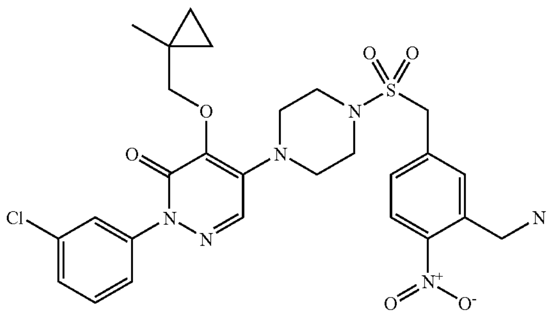 | 603 |
| 15742Z-41 | 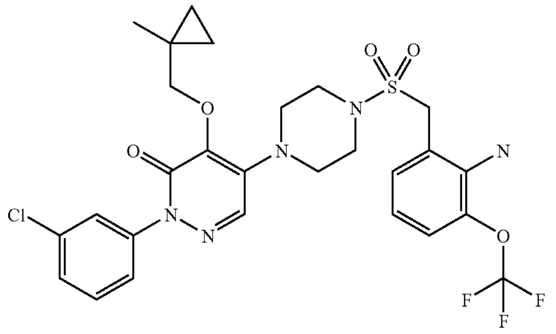 | 628 |

TABLE 23-continued
| Oxygen Linked Analogs with Sulfonamide Using the procedures described above, the following compounds were synthesized. | | |
|---|---|---|
| Comp. No. | Structure | MS M + 1 |
| 1574Z-42 | 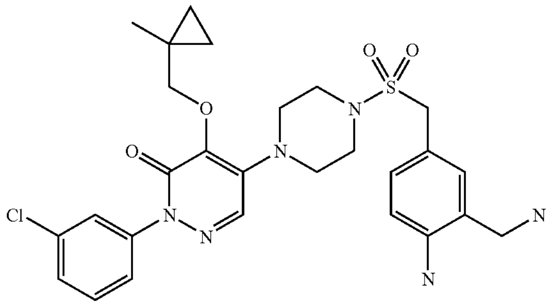 | 573 |
| 1574Z-43 | 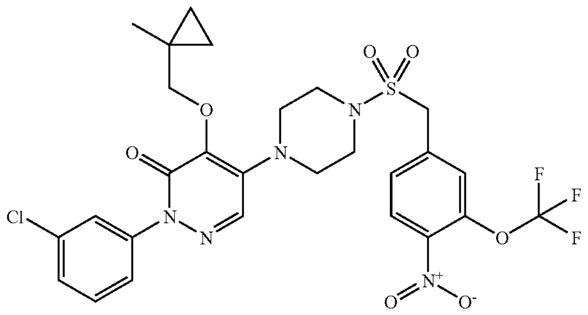 | 658 |
| 1574Z-44 | 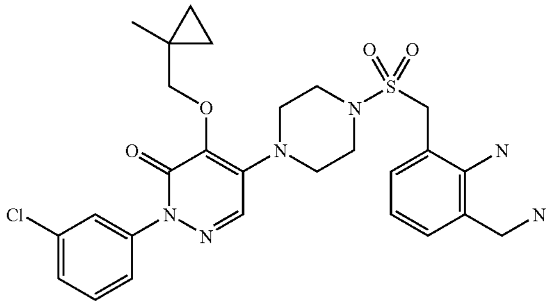 | 573 |
| 1574Z-45 | 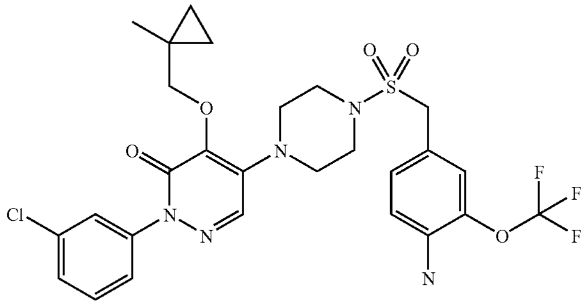 | 628 |

TABLE 23-continued
Oxygen Linked Analogs with Sulfonamide
Using the procedures described above, the following compounds were synthesized.
| Comp. No. | Structure | MS M + 1 |
|---|---|---|
| 1574Z-46 | 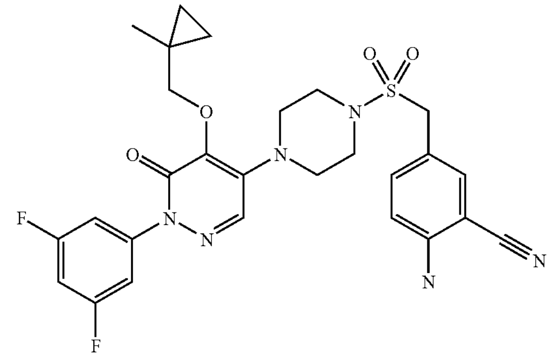 | 571 |
| 1574Z-47 | 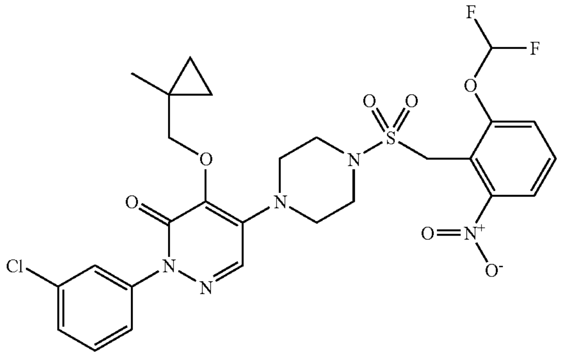 | 640 |
| 1574Z-48 | 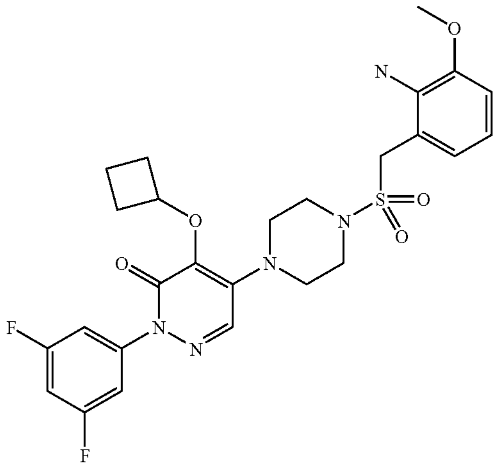 | 562 |
| 1574Z-49 | 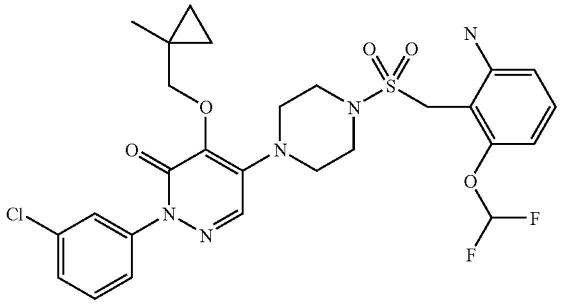 | 610 |

TABLE 23-continued
| Oxygen Linked Analogs with Sulfonamide<br>Using the procedures described above, the following compounds were synthesized. | | |
|---|---|---|
| Comp. No. | Structure | MS M + 1 |
| 1574Z-50 | 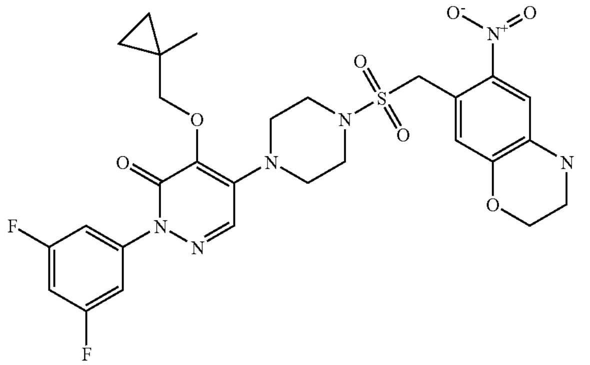 | 629 |
| 1574Z-51 | 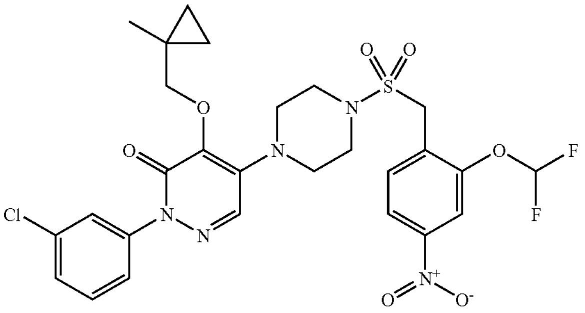 | 640 |
| 1574Z-52 | 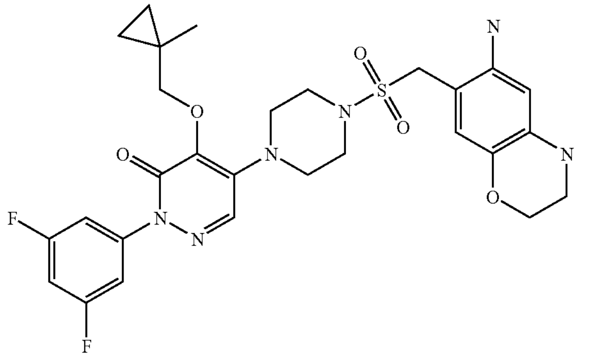 | 601 |
| 1574Z-53 | 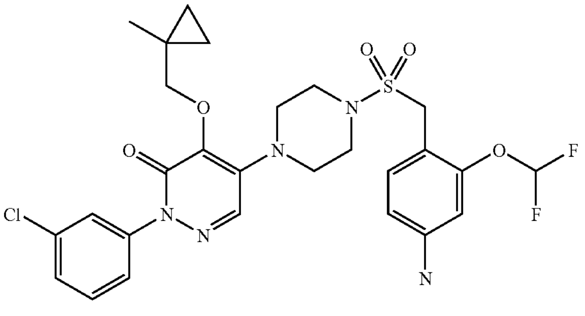 | 610 |

TABLE 23-continued
| Comp. No. | Structure | MS M + 1 |
|---|---|---|
| Oxygen Linked Analogs with Sulfonamide<br>Using the procedures described above, the following compounds were synthesized. | | |
| 1574Z-54 | 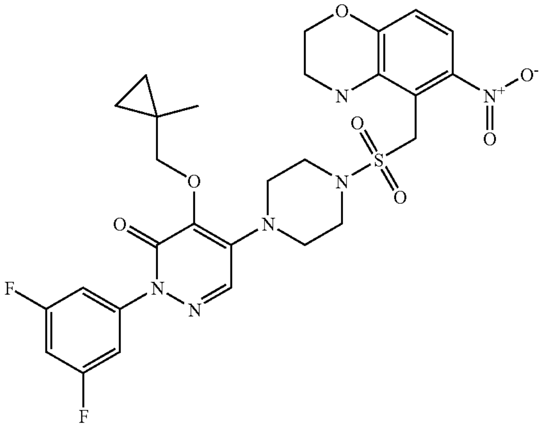 | 629 |
| 1574Z-55 | 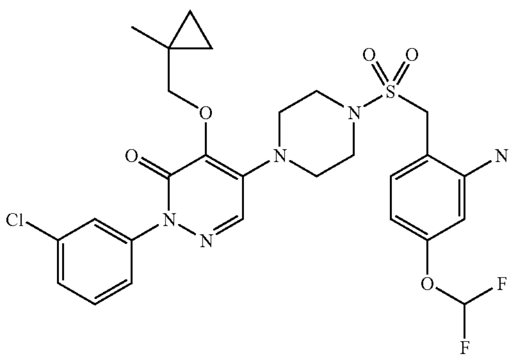 | 610 |
| 1574Z-56 | 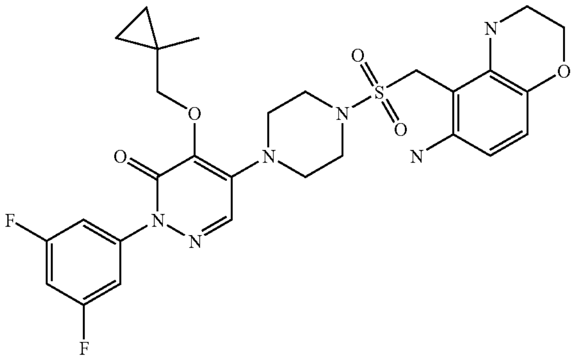 | 601 |

TABLE 23-continued
| Comp. No. | Structure | MS M + 1 |
|---|---|---|
| Oxygen Linked Analogs with Sulfonamide<br>Using the procedures described above, the following compounds were synthesized. | | |
| 1574Z-57 | 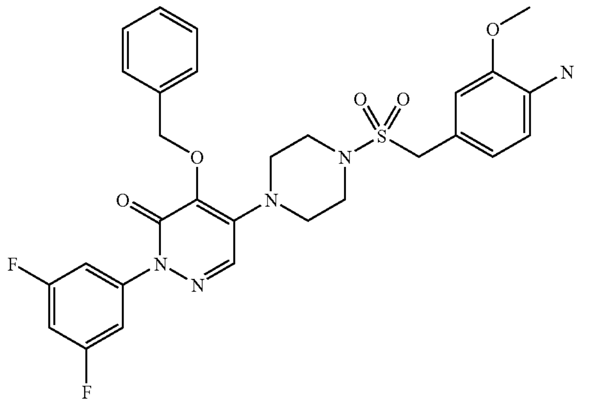 | 598 |
| 1574Z-58 | 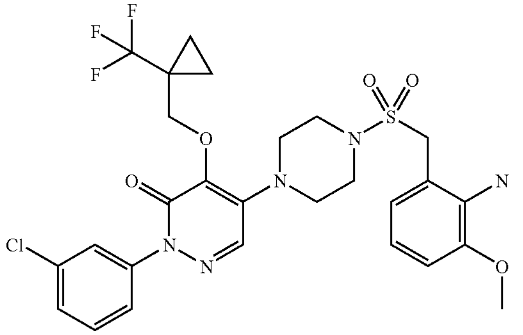 | 628 |
| 1574Z-59 | 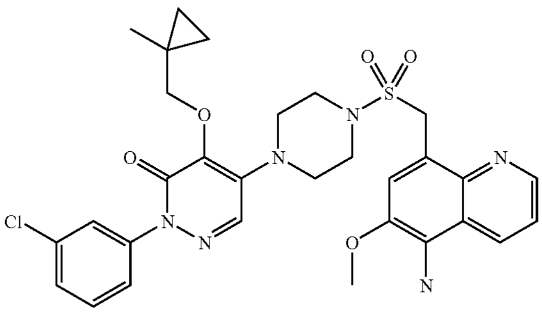 | 625 |
| 1574Z-60 | 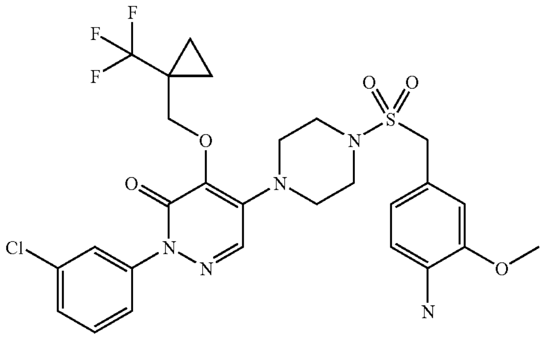 | 628 |

TABLE 23-continued
Oxygen Linked Analogs with Sulfonamide
Using the procedures described above, the following compounds were synthesized.
| Comp. No. | Structure | MS M + 1 |
|---|---|---|
| 1574Z-61 | 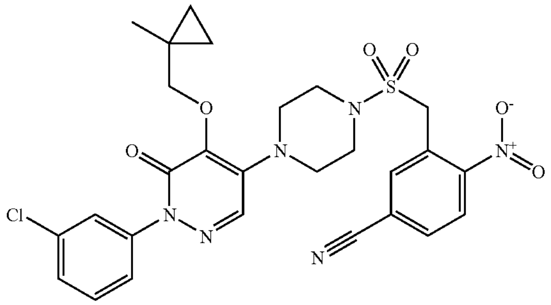 | 599 |
| 1574Z-62 | 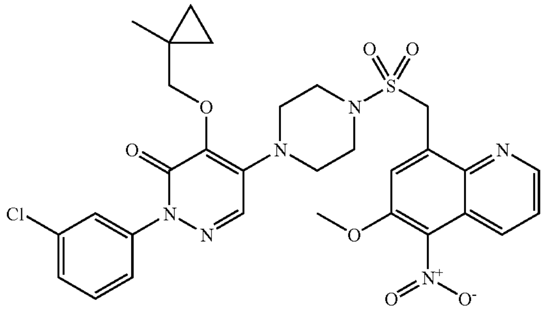 | 655 |
| 1574Z-63 | 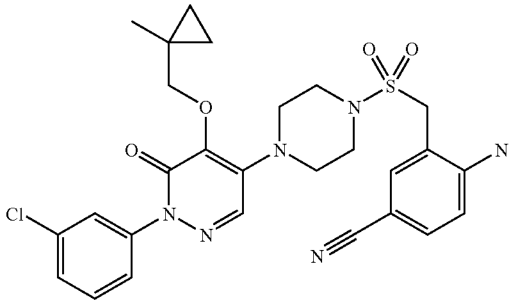 | 569 |
| 1574Z-64 | 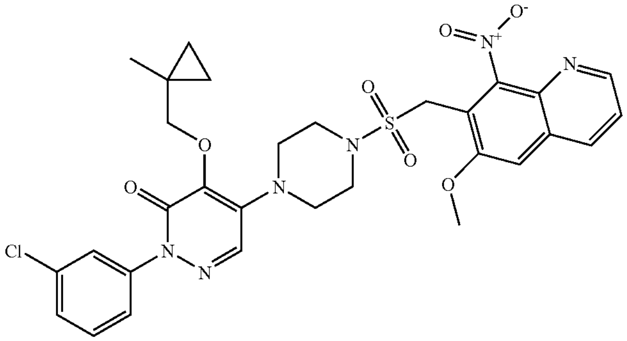 | 655 |

TABLE 23-continued
| Comp. No. | Structure | MS M + 1 |
|---|---|---|
| | Oxygen Linked Analogs with Sulfonamide<br>Using the procedures described above, the following compounds were synthesized. | |
| 1574Z-65 | 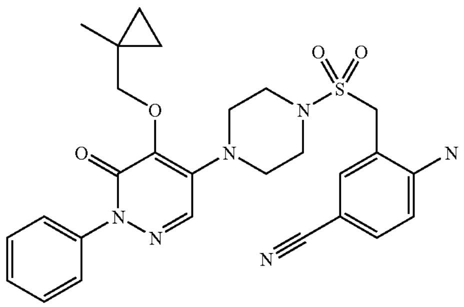 | 535 |
| 1574Z-66 | 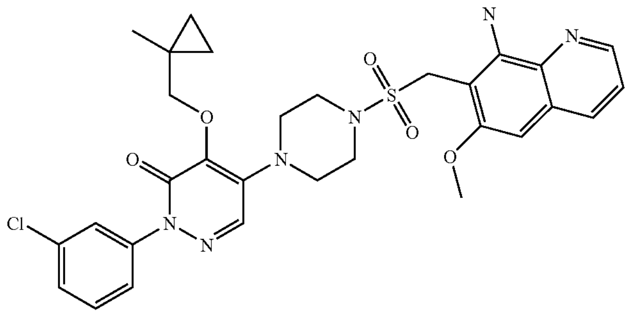 | 625 |
| 1574Z-67 | 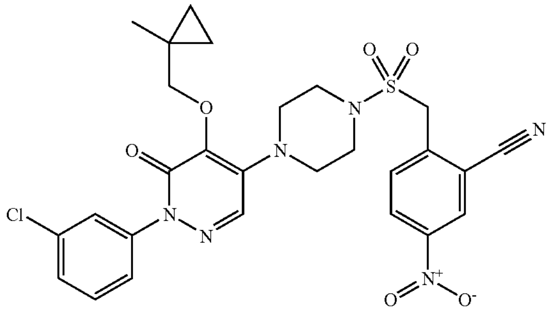 | 599 |
| 1574Z-68 | 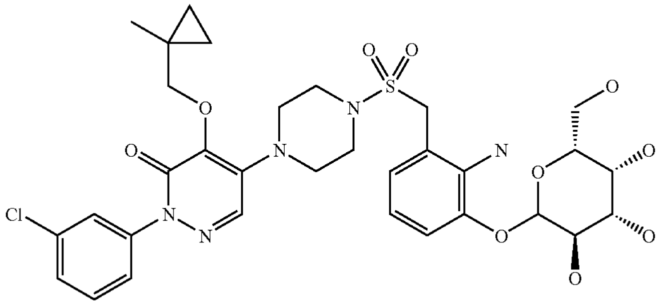 | 722 |

TABLE 23-continued
| Comp. No. | Structure | MS M + 1 |
|---|---|---|
| Oxygen Linked Analogs with Sulfonamide<br>Using the procedures described above, the following compounds were synthesized. | | |
| 1574Z-69 | 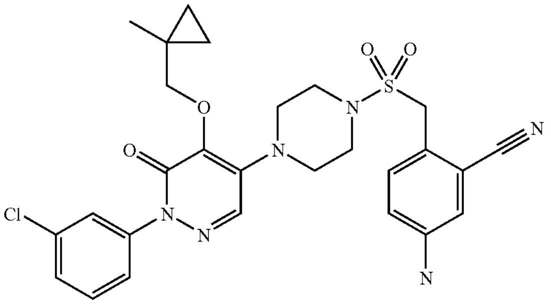 | 569 |
| 1574Z-70 | 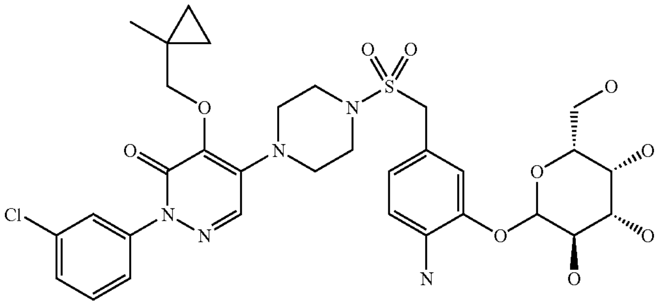 | 722 |
| 1574Z-71 | 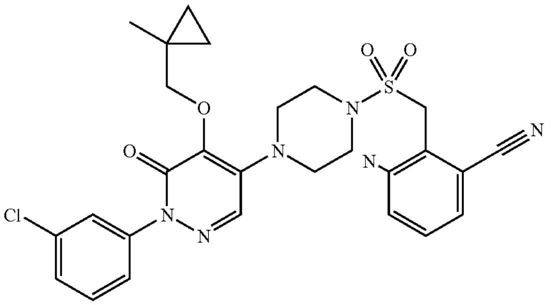 | 569 |
| 1574Z-72 | 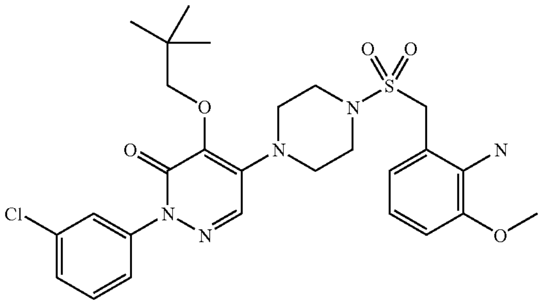 | 576 |

TABLE 23-continued
| Oxygen Linked Analogs with Sulfonamide Using the procedures described above, the following compounds were synthesized. | | |
|---|---|---|
| Comp. No. | Structure | MS M + 1 |
| 1574Z-73 | 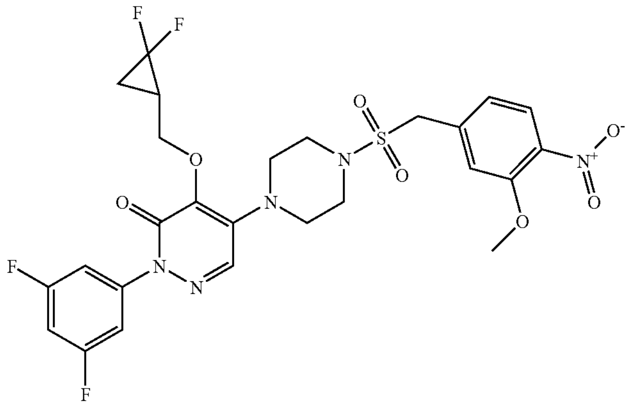 | 626 |
| 1574Z-74 | 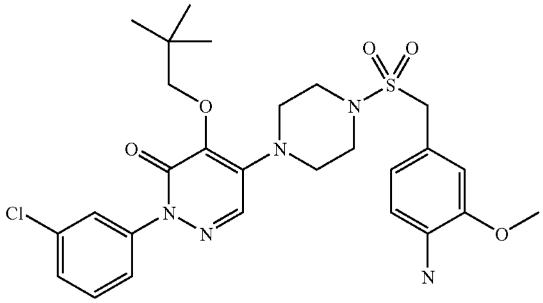 | 576 |
| 1574Z-75 | 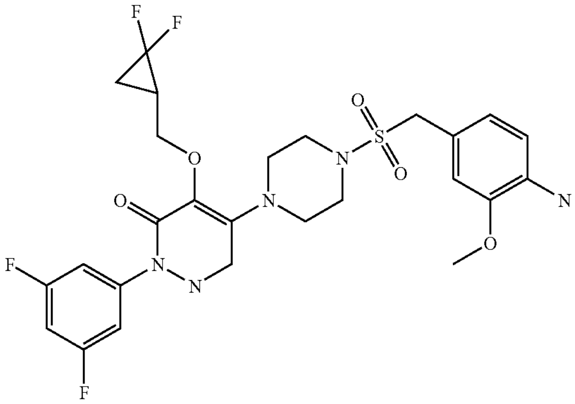 | 600 |
| 1574Z-76 | 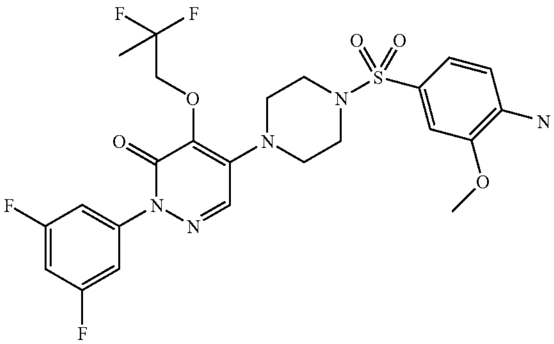 | 602 |

TABLE 23-continued
| Comp. No. | Oxygen Linked Analogs with Sulfonamide<br>Using the procedures described above, the following compounds were synthesized.<br>Structure | MS M + 1 |
|---|---|---|
| 1574Z-77 | 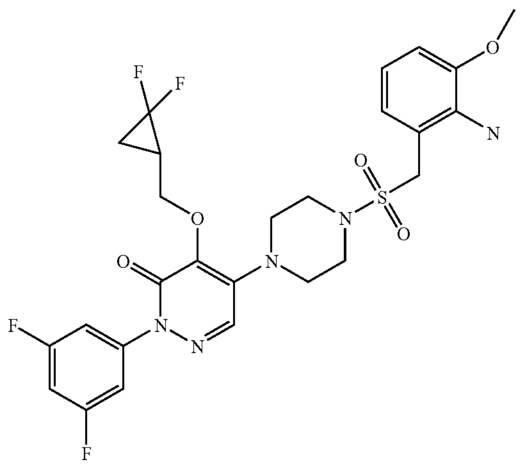 | 598 |
| 1574Z-78 | 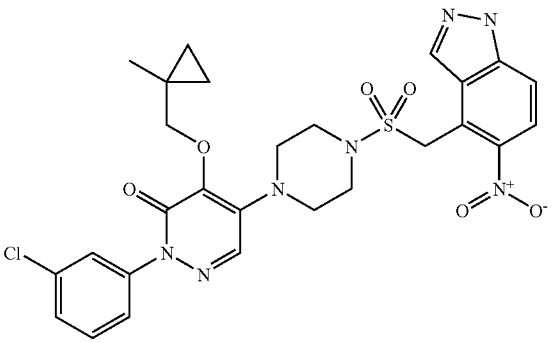 | 614 |
| 1574Z-79 | 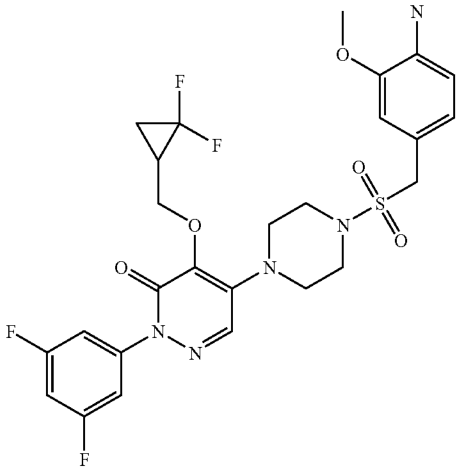 | 598 |

TABLE 23-continued
| Comp. No. | Structure | MS M + 1 |
|---|---|---|
| Oxygen Linked Analogs with Sulfonamide. Using the procedures described above, the following compounds were synthesized. | | |
| 1574Z-80 | 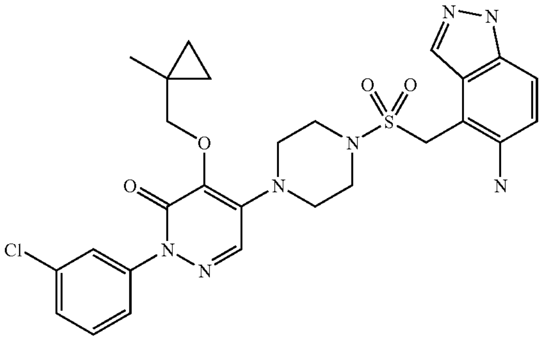 | 584 |
| 1574Z-81 | 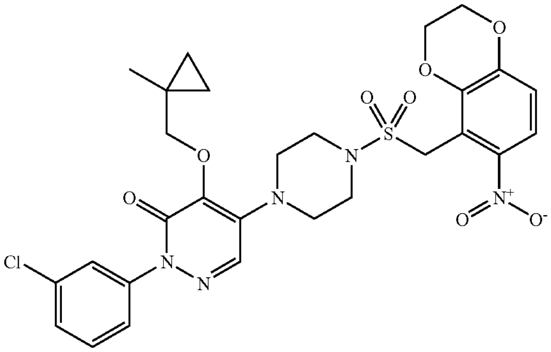 | 632 |
| 1574Z-82 | 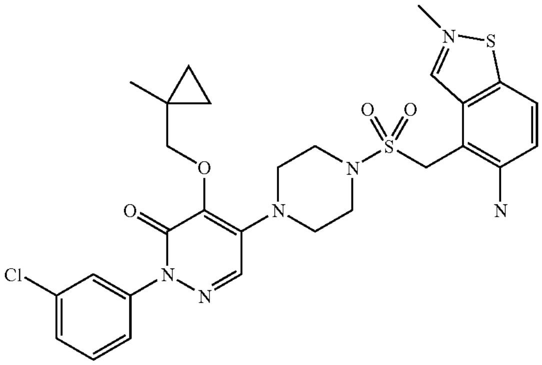 | 615 |
| 1574Z-83 | 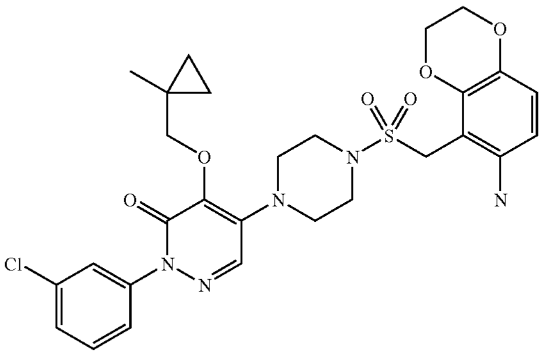 | 602 |

TABLE 23-continued
| Oxygen Linked Analogs with Sulfonamide<br>Using the procedures described above, the following compounds were synthesized. | | |
|---|---|---|
| Comp. No. | Structure | MS M + 1 |
| 1574Z-84 | 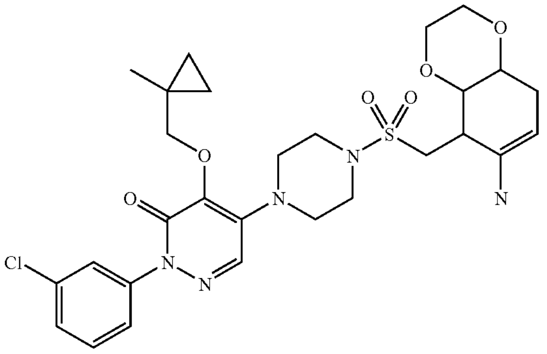 | 606 |
| 1574Z-85 | 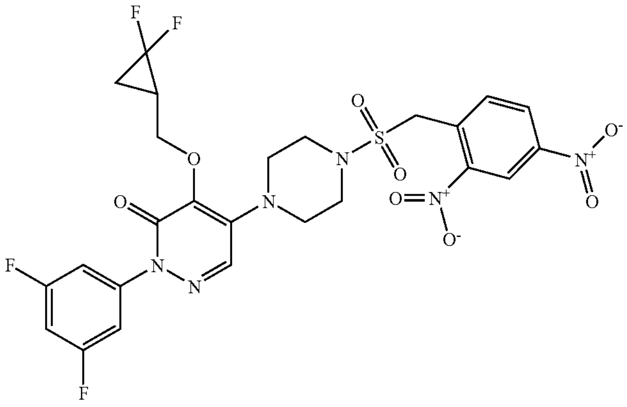 | 643 |
| 1574Z-86 | 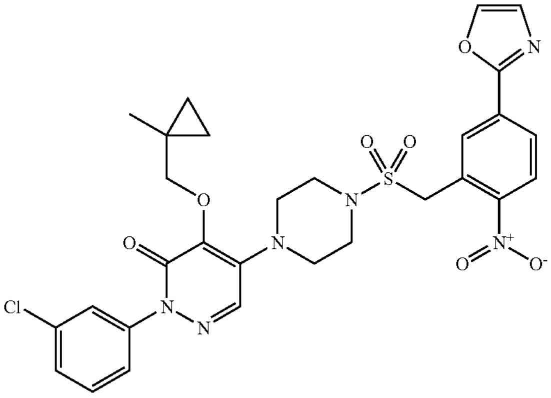 | 641 |
| 1574Z-87 | 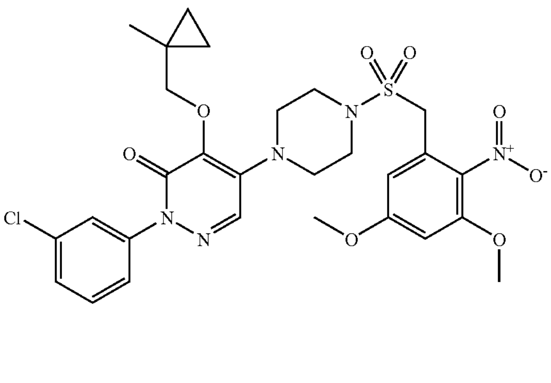 | 634 |

TABLE 23-continued
| Oxygen Linked Analogs with Sulfonamide<br>Using the procedures described above, the following compounds were synthesized. | | |
|---|---|---|
| Comp. No. | Structure | MS M + 1 |
| 1574Z-88 | 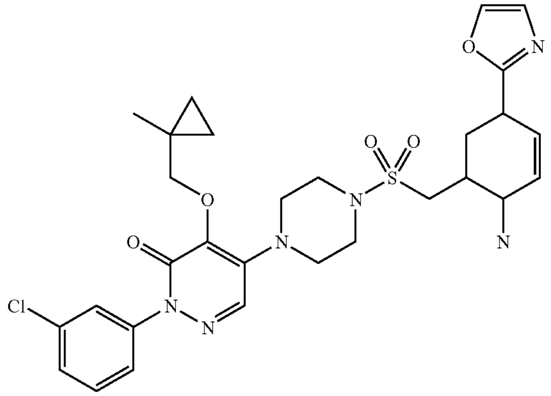 | 615 |
| 1574Z-89 | 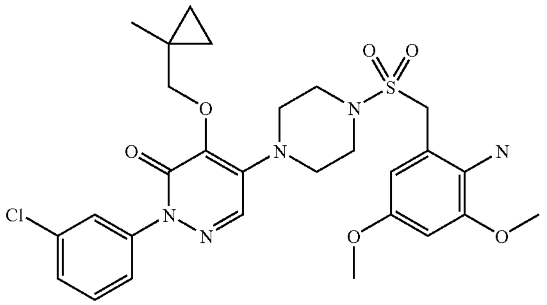 | 604 |
| 1574Z-90 | 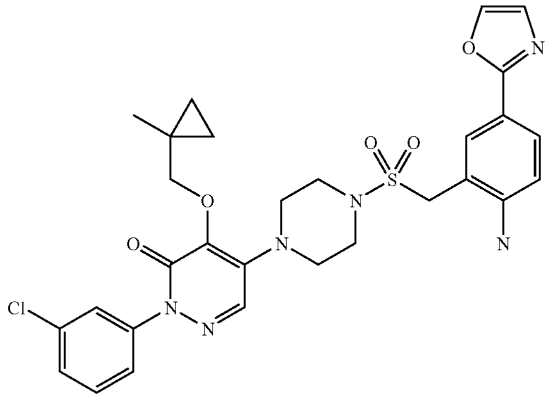 | 611 |
| 1574Z-91 | 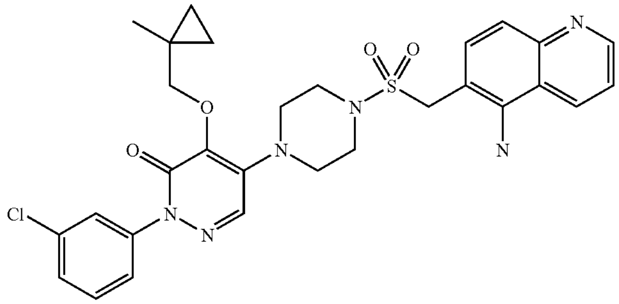 | 595 |

TABLE 23-continued
| Comp. No. | Structure | MS M + 1 |
|---|---|---|
| Oxygen Linked Analogs with Sulfonamide Using the procedures described above, the following compounds were synthesized. | | |
| 1574Z-92 | 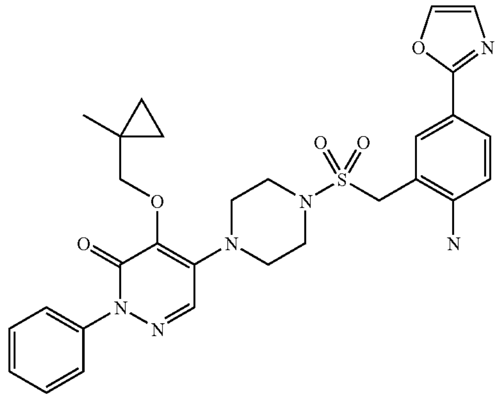 | 577 |
| 1574Z-93 | 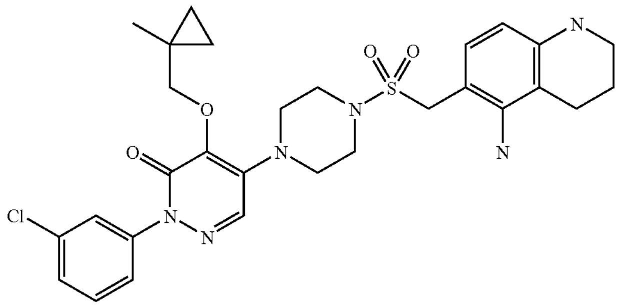 | 599 |
| 1574Z-94 | 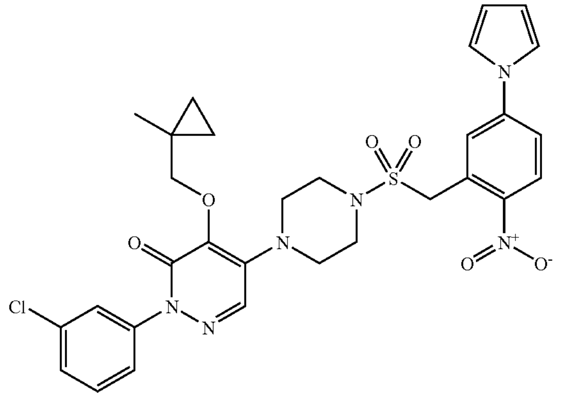 | 639 |
| 1574-95 | 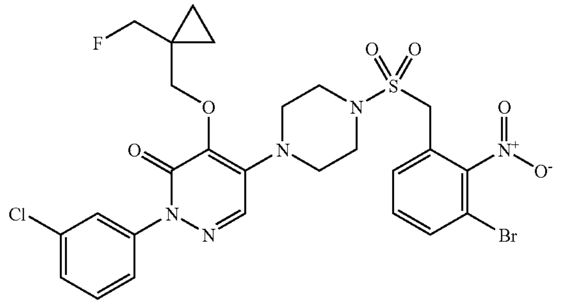 | 672 |

TABLE 23-continued
| Oxygen Linked Analogs with Sulfonamide<br>Using the procedures described above, the following compounds were synthesized. | | |
|---|---|---|
| Comp. No. | Structure | MS M + 1 |
| 1574Z-96 | 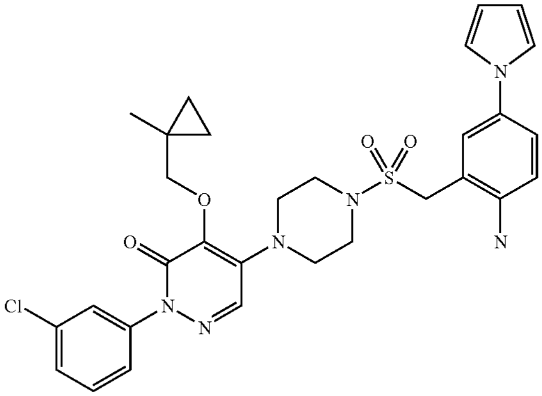 | 609 |
| 1574Z-97 | 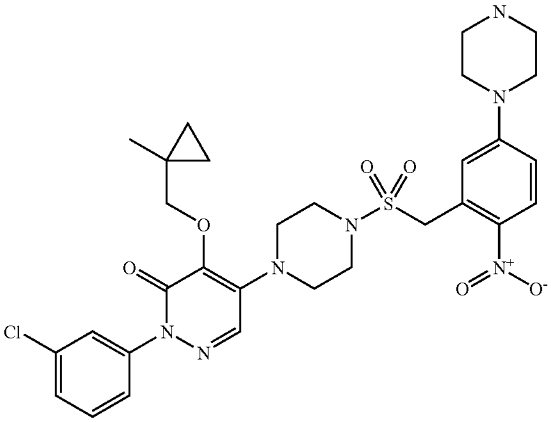 | 658 |
| 1574Z-98 | 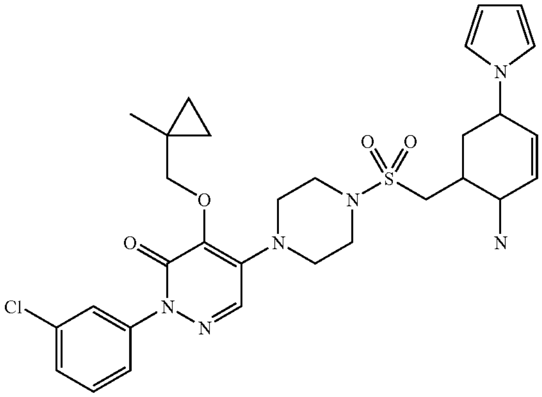 | 613 |

TABLE 23-continued
| Comp. No. | Structure | MS M + 1 |
|---|---|---|
| | Oxygen Linked Analogs with Sulfonamide Using the procedures described above, the following compounds were synthesized. | |
| 1574Z-99 | 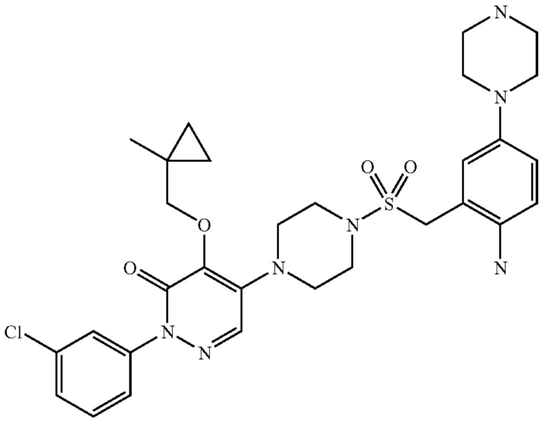 | 628 |
| 1574Z-100 | 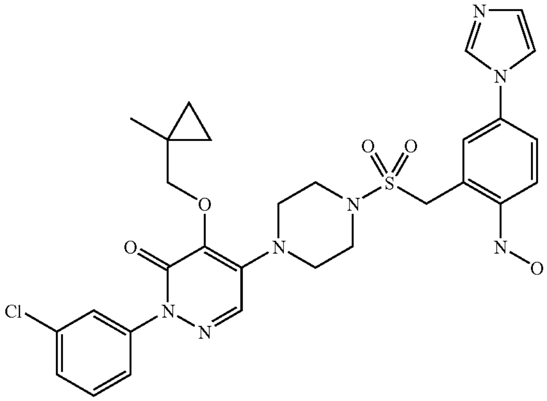 | 617 |
| 1574Z-101 | 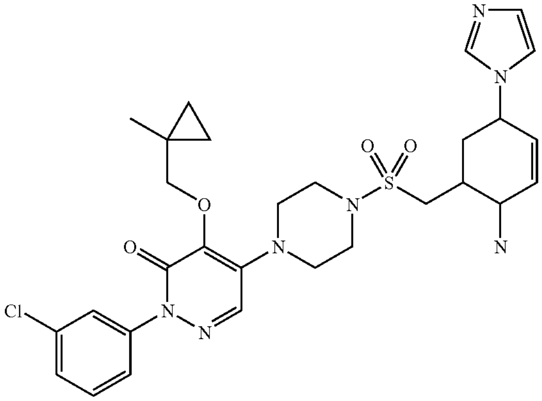 | 610 |

Scheme 22

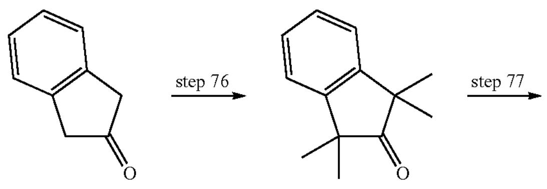

110 111

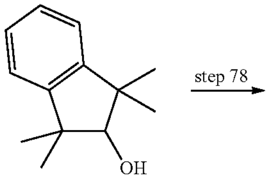

112

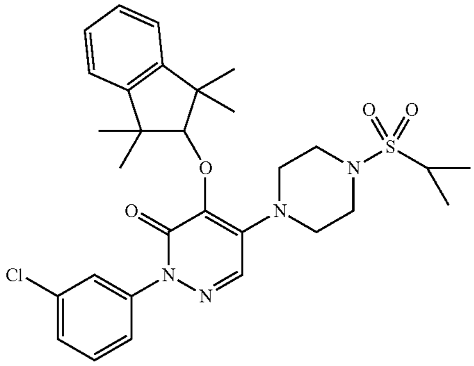

113

Step 76:

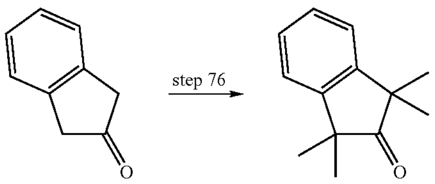

110 111

In a three necked flask containing a reflux condenser, dropping funnel, inner thermometer, a mixture of ketone 110 (2.64 g, 0.020 mol) and MeI (10 mL, 0.160 mol) was added to a suspension of KOH (22.40 g, 0.400 mol) in DMSO (30 mL) at 50-60° C. The reaction mixture was stirred at this temperature for 1.5 h and then the slurry was poured into ice water. The mixture was extracted with pentane (3×50 mL). The combined organic extract was washed with 120 (2×10 mL), brine (10 mL), dried (MgSO4) filtered, and concentrated. Purification by silica get chromatography (50:1 hexanes:EtOAc) gave the product 111 as a colorless oil (2.10 g, 56%). MS (M+1): m/e 187

Step 77:

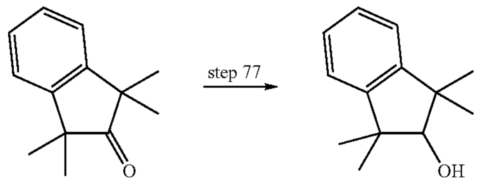

111 112

A solution of lithium aluminum hydride (5.0 mL, 1.0 M in TH, 5.0 mmol) was added to compound 111 (1.88 g, 10 mmol) dissolved in anhydrous ether (20 mL) and cooled to 0° C. The reaction mixture was stirred for 4 h and then water (0.2 mL), 1 N NaOH (0.2 ml), and water (0.6 mL) were added sequentially. The mixture was filtered through celite and washed with ether. The filtrate was concentrated and purification by silica gel chromatography (20:1 hexanes:EtOAc) gave 1.0 g (53%) of the product 112 as a colorless oil.

Step 78:

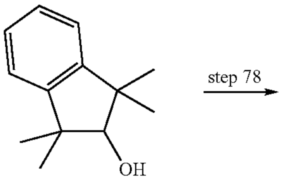

112

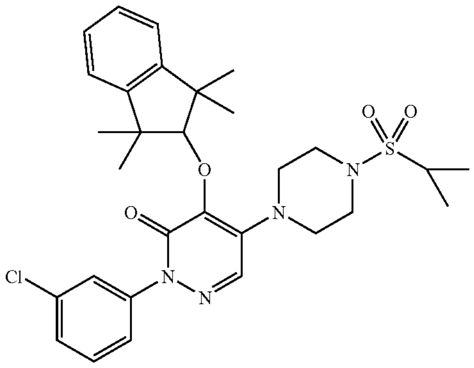

113

A mixture of anhydrous NaH (0.011 g, 0.30 mmol, 60%) and methoxylindanol 112 (0.062 g, 0.33 mmol) in anhydrous THF (5 mL) was stirred at room temperature for 10 mins. To this mixture, a solution of compound 14A (0.070 g, 0.16 mmol) in anhydrous THF (5 mL) was added dropwise at room temperature. The resulting solution was refluxed for 8 h, and then the solvent was evaporated. Aqueous $NH_4Cl$ (10 mL) was added and the aqueous solution was extracted with $CH_2Cl_2$ (3×50 mL). The combined organic extract was washed with $H_2O$ (2×10 mL) and brine (10 mL), dried ($MgSO_4$), filtered, and concentrated. Purification by silica gel chromatography (10:1 hexanes:EtOAc) gave the product 113 as a colorless oil (0.042 g, 46%). MS (M+1): m/e 569.

Scheme 23

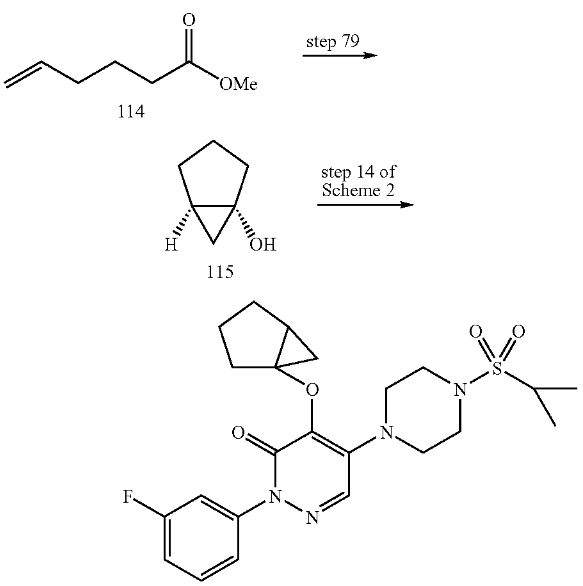

114

115

116

-continued

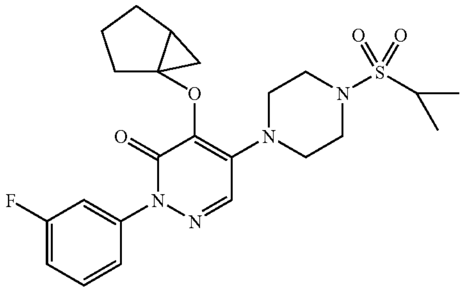

116

Using the procedure described above, compound 116 was synthesized. MS (M+1): m/e 477.

Step 79. *Organic Syntheses, Vol.* 80, *p.* 111 (2003).

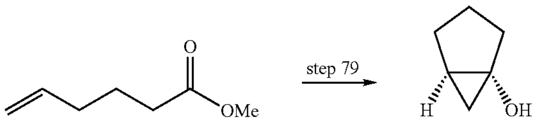

114

115

To compound 114 (2.0 g, 15.6 mmol) and chlorotitanium triisopropoxide (11.2 mL, 11.2 mmol of 1 M in hexane) dissolved in anhydrous ether (54 mL) under a nitrogen atmosphere was added n-butylmagnesium chloride in ether (1 M, 52 mL, 52 mmol) over 6.5 h via a syringe pump at room temperature. After the addition is complete, the resulting black reaction mixture is stirred for an additional 20 mins and then cooled to 0° C. Ether (50 mL) was added followed by the slow addition of water (14 mL). The resulting mixture was stirred for 3 h at room temperature. The organic phase was separated, and the aqueous phase was extracted with ether (3×100 mL). The combined organic extract was washed with brine (2×50 mL), dried ($MgSO_4$), filtered, and concentrated. Purification by silica gel chromatography (eluant: 5-10% ether/pentane) gave 1.09 g (71%) of the product 115 as a colorless oil.

Step 14 of Scheme 2:

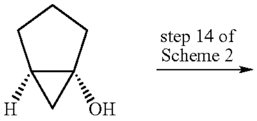

115

Scheme 24

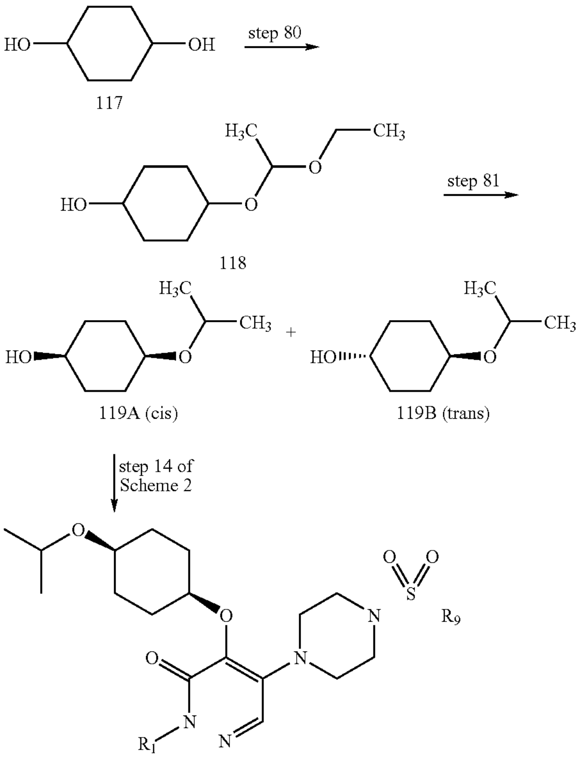

117

118

119A (cis)

119B (trans)

116

Step 80:

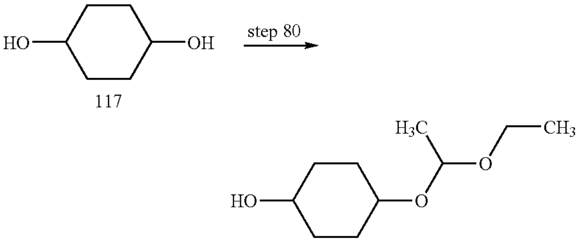

117

118

Ethyl vinyl ether (43 mL, 0.45 mol) was added to a suspension of cyclohexane-1,4-diol (117, 52 g, 0.45 mol, mixture of cis and trans isomers) in anhydrous tetrahydrofuran (300 mL) at 0° C. under nitrogen, after which 4-toluenesulfonic acid (15 mg, catalytic amount) was added. The mixture was warmed to room temperature and stirred for 1 h, after which sodium carbonate (30 g) was added to the clear solution. The solids were removed by filtration and the solvent was evaporated. Purification by flash column chromatography on silica gel (eluant: 1:1 ethyl acetate:hexanes) gave acetal 118 (19 g, 22%, mixture of cis and trans isomers) as a colorless oil.

Step 81:

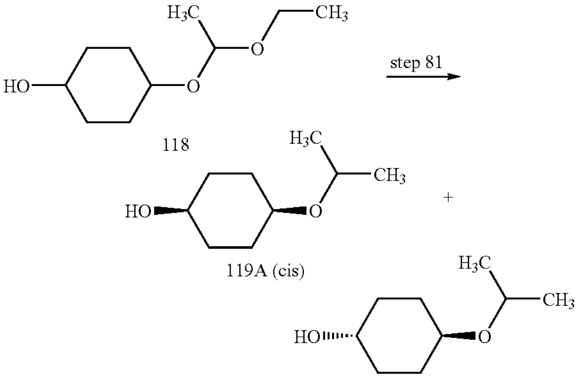

118

119A (cis)

119B (trans)

Methylmagnesium bromide (55 mL, 165 mmol, 3.0 M in tetrahydrofuran) was added to a solution of acetal 118 (7.8 g, 41.3 mmol, mixture of cis and trans isomers) in anhydrous toluene (500 mL) at room temperature under nitrogen, and the mixture was heated at 105° C. for 36 h. The mixture was cooled to 0° C., diluted with water (100 mL) and the pH was adjusted to 4-5 with 2 N HCl. The mixture was extracted with diethyl ether (100 mL) and the organic extract was washed with brine (3×200) dried ($Na_2SO_4$), filtered, and concentrated. Purification by flash column chromatography on silica gel (eluant: 1:1 ethyl acetate:hexanes) to first produce cis compound 119a (1.8 g, 28%) as a colorless oil. Additional elution produced the trans compound 119b (0.9 g, 14%) as a colorless oil

TABLE 24

Oxygen Linked Analogs with Sulfonamide
Step 14 of Scheme 2:
Using the procedure described above, the following compounds were synthesized.

| Comp. No. | Structure | MS M + 1 |
|---|---|---|
| 1575Z | 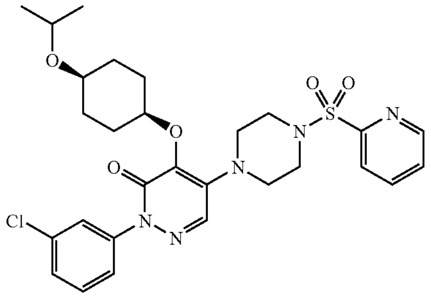 | 588 |

TABLE 24-continued

Oxygen Linked Analogs with Sulfonamide
Step 14 of Scheme 2:
Using the procedure described above, the following compounds were synthesized.

| Comp. No. | Structure | MS M + 1 |
|---|---|---|
| 1576Z | 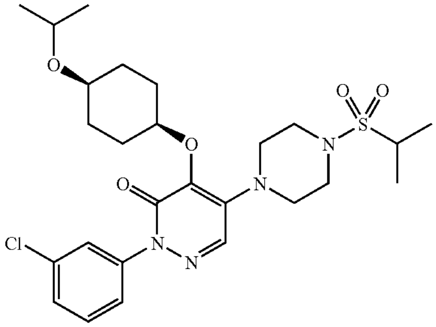 | 554 |
| 1577Z | 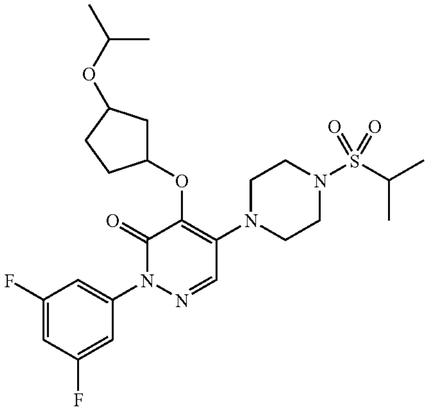 | 541 |
| 1578Z | 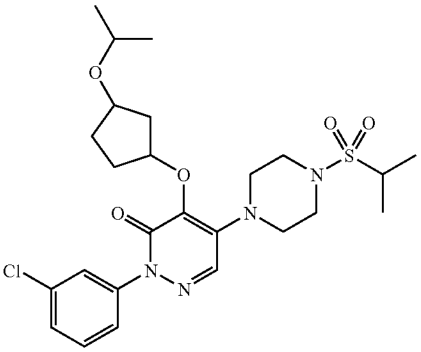 | 539 |
| 1579Z | 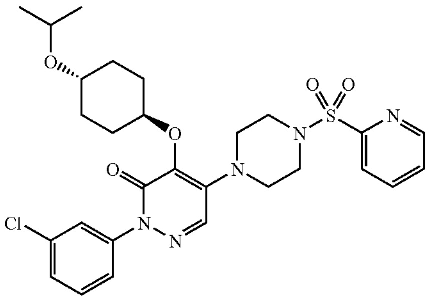 | 588 |

TABLE 24-continued

Oxygen Linked Analogs with Sulfonamide
Step 14 of Scheme 2:
Using the procedure described above, the following compounds were synthesized.

| Comp. No. | Structure | MS M + 1 |
|---|---|---|
| 1580Z | 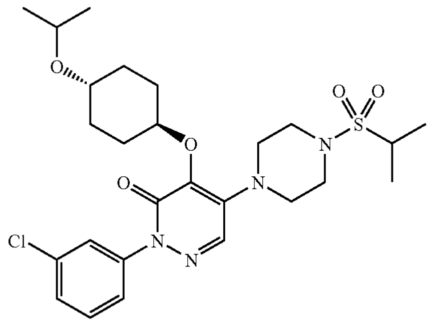 | 554 |
| 1581Z | 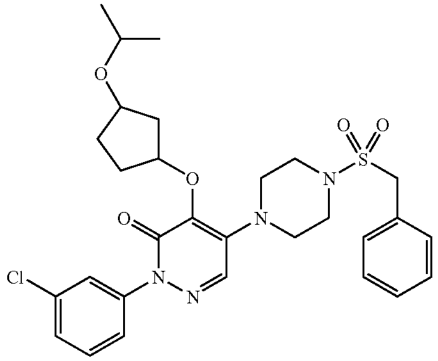 | 587 |

Scheme 25

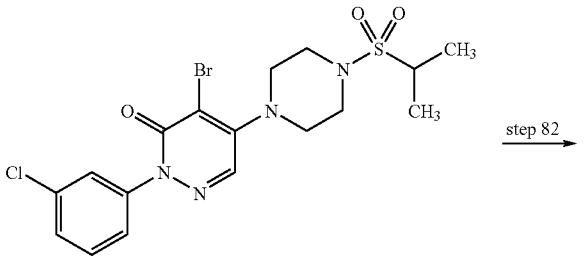

117

-continued

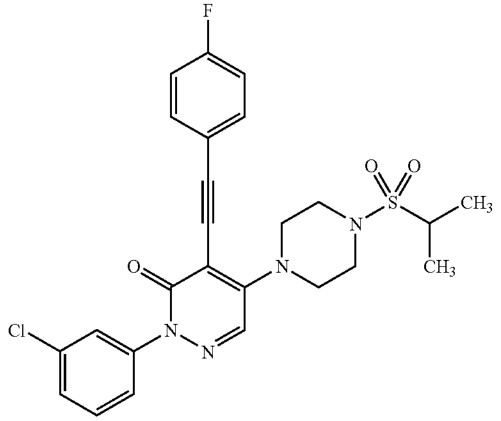

118

Compound 117 can be synthesized using steps 1 and 2 of Scheme 1 and steps 11 and 12 of Scheme 2.

Step 82:

A mixture of 117 (238 mg, 0.500 mmol), p-fluorophenylacetylene (0.10 mL, 0.10 g, 0.87 mmol), triethylamine (0.70 mL, 0.51 g, 5.0 mmol), bis(triphenylphosphine)palladium(II) dichloride (20 mg, 0.028 mmol) and copper(I) iodide (50 mg, 0.26 mmol) in anhydrous acetonitrile (3 mL) was sealed under nitro-en in a microwave tube. The mixture was heated to 130° C. over 5 mins and irradiated at 150° C. for 30 mins. The cooled mixture was poured into water (100 mL) and extracted with ethyl acetate (2×100 mL). The combined organic extracts were dried ($Na_2SO_4$), filtered, and concentrated. Purification by flash column chromatography on silica gel (eluant: 1:1 ethyl acetate:hexanes) gave the product 118 (50 mg, 19%) as a yellow solid: MS (M+1): m/e 515.

Scheme 26

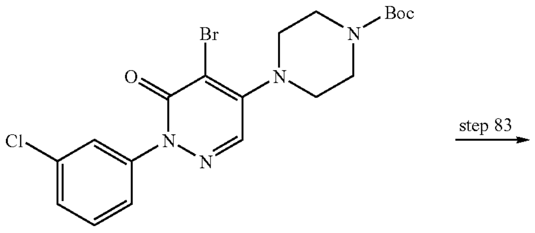

119

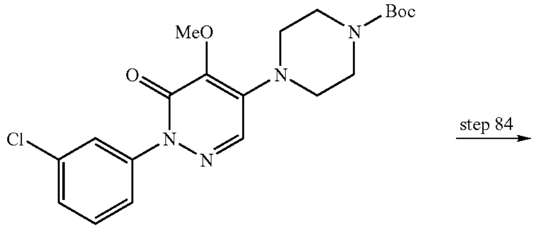

121

-continued

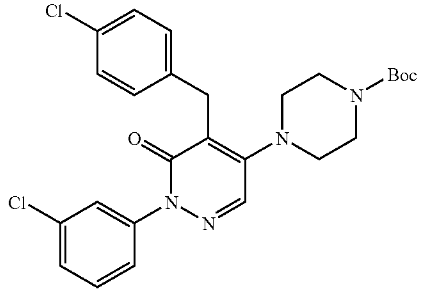

120

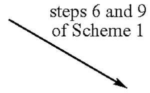

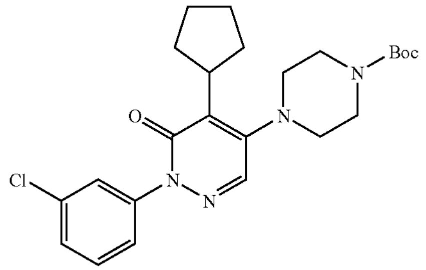

122

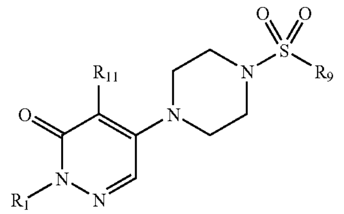

123

Compound 119 can be synthesized using steps 1 and 2 of Scheme 1.

Compound 121 can be synthesized using steps 1, 2, and 4 of Scheme 1.

Step 83:

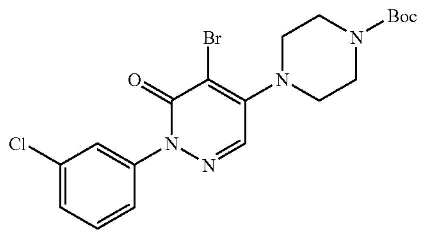

119

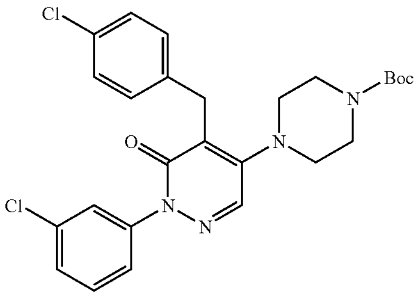

120

Argon was bubbled through a mixture of compound 119 (1.00 g, 2.13 mmol) and trans-benzyl(chloro)bis(triphenylphosphine)palladium(II) (81 mg, 0.11 mmol) in anhydrous tetrahydrofuran (25 mL) at room temperature under nitrogen. The yellow solution was heated to reflux and p-chlorobenzylzinc chloride (5.0 mL, 2.5 mmol, 0.5 M in tetrahydrofuran) was added dropwise, after which the mixture was heated at reflux for 12 h. The cooled mixture was treated with saturated aqueous $NH_4Cl$ solution (10 mL) followed by water (200 mL), and the mixture was extracted with ethyl acetate (3×100 mL). The combined organic extract was dried ($Na_2SO_4$), filtered, and concentrated. Purification by flash column chromatography on silica gel (eluant: 0:100 to 3:7 gradient of ethyl acetate:hexanes) gave the product 120 (807 mg, 74%) as a white solid: MS (M+1): m/e 515.

Step 84:

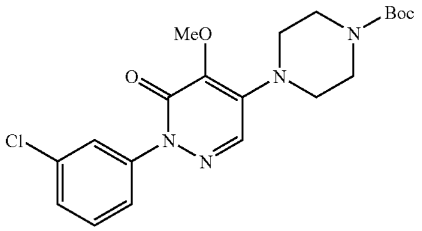

121

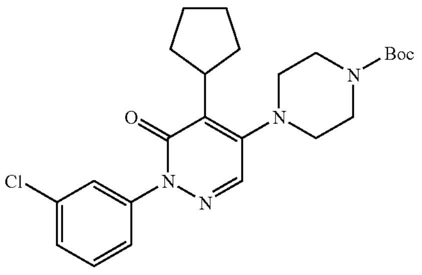

122

To a solution of 121 (350 mg, 0.832 mmol) in anhydrous tetrahydrofuran (20 mL) at −78° C. under nitrogen was added cyclopentylmagnesium chloride (0.85 mL, 1.7 mmol, 2.0 M in diethyl ether) at a rate which kept the internal reaction temperature below −70° C. The mixture was slowly warmed to room temperature, stirring for a total of 18 h. The mixture was diluted with saturated aqueous $NH_4Cl$ solution (10 mL) and water (100 mL) and extracted with ethyl acetate (2×100 mL). The combined organic extract was dried ($Na_2SO_4$), filtered, and concentrated. Purification by flash column chromatography on silica gel (eluant: 3:7 ethyl acetate:hexanes) gave the product 122 (351 mg, 92%) as a white solid: MS (M+1): m/e 45%.

TABLE 25
| Carbon Linked Analogs with Sulfonamide<br>Steps 6 and 9 of Scheme 1:<br>Using the procedures described above, the following compounds were synthesized. | | |
|---|---|---|
| Comp. No. | Structure | MS M + 1 |
| 1582Z | 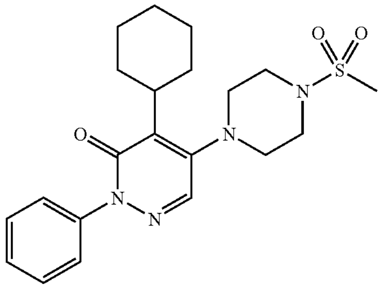 | 417 |
| 1583Z | 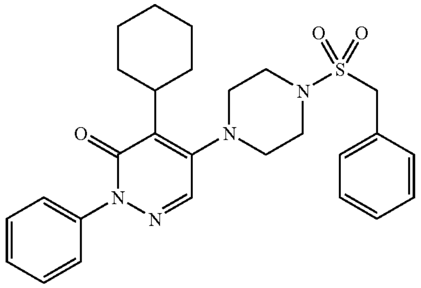 | 493 |
| 1584Z | 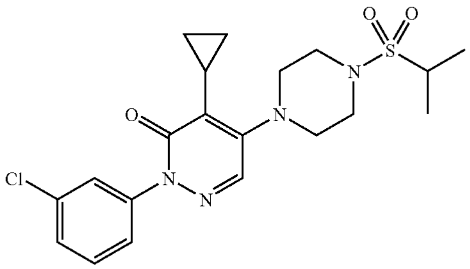 | 437 |
| 1585Z | 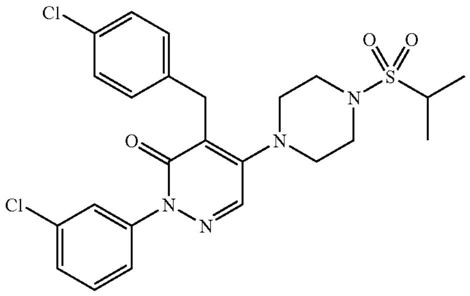 | 521 |
| 1586Z | 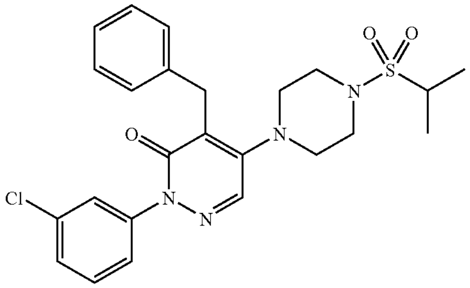 | 487 |

TABLE 25-continued
Carbon Linked Analogs with Sulfonamide
Steps 6 and 9 of Scheme 1:
Using the procedures described above, the following compounds were synthesized.
| Comp. No. | Structure | MS M + 1 |
| --- | --- | --- |
| 1587Z | 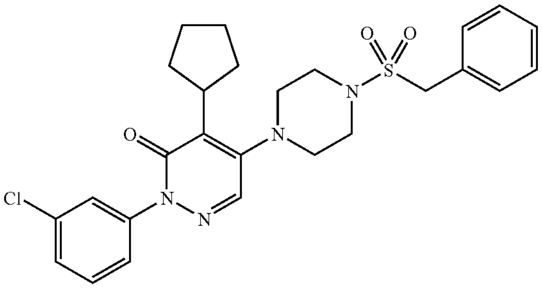 | 513 |
| 1588Z | 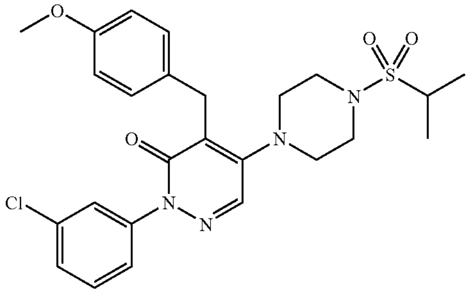 | 517 |
| 1589Z | 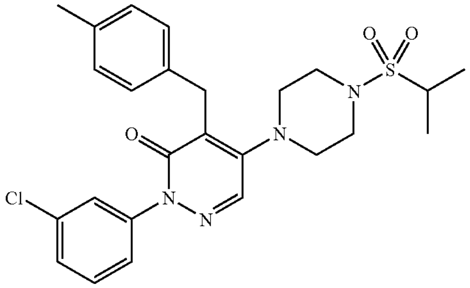 | 501 |
| 1590Z | 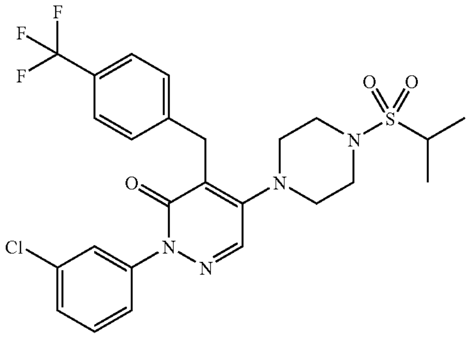 | 555 |
| 1591Z | 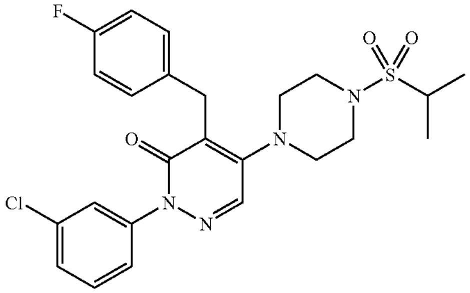 | 505 |

TABLE 25-continued
| Comp. No. | Structure | MS M + 1 |
|---|---|---|
| Carbon Linked Analogs with Sulfonamide<br>Steps 6 and 9 of Scheme 1:<br>Using the procedures described above, the following compounds were synthesized. | | |
| 1592Z | 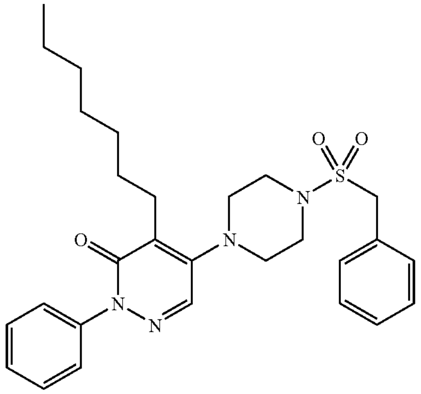 | 509 |
| 1593Z | 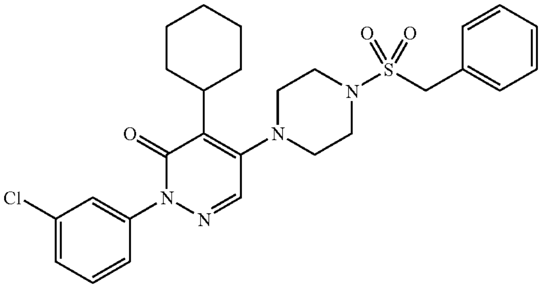 | 527 |
| 1594Z | 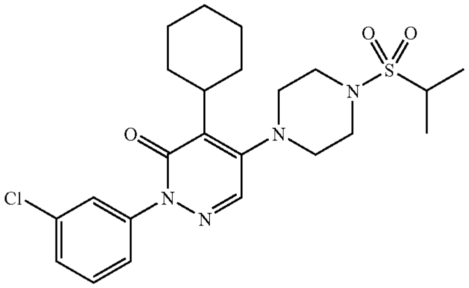 | 479 |
| 1595Z | 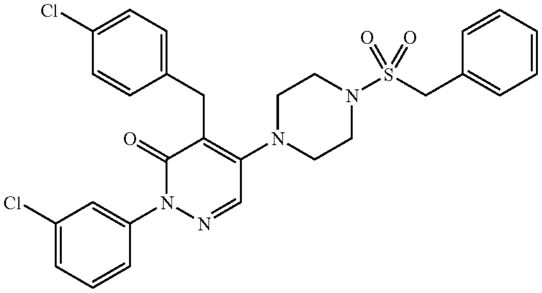 | 569 |

TABLE 25-continued
| Carbon Linked Analogs with Sulfonamide<br>Steps 6 and 9 of Scheme 1:<br>Using the procedures described above, the following compounds were synthesized. | | |
|---|---|---|
| Comp. No. | Structure | MS M + 1 |
| 1596Z | 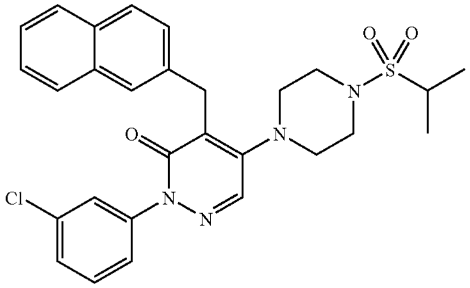 | 537 |
| 1597Z | 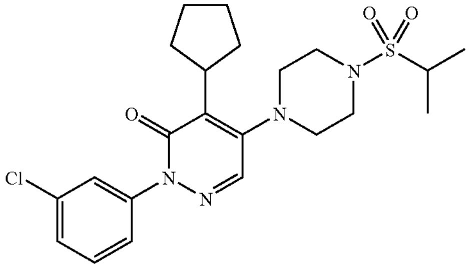 | 465 |
| 1598Z | 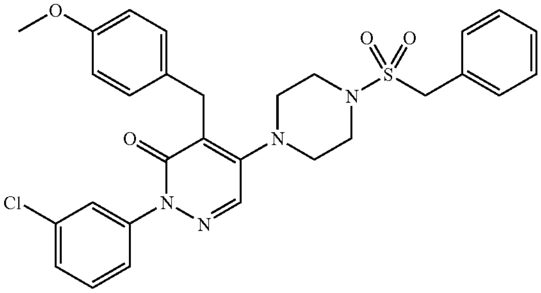 | 565 |
| 1599Z | 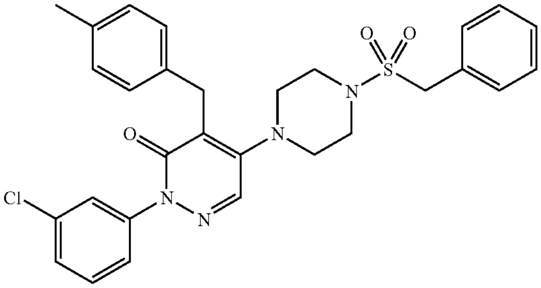 | 549 |
| 1600Z | 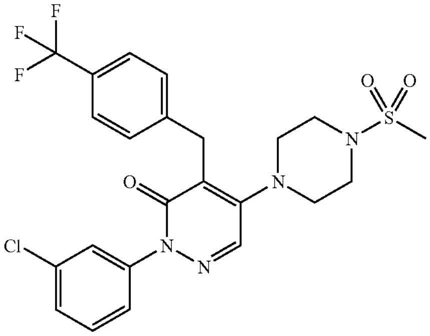 | 527 |

TABLE 25-continued

| Carbon Linked Analogs with Sulfonamide<br>Steps 6 and 9 of Scheme 1:<br>Using the procedures described above, the following compounds were synthesized. | | |
|---|---|---|
| Comp. No. | Structure | MS M + 1 |
| 1601Z | 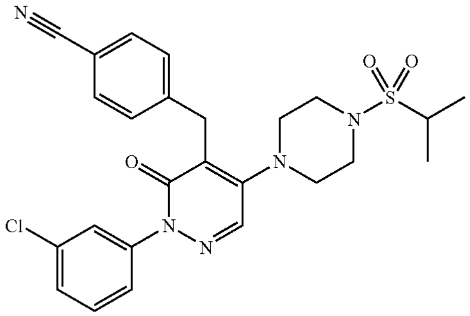 | 512 |

Scheme 27

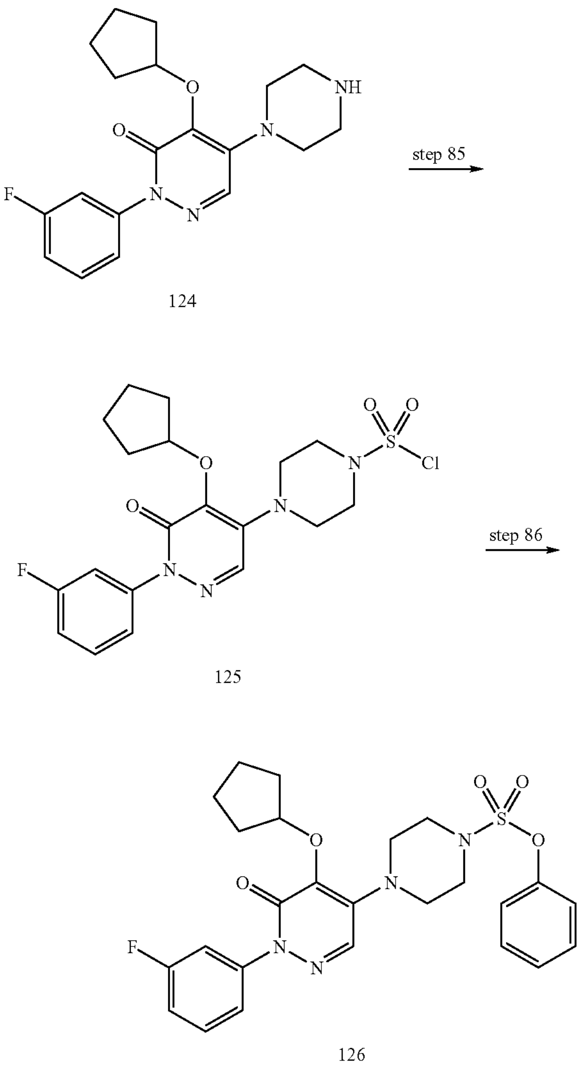

124

125

126

Step 85:

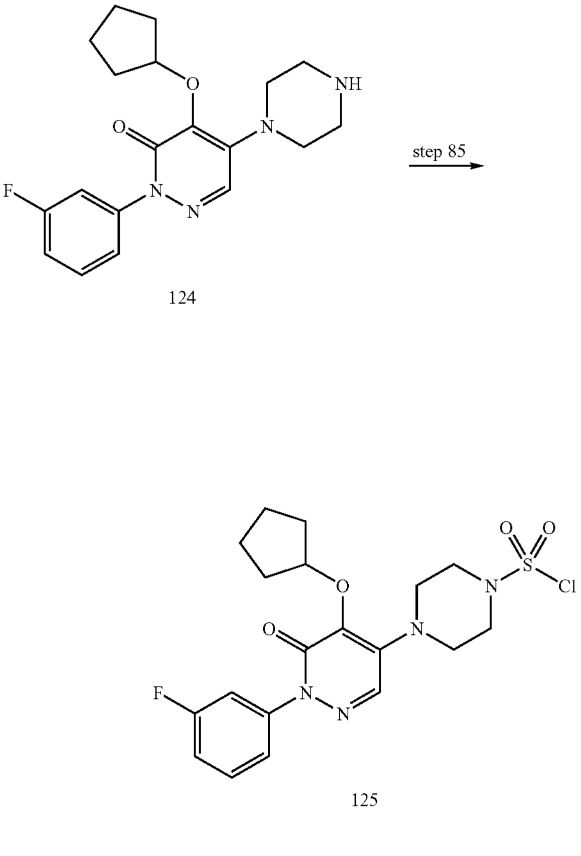

124

125

To a solution of $SO_2Cl_2$ (0.08 mL, 1.0 mmol) in $CH_2Cl_2$ (5 mL) at −78° C. was added a solution of the compound 124 (0.36 g, 1.0 mmol) and $Et_3N$ (0.16 mL, 1.1 mmol) in $CH_2Cl_2$ (5 mL). The reaction was slowly warmed up from −78 to −20° C. over a period of 1 h. The solvent was evaporated and purification by silica gel chromatography (eluant 20:1 $CH_2Cl_2$:EtOAc) gave 82 mg (18%) of the product 125 as a white solid. MS (M+1): m/e 457.

Step 86:

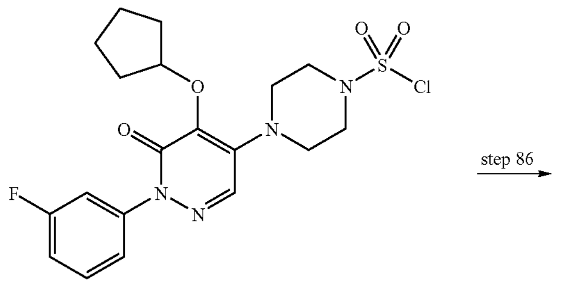

125

-continued

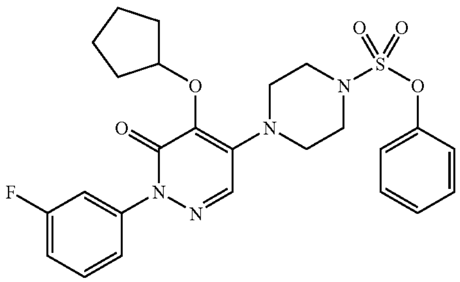

126

To a solution of phenol (47 mg, 0.50 mmol) in dry THF (3 mL), was added NaH (20 mg 60% by weight in oil, 0.50 mmol). The reaction mixture was stirred for 15 min at room temperature. A solution of the compound 125 (0.11 g 0.25 mmol) in THF (2 mL) was added, and the reaction mixture was stirred for 1 h. The mixture was diluted with EtOAc (20 mL) and washed with 1 N HCl and brine, dried ($MgSO_4$), filtered, and concentrated. Purification by silica gel chromatography (eluant: 0-25%. EtOAc in hexanes) gave 40 mg (31%) of the product 126 as a pale yellow solid. MS (M+1): m/e 515.

Scheme 28

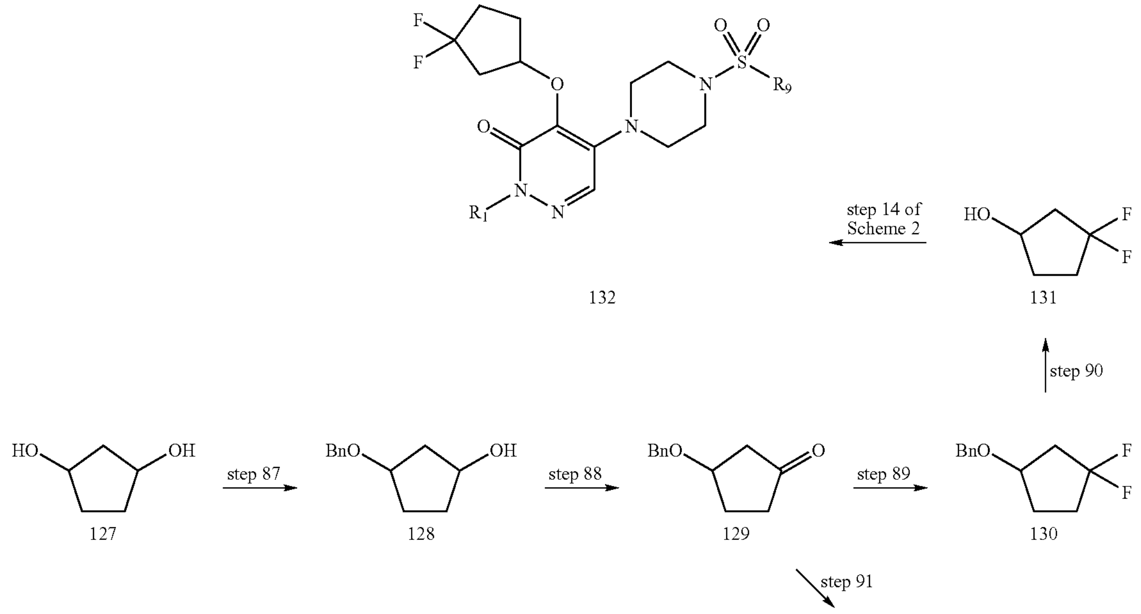

-continued

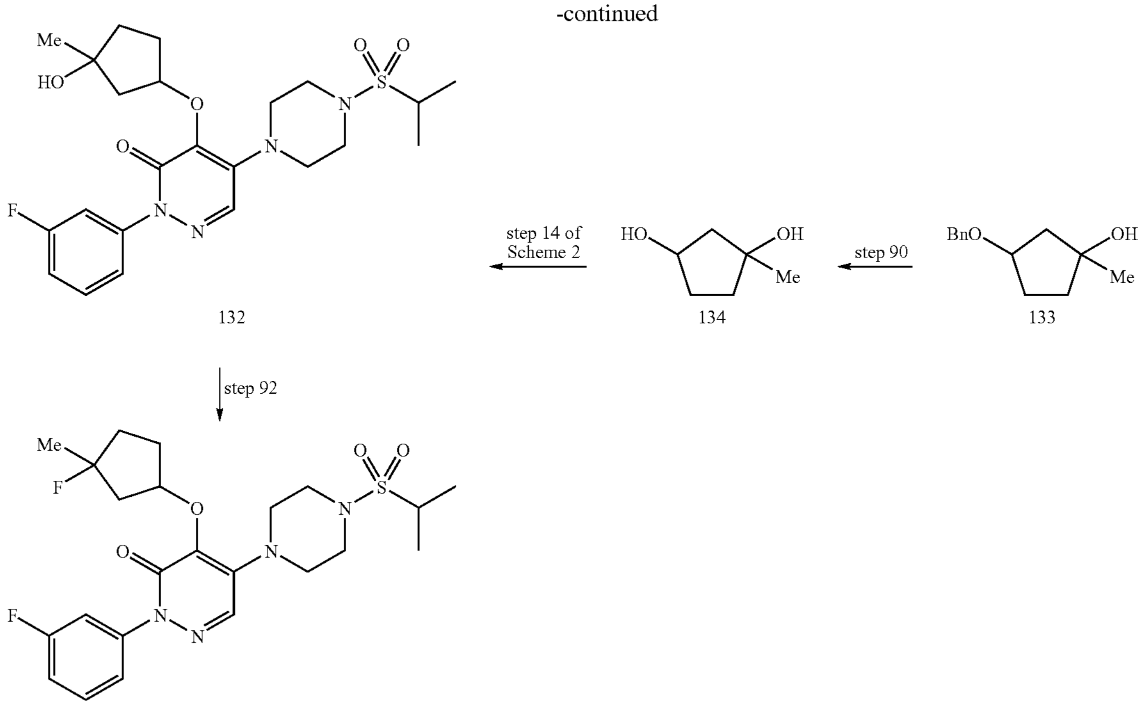

132 134 133

133

Step 87:

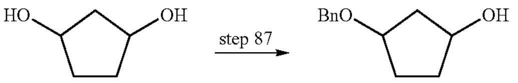

127 128

Sodium hydride (60%, 2.40 g, 60 mmol) was added to a solution of 1,3-cyclopentadiol 127 (8.16 g, 80 mmol) in THF (200 mL) and the mixture was stirred for 15 mins at room temperature. Benzyl bromide (6.80 g, 40 mmol) was then added, and the resulting mixture was stirred at room temperature for 20 h. Solid sodium bicarbonate 10 g) was added, and stirring was continued for 30 mins. The reaction mixture was filtered, and the filtrate was concentrated. Purification by silica gel chromatography (eluant: 0-30% EtOAc in hexanes) gave 3.5 g (46%) of the product 128 as colorless oil.

Step 88:

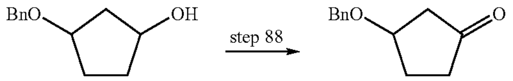

128 129

To a solution of the compound 128 (2.77 g, 14.4 mmol) in $CH_2Cl_2$ (50 mL) was added Dess-Martin periodinane (12.22 g, 28.8 mmol) followed by stirring for 2 h at room temperature. The reaction mixture was treated with 2.0 M NaOH (50 mL). The organic phase was separated, and the aqueous solution was extracted with 110 mL of EtOAc. The combined organic extract was washed with brine, dried ($MgSO_4$), filtered, and concentrated to give 2.5 g (93%) of the product 129 as a colorless oil.

Step 89:

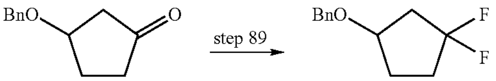

129 130

DAST (3.18 g, 19.7 mmol) was added dropwise to a solution of compound 129 (1.50 g, 7.9 mmol) in 1,2-dichloroethane at room temperature. The reaction was heated at 90° C. for 24 h. After cooling to room temperature, the reaction mixture was filtered through a short silica gel plug and washed with $CH_2Cl_2$. The filtrate was concentrated and purification by silica gel chromatography (eluant: hexane) gave 0.99 g (59%) of the product 130 as colorless oil.

Step 90:

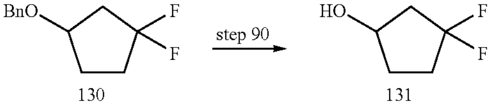

130 131

A flask was charged with Pd/C (10% wt, 1.00 g). Compound 130 (0.90 g, 4.3 mmol) dissolved in 5:1 MeOH:AcOH (30 mL) was added under nitrogen. The reaction mixture was shaken under hydrogen (50 psi) at room temperature for 48 h. The Pd/C catalyst was filtered and washed with $CH_2Cl_2$. The solvent was removed from the filtrate by distillation at 90° C. The residue was diluted with $Et_2O$ and treated with $Na_2CO_3$ (4.5 g) over 30 mins at room temperature. The solid was filtered off, and the filtrate was concentrated to give 0.37 g (71%) of the product 131 as a colorless oil.

Step 91:

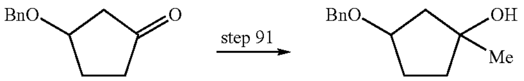

129 133

A solution of compound 129 (0.49 g, 2.6 mmol) in THF (10 mL) was cooled to −78° C., and MeMgBr (1.4 M, 2.8 ml, 3.9 mmol) was added dropwise. The reaction mixture was warmed slowly from −78 to −10° C. over 1 h. Saturated $NH_4Cl$ solution (5 mL) and then EtOAc were added. The organic solution was washed with brine, dried ($MgSO_4$), filtered, and concentrated. Purification by silica gel chromatography (eluant: 0-10% EtOAc in $CH_2Cl_2$) to give 0.20 g (37%) of the product 133 as a colorless oil.

TABLE 26

Oxygen Linked Analogs with Sulfonamide
Step 14 of Scheme 2:
Using the procedures described above, the following compounds were synthesized.

| Comp. No. | Structure | MS M + 1 |
|---|---|---|
| 1601Z | 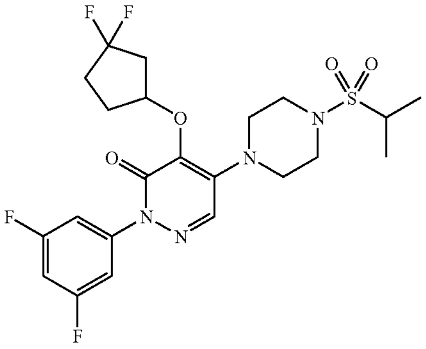 | 519 |
| 1602Z | 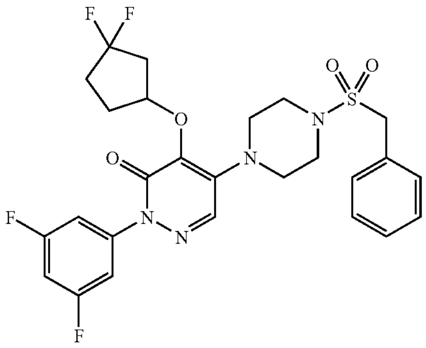 | 567 |

TABLE 26-continued

Oxygen Linked Analogs with Sulfonamide
Step 14 of Scheme 2:
Using the procedures described above, the following compounds were synthesized.

| Comp. No. | Structure | MS M + 1 |
|---|---|---|
| 1603Z | 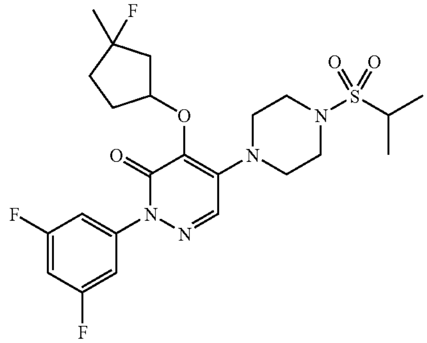 | 515 |
| 1604Z | 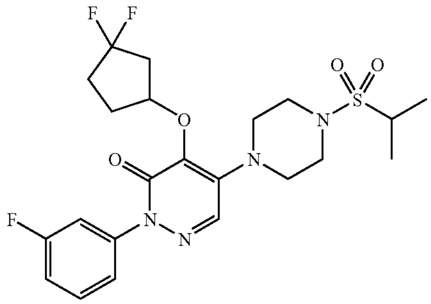 | 501 |
| 1605Z | 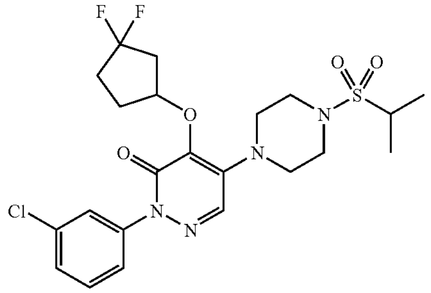 | 517 |
| 1606Z | 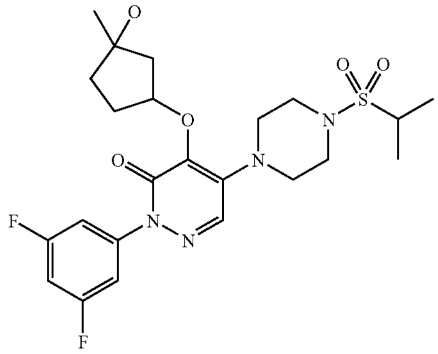 | 495 |

Step 92:

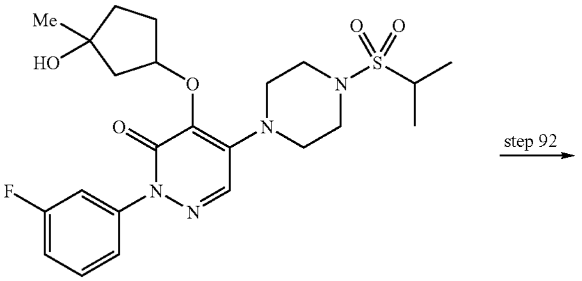

132

-continued

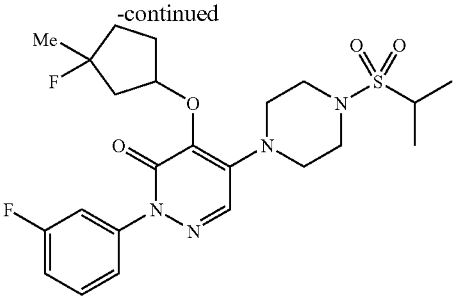

133

A solution of DAST (52 mg, 0.325 mmol) dissolved in $CH_2Cl_2$ (5 mL) and cooled to −78° C. was added dropwise a solution of the alcohol 132 (80 mg, 0.16 mmol) in $CH_2Cl_2$ (5 mL). The reaction mixture was slowly warmed up to room temperature and stirred for 3 h. Saturated $NaHCO_3$ solution (0.1 mL) was added. Purification of the mixture by silica gel chromatography (eluant: 0-359%. EtOAc in hexanes) gave 68 mg (86%) of the product 133 as a pale yellow solid (86%). MS (M+1): m/e 497.

Scheme 29

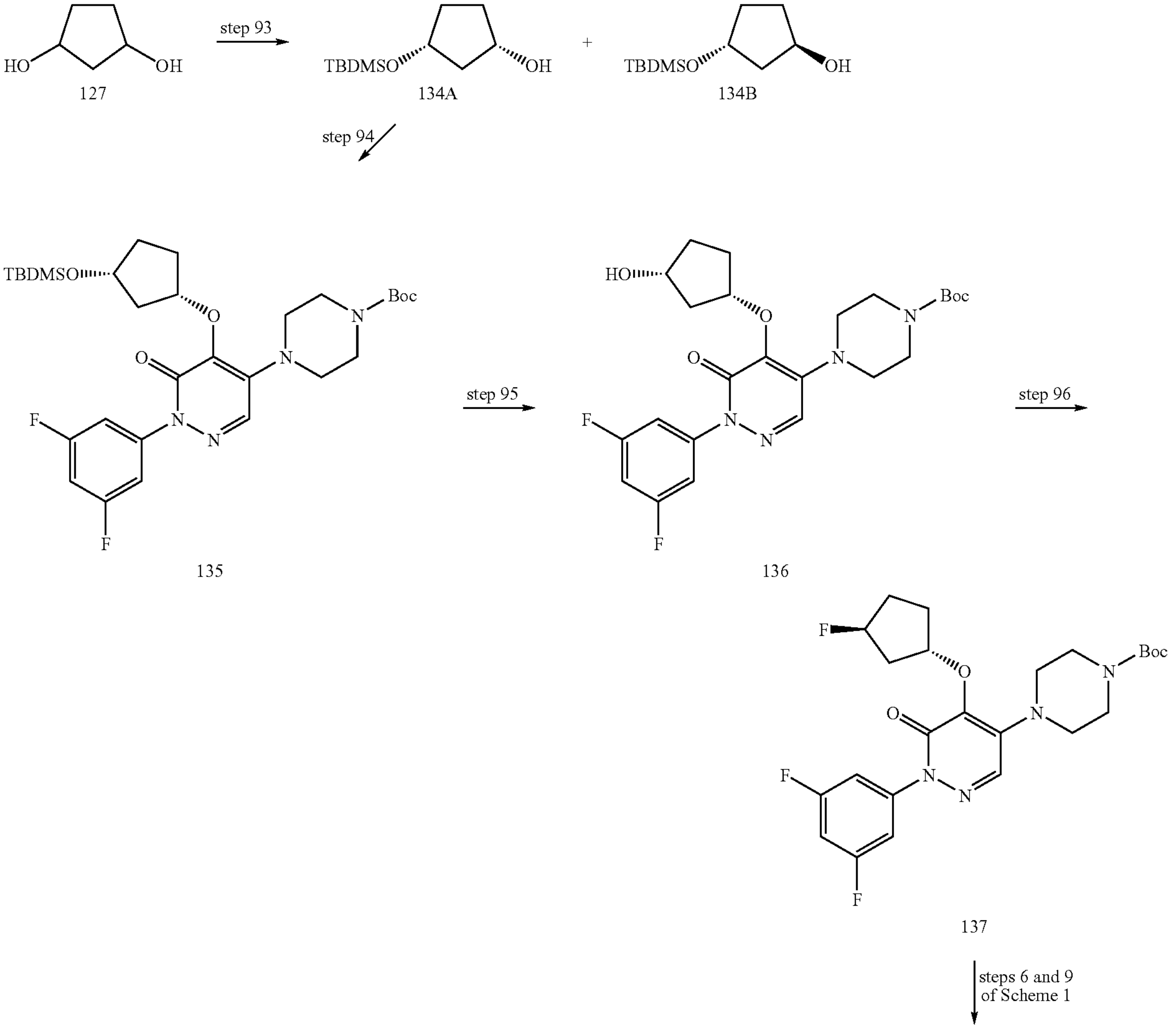

127 134A 134B 135 136

137

-continued

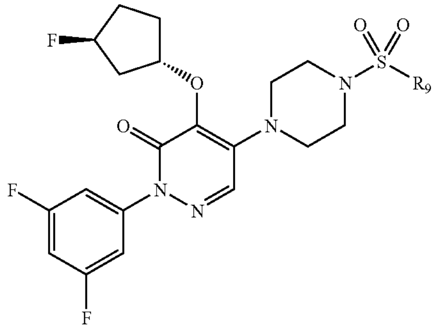

138

Step 93: Tetrahedron v. 53, p. 1983 (1997) and Org. Process Res. Dev. v 2, p. 357 (1998)

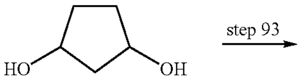

127

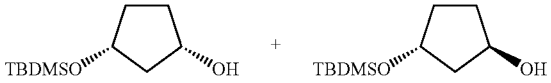

134A 134B

Sodium hydride (11.6 g, 289 mmol, 60% dispersion in mineral oil) was added to a solution of 1,3-cyclopentanediol 127 (28.1 g, 275 mmol, mixture of cis and trans isomers) in anhydrous tetrahydrofuran (500 mL) at 0° C. under nitrogen. The mixture was stirred for 1 h after which a solution of tert-butyldimethylchlorosilane (49.8 g, 330 mmol) in anhydrous tetrahydrofuran (200 mL) was added. The mixture was slowly warmed to room temperature and stirred for a total of 18 h after which the mixture was diluted with brine (500 mL) and extracted with ethyl acetate (2×200 mL). The combined organic extract was dried ($MgSO_4$), filtered, and concentrated. The residue was purified in two batches by CombiFlash Companion (330-g silica gel cartridge), eluting with ethyl acetate/hexanes (1:9 to 3:7), to provide the cis isomer 134A (2.45 g, 4%) as a colorless oil. The later eluting trans isomer 134B (15.18 g, 25%) was also isolated as a colorless oil.

Step 94:

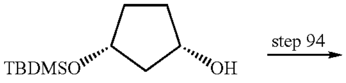

134A

-continued

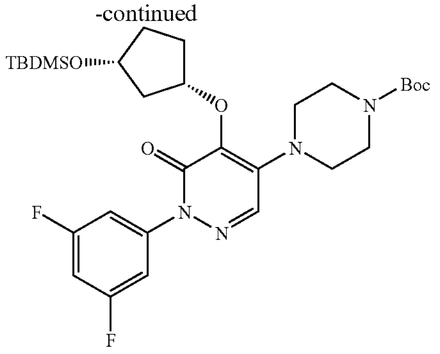

135

To a solution of compound 134A (2.4 g, 11.1 mmol) in anhydrous THF (100 mL) at room temperature under nitrogen was added sodium bis(trimethylsilyl)amide (12 mL, 12.1 mmol, 1.0 M in THF). The mixture was stirred for 10 mins, after which chloropyridazinone (4.3 g, 10.1 mmol) was added portion wise. The mixture was stirred for 28 h after which the mixture was diluted with brine (100 mL) and extracted with ethyl acetate (300 mL). The organic extract was dried ($MgSO_4$), filtered and concentrated. The residue was purified by CombiFlash Companion (120-g silica gel cartridge), eluting with ethyl acetate/hexanes (9:1 to 8:2), to give the product 135 (4.3 g, 71%) as an off-white solid. MS (M−H—$SiMe_2tBu$): m/e 491.

Step 95:

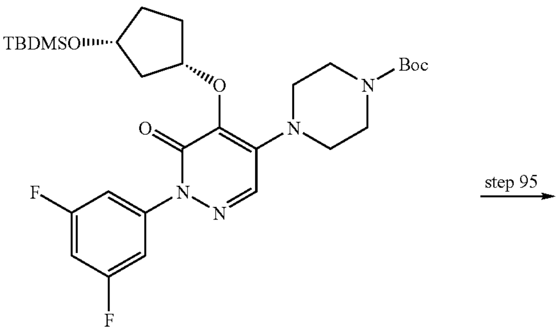

135

-continued

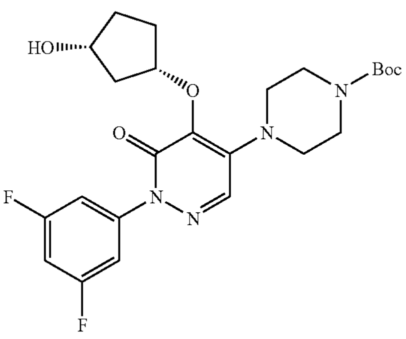

136

To a solution of compound 135 (4.3 g, 7.1 mmol) in anhydrous THF (50 mL) at 0° C. under nitrogen was added tetra-n-butylammonium fluoride (8.5 mL, 8.5 mmol, 1 M in THF), and the mixture was slowly warmed to room temperature and stirred for a total of 18 h. The mixture was diluted with ethyl acetate (200 mL), washed with brine (100 mL), dried ($MgSO_4$), filtered, and concentrated. Purification by CombiFlash Companion (80-g silica gel cartridge), eluting with ethyl acetate/hexanes (2:8 to 8:2) gave the product 136 (2.88 g 82% c) as an off-white solid. MS (M−H): m/e 491.

Step 96:

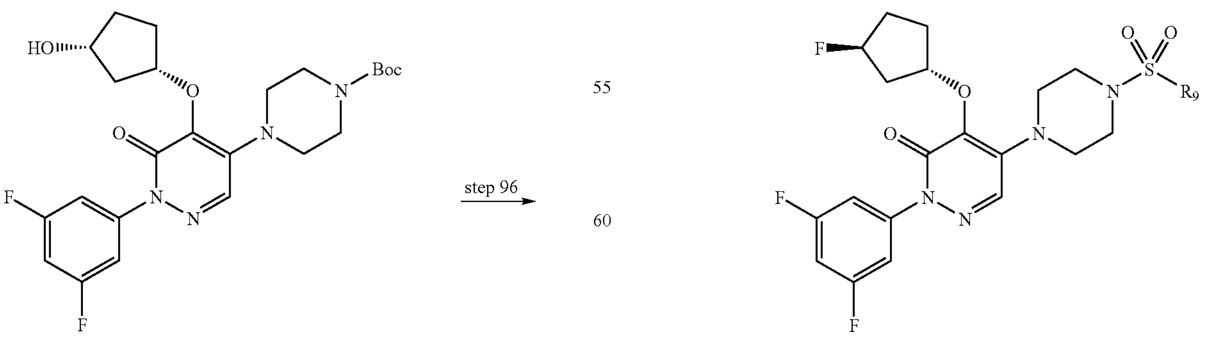

136

138

-continued

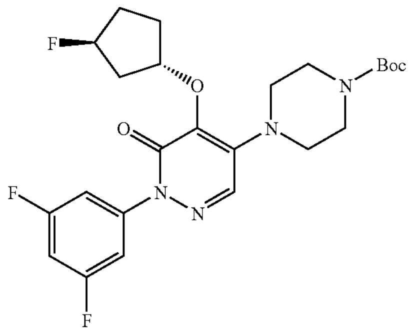

137

Diethylaminosulfur trifluoride (DAST, 1.2 mL, 8.8 mmol) was added dropwise to a solution of compound 136 (2.88 g, 5.8 mmol) in anhydrous methylene chloride (100 mL) at −20° C. under nitrogen. The mixture was stirred for 3.5 h after which it was warmed to 0° C. and diluted with saturated aqueous sodium bicarbonate solution (50 mL) and extracted with methylene chloride (2×100 mL). The combined organic extract was washed with brine (100 mL) and then concentrated. Purification by CombiFlash Companion (80-g silica gel cartridge), eluting with ethyl acetate/hexanes (1:9 to 4:6) gave the product 137 (2.16 g, 75%) as a white solid. MS (M+1): m/e 495.

Steps 6 and 9 of Scheme 1:

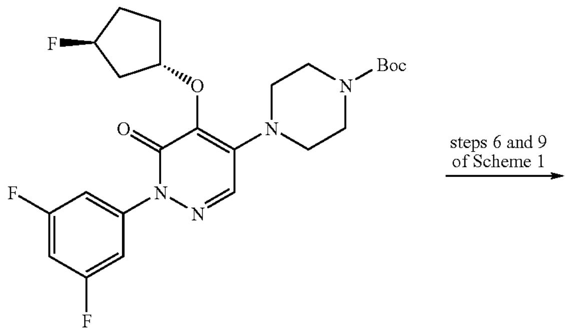

137

TABLE 27
| Oxygen Linked Analogs with Sulfonamide<br>Using the procedures described above, the following compounds were synthesized. | | |
|---|---|---|
| Comp. No. | Structure | MS M + 1 |
| 1607Z | 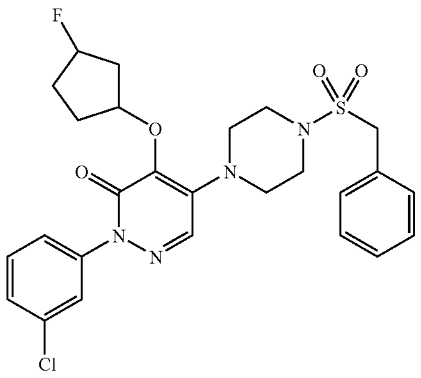 | 547 |
| 1608Z | 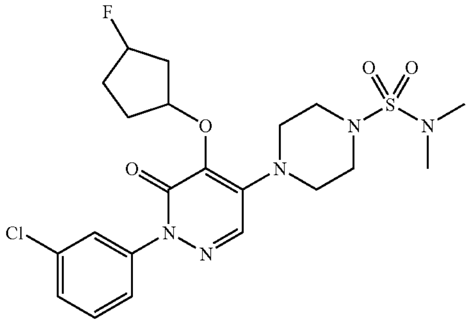 | 500 |
| 1609Z | 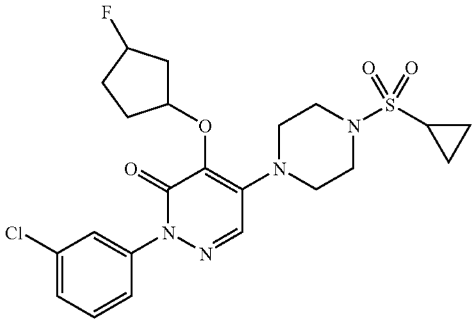 | 497 |
| 1610Z | 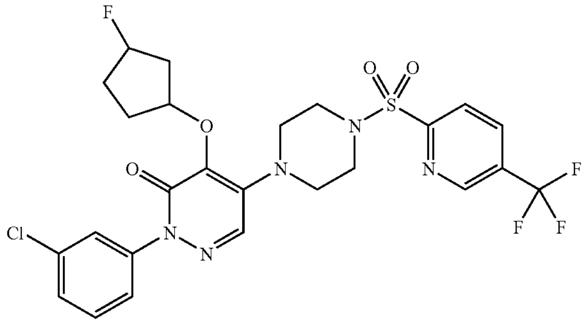 | 602 |

TABLE 27-continued
Oxygen Linked Analogs with Sulfonamide
Using the procedures described above, the following compounds were synthesized.
| Comp. No. | Structure | MS M + 1 |
|---|---|---|
| 1611Z | 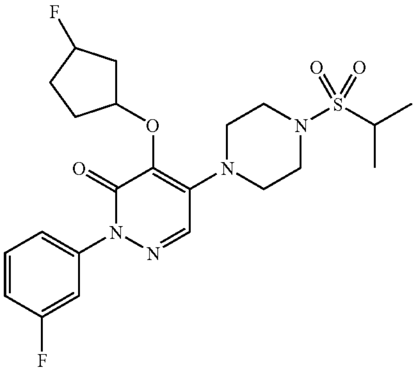 | 483 |
| 1612Z | 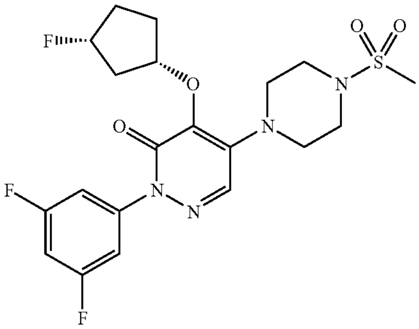 | 473 |
| 1613Z | 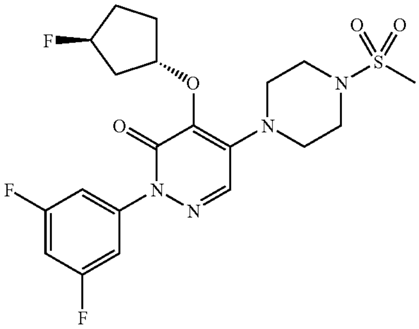 | 473 |
| 1614Z | 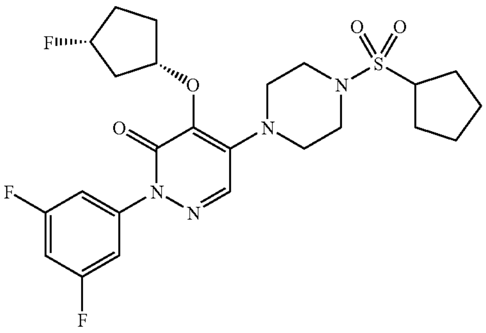 | 527 |

TABLE 27-continued
| Oxygen Linked Analogs with Sulfonamide<br>Using the procedures described above, the following compounds were synthesized. | | |
|---|---|---|
| Comp. No. | Structure | MS M + 1 |
| 1615Z | 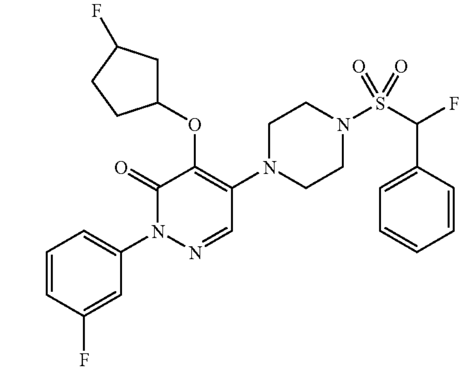 | 549 |
| 1616Z | 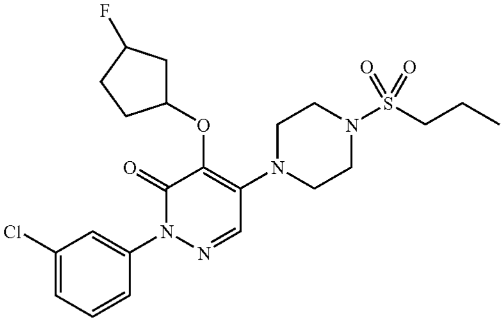 | 499 |
| 1617Z | 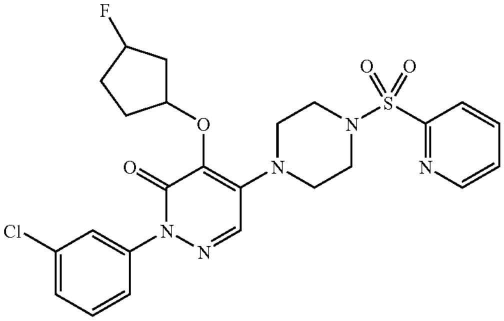 | 534 |
| 1618Z | 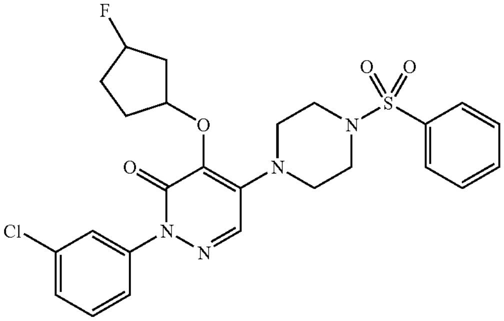 | 533 |

TABLE 27-continued
| Oxygen Linked Analogs with Sulfonamide Using the procedures described above, the following compounds were synthesized. | | |
|---|---|---|
| Comp. No. | Structure | MS M + 1 |
| 1619Z | 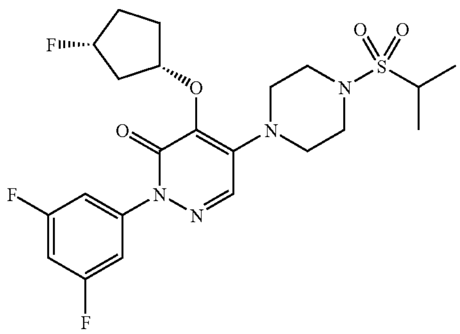 | 501 |
| 1620Z | 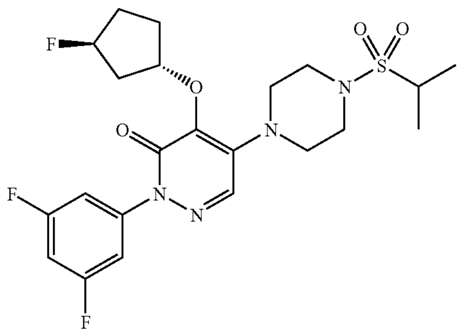 | 501 |
| 1621Z | 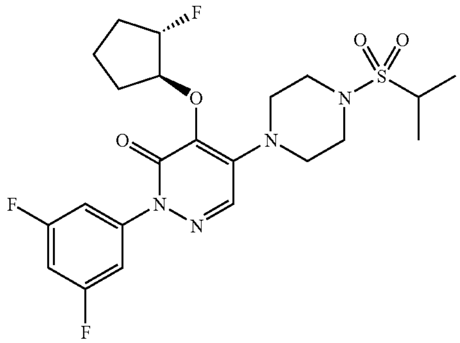 | 501 |
| 1622Z | 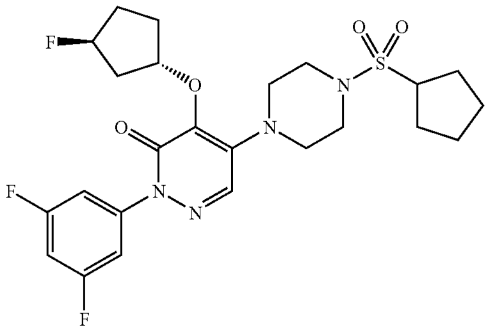 | 527 |

Using the procedure of Scheme 29, the following, compounds listed above in Tables 10 and 11 are prepared: 448Z, 569Z, 570Z, 678Z, 733Z, 765Z, 766Z, 779Z, 793Z, 803Z, 804Z, 821Z, 847Z, 850Z, 851Z, 859Z, 875Z, 888Z, 902Z, 919Z, 925Z, 928Z, 1055Z, 1085Z, 1089Z, 1128Z, 1132Z, 1152Z, 1173Z, 1224Z and 1477Z.

Scheme 30

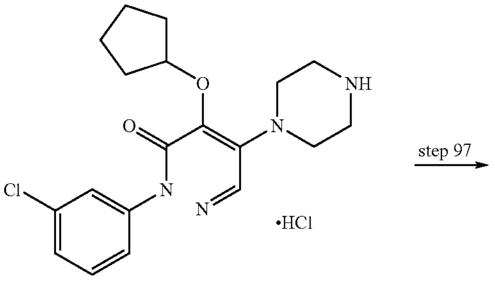

62

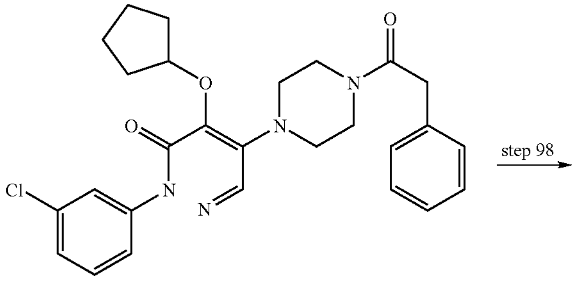

139

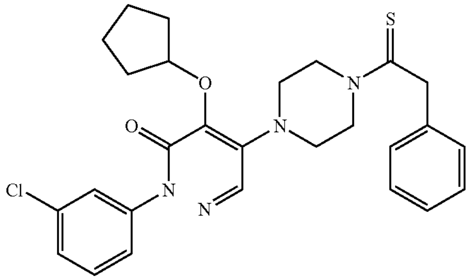

140

Step 97:

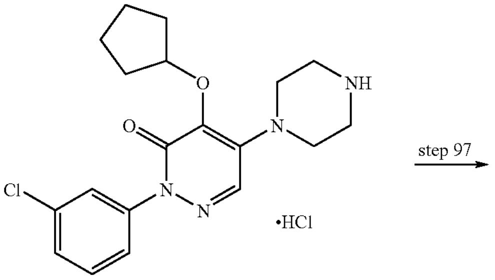

62

-continued

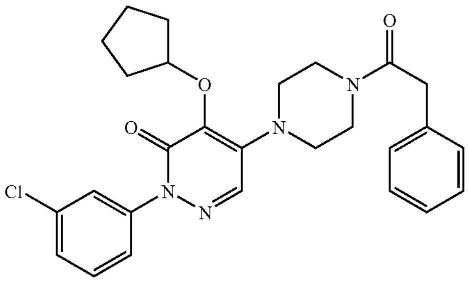

139

Diisopropylethylamine (0.50 mL, 3.0 mmol) was added to a suspension of phenylacetyl chloride (0.16 mL, 1.2 mmol) and amine hydrochloride salt 62 (500 mg, 1.2 mmol) in anhydrous methylene chloride (10 mL) at room temperature under nitrogen. The mixture was stirred for 4 h after which it was directly purified by CombiFlash Companion (80-g silica gel cartridge), eluting with ethyl acetate/hexanes (2:8 to 100% ethyl acetate), to provide the product 139 (460 mg, 77%) as an off-white solid: MS (M+1): m/e 493.

Step 98:

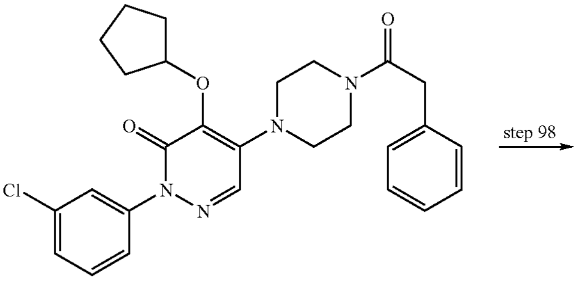

139

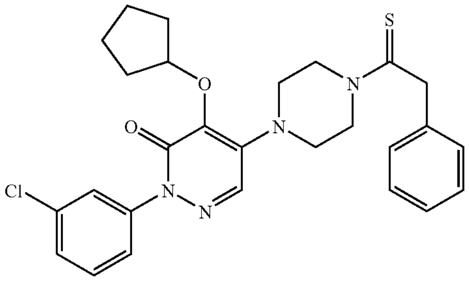

140

A mixture of benzamide 139 (400 mg, 0.81 mmol) and p-methoxyphenyl-thionophosphine sulfide dimer (Lawesson's reagent, 164 mg, 0.41 mmol) in anhydrous toluene (10 mL) was heated at reflux under nitrogen for 3 h. The solvent was removed from the cooled mixture under reduced pressure, and the residue was purified by CombiFlash Companion (80-g silica gel cartridge), eluting with ethyl acetate/hexanes (2:8 to 4:6), to provide the product 140 (420 mg, 99%) as a light yellow solid: MS (M+1): m/e 509.

TABLE 28
| Oxygen Linked Analogs with Sulfamide<br>Using the procedures described above, the following compounds were synthesized. | | |
|---|---|---|
| Comp. No. | Structure | MS M + 1 |
| 1623Z | 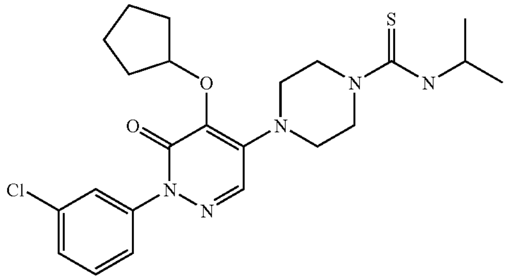 | 476 |
| 1624Z | 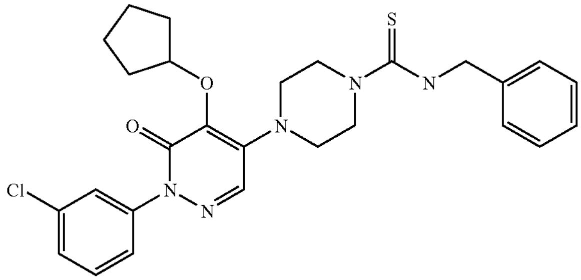 | 524 |
| 1625Z | 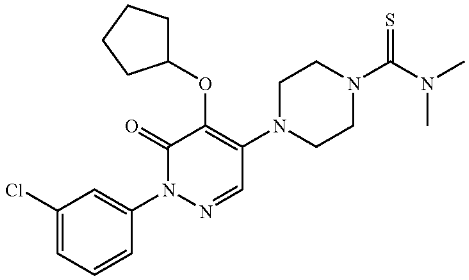 | 462 |
| 1626Z | 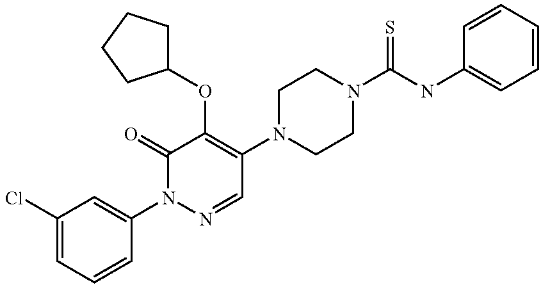 | 510 |
| 1627Z | 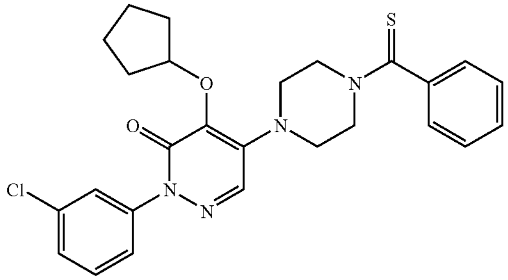 | 495 |

TABLE 28-continued
Oxygen Linked Analogs with Sulfamide
Using the procedures described above, the following compounds were synthesized.
| Comp. No. | Structure | MS M + 1 |
|---|---|---|
| 1628Z | 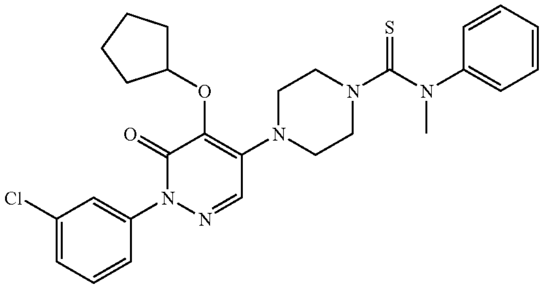 | 524 |
Scheme 31
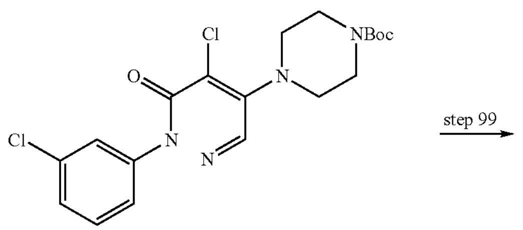
141
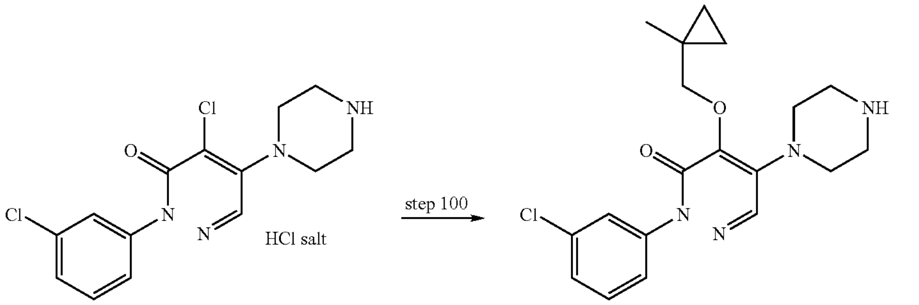
142
143
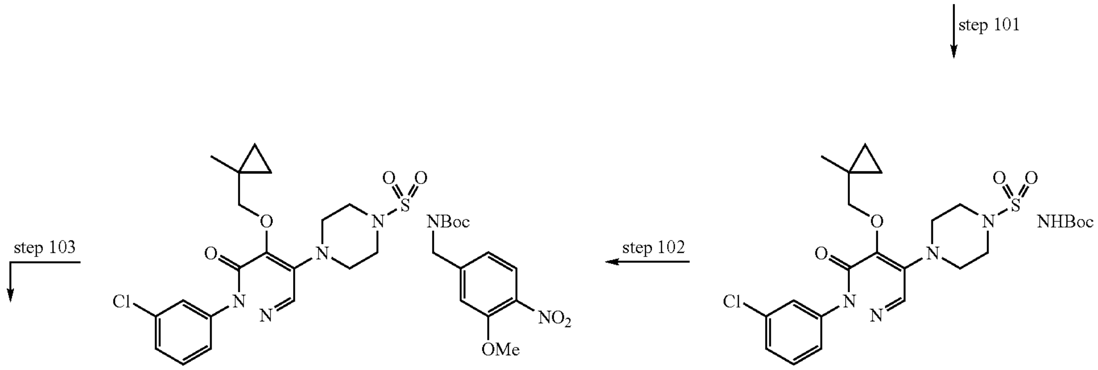
145
144

-continued

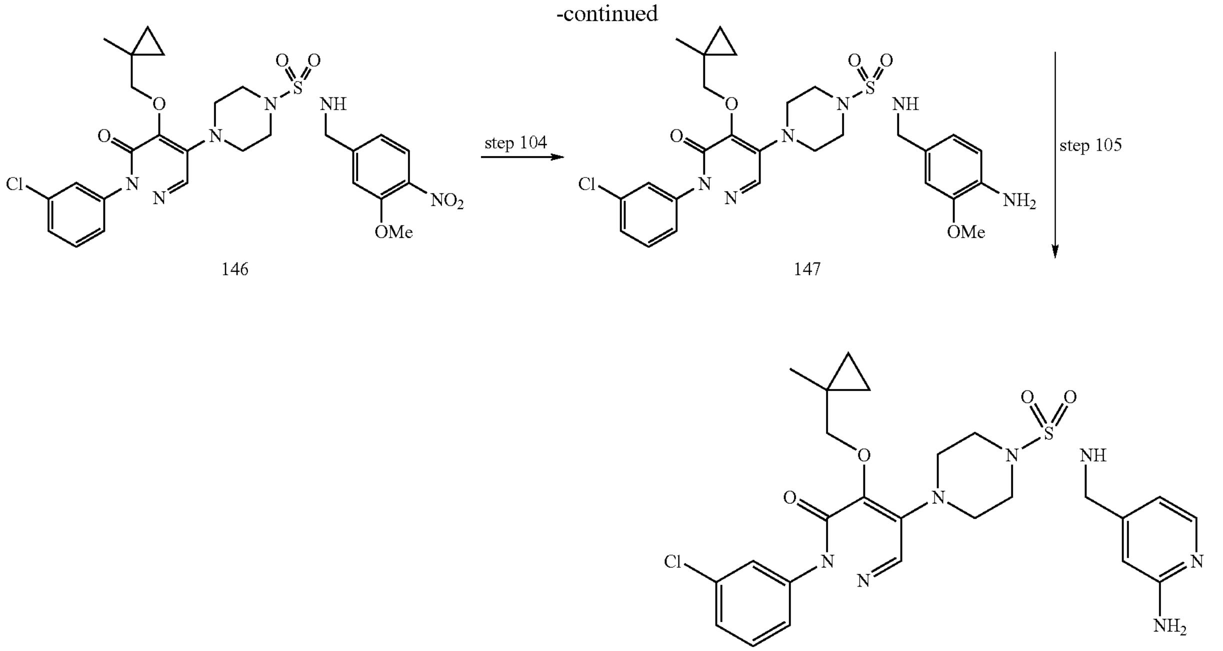

146 147 148

Step 99:

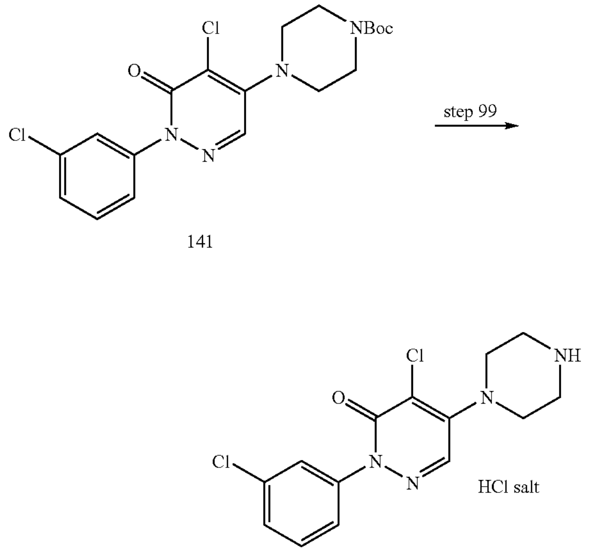

141 142

Compound 141 (20 g) in 50 mL of $CH_2Cl_2$ was treated with 150 mL of 4N HCl/dioxane solution at room temperature for 2 days. Ether (300 mL) was added, and the precipitate was collected by filtration and further washed with ether. The white solid was dried in a vacuum oven at 50° C. overnight to give 16.2 g of the product 142 as the HCl salt. MS (M+1): m/e 325.

Step 100:

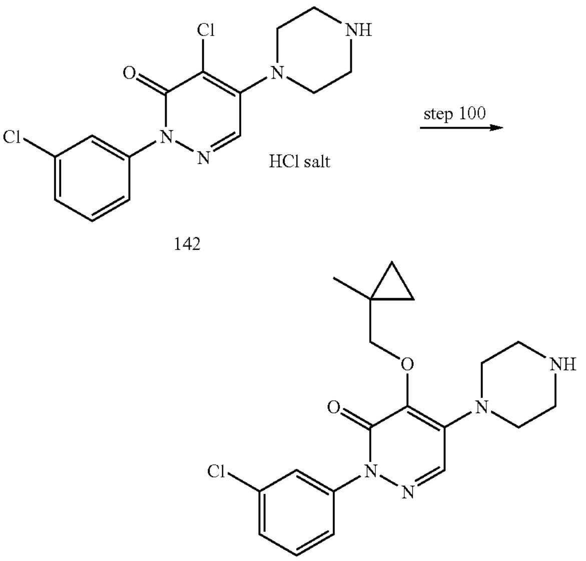

142 143

Compound 142 (7.2 g, 20 mmol) was mixed with methylcyclopropanemethanol (2.6 g, 30 mmol) in 100 mL of dry THF. NaH (60%, 2.0 g, 50 mmol) was added. The resulting mixture was stirred at room temperature for one hour, then heated to 70° C. for 30 mins. The reaction mixture was cooled to room temperature, and water (100 mL) was added. The aqueous solution was extracted with ethyl ether (3×100 mL). The combined organic solutions were washed with brine, concentrated, and further dried by co-evaporation with toluene to give the product 143 as the free amine, which is used in the next step without further purification.

Step 101:

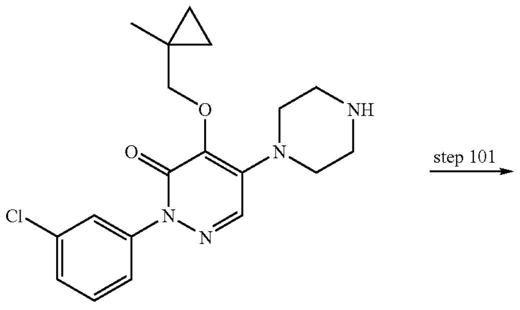

143

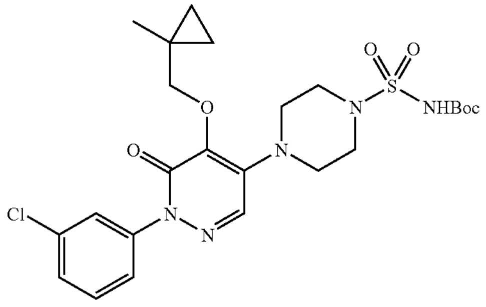

144

-continued

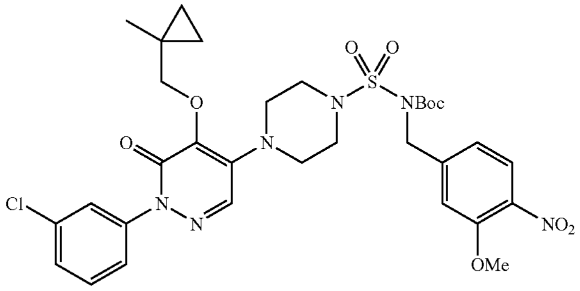

145

Dry t-butanol (4.0 mL, 42 mmol) in 80 mL of dry $CH_2Cl_2$ was cooled to 0° C. Chlorosulfonyl isocyanate (3.5 mL, 40 mmol) was then added dropwise. The resulting solution was stirred at 0° C. for 3 h. This 0.5 M solution of $BocNHSO_2Cl$ was used directly in the next step. Compound 143 (20 mmol) in 100 mL of dry $CH_2Cl_2$ was mixed with isopropyldiethylamine (7 mL, 40 mmol), and cooled to 0° C. in an ice-water bath. A 0.5 M solution of $BocNHSO_2Cl$ (50 mL, 25 mmol) was added dropwise. The resulting mixture was then stirred at room temperature overnight. The mixture was diluted with 500 mL of $CH_2Cl_2$, and washed with 0.5 N HCl solution and water. The organic layer was separated and dried over anhydrous $Na_2SO_4$. The solution was concentrated to about 70 mL, and the precipitate was collected by filtration to give the first batch of product 144 (9.1 g after drying). Further concentration of the solution affords another 1.5 g of the product 144. The product was dried in vacuum over at 50° C. for 2 days before use in the next step.

Step 102:

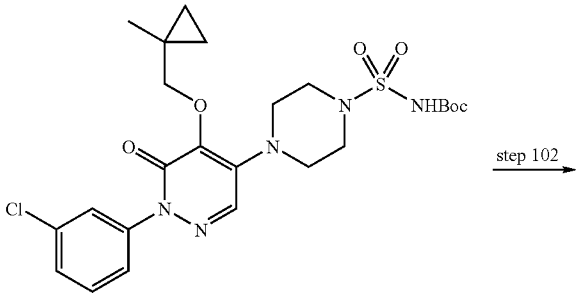

144

Compound 144 (0.11 g, 0.2 mmol) was mixed with (4-bromomethyl)-2-methoxy-1-nitrobenzene (0.054 g, 0.22 mmol) and phosphazene base P1-t-Bu (60 □L, 0.24 mmol) in 2 mL of dry THF. The resulting mixture was stirred at room temperature overnight, and the whole mixture was used directly in the next step.

Step 103:

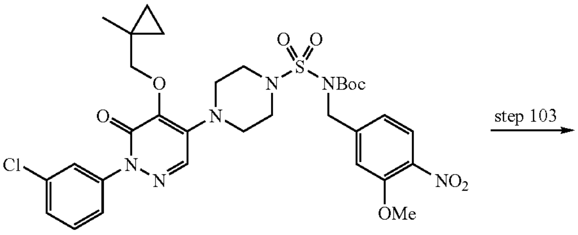

145

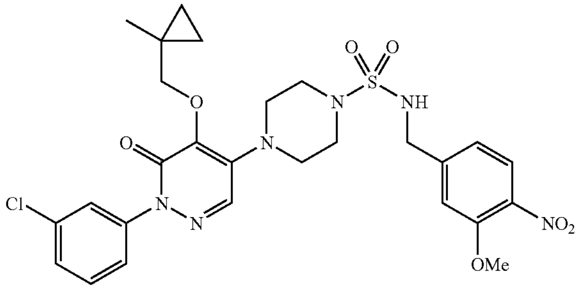

146

Water (0.5 mL) was added to the reaction mixture from step 104. The resulting mixture was heated to 155° C. for 5 mins in the microwave reactor. After cooling to room temperature, the mixture was concentrated and purified by flash chromatography (eluant: 0%-10% EtOAc—$CH_2Cl_2$ gradient) to give 98 mg of compound 146 as a yellow solid. MS (M+1): m/e 619.

Step 104:

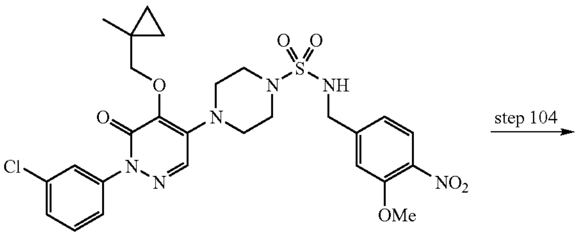

146

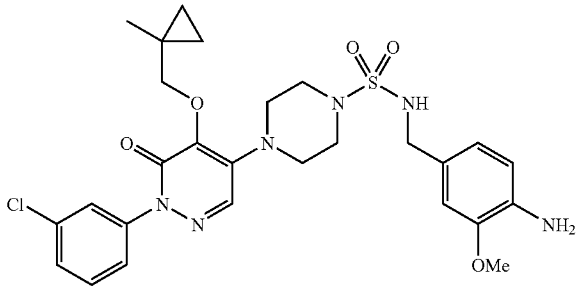

147

Compound 146 (93 mg) was dissolved in 8 mL of EtOAc/MeOH (3:1) mixed solvent system, $PtO_2$ (20 mg) was added. The mixture was stirred under atmospheric $H_2$ for one h. The reaction mixture was concentrated, and the crude product was purified by flash chromatography (eluant: 0%-20% EtOAc—$CH_2Cl_2$ gradient) to give 75 mg of compound 147 as a yellow solid. MS (M+1): m/e 589.

Step 105:

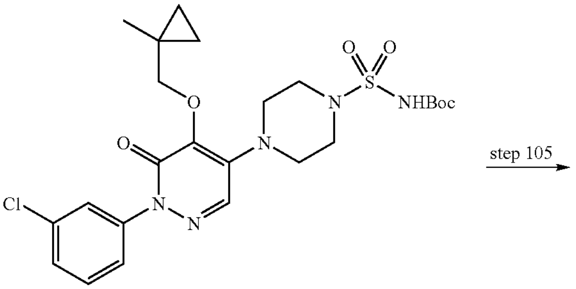

144

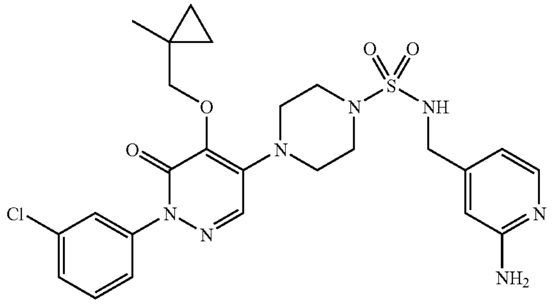

148

Compound 144 (0.11 g, 0.2 mmol) was mixed with (4-hydroxymethyl)-2-amino-pyridine (37 mg, 0.3 mmol), triphenylphosphine (0.12 g, 0.44 mmol), and DEAD (88 mg, 0.48 mmol) in 2 mL of dry THF. The mixture was stirred at room temperature for 3 days.

Water (0.5 mL) was added, and the mixture was heated to 155° C. for 5 mins in the microwave reactor. After cooling to room temperature, the mixture was concentrated and purified by Gilson prep HPLC to give 65 mg (56%) of compound 148 as a white solid. MS (M+1): m/e 560.

Using the procedures described above, the following compounds were synthesized.

TABLE 29

Oxygen Analogues with Sulfamide Tails

Using the procedures described above, the following compounds were synthesized.

| Comp. No. | Structure | MS M + 1 |
|---|---|---|
| 1629Z | 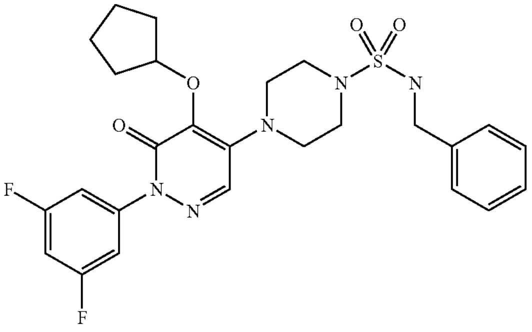 | 544 (M − 1) |

TABLE 29-continued
| Oxygen Analogues with Sulfamide Tails<br>Using the procedures described above, the following compounds were synthesized. | | |
|---|---|---|
| Comp. No. | Structure | MS M + 1 |
| 1630Z | 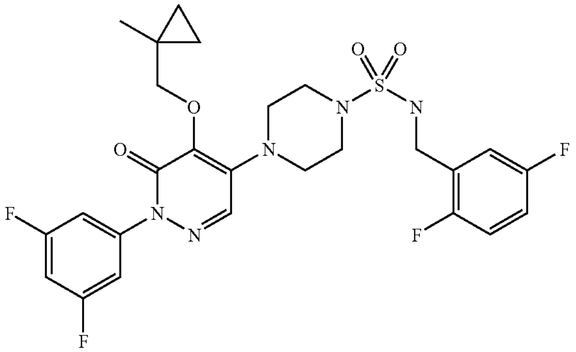 | 582 |
| 1631Z | 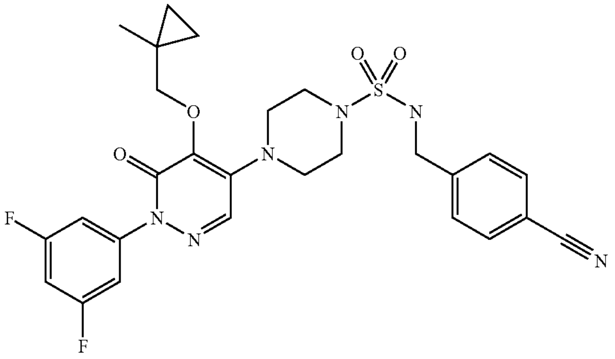 | 571 |
| 1632Z | 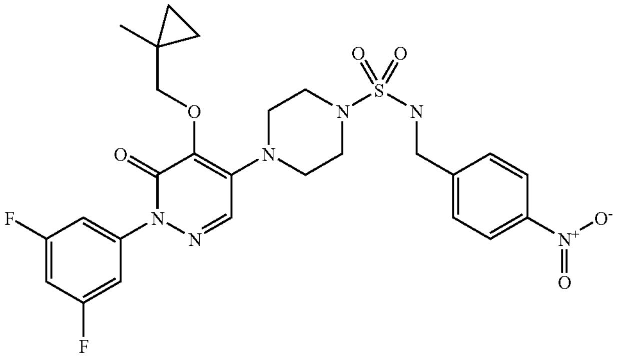 | 591 |
| 1633Z | 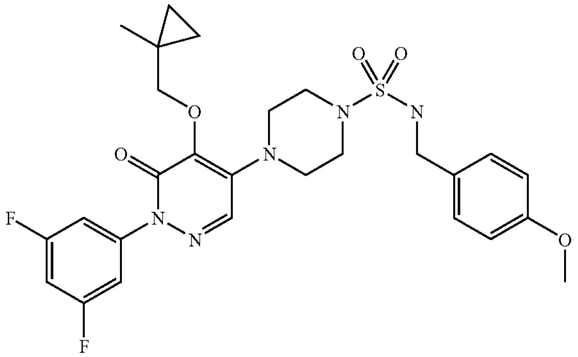 | 576 |

TABLE 29-continued
| Comp. No. | Structure | MS M + 1 |
|---|---|---|
| | Oxygen Analogues with Sulfamide Tails<br>Using the procedures described above, the following compounds were synthesized. | |
| 1634Z | 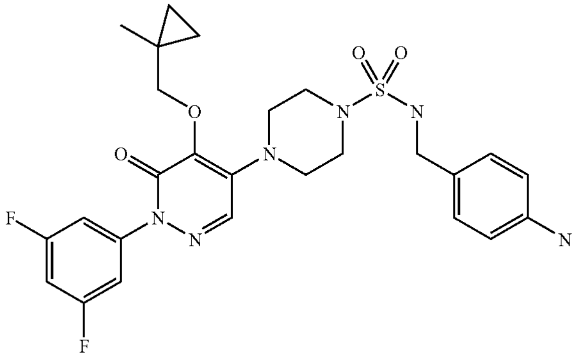 | 561 |
| 1635Z | 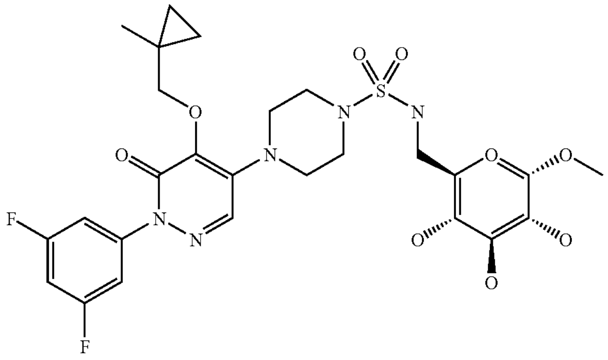 | 632 |
| 1636Z | 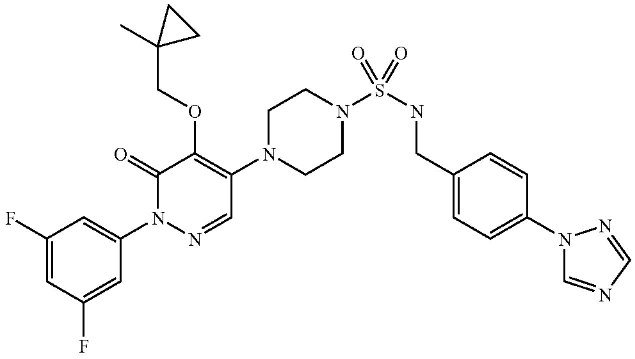 | 613 |
| 1637Z | 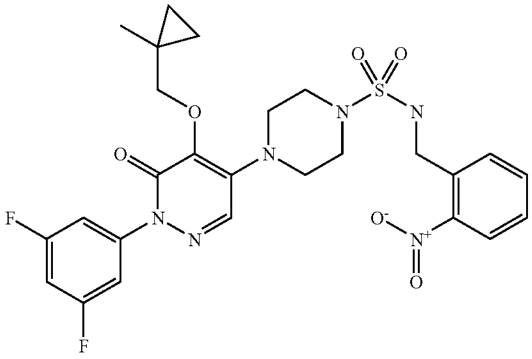 | 591 |

TABLE 29-continued
Oxygen Analogues with Sulfamide Tails
Using the procedures described above, the following compounds were synthesized.
| Comp. No. | Structure | MS M + 1 |
|---|---|---|
| 1638Z | 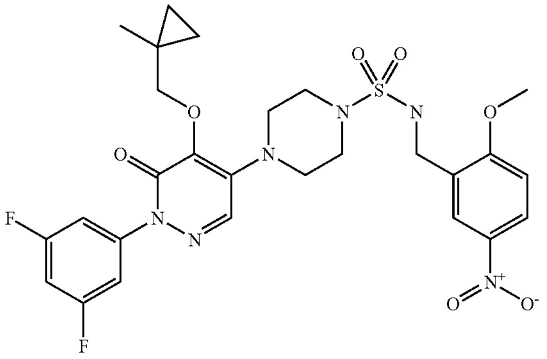 | 621 |
| 1639Z | 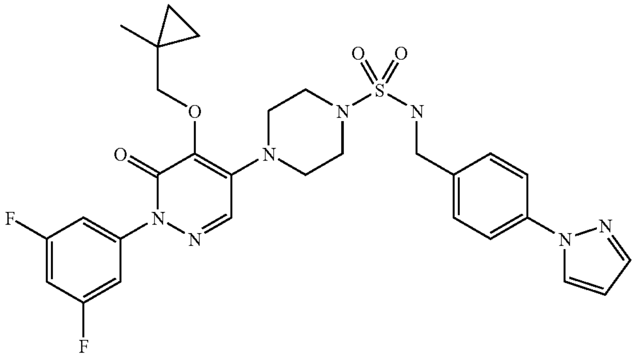 | 612 |
| 1640Z | 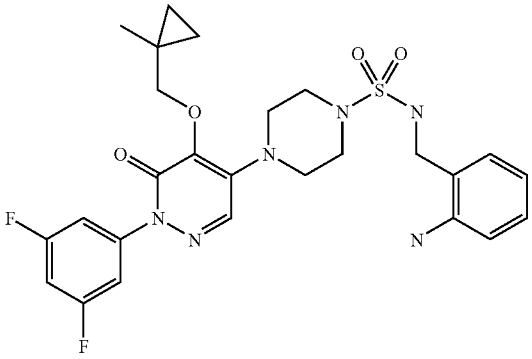 | 561 |
| 1641Z | 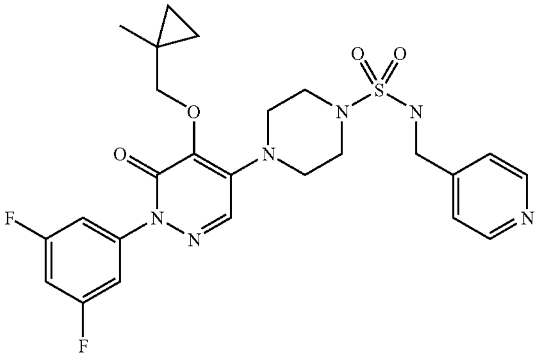 | 547 |

TABLE 29-continued
| Comp. No. | Structure | MS M + 1 |
| --- | --- | --- |
| Oxygen Analogues with Sulfamide Tails Using the procedures described above, the following compounds were synthesized. | | |
| 1642Z | 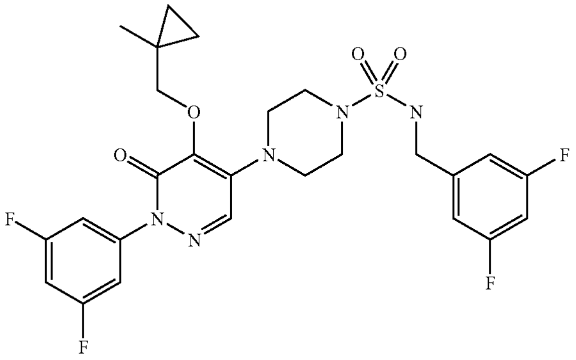 | 582 |
| 1643Z | 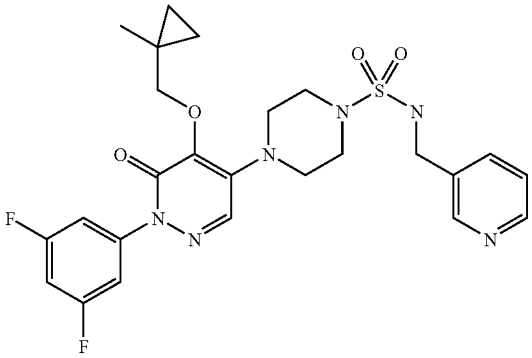 | 547 |
| 1644Z | 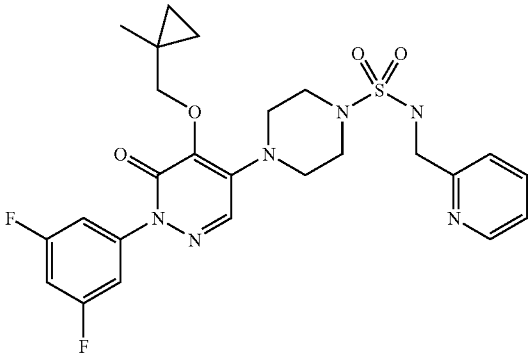 | 547 |
| 1645Z | 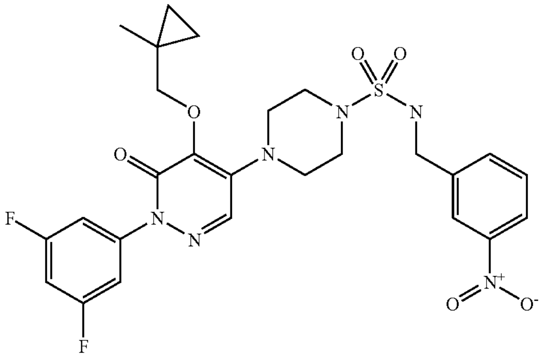 | 591 |

TABLE 29-continued
Oxygen Analogues with Sulfamide Tails
Using the procedures described above, the following compounds were synthesized.
| Comp. No. | Structure | MS M + 1 |
|---|---|---|
| 1646Z | 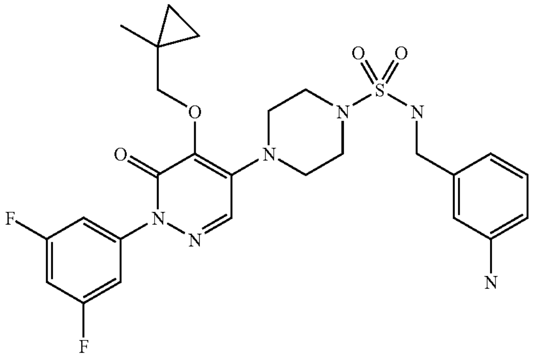 | 561 |
| 1647Z | 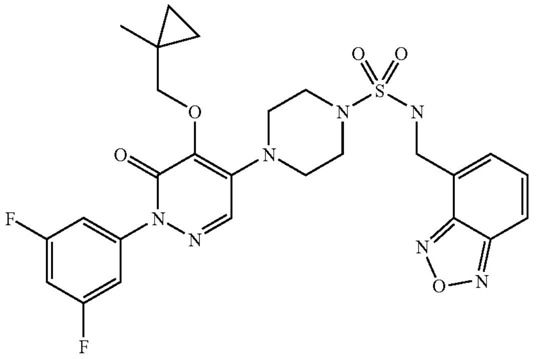 | 588 |
| 1648Z | 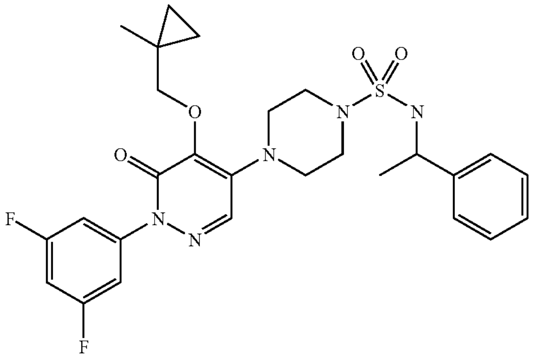 | 560 |
| 1649Z | 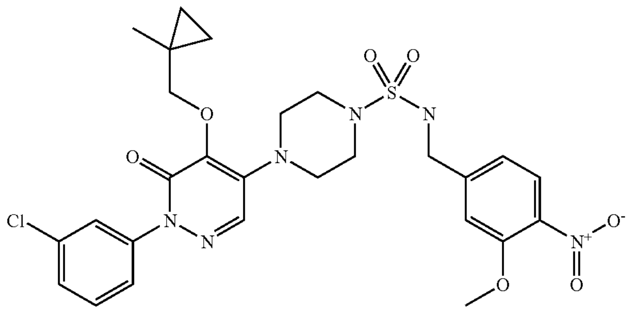 | 619 |

TABLE 29-continued
Oxygen Analogues with Sulfamide Tails
Using the procedures described above, the following compounds were synthesized.
| Comp. No. | Structure | MS M + 1 |
|---|---|---|
| 1650Z | 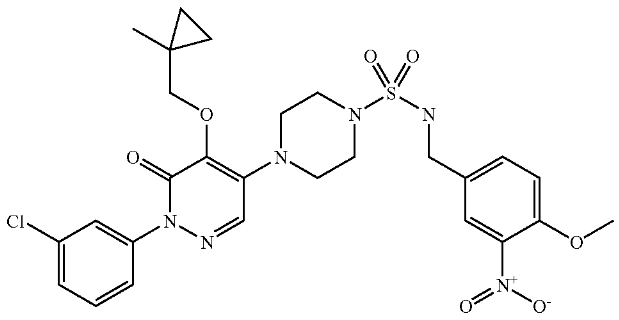 | 619 |
| 1651Z | 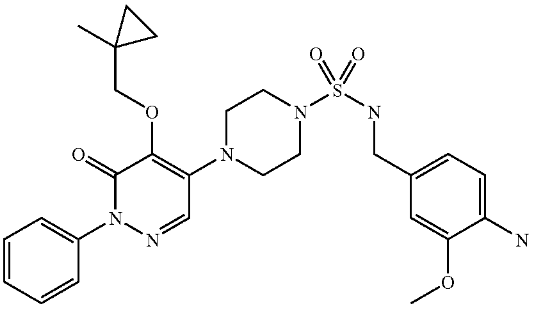 | 555 |
| 1652Z | 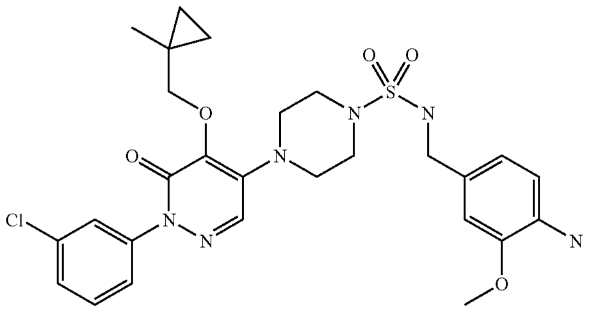 | 589 |
| 1653Z | 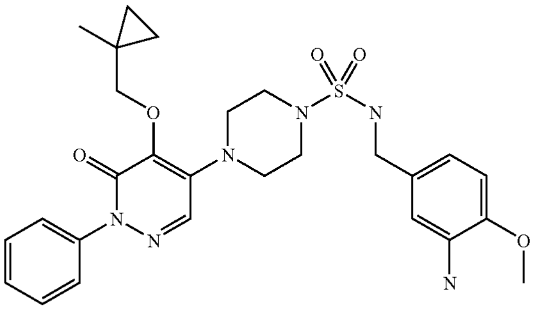 | 555 |

TABLE 29-continued
| Oxygen Analogues with Sulfamide Tails<br>Using the procedures described above, the following compounds were synthesized. | | |
|---|---|---|
| Comp. No. | Structure | MS M + 1 |
| 1654Z | 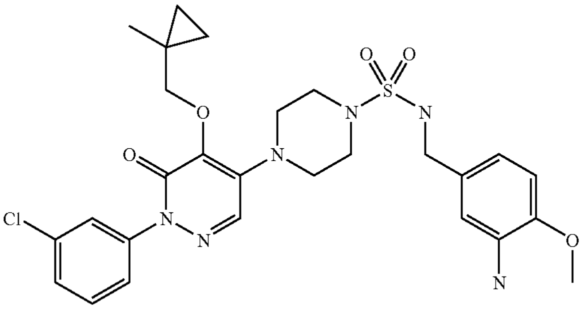 | 589 |
| 1655Z | 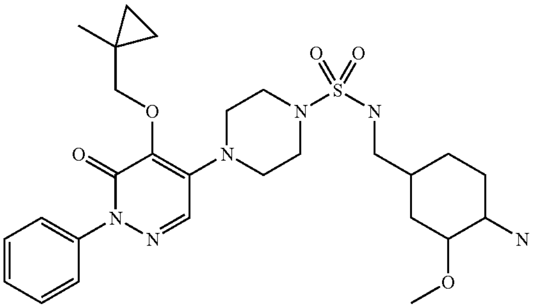 | 561 |
| 1656Z | 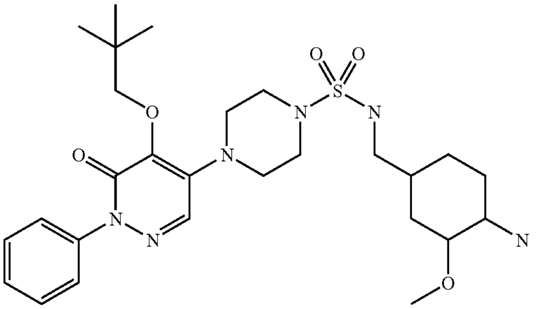 | 563 |
| 1657Z | 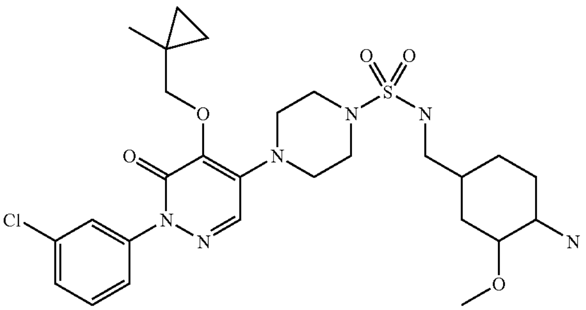 | 595 |

TABLE 29-continued
Oxygen Analogues with Sulfamide Tails
Using the procedures described above, the following compounds were synthesized.
| Comp. No. | Structure | MS M + 1 |
|---|---|---|
| 1658Z | 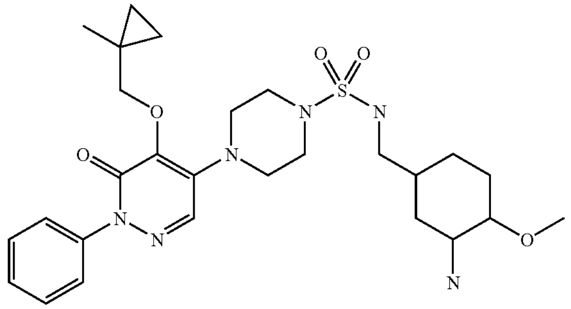 | 561 |
| 1659Z | 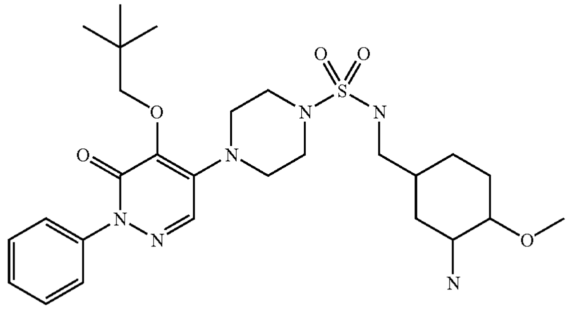 | 563 |
| 1660Z | 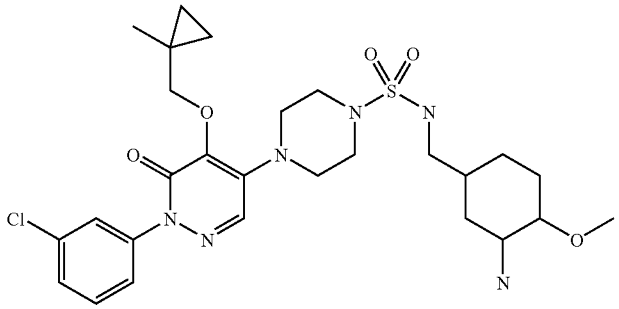 | 595 |
| 1661Z | 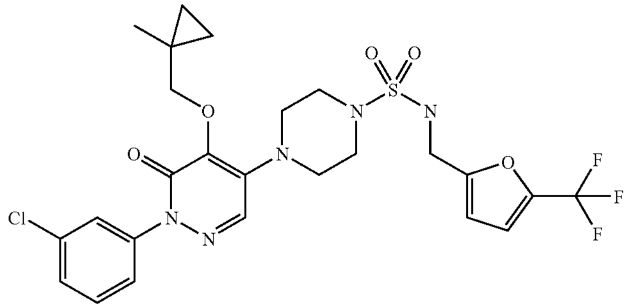 | 602 |

TABLE 29-continued
| Oxygen Analogues with Sulfamide Tails<br>Using the procedures described above, the following compounds were synthesized. | | |
|---|---|---|
| Comp. No. | Structure | MS M + 1 |
| 1662Z | 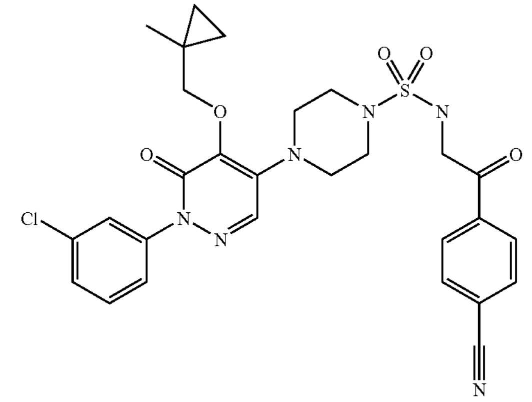 | 597 |
| 1663Z | 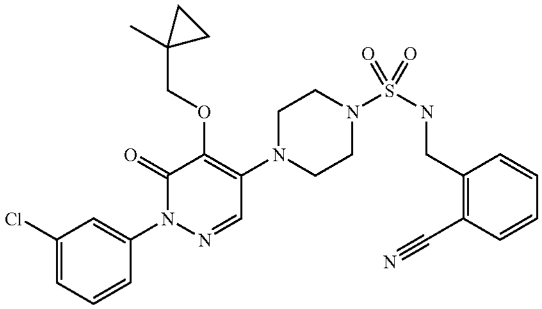 | 569 |
| 1664Z | 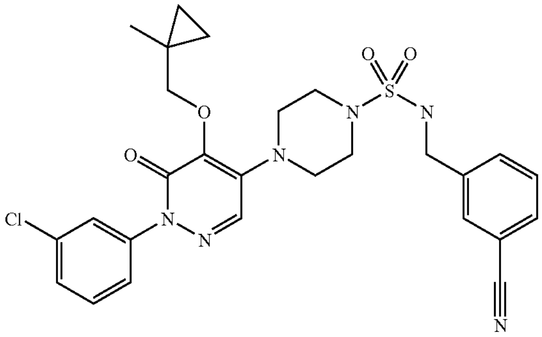 | 569 |
| 1665Z | 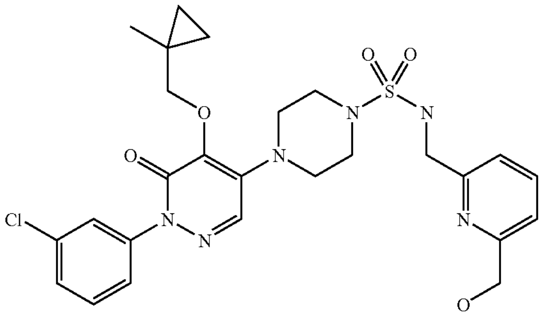 | 575 |

TABLE 29-continued
| Oxygen Analogues with Sulfamide Tails<br>Using the procedures described above, the following compounds were synthesized. | | |
|---|---|---|
| Comp. No. | Structure | MS M + 1 |
| 1666Z | 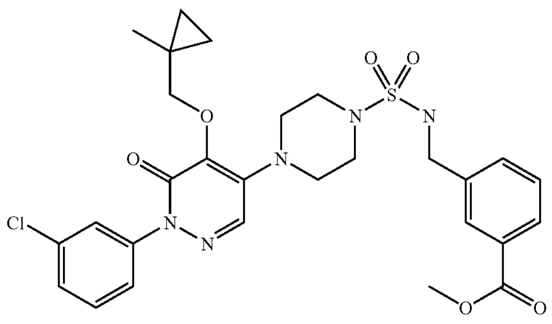 | 602 |
| 1667Z | 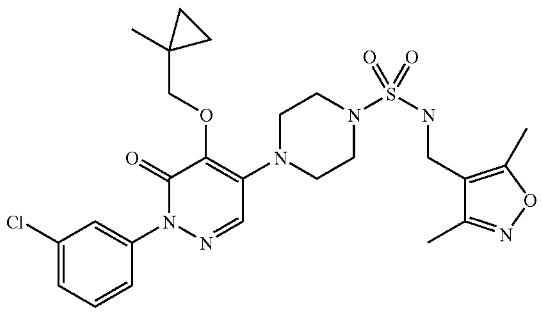 | 563 |
| 1668Z | 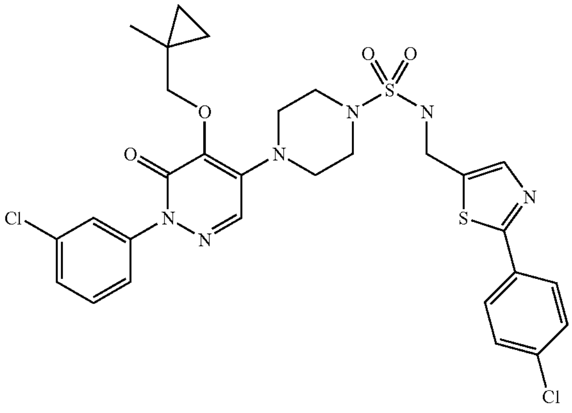 | 661 |

TABLE 29-continued
| Oxygen Analogues with Sulfamide Tails<br>Using the procedures described above, the following compounds were synthesized. | | |
|---|---|---|
| Comp. No. | Structure | MS M + 1 |
| 1669Z | 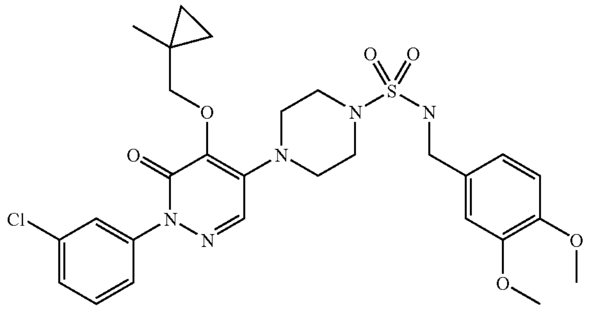 | 604 |
| 1670Z | 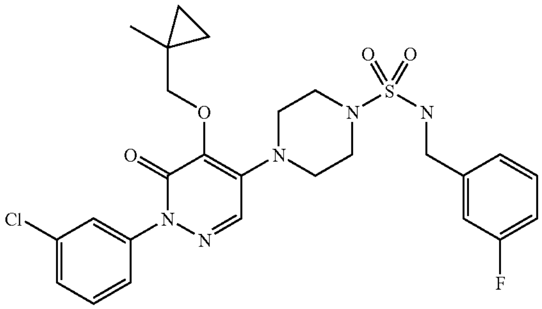 | 562 |
| 1671Z | 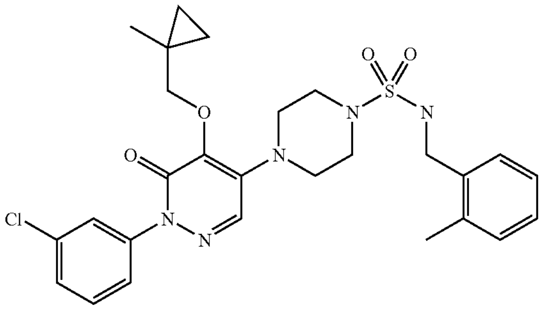 | 558 |
| 1672Z | 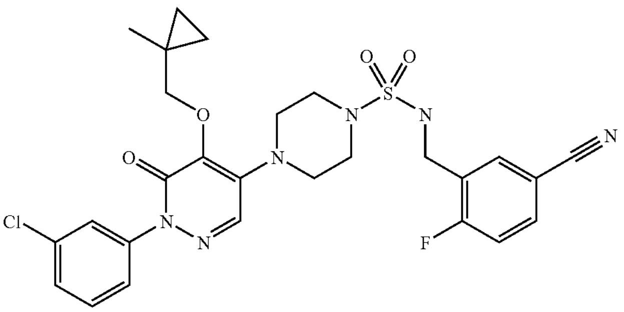 | 587 |

TABLE 29-continued
| Oxygen Analogues with Sulfamide Tails<br>Using the procedures described above, the following compounds were synthesized. | | |
|---|---|---|
| Comp. No. | Structure | MS M + 1 |
| 1673Z | 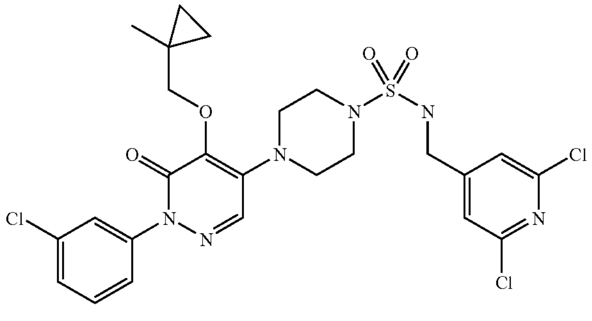 | 615 |
| 1674Z | 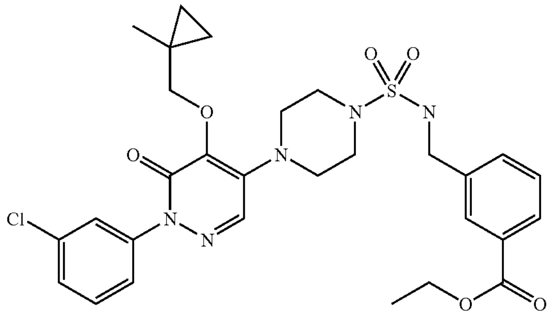 | 616 |
| 1675Z | 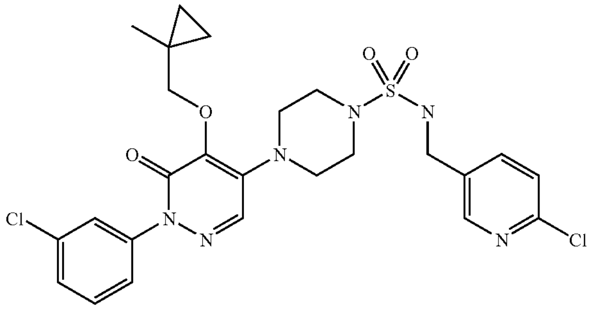 | 579 |
| 1676Z | 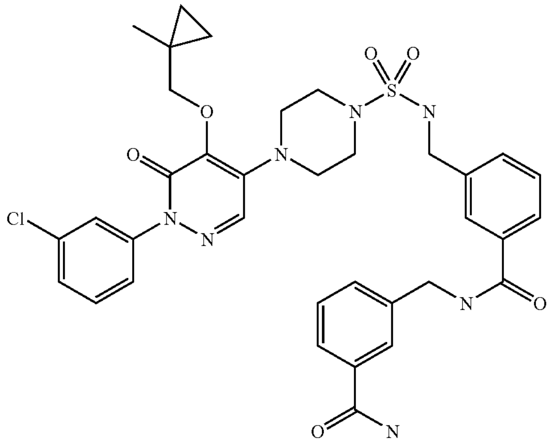 | 720 |

TABLE 29-continued
| Comp. No. | Structure | MS M + 1 |
|---|---|---|
| | Oxygen Analogues with Sulfamide Tails<br>Using the procedures described above, the following compounds were synthesized. | |
| 1677Z | 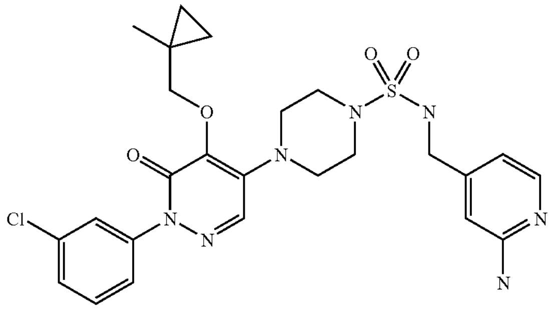 | 560 |
| 1678Z | 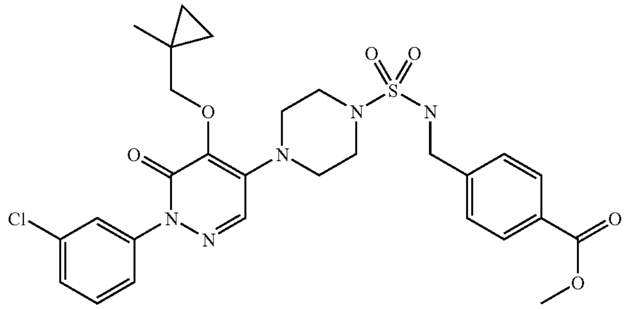 | 602 |
| 1679Z | 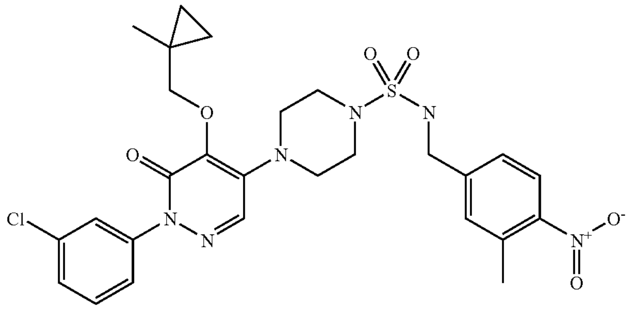 | 603 |
| 1680Z | 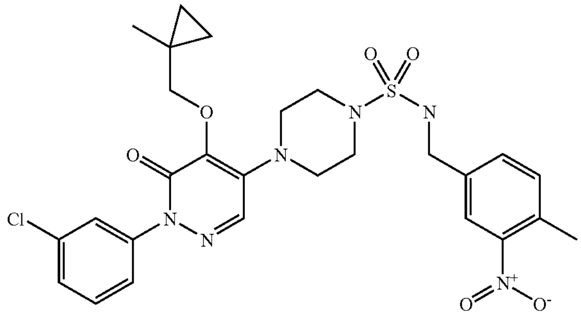 | 603 |

TABLE 29-continued
Oxygen Analogues with Sulfamide Tails
Using the procedures described above, the following compounds were synthesized.
| Comp. No. | Structure | MS M + 1 |
|---|---|---|
| 1681Z | 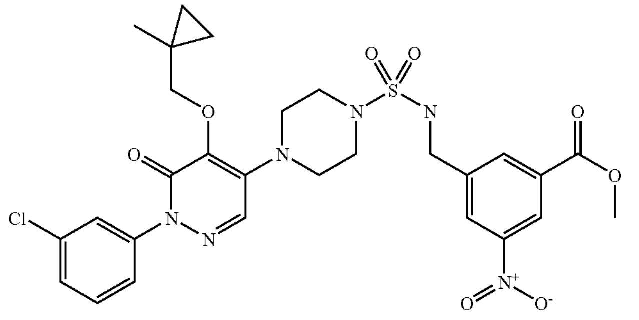 | 647 |
| 1682Z | 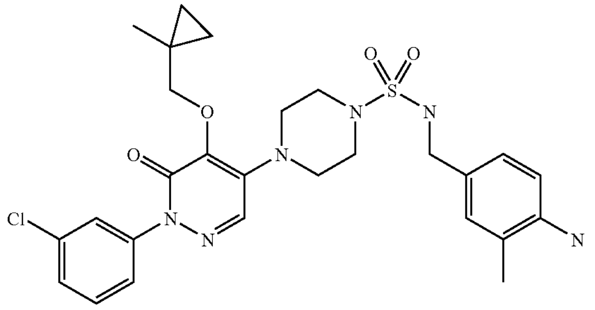 | 573 |
| 1683Z | 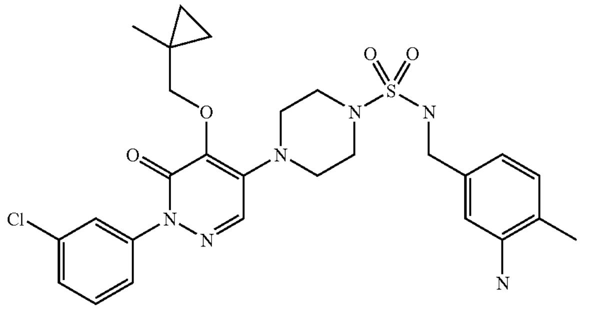 | 573 |
| 1684Z | 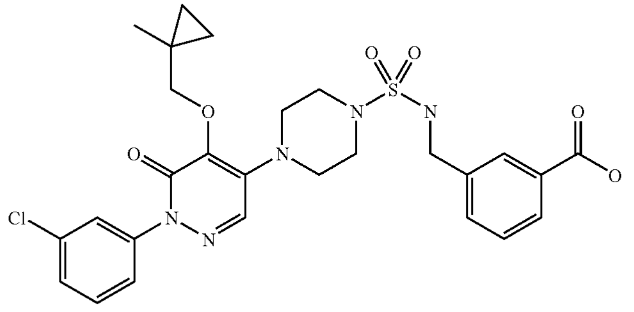 | 588 |

TABLE 29-continued
| Oxygen Analogues with Sulfamide Tails<br>Using the procedures described above, the following compounds were synthesized. | | |
|---|---|---|
| Comp. No. | Structure | MS M + 1 |
| 1685Z | 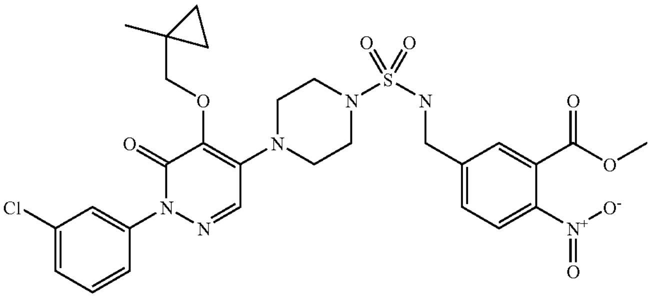 | 647 |
| 1686Z | 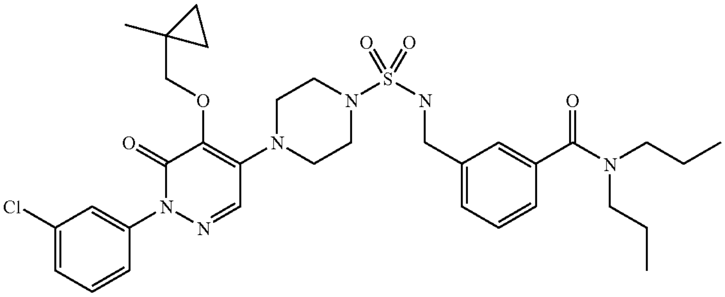 | 671 |
| 1687Z | 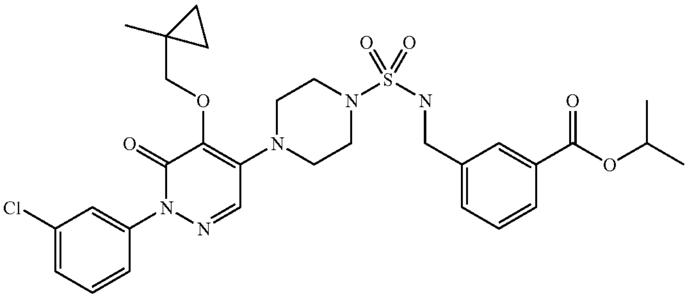 | 630 |
| 1688Z | 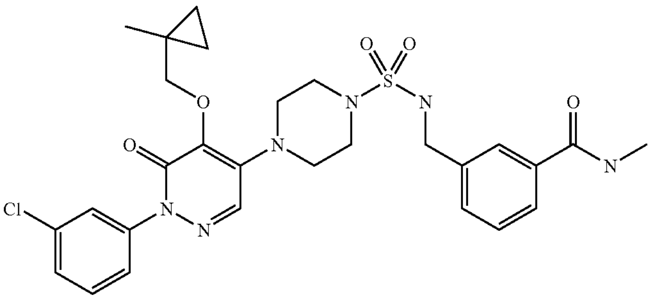 | 601 |

TABLE 29-continued
Oxygen Analogues with Sulfamide Tails
Using the procedures described above, the following compounds were synthesized.
| Comp. No. | Structure | MS M + 1 |
|---|---|---|
| 1689Z | 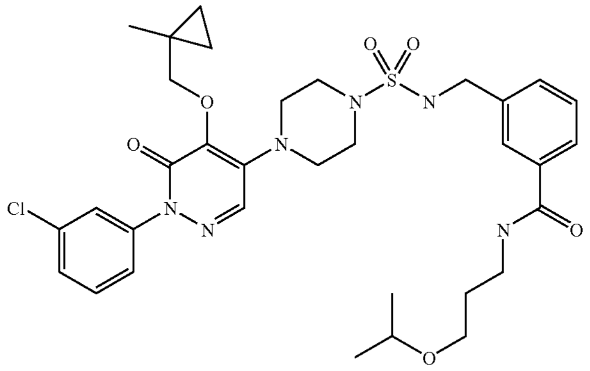 | 687 |
| 1690Z | 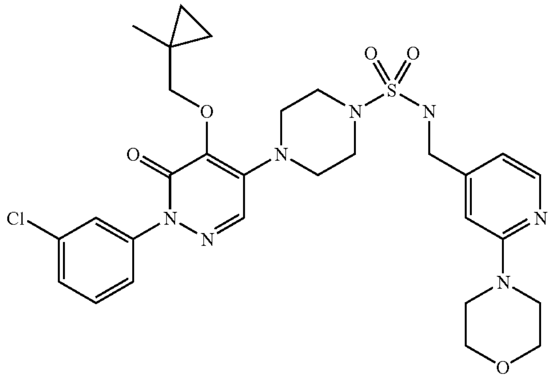 | 630 |
| 1691Z | 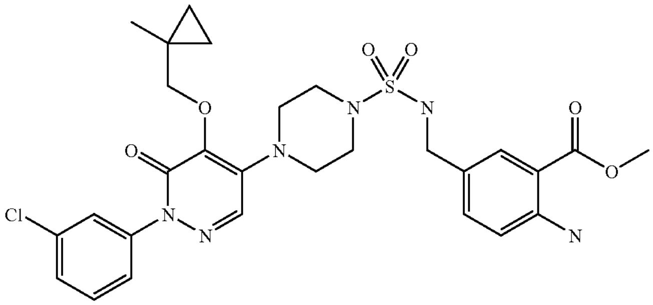 | 617 |
| 1692Z | 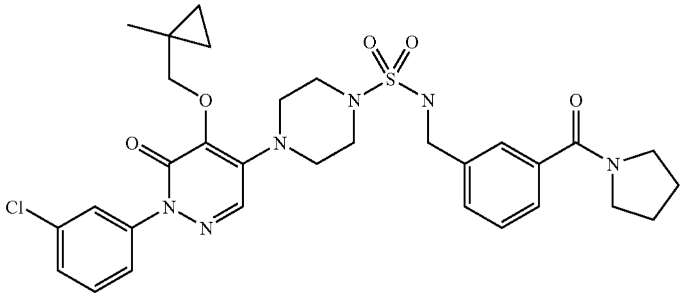 | 641 |

TABLE 29-continued
Oxygen Analogues with Sulfamide Tails
Using the procedures described above, the following compounds were synthesized.
| Comp. No. | Structure | MS M + 1 |
|---|---|---|
| 1693Z | 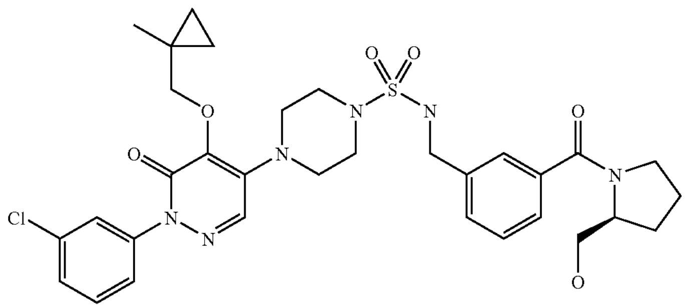 | 671 |
| 1694Z | 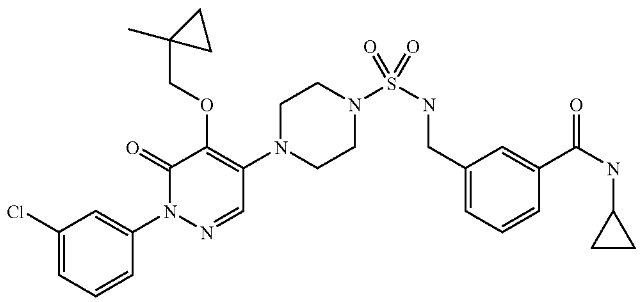 | 627 |
| 1695Z | 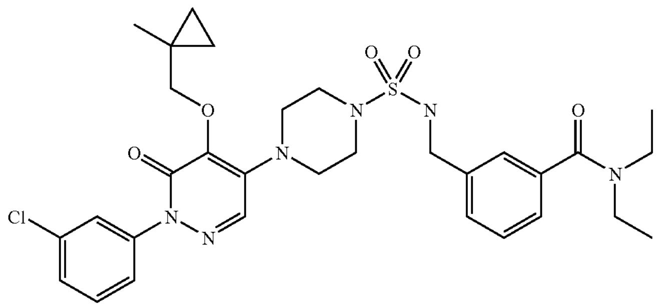 | 643 |
| 1696Z | 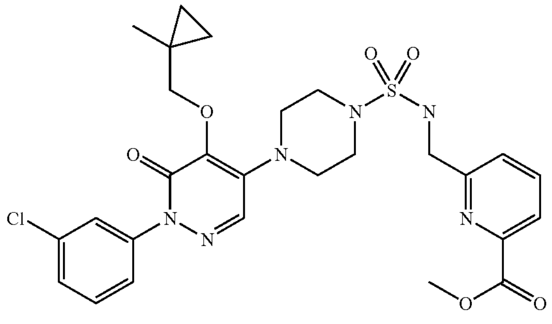 | 603 |

TABLE 29-continued
Oxygen Analogues with Sulfamide Tails
Using the procedures described above, the following compounds were synthesized.
| Comp. No. | Structure | MS M + 1 |
| --- | --- | --- |
| 1697Z | 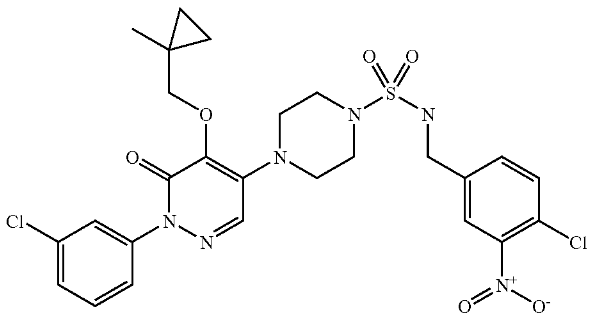 | 623 |
| 1698Z | 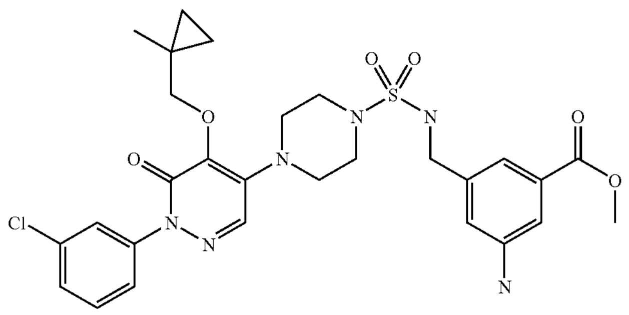 | 617 |
| 1699Z | 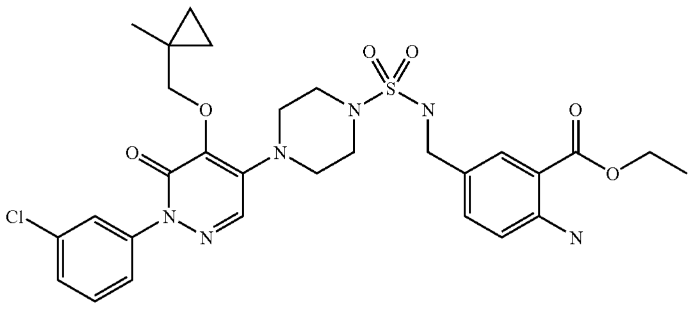 | 631 |
| 1700Z | 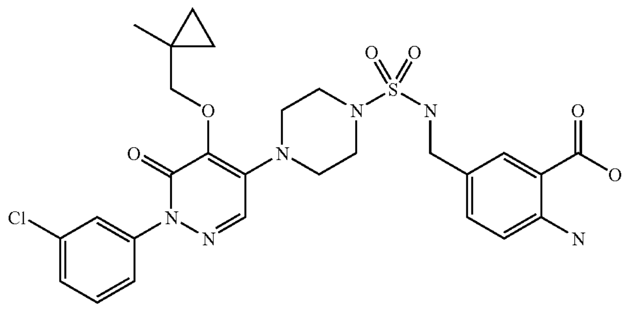 | 603 |

TABLE 29-continued
| Comp. No. | Oxygen Analogues with Sulfamide Tails<br>Using the procedures described above, the following compounds were synthesized.<br>Structure | MS M + 1 |
|---|---|---|
| 1701Z | 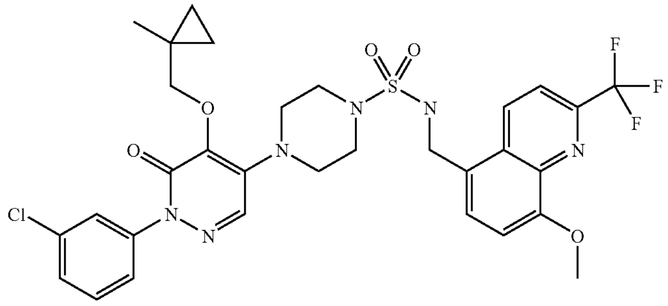 | 693 |
| 1702Z | 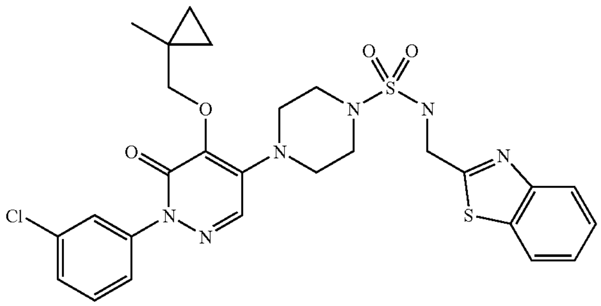 | 601 |
| 1703Z | 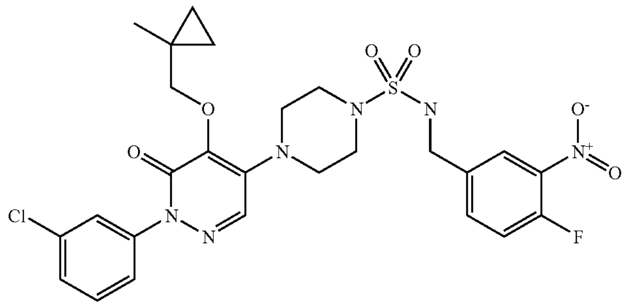 | 607 |
| 1704Z | 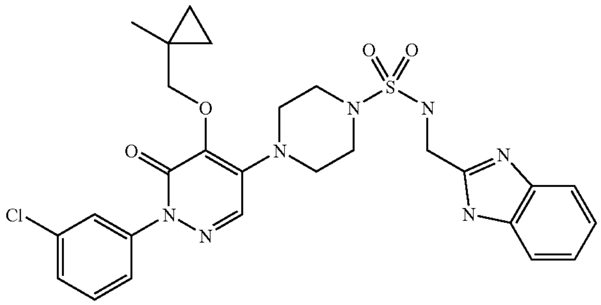 | 584 |

TABLE 29-continued
| Oxygen Analogues with Sulfamide Tails<br>Using the procedures described above, the following compounds were synthesized. | | |
|---|---|---|
| Comp. No. | Structure | MS M + 1 |
| 1705Z | 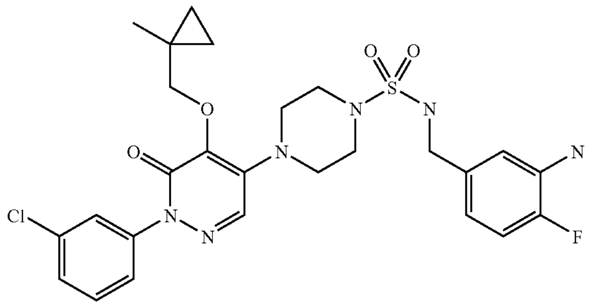 | 577 |
| 1706Z | 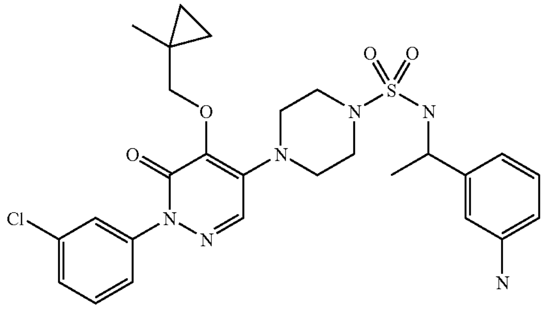 | 573 |
| 1707Z | 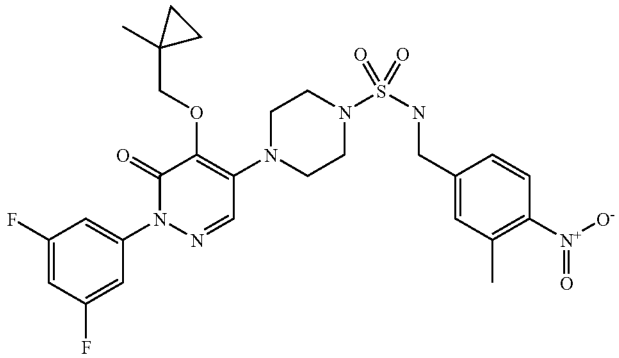 | 605 |
| 1708Z | 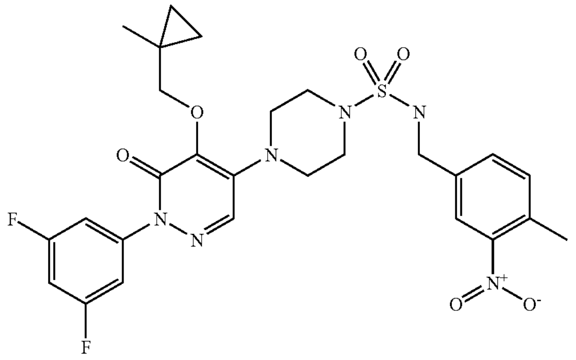 | 605 |

TABLE 29-continued
| Oxygen Analogues with Sulfamide Tails<br>Using the procedures described above, the following compounds were synthesized. | | |
|---|---|---|
| Comp. No. | Structure | MS M + 1 |
| 1709Z | 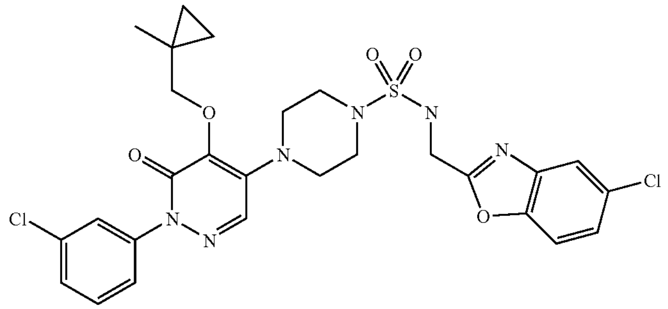 | 621 |
| 1710Z | 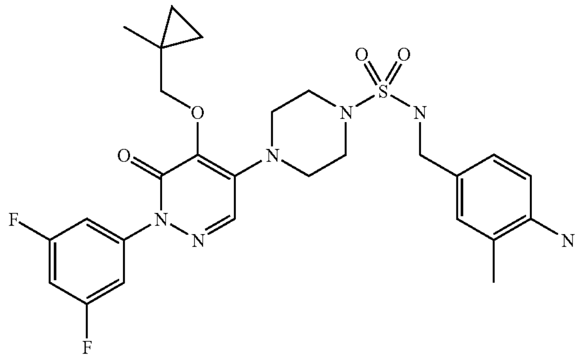 | 575 |
| 1711Z | 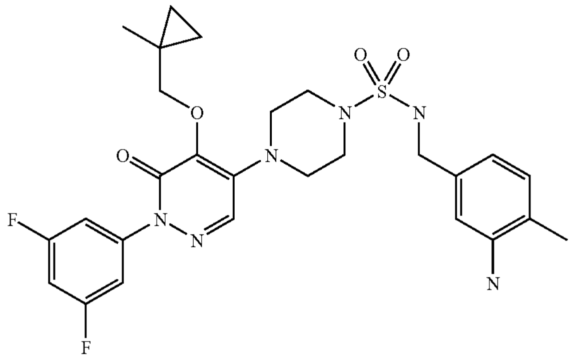 | 575 |
| 1712Z | 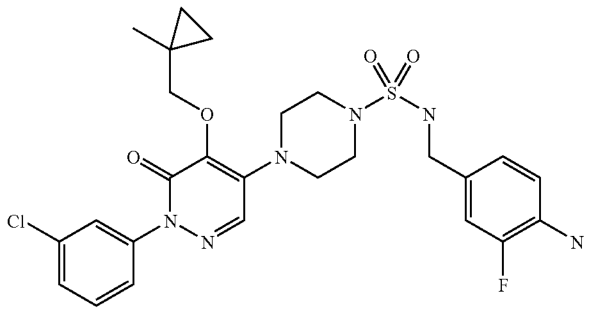 | 577 |

TABLE 29-continued
| Comp. No. | Structure | MS M + 1 |
|---|---|---|
| | Oxygen Analogues with Sulfamide Tails<br>Using the procedures described above, the following compounds were synthesized. | |
| 1713Z | 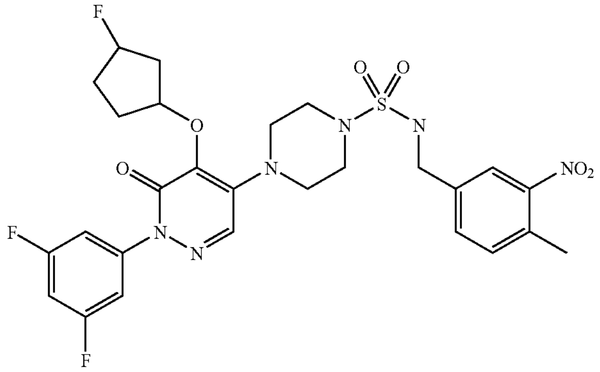 | 623 |
| 1714Z | 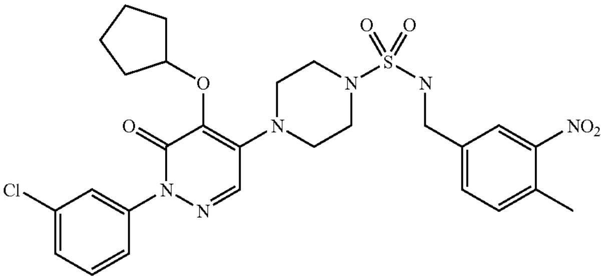 | 603 |
| 1715Z | 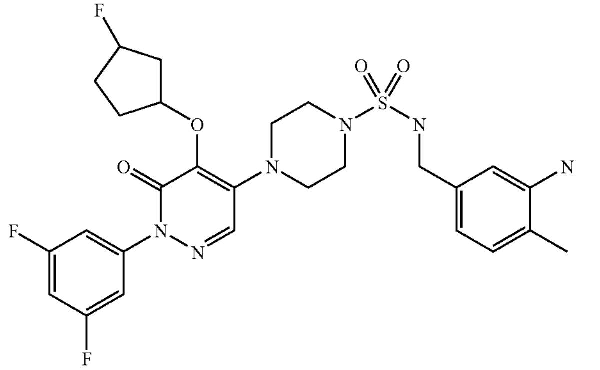 | 593 |
| 1716Z | 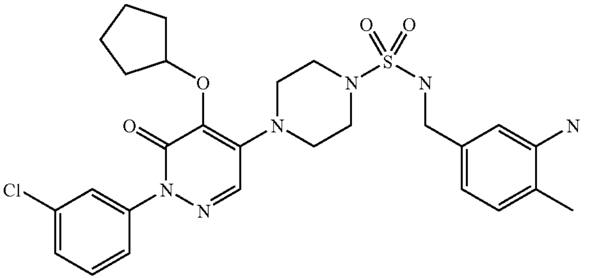 | 573 |

TABLE 29-continued
| Comp. No. | Structure | MS M + 1 |
| --- | --- | --- |
| | Oxygen Analogues with Sulfamide Tails<br>Using the procedures described above, the following compounds were synthesized. | |
| 1717Z | 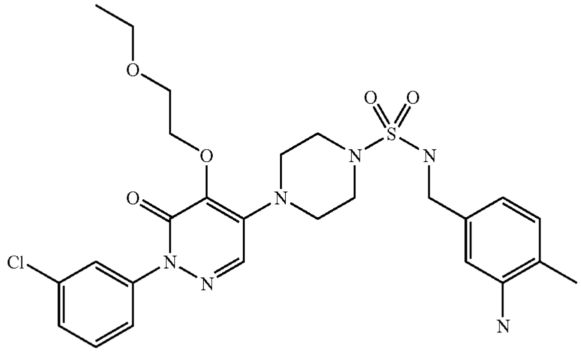 | 577 |
| 1718Z | 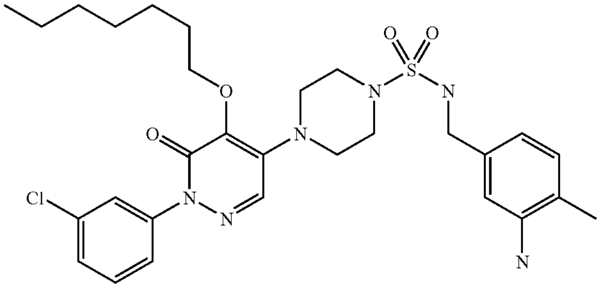 | 603 |
| 1719Z | 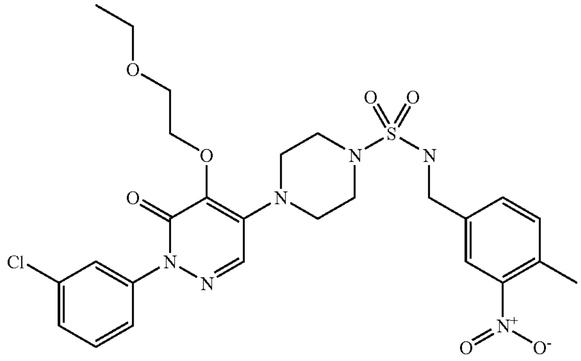 | 607 |
| 1720Z | 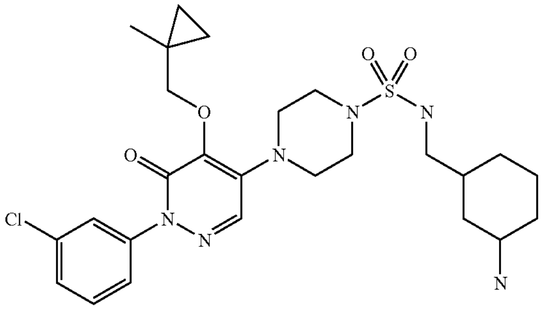 | 565 |

TABLE 29-continued
| Oxygen Analogues with Sulfamide Tails<br>Using the procedures described above, the following compounds were synthesized. | | |
|---|---|---|
| Comp. No. | Structure | MS M + 1 |
| 1721Z | 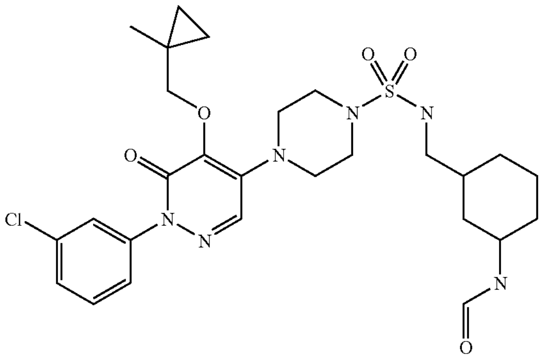 | 593 |
| 1722Z | 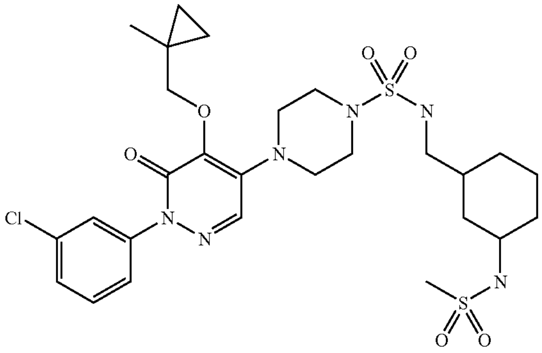 | 643 |
| 1723Z | 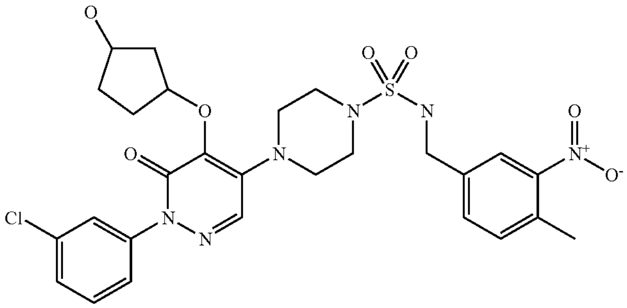 | 619 |
| 1724Z | 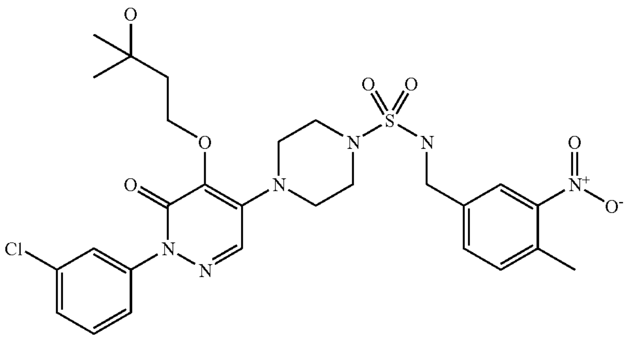 | 621 |

TABLE 29-continued
| Comp. No. | Structure | MS M + 1 |
|---|---|---|
| | Oxygen Analogues with Sulfamide Tails<br>Using the procedures described above, the following compounds were synthesized. | |
| 1725Z | 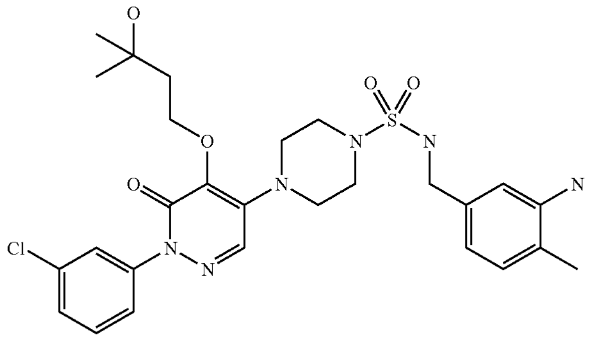 | 591 |
| 1726Z | 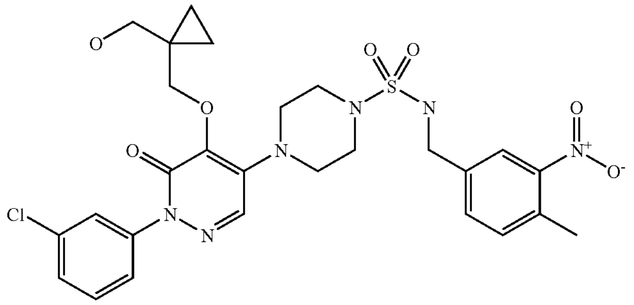 | 619 |
| 1727Z | 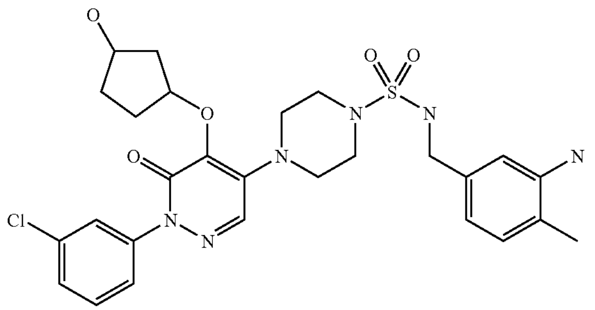 | 589 |
| 1728Z | 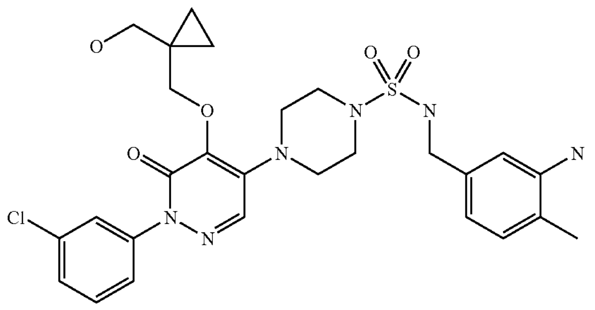 | 589 |

TABLE 29-continued
Oxygen Analogues with Sulfamide Tails
Using the procedures described above, the following compounds were synthesized.
| Comp. No. | Structure | MS M + 1 |
| --- | --- | --- |
| 1729Z | 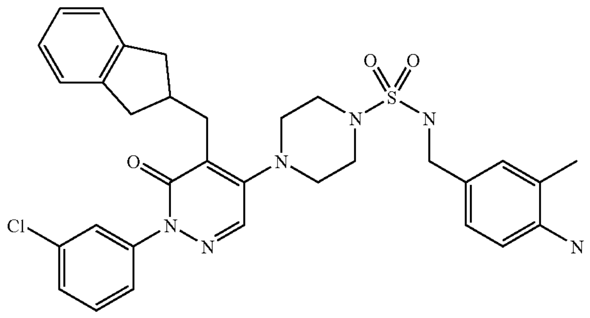 | 621 |
| 1730Z | 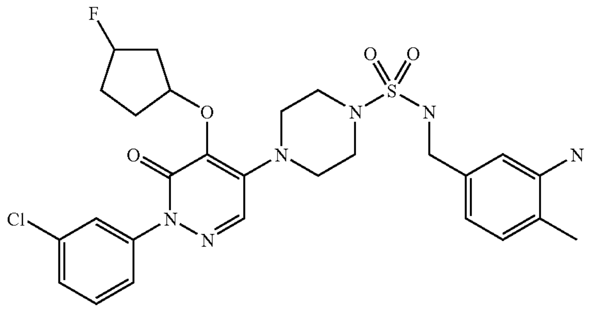 | 591 |
| 1731Z | 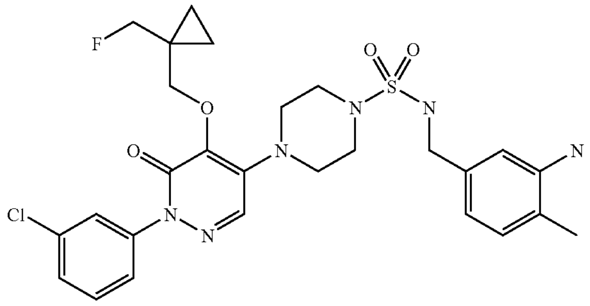 | 591 |
| 1732Z | 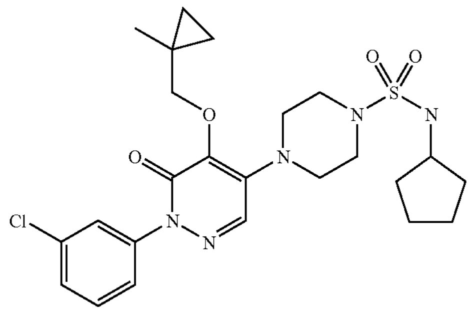 | 522 |

TABLE 29-continued
| Oxygen Analogues with Sulfamide Tails<br>Using the procedures described above, the following compounds were synthesized. | | |
|---|---|---|
| Comp. No. | Structure | MS M + 1 |
| 1733Z | 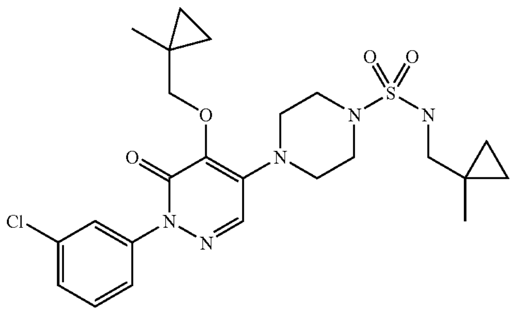 | 522 |
| 1734Z | 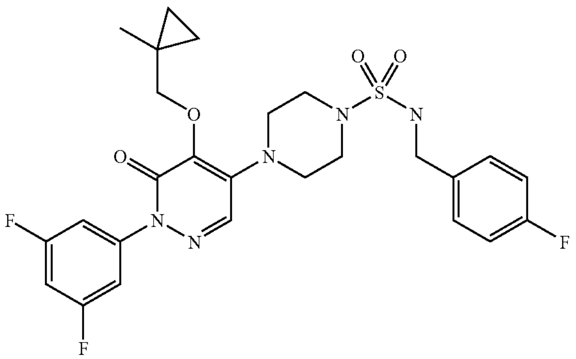 | 564 |
| 1735Z | 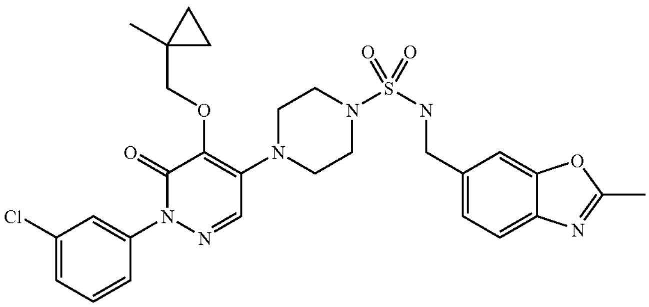 | 599 |
| 1736Z | 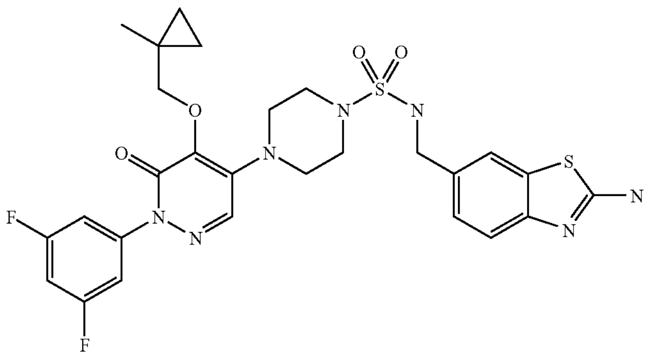 | 618 |

TABLE 29-continued
Oxygen Analogues with Sulfamide Tails
Using the procedures described above, the following compounds were synthesized.
| Comp. No. | Structure | MS M + 1 |
|---|---|---|
| 1737Z | 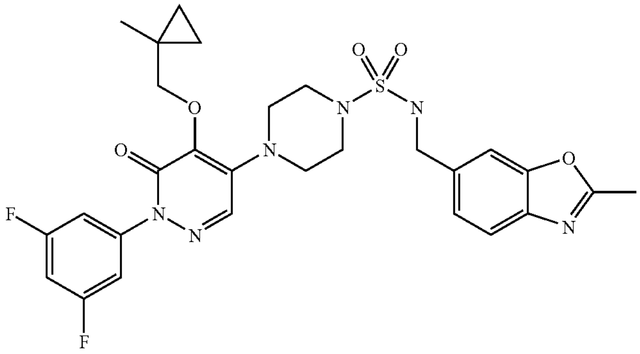 | 601 |
| 1738Z | 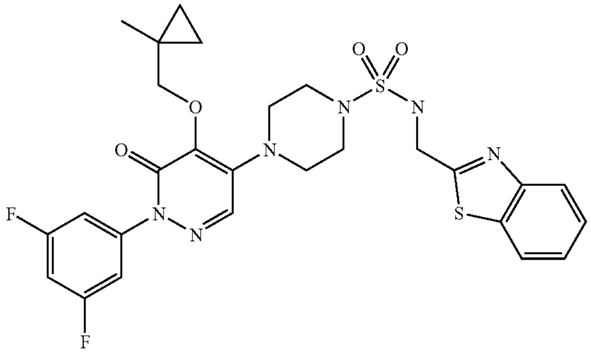 | 603 |
| 1739Z | 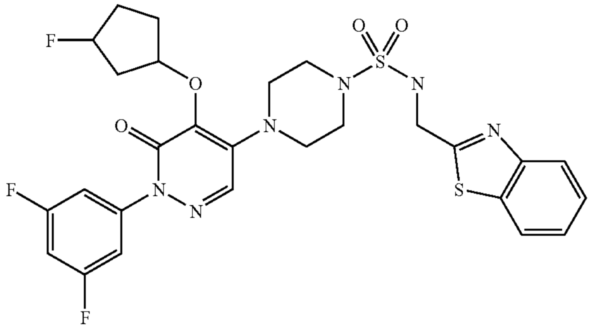 | 621 |
| 1740Z | 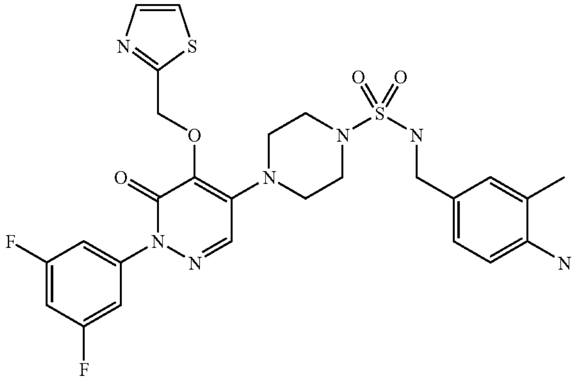 | 604 |

TABLE 29-continued
| Comp. No. | Structure | MS M + 1 |
| --- | --- | --- |
| | Oxygen Analogues with Sulfamide Tails<br>Using the procedures described above, the following compounds were synthesized. | |
| 1741Z | 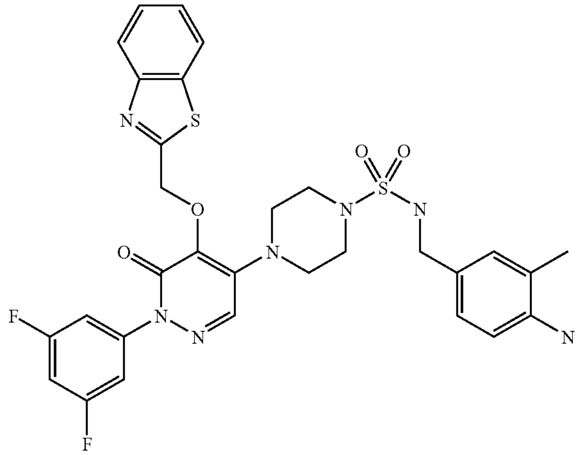 | 654 |
| 1742Z | 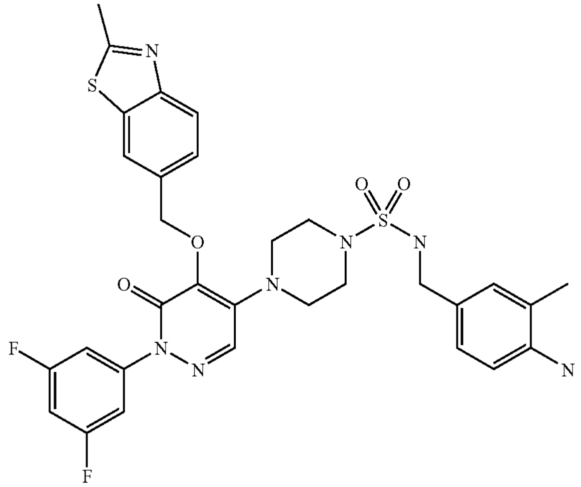 | 668 |
| 1743Z | 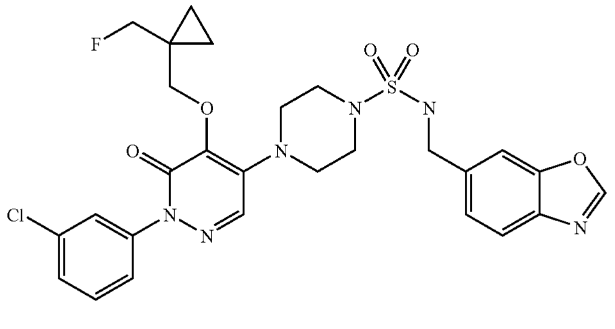 | 603 |

TABLE 29-continued
| Oxygen Analogues with Sulfamide Tails<br>Using the procedures described above, the following compounds were synthesized. | | |
|---|---|---|
| Comp. No. | Structure | MS M + 1 |
| 1744Z | 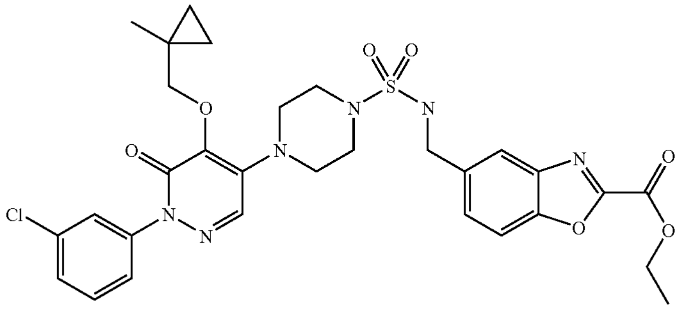 | 657 |
| 1745Z | 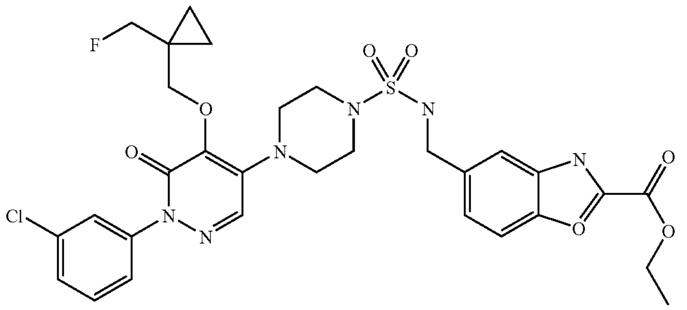 | 675 |
| 1745Za | 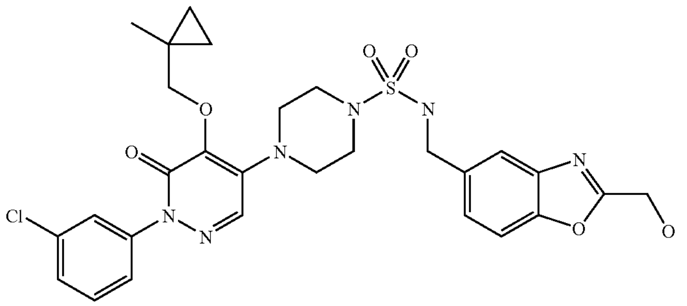 | 615 |
| 1745Zb | 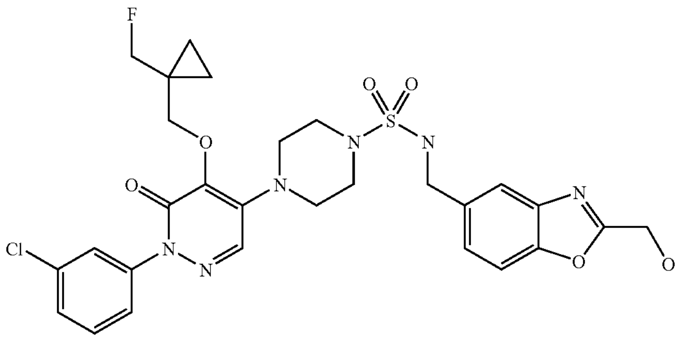 | 633 |

TABLE 29-continued
Oxygen Analogues with Sulfamide Tails
Using the procedures described above, the following compounds were synthesized.
| Comp. No. | Structure | MS M + 1 |
| --- | --- | --- |
| 1745c | 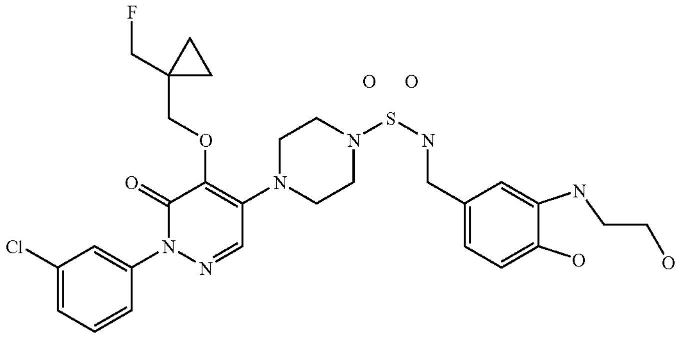 | 637 |
| 1745d | 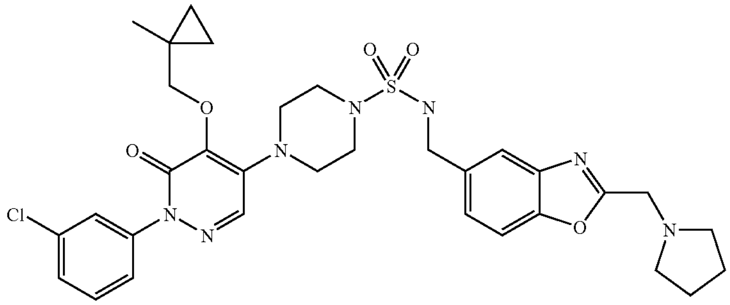 | 668 |
Scheme 32
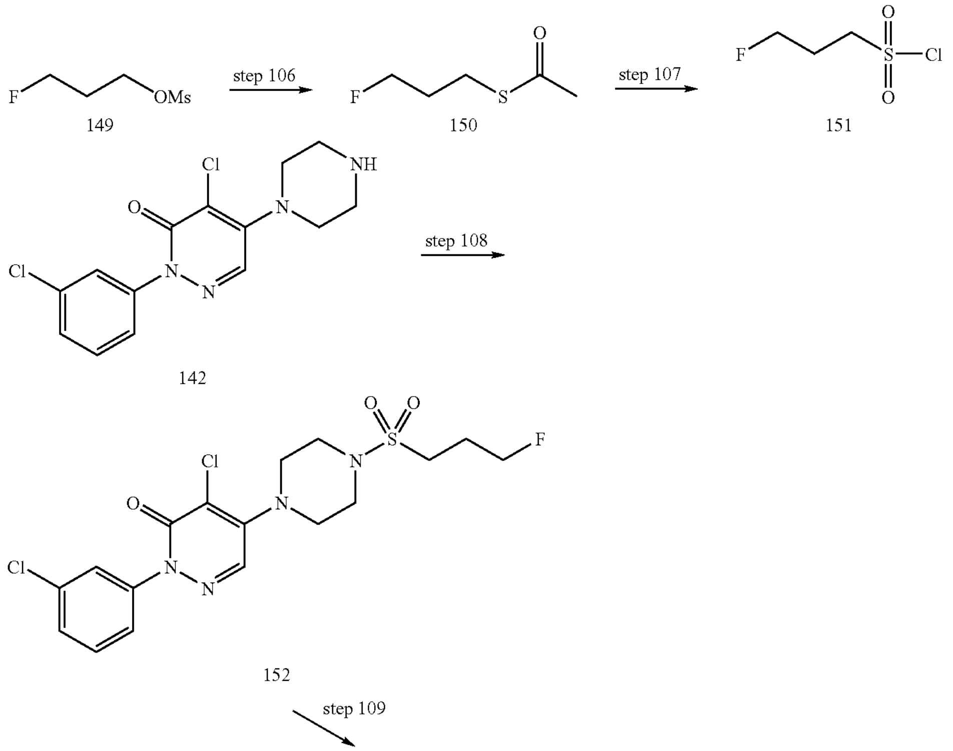
149 150 151
142
152

-continued

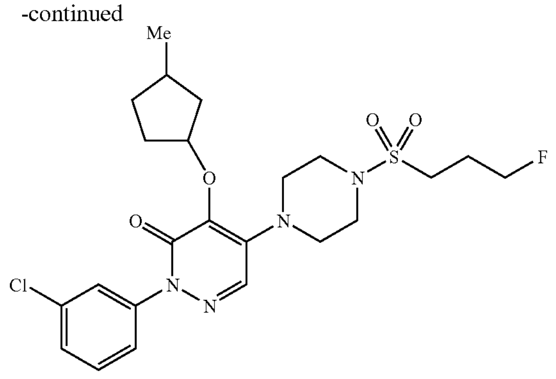

153

Step 106:

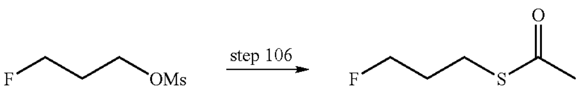

149 150

To a solution of fluoropropyl methylsulfonate 149 (4.7 g, 30 mmol) in DMF (40 mL) was added potassium thioacetate (7 g, 60 mmol) at room temperature. The reaction mixture was warmed to 70° C. for 12 h. After cooling to room temperature, saturated aqueous $NH_4Cl$ solution was added, and the aqueous solution was extracted with EtOAc. The combined organic extract was washed with brine, dried ($Na_2SO_4$), filtered, and concentrated. Purification by silica gel chromatography (eluant: 257 EtOAc-hexane) gave 5.2 g (100% yield) of the product 150 as a colorless liquid.

Step 107:

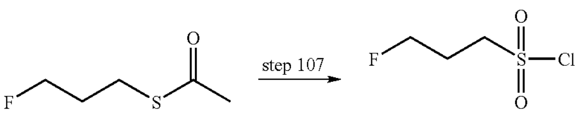

150 151

Chlorine gas was bubbled through a stirred solution of fluoropropyl thioacetate 150 (2 g, 14.7 mmol) in $CH_2Cl_2$ (30 mL) and $H_2O$ (6 mL) at 6° C. to 9° C. After compound 150 was completely consumed, water and $CH_2Cl_2$ were added, and the $CH_2Cl_2$ layer was separated, washed with brine, dried ($Na_2SO_4$), filtered, and concentrated to give 2.3 g (100% yield) of the product 151 as a colorless liquid.

Step 108:

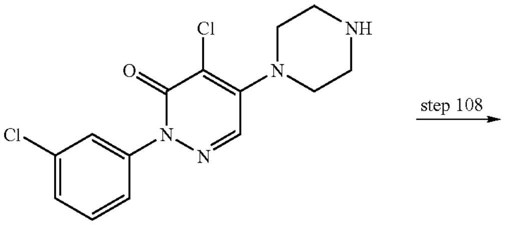

142

-continued

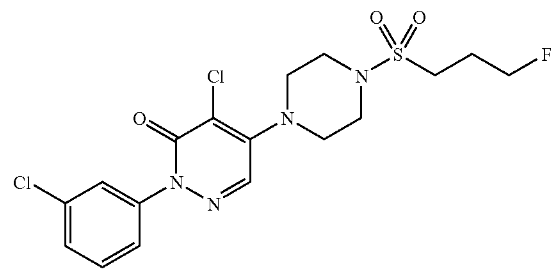

152

To a suspension of chloropyridazinone 142 (468 mg, 1.29 mmol, HCl salt) in $CH_2Cl_2$ (5 mL) at 0° C. was added $iPr_2NEt$ (673 uL, 3.87 mmol) followed by the addition of fluoropropylsulfonyl chloride 151 (250 mg, 1.55 mol) in $CH_2Cl_2$ (2.5 mL) over 2 mins. After 2 h at 0° C. and 1.5 h at room temperature, water was added to the reaction mixture, and the aqueous solution was extracted with $CH_2Cl_2$. The combined organic extract was washed with brine, dried ($Na_2SO_4$), filtered, and concentrated to provide 560 mg (96% yield) of the product 152 as a white solid. MS (M+1): 449.

Step 109:

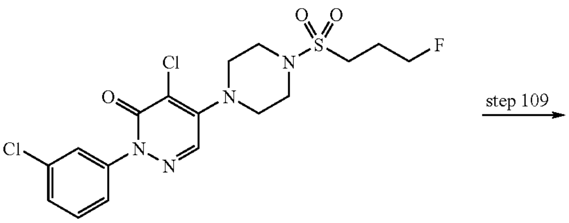

152

-continued

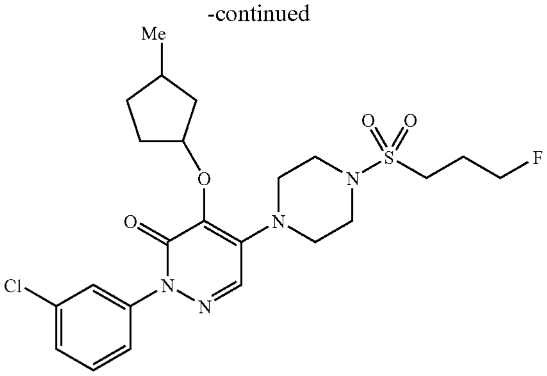

153

To a solution of 3-methylcyclopentanol (95 mg, 0.21 mmol) in THF (3 mL) at room temperature was added NaN$(TMS)_2$ (0.63 mL, 0.63 mmol) over 2 mins. After 15 mins, dichloropyridazinone 152 was added as a solid in one portion. The reaction mixture was stirred for 1 h and quenched with saturated aqueous $NH_4Cl$ solution, and the aqueous solution was extracted with EtOAc. The combined organic extract was washed with brine, dried ($Na_2SO_4$), filtered, and concentrated. Purification by Gilson reverse phase chromatography (eluant: $CH_3CN$—$H_2O$) gave 82 mg (80% yield) of the product 153 as a white solid. MS (M+1): 513.

Using the procedures described above, the following compounds were synthesized.

TABLE 30

Oxygen Analogues with Fluoropropyl Sulfonamide

| Cmpd. No. | Structure | MS M + 1 |
|---|---|---|
| 1746Z | 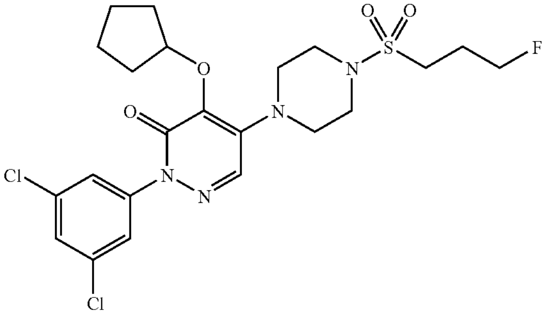 | 533 |
| 1747Z | 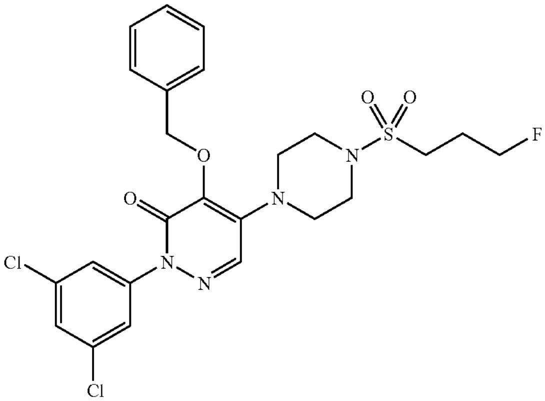 | 555 |
| 1748Z | 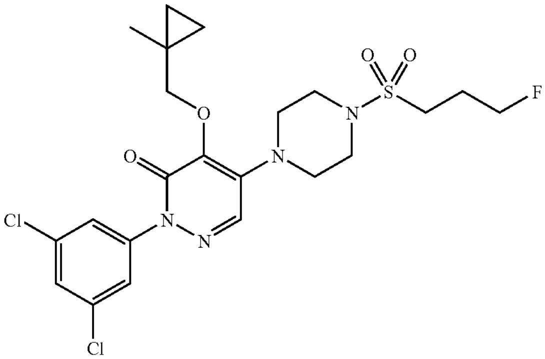 | 533 |

TABLE 30-continued
| Oxygen Analogues with Fluoropropyl Sulfonamide | | |
|---|---|---|
| Cmpd. No. | Structure | MS M + 1 |
| 1749Z | 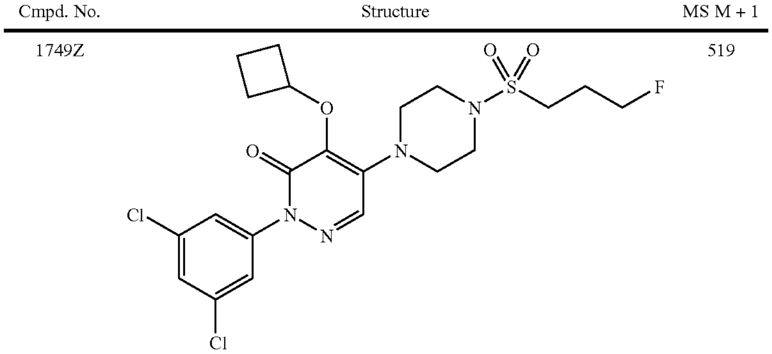 | 519 |
| 1750Z | 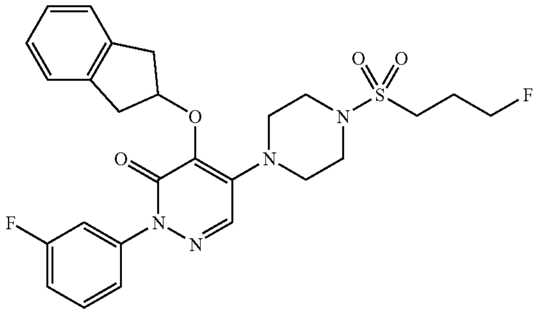 | 531 |
| 1751Z | 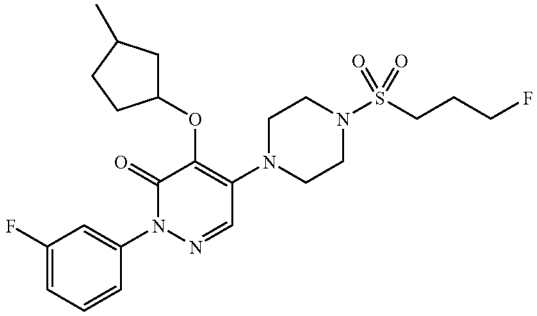 | 497 |
| 1752Z | 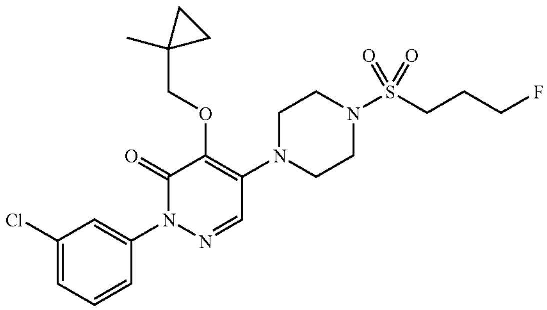 | 499 |
| 1753Z | 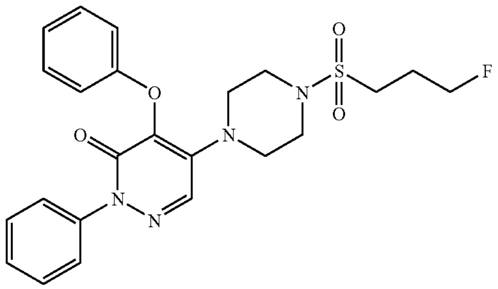 | 487 |

TABLE 30-continued
| Oxygen Analogues with Fluoropropyl Sulfonamide | | |
|---|---|---|
| Cmpd. No. | Structure | MS M + 1 |
| 1754Z | 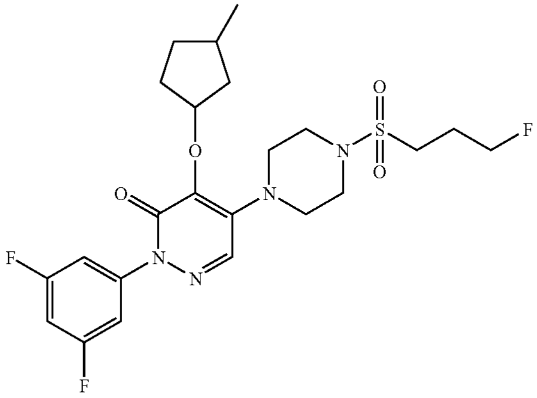 | 515 |
| 1755Z | 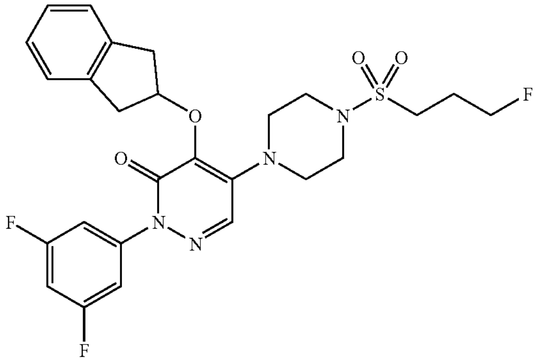 | 549 |
| 1756Z | 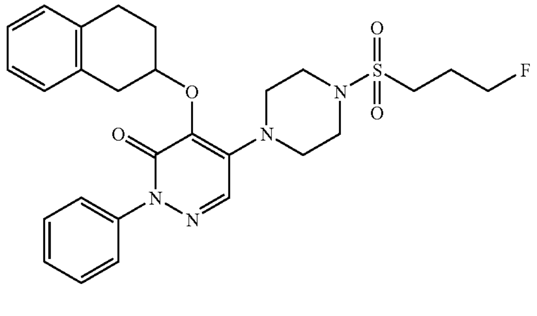 | 527 |
| 1757Z | 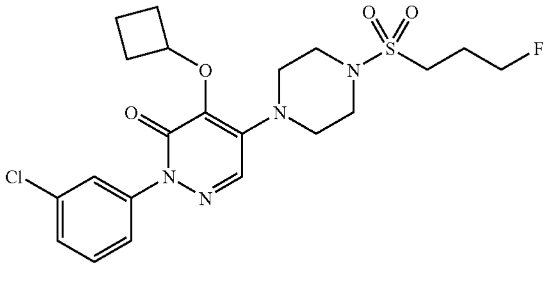 | 485 |

TABLE 30-continued
| Oxygen Analogues with Fluoropropyl Sulfonamide | | |
|---|---|---|
| Cmpd. No. | Structure | MS M + 1 |
| 1758Z | 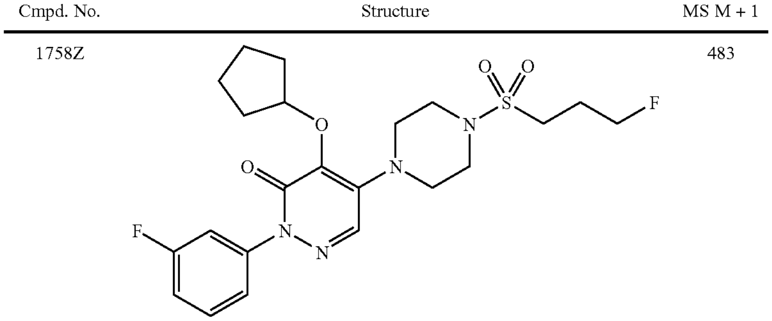 | 483 |
| 1759Z | 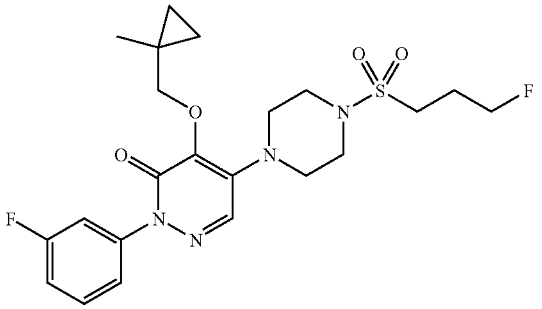 | 483 |
| 1760Z | 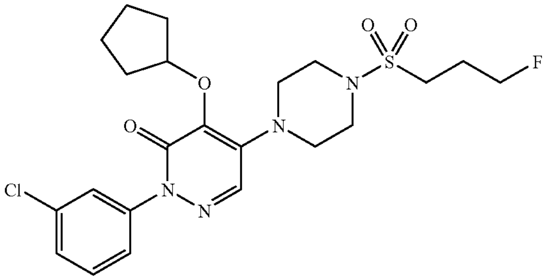 | 499 |
| 1761Z | 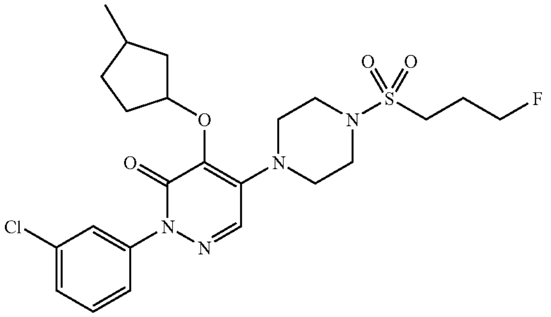 | 513 |
| 1762Z | 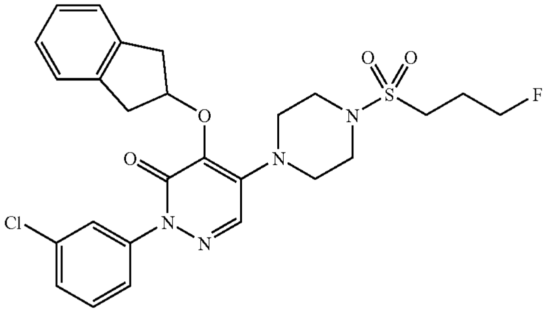 | 547 |

TABLE 30-continued
| Oxygen Analogues with Fluoropropyl Sulfonamide | | |
| --- | --- | --- |
| Cmpd. No. | Structure | MS M + 1 |
| 1763Z | 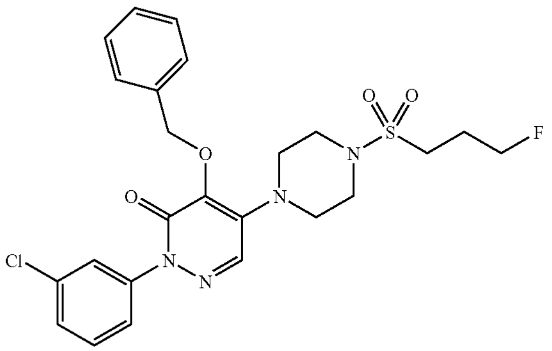 | 521 |
| 1764Z | 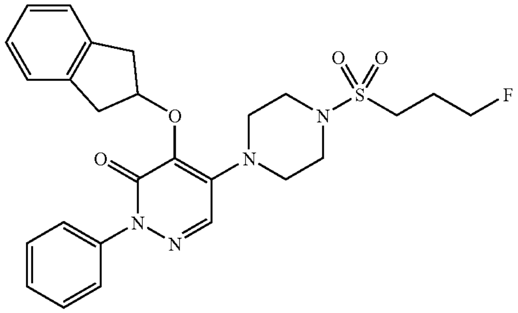 | 513 |
| 1765Z | 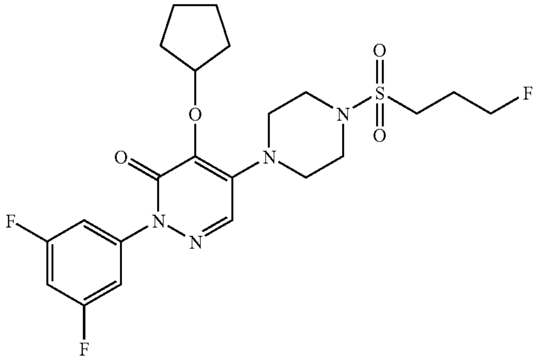 | 501 |
| 1766Z | 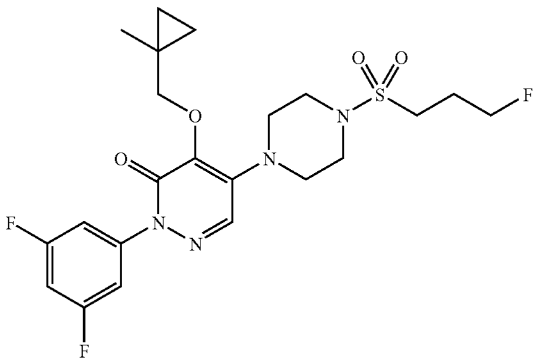 | 501 |

TABLE 30-continued
| Oxygen Analogues with Fluoropropyl Sulfonamide | | |
|---|---|---|
| Cmpd. No. | Structure | MS M + 1 |
| 1767Z | 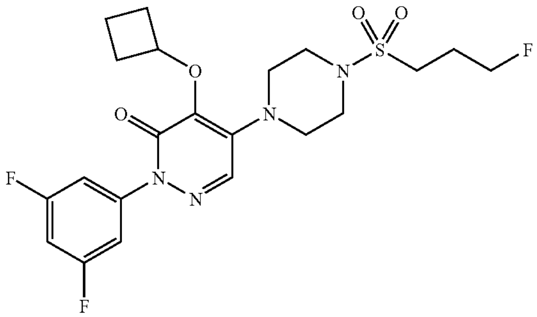 | 487 |
| 1768Z | 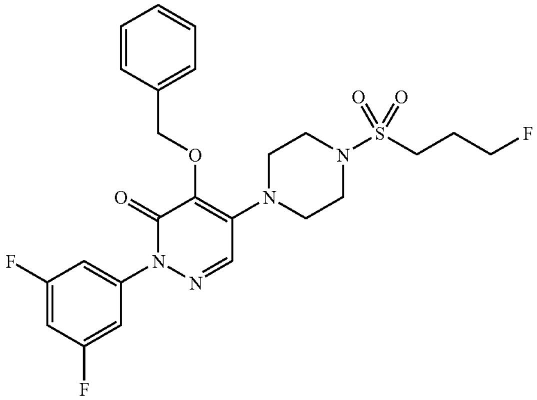 | 523 |
| 1769Z | 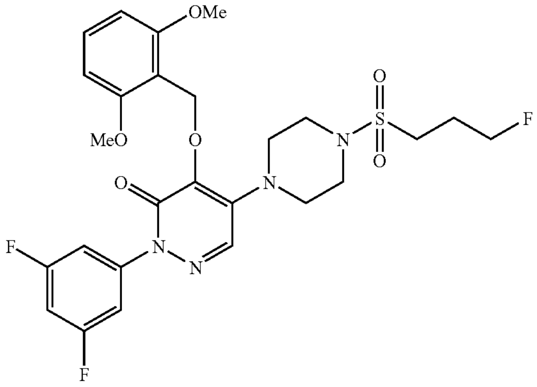 | 583 |
| 1770Z | 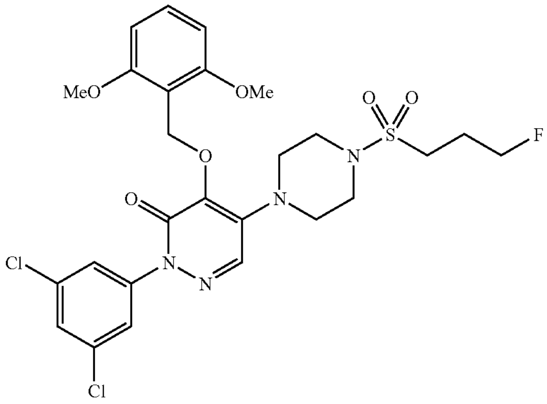 | 614 |

Scheme 33

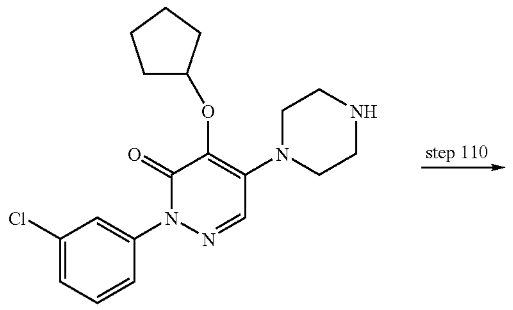

154

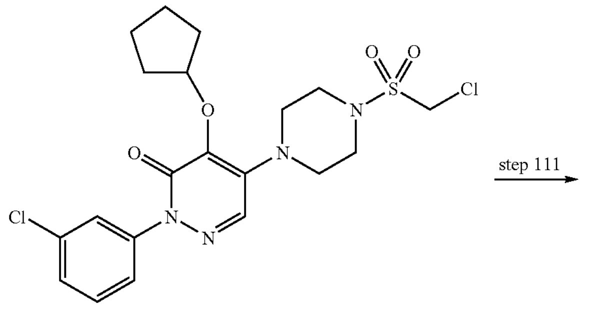

155

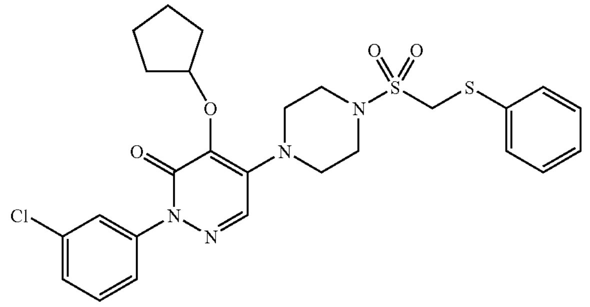

156

Step 110:

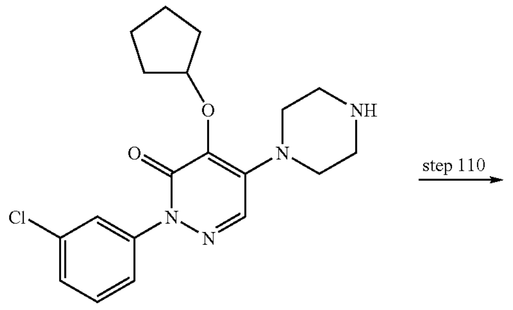

154

-continued

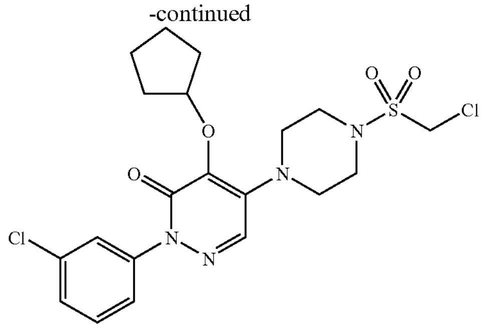

155

To a suspension of chloropyridazinone 154 (1.95 g, 4.74 mmol, HCl salt) in $C_2Cl_2$ (30 mL) at −35° C. was added $iPr_2NEt$ (2.06 mL, 11.85 mmol) followed by the addition of chloromethylsulfonyl chloride (918 mg, 6.16 mmol) in $CH_2Cl_2$ (20 mL) over 20 mins. After 2 h at −35° C. to 10° C., water was added to the reaction mixture and the aqueous solution was extracted with $CH_2Cl_2$. The combined organic extract was washed with 1 N HCl, brine, dried ($Na_2SO_4$), filtered, and concentrated. Purification by ISCO silica gel chromatography (eluant: EtOAc-hexane) gave 1.5 g (65% yield) of the product 155 as a white foam. MS (M+1): 487.

Step 111:

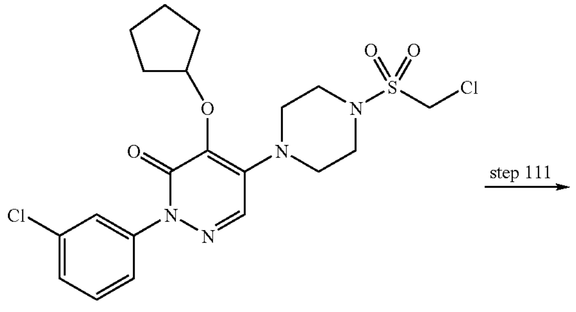

155

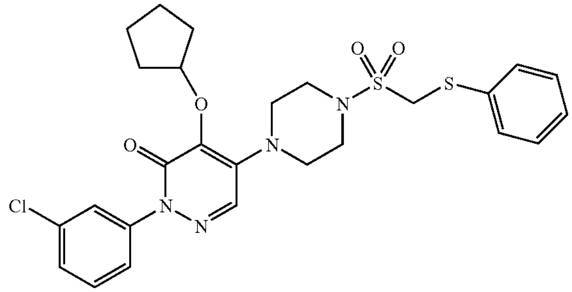

156

A reaction mixture of chloropyridazinone 155 (292 mg, 0.6 mmol), thiophenol (79 mg, 0.72 mmol) and $K_2CO_3$ (124 mg, 0.9 mmol) in DMF (3 mL) was heated to 80° C. for 30 mins via microwave irradiation. The reaction mixture was quenched with saturated aqueous $NH_4Cl$ solution, and the aqueous solution was extracted with EtOAc. The combined organic extract was washed with brine, dried ($Na_2SO_4$), filtered, and concentrated. Purification by Gilson reverse phase chromatography (eluant: $CH_3CN—H_2O$) gave 242 mg (72% yield) of the product 156 as a white solid. MS (M+1): 561.

Using the procedures described above, the following compounds were synthesized.

TABLE 31
| Oxygen Analogues with Thioether/Ether Sulfonamide | | |
|---|---|---|
| Cmpd. No. | Structure | MS M + 1 |
| 1771Z | 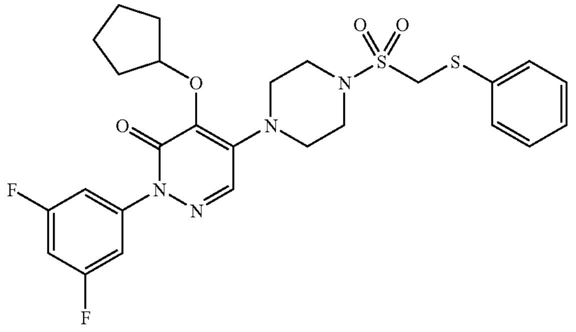 | 563 |
| 1772Z | 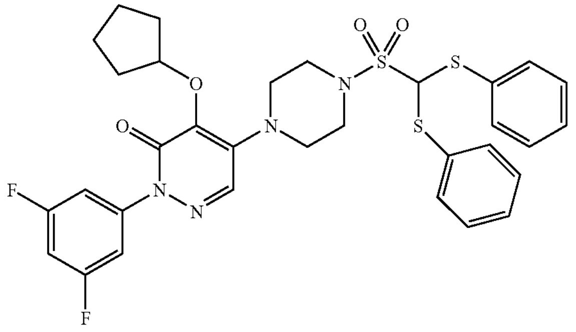 | 671 |
| 1773Z | 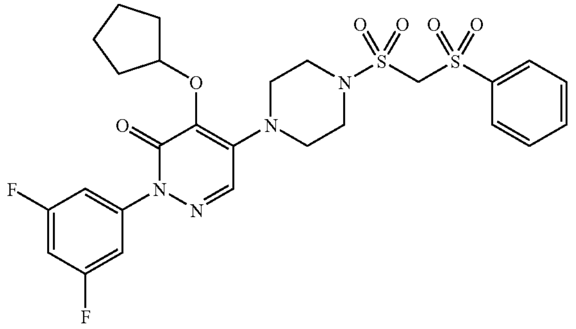 | 595 |
| 1774Z | 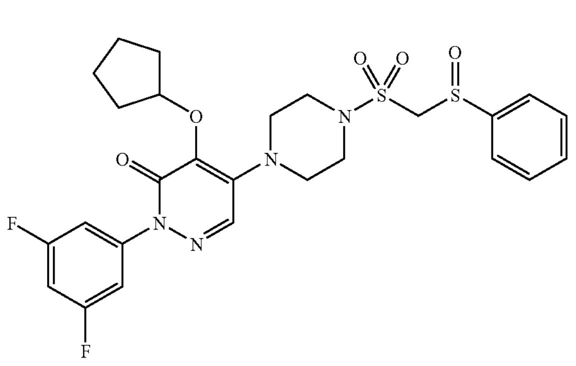 | 579 |

TABLE 31-continued
| Cmpd. No. | Structure | MS M + 1 |
|---|---|---|
| | Oxygen Analogues with Thioether/Ether Sulfonamide | |
| 1775Z | 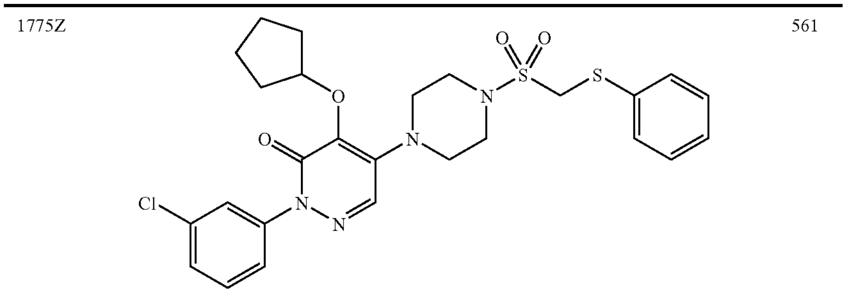 | 561 |
| 1776Z | 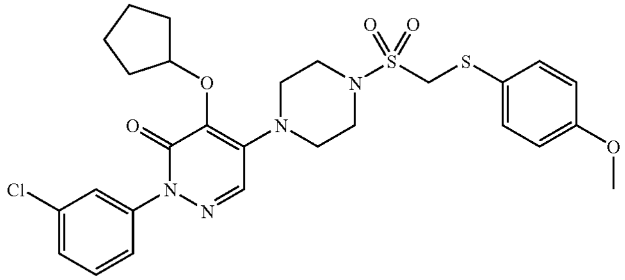 | 591 |
| 1777Z | 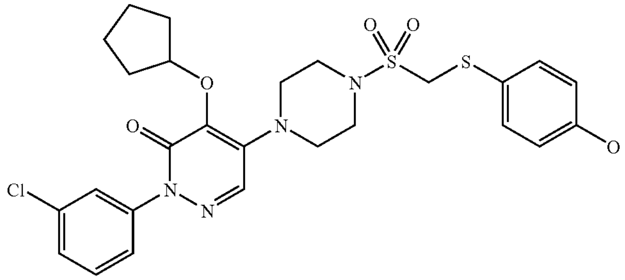 | 577 |
| 1778Z | 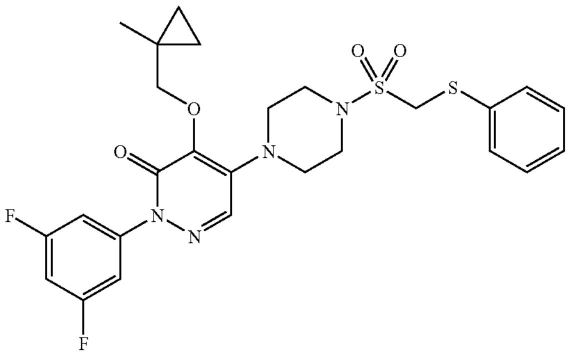 | 563 |
| 1779Z | 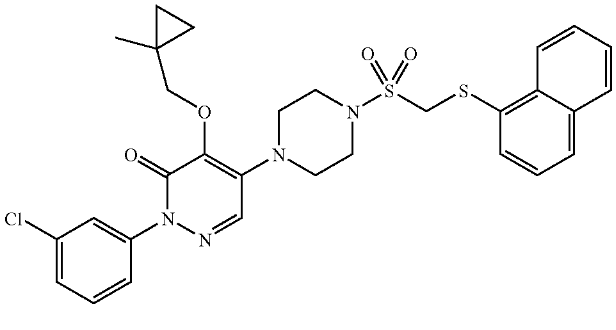 | 611 |

TABLE 31-continued
Oxygen Analogues with Thioether/Ether Sulfonamide
| Cmpd. No. | Structure | MS M + 1 |
| --- | --- | --- |
| 1780Z | 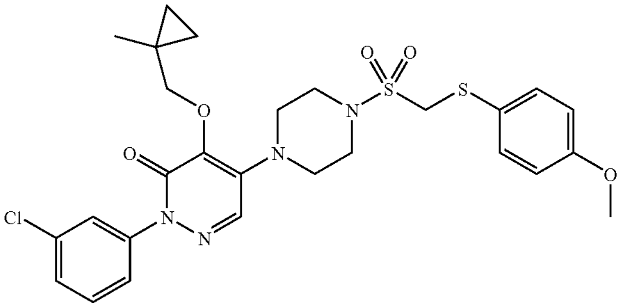 | 591 |
| 1781Z | 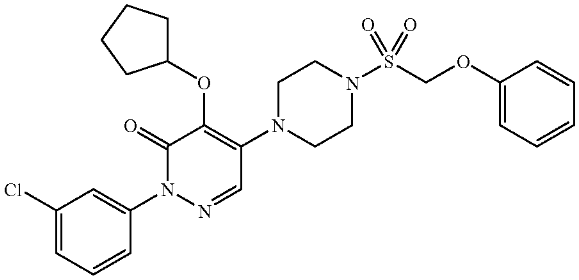 | 545 |
| 1782Z | 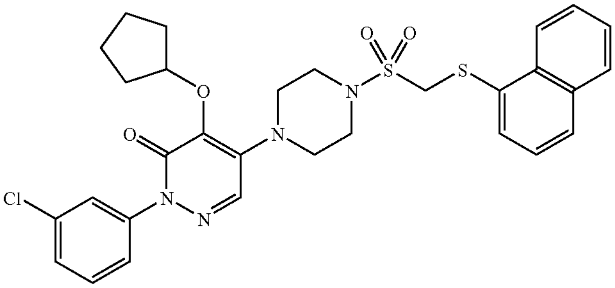 | 611 |
| 1783Z | 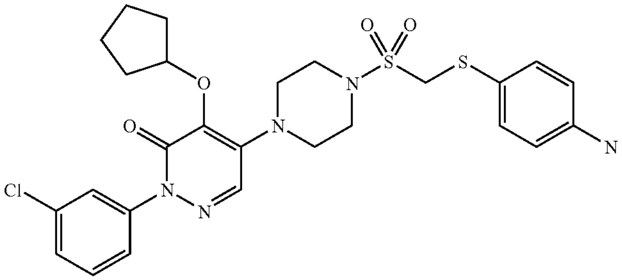 | 576 |
| 1784Z | 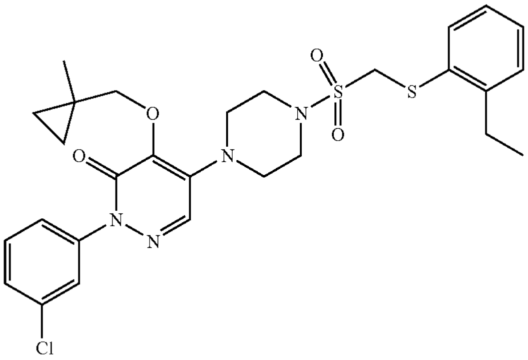 | 589 |

TABLE 31-continued
| Oxygen Analogues with Thioether/Ether Sulfonamide | | |
|---|---|---|
| Cmpd. No. | Structure | MS M + 1 |
| 1785Z | 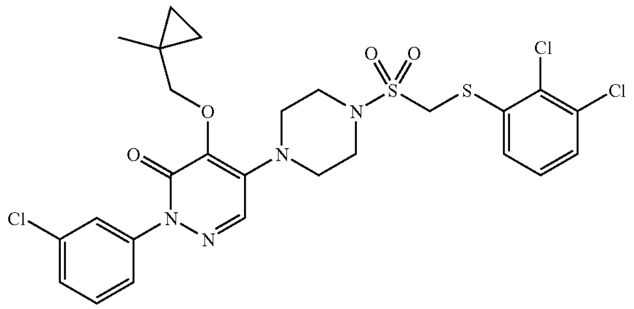 | 633 |
| 1786Z | 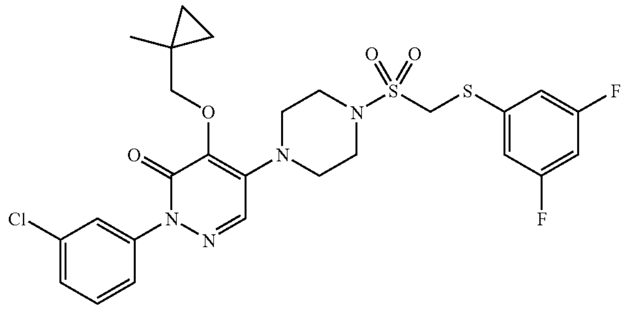 | 597 |
| 1787Z | 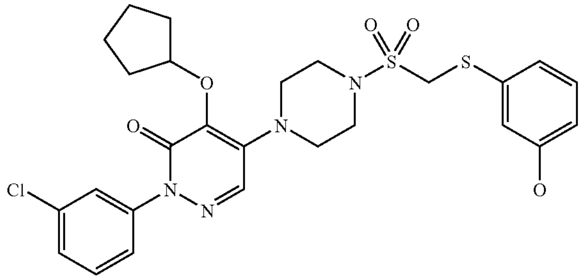 | 577 |
| 1788Z | 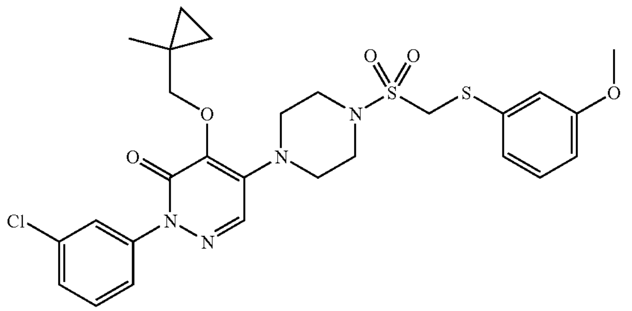 | 591 |

TABLE 31-continued
| Oxygen Analogues with Thioether/Ether Sulfonamide | | |
|---|---|---|
| Cmpd. No. | Structure | MS M + 1 |
| 1789Z | 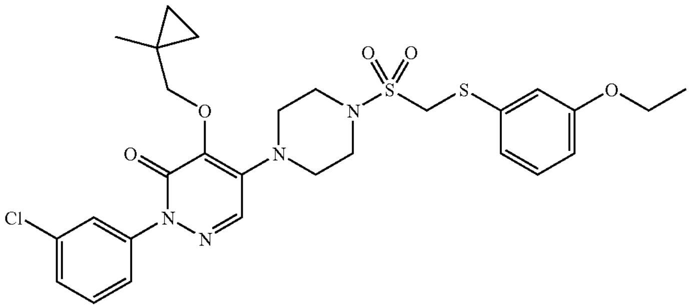 | 605 |
| 1790Z | 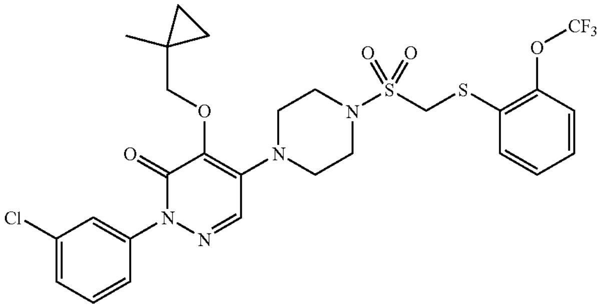 | 645 |
| 1791Z | 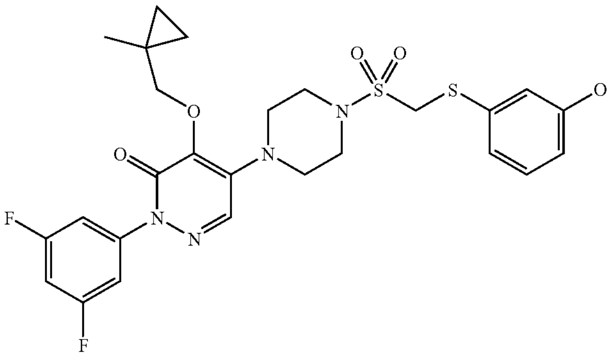 | 579 |
| 1792Z | 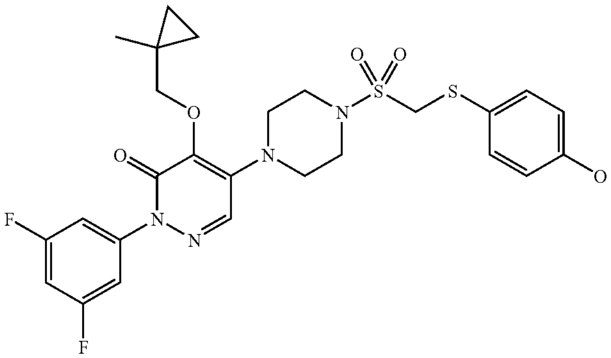 | 579 |

TABLE 31-continued
| Oxygen Analogues with Thioether/Ether Sulfonamide | | |
|---|---|---|
| Cmpd. No. | Structure | MS M + 1 |
| 1793Z | 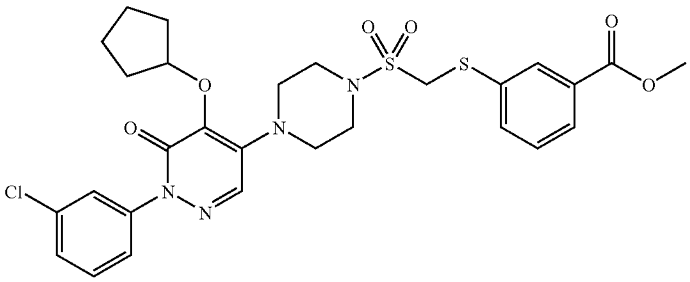 | 619 |
| 1794Z | 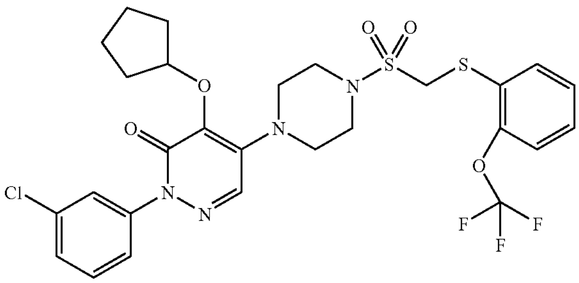 | 645 |
| 1795Z | 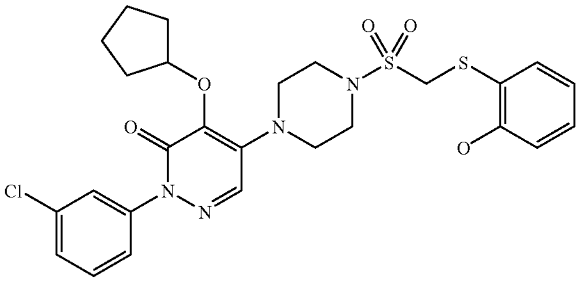 | 577 |
| 1796Z | 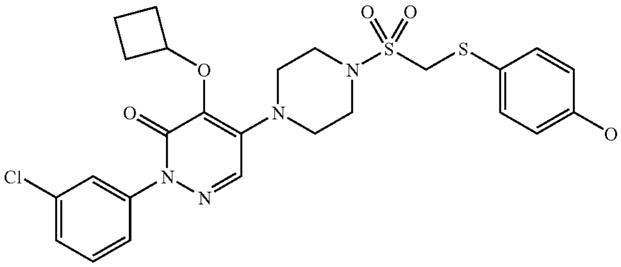 | 563 |
| 1797Z | 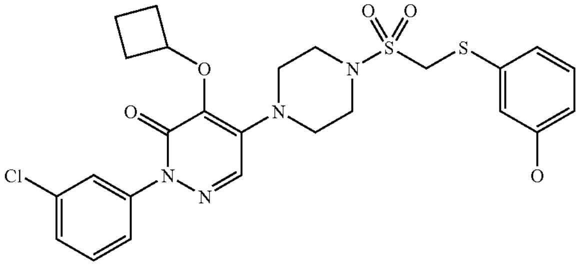 | 563 |

TABLE 31-continued
| Oxygen Analogues with Thioether/Ether Sulfonamide | | |
|---|---|---|
| Cmpd. No. | Structure | MS M + 1 |
| 1798Z | 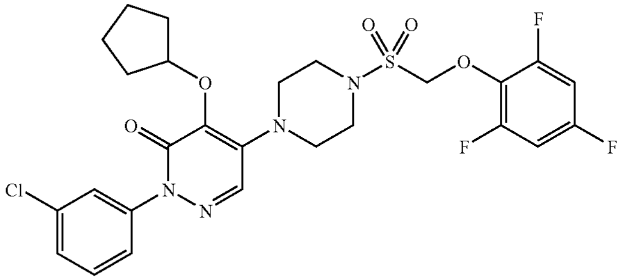 | 599 |
| 1799Z | 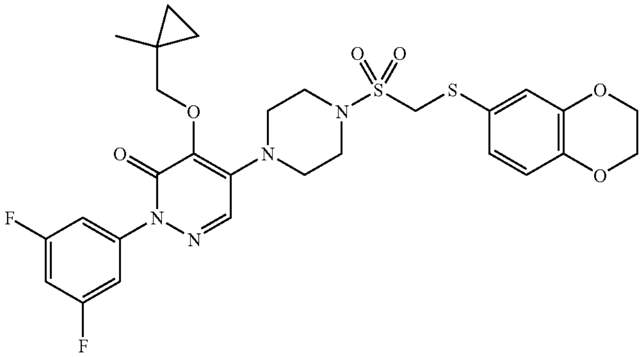 | 621 |
| 1800Z | 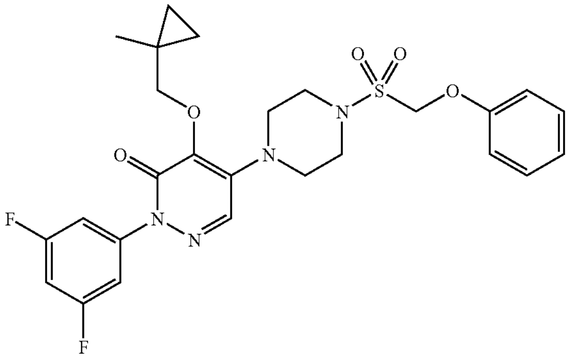 | 547 |
| 1801Z | 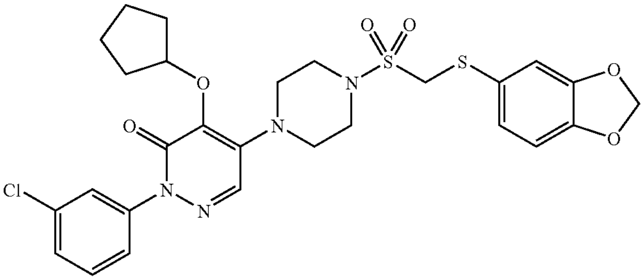 | 605 |

TABLE 31-continued
| Oxygen Analogues with Thioether/Ether Sulfonamide | | |
|---|---|---|
| Cmpd. No. | Structure | MS M + 1 |
| 1802Z | 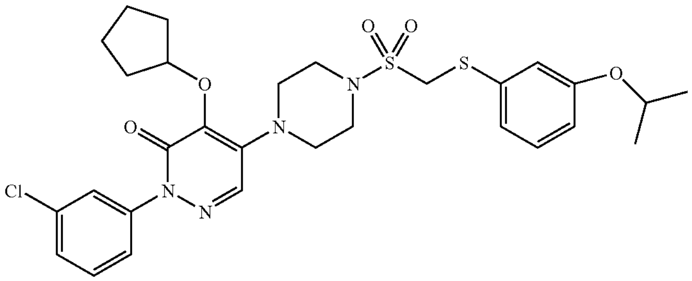 | 619 |
| 1803Z | 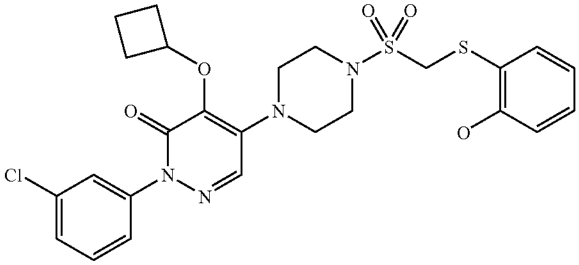 | 563 |
| 1804Z | 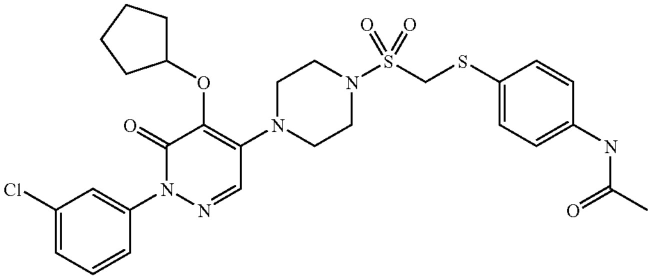 | 618 |
| 1805Z | 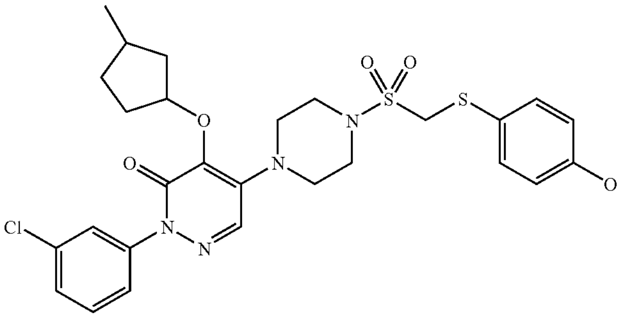 | 591 |
| 1806Z | 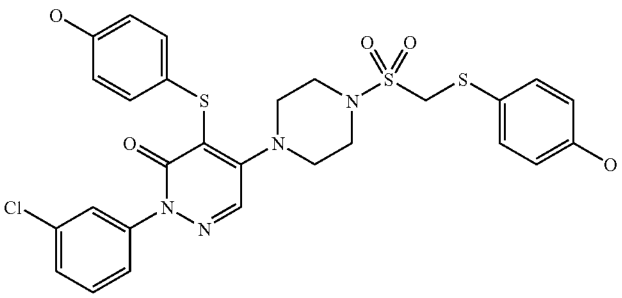 | 617 |

TABLE 31-continued
| Oxygen Analogues with Thioether/Ether Sulfonamide | | |
|---|---|---|
| Cmpd. No. | Structure | MS M + 1 |
| 1807Z | 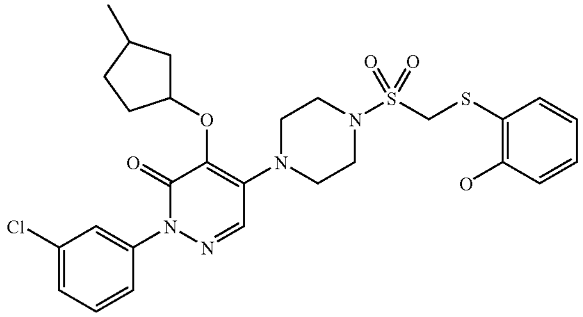 | 591 |
| 1808Z | 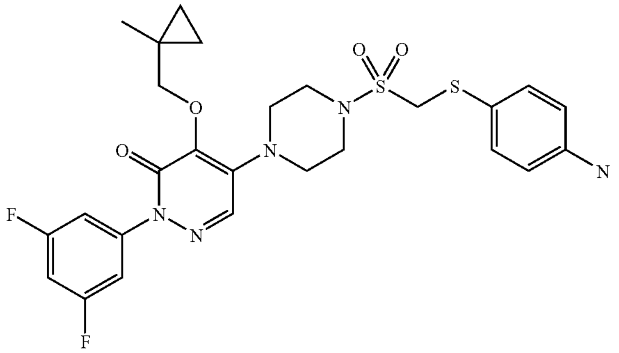 | 578 |
| 1809Z | 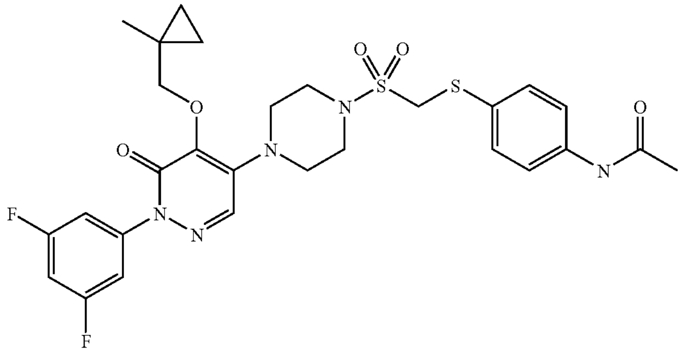 | 620 |
Scheme 34
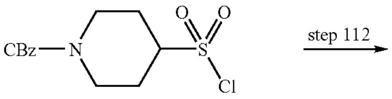
157
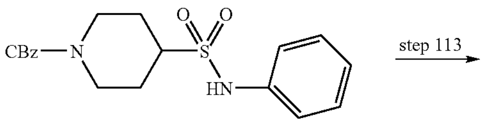
158
-continued
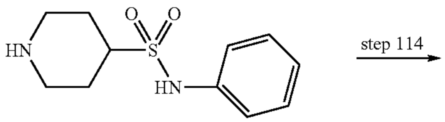
159
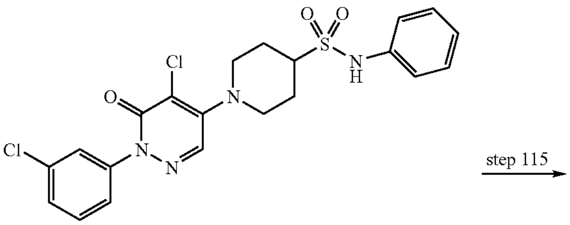
160

-continued

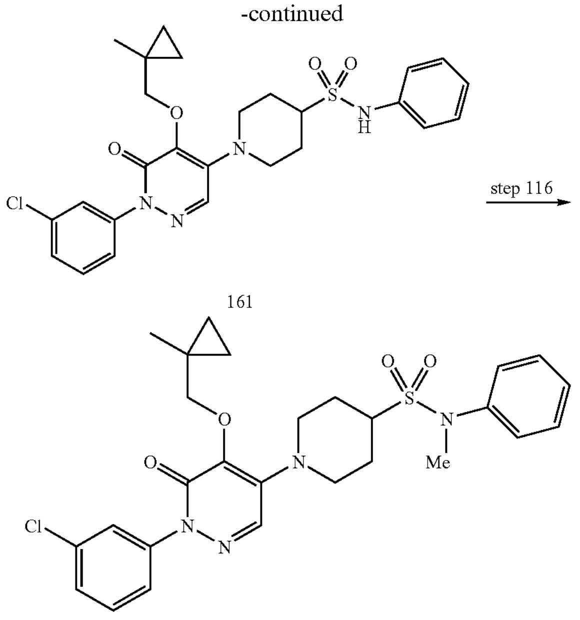

161

162

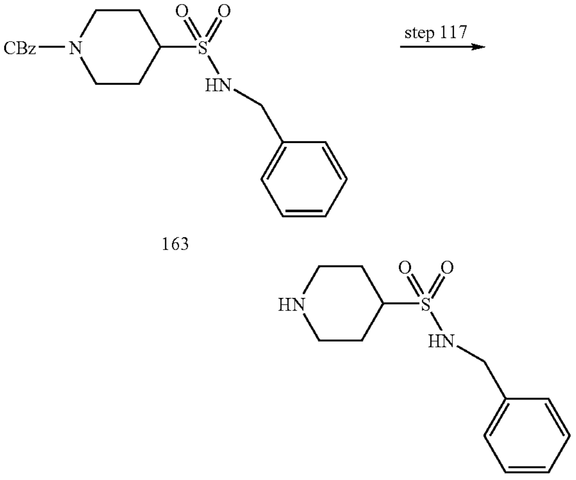

163

164

Step 112:

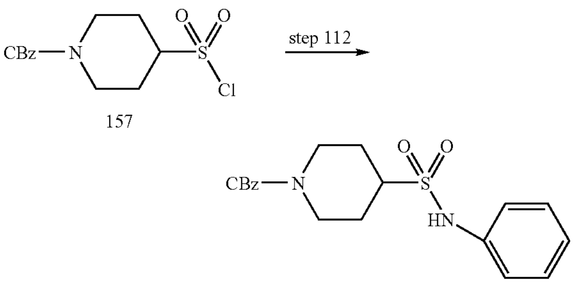

157

158

To a solution of aniline (2.3 g, 25.12 mmol) and $iPr_2NEt$ (3.3 mL, 18.84 mmol) in $CH_2Cl_2$ (50 mL) at 0° C. was added a solution of Cbz-piperidinylsulfonyl chloride 157 (4.0 g, 12.56 mmol) in $CH_2Cl_2$ (20 mL) over 10 mins. After 1 h at 0° C. and 2.5 h at room temperature, water was added to the reaction mixture, and the aqueous solution was extracted with $Cl_2Cl_2$. The combined organic extract was washed with 1 N HCl, brine, dried ($Na_2SO_4$), filtered and concentrated. Purification by ISCO silica gel chromatography (eluant: EtOAc hexane) gave 3.7 g (79% yield) of the product 158 as a white solid. MS (M+1): 375.

Step 113:

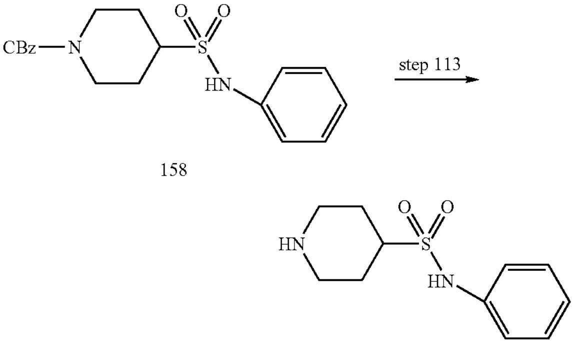

158

159

To a solution of sulfonamide 158 (810 mg, 2.16 mmol) in MeOH (50 mL) and EtOAc (15 mL) was added Pd/C (500 mg) and the reaction mixture was treated with $H_2$ (44 psi) for 18 h. The reaction mixture was filtered, and the filtrate was concentrated to give 440 mg (85% yield) of the product 159 as a white solid. MS (M+1): 241.

Step 114:

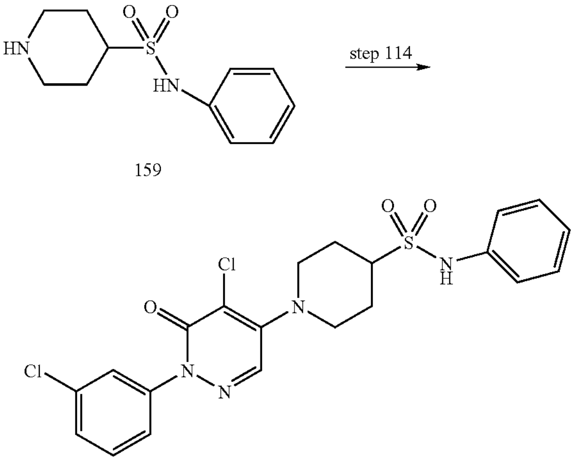

159

160

The reaction mixture of sulfonamide 159 (400 mg, 1.67 mmol), dichloropyridazinone (460 mg, 1.67 mmol) and $iPr_2NEt$ (580 uL, 3.34 mmol) in EtOH (8 mL) was heated to 92° C. for 15 h, and then concentrated to provide a solid residue. To the above residue was added saturated aqueous $NH_2Cl$ solution and the aqueous solution was extracted with $C_2Cl_2$. The combined organic extract was washed with brine, dried ($Na_2SO_4$), filtered, and concentrated. ISCO silica gel chromatography (eluant: $CH_2Cl_2$-MeOH) gave 551 mg (69% yield) of the product 160 as a white solid. MS (M+1): 480.

Step 115:

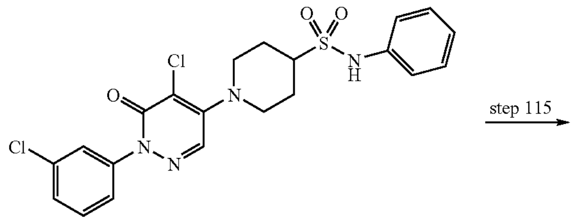

160

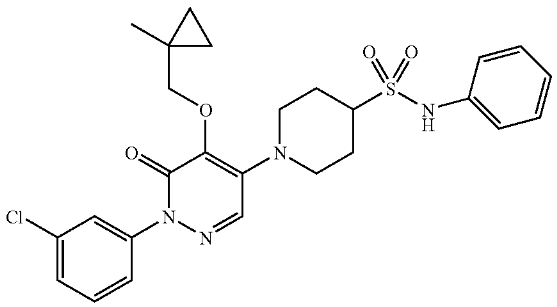

161

To a solution of methylcyclopropylmethanol (158 mg, 1.84 mmol) in THF (3 mL) and DMF (1 mL) at room temperature was added $NaN(TMS)_2$ (1.84 mL, 1.84 mmol) over 2 mins. After 20 mins, dichloropyridazinone 160 was added as a solid in one portion. The reaction mixture was stirred for 1 h and quenched with saturated aqueous $NH_4Cl$ solution, and the aqueous solution was extracted with EtOAc. The combined organic extract was washed with brine, dried ($Na_2SO_4$), filtered, and concentrated. Purification by Gilson reverse phase chromatography (eluant: $CH_3CN—H_2O$) gave 148 mg (61% yield) of the product 161 as a white solid. MS (M+1): 529.

Step 116:

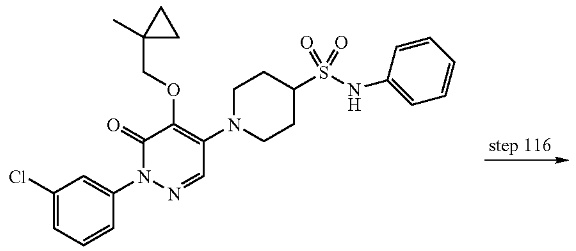

161

-continued

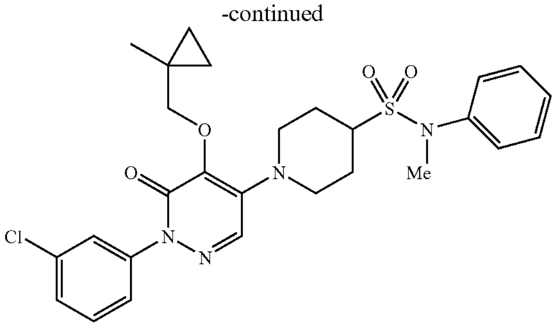

162

To a solution of sulfonamide 161 (110 mg, 0.21 mmol) in DMF (2 mL) at room temperature was added NaH (17 mg, 0.42 mmol, 60% in oil) in one portion. After 25 mins, methyl iodide (60 mg, 0.42 mmol) was added in one portion. After 1 h, the reaction mixture was added slowly to a saturated aqueous $NH_4Cl$ solution, and the aqueous solution was extracted with EtOAc. The combined organic extract was washed with brine, dried ($Na_2SO_4$), filtered, and concentrated. Purification by Gilson reverse phase chromatography (eluant: $CH_3CN—H_2O$) gave 85 mg (79% yield) of the product 162 as a white solid. MS (M+1): 543.

Step 117:

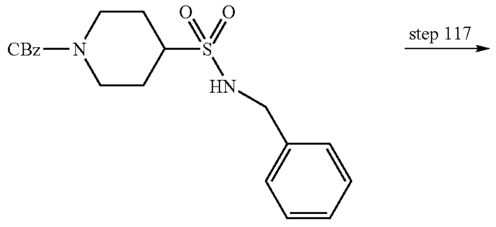

163

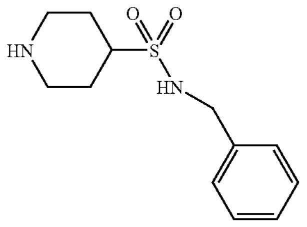

164

The reaction mixture of sulfonamide 163 (1.1 g, 2.83 mmol) in 33% HBr/HOAc (26 mL) was stirred at room temperature for 2 h, and then poured into ice water. To the aqueous reaction mixture was added NaOH solution until the pH 12-13, then the aqueous solution was extracted with EtOAc. The combined organic extract was washed with brine, dried ($Na_2SO_4$), filtered, and concentrated to give a solid. The solid was washed with a mixture of $Et_2O$ and hexane to remove the benzyl bromide impurity and dried to give 530 mg (68% yield) of the product 164 as a white solid. MS (M+1): 276.

Using the procedures described above, the following compounds were synthesized.

TABLE 32
| Oxygen Analogues with Reverse Sulfonamide | | |
|---|---|---|
| Cmpd. No. | Structure | MS M + 1 |
| 1810Z | 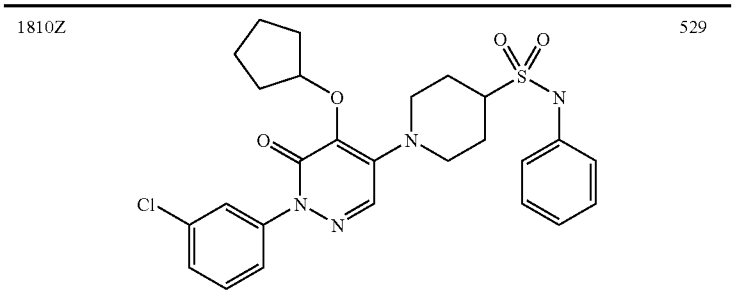 | 529 |
| 1811Z | 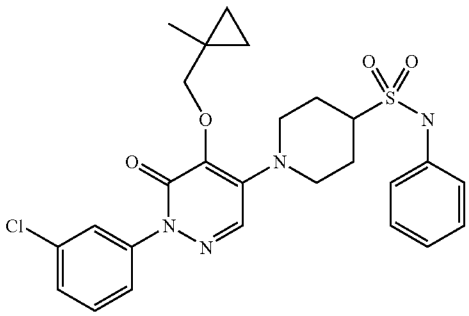 | 529 |
| 1812Z | 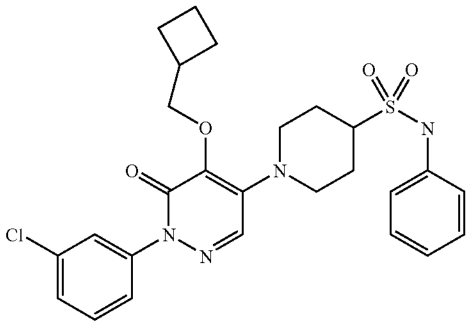 | 529 |
| 1813Z | 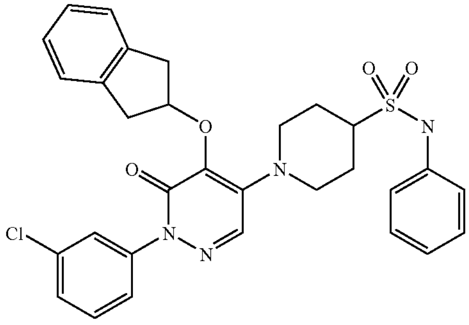 | 577 |
| 1814Z | 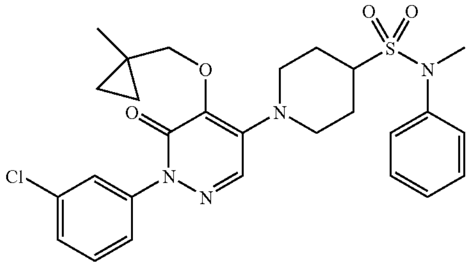 | 543 |

TABLE 32-continued
| Oxygen Analogues with Reverse Sulfonamide | | |
|---|---|---|
| Cmpd. No. | Structure | MS M + 1 |
| 1815Z | 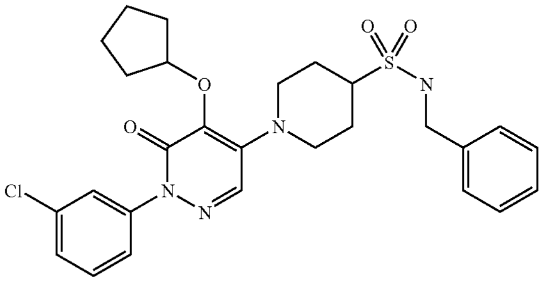 | 543 |
| 1816Z | 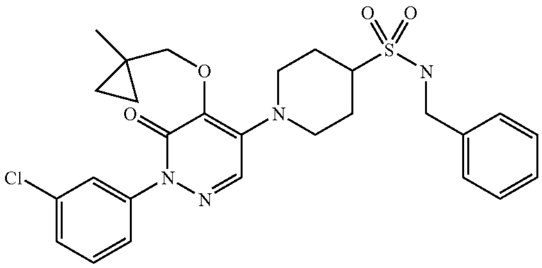 | 543 |
| 1817Z | 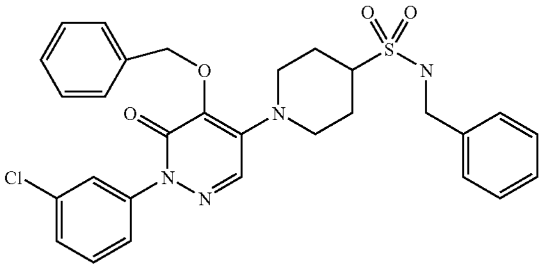 | 565 |
| 1818Z | 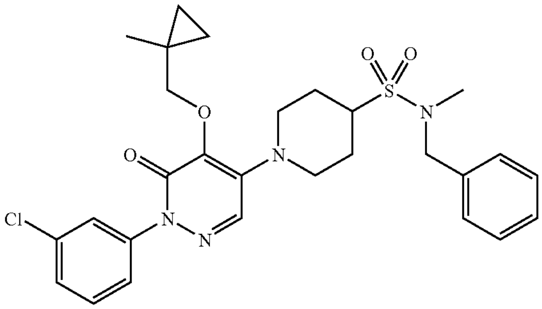 | 557 |
| 1819Z | 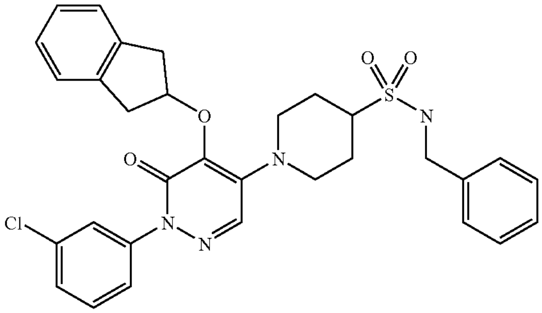 | 591 |

TABLE 32-continued
| Oxygen Analogues with Reverse Sulfonamide | | |
|---|---|---|
| Cmpd. No. | Structure | MS M + 1 |
| 1820Z | 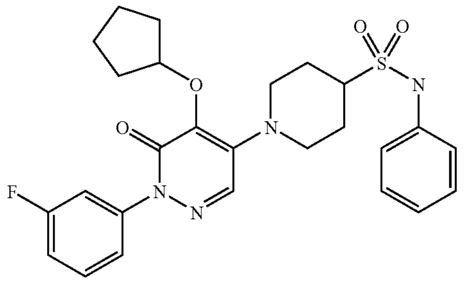 | 513 |
| 1821Z | 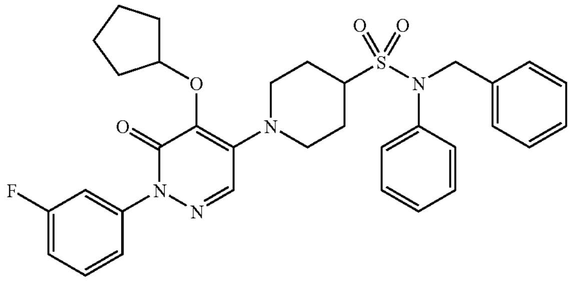 | 603 |
| 1822Z | 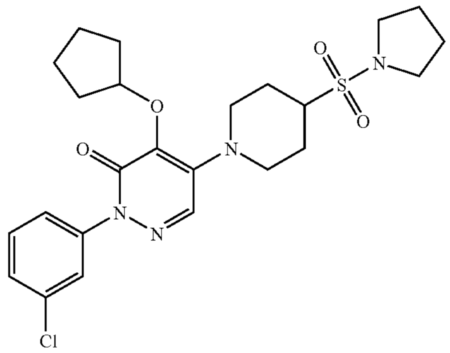 | 507 |
| 1823Z | 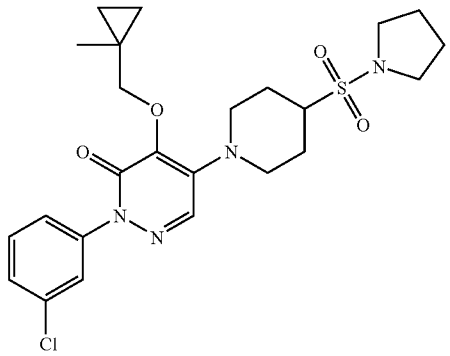 | 507 |

Scheme 35

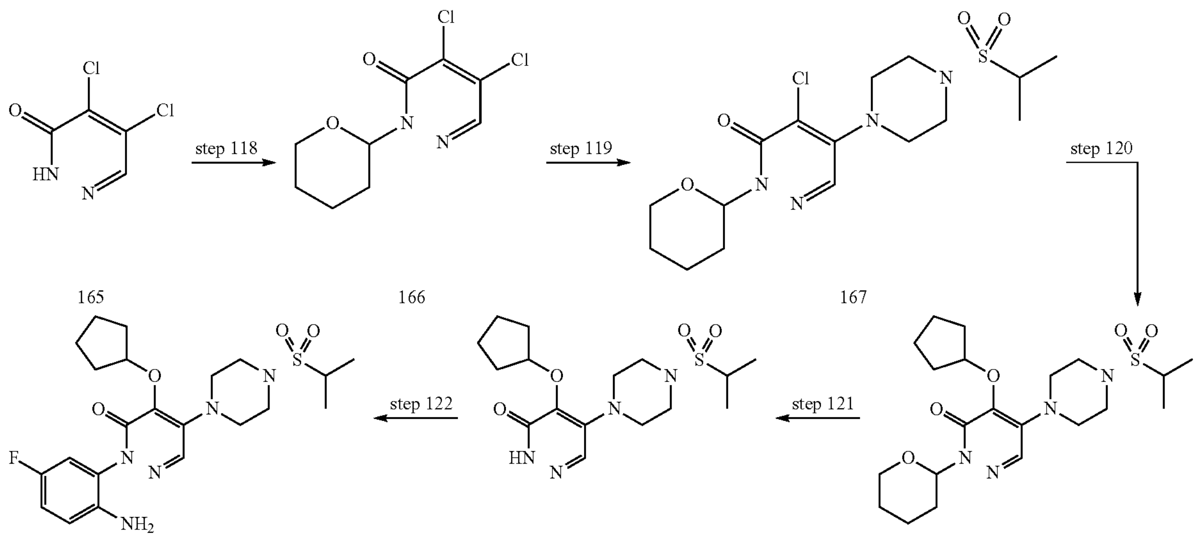

165 166 167

170 169 168

Step 118:

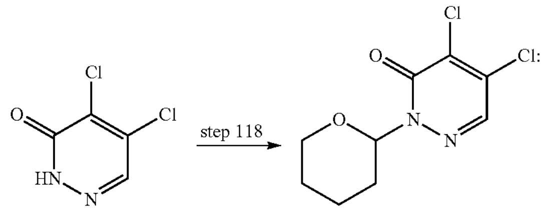

165 166

4,5-Dichloropyridazinone (25 g, 150 mmol) was mixed with dihydropyrane (41 mL, 450 mmol), and p-toluenesulfonic acid monohydrate (1.0 g) in a mixed solvent of toluene (120 mL) and THF (20 mL). The mixture was heated at reflux for 4 h. After cooling, the mixture was then diluted with 300 mL of EtOAc and 150 mL of water. The solid was removed by filtration. The organic layer was washed with diluted $NaHCO_3$ then brine, dried over anhydrous sodium sulfate, and concentrated. Purification by flash chromatography gave 24.4 g of the product 166 as an oil.

Step 119:

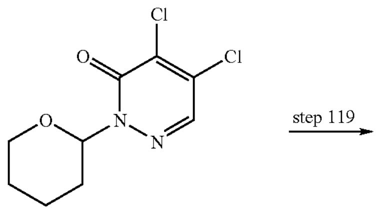

166

-continued

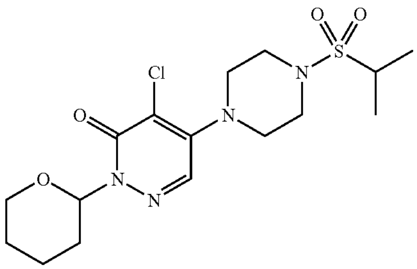

167

Compound 166 (12.5 g, 50 mmol) was mixed with 1-(isopropylsulfonyl)-piperazine HCl salt (16.8 g, 52.5 mmol) and triethylamine (14.6 mL, 105 mmol) in 180 mL of ethanol. The mixture was heated to 70° C. overnight. After cooling, the solvent was evaporated. The crude product was stirred in 200 mL of MeOH/water (1:1). The product was collected by filtration, washed with water and MeOH/water (1:1), and dried in a vacuum oven at 70° C. for 3 days to give 13.6 g of the product 167. MS (M+1): m/e 405.

Step 120:

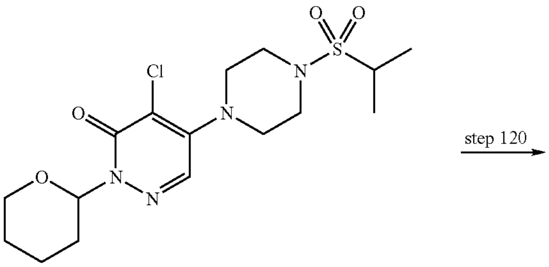

167

-continued

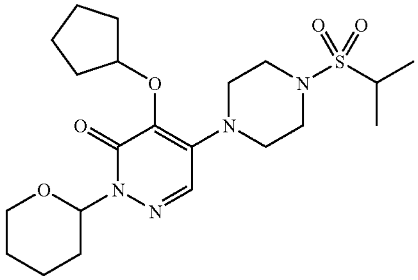

168

Compound 167 (6.1 g, 15 mmol) was mixed with cyclopentanol (2.1 mL, 23 mmol) in 80 mL of dry THF. NaH (60%, 0.72 g, 18 mmol) was added. The resulting mixture was stirred at room temperature overnight. The mixture was diluted with EtOAc and washed with water and brine. The organic layer was dried over anhydrous sodium sulfate, filtered, and concentrated to give the product 168 as an oil, which was dried under high vacuum overnight before use in the next step.

Step 121:

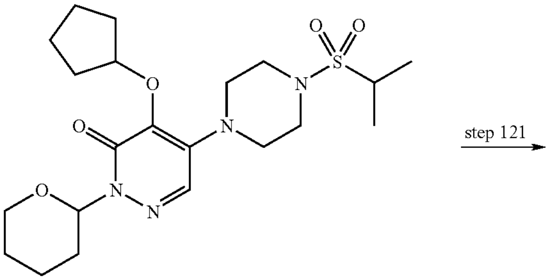

168

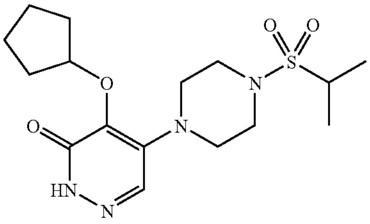

169

Compound 168 (~15 mmol) in 150 mL of dry methylene chloride was cooled to 0° C. $BF_3.Et_2O$ (5.6 mL, 45 mmol) was added slowly. The mixture was then stirred at 0° C. for 1 h. Ice-water was added to quench the reaction. The mixture was diluted with methylene chloride then washed with water, diluted sodium bicarbonate, and brine. The organic solution was dried over anhydrous sodium sulfate, filtered, and concentrated. The product was further dried in a vacuum oven to give 5.2 g of the product 169 as a pale yellow solid. MS (M+1): m/e 371.

Step 122 (Method A):

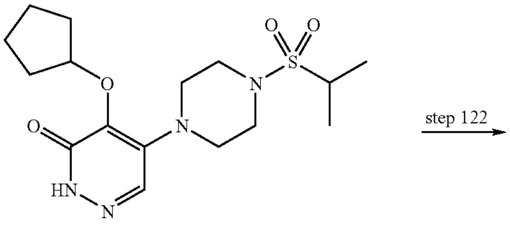

169

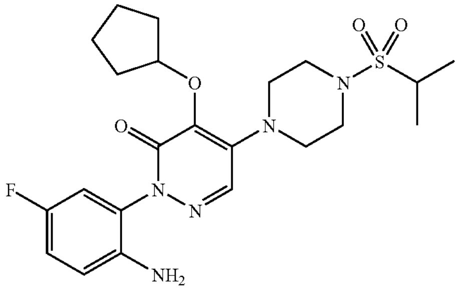

170A

Compound 169 (100 mg) was mixed with 2-iodo-4-fluoroaniline (100 mg), CuI (10 mg), 8-hydroxylquinoline (10 mmol), and potassium carbonate (100 mg) in 3.5 mL of dry pyridine. The mixture was heated to 175° C. for 30 mins in a microwave reactor. After cooling, the mixture was filtered through celite which was washed with EtOAc. The filtrate was concentrated, and the crude product was purified by Gilson prep HPLC (eluant: $CH_3CN$-water gradient with 0.1% HCOOH) to give 60 mg of pure product 170A as pale solid. MS (M+1): m/e 480.

Step 122 (Method B):

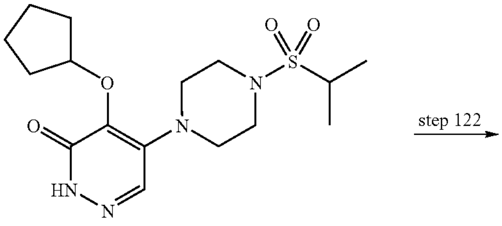

169

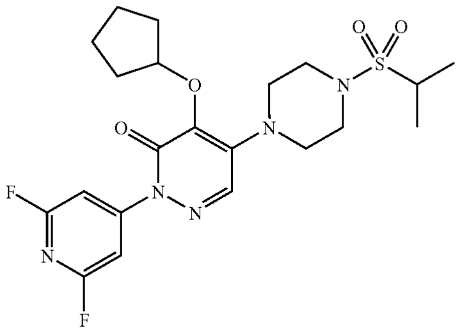

170B

Compound 169 (100 mg, 0.27 mmol) was mixed with 2,4,6-trifluoropyridine (53 mg, 0.4 mmol), and phosphazene base $P_1$-t-Bu (0.13 mL, 0.5 mmol) in 0.7 mL of dry DMF. The mixture was stirred at room temperature overnight then diluted to 4 mL with DMF, and purified by Gilson prep HPLC (eluant: $CH_3CN$-water gradient with 0.1% HCOOH) to give 51 mg of compound 170B as light-yellow solid. MS (M+1): m/e 484.

Using the procedures described above, the following compounds were synthesized.

TABLE 33

R$^3$ Substituent Analogs

| Cmpd. No. | Structure | MS M + 1 |
|---|---|---|
| 1824Z | 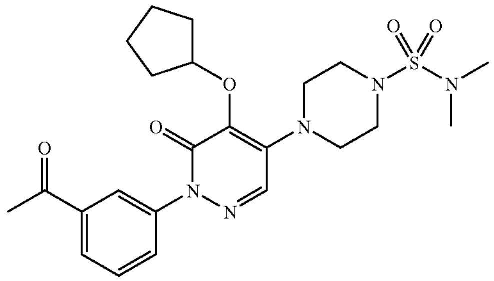 | 489 |
| 1825Z | 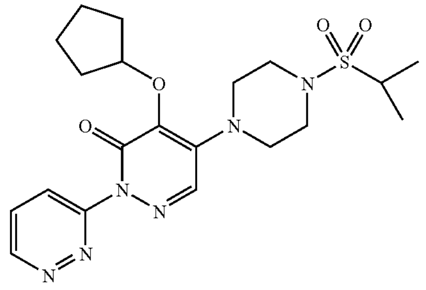 | 449 |
| 1826Z | 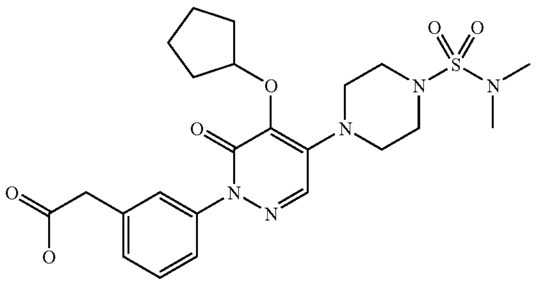 | 505 |
| 1827Z | 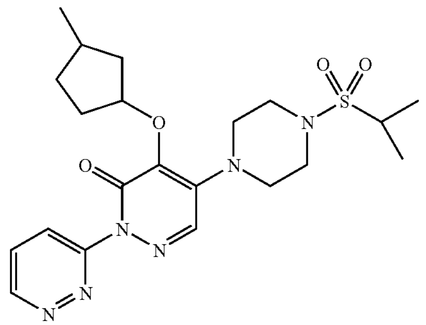 | 463 |

TABLE 33-continued
| R$^3$ Substituent Analogs | | |
|---|---|---|
| Cmpd. No. | Structure | MS M + 1 |
| 1828Z | 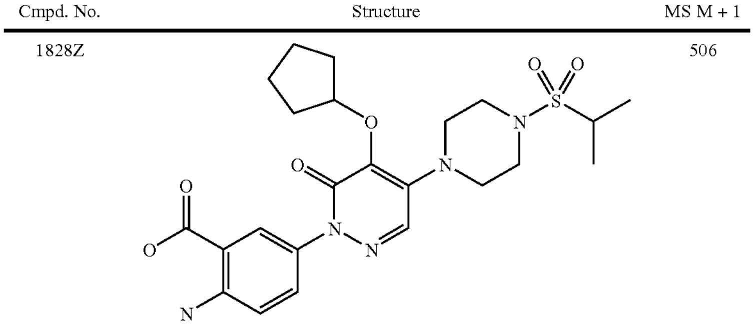 | 506 |
| 1829Z | 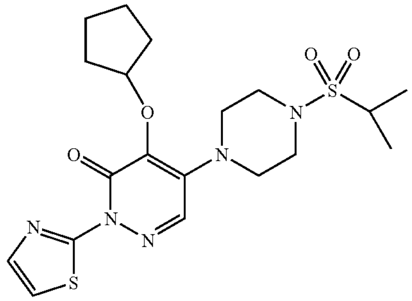 | 454 |
| 1830Z | 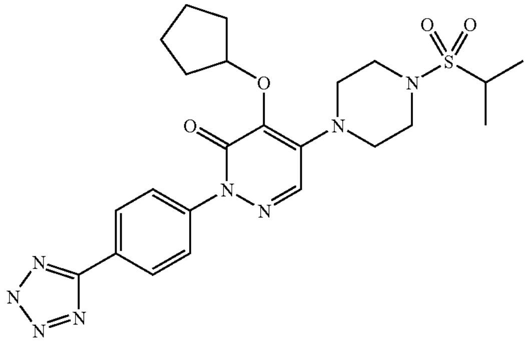 | 515 |
| 1831Z | 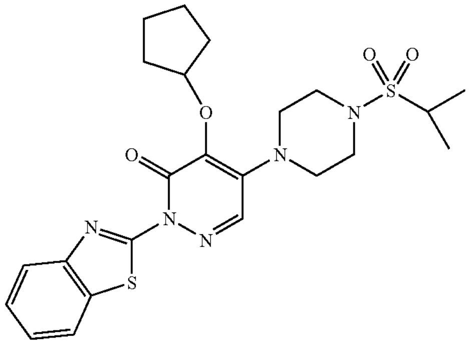 | 504 |
| 1832Z | 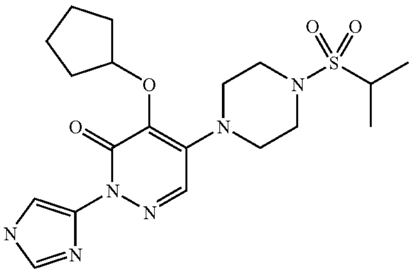 | 437 |

TABLE 33-continued

| R3 Substituent Analogs | | |
|---|---|---|
| Cmpd. No. | Structure | MS M + 1 |
| 1833Z | 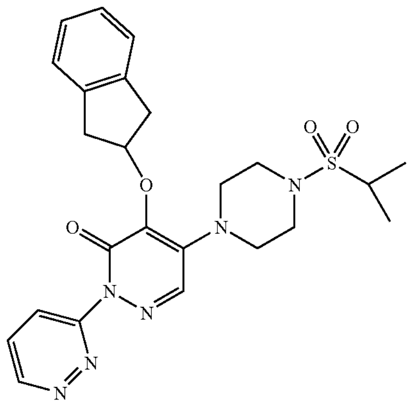 | 497 |
| 1834Z | 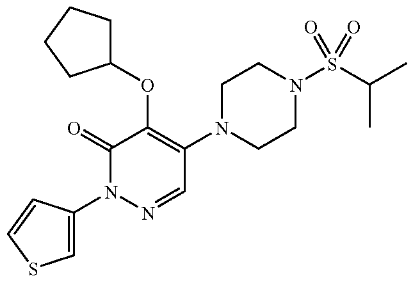 | 453 |

Scheme 36

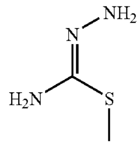

•HI +

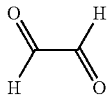

step 123

171

172

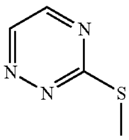

173

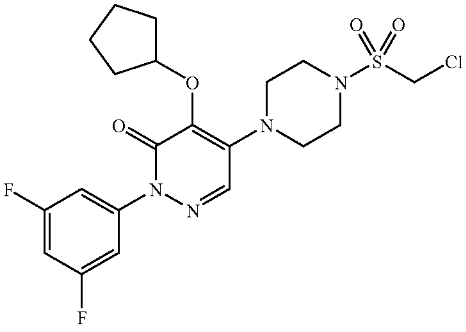

174

+

-continued

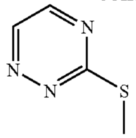

173 step 124

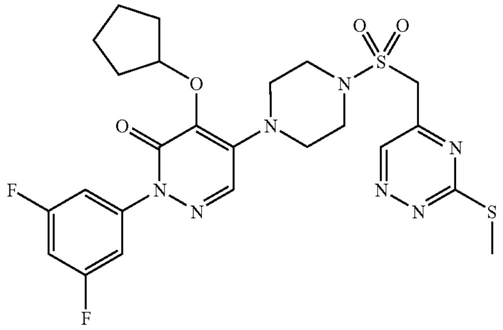

175

Step 123:

Compound 173 was prepared via the method of William W. Paudler and The-Kuei Chen, *J. Hetero. Chem. Vol.* 7 (1970) 767-771.

A solution of sodium bicarbonate (3.7 g, 44 mmol) and 40% glyoxal 172 (7 g, 48 mmol) in ice water (100 mL) was added to a solution of S-methylthiosemicarbazide hydroiodide 171 (9.32 g, 40 mmol) dissolved in ice water (60 mL) set in an ice bath. The resulting mixture was placed in the refrigerator (about −10° C.) for 5 h. The reaction mixture was extracted several times with $CH_2Cl_2$. The combined organic extract was dried ($Na_2SO_4$), filtered, and concentrated to give an oil (4.37 g, 86% yield). $^1$H-NMR 9.0 ppm s (1H), 8.4 ppm s (1H), 2.7 ppm s (3H).

Step 124:

A solution of compound 174 (430 mg, 0.88 mmol) and compound 173 (102 mg, 0.8 mmol) in DMSO (1 mL) was added dropwise to a mixture of potassium hydroxide powder (320 mg, 5.7 mmol) in DMSO (1.5 mL) at room temperature. The darkened mixture was stirred for 1 h, then poured into a saturated ammonium chloride solution. The precipitate was collected by filtration. Purification by silica gel chromatography (eluant: 0%-40% EtOAc-hexanes gradient) gave 300 mg (65% yield) of the product 175 as a pale-yellow foam. MS (M+1): m/e 580.

Using the procedures described above, the following compounds were synthesized.

| Cmpd. No | Structure | MS M + 1 |
|---|---|---|
| 1835Z | 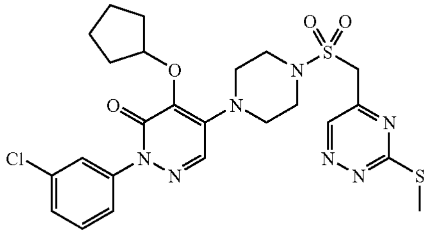 | 578 |
| 1836Z | 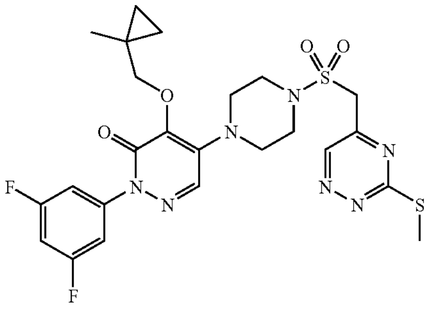 | 580 |
| 1837Z | 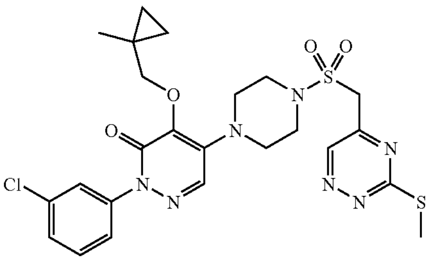 | 578 |

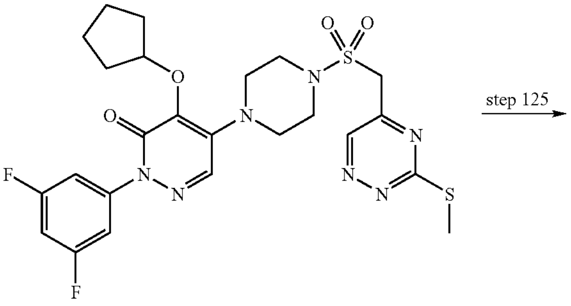

175

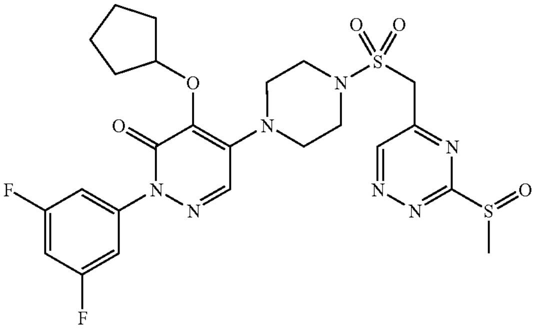

176

Step 125:

m-Chloroperbenzoic acid (77%, 23 mg, 0.1 mmol) was added to compound 175 (58 mg, 0.1 mmol) in $CH_2Cl_2$ (1.5 mL) at 0° C. The mixture was allowed to warm to 25° C. and stir for 15 h. A second dose of m-chloroperbenzoic acid (77%, 23 mg, 0.1 mmol) was added. After 5 h, additional $CH_2Cl_2$ was added, and the solution was washed with 10% sodium thiosulfate, saturated sodium bicarbonate, then brine. The dried ($Na_2SO_4$) organic layer was concentrated to a residue. Purification by silica gel chromatography (eluant: 0%-100% EtOAc hexanes gradient) gave 44 mg (74% yield) of the product 176 as a beige solid. MS (M+1): m/e 596.

Scheme 38

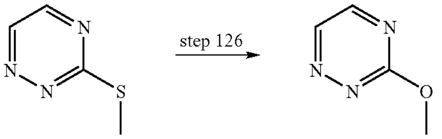

173 177

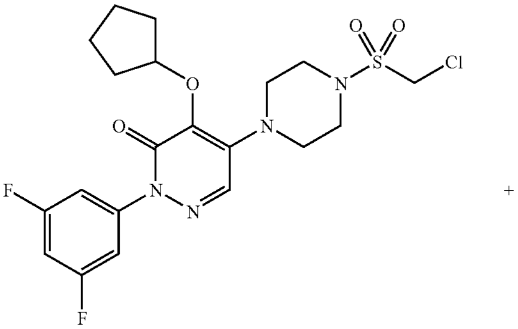

174

-continued

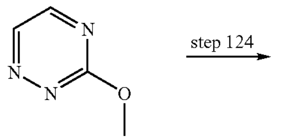

177

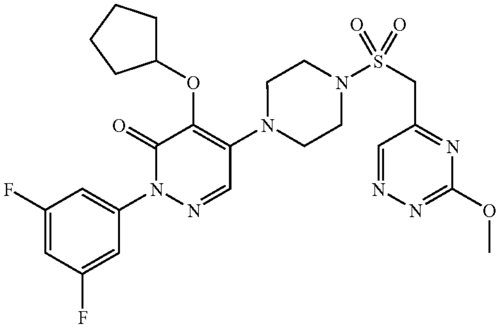

178

Step 126:

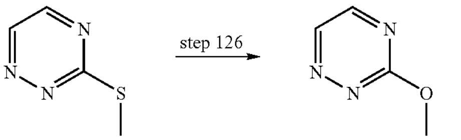

173 177

Compound 177 was prepared via the method of William W. Paudler and The-Kuei Chen, *J. Hetero. Chem. Vol.* 7 (1970) 767-771

Sodium methoxide (1.18 g, 21.8 mmol) was added to compound 173 (2.54 g, 20 mmol) in absolute methanol (35 mL). The mixture was stirred for 15 h. Ground dry ice was added slowly, and the mixture was filtered with a methanol rinse. The filtrate was concentrated to a residue. Purification by silica gel chromatography (eluant: 0%-40% EtOAc-hexanes gradient) gave 804 mg (36% yield) of the product 177 as a solid. MS (M+1): m/e 112.

Step 127:

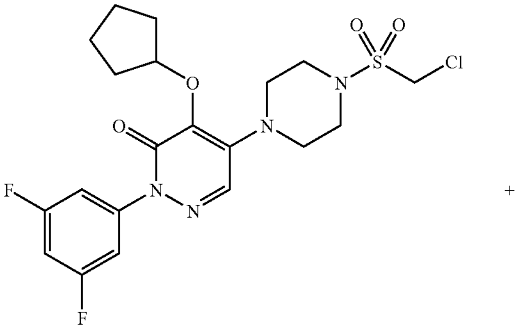

174

-continued

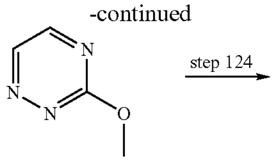

177

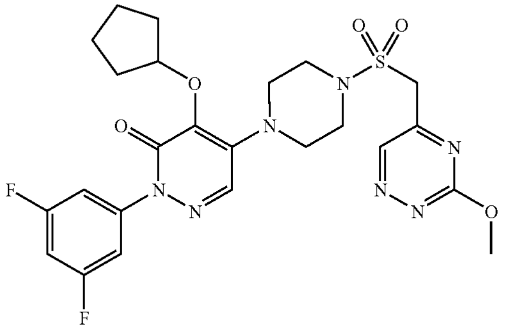

178

Using the procedure described in step 124, with compounds 174 and 177, compound 178 was prepared (53% yield) as a yellow solid. MS (M+1): m/e 564.

Scheme 39

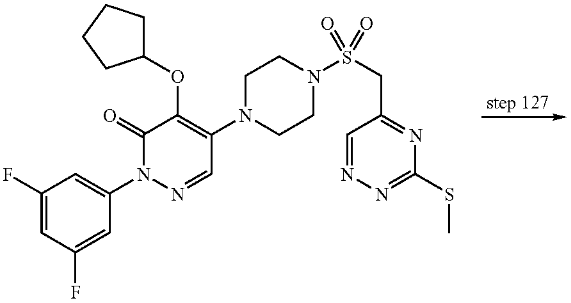

175

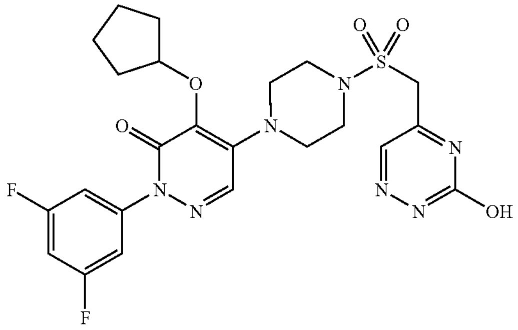

179 m-Chloroperbenzoic acid (77%, 48.6 mg, 0.22 mmol) was added to compound 175 (53 mg, 0.09 mmol) in $CH_2Cl_2$ (2 mL) at 25° C. The mixture was allowed to stir for 12 days. The solution was diluted with $CH_2Cl_2$ washed with 10% sodium thiosulfate, saturated sodium bicarbonate and brine. The dried ($Na_2SO_4$) organic layer was concentrated to a residue. Exposure to silica gel thin layer chromatography (60% EtOAc hexanes) for 15 h gave 32 mg (65% yield) of the product 179 as a solid. MS (M+1): m/e 550.

Scheme 40
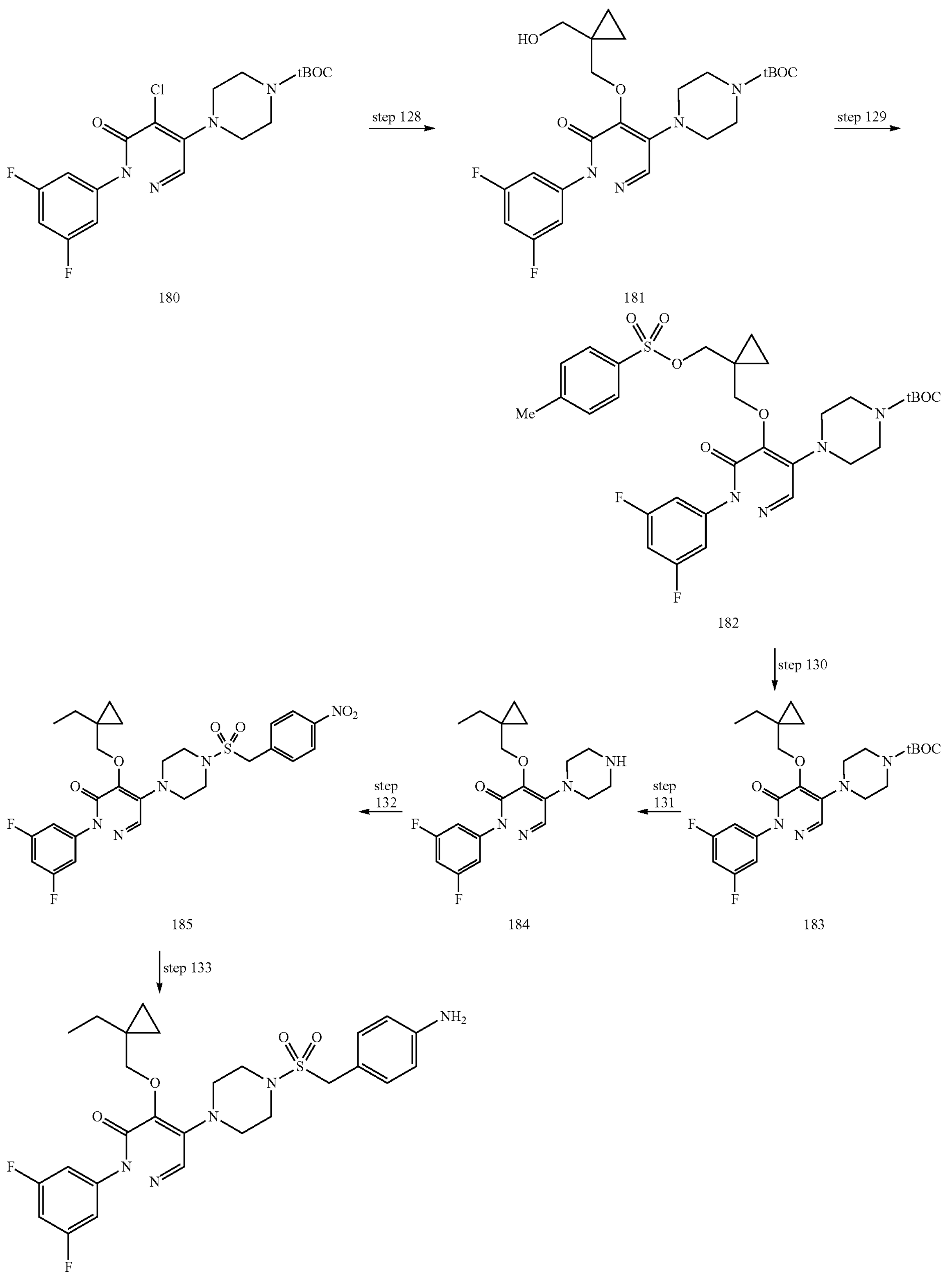
180
181
182
183
184
185
186

Step 128:

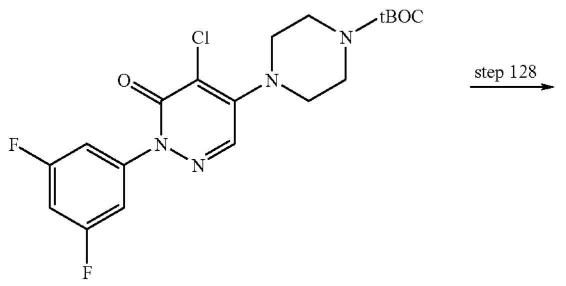

180

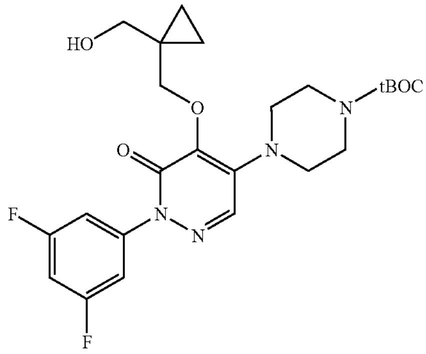

181

To cyclopropanedimethanol (11.2 g, 98.7 mmol) dissolved in dry THF (200 mL) under a nitrogen atmosphere was added sodium hexamethyldisilazane (1.0 M in THF, 49 mL, 49 mmol). The cloudy reaction mixture was stirred at room temperature for 20 mins then chloropyridazinone 180 (10.4 g, 24.4 mmol) was added. The reaction mixture was stirred at room temperature for 20 mins then heated at 80° C. for 10 h. The solvent was evaporated from the cooled mixture. Water (300 mL) was added, and the aqueous solution was extracted with $CH_2Cl_2$. The combined organic extract was dried ($MgSO_4$), filtered, and concentrated. Purification by silica gel chromatography (eluant: 20% EtOAc—$CH_2Cl_2$) gave 8.8 g (73% yield) of the product 181 as a yellow solid. MS (M+1): m/e 493.

Step 129:

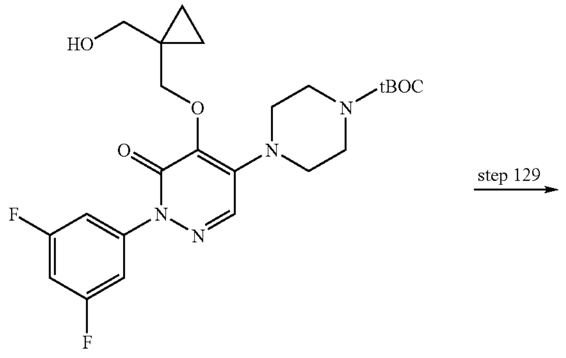

181

-continued

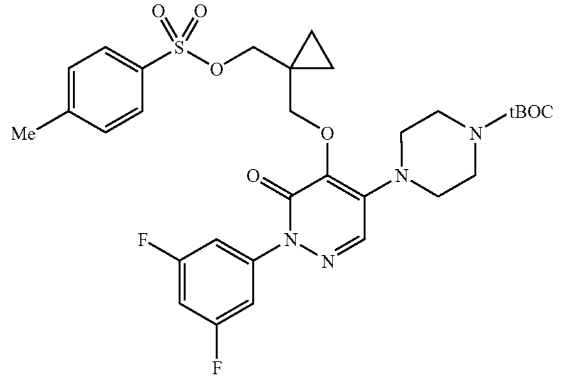

182

To compound 181 (2.00 g, 4.06 mmol) dissolved in $CH_2Cl_2$ (40 mL) was added dimethylaminopyridine (0.25 g, 2.03 mmol), triethylamine (1.23 g, 1.7 mL, 12.2 mmol), and then p-toluenesulfonyl chloride (1.93 g, 10.2 mmol). The reaction mixture was stirred at room temperature for 24 h. Water (50 mL) was added, and the aqueous solution was extracted with $CH_2Cl_2$. The combined organic extract was dried ($MgSO_4$), filtered, and concentrated. Purification by silica gel chromatography (eluant: 5% 10% EtOAc—$CH_2Cl_2$ gradient) gave 1.69 g (64% yield) of the product 182 as a yellow foam. MS (M+1): m/e 647.

Step 130:

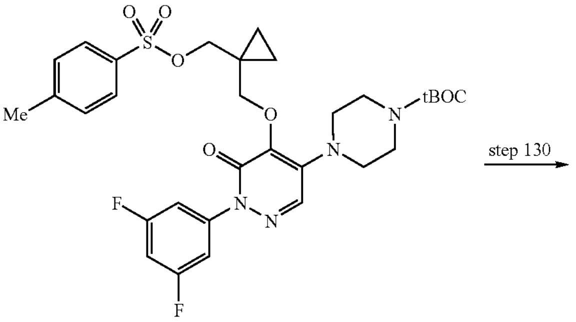

182

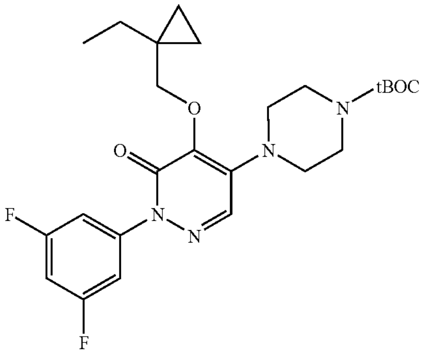

183

To copper iodide (1.48 g, 7.79 mmol) suspended in dry diethyl ether (20 mL) and cooled in −10° C. isopropanol bath (Neslab ethylene glycol circulator) under a nitrogen atmosphere was added methyl lithium (1.6 M in diethyl ether, 9.7 mL, 15.6 mmol) via syringe. The reaction mixture became cloudy yellow then colorless and was stirred for 30 mins in the −10° C. bath. The tosylate compound 182 (1.68 g, 2.60 mmol) was dissolved in diethyl ether (50 mL) and added via addition funnel. The reaction mixture was stirred in the −10° C. bath for 45 mins, then warmed slowly to room temperature, and stirred at room temperature for 16 h. Saturated $NH_4Cl$ (50 mL) was added, and the aqueous solution was extracted with EtOAc. The combined organic extract was dried ($MgSO_4$), filtered, and concentrated. Purification by silica gel chromatography (eluant: 5% EtOAc—$CH_2Cl_2$) gave 0.51 g (40% yield) of the product 183 as a yellow oil. MS (M+1): m/e 491.

Step 131:

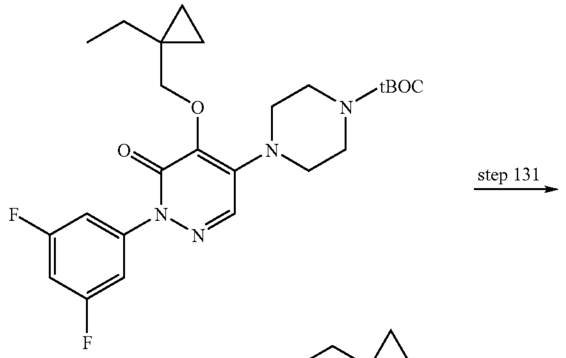

183

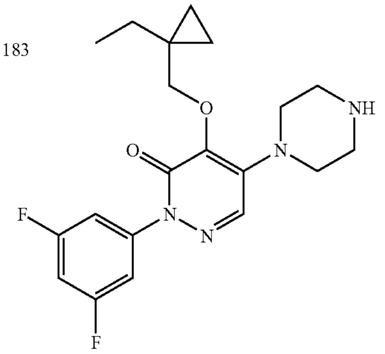

184

To compound 183 (0.50 g, 1.02 mmol) dissolved in $CH_2Cl_2$ (10 mL) and cooled to 0° C. was added trifluoroacetic acid (2 mL). The reaction mixture was stirred at 0° C. for 2 h then the solvent was evaporated. Aqueous 0.5 N NaOH (15 mL) was added, and the aqueous solution was extracted with $CH_2Cl_2$. The combined organic extract was dried ($MgSO_4$), filtered, and concentrated to give 0.25 g (63% yield) of the product 184 as a yellow oil. MS (M+1): m/e 391.

Step 132:

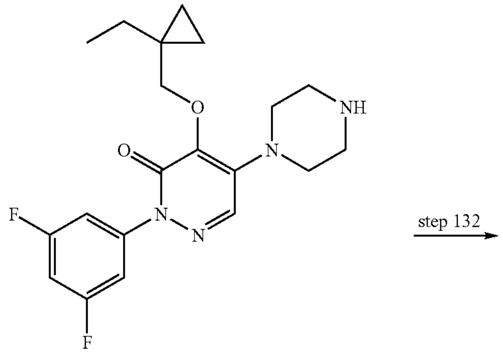

184

-continued

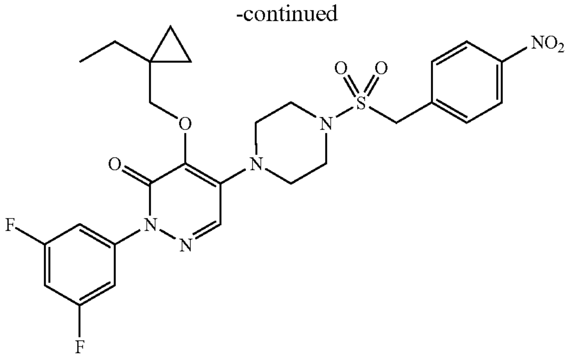

185

To compound 184 (185 mg, 0.474 mmol) dissolved in $CH_2Cl_2$ (8 mL) was added pyridine (0.11 mL, 1.4 mmol) then (4-nitrophenyl)methanesulfonyl chloride (160 mg, 0.62 mmol). The reaction mixture was stirred at room temperature for 4 h. Water was added, and the aqueous solution was extracted with $CH_2C_2$. The combined organic extract was dried ($MgSO_4$), filtered, and concentrated. Purification by silica gel chromatography (eluant: 10% EtOAc—$CH_2Cl_2$) gave 110 mg (39% yield) of the product 185 as a yellow oil. MS (M+1): m/e 590.

Step 133:

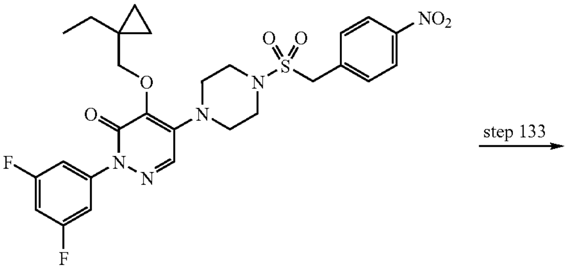

185

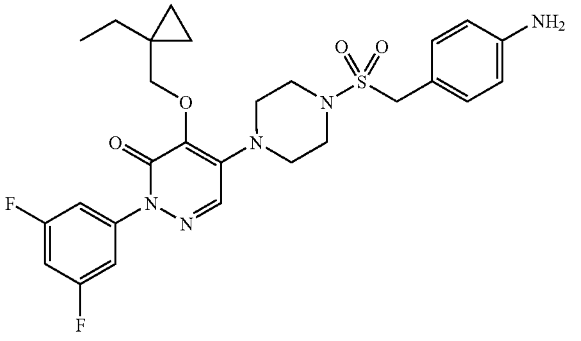

186

To compound 185 (116 mg, 0197 mmol) suspended in EtOAc (20 mL) and iPrOH (10 mL) was added platinum oxide (26.7 mg, 0.098 mmol). The reaction mixture was stirred under a hydrogen balloon for 4 h. The platinum oxide catalyst was removed by filtration, washed with iPrOH, and the filtrate was evaporated. Purification by silica gel chromatography (eluant: 40% EtOAc-hexane) gave 65 mg (56% yield) of the product 186 as a yellow foam. MS (M+1): m/e 560.

Using the procedures described above, the following compounds were synthesized.

-continued
| Cmpd. No. | Structure | MS M + 1 |
|---|---|---|
| 1838Z | 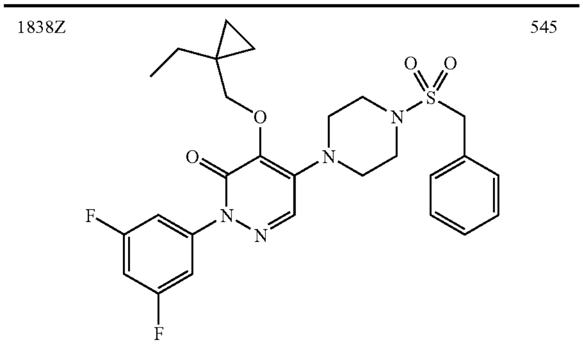 | 545 |
| 1839Z | 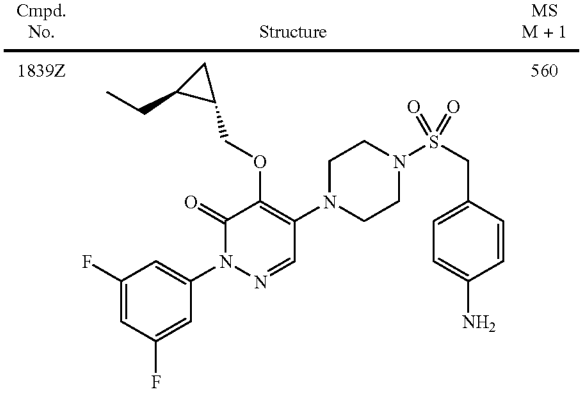 | 560 |
Scheme 41
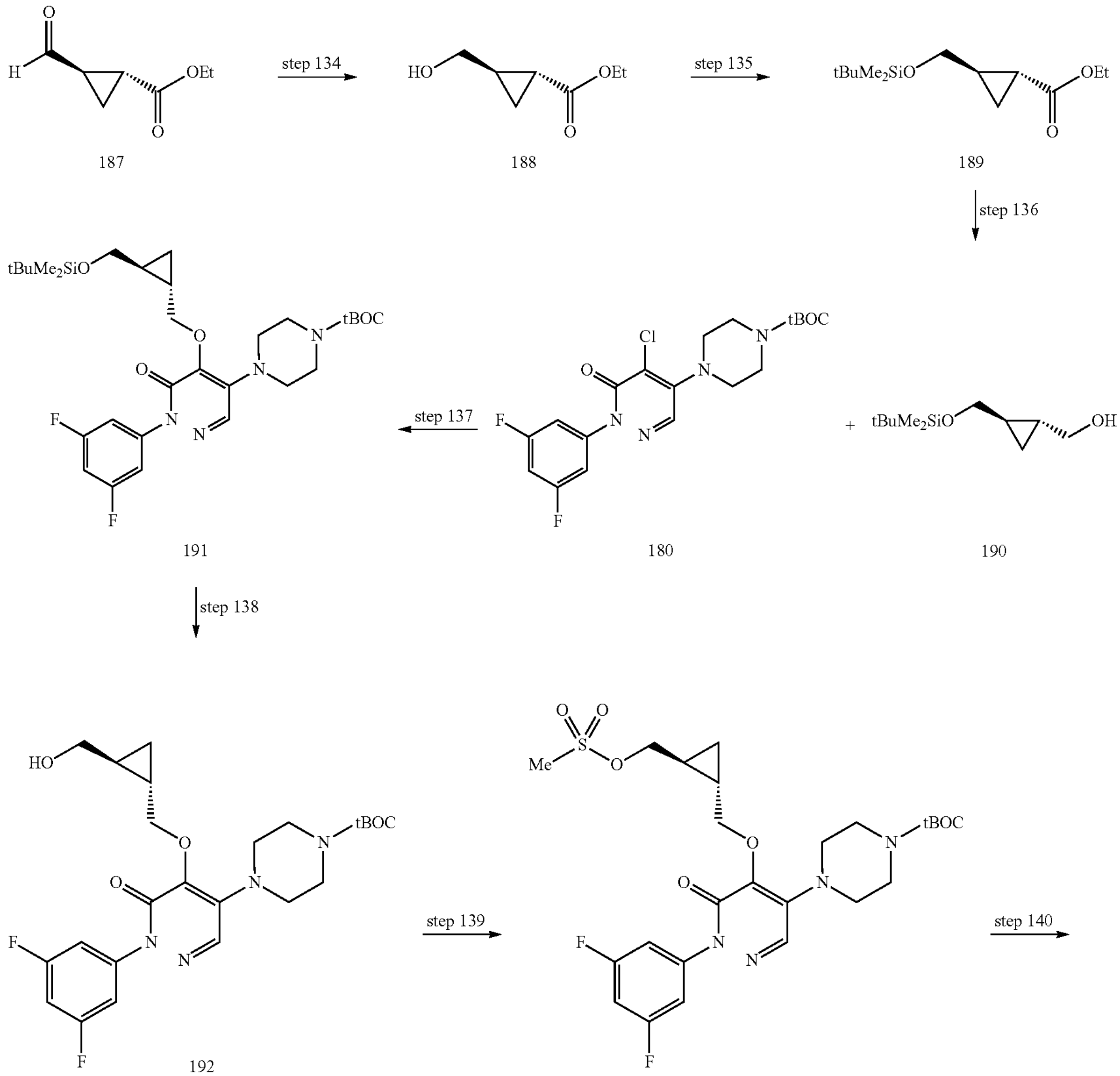
187
188
189
191
180
190
192
193

-continued

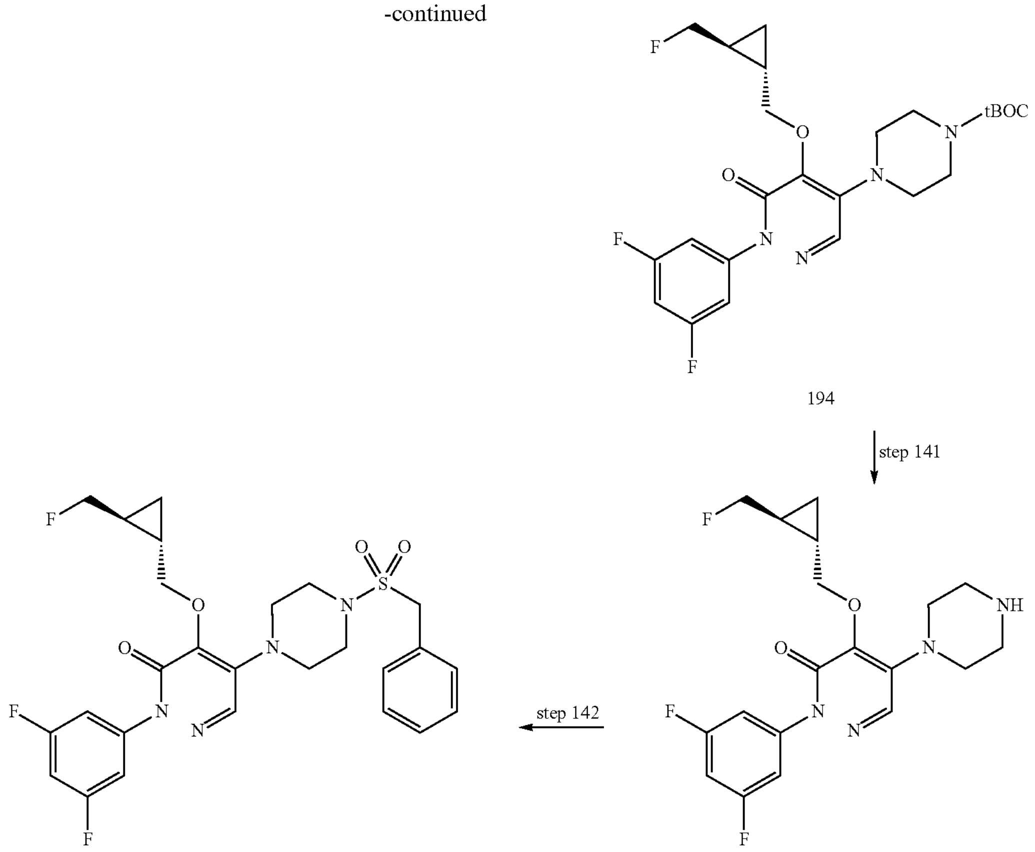

194

195

196

Step 134:

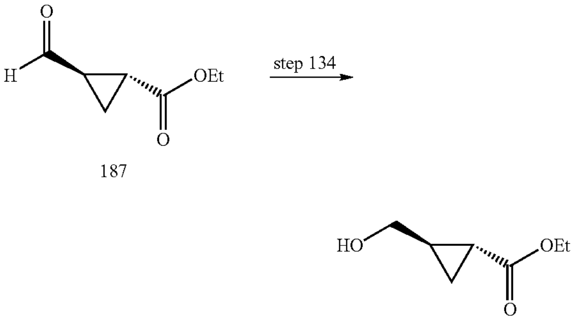

187

188

Step 135:

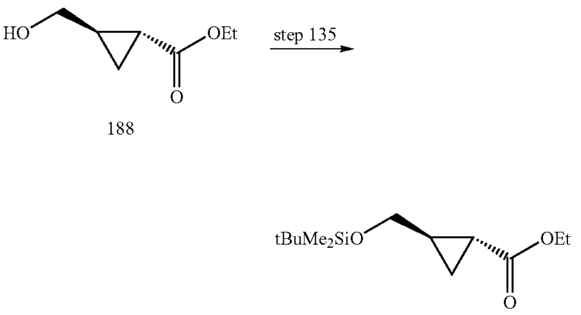

188

189

To ethyl 2-formyl-1-cyclopropane carboxylate 187 (10.00 g, 0.0703 mol) dissolved in ethanol (250 mL) was added sodium borohydride (3.99 g, 0.106 mol). The reaction mixture was stirred at room temperature for 5 h. The solvent was evaporated, and water (200 mL) was added. The aqueous solution was extracted with $CH_2Cl_2$. The combined organic extract was dried ($MgSO_4$), filtered, and concentrated. Purification by silica gel chromatography (eluant: 5-8% MeOH—$CH_2Cl_2$) gave 9.19 g (91% yield) of the product 188 as a colorless oil. MS (M−17): m/e 127.

To compound 188 (2.00 g, 13.9 mmol) dissolved in $CH_2Cl_2$ (50 mL) was added dimethylaminopyridine (0.42 g, 3.47 mmol), triethylamine (2.11 g, 2.9 mL, 20.8 mmol), and t-butyldimethylsilyl chloride (2.72 g, 18.0 mmol). The reaction mixture was stirred at room temperature for 18 h. Water (50 mL) was added, and the aqueous solution was extracted with $CH_2Cl_2$. The combined organic extract was dried ($MgSO_4$), filtered, and concentrated. Purification by silica gel chromatography (eluant: 3% EtOAc—$CH_2Cl_2$) gave 3.59 g (100% yield) of the product 189 as a colorless oil. MS (M+1): m/e 259.

Step 136:

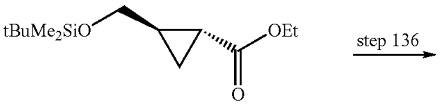

189

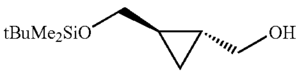

190

To compound 189 (3.59 g, 13.9 mmol) dissolved in dry THF (50 mL) was added solid lithium aluminum hydride (0.53 g, 13.9 mmol) portionwise. The reaction mixture was stirred at room temperature for 16 h under nitrogen. Carefully added water (0.5 mL), 1 N NaOH (0.5 mL) then water (1.5 mL) to precipitate the aluminum salts. Additional $CH_2Cl_2$ (50 mL) and $MgSO_4$ was added and stirred. The mixture was filtered, and the aluminum salts washed with $CH_2Cl_2$. The filtrate was evaporated. Purification by silica gel chromatography (eluant: 20% EtOAc—$CH_2Cl_2$) gave 2.15 g (71% yield) of the product 190 as a colorless oil. MS (M+1): m/e 217.

Step 137:

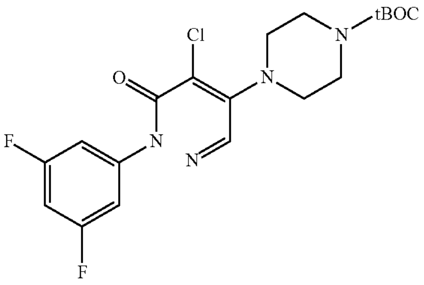

180

+

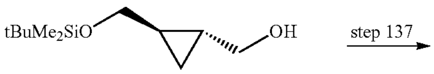

190

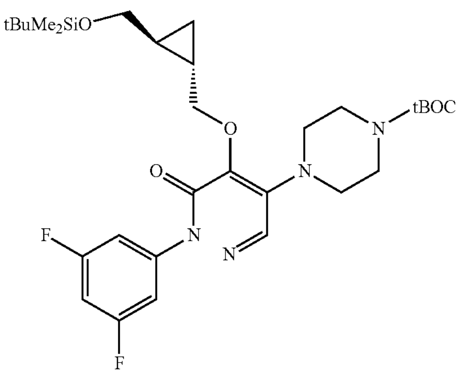

191

To compound 190 (2.14 g, 9.89 mmol) dissolved in dry THF (50 mL) was added sodium bis(trimethylsilyl)amide (1.0 M in THF, 9.5 mL, 9.50 mmol) via syringe. The reaction mixture was stirred at room temperature for 15 mins under nitrogen. Chloropyridazinone 180 (3.52 g, 8.24 mmol) was added, and the reaction mixture was heated at 80° C. for 1 h then stirred at room temperature for 16 h. The solvent was evaporated. Water (75 mL) was added, and the aqueous solution was extracted with $CH_2Cl_2$. The combined organic extract was dried ($MgSO_4$), filtered, and concentrated. Purification by silica gel chromatography (eluant: 5-10% EtOAc—$CH_2Cl_2$) gave 4.94 g (99% yield) of the product 191 as a yellow oil. MS (M+1): m/e 607.8.

Step 138:

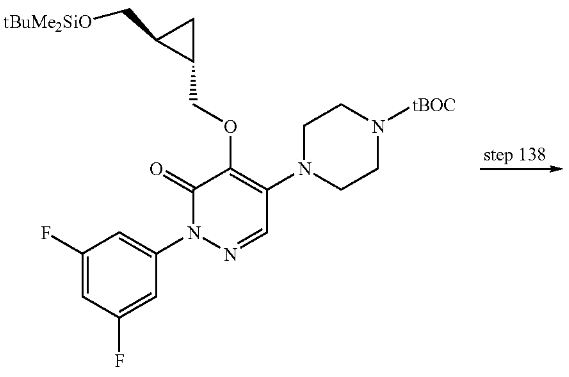

191

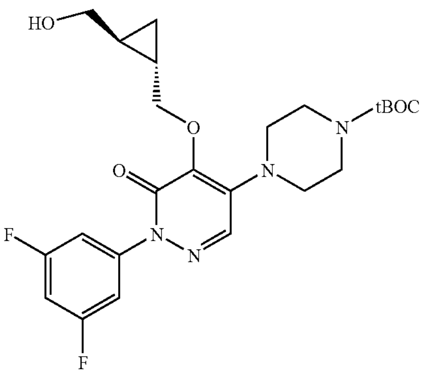

192

To compound 191 (4.93 g, 8.12 mmol) dissolved in dry THF (60 mL) was added tetrabutylammonium fluoride (1.0 M in THF, 12.2 mL, 12.2 mmol). The reaction mixture was stirred at room temperature for 16 h. The solvent was evaporated. Water (75 mL) was added, and the aqueous solution was extracted with $CH_2Cl_2$. The combined organic extract was dried ($MgSO_4$), filtered, and concentrated. Purification by silica gel chromatography (eluant: 5% MeOH($CH_2Cl_2$)) gave 4.00 g (100% yield) of the product 192 as a yellow oil. MS (M+1): m/e 493.

Step 139:

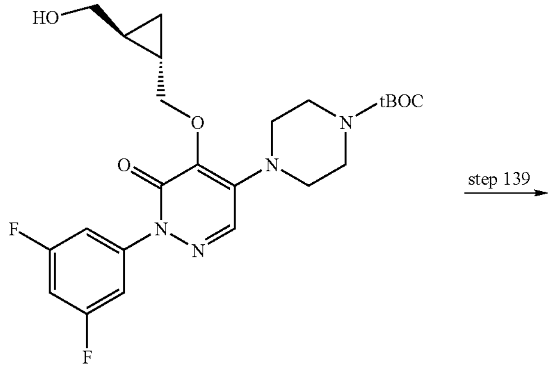

192

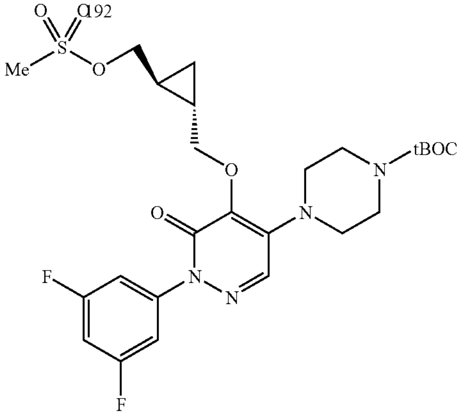

193

To compound 192 (1.07 g, 2.17 mmol) dissolved in $CH_2Cl_2$ (25 mL) was added dimethylaminopyridine (0.053 g, 0.434 mmol), triethylamine (0.33 g, 0.45 mL, 3.26 mmol), and methanesulfonic anhydride (0.45 g, 2.61 mmol). The reaction mixture was stirred at room temperature for 5 h. Saturated $NaHCO_3$ (30 mL) was added, and the aqueous solution was extracted with $CH_2Cl_2$. The combined organic extract was dried ($MgSO_4$), filtered, and concentrated to give 1.24 g (100% yield) of the product 193 as a yellow oil. MS (M+1): m/e 571.

Step 140:

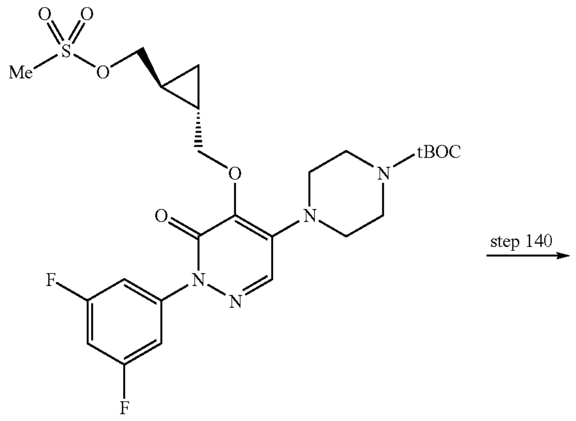

193

-continued

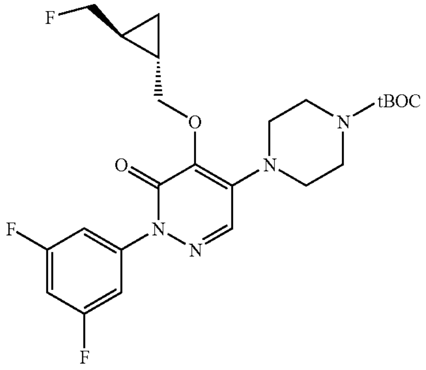

194

To compound 193 (1.24 g, 2.17 mmol) dissolved in dry THF (25 mL) was added tetrabutylammonium fluoride (1.0 M in THF, 3.3 mL, 3.3 mmol). The reaction mixture was heated at 45° C. for 4.5 h. The solvent was evaporated. Water (30 mL) was added, and the aqueous solution was extracted with $CH_2Cl_2$. The combined organic extract was dried ($MgSO_4$), filtered, and concentrated. Purification by silica gel chromatography (eluant: 5-10% EtOAc—$CH_2Cl_2$) gave 0.67 g (63% yield) of the product 194 as a yellow oil. MS (M+1): m/e 495.

Step 141:

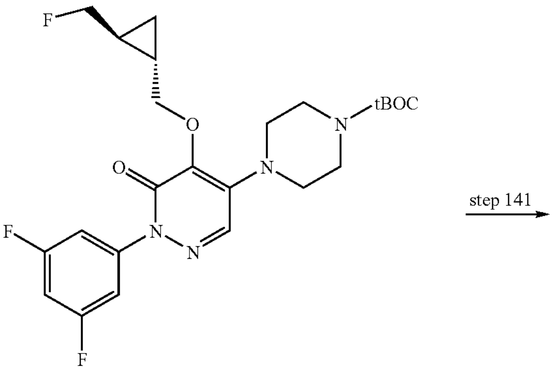

194

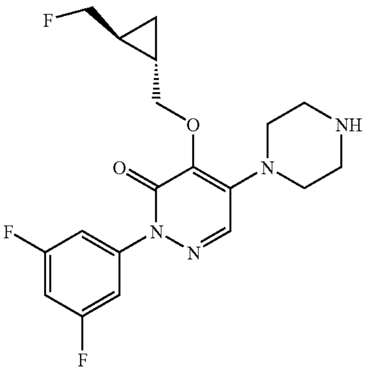

195

To compound 194 (0.66 g, 1.33 mmol) dissolved in $CH_2Cl_2$ (15 mL) was added trifluoroacetic acid (2 mL). The reaction mixture was stirred at room temperature for 3.5 h then the solvent was evaporated. Aqueous 0.5 N NaOH (20 mL) was added, and the aqueous solution was extracted with $CH_2Cl_2$. The combined organic extract was dried ($MgSO_4$), filtered, and concentrated to give 0.52 g (100% yield) of the product 195 as a yellow oil. MS (M+1): m/e 395.7.

Step 142:

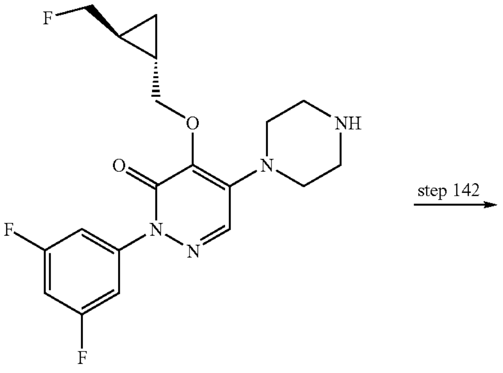

195

-continued

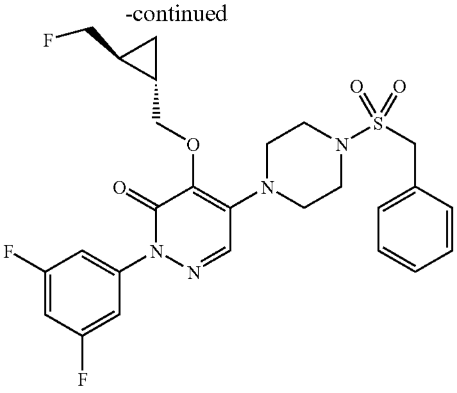

196

To compound 195 (100 mg, 0.254 mmol) dissolved in $CH_2Cl_2$ (5 mL) was added pyridine (0.062 mL, 0.762 mmol) then □-toluenesulfonyl chloride (63 mg, 0.33 mmol). The reaction mixture was stirred at room temperature for 7 h. Water was added, and the aqueous solution was extracted with $CH_2Cl_2$. The combined organic extract was dried ($MgSO_4$), filtered, and concentrated. Purification by silica gel chromatography (eluant: 5% EtOAc—$CH_2Cl_2$) gave 74 mg (53% yield) of the product 196 as a yellow oil. MS (M+1): m/e 549.

Using the procedures described above, the following compounds were synthesized.

| Cmpd. No. | Structure | MS M + 1 |
| --- | --- | --- |
| 1840Z | 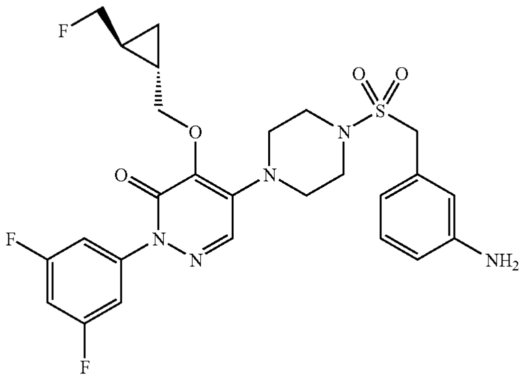 | 564 |
| 1841Z | 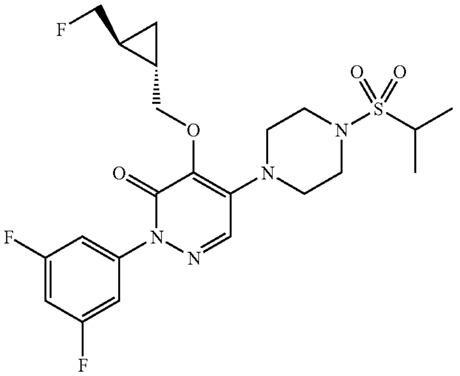 | 501 |

-continued
| Cmpd. No. | Structure | MS M + 1 |
|---|---|---|
| 1842Z | 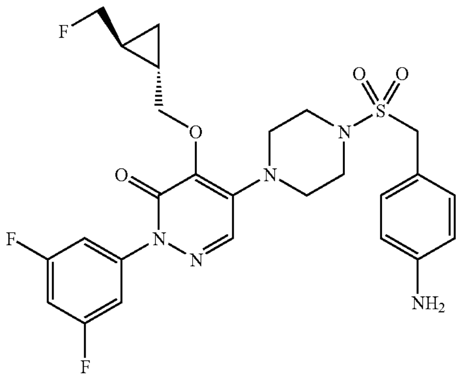 | 564 |
Scheme 42
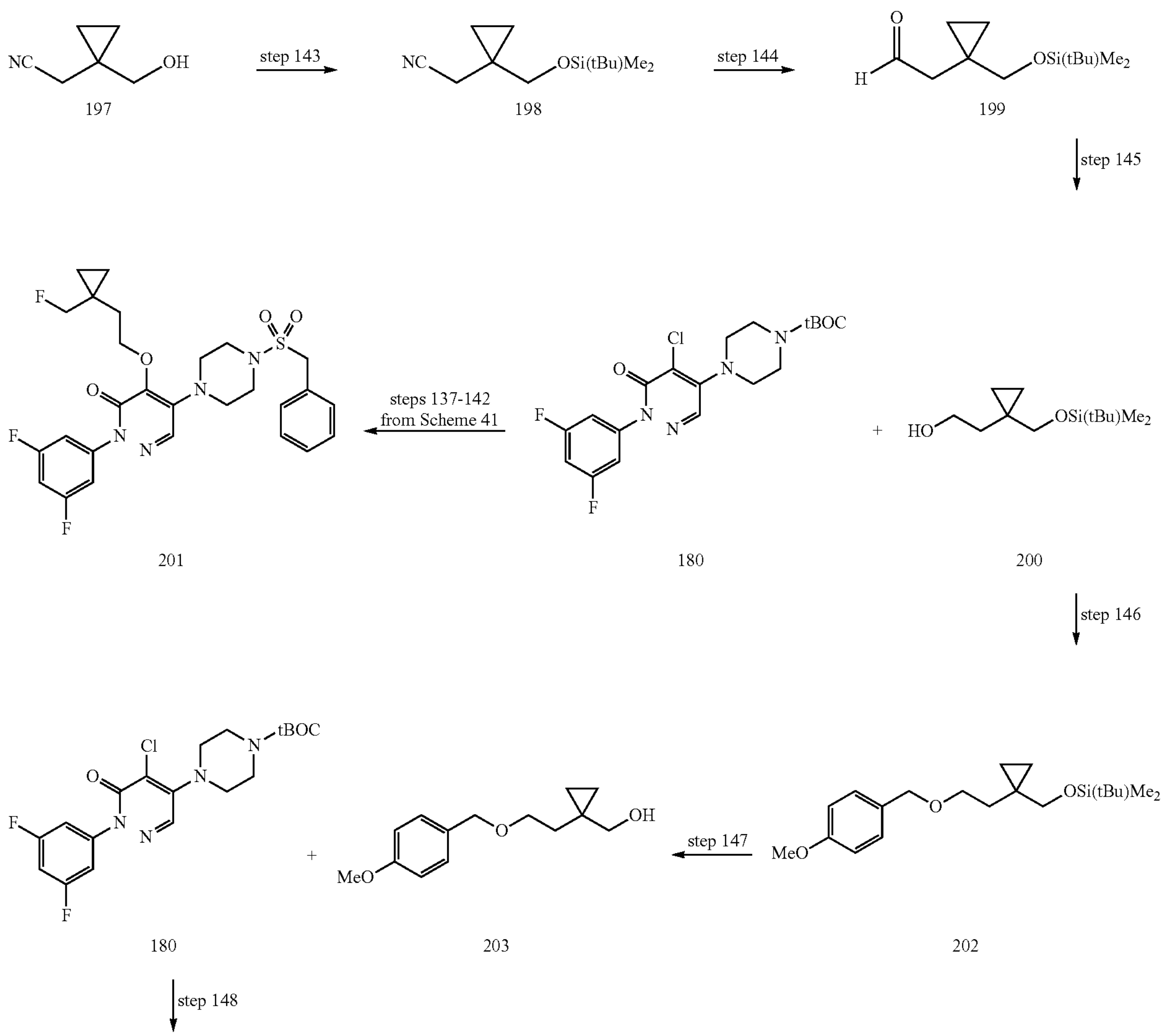
197 198 199
201 180 200
180 203 202

-continued

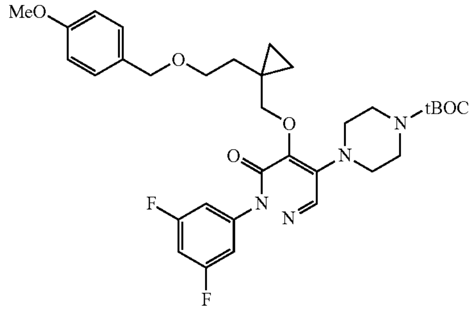

204

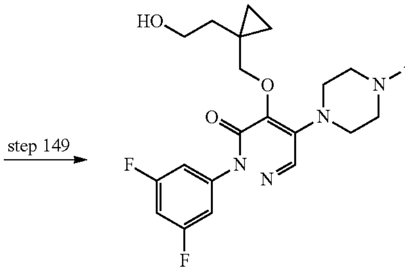

205

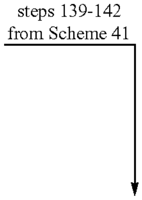

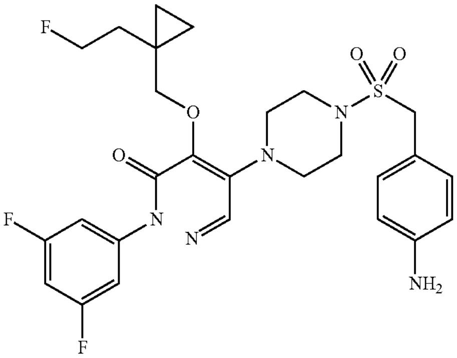

206

Step 143:

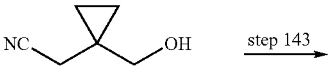

197

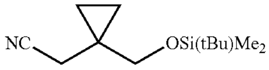

198

To compound 197 (5.00 g, 45.0 mmol) dissolved in $CH_2Cl_2$ (200 mL) was added dimethylaminopyridine (1.37 g, 11.2 mmol), triethylamine (6.83 g, 9.4 mL, 67.5 mmol), and t-butyldimethylsilyl chloride (8.82 g, 58.5 mmol). The reaction mixture was stirred at room temperature for 5 h. Water (150 mL) was added, and the aqueous solution was extracted with $CH_2Cl_2$. The combined organic extract was dried ($MgSO_4$), filtered, and concentrated. Purification by silica gel chromatography (eluant: 3% EtOAc—$CH_2Cl_2$) gave 9.57 g (94% yield) of the product 198 as a colorless oil. MS (M+1): m/e 226.

Step 144:

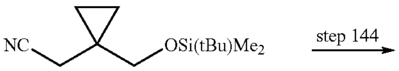

198

-continued

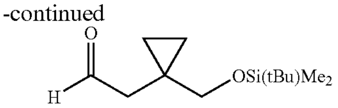

199

To compound 198 (9.56 g, 49.4 mmol) dissolved in $CH_2Cl_2$ (150 mL) and cooled to −78° C. under nitrogen was added diisobutylaluminum hydride (1 M in hexane, 46.7 mL, 46.7 mmol) via addition funnel over 10 mins. The reaction mixture was warmed slowly to 0° C. over 45 mins and stirred at 0° C. for 30 mins. Carefully added 1 N HCl (200 mL) and then extracted with $CH_2Cl_2$. The combined organic extract was dried ($MgSO_4$), filtered, and concentrated to give 9.69 g (100% yield) of the product 199 as a yellow oil. MS (M+1): m/e 228.

Step 145:

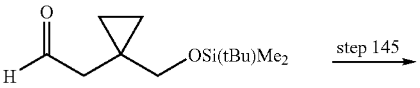

199

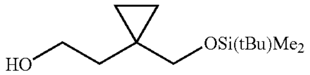

200

To compound 199 (9.69 g, 42.4 mmol) dissolved in ethanol (200 mL) was added sodium borohydride (2.41 g, 63.6 mmol). The reaction mixture was stirred at room temperature for 3 h. The solvent was evaporated. Water (200 mL) was added, and the aqueous solution was extracted with $CH_2Cl_2$. The combined organic extract was dried ($MgSO_4$), filtered, and concentrated. Purification by silica gel chromatography (eluant: 10% EtOAc—$CH_2Cl_2$) gave 6.86 g (70% yield) of the product 200 as a yellow oil. MS (M+1): m/e 231.
Steps 137-142 from Scheme 41:
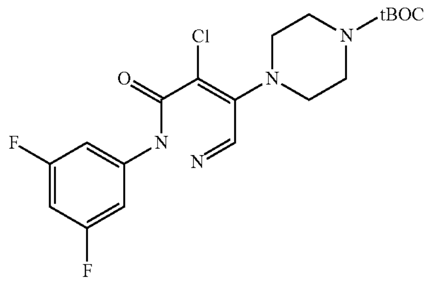
180
+
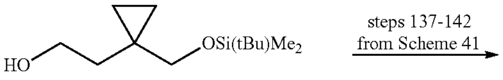
200
-continued
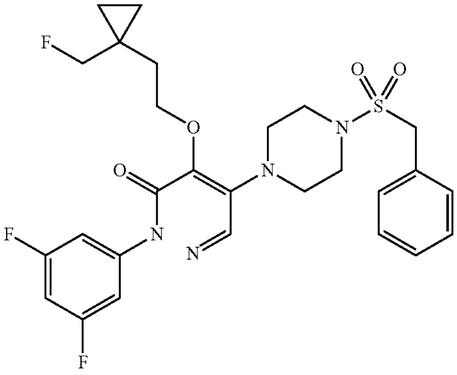
201
Using the procedures from steps 137-142 from Scheme 41, the following compounds were synthesized.
| Cmpd. No. | Structure | MS M + 1 |
|---|---|---|
| 1843Z | 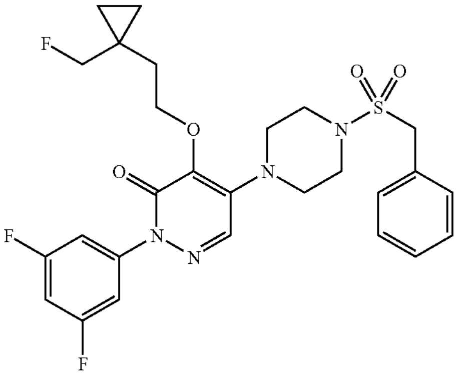 | 563 |
| 1844Z | 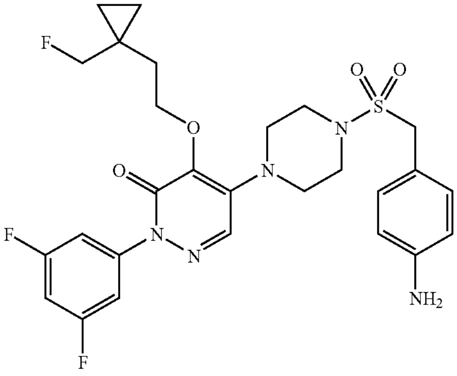 | 578 |

-continued

| Cmpd. No. | Structure | MS M + 1 |
|---|---|---|
| 1845Z | 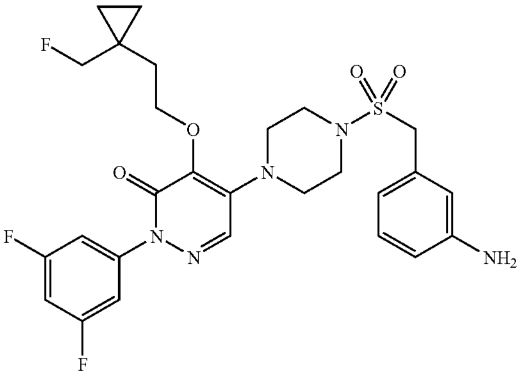 | 578 |

Step 146:

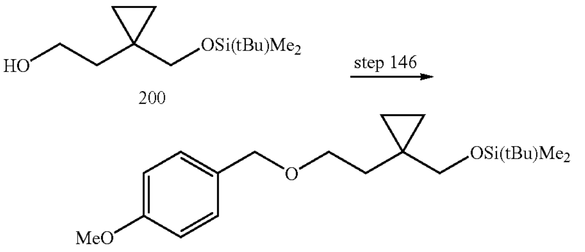

200

202

To compound 200 (5.45 g, 23.7 mmol) dissolved in dry THF (100 mL) under nitrogen was added sodium bis(trimethylsilyl)amide via syringe. The reaction mixture was stirred at room temperature for 15 mins then p-methoxybenzylbromide (6.18 g, 30.8 mmol) was added. The resulting mixture was stirred at room temperature for 18 h. The solvent was evaporated. Water (100 mL) was added, and the aqueous solution was extracted with $CH_2Cl_2$. The combined organic extract was dried ($MgSO_4$), filtered, and concentrated. Purification by silica gel chromatography (eluant: 2% EtOAc—$CH_2Cl_2$) gave 7.59 g (92% yield) of the product 202 as a colorless oil. MS (M+1): m/e 351.

Step 147:

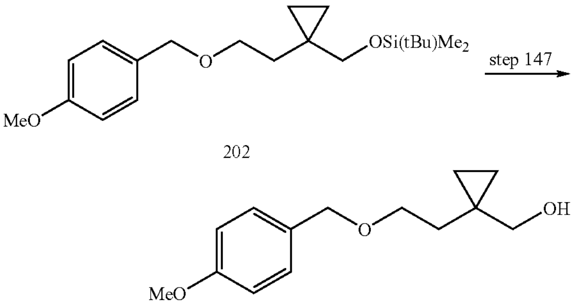

202

203

To compound 202 (7.58 g, 21.6 mmol) dissolved in dry THF (100 mL) was added tetrabutylammonium fluoride (1.0 M in THF, 27.0 mL 27.0 mmol). The reaction mixture was stirred at room temperature for 16 h. The solvent was evaporated. Water (100 mL) was added, and the aqueous solution was extracted with $CH_2Cl_2$. The combined organic extract was dried ($MgSO_4$), filtered, and concentrated. Purification by silica gel chromatography (eluant: 15% EtOAc—$CH_2Cl_2$) gave 5.03 g (98% yield) of the product 203 as a colorless oil. MS (M+1): m/e 237.

Step 148:

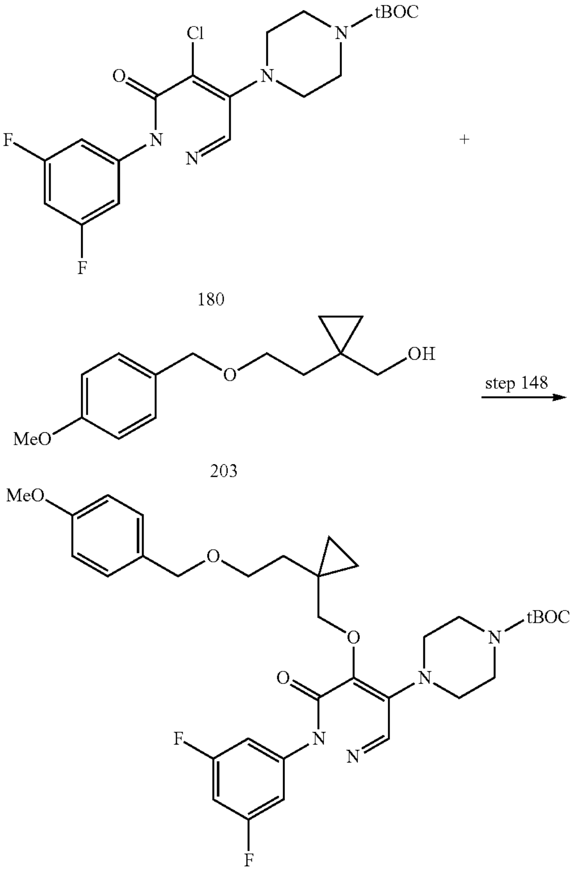

180

203

204

To compound 203 (2.16 g, 9.14 mmol) dissolved in dry THF (40 mL) was added sodium bis(trimethylsilyl)amide (1.0 M in THF, 8.4 mL, 8.40 mmol) via syringe. The reaction mixture was stirred at room temperature for 15 mins under nitrogen. Chloropyridazinone 180 (3.00 g, 7.03 mmol) was added, and the reaction mixture was heated at 80° C. for 1 h then stirred at room temperature for 16 h. The solvent was evaporated. Water (50 mL) was added, and the aqueous solution was extracted with EtOAc. The combined organic extract was dried ($MgSO_4$), filtered, and concentrated. Purification by silica gel chromatography (eluant: 5-15% EtOAc—$CH_2Cl_2$) gave 4.40 g (100% yield) of the product 204 as a yellow oil. MS (M+1): m/e 628.

Step 149:

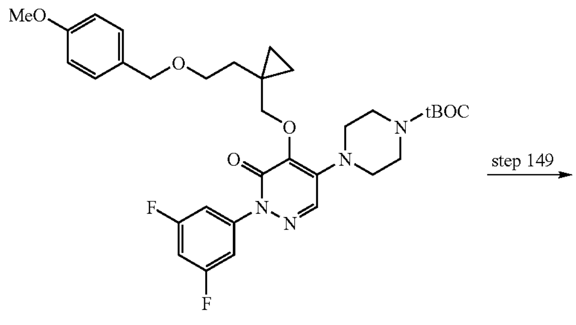

204

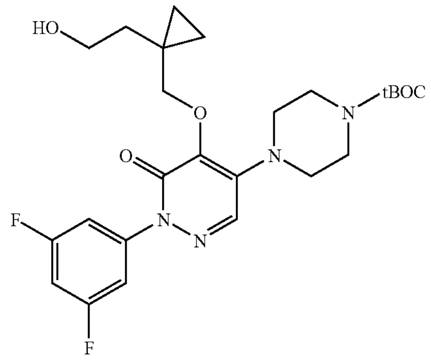

205

To compound 204 (4.40 g, 7.03 mmol) dissolved in $CH_2Cl_2$ (50 mL) and water (3 mL) was added 2,3-dichloro-5,6-dicyano-benzoquinone (1.92 g, 8.44 mmol). The reaction mixture was stirred at room temperature for 60 mins. Saturated $NaHCO_3$ (100 mL) was added and the aqueous solution was extracted with EtOAc. The combined organic extract was dried ($MgSO_4$), filtered, and concentrated. Purification by silica gel chromatography (eluant: 15% EtOAc—$CH_2Cl_2$ then 5% MeOH—$CH_2Cl_2$) gave 2.90 g (81% yield) of the product 205 as a white foam. MS (M+1): m/e 508.

Step 139-142 from Scheme 41:

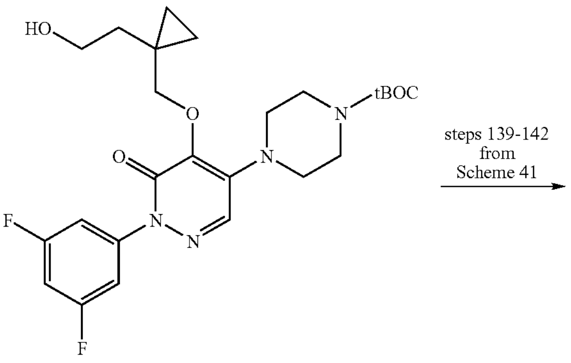

205

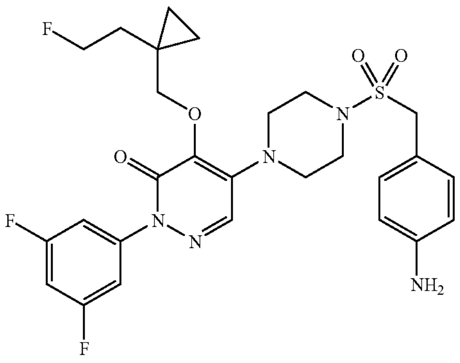

206

Using the procedures from steps 139-142 from Scheme 41, the following compounds were synthesized.

| Cmpd. No. | Structure | MS M + 1 |
| --- | --- | --- |
| 1846Z | 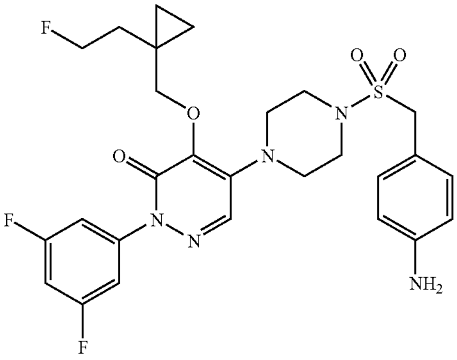 | 578 |

-continued
| Cmpd. No. | Structure | MS M + 1 |
|---|---|---|
| 1847Z | 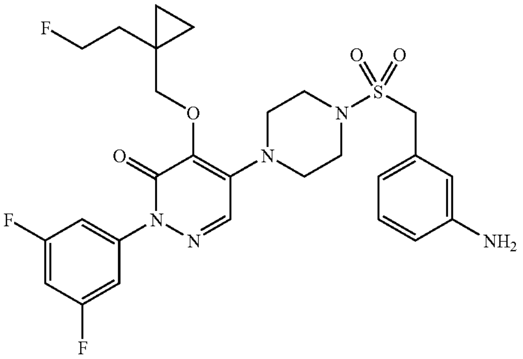 | 578 |
Scheme 43
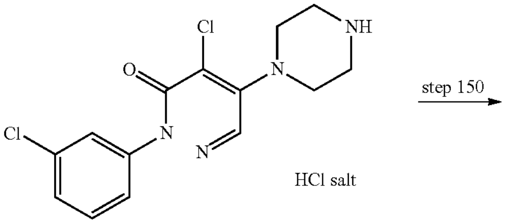
207
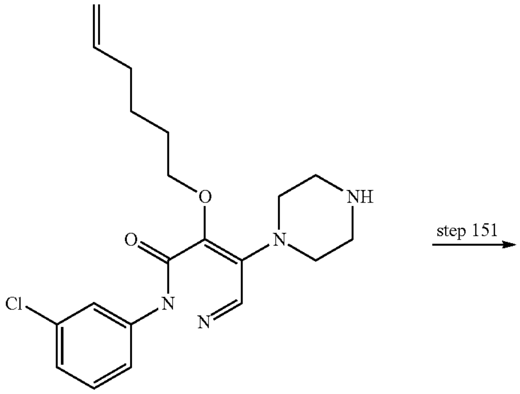
208
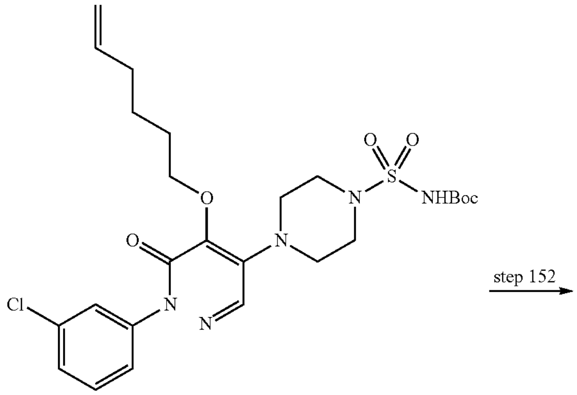
209
-continued
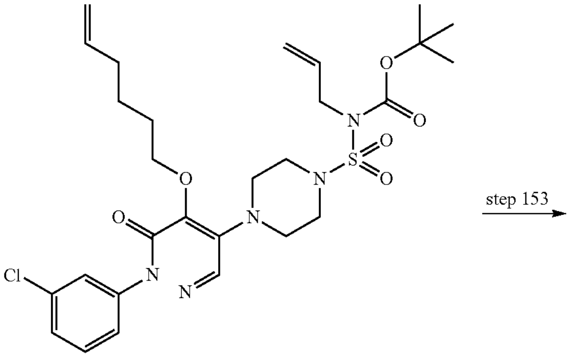
210
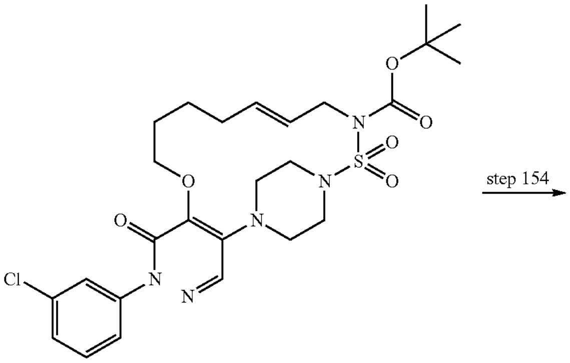
211
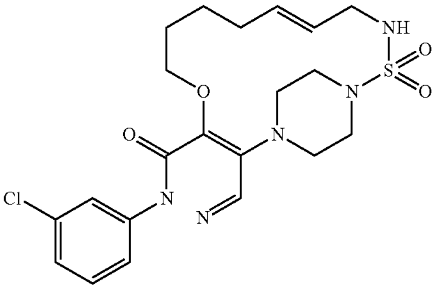
212

Step 150:

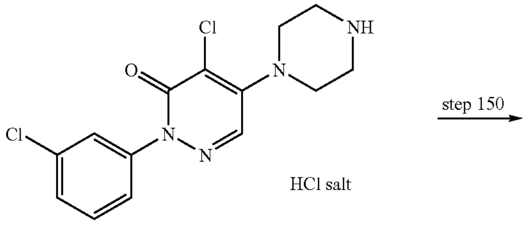

207

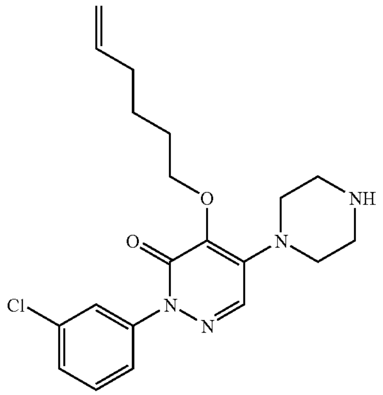

208

Compound 207 (1.0 g, 2.8 mmol) and 5-hexenol-1 (0.83 g, 8.3 mmol) were mixed in 15 mL of dry THF. NaH (60%, 0.28 g, 7 mmol) was added. The resulting mixture was stirred at room temperature overnight. The reaction was quenched with 10 mL of water, extracted with ethyl acetate, dried over anhydrous sodium sulfate, and concentrated. The crude product was purified by flash chromatography (eluant: 0-0.5% 7 M $NH_3$/MeOH in $CH_2Cl_2$ gradient) to give 1.1 g (100%) of compound 208 as a colorless oil. MS (M+1): m/e 389.

Step 151:

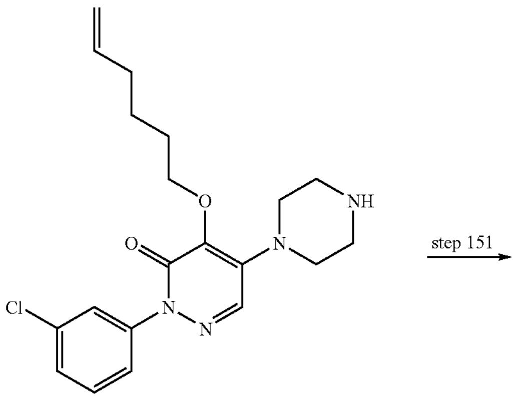

208

-continued

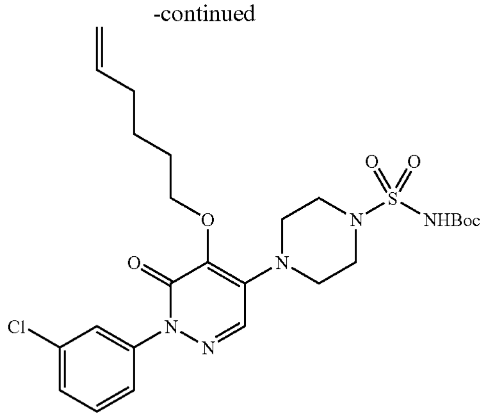

209

Compound 208 (2.7 mmol) dissolved in 10 mL of dry $CH_2Cl_2$ was mixed with isopropyldiethylamine (1.5 ml, 8.8 mmol), and cooled to 0° C. with an ice-water bath. A freshly prepared 0.5 M solution of $BocNHSO_2Cl$ in $CH_2Cl_2$ (8 mL, 4 mmol) was added dropwise. The resulting mixture was then stirred at room temperature overnight. The mixture was diluted with 500 mL of $CH_2Cl_2$, and washed with 1 N HCl solution then water. The organic layer was separated, dried over anhydrous $Na_2SO_4$, and concentrated. Purification by flash chromatography gave 1.4 g of compound 209 as a white solid. MS (M+1): m/e 568.

Step 152:

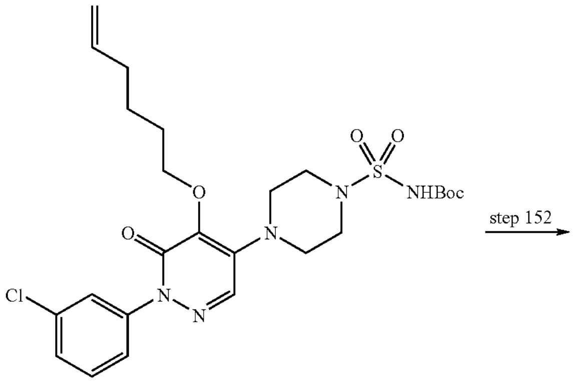

209

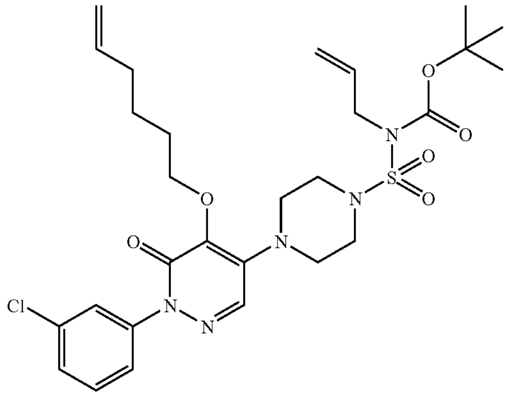

210

Compound 209 (0.38 g, 0.7 mmol) was mixed with allyl bromide (0.3 mL), and phosphazene base P1-t-Bu (0.25 mL, 1 mmol) in 5 mL of dry THF. The resulting mixture was stirred at room temperature overnight. The mixture was diluted with EtOAc, and washed with water then brine. The organic layer was dried over anhydrous $Na_2SO_4$, and then concentrated. Purification by flash chromatography gave 0.35 g of compound 210 as a white solid. MS (M+1): m/e 608.

Step 153:

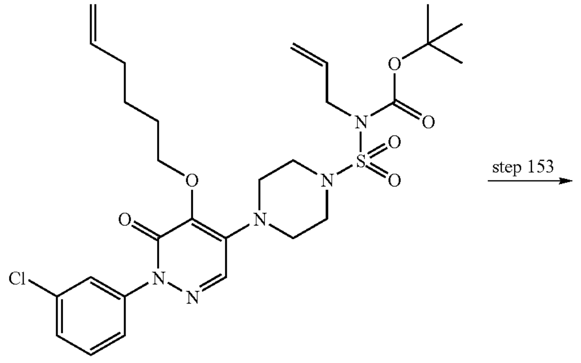

210

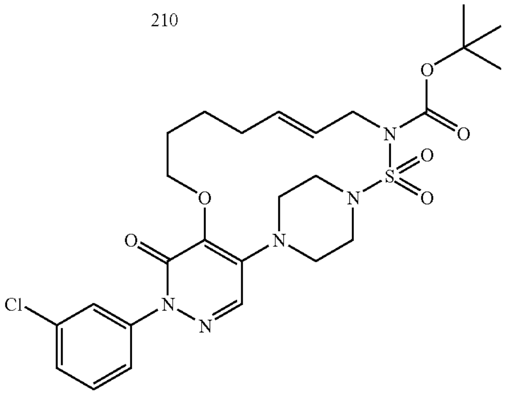

211

Compound 210 (92 mg, 0.15 mmol) in 60 mL of $CH_2Cl_2$ was mixed with 25 mg of 2$^{nd}$ generation Grubbs' catalyst under nitrogen. The mixture was then heated to 50° C. under nitrogen overnight. After cooling, the mixture was concentrated. Purification by flash chromatography (eluant: 10% 30% EtOAc-hexane gradient) gave 81 mg of compound 211 as a white solid. MS (M+1): m/e 580.

Step 154:

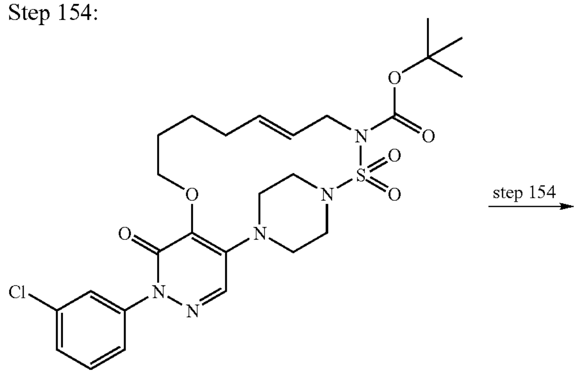

211

-continued

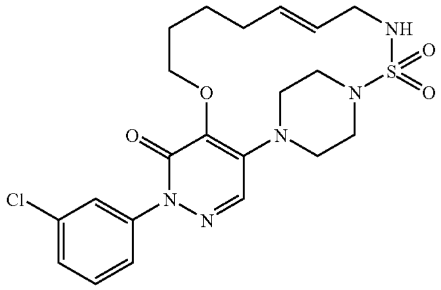

212

Compound 211 (70 mg) was treated with 10 mL of 4 N HCl in dioxane at room temperature overnight. The mixture was concentrated, and the crude product was purified by flash chromatography (eluant: 10%-40% EtOAc-hexane gradient) to give 51 mg of compound 212 as a white solid. MS (M+1): m/e 480.

Scheme 44

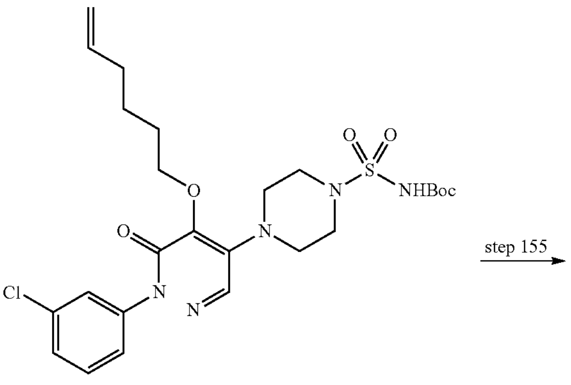

209

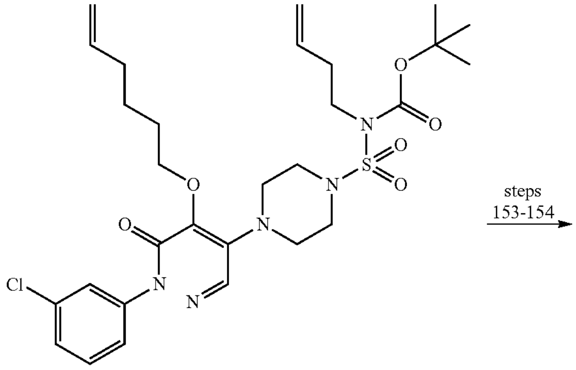

213

-continued

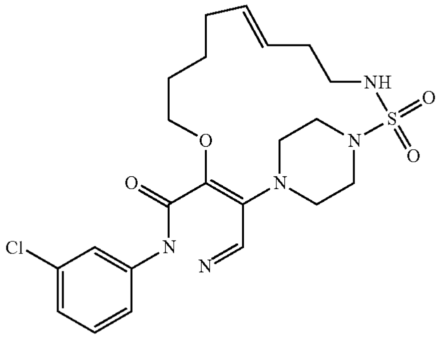

214

Step 155:

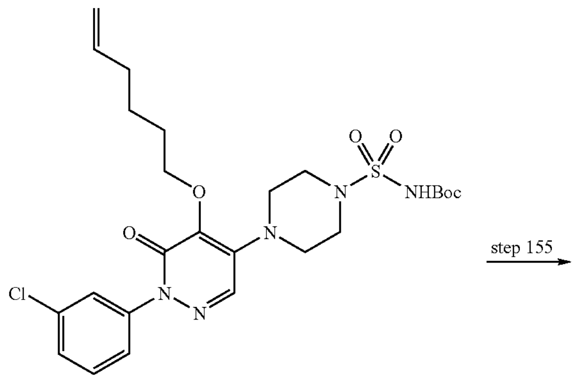

209

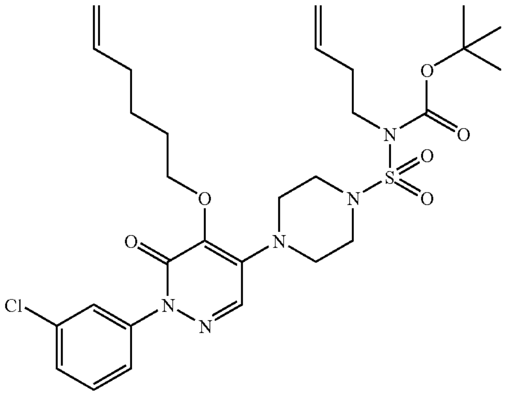

213

Compound 209 (0.20 g, 0.35 mmol) was mixed with 3-buten-1-ol (0.06 mL, 0.7 mmol), triphenylphosphine (0.18 g, 0.7 mmol), and DIAD (0.14 mL, 0.7 mmol) in 3 mL of dry THF. The mixture was stirred at room temperature overnight then concentrated. Purification by flash chromatography (eluant: 10%-30% EtOAc-hexane gradient) gave 0.21 g of compound 213 as a white solid. MS (M+1): m/e 622.

Steps 153-154:

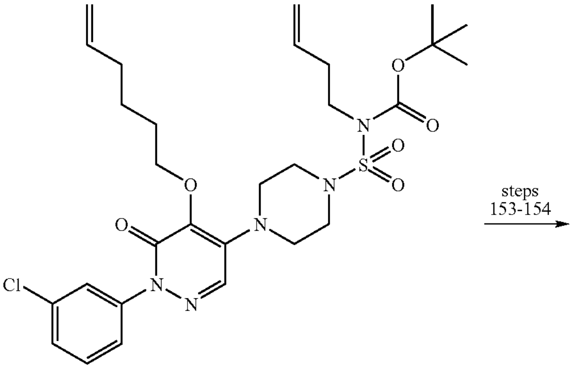

213

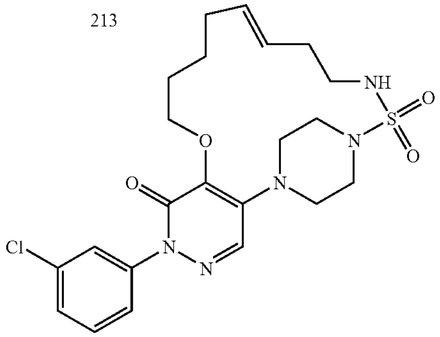

214

Using the procedures from step 153-154 from Scheme 43, the following compounds were synthesized.

| Cmpd. No | Structure | MS M + 1 |
|---|---|---|
| 1848Z | 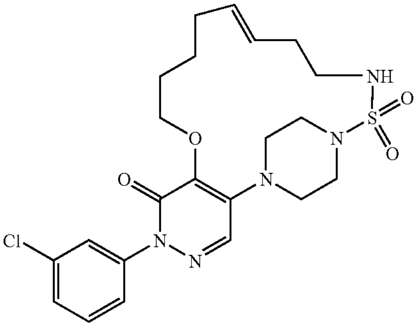 | 493 |
| 1849Z | 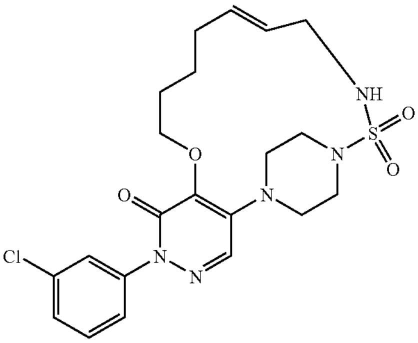 | 479 |

-continued
| Cmpd. No | Structure | MS M + 1 |
|---|---|---|
| 1850Z | 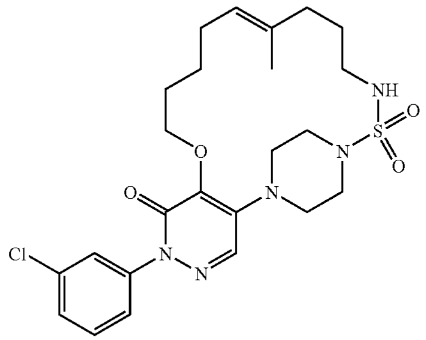 | 521 |
| 1851Z | 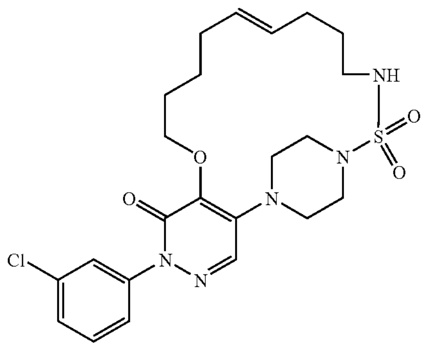 | 507 |
Scheme 45
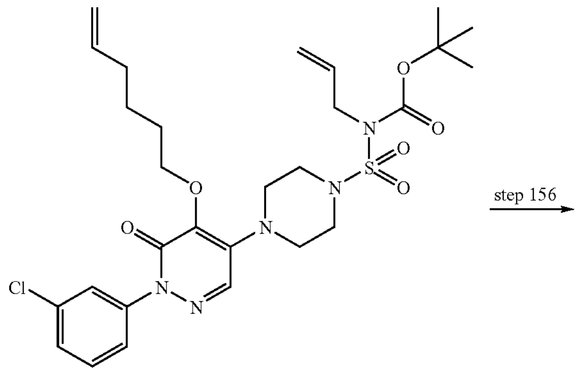
210
-continued
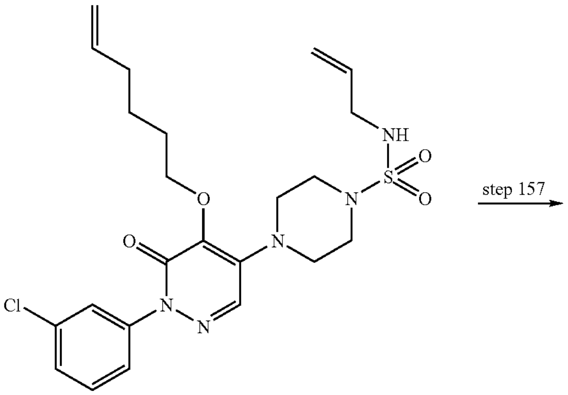
215
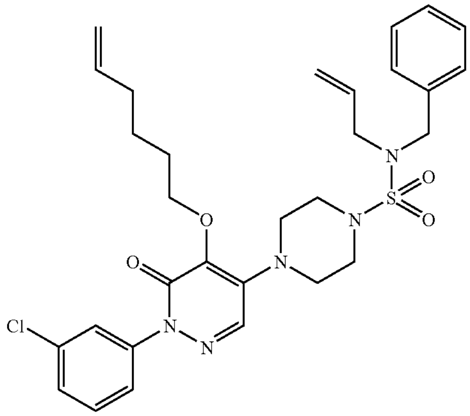
216
step 158
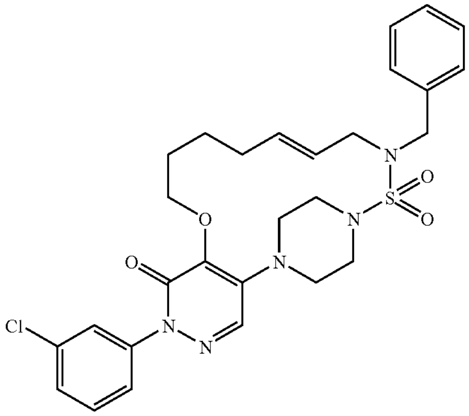
217

Step 156:

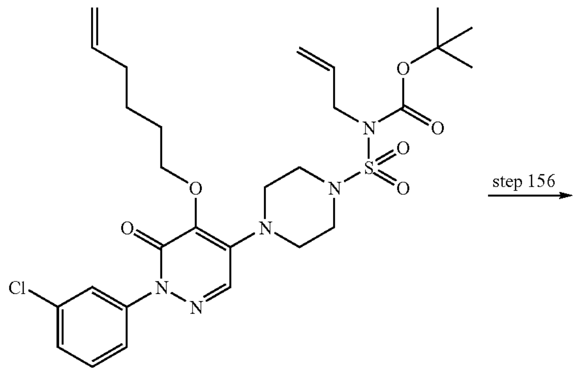

210

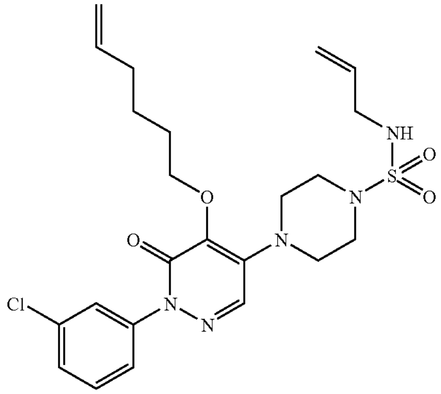

215

Compound 210 (220 mg) was treated with 10 mL of 4 N HCl in dioxane at room temperature overnight. Mixture was concentrated, and the crude was purified by flash chromatography (eluant: 10%-40% EtOAc-hexane gradient) to give 180 mg of compound 215 as a white solid. MS (M+1): m/e 508.

Step 157:

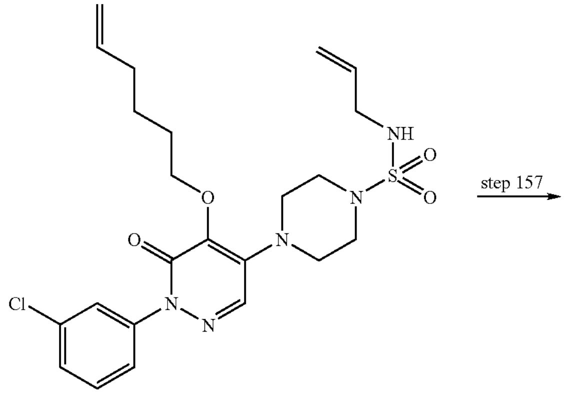

215

-continued

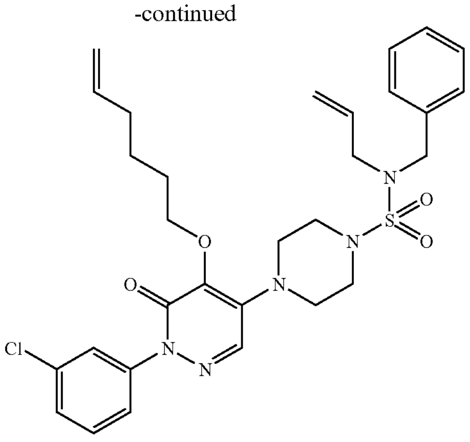

216

Compound 215 (0.11 g, 0.22 mmol) was mixed with benzyl bromide (40 mg, 0.23 mmol), and 60% NaH (10 mg, 0.24 mmol) in 2 mL of dry DMF at 0° C. The resulting mixture was stirred at room temperature overnight. The mixture was diluted with EtOAc, and washed with water then brine. The organic layer was dried over anhydrous $Na_2SO_4$, and concentrated. Purification by flash chromatography gave 0.10 g of compound 216 as a white solid. MS (M+1): m/e 598.

Step 158:

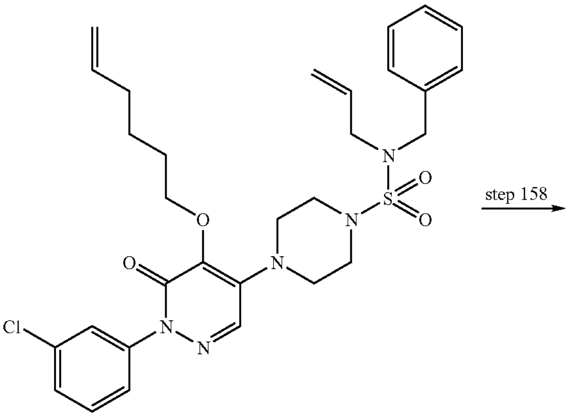

216

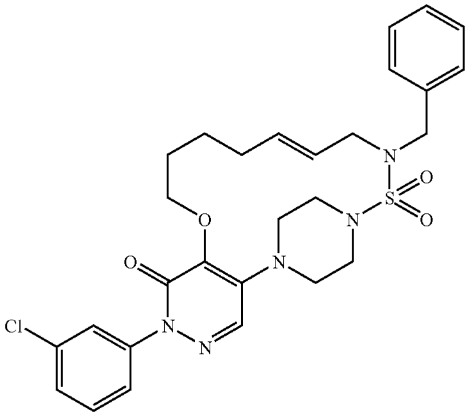

217

Compound 216 (90 mg, 0.15 mmol) in 50 mL of $CH_2Cl_2$ was mixed with 25 mg of $2^{nd}$ generation Grubbs' catalyst under nitrogen. The mixture was then heated to 50° C. under nitrogen overnight. After cooling, the mixture was concentrated, and the crude product was purified by Gilson Prep HPLC (eluant: $CH_3CN$-water gradient) to give 69 mg of compound 217 as a white solid. MS (M+1): m/e 570.

Scheme 46

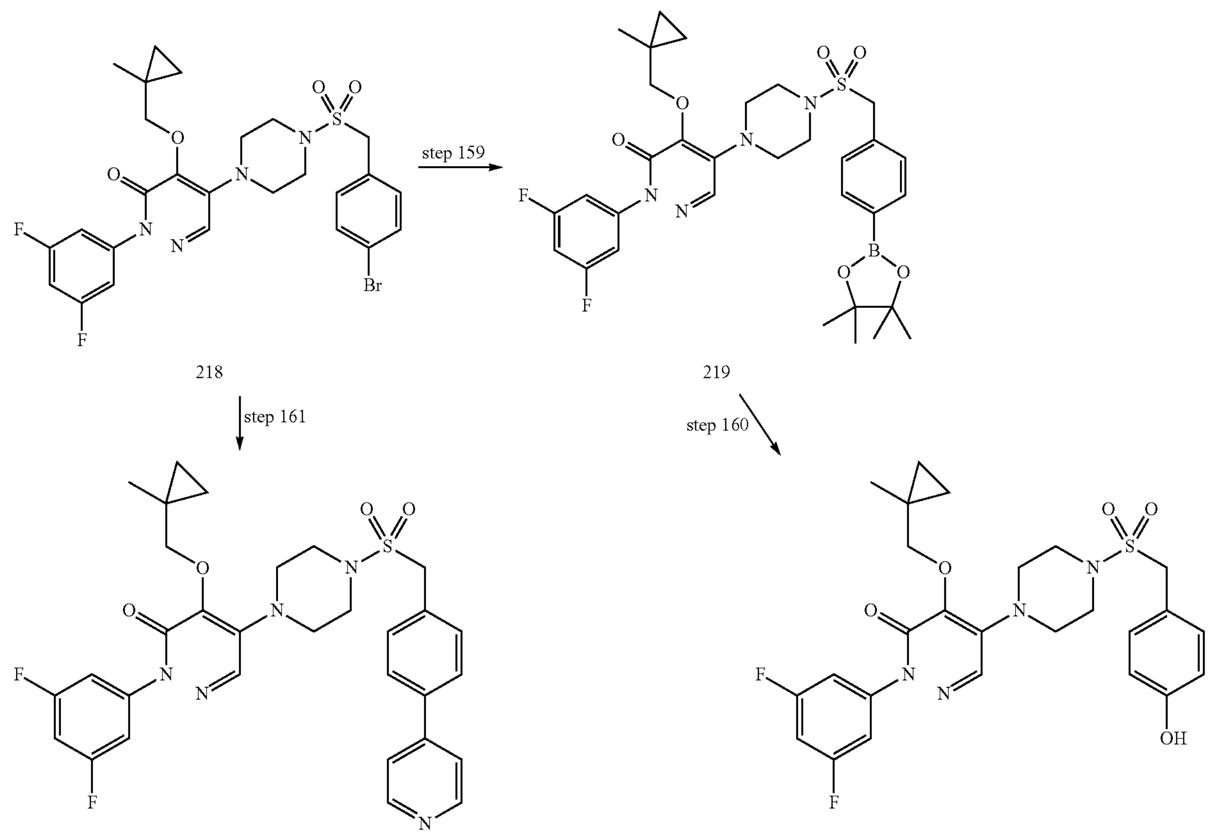

218, 219, 221, 220

Step 159:

-continued

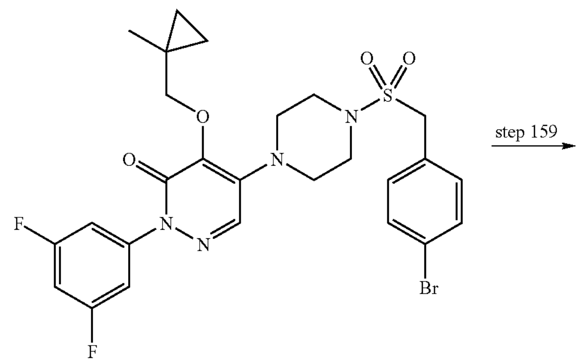

218 step 159

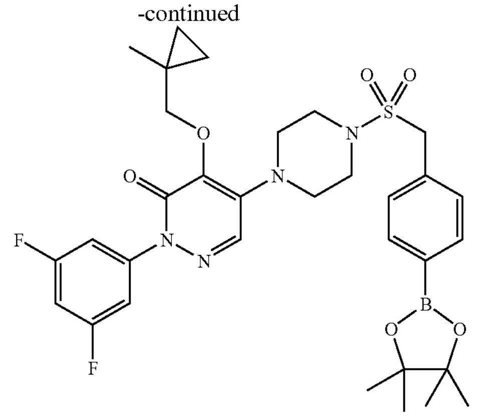

219

A round bottom flask was charged with [1,1'-Bis(diphenylphosphino)ferrocene]-dichloropalladium(II), complex with dichloromethane (1:1) (6.70 mg, 0.00820 mmol); compound 218 (100 mg, 0.164 mmol); bis(pinacolato)diboron (50.0 mg, 0.197 mmol); and potassium acetate (80.5 mg, 0.820 mmol) in 14-dioxane (20 mL). The reaction mixture was placed under a nitrogen atmosphere and was degassed under vacuum three times. The reaction was stirred at 100° C. overnight. After cooling, the mixture was filtered through a short path silica column (eluant: ethyl acetate). The solvent was concentrated then purification by flash chromatography (eluant: 1:1 hexane:EtOAc) gave 75 mg (70% yield) of the product 219. MS (M+1): m/e 657.

Step 160:

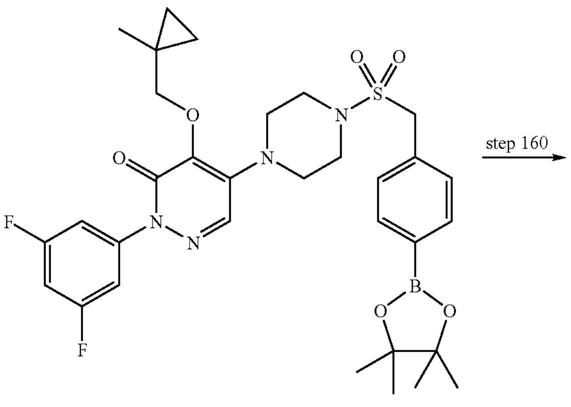

219

-continued

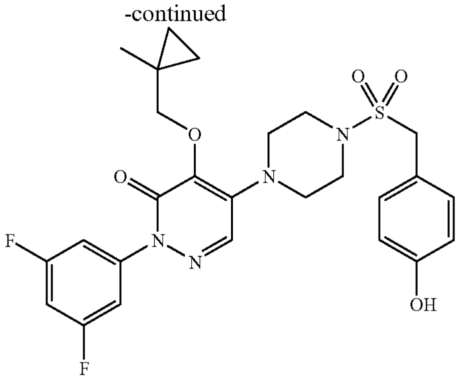

220

Compound 219 (80 mg, 0.1 mmol) was dissolved in ethanol, and 1 M of sodium bicarbonate (200 uL) and hydrogen peroxide (50 uL, 0.5 mmol) were added at 0° C. The reaction was stirred at 0° C. overnight then concentrated. 1 M Hydrogen chloride in water (5 mL) was added, the mixture was extracted with ethyl acetate (150 mL), dried over sodium sulfate, and concentrated. Purification by silica gel chromatography (eluant: 1:1 hexane:EtOAc) gave 42 mg (63% yield) of the product 220. MS (M+1): m/e 547.

Using the procedures described above, the following compounds were synthesized.

| Cmpd. No | Structure | MS M + 1 |
|---|---|---|
| 1852Z | 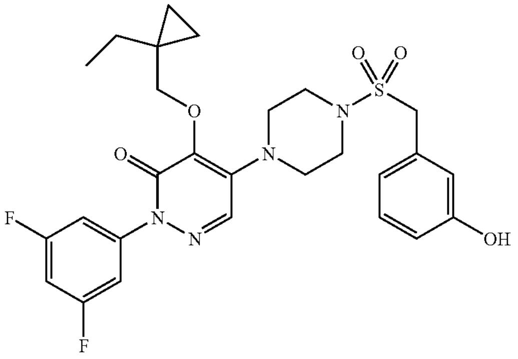 | 547 |
| 1853Z | 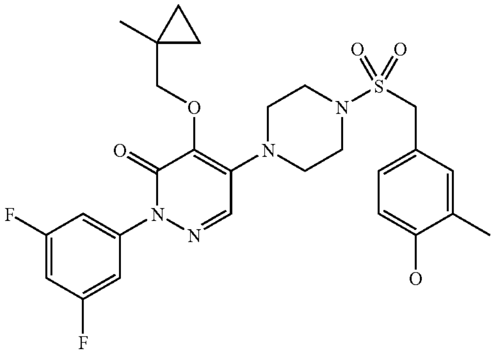 | 562 |

Step 161:

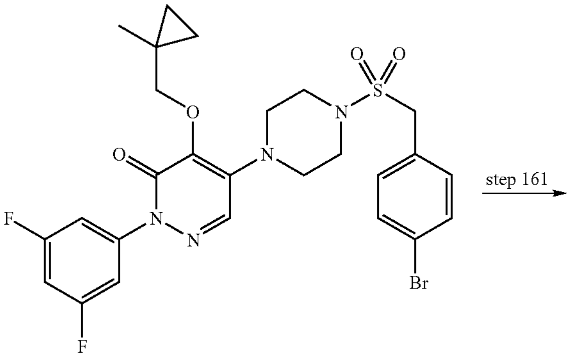

218

-continued

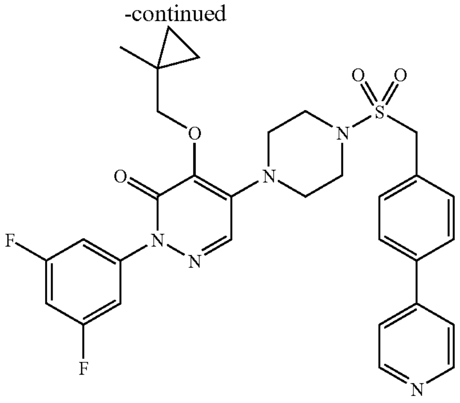

221

A round bottom flask was charged with compound 218 (70.0 mg, 0.115 mmol), tetrakis(triphenylphosphine)palladium(0) (5.69 mg, 0.00492 mmol), 4-pyridylboronic acid (20.0 mg, 0.163 mmol), and cesium carbonate (38.5 mg, 0.118 mmol) in 1,4-dioxane (20 mL) and water (2 mL). The reaction was placed under an atmosphere of nitrogen and degassed under vacuum three times. The reaction mixture was stirred at 100° C. overnight. After cooling, the mixture was filtered through a short path silica column (eluant: ethyl acetate). The solvent was concentrated, and purification by silica gel chromatography (eluant: 1:2 hexane:EtOAc) gave 70 mg (100% yield) of the product 221. MS (M+1): m/e 608.

Using the procedures described above, the following compounds were synthesized.

| Cmpd. No. | Structure | MS M + 1 |
|---|---|---|
| 1854Z | 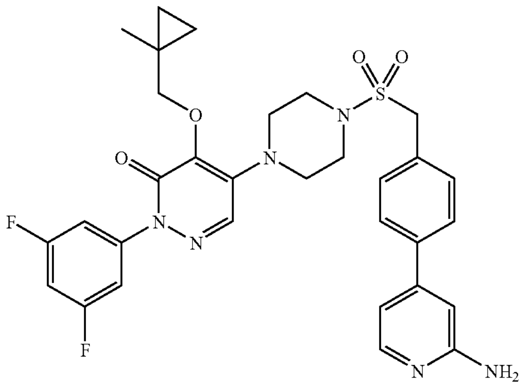 | 624 |
| 1855Z | 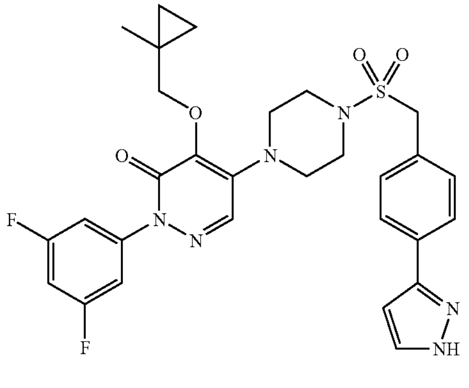 | 598 |

-continued
| Cmpd. No. | Structure | MS M + 1 |
|---|---|---|
| 1856Z | 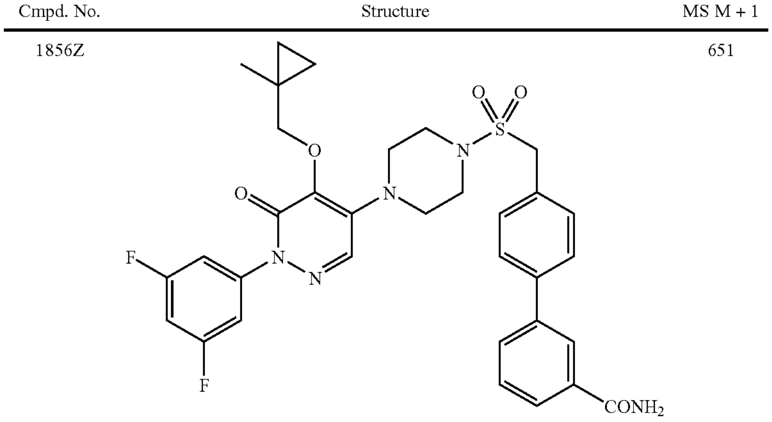 | 651 |
| 1857Z | 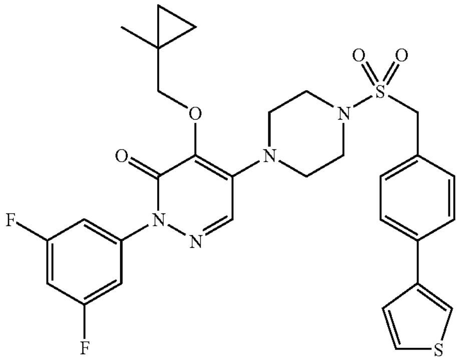 | 614 |
| 1858Z | 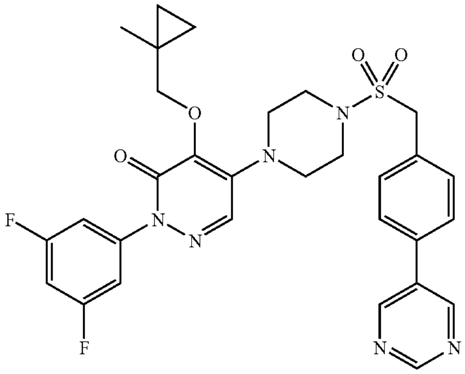 | 610 |
Scheme 47
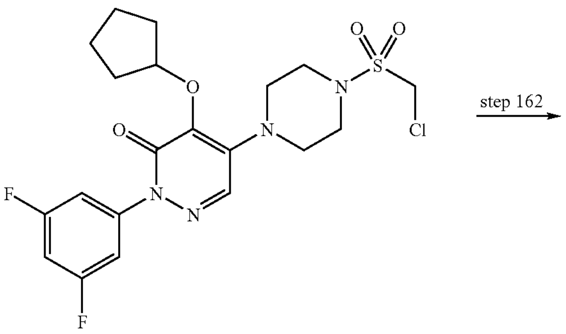
222
-continued
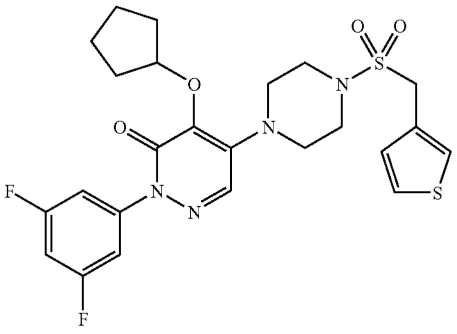
223

Step 162:

A round bottom flask was charged with compound 222 (50 mg, 0.102 mmol), 3 thienylboronic acid (26.2 mg, 0.204 mmol), L-proline (2.82 mg, 0.0245 mmol), potassium bis (trimethylsilyl)amide (40.8 mg, 0.204 mmol), isopropyl alcohol (0.5 mL, 6 mmol), and nickel chloride dimethoxyethane (2.70 mg, 0.0123 mmol). The reaction was placed under an atmosphere of nitrogen and degassed under vacuum three times. The reaction was filtered through a short path silica get column (eluant: ethyl acetate), and the solvent was concentrated. Purification by silica gel chromatography (eluant: 1:2 hexane:EtOAc) gave the product which was further purified on the Gilson reverse phase HPLC (eluant: water:$CH_3CN$ gradient) to give 5 mg (9% yield) of the product 223. MS (M+1): m/e 537.

Scheme 48

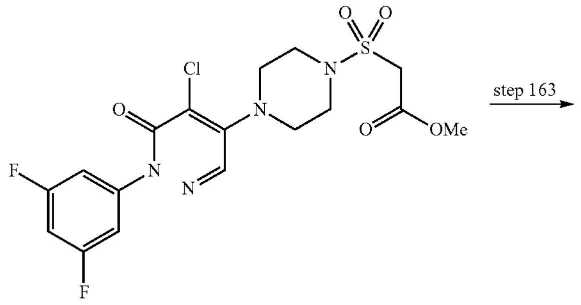

224

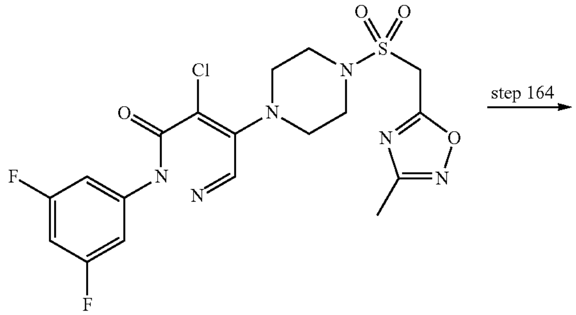

225

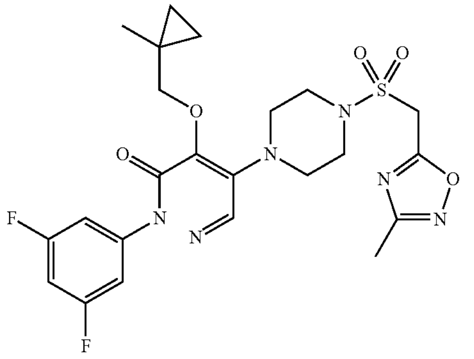

226

Step 163:

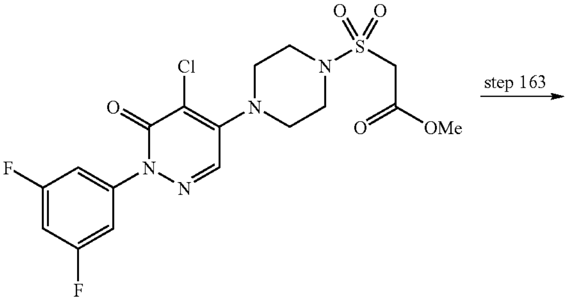

224

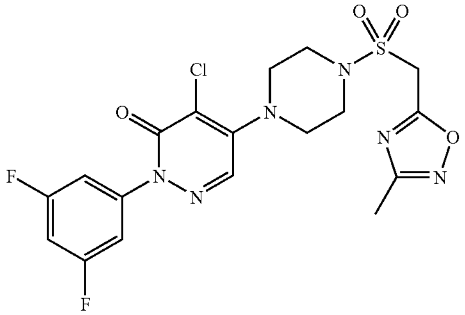

225

Compound 224 (100 mg, 0.216 mmol), potassium carbonate (60 mg, 0.432 mmol), and N-hydroxyacetimidamide (18 mg, 0.24 mmol) in toluene (10 mL) was heated at reflux for 48 h. After cooling, the reaction mixture was filtered through a short path silica gel column (eluant: ethyl acetate). The solvent was concentrated, and purification by silica gel chromatography (eluant: 1:2 hexane:ethyl acetate) gave 81 mg (77% yield) of the product 225. MS (M+1): m/e 487.

Step 164:

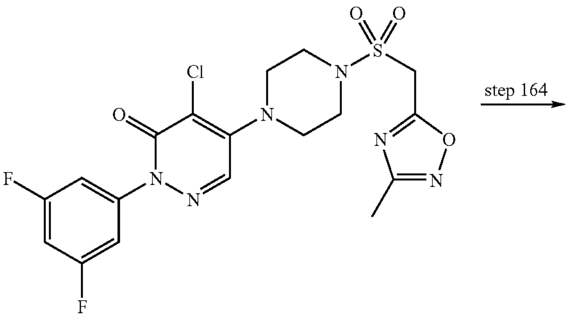

225

-continued

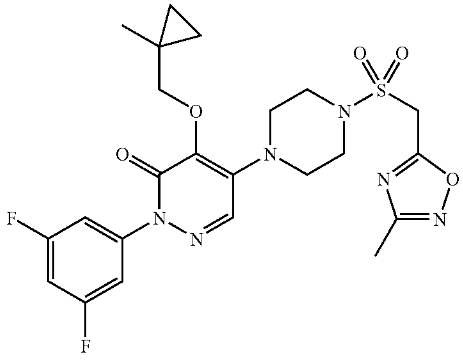

226

To methylcyclopropanemethanol (168 mg, 1.94 mmol) in dry THF (6 mL) was added sodium hydride (60.2 mg of 60 wt % in oil, 1.50 mmol). The reaction mixture was stirred at room temperature for 10 mins, and then compound 225 (50 mg, 0.103 mmol) was added. The reaction mixture was stirred at room temperature overnight and then the solvent was concentrated. Water was added, and the aqueous solution was extracted with ethyl acetate. The organic phase was dried over magnesium sulfate, filtered, and concentrated. Purification by silica gel chromatography (eluant: 1:1 hexane:EtOAc) gave 30 mg (54% yield) of the product 226. MS (M+1): m/e 537.

Scheme 49

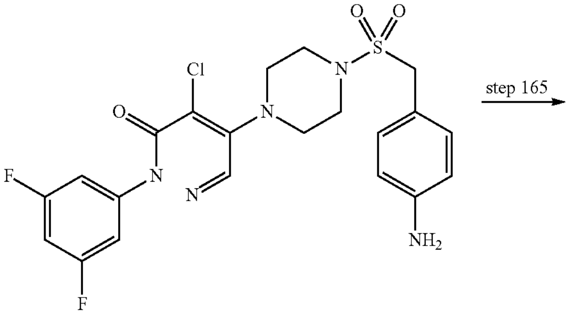

227

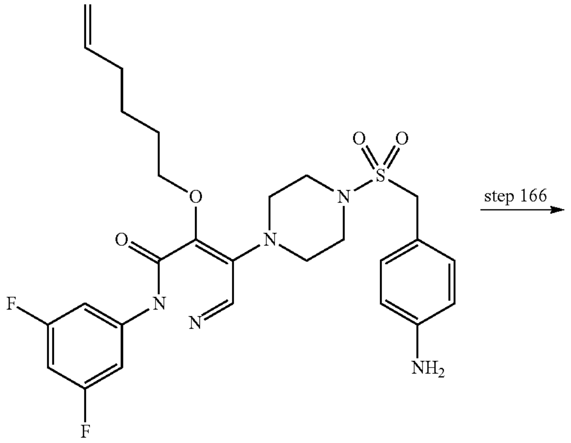

228

-continued

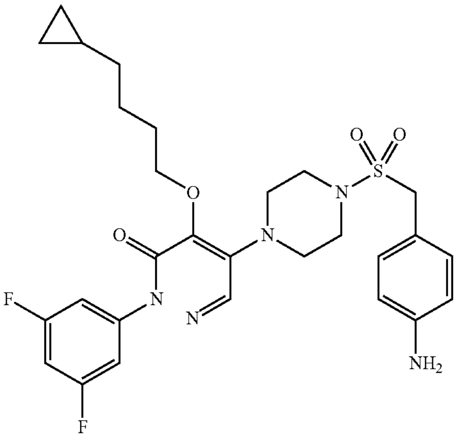

229

+

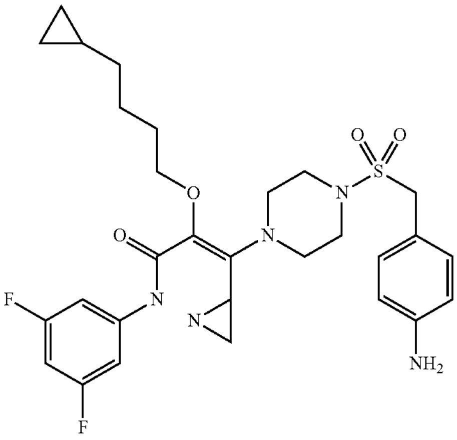

230

Step 165:

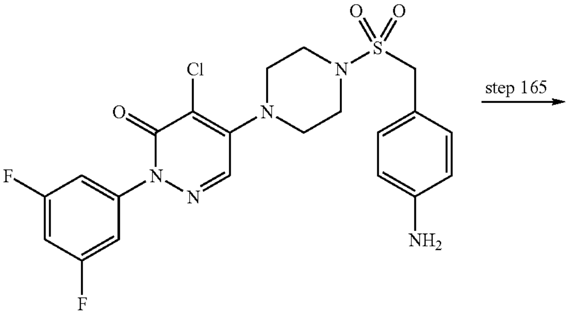

227

-continued

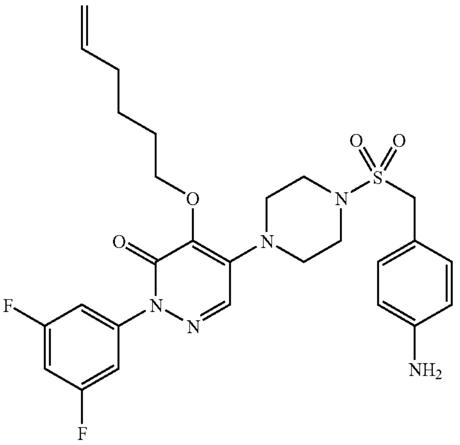

228

To 5-hexen-1-ol (48 mg, 0.483 mmol) dissolved in dry THF (5 mL) was added 1 M sodium hexamethyldisilazane in THF (0.323 mL, 0.323 mmol). The reaction was stirred at room temperature for 10 mins then compound 227 (80.0 mg, 0.161 mmol) was added. The reaction was stirred at room temperature overnight, and the solvent was evaporated. Water was added, and the mixture was extracted with ethyl acetate. The organic phase was dried over magnesium sulfate, filtered, and concentrated. Purification by silica gel chromatography (eluant: 1:1 hexane:EtOAc) gave 80 mg (89% yield) of the product 228. MS (M+1): m/e 560.

Step 166:

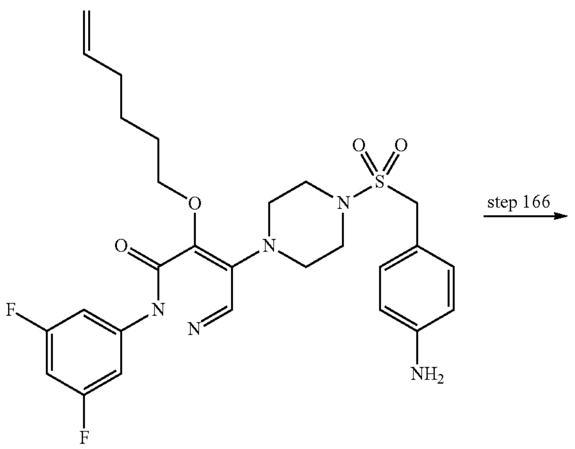

228

-continued

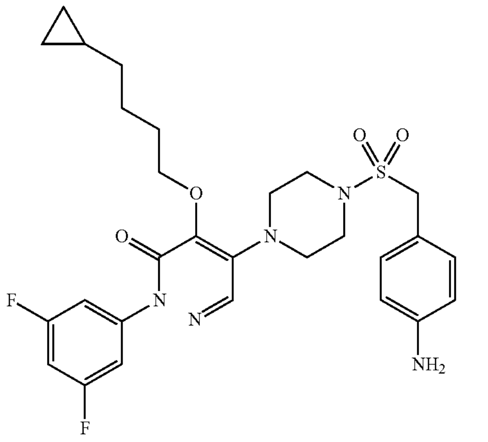

229

+

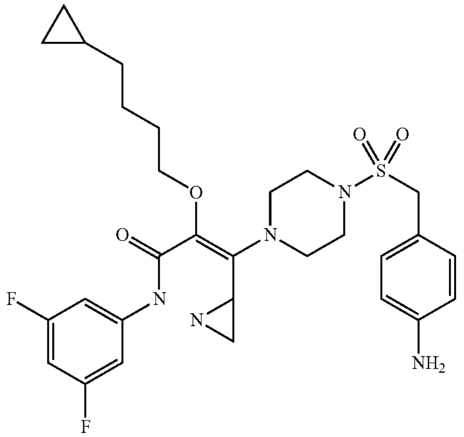

230

To a Schlenk flask charged with diiodomethane (0.034 mL, 0.43 mmol) in methylene chloride (10 mL) was slowly added trifluoroacetic acid (49 mg, 0.032 mL, 0.43 mmol) then 1.0 M of diethyl zinc in pentane (0.43 mL, 0.43 mmol). The reaction mixture was stirred for 30 mins at 0° C. Compound 228 (80 mg, 0.143 mmol) in methylene chloride was added. The reaction mixture was warmed slowly to room temperature and stirred overnight. Saturated ammonium chloride was added, and the aqueous solution was extracted with methylene chloride, dried over MgSO4, filtered, and concentrated. Purification by silica gel chromatography (eluant: 1:1 hexane:EtOAc) gave 10 mg (12% yield) of the product 229 MS (M+1): m/e 574 and 30 mg (36% yield) of the product 230 MS (M+1): m/e 588.

Using the procedures described above, the following compounds were synthesized.

-continued
| Cmpd. No. | Structure | MS M + 1 |
|---|---|---|
| 1859Z | 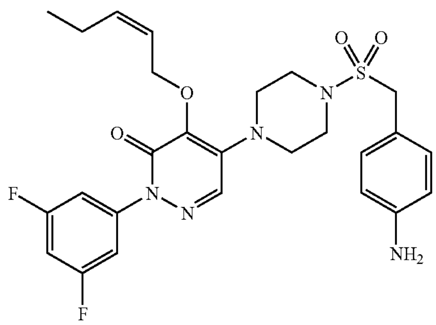 | 546 |
| 1860Z | 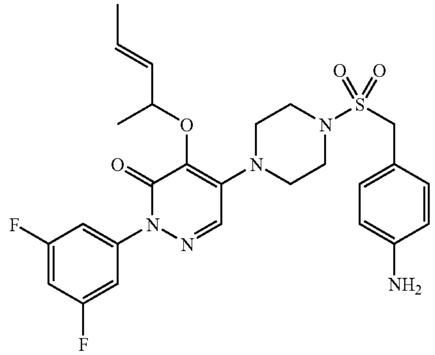 | 546 |
| 1861Z | 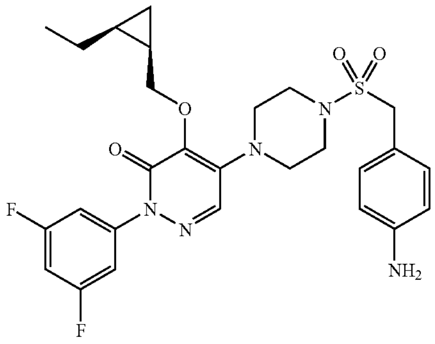 | 560 |
| 1862Z | 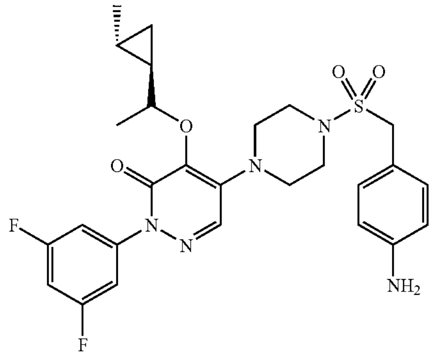 | 560 |
Scheme 50
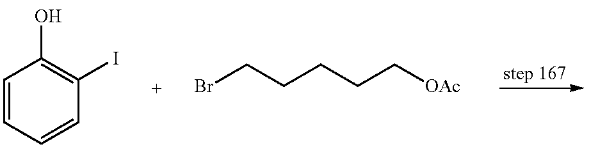
231 232
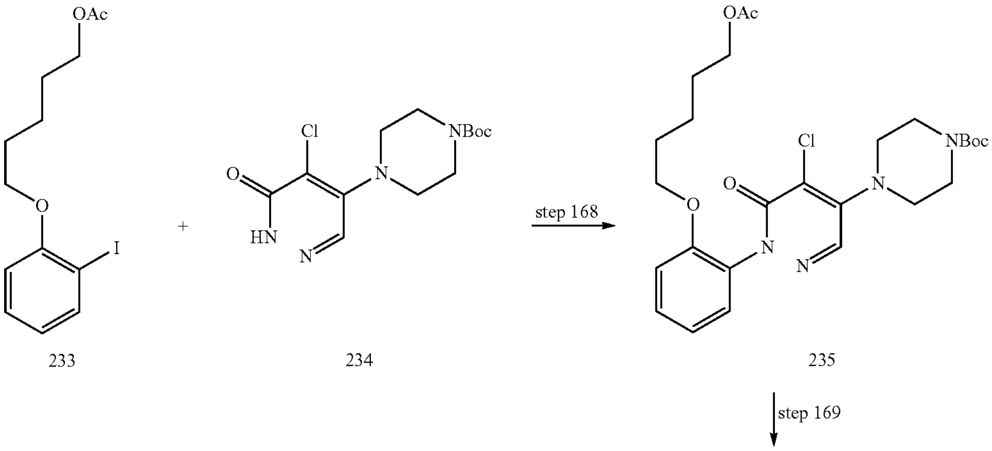
233 234 235

-continued

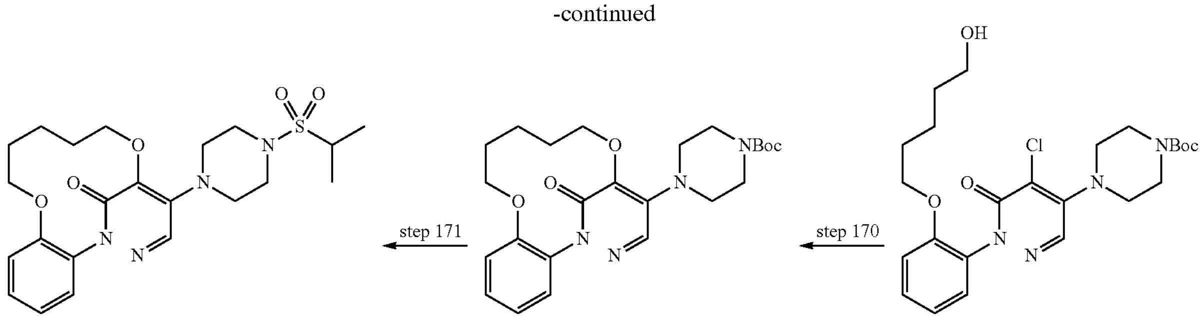

238 237 236

Step 167:

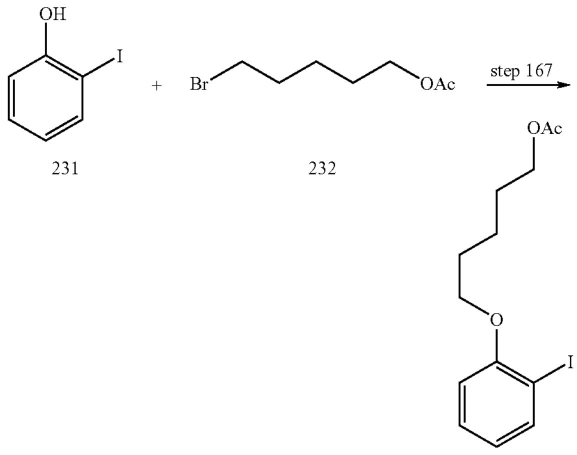

231 232 233

To a solution of 2-iodophenol 231 (2.0 g, 9.09 mmol) in dry DMF (40 mL) was added $K_2CO_3$ (4.93 g, 35.7 mmol) and 5-bromopentyl acetate (4.16 mL, 25.0 mmol) under a nitrogen atmosphere. The reaction mixture was heated to 50° C. and stirred for 17 h. The reaction mixture was diluted with ethyl acetate then washed with brine. The organic extract was dried with $MgSO_4$, filtered, and concentrated. Purification by silica gel chromatography (eluant: 5% ethyl acetate in hexanes) yielded 1.81 g (57% yield) of the product 233 as a yellow liquid.

Step 168:

-continued

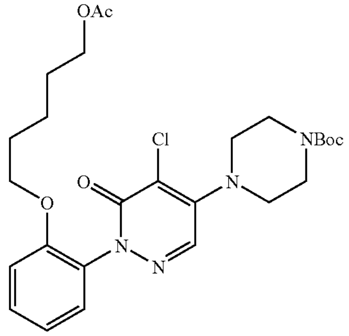

235

Reference: Pu, Y. M. et. al. *Tet. Lett.* 2006, 47, 149-153.

To a solution of iodide 233 (829.6 mg, 2.38 mmol) and pyridazinone 234 (500 mg, 1.59 mmol) in dry DMF (10 mL) in a sealed flask was added $K_2CO_3$ (329.3 mg, 2.38 mmol) and Cu catalyst (69.2 mg, 0.159 mmol) and flushed with nitrogen. The reaction mixture was heated to 120° C. for 17 h. The reaction mixture was diluted with ethyl acetate and washed with 1 N HCl then brine. The organic extract was dried with $MgSO_4$, filtered, and concentrated. Purification by silica gel chromatography (eluant: 50% ethyl acetate in hexanes) yielded 81 mg (10%) of the product 235 as a yellow oil. MS (M+1): m/e 535.

Step 169:

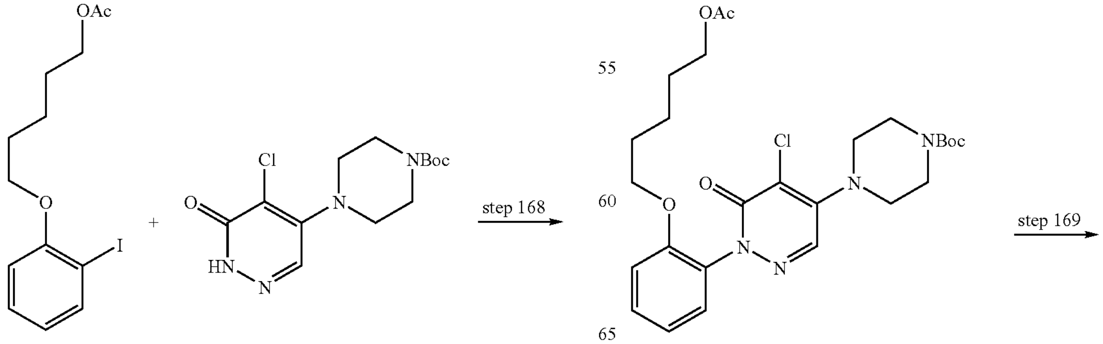

233 234 235

-continued

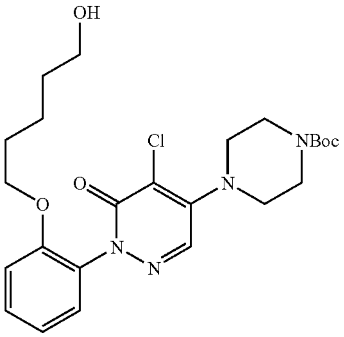

236

To a solution of acetate 235 (81 mg, 0.151 mmol) in MeOH (5 mL) was added water (3 drops) and $K_2CO_3$ (105 mg, 0.760 mmol) under a nitrogen atmosphere. The reaction mixture was stirred at room temperature for 18 h. The reaction mixture was quenched with saturated $NH_2Cl$, then extracted with ethyl acetate. The organic extract was washed with brine, dried with $MgSO_4$, filtered, and concentrated. Purification by silica gel chromatography (eluant: 65% ethyl acetate in hexanes) yielded 52.6 mg (71%) of the product 236 as a white foam. MS (M+1): m/e 493.

Step 170:

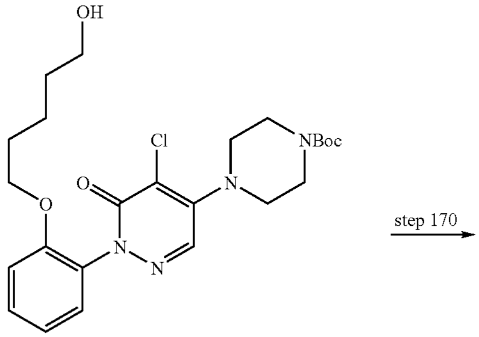

236

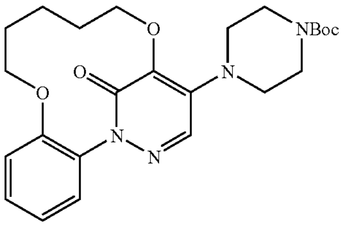

237

To a solution alcohol 236 (42.3 mg, 0.086 mmol) in THF (15 mL) was added NaH (60%, 6.9 mg, 0.479 mmol) under a nitrogen atmosphere. The reaction mixture was stirred at room temperature for 18 h. The reaction mixture was quenched with saturated $NH_4Cl$ then extracted with ethyl acetate. The organic extract was washed with brine, dried with $MgSO_4$, filtered, and concentrated. Purification by silica gel chromatography (eluant: 35% ethyl acetate in hexanes) yielded 12 mg (31%) of the product 237 as a white solid. MS (M+1): m/e 457.

Step 171:

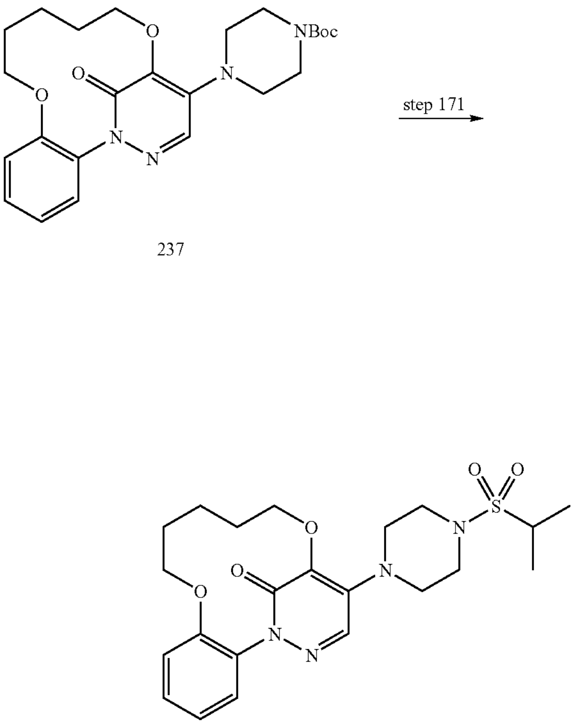

237

238

4 N HCl in dioxane (5 mL) was added to macrocycle 237 (52 mg, 0.114 mmol) under a nitrogen atmosphere. The reaction mixture was stirred at room temperature for 1.5 h. The reaction was then concentrated and dried under high vacuum. To a solution of this crude product in $CH_2Cl_2$ (10 mL) was added isopropyl sulfonyl chloride (51.2 uL, 0.456 mol) and Hunig's base (119 uL, 0.683 mmol). The reaction was stirred at room temperature for 17 h then concentrated. Purification by silica gel chromatography yielded 16.3 mg (31%) of the product 238 as a brown solid. MS (M+1): m/e 463.

Scheme 51
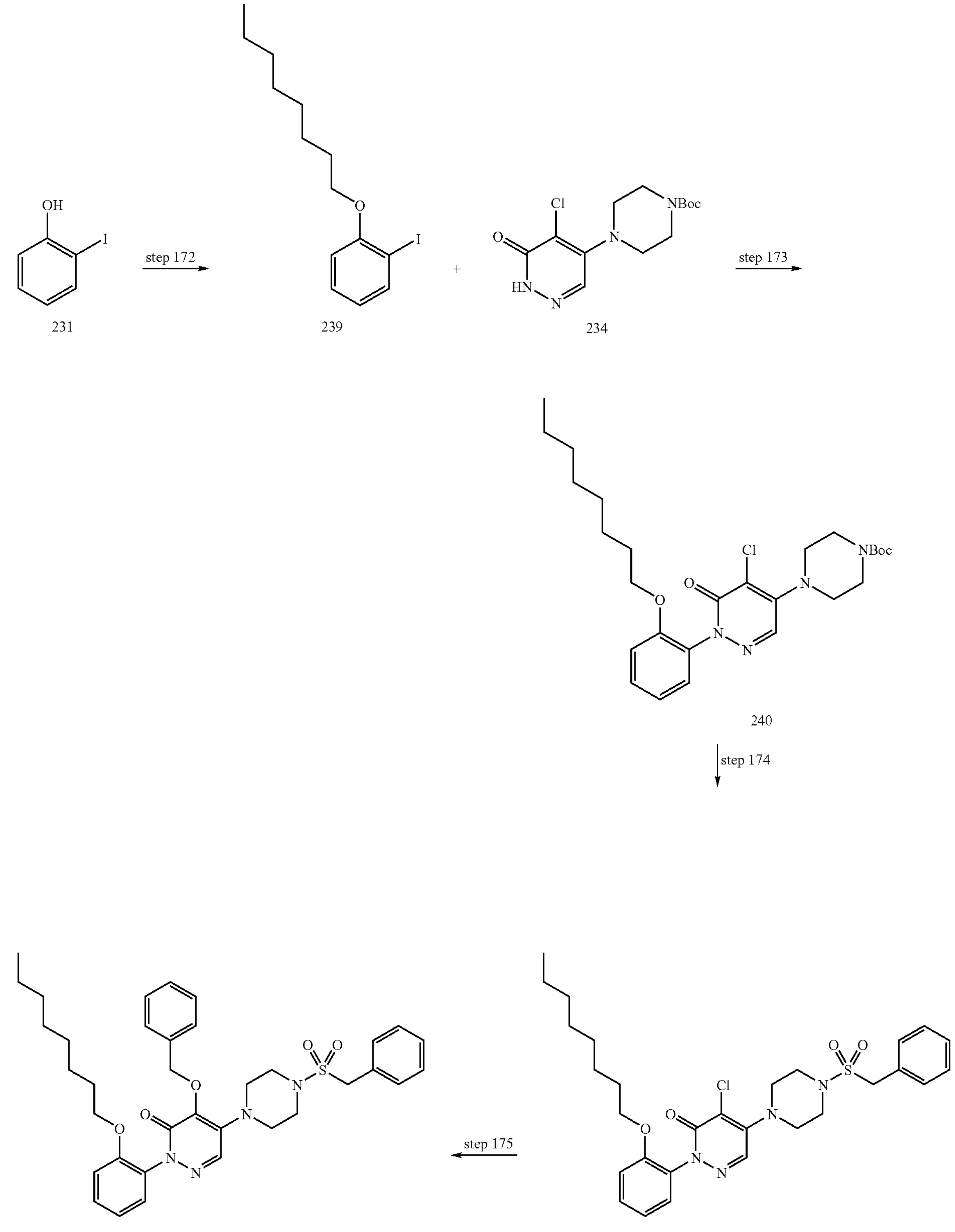
231 239 234 240 241 242

Step 172:

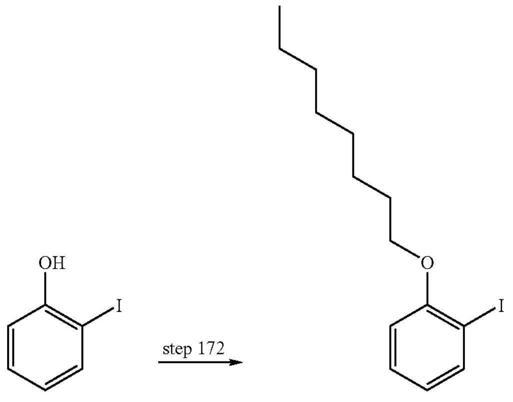

231

239

To a solution of 2-iodophenol 231 (2.0 g, 9.09 mmol) in dry DMF (40 mL) was added $K_2CO_3$ (3.77 g, 27.3 mmol) and 1-iodooctane (1.98 mL, 10.9 mmol) under a nitrogen atmosphere. The reaction mixture was heated to 40° C. and stirred for 17 h. The reaction mixture was diluted with ethyl acetate then washed with brine. The organic extract was dried with $MgSO_4$, filtered, and concentrated. Purification by silica gel chromatography (eluant: 3% ethyl acetate in hexanes) yielded 3.02 g (99% yield) of the product 239 as a yellow liquid.

Step 173:

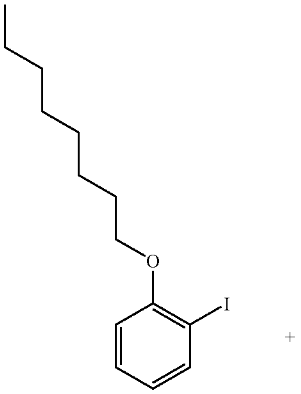

239

+

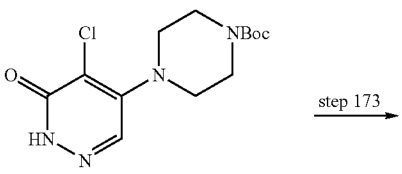

234

-continued

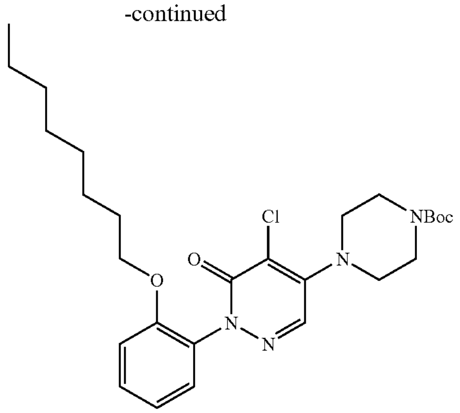

240

To a solution of iodide 239 (1.27 g, 3.82 mmol) and pyridazinone 234 (1 g, 3.18 mmol) in dry DMF (14 mL) in a sealed flask was added $K_2CO_3$ (483 mg, 3.50 mmol) and Cu catalyst (139 mg, 0.319 mmol) and flushed with nitrogen. The reaction mixture was heated to 120° C. for 17 h. The reaction mixture was diluted with ethyl acetate and washed with 1 N HCl then brine. The organic extract was dried with $MgSO_4$, filtered, and concentrated. Purification by silica gel chromatography (eluant: 50% ethyl acetate in hexanes) yielded 300 mg (15%) of the product 240 as a yellow oil. MS (M+1): m/e 519.

Step 174:

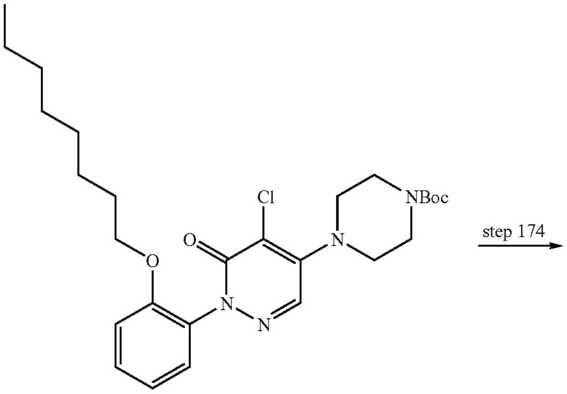

240

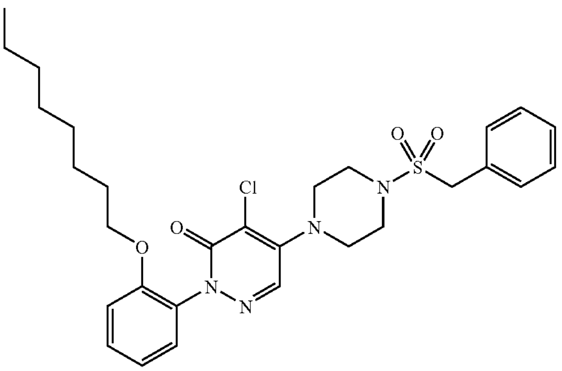

241

4 N HCl in dioxane (5 mL) was added to compound 240 (50 mg, 0.096 mmol) under a nitrogen atmosphere. The reaction mixture was stirred at room temperature for 1.5 h. The reaction was then concentrated and dried under high vacuum. To a solution of this crude product in $CH_2Cl_2$ (5 mL) was added □-toluenesulfonyl chloride (55.1 mg, 0.289 mmol) and Hunig's base (100 uL, 0.574 mmol). The reaction was stirred at room temperature for 17 h then concentrated. Purification by silica gel chromatography yielded 44.9 mg (81%) of the product 241 as a colorless oil. MS (M+1): m/e 573.

Step 175:

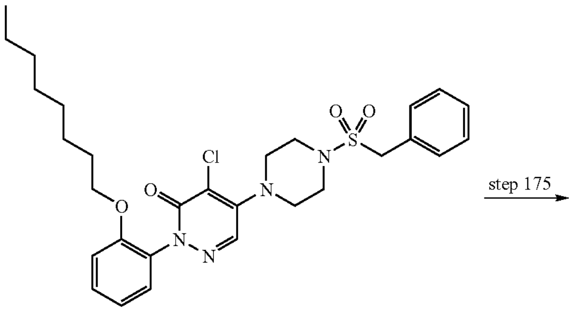

241

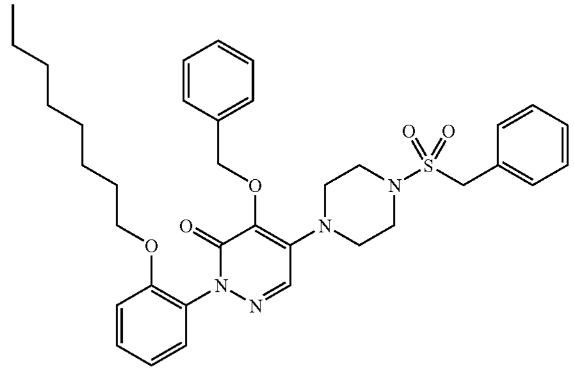

242

To a solution of benzyl alcohol (39.1 mg, 0.362 mmol) in THF (10 mL) was added NaH (60% in oil, 11.6 mg, 0.290 mmol) under a nitrogen atmosphere. To the reaction solution was added chloride 241 (41.4 mg, 0.072 mmol), and the reaction mixture was stirred at room temperature for 17 h. The reaction was quenched with saturated $NH_4Cl$ and extracted with ethyl acetate. The organic extract was then washed with brine, dried with $MgSO_4$, filtered, and concentrated. Purification by silica gel chromatography (eluant: 65% ethyl acetate in hexanes) yielded 34.6 mg (74%) of the product 242 as a brown oil. MS (M+1): m/e 645.

Scheme 52

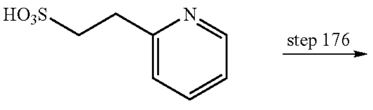

243

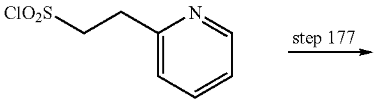

244

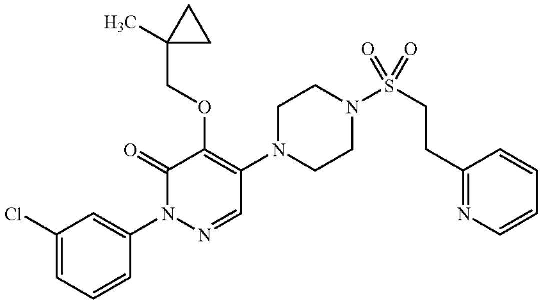

245

Steps 176 and 177:

A mixture of 2-(pyridin-2-yl)ethanesulfonic acid (243) (60 mg, 0.32 mmol) and thionyl chloride (2.3 mL, 31.6 mmol) under nitrogen was stirred at 55° C. for 5 h. The mixture was cooled to room temperature and concentrated to dryness under reduced pressure. The resulting residue was further diluted with toluene (5 mL), which was removed under reduced pressure to give crude 2-(pyridin-2-yl)ethanesulfonyl chloride (244) as a fine powder. Compound 244 was diluted with methylene chloride (2 mL) and the solution was cooled to 0° C. and a cold solution of 2-(3-chlorophenyl)-4-((1-methyl cyclopropyl)methoxy)-5-(piperazin-1-yl)pyridazin-3(2H)-one (120 mg, 0.32 mmol) and triethylamine (0.54 mL, 3.87 mmol) in methylene chloride (3 mL) was added dropwise. The reaction mixture was slowly warmed to room temperature, stirring for a total of 18 h after which the solvents were removed under reduced pressure. The residue was purified by CombiFlash Companion (80-g silica gel cartridge), eluting with ethyl acetate/hexanes (1:9 to 7:3), to provide the product 245 (66 mg, 38%) as a white solid. MS (M+1): m/e 544.

Scheme 53
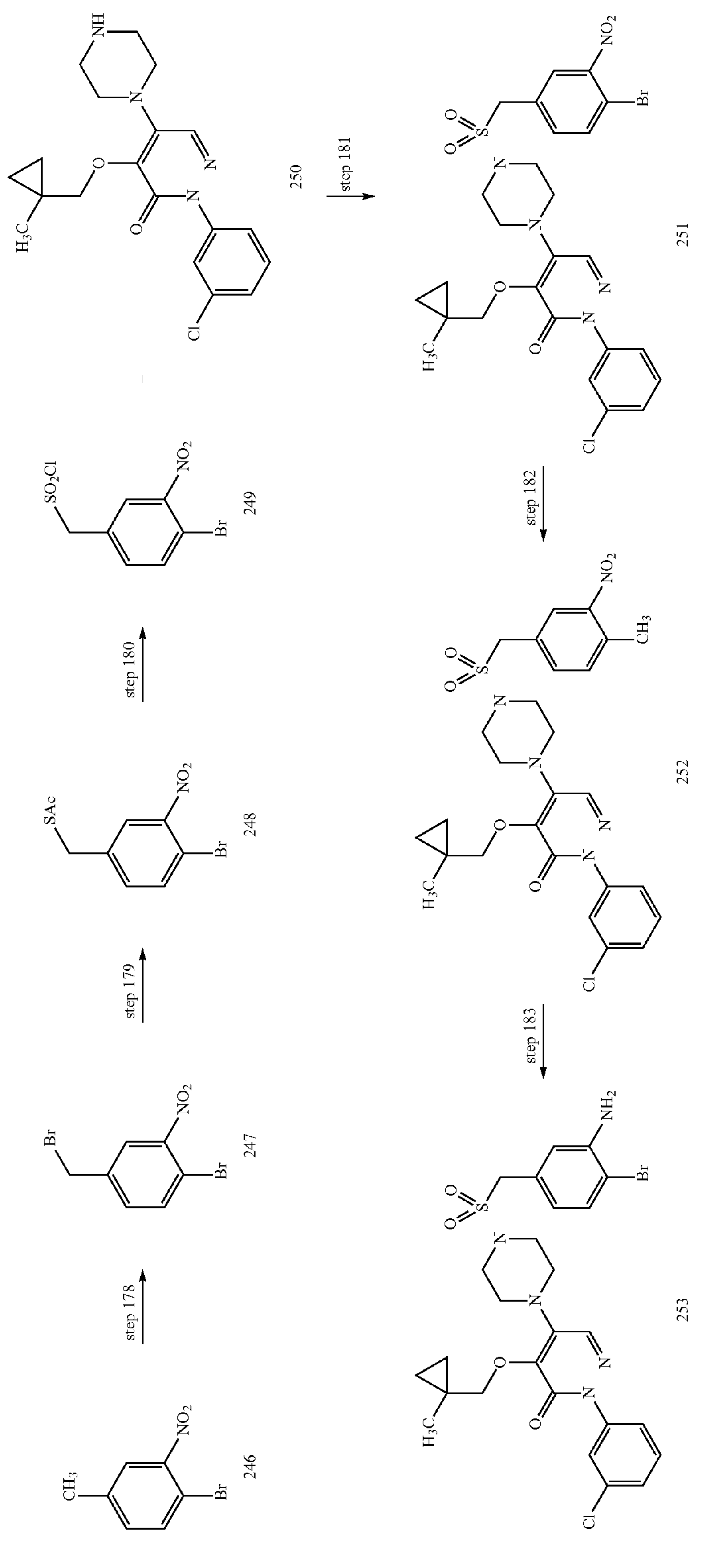
246 247 248 249 250 251 252 253

Step 178:

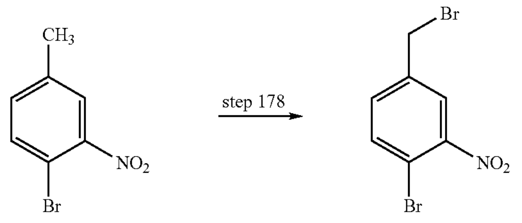

246 247

A mixture of 1-bromo-4-methyl-2-nitrobenzene 246 (10.0 g, 46.29 mmol), N-bromosuccinimide (9.06 g, 50.92 mmol) and AIBN (0.76 g, 4.63 mmol) in carbon tetrachloride (50 mL) at room temperature was purged with nitrogen (subsurface bubbling) for 10 mins after which the mixture was heated to reflux and stirred for 17 h. The cooled mixture was vacuum filtered, and the filtrate was concentrated. The resulting residue was purified by CombiFlash Companion (330-g silica gel cartridge), eluting with ethyl acetate/hexanes (3:97 to 1:9), to provide 6.88 g (50% yield) of the product 247 as a yellow solid.

Step 179:

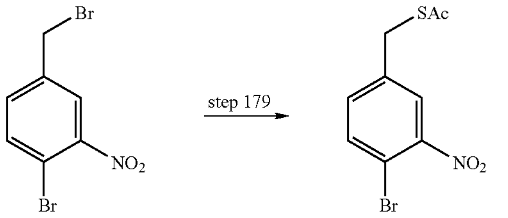

247 248

A solution of 1-bromo-4-(bromomethyl)-2-nitrobenzene 247 (6.88 g, 23.33 mmol) and potassium thioacetate (3.46 g, 30.33 mmol) in anhydrous DMF (100 mL) was heated at 55° C. under nitrogen for 17 h. The cooled mixture was diluted with water (300 mL) and extracted with ethyl acetate (3×200 mL). The combined organic extracts were washed with water (3×50 mL), brine (100 mL) and then concentrated to afford the product 248 (6.73 g, 99% yield) as a dark-red oil that was used in the next step without further purification.

Step 180:

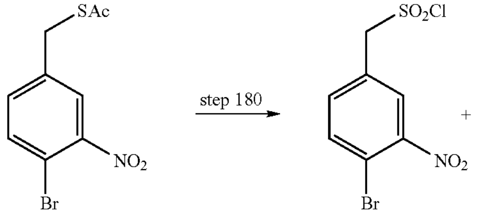

248 249

Chlorine gas was slowly bubbled through a biphasic mixture of S-4-bromo-3-nitrobenzyl ethanethioate 8 (6.73 g, 23.2 mmol) in methylene chloride (100 mL) and water (20 mL) at 0° C. for 45 mins, during which time the solution became a persistent yellow color. Nitrogen gas was slowly bubbled through the solution to displace the chlorine gas, and the reaction mixture was extracted with methylene chloride (100 mL). The aqueous layer was further extracted with methylene chloride (2×30 mL), and the combined organic extracts were washed with brine (100 mL), dried ($Na_2SO_4$), filtered, and concentrated to afford (4-bromo-3-nitrophenyl)methanesulfonyl chloride 9 (7.00 g, 96% yield) as a yellow solid which was used in the next step without further purification.

Step 181:

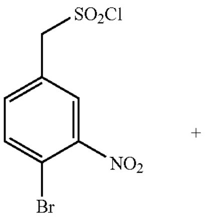

249

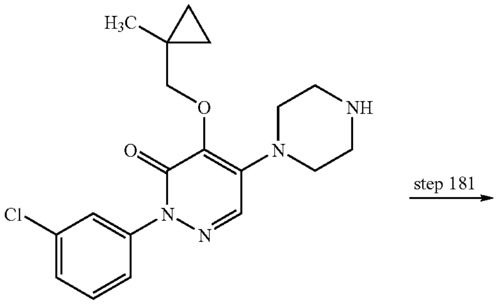

250

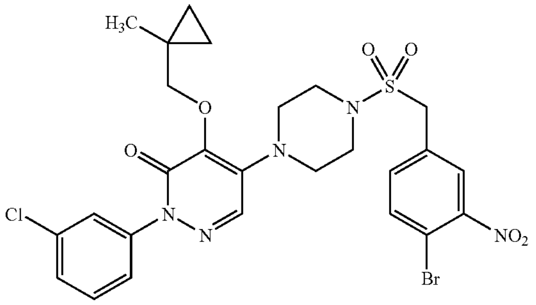

251

Triethylamine (1.64 mL, 11.8 mmol) was added to a mixture of 2-(3-chlorophenyl)-4-((1-methylcyclopropyl)methoxy)-5-(piperazin-1-yl)pyridazin-3(2H)-one 250 (2.21 g, 5.89 mmol) and (4-bromo-3-nitrophenyl)methanesulfonyl chloride 249 (1.86 g, 5.91 mmol) in anhydrous methylene chloride (25 mL) at 0° C. under nitrogen. The mixture was stirred at 0° C. for 1 h after which it was slowly warmed to room temperature, stirring for a total of 16 h. The mixture was diluted with methylene chloride (150 mL), washed with water (50 mL) then brine (50 mL), and the solvents were removed under reduced pressure. The residue was purified by CombiFlash Companion (120-g $SiO_2$ cartridge), eluting with ethyl acetate/hexanes (1:9 to 4:6), to provide 980 mg (25% yield) of the product 251 as a yellow solid. MS (M+1): m/e 652.

Step 182:

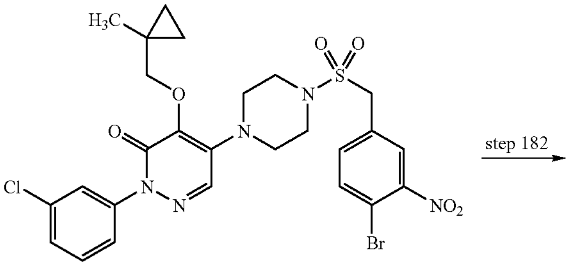

251

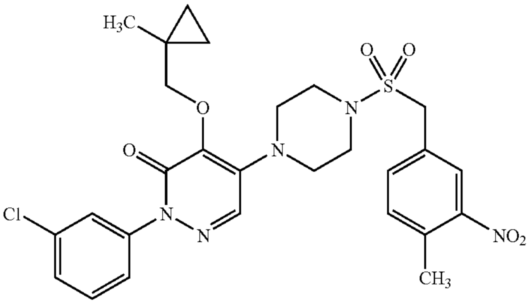

252

Cesium carbonate (46 mg, 0.14 mmol) and potassium carbonate (39 mg, 0.28 mmol) were added to a degassed solution of 5-(4-(4-bromo-3-nitrobenzylsulfonyl)piperazin-1-yl)-2-(3-chlorophenyl)-4-((1-methylcyclopropyl)methoxy)pyridazin-3(2H)-one 10 (93 mg, 0.142 mmol) in 1,4-dioxane (5 mL) at room temperature under nitrogen after which $Pd(PPh_3)_4$ (16 mg, 0.014 mmol) and trimethylboroxine (44 uL, 0.315 mmol) were added. The reaction mixture was stirred at reflux for 16 h after which the cooled mixture was concentrated. The resulting residue was diluted with water (30 mL) and extracted with methylene chloride (2×30 mL). The combined organic extracts were washed with brine (50 mL) then concentrated. The residue was purified by CombiFlash Companion (40-g $SiO_2$ cartridge), eluting with ethyl acetate/hexanes (1:9 to 4:6), to provide 75 mg (90% yield) of the product 252 as a yellow solid. MS (M+1): m/e 588.

Step 183:

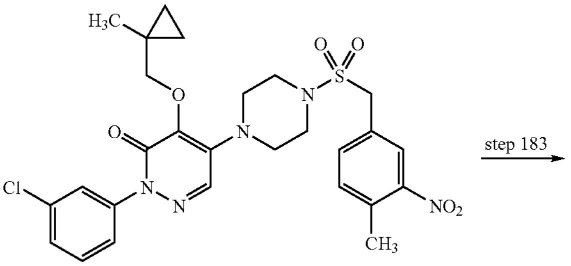

252

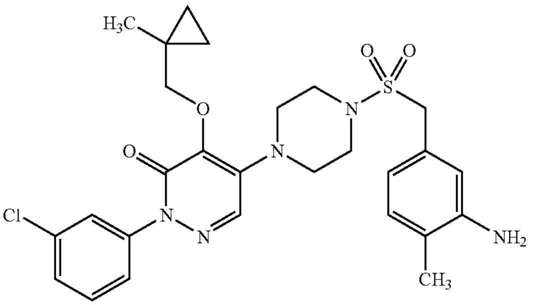

253

A mixture of 2-(3-chlorophenyl)-5-(4-(4-methyl-3-nitrobenzylsulfonyl)piperazin-1-yl)-4-((1-methylcyclopropyl)methoxy)pyridazin-3(2H)-one 252 (75 mg, 0.13 mmol) and platinum(II) oxide (11 mg, 0.048 mmol) in ethanol (5 mL) and THF (5 mL) at room temperature was stirred under an atmosphere of hydrogen (balloon) for 18 h. The mixture was filtered through a plug of celite under reduced pressure, and the filtrate was concentrated. The residue was purified by CombiFlash Companion (40-g $SiO_2$ cartridge), eluting with ethyl acetate/hexanes (15:85 to 8:2), to provide 36 mg (51% yield) of the product 253 as a white solid. MS (M+1): m/e 558.

Using the procedures described above, the following compounds were synthesized.

TABLE 34

Oxygen Analogs with Methyl-or Methoxy-Substituted Sulfonamide

| Cmpd. No. | Structure | MS M + 1 |
|---|---|---|
| 1863Z | 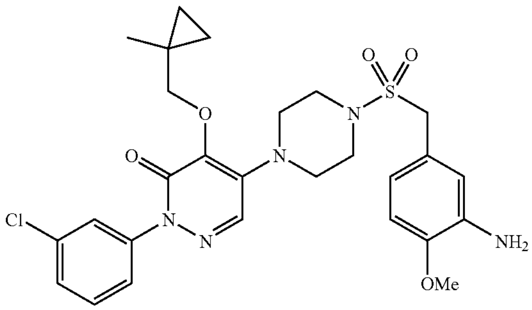 | 574 |

TABLE 34-continued
| Oxygen Analogs with Methyl-or Methoxy-Substituted Sulfonamide | | |
|---|---|---|
| Cmpd. No. | Structure | MS M + 1 |
| 1864Z | 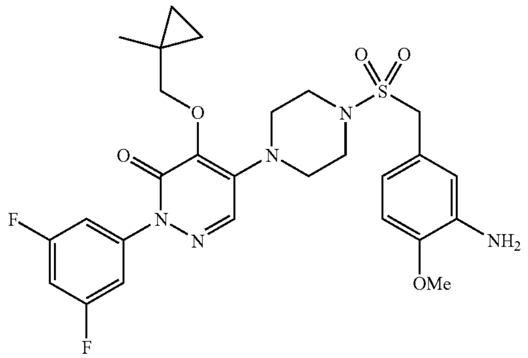 | 576 |
| 1865Z | 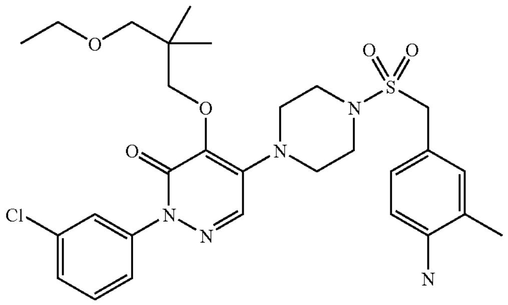 | 604 |
| 1866Z | 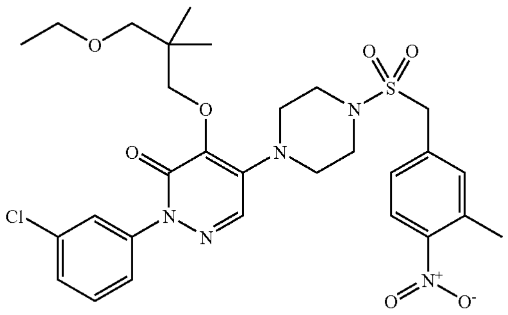 | 634 |
| 1867Z | 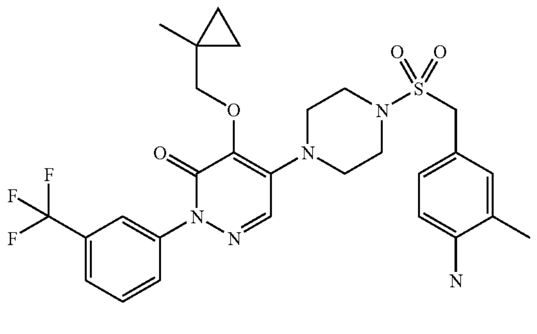 | 592 |

TABLE 34-continued
| Oxygen Analogs with Methyl-or Methoxy-Substituted Sulfonamide | | |
|---|---|---|
| Cmpd. No. | Structure | MS M + 1 |
| 1868Z | 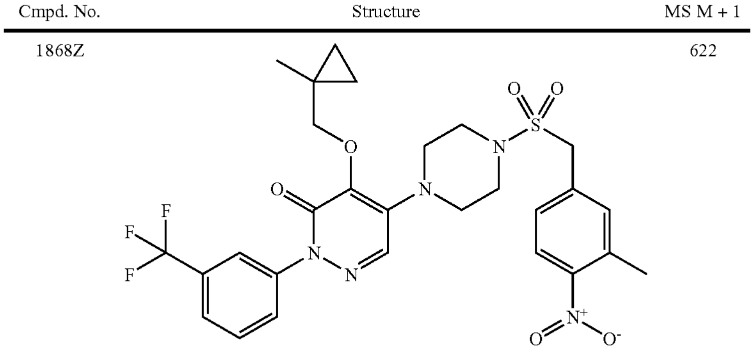 | 622 |
| 1869Z | 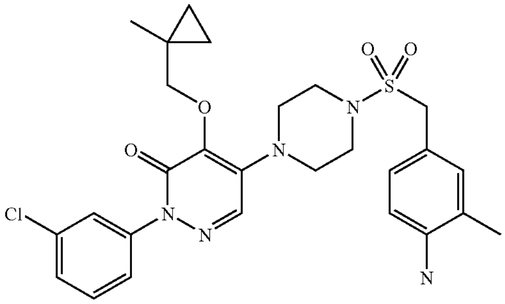 | 558 |
| 1870Z | 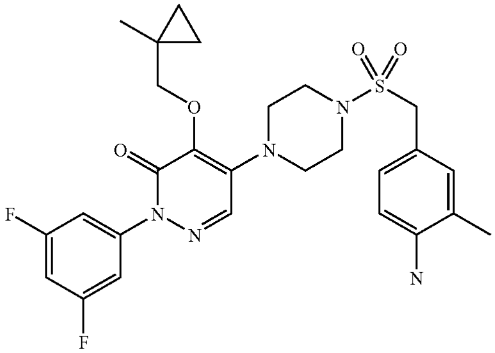 | 560 |
| 1871Z | 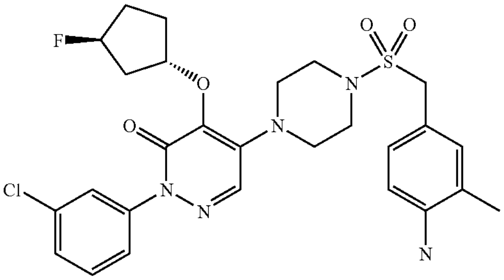 | 576 |
| 1872Z | 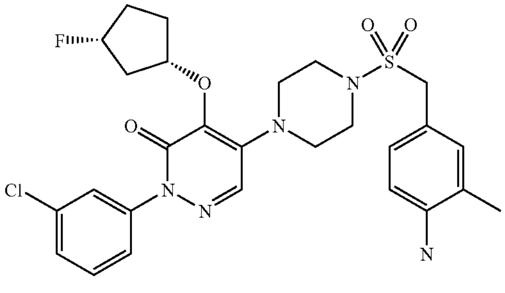 | 576 |

TABLE 34-continued
| Oxygen Analogs with Methyl-or Methoxy-Substituted Sulfonamide | | |
|---|---|---|
| Cmpd. No. | Structure | MS M + 1 |
| 1873Z | 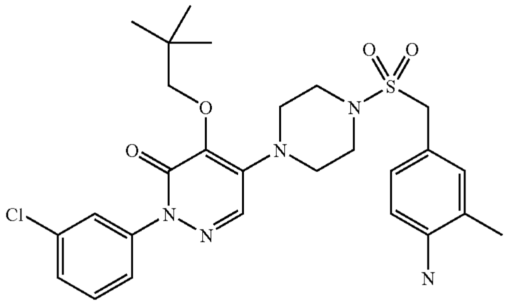 | 560 |
| 1874Z | 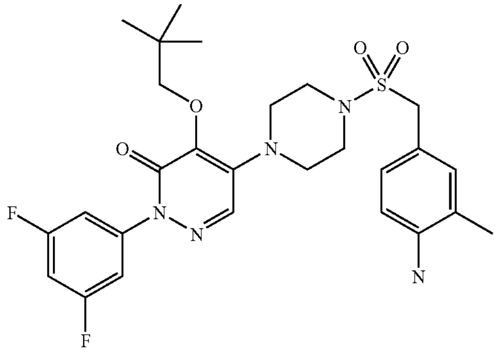 | 562 |
| 1875Z | 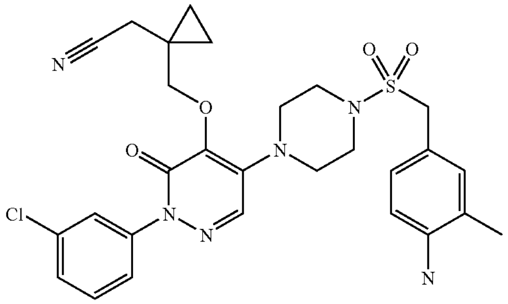 | 583 |
| 1876Z | 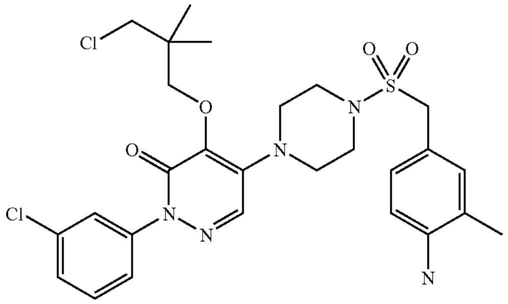 | 594 |

TABLE 34-continued
| Oxygen Analogs with Methyl-or Methoxy-Substituted Sulfonamide | | |
|---|---|---|
| Cmpd. No. | Structure | MS M + 1 |
| 1877Z | 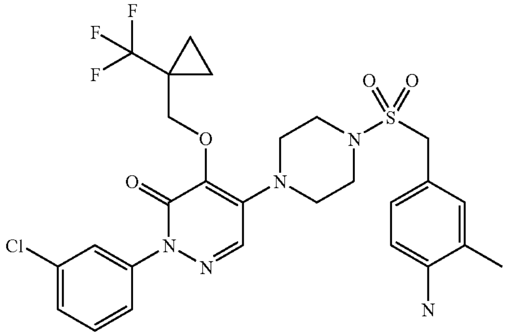 | 612 |
| 1878Z | 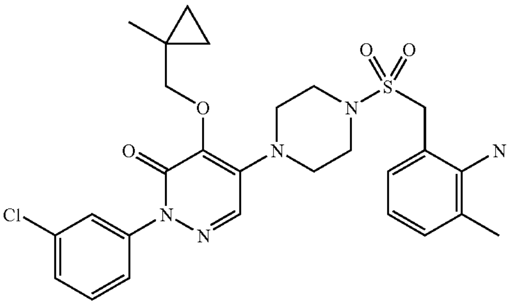 | 558 |
Scheme 54
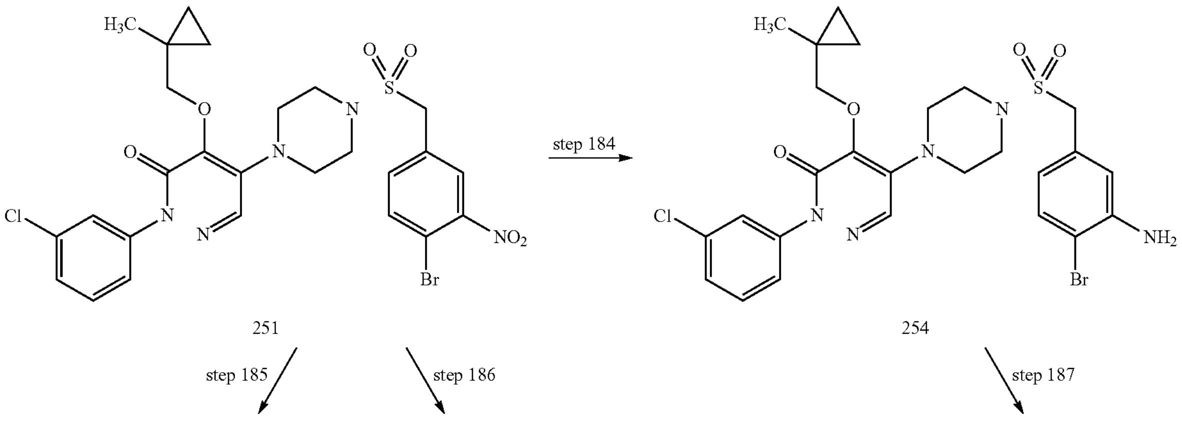
251
254

-continued

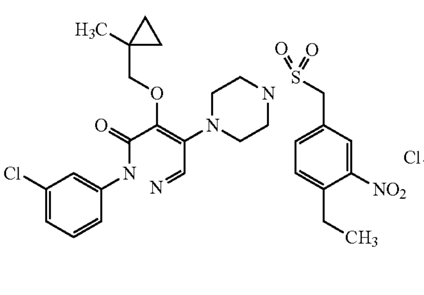

255

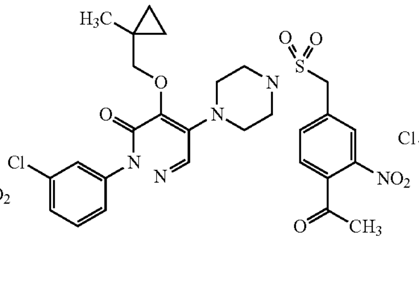

257

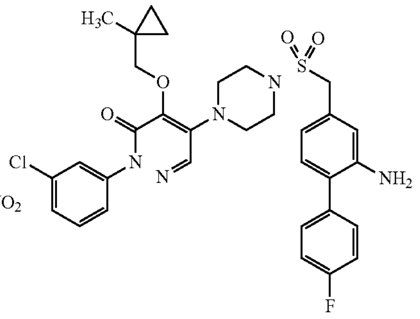

259 step 184 step 184

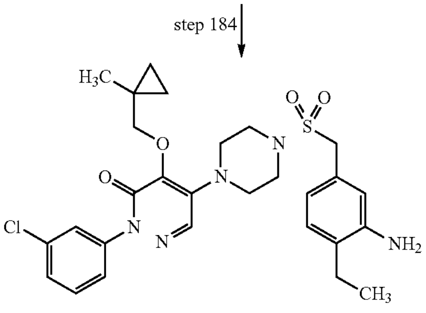

256

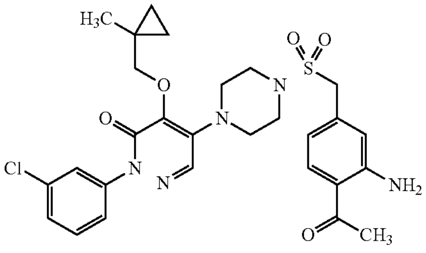

258

Step 184:

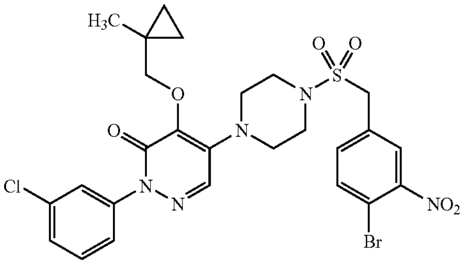

251 step 184

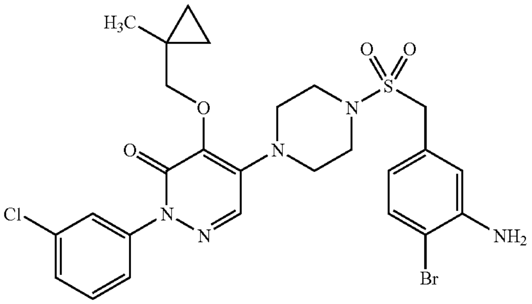

254

A mixture of 5-(4-(4-bromo-3-nitrobenzylsulfonyl)piperazin-1-yl)-2-(3-chlorophenyl)-4-((1-methylcyclopropyl)methoxy)pyridazin-3(2H)-one 251 (49 mg, 0.075 mmol) and platinum(II) oxide (10 mg 0.044 mmol) in ethanol (5 mL) and THF (2 mL) at room temperature was stirred under an atmosphere of hydrogen (balloon) for 16 h. The mixture was filtered through a plug of celite under reduced pressure, and the filtrate was concentrated. The residue was purified by CombiFlash Companion (40-g, $SiO_2$ cartridge), eluting with ethyl acetate/hexanes (1:9 to 8:2) to provide 11 mg (45% yield) of the product 254 as a white solid. MS (M+1): m/e 622.

Step 185:

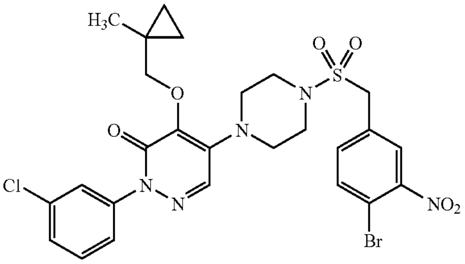

251 step 185

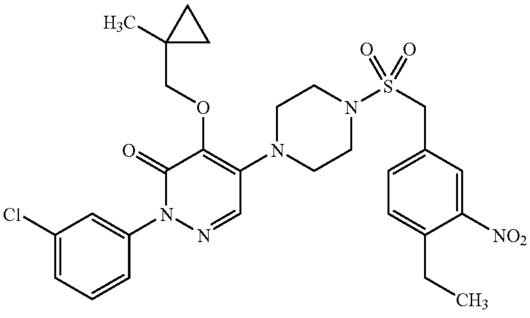

255

A solution of potassium phosphate (66 mg, 0.31 mmol) in water (2 mL) was added to a degassed solution of 5-(4-(4-bromo-3-nitrobenzylsulfonyl)piperazin-1-yl)-2-(3-chlorophenyl)-4-((1-methylcyclopropyl)methoxy)pyridazin-3

(2H)-one 251 (92 mg, 0.141 mmol) in THF (5 mL) after which $PdCl_2$(dppf) (8 mg, 0.01 mmol) and triethyl borane (1.0 M in THF 0.17 mL, 0.17 mmol) were added, and the mixture was heated to reflux, stirring for a total of 18 h. The cooled mixture was diluted with water (30 mL) and extracted with methylene chloride (3×30 mL). The combined organic extracts were washed with brine (50 mL) then concentrated. The residue was purified by CombiFlash Companion (40-g $SiO_2$ cartridge), eluting with ethyl acetate/hexanes (1:9 to 4:6), to provide 34 mg (40% yield) of the product 255 as a yellow solid. MS (M+1): m/e 602.

Step 184:

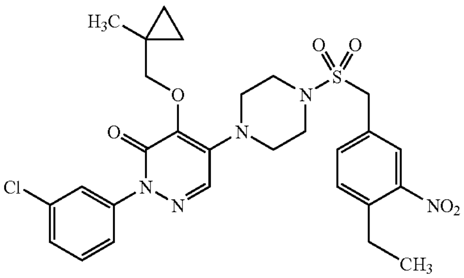

255 step 184

-continued

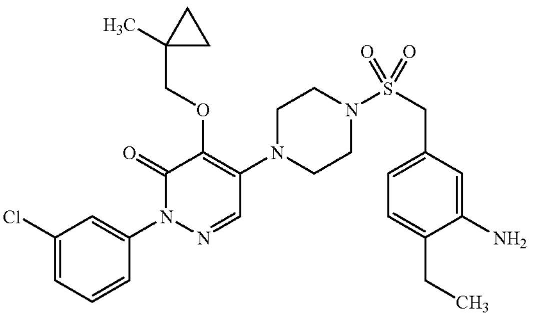

256

Hydrogenation of 2-(3-chlorophenyl)-5-(4-(4-ethyl-3-nitrobenzylsulfonyl)piperazin-1-yl)-4-((1-methylcyclopropyl)methoxy)pyridazin-3(2H)-one 255 (34 mg, 0.057 mmol) was performed as described above to provide 26 mg (80% yield) of the product 256 as a white solid. MS (M+1): m/e 572.

Using the procedures described above, the following compounds were synthesized.

| Cmpd. No. | Structure | MS M + 1 |
|---|---|---|
| 1879Z | 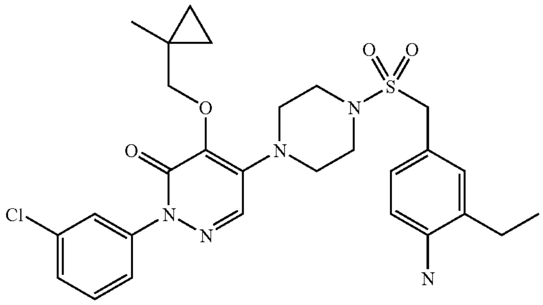 | 572 |
| 1880Z | 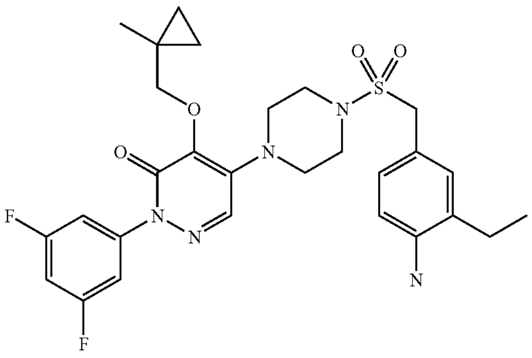 | 574 |

Step 186:

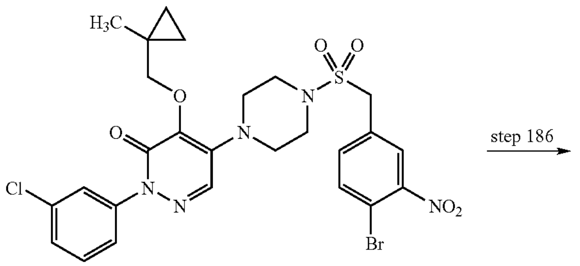

251

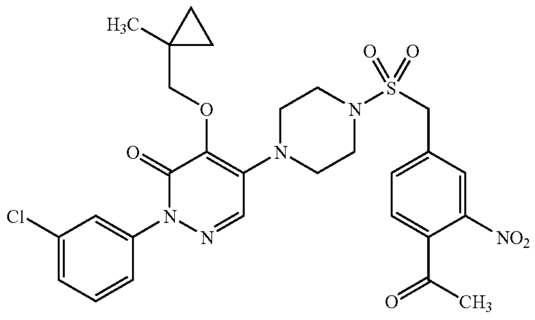

257

Tributylethoxyvinyltin (126 uL, 0.373 mmol) and $PdCl_2(PPh_3)_2$ (20 mg, 0.028 mmol) were added to a degassed solution of 5-(4-(4-bromo-3-nitrobenzylsulfonyl)piperazin-1-yl)-2-(3-chlorophenyl)-4-((1-methylcyclopropyl)methoxy)pyridazin-3(2H)-one 251 (187 mg, 0.286 mmol) in 1,4-dioxane (6 mL) at room temperature under nitro-en after which the mixture was heated to reflux, stirring for a total of 18 h. The cooled mixture was diluted with 1 M HCl (4 mL) and stirred at room temperature for an additional 90 mins. Aqueous sodium hydroxice (1 M, 4.5 mL) was added, and the mixture was extracted with methylene chloride (60 mL×2). The solvent was concentrated, and the residue was purified by CombiFlash Companion (40-g $SiO_2$ cartridge), eluting with ethyl acetate/hexanes (1:9 to 6:4), to provide 139 mg (79% yield) of the product 257 as a white solid. MS (M+1): m/e 616.

Step 184:

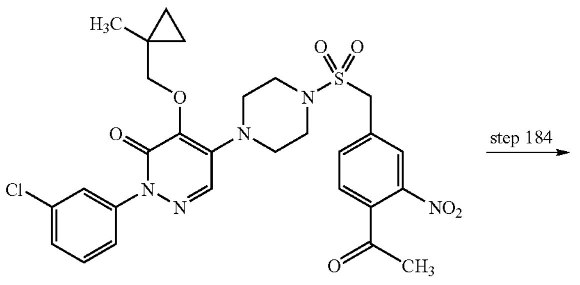

257

-continued

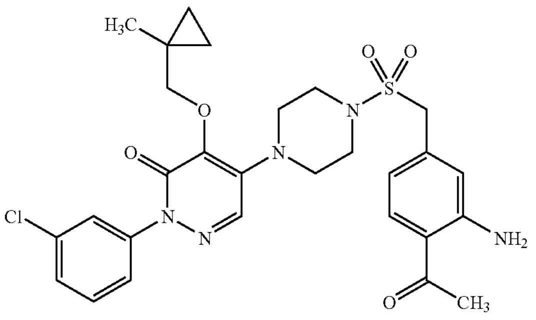

258

Hydrogenation of 5-(4-(4-acetyl-3-nitrobenzylsulfonyl)piperazin-1-yl)-2-(3-chloro phenyl)-4-((1-methylcyclopropyl)methoxy)pyridazin-3(2H)-one 257 (139 mg, 0.226 mmol) was performed as described above to provide 99 mg (74% yield) of the product 258 as a yellow solid. MS (M+1): m/e 586.

Step 187:

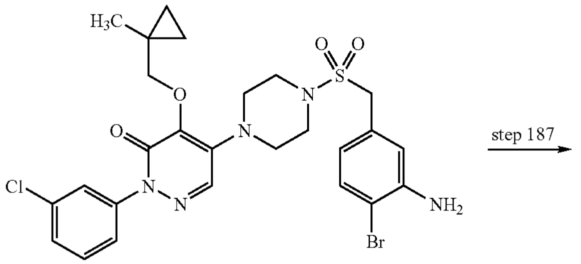

254

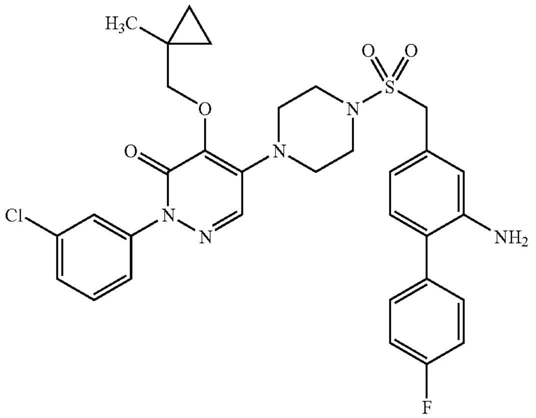

259

A solution of sodium carbonate (2 M, 0.4 mL, 0.8 mmol) and 4-fluorophenylboronic acid (34 mg, 0.24 mmol) was added to a degassed solution of 5-(4-(3-amino-4-bromobenzylsulfonyl)piperazin-1-yl)-2-(3-chloro phenyl)-4-((1-methylcyclopropyl)methoxy)pyridazin-3(2H)-one 254 (60 mg, 0.096 mmol) in 1,4-dioxane (4 mL) at room temperature under nitrogen, after which $Pd(PPh_3)_4$ (20 mg, 0.017 mmol) was added, and the mixture was stirred at 95° C. 16 h. The cooled mixture was diluted with methylene chloride (150 mL), washed with brine (40 mL) and then concentrated. The residue was purified by CombiFlash Companion (40-g $SiO_2$ cartridge), eluting with ethyl acetate/hexanes (1:9 to 4:6), to provide 14 mg (23% yield) of the product 259 as a white solid. MS (M+1): m/e 638.

Scheme 55

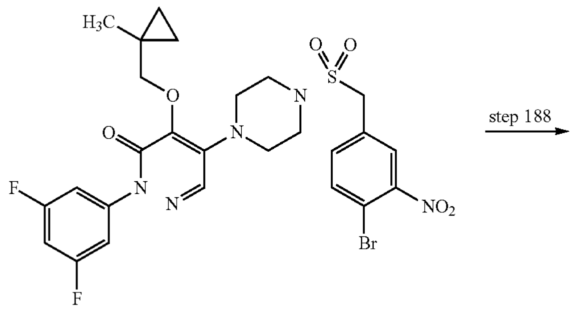

260

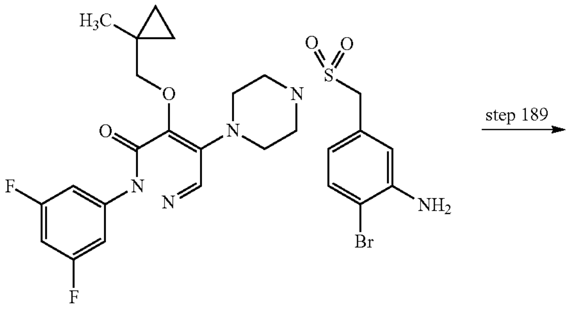

261

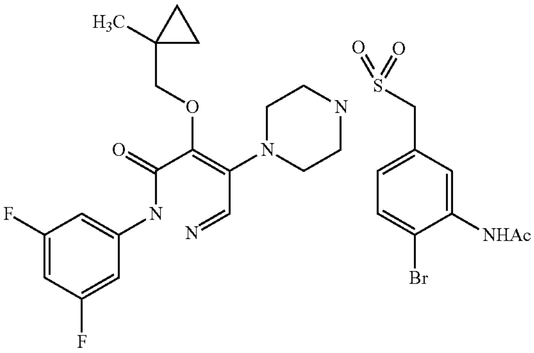

262

Step 188:

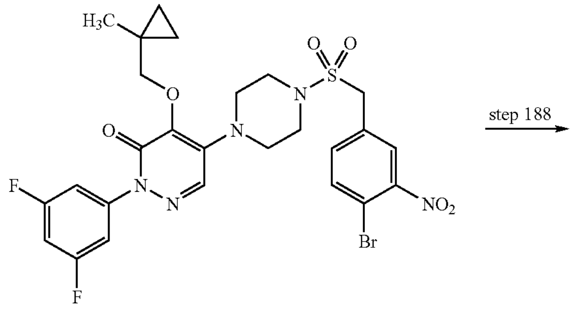

260

-continued

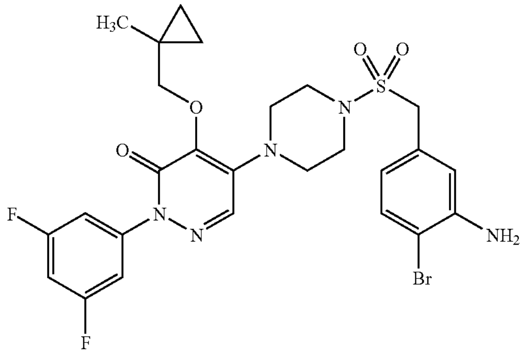

261

Iron powder (448 mg, 8.02 mmol) was added portionwise to a solution of 5-(4-(4-bromo-3-nitrobenzylsulfonyl)piperazin-1-yl)-2-(3,5-difluoro phenyl)-4-((1-methylcyclopropyl)methoxy)pyridazin-3(2H)-one 260 (105 mg, 0.160 mmol) in THF (3 mL) at room temperature under nitrogen, after which acetic acid (3.7 mL, 64 mmol) was added slowly. The reaction mixture was stirred at room temperature for 4 h then the solids were removed by vacuum filtration. The filtrate was concentrated, and the residue was purified by CombiFlash Companion (40-g $SiO_2$ cartridge), eluting with ethyl acetate/hexanes (1:9 to 1:1), to provide 82 mg (82% yield) of the product 261 as a white solid. MS (M+1): m/e 624.

Step 189:

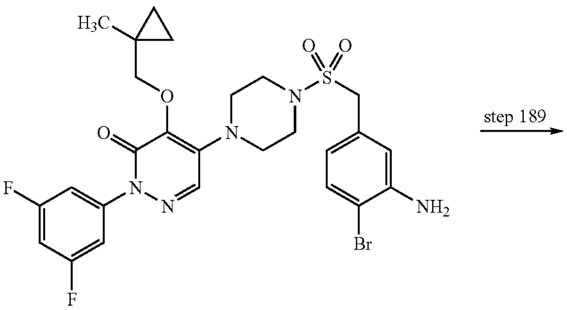

261

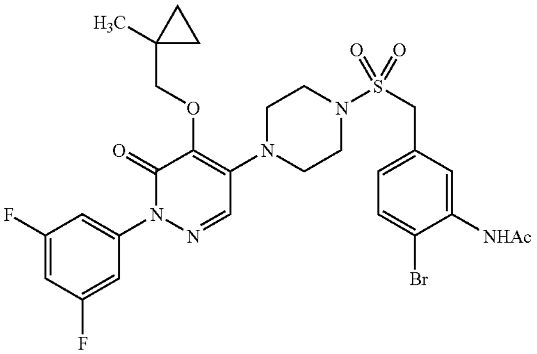

262

Acetyl chloride (28 uL, 0.394 mmol) was added to a solution of 5-(4-(3-amino-4-bromobenzyl sulfonyl)piperazin-1-yl)-2-(3,5-difluorophenyl)-4-((1-methylcyclopropyl)methoxy)pyridazin-3(2H)-one 261 (82 mg, 0.131 mmol) and triethylamine (110 uL, 0.79 mmol) in THF (3 mL) at room temperature under nitrogen, and the mixture was stirred for 18 h then concentrated. The crude product was purified by CombiFlash Companion (40-g $SiO_2$ cartridge), eluting with ethyl acetate/hexanes (1:9 to 6:4), to provide 57 mg (65% yield) of the product 262 as a yellow solid. MS (M+1): m/e 666.
Scheme 56
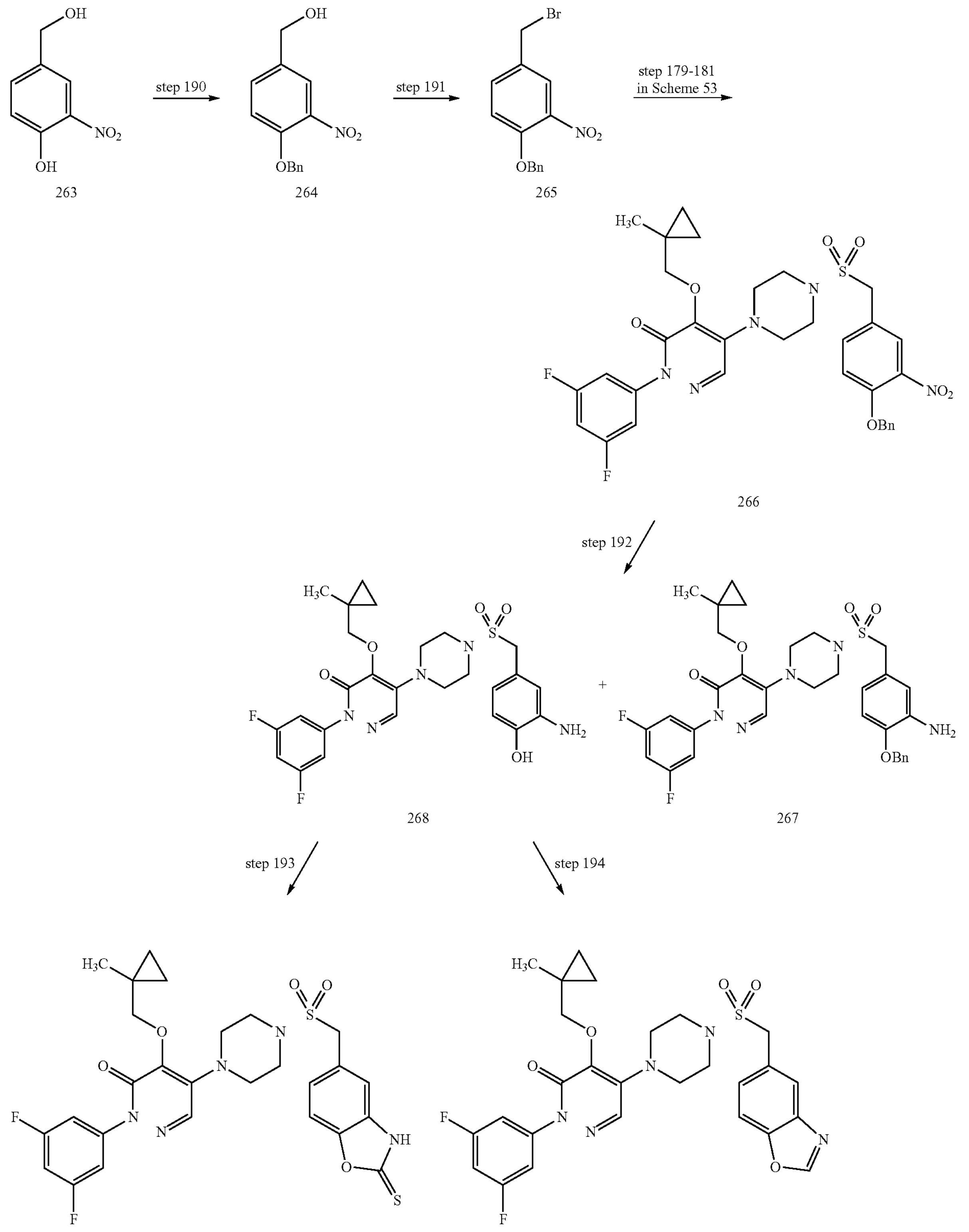
263 264 265
266
268 + 267
269 270

Step 190:

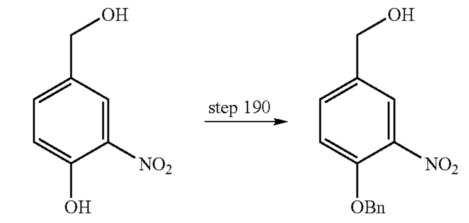

263 264

A mixture of 4-(hydroxymethyl)-2-nitrophenol 263 (3.27 g, 19.33 mmol), potassium carbonate (5.34 g, 38.64 mmol) and benzyl bromide (2.53 mL, 21.30 mmol) in acetone (200 mL) was stirred at reflux for 18 h. After cooling, the solvent was concentrated, and the residue was triturated with methylene chloride (300 mL) and vacuum filtered. The filtrate was concentrated, and the residue was purified by CombiFlash Companion (80-g silica gel cartridge), eluting with ethyl acetate/hexanes (1:1), to provide 5.49 g (95% yield) of the product 264 as a yellow solid.

Step 191:

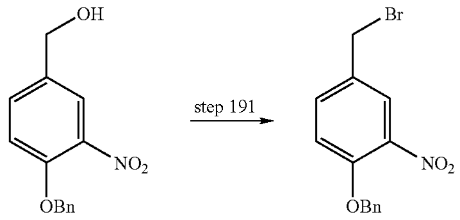

264 265

Triphenylphosphine (1112 g, 42.39 mmol) was added to a solution of N-bromosaccharin (11.11 g, 42.39 mmol) in methylene chloride (180 mL) at 0° C. under nitrogen, and the mixture was stirred for 5 mins. The mixture was warmed to room temperature, and a solution of (4-(benzyloxy)-3-nitrophenyl)methanol 264 (5.49 g, 21.17 mmol) in methylene chloride (60 mL) was added dropwise. The mixture was stirred at room temperature for 1 h after which the white precipitate was removed by filtration under reduced pressure. The filtrate was concentrated, and the residue was purified by CombiFlash Companion (80-g silica gel cartridge), eluting with methylene chloride/hexanes (1:1), to provide 5.57 g (82% yield) of the product 265 as a yellow solid.

Steps 179-181 in Scheme 53:

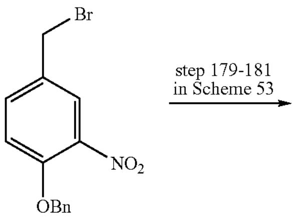

265

-continued

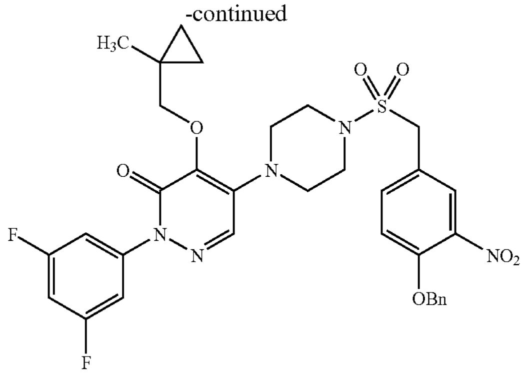

266

Using the described procedures for step 179-181 in Scheme 53, compound 266 was synthesized. MS (M+1): m/e 682.

Step 192:

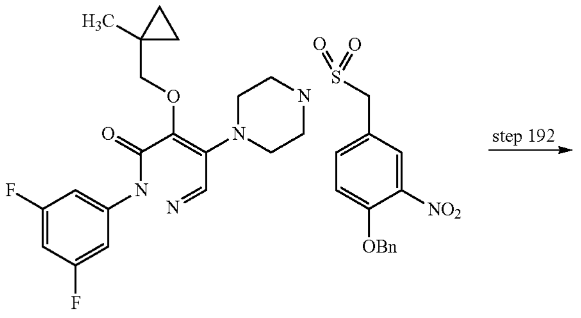

266

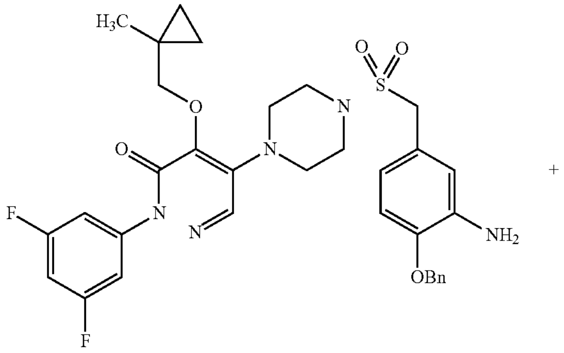

267

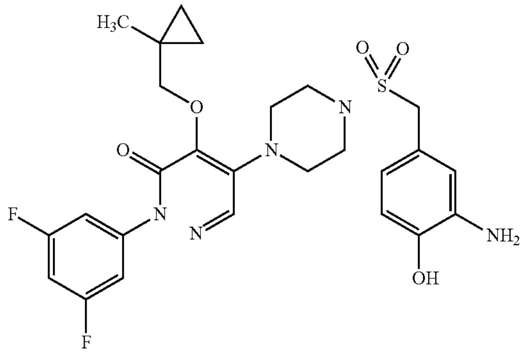

268

A mixture of 5-(4-(4-(benzyloxy)-nitrobenzylsulfonyl) piperazin-1-yl-(3,5-difluorophenyl)-4-((1-methylcyclopropyl)methoxy)pyridazin-3(2H)-one 266 (166 mg, 0.244 mmol) and platinum(II) oxide (24 mg, 0.098 mmol) in ethyl acetate (6 mL) and ethanol (6 mL) was stirred at room temperature under an atmosphere of hydrogen (balloon) for 18 h. The mixture, was filtered through a plug of celite, and the filtrate was concentrated. The resulting residue was purified by CombiFlash Companion (40-g $SiO_2$ cartridge), eluting with ethyl acetate/hexanes (1:9 to 8:2), to provide 85 mg (54% yield) of the product 267 as a white solid: MS (M+1): m/e 652 and 10 mg (7% yield) of the product 268; MS (M+1): m/e 562.

Step 193:

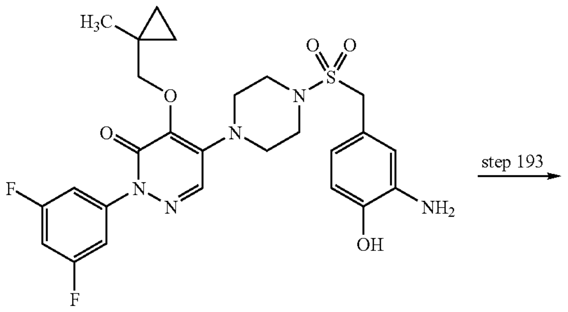

268

-continued

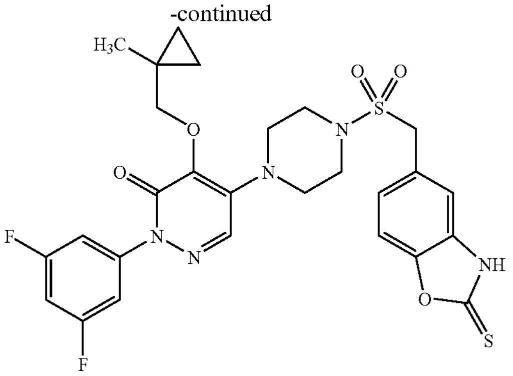

269

A mixture of 5-(4-(3-amino-4-hydroxybenzylsulfonyl) piperazin-1-yl)-2-(3,5-difluorophenyl)-4-((1-methylcyclopropyl)methoxy)pyridazin-3(2H)-one 268 (66 mg, 0.12 mmol) and 1,1'-thiocarbonyldiimidazole (42 mg, 0.24 mmol) in DMF (3 mL) at room temperature under nitrogen was stirred for 24 h, after which the mixture was diluted with water (30 mL) and extracted with ethyl acetate (50 mL×3). The combined organic extracts were washed with water (30 mL×3) then brine (70 mL), and the solvent was concentrated. The resulting residue was purified by CombiFlash Companion (40-g silica gel cartridge), eluting with ethyl acetate/hexanes (1:9 to 6:4), to provide 56 mg (79% yield) of the product 269 as a white solid. MS (M+1): m/e 604.

Using the procedures described above, the following compounds were synthesized.

TABLE 35

Oxygen Analogs with Cyclized Sulfonamide

| Cmpd. No. | Structure | MS M + 1 |
|---|---|---|
| 1881Z | 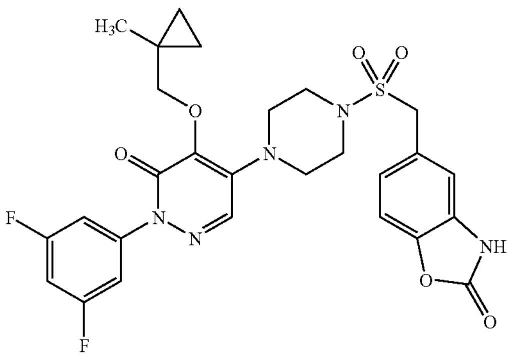 | 588 |
| 1882Z | 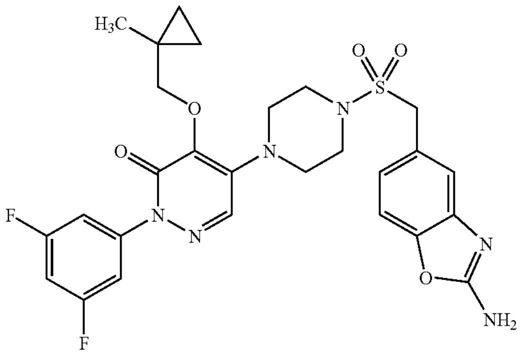 | 587 |

TABLE 35-continued
| Oxygen Analogs with Cyclized Sulfonamide | | |
|---|---|---|
| Cmpd. No. | Structure | MS M + 1 |
| 1883Z | 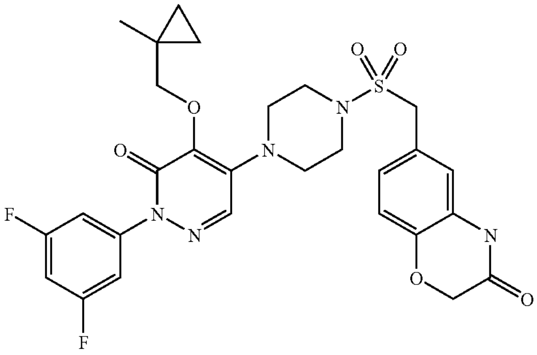 | 602 |
| 1884Z | 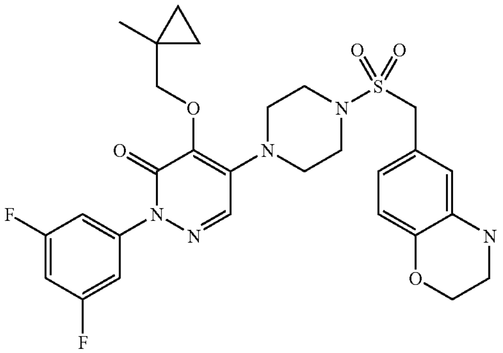 | 588 |
| 1885Z | 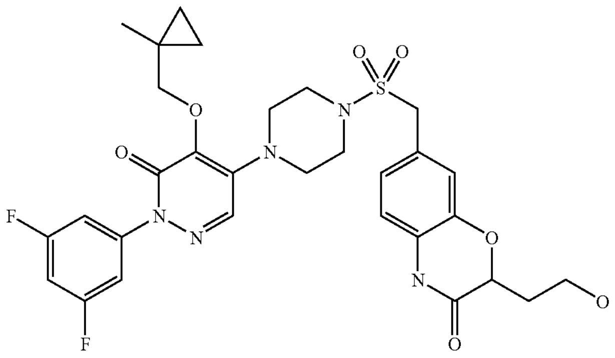 | 646 |

TABLE 35-continued
| Cmpd. No. | Structure | MS M + 1 |
|---|---|---|
| 1886Z | 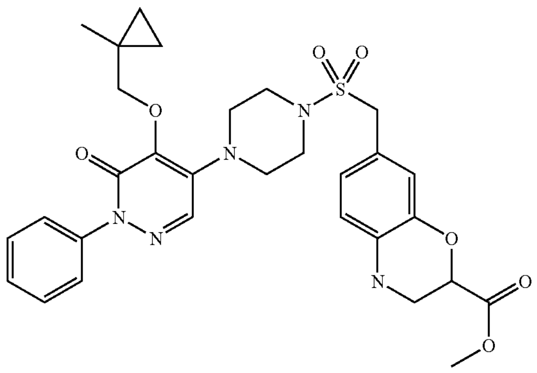 | 610 |
| 1887Z | 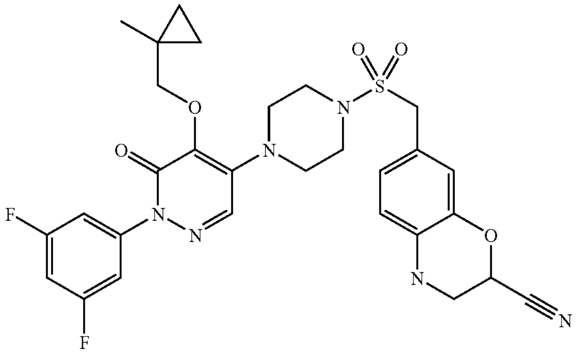 | 613 |
Oxygen Analogs with Cyclized Sulfonamide
Step 194:
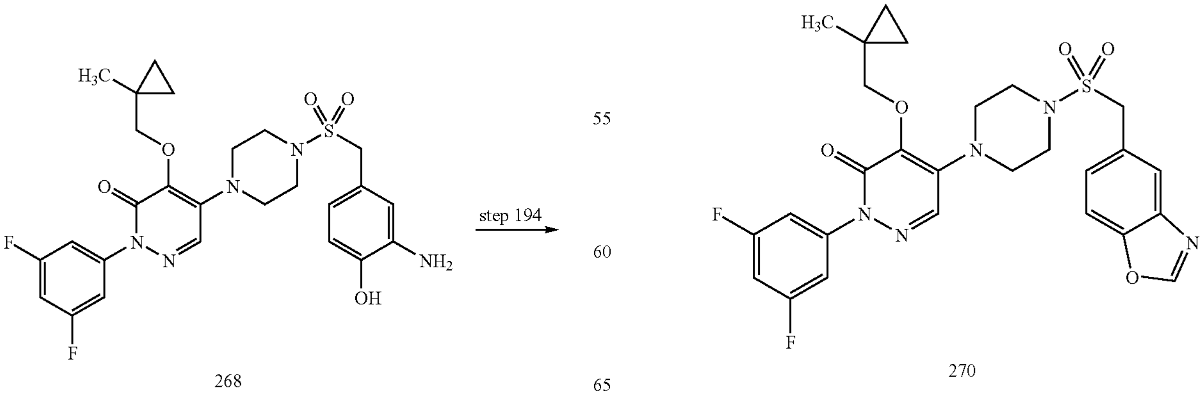
268
-continued
270

A mixture of 5-(4-(3-amino-4-hydroxybenzylsulfonyl)piperazin-1-yl)-2-(3,5-difluorophenyl)-4-((1 methylcyclopropyl)methoxy)pyridazin-3(2H)-one 268 (110 mg, 0.196 mmol) and trimethyl orthoformate (4 mL, 36.6 mmol) was heated at 100° C. under nitrogen for 24 h. The cooled mixture was concentrated, and the resulting residue was purified by CombiFlash Companion (40-g silica gel cartridge), eluting with ethyl acetate/methylene chloride (3:7), to provide 91 mg (81% yield) of the product 270 as a white solid, MS (M+1): m/e 572.

Using the procedures described above, the following compound was synthesized.

TABLE 36

Oxygen Analogs with Cyclized Sulfonamide

| Cmpd. No. | Structure | MS M + 1 |
|---|---|---|
| 1888Z | 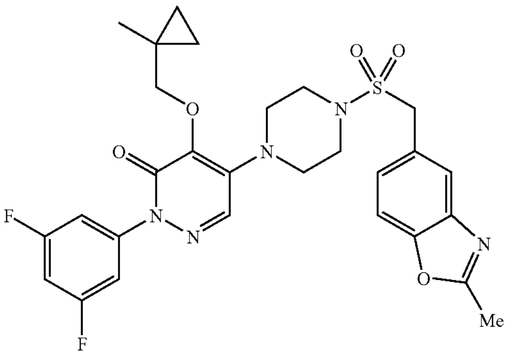 | 586 |
| 1889Z | 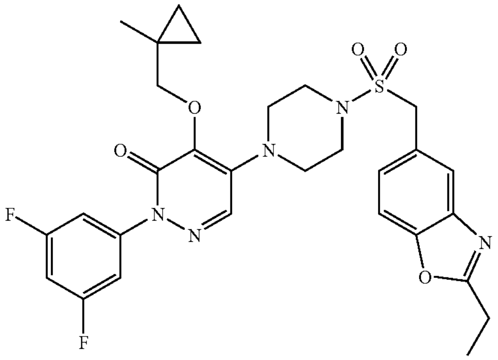 | 600 |
| 1890Z | 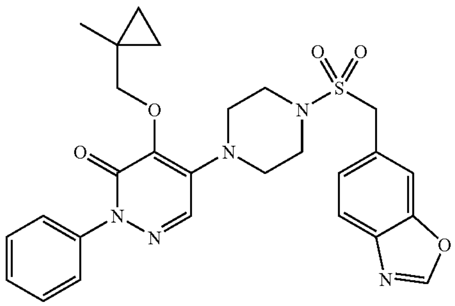 | 536 |
| 1891Z | 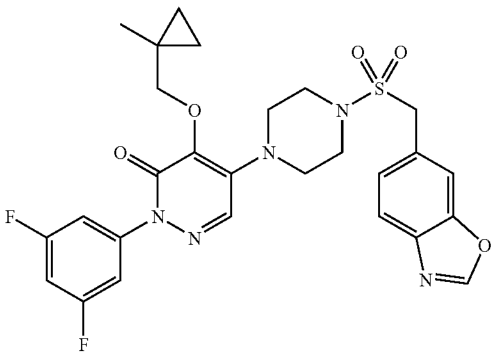 | 572 |

TABLE 36-continued
| Oxygen Analogs with Cyclized Sulfonamide | | |
|---|---|---|
| Cmpd. No. | Structure | MS M + 1 |
| 1892Z | 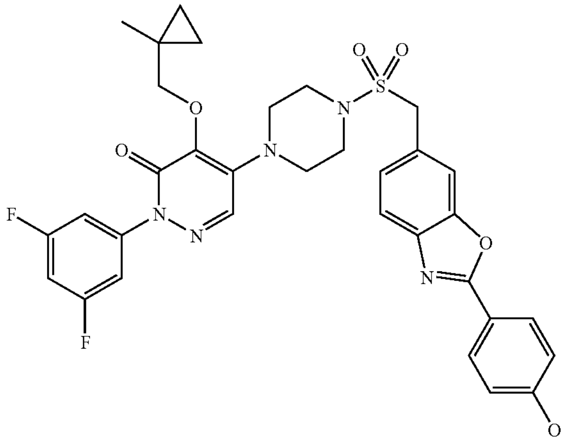 | 664 |
| 1893Z | 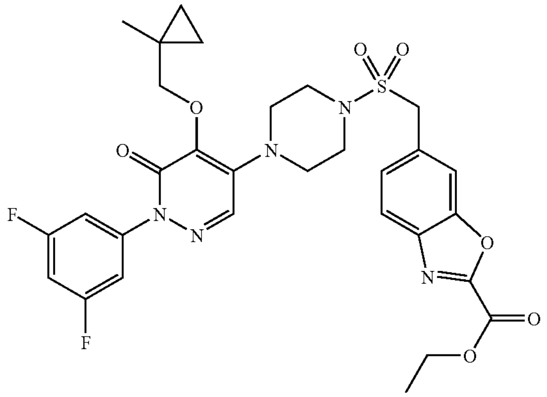 | 644 |
| 1894Z | 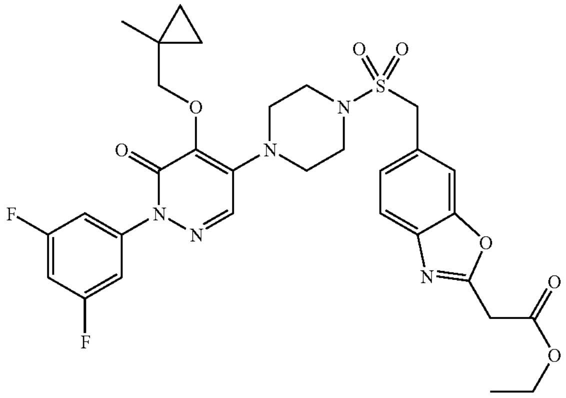 | 658 |

TABLE 36-continued
Oxygen Analogs with Cyclized Sulfonamide
| Cmpd. No. | Structure | MS M + 1 |
|---|---|---|
| 1895Z | 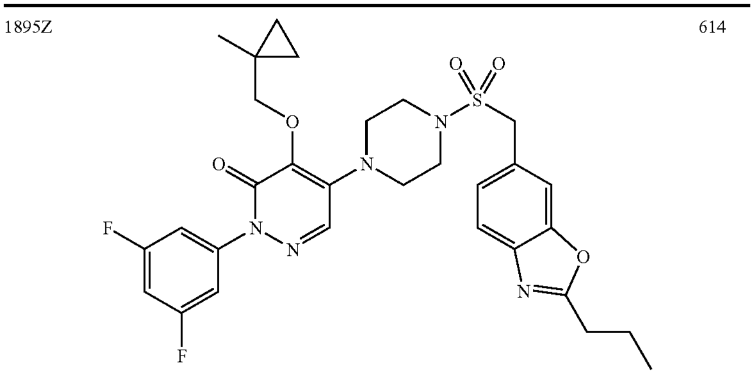 | 614 |
| 1896Z | 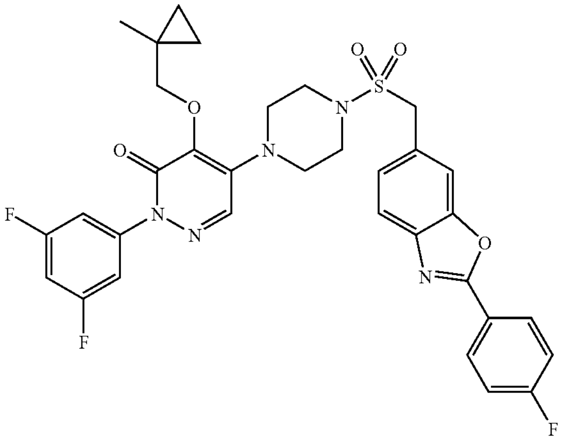 | 666 |
| 1897Z | 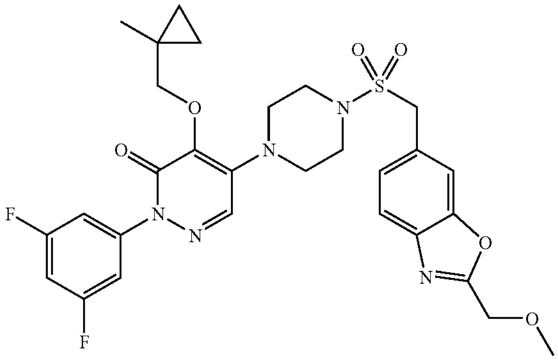 | 616 |
| 1898Z | 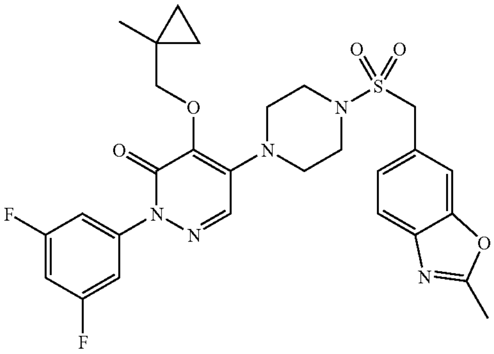 | 586 |

TABLE 36-continued
| Oxygen Analogs with Cyclized Sulfonamide | | |
|---|---|---|
| Cmpd. No. | Structure | MS M + 1 |
| 1899Z | 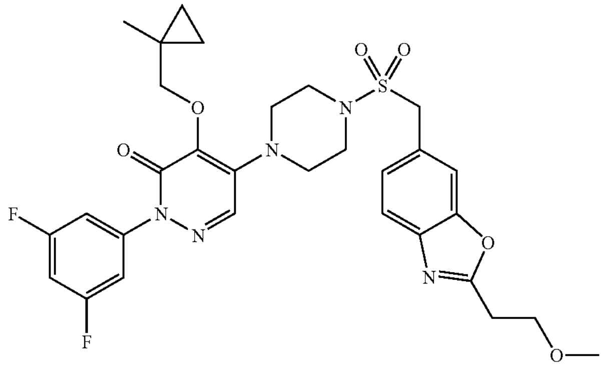 | 630 |
| 1900Z | 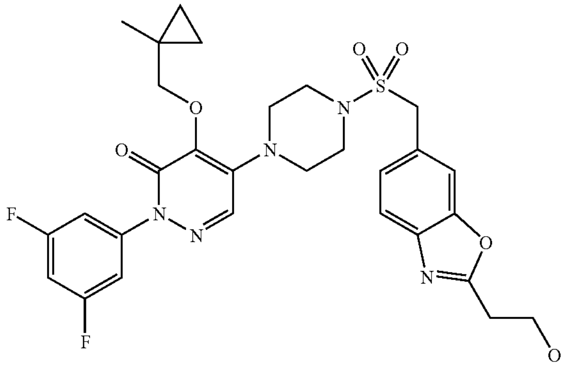 | 616 |
| 1901Z | 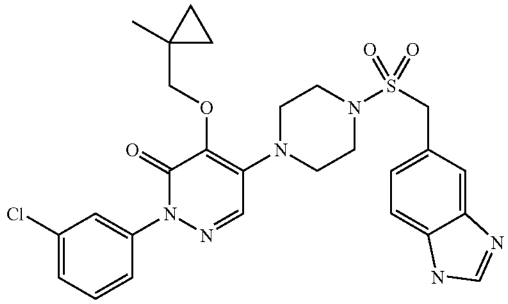 | 569 |
| 1902Z | 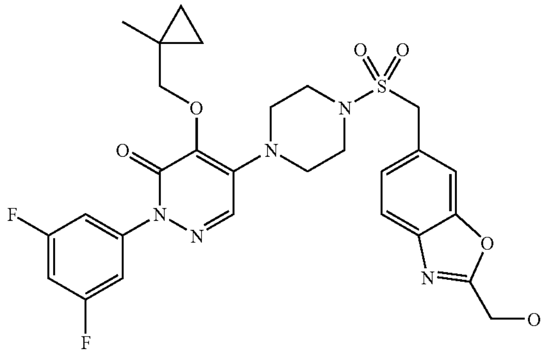 | 602 |

TABLE 36-continued
| Oxygen Analogs with Cyclized Sulfonamide | | |
|---|---|---|
| Cmpd. No. | Structure | MS M + 1 |
| 1902ZA | 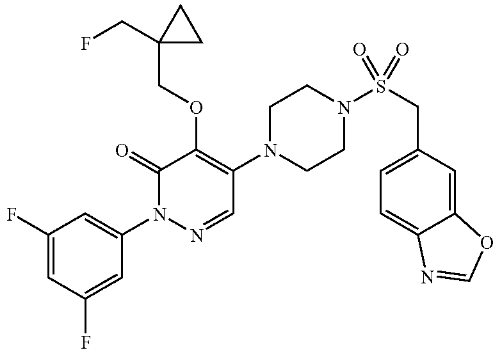 | 590 |
| 1902ZB | 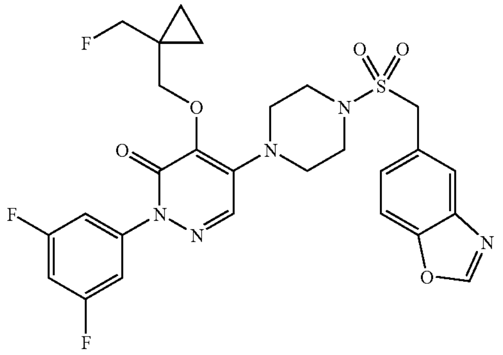 | 590 |
Scheme 57
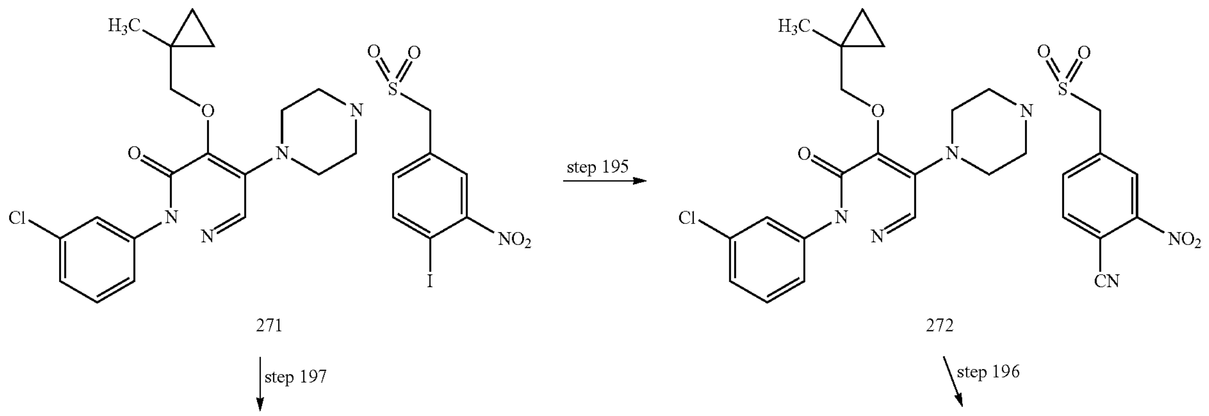

-continued
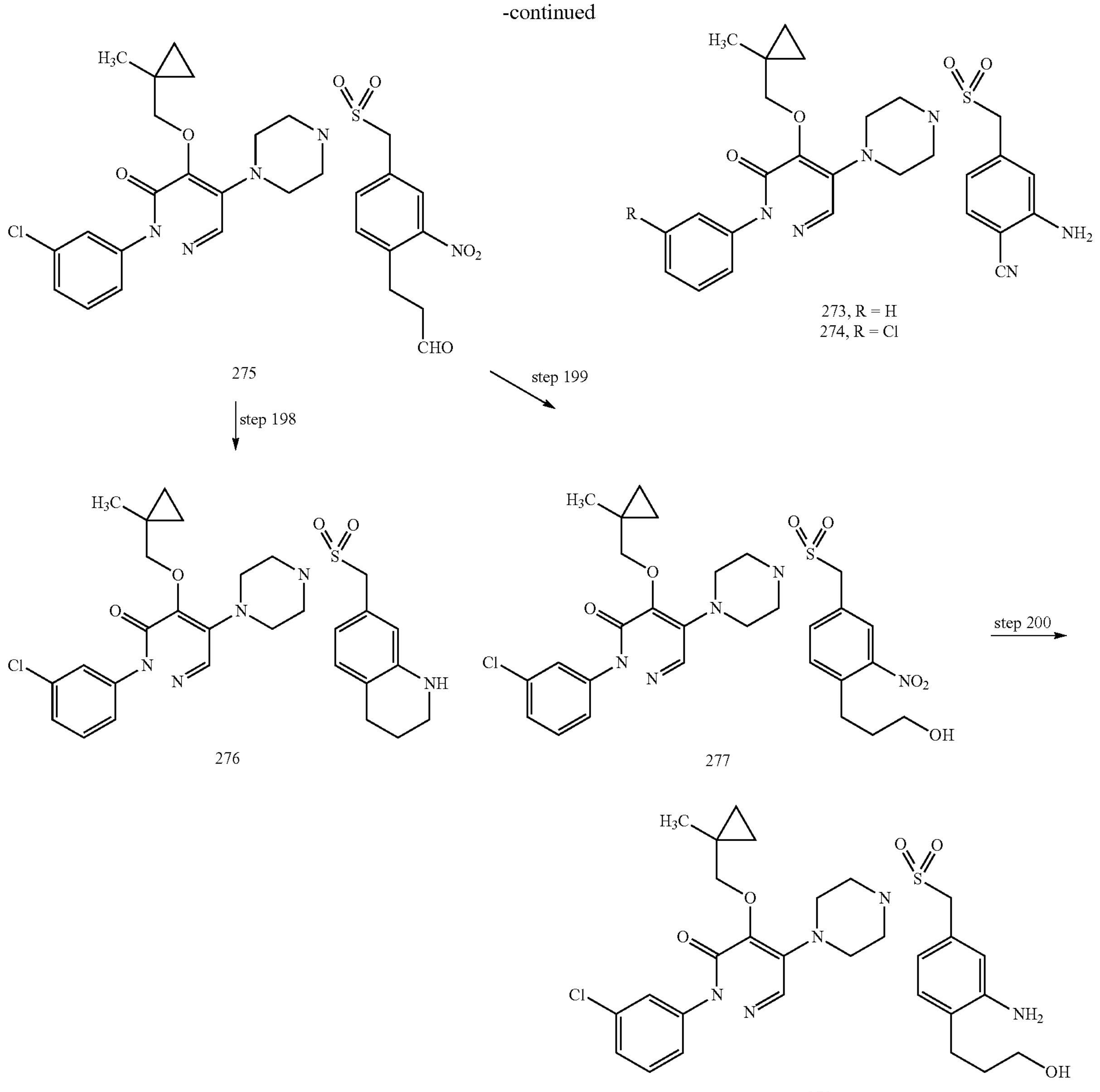
273, R = H
274, R = Cl
275
276
277
278
Step 195:
-continued
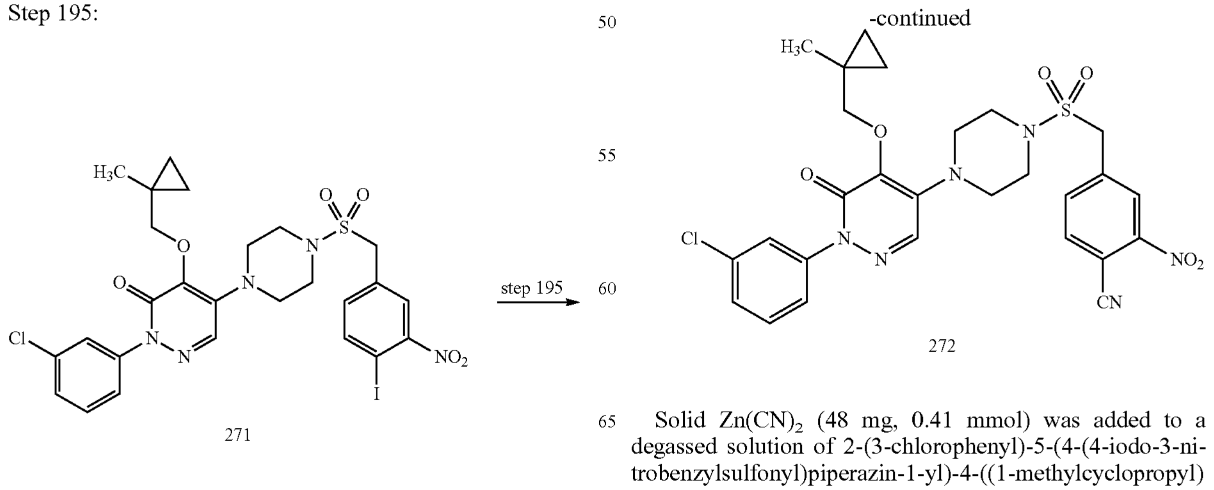
271
272
Solid $Zn(CN)_2$ (48 mg, 0.41 mmol) was added to a degassed solution of 2-(3-chlorophenyl)-5-(4-(4-iodo-3-nitrobenzylsulfonyl)piperazin-1-yl)-4-((1-methylcyclopropyl)

methoxy)pyridazin-3(2H)-one 271 (260 mg, 0.371 mmol) in DMF (5 mL) at room temperature under nitrogen, after which $Pd(PPh_3)_4$ (64 mg, 0.056 mmol) was added and the mixture was stirred at 85° C. under nitrogen for 18 h. The cooled mixture was diluted with ethyl acetate (150 mL), washed with water (15 mL×3) and brine (75 mL), and the solvent was concentrated. The resulting residue was purified by CombiFlash Companion (40-g $SiO_2$ cartridge), eluting, with ethyl acetate/hexanes (1:9 to 1:1), to provide 196 mg (88% yield) of the product 272 as a yellow solid. MS (M+1): m/e 599.

Step 196:

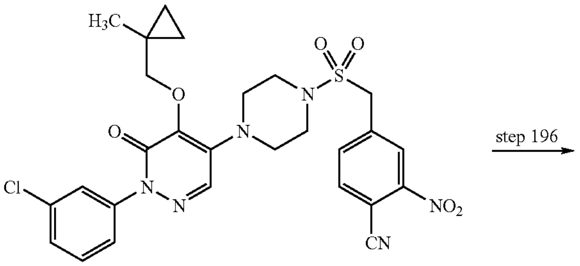

272

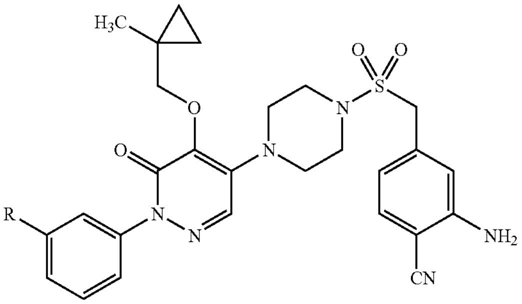

273, R = H
274, R = Cl

A mixture of 4-((4-(1-(3-chlorophenyl)-5-((1-methylcyclopropyl)methoxy)-6-oxo-1,6-dihydropyridazin-4-yl)piperazin-1-ylsulfonyl)methyl)-2-nitrobenzonitrile 272 (172 mg, 0.287 mmol) and palladium on carbon (100 mg) in methylene chloride (6 mL) and methanol (12 mL) at room temperature was stirred under an atmosphere of hydrogen (45 psi) for 3 h. The mixture was filtered through a plug of celite under reduced pressure, after which the filtrate was concentrated. The resulting residue was purified by CombiFlash Companion (40-g $SiO_2$ cartridge), eluting with ethyl acetate/hexanes (1:9 to 1:1), to provide first 95 mg (58% yield) of the product 274 as an off-white solid. MS (M+1): m/e 569 and second 27 mg (18% yield) of the product 273 as a white solid: MS (M+1): m/e 535.

Step 197:

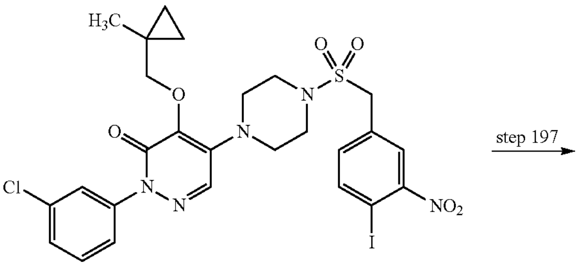

271

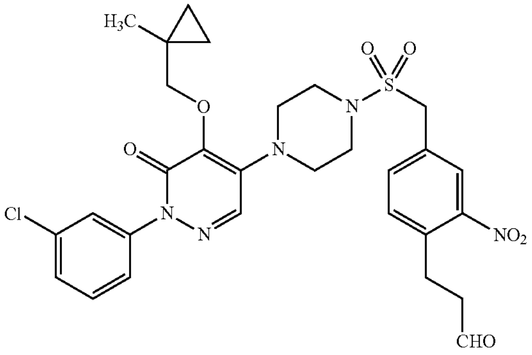

275

Sodium bicarbonate (89 mg, 1.06 mmol), $Bu_4NBr$ (151 mg, 0.468 mmol), allyl alcohol (102 uL, 1.50 mmol) and $Pd(OAc)_2$ (8 mg, 0.03 mmol) were sequentially added to a degassed solution of 2-(3-chlorophenyl)-5-(4-(4-iodo-3-nitrobenzylsulfonyl)piperazin-1)-4-((1 methylcyclopropyl) methoxy pyridazin-3(2H)-one 271 (298 mg, 0.426 mmol) in DMF (8 mL) at room temperature under nitrogen, after which the mixture was stirred at 50° C. for 24 h. The cooled mixture was diluted with water (80 mL) and extracted with ethyl acetate (80 mL×3). The combined organic extracts were washed with water (30 mL×3) and brine (80 mL), and the solvents was concentrated. The resulting residue was purified by CombiFlash Companion (40-g $SiO_2$ cartridge), eluting with ethyl acetate/methylene chloride (5:95 to 3:7), to provide 177 mg (66% yield) of the product 275 as a yellow solid. MS (M+1): m/e 630.

Step 198:

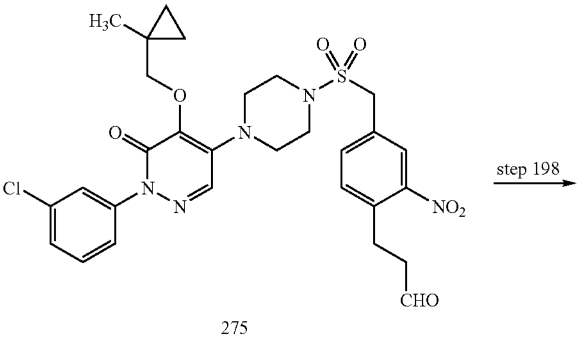

275

-continued

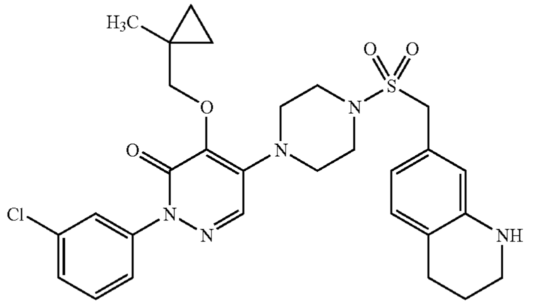

276

A mixture of 3-(4-((4-(1-(3-chlorophenyl)-5-((1-methylcyclopropyl)methoxy)-6-oxo-1,6-dihydropyridazin-4-yl)piperazin-1-ylsulfonyl)methyl)-2-nitrophenyl)propanal 275 (100 mg, 0.159 mmol) and platinum(IV) oxide (14 mg, 0.062 mmol) in ethyl acetate (8 mL) and methanol (8 mL) at room temperature was stirred under an atmosphere of hydrogen (balloon) for 18 h. The mixture was filtered through a plug of celite under reduced pressure and the filtrate was concentrated. The resulting residue was purified by CombiFlash Companion (40-g $SiO_2$ cartridge), eluting with ethyl acetate/methylene chloride (1:99 to 15:85) to provide 47 mg (51% yield) of the product 276. MS (M+1): m/e 584.

Step 199:

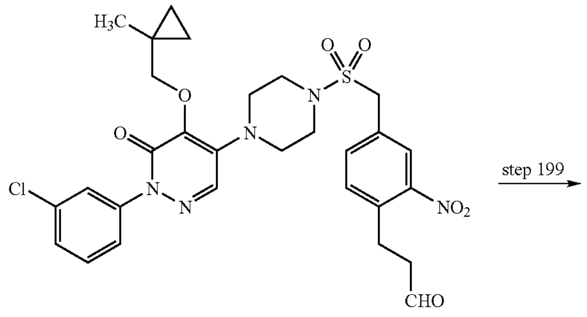

275

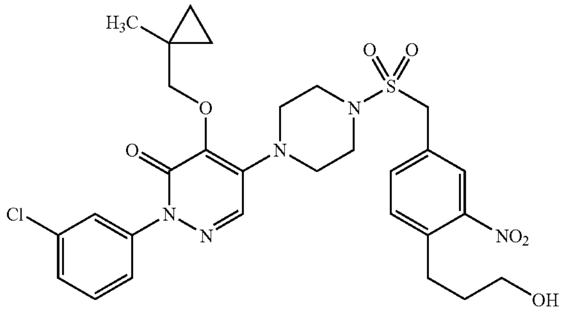

277

Sodium borohydride (14 mg, 0.37 mmol) was added to a solution of 3-(4-((4-(1-(3-chlorophenyl)-5-((1-methylcyclopropyl)methoxy)-6-oxo-1,6-dihydropyridazin-4-yl)piperazin-1-ylsulfonyl)methyl)-2-nitrophenyl)propanal 275 (77 mg, 0.122 mmol) in methanol (8 mL) at 0° C. under nitrogen and the mixture was stirred for 90 mins. Water (0.5 mL) was added, and the mixture was concentrated. The residue was diluted with water (15 mL) and adjusted to pH ~7 with 1 M HCl and then extracted with ethyl acetate (30 mL×2). The combined organic extracts were washed with brine (30 mL) and the solvent was concentrated. The resulting residue was purified by CombiFlash Companion (40 g silica gel cartridge), eluting with ethyl acetate/methylene chloride (5:95 to 3:7), to provide 56 mg (72% yield) of the product 277 as a white solid. MS (M+1): m/e 632.

Step 200:

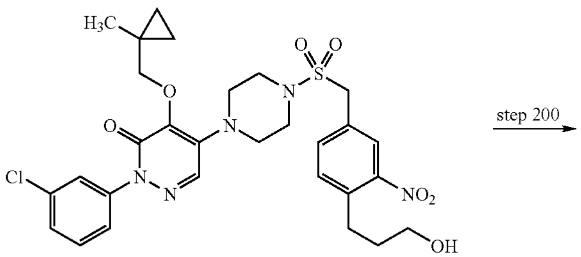

277

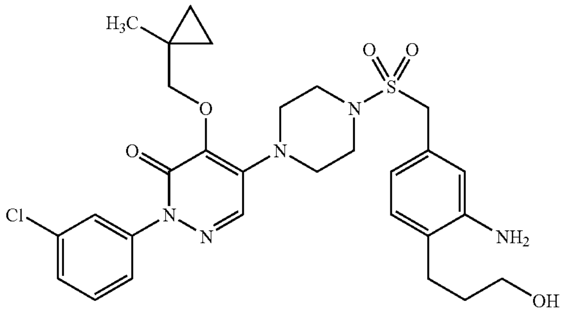

278

A mixture of 2-(3-chlorophenyl)-5-(4-(4-(3-hydroxypropyl)-3-nitrobenzylsulfonyl)piperazin-1-yl)-4-((1-methylcyclopropyl)methoxy)pyridazin-3(2H)-one 277 (42 mg, 0.066 mmol) and platinum(IV) oxide (8 mg, 0.033 mmol) in ethyl acetate (6 mL) and methanol (6 mL) at room temperature was stirred under an atmosphere of hydrogen (balloon) for 18 h. The mixture was filtered through a plug of celite under reduced pressure and the filtrate was concentrated. The resulting residue was purified by CombiFlash Companion (40-g silica gel cartridge), eluting with ethyl acetate/methylene chloride (5:95 to 8:2), to provide 31 mg (77% yield) of the product 278 as a white solid. MS (M+1): m/e 602.

Scheme 58

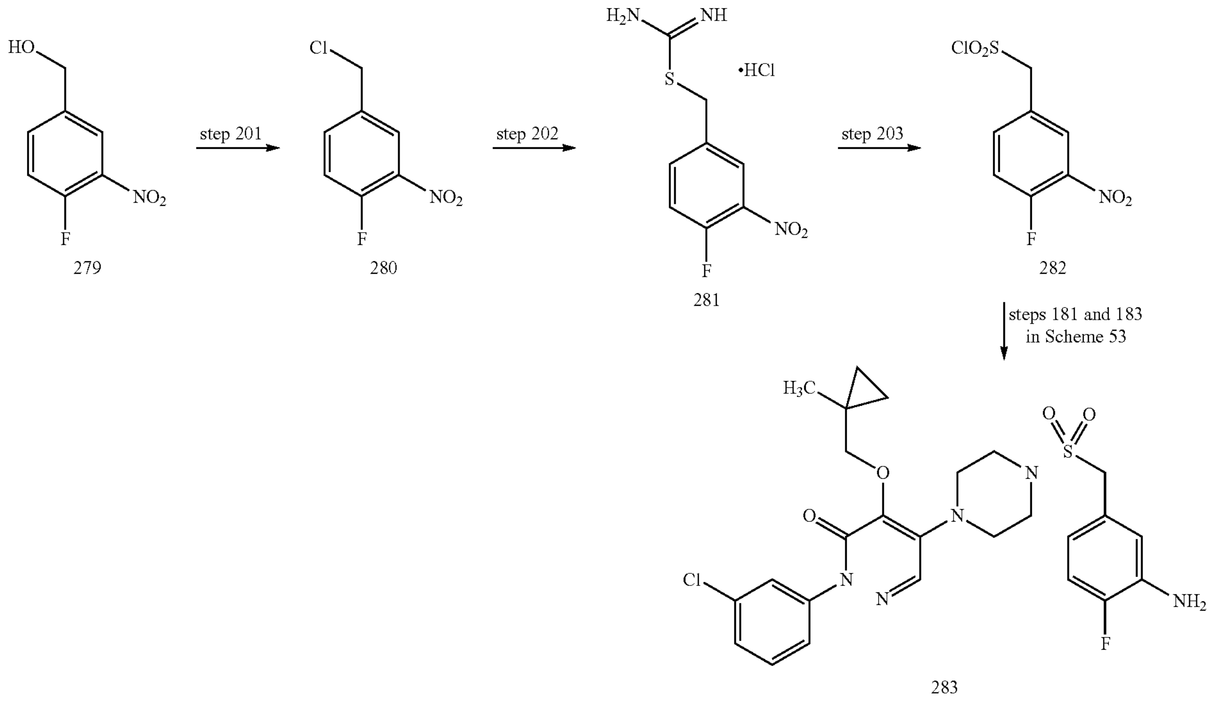

Step 201:

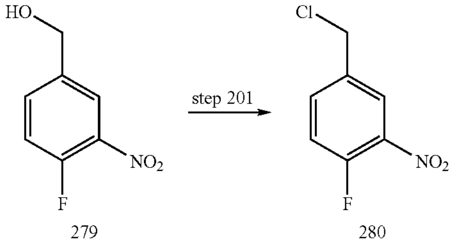

Methylene chloride (30 mL) was added to a solution of cyanuric chloride (1.84 g, 10.0 mmol) in dimethylformamide (1.90 g, 25.8 mmol) at room temperature under nitrogen, after which (4-fluoro-3-nitrophenyl)methanol 279 (2.22 g, 9.5 mmol) was added. The mixture was stirred for 3 h, diluted with methylene chloride, and washed sequentially with water (125 mL), saturated sodium carbonate solution (125 mL), 1 N hydrochloric acid (125 mL) and brine (150 mL). The organic solution was dried over sodium sulfate, filtered, and concentrated. The residue was purified by CombiFlash Companion (40-g silica cartridge), eluting with methylene chloride, to provide 1.62 g (90% yield) of the product 280 as a clear oil which solidified upon refrigeration, and was used without purification.

Step 202:

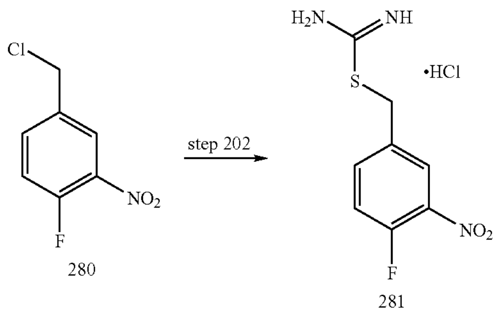

A mixture of 4-(chloromethyl)-1-fluoro-2-nitrobenzene 280 (1.62 g, 8.54 mmol) and thiourea (0.65 g, 8.54 mmol) in ethanol (10 mL) was heated at reflux under nitrogen for 15 h. The solvent was removed from the cooled mixture under reduced pressure, and the residue triturated with ethyl acetate (75 mL) for 30 mins at room temperature. The solids were collected by filtration, washed with ethyl acetate, and dried under reduced pressure to provide 1.32 g (58% yield) of the product 281 as a white solid that was used without purification.

Step 203:

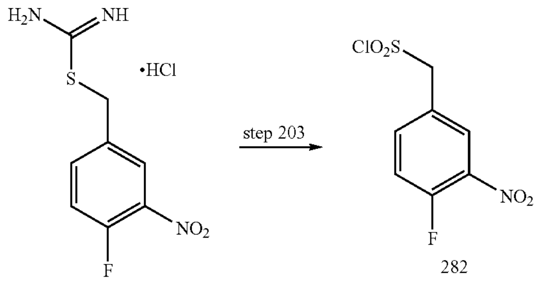

281 282

A stream of chlorine gas was introduced subsurface for 30 mins to a rapidly-stirred suspension of 4-fluoro-3-nitrobenzylcarbamimidothioate hydrochloride 281 (1.30 g, 4.96 mmol) in 1 N hydrochloric acid (40 mL) at 0° C., after which the ice-bath was removed, and chlorine addition was continued for an additional 30 mins. The solids were collected by filtration under reduced pressured washed with watery and dried under reduced pressure to provide 1.02 g (81% yield) of the product 282 as a white solid that was used without purification.

Steps 181 and 183 in Scheme 53:

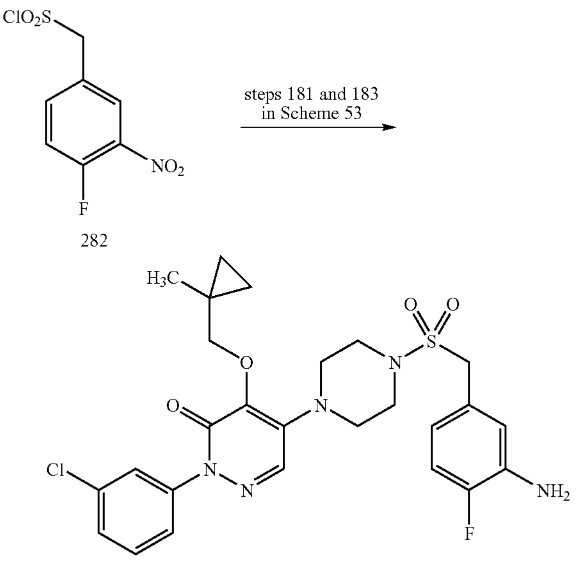

282

283

Using the described procedures for steps 181 and 183 in Scheme 53, compound 283 was synthesized. MS (M+1): m/e 562.

Using the procedures described above, the following compounds were synthesized.

| Cmpd. No. | Structure | MS M + 1 |
| --- | --- | --- |
| 1903Z | 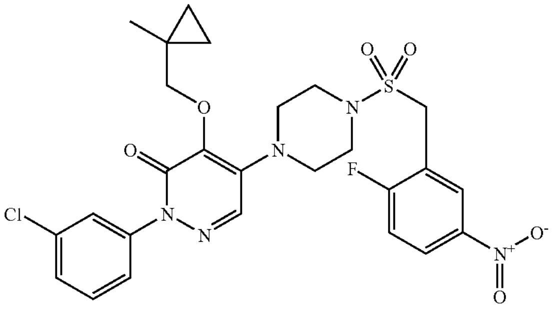 | 592 |
| 1904Z | 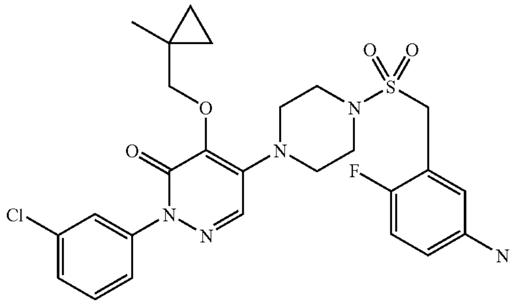 | 562 |

-continued
| Cmpd. No. | Structure | MS M + 1 |
|---|---|---|
| 1905Z | 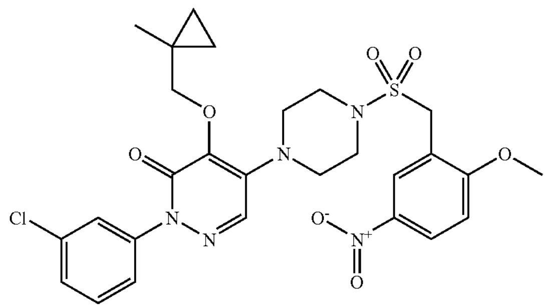 | 604 |
| 1906Z | 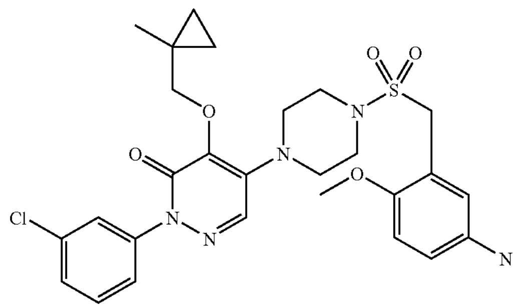 | 574 |
| 1907Z | 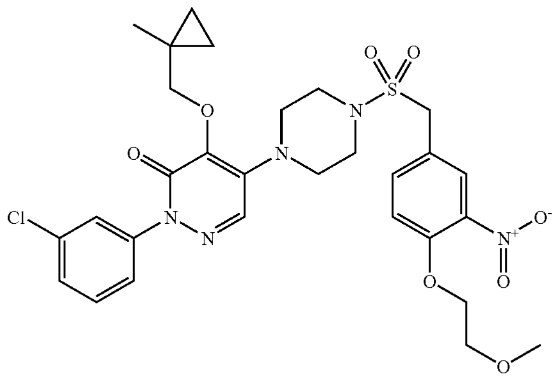 | 648 |
| 1908Z | 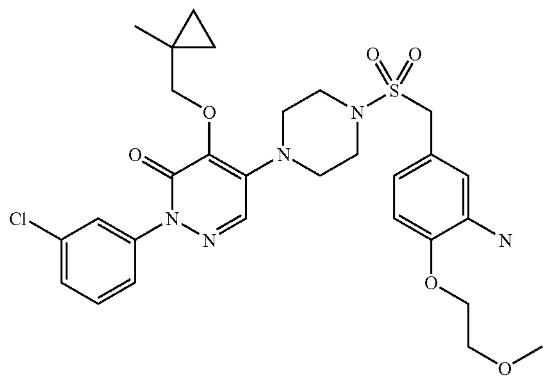 | 618 |

-continued
| Cmpd. No. | Structure | MS M + 1 |
|---|---|---|
| 1909Z | 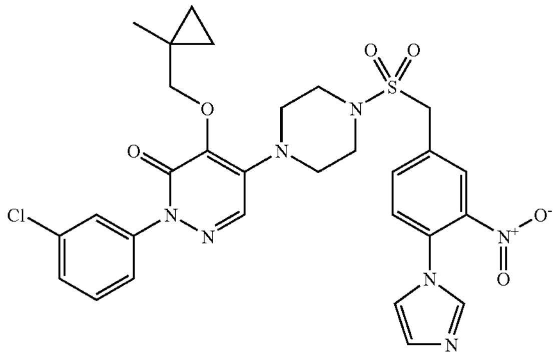 | 640 |
| 1910Z | 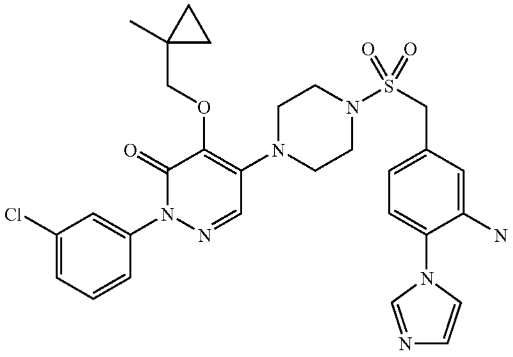 | 610 |
| 1910ZA | 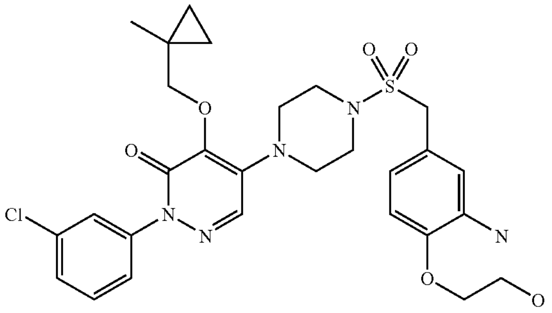 | 604 |
Scheme 59
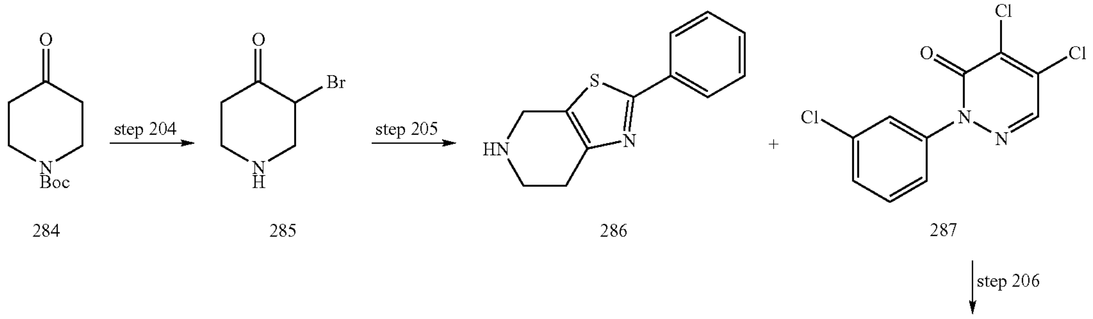
284 285 286 287

-continued

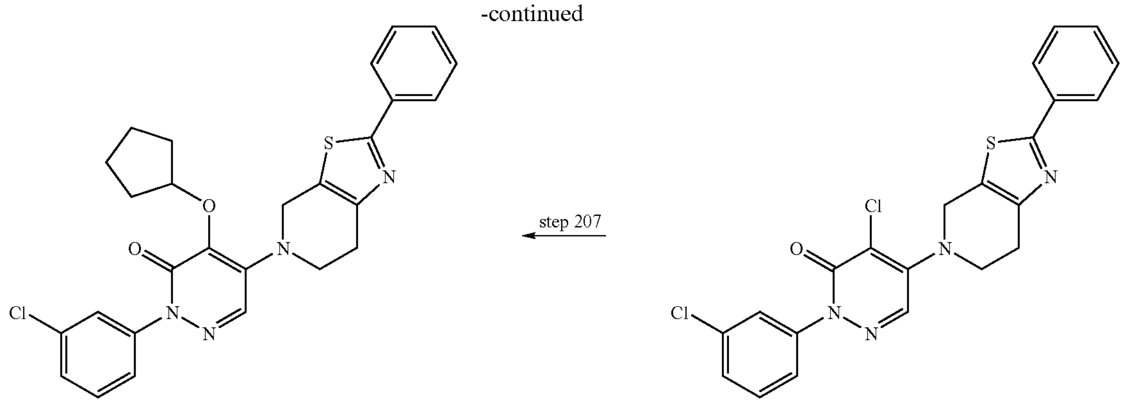

289 288

Step 204:

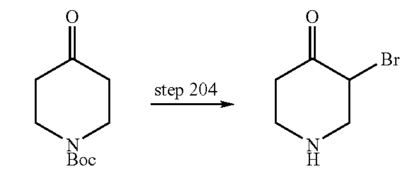

284 285

To a solution of 1-Bloc-4-piperidone 284 (1 g, 5.01 mmol) in chloroform (20 mL) was slowly added bromine (0.26 mL, 5.02 mmol) over 30 mins under a nitrogen atmosphere. The reaction mixture was stirred at room temperature for 2 h. The resulting solid was filtered and dried to give 684 mg (53% yield) of the product 285 as brown solid. MS (M+1): m/e 179.

Step 205:

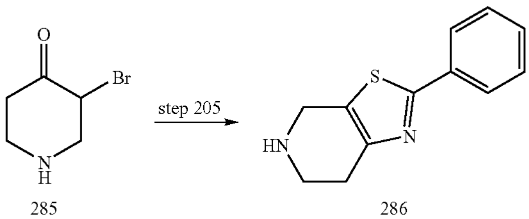

285 286

To a solution of bromine 285 (494 mg, 1.91 mmol) in DMF (10 mL) was added thiobenzamide (314 mg, 2.29 mmol) under a nitrogen atmosphere. The reaction mixture was heated to 100° C. for 7 h then cooled to room temperature and stirred for 11 h. The reaction mixture was diluted with ethyl acetate and washed with water. The aqueous extract was concentrated to give 312 mg (59% yield) of thiazole 286 as brown oil. MS (M+1): m/e 217.

Step 206:

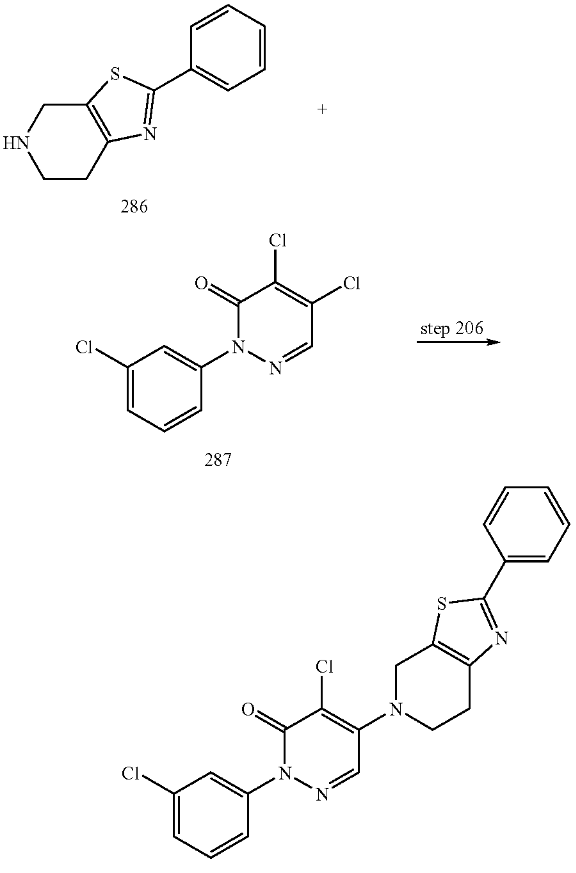

286 287 288

To a solution of thiazole 286 (1.12 g, 5.18 mmol) in EtOH (20 mL) was added pyradizinone 287 (1.26 g, 4.57 mmol) and triethylamine (960 ul, 6.89 mmol) under a nitrogen atmosphere. The reaction mixture was heated to 80° C. for 17 h. The reaction was concentrated and purification with silica gel chromatography (eluant: 25% ethyl acetate in hexanes) gave 816 mg (39% yield) of the product 288 as a brown oil. MS (M+1): m/e 455.

Step 207:

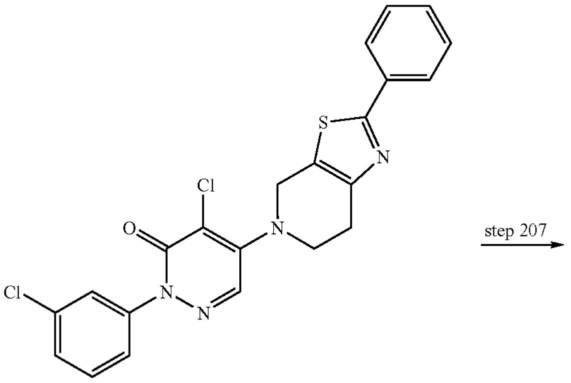

288

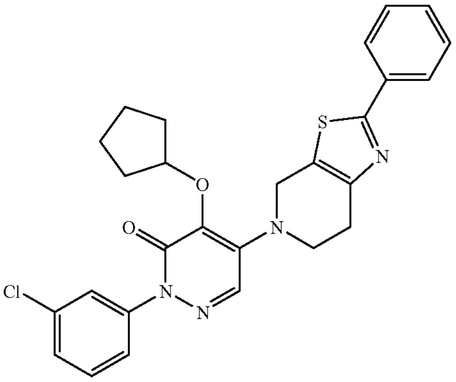

289

To a solution of cyclopentanol (47.3 mg, 0.549 mmol) in THF (10 mL) was added NaH (60%, 17.6 mg, 0.440 mmol) under a nitrogen atmosphere. To the solution was added compound 288 (50 mg, 0.110 mmol), and the reaction mixture was stirred at room temperature for 17 h. The reaction was quenched with saturated $NH_4Cl$ and extracted with ethyl acetate. The organic extract was then washed with brine, dried with $MgSO_4$, filtered, and concentrated. Purification with silica gel chromatography (eluant: 25% ethyl acetate in hexanes) gave 23.5 mg (42% yield) of the product 289 as brown oil. MS (M+1): m/e 505.

-continued

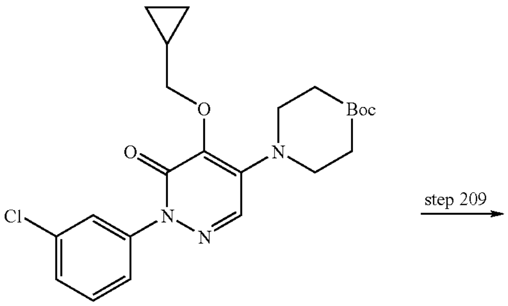

292

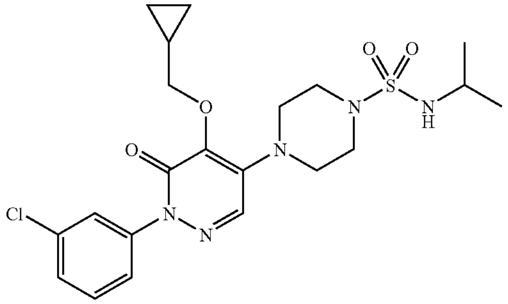

293

Step 208:

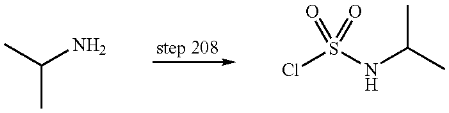

290

291

To a solution of sulfuryl chloride (4.57 mL, 56.38 mmol) in acetonitrile (9 mL) was added very slowly isopropylamine (1.44 mL, 16.91 mmol) under a nitrogen atmosphere. The reaction was then heated to 55° C. for 17 h. The reaction mixture was concentrated then diluted with water and extracted with ether. The organic extract was washed with brine, dried with $MgSO_4$, filtered, and concentrated to give 683 mg (26% yield) of the product 291 as a white solid.

Step 209:

Scheme 60

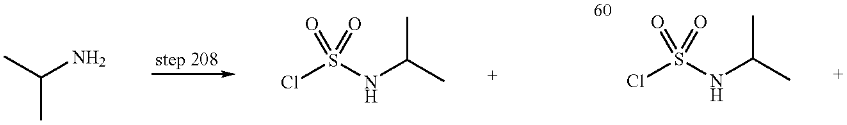

290

291

291

-continued

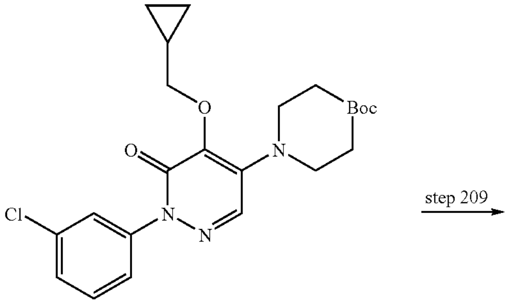

292

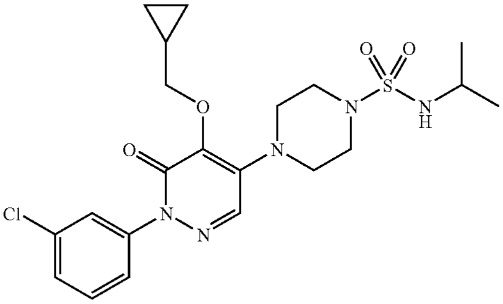

293

4N HCl in dioxane (5 mL) was added to ether 292 (50 mg, 0.145 mmol) under a nitrogen atmosphere. The reaction mixture was stirred at room temperature for 1.5 h. The reaction was then concentrated and dried under high vacuum. To a solution of the crude product in $CH_2Cl_2$ (5 mL) was added sulfamoyl chloride 291 (51.3 mg, 0.325 mmol) and Hunig's base (113.3 uL, 0.650 mmol). The reaction was stirred at room temperature for 17 h then concentrated. Purification with silica gel chromatography (eluant: 20% ethyl acetate in hexanes) gave 19.6 mg (38% yield) of the product 293 as a yellow oil. MS (M+1): m/e 482.

Using the procedures described above, the following compounds were synthesized.

| Cmpd. No. | Structure | MS M + 1 |
|---|---|---|
| 1911Z | 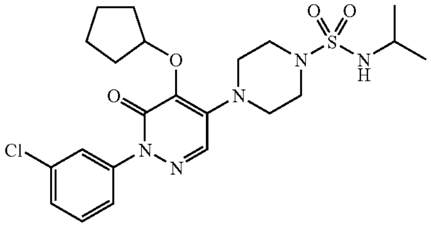 | 496 |

-continued

| Cmpd. No. | Structure | MS M + 1 |
|---|---|---|
| 1912Z | 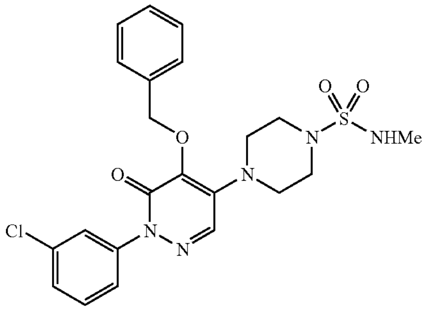 | 490 |
| 1913Z | 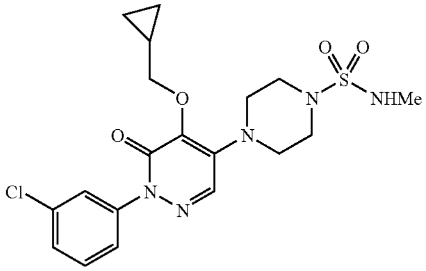 | 454 |

Scheme 61

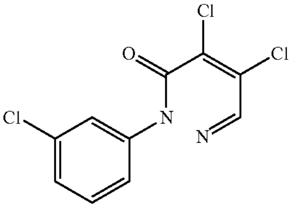

294

+

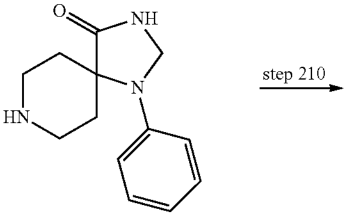

295

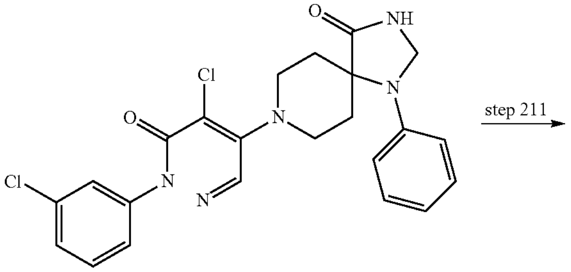

296

-continued

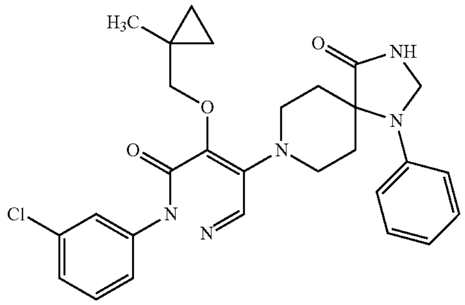

297

Step 210:

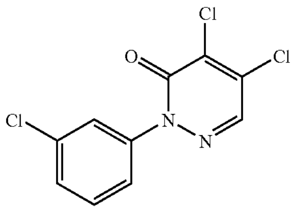

294

+

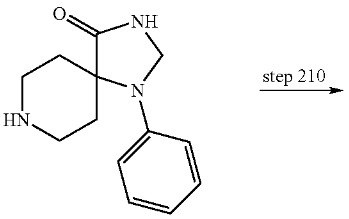

295

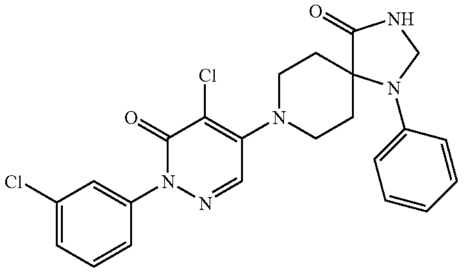

296

A mixture of 4,5-dichloro-2-(3-chlorophenyl)pyridazin-3(2H)-one 294 (1.0 g, 3.6 mmol), diisopropylethylamine (1.0 mL, 5.43 mmol) and 1-phenyl-1,3,8-triazaspiro[45]decan-4-one 295 (1.0 g, 4.4 mmol) in absolute ethanol (15 mL) was heated at reflux under nitrogen for 16 h. The mixture was cooled to room temperature and purified by CombiFlash Companion (80-g silica gel cartridge), eluting with ethyl acetate, to provide 1.1 (64% yield) of the product 296 as an off-white solid. MS (M+1): m/e 470.

Step 211:

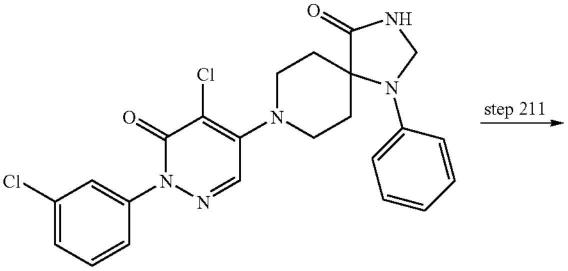

296

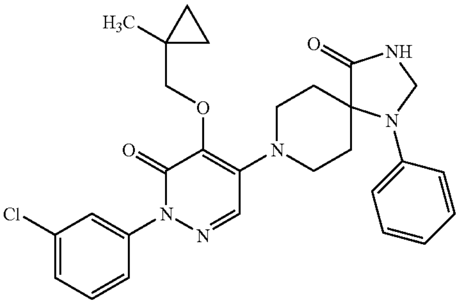

297

Sodium hydride (45 mg, 1.1 mmol, 60%; suspension in mineral oil) was added to a solution of 1-methylcyclopropylmethanol (55 mg, 0.64 mmol) and 8-(5-chloro-1-(3-chlorophenyl)-6-oxo-1,6-dihydropyridazin-4-yl)-1-phenyl-1,3,8-triazaspiro[4.5]decan-4-one 296 (200 mg, 0.43 mmol) in anhydrous tetrahydrofuran (5 mL) at room temperature tinder nitrogen and the mixture was heated at reflux for 4 h. The cooled mixture was diluted with ethyl acetate (200 mL), washed with water (100 mL) and brine (100 mL), dried ($MgSO_4$) and filtered. The solvent was concentrated, and the residue was purified by CombiFlash Companion (40-g silica gel cartridge), eluting with ethyl acetate/hexanes (1:1 to 100% ethyl acetate), to provide 60 mg (27% yield) of the product 297 as a yellow solid. MS (M+1): m/e 520.

Using the procedures described above, the following compounds were synthesized.

| Cmpd. No. | Structure | MS M + 1 |
|---|---|---|
| 1914Z | 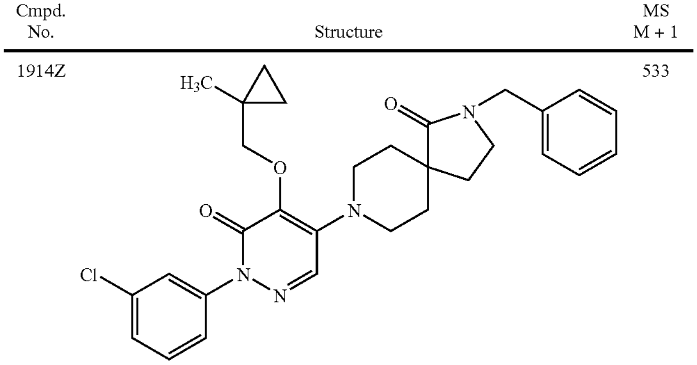 | 533 |
| 1915Z | 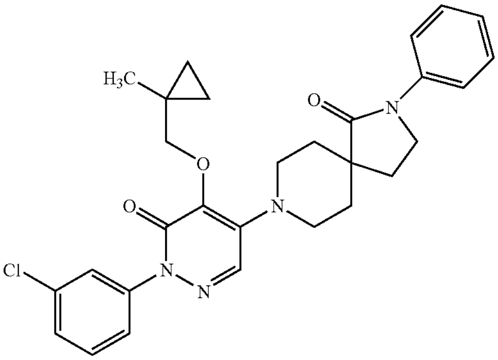 | 519 |
Scheme 62
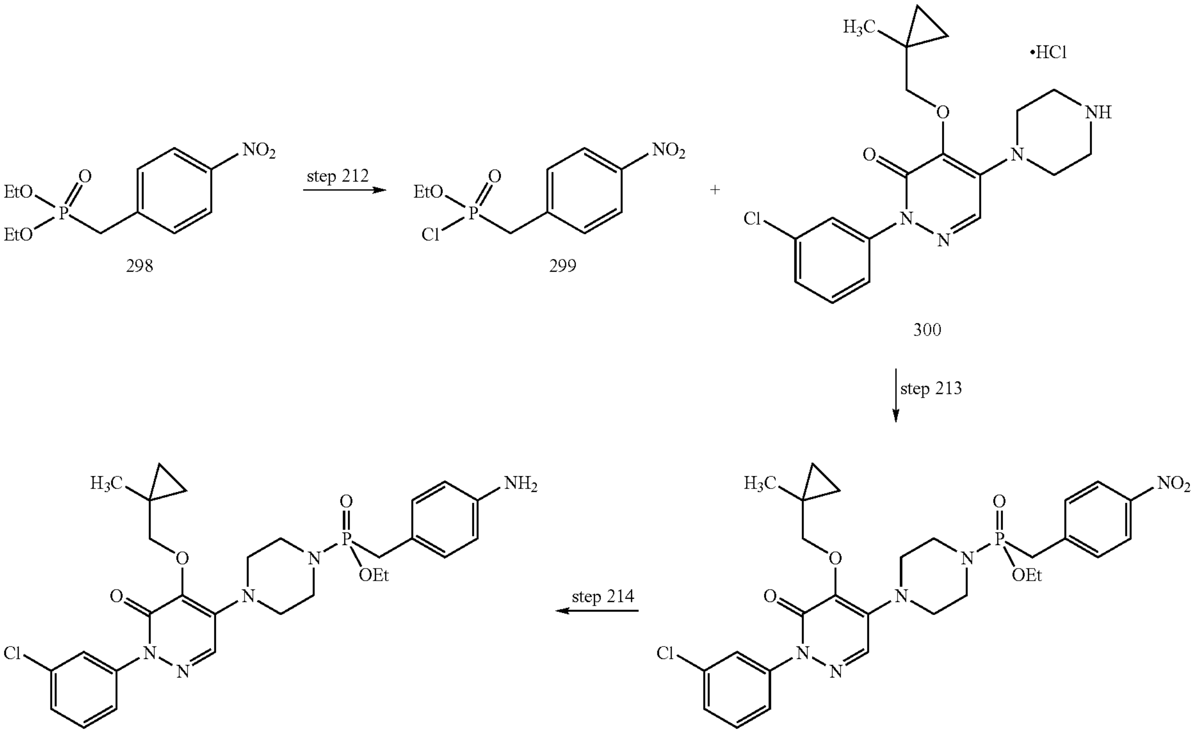
298 299 300 301 302

Step 212:

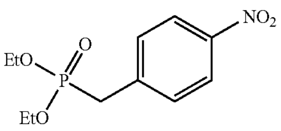

298

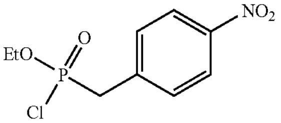

299

Oxalyl chloride (4.8 mL, 9.6 mmol, 2 M solution in methylene chloride) was added to a solution of diethyl 4-nitrobenzylphosphonate 298 (546 mg, 2.0 mmol) in methylene chloride (10 mL) at room temperature under nitrogen, and the mixture was stirred for 48 h. The mixture was diluted with chloroform (10 mL), and the solvent was concentrated to provide 520 mg (99% yield) of ethyl 4-nitrobenzylphosphonochloridate 299 as a thick yellow oil that was used in the next step without purification.

Step 213:

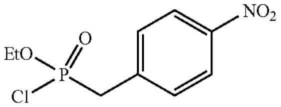

299

+

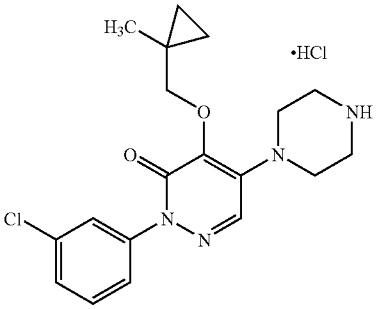

300

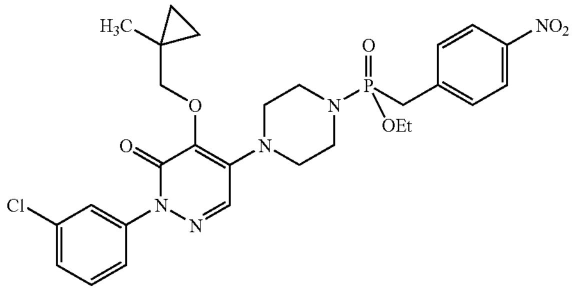

301

A solution of ethyl 4-nitrobenzylphosphonochloridate 299 (197 mg, 0.75 mmol) in methylene chloride (1 mL) was added dropwise to a mixture of 4,5-dichloro-2-(3-chlorophenyl)-pyridazin-3(2H)-one hydrochloride 300 (205 mg, 0.50 mmol) and diisopropylethylamine (0.22 mL, 1.25 mmol) in methylene chloride (5 mL) at 0° C. under nitrogen, and the mixture was slowly warmed to room temperature, stirring for a total of 16 h. The solvent was concentrated, and the residue was purified by CombiFlash Companion (12-g silica gel cartridge), eluting with ethyl acetate/hexanes (1:9 to 100% ethyl acetate), to provide 96 mg (32% yield) of the product 301 as a light yellow solid. MS (M+1): m/e 600.

Using the procedures described above, the following compounds were synthesized.

| Cmpd. No. | Structure | MS M + 1 |
|---|---|---|
| 1916Z | 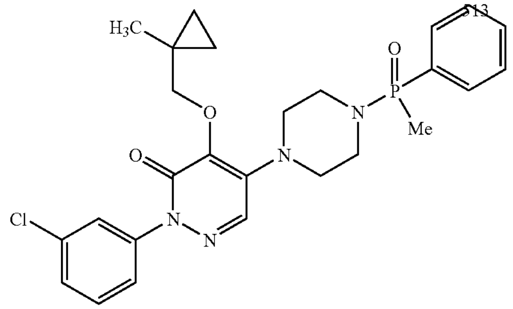 | 513 |

Step 214:

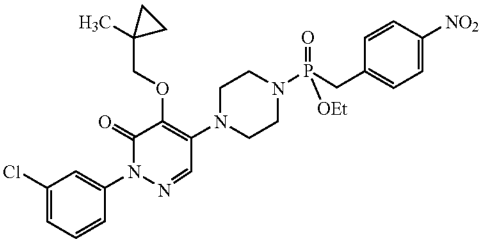

301

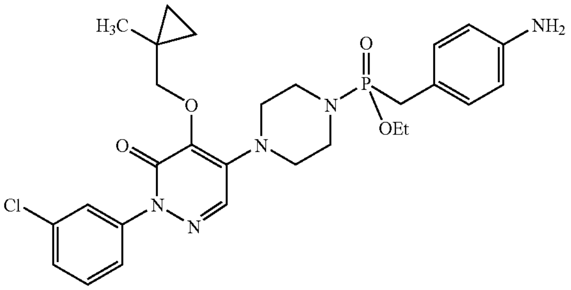

302

A mixture of ethyl 4-(1-(3-chlorophenyl)-5-((1-methylcyclopropyl)methoxy)-6-oxo-1,6 dihydropyridazin-4-yl)piperazin-1-yl(4-nitrobenzyl)phosphinate 301 (130 mg, 0.22 mmol) and platinum(II) oxide (24 mg, 0.11 mmol) in ethanol (4 mL) and ethyl acetate (4 mL) at room temperature was stirred under an atmosphere of hydrogen (balloon) for 90 mins. The mixture was filtered through a plug of celite under reduced pressure and the filtrate was concentrated. The residue was purified by CombiFlash Companion (40-g $SiO_2$ cartridge), eluting with methanol/methylene chloride (1:99 to 1:9), to provide 88 mg (71% yield) of the product 302 as an off-white solid. MS (M+1): m/e 572.

Scheme 63

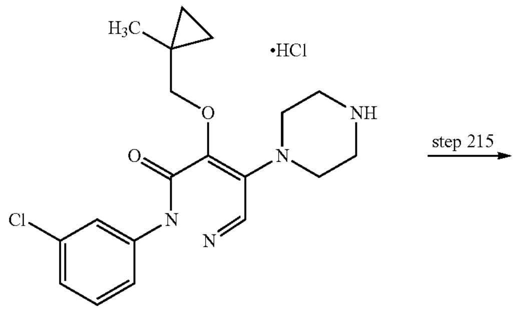

300

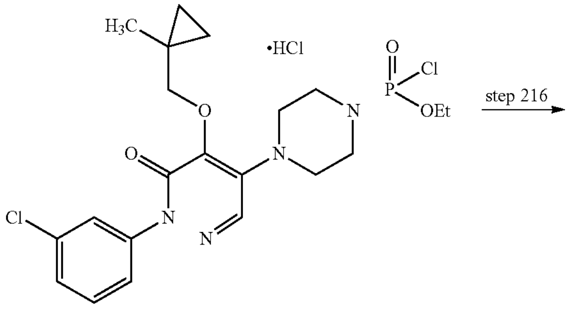

303

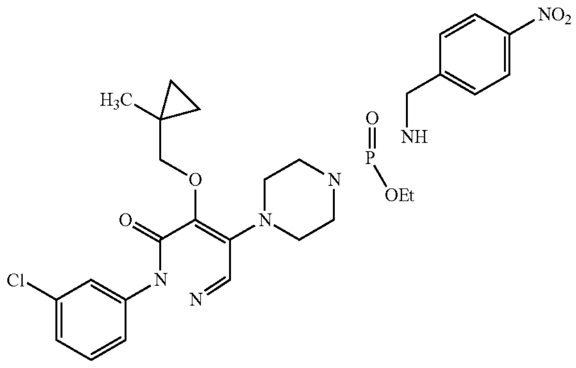

304

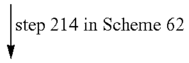

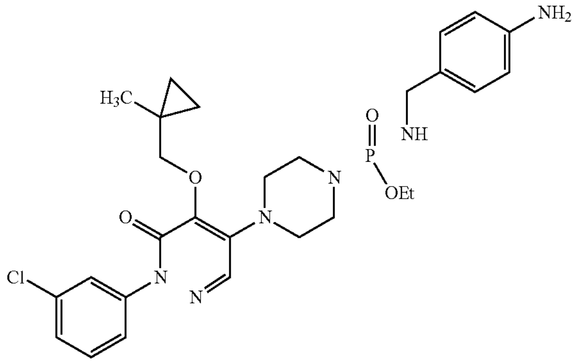

305

Step 215:

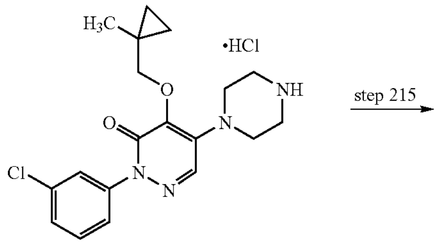

300

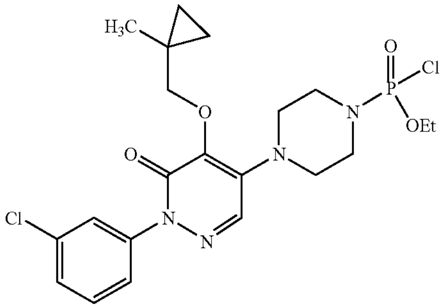

303

A solution of ethyl phosphorodichloridate (90 mg, 0.55 mmol) in methylene chloride (1 mL) was added dropwise to a solution of 4,5-dichloro-2-(3-chlorophenyl)pyridazin-3 (2H)-one hydrochloride 300 (205 mg, 0.50 mmol) and diisopropylethylamine (0.26 mL, 1.50 mmol) in methylene chloride (5 mL) at room temperature under nitrogen, after which the mixture was slowly warmed to room temperature, stirring for a total of 16 h. The solvent was concentrated, and the residue was purified by CombiFlash Companion (12-g $SiO_2$ cartridge), eluting with ethyl acetate/hexanes (1:9 to 2:3), to provide 121 mg (48% yield) of the product 303 as a viscous yellow oil that was used without purification.

Step 216:

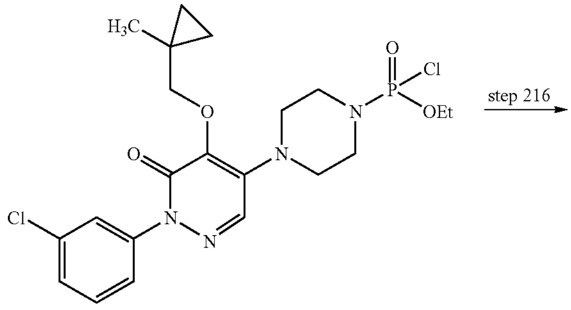

303

-continued

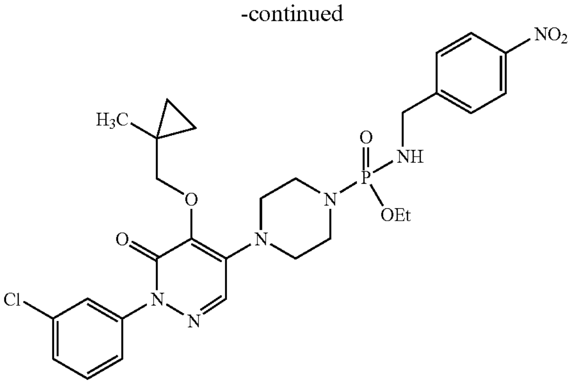

304

Diisopropylethylamine (84 uL, 0.48 mmol) was added over a period of 10 mins to a solution of ethyl 4-(1-(3-chlorophenyl)-5-((1-methylcyclopropyl)methoxy)-6-oxo-1,6-dihydropyridazin-4-yl)piperazin-1-ylphosphonochloridate 303 (110 mg, 0.22 mmol) and (4-nitrophenyl)methylamine hydrochloride (38 mg, 0.20 mmol) in methylene chloride (1 mL) at 0° C. under nitrogen, and the mixture was slowly warmed to room temperature, stirring for a total of 16 h. The solvent was concentrated, and the residue purified by CombiFlash Companion (12-g $SiO_2$ cartridge), eluting with ethyl acetate/hexanes (2:3 to 100% ethyl acetate), to provide 96 mg (78% yield) of the product 304 as a light yellow foam. MS (M−1): m/e 615.

Using the procedures described above, the following compounds were synthesized.

| Cmpd. No. | Structure | MS M + 1 |
|---|---|---|
| 1917Z | 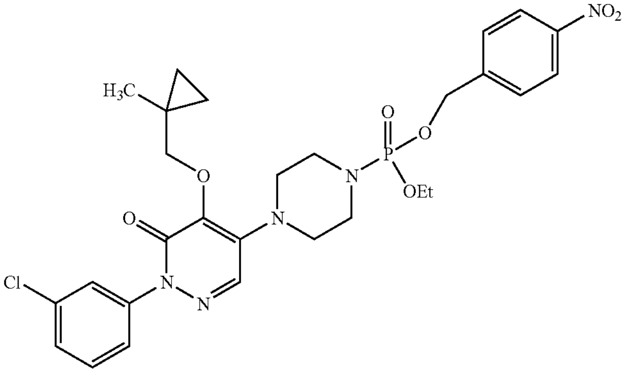 | 618 |
| 1918Z | 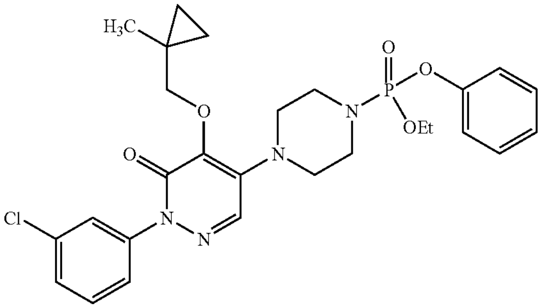 | 559 |
| 1918ZA | 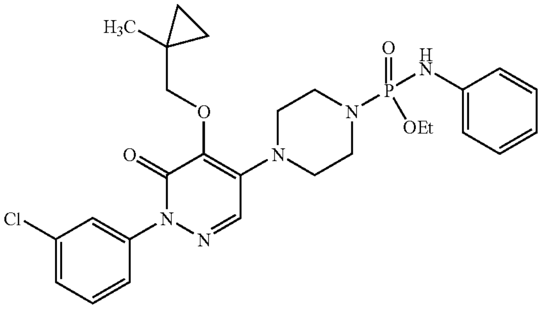 | 558 |

Step 214:
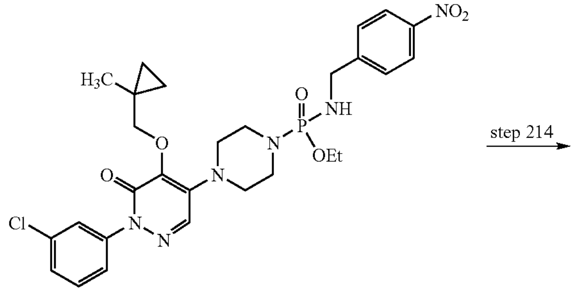
304
-continued
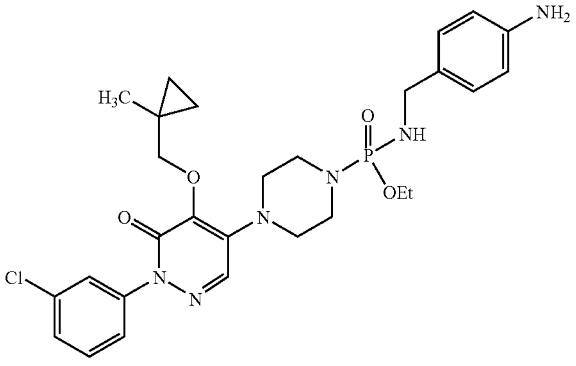
305
Using the procedure described above in step 214 in Scheme 62, compound 305 was synthesized. MS (M+1): m/e 587.
Scheme 64
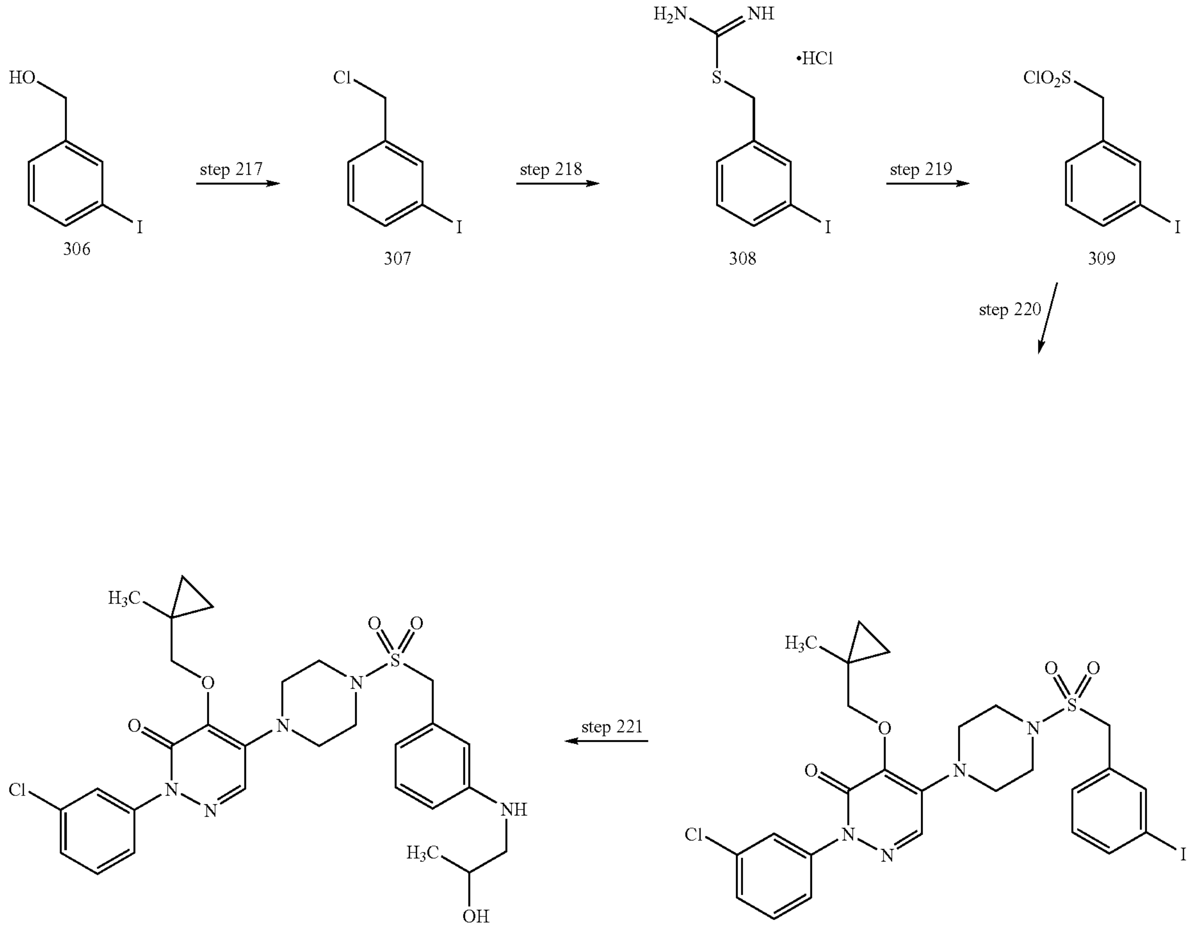
306 307 308 309
311 310

-continued

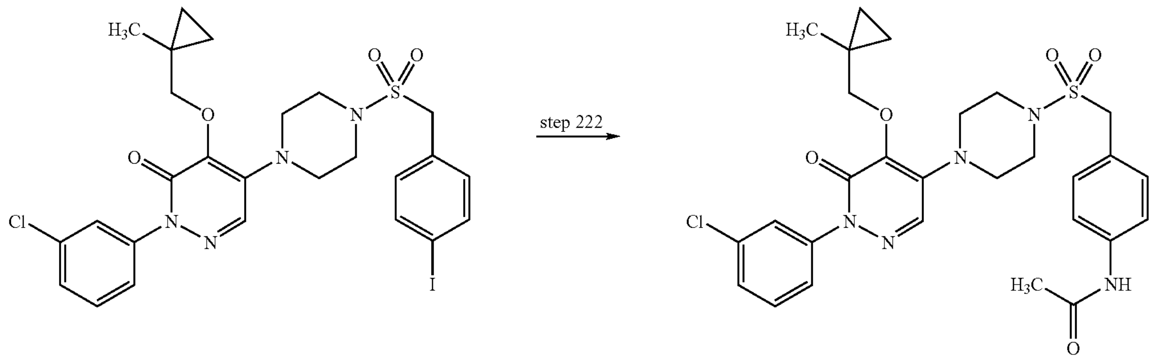

312 313

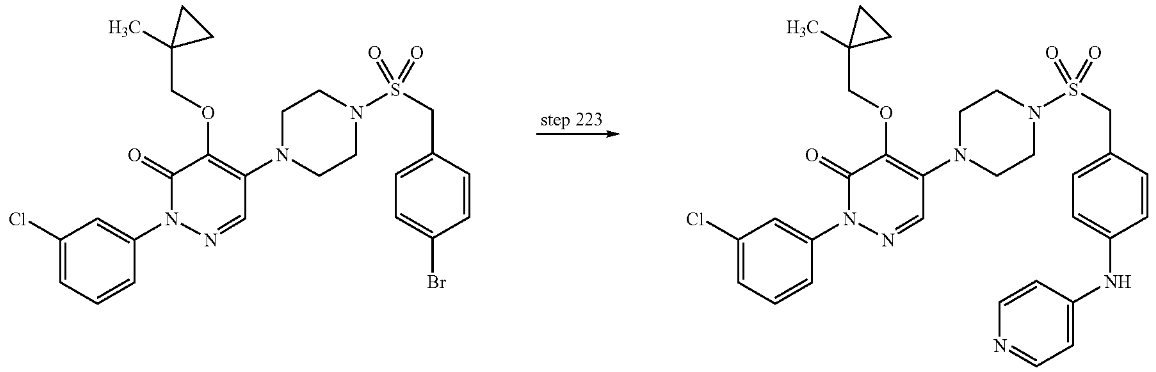

314 315

Step 217:

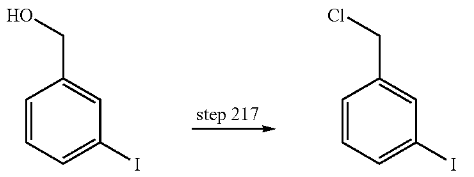

306 307

Methylene chloride (30 mL) was added to a mixture of cyanuric chloride (1.83 g, 100 mmol) in dimethylformamide (1.89 g, 25.8 mmol) at room temperature under nitrogen, after which (3-iodophenyl)methanol 306 (2.22 g, 9.5 mmol) was added, and the mixture was stirred for 1 h. The mixture was washed sequentially with water (25 mL), saturated sodium carbonate solution (125 mL), 1 N hydrochloric acid (125 mL) and brine (150 mL), dried over sodium sulfate, filtered, and concentrated. The residue was purified by CombiFlash Companion (40-g $SiO_2$ cartridge), eluting with hexanes, to provide 1.64 g (68% yield) of the product 307 as a clear, colorless oil.

Step 218:

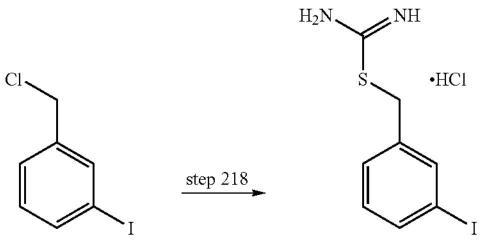

307 308

A mixture of 1-(chloromethyl)-3-iodobenzene 307 (1.64 g, 6.50 mmol) and thiourea (0.49 g, 6.50 mmol) in ethanol (10 mL) was heated at reflux under nitrogen for 20 h, after which the solvent was removed from the cooled mixture under reduced pressure. The residue was triturated with ethyl acetate (75 mL) for 30 mins, after which the solids were collected by filtration, washed with ethyl acetate (75 mL) and dried under reduced pressure to provide 2.02 g (94% yield) of the product 308 as a white solid that was used in the next step without purification.

Step 219:

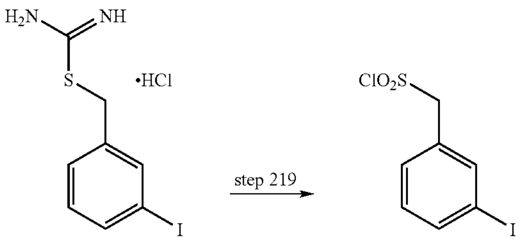

308 309

A stream of chlorine gas was introduced subsurface for 30 mins to a rapidly-stirred suspension of 3-iodobenzyl carbamimidothioate hydrochloride 308 (2.00 g, 6.09 mmol) in 1 N hydrochloric acid (100 mL) at 0° C., after which the ice-bath was removed, and chlorine addition was continued for an additional 30 mins. The solids were collected by filtration under reduced pressure, washed with water, and dried under reduced pressure. The dried solid was then suspended in hot toluene (45 mL), and the solids were removed by decantation. The filtrate was diluted with hexanes (15 mL), and the mixture was allowed to stand for 3 h at room temperature, and then placed into a freezer for 12 h. The resulting crystals were collected by filtration, washed with hexanes (75 mL), and dried under reduced pressure to give 1.02 g (53% yield) of the product chloride 309 as opaque crystals.

Step 220:

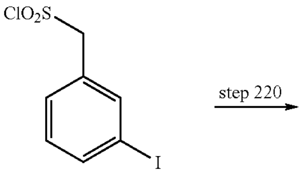

309

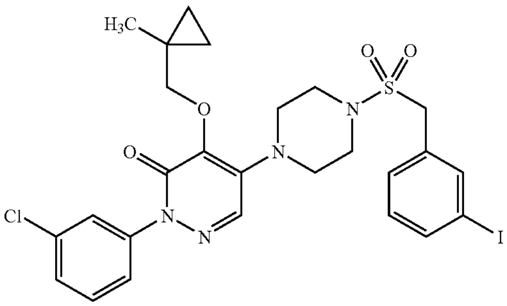

310

Diisopropylamine (2.80 mL, 16.60 mmol) was added dropwise to a mixture of 2-(3-chlorophenyl)-4-((1-methylcyclopropyl)methoxy)-5-(piperazin-1-yl)pyridazin-3(2H)-one hydrochloride (3.00 g, 7.30 mmol) and (3-iodophenyl)methanesulfonyl chloride 309 (2.55 g, 8.03 mmol) in anhydrous dimethylformamide (5 mL) at 0° C. under nitrogen. The mixture was slowly warmed to room temperature and stirred for a total of 17 h. The mixture was poured into rapidly-stirred cold water (200 mL) and stirred for 30 mins. The precipitated solid was collected by filtration under reduced pressure, washed with water, and dried under reduced pressure at 45° C. The crude product was purified by CombiFlash Companion (40-g $SiO_2$ cartridge), eluting with ethyl acetate/methylene chloride (100% methylene chloride to 1:9), to provide 2.48 g (52% yield) of the product 310 as a light-yellow foam: MS (M+1): m/e 655.

Step 221:

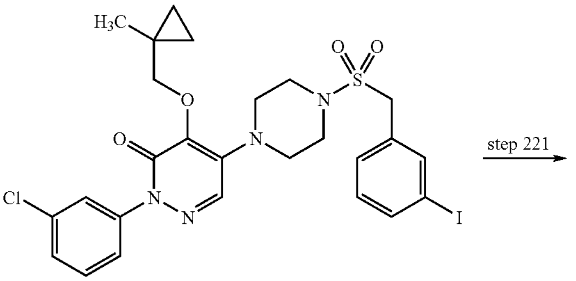

310

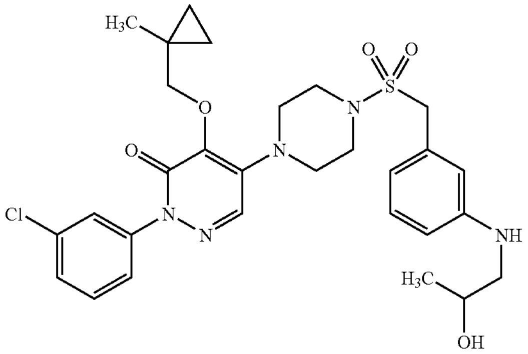

311

A degassed mixture of 2-(3-chlorophenyl)-5-(4-(3-iodobenzylsulfonyl)piperazin-1-yl)-4-((1-methylcyclopropyl)methoxy)pyridazin-3(2H)-one 310 (150 mg, 0.23 mmol), (+/−)-1-aminopropan-2-ol (35 mg, 0.46 mmol), copper(I) iodide (11 mg, 0.06 mmol), L-proline (13 mg, 0.11 mmol), and potassium carbonate (63 mg, 0.46 mmol) in anhydrous dimethyl sulfoxide (1.0 mL) was heated at 95° C. under nitrogen for 16 h. The cooled mixture was diluted with dimethyl sulfoxide (3 mL), filtered through a pad of celite under reduced pressure, and washed with ethyl acetate (35 mL). The filtrate was washed with brine (3×15 mL), dried over sodium sulfate, filtered, and concentrated. The residue was purified by CombiFlash Companion (12-g $SiO_2$ cartridge), eluting with hexanes/ethyl acetate (1:4 to 1:1), to provide 88 mg (64% yield) of the product 311 as a white solid: MS (M+1): m/e 602.

Step 222:

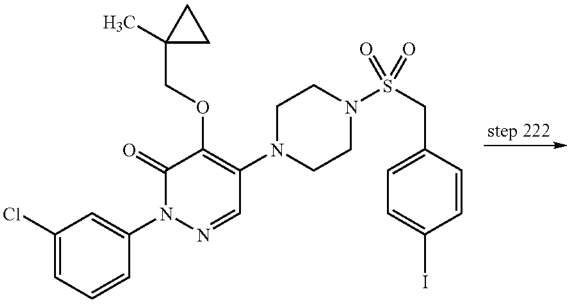

312

-continued

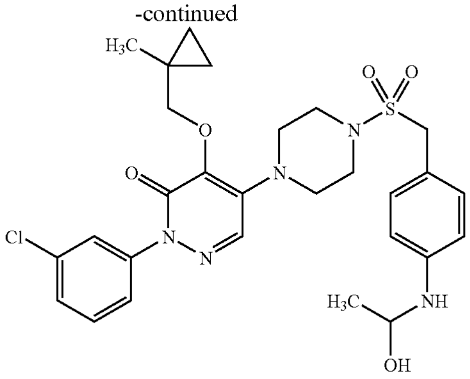

313

A degassed mixture of 2-(3-chlorophenyl)-5-(4-(4-iodobenzylsulfonyl)piperazin-1-yl)-4-((1-methylcyclopropyl)methoxy)pyridazin-3(2H)-one 312 (328 mg, 0.50 mmol), acetamide (36 mg, 0.61 mmol), copper(I) iodide (18 mg, 0.09 mmol), N,N'-dimethylethylene-diamine (12 mg, 0.14 mmol), and potassium carbonate (212 mg, 2.0 mmol) in dimethylformamide (3 mL) was heated in a resealable reaction vessel at 85° C. for 18 h. The cooled mixture was diluted with ethyl acetate (35 mL), washed with brine (35 mL), dried over sodium sulfate, filtered, and concentrated. The residue was purified by CombiFlash Companion (40-g $SiO_2$ cartridge), eluting with ethyl acetate/hexanes (1:1 to 100% ethyl acetate), to provide 165 mg (57% yield) of the product 313 as a white solid: MS (M+1): m/e 586.

Step 223:

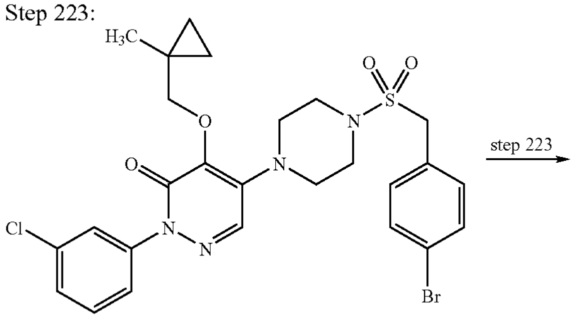

314

-continued

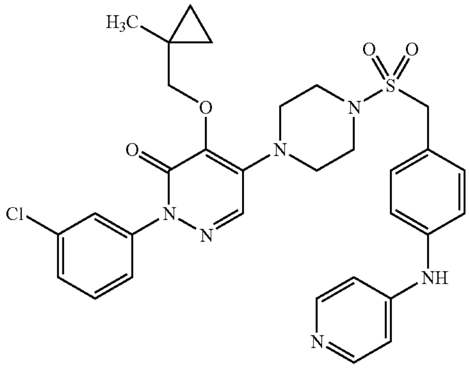

315

A degassed mixture of 5-(4-(4-bromobenzylsulfonyl)piperazin-1-yl)-2-(3-chlorophenyl)-4-((1-methylcyclopropyl)methoxy)pyridazin-3(2H)-one 314 (152 mg, 0.25 mmol), 4-aminopyridine (26 mg, 0.28 mmol), tris(dibenzylideneacetone)dipalladium (4 mg, 0.008 mmol), 2-dicyclohexylphosphino-2',4',6'-triisopropylbiphenyl (XPhos, 12 mg, 0.012 mmol), and potassium phosphate (74 mg, 0.35 mmol) in anhydrous 1,4-dioxane (1.0 mL) was heated in a resealable reaction vessel at 105° C. for 18 h. The cooled mixture was diluted with ethyl acetate (2 mL), methylene chloride (2 mL) and methanol (2 mL), filtered through a plug of celite under reduced pressure, and the filtrate was concentrated. The residue was purified by CombiFlash Companion (12-g $SiO_2$ cartridge) eluting with methanol/methylene chloride (1:99 to 1:9), to provide 35 mg (23% yield) of the product 315 as a light brown solid: MS (M+1): m/e 621.

Using the procedures described above, the following compounds were synthesized.

TABLE 37

Oxygen Analogs with Substituted Sulfonamide

| Cmpd. No. | Structure | MS M + 1 |
|---|---|---|
| 1919Z | 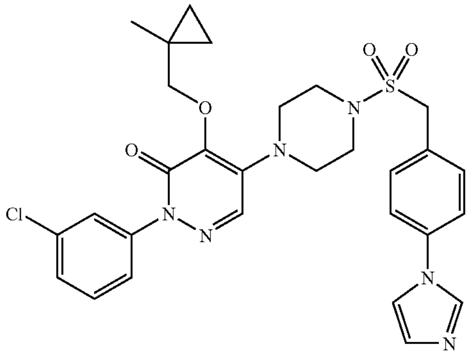 | 595 |

TABLE 37-continued
| Oxygen Analogs with Substituted Sulfonamide | | |
|---|---|---|
| Cmpd. No. | Structure | MS M + 1 |
| 1920Z | 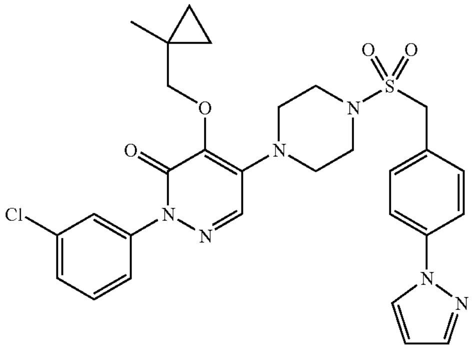 | 593 (M − 1) |
| 1921Z | 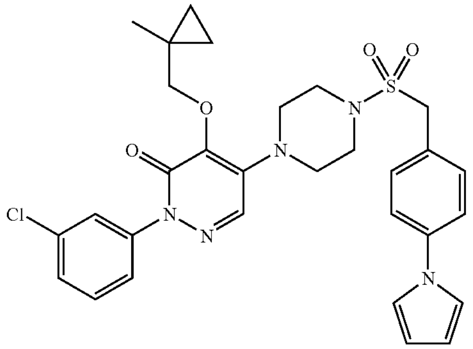 | 592 (M − 1) |
| 1922Z | 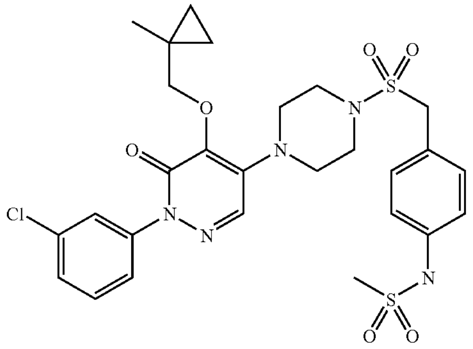 | 620 (M − 1) |
| 1923Z | 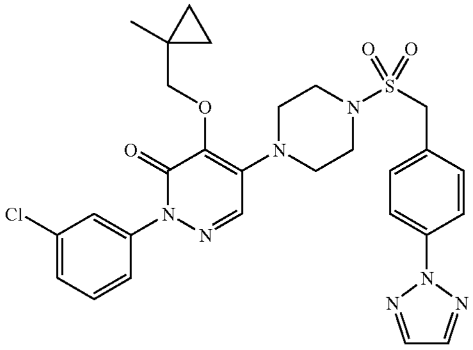 | 594 (M − 1) |

TABLE 37-continued
| Oxygen Analogs with Substituted Sulfonamide | | |
|---|---|---|
| Cmpd. No. | Structure | MS M + 1 |
| 1924Z | 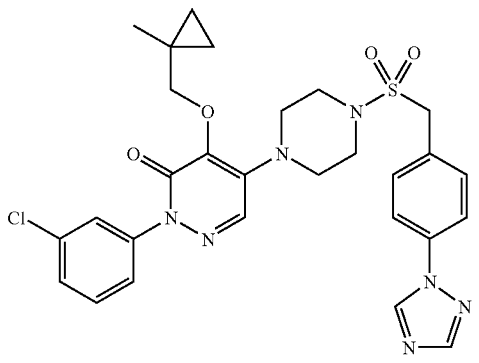 | 594 (M − 1) |
| 1925Z | 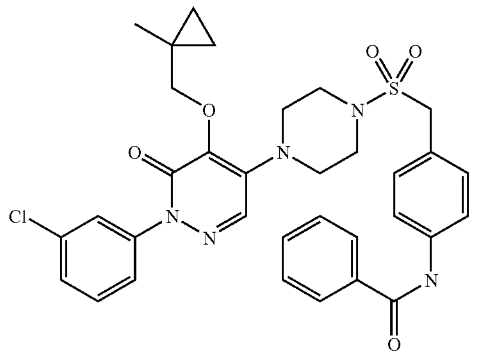 | 646 (M − 1) |
| 1926Z | 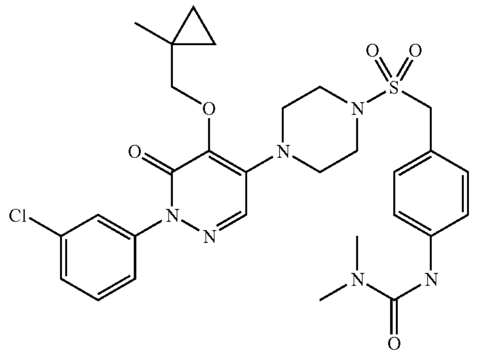 | 613 (M − 1) |
| 1927Z | 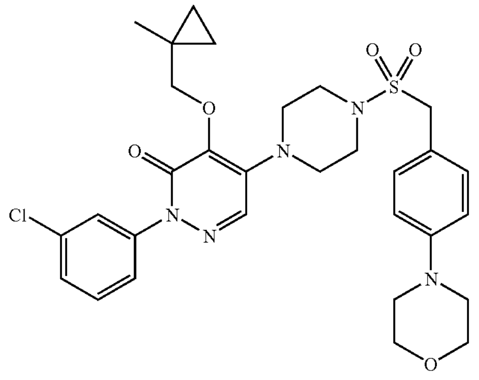 | 614 |

TABLE 37-continued
| Oxygen Analogs with Substituted Sulfonamide | | |
|---|---|---|
| Cmpd. No. | Structure | MS M + 1 |
| 1928Z | 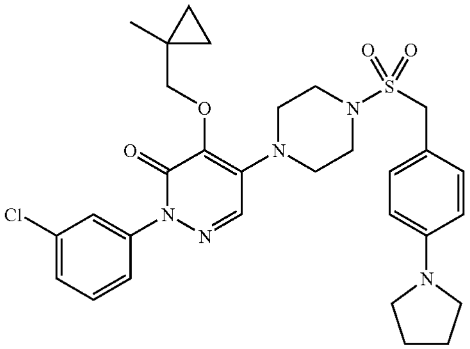 | 598 |
| 1929Z | 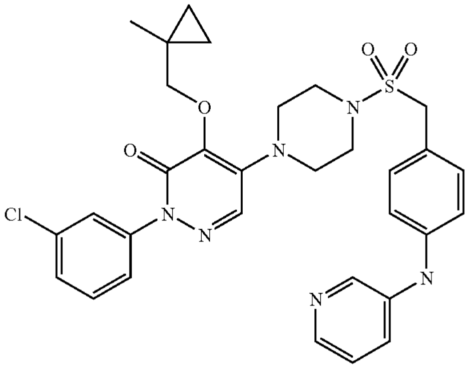 | 621 |
| 1930Z | 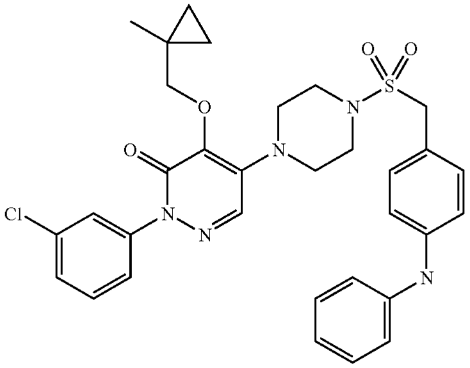 | 620 |
| 1931Z | 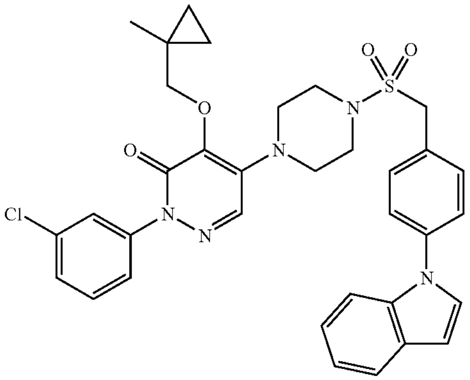 | 642 (M − 1) |

TABLE 37-continued
| Oxygen Analogs with Substituted Sulfonamide | | |
|---|---|---|
| Cmpd. No. | Structure | MS M + 1 |
| 1932Z | 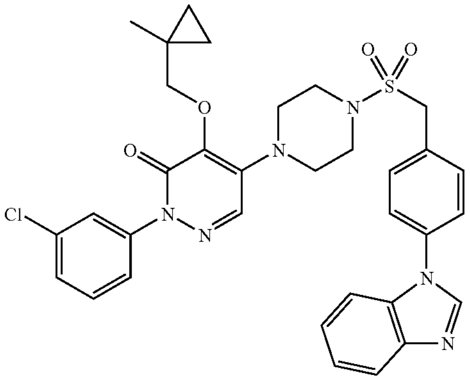 | 645 |
| 1933Z | 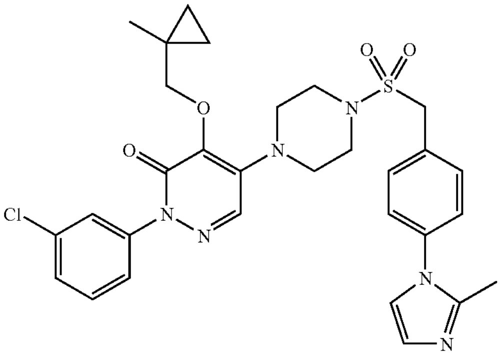 | 609 |
| 1934Z | 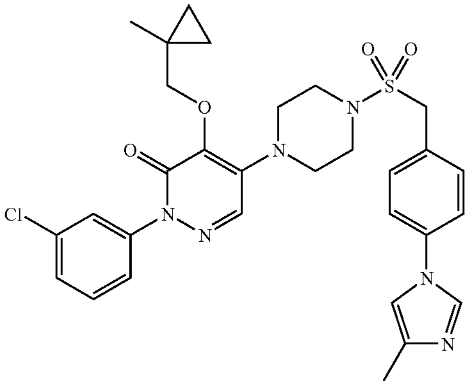 | 609 |
| 1935Z | 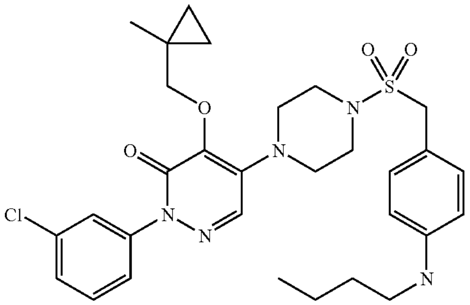 | 600 |

TABLE 37-continued
| Cmpd. No. | Structure | MS M + 1 |
|---|---|---|
| Oxygen Analogs with Substituted Sulfonamide | | |
| 1936Z | 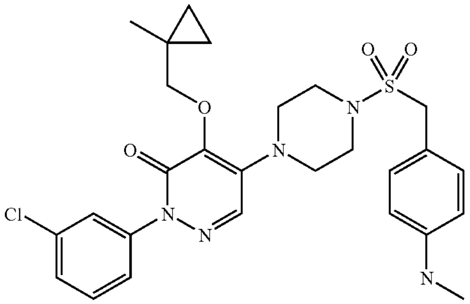 | 558 |
| 1937Z | 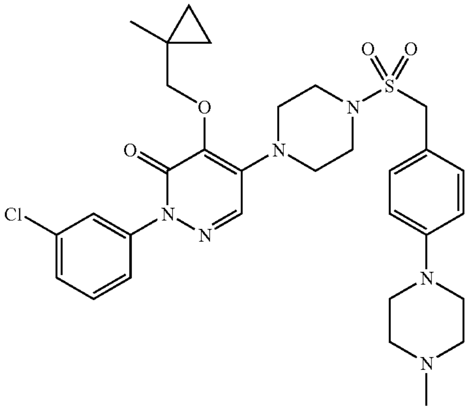 | 627 |
| 1938Z | 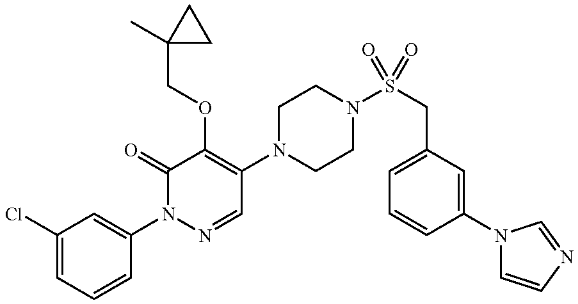 | 595 |
| 1939Z | 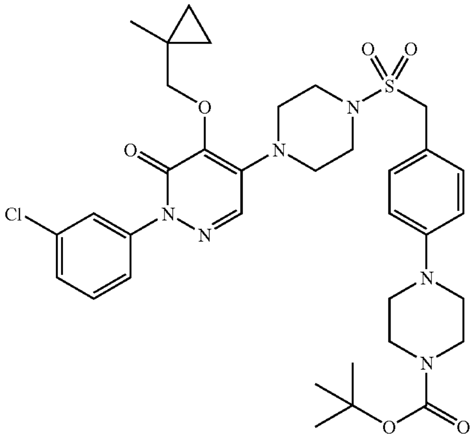 | 713 |

TABLE 37-continued
| Oxygen Analogs with Substituted Sulfonamide | | |
|---|---|---|
| Cmpd. No. | Structure | MS M + 1 |
| 1940Z | 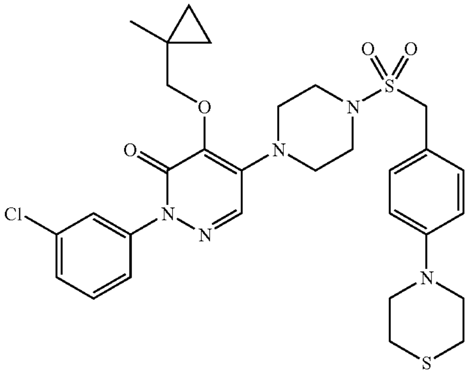 | 630 |
| 1941Z | 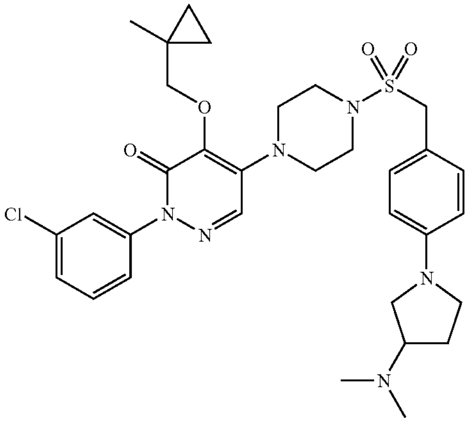 | 641 |
| 1942Z | 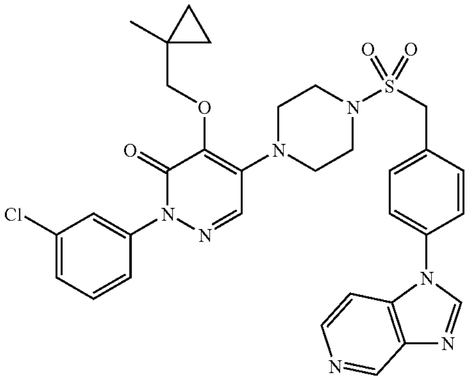 | 646 |
| 1943Z | 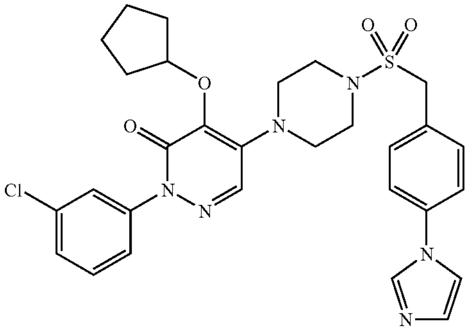 | 595 |

TABLE 37-continued
| Oxygen Analogs with Substituted Sulfonamide | | |
|---|---|---|
| Cmpd. No. | Structure | MS M + 1 |
| 1944Z | 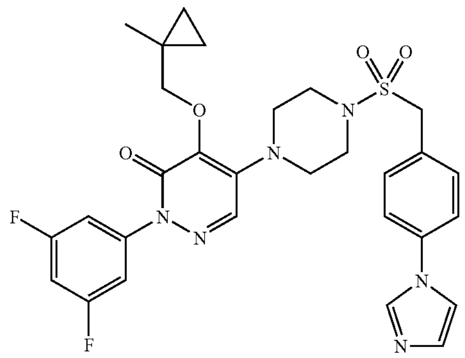 | 597 |
| 1945Z | 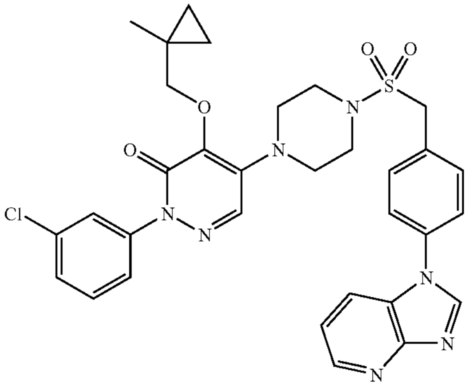 | 646 |
| 1946Z | 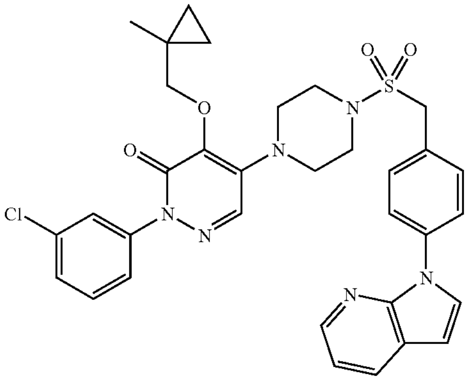 | 645 |
| 1947Z | 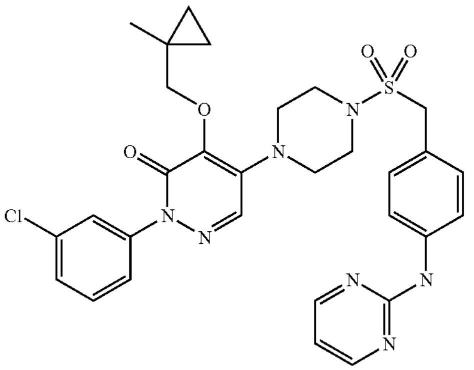 | 623 |

TABLE 37-continued
| Oxygen Analogs with Substituted Sulfonamide | | |
|---|---|---|
| Cmpd. No. | Structure | MS M + 1 |
| 1948Z | 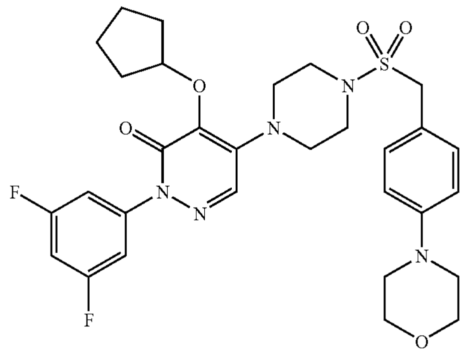 | 614 (M − 1) |
| 1949Z | 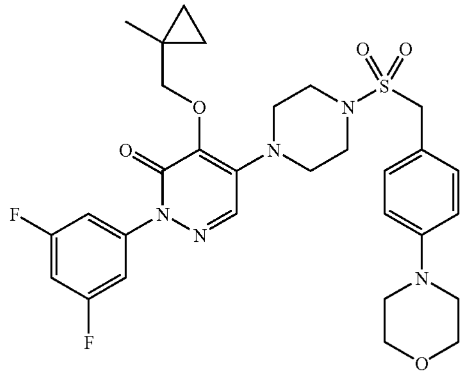 | 616 |
| 1950Z | 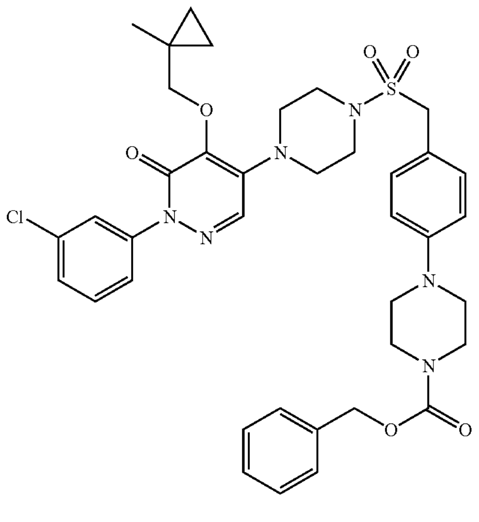 | 747 |

TABLE 37-continued
Oxygen Analogs with Substituted Sulfonamide
| Cmpd. No. | Structure | MS M + 1 |
| --- | --- | --- |
| 1951Z | 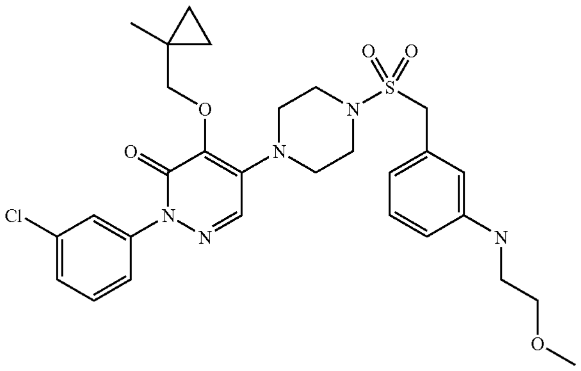 | 602 |
| 1952Z | 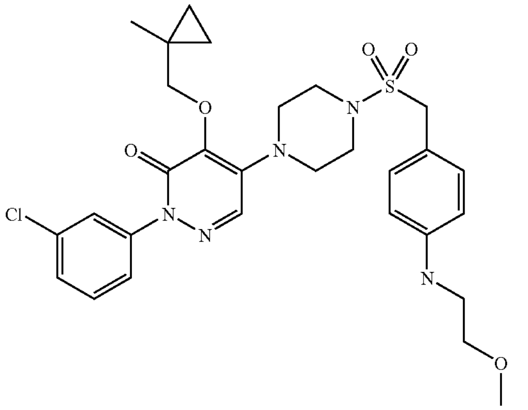 | 602 |
| 1953Z | 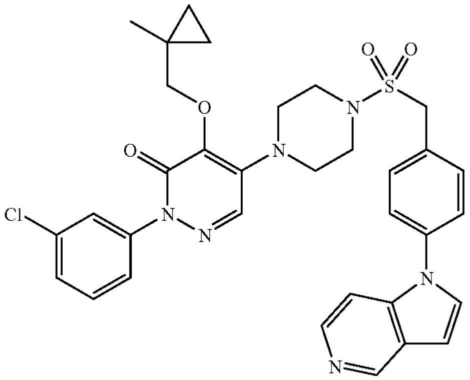 | 645 |
| 1954Z | 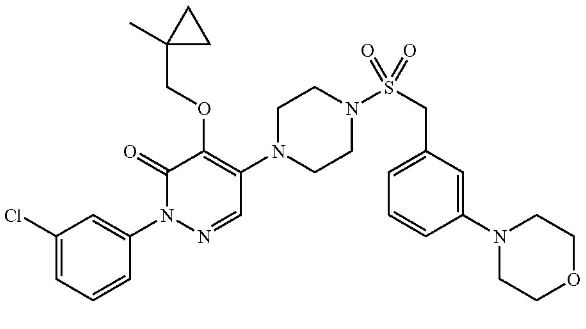 | 614 |

TABLE 37-continued
| Oxygen Analogs with Substituted Sulfonamide | | |
|---|---|---|
| Cmpd. No. | Structure | MS M + 1 |
| 1955Z | 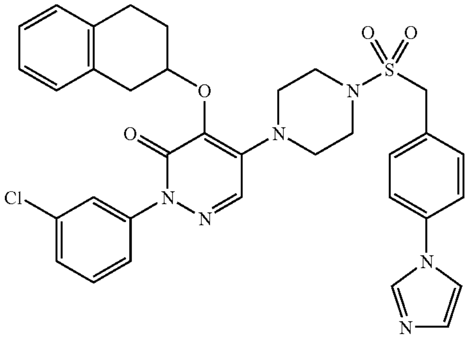 | 657 |
| 1956Z | 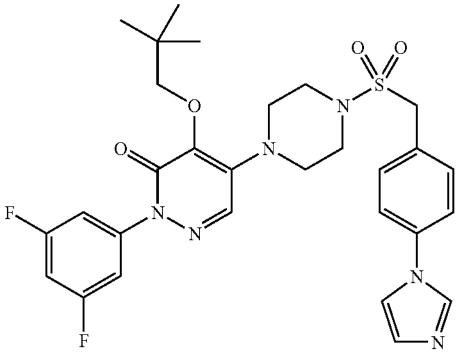 | 599 |
| 1957Z | 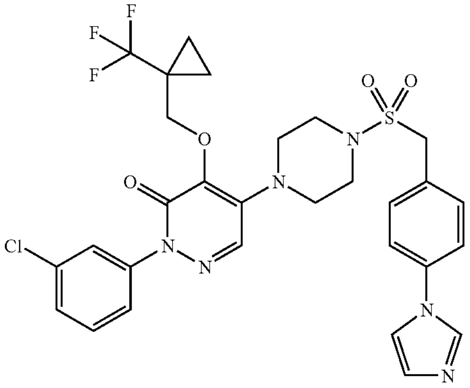 | 649 |
| 1958Z | 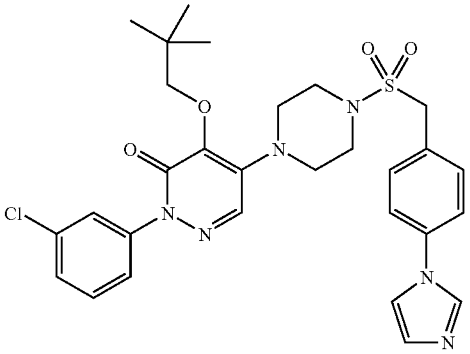 | 597 |

TABLE 37-continued
| Oxygen Analogs with Substituted Sulfonamide | | |
|---|---|---|
| Cmpd. No. | Structure | MS M + 1 |
| 1959Z | 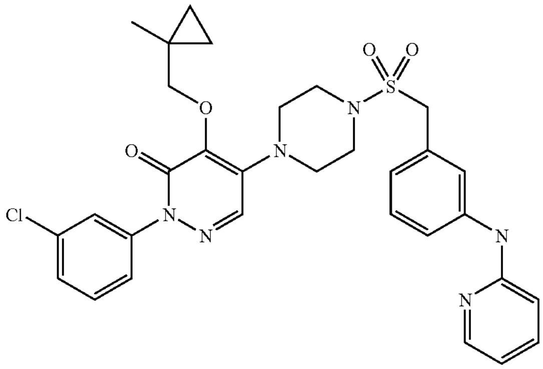 | 621 |
| 1960Z | 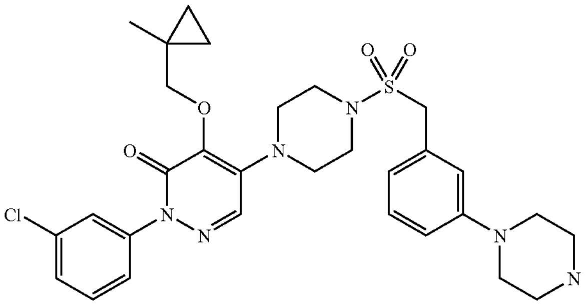 | 613 |
| 1961Z | 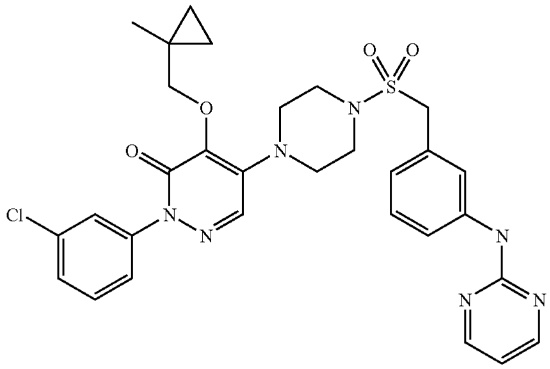 | 622 |
| 1962Z | 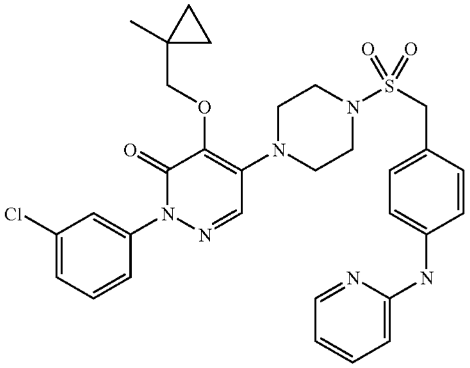 | 621 |

TABLE 37-continued
| Oxygen Analogs with Substituted Sulfonamide | | |
|---|---|---|
| Cmpd. No. | Structure | MS M + 1 |
| 1963Z | 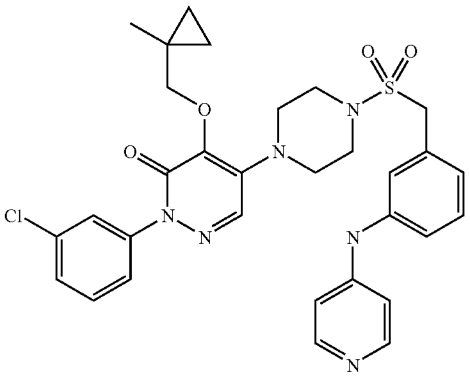 | 621 |
| 1964Z | 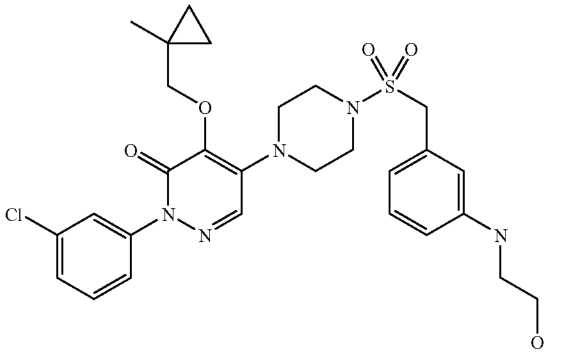 | 588 |
| 1965Z | 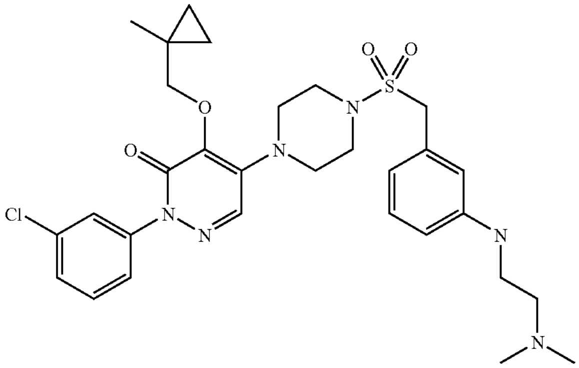 | 615 |
| 1966Z | 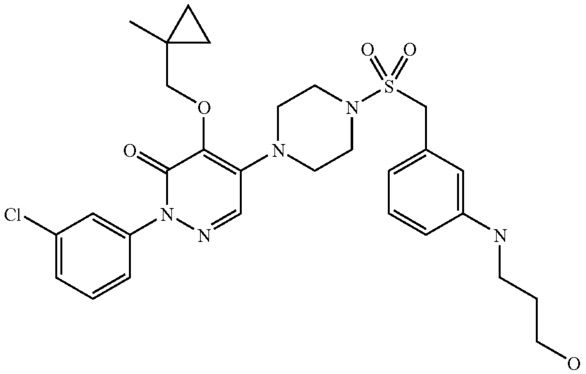 | 602 |

TABLE 37-continued
| Oxygen Analogs with Substituted Sulfonamide | | |
|---|---|---|
| Cmpd. No. | Structure | MS M + 1 |
| 1967Z | 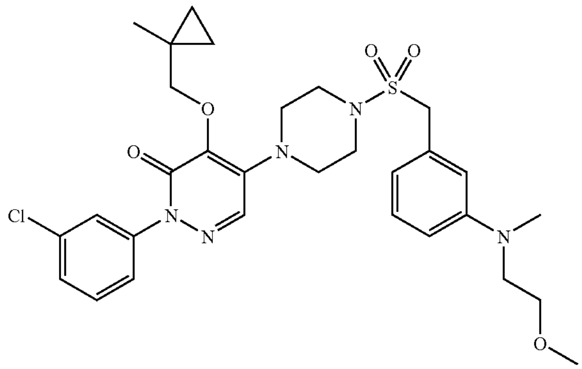 | 616 |
| 1968Z | 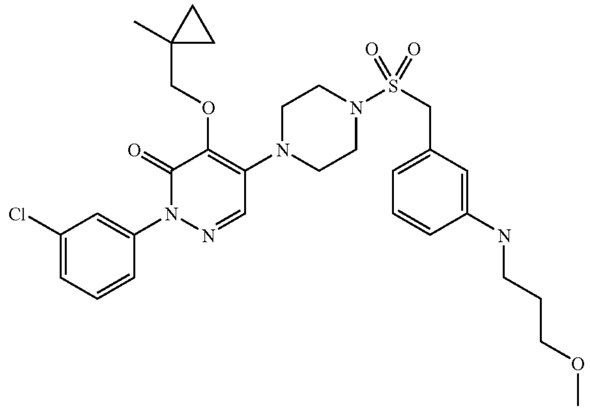 | 616 |
| 1969Z | 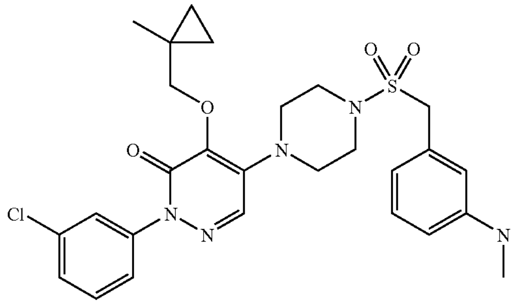 | 558 |
| 1970Z | 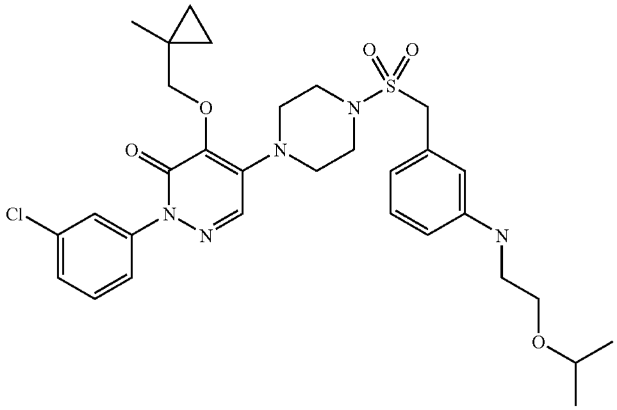 | 630 |

TABLE 37-continued
| Cmpd. No. | Structure | MS M + 1 |
|---|---|---|
| | Oxygen Analogs with Substituted Sulfonamide | |
| 1971Z | 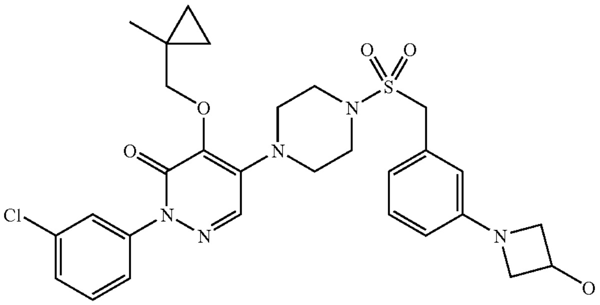 | 600 |
| 1972Z | 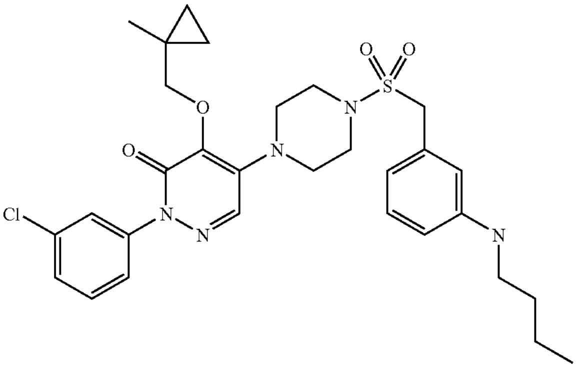 | 600 |
| 1973Z | 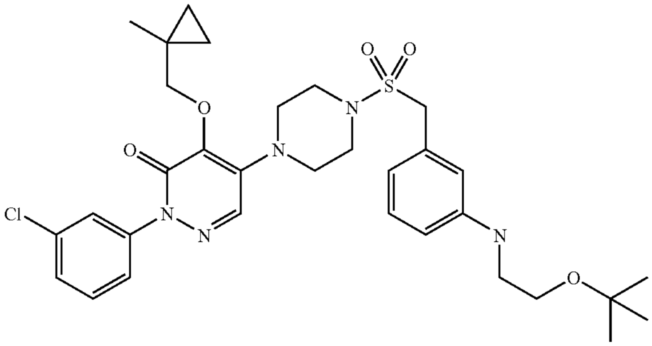 | 644 |
| 1974Z | 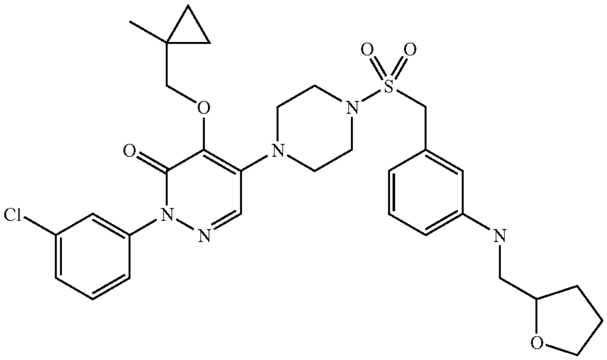 | 628 |

TABLE 37-continued
| Oxygen Analogs with Substituted Sulfonamide | | |
|---|---|---|
| Cmpd. No. | Structure | MS M + 1 |
| 1975Z | 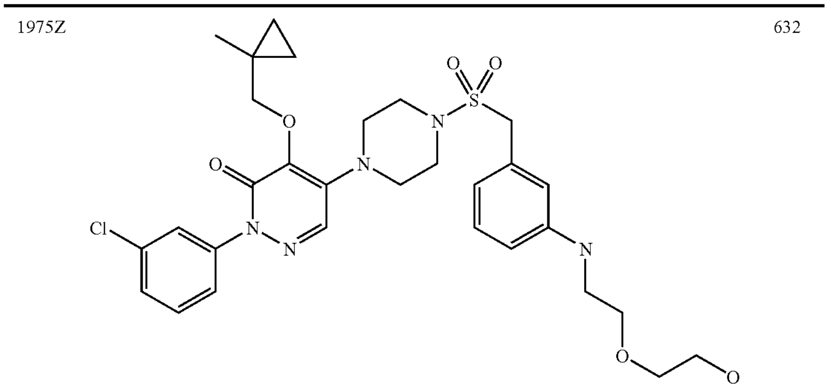 | 632 |
| 1976Z | 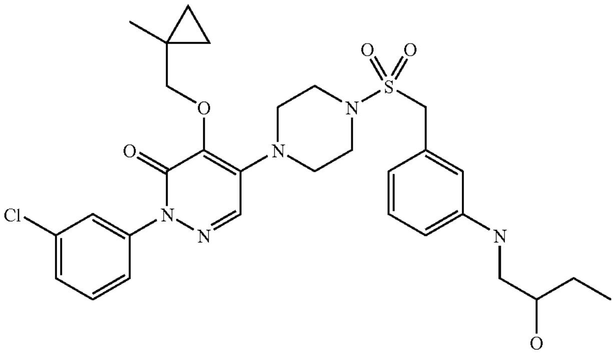 | 616 |
| 1977Z | 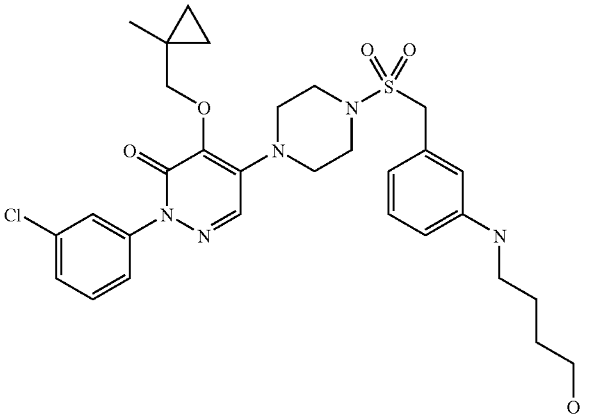 | 616 |
| 1978Z | 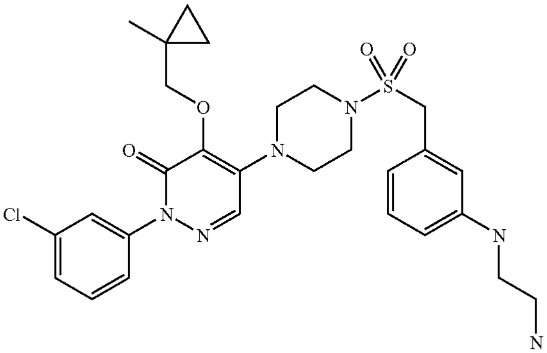 | 587 |

TABLE 37-continued
| Oxygen Analogs with Substituted Sulfonamide | | |
|---|---|---|
| Cmpd. No. | Structure | MS M + 1 |
| 1979Z | 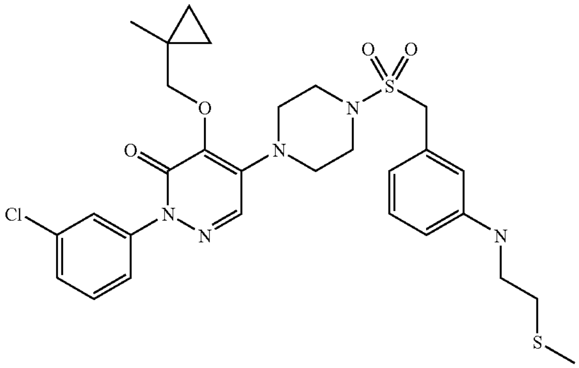 | 618 |
| 1980Z | 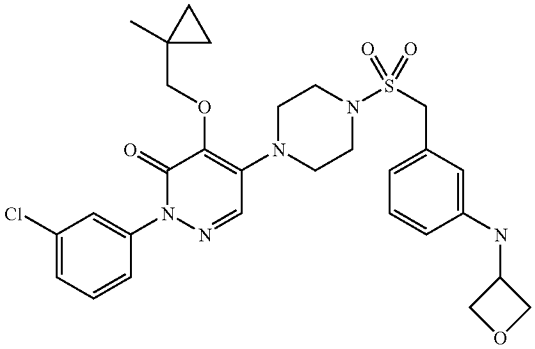 | 601 |
| 1981Z | 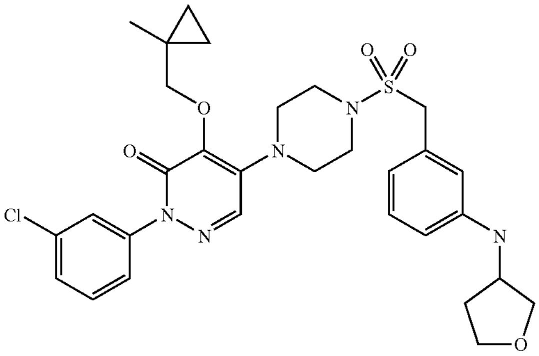 | 615 |
| 1982Z | 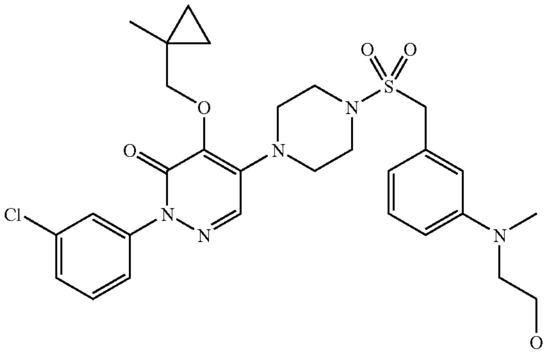 | 603 |

TABLE 37-continued

| Oxygen Analogs with Substituted Sulfonamide | | |
|---|---|---|
| Cmpd. No. | Structure | MS M + 1 |
| 1983Z | 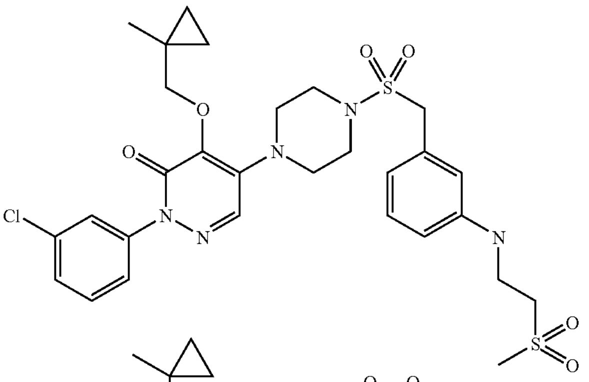 | 651 |
| 1984Z | 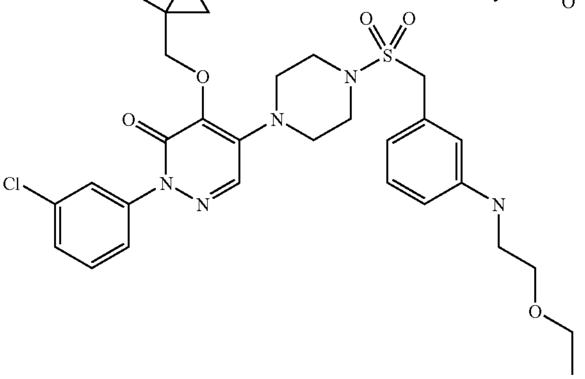 | 617 |

Scheme 65

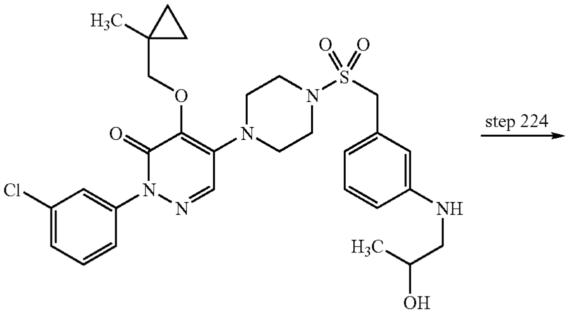

316

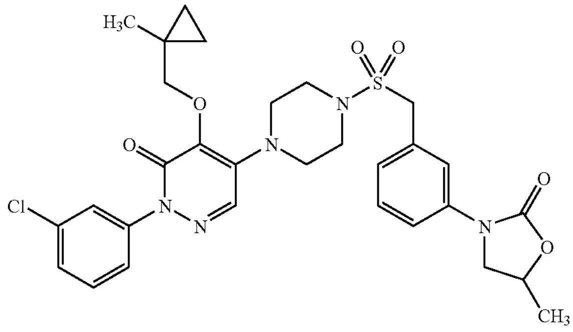

317

Step 224:

A mixture of (+/−)-2-(3-chlorophenyl)-5-(4-(3-(2-hydroxypropylamino)-benzylsulfonyl)piperazin-1-yl)-4-((1-methylcyclopropyl)methoxy)pyridazin-3 (2H)-one 316 (43 mg, 0.071 mmol), carbonyl diimidazole (46 mg, 0.29 mmol), and 4-dimethylaminopyridine (2 mg, 0.016 mmol) in tetrahydrofuran (5 mL) was heated at 80° C. under nitrogen for 6 h. The solvent was removed from the cooled mixture under reduced pressure, and the residue was purified by CombiFlash Companion (4-g $SiO_2$ cartridge), eluting with hexanes/ethyl acetate (1:19 to 1:1), to provide 28 mg (62% yield) of the product 317 as a light yellow solid: MS (M+1): m/e 628.

Scheme 66

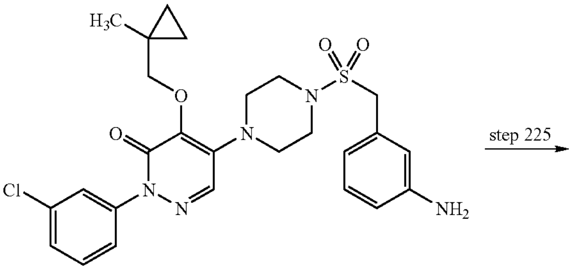

318

-continued

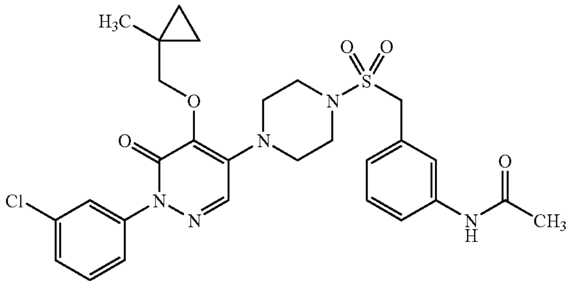

319

Step 225:

Acetyl chloride (22 mg, 0.28 mmol) was added dropwise to a mixture of 5-(4-(3-aminobenzylsulfonyl)piperazin-1-yl)-2-(3-chlorophenyl)-4-((1-methylcyclopropyl)-methoxy)pyridazin-3(2H)-one 318 (125 mg, 0.23 mmol) in pyridine (0.5 mL) at 0° C. under nitrogen. The mixture was slowly warmed to room temperature, stirring for a total of 22 h. The mixture was diluted with water (50 mL) and extracted with ethyl acetate (25 mL). The combined organic extracts were washed with 0.2 N HCl (4×50 mL), water (50 mL) and brine (50 mL), dried over sodium sulfate, filtered, and concentrated to provide 112 mg (83% yield) of the product 319 as an off-white foam: MS (M+1): m/e 586.

Using the procedure described above, the following compounds were synthesized,

| Cmpd. No. | Structure | MS M + 1 |
| --- | --- | --- |
| 1985Z | 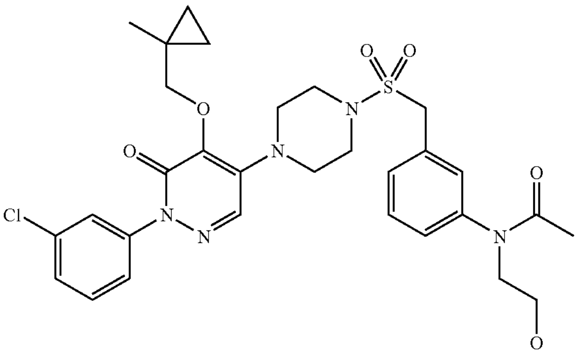 | 630 |
| 1986Z | 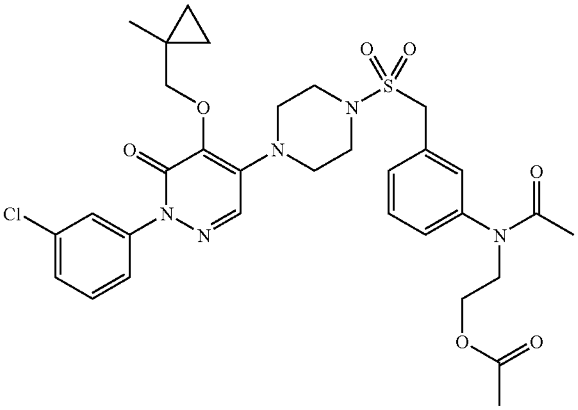 | 673 |
| 1987Z | 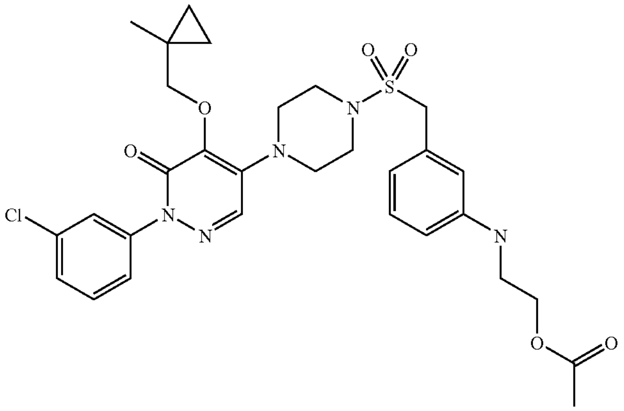 | 631 |

Scheme 67

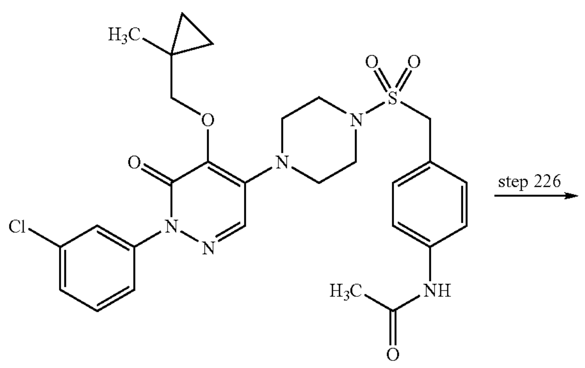

320

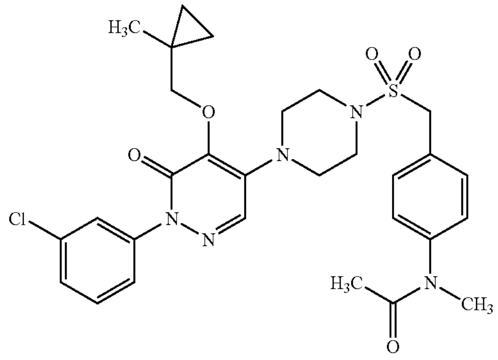

321

Step 226:

Dimethyl sulfate (26 mg, 0.22 mmol) was added to a mixture of N-(4-((4-(1-(3-chlorophenyl)-5-((1-methylcyclopropyl)methoxy)-6-oxo-1,6-dihydropyridazin-4-yl)piperazin-1-ylsulfonyl)methylphenyl)acetamide 320 (100 mg, 0.17 mmol) and potassium hydroxide (14 mg, 0.26 mmol) in dimethylformamide (0.5 mL) at room temperature under nitrogen, and the mixture was stirred for 15 h. The mixture was poured into cold water (30 mL), and the solids were removed by filtration under reduced pressure. The filtrate was concentrated, and the residue was purified by preparative TLC on silica gel, eluting with ethyl acetate, to provide 10 mg (10% yield) of the product 321 as an off-white solid: MS (M+1): m/e 600.

Scheme 68

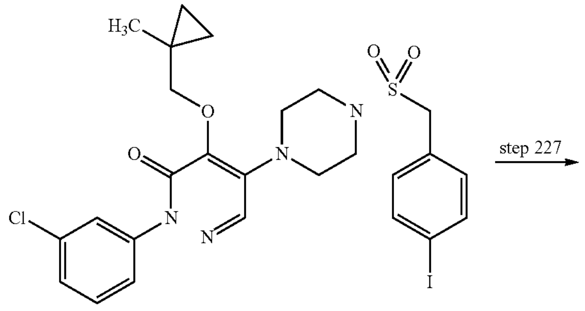

322

-continued

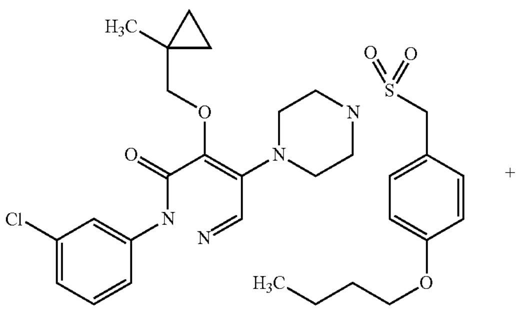

323

+

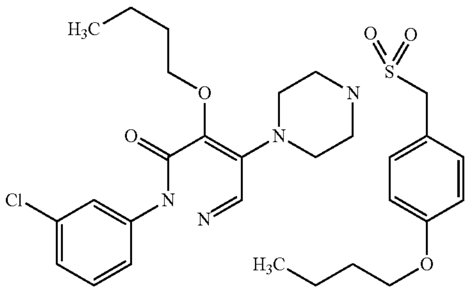

324

Step 227:

A mixture of 2-(3-chlorophenyl)-5-(4-(4-iodobenzylsulfonyl)piperazin-1-yl)-4-((1-methylcyclopropyl)methoxy)pyridazin-3(2H)-one 322 (66 mg, 0.10 mmol), n-butanol (15 mg, 0.20 mmol), copper(I) iodide (2 mg, 0.01 mmol), cesium carbonate (65 mg, 0.20 mmol) and 1,10-phenanthroline (4 mg, 0.02 mmol) in toluene (0.5 mL) was heated at 105° C. under nitrogen for 16 h. Then additional 1,10-phenanthroline (8 mg, 0.04 mmol), cesium carbonate (130 mg, 0.40 mmol), n-butanol (30 mg, 0.40 mmol) and copper(I) iodide (4 mg, 0.02 mmol) were added, and the reaction was heated for an additional 16 h. The cooled mixture was triturated with methylene chloride (5 mL) and methanol (5 mL), and the solids were removed by filtration. The filtrate was concentrated, and the residue was purified by CombiFlash Companion (12-g $SiO_2$ cartridge), eluting with ethyl acetate/hexanes (1:19 to 2:3), to provide 10 mg, (17% yield) of the product 323 as an off-white solid: MS (M+1): m/e 601. The byproduct 324 was also isolated as a white solid: MS (M+1): m/e 589.

Using the procedure described above, the following compounds were synthesized.

| Cmpd. No. | Structure | MS M + 1 |
|---|---|---|
| 1988Z | 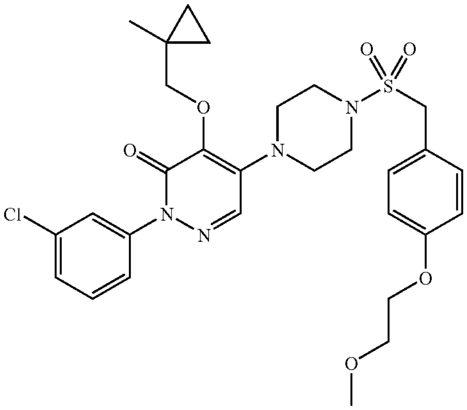 | 603 |
| 1989Z | 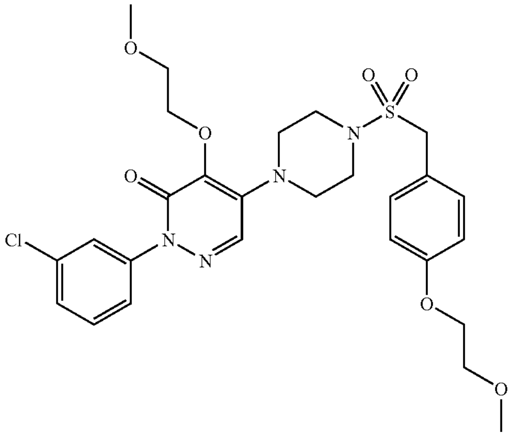 | 594 |
| 1990Z | 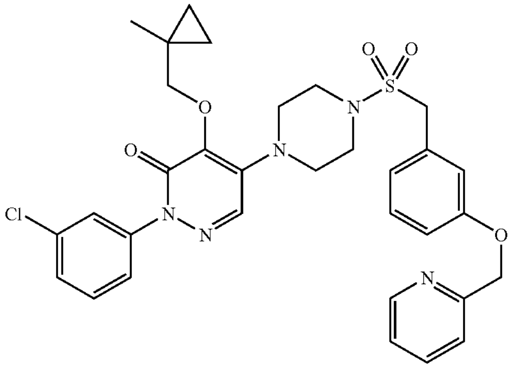 | 637 |
| 1991Z | 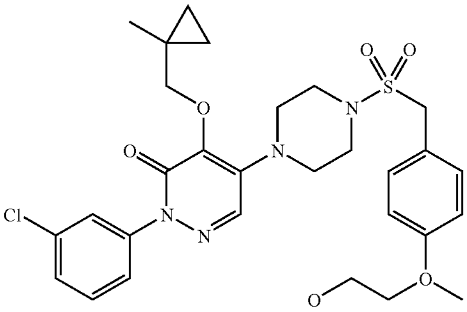 | 590 |

Scheme 69

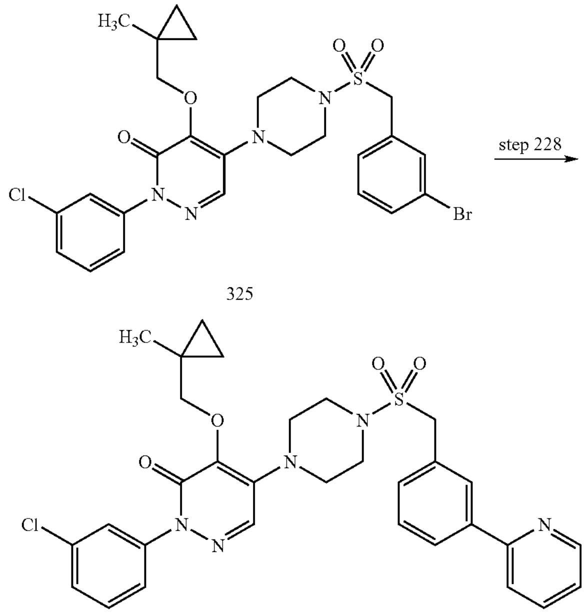

325

326

Step 228:

To a solution of 5-(4-(3-bromobenzylsulfonyl)piperazin-1-yl)-2-(3-chlorophenyl)-4-((1-methylcyclopropyl)methoxy)pyridazin-3(2H)-one 325 (200 mg, 0.329 mmol) in anhydrous DMF (6.0 mL) was added Pd(dppf)$Cl_2$ (24.1 mg, 0.0329 mmol), bis(pinacolato)diboron (94.4 mg, 0.372 mmole), and potassium acetate (96.7 mg, 0.987 mmole), the reaction mixture was heated to 95° C. for a total of 18 h. LCMS confirmed the boron ester intermediate. Into the reaction mixture was added Pd(dppf)$Cl_2$ (24.1 mg, 0.0329 mmol), 2-chloropyridine (56.0 mg, 0.494 mmole), and sodium carbonate (0.5 mL, 2 N). The reaction mixture was heated to 95° C. for a total of 18 h. The mixture was diluted with ethyl acetate (100 mL), washed with water/brine (100 mL), dried over anhydrous sodium sulfate, filtered, and concentrated. The residue was purified by preparatory TLC (Analtech silica gel GF, 200 microns) eluting with hexanes/ethyl acetate (3:2), to provide 14 mg (7% yield) of the product 326 as a white solid: MS (M+1): m/e 606.

Using the procedure described above, the following compounds were synthesized.

TABLE 38

Oxygen Analogs with C-Linked Substituted Sulfonamide

| Cmpd. No. | Structure | MS M + 1 |
|---|---|---|
| 1992Z | 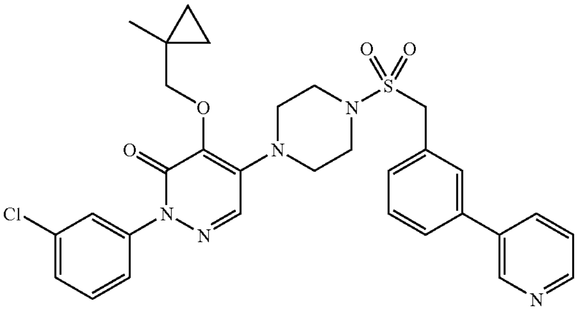 | 606 |
| 1993Z | 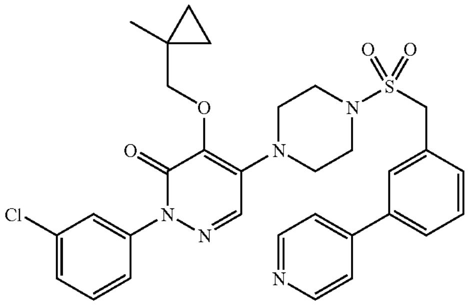 | 606 |

TABLE 38-continued
| Oxygen Analogs with C-Linked Substituted Sulfonamide | | |
|---|---|---|
| Cmpd. No. | Structure | MS M + 1 |
| 1994Z | 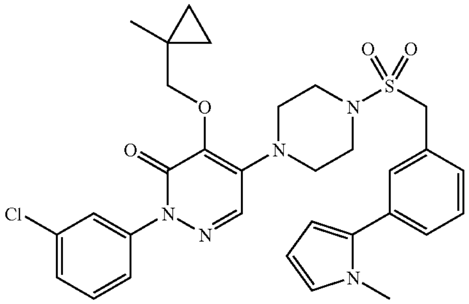 | 608 |
| 1995Z | 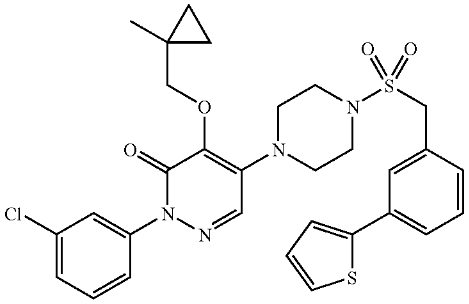 | 611 |
| 1996Z | 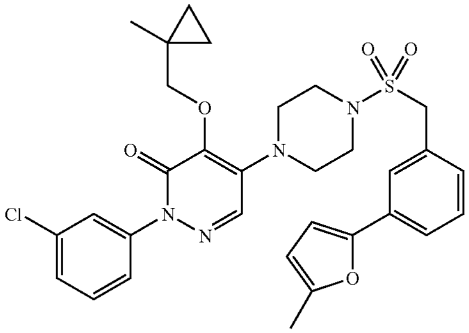 | 609 |
| 1997Z | 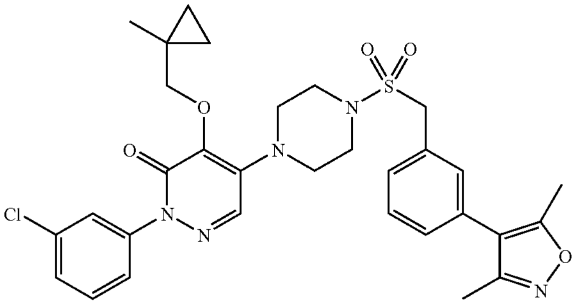 | 624 |

TABLE 38-continued
| Oxygen Analogs with C-Linked Substituted Sulfonamide | | |
|---|---|---|
| Cmpd. No. | Structure | MS M + 1 |
| 1998Z | 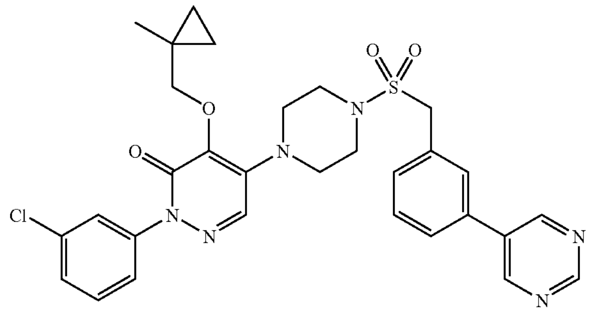 | 607 |
| 1999Z | 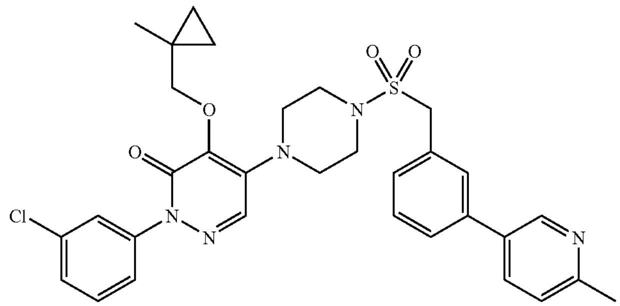 | 620 |
| 2000Z | 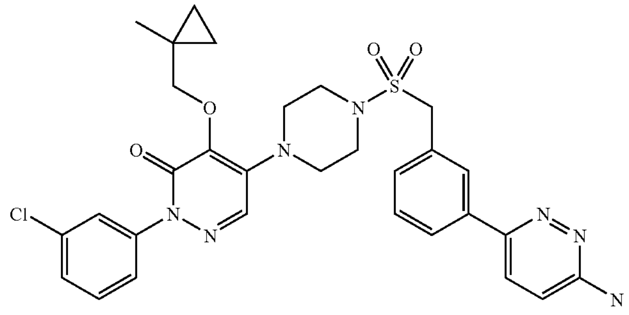 | 622 |
| 2001Z | 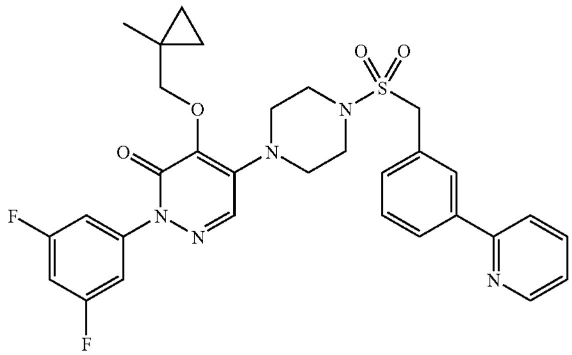 | 608 |

TABLE 38-continued
| Oxygen Analogs with C-Linked Substituted Sulfonamide | | |
|---|---|---|
| Cmpd. No. | Structure | MS M + 1 |
| 2002Z | 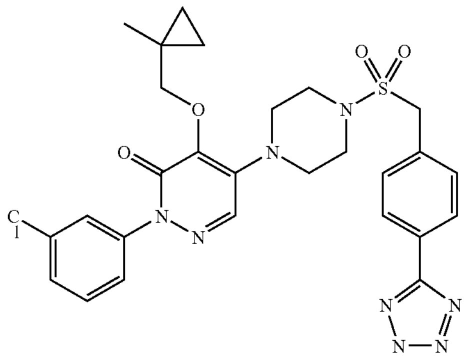 | 597 |
| 2003Z | 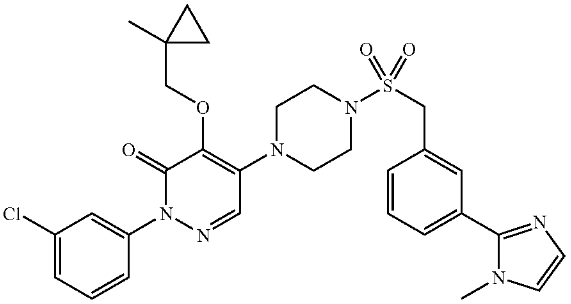 | 609 |
| 2004Z | 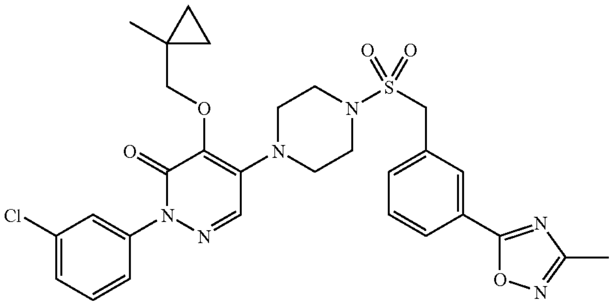 | 611 |
| 2005Z | 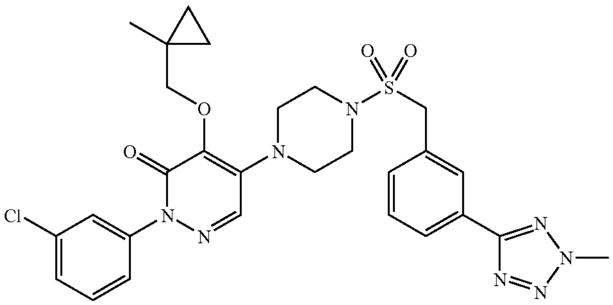 | 611 |

TABLE 38-continued

| Oxygen Analogs with C-Linked Substituted Sulfonamide | | |
|---|---|---|
| Cmpd. No. | Structure | MS M + 1 |
| 2006Z | 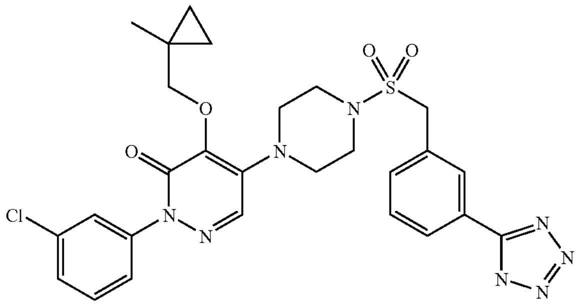 | 611 |
| 2007Z | 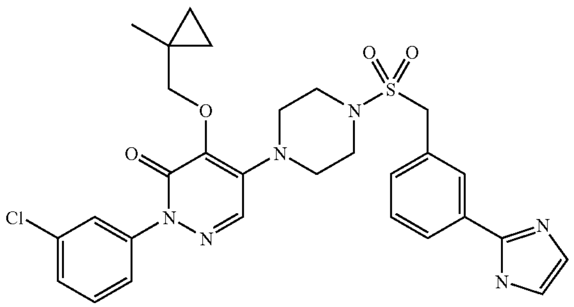 | 595 |

Scheme 70

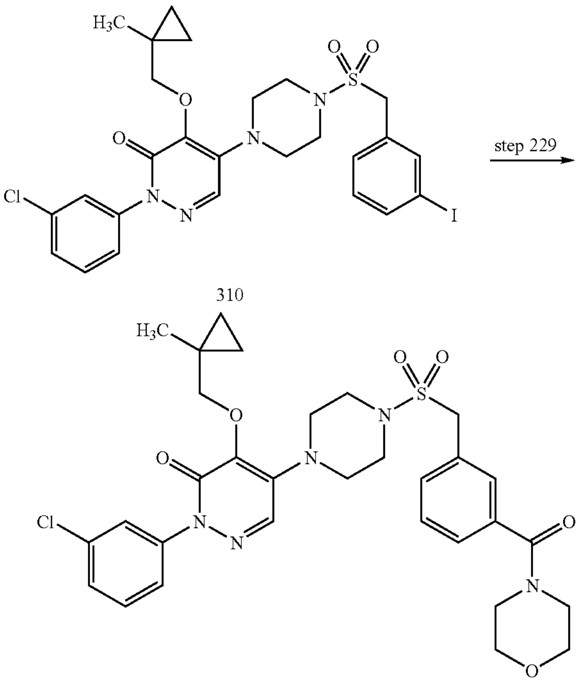

310

327

Step 229:

A mixture of 2-(3-chlorophenyl)-5-(4-(3-iodobenzylsulfonyl piperazin-1-yl)-4-((1 methylcyclopropyl)methoxy)pyridazin-3(2H)-one 310 (200 mg, 0.305 mmol), morpholine (39.9 mg, 0.458 mmol), and Pd(dppf)$Cl_2$ (22.3 mg, 0.03 mmole) in anhydrous DMSO (12 mL) at room temperature was charged with an atmosphere of carbon monoxide, after which the mixture was heated at 80° C. for 16 h. The cooled mixture was diluted with ethyl acetate (200 mL), washed with brine (300 mL), died over anhydrous sodium sulfate, filtered, and concentrated. The residue was purified by preparative TLC on silica gel, eluting with ethyl acetate, to provide 79 mg (41% yield) of the product 327 as a light brown solid: MS (M+1): m/e 642.

Using the procedure described above, the following compounds were synthesized.

TABLE 39
| Cmpd. No. | Structure | MS M + 1 |
| --- | --- | --- |
| Oxygen Analogs with Carbonyl Substituted Sulfonamide | | |
| 2008Z | 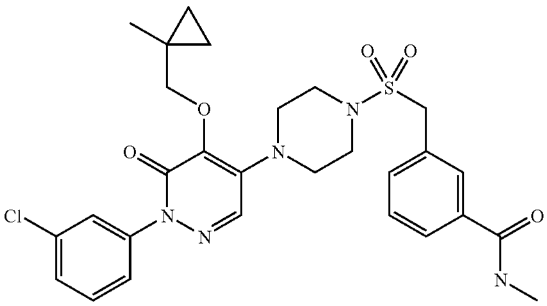 | 586 |
| 2009Z | 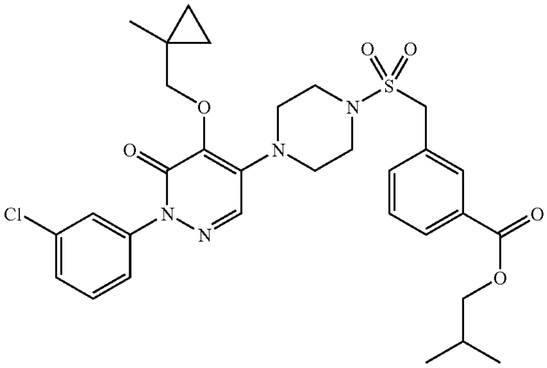 | 629 |
| 2010Z | 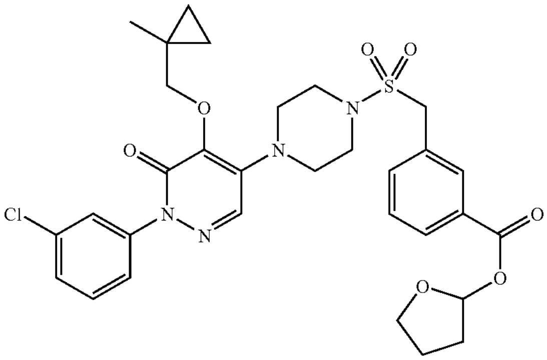 | 643 |
| 2011Z | 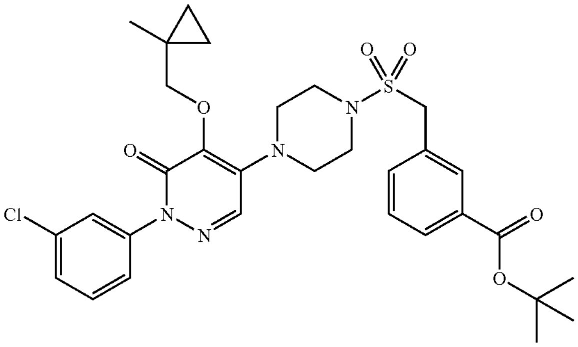 | 629 |

TABLE 39-continued
| Oxygen Analogs with Carbonyl Substituted Sulfonamide | | |
|---|---|---|
| Cmpd. No. | Structure | MS M + 1 |
| 2012Z | 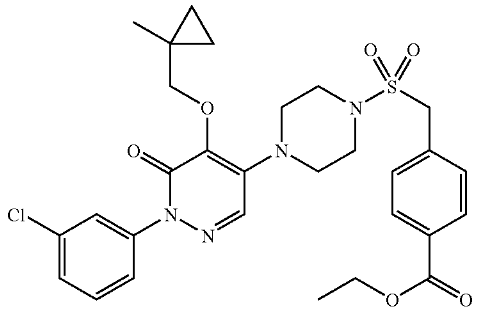 | 602 |
| 2013Z | 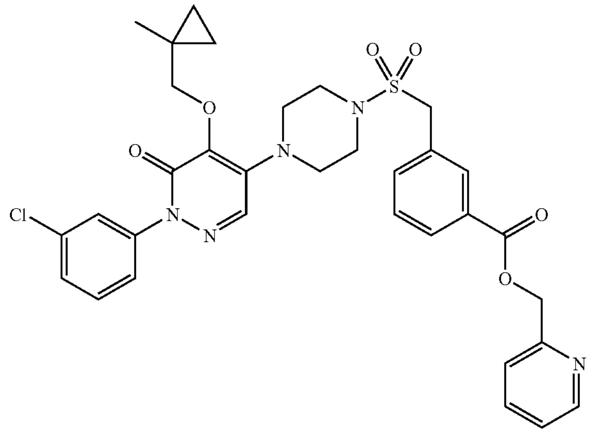 | 665 |
| 2014Z | 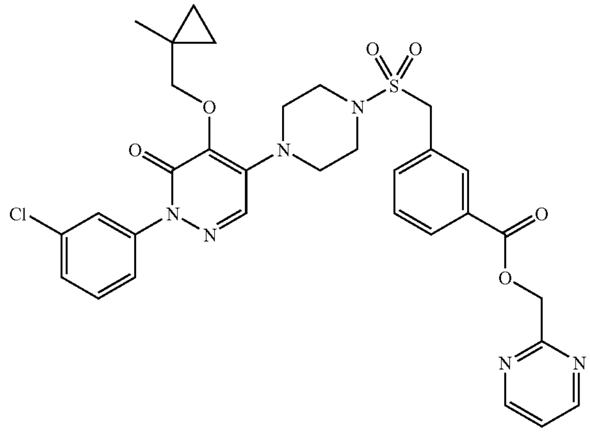 | 665 |

TABLE 39-continued
| Cmpd. No. | Structure | MS M + 1 |
| --- | --- | --- |
| | Oxygen Analogs with Carbonyl Substituted Sulfonamide | |
| 2015Z | 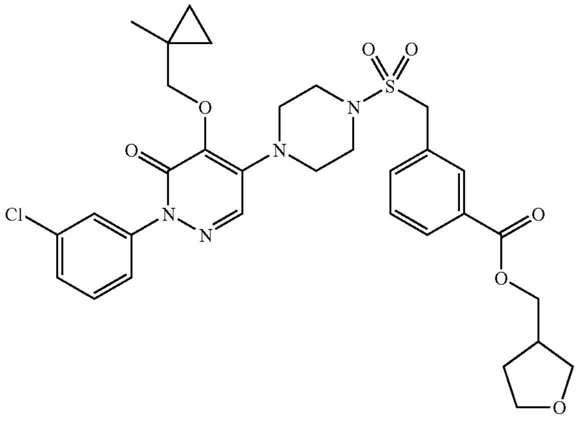 | 658 |
| 2016Z | 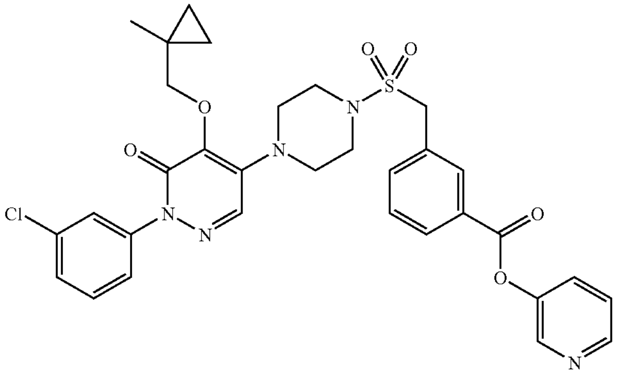 | 651 |

Scheme 71
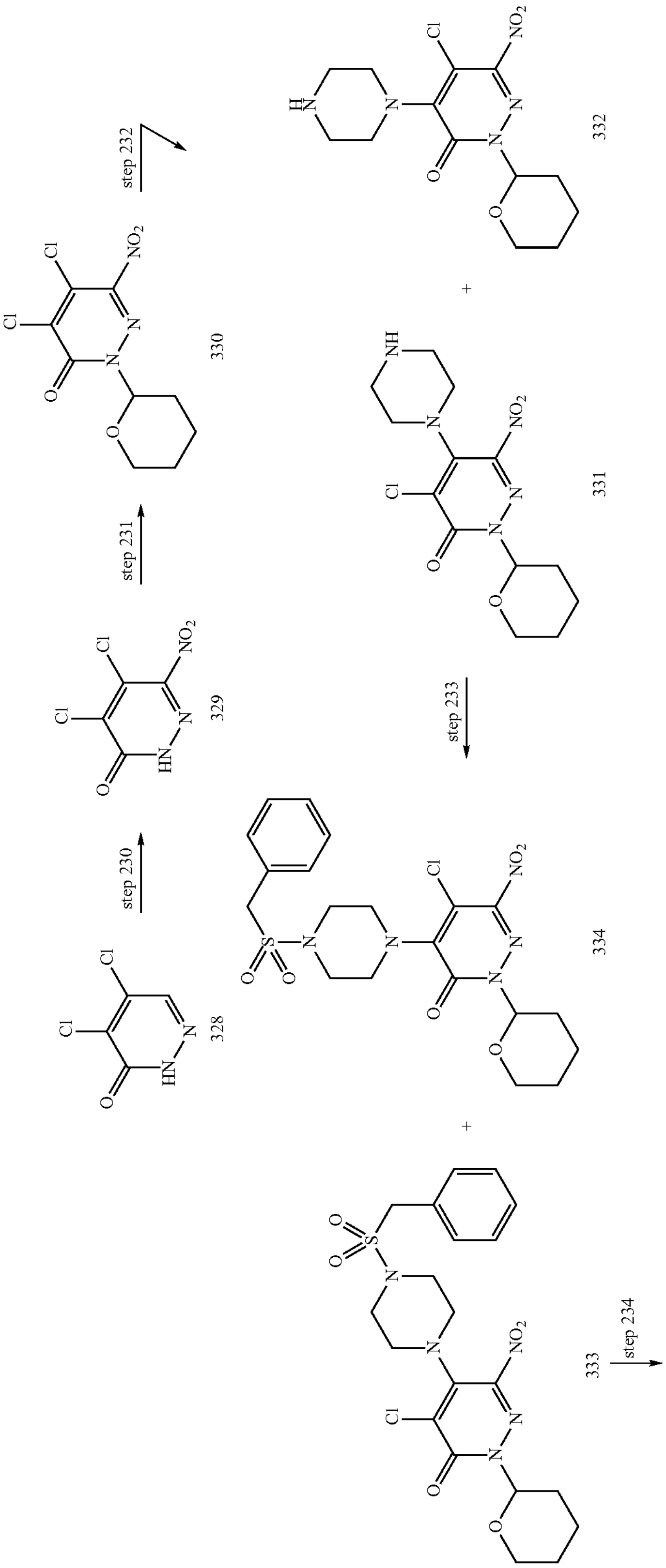
328 329 330 331 332 334 333

-continued
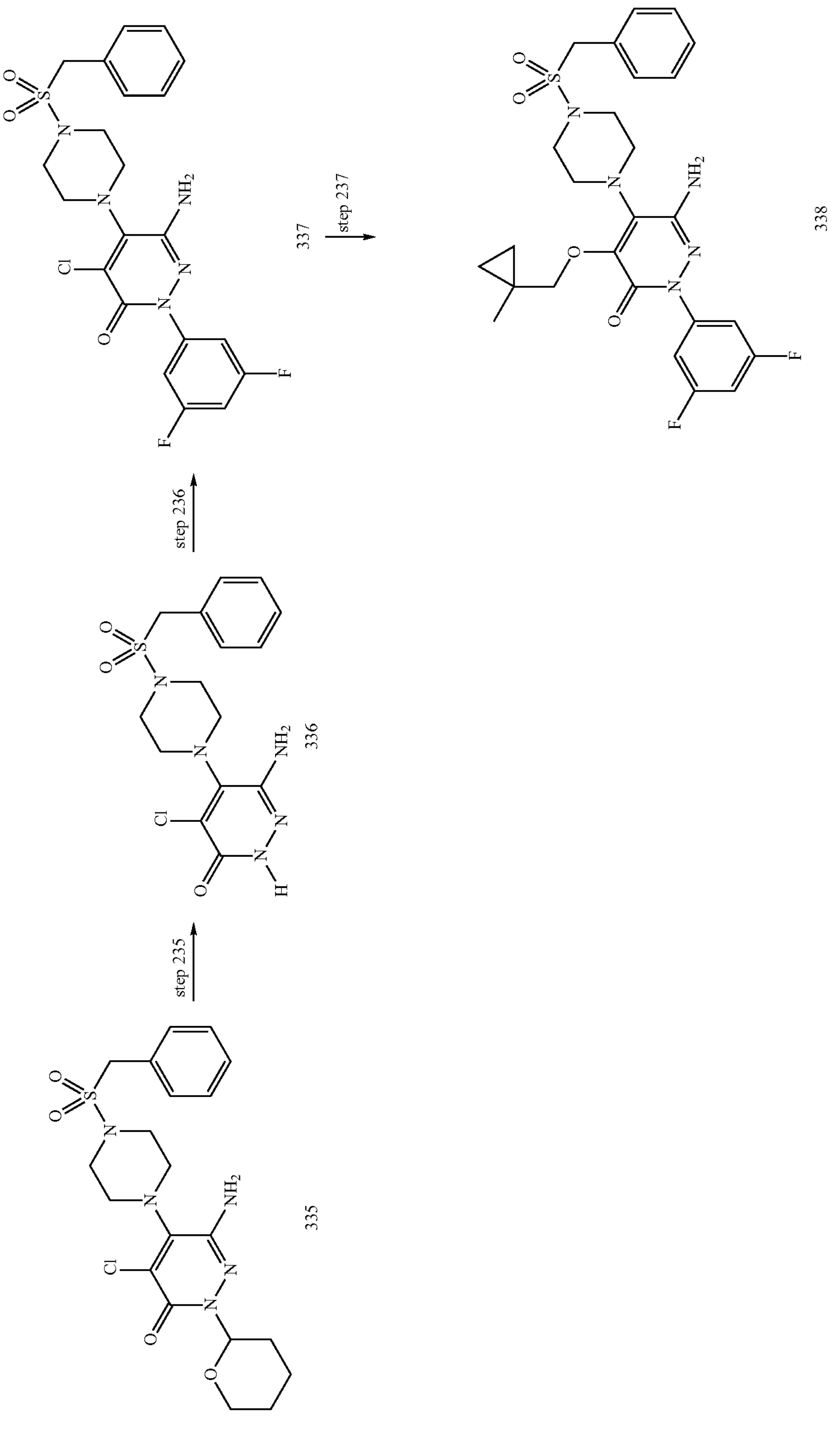
335
336
337
338

Step 230:

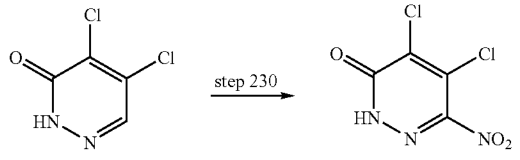

328 329

$KNO_3$ (20.0 g, mmol) was added portionwise to a mixture of fuming $H_2SO_4$ (30.0 mL) and 98%. $H_2SO_4$ (16.0 mL) at 0° C. followed by stirring for 5 mins. Then 4,5-dichloropyridazinone 328 (1.0 g, 6.1 mmol) was added, and the reaction mixture was heated at 100° C. for 6 h. The reaction mixture was cooled to room temperature, poured into ice-water, and stirred for 5 mins to obtain a precipitate. The precipitate was collected by filtration, washed with $H_2O$ (3×50 mL), and dried in a vacuum oven at 50° C. to afford 5.2 g (32% yield) of the crude product 329 as a white solid.

Step 231:

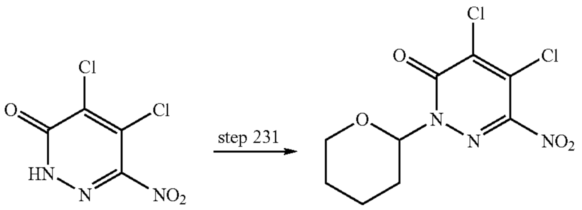

329 330

Compound 329 (6.16 g, 29.3 mmol) was added to a solution of 3,4-dihydropyran (24.7 g 293 mmol) and p-toluene sulfuric acid monohydrate (0.56 g, 2.93 mmol) in THF (200 mL) The solution was refluxed for 29 h at 80° C. then cooled to room temperature, and the solvent was concentrated. The residue was purified by chromatography on a silica-gel column (eluant: 0-8% EtOAc/hexane gradient) to afford 6.5 g (75% yield) of the product 330 as pale yellow solid.

Step 232:

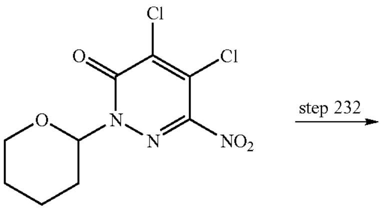

330

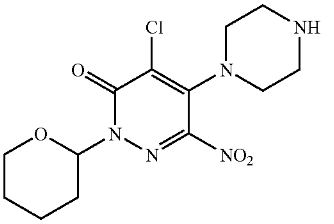

331

+

-continued

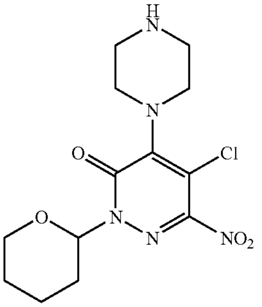

332

A solution of compound 330 (6.5 g, 22.1 mmol) and piperazine (3.8 g, 44.2 mmol) in EtOH (100 mL) was refluxed for 4 h at 80° C. then cooled to room temperature. The solvent was concentrated, and the residue was purified by chromatography on a silica-gel column (eluant: 4:1 to 1:2 EtOAc/MeOH gradient) to afford 5.1 g (67% yield) of a 1:1 mixture of products 331 and 332 as a yellow solid. MS (M+1): m/e 344.

Step 233:

α-Toluenesulfonyl chloride (0.81 g, 6.3 mmol) was added to a solution of the compounds 4 and 5 (1.8 g, 5.2 mmol) and i-$Pr_2NEt$ (0.81 g, 6.3 mmol) in $CH_2Cl_2$ (50 mL) at 0° C. followed by slowly warming to room temperature over 2 h. The solvent was concentrated. The residue was purified by chromatography on a silica-gel column (eluant: 0-40% EtOAc/hexane gradient) to afford 0.65 g (25% yield) of the first isomer 332 as pale yellow solid, MS (M+1): m/e 498; and 0.68 g (26% yield) of the second isomer 331 as pale yellow solid, MS (M+1): m/e 498.

Step 234:

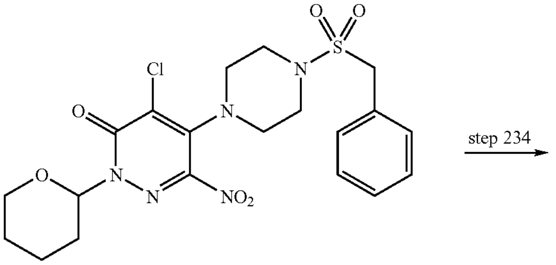

333

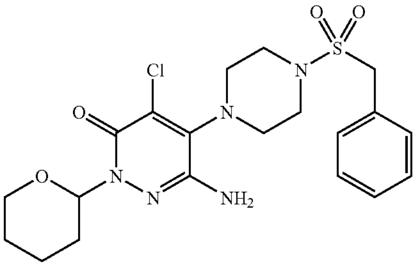

335

Compound 333 (0.68 g, 1.4 mmol) and $PtO_2$ (68 mg) dissolved in EtOAc/MeOH (15/30 mL) was stirred under a hydrogen atmosphere. The reaction was stirred overnight at room temperature under a hydrogen balloon. The solution was filtered through celite to remove the $PtO_2$. The filtrate was concentrated, and the product was purified by Prep Gilson HPLC to afford 0.48 g (75% yield) of the product 335 as a pale yellow solid. MS (M+1): m/e 468.

Step 235:

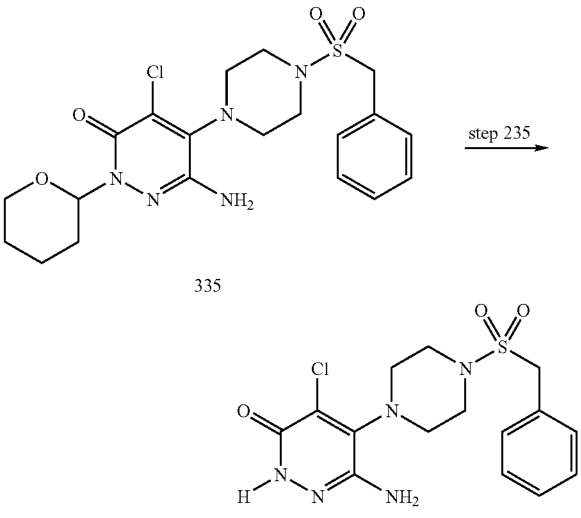

335

336

To compound 335 (0.24 g, 0.5 mmol) in MeOH (5 mL) was added a solution of 6 M aqueous HCl (2.5 mL) followed by stirring for 1 h at 75° C. The reaction mixture was cooled to room temperature, and the solvent was concentrated. The residue was dissolved in EtOAc (25 mL) and washed with saturated $NaHCO_3$ (20 mL). The organic phase was separated, dried over $MgSO_4$, filtered, and concentrated to afford 75 mg (39% yield) of the product 336 as a pale yellow solid. MS (M+1): m/e 384.

Step 236:

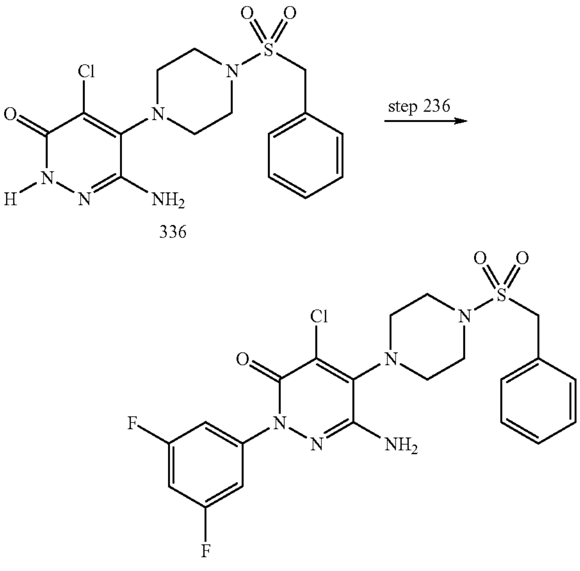

336

337

A suspension of compound 336 (75 mg, 0.20 mmol), 3,5-difluoroiodobenzene (72 mg, 0.30 mmol), 8-hydroxyquinoline (11 mg, 0.08 mmol), CuI (10 mg, 0.05 mmol), and $K_2CO_3$ (55 mg, 0.40 mmol) in pyridine (5 mL) was heated for 1.5 h at 170° C. in a microwave reactor. The reaction mixture was cooled to room temperature, and the solution was filtered to remove the solid. The filtrate was concentrated and purified by prep Gilson HPLC to afford 51 mg (52% yield) of the product 337 as a pale yellow solid. MS (M+1): m/e 496.

Step 237:

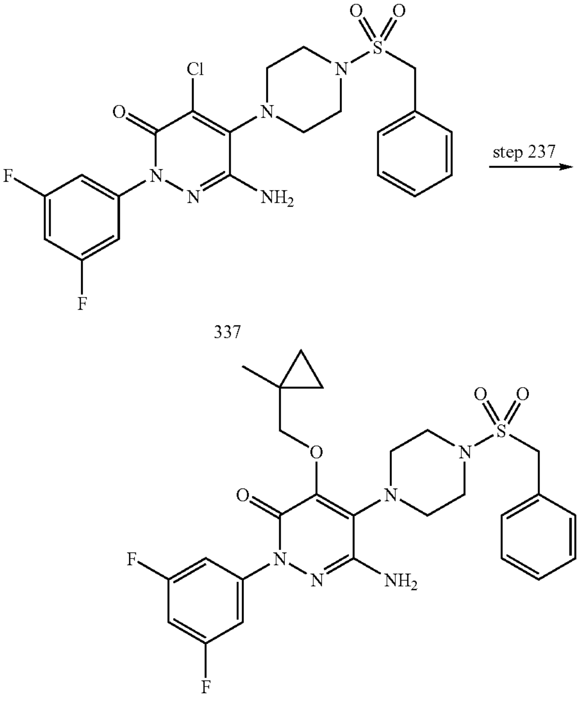

337

338

NaH (11 mg, 0.27 mmol) was added to a solution of 1-methylcyclopropanemethanol (26 μL, 0.27 mmol) in THF (3.0 mL) followed by stirring for 5 mins at room temperature. Compound 337 (45 mg, 0.09 mmol) was then added, and the reaction was heated for 2 h at 75° C. The reaction mixture was cooled to room temperature, concentrated, and purified by chromatography on a silica-gel column (eluant: 0-35% EtOAc/hexane gradient) to afford 24 mg (49% yield) of the product 338 as a pale yellow solid. MS (M+1): m/e 546.

Using the procedures described above, the following compounds were synthesized.

| Cmpd. No. | Structure | MS M + 1 |
|---|---|---|
| 2017Z | 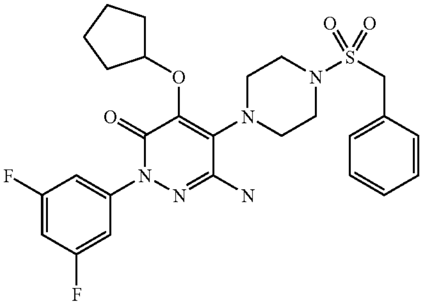 | 546 |

| Cmpd. No. | Structure | MS M + 1 |
|---|---|---|
| 2018Z | 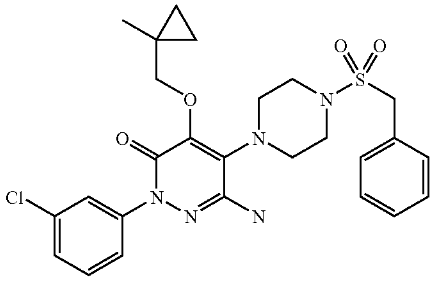 | 544 |
| 2019Z | 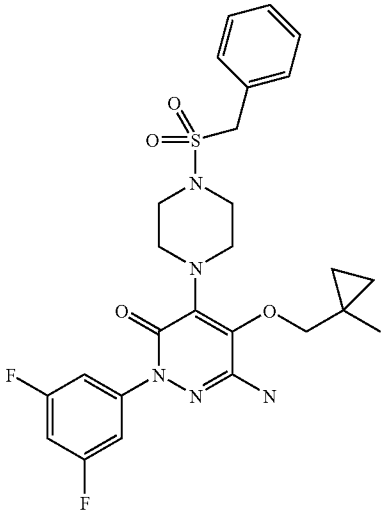 | 546 |

Scheme 72

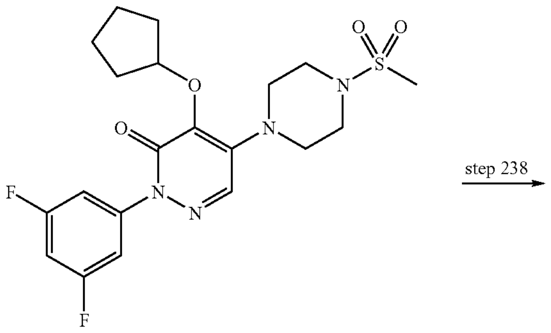

339

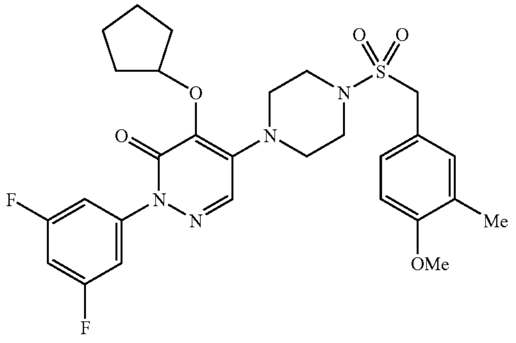

340

Step 238:

To compound 339 (45.4 mg, 0.0999 mmol) and 4-bromo-2-methylanisole (42.5 mg, 0.211 mmol) dissolved in anhydrous toluene (2 mL) at room temperature was added lithium hexamethyldisilazide in THF (0.200 mL, 1.0 M), palladium acetate (1.79 mg, 0.00799 mmol) and triphenylphosphine (6.55 mg, 0.0250 mmol). The reaction was degassed, placed under an atmosphere of nitrogen, and stirred at 100° C. overnight. The reaction mixture was filtered through a short path silica column and washed with ethyl acetate (150 mL). The solvent was concentrated, and the product was chromatographed on silica gel (eluant: 1:2 hexanes:EtOAc) to give 36 mg (63% yield) of the product 340. MS (M+1): m/e 575.

Using the procedure described above, the following compound was synthesized.

| Cmpd. No. | Structure | MS M + 1 |
|---|---|---|
| 2020Z | 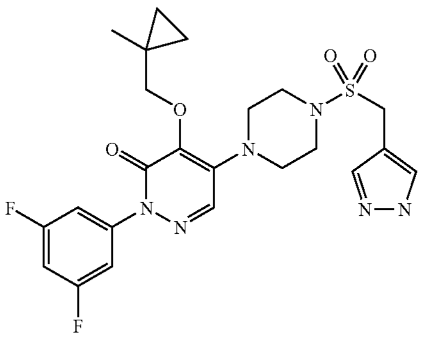 | 521 |

Scheme 73

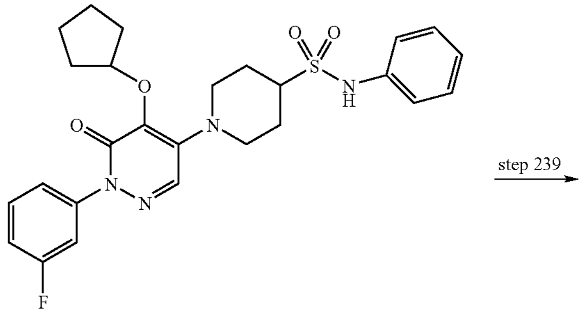

341

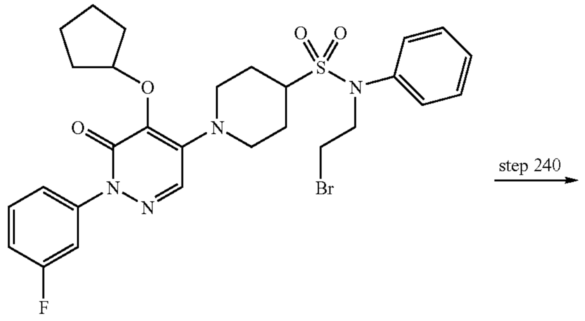

342

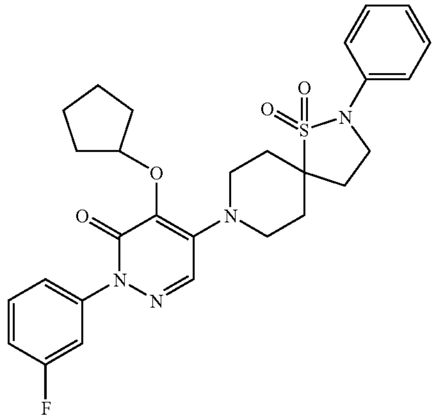

343

Step 239:

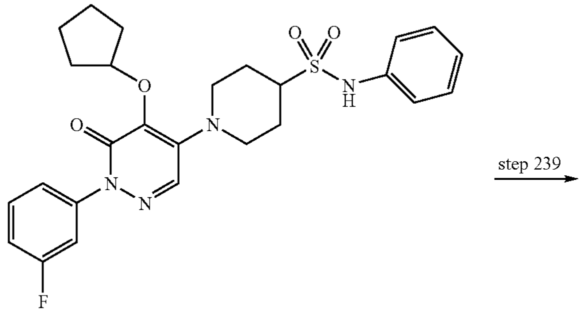

341

-continued

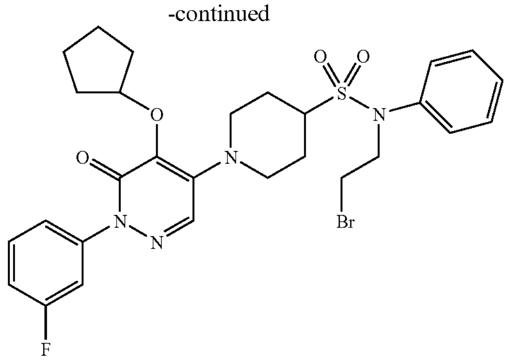

342

Compound 341 can be prepared according to Scheme 34.

To a solution of sulfonamide 341 (200 mg, 0.39 mmol) in DMF (4 mL) at room temperature was added NaH (39 mg, 0.98 mmol, 60% in oil) in one portion. After stirring for 20 mins, 1,2-dibromoethane (840 mg, 4.2 mmol) was added in one portion followed by the addition of $K_2CO_3$ (540 mg, 3.9 mmol). The reaction mixture was heated at 120° C. for 8 h then cooled and slowly added to a saturated aqueous $NH_4Cl$ solution. The aqueous solution was extracted with EtOAc. The combined organic extract was washed with brine, dried ($Na_2SO_4$), filtered, and concentrated. Purification by Gilson reverse phase chromatography (eluant: $CH_3CN$—$H_2O$) gave 180 mg (74% yield) of the product 342 as a white solid. MS (M+1): 621.

Step 240:

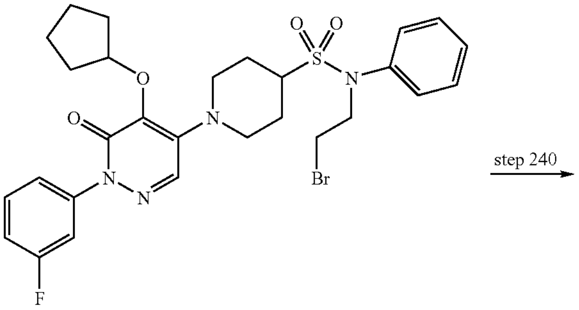

342

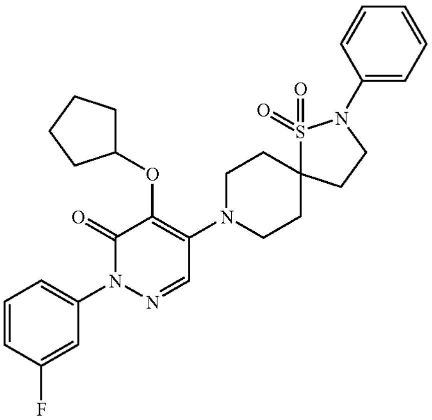

343

To a solution of bromosulfonamide 342 (160 mg, 0.26 mmol) in THF/HMPA (2 mL/0.4 mL) at −78° C. was added KN(TMS)$_2$ (1.55 mL, 0.77 mmol) over 2 mins. After stirring for 30 mins, the reaction mixture was raised to room temperature and stirred over night. Saturated aqueous $NH_4Cl$ solution was then added, and the aqueous solution was extracted with EtOAc. The combined organic extract was washed with brine, dried ($Na_2SO_4$), filtered, and concentrated. Purification by Gilson reverse phase chromatography (eluant: $CH_3CN$—$H_2O$) gave 10 mg (7.4% yield) of the product 343 as a solid. MS (M+1): 539.

Scheme 74

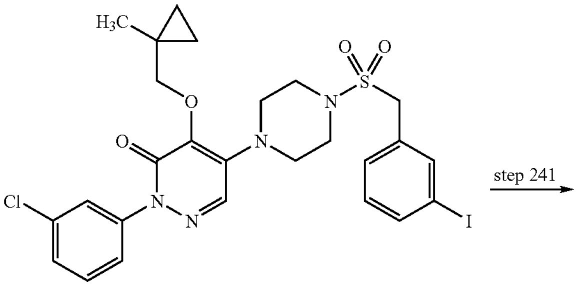

344

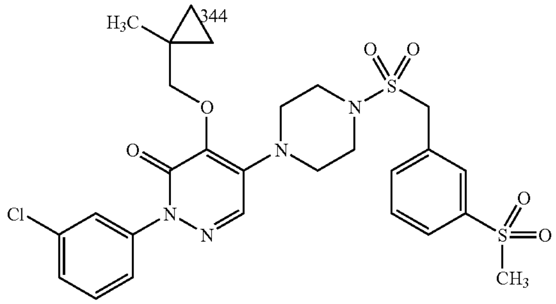

345

Step 241:

A mixture of 2-(3-chlorophenyl)-5-(4-(3-iodobenzylsulfonyl)piperazin-1-yl)-4-((1-methylcyclopropyl)methoxy)pyridazin-3(2H)-one 344 (100 mg, 0.153 mmol), methylsulfonyl sodium (19 mg, 0.18 mmol), copper iodide (6 mg, 0.03 mmole), L-proline (7.0 mg, 0.06 mmole) and sodium hydroxide (3 mg, 0.06 mmole) in anhydrous DMSO (0.5 mL) was heated at 90° C. under nitrogen for 17 h. The cooled mixture was diluted with ethyl acetate (200 mL), washed with brine (300 mL), dried over anhydrous sodium sulfate, filtered, and concentrated. The residue was purified by preparatory TLC (Analtech silica gel GF, 200 microns) eluting with methylene chloride/methanol (19:1), to provide 21.8 mg (24% yield) of the product 345 as a white solid: MS (M+1): m/e 607.

Scheme 75

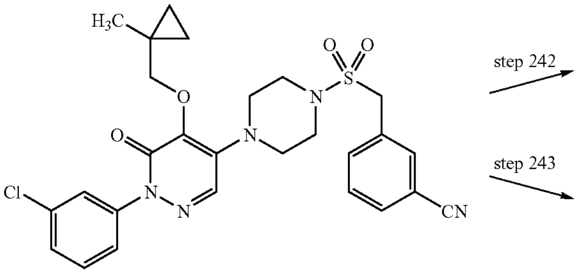

346

-continued

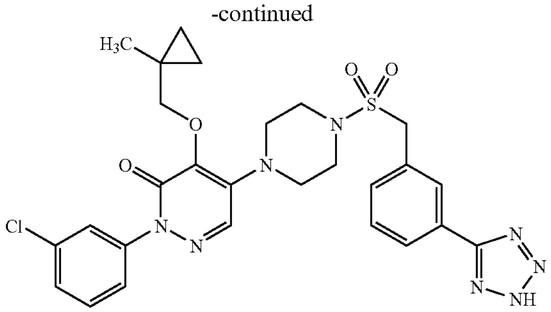

347

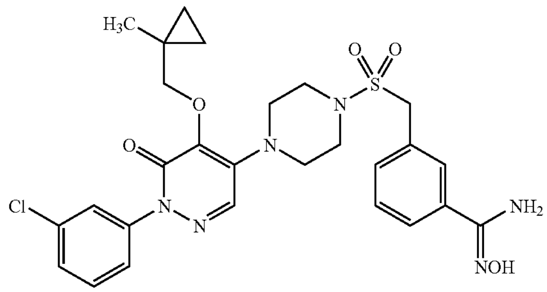

348

Step 242:

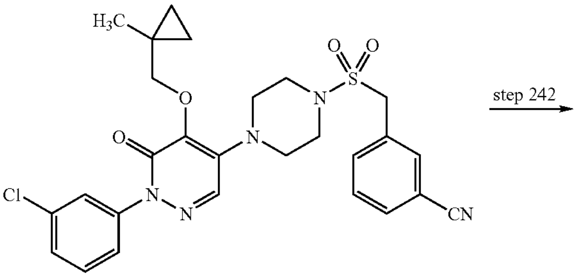

346

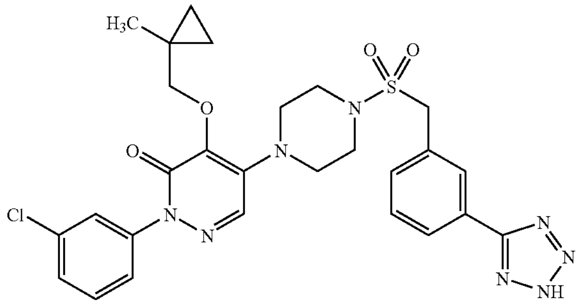

347

Compound 346 can be synthesized according to Scheme 64.

A mixture of 3-[(4-(1-(3-chlorophenyl]-5-[(1-methylcyclopropyl)methoxy-6-oxo-1,6-dihydropyridazin-4-yl)piperazin-1-ylsulfonyl)methyl]benzonitrile 346 (100 mg, 0.180 mmol), sodium azide (36.6 mg, 0.564 mmol) and triethylamine hydrochloride (74.5 mg, 0.541 mmol) in anhydrous toluene (1 mL) was heated at 90° C. under nitrogen for 16 h. The cooled mixture was diluted with brine (100 mL), extracted with ethyl acetate (150 mL) dried over anhydrous sodium sulfate, filtered, and concentrated. The residue was purified by CombiFlash Companion (40-g silica gel cartridge), eluting with methylene chloride/methanol (19:1 to 3:1), to provide 44 mg (41% yield) of the product 347 as a yellow solid: MS (M+1): m/e 597.

Step 243:

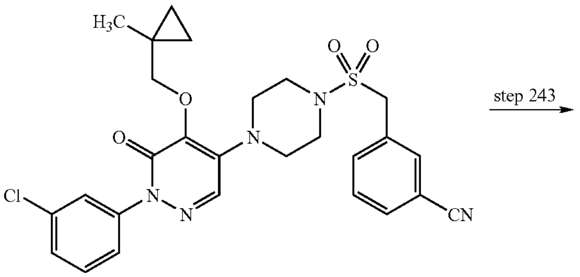

346

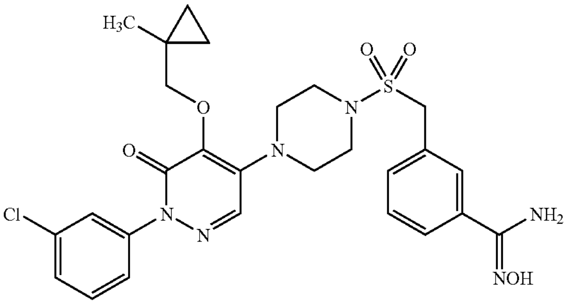

348

A mixture of 3-[(4-(1-(3-chlorophenyl]-5-[(1-methylcyclopropyl)methoxy-6-oxo-1,6-dihydropyridazin-4-yl)piperazin-1-ylsulfonyl)methyl]benzonitrile 346 (100 mg, 0.180 mmol), hydroxylamine hydrochloride (56.0 mg, 0.80 mmol), and sodium carbonate (84.0 mg, 1.01 mmol) in a biphasic mixture of water, (3 mL), methylene chloride (1 mL), and ethanol (9 mL) was heated at reflux under nitrogen for 19 h. The cooled suspension was diluted with water (100 mL), extracted with methylene chloride (100 mL), dried over anhydrous sodium sulfate, filtered, and concentrated to provide a clear oil, which was triturated with diethyl ether (20 mL). The resulting solids were collected under reduced pressure to provide 130 mg (64% yield) of the product 348 as a yellow solid: MS (M+1): m/e 587.

Using the procedures described above, the following compound was synthesized.

| Cmpd. No | Structure | MS M + 1 |
| --- | --- | --- |
| 2021Z | 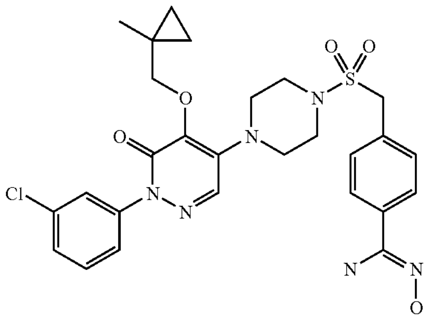 | 587 |

Scheme 76

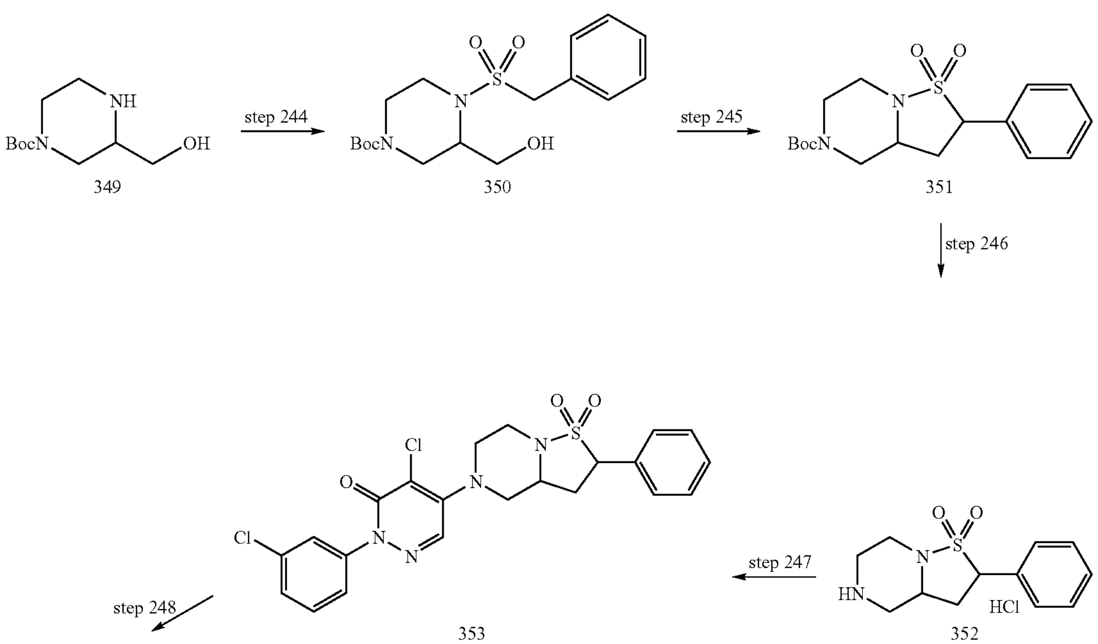

349 350 351 352 353

-continued

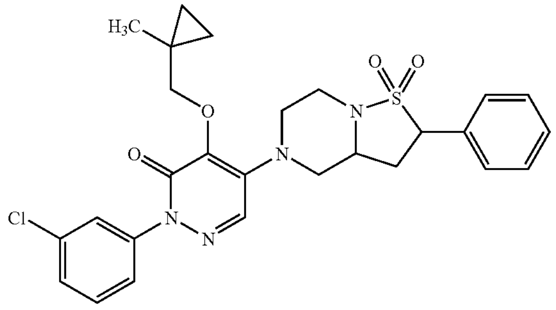

354

Step 244:

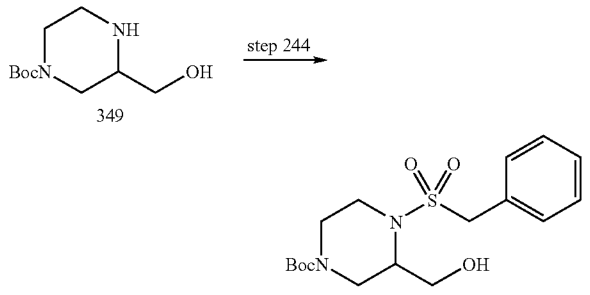

349

350

A solution of benzylsulfonyl chloride (210 mg, 1.1 mmol) in methylene chloride (0.5 mL) was added dropwise to a mixture of (+/−)-tert-butyl 3-(hydroxymethyl)piperazine-1-carboxylate 349 (216 mg, 1.0 mmol) and diisopropylethylamine (0.35 mL, 2.0 mmol) in methylene chloride (1.0 mL) at 0° C. under nitrogen, after which the mixture was slowly warmed to room temperature, stirring for a total of 2 h. The solvent was concentrated, and the residue was purified by CombiFlash Companion (12-g silica gel cartridge), eluting with ethyl acetate/hexanes (1:19 to 1:1), to provide 102 mg (28% yield) of the product 350 as a white solid.

Step 245:

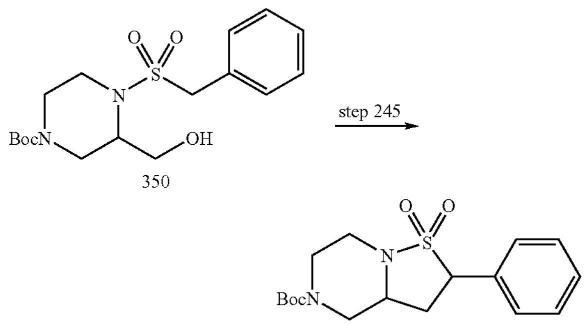

350

351

A solution of (+/−)-tert-butyl 4-(benzylsulfonyl)-3-(hydroxymethyl)piperazine-1-carboxylate 350 (222 mg, 0.60 mmol) and (cyanomethylene)tributylphosphorane (0.30 g, 1.24 mmol) in toluene (5 mL) was heated at 105° C. under nitrogen for 16 h. The solvents were removed from the cooled mixture under reduced pressure, and the residue was purified by CombiFlash Companion (12-g silica gel cartridge), eluting with ethyl acetate/hexanes (100% hexanes to 1:1), to provide 162 mg (77% yield) of the product 351 as a light brown oil.

Step 246:

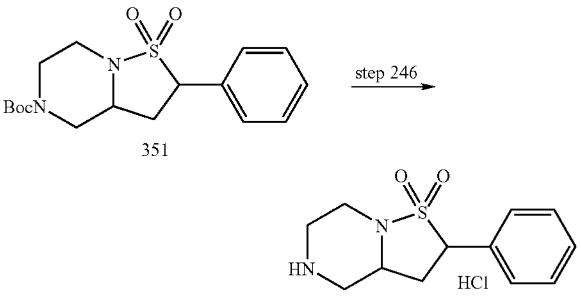

351

352

Solid (+/−)-bicyclic sulfonamide 351 (75 mg, 0.21 mmol) was treated with hydrochloric acid (2 mL, 8 mmol, 4 N in dioxane), and the mixture was stirred at room temperature for 2 h. The thick suspension was dissolved in methanol (25 mL), and the solvents were removed under reduced pressure to provide 63 mg (100% yield) of the product 352 as an off-white solid.

Step 247:

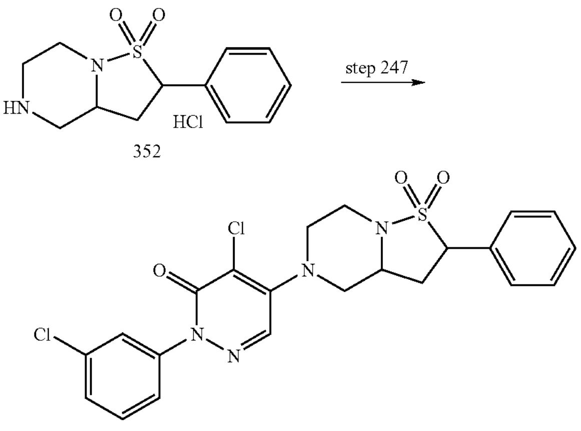

352

353

Diisopropylethylamine (0.11 mL, 0.63 mmol) was added to a mixture of 4,5-dichloro-2-(3-chlorophenyl)pyridazin-3(2H)-one (57 mg, 0.21 mmol) and (+/−)-bicyclic sulfonamide hydrochloride 352 (60 mg, 0.21 mmol) in DMF (0.5 mL) at room temperature under nitrogen, and the mixture was heated at 95° C. for 17 h. The cooled mixture was diluted with ethyl acetate (15 mL), washed with brine (3×15 mL), dried over sodium sulfate, filtered and concentrated. The residue was purified by CombiFlash Companion (4-g silica gel cartridge), eluting with ethyl acetate/hexanes (1:19 to 1:1), to provide 61 mg (59% yield) of the product 353 as a tan solid: MS (M+1): m/e 491.

Step 248:

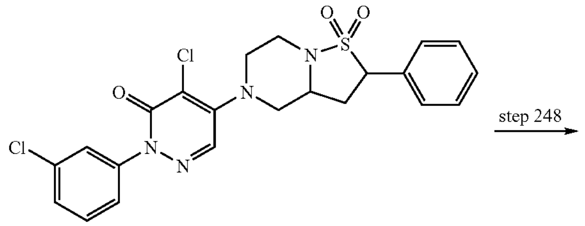

353

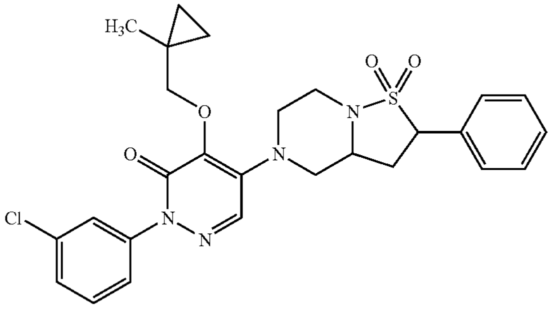

354

A solution of (1-methylcyclopropyl)methanol (20 mg, 0.23 mmol) and sodium hexamethyldisilazide (0.17 mL, 0.17 mmol, 1 N in THF) combined in THF (1 mL) was added dropwise to a solution of (+/−)-bicyclic sulfonamide pyridazinone 353 (55 mg, 0.11 mmol) dissolved in THF (1 mL) at room temperature under nitrogen. The mixture was heated at reflux for 6 h then cooled to room temperature and concentrated. The residue was purified by CombiFlash Companion (12-g silica gel cartridge), elating with ethyl acetate/hexanes (1:19 to 1:1), to provide 17 mg (28% yield) of the product 354 as an off-white solid: MS (M+1) m/e 541.

Scheme 77

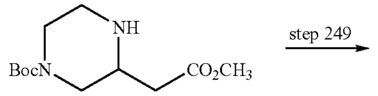

355

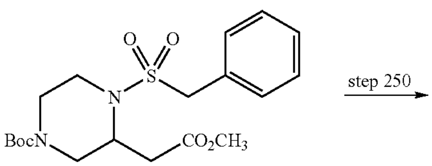

356

-continued

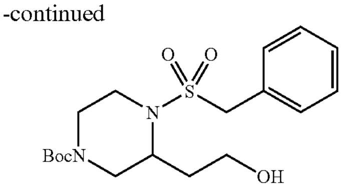

357

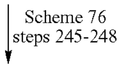

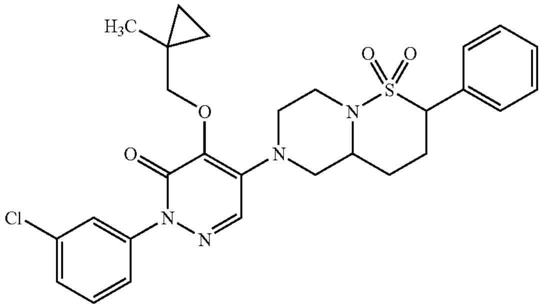

358

Step 249:

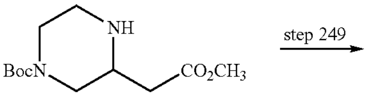

355

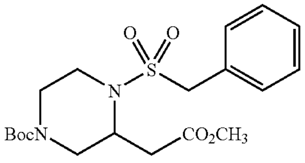

356

A solution of benzylsulfonyl chloride (458 mg, 2.4 mmol) in methylene chloride (5 mL) was added dropwise to a mixture of (+/−)-tert-butyl 3-(2-methoxy-2-oxoethyl)piperazine-1-carboxylate 355 (517 mg, 2.0 mmol) and diisopropylethylamine (0.52 mL, 3.0 mmol) in methylene chloride (10.0 mL) at 0° C. under nitrogen after which the mixture was slowly warmed to room temperature, stirring for a total of 5 days. The solvents were removed under reduced pressure, and the residue was purified by CombiFlash Companion (40-g silica gel cartridge), eluting with ethyl acetate/hexanes (100% hexanes to 2:3), to provide 450 mg (55% yield) of the product 356 as a white foam.

Step 250:

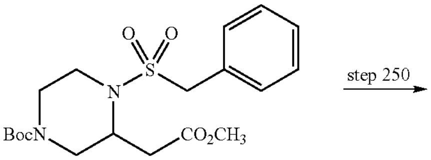

356

-continued

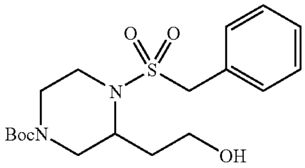

357

A mixture of (+/−)-tert-butyl 4-(benzylsulfonyl)-3-(2-methoxy-2-oxoethyl)piperazine-1-carboxylate 356 (1.29 g, 3.12 mmol) and sodium borohydride in THF (25 mL) was heated at reflux under nitrogen, after which methanol (0.75 mL) was added in small portions over 1 h. The resulting mixture was heated at reflux for an additional 4 h, after which the cooled mixture was diluted with brine (15 mL) and aqueous HCl (40 mL, 0.1 N). The mixture was extracted with ethyl acetate (10 mL), washed with brine (10 mL), dried over sodium sulfate, filtered and concentrated. The residue was purified by CombiFlash Companion (80-g silica gel cartridge), eluting with ethyl acetate/hexanes (1:9 hexanes to 1:1), to provide 0.95 g (79% yield) of the product 357 as a colorless viscous oil.

Steps 245-248 from Scheme 76:

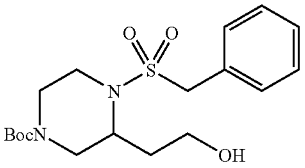

357

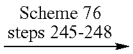

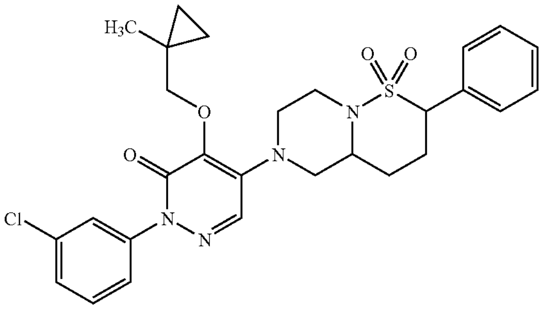

358

Using the procedures described above, compound 358 was synthesized. MS (M+1): m/e 555.

Scheme 78

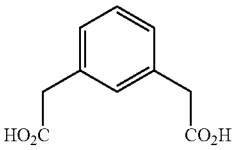

359

-continued

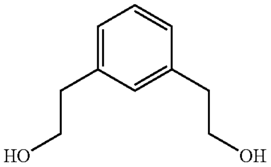

360

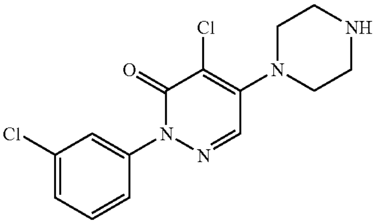

361

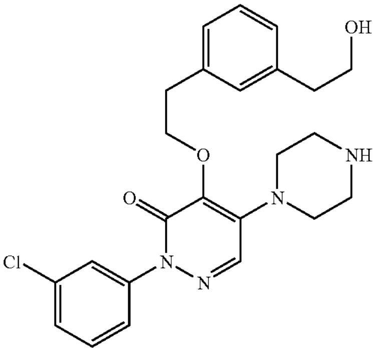

362

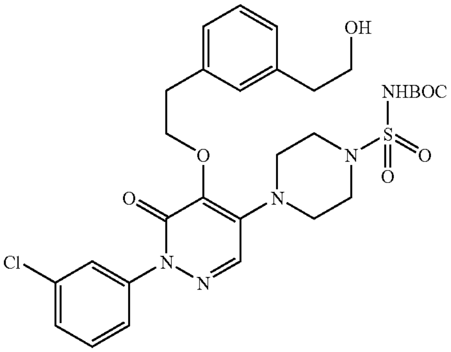

363

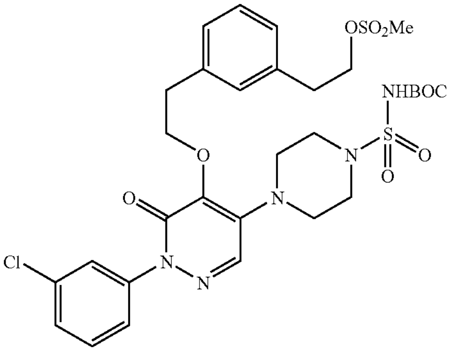

364

-continued

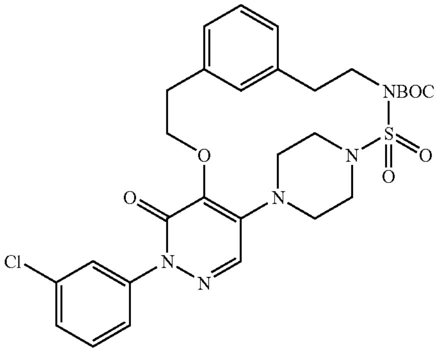

365

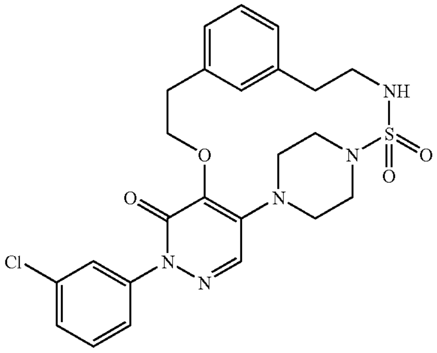

366

Step 251:

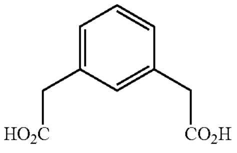

359

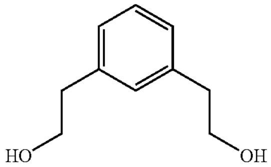

360

$BH_3.SMe_2$ (1.65 ml, 16.5 mmol) was added dropwise to a solution of 1,3-phenylenediacetic acid 359 (0.80 g, 4.12 mmol) in THF (20 mL) at room temperature followed by heating at 75° C. for 3. After cooling, the reaction mixture was diluted with EtOAc (20 mL) and treated with saturated aq. $NH_4Cl$. The organic phase was separated, and the aqueous solution was extracted with EtOAc (20 mL). The combined organic phase was washed with sat. $NaHCO_3$, dried ($MgSO_4$), filtered, and concentrated. The crude product was purified on a silica-gel column (eluant: 5:1 to 1:1 $CH_2Cl_2$/EtOAc gradient) to afford 0.53 g (78% yield) of the product 360 as a white solid.

Step 252:

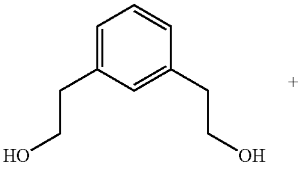

360

+

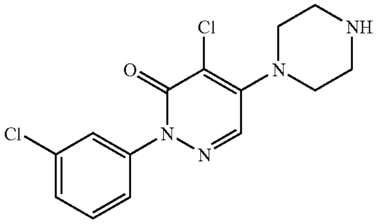

361

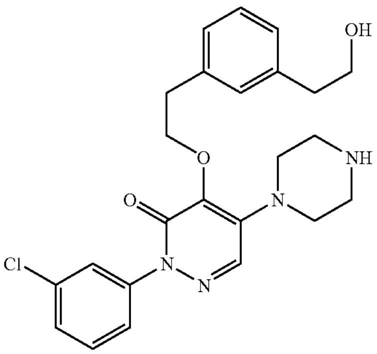

362

Sodium hydride (0.13 mg, 3.2 mmol) was added to a solution of 1,3-diphenylenediethanol 360 (0.53 g, 3.2 mmol) in THF at 0° C. followed by stirring for 15 mins. To the above mixture was added compound 361 (0.54 g, 1.5 mmol), and the reaction was heated for 1 h at 60° C. The reaction mixture was cooled, concentrated, and purified by chromatography on a silica-gel column (eluant: 2:1 $CH_2Cl_2$/EtOAc mixed with 2 M ammonia in 5-20% $CH_3OH$ gradient) to afford 0.41 g (60% yield) of the product 362 as a pale yellow solid. MS (M+1): m/e 455.

Step 253:

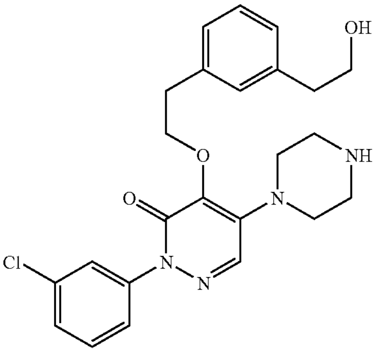

362

-continued

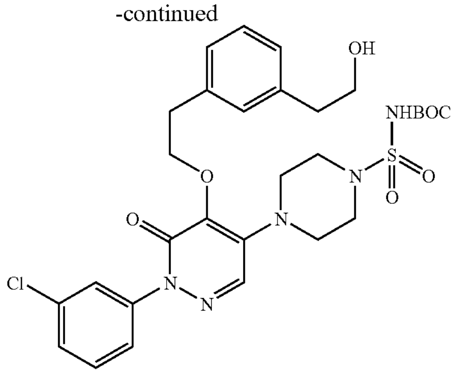

363 tBuOH (61 mg, 0.9 mmol) was added dropwise to a solution of $ClSO_2NCO$ (127 mg, 0.9 mmol) in $CH_2Cl_2$ (10 mL) at 0° C. followed by stirring for 30 mins. The resulting solution was then added to a solution of compound 362 (410 mg, 0.9 mmol) and i-$Pr_2NEt$ (174 mg, 1.35 mmol) in $CH_2Cl_2$ (10 mL) at 0° C. followed by stirring for 2 h, while temperature was slowly allowed to rise to room temperature. The mixture was concentrated, and the residue was purified by chromatography on a silica-gel column (eluant: 0-60% EtOAc/hexane gradient) to afford 0.30 g (53% yield) of the product 363 as a pale yellow solid. MS (M+1): m/e 634.

Step 254:

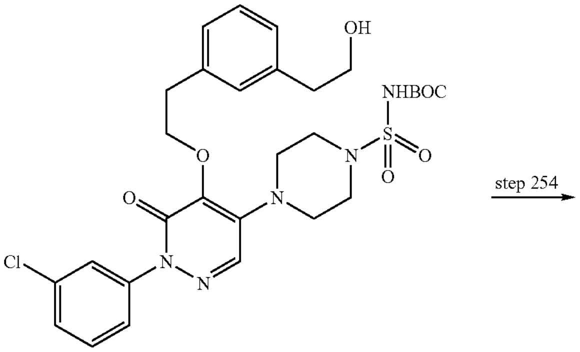

363

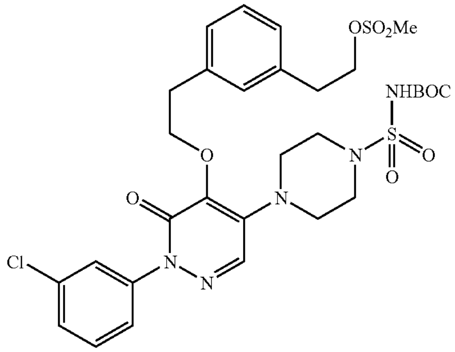

364

Methanesulfonic anhydride (42 mg, 0.24 mmol) was added to a solution of compound 363 (140 mg, 0.22 mmol), DMAP (54 mg, 0.44 mmol) and $Et_3N$ in $CH_2Cl_2$ (5 mL) at 0° C. After the reaction mixture was warmed to room temperature, the reaction was stirred for 2 h. The solvent was concentrated, and the crude product was purified by Prep Gilson HPLC to afford 0.12 g (92% yield) of the product 364 as a pale yellow solid. MS (M+1): m/e 612.

Step 255:

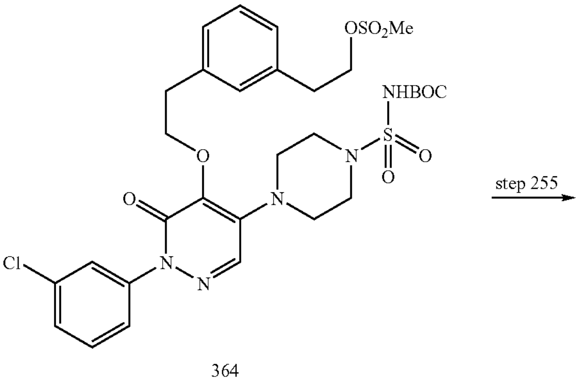

364

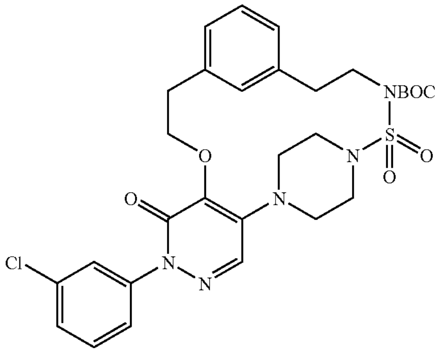

365

Compound 364 (52 mg, 0.07 mmol), $K_2CO_3$ (39 mg, 0.28 mmol) and DMF (5 mL) were mixed in a microwave reaction vial, which was then capped and heated to 90° C. for 1~2 h in a microwave reactor. The progress of the reaction was monitored by mass spectral data. After the reaction was complete, the mixture was diluted with EtOAc (25 mL) and washed with $H_2O$ (20 mL). The organic phase was separated, and the aqueous solution was extracted with EtOAc (20 mL). The organic phase was combined, dried ($MgSO_4$), filtered, and concentrated. The residue was purified by Prep Gilson HPLC to afford 18 mg (42% yield) of the product 365 as a pale yellow solid. MS (M+1): m/e 616.

Step 256:

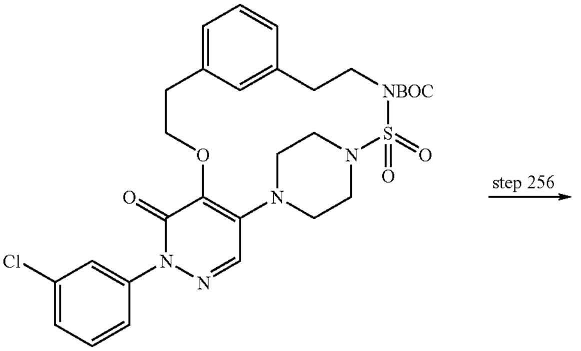

365

-continued
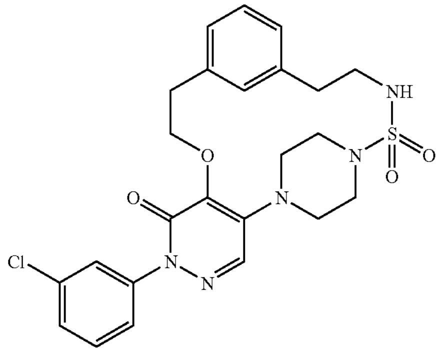
366
Compound 365 (18 mg, 0.03 mmol) and THF/$H_2O$ (4 mL, 3:1) was mixed in a microwave reaction vial, which was then capped and heated at 145° C. for 20 mins in a microwave reactor. After cooling, the reaction mixture was concentrated and purified on a silica-gel column (eluant: 0-35% EtOAc/hexane gradient) to afford 12 mg (80% yield) of the product 366 as a pale yellow solid. MS (M+1): m/e 516.
Scheme 79
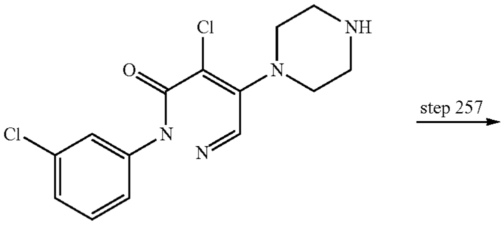
361
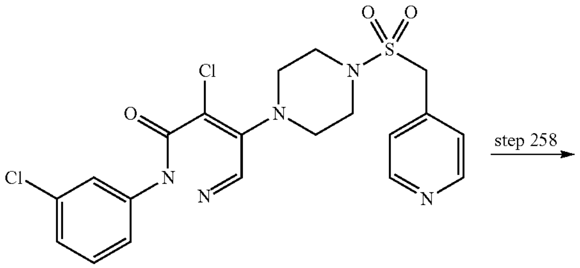
367
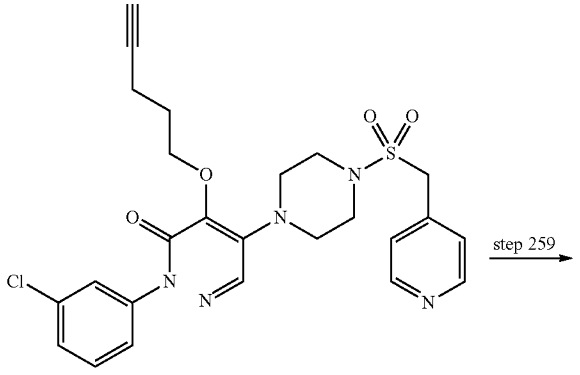
368
-continued
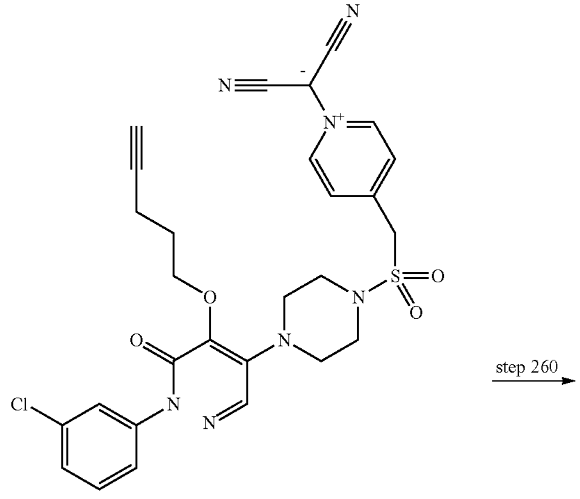
369
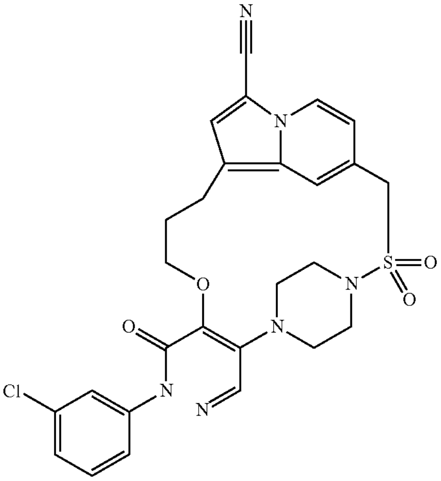
370
Step 257:
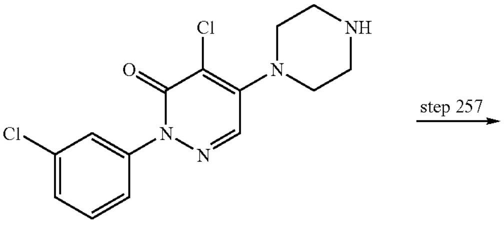
361

-continued

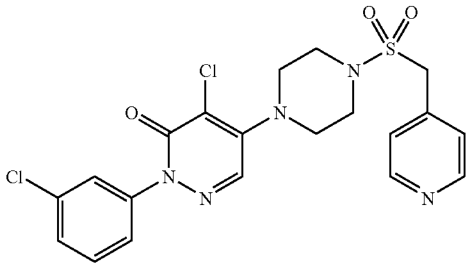

367

Compound 361 (1.06 g, 2.9 mmol) dissolved in $CH_2Cl_2$ (20 mL) was mixed with diisopropylethylamine (0.6 mL) at 0° C. 4-Pyridylmethanesulfonyl chloride TfOH (1.0 g 2.9 mmol) was added. The mixture was stirred at room temperature overnight then diluted with ethyl acetate (100 mL). The organic solution was washed with water then brine, dried over anhydrous sodium sulfate, filtered, and concentrated. Purification by flash chromatography gave 0.81 g (59% yield) of the product 367 as a solid. MS (M+1): m/e 480.

Step 258:

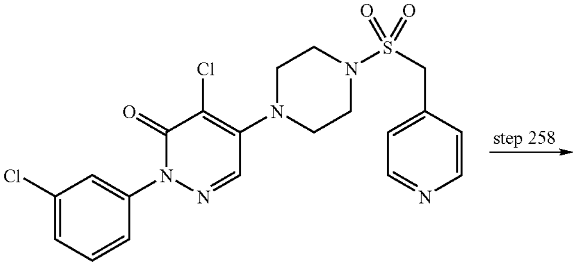

367

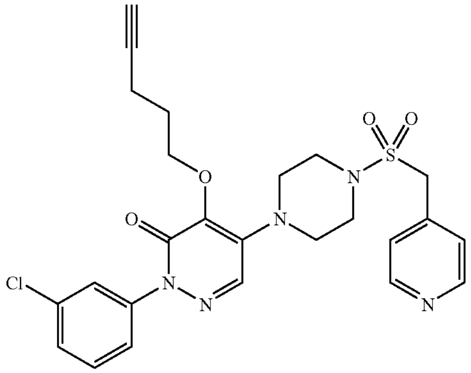

368

Compound 367 (0.1 g, 0.21 mmol) and 4-pentyn-1-ol (0.06 mL, 0.63 mmol) in dry THF (3 mL) were mixed with 60% NaH (12 mg, 0.3 mmol). The mixture was stirred at room temperature for 2 h then diluted with ethyl acetate. The organic solution washed with water then brine, dried over anhydrous sodium sulfate, filtered, and concentrated. Purification by flash chromatography gave 0.081 g (73% yield) of the product 368 as a solid. MS (M+1): m/e 528.

Step 259:

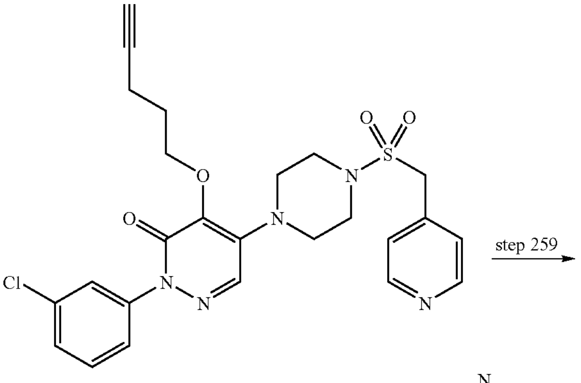

368

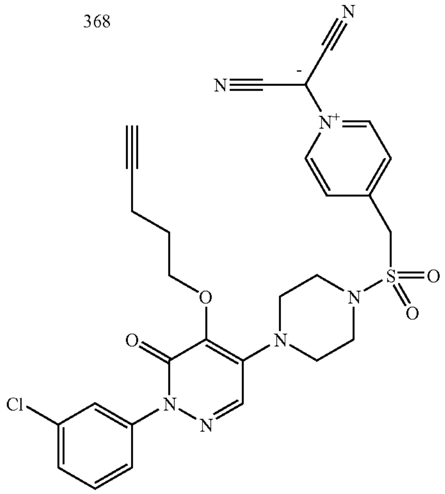

369

Compound 368 (90 mg, 0.17 mmol) in dry THF (5 mL) was mixed with TCNEO (tetracyanoethylene oxide, 0.1 g). The resulting mixture was then stirred at room temperature overnight then concentrated. Purification by prep Gilson HPLC gave 62 mg (62% yield) of the product 369 as a bright yellow solid. MS (M+1): m/e 592.

Step 260:

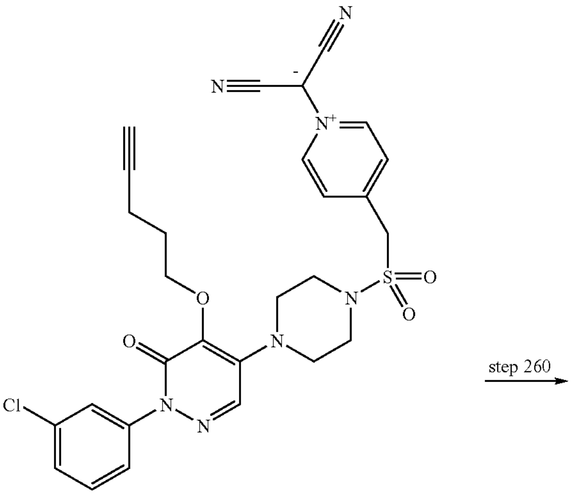

369

-continued
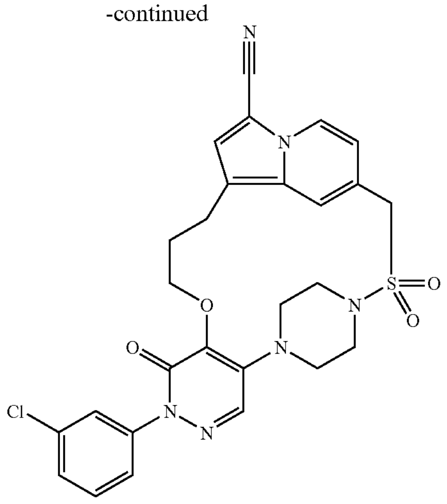
370
Compound 369 (20 mg, 0.034 mmol) in 3 mL of toluene and 0.5 mL of acetonitrile was heated to 180° C. for 15 mins in a microwave reactor. The mixture was concentrated and then purified by prep Gilson HPLC to give 9.5 mg (50% yield) of the product 370. MS (M+1): m/e 565.
Using the procedure above, the following compound was synthesized.
| Cmpd. | Structure | MS M + 1 |
|---|---|---|
| 2022Z | 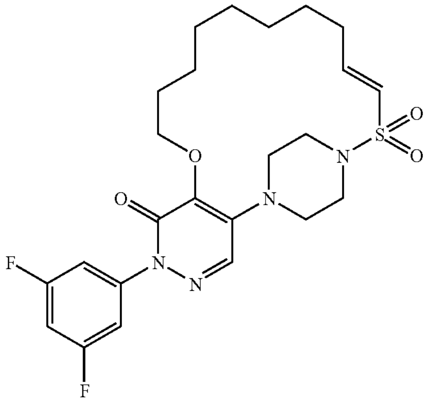 | 509 |
Scheme 80
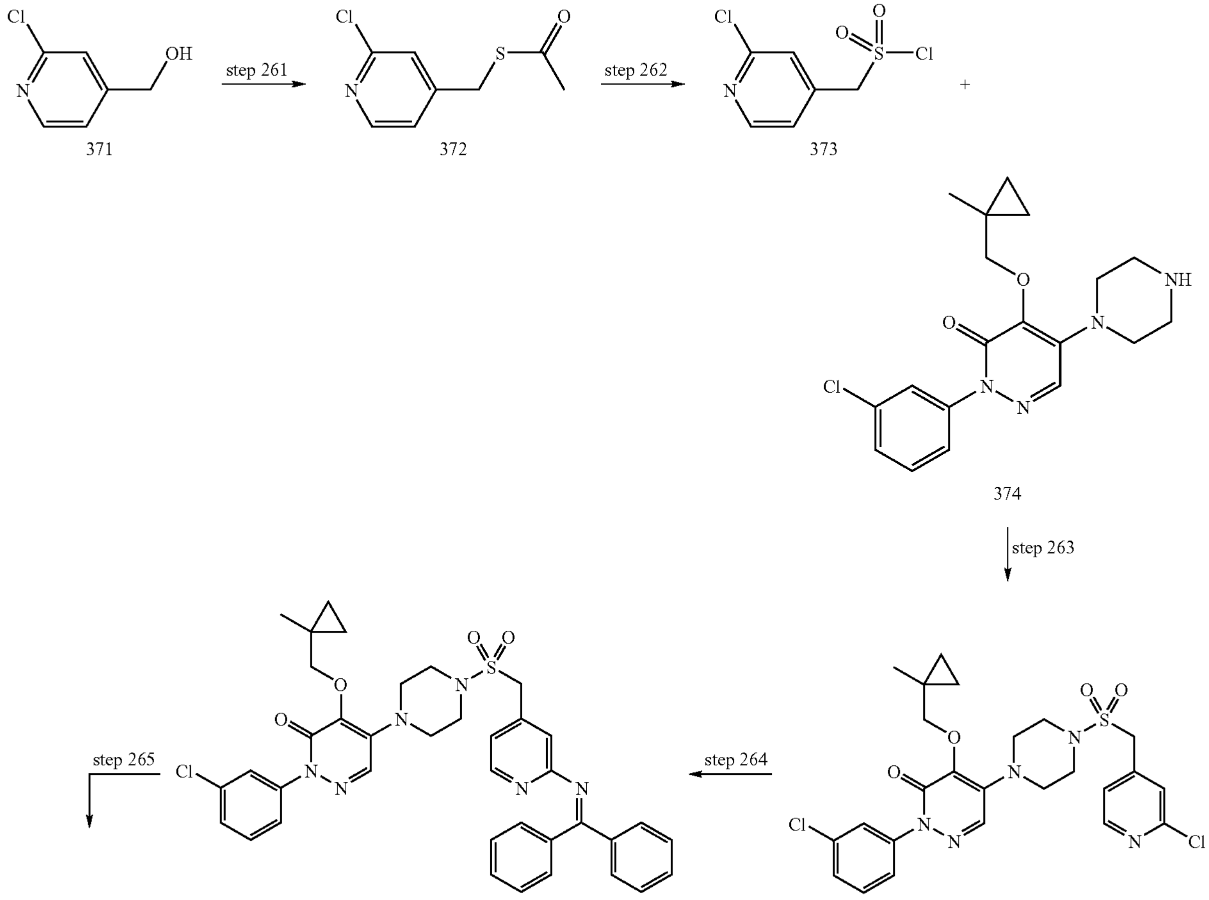
371 372 373 374 375 376

-continued

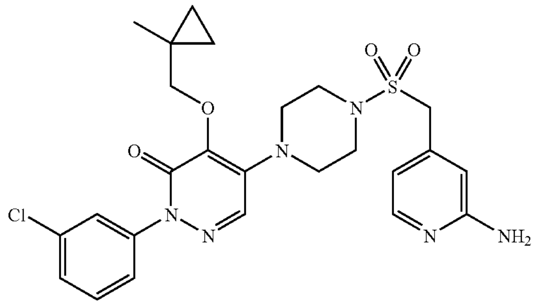

377

Step 261:

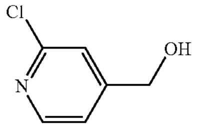

371

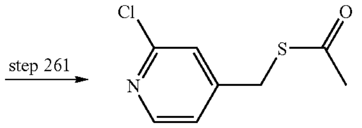

372

Compound 371 (2.15 g, 15 mmol) was mixed with triphenylphosphine (5.24 g, 20 mmol) and thioacetic acid (1.2 mL, 16 mmol) in dry THF (20 mL). DIAD (diisopropyl azodicarboxylate, 3.9 mL, 20 mmol) was added at 0° C. The mixture was stirred at room temperature for 6 h and then concentrated. Purification by flash chromatography gave 1.9 g (63% yield) of the product 372 as a solid. MS (M+1): m/e 202.

Step 262:

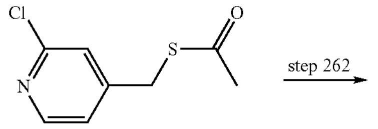

372

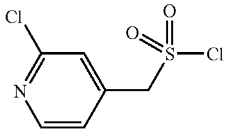

373

Compound 372 (0.35 g, 1.7 mmol) was mixed with water (0.09 mL, 5 mmol) and trifluoromethanesulfonic acid (0.3 mL, 3.4 mmol) in $CH_2Cl_2$ (15 mL) and cooled to 0° C. Chlorine gas was bubbled into the solution for 5 mins. The yellow solution was stirred at 0° C. for 1 h. Dry diethyl ether and hexane were added to the mixture, which was immediately cooled to −78° C. A solid formed at the bottom of the solution, and the solvent was decanted. The solid was washed again with cold hexane, cooled to −78° C., and the solvent was decanted to give the sulfonyl chloride product 373 as the triflate salt which was used in the next step immediately.

Step 263:

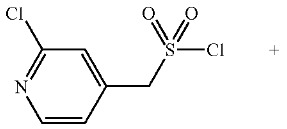

373

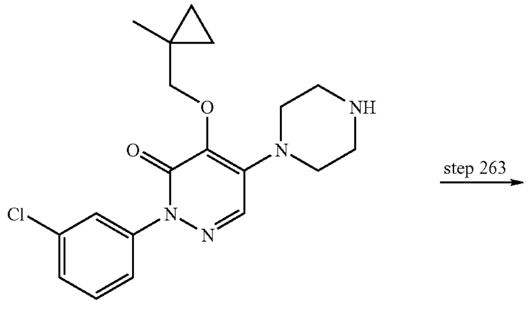

374

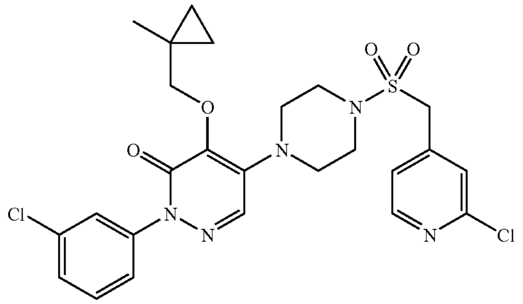

375

Compound 373 (~1.7 mmol) at −78° C. was mixed with compound 374 (750 mg, 2 mmol) and diisopropylethylamine (5 mmol) in $CH_2Cl_2$ (10 mL). The mixture was stirred at room temperature overnight then diluted with ethyl acetate (100 mL). The organic solution was washed with water then brine, dried over anhydrous sodium sulfate, filtered, and concentrated. Purification by flash chromatography gave 0.26 g (27% yield) of the product 375 as a solid. MS (M+1): m/e 564.

Step 264:

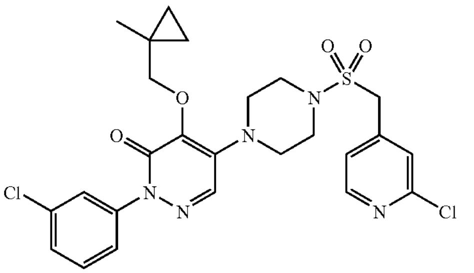

375

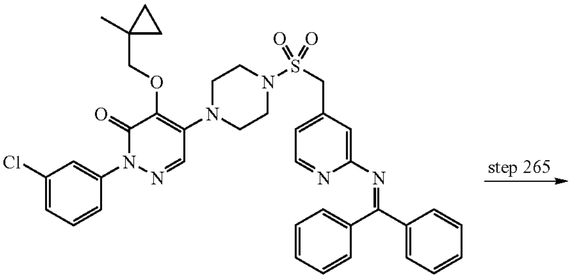

376

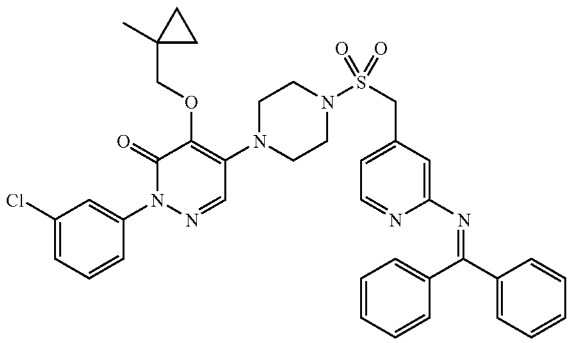

376

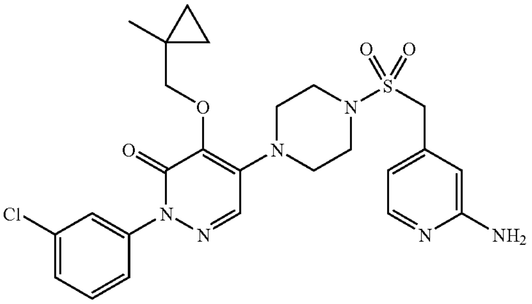

377

Compound 375 (35 mg) was mixed with palladium acetate (0.5 mg), BINAP (1.5 mg), benzophenone imine (20 mg), and cesium carbonate (100 mg). The mixture was heated to at 90° C. under nitrogen overnight then diluted with EtOAc (50 mL). The organic solution was washed with water then brine, dried, filtered, and concentrated. The crude product 376 was used in the next step without further purification.

Step 265:

Compound 376 was treated with sodium acetate (0.1 g) and hydroxylamine hydrochloride (0.1 g) in methanol (3 mL) at room temperature for 1 h. The mixture was concentrated and then purified by prep Gilson HPLC to give 12 mg of the product 377 as the formate salt. MS (M+1): m/e 545.

Scheme 81

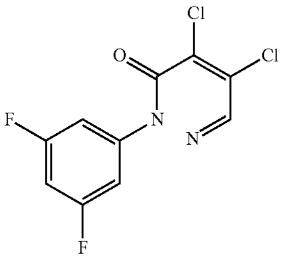

378

+

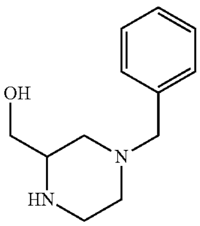

379

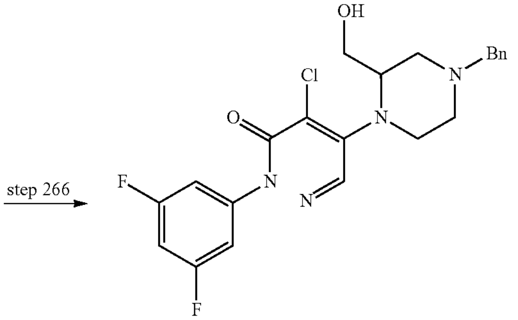

380

-continued

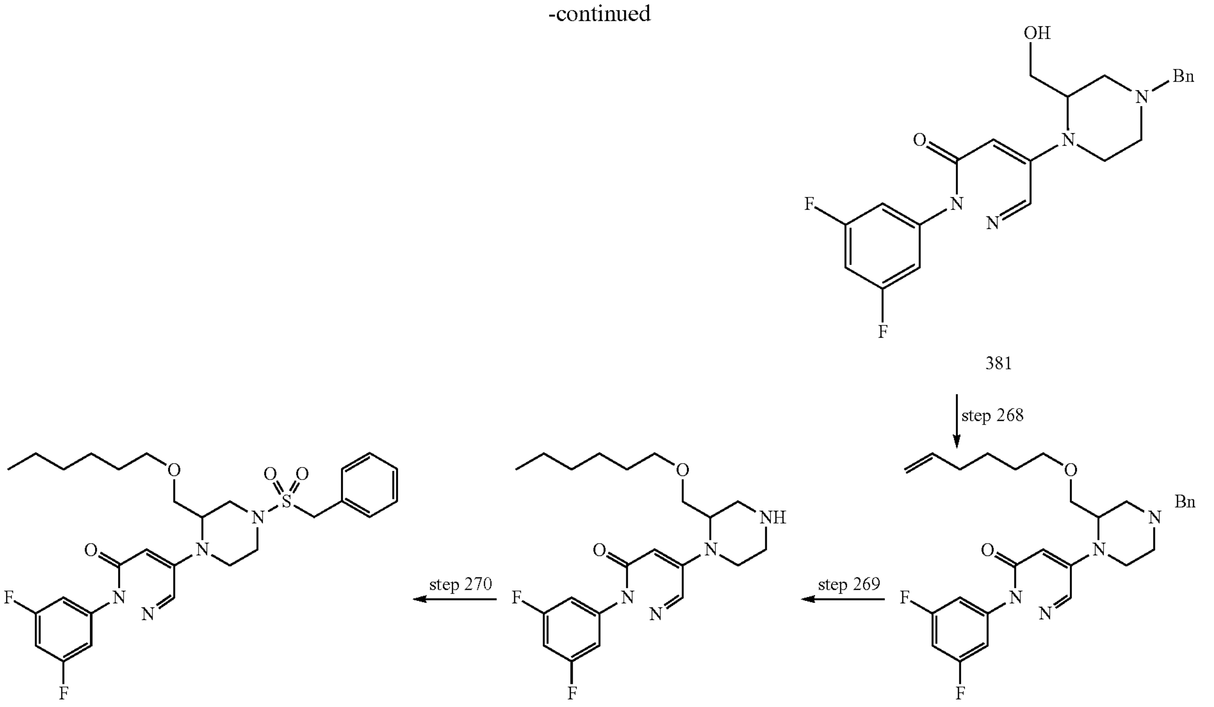

381

384 383 382

Step 266:

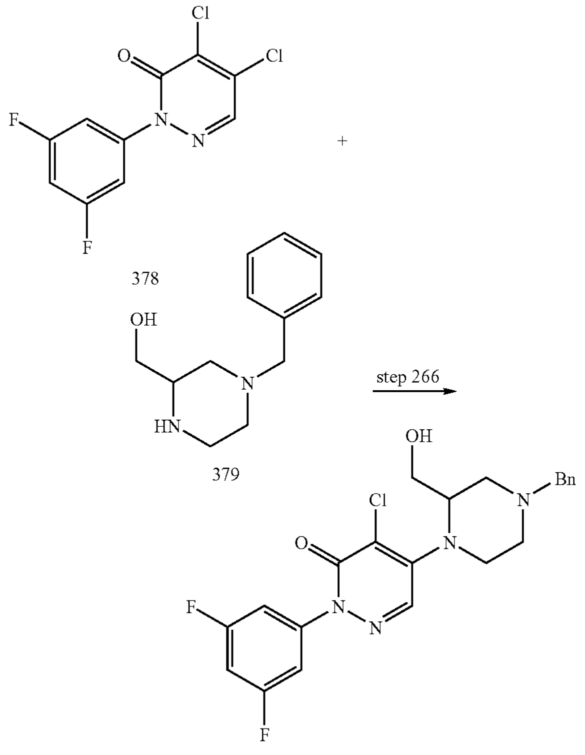

378

379

380

N-benzylhydroxymethylpiperazine was prepared according to the reported literature procedure: A. Naylor et al, *J. Med. Chem.* 1993, 36, 2075-2083. To compound 379 (2.48 g, 12.00 mmol), which was dried just before use by azeotropic distillation with toluene under reduced pressure, dissolved in anhydrous DMF (24 mL) under an argon atmosphere was successively added N,N-diisopropylethylamine (3.15 mL, 17.95 mmol), 4 Å molecular sieves and dichloropyridazinone 378 (1.68 g, 5.98 mmol). The reaction mixture was heated at 100° C. for 23 h. Upon cooling to room temperature, the mixture was poured into an aqueous pH 7 phosphate buffer solution (400 mL) and diluted with ethyl acetate (300 mL). After decantation, the aqueous solution was extracted with ethyl acetate (3x350 mL). The combined organic extract was successively washed with water (400 mL) then brine (400 mL), dried ($MgSO_4$), filtered, and concentrated. The crude oil was recrystallized from boiling ethyl acetate (250 mL), filtered and rinsed with cold methylene chloride (70 mL) to give 1.08 g of the product 380 (41% yield) as an off-white solid. MS (M+1): m/e 447.

Step 267:

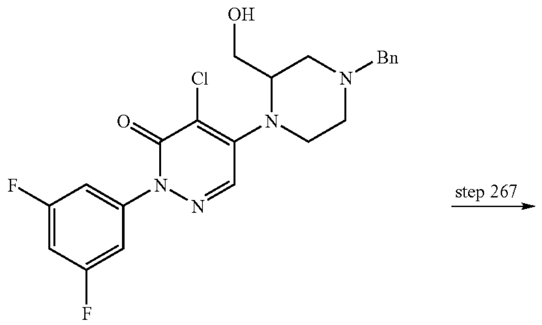

380

-continued

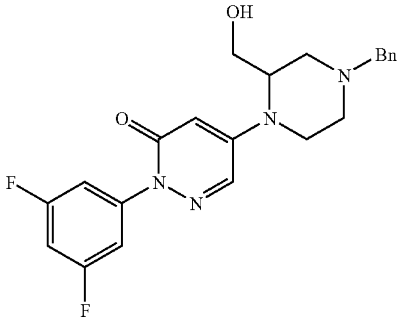

381

To chloropyridazinone 380 (100.0 mg, 0.224 mmol) dissolved in ethyl acetate (0.84 mL) and methanol (0.28 mL) at room temperature was added platinum oxide (20.4 mg, 0.090 mmol). A hydrogen atmosphere was introduced using a rubber balloon as the gas source, and the reaction mixture was stirred at room temperature for 6 h. The crude suspension was filtered over a ¼ inch celite pad under a positive pressure of nitrogen, thoroughly rinsed with methanol (50 mL) and concentrated. Purification by silica gel chromatography (eluant: 100% $CH_2Cl_2$ to 100% EtOAc gradient) gave 19.6 mg (20% yield) of the product 381 as a pale yellow oil. MS (M+1): m/e 413.

Step 268:

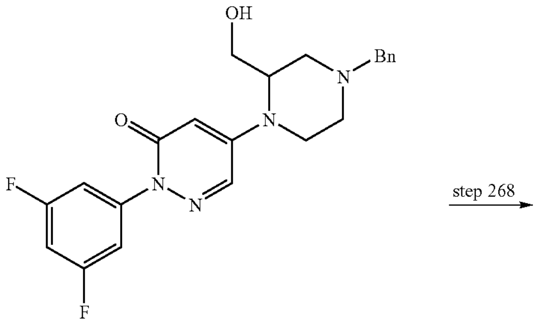

381

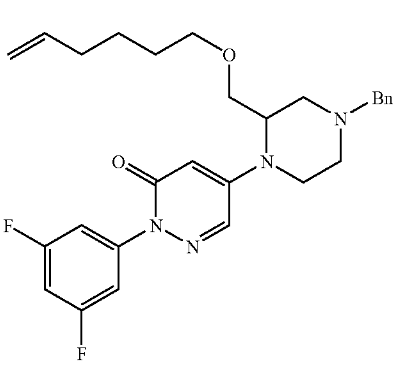

382

To compound 381 (19.0 mg, 0.045 mmol), dissolved in anhydrous THF (0.45 mL) under an argon atmosphere at 0° C. was added tetrabutylammonium iodide (16.6 mg, 0.045 mmol), followed by 6-bromo-1-hexene (30.1 μL, 0.225 mmol). Sodium hydride was then added (60% dispersion in oil, 3 mg, ca. 0.068 mmol). The milky reaction mixture was then vigorously stirred at room temperature. Additional portions of 6-bromo-1-hexene (30.1 μL, 0.225 mmol) and NaH (60% dispersion in oil, 3 mg, ca. 0.068 mmol) were added until complete consumption of starting material was indicated by TLC and MS. The reaction mixture was diluted with $Et_2O$ (30 mL) and carefully quenched with an aqueous pH 7 phosphate buffer solution (20 mL). The aqueous solution was extracted with $Et_2O$ (3×30 mL). The combined organic extract was washed successively with an aqueous pH 7 phosphate buffer solution (30 mL) then brine (30 mL), dried ($MgSO_4$), filtered, and concentrated to give 23.7 mg (98% yield) of the product 382 as a light yellow oil which was used for the next step without purification. MS (M+1): m/e 495.

Step 269:

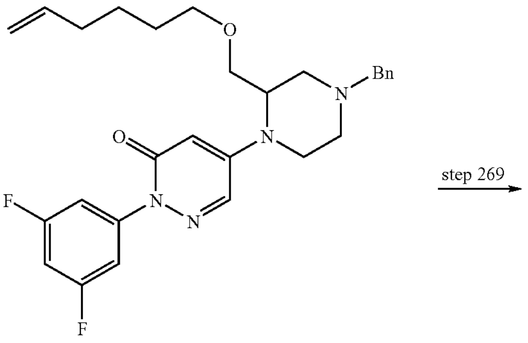

382

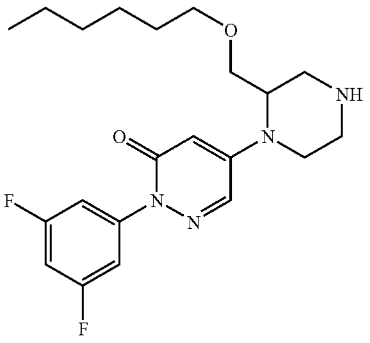

383

To compound 382 (23.7 mg, 0.045 mmol) dissolved in a methanolic solution of formic acid (v/v 5%, 0.45 mL) at room temperature was added 5% palladium over carbon (37.0 mg). The reaction mixture was vigorously stirred for 4 h, after which an additional portion of 5% Pd—C (20 mg) and methanolic solution of formic acid (v/v 5%, 0.1 mL) were added. After 3 h of additional stirring, the crude suspension was filtered over a celite pad under a positive pressure of nitrogen, thoroughly rinsed with methanol (50 mL) and concentrated to give 10.8 mg of crude oil containing the product 383. MS (M+1): m/e 407. This material was used for the next step without purification.

Step 270:

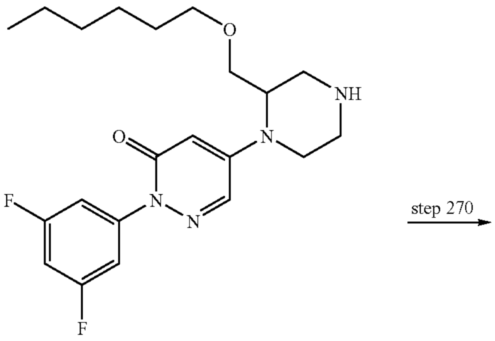

383

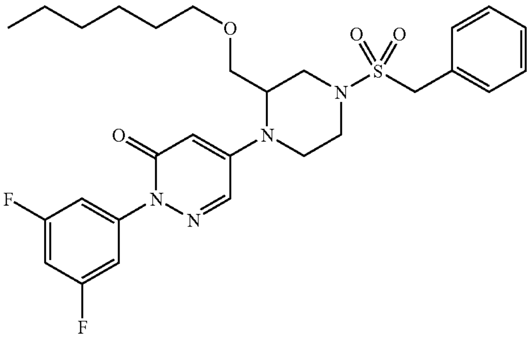

384

To compound 383 (10.8 mg of crude material from step 269, ca. 0.045 mmol) dissolved in $CH_2Cl_2$ (0.25 mL) was successively added triethylamine (10 μL, 0.062 mmol) and α-toluenesulfonyl chloride (7.1 mg, 0.037 mmol) at 0° C. The reaction mixture was stirred at room temperature for 18 h and then concentrated to dryness. Purification by silica gel chromatography (eluant: 100% hexanes to 100% EtOAc gradient) gave 2.8 mg (21% yield over steps 267 and 270 combined) of the product 384 as a white solid. MS (M+1): m/e 561.

Using procedures similar to the ones described above, the following compounds were synthesized.

| Cmpd. No | Structure | MS M + 1 |
|---|---|---|
| 2023Z | 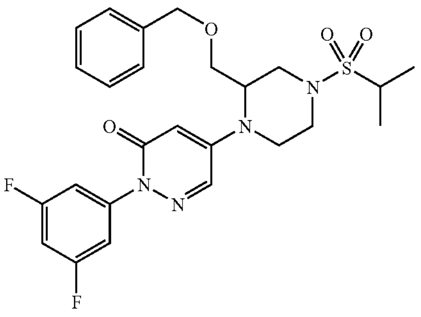 | 519 |

-continued

| Cmpd. No | Structure | MS M + 1 |
|---|---|---|
| 2024Z | 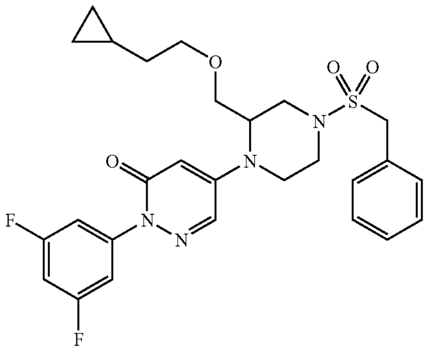 | 545 |
| 2025Z | 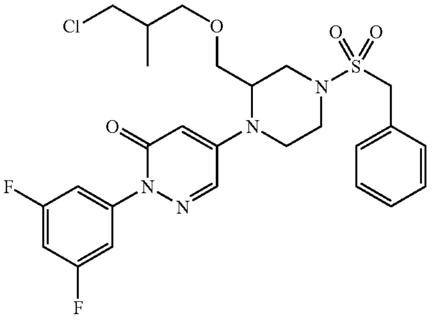 | 567 |
| 2026Z | 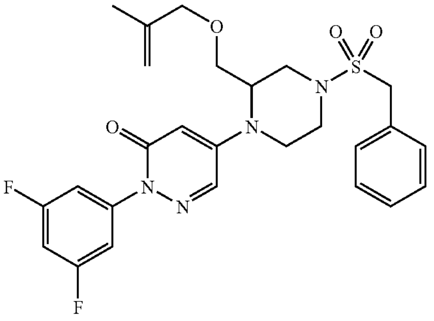 | 531 |

Scheme 82
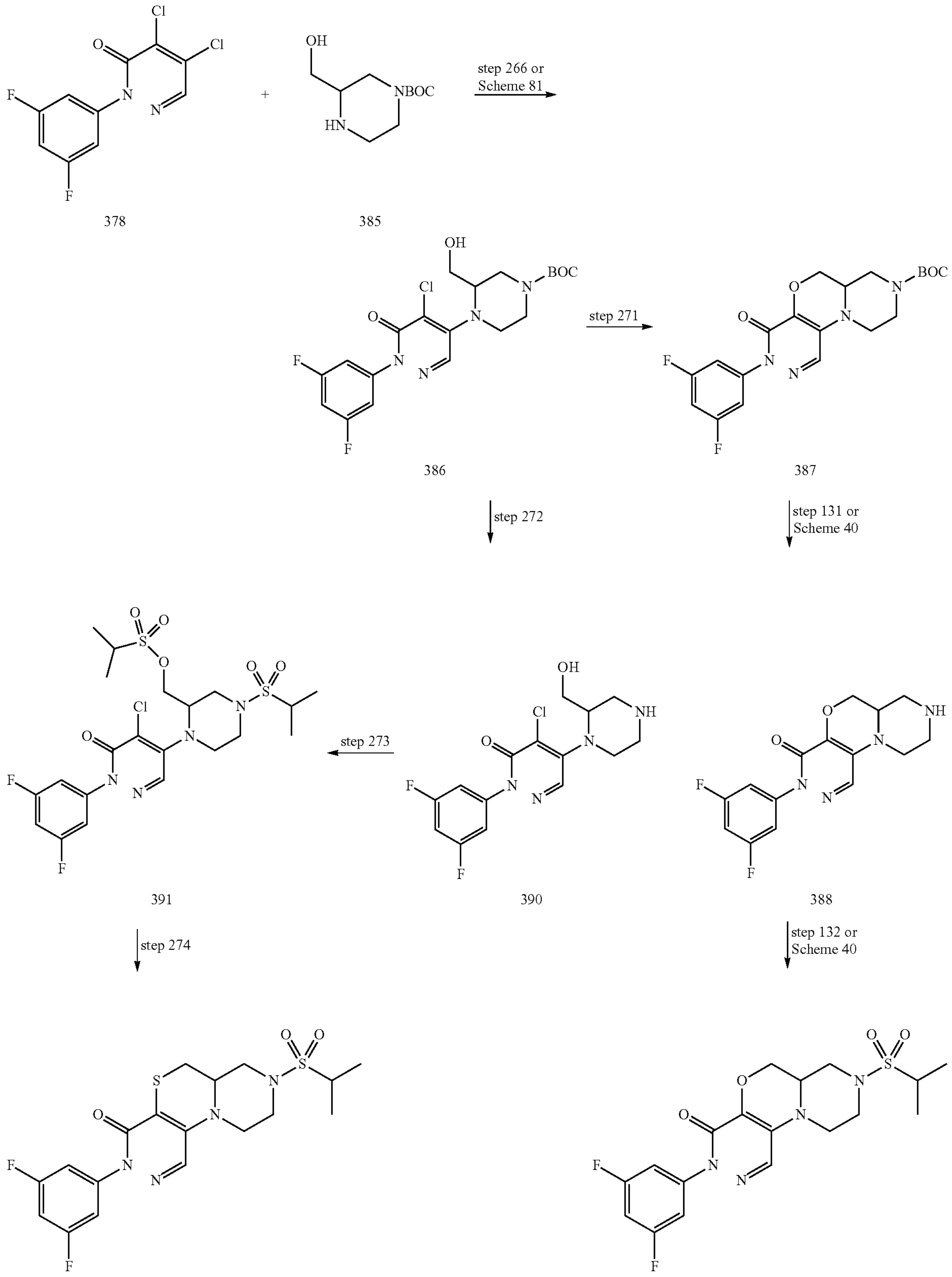
378 385 386 387 391 390 388 392 389

Step 266 from Scheme 81:

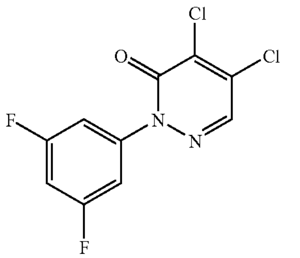

378

+

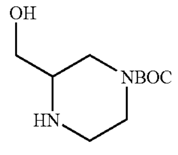

385 step 266 of
Scheme 81

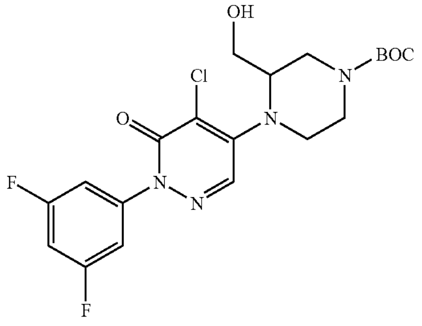

386

Using the procedure of step 266 from Scheme 81, compound 386 was synthesized. MS (M+1): m/e 457.

Step 271:

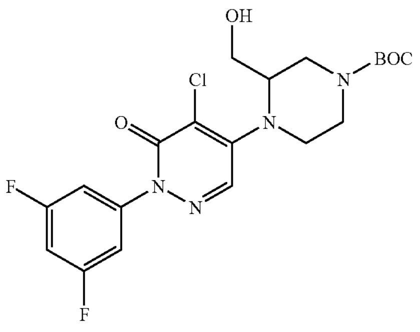

386 step 271

-continued

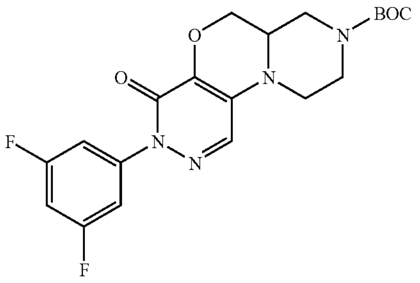

387

To chloropyridazinone 386 (176 mg, 0.385 mmol) dissolved in dry THF (10 mL) was added sodium hexamethyldisilazide (1.0 M in THF, 2.0 mL, 2.0 mmol). The reaction mixture was stirred at room temperature for 16 h. Saturated $NH_4Cl$ (5 mL) and water were added, and the aqueous solution was extracted with $CH_2Cl_2$. The organic solution was dried ($MgSO_4$), filtered, and concentrated. Purification by silica gel chromatography (eluant: EtOAc-hexanes gradient) gave 58 mg (36% yield) of the product 387 as a yellow solid. MS (M+1): m/e 421.

Steps 131-132 from Scheme 40:

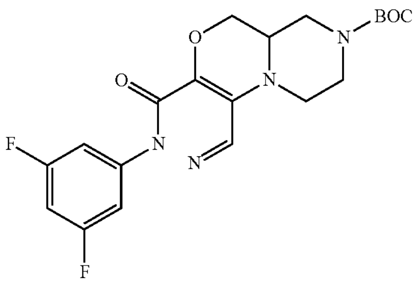

387 steps 131-132
of Scheme 40

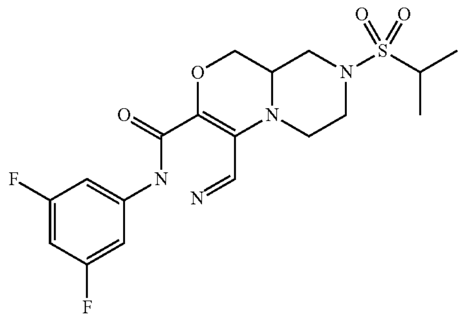

389

Using the procedures of steps 131-132 from Scheme 40, compound 389 was synthesized. MS (M+1): m/e 427.

Step 272:

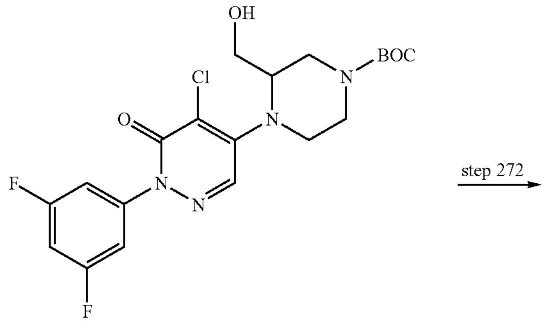

386

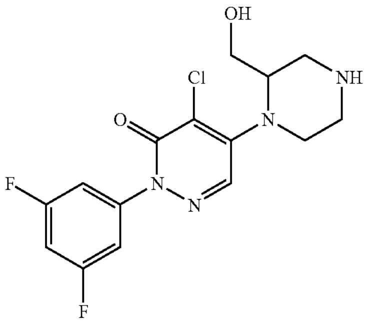

390

To compound 386 (250 mg, 0.547 mmol) dissolved in $CH_2Cl_2$ (20 mL) was added 4 N HCl in dioxane (2 mL, 8 mmol). The reaction mixture was stirred at room temperature for 4 h then concentrated. Additional MeOH and $CH_2Cl_2$ were added, and the solution was concentrated again to give 215 mg (100% yield) of the product 390 as the hydrochloride salt as a white solid. MS (M+1): m/e 357.

Step 273:

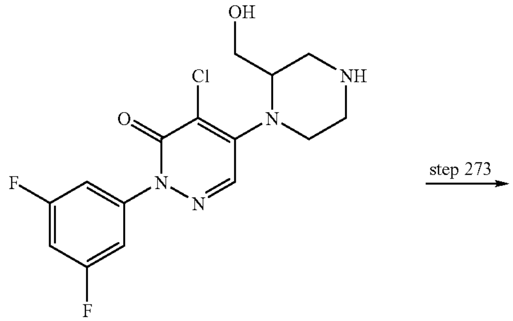

390

-continued

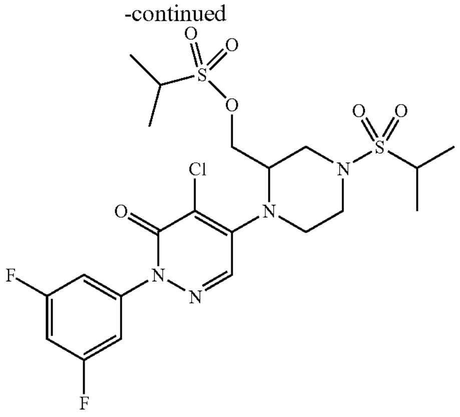

391

To compound 390 (108 mg, 0.275 mmol) dissolved in $CH_2Cl_2$ (10 mL) was added Hunig's base (0.20 mL, 0.15 g, 1.1 mmol) and isopropylsulfonyl chloride (0.10 mL, 0.13 g, 0.89 mmol). The reaction mixture was stirred at room temperature for 4 h and then water was added. The aqueous solution was extracted with $CH_2Cl_2$. The organic solution was dried ($MgSO_4$), filtered, and concentrated to give 156 mg (100% yield) of the product 391 as an orange solid. MS (M+1): m/e 569.

Step 274:

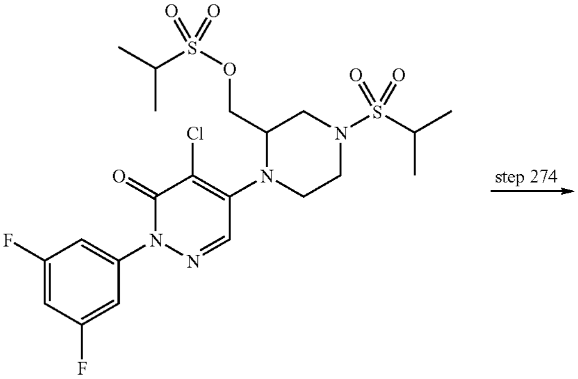

391

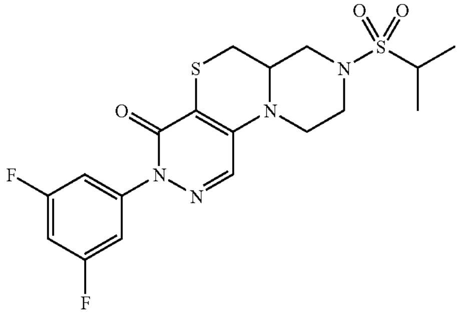

392

To compound 391 (156 mg, 0.275 mmol) dissolved in dry DMSO (3 mL) was added disodiumsulfide (108 mg, 0.450 mmol). The reaction mixture was stirred at room temperature for 16 h and then water was added. The aqueous solution was extracted with EtOAc. The organic solution was dried ($MgSO_4$), filtered, and concentrated. Purification by silica gel chromatography (eluant: 50% EtOAc in hexanes) gave 30 mg (25% yield) of the product 392 as an oil. MS (M+1): m/e 443.
Scheme 83
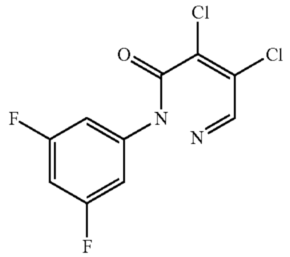
378
+
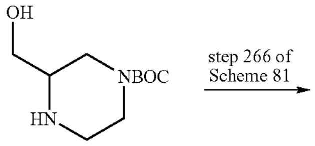
385
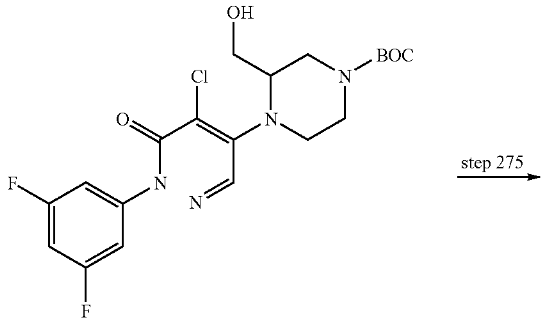
386
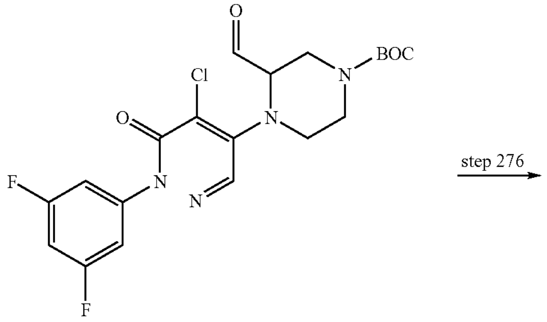
393
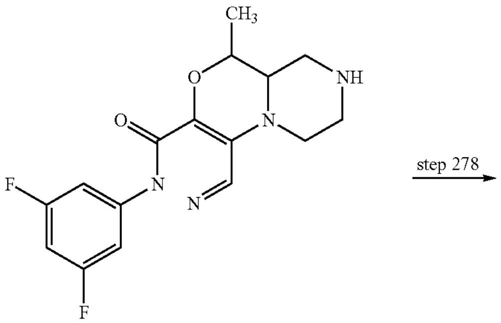
396
-continued
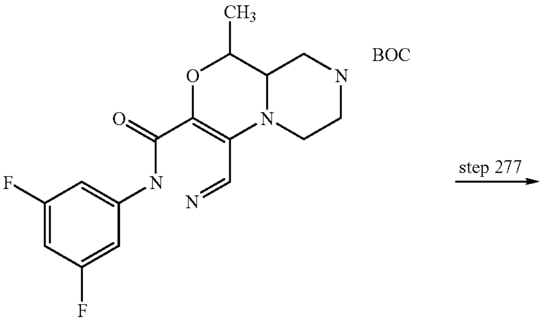
395
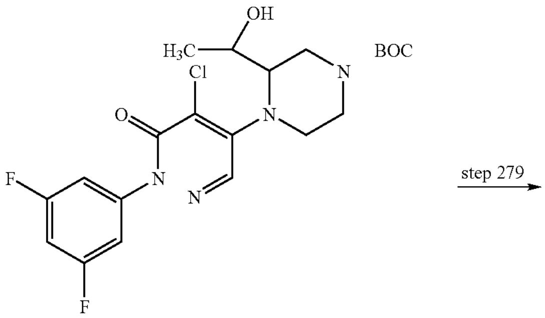
394
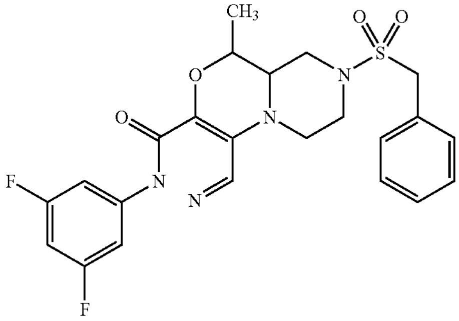
397
Step 266 from Scheme 81:
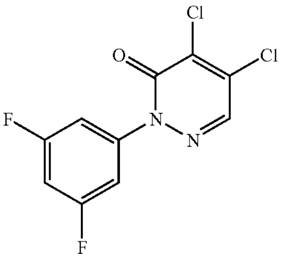
378
+
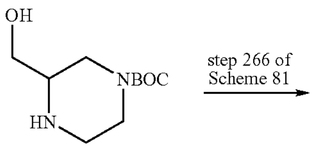
385

-continued

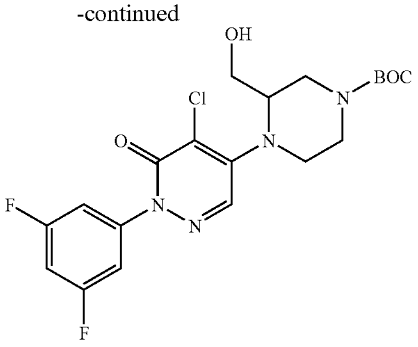

386

Using the procedure of step 266 from Scheme 81, compound 386 was synthesized. MS (M+1): m/e 457.

Step 275:

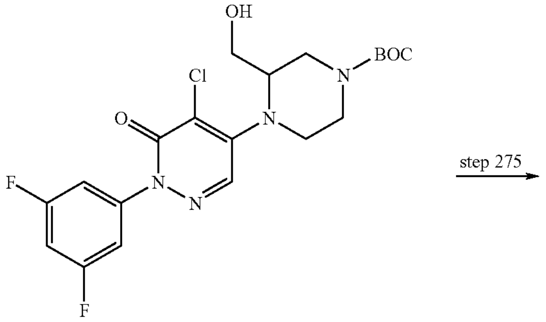

386

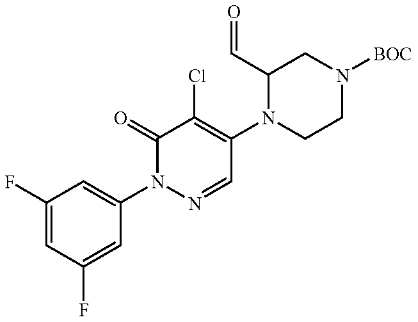

393

To oxalyl chloride (33.0 μL, 0.394 mmol) in anhydrous methylene chloride (0.20 mL) at −78° C. was added dropwise a solution of anhydrous DMSO (58.0 μL, 0.788 mmol) in anhydrous methylene chloride (0.20 mL). After stirring for 10 mins, chloropyridazinone 386 (100.0 mg, 0.197 mmol) suspended in anhydrous methylene chloride (1.00 mL) was added using a canula. After 40 mins additional stirring at −78° C., anhydrous triethylamine (220.0 μL, 1.576 mmol) was added, and the reaction mixture was allowed to warm up to −10° C. over 1 h. The reaction mixture was then quenched with an aqueous pH 7 phosphate buffer solution (20 mL) and diluted with ethyl acetate (30 mL). After decantation, the aqueous solution was extracted with diethyl ether (2×30 mL) and finally once with ethyl acetate (30 mL). The combined organic extract was successively washed with an aqueous pH 7 phosphate buffer solution (40 mL), water (40 mL) and then brine (40 mL), dried ($MgSO_4$), filtered, and concentrated. Purification by silica gel chromatography (eluant: EtOAc-methylene chloride gradient) gave 34.9 mg (39% yield) of the product 393 as a yellow solid. MS (M+1): m/e 455.

Step 276:

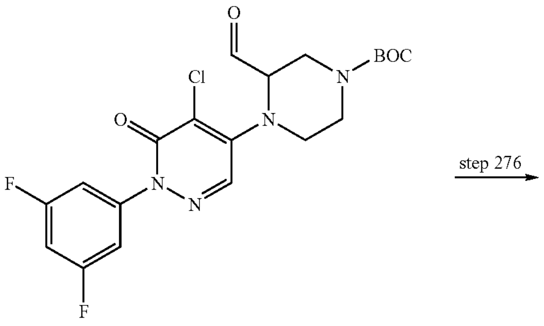

393

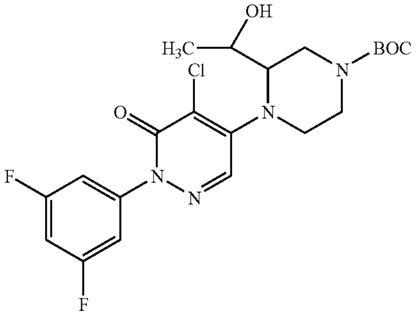

394

To chloropyridazinone 393 (63.5 mg, 0.138 mmol), which was dried just before use by azeotropic distillation with toluene under reduced pressure, dissolved in anhydrous THF (1.20 mL) at −40° C. was added dropwise a solution of methylmagnesium bromide (116.0 μL, 3.0 M in diethyl ether). After 40 mins, the reaction mixture was quenched at −40° C. with an aqueous pH 7 phosphate buffer solution (20 mL) and diluted with ethyl acetate (20 mL). After decantation, the aqueous solution was extracted with ethyl acetate (2×40 mL). The combined organic extract was successively washed with an aqueous pH 7 phosphate buffer solution (40 mL), and then brine (40 mL), dried ($MgSO_4$), filtered, and concentrated. The crude material (82.1 mg, obtained with trace-amount of residual solvents) showed exclusively the product 394 by MS and NMR and was used for the next step without additional purification. MS (M+1): m/e 471

Step 277:

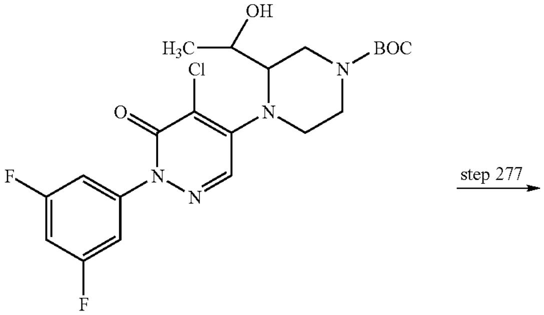

394

-continued

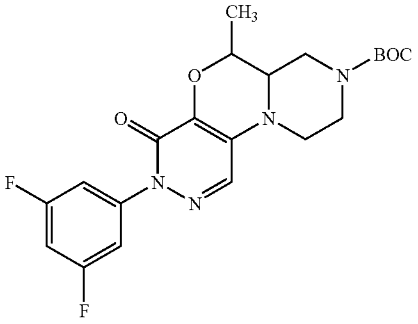

395

To compound 394 (80.0 mg, ca 0.112 mmol crude), which was dried just before use by azeotropic distillation with toluene under reduced pressure, dissolved in anhydrous THF (111.20 mL) at room temperature was added sodium hydride (4.5 mg, 60% dispersion in oil, 0.112 mmol), followed by palladium acetate (1.3 mg, 0.0056 mmol) and rac-BINAP (3.5 mg, 0.0056 mmol). After stirring for 3 h at room temperature, sodium hydride (2.0 mg, 60% dispersion in oil, 0.050 mmol) was then added, and the mixture was heated to 35° C. for an additional 3 h period. The reaction mixture was quenched with an aqueous pH 7 phosphate buffer solution (20 mL) and diluted with diethyl ether (30 mL). After decantation, the aqueous solution was extracted with diethyl ether (2×30 mL) and finally once with ethyl acetate (40 mL). The combined organic extract was successively washed with an aqueous pH 7 phosphate buffer solution (20 mL), and then brine (20 mL), dried ($MgSO_4$), filtered, and concentrated. Purification by silica gel chromatography (eluant: EtOAc-methylene chloride gradient) gave 49.2 mg of a mixture of alcohol 394 (31% yield based on 393) and the product 395 (40% yield over two steps) as a yellow oil. MS for 395 (M+1): m/e 435. Further purification is possible but the mixture was used as such for the next step.

Step 278:

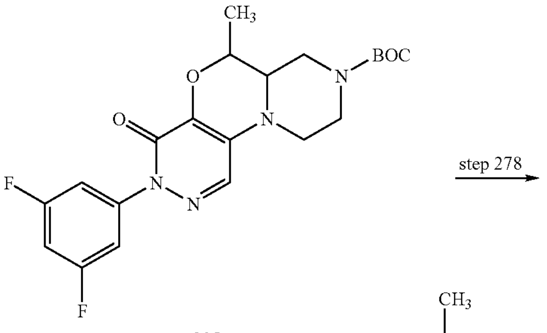

395

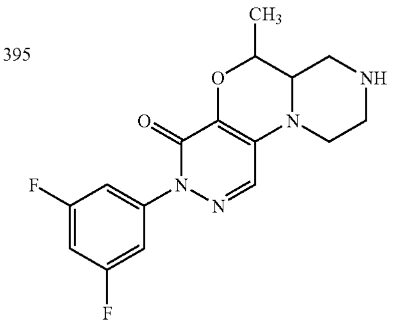

396

To compound 395 (48.0 mg of a mixture with 394, 0.098 mmol total), dissolved in dry methylene chloride (0.80 mL) was added TFA (0.14 mL, 1.88 mmol). The reaction mixture was stirred at room temperature for 70 mins and then quenched with a saturated aqueous solution of $Na_2CO_3$ (30 mL) and diluted with ethyl acetate (30 mL). The aqueous solution was extracted with ethyl acetate (3×30 mL). The combined organic extract was successively washed with a saturated aqueous solution of $Na_2CO_3$ (30 mL) and brine (20 mL), dried ($MgSO_4$), filtered, and concentrated to give 37.7 mg of yellow foam which was used for the next step without purification. MS analysis showed exclusively 396 and the amine corresponding to residual 394. MS for 396 (M+1): m/e 335.

Step 279:

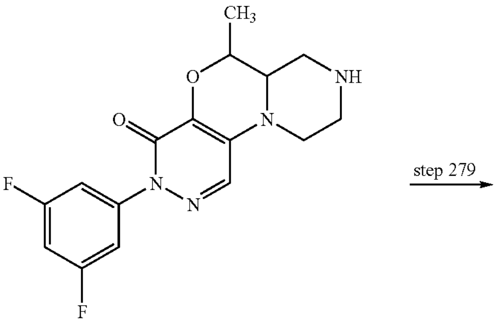

396

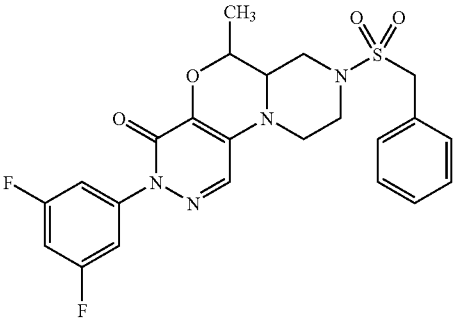

397

To compound 396 (37.7 mg of mixture, ca 0.090 mmol total), which was dried just before use by azeotropic distillation with toluene under reduced pressure, dissolved in anhydrous $CH_2Cl_2$ (0.30 mL) was added dry diisopropylethylamine (0.235 ml, 1.35 mmol), followed by α-tosyl chloride (120.0 mg, 0.63 mmol). The reaction mixture was stirred at room temperature for 48 h, then quenched with an aqueous pH 7 phosphate buffer solution (25 mL) and diluted with diethyl ether (30 mL). After decantation, the aqueous solution was extracted with ethyl acetate (2×35 mL). The combined organic extract was successively washed with an aqueous pH 7 phosphate buffer solution (30 mL), and then brine (30 mL), dried ($MgSO_4$), filtered, and concentrated. Purification by silica gel chromatography (eluant: EtOAc-methylene chloride gradient) gave 7.8 mg (26% yield) of the product 397 as a yellow glass. MS (M+1): m/e 489.

Scheme 84
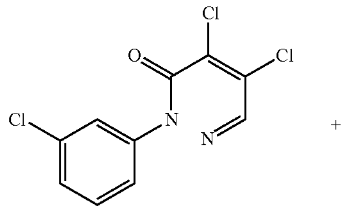
2
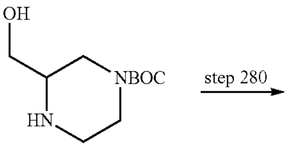
385
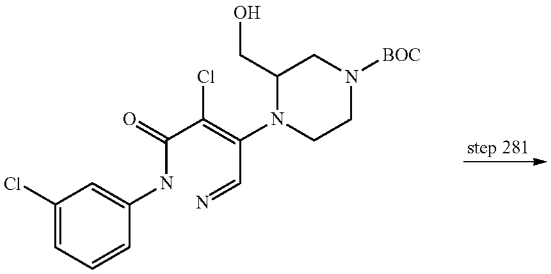
398
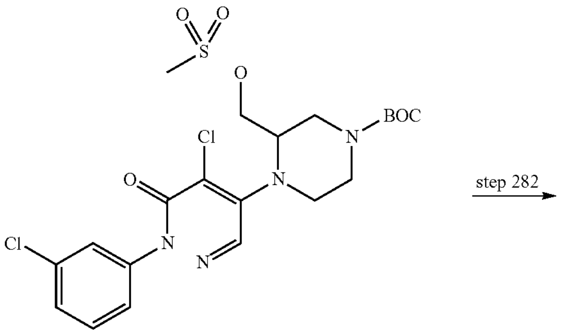
399
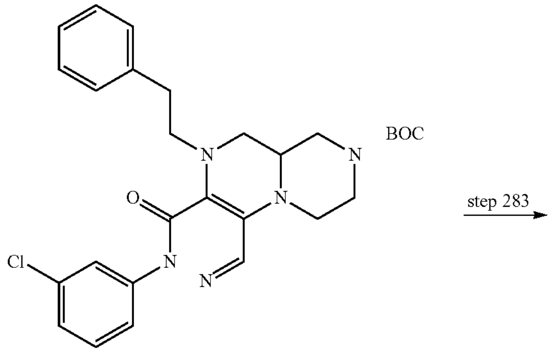
400
-continued
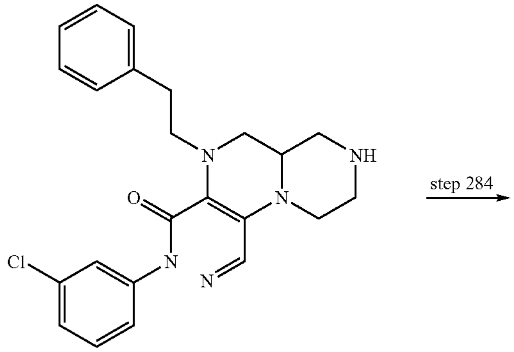
401
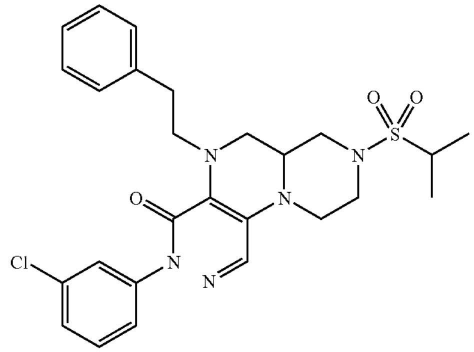
402
Step 280:
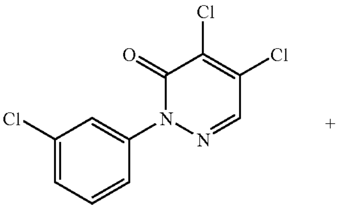
2
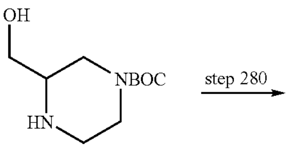
385
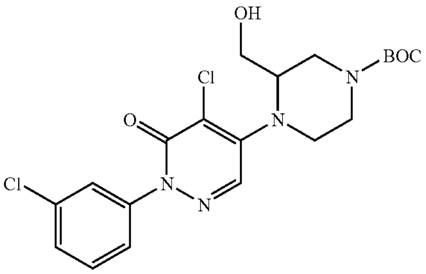
398

To chloropyridazinone 2 (955.4 mg, 3.47 mmol) and N—BOC hydroxypiperazine 385 (1.50 g, 6.936 mmol) dissolved in anhydrous DMF (13.90 mL) was added 4 Å molecular sieves and dry diisopropylethylamine (1.81 mL, 10.40 mmol). The reaction mixture was heated at 100° C. for 12 h, then cooled down to room temperature, poured onto water (60 mL) and diluted with ethyl acetate (100 mL). After decantation, the aqueous solution was extracted with ethyl acetate (3×120 mL). The combined organic extract was successively washed with water (100 mL), and then brine (100 mL), dried ($MgSO_4$), filtered, and concentrated. Purification by silica gel chromatography (eluant: EtOAc-methylene chloride gradient) gave 1.10 g (70% yield) of the product 398 as a light yellow solid. MS (M+1): m/e 455.

Step 281:

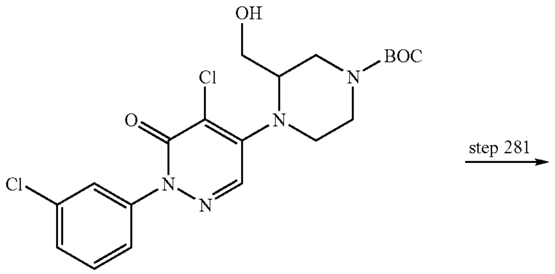

398

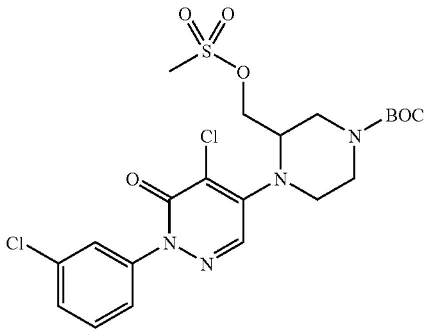

399

To chloropyridazinone 398 (100.0 mg, 0.210 mmol) dissolved in anhydrous methylene chloride (1.05 mL) at 0° C. was added dry triethylamine (117.0 μL, 0.840 mmol) and methanesulfonyl anhydride (54.9 mg, 0.315 mmol). The reaction mixture was stirred at 0° C. for 30 mins, then quenched with an aqueous pH 7 phosphate buffer solution (20 mL) and diluted with ethyl acetate (20 mL). After decantation, the aqueous solution was extracted with ethyl acetate (2×30 mL). The combined organic extract was successively washed with an aqueous pH 7 phosphate buffer solution (30 mL), and then brine (30 mL), dried ($MgSO_4$), filtered, and concentrated. The crude light tan solid obtained (123.0 mg, ca. 99% yield) showed exclusively the mesylate 399 by MS and NMR. MS (M+1): m/e 533.

Step 282:

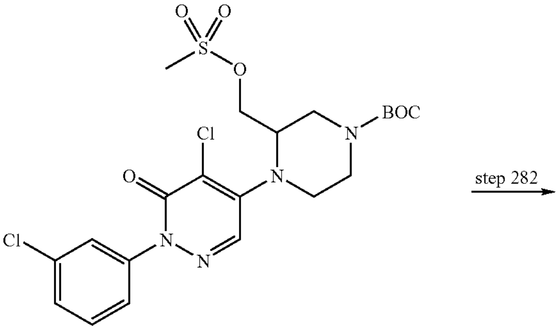

399

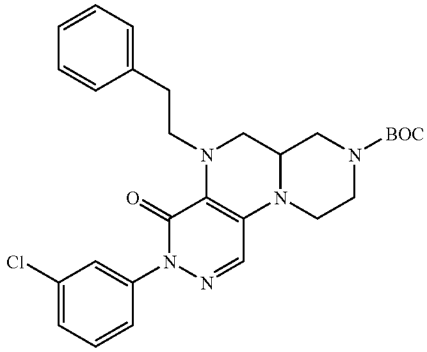

400

To chloropyridazinone 399 (115.0 mg, 0.210 mmol) dissolved in anhydrous toluene (1.50 mL) was added palladium acetate (2.4 mg, 0.011 mmol) and rac-BINAP (6.6 mg, 0.011 mmol), followed by $K_2CO_3$ (72.6 mg, 0.525 mmol) and phenethylamine (132 μL, 1.05 mmol). The reaction mixture was stirred at 110° C. for 16 h, then cooled to room temperature, quenched with an aqueous pH 7 phosphate buffer solution (20 mL) and diluted with ethyl acetate (20 mL). After decantation, the aqueous solution was extracted with ethyl acetate (3×20 mL). The combined organic extract was successively washed with an aqueous pH 7 phosphate buffer solution (30 mL), and then brine (30 mL), dried ($MgSO_4$), filtered, and concentrated. Purification by silica gel chromatography (eluant: hexanes-ethyl acetate gradient) gave 30.0 mg of the product 400 (25% yield) as a light tan solid. MS (M+1): m/e 522.

Step 283:

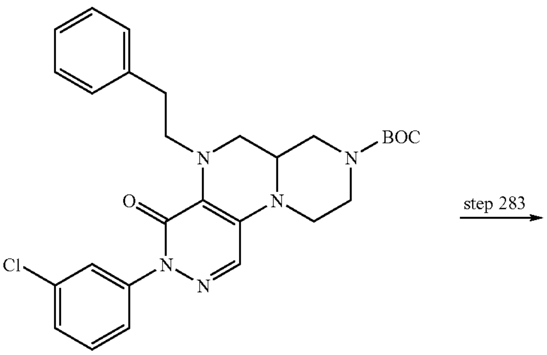

400

-continued

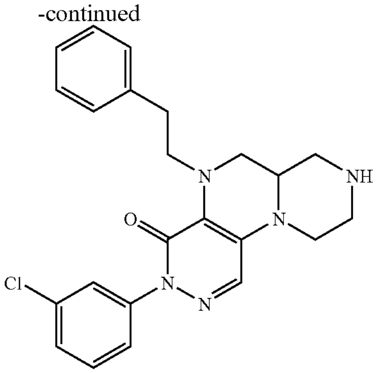

401

To compound 400 (28.0 mg, 0.051 mmol), dissolved in dry methylene chloride (0.80 mL) was added TFA (0.135 mL, 1.79 mmol). The reaction mixture was stirred at room temperature for 3.5 h, then quenched with a saturated aqueous solution of $Na_2CO_3$ (20 mL) and diluted with ethyl acetate (30 mL). The aqueous solution was extracted with ethyl acetate (2×30 mL). The combined organic extract was successively washed with water (20 mL) and brine (20 mL), dried ($MgSO_4$), filtered, and concentrated to give 23.6 mg of yellow foam which was used for the next step without purification. MS and NMR analysis showed exclusively the product 401 (ca. 91% yield from crude). MS (M+1): m/e 422.

Step 284:

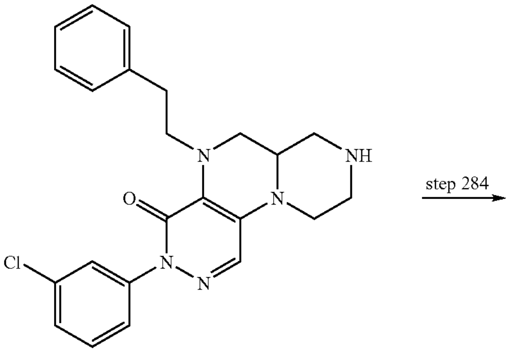

401

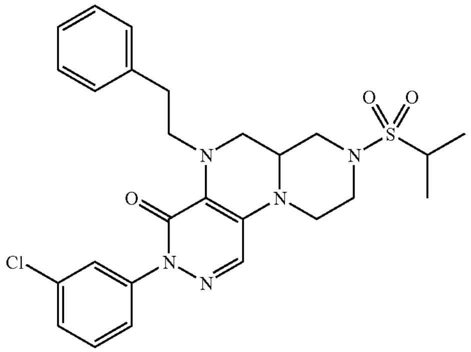

402

To compound 401 (23.5 mg, 0.045 mmol), which was dried just before use by azeotropic distillation with toluene under reduced pressure, dissolved in anhydrous methylene chloride (0.75 mL) was added dry diisopropylethylamine (0.118 mL, 0.675 mmol), followed by isopropylsulfonyl chloride (36.0 μL, 0.315 mmol). The reaction mixture was stirred at room temperature for 48 h, then quenched with an aqueous pH 7 phosphate buffer solution (40 mL) and diluted with diethyl ether (25 mL). After decantation, the aqueous solution was extracted with diethyl ether (3×30 mL) and finally with ethyl acetate (2×50 mL). The combined organic extract was successively washed with an aqueous pH 7 phosphate buffer solution (30 mL), and then brine (40 mL), dried ($MgSO_4$), filtered, and concentrated. Purification by reverse phase HPLC (eluant: $H_2O$-acetonitrile gradient) gave 7.0 mg (28% yield) of the product 402 as a light yellow glass. MS (M+1): m/e 528.

Results of the in vitro fungal enzyme activity assay for representative compounds of Formula I are listed in Table 40:

TABLE 40

| Biological Data | | |
|---|---|---|
| Compound No. | $IC_{50}$ (μg/mL) *Saccharomyces cerevisiae* | $IC_{50}$ (μg/mL) *Candida albicans* |
| 1Z | NT | 10 |
| 7Z | 0.34 | 1.1 |
| 11Z | 1.2 | 6.2 |
| 19Z | 0.081 | 1.7 |
| 25Z | NT | 48 |
| 30Z | 0.4 | 9 |
| 47Z | 0.025 | 0.23 |
| 61Z | 0.32 | 1.3 |
| 82Z | 0.048 | 0.45 |
| 96Z | 0.22 | 0.94 |
| 119Z | 0.063 | 0.81 |
| 197Z | 0.078 | 1.9 |
| 204Z | 103 | 35 |
| 208Z | 0.11 | 1.4 |
| 214Z | 0.75 | 0.28 |
| 227Z | 152 | 152 |
| 232Z | 2 | 8.2 |
| 240Z | 98 | 98 |
| 244Z | 0.093 | 0.41 |
| 402Z | 0.073 | 0.38 |
| 553Z | 0.11 | 0.21 |
| 1402Z | 0.02 | 0.06 |
| 974Z | 0.13 | 0.33 |
| 1035Z | 0.04 | 0.03 |
| 1122Z | 0.03 | 0.03 |
| 1267Z | 0.11 | 0.35 |
| 738Z | 0.04 | 0.07 |
| 801Z | 0.01 | 0.03 |
| 808Z | 0.03 | 0.05 |
| 1629Z | 0.02 | 0.05 |
| 1734Z | 0.06 | 0.13 |
| 1574Zq | 0.04 | 0.08 |
| 312* | 0.06 | 0.07 |
| 1529Z-33 | 0.01 | 0.02 |
| 1633Z | 0.08 | 0.05 |
| 1634Z | 0.17 | 0.11 |
| 1529Z-56 | 0.17 | 0.06 |
| 1574ZI | 0.05 | 0.05 |
| 1529Z-150 | 0.04 | 0.10 |
| 1574Z-82 | 0.16 | 0.29 |
| 1529Z-180 | 0.001 | 0.003 |
| 1529Z-182 | 0.001 | 0.01 |
| 1529Z-185 | 0.006 | 0.02 |
| 1675Z | 0.08 | 0.20 |
| 1529Z-191 | 0.11 | 0.02 |
| 1712Z | 0.08 | 0.06 |
| 1761Z | 0.07 | 0.16 |
| 270* | 0.03 | 0.02 |
| 1891Z | 0.05 | 0.07 |
| 1898Z | 0.05 | 0.06 |
| 1743Z | 0.07 | 0.06 |
| 2022Z | 0.04 | 0.08 |
| 745Z | 0.04 | 0.06 |
| 755Z | 0.05 | 0.04 |
| 767Z | 0.05 | 0.13 |

TABLE 40-continued

| Biological Data | | |
|---|---|---|
| Compound No. | $IC_{50}$ (μg/mL) *Saccharomyces cerevisiae* | $IC_{50}$ (μg/mL) *Candida albicans* |
| 809Z | 0.04 | 0.11 |
| 932Z | 0.04 | 0.13 |
| 1529Z-6 | 0.02 | 0.06 |
| 1574Zo | 0.03 | 0.04 |
| 1529Z-19 | 0.04 | 0.13 |
| 1529Z-40 | 0.03 | 0.03 |
| 1574Zr | 0.06 | 0.13 |
| 1529Z-70 | 0.07 | 0.08 |
| 1529Z-73 | 0.09 | 0.19 |
| 1951Z | 0.06 | 0.05 |
| 1869Z | 0.03 | 0.08 |
| 1864Z | 0.06 | 0.05 |
| 1529Z-151 | 0.07 | 0.09 |
| 1529Z-174 | 0.07 | 0.10 |
| 186* | 0.05 | 0.12 |
| 1529Z-190 | 0.05 | 0.12 |
| 1683Z | 0.08 | 0.07 |
| 1870Z | 0.03 | 0.07 |
| 1969Z | 0.12 | 0.12 |
| 1715Z | 0.10 | 0.31 |
| 1529Z-131 | 0.03 | 0.06 |
| 1904Z | 0.06 | 0.08 |
| 971Zbb | 0.33 | 1.6 |

NT = not tested;
*numbers refer to structures in the reaction Schemes

The compounds listed above can be administered to an animal orally, intravenously, subcutaneously, intrathecally, by inhalation (e.g., to treat fungal infections in the lungs) or topically (e.g. to treat fungal infections of the skin or mucous membranes). Preferably the compound(s) of the invention listed above is administered orally or intravenously, more preferably orally.

For preparing pharmaceutical compositions from the compounds useful in the method of this invention, inert, pharmaceutically acceptable carriers can be either solid or liquid. Solid form preparations include powders, tablets, dispersible granules, capsules, cachets and suppositories. The powders and tablets may be comprised of from about 0.1 to about 99 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds useful in the method of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active component, e.g., an effective amount to achieve the desired purpose.

The quantity of compound listed above in a unit dose of preparation may be varied or adjusted from about 0.1 mg to 1000 mg, more preferably from about 1 mg to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compound listed above useful in the method of the invention will be regulated according to the judgment of the attending clinician considering such factors as age, condition and size of the patient as well as severity of the symptoms being treated. A typical recommended dosage regimen for a compound listed above is oral administration of about 10 mg to 2000 mg/day preferably 10 to 1000 mg/day, in two to four divided doses to provide relief from the fungal infection.

When the invention comprises a combination of one or more compounds listed above and one or more other antifungal agents, the active components may be co-administered simultaneously or sequentially, or a single pharmaceutical composition comprising one or more compounds listed above and one or more other antifungal agents in a pharmaceutically acceptable carrier can be administered. The components of the combination can be administered individually or together in any conventional dosage form such as capsule, tablet, powder, cachet, suspension, solution, suppository, nasal spray, etc. The dosages of the other antifungal agents can be determined from published material, and may range from 1 to 1000 mg per dose. When used in combination, the dosage levels of the individual components are preferably lower than the recommended individual dosages because of the advantageous effect of the combination.

When separate pharmaceutical compositions of compounds listed above and other antifungal agents are to be administered, they can be provided in a kit comprising in a single package, one container comprising one or more compounds of the present invention listed above in a pharmaceutically acceptable carrier, and a separate container comprising one or more other antifungal agents in a pharmaceutically acceptable carrier, with the compounds listed above and the other antifungal agents being present in amounts such that the combination is therapeutically effective. A kit is advantageous for administering a combination when, for example, the components must be administered at different time intervals or when they are in different dosage forms.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound of Formula I:

Formula I

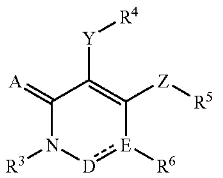

or a pharmaceutically acceptable salt, or ester thereof, wherein:

═══ represents a double bond or a single bond, as permitted by the valency requirement, with the proviso that when E is N, the double bond is present and $R^6$ is absent;

A is O or S;

D and E are independently C or N, provided that when D is carbon, D is substituted with hydrogen, alkyl, —Oalkyl, —Nalkyl or —Salkyl;

$R^3$ is a moiety selected from the group consisting of aryl, arylalkyl, arylalkenyl, heteroaryl, heteroarylalkyl, heteroarylalkenyl, cycloalkyl, cycloalkylalkyl, cycloalkylalkenyl, cyclenyl, cyclenylalkyl, cyclenylalkenyl, heterocyclyl, heterocyclylalkyl, heterocyclylalkenyl, heterocyclenyl, heterocyclenylalkyl, heterocyclenylalkenyl, cycloalkoxylalkyl, cycloalkoxylalkenyl, cycloalkenoxylalkyl, and cycloalkenyoxylalkenyl, wherein each of said alkyl, alkenyl, aryl, arylalkyl, arylalkenyl, heteroaryl, heteroarylalkyl, heteroarylalkenyl, cycloalkyl, cycloalkylalkyl, cycloalkylalkenyl, cyclenyl, cyclenylalkyl, cyclenylalkenyl, heterocyclyl, heterocyclylalkyl, heterocyclylalkenyl, heterocyclenyl, heterocyclenylalkyl, heterocyclenylalkenyl, arylalkoxylalkyl, arylalkoxylalkenyl, cycloalkoxylalkyl, cycloalkoxylalkenyl, cycloalkenoxylalkyl, cycloalkenyoxylalkenyl can be unsubstituted or substituted with one or more moieties, which can be the same or different, each moiety being independently selected from the group consisting of alkyl, alkenyl, alkynyl, cycloalkyl, halogen, trihaloalkyl, dihaloalkyl, monohaloalkyl, $—NR^9{}_2$, $—OR^9$, $—SR^9$, $—NO_2$, —CN, $—NR^{16}COR^9$, $—NR^{16}SO_2R^9$, $—COR^9$, $—CO_2R^9$, $—SO_2R^9$, $—CONR^9$, $R^{16}$, and —N═C═O;

Y is

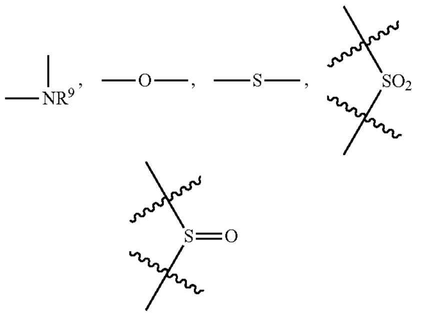

or a single bond, provided that when Y is O, Y—$R^4$ taken together is not alkoxyl of the formula

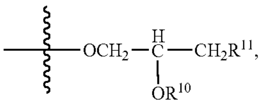

wherein $—CH_2R^{11}$ and $—OR^{10}$ together with the CH to which they are attached, form a heterocyclyl that is substituted with one or more moieties, which can be the same or different , selected from the group consisting of alkyl and aryl, or wherein $R^{10}$ is H and $R^{11}$ is hydroxyl or butylamine;

$R^4$ is alkyl, alkenyl, alkynyl, alkoxyalkyl, alkenyl-O-alkyl, alkoxyalkenyl, alkenyl-O-alkenyl, alkynyl-O-alkyl, hydroxyalkyl, hydroxyalkenyl, alkyl-S-alkyl, alkenyl-S-alkyl, alkyl-S-alkenyl, alkenyl-S-alkenyl, alkyl-SO-alkyl, alkenyl-SO-alkyl, alkyl-SO-alkenyl, alkenyl-SO-alkenyl, alkyl-$SO_2$-alkyl, alkenyl-$SO_2$-alkyl, alkyl-$SO_2$-alkenyl, alkenyl-$SO_2$-alkenyl, alkyl-$NR^9$-alkyl, alkenyl-$NR^9$-alkyl, alkyl-$NR^9$-alkenyl, alkenyl-$NR^9$-alkenyl, alkyl-$CO_2$-alkyl, alkenyl-$CO_2$-alkyl, alkyl-$CO_2$-alkenyl, alkenyl-$CO_2$-alkenyl, alkyl-$O_2C$-alkyl, alkenyl-$O_2C$-alkyl, alkyl-$O_2C$-alkenyl, alkenyl-$O_2C$-alkenyl, alkyl-CO-alkyl, alkenyl-CO-alkyl, alkyl-CO-alkenyl, alkenyl-CO-alkenyl, cycloalkyl, cycloalkylalkyl, spiroheteroaryl, spiroheterocyclenyl, spiroheterocyclyl, spiroheteroarylalkyl, spiroheteroarylalkenyl, spiroheterocyclenylalkyl, spiroheterocyclenylalkenyl, spiroheterocyclylalkyl, spiroheterocyclylalkenyl, spirocycloalkyl, spirocycloalkylalkyl, spirocycloalkylalkenyl, spirocyclenyl, spirocyclenylalkyl, spirocyclenylalkenyl, spiroaryl, spiroarylalkyl, spiroarylalkenyl, alkylcycloalkyl, cyclenyl, cyclenylalkyl, cyclenylalkenyl, aryl, arylalkyl, arylalkenyl, heteroaryl, heteroarylalkyl, heteroarylalkenyl, heterocyclyl, heterocyclenyl, heterocyclenylalkyl heterocyclenylalkenyl, heterocyclylalkyl, heterocyclylalkenyl, benzofused-cycloalkyl, benzofused-heterocycloalkyl, benzofused-cycloalkylalkyl or benzofused-heterocycloalkylalkyl;

wherein said alkyl, alkenyl, alkynyl, alkoxyalkyl, alkoxyalkoxyalkyl, alkenyl-O-alkyl, alkoxyalkenyl, alkenyl-O-alkenyl, alkynyl-O-alkyl, hydroxyalkyl, hydroxyalkenyl, alkyl-S-alkyl, alkenyl-S-alkyl, alkyl-S-alkenyl, alkenyl-S-alkenyl, alkyl-SO-alkyl, alkenyl-SO-alkyl, alkyl-SO-alkenyl, alkenyl-SO-alkenyl, alkyl-$SO_2$-alkyl, alkenyl-$SO_2$-alkyl, alkyl-$SO_2$-alkenyl, alkenyl-$SO_2$-alkenyl, alkyl-$NR^9$-alkyl, alkenyl-$NR^9$-alkyl, alkyl-$NR^9$-alkenyl, alkenyl-$NR^9$-alkenyl, alkyl-$CO_2$-alkyl, alkenyl-$CO_2$-alkyl, alkyl-$CO_2$-alkenyl, alkenyl-$CO_2$-alkenyl, alkyl-$O_2C$-alkyl, alkenyl-$O_2C$-alkyl, alkyl-$O_2C$-alkenyl, alkenyl-$O_2C$-alkenyl, alkyl-CO-alkyl, alkenyl-CO-alkyl, alkyl-CO-alkenyl, alkenyl-CO-alkenyl, cycloalkyl, cycloalkylalkyl, spiroheteroaryl, spiroheterocyclenyl, spiroheterocyclyl, spiroheteroarylalkyl, spiroheteroarylalkenyl, spiroheterocyclenylalkyl, spiroheterocyclenylalkenyl, spiroheterocyclylalkyl, spiroheterocyclylalkenyl, spirocycloalkyl, spirocycloalkylalkyl, spirocycloalkylalkenyl, spirocyclenyl, spirocyclenylalkyl, spirocyclenylalkenyl, spiroaryl, spiroarylalkyl, spiroarylalkenyl, alkylcycloalkyl, alkylcycloalkylalkyl, cyclenyl, cyclenylalkyl, cyclenylalkenyl, aryl, arylalkyl, arylalkenyl, heteroaryl, heteroarylalkyl, heteroarylalkenyl, heterocyclyl, heterocyclenyl, heterocyclenylalkyl heterocyclenylalkenyl, heterocyclylalkyl, heterocyclylalkenyl, benzofused-cycloalkyl, benzofused-heterocycloalkyl, benzofused-cycloalkylalkyl or benzofused-heterocycloalkylalkyl can be unsubstituted or substituted with at least one moiety independently selected from the group consisting of alkyl, alkenyl, aryl, $OR^9$, arylalkyl, arylalkenyl, cyclenylalkyl, cyclenylalkenyl, cycloalkylalkyl, cycloalkylalkenyl, alkyl$CO_2$alkyl-, halogen, trihaloalkyl, dihaloalkyl, monohaloalkyl, cycloalkyl, cyclenyl, hydroxyalkyl, hydroxyalkenyl, thiohydroxyalkyl, thiohydroxyalkenyl, hydroxyalkenyl, heteroaryl, heteroarylalkyl, heterocyclenyl, heterocyclenylalkyl, heterocyclyl, heterocyclylalkyl, alkoxyalkyl, —CN, —$NO_2$, —$OSiR^9_3$, —$NR^{16}COR^9$, —$OCONR^9_2$, —$NR^{16}CONR^9_2$, —$NR^{16}SO_2R^9$, —$NR^9_2$, —N═C═O,

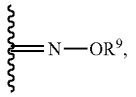

—$NR^{16}CO_2R^9$, —$COR^9$, —$CO_2R^9$, —$OCOR^9$, —$SO_2R^9$, —$SOR^9$, —$SR^9$, —$SO_2N(R^9)_2$ or —$CONR^9R^{16}$, wherein each of said alkyl, alkenyl, aryl, arylalkyl, arylalkenyl, cyclenylalkyl, cyclenylalkenyl, cycloalkylalkyl, cycloalkylalkenyl, halogen, trihaloalkyl, dihaloalkyl, monohaloalkyl, cycloalkyl, cyclenyl, hydroxyalkyl, hydroxyalkenyl, thiohydroxyalkyl, thiohydroxyalkenyl, hydroxyalkenyl, heteroaryl, heteroarylalkyl, heterocyclenyl, heterocyclenylalkyl, heterocyclyl, heterocyclylalkyl, alkoxyalkyl, can be unsubstituted or substituted with one or more moieties which can be the same or different, each moiety being independently selected from $R^9$;

Z is a linker attached at either end of said linker to the parent ring of Formula I, wherein said linker is selected from the group consisting of:

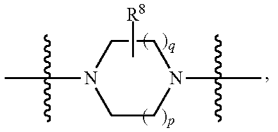

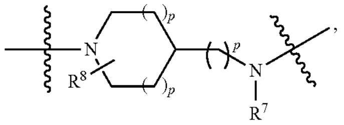

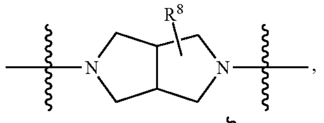

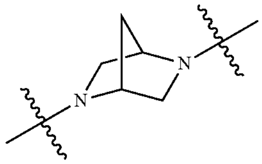

wherein n is 1 to 4, p is 0 to 2, q is 1 to 3;

$R^5$ is

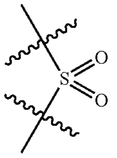

or

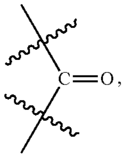

wherein each of said

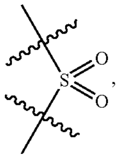

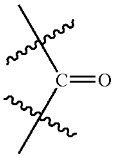

or —$CR^9_2$— is attached at one end to Z and at the second end substituted with a moiety, selected from the group consisting of alkyl, alkenyl, cycloalkyl, cyclenyl, aryl, heterocyclyl, heterocyclenyl, cycloalkylalkyl, cyclenylalkyl, arylalkyl, heterocyclylalkyl, heterocyclenylalkyl, heteroarylalkyl, cycloalkylalkenyl, cyclenylalkenyl, arylalkenyl, heterocyclylalkenyl, heterocyclenylalkenyl, heteroarylalkenyl, —$OR^9$ and —$NR^9_2$, further, wherein each of said alkyl, alkenyl, cycloalkyl, cyclenyl, aryl, heterocyclyl, heterocyclenyl, heteroaryl, cycloalkylalkyl, cyclenylalkyl, arylalkyl, heterocyclylalkyl, heterocyclenylalkyl, heteroarylalkyl, cycloalkylalkenyl, cyclenylalkenyl, arylalkenyl, heterocyclylalkenyl, heterocyclenylalkenyl, or heteroarylalkenyl can be unsubstituted or substituted with one or more moieties, which can be the same or different, each moiety being independently selected from the group consisting of halogen, alkyl, alkenyl, cycloalkyl, —$OR^9$, alkyl$OR^9$, alkyl$CO_2R^9$, alkyl$NR^{16}COR^9$, alkyl$NR^{16}CONR^9$, alkyl$SO_2R^9$, alkyl$COR^9$, alkyl$SO_2NR^9_2$, alkyl$NR^9_2$, alkylaryl, alkylheteroaryl, alkyl$SR^9$, alkyl$SOR^9$, —CN, —$CO_2R^9$, trihaloalkyl, dihaloalkyl, monohaloalkyl, —$NR^{16}COR^9$, —$NR^{16}CONR^9_2$, —$NR^{16}SO_2$—$R^{13}$, —$SO_2R^9$, —$COR^9$, —$NO_2$, —$SO_2NR^9_2$, aryl, heteroaryl, —$NR^9_2$, —$SR^9$, —$SOR^9$, —C(═NOH)—$NR^{13}$,

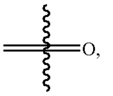

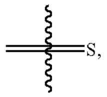

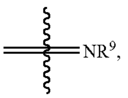

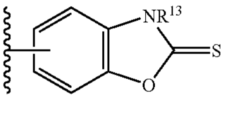

and

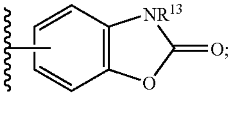

or Y—$R^4$ taken together are H, provided that $R^6$ is not H; or Y—$R^4$ taken together are H and $R^6$ is H, provided that when Z is

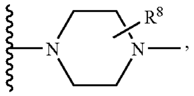

$R^8$ is not H;

or Z and $R^5$ taken together is

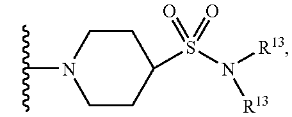,
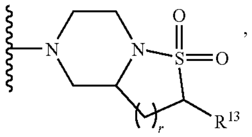,

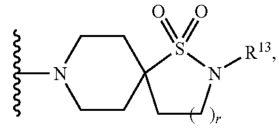,
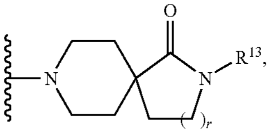,

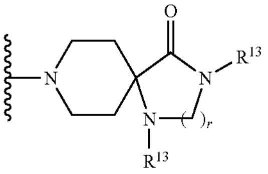 or
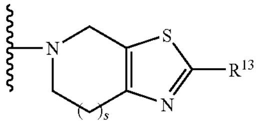, wherein r is 1 or 2;

s is 0 or 1;

or —Y—$R^4$, —$ZR^5$ and the carbons to which they are attached form the group

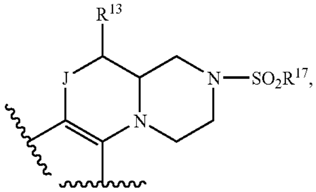

wherein J is —O—, —S—, or —$NR^{13}$—;

$R^6$ is H, alkyl, aryl, arylalkyl, arylalkenyl, heteroaryl, heteroarylalkyl, heteroarylalkenyl, cycloalkyl, cycloalkylalkyl, cycloalkylalkenyl, arylalkoxylalkyl, arylalkoxylalkenyl, arylalkoxyl, cycloalkoxyl, cycloalkoxylalkyl, cycloalkoxylalkenyl, cycloalkylalkoxyl, cycloalkenoxyl, cycloalkenoxylalkyl, cycloalkenyoxylalkenyl, —$NR^9_2$, —$OR^9$, —$NO_2$, —$NR^{16}COR^9$, —$NR^{16}CON(R^{17})_2$, —$NR^{16}SO_2R^9$, —$COR^9$, —$CO_2R^9$, or —$CONR^9R^{16}$;

wherein each of said alkyl, aryl, arylalkyl, arylalkenyl, heteroaryl, heteroarylalkyl, heteroarylalkenyl, cycloalkyl, cycloalkylalkyl, cycloalkylalkenyl, arylalkoxylalkyl, arylalkoxylalkenyl, arylalkoxyl, cycloalkoxyl, cycloalkoxylalkyl, cycloalkoxylalkenyl, cycloalkylalkoxyl, cycloalkenoxyl, cycloalkenoxylalkyl, cycloalkenyoxylalkenyl can be unsubstituted or substituted with one or more moieties, which can be the same or different, each moiety being independently selected from the group consisting of halogen, alkyl, trihaloalkyl, dihaloalkyl, monohaloalkyl, —$NR^9_2$, —$OR^9$, —$SR^9$, —$NO_2$, —CN, —$NR^{16}COR^9$, —$NR^{16}SO_2R^9$, —$COR^9$, —$CO_2R^9$, —$SO_2R^9$, —$CONR^9R^{16}$ and —$NR^{16}CON(R^{17})_2$;

each $R^7$ is independently selected from the group consisting of H and alkyl;

$R^8$ is one or more moieties, which can be the same or different, each being independently selected from the group consisting of H, aryl, arylalkyl, alkyl,

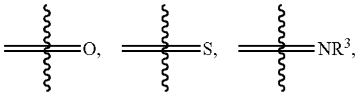

arylalkenyl, heteroaryl, heteroarylalkyl, heteroarylalkenyl, cycloalkyl, cycloalkylalkyl, cycloalkylalkenyl, cyclenyl, cyclenylalkyl, cyclenylalkenyl, alkenyl, alkynyl, trihaloalkyl, dihaloalkyl, monohaloalkyl, —$NR^9_2$, —$OR^9$, —$SR^9$, —$NR^{16}COR^9$, —$NR^{16}CON(R^{17})_2$, —$NR^{16}SO_2R^9$, —$COR^9$, —$CO_2R^9$, —$SO_2R^9$, and —$CONR^9R^{16}$, wherein each of said aryl, arylalkyl, alkyl, arylalkenyl, heteroaryl, heteroarylalkyl, heteroarylalkenyl, cycloalkyl, cycloalkylalkyl, cycloalkylalkenyl, cyclenyl, cyclenylalkyl, cyclenylalkenyl, alkenyl and alkynyl can be unsubstituted or substituted with one or more moieties which can be the same or different, each moiety being independently selected from the group consisting of halogen, alkyl, trihaloalkyl, dihaloalkyl, monohaloalkyl, —$NR^9_2$, —$OR^9$, —$SR^9$, —$NO_2$, —CN, —$NR^{16}COR^9$, —$NR^{16}SO_2R^9$, —$COR^9$, —$CO_2R^9$, —$SO_2R^9$, —$CONR^9R^{16}$ and —$NR^{16}CON(R^{17})_2$;

$R^9$ is one or more moieties, which can be the same or different, each moiety being independently selected from the group consisting of H, alkyl, alkenyl, alkynyl, cycloalkyl, cyclenyl, aryl, heteroalkyl, heterocycloalkyl, heterocyclenyl, heteroaryl, hydroxyalkyl, hydroxyalkenyl, alkylthioalkyl, alkylthioalkenyl, alkenylthioalkyl, alkenylthioalkenyl, alkoxylalkyl, arylalkyl, cycloalkylalkyl, cyclenylalkyl, heterocyclylalkyl, heterocyclenylalkyl, heteroarylalkyl, arylalkenyl, cycloalkyalkenyl, cyclenylalkenyl, heterocyclylalkenyl, heterocyclenylalkenyl, heteroarylalkenyl, alkoxyaryl, trihaloalkyl, trihaloalkenyl, dihaloalkyl, dihaloalkenyl, monohaloalkyl, and monohaloalkenyl, wherein each of said alkyl, alkenyl, alkynyl, cycloalkyl, cyclenyl, aryl, heterocycloalkyl, heterocyclenyl, heteroaryl, hydroxyalkyl, hydroxyalkenyl, alkoxylalkyl, arylalkyl, cycloalkylalkyl, cyclenylalkyl, heterocyclylalkyl, heterocyclenylalkyl, heteroarylalkyl, arylalkenyl, cycloalkyalkenyl, cyclenylalkenyl, heterocyclylalkenyl, heterocyclenylalkenyl, heteroarylalkenyl, and alkoxyaryl can be unsubstituted or substituted with one or more moieties, which can be the same or different, each moiety being independently selected from the group consisting of halogen, trihaloalkyl, dihaloalkyl, monohaloalkyl, trihaloalkenyl, dihaloalkenyl, monohaloalkenyl, hydroxyl, alkoxy, hydroxyalkyl, —$N(R^{12})_2$, alkyl, alkynyl , cycloalkyl, alkenyl, cyclenyl, aryl, heteroaryl, heterocycloalkyl, heterocyclenyl, cycloalkylalkyl, cyclenylalkyl, arylalkyl, heteroarylalkyl, heterocycloalkylalkyl, heterocyclenylalkyl, cycloalkylalkenyl, cyclenylalkenyl, arylalkenyl, heteroarylalkenyl, heterocycloalkylalkenyl, heterocyclenylalkenyl, —CN, —$NO_2$, —$SO_2R^{17}$, —$C(O)N(R^{20})_2$, —$CO_2R^{19}$,

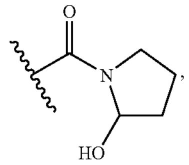

$-NR^{16}-C(O)R^{19}$, $-NR^{16}CON(R^{17})_2$, $-NR^{16}SO_2R^{17}$, trihaloalkoxy, dihaloalkoxy, monohaloalkoxy,

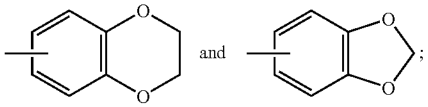

further wherein when two $R^9$ moieties are attached to a N, the two $R^9$ moieties, together with the N to which they are attached, can form a heterocyclyl or heterocyclenyl ring of 4 to 7 members, wherein 1 or 2 of said ring members can be —O—, —S— or $-NR^{18}-$, provided that there are no heteroatoms adjacent to each other; and wherein the heterocyclyl or heterocyclenyl ring is optionally substituted on 1 or 2 ring carbon atoms by a substituent independently selected from the group consisting of alkyl, alkoxy, —OH and $-NR^{16}$, or two hydrogen atoms on the same carbon are replaced by =O;

each $R^{12}$ is independently selected from the group consisting of H, alkyl, aryl and arylalkyl;

each $R^{13}$ is independently selected from the group consisting of H, alkyl, aryl, arylalkyl, cycloalkyl and cycloalkylalkyl;

$R^{14}$ is alkyl or alkoxy;

$R^{15}$ is aryl, arylalkyl, $-N(R^{13})$-aryl, $-N(R^{13})$-alkylaryl, —O-aryl or —O-alkylaryl;

$R^{16}$ is independently selected from the group consisting of H and alkyl;

$R^{17}$ is alkyl, aryl or arylalkyl;

$R^{18}$ is H, alkyl, $-COOR^{19}$, $-COR^{17}$ or $-CON(R^{17})_2$;

each $R^{19}$ is independently selected from the group consisting of H, alkyl and benzyl;

each $R^{20}$ is independently selected from the group consisting of H, alkyl, aryl, arylalkyl, cycloalkyl, cycloalkylalkyl, and alkoxyalkyl;

provided that Formula I does not include the compounds of Table A:

TABLE A

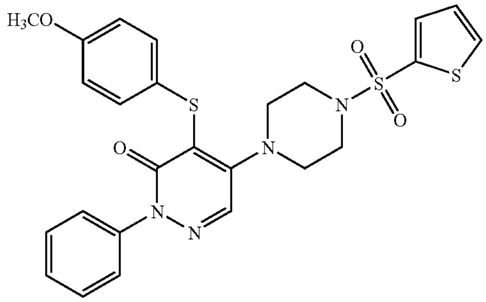

TABLE A-continued

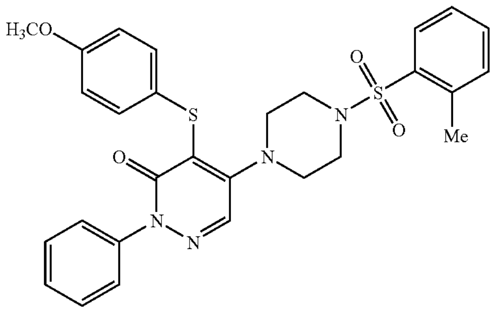

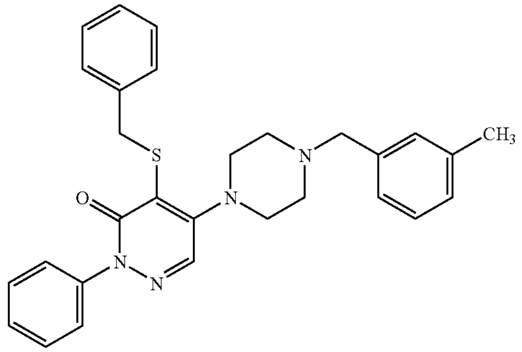

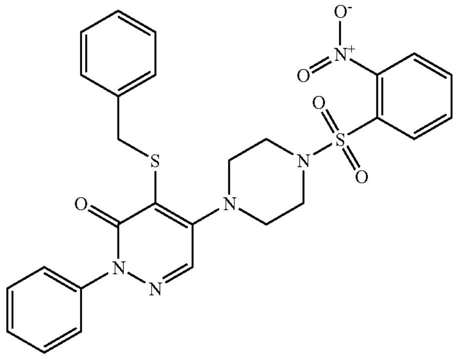

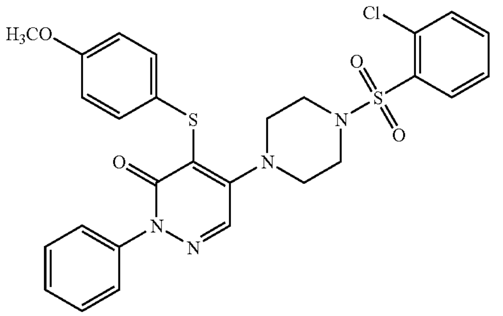

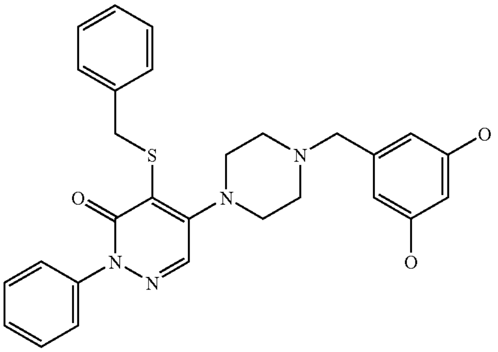
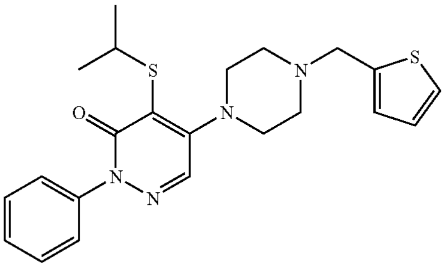
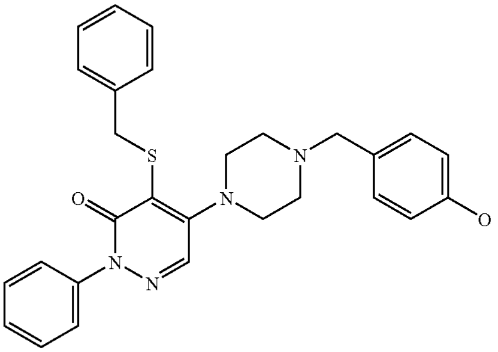
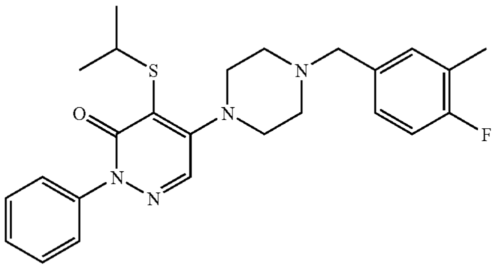
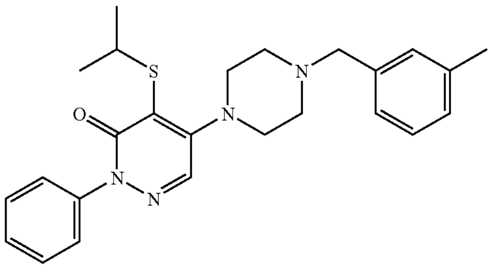
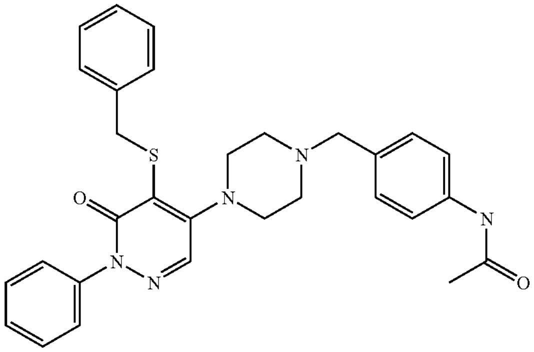
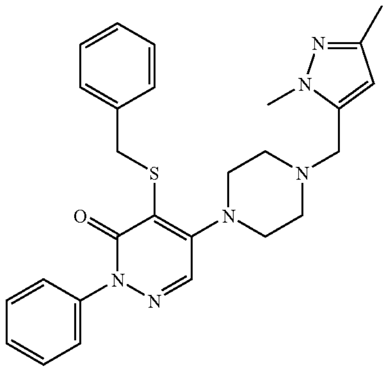
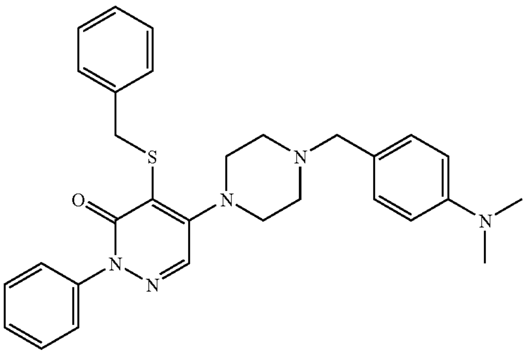
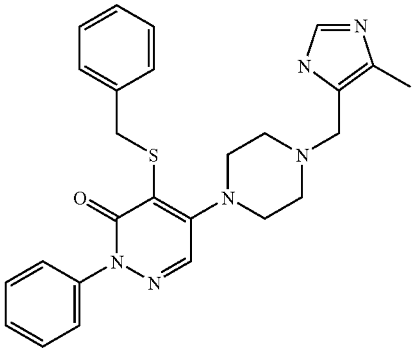

TABLE A-continued
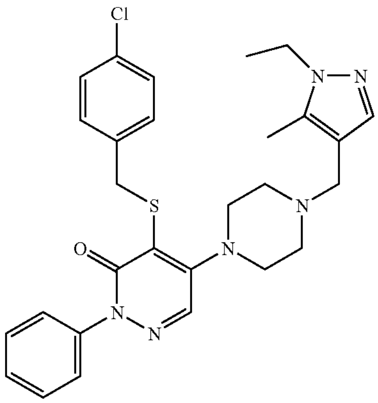
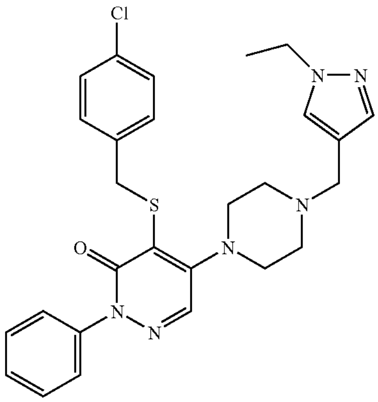
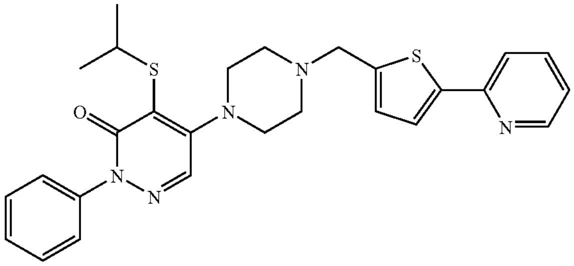
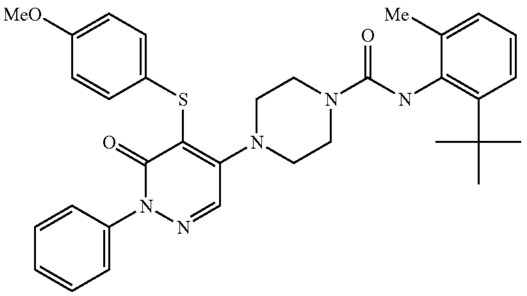
TABLE A-continued
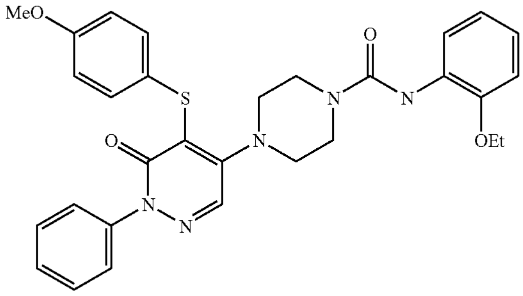
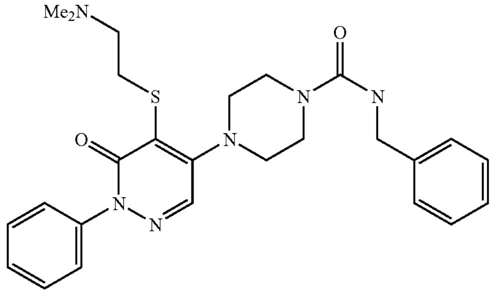
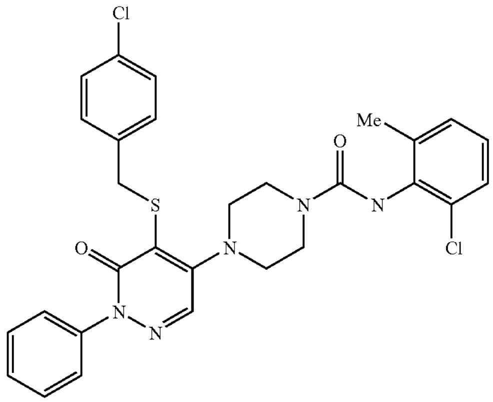
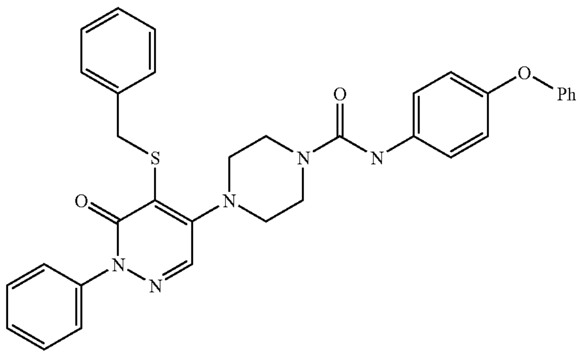

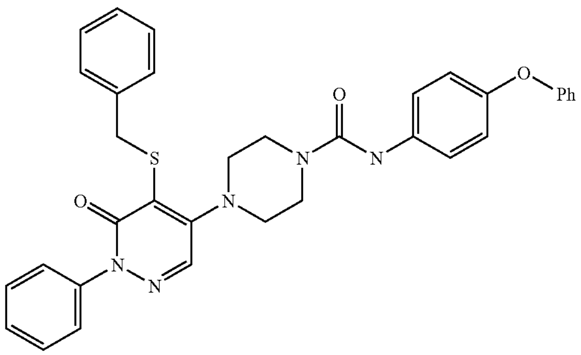
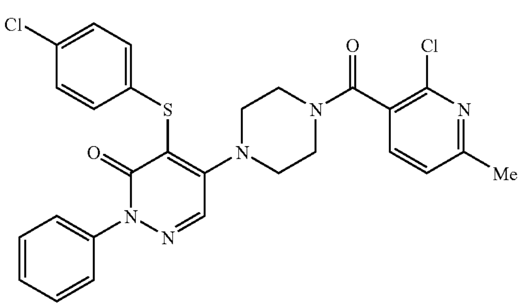
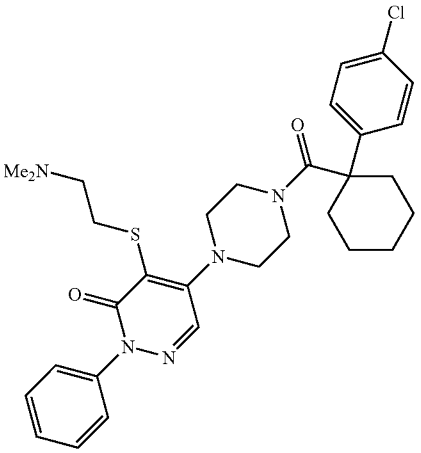
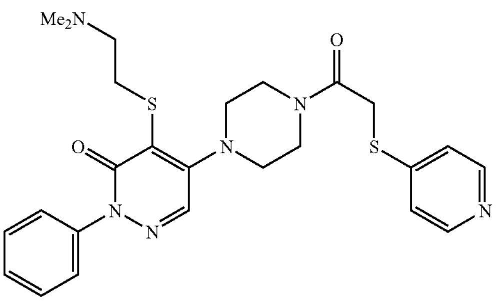
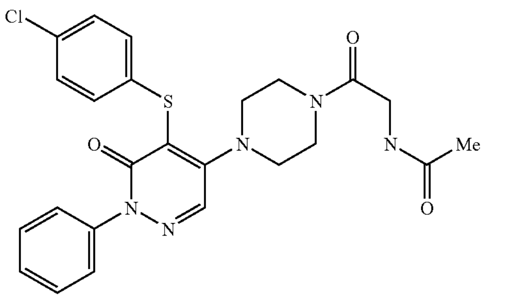
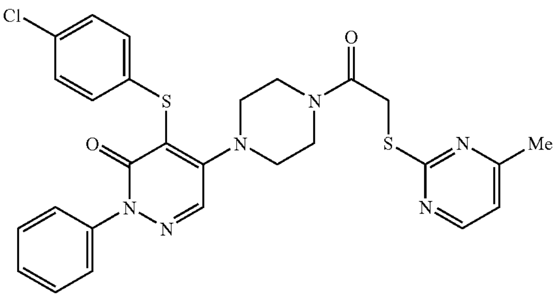
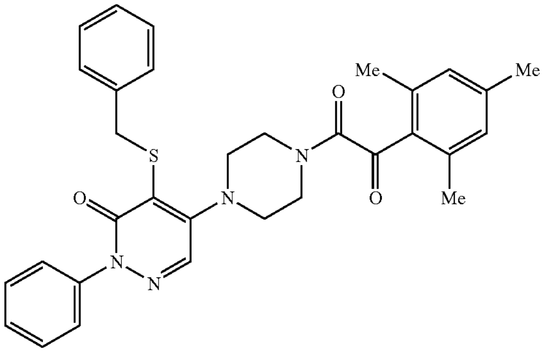
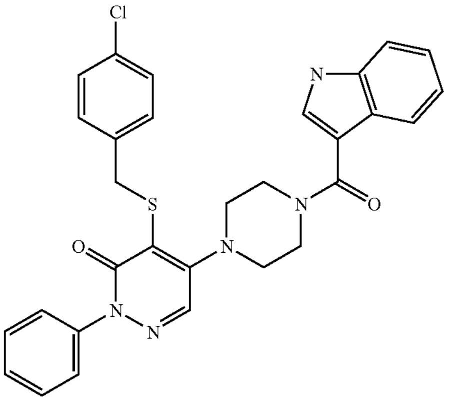

TABLE A-continued
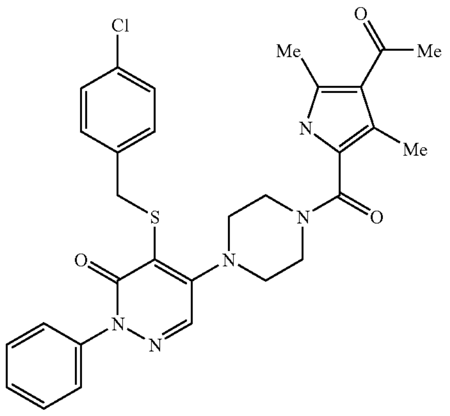
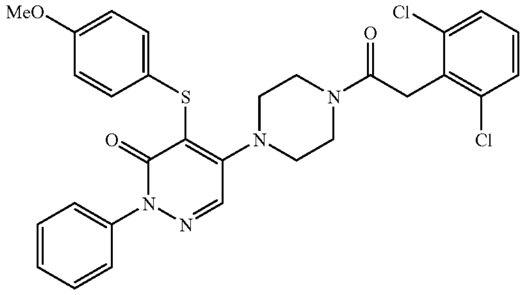
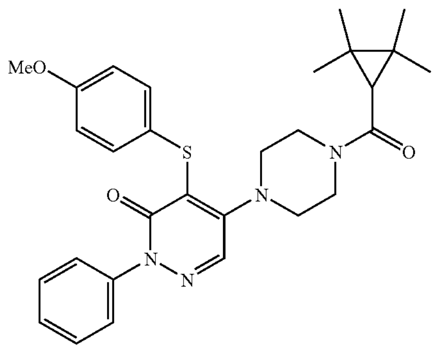
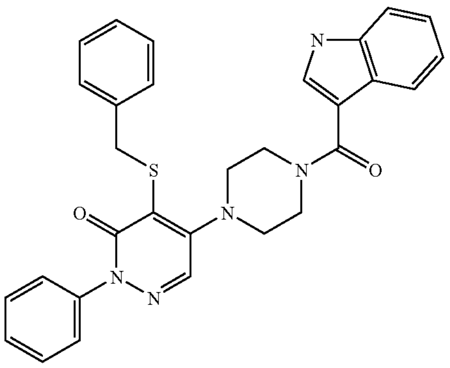
TABLE A-continued
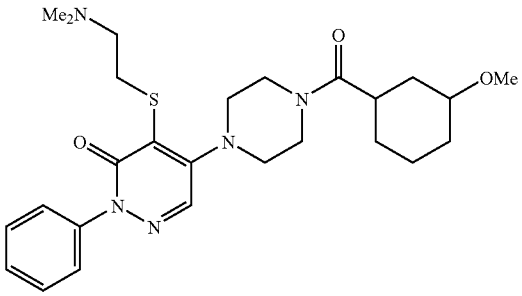
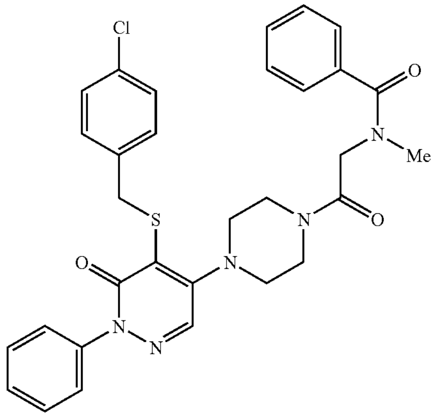
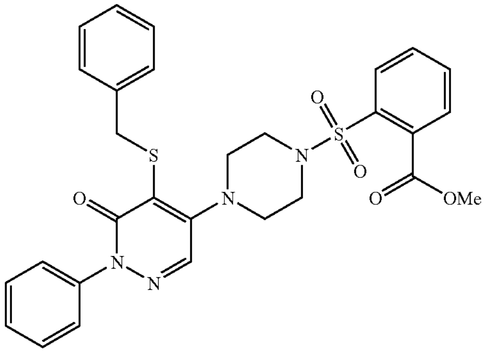
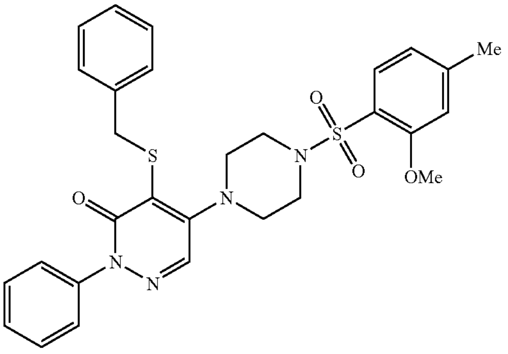

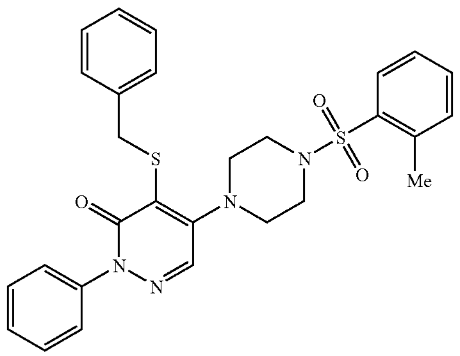
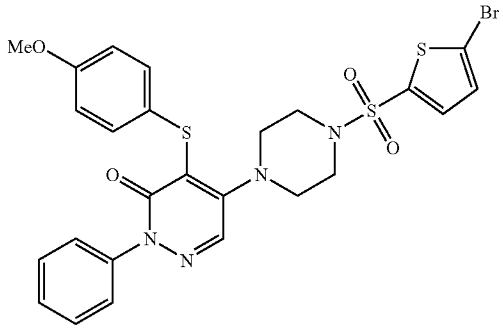
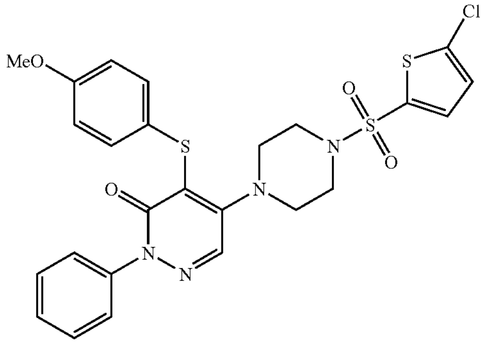
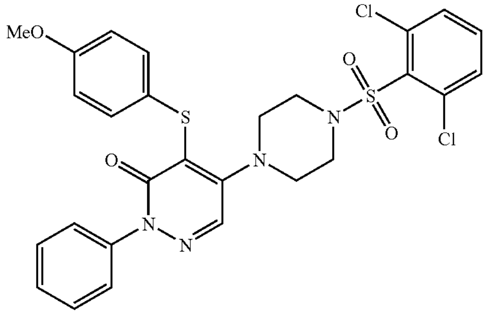
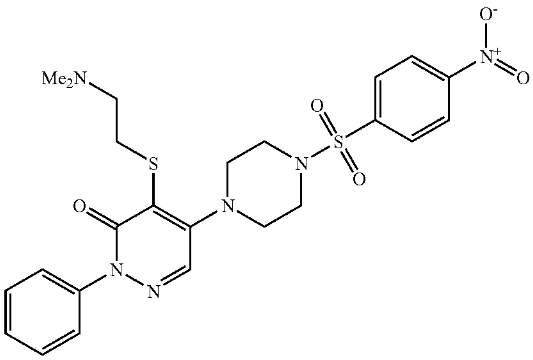
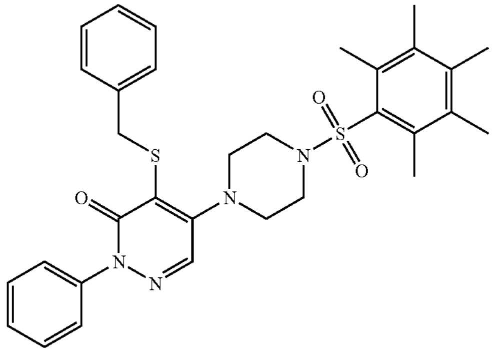
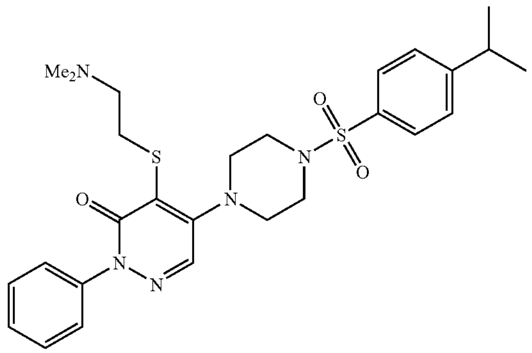
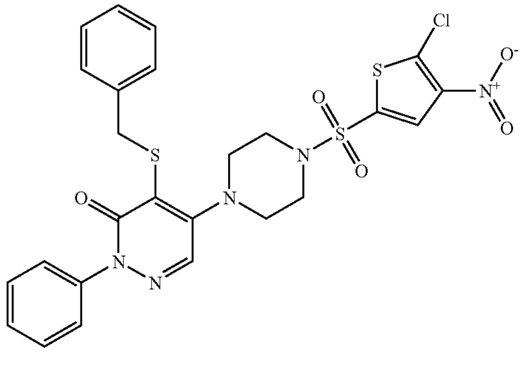

TABLE A-continued
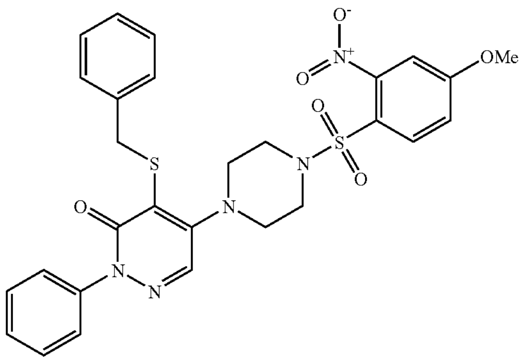
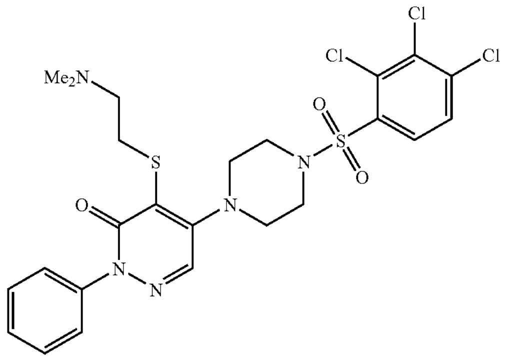
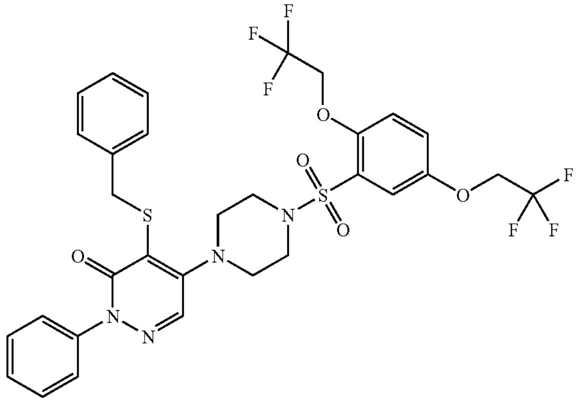
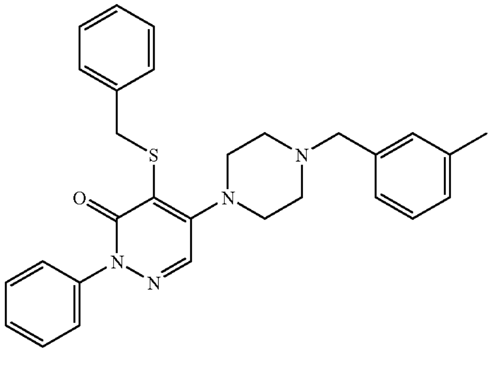
TABLE A-continued
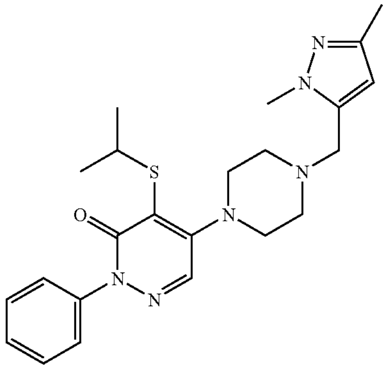
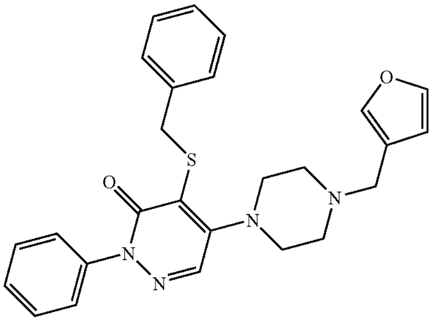
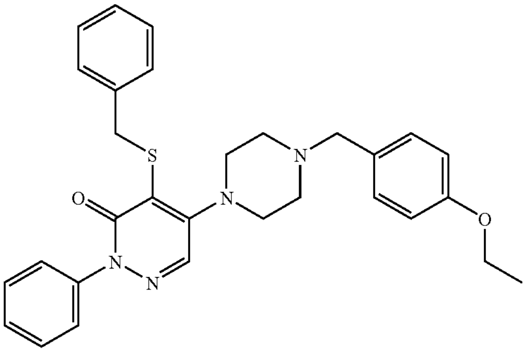
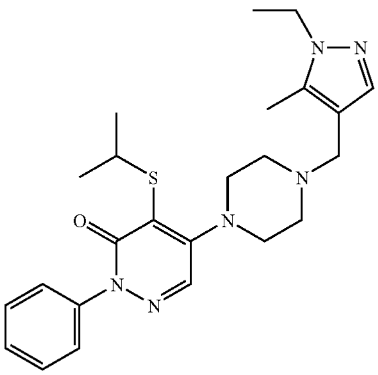

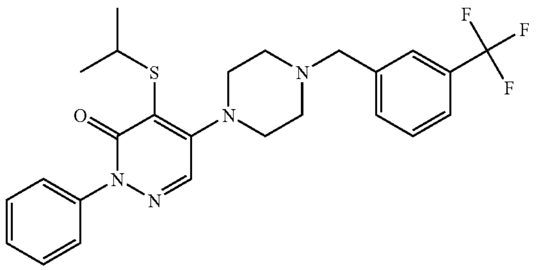
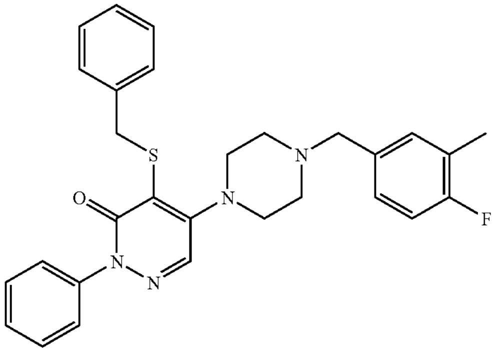
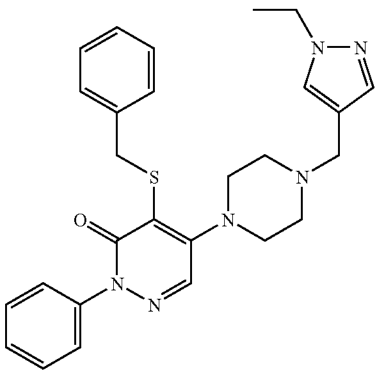
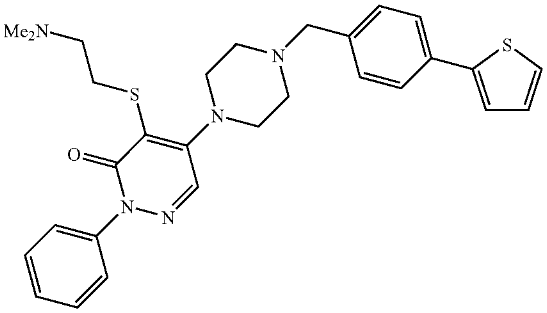
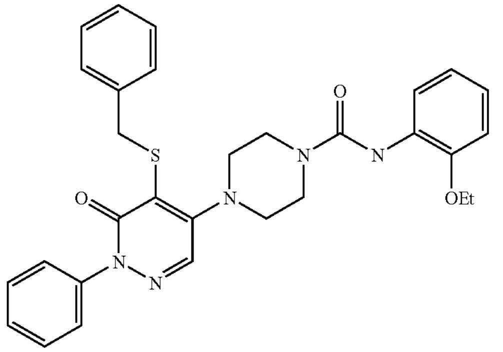
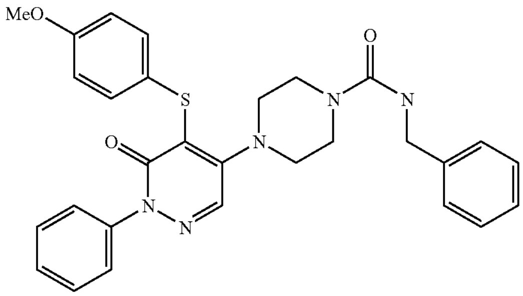
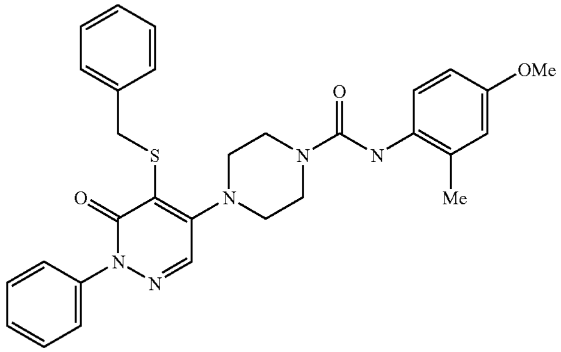
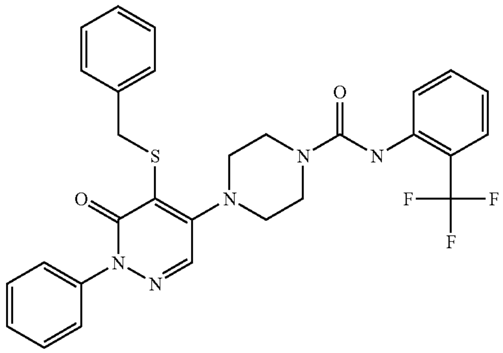

TABLE A-continued
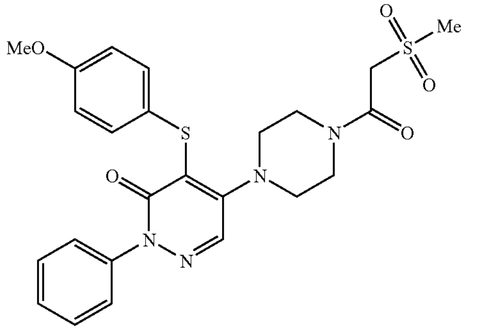
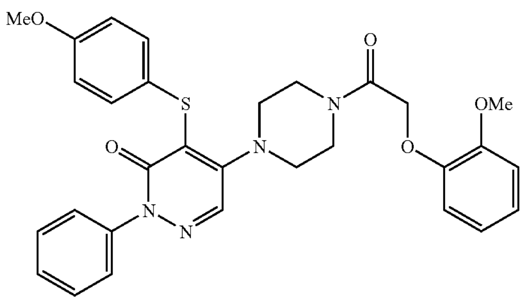
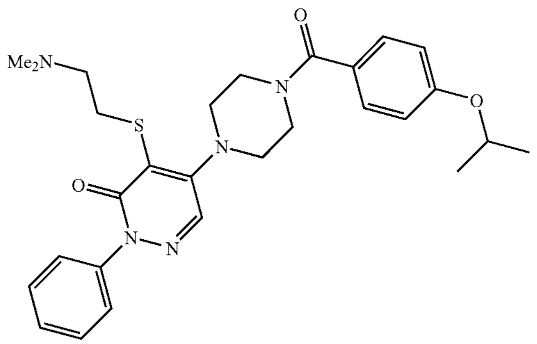
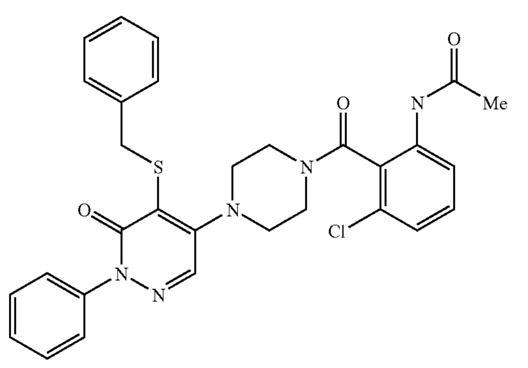
TABLE A-continued
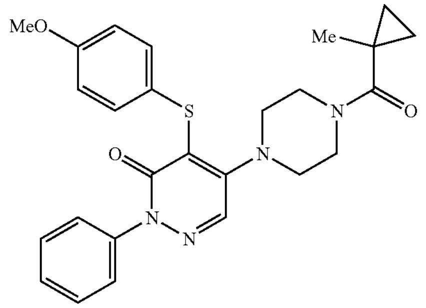
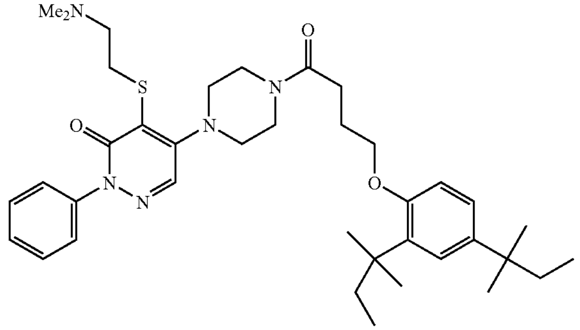
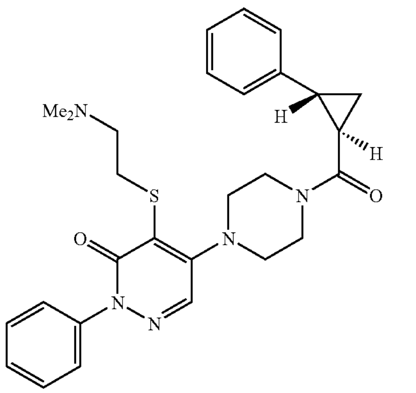
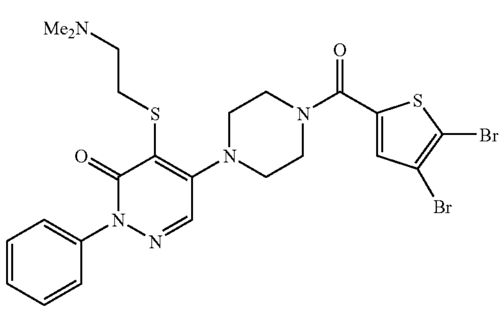

TABLE A-continued
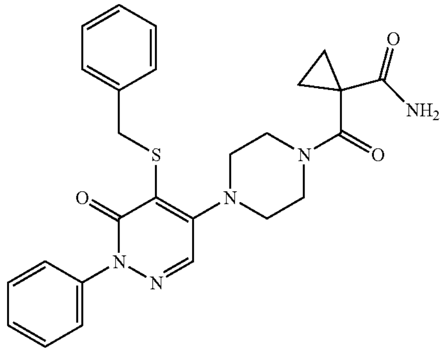
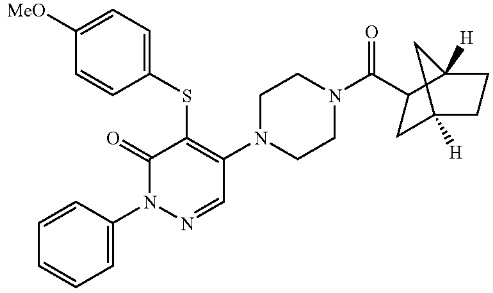
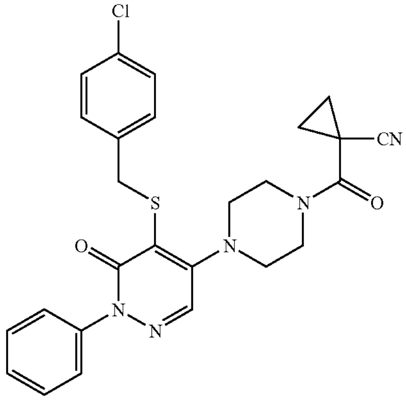
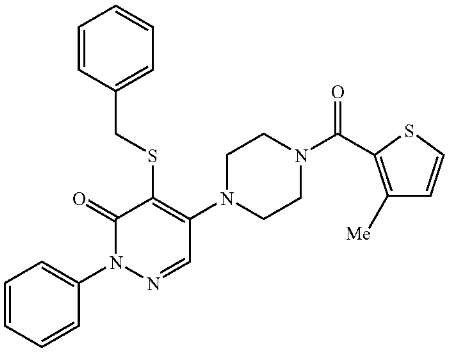
TABLE A-continued
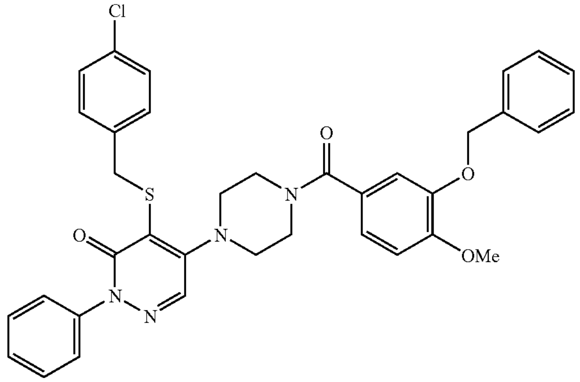
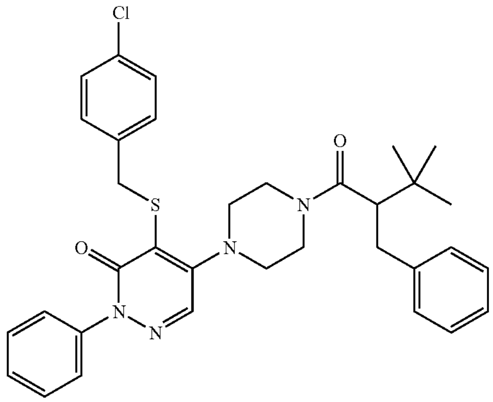
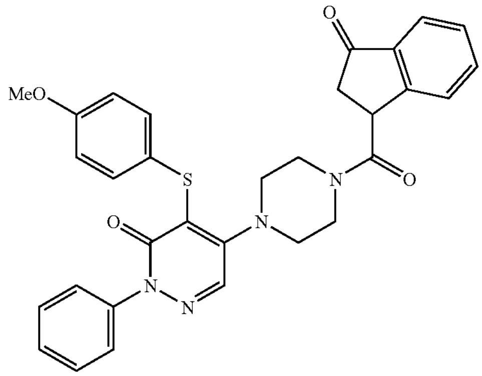
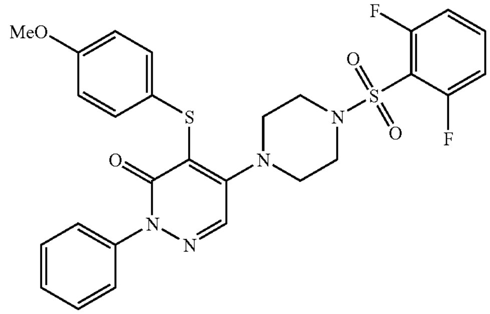

TABLE A-continued
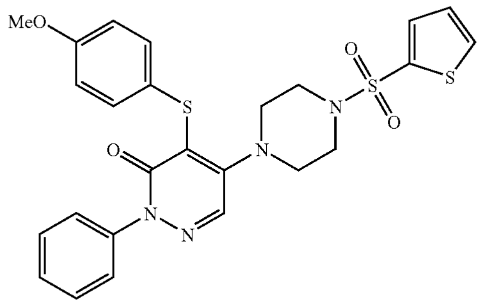
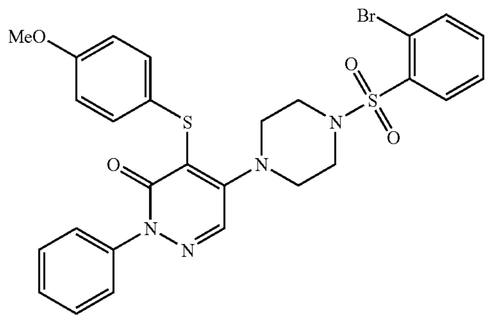
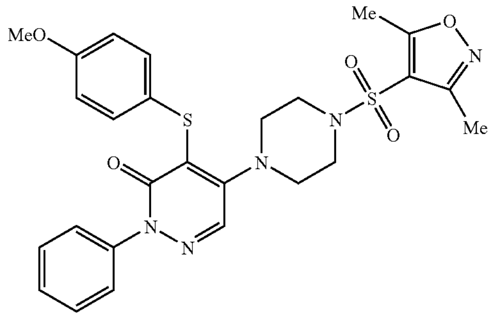
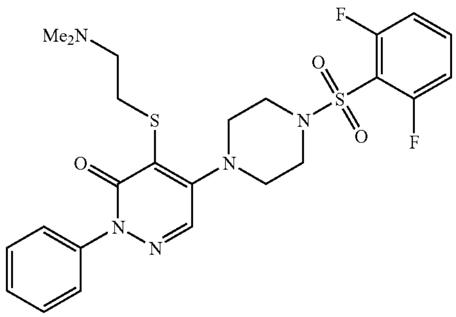
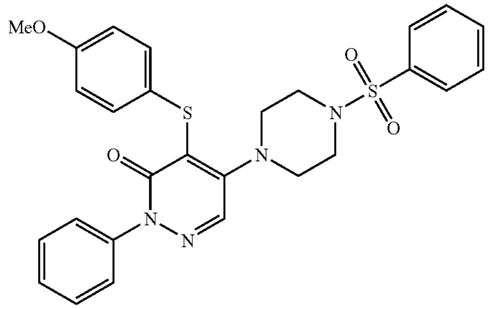
TABLE A-continued
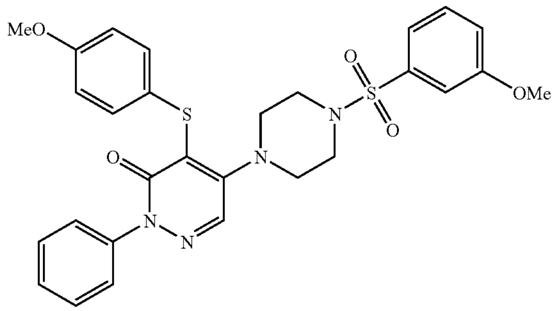
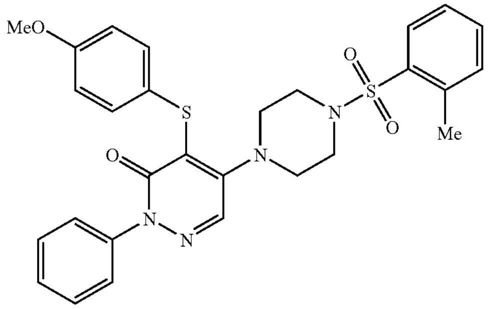
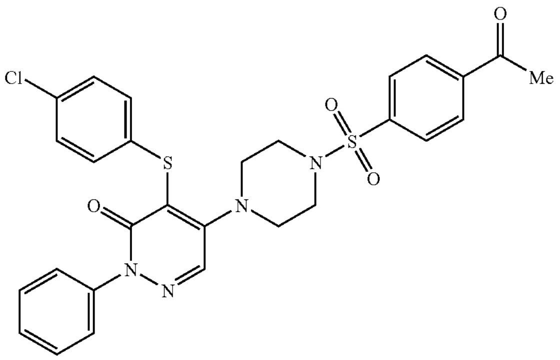
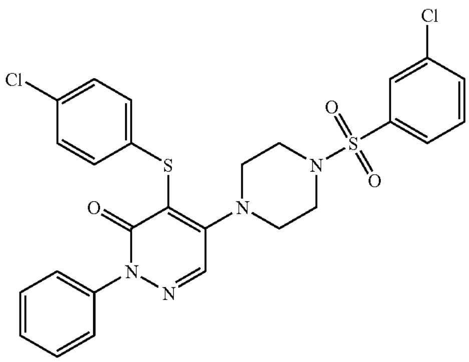

TABLE A-continued
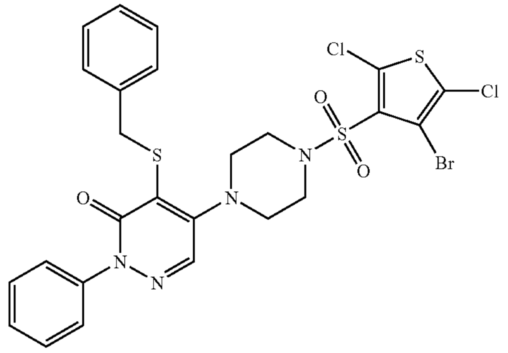
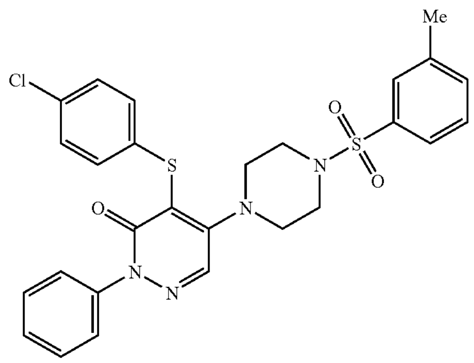
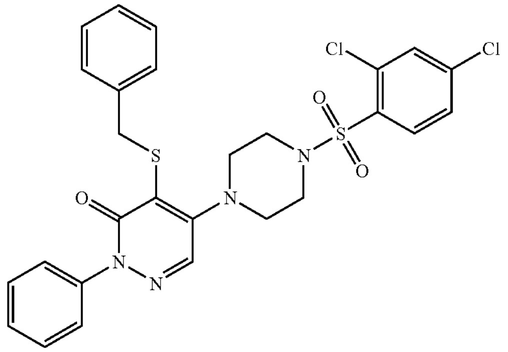
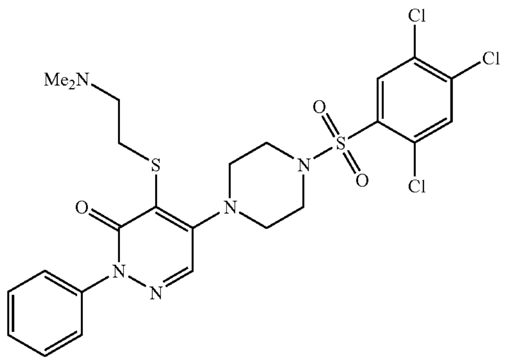
TABLE A-continued
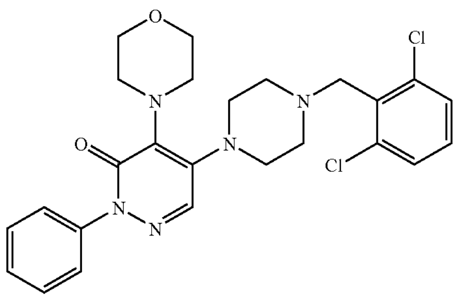
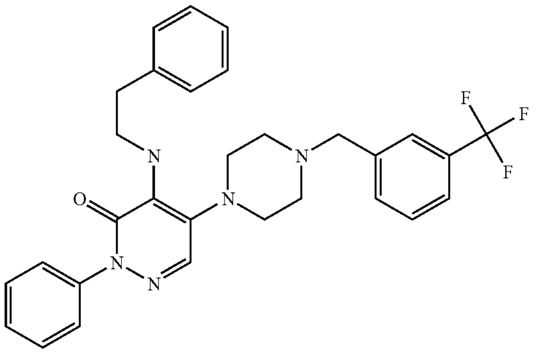
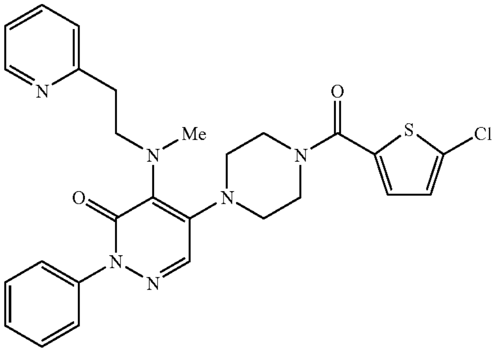
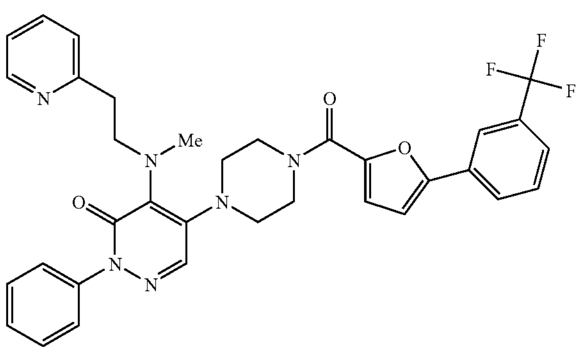

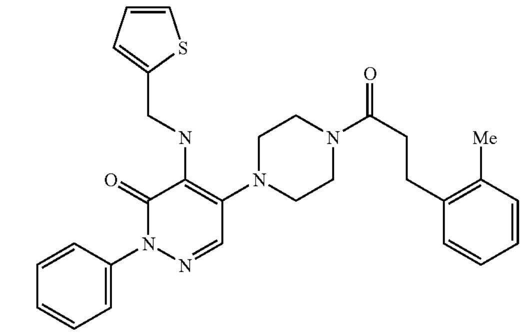
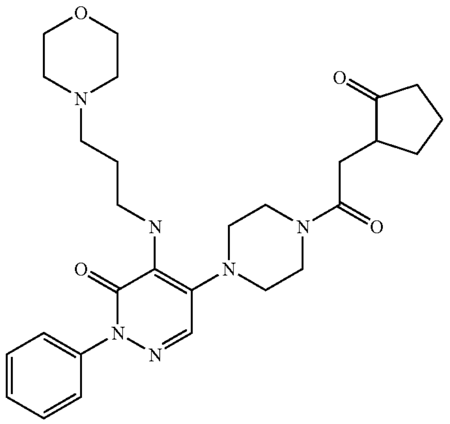
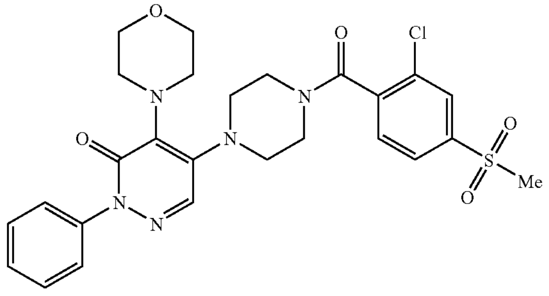
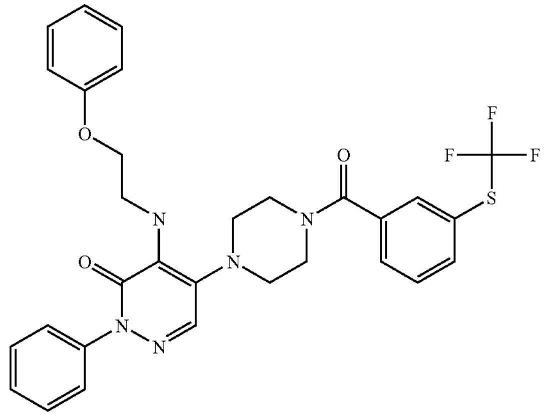
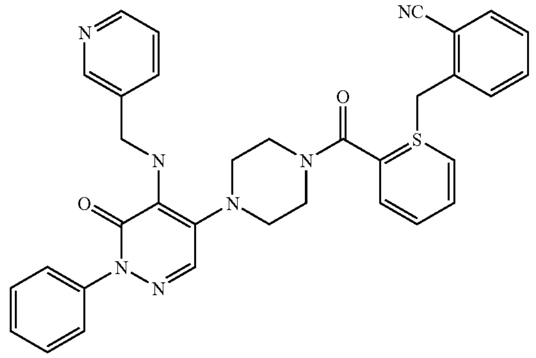
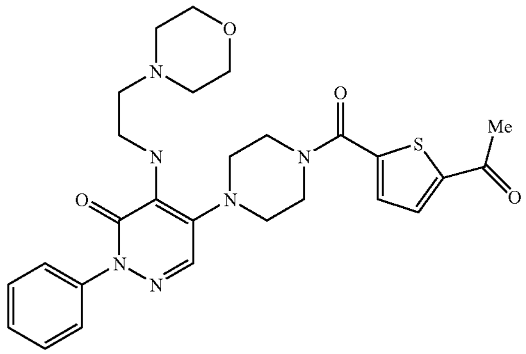
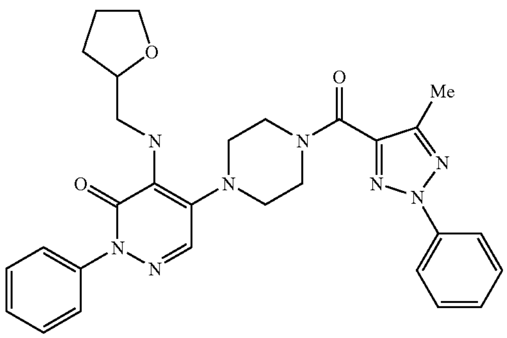
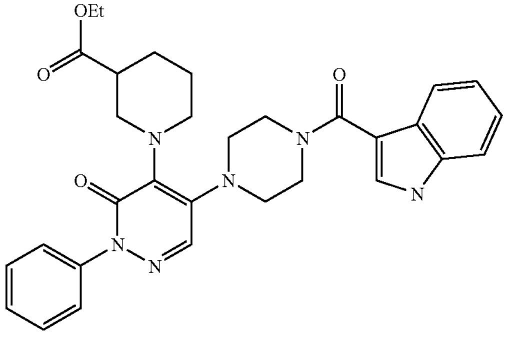

TABLE A-continued
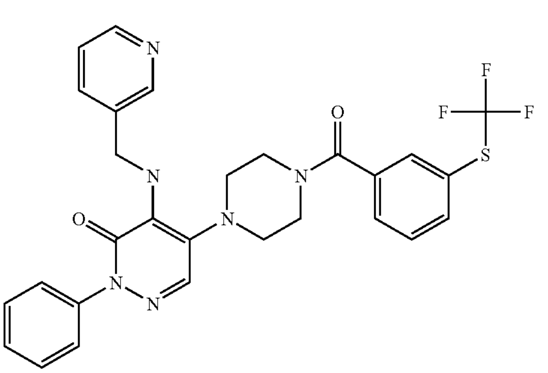
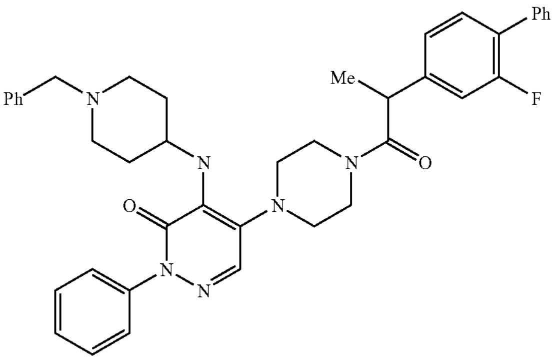
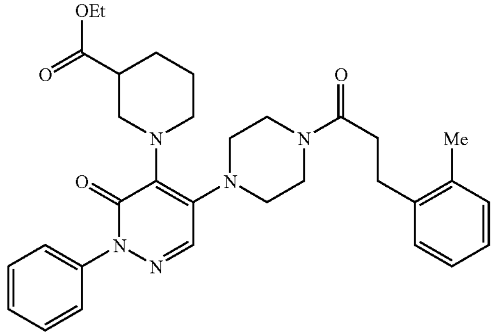
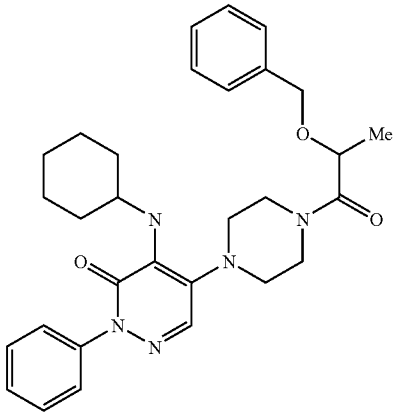
TABLE A-continued
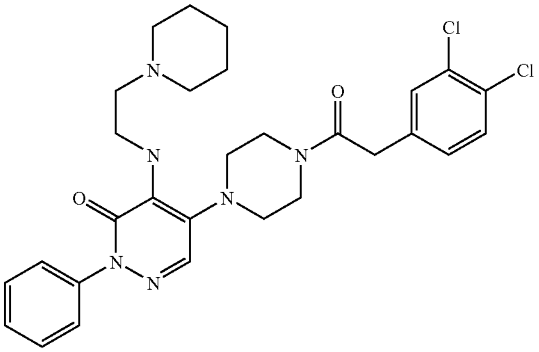
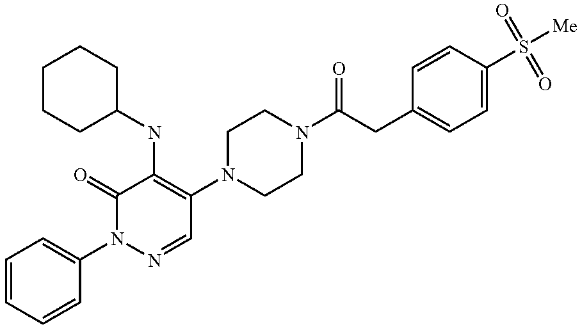
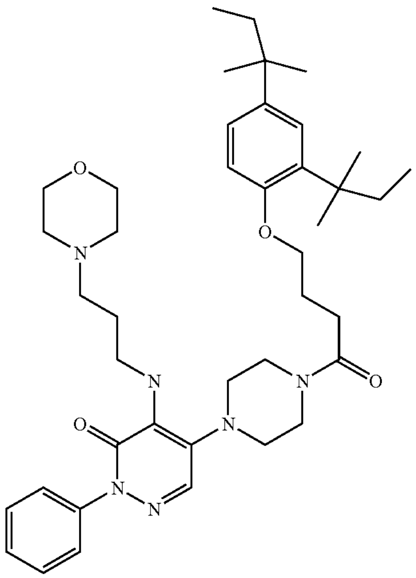
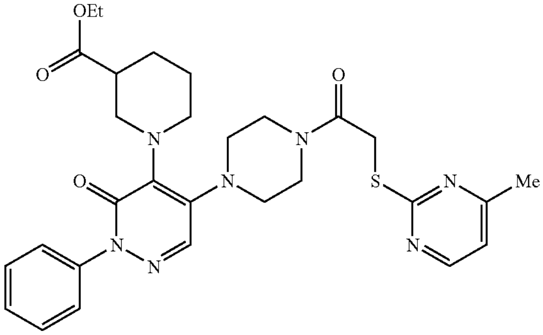

TABLE A-continued
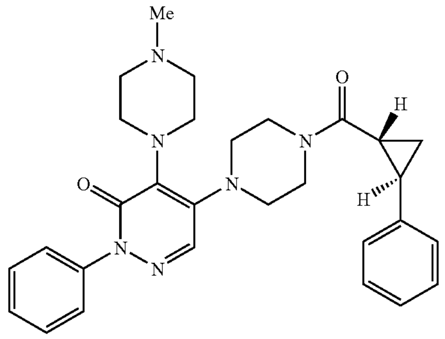
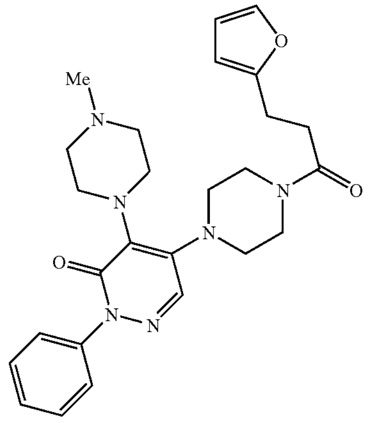
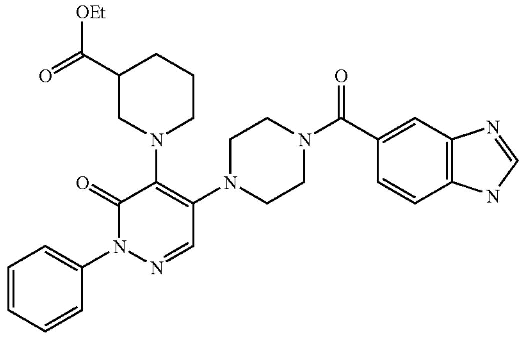
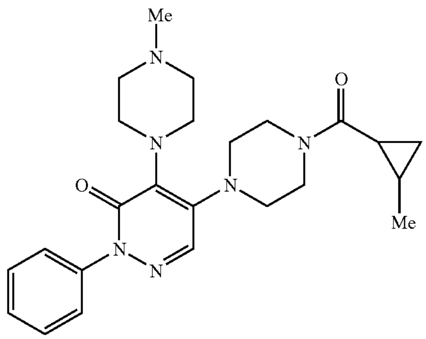
TABLE A-continued
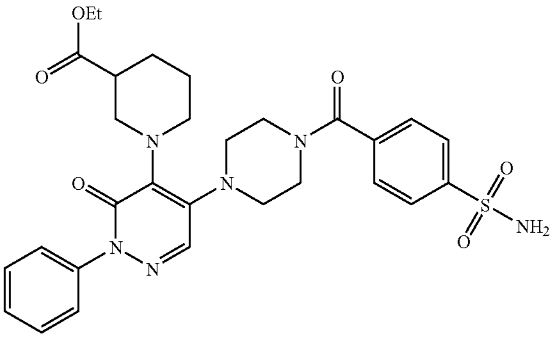
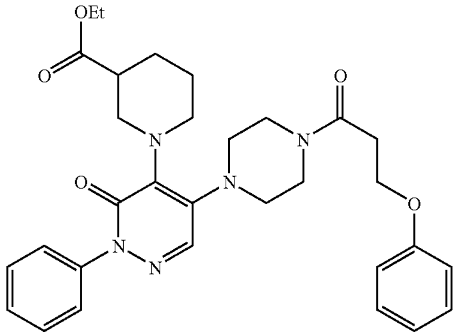
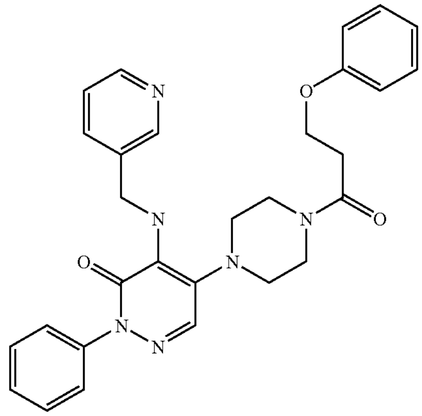
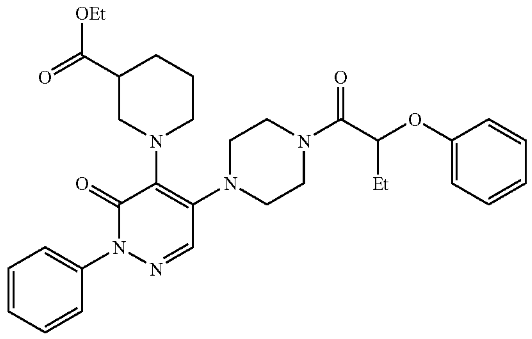

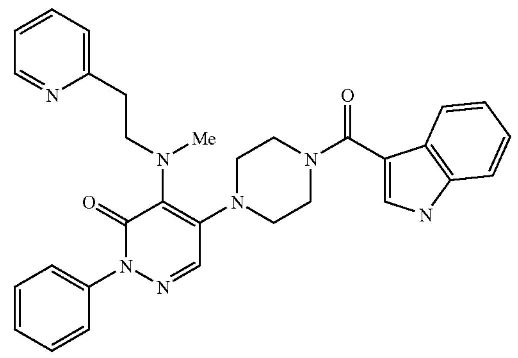
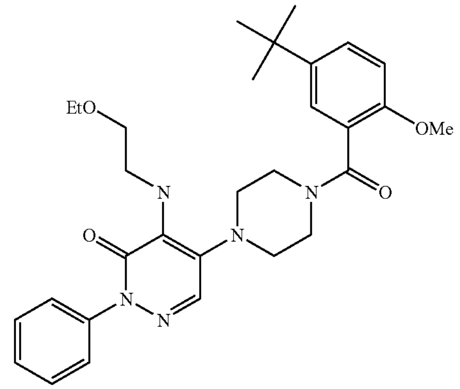
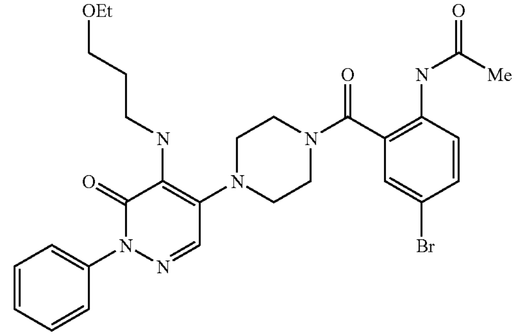
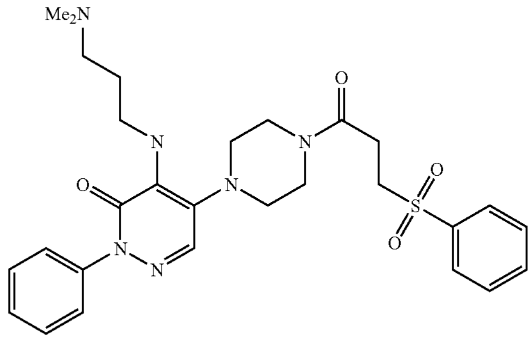
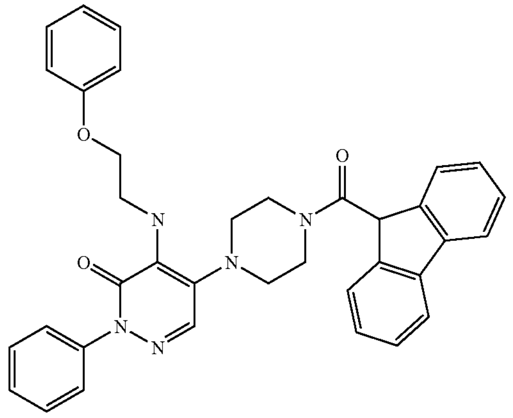
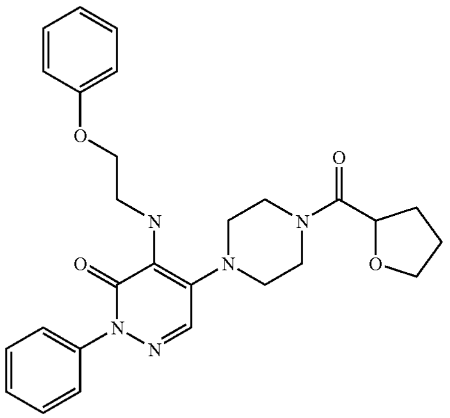
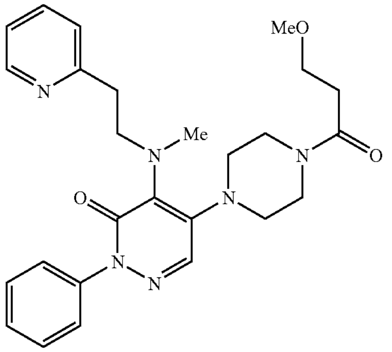
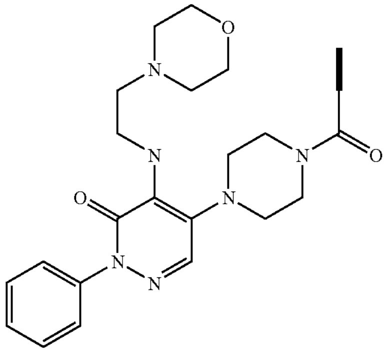

TABLE A-continued
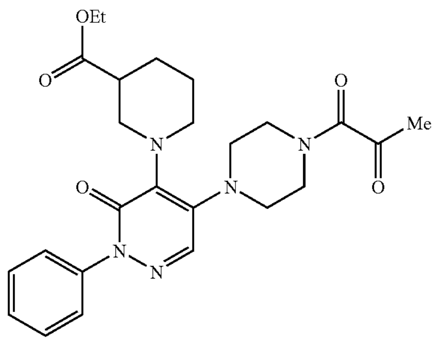
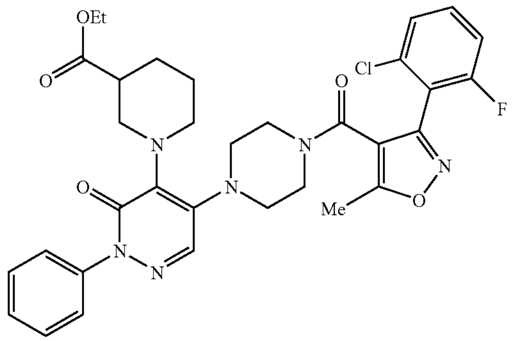
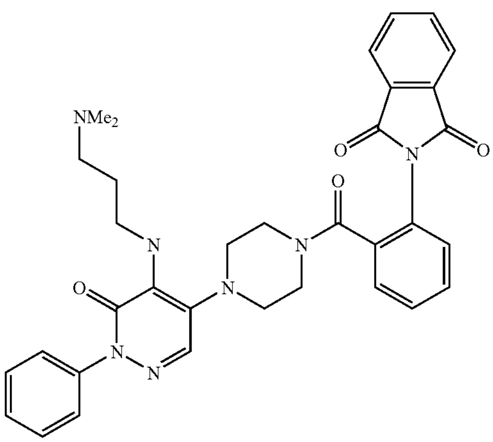
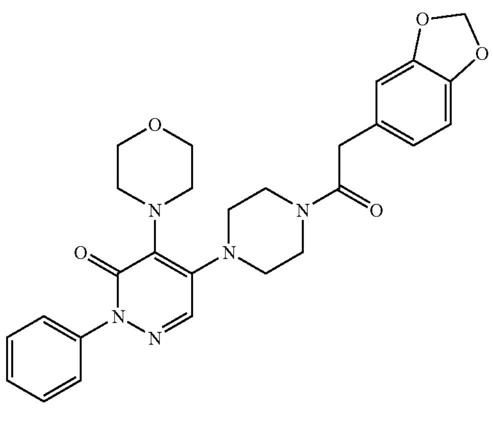
TABLE A-continued
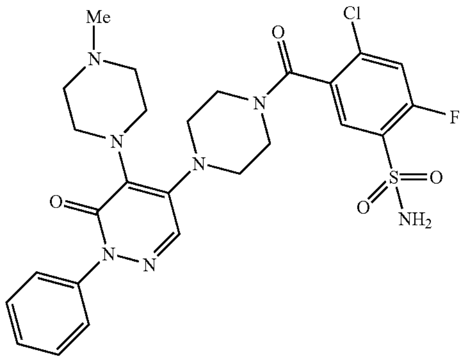
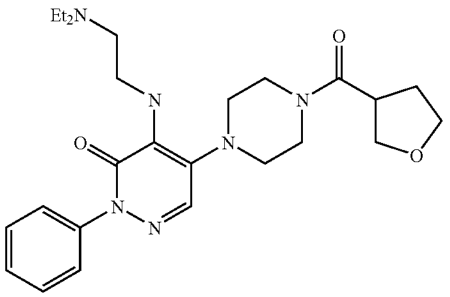
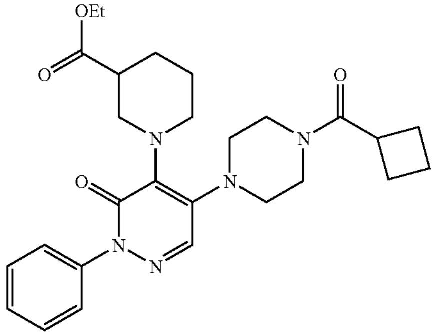
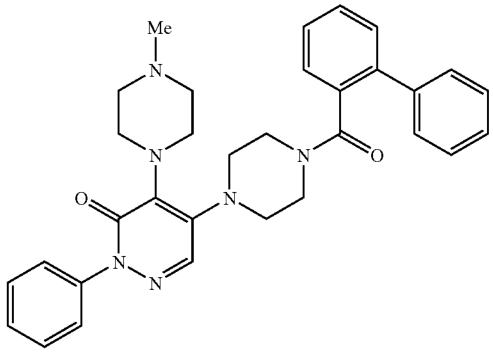

TABLE A-continued
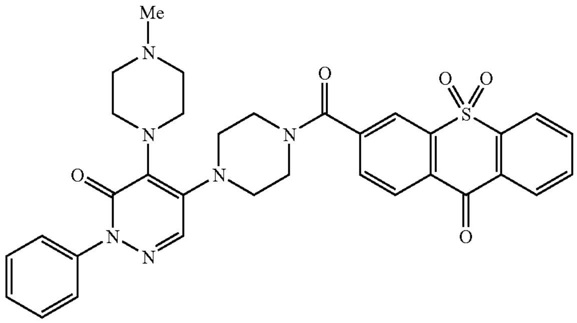
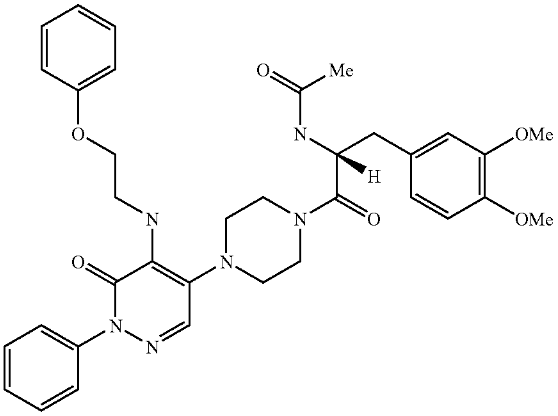
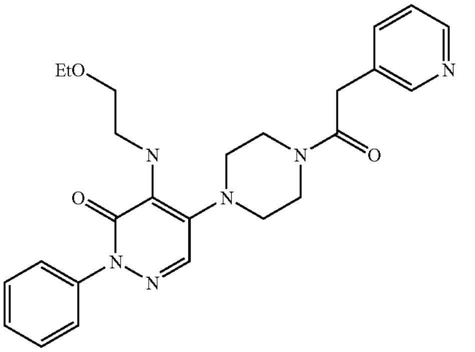
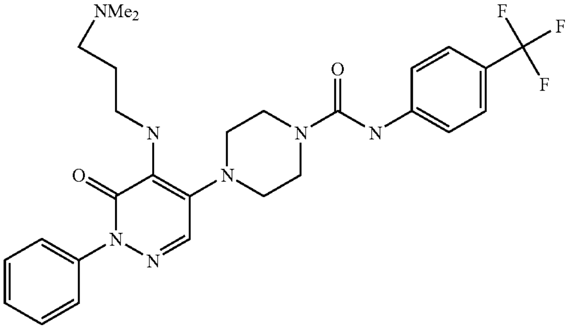
TABLE A-continued
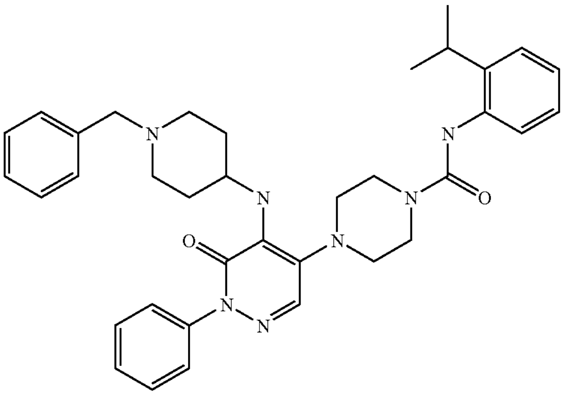
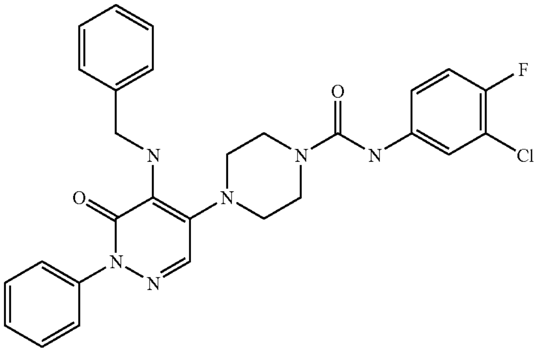
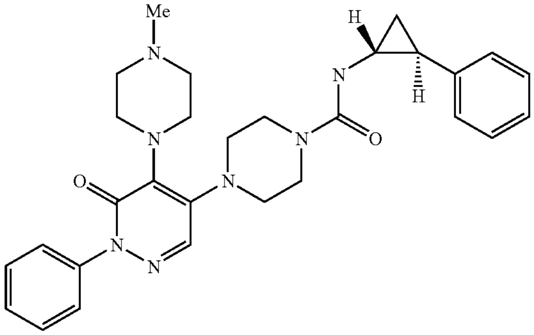
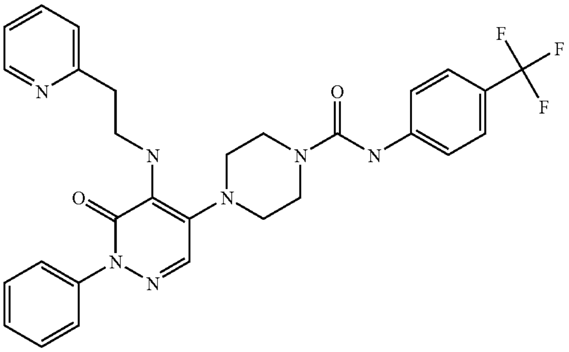

TABLE A-continued
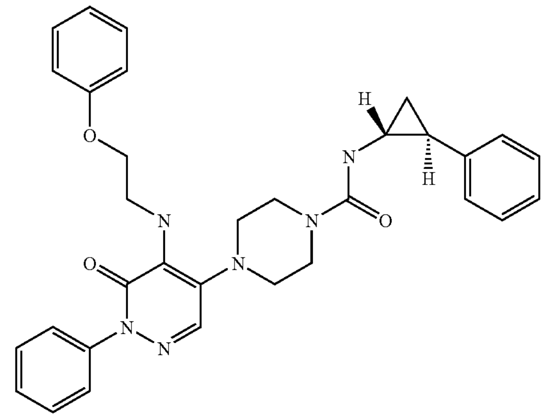
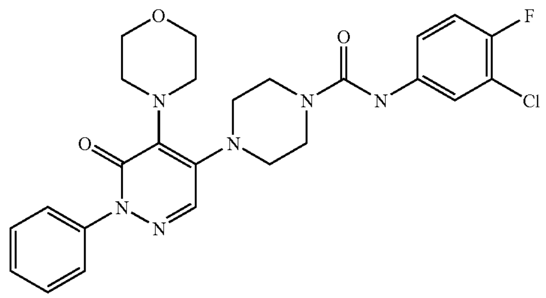
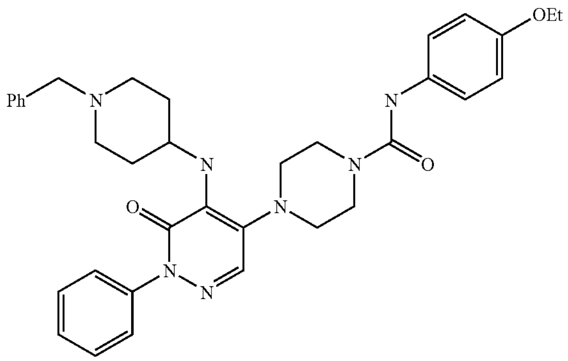
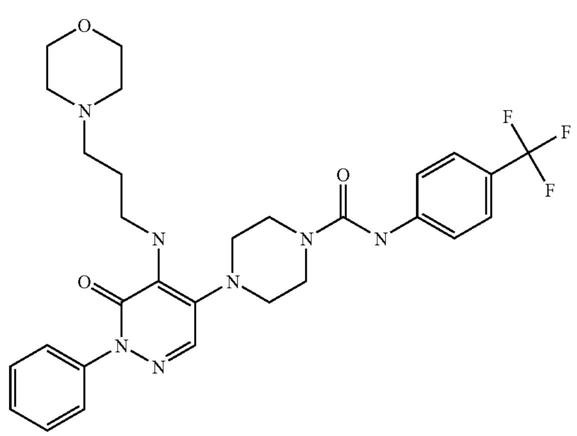
TABLE A-continued
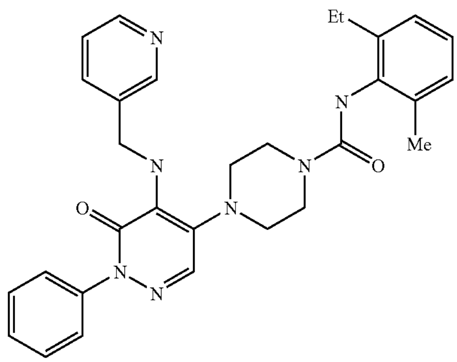
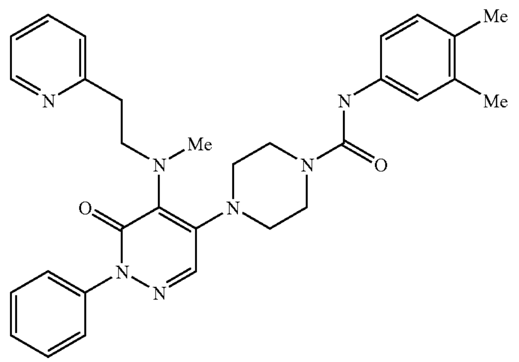
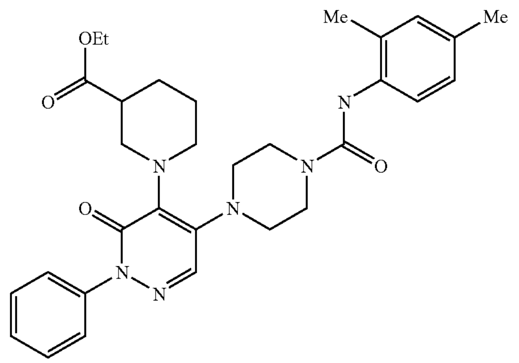
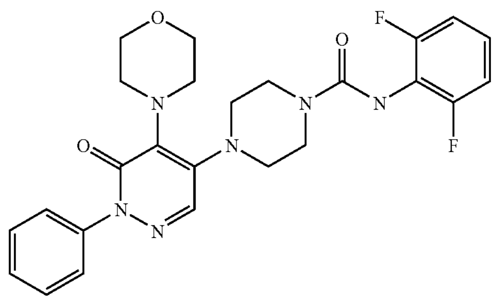

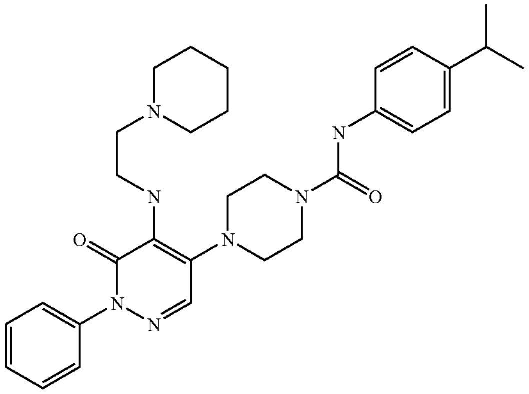
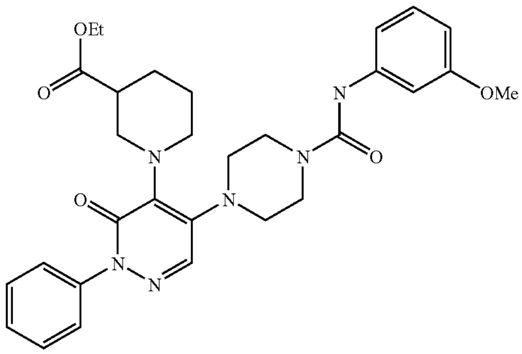
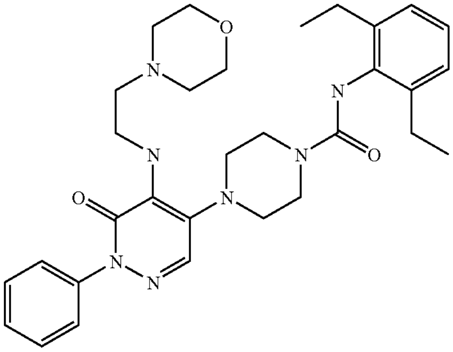
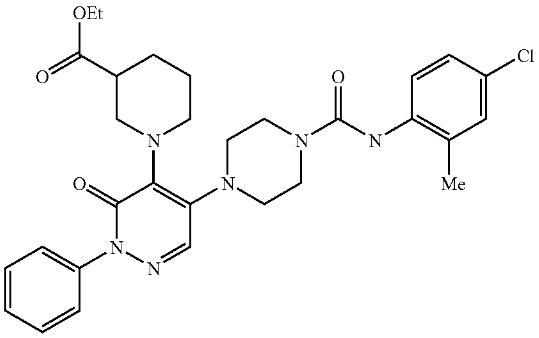
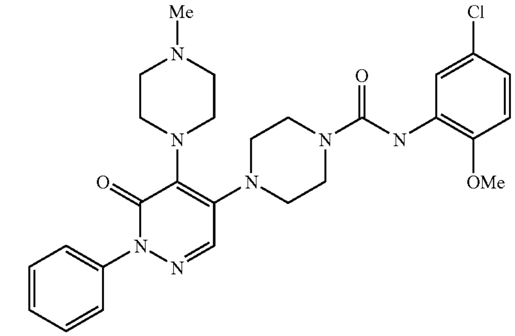
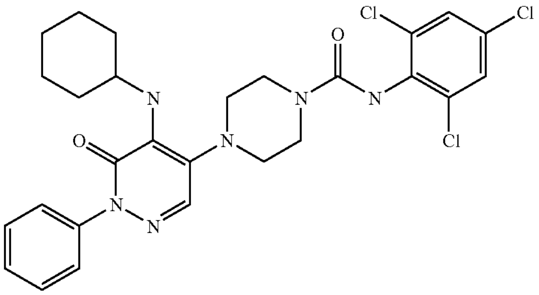
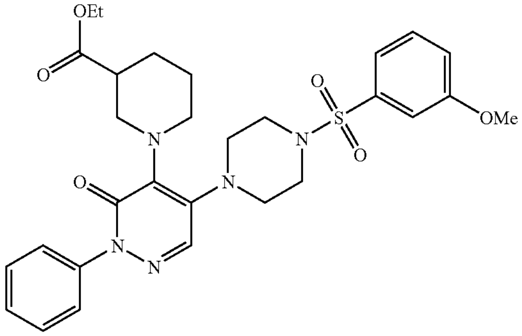
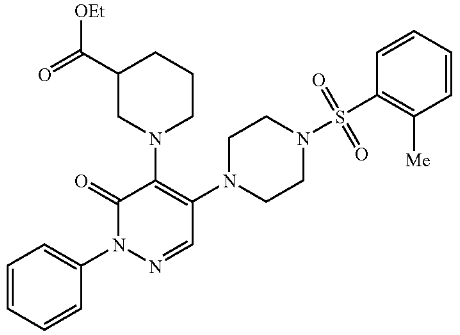

TABLE A-continued
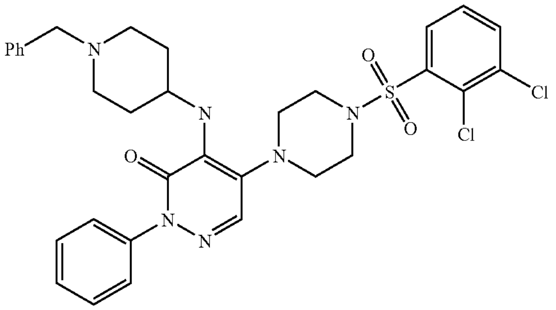
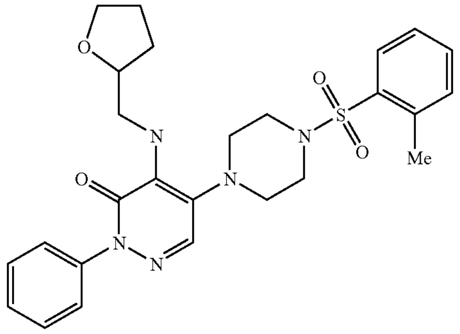
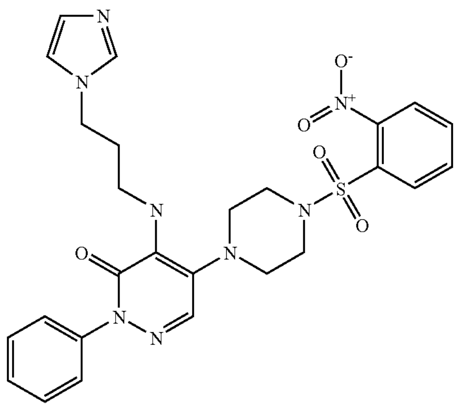
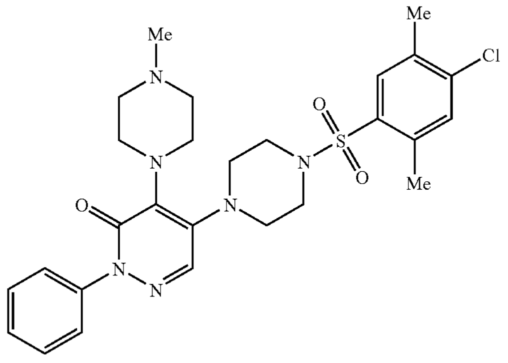
TABLE A-continued
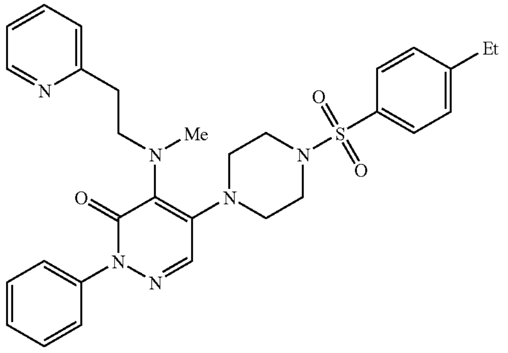
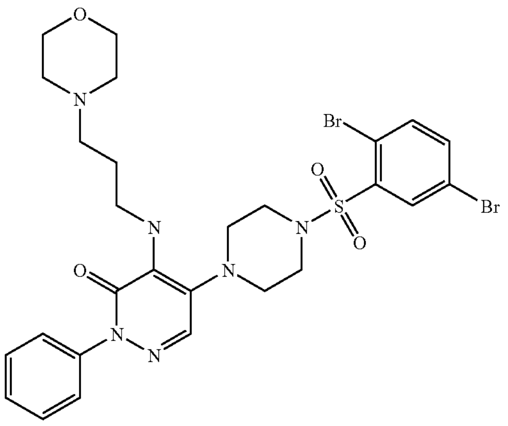
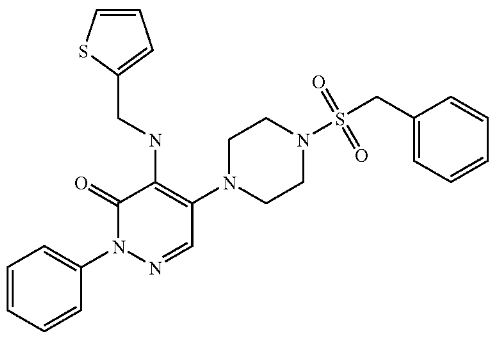
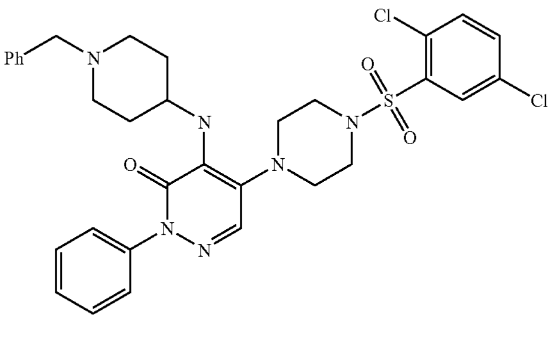

TABLE A-continued
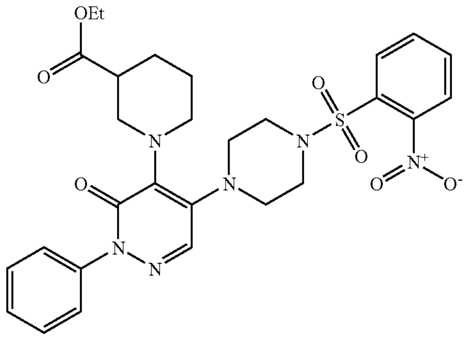
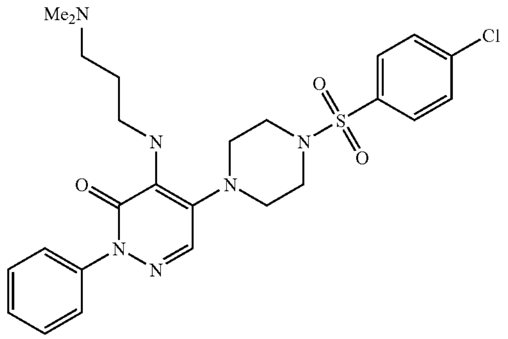
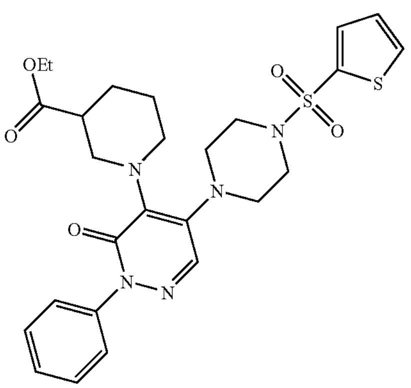
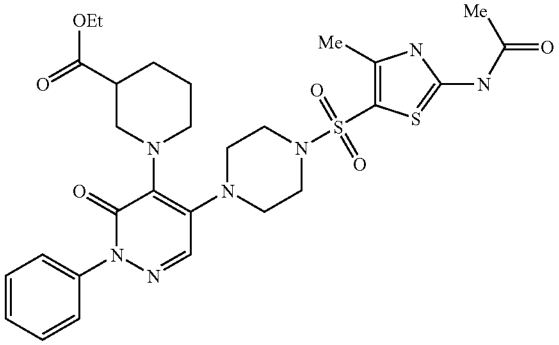
TABLE A-continued
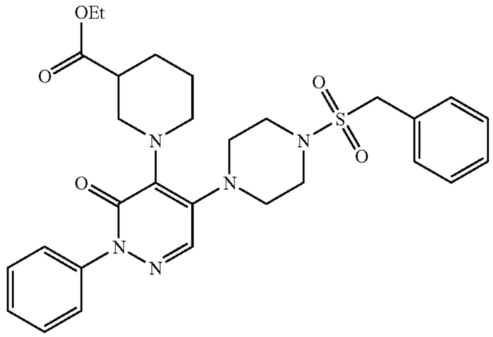
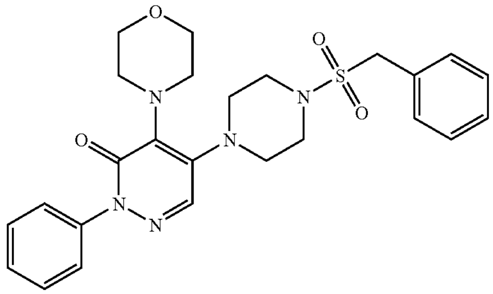
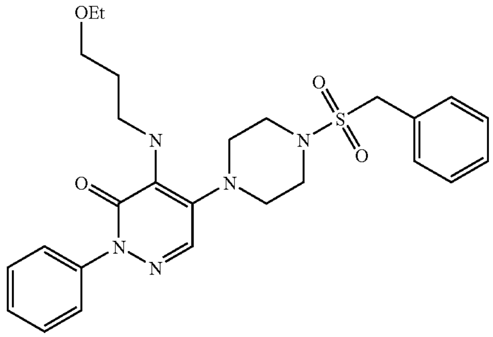
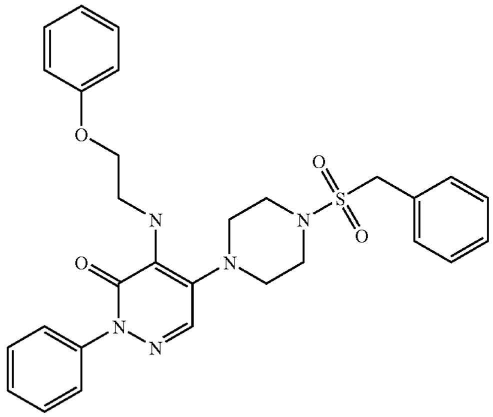

TABLE A-continued
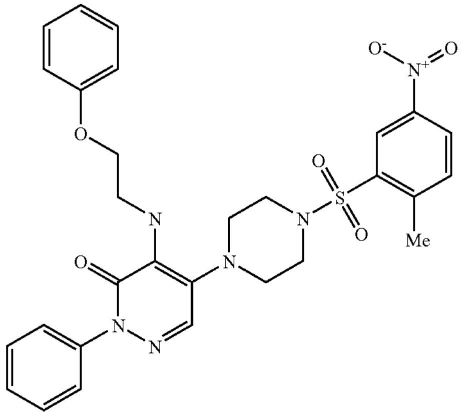
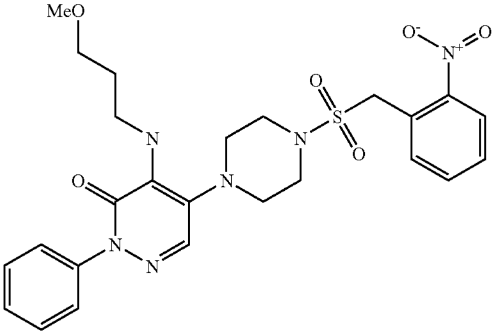
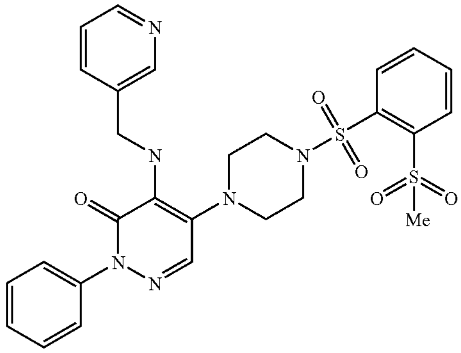
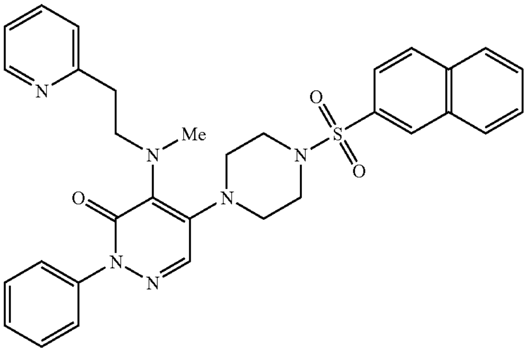
TABLE A-continued
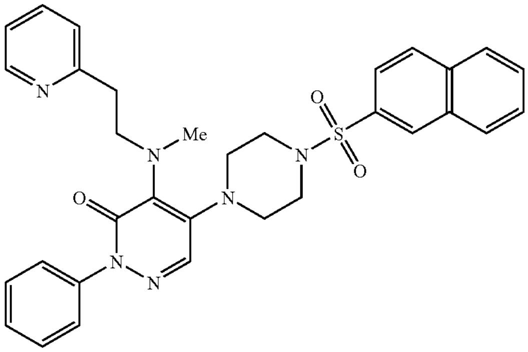
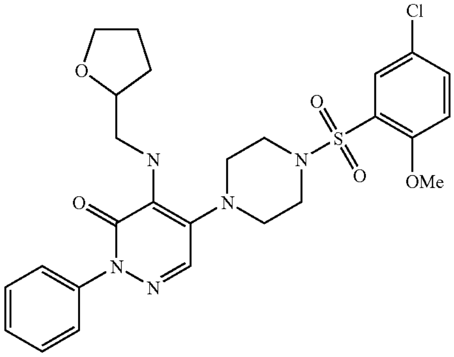
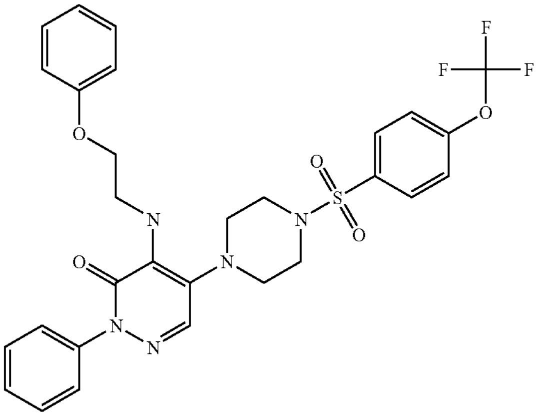
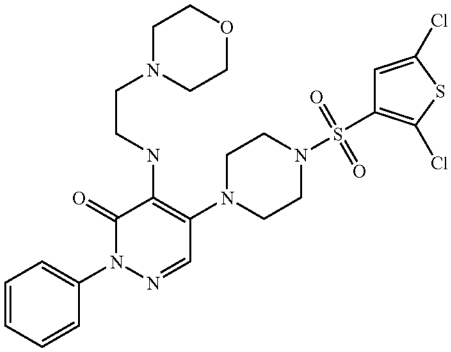

TABLE A-continued
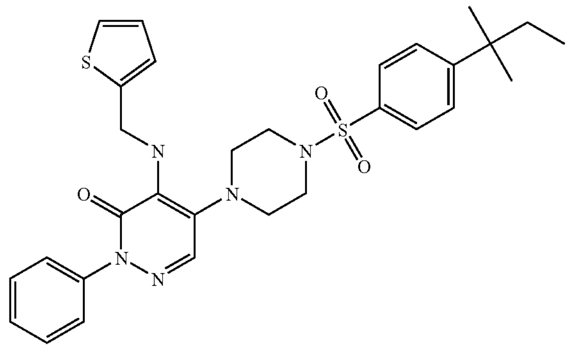
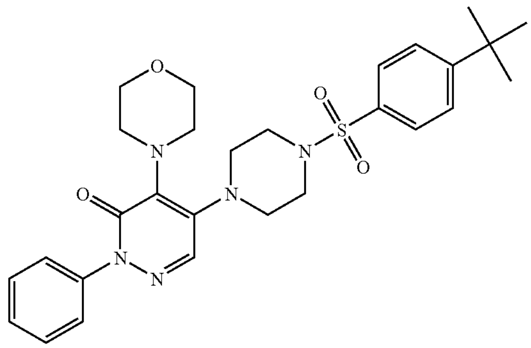
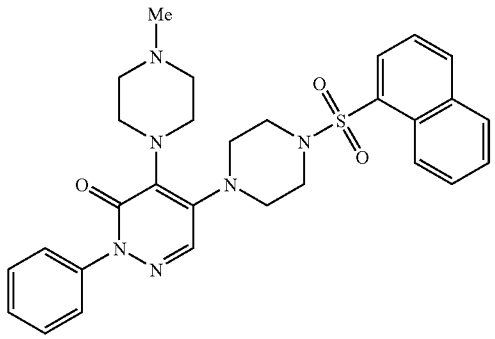
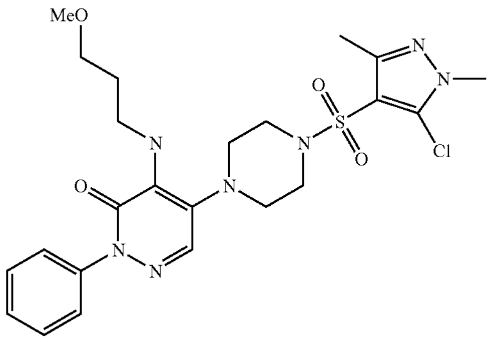
TABLE A-continued
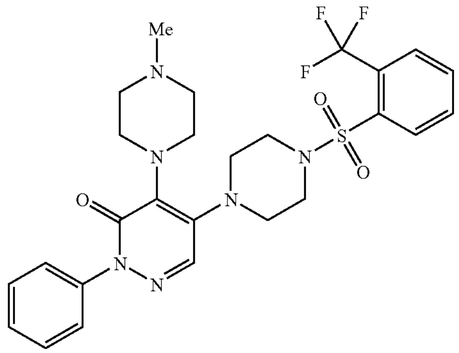
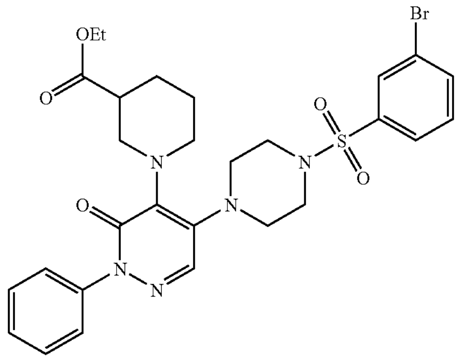
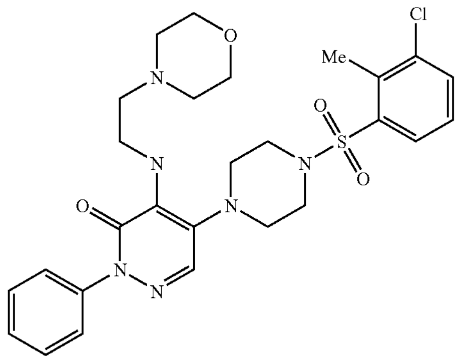
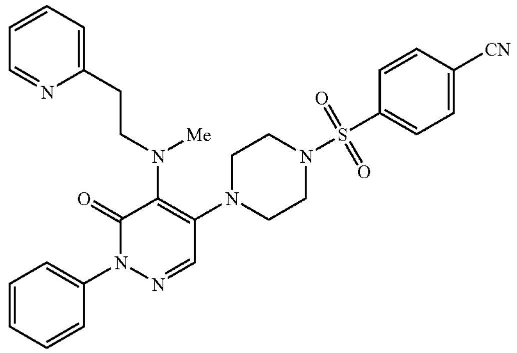

TABLE A-continued
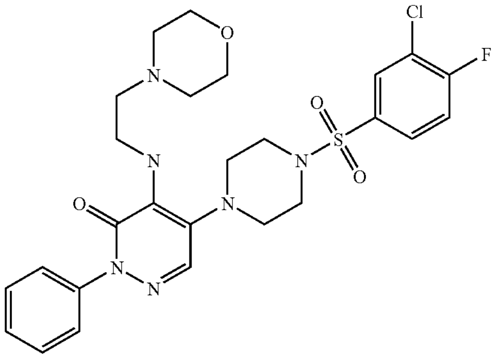
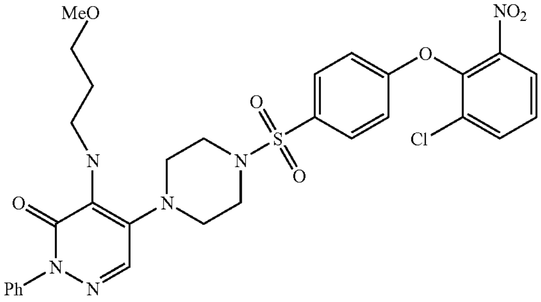
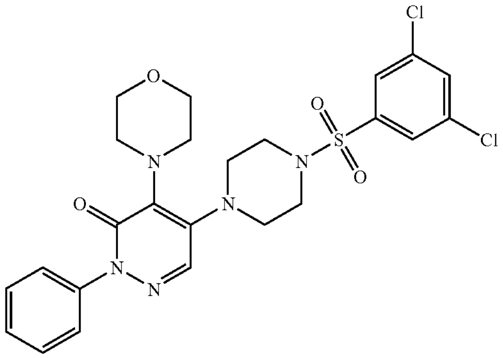
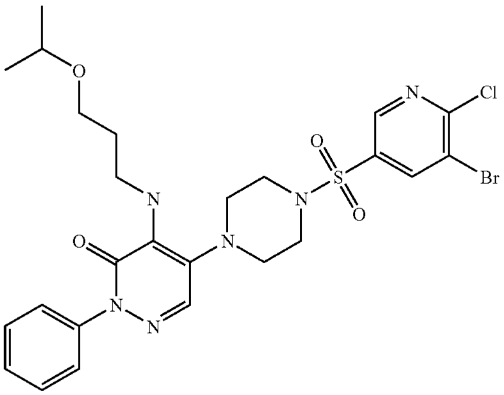
TABLE A-continued
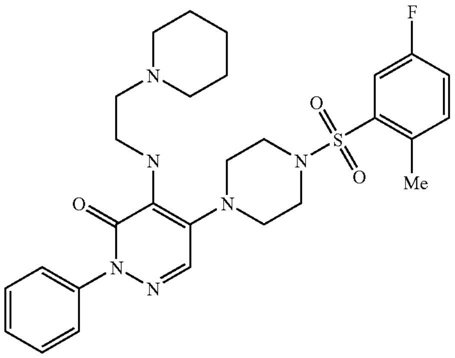
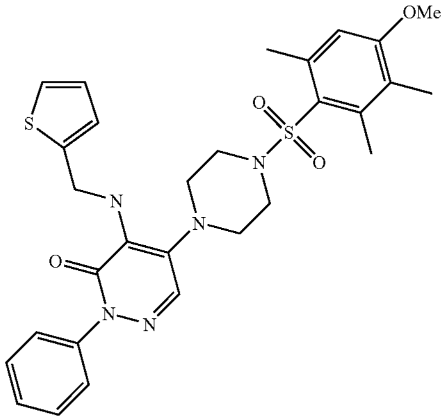
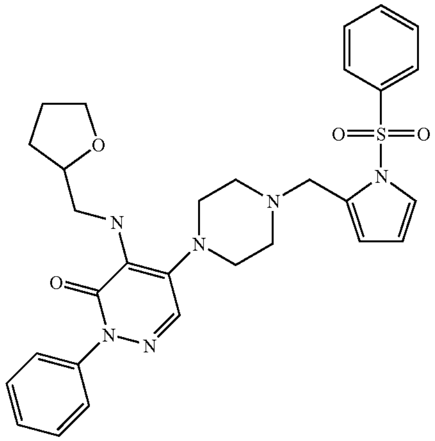

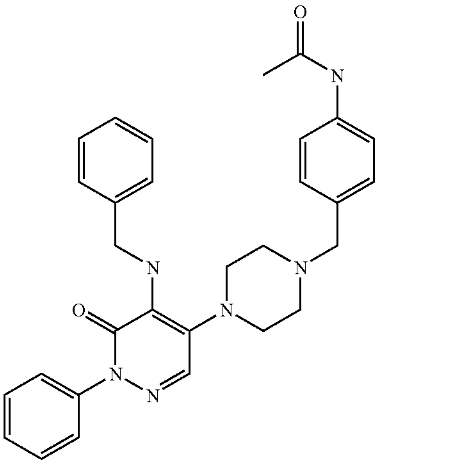
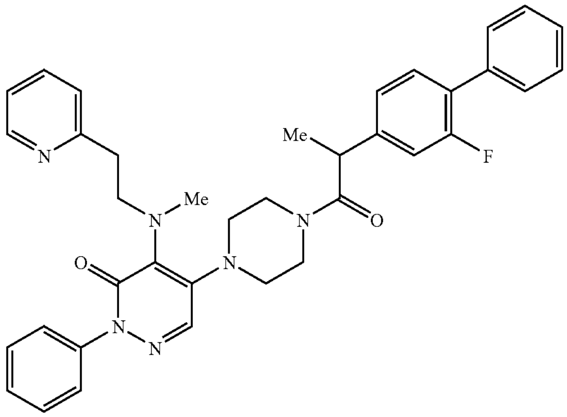
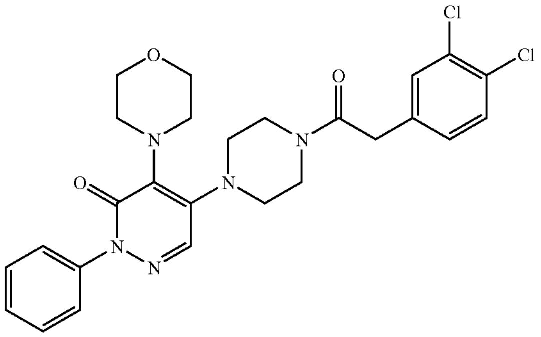
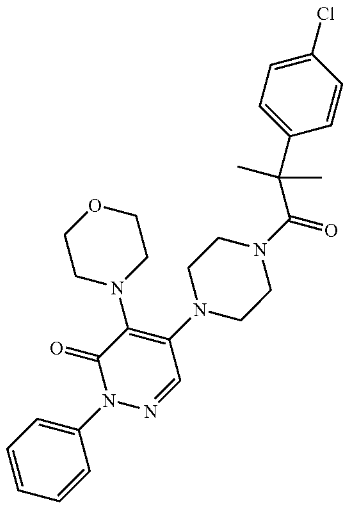
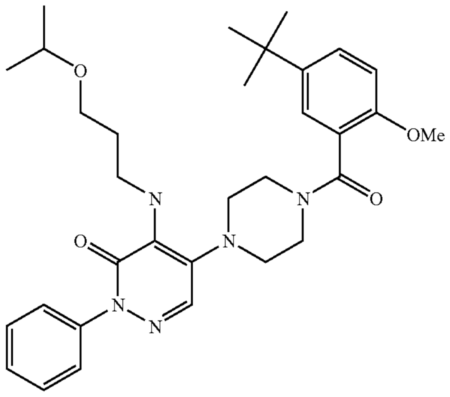
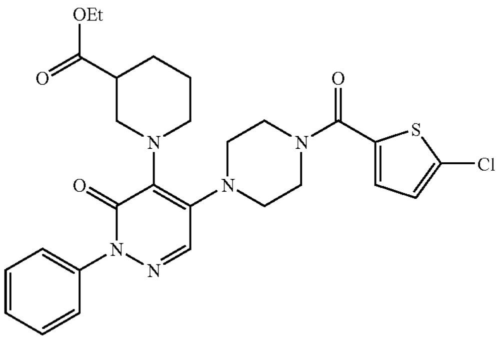

TABLE A-continued
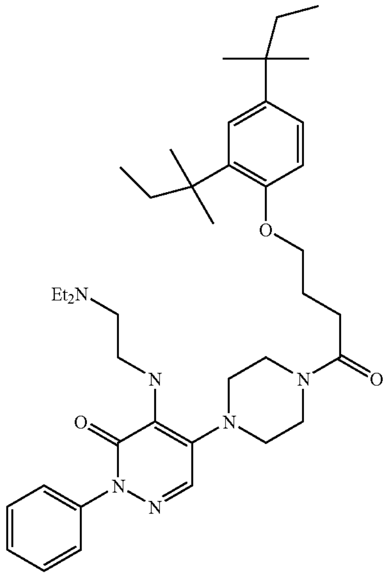
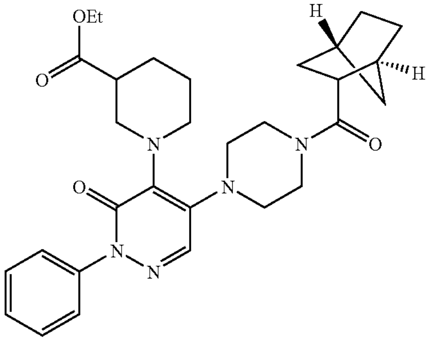
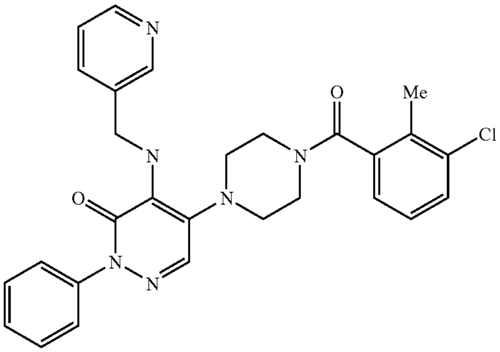
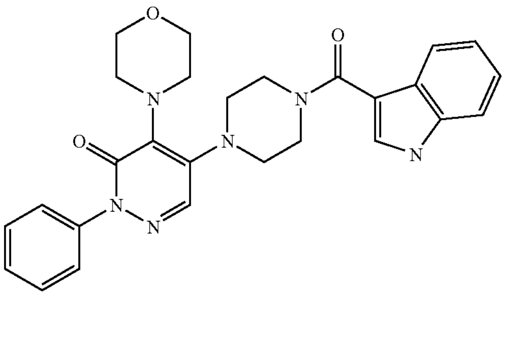
TABLE A-continued
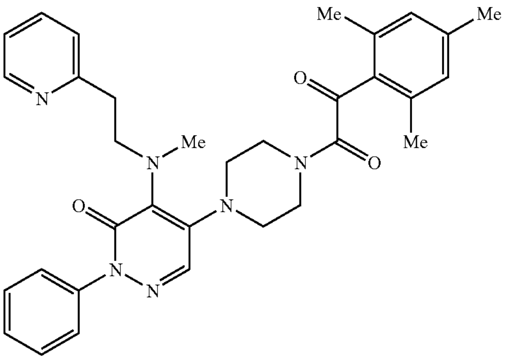
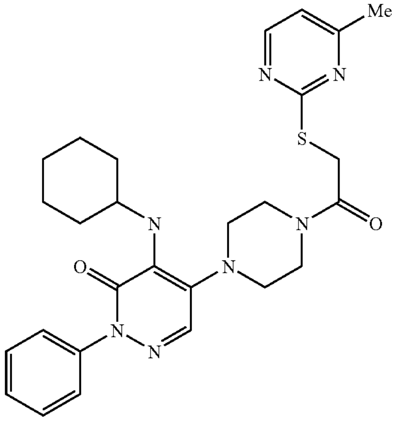
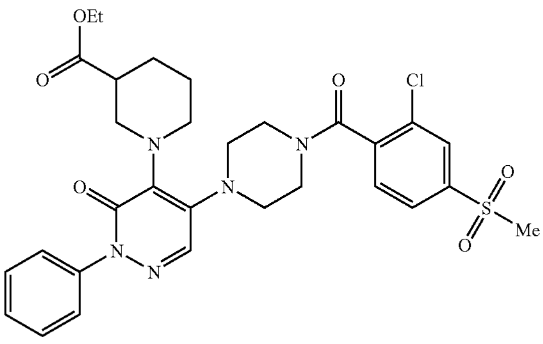
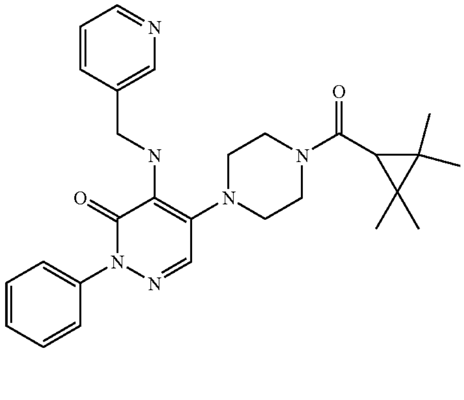

TABLE A-continued
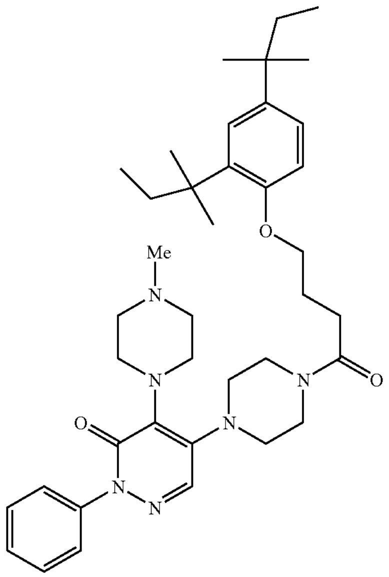
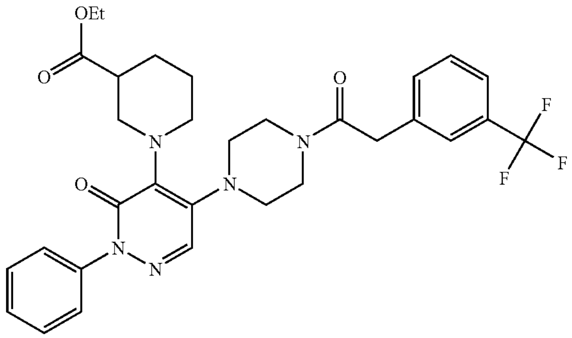
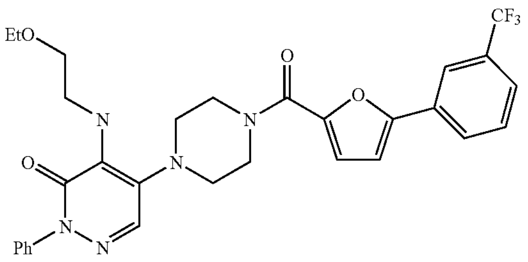
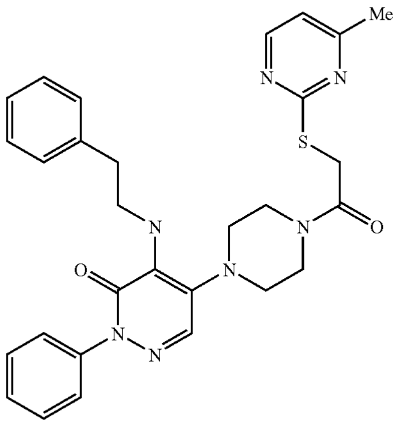
TABLE A-continued
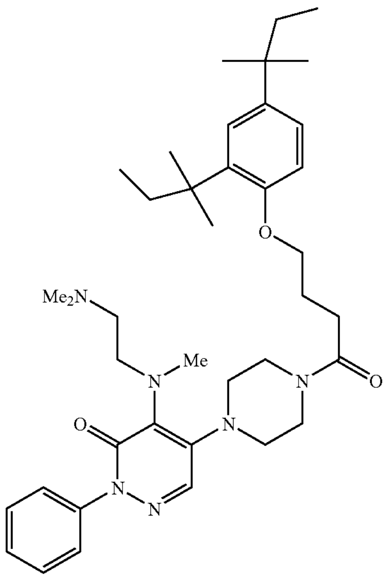
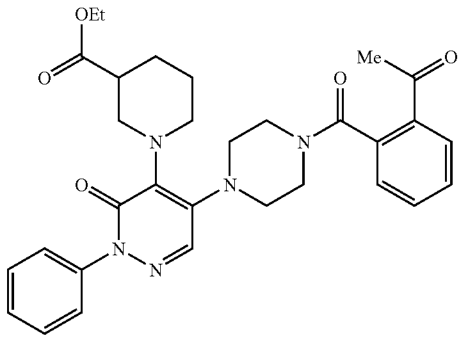
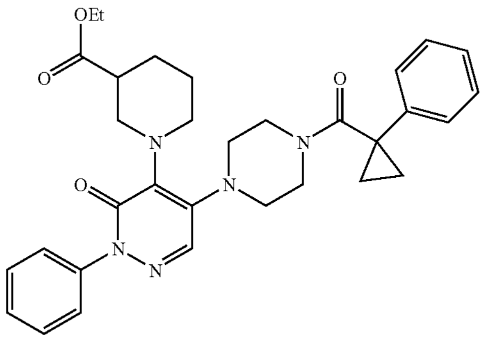
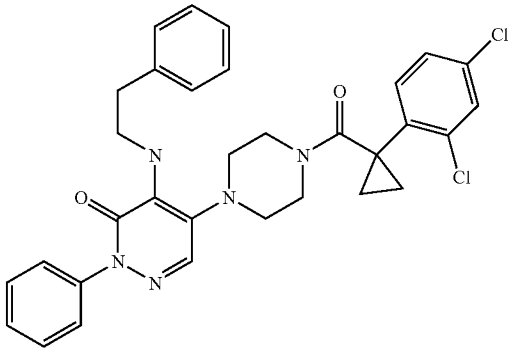

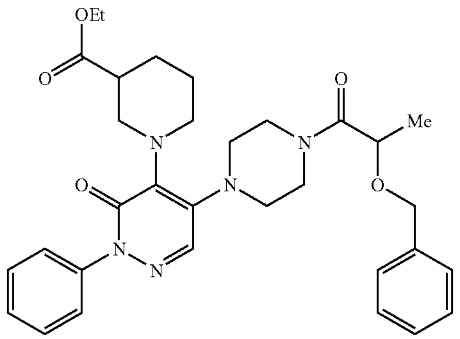
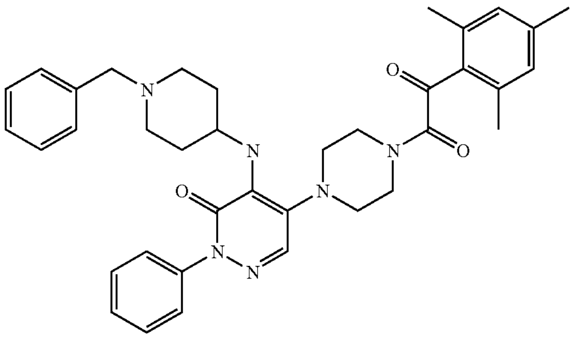
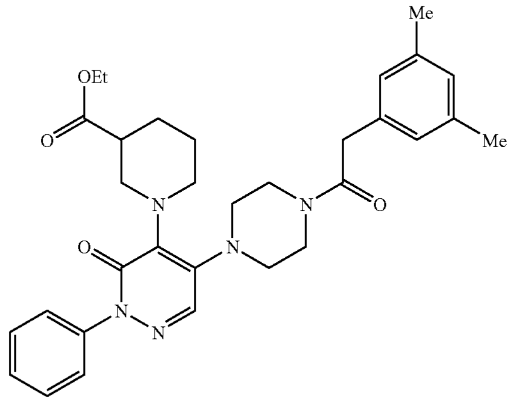
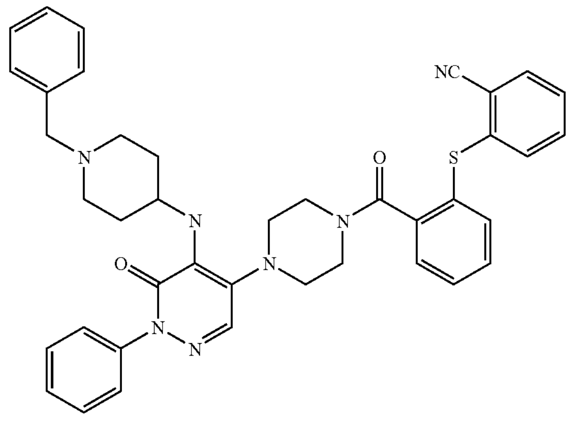
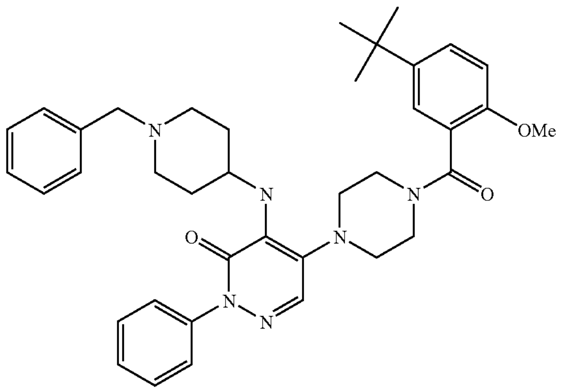
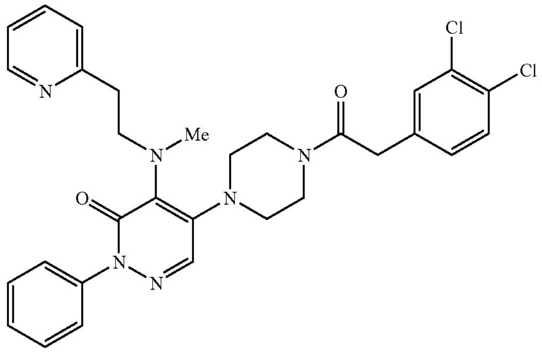
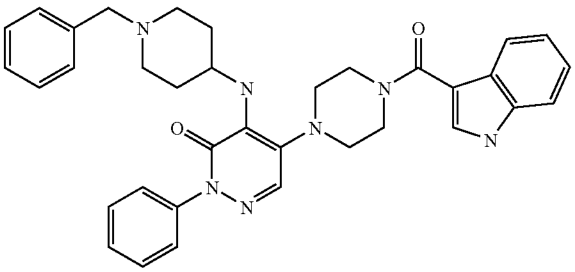
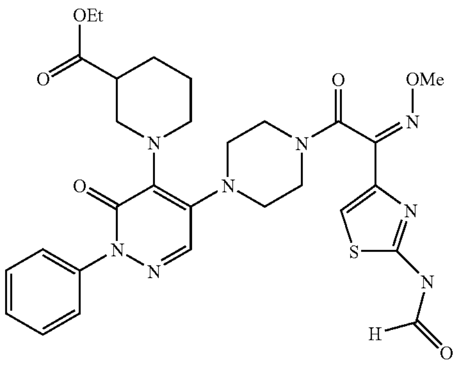

TABLE A-continued
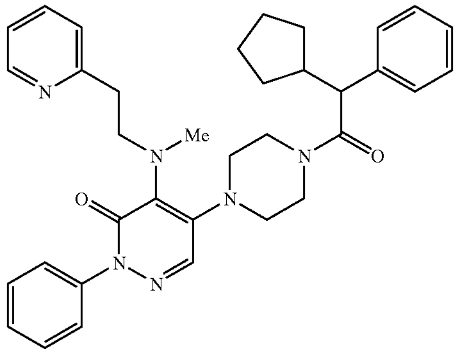
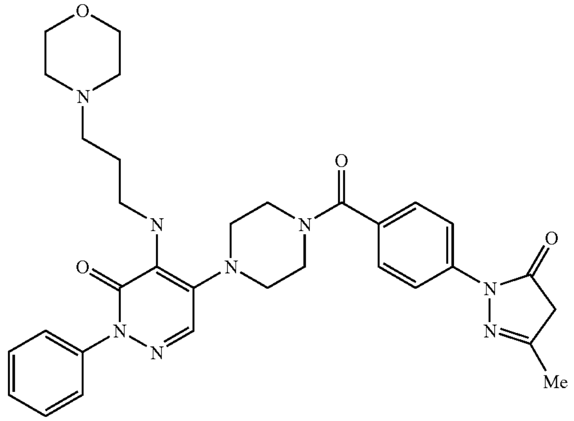
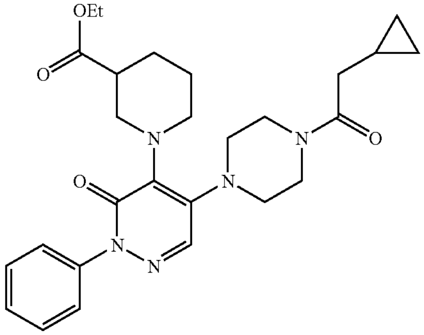
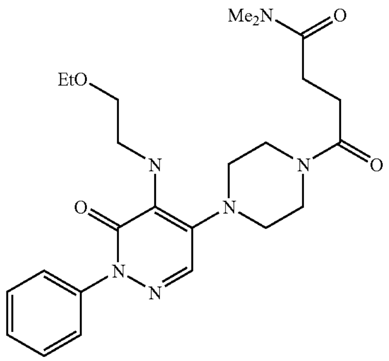
TABLE A-continued
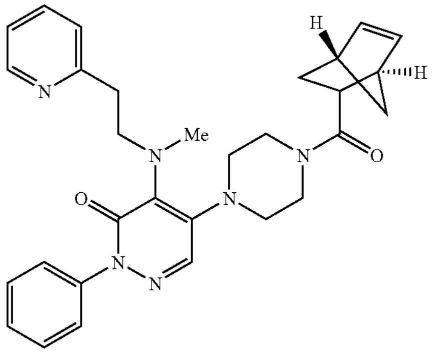
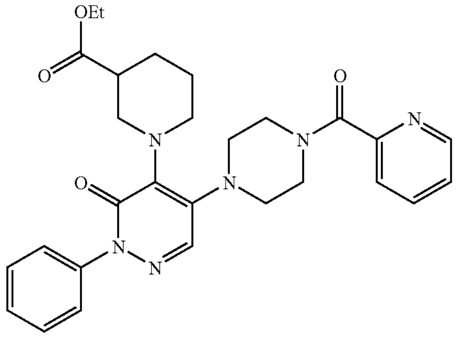
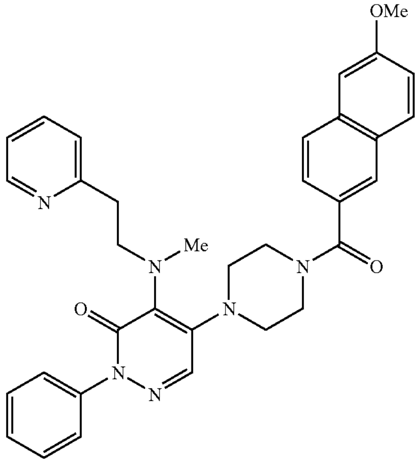
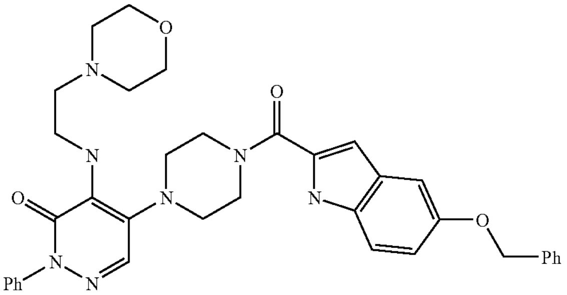

TABLE A-continued
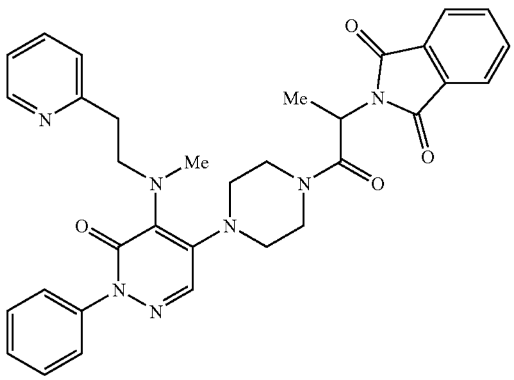
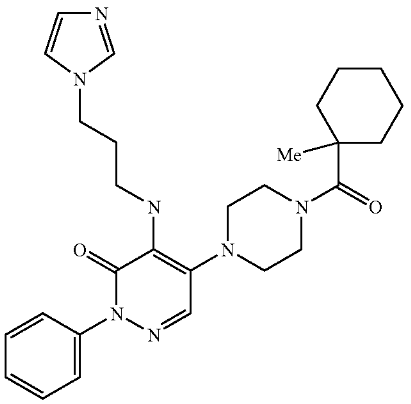
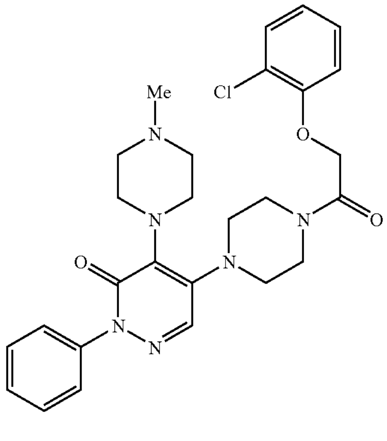
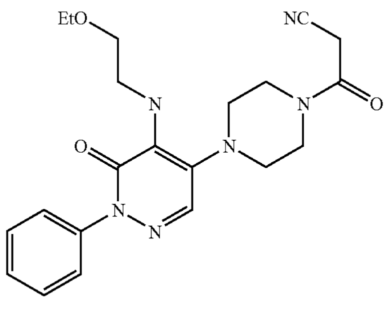
TABLE A-continued
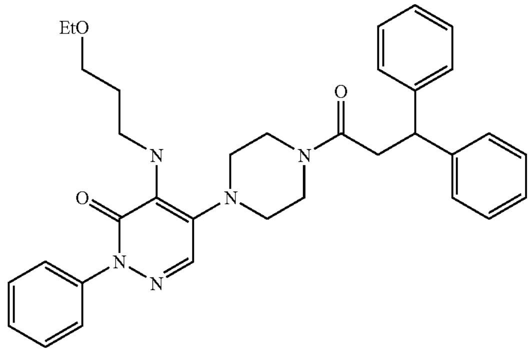
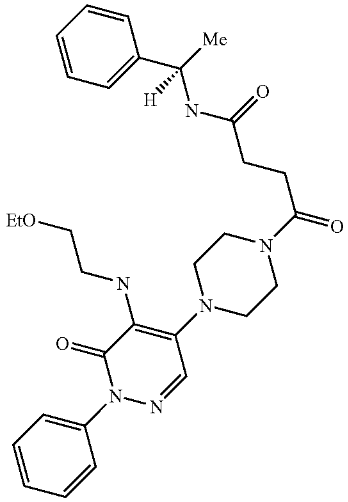
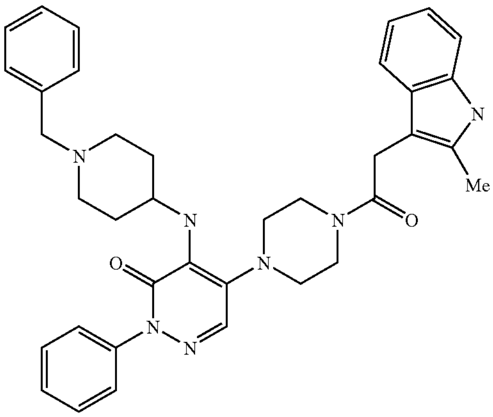
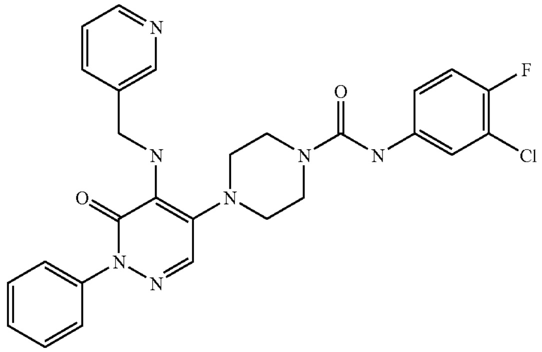

TABLE A-continued
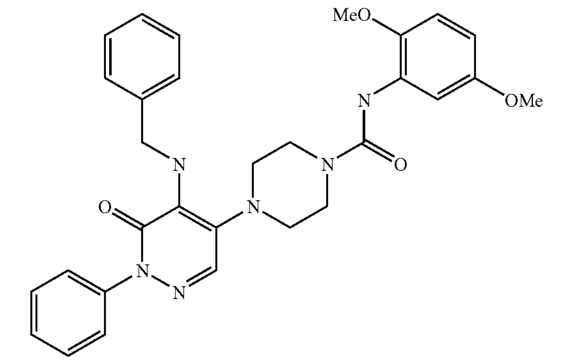
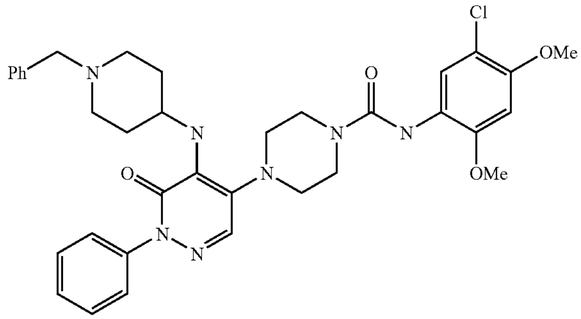
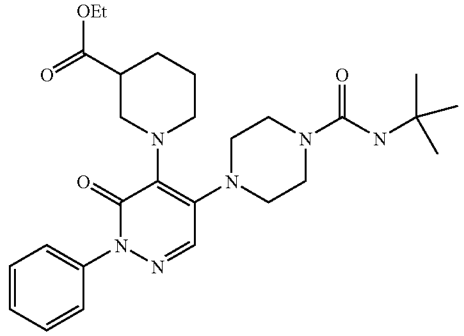
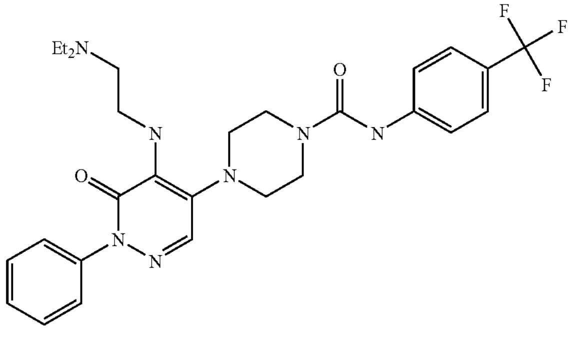
TABLE A-continued
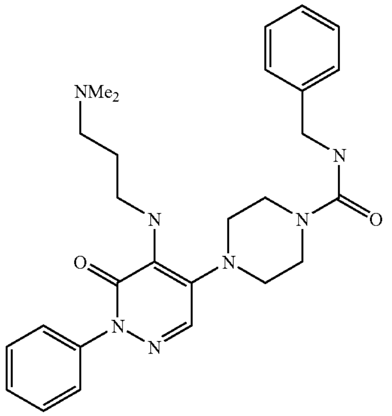
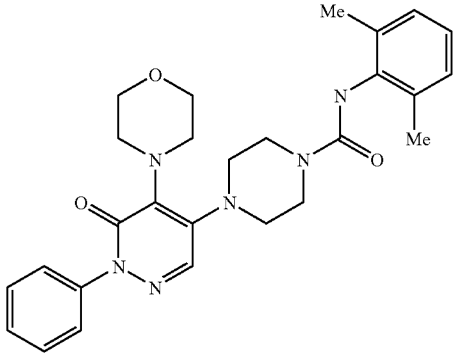
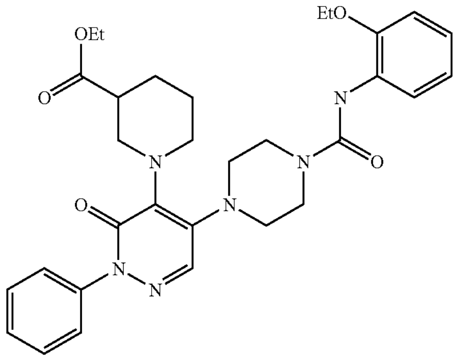
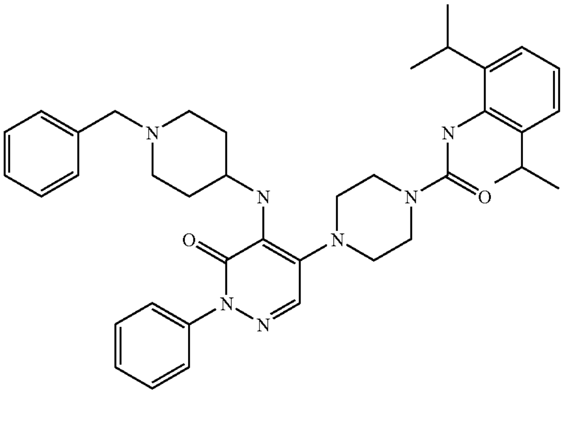

TABLE A-continued
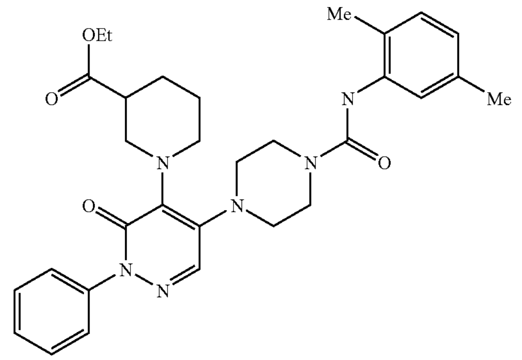
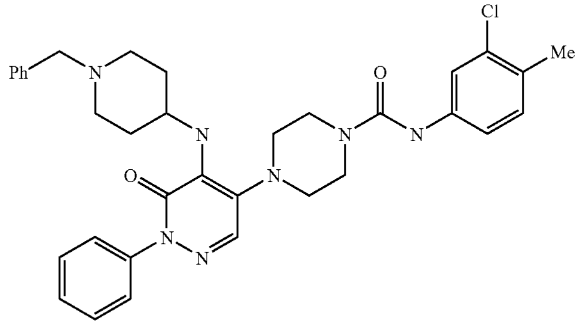
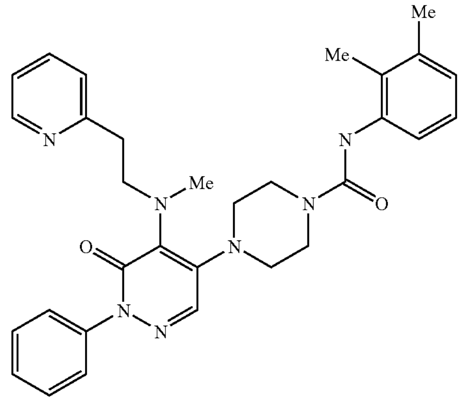
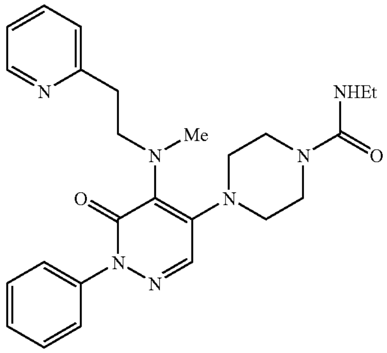
TABLE A-continued
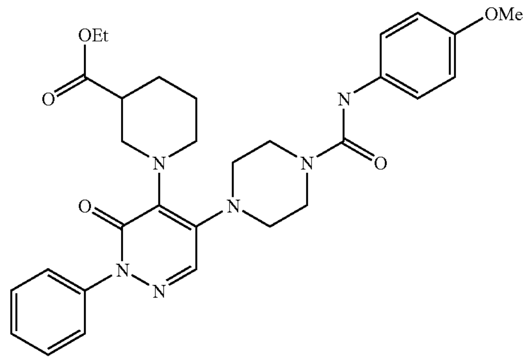
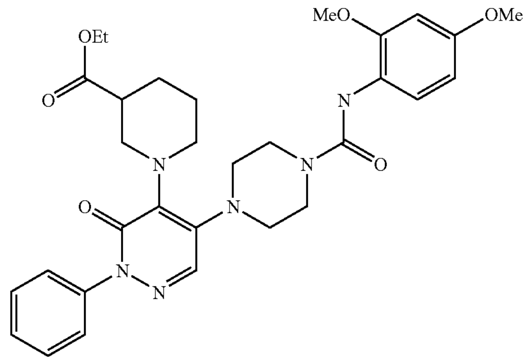
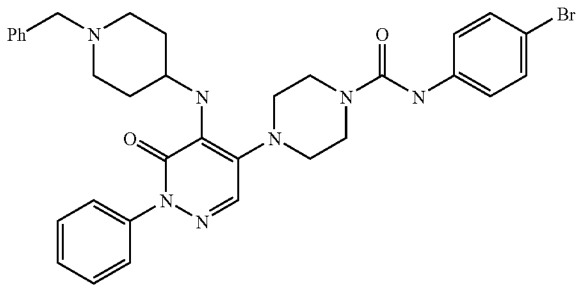
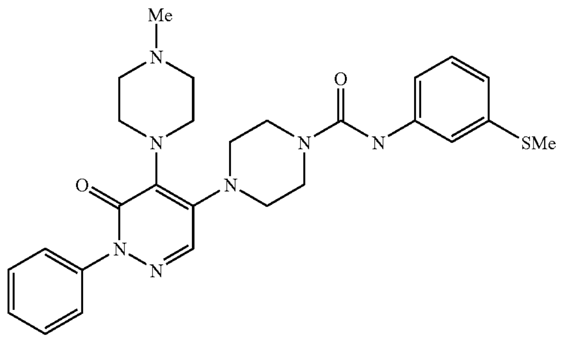

TABLE A-continued
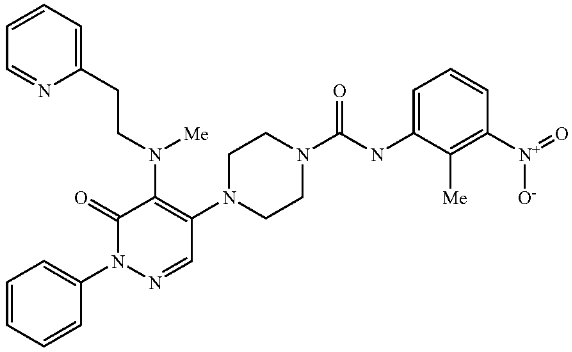
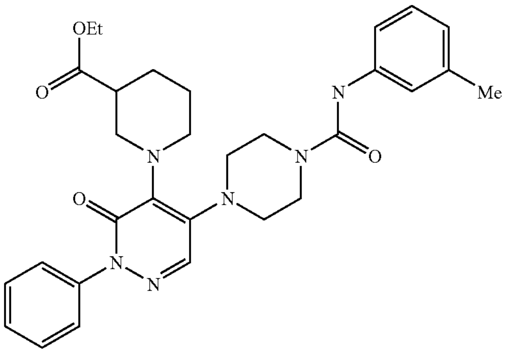
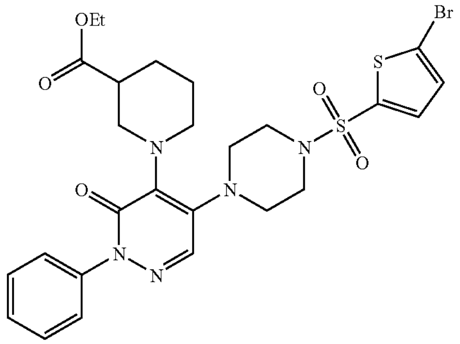
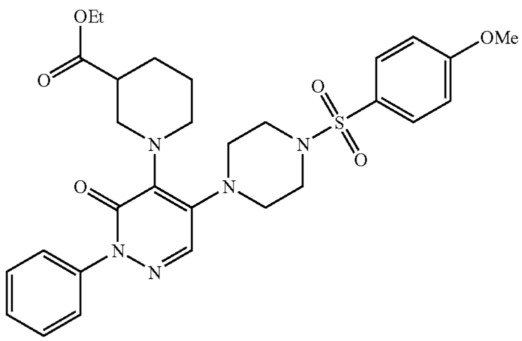
TABLE A-continued
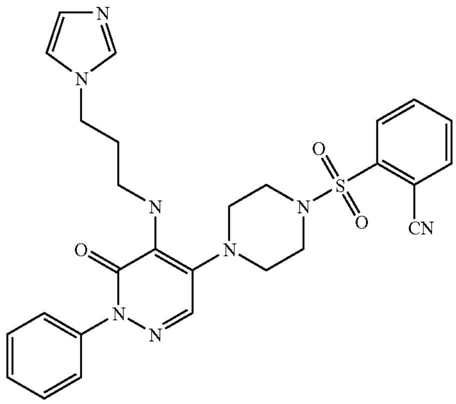
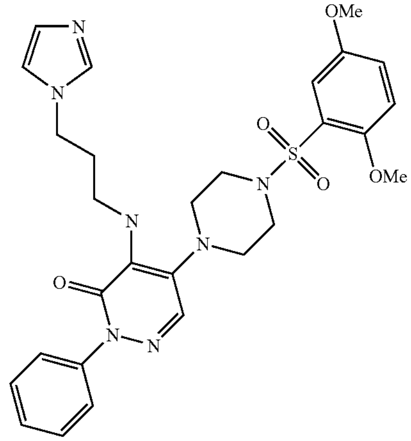
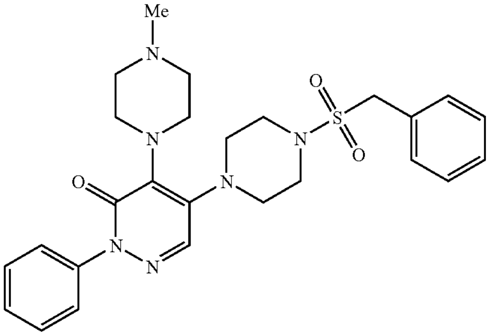
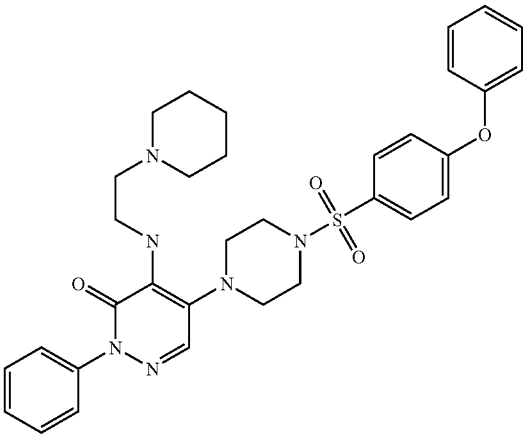

TABLE A-continued
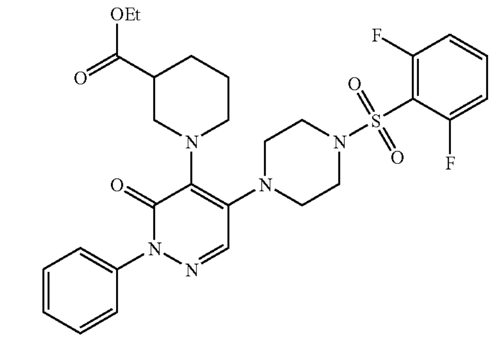
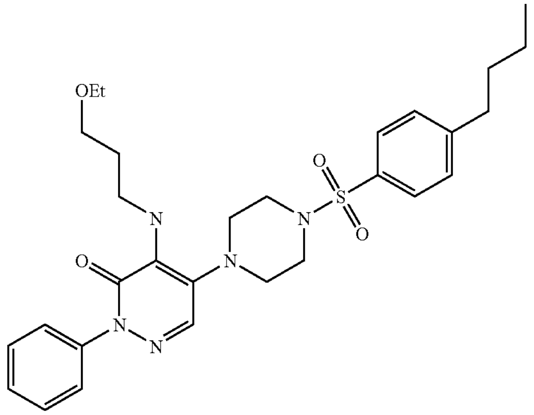
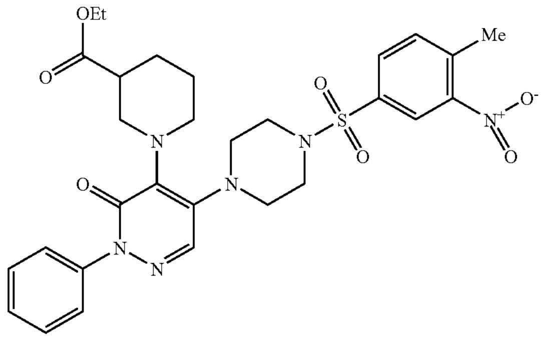
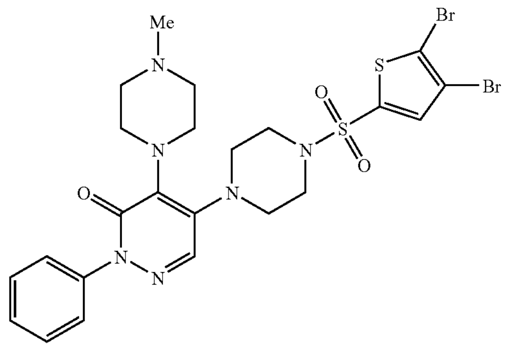
TABLE A-continued
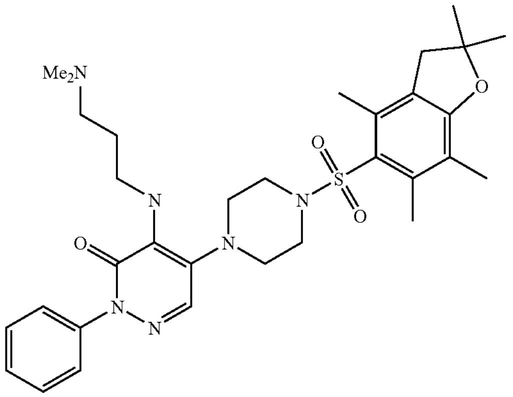
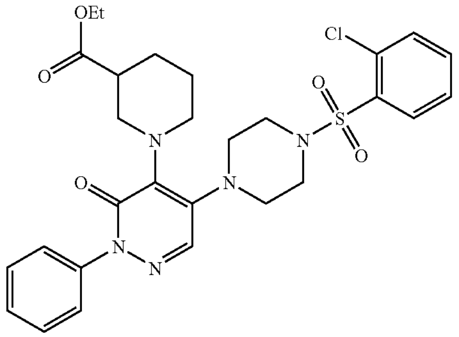
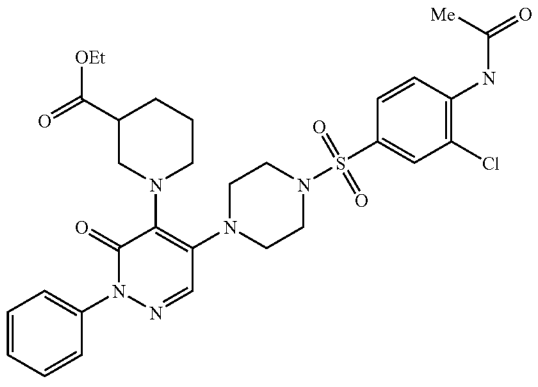
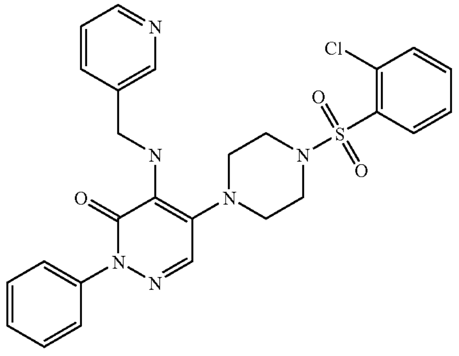

TABLE A-continued
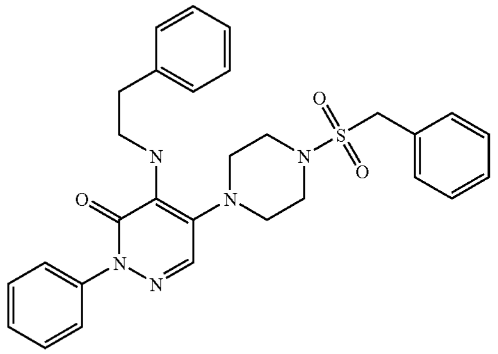
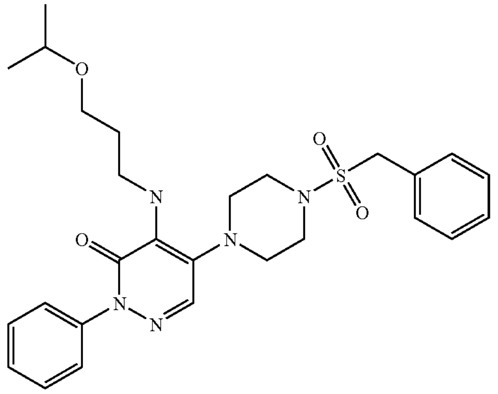
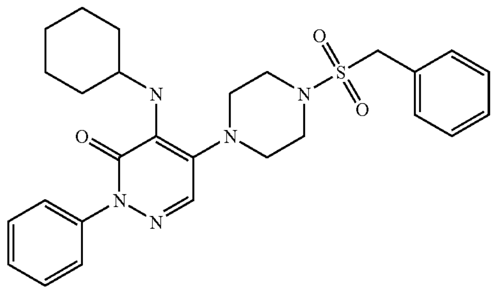
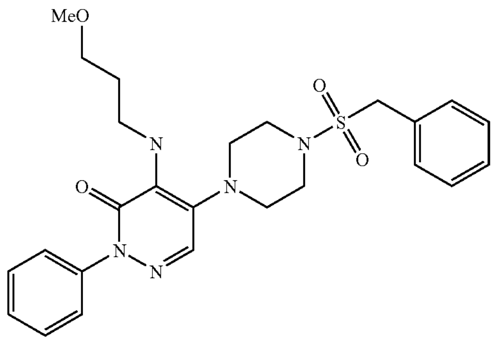
TABLE A-continued
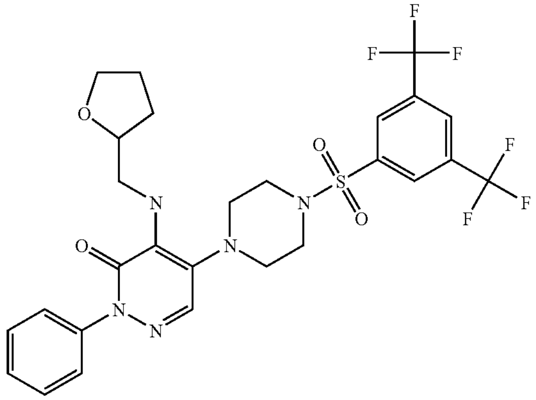
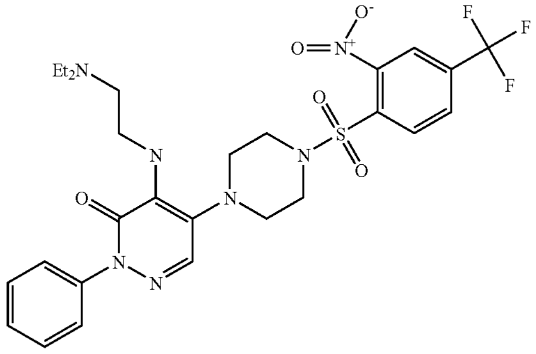
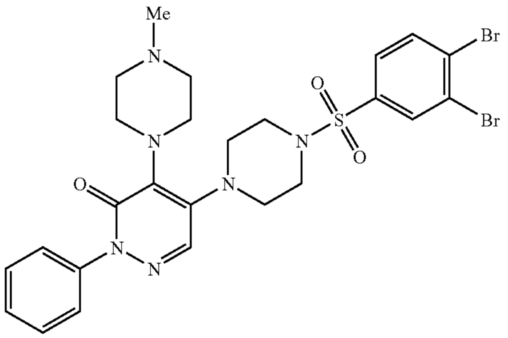
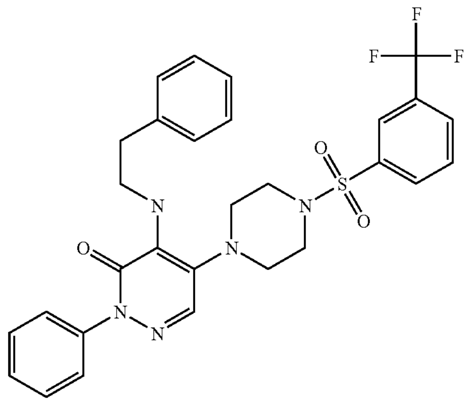

TABLE A-continued
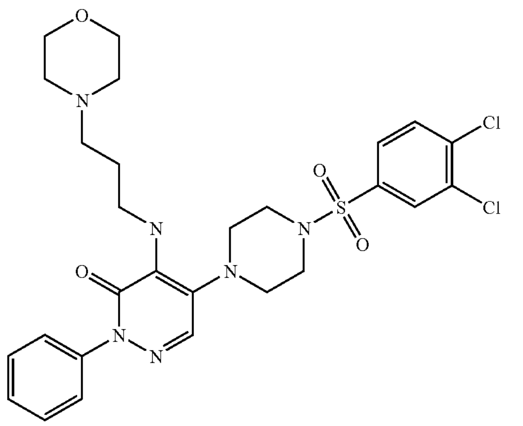
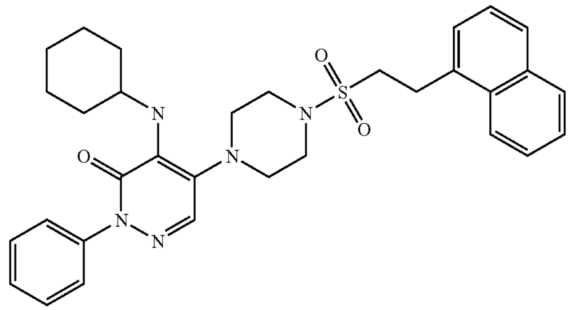
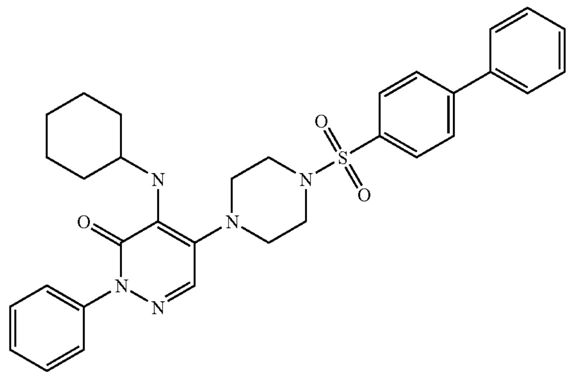
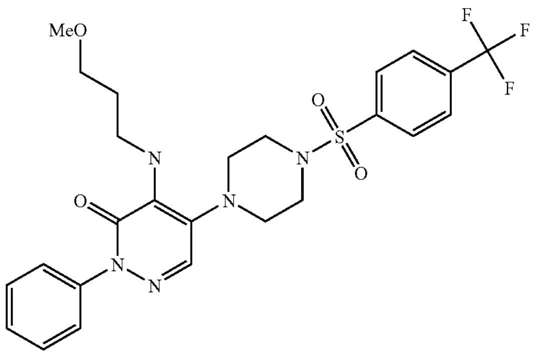
TABLE A-continued
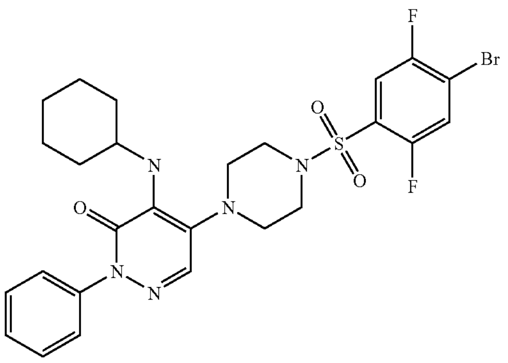
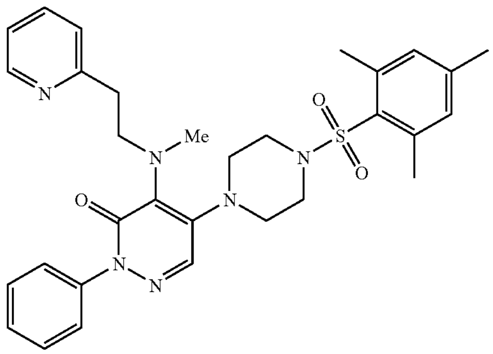
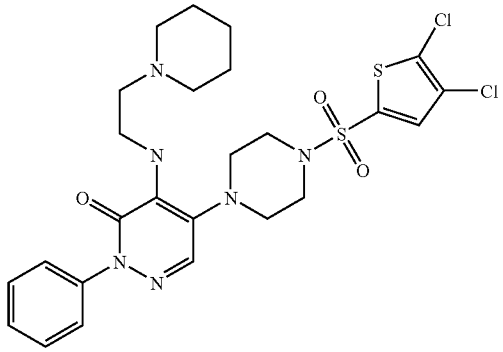
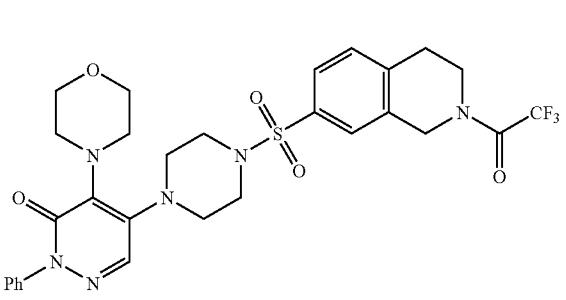

TABLE A-continued
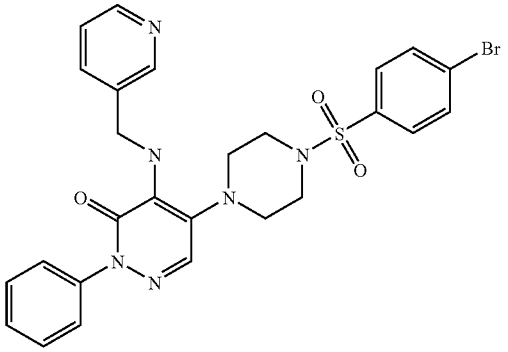
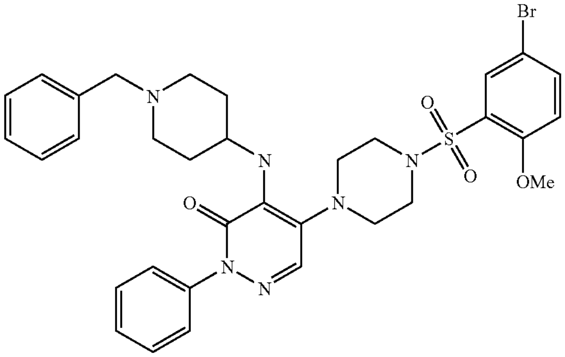
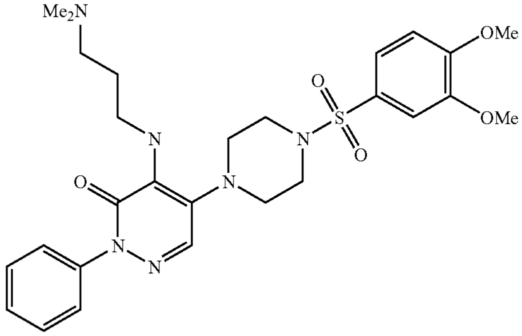
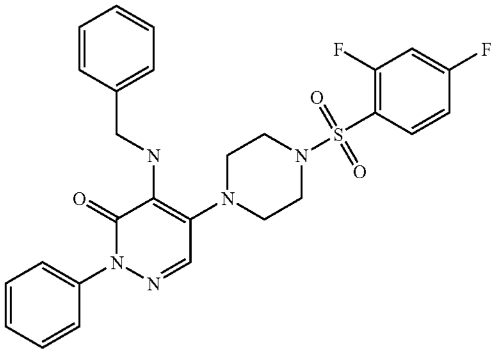
TABLE A-continued
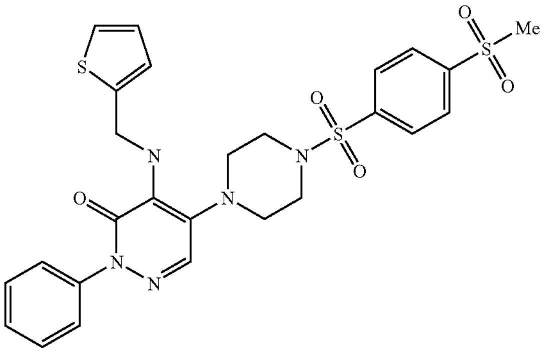
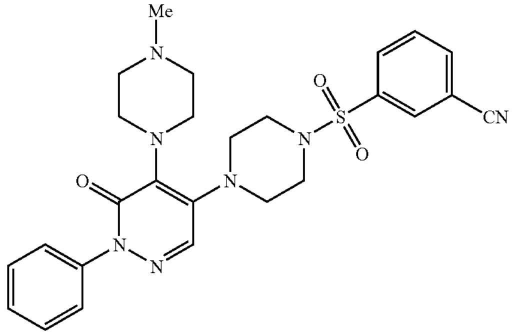
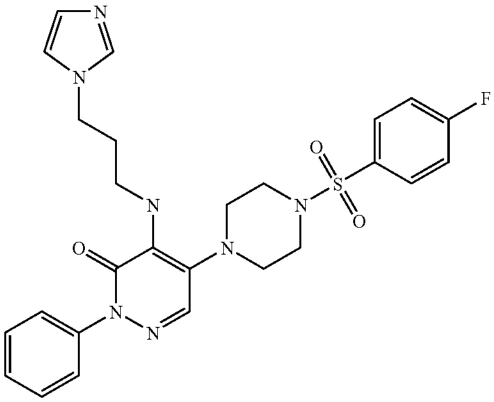
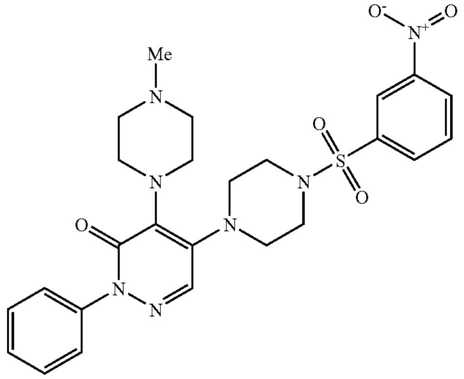

TABLE A-continued
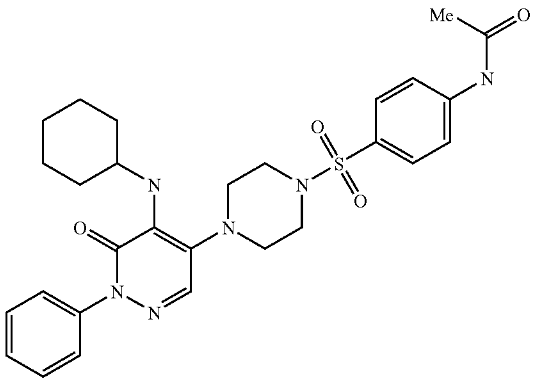
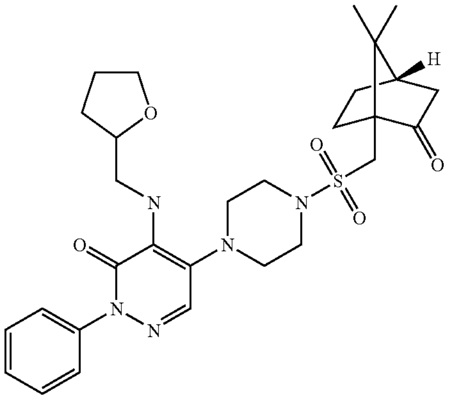
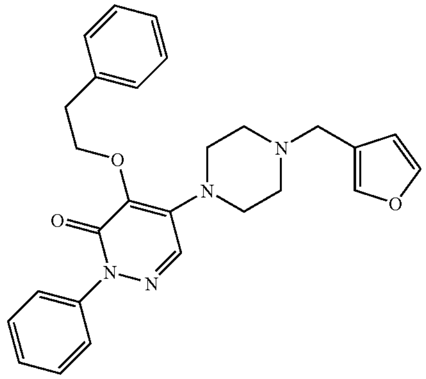
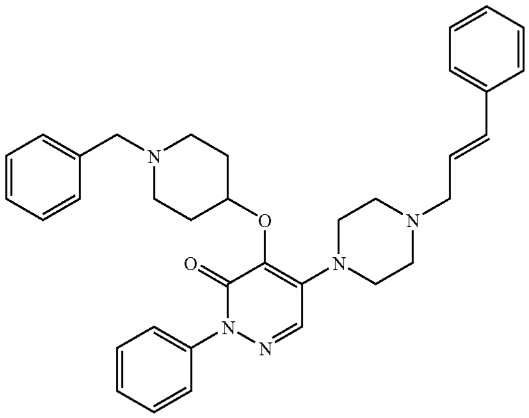
TABLE A-continued
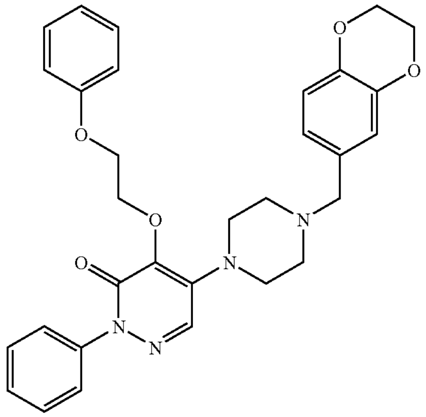
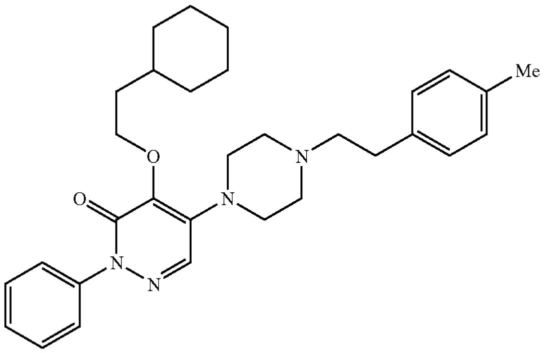
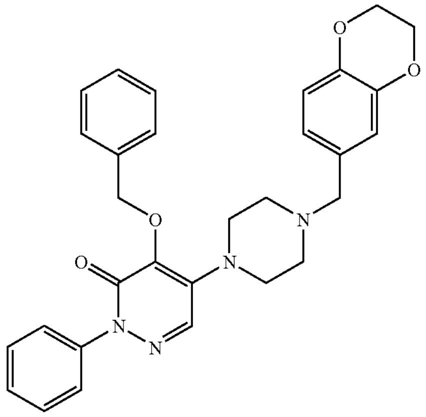
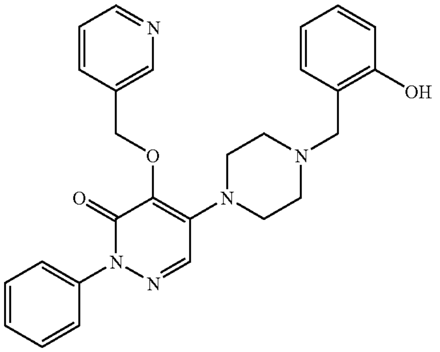

TABLE A-continued
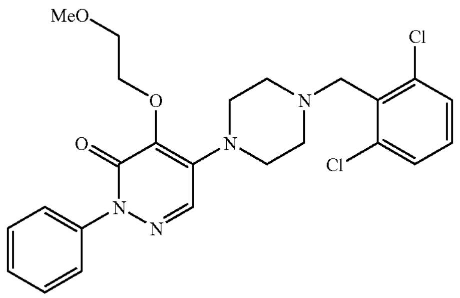
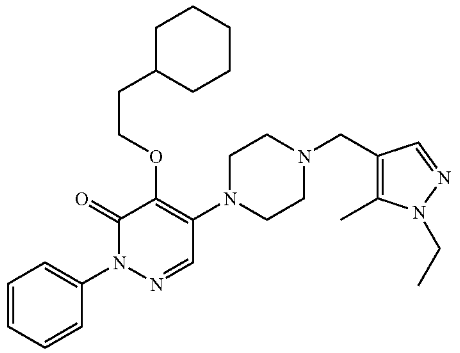
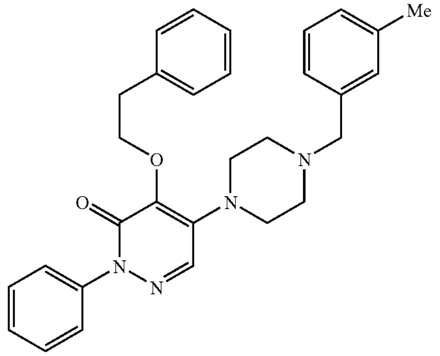
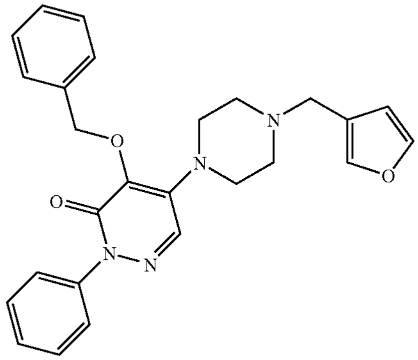
TABLE A-continued
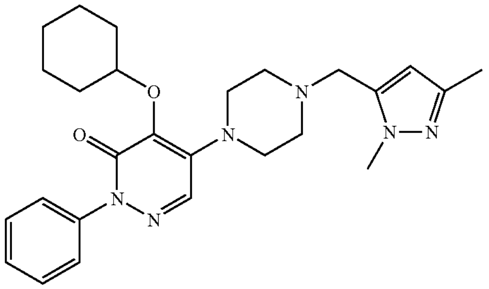
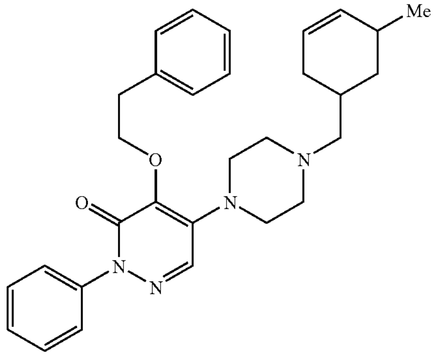
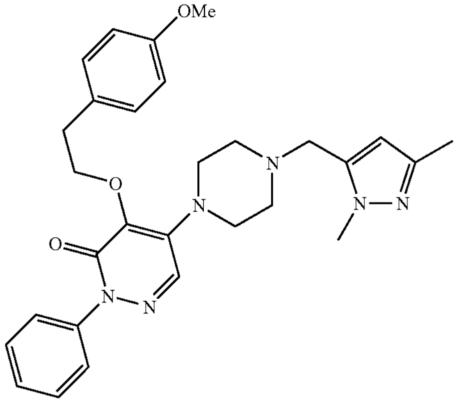
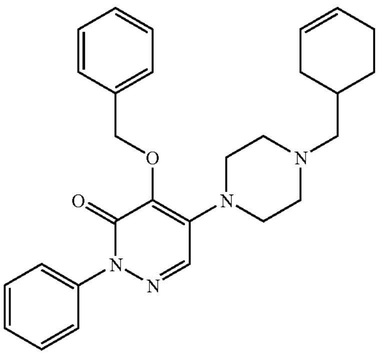

TABLE A-continued
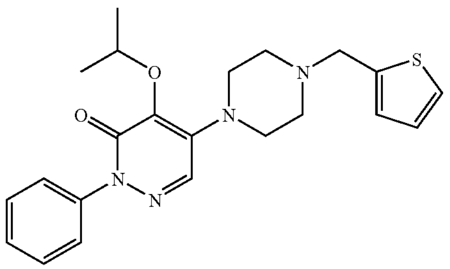
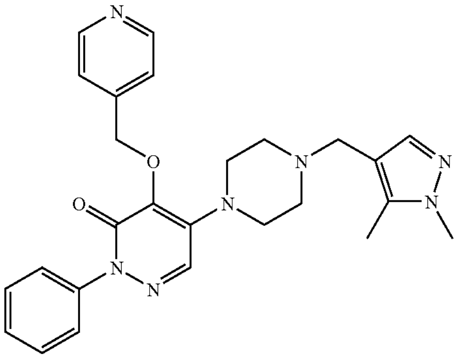
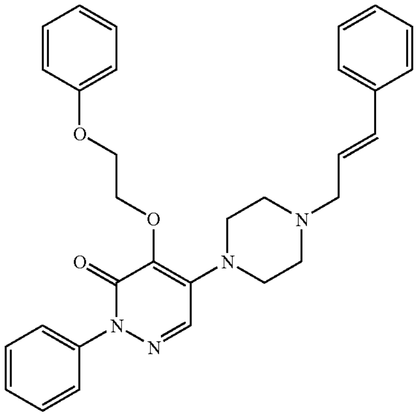
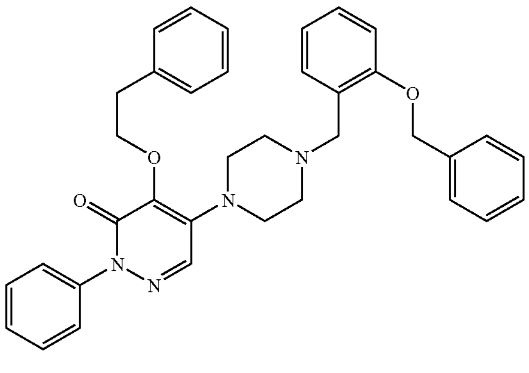
TABLE A-continued
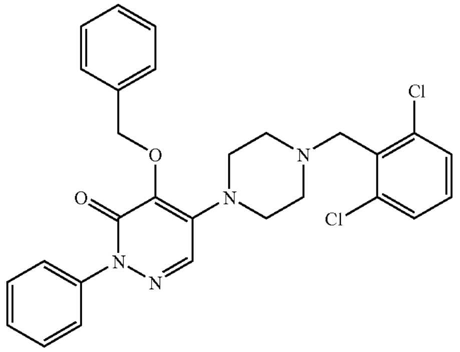
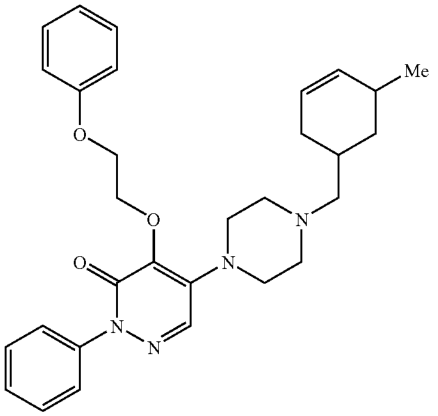
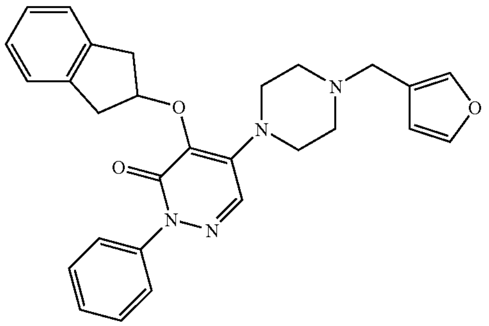
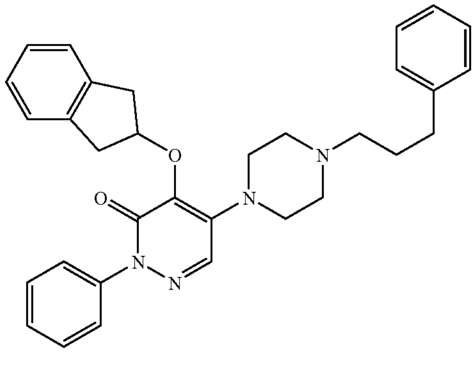

TABLE A-continued
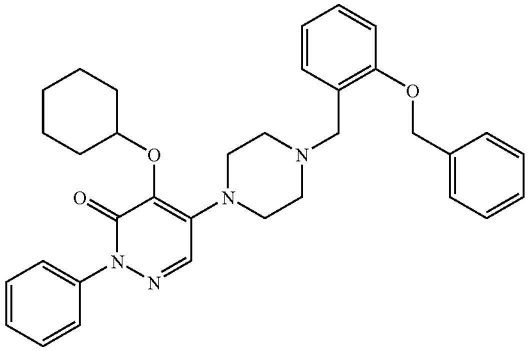
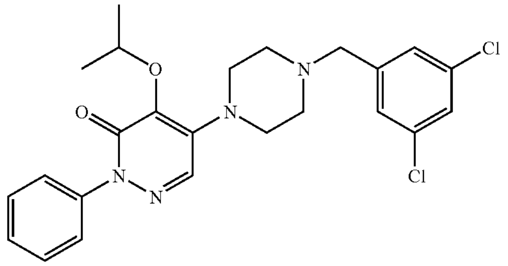
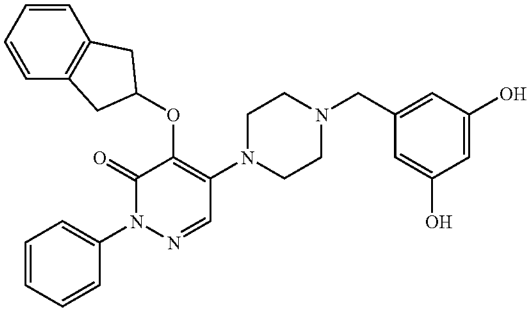
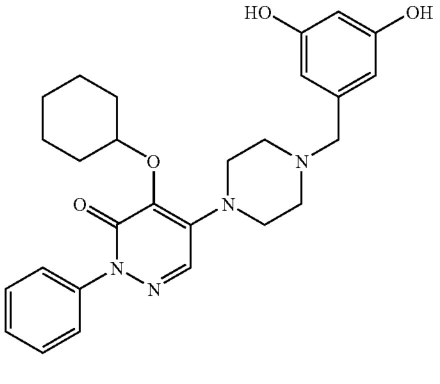
TABLE A-continued
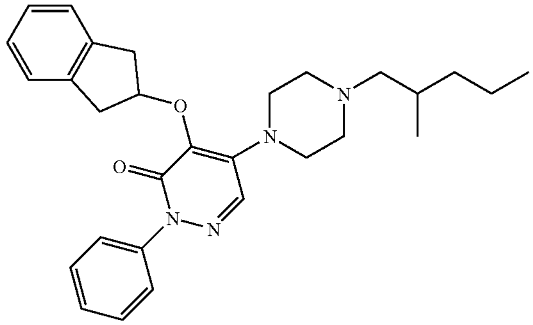
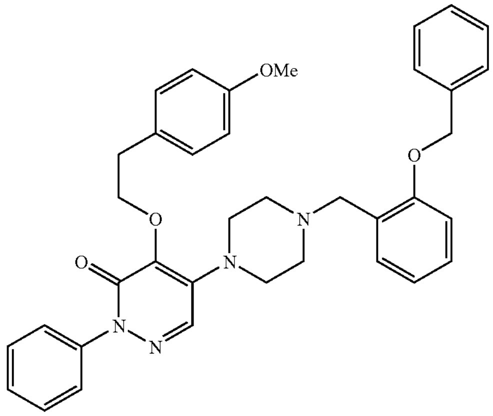
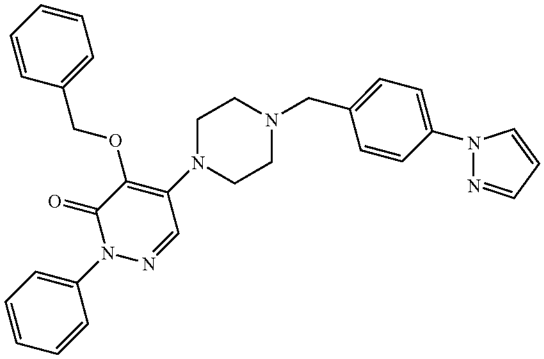
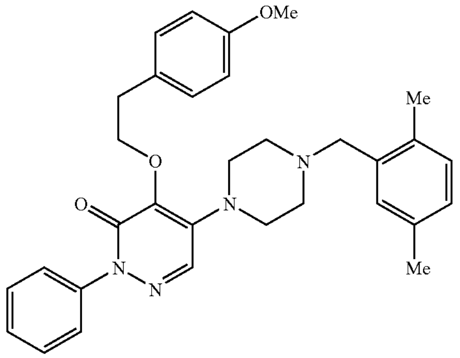

TABLE A-continued
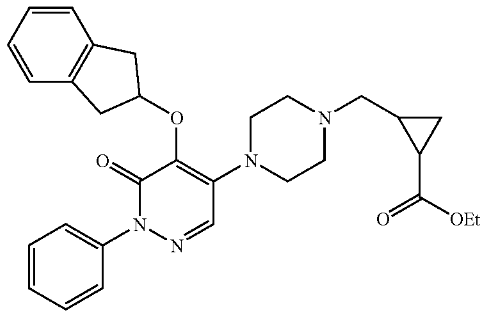
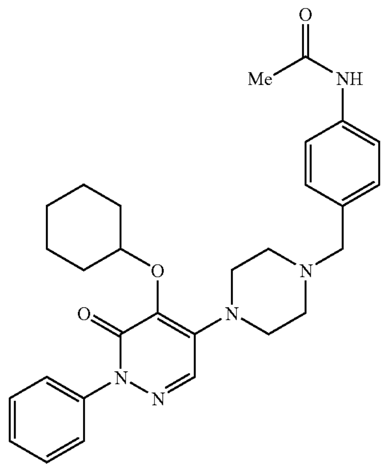
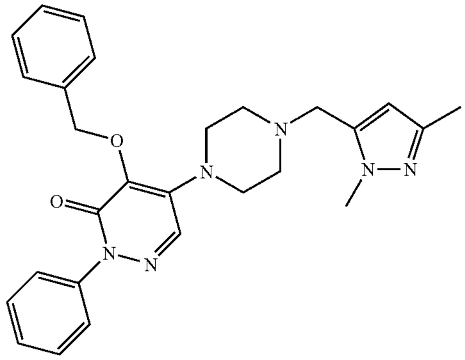
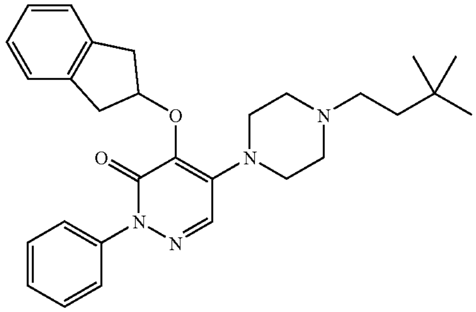
TABLE A-continued
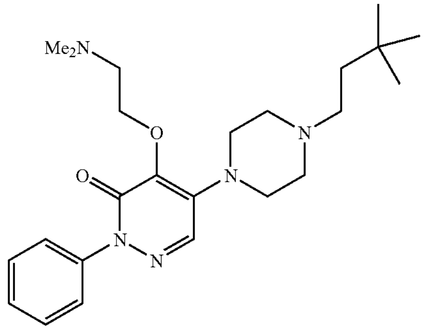
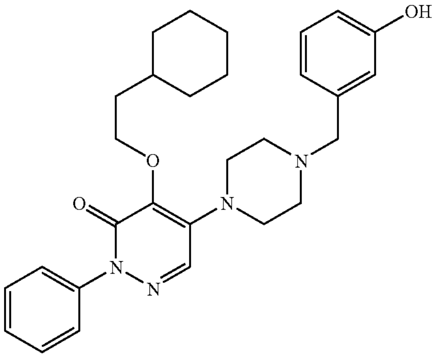
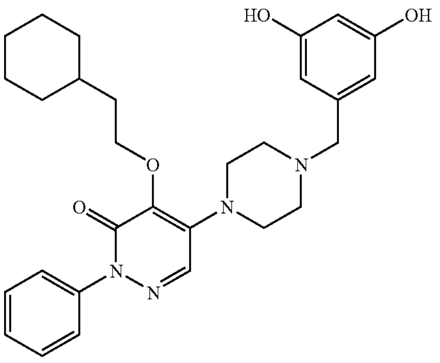
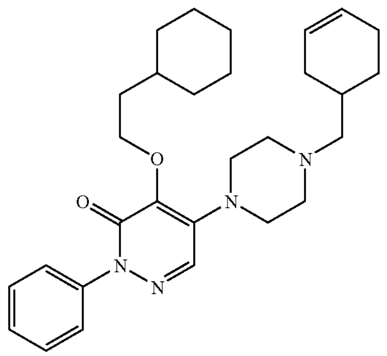

TABLE A-continued
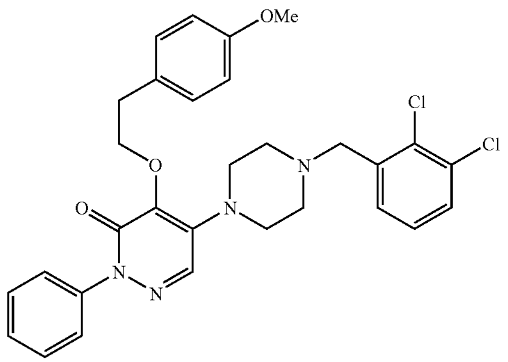
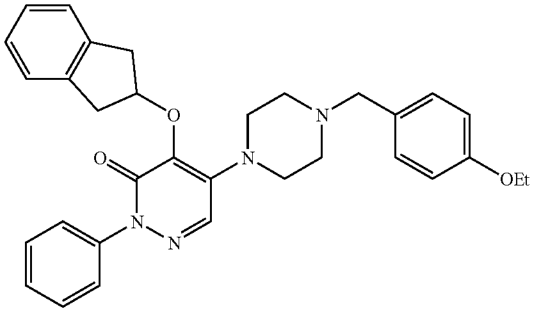
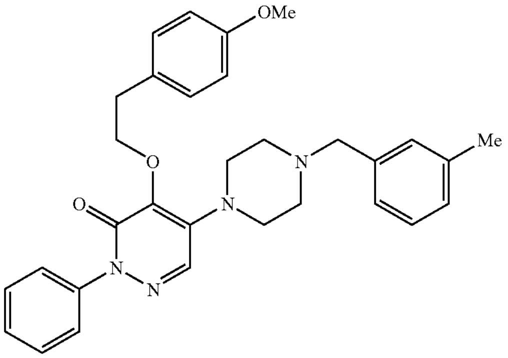
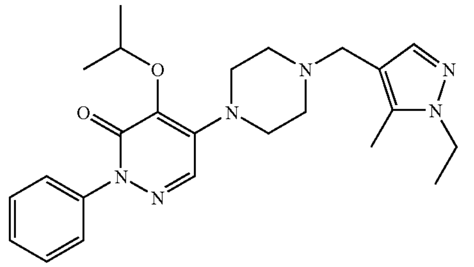
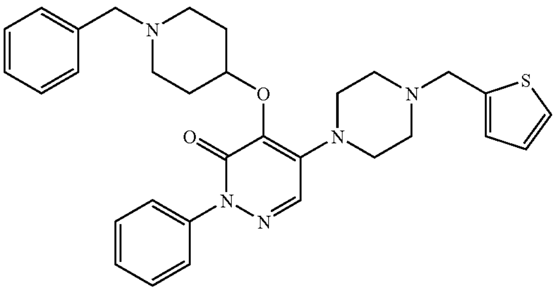
TABLE A-continued
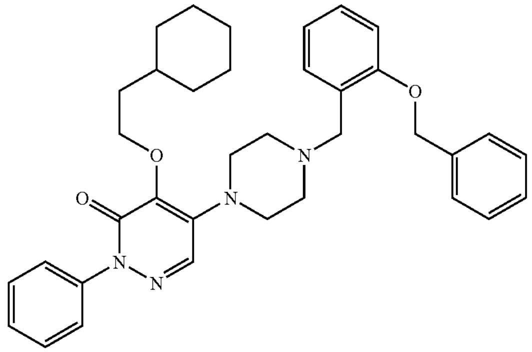
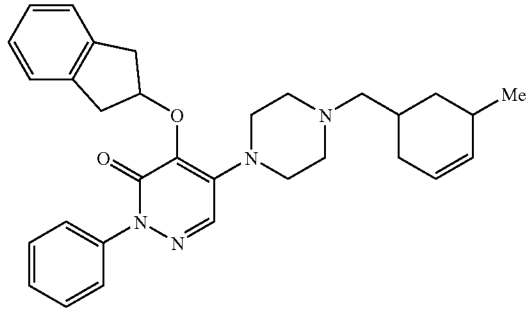
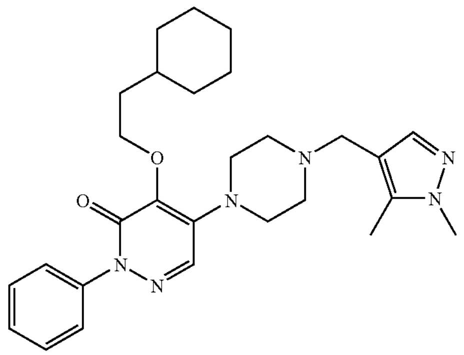
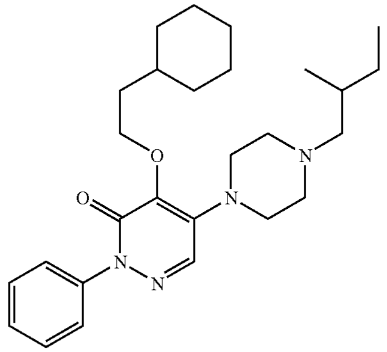

TABLE A-continued
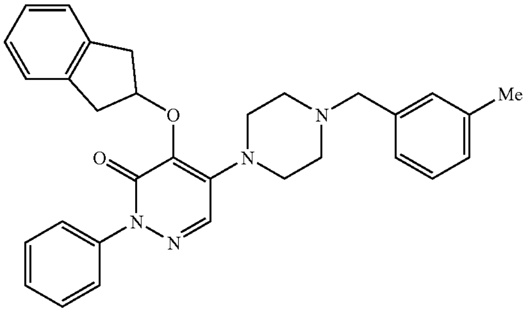
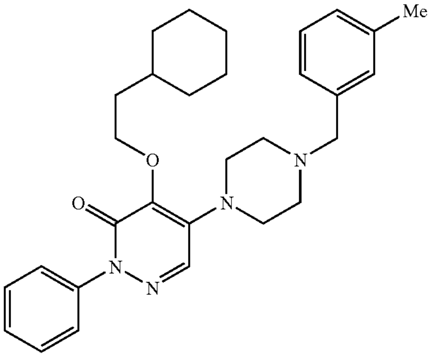
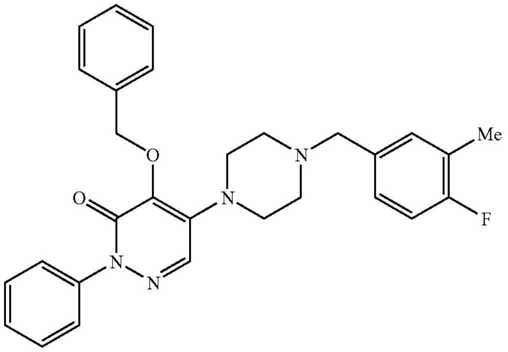
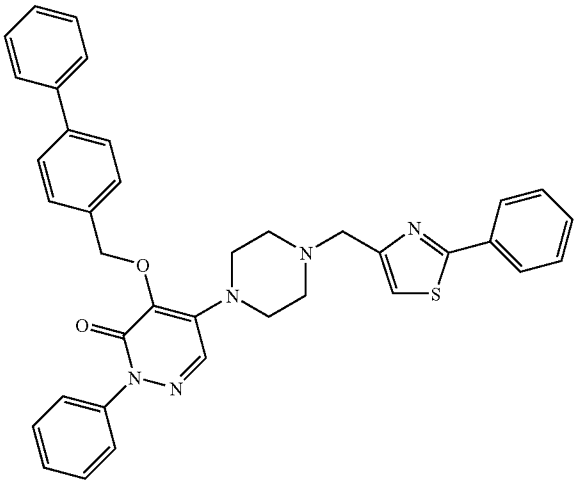
TABLE A-continued
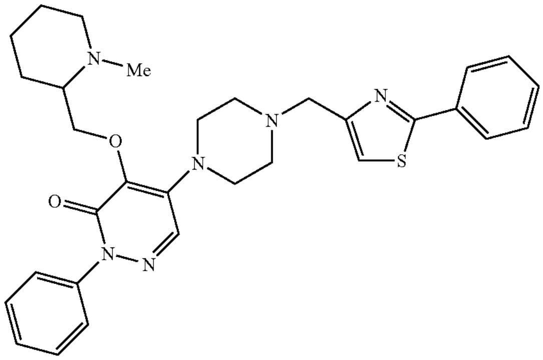
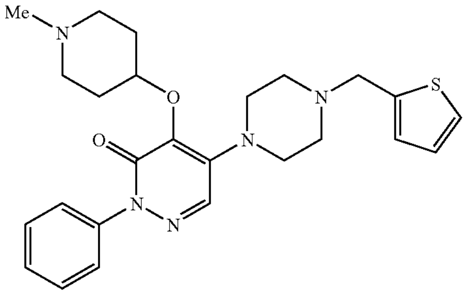
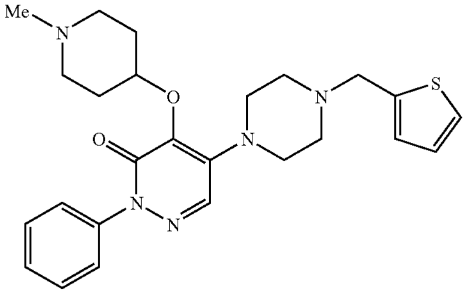
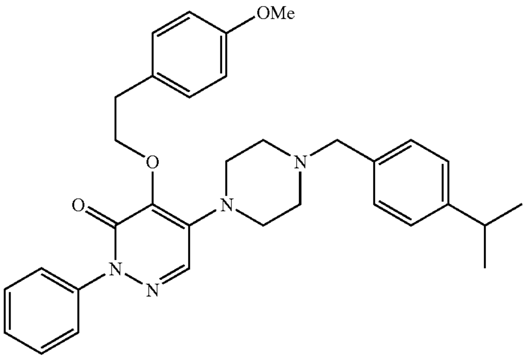

TABLE A-continued
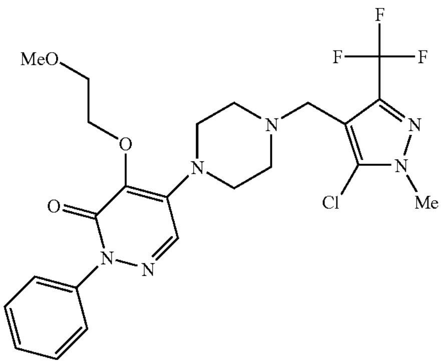
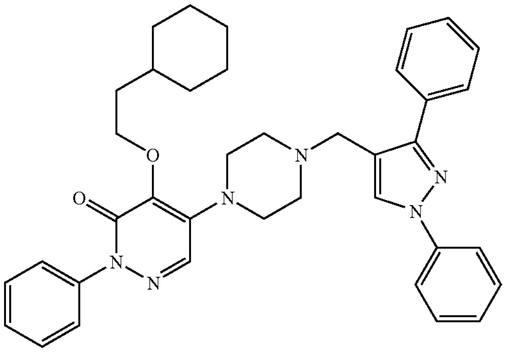
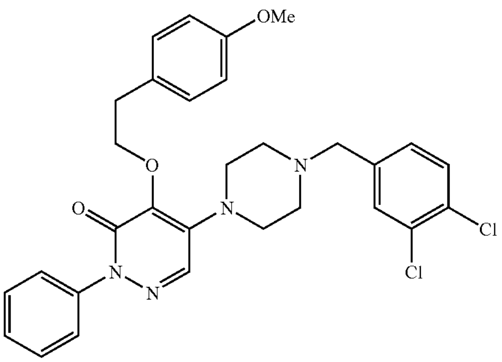
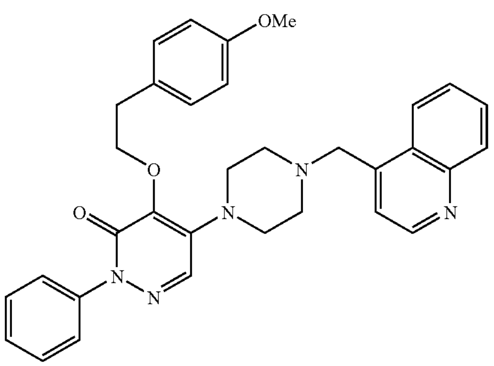
TABLE A-continued
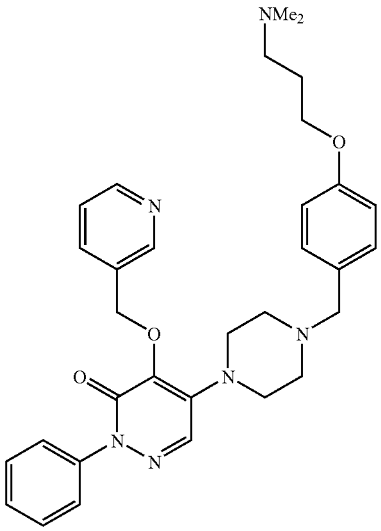
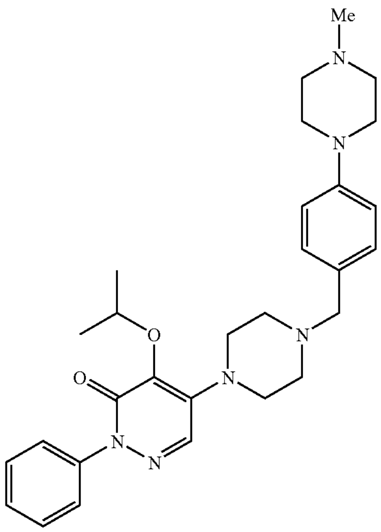
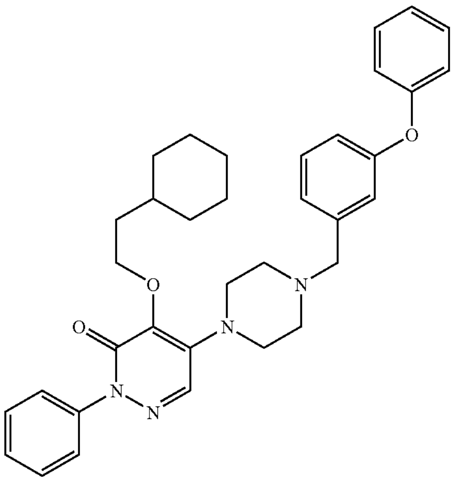

TABLE A-continued
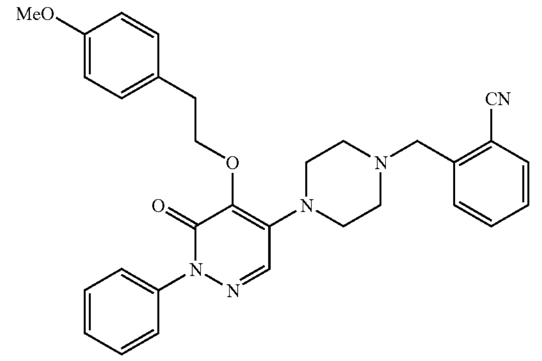
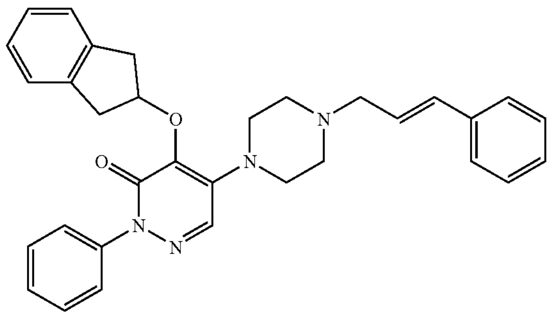
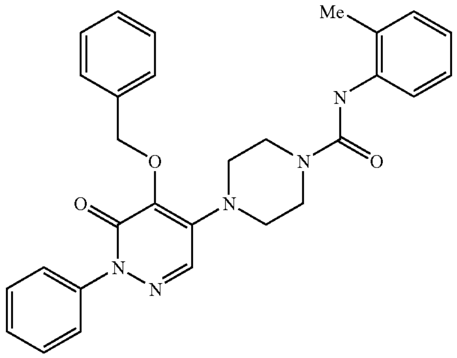
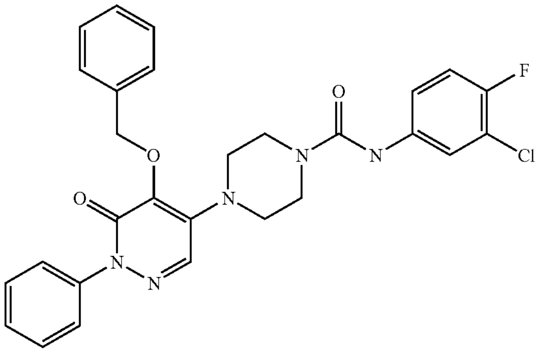
TABLE A-continued
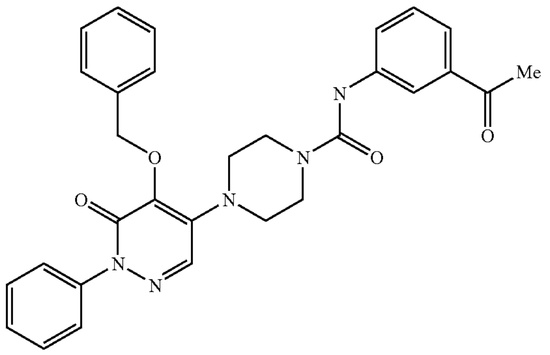
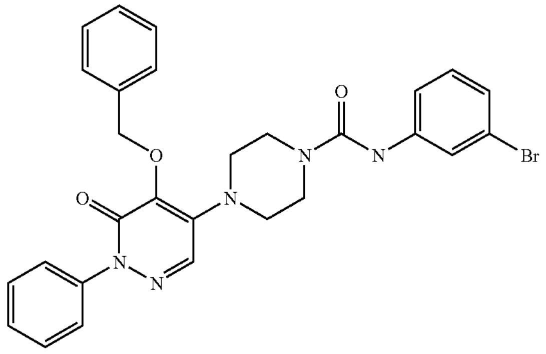
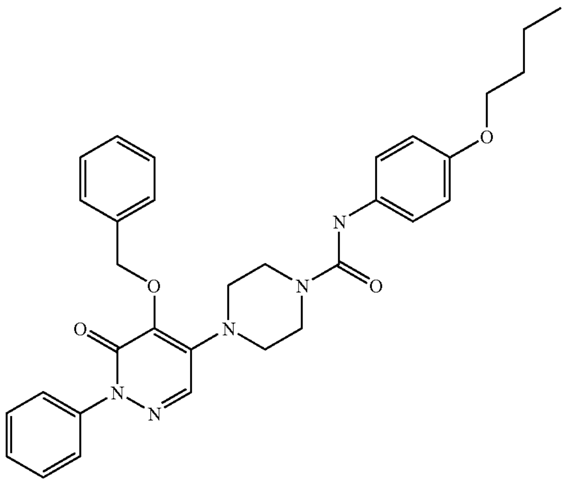

TABLE A-continued
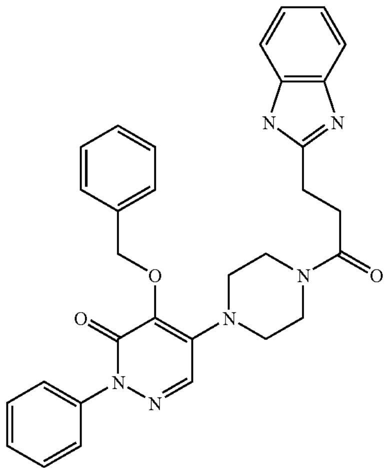
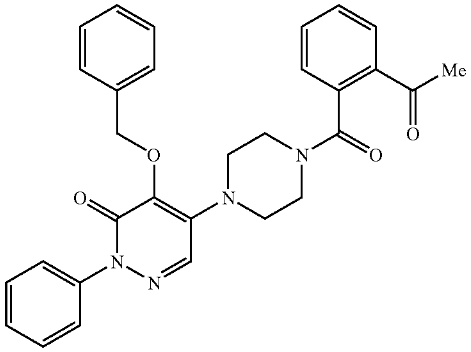
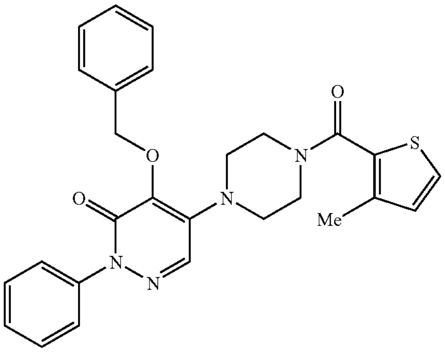
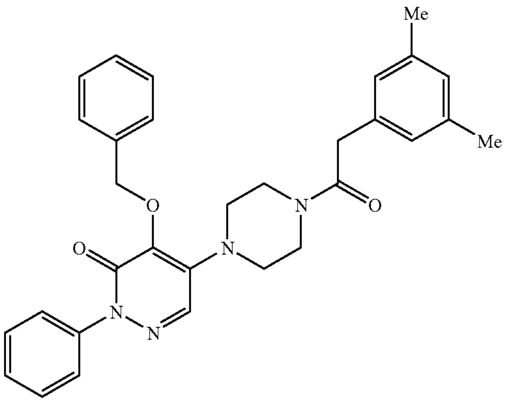
TABLE A-continued
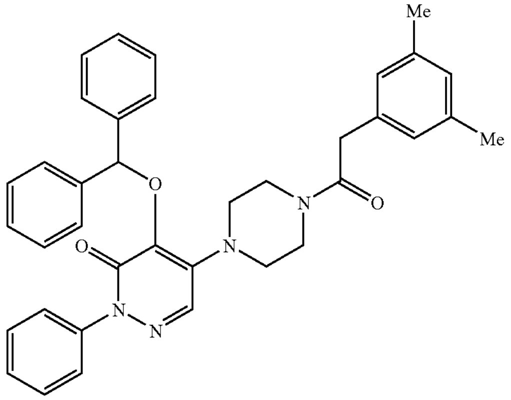
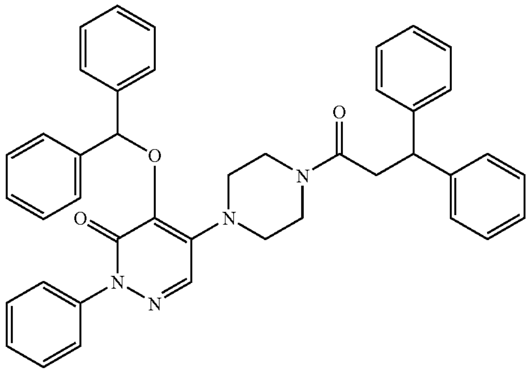
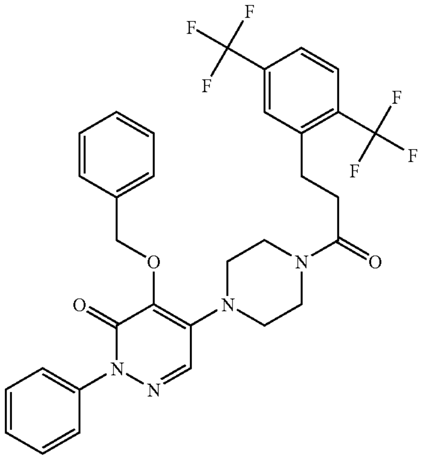
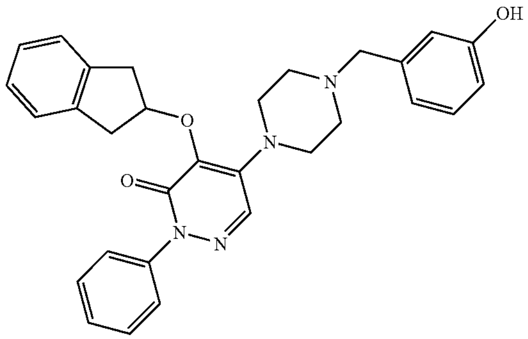

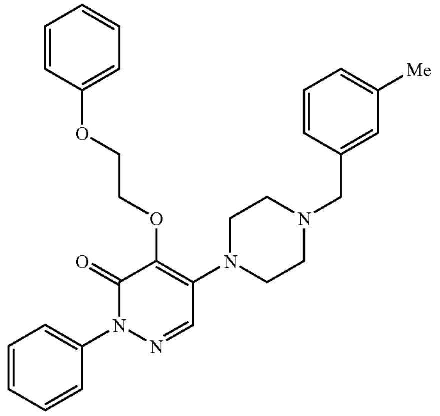
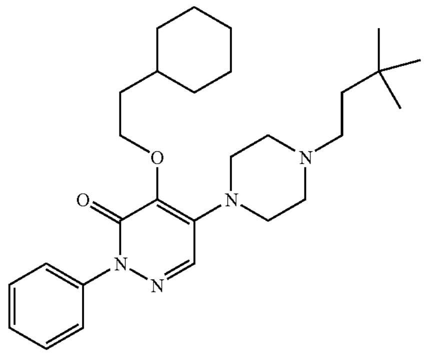
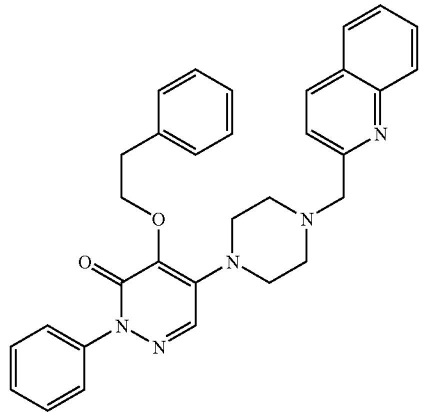
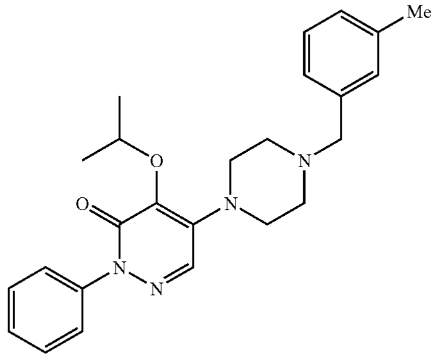
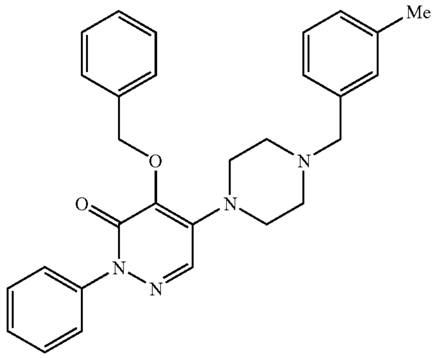
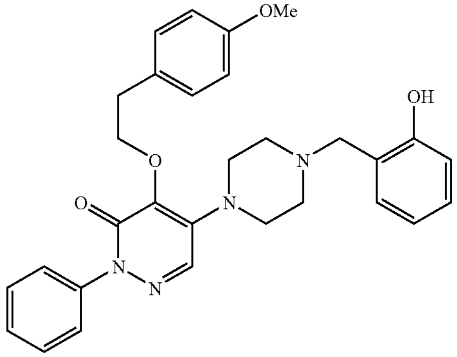
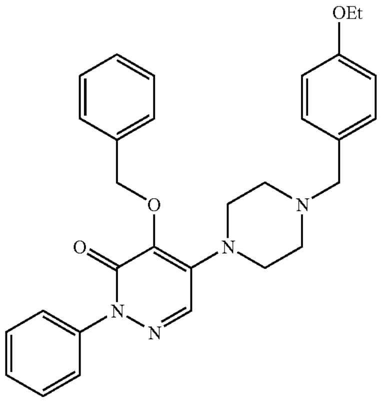
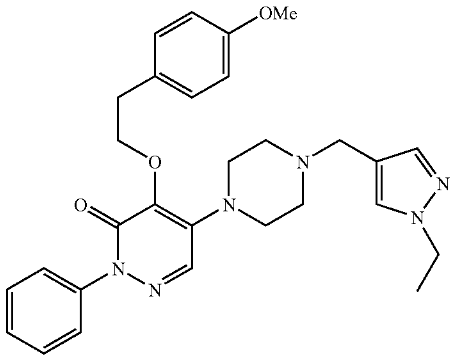

TABLE A-continued
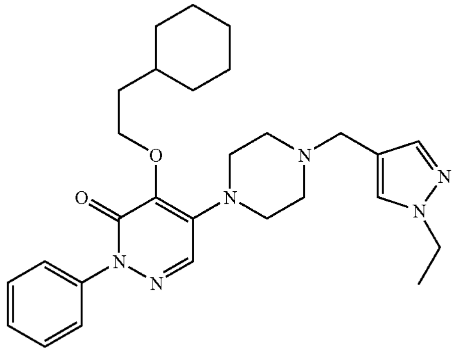
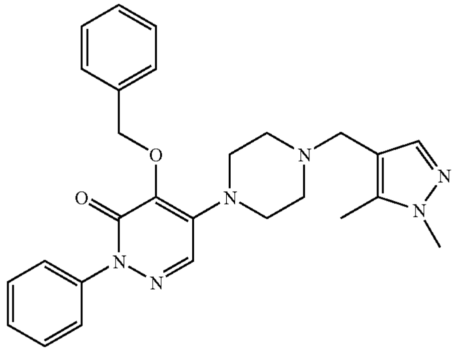
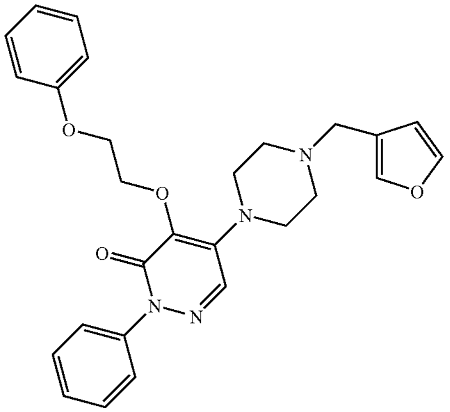
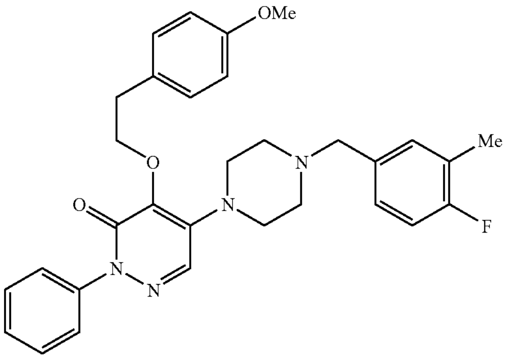
TABLE A-continued
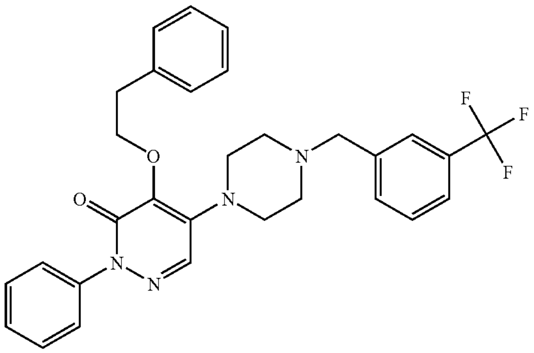
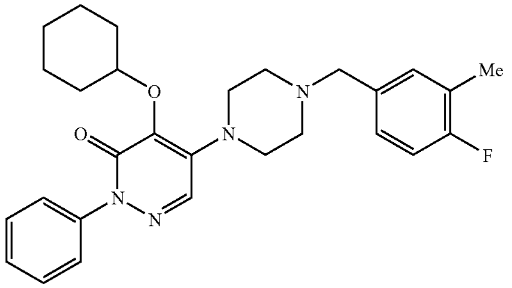
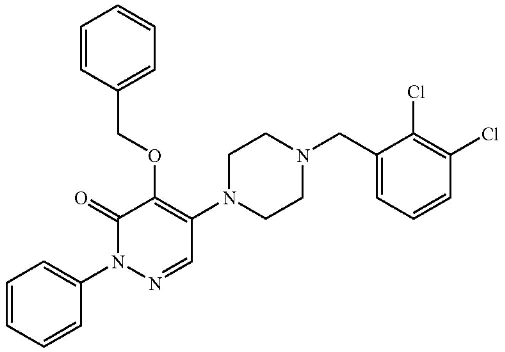
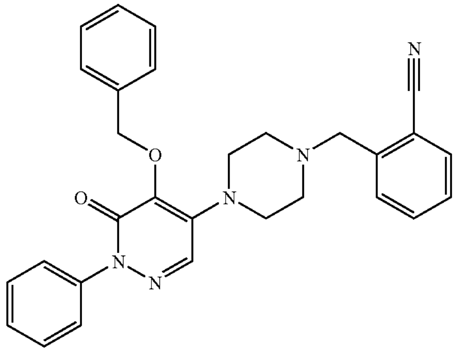

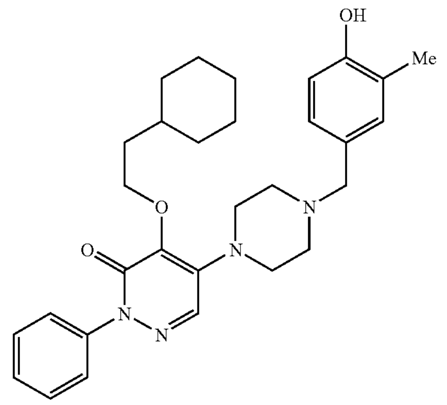
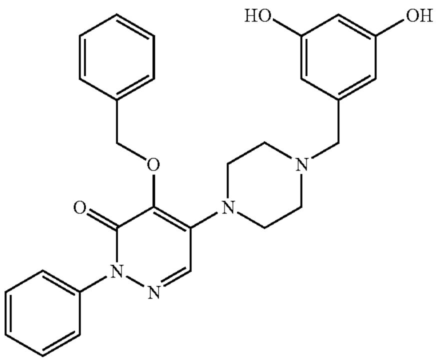
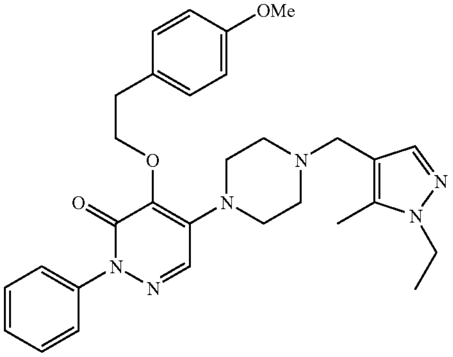
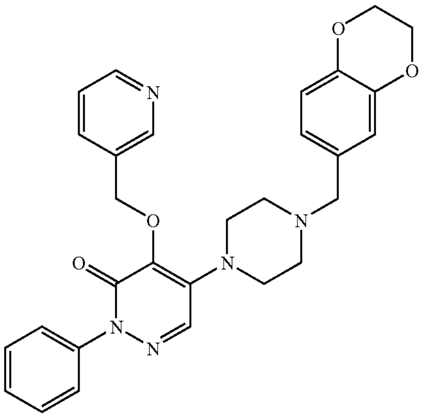
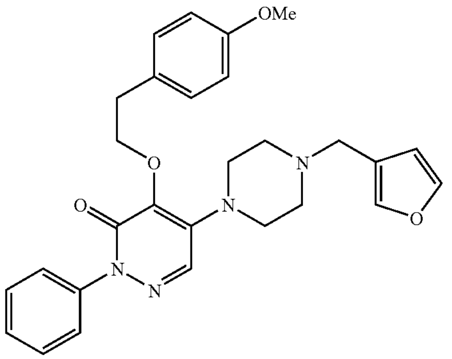
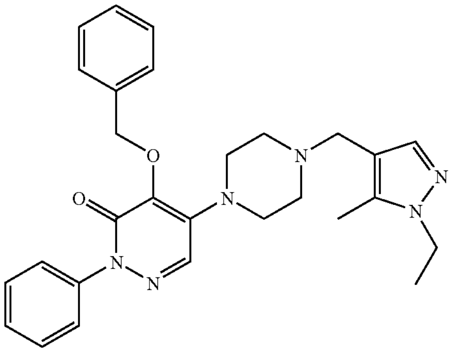
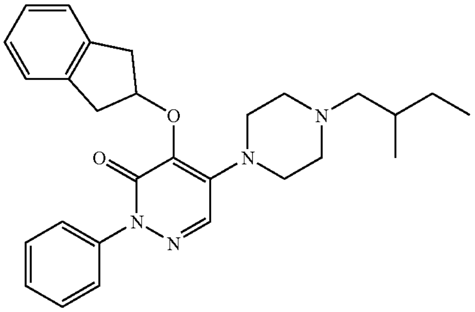
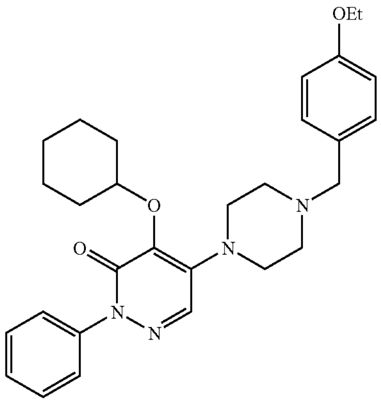

TABLE A-continued
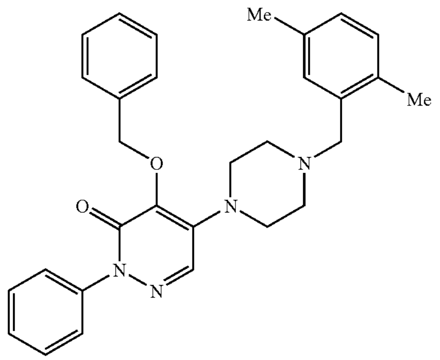
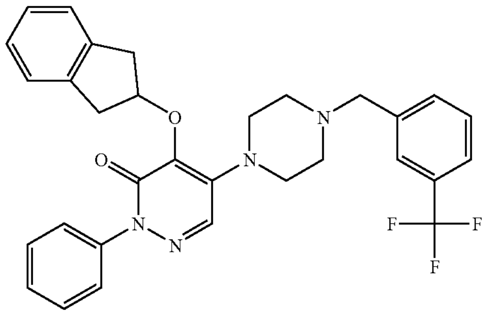
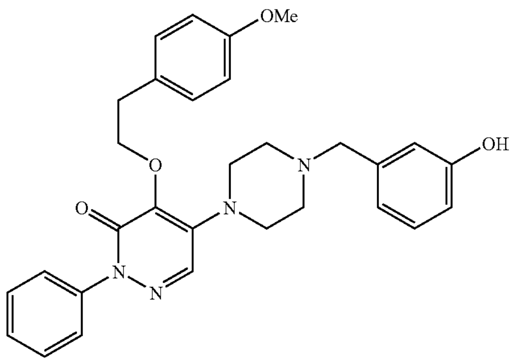
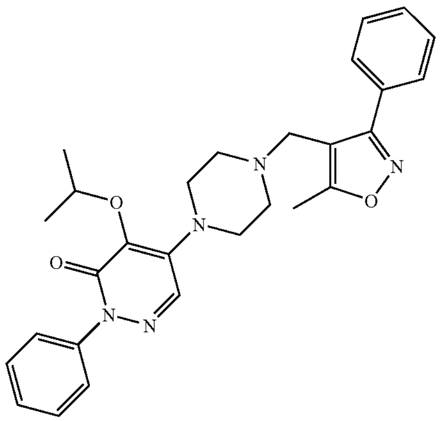
TABLE A-continued
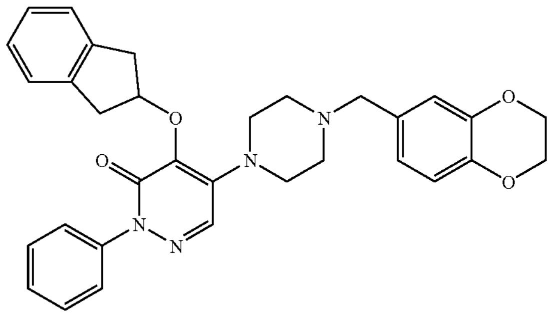
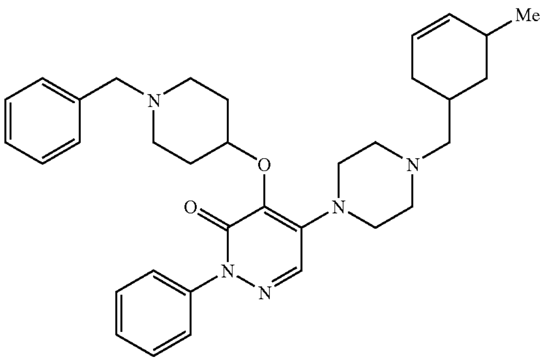
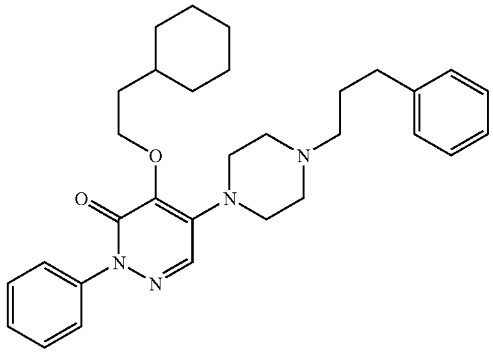
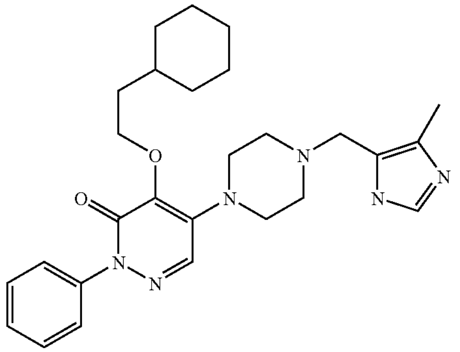

TABLE A-continued
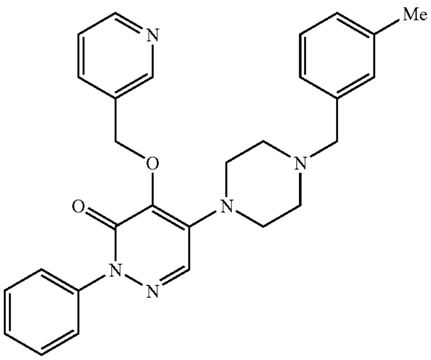
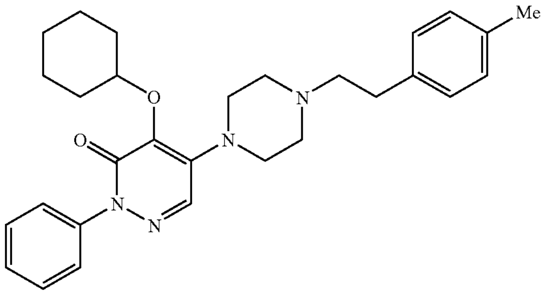
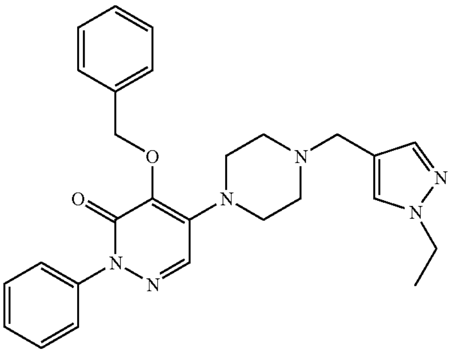
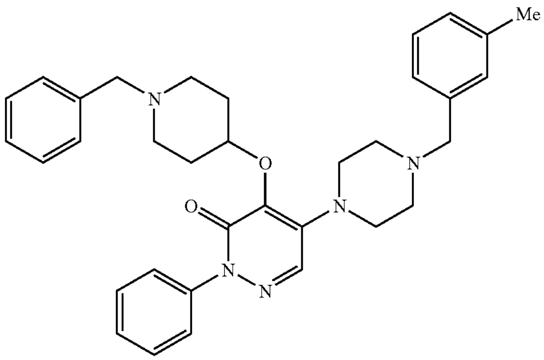
TABLE A-continued
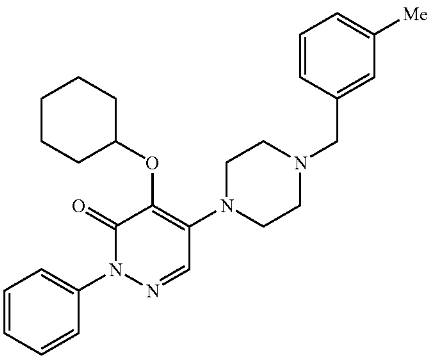
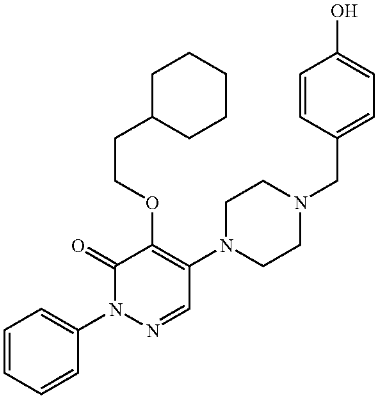
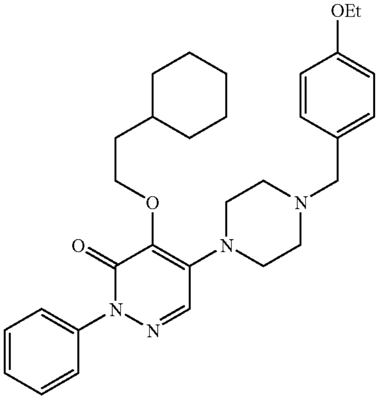
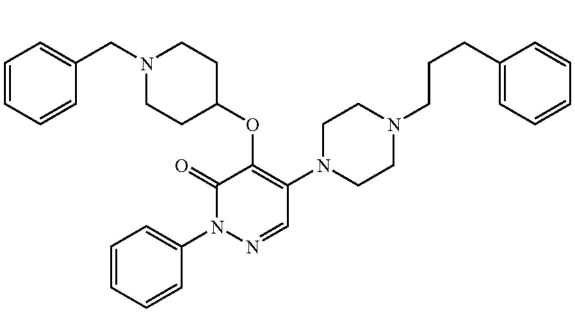

TABLE A-continued
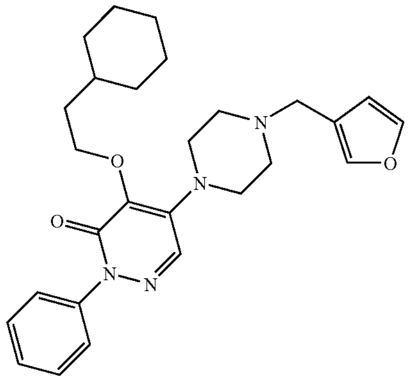
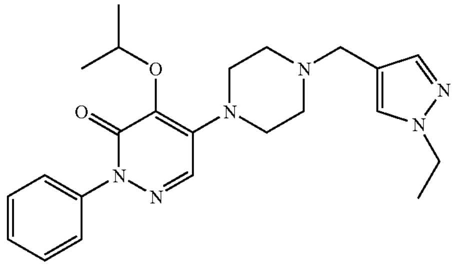
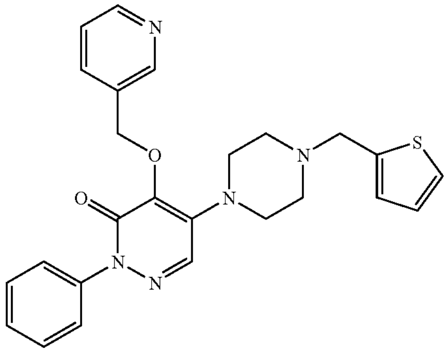
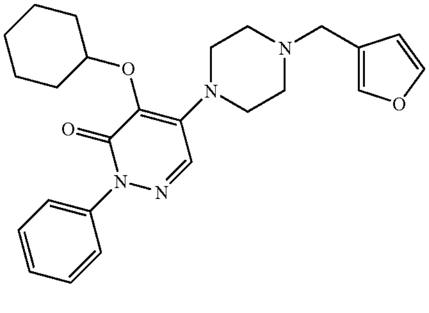
TABLE A-continued
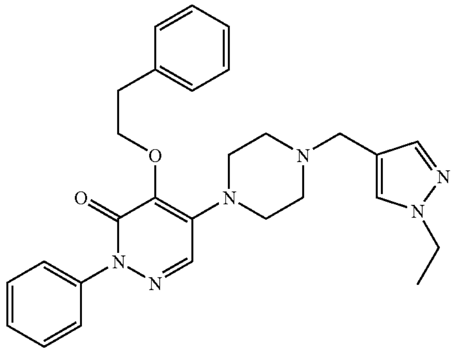
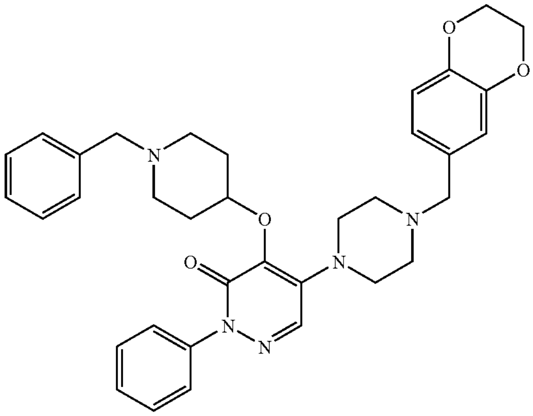
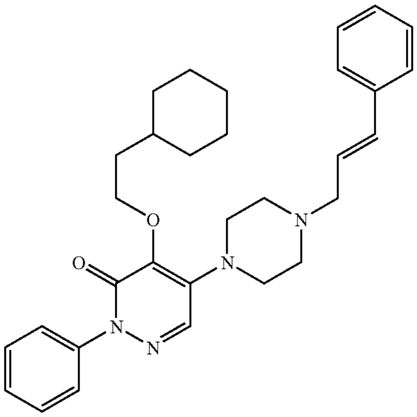
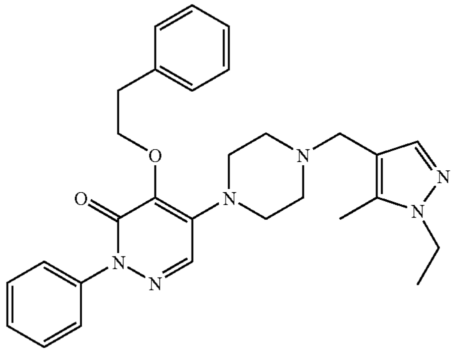

TABLE A-continued
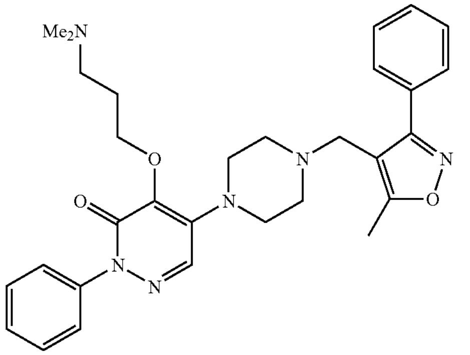
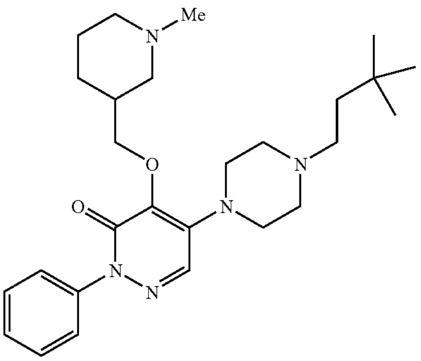
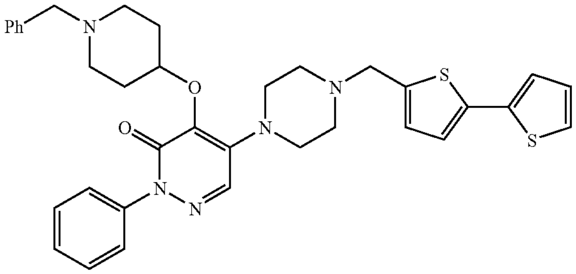
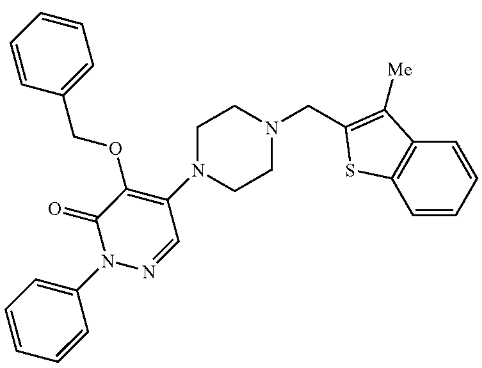
TABLE A-continued
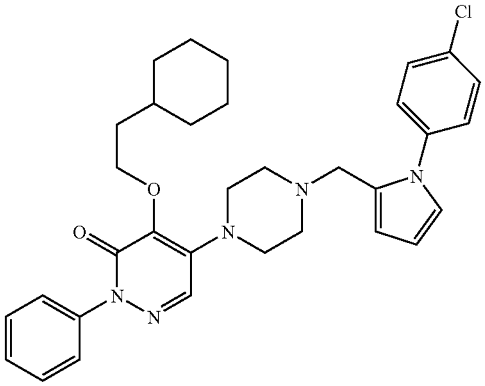
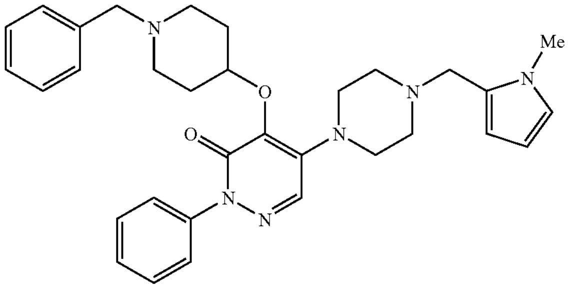
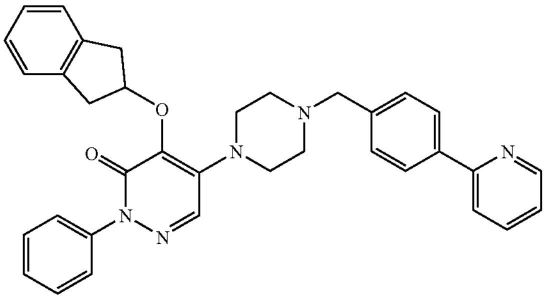
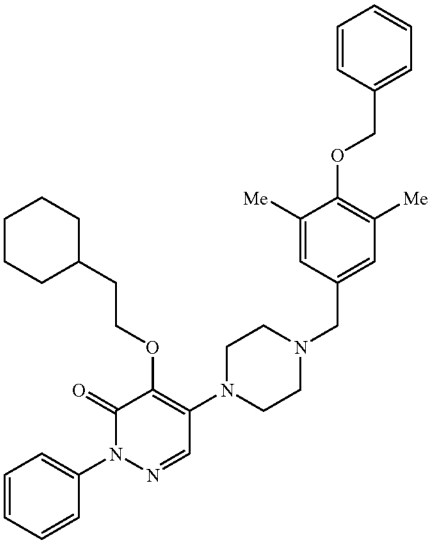

TABLE A-continued
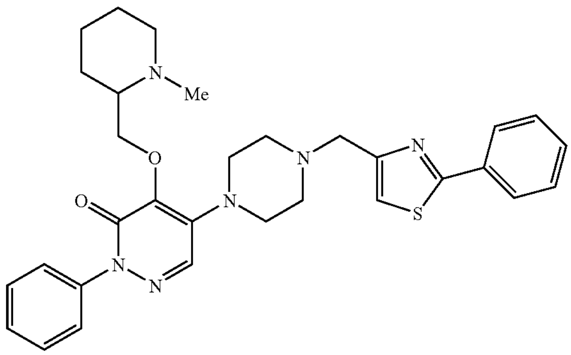
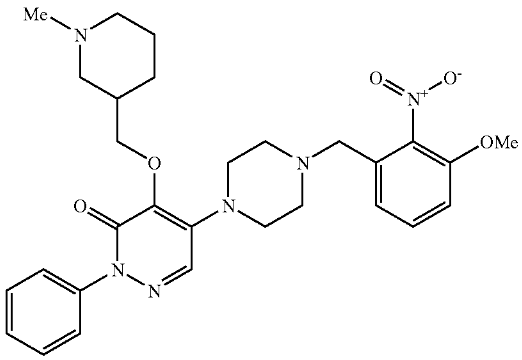
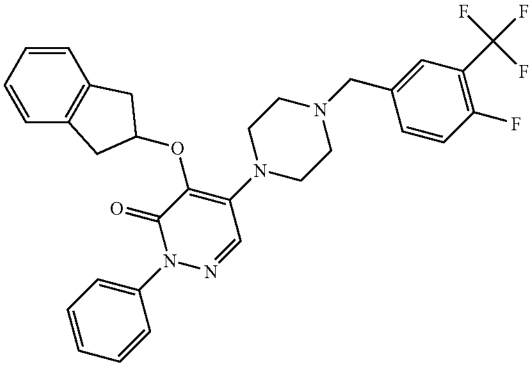
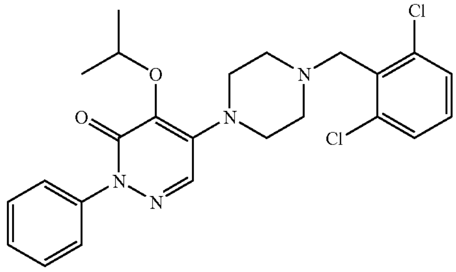
TABLE A-continued
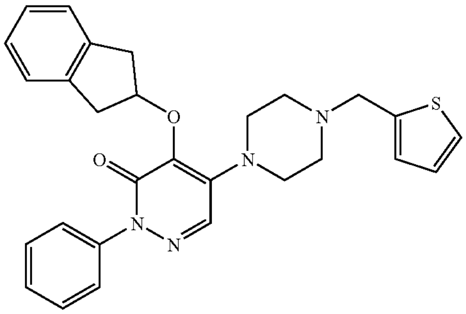
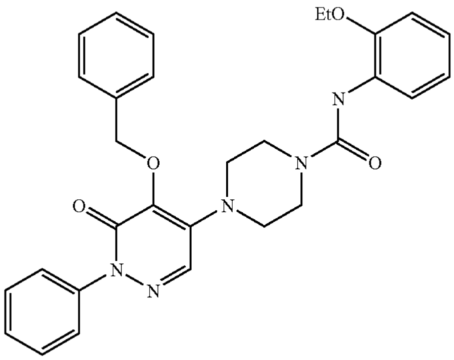
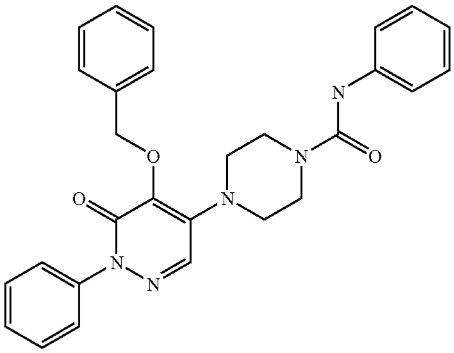
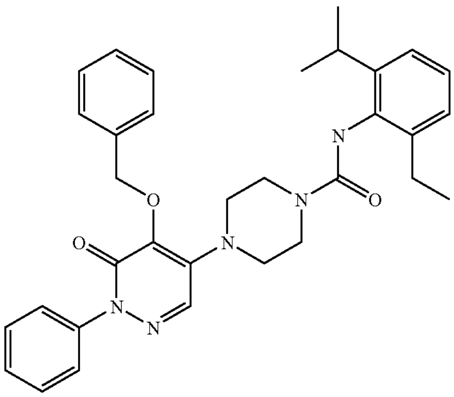

TABLE A-continued
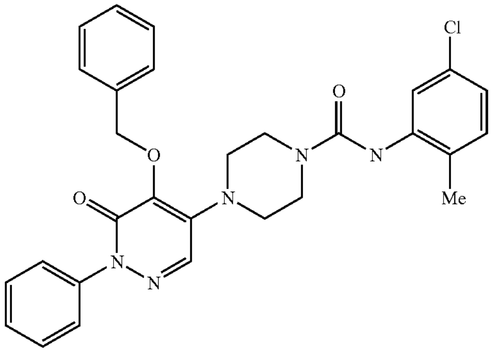
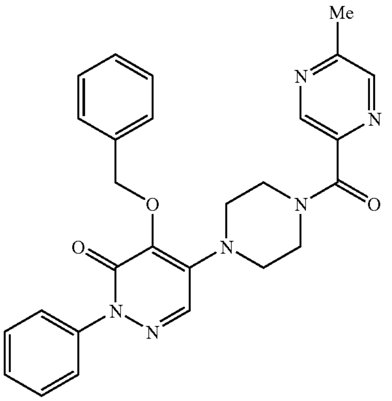
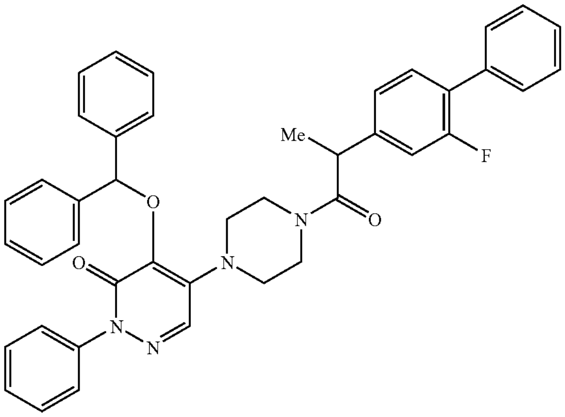
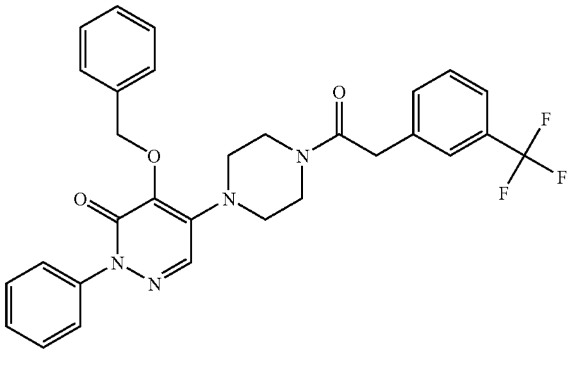
TABLE A-continued
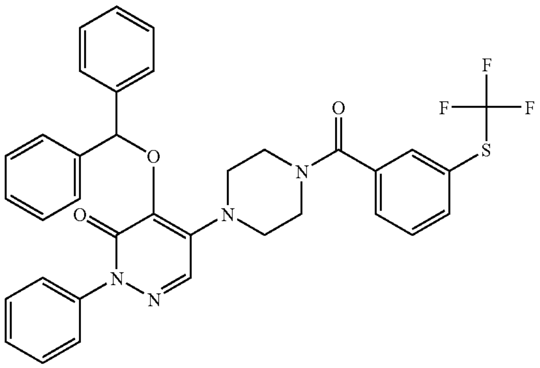
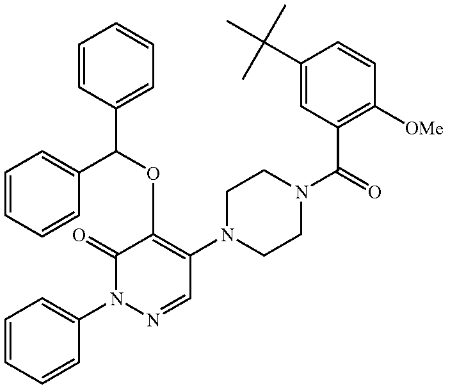
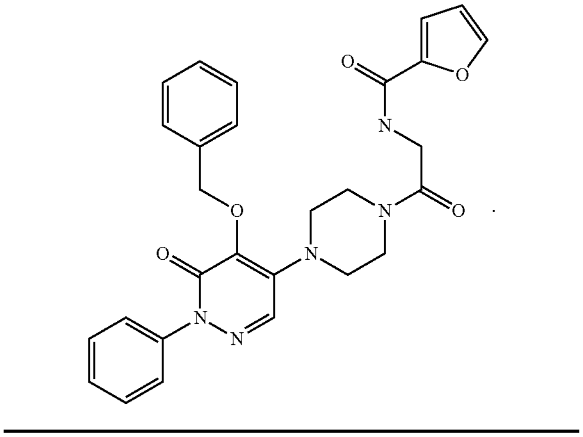
2. The compound of claim 1, wherein A is O.
3. The compound of claim 1, wherein D is N.
4. The compound of claim 1, wherein E is C.
5. The compound of claim 1, wherein Y is O.
6. The compound of claim 1, wherein Y is
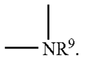

7. The compound of claim 1, wherein Y is —S—,

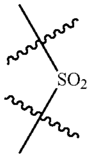

or

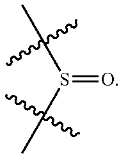

8. The compound of claim 1, wherein Y a single bond.

9. The compound of claim 1, wherein Z is

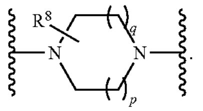

10. The compound of claim 1, wherein $R^5$ is

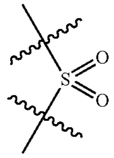

or

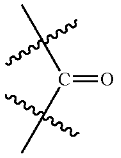

11. The compound of claim 1, wherein $R^5$ is

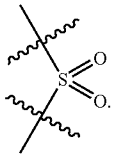

12. The compound of claim 1, wherein $R^5$ is

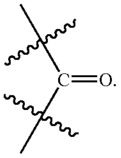

13. The compound of claim 1, wherein E is C and $R^6$ is H.

14. A compound of claim 1 having the structure

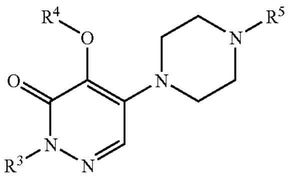

wherein $R^3$ is mono- or dihalo-phenyl;

$R^4$ is alkyl, haloalkyl, optionally substituted cycloalkyl, optionally substituted cycloalkylalkyl, optionally substituted benzyl, or optionally substituted benzofused cycloalkyl;

$R^5$ is —$SO_2$—, wherein the second end substituent is alkyl, haloalkyl, optionally substituted arylalkyl, or optionally substituted heteroarylalkyl; or —$N(R^9)_2$, wherein one $R^9$ is H and the other is optionally substituted arylalkyl or optionally substituted heteroarylalkyl.

15. A compound selected from the group consisting of:

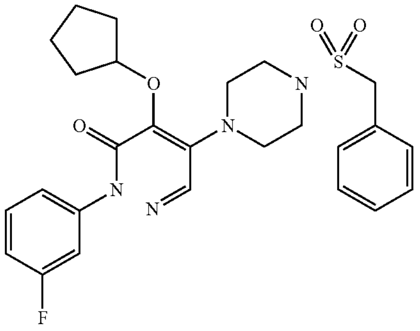

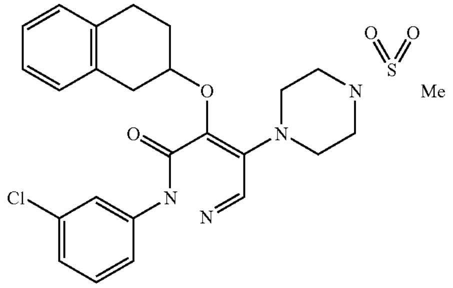

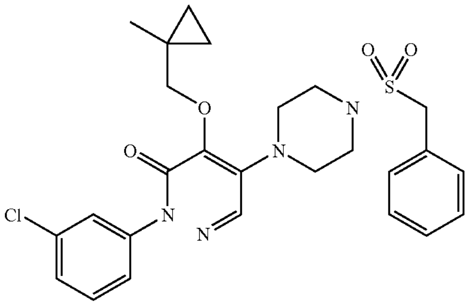

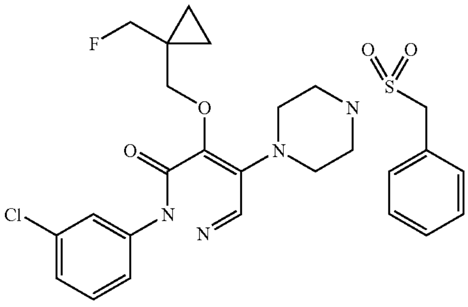

-continued
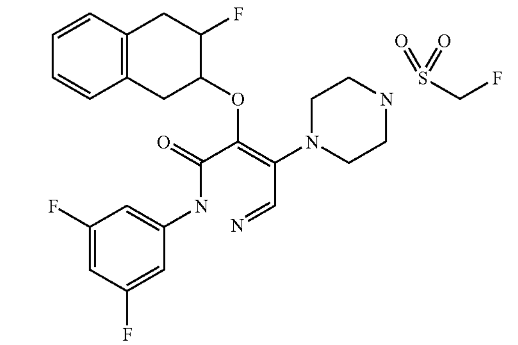
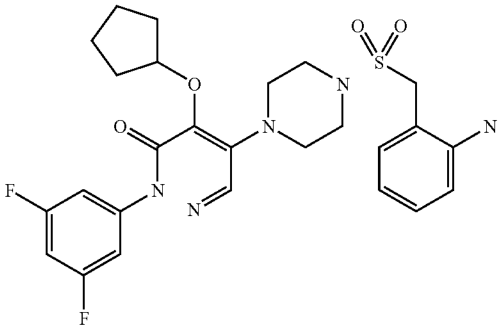
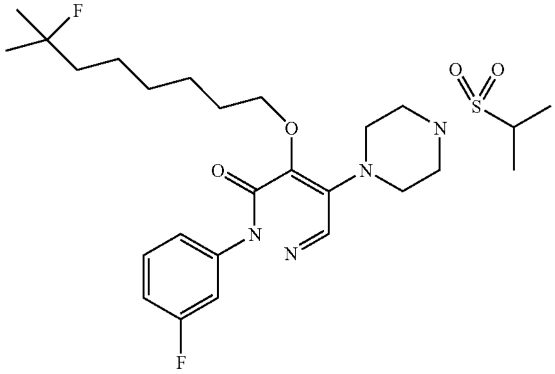
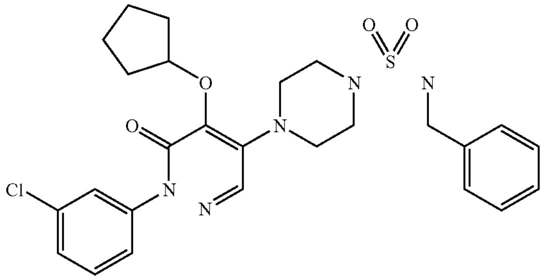
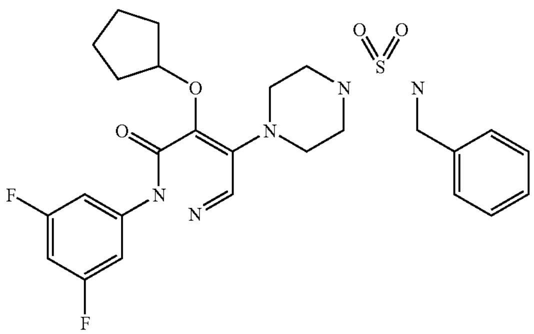
-continued
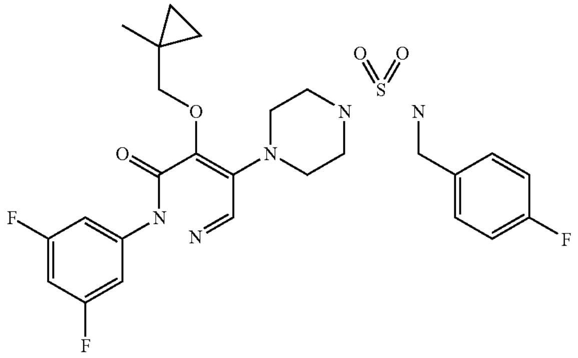
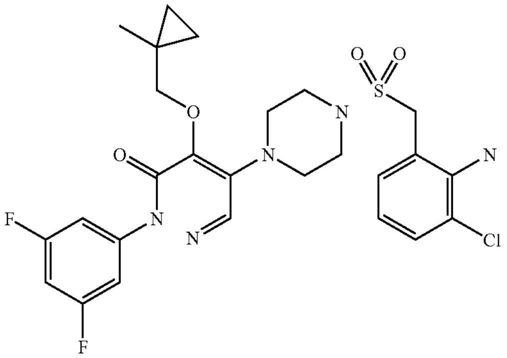
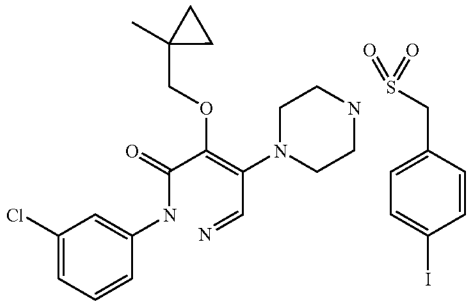
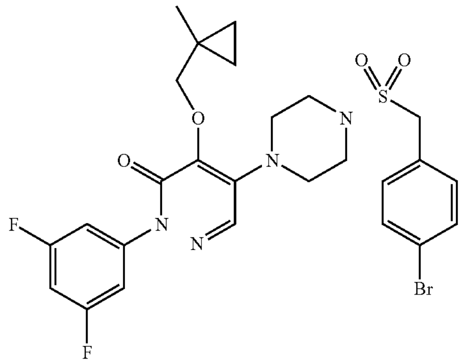
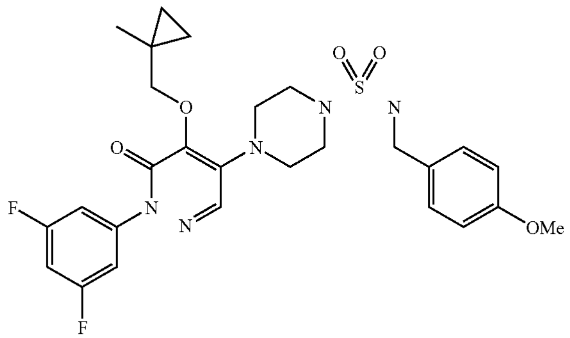

-continued
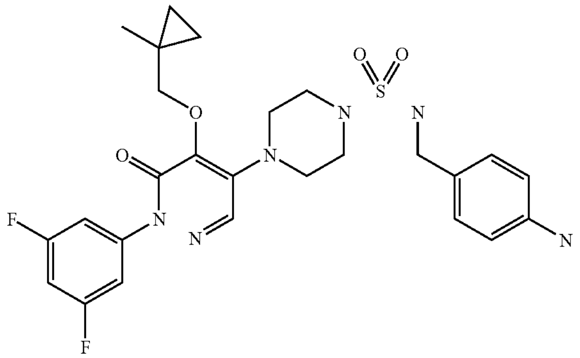
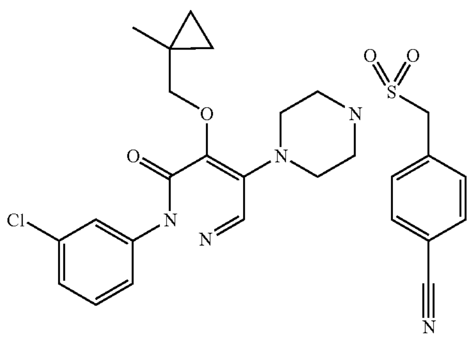
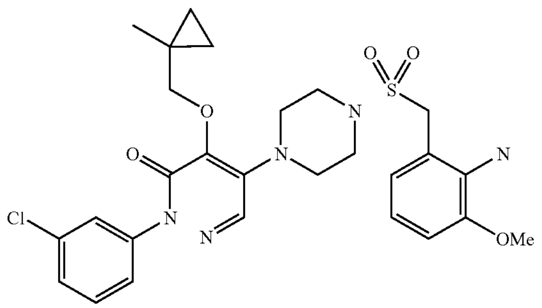
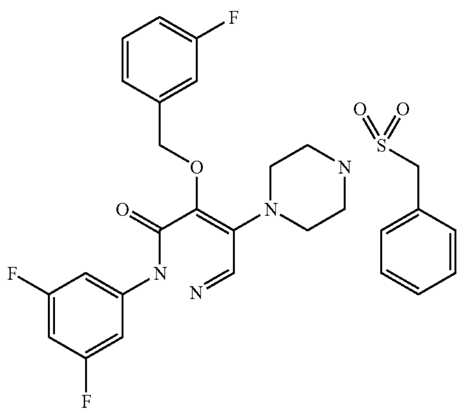
-continued
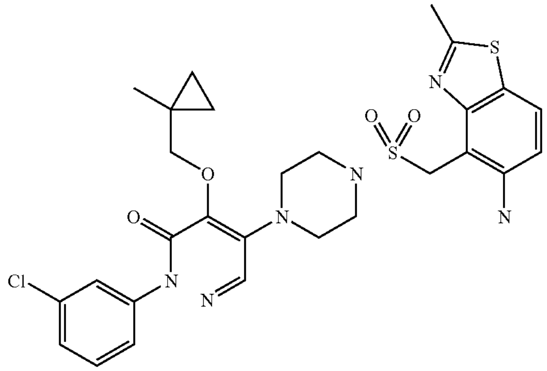
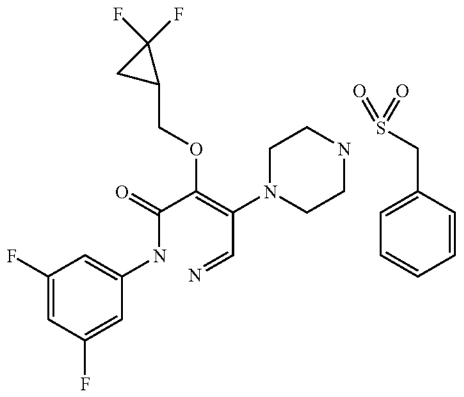
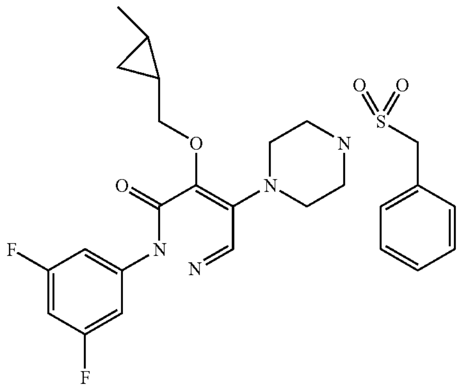
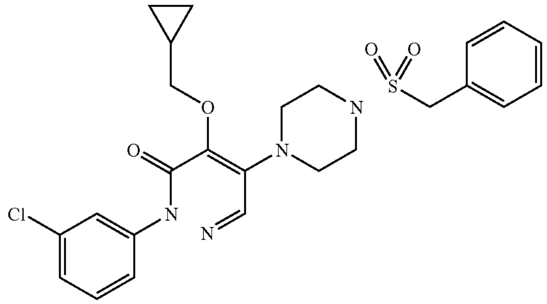

-continued
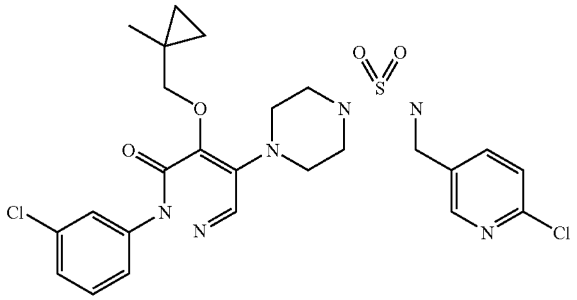
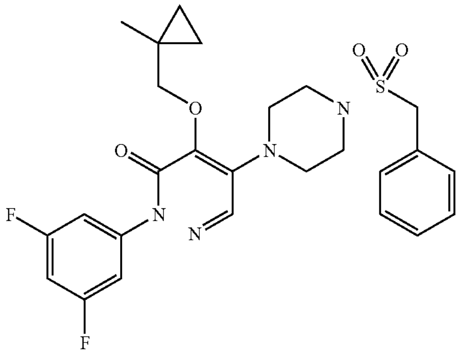
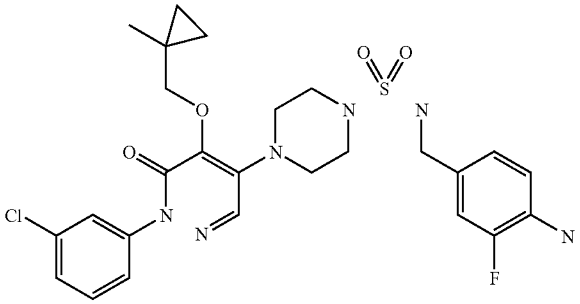
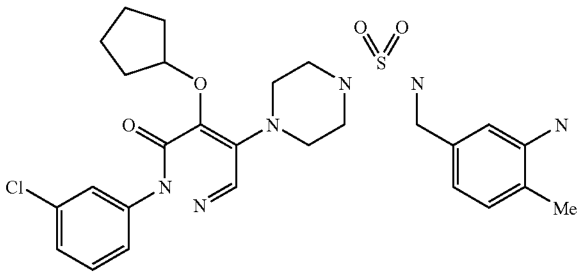
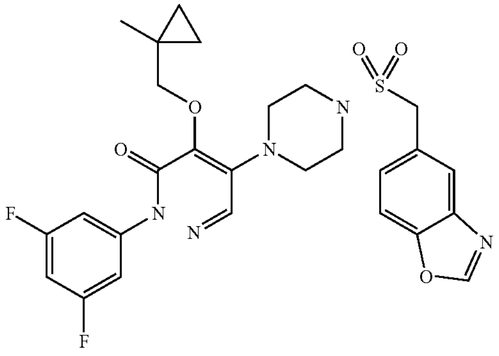
-continued
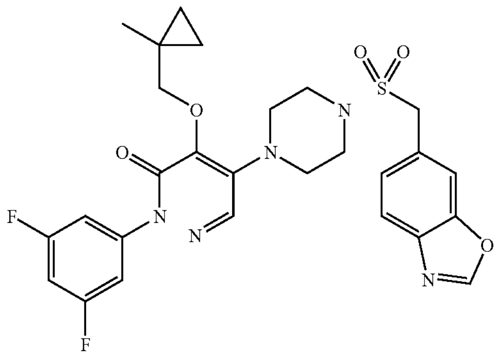
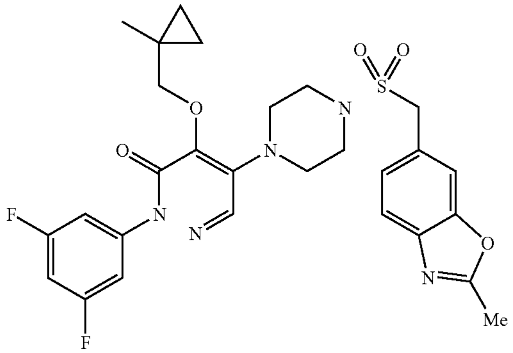
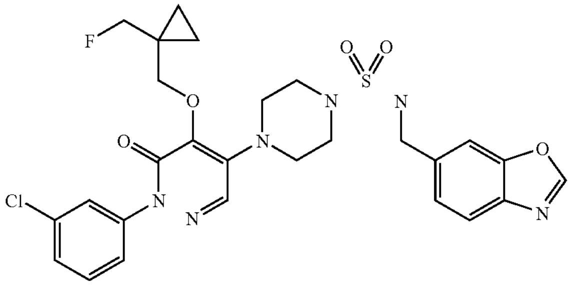
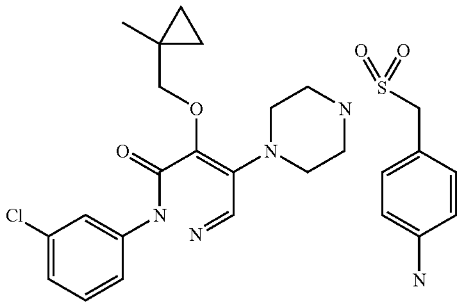
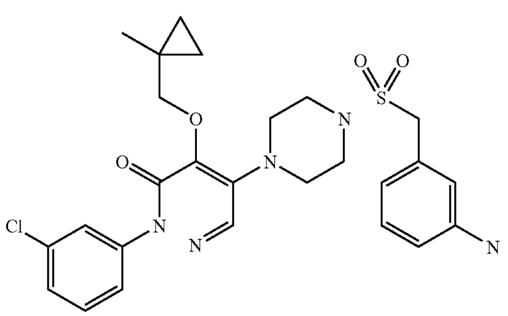

-continued
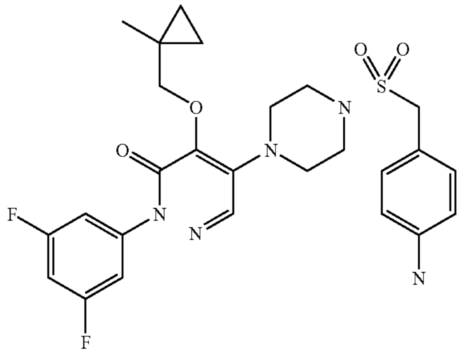
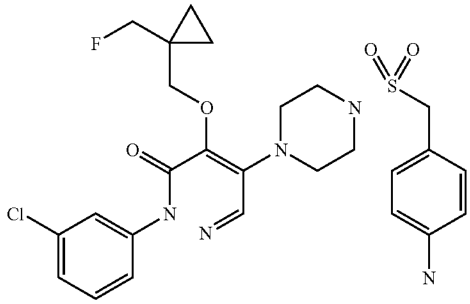
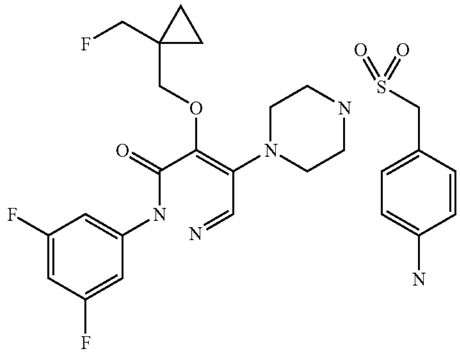
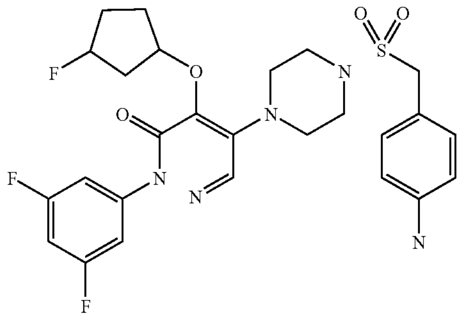
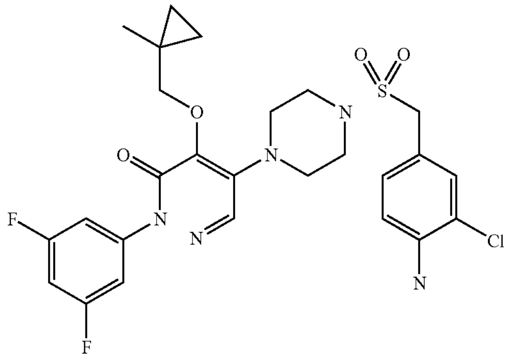
-continued
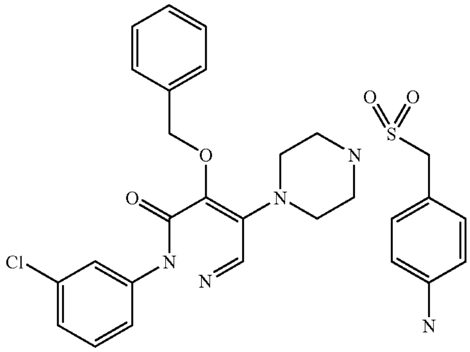
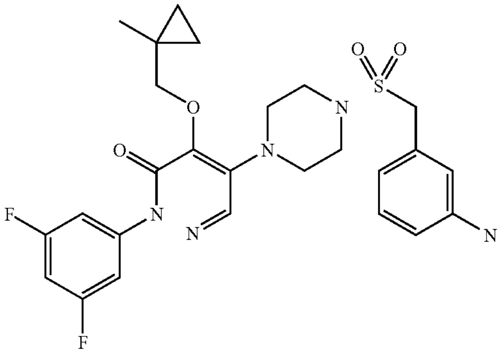
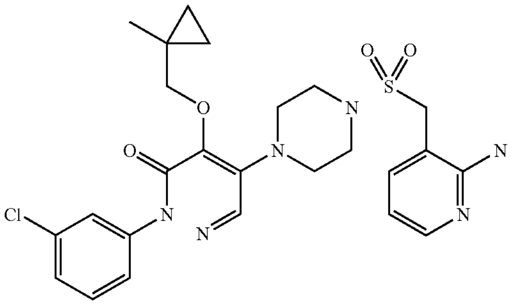
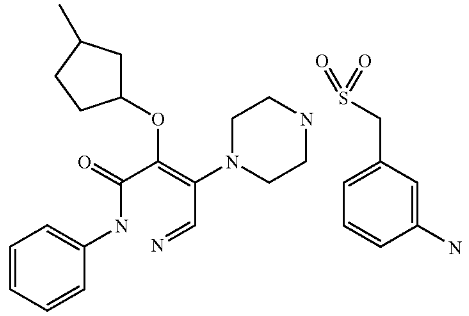
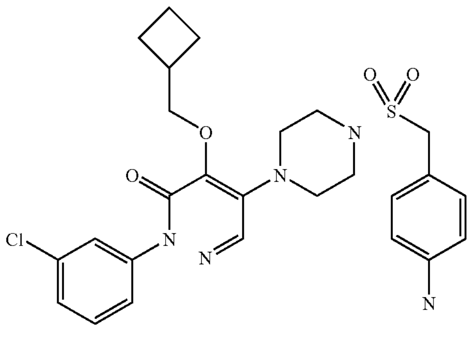

-continued
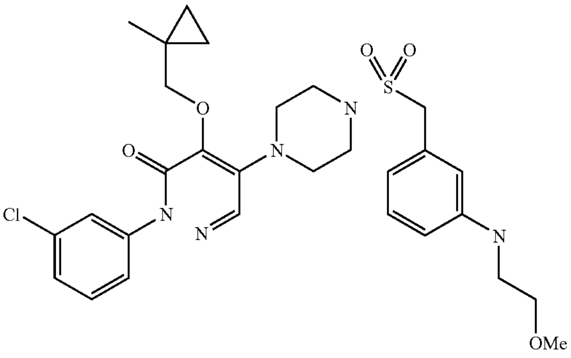
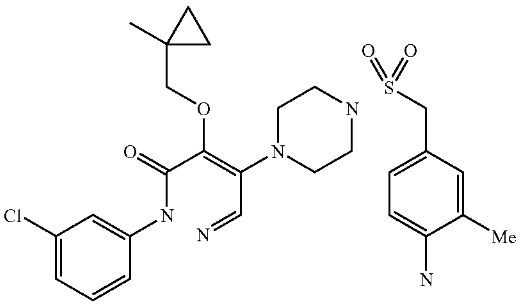
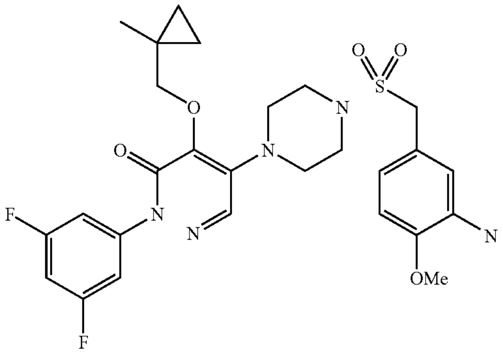
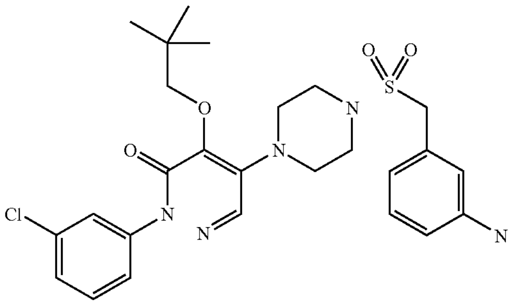
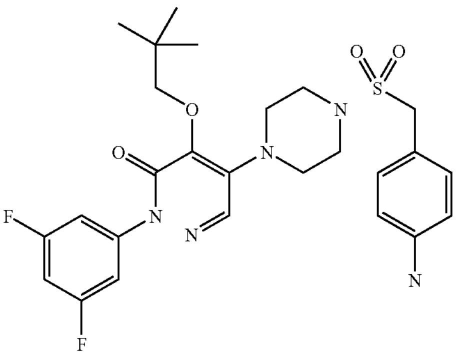
-continued
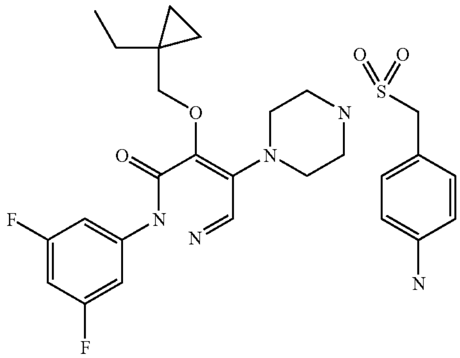
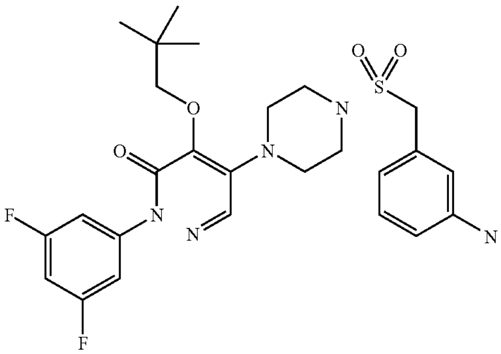
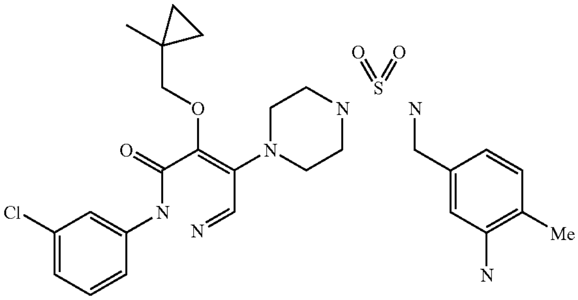
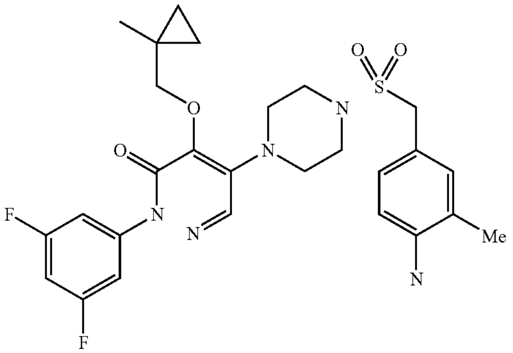
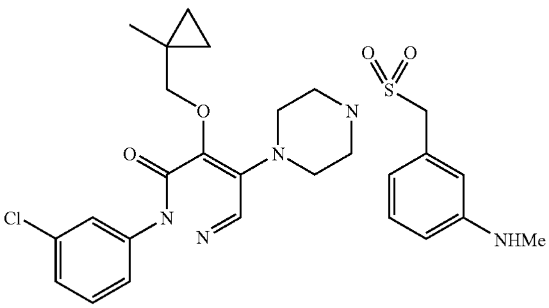

-continued
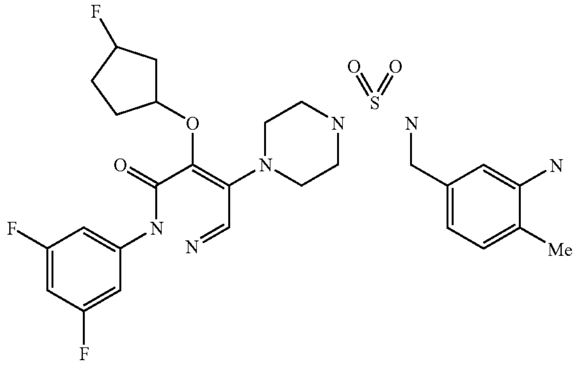
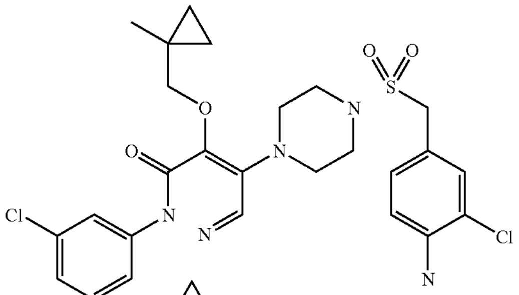
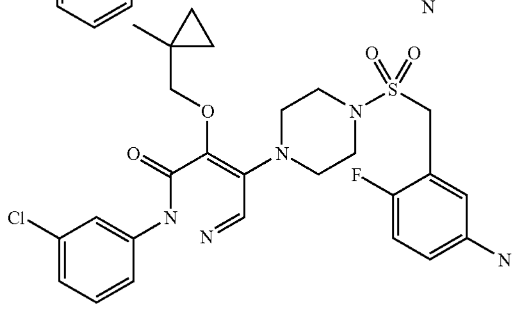
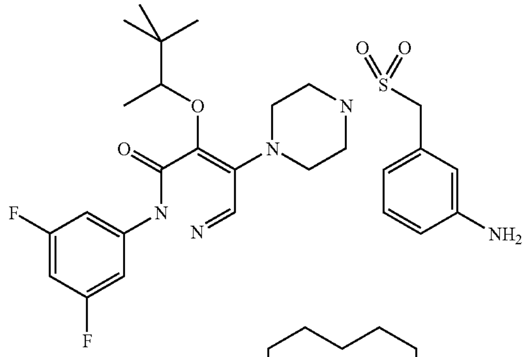
and
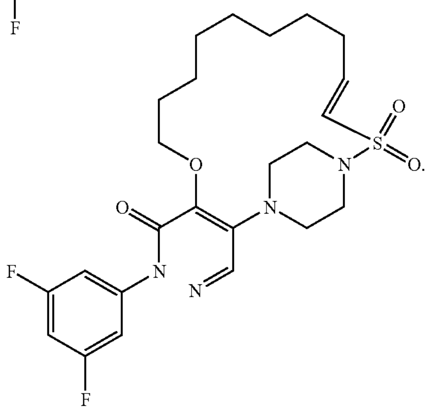
or a pharmaceutically acceptable salt thereof.
16. A compound selected from the group consisting of
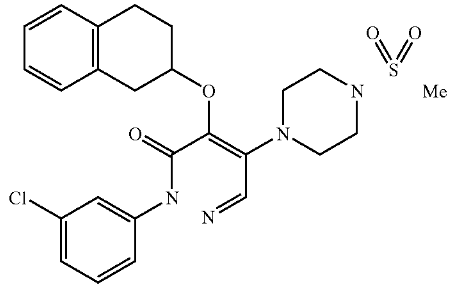
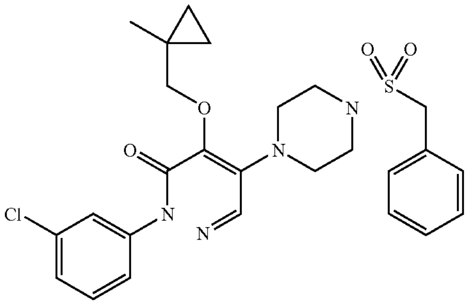
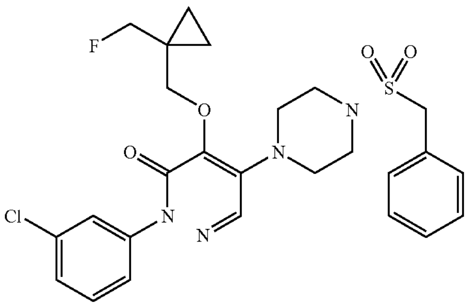
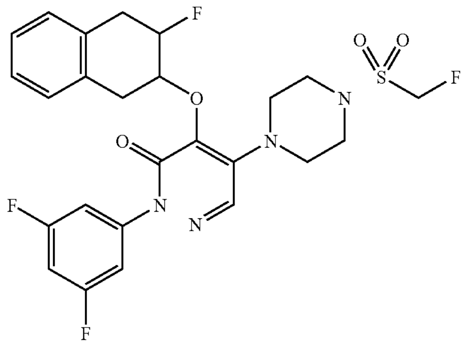
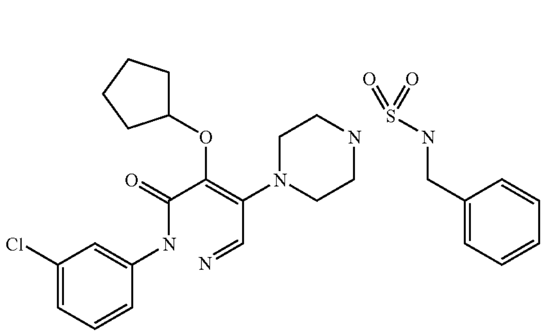

-continued
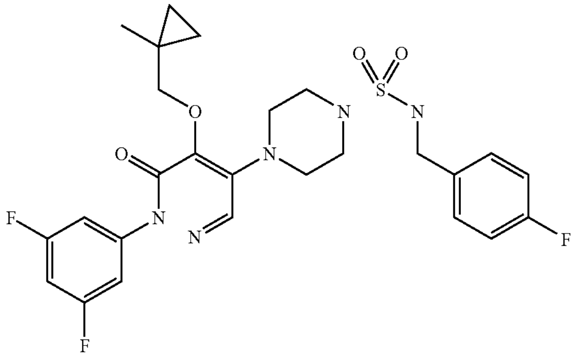
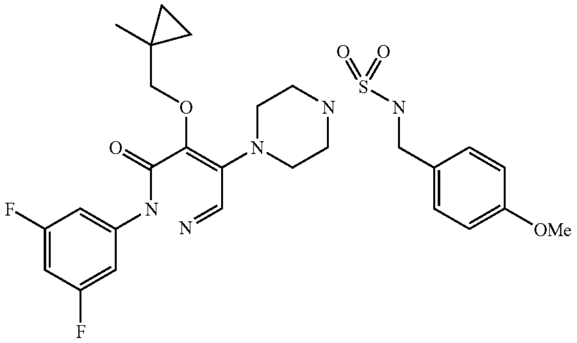
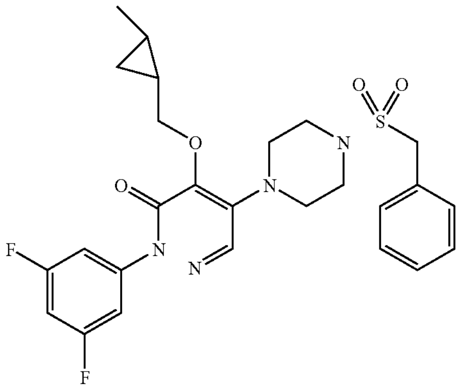
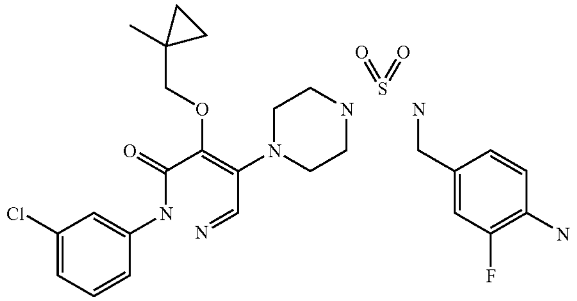
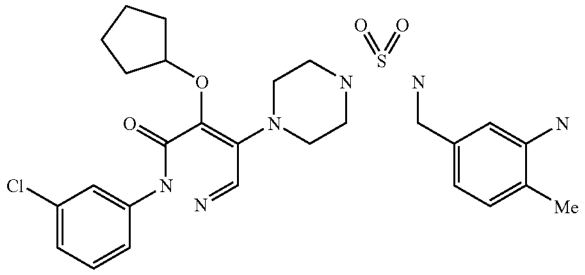
-continued
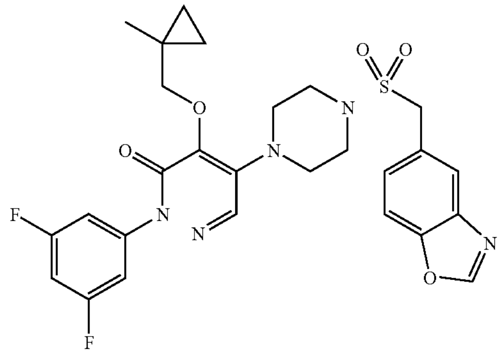
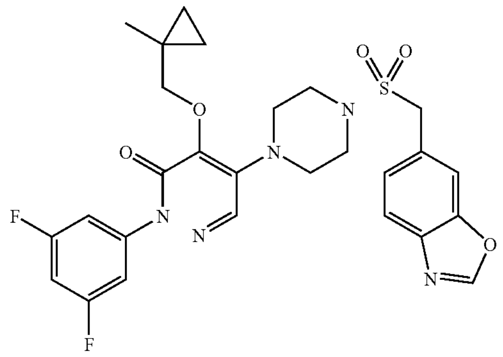
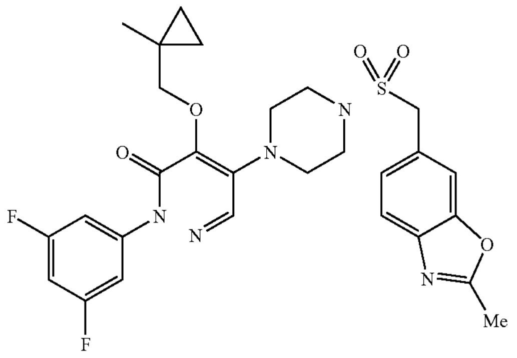
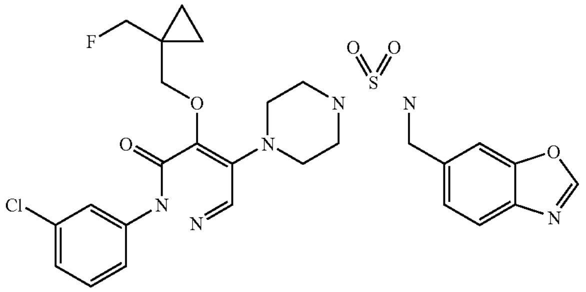
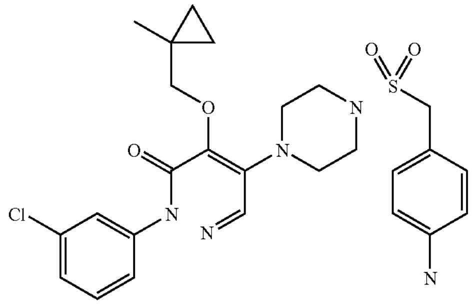

-continued
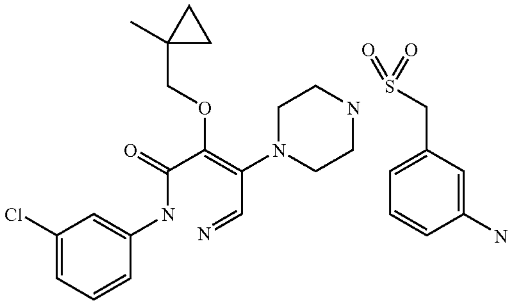
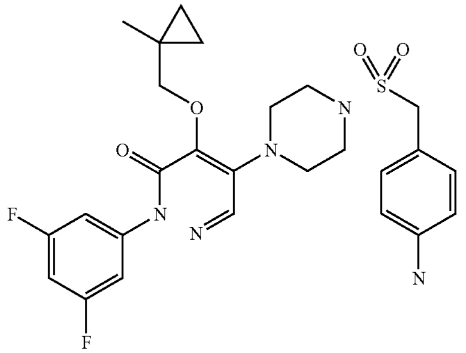
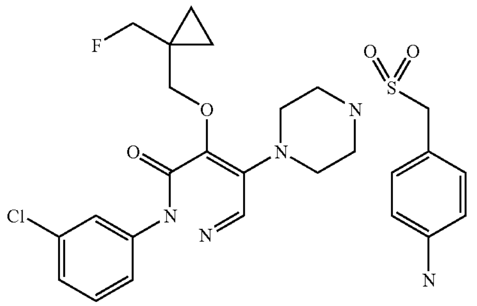
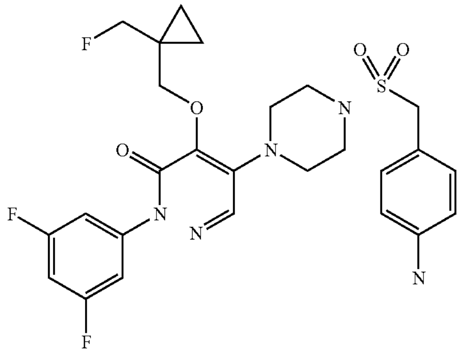
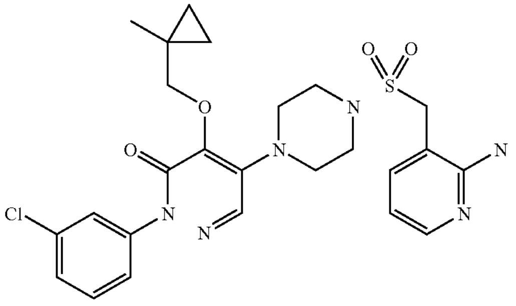
-continued
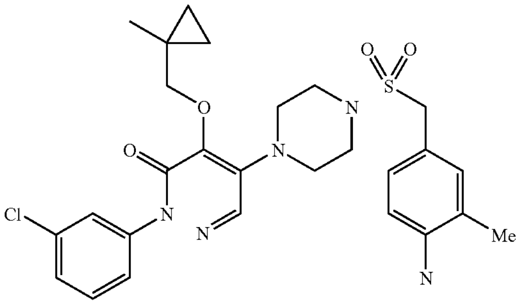
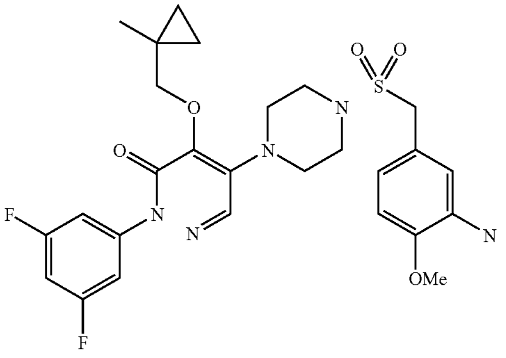
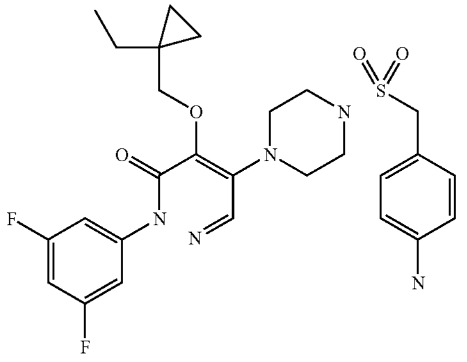
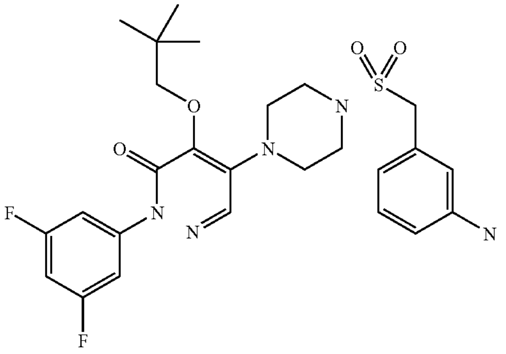

-continued

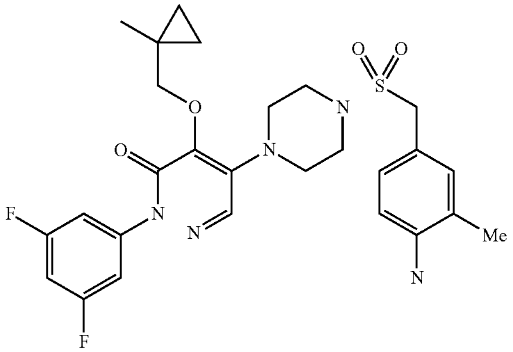

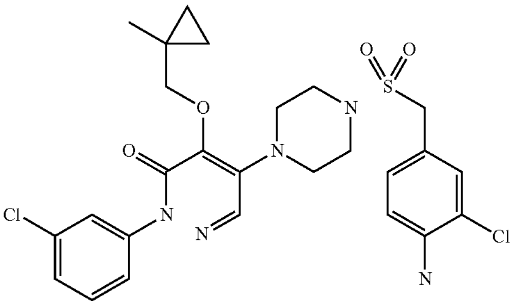

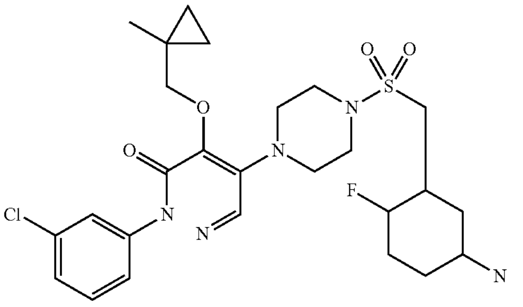

and

-continued

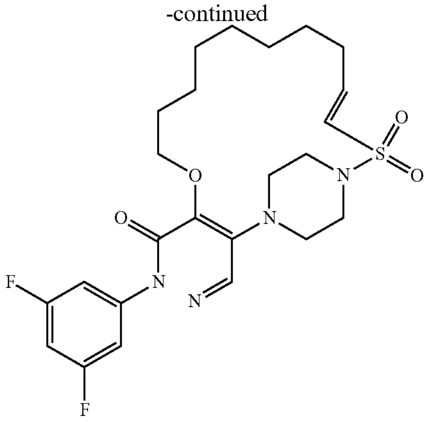

or a pharmaceutically acceptable salt thereof.

17. A pharmaceutical composition comprising a therapeutically effective amount of at least one compound of claim 1 or a pharmaceutically acceptable salt, or ester thereof, in combination with at least one pharmaceutically acceptable carrier.

18. The pharmaceutical composition according to claim 17, further comprising one or more anti-fungal agents different from the compound of claim 1.

19. The pharmaceutical composition according to claim 18, wherein the one or more anti-fungal agents are selected from the group consisting of azoles, echinocandins, polyenes, allylamines, thiocarbamates, nikkomycins, pradimicins, 5-fluorocytosines, oxaboroles, ciclopiroxolamine, griseofulvin and morpholines.

20. The pharmaceutical composition according to claim 18, wherein the one or more anti-fungal agents are selected from the group consisting of fluconazole, miconazole, itraconazole, voriconazole, posaconazole, caspofungin, micafungin, anidulafungin, amphotericin B, liposomal formulations of amphotericin B, nystatin, terbinafine, tolnaftate, ciclopiroxolamine, griseofulvin and fenpropimorph.

* * * * *